United States Patent
Liu et al.

(10) Patent No.: US 11,702,651 B2
(45) Date of Patent: Jul. 18, 2023

(54) ADENOSINE NUCLEOBASE EDITORS AND USES THEREOF

(71) Applicant: President and Fellows of Harvard College, Cambridge, MA (US)

(72) Inventors: David R. Liu, Cambridge, MA (US); Nicole Gaudelli, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 256 days.

(21) Appl. No.: 17/148,059

(22) Filed: Jan. 13, 2021

(65) Prior Publication Data

US 2021/0317440 A1    Oct. 14, 2021

Related U.S. Application Data

(63) Continuation of application No. 16/143,370, filed on Sep. 26, 2018, now Pat. No. 10,947,530, which is a continuation of application No. 15/791,085, filed on Oct. 23, 2017, now Pat. No. 10,113,163, which is a continuation of application No. PCT/US2017/045381, filed on Aug. 3, 2017.

(60) Provisional application No. 62/473,714, filed on Mar. 20, 2017, provisional application No. 62/454,035, filed on Feb. 2, 2017, provisional application No. 62/370,684, filed on Aug. 3, 2016.

(51) Int. Cl.
C12N 15/10    (2006.01)
C12N 9/78    (2006.01)
C12N 9/22    (2006.01)

(52) U.S. Cl.
CPC ........... *C12N 15/1024* (2013.01); *C12N 9/22* (2013.01); *C12N 9/78* (2013.01); *C12Y 305/04004* (2013.01)

(58) Field of Classification Search
CPC ......... C12N 15/1024; C12N 9/22; C12N 9/78
See application file for complete search history.

(56) References Cited

U.S. PATENT DOCUMENTS

| | | |
|---|---|---|
| 4,182,449 A | 1/1980 | Kozlow |
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,663,290 A | 5/1987 | Weis et al. |
| 4,737,323 A | 4/1988 | Martin et al. |
| 4,774,085 A | 9/1988 | Fidler |
| 4,797,368 A | 1/1989 | Carter et al. |
| 4,837,028 A | 6/1989 | Allen |
| 4,873,316 A | 10/1989 | Meade et al. |
| 4,880,635 A | 11/1989 | Janoff et al. |
| 4,889,818 A | 12/1989 | Gelfand et al. |
| 4,897,355 A | 1/1990 | Eppstein et al. |
| 4,906,477 A | 3/1990 | Kurono et al. |
| 4,911,928 A | 3/1990 | Wallach |
| 4,917,951 A | 4/1990 | Wallach |
| 4,920,016 A | 4/1990 | Allen et al. |
| 4,921,757 A | 5/1990 | Wheatley et al. |
| 4,946,787 A | 8/1990 | Eppstein et al. |
| 4,965,185 A | 10/1990 | Grischenko et al. |
| 5,017,492 A | 5/1991 | Kotewicz et al. |
| 5,047,342 A | 9/1991 | Chatterjee |
| 5,049,386 A | 9/1991 | Eppstein et al. |
| 5,079,352 A | 1/1992 | Gelfand et al. |
| 5,139,941 A | 8/1992 | Muzyczka et al. |
| 5,173,414 A | 12/1992 | Lebkowski et al. |
| 5,223,409 A | 6/1993 | Ladner et al. |
| 5,244,797 A | 9/1993 | Kotewicz et al. |
| 5,270,179 A | 12/1993 | Chatterjee |
| 5,374,553 A | 12/1994 | Gelfand et al. |
| 5,405,776 A | 4/1995 | Kotewicz et al. |
| 5,436,149 A | 7/1995 | Barnes |
| 5,449,639 A | 9/1995 | Wei et al. |
| 5,496,714 A | 3/1996 | Comb et al. |
| 5,512,462 A | 4/1996 | Cheng |
| 5,580,737 A | 12/1996 | Polisky et al. |
| 5,614,365 A | 3/1997 | Tabor et al. |
| 5,658,727 A | 8/1997 | Barbas et al. |
| 5,668,005 A | 9/1997 | Kotewicz et al. |
| 5,677,152 A | 10/1997 | Birch et al. |
| 5,767,099 A | 6/1998 | Harris et al. |
| 5,780,053 A | 7/1998 | Ashley et al. |

(Continued)

FOREIGN PATENT DOCUMENTS

AU    2012244264 A1    11/2012
AU    2012354062 A1    7/2014

(Continued)

OTHER PUBLICATIONS

U.S. Appl. No. 14/234,031, filed Mar. 24, 2014, Liu et al.
U.S. Appl. No. 14/320,271, filed Jun. 30, 2014, Liu et al.
U.S. Appl. No. 16/441,751, filed Jun. 14, 2019, Liu et al.
U.S. Appl. No. 14/320,519, filed Jun. 30, 2014, Liu et al.
U.S. Appl. No. 14/913,458, filed Feb. 22, 2016, Liu et al.

(Continued)

*Primary Examiner* — Paul J Holland
(74) *Attorney, Agent, or Firm* — Wolf, Greenfield & Sacks, P.C.

(57) ABSTRACT

The disclosure provides adenosine deaminases that are capable of deaminating adenosine in DNA. The disclosure also provides fusion proteins comprising a Cas9 (e.g., a Cas9 nickase) domain and adenosine deaminases that deaminate adenosine in DNA. In some embodiments, the fusion proteins further comprise a nuclear localization sequence (NLS), and/or an inhibitor of base repair, such as, a nuclease dead inosine specific nuclease (dISN).

61 Claims, 248 Drawing Sheets

Specification includes a Sequence Listing.

(56) References Cited

U.S. PATENT DOCUMENTS

| | | |
|---|---|---|
| 5,830,430 A | 11/1998 | Unger et al. |
| 5,834,247 A | 11/1998 | Comb et al. |
| 5,835,699 A | 11/1998 | Kimura |
| 5,851,548 A | 12/1998 | Dattagupta et al. |
| 5,855,910 A | 1/1999 | Ashley et al. |
| 5,962,313 A | 10/1999 | Podsakoff et al. |
| 5,981,182 A | 11/1999 | Jacobs, Jr. et al. |
| 6,057,153 A | 5/2000 | George et al. |
| 6,063,608 A | 5/2000 | Kotewicz et al. |
| 6,156,509 A | 12/2000 | Schellenberger |
| 6,183,998 B1 | 2/2001 | Ivanov et al. |
| 6,429,298 B1 | 8/2002 | Ellington et al. |
| 6,453,242 B1 | 9/2002 | Eisenberg et al. |
| 6,479,264 B1 | 11/2002 | Louwrier |
| 6,503,717 B2 | 1/2003 | Case et al. |
| 6,534,261 B1 | 3/2003 | Cox, III et al. |
| 6,589,768 B1 | 7/2003 | Kotewicz et al. |
| 6,599,692 B1 | 7/2003 | Case et al. |
| 6,607,882 B1 | 8/2003 | Cox, III et al. |
| 6,610,522 B1 | 8/2003 | Kotewicz et al. |
| 6,689,558 B2 | 2/2004 | Case |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,078,208 B2 | 7/2006 | Smith et al. |
| 7,163,824 B2 | 1/2007 | Cox, III et al. |
| 7,479,573 B2 | 1/2009 | Chu et al. |
| 7,595,179 B2 | 9/2009 | Chen et al. |
| 7,670,807 B2 | 3/2010 | Lampson et al. |
| 7,794,931 B2 | 9/2010 | Breaker et al. |
| 7,919,277 B2 | 4/2011 | Russell et al. |
| 7,993,672 B2 | 8/2011 | Huang et al. |
| 8,067,556 B2 | 11/2011 | Hogrefe et al. |
| 8,361,725 B2 | 1/2013 | Russell et al. |
| 8,394,604 B2 | 3/2013 | Liu et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,492,082 B2 | 7/2013 | De Franciscis et al. |
| 8,546,553 B2 | 10/2013 | Terns et al. |
| 8,569,256 B2 | 10/2013 | Heyes et al. |
| 8,586,363 B2 | 11/2013 | Voytas et al. |
| 8,680,069 B2 | 3/2014 | de Fougerolles et al. |
| 8,691,750 B2 | 4/2014 | Constien et al. |
| 8,697,359 B1 | 4/2014 | Zhang |
| 8,697,853 B2 | 4/2014 | Voytas et al. |
| 8,709,466 B2 | 4/2014 | Coady et al. |
| 8,728,526 B2 | 5/2014 | Heller |
| 8,748,667 B2 | 6/2014 | Budzik et al. |
| 8,758,810 B2 | 6/2014 | Okada et al. |
| 8,759,103 B2 | 6/2014 | Kim et al. |
| 8,759,104 B2 | 6/2014 | Unciti-Broceta et al. |
| 8,771,728 B2 | 7/2014 | Huang et al. |
| 8,790,664 B2 | 7/2014 | Pitard et al. |
| 8,795,965 B2 | 8/2014 | Zhang |
| 8,822,663 B2 | 9/2014 | Schrum et al. |
| 8,846,578 B2 | 9/2014 | McCray et al. |
| 8,900,814 B2 | 12/2014 | Yasukawa et al. |
| 8,993,233 B2 | 3/2015 | Zhang et al. |
| 8,999,641 B2 | 4/2015 | Zhang et al. |
| 9,023,594 B2 | 5/2015 | Liu et al. |
| 9,068,179 B1 | 6/2015 | Liu et al. |
| 9,163,284 B2 | 10/2015 | Liu et al. |
| 9,181,535 B2 | 11/2015 | Liu et al. |
| 9,228,207 B2 | 1/2016 | Liu et al. |
| 9,234,213 B2 | 1/2016 | Wu |
| 9,267,127 B2 | 2/2016 | Liu et al. |
| 9,322,006 B2 | 4/2016 | Liu et al. |
| 9,322,037 B2 | 4/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,388,430 B2 | 7/2016 | Liu et al. |
| 9,394,537 B2 | 7/2016 | Liu et al. |
| 9,458,484 B2 | 10/2016 | Ma et al. |
| 9,512,446 B1 | 12/2016 | Joung et al. |
| 9,526,724 B2 | 12/2016 | Oshlack et al. |
| 9,526,784 B2 | 12/2016 | Liu et al. |
| 9,534,210 B2 | 1/2017 | Park et al. |
| 9,580,698 B1 | 2/2017 | Xu et al. |
| 9,637,739 B2 | 5/2017 | Šikšnys et al. |
| 9,737,604 B2 | 8/2017 | Liu et al. |
| 9,738,693 B2 | 8/2017 | Telford et al. |
| 9,771,574 B2 | 9/2017 | Liu et al. |
| 9,783,791 B2 | 10/2017 | Hogrefe et al. |
| 9,816,093 B1 | 11/2017 | Donohoue et al. |
| 9,840,538 B2 | 12/2017 | Telford et al. |
| 9,840,690 B2 | 12/2017 | Karli et al. |
| 9,840,699 B2 | 12/2017 | Liu et al. |
| 9,840,702 B2 | 12/2017 | Collingwood et al. |
| 9,850,521 B2 | 12/2017 | Braman et al. |
| 9,873,907 B2 | 1/2018 | Zeiner et al. |
| 9,879,270 B2 | 1/2018 | Hittinger et al. |
| 9,932,567 B1 | 4/2018 | Xu et al. |
| 9,938,288 B1 | 4/2018 | Kishi et al. |
| 9,944,933 B2 | 4/2018 | Storici et al. |
| 9,982,279 B1 | 5/2018 | Gill et al. |
| 9,999,671 B2 | 6/2018 | Liu et al. |
| 10,059,940 B2 | 8/2018 | Zhong |
| 10,077,453 B2 | 9/2018 | Liu et al. |
| 10,113,163 B2 | 10/2018 | Liu et al. |
| 10,150,955 B2 | 12/2018 | Lambowitz et al. |
| 10,167,457 B2 | 1/2019 | Liu et al. |
| 10,179,911 B2 | 1/2019 | Liu et al. |
| 10,189,831 B2 | 1/2019 | Arrington et al. |
| 10,202,658 B2 | 2/2019 | Parkin et al. |
| 10,227,581 B2 | 3/2019 | Liu et al. |
| 10,323,236 B2 | 6/2019 | Liu et al. |
| 10,336,997 B2 | 7/2019 | Liu et al. |
| 10,358,670 B2 | 7/2019 | Janulaitis et al. |
| 10,392,674 B2 | 8/2019 | Liu et al. |
| 10,407,697 B2 | 9/2019 | Doudna et al. |
| 10,465,176 B2 | 11/2019 | Liu et al. |
| 10,508,298 B2 | 12/2019 | Liu et al. |
| 10,597,679 B2 | 3/2020 | Liu et al. |
| 10,612,011 B2 | 4/2020 | Liu et al. |
| 10,858,639 B2 | 12/2020 | Liu et al. |
| 10,912,833 B2 | 2/2021 | Liu et al. |
| 10,947,530 B2 | 3/2021 | Liu et al. |
| 10,954,548 B2 | 3/2021 | Liu et al. |
| 2003/0082575 A1 | 5/2003 | Schultz et al. |
| 2003/0087817 A1 | 5/2003 | Cox et al. |
| 2003/0096337 A1 | 5/2003 | Hillman et al. |
| 2003/0108885 A1 | 6/2003 | Schultz et al. |
| 2003/0119764 A1 | 6/2003 | Loeb et al. |
| 2003/0167533 A1 | 9/2003 | Yadav et al. |
| 2003/0203480 A1 | 10/2003 | Kovesdi et al. |
| 2004/0003420 A1 | 1/2004 | Kuhn et al. |
| 2004/0115184 A1 | 6/2004 | Smith et al. |
| 2004/0203109 A1 | 10/2004 | Lal et al. |
| 2005/0136429 A1 | 6/2005 | Guarente et al. |
| 2005/0222030 A1 | 10/2005 | Allison |
| 2005/0260626 A1 | 11/2005 | Lorens et al. |
| 2006/0088864 A1 | 4/2006 | Smolke et al. |
| 2006/0104984 A1 | 5/2006 | Littlefield et al. |
| 2006/0246568 A1 | 11/2006 | Honjo et al. |
| 2007/0264692 A1 | 11/2007 | Liu et al. |
| 2007/0269817 A1 | 11/2007 | Shapero |
| 2008/0051317 A1 | 2/2008 | Church et al. |
| 2008/0124725 A1 | 5/2008 | Barrangou et al. |
| 2008/0182254 A1 | 7/2008 | Hall et al. |
| 2008/0220502 A1 | 9/2008 | Schellenberger et al. |
| 2009/0130718 A1 | 5/2009 | Short |
| 2009/0215878 A1 | 8/2009 | Tan et al. |
| 2009/0234109 A1 | 9/2009 | Han et al. |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0273857 A1 | 10/2010 | Thakker et al. |
| 2010/0305197 A1 | 12/2010 | Che |
| 2010/0316643 A1 | 12/2010 | Eckert et al. |
| 2011/0016540 A1 | 1/2011 | Weinstein et al. |
| 2011/0059160 A1 | 3/2011 | Essner et al. |

(56) References Cited

U.S. PATENT DOCUMENTS

| | | |
|---|---|---|
| 2011/0059502 A1 | 3/2011 | Chalasani |
| 2011/0104787 A1 | 5/2011 | Church et al. |
| 2011/0177495 A1 | 7/2011 | Liu et al. |
| 2011/0189776 A1 | 8/2011 | Terns et al. |
| 2011/0217739 A1 | 9/2011 | Terns et al. |
| 2011/0301073 A1 | 12/2011 | Gregory et al. |
| 2012/0129759 A1 | 5/2012 | Liu et al. |
| 2012/0141523 A1 | 6/2012 | Castado et al. |
| 2012/0244264 A1 | 9/2012 | Karpinsky et al. |
| 2012/0244601 A1 | 9/2012 | Bertozzi et al. |
| 2012/0270273 A1 | 10/2012 | Zhang et al. |
| 2013/0059931 A1 | 3/2013 | Petersen-Mahrt et al. |
| 2013/0117869 A1 | 5/2013 | Duchateau et al. |
| 2013/0130248 A1 | 5/2013 | Haurwitz et al. |
| 2013/0158245 A1 | 6/2013 | Russell et al. |
| 2013/0165389 A1 | 6/2013 | Schellenberger et al. |
| 2013/0309720 A1 | 11/2013 | Schultz et al. |
| 2013/0344117 A1 | 12/2013 | Mirosevich et al. |
| 2013/0345064 A1 | 12/2013 | Liu et al. |
| 2014/0004280 A1 | 1/2014 | Loomis |
| 2014/0005269 A1 | 1/2014 | Ngwuluka et al. |
| 2014/0017214 A1 | 1/2014 | Cost |
| 2014/0018404 A1 | 1/2014 | Chen et al. |
| 2014/0044793 A1 | 2/2014 | Goll et al. |
| 2014/0065711 A1 | 3/2014 | Liu et al. |
| 2014/0068797 A1 | 3/2014 | Doudna et al. |
| 2014/0127752 A1 | 5/2014 | Zhou et al. |
| 2014/0141094 A1 | 5/2014 | Smyth et al. |
| 2014/0141487 A1 | 5/2014 | Feldman et al. |
| 2014/0179770 A1 | 6/2014 | Zhang et al. |
| 2014/0186843 A1 | 7/2014 | Zhang et al. |
| 2014/0186958 A1 | 7/2014 | Zhang et al. |
| 2014/0201858 A1 | 7/2014 | Ostertag et al. |
| 2014/0234289 A1 | 8/2014 | Liu et al. |
| 2014/0248702 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0295556 A1 | 10/2014 | Joung et al. |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0010526 A1 | 1/2015 | Liu et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |
| 2015/0044192 A1 | 2/2015 | Liu et al. |
| 2015/0044772 A1 | 2/2015 | Zhao |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0064138 A1 | 3/2015 | Lu et al. |
| 2015/0064789 A1 | 3/2015 | Paschon et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071902 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0079681 A1 | 3/2015 | Zhang |
| 2015/0098954 A1 | 4/2015 | Hyde et al. |
| 2015/0118216 A1 | 4/2015 | Liu et al. |
| 2015/0132269 A1 | 5/2015 | Orkin et al. |
| 2015/0140664 A1 | 5/2015 | Byrne et al. |
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0166981 A1 | 6/2015 | Liu et al. |
| 2015/0166982 A1 | 6/2015 | Liu et al. |
| 2015/0166984 A1 | 6/2015 | Liu et al. |
| 2015/0166985 A1 | 6/2015 | Liu et al. |
| 2015/0191744 A1 | 7/2015 | Wolfe et al. |
| 2015/0197759 A1 | 7/2015 | Xu et al. |
| 2015/0211058 A1 | 7/2015 | Carstens |
| 2015/0218573 A1 | 8/2015 | Logue et al. |
| 2015/0225773 A1 | 8/2015 | Farmer et al. |
| 2015/0252358 A1 | 9/2015 | Maeder et al. |
| 2015/0275202 A1 | 10/2015 | Liu et al. |
| 2015/0307889 A1 | 10/2015 | Petolino et al. |
| 2015/0315252 A1 | 11/2015 | Haugwitz et al. |
| 2015/0344549 A1 | 12/2015 | Muir et al. |
| 2016/0015682 A2 | 1/2016 | Cawthorne et al. |
| 2016/0017393 A1 | 1/2016 | Jacobson et al. |
| 2016/0017396 A1 | 1/2016 | Cann et al. |
| 2016/0032292 A1 | 2/2016 | Storici et al. |
| 2016/0032353 A1 | 2/2016 | Braman et al. |
| 2016/0040155 A1 | 2/2016 | Maizels et al. |
| 2016/0046952 A1 | 2/2016 | Hittinger et al. |
| 2016/0046961 A1 | 2/2016 | Jinek et al. |
| 2016/0046962 A1 | 2/2016 | May et al. |
| 2016/0053272 A1 | 2/2016 | Wurtzel et al. |
| 2016/0053304 A1 | 2/2016 | Wurtzel et al. |
| 2016/0074535 A1 | 3/2016 | Ranganathan et al. |
| 2016/0076093 A1 | 3/2016 | Shendure et al. |
| 2016/0090603 A1 | 3/2016 | Carnes et al. |
| 2016/0090622 A1 | 3/2016 | Liu et al. |
| 2016/0115488 A1 | 4/2016 | Zhang et al. |
| 2016/0138046 A1 | 5/2016 | Wu |
| 2016/0186214 A1 | 6/2016 | Brouns et al. |
| 2016/0200779 A1 | 7/2016 | Liu et al. |
| 2016/0201040 A1 | 7/2016 | Liu et al. |
| 2016/0201089 A1 | 7/2016 | Gersbach et al. |
| 2016/0206566 A1 | 7/2016 | Lu et al. |
| 2016/0208243 A1 | 7/2016 | Zhang et al. |
| 2016/0208288 A1 | 7/2016 | Liu et al. |
| 2016/0215275 A1 | 7/2016 | Zhong |
| 2016/0215276 A1 | 7/2016 | Liu et al. |
| 2016/0215300 A1 | 7/2016 | May et al. |
| 2016/0244784 A1 | 8/2016 | Jacobson et al. |
| 2016/0244829 A1 | 8/2016 | Bang et al. |
| 2016/0264934 A1 | 9/2016 | Giallourakis et al. |
| 2016/0272965 A1 | 9/2016 | Zhang et al. |
| 2016/0281072 A1 | 9/2016 | Zhang |
| 2016/0298136 A1 | 10/2016 | Chen et al. |
| 2016/0304846 A1 | 10/2016 | Liu et al. |
| 2016/0304855 A1 | 10/2016 | Stark et al. |
| 2016/0312304 A1 | 10/2016 | Sorrentino et al. |
| 2016/0319262 A1 | 11/2016 | Doudna et al. |
| 2016/0333389 A1 | 11/2016 | Liu et al. |
| 2016/0340622 A1 | 11/2016 | Abdou |
| 2016/0340662 A1 | 11/2016 | Zhang et al. |
| 2016/0345578 A1 | 12/2016 | Barrangou et al. |
| 2016/0346360 A1 | 12/2016 | Quake et al. |
| 2016/0346361 A1 | 12/2016 | Quake et al. |
| 2016/0346362 A1 | 12/2016 | Quake et al. |
| 2016/0348074 A1 | 12/2016 | Quake et al. |
| 2016/0348096 A1 | 12/2016 | Liu et al. |
| 2016/0350476 A1 | 12/2016 | Quake et al. |
| 2016/0355796 A1 | 12/2016 | Davidson et al. |
| 2016/0369262 A1 | 12/2016 | Reik et al. |
| 2017/0009224 A1 | 1/2017 | Liu et al. |
| 2017/0009242 A1 | 1/2017 | McKinley et al. |
| 2017/0014449 A1 | 1/2017 | Bangera et al. |
| 2017/0020922 A1 | 1/2017 | Wagner et al. |
| 2017/0037432 A1 | 2/2017 | Donohoue et al. |
| 2017/0044520 A1 | 2/2017 | Liu et al. |
| 2017/0044592 A1 | 2/2017 | Peter et al. |
| 2017/0053729 A1 | 2/2017 | Kotani et al. |
| 2017/0058271 A1 | 3/2017 | Joung et al. |
| 2017/0058272 A1 | 3/2017 | Carter et al. |
| 2017/0058298 A1 | 3/2017 | Kennedy et al. |
| 2017/0073663 A1 | 3/2017 | Wang et al. |
| 2017/0073670 A1 | 3/2017 | Nishida et al. |

(56) References Cited

U.S. PATENT DOCUMENTS

| | | |
|---|---|---|
| 2017/0087224 A1 | 3/2017 | Quake |
| 2017/0087225 A1 | 3/2017 | Quake |
| 2017/0088587 A1 | 3/2017 | Quake |
| 2017/0088828 A1 | 3/2017 | Quake |
| 2017/0107536 A1 | 4/2017 | Zhang et al. |
| 2017/0107560 A1 | 4/2017 | Peter et al. |
| 2017/0114367 A1 | 4/2017 | Hu et al. |
| 2017/0121693 A1 | 5/2017 | Liu et al. |
| 2017/0145394 A1 | 5/2017 | Yeo et al. |
| 2017/0145405 A1 | 5/2017 | Tang et al. |
| 2017/0145438 A1 | 5/2017 | Kantor |
| 2017/0152528 A1 | 6/2017 | Zhang |
| 2017/0152787 A1 | 6/2017 | Kubo et al. |
| 2017/0159033 A1 | 6/2017 | Kamtekar et al. |
| 2017/0166928 A1 | 6/2017 | Vyas et al. |
| 2017/0175104 A1 | 6/2017 | Doudna et al. |
| 2017/0175142 A1 | 6/2017 | Zhang et al. |
| 2017/0191047 A1 | 7/2017 | Terns et al. |
| 2017/0191078 A1 | 7/2017 | Zhang et al. |
| 2017/0198269 A1 | 7/2017 | Zhang et al. |
| 2017/0198277 A1 | 7/2017 | Kmiec et al. |
| 2017/0198302 A1 | 7/2017 | Feng et al. |
| 2017/0226522 A1 | 8/2017 | Hu et al. |
| 2017/0233703 A1 | 8/2017 | Xie et al. |
| 2017/0233756 A1 | 8/2017 | Begemann et al. |
| 2017/0247671 A1 | 8/2017 | Yung et al. |
| 2017/0247703 A1 | 8/2017 | Sloan et al. |
| 2017/0268022 A1 | 9/2017 | Liu et al. |
| 2017/0275665 A1 | 9/2017 | Silas et al. |
| 2017/0283797 A1 | 10/2017 | Robb et al. |
| 2017/0283831 A1 | 10/2017 | Zhang et al. |
| 2017/0314016 A1 | 11/2017 | Kim et al. |
| 2017/0362635 A1 | 12/2017 | Chamberlain et al. |
| 2018/0064077 A1 | 3/2018 | Dunham et al. |
| 2018/0066258 A1 | 3/2018 | Powell |
| 2018/0068062 A1 | 3/2018 | Zhang et al. |
| 2018/0073012 A1 | 3/2018 | Liu et al. |
| 2018/0080051 A1 | 3/2018 | Sheikh et al. |
| 2018/0087046 A1 | 3/2018 | Badran et al. |
| 2018/0100147 A1 | 4/2018 | Yates et al. |
| 2018/0105867 A1 | 4/2018 | Xiao et al. |
| 2018/0119118 A1 | 5/2018 | Lu et al. |
| 2018/0127780 A1 | 5/2018 | Liu et al. |
| 2018/0155708 A1 | 6/2018 | Church et al. |
| 2018/0155720 A1 | 6/2018 | Donohoue et al. |
| 2018/0163213 A1 | 6/2018 | Aneja et al. |
| 2018/0170984 A1 | 6/2018 | Harris et al. |
| 2018/0179503 A1 | 6/2018 | Maianti et al. |
| 2018/0179547 A1 | 6/2018 | Zhang et al. |
| 2018/0201921 A1 | 7/2018 | Malcolm |
| 2018/0230464 A1 | 8/2018 | Zhong |
| 2018/0230471 A1 | 8/2018 | Storici et al. |
| 2018/0236081 A1 | 8/2018 | Liu et al. |
| 2018/0237758 A1 | 8/2018 | Liu et al. |
| 2018/0237787 A1 | 8/2018 | Maianti et al. |
| 2018/0245066 A1 | 8/2018 | Yao et al. |
| 2018/0258418 A1 | 9/2018 | Kim |
| 2018/0265864 A1 | 9/2018 | Li et al. |
| 2018/0273939 A1 | 9/2018 | Yu et al. |
| 2018/0282722 A1 | 10/2018 | Jakimo et al. |
| 2018/0298391 A1 | 10/2018 | Jakimo et al. |
| 2018/0305688 A1 | 10/2018 | Zhong |
| 2018/0305704 A1 | 10/2018 | Zhang |
| 2018/0312822 A1 | 11/2018 | Lee et al. |
| 2018/0312825 A1 | 11/2018 | Liu et al. |
| 2018/0312828 A1 | 11/2018 | Liu et al. |
| 2018/0312835 A1 | 11/2018 | Yao et al. |
| 2018/0327756 A1 | 11/2018 | Zhang et al. |
| 2019/0010481 A1 | 1/2019 | Joung et al. |
| 2019/0055543 A1 | 2/2019 | Tran et al. |
| 2019/0093099 A1 | 3/2019 | Liu et al. |
| 2019/0185883 A1 | 6/2019 | Liu et al. |
| 2019/0225955 A1 | 7/2019 | Liu et al. |
| 2019/0233847 A1 | 8/2019 | Savage et al. |
| 2019/0241633 A1 | 8/2019 | Fotin-Mleczek et al. |
| 2019/0256842 A1 | 8/2019 | Liu et al. |
| 2019/0264202 A1 | 8/2019 | Church et al. |
| 2019/0276816 A1 | 9/2019 | Liu et al. |
| 2019/0322992 A1 | 10/2019 | Liu et al. |
| 2019/0352632 A1 | 11/2019 | Liu et al. |
| 2019/0367891 A1 | 12/2019 | Liu et al. |
| 2020/0010818 A1 | 1/2020 | Liu et al. |
| 2020/0010835 A1 | 1/2020 | Maianti et al. |
| 2020/0063127 A1 | 2/2020 | Lu et al. |
| 2020/0071722 A1 | 3/2020 | Liu et al. |
| 2020/0109398 A1 | 4/2020 | Rubens et al. |
| 2020/0216833 A1 | 7/2020 | Liu et al. |
| 2020/0255868 A1 | 8/2020 | Liu et al. |
| 2020/0277587 A1 | 9/2020 | Liu et al. |
| 2020/0323984 A1 | 10/2020 | Liu et al. |
| 2020/0399619 A1 | 12/2020 | Maianti et al. |
| 2021/0054416 A1 | 2/2021 | Liu et al. |

FOREIGN PATENT DOCUMENTS

| | | |
|---|---|---|
| AU | 2015252023 A1 | 11/2015 |
| AU | 2015101792 A4 | 1/2016 |
| BR | 112015013786 A2 | 7/2017 |
| CA | 2894668 A1 | 6/2014 |
| CA | 2894681 A1 | 6/2014 |
| CA | 2894684 A1 | 6/2014 |
| CA | 2 852 593 A1 | 11/2015 |
| CN | 1069962 A | 3/1993 |
| CN | 103224947 A | 7/2013 |
| CN | 103233028 A | 8/2013 |
| CN | 103388006 A | 11/2013 |
| CN | 103614415 A | 3/2014 |
| CN | 103642836 A | 3/2014 |
| CN | 103668472 A | 3/2014 |
| CN | 103820441 A | 5/2014 |
| CN | 103820454 A | 5/2014 |
| CN | 103911376 A | 7/2014 |
| CN | 103923911 A | 7/2014 |
| CN | 103981211 A1 | 8/2014 |
| CN | 103981212 A | 8/2014 |
| CN | 104004778 A | 8/2014 |
| CN | 104004782 A | 8/2014 |
| CN | 104017821 A | 9/2014 |
| CN | 104109687 A | 10/2014 |
| CN | 104178461 A | 12/2014 |
| CN | 104342457 A | 2/2015 |
| CN | 104404036 A | 3/2015 |
| CN | 104450774 A | 3/2015 |
| CN | 104480144 A | 4/2015 |
| CN | 104498493 A | 4/2015 |
| CN | 104504304 A | 4/2015 |
| CN | 104531704 A | 4/2015 |
| CN | 104531705 A | 4/2015 |
| CN | 104560864 A | 4/2015 |
| CN | 104561095 A | 4/2015 |
| CN | 104593418 A | 5/2015 |
| CN | 104593422 A | 5/2015 |
| CN | 104611370 A | 5/2015 |
| CN | 104651392 A | 5/2015 |
| CN | 104651398 A | 5/2015 |
| CN | 104651399 A | 5/2015 |
| CN | 104651401 A | 5/2015 |
| CN | 104673816 A | 6/2015 |
| CN | 104725626 A | 6/2015 |
| CN | 104726449 A | 6/2015 |
| CN | 104726494 A | 6/2015 |
| CN | 104745626 A | 7/2015 |
| CN | 104762321 A | 7/2015 |
| CN | 104805078 A | 7/2015 |
| CN | 104805099 A | 7/2015 |
| CN | 104805118 A | 7/2015 |
| CN | 104846010 A | 8/2015 |
| CN | 104894068 A | 9/2015 |
| CN | 104894075 A | 9/2015 |
| CN | 104928321 A | 9/2015 |
| CN | 105039339 A | 11/2015 |
| CN | 105039399 A | 11/2015 |
| CN | 105063061 A | 11/2015 |
| CN | 105087620 A | 11/2015 |

(56) References Cited

FOREIGN PATENT DOCUMENTS

| | | |
|---|---|---|
| CN | 105112422 A | 12/2015 |
| CN | 105112445 A | 12/2015 |
| CN | 105112519 A | 12/2015 |
| CN | 105121648 A | 12/2015 |
| CN | 105132427 A | 12/2015 |
| CN | 105132451 A | 12/2015 |
| CN | 105177038 A | 12/2015 |
| CN | 105177126 A | 12/2015 |
| CN | 105210981 A | 1/2016 |
| CN | 105219799 A | 1/2016 |
| CN | 105238806 A | 1/2016 |
| CN | 105255937 A | 1/2016 |
| CN | 105274144 A | 1/2016 |
| CN | 105296518 A | 2/2016 |
| CN | 105296537 A | 2/2016 |
| CN | 105316324 A | 2/2016 |
| CN | 105316327 A | 2/2016 |
| CN | 105316337 A | 2/2016 |
| CN | 105331607 A | 2/2016 |
| CN | 105331608 A | 2/2016 |
| CN | 105331609 A | 2/2016 |
| CN | 105331627 A | 2/2016 |
| CN | 105400773 A | 3/2016 |
| CN | 105400779 A | 3/2016 |
| CN | 105400810 A | 3/2016 |
| CN | 105441451 A | 3/2016 |
| CN | 105462968 A | 4/2016 |
| CN | 105463003 A | 4/2016 |
| CN | 105463027 A | 4/2016 |
| CN | 105492608 A | 4/2016 |
| CN | 105492609 A | 4/2016 |
| CN | 105505976 A | 4/2016 |
| CN | 105505979 A | 4/2016 |
| CN | 105518134 A | 4/2016 |
| CN | 105518135 A | 4/2016 |
| CN | 105518137 A | 4/2016 |
| CN | 105518138 A | 4/2016 |
| CN | 105518139 A | 4/2016 |
| CN | 105518140 A | 4/2016 |
| CN | 105543228 A | 5/2016 |
| CN | 105543266 A | 5/2016 |
| CN | 105543270 A | 5/2016 |
| CN | 105567688 A | 5/2016 |
| CN | 105567689 A | 5/2016 |
| CN | 105567734 A | 5/2016 |
| CN | 105567735 A | 5/2016 |
| CN | 105567738 A | 5/2016 |
| CN | 105593367 A | 5/2016 |
| CN | 105594664 A | 5/2016 |
| CN | 105602987 A | 5/2016 |
| CN | 105624146 A | 6/2016 |
| CN | 105624187 A | 6/2016 |
| CN | 105646719 A | 6/2016 |
| CN | 105647922 A | 6/2016 |
| CN | 105647962 A | 6/2016 |
| CN | 105647968 A | 6/2016 |
| CN | 105647969 A | 6/2016 |
| CN | 105671070 A | 6/2016 |
| CN | 105671083 A | 6/2016 |
| CN | 105695485 A | 6/2016 |
| CN | 105779448 A | 7/2016 |
| CN | 105779449 A | 7/2016 |
| CN | 105802980 A | 7/2016 |
| CN | 105821039 A | 8/2016 |
| CN | 105821040 A | 8/2016 |
| CN | 105821049 A | 8/2016 |
| CN | 105821072 A | 8/2016 |
| CN | 105821075 A | 8/2016 |
| CN | 105821116 A | 8/2016 |
| CN | 105838733 A | 8/2016 |
| CN | 105861547 A | 8/2016 |
| CN | 105861552 A | 8/2016 |
| CN | 105861554 A | 8/2016 |
| CN | 105886498 A | 8/2016 |
| CN | 105886534 A | 8/2016 |
| CN | 105886616 A | 8/2016 |
| CN | 105907758 A | 8/2016 |
| CN | 105907785 A | 8/2016 |
| CN | 105925608 A | 9/2016 |
| CN | 105950560 A | 9/2016 |
| CN | 105950626 A | 9/2016 |
| CN | 105950633 A | 9/2016 |
| CN | 105950639 A | 9/2016 |
| CN | 105985985 A | 10/2016 |
| CN | 106011104 A | 10/2016 |
| CN | 106011150 A | 10/2016 |
| CN | 106011167 A | 10/2016 |
| CN | 106011171 A | 10/2016 |
| CN | 106032540 A | 10/2016 |
| CN | 106047803 A | 10/2016 |
| CN | 106047877 A | 10/2016 |
| CN | 106047930 A | 10/2016 |
| CN | 106086008 A | 11/2016 |
| CN | 106086028 A | 11/2016 |
| CN | 106086061 A | 11/2016 |
| CN | 106086062 A | 11/2016 |
| CN | 106109417 A | 11/2016 |
| CN | 106119275 A | 11/2016 |
| CN | 106119283 A | 11/2016 |
| CN | 106148286 A | 11/2016 |
| CN | 106148370 A | 11/2016 |
| CN | 106148416 A | 11/2016 |
| CN | 106167525 A | 11/2016 |
| CN | 106167808 A | 11/2016 |
| CN | 106167810 A | 11/2016 |
| CN | 106167821 A | 11/2016 |
| CN | 106172238 A | 12/2016 |
| CN | 106190903 A | 12/2016 |
| CN | 106191057 A | 12/2016 |
| CN | 106191061 A | 12/2016 |
| CN | 106191062 A | 12/2016 |
| CN | 106191064 A | 12/2016 |
| CN | 106191071 A | 12/2016 |
| CN | 106191099 A | 12/2016 |
| CN | 106191107 A | 12/2016 |
| CN | 106191113 A | 12/2016 |
| CN | 106191114 A | 12/2016 |
| CN | 106191116 A | 12/2016 |
| CN | 106191124 A | 12/2016 |
| CN | 106222177 A | 12/2016 |
| CN | 106222193 A | 12/2016 |
| CN | 106222203 A | 12/2016 |
| CN | 106244555 A | 12/2016 |
| CN | 106244591 A | 12/2016 |
| CN | 106244609 A | 12/2016 |
| CN | 106282241 A | 1/2017 |
| CN | 106318934 A | 1/2017 |
| CN | 106318973 A | 1/2017 |
| CN | 106350540 A | 1/2017 |
| CN | 106367435 A | 2/2017 |
| CN | 106399306 A | 2/2017 |
| CN | 106399311 A | 2/2017 |
| CN | 106399360 A | 2/2017 |
| CN | 106399367 A | 2/2017 |
| CN | 106399375 A | 2/2017 |
| CN | 106399377 A | 2/2017 |
| CN | 106434651 A | 2/2017 |
| CN | 106434663 A | 2/2017 |
| CN | 106434688 A | 2/2017 |
| CN | 106434737 A | 2/2017 |
| CN | 106434748 A | 2/2017 |
| CN | 106434752 A | 2/2017 |
| CN | 106434782 A | 2/2017 |
| CN | 106446600 A | 2/2017 |
| CN | 106479985 A | 3/2017 |
| CN | 106480027 A | 3/2017 |
| CN | 106480036 A | 3/2017 |
| CN | 106480067 A | 3/2017 |
| CN | 106480080 A | 3/2017 |
| CN | 106480083 A | 3/2017 |
| CN | 106480097 A | 3/2017 |
| CN | 106544351 A | 3/2017 |
| CN | 106544353 A | 3/2017 |
| CN | 106544357 A | 3/2017 |

(56) References Cited

FOREIGN PATENT DOCUMENTS

| | | |
|---|---|---|
| CN | 106554969 A | 4/2017 |
| CN | 106566838 A | 4/2017 |
| CN | 106701763 A | 5/2017 |
| CN | 106701808 A | 5/2017 |
| CN | 106701818 A | 5/2017 |
| CN | 106701823 A | 5/2017 |
| CN | 106701830 A | 5/2017 |
| CN | 106754912 A | 5/2017 |
| CN | 106755026 A | 5/2017 |
| CN | 106755077 A | 5/2017 |
| CN | 106755088 A | 5/2017 |
| CN | 106755091 A | 5/2017 |
| CN | 106755097 A | 5/2017 |
| CN | 106755424 A | 5/2017 |
| CN | 106801056 A | 6/2017 |
| CN | 106834323 A | 6/2017 |
| CN | 106834341 A | 6/2017 |
| CN | 106834347 A | 6/2017 |
| CN | 106845151 A | 6/2017 |
| CN | 106868008 A | 6/2017 |
| CN | 106868031 A | 6/2017 |
| CN | 106906240 A | 6/2017 |
| CN | 106906242 A | 6/2017 |
| CN | 106916820 A | 7/2017 |
| CN | 106916852 A | 7/2017 |
| CN | 106939303 A | 7/2017 |
| CN | 106947750 A | 7/2017 |
| CN | 106947780 A | 7/2017 |
| CN | 106957830 A | 7/2017 |
| CN | 106957831 A | 7/2017 |
| CN | 106957844 A | 7/2017 |
| CN | 106957855 A | 7/2017 |
| CN | 106957858 A | 7/2017 |
| CN | 106967697 A | 7/2017 |
| CN | 106967726 A | 7/2017 |
| CN | 106978428 A | 7/2017 |
| CN | 106987570 A | 7/2017 |
| CN | 106987757 A | 7/2017 |
| CN | 107012164 A | 8/2017 |
| CN | 107012174 A | 8/2017 |
| CN | 107012213 A | 8/2017 |
| CN | 107012250 A | 8/2017 |
| CN | 107022562 A | 8/2017 |
| CN | 107034188 A | 8/2017 |
| CN | 107034218 A | 8/2017 |
| CN | 107034229 A | 8/2017 |
| CN | 107043775 A | 8/2017 |
| CN | 107043779 A | 8/2017 |
| CN | 107043787 A | 8/2017 |
| CN | 107058320 A | 8/2017 |
| CN | 107058328 A | 8/2017 |
| CN | 107058358 A | 8/2017 |
| CN | 107058372 A | 8/2017 |
| CN | 107083392 A | 8/2017 |
| CN | 107099533 A | 8/2017 |
| CN | 107099850 A | 8/2017 |
| CN | 107119053 A | 9/2017 |
| CN | 107119071 A | 9/2017 |
| CN | 107129999 A | 9/2017 |
| CN | 107130000 A | 9/2017 |
| CN | 107142272 A | 9/2017 |
| CN | 107142282 A | 9/2017 |
| CN | 107177591 A | 9/2017 |
| CN | 107177595 A | 9/2017 |
| CN | 107177625 A | 9/2017 |
| CN | 107177631 A | 9/2017 |
| CN | 107190006 A | 9/2017 |
| CN | 107190008 A | 9/2017 |
| CN | 107217042 A | 9/2017 |
| CN | 107217075 A | 9/2017 |
| CN | 107227307 A | 10/2017 |
| CN | 107227352 A | 10/2017 |
| CN | 107236737 A | 10/2017 |
| CN | 107236739 A | 10/2017 |
| CN | 107236741 A | 10/2017 |
| CN | 107245502 A | 10/2017 |
| CN | 107254485 A | 10/2017 |
| CN | 107266541 A | 10/2017 |
| CN | 107267515 A | 10/2017 |
| CN | 107287245 A | 10/2017 |
| CN | 107298701 A | 10/2017 |
| CN | 107299114 A | 10/2017 |
| CN | 107304435 A | 10/2017 |
| CN | 107312785 A | 11/2017 |
| CN | 107312793 A | 11/2017 |
| CN | 107312795 A | 11/2017 |
| CN | 107312798 A | 11/2017 |
| CN | 107326042 U | 11/2017 |
| CN | 107326046 A | 11/2017 |
| CN | 107354156 A | 11/2017 |
| CN | 107354173 A | 11/2017 |
| CN | 107356793 A | 11/2017 |
| CN | 107362372 A | 11/2017 |
| CN | 107365786 A | 11/2017 |
| CN | 107365804 A | 11/2017 |
| CN | 107384894 A | 11/2017 |
| CN | 107384922 A | 11/2017 |
| CN | 107384926 A | 11/2017 |
| CN | 107400677 A | 11/2017 |
| CN | 107418974 A | 12/2017 |
| CN | 107435051 A | 12/2017 |
| CN | 107435069 A | 12/2017 |
| CN | 107446922 A | 12/2017 |
| CN | 107446923 A | 12/2017 |
| CN | 107446924 A | 12/2017 |
| CN | 107446932 A | 12/2017 |
| CN | 107446951 A | 12/2017 |
| CN | 107446954 A | 12/2017 |
| CN | 107460196 A | 12/2017 |
| CN | 107474129 A | 12/2017 |
| CN | 107475300 A | 12/2017 |
| CN | 107488649 A | 12/2017 |
| CN | 107502608 A | 12/2017 |
| CN | 107502618 A | 12/2017 |
| CN | 107513531 A | 12/2017 |
| CN | 107519492 A | 12/2017 |
| CN | 107523567 A | 12/2017 |
| CN | 107523583 A | 12/2017 |
| CN | 107541525 A | 1/2018 |
| CN | 107557373 A | 1/2018 |
| CN | 107557378 A | 1/2018 |
| CN | 107557381 A | 1/2018 |
| CN | 107557390 A | 1/2018 |
| CN | 107557393 A | 1/2018 |
| CN | 107557394 A | 1/2018 |
| CN | 107557455 A | 1/2018 |
| CN | 107574179 A | 1/2018 |
| CN | 107586777 A | 1/2018 |
| CN | 107586779 A | 1/2018 |
| CN | 107604003 A | 1/2018 |
| CN | 107619829 A | 1/2018 |
| CN | 107619837 A | 1/2018 |
| CN | 107630006 A | 1/2018 |
| CN | 107630041 A | 1/2018 |
| CN | 107630042 A | 1/2018 |
| CN | 107630043 A | 1/2018 |
| CN | 107641631 A | 1/2018 |
| CN | 107653256 A | 2/2018 |
| CN | 107686848 A | 2/2018 |
| CN | 206970581 U | 2/2018 |
| CN | 107760652 A | 3/2018 |
| CN | 107760663 A | 3/2018 |
| CN | 107760684 A | 3/2018 |
| CN | 107760715 A | 3/2018 |
| CN | 107784200 A | 3/2018 |
| CN | 107794272 A | 3/2018 |
| CN | 107794276 A | 3/2018 |
| CN | 107815463 A | 3/2018 |
| CN | 107828738 A | 3/2018 |
| CN | 107828794 A | 3/2018 |
| CN | 107828826 A | 3/2018 |
| CN | 107828874 A | 3/2018 |
| CN | 107858346 A | 3/2018 |
| CN | 107858373 A | 3/2018 |

(56) References Cited

FOREIGN PATENT DOCUMENTS

| | | |
|---|---|---|
| CN | 107880132 A | 4/2018 |
| CN | 107881184 A | 4/2018 |
| CN | 107893074 A | 4/2018 |
| CN | 107893075 A | 4/2018 |
| CN | 107893076 A | 4/2018 |
| CN | 107893080 A | 4/2018 |
| CN | 107893086 A | 4/2018 |
| CN | 107904261 A | 4/2018 |
| CN | 107937427 A | 4/2018 |
| CN | 107937432 A | 4/2018 |
| CN | 107937501 A | 4/2018 |
| CN | 107974466 A | 5/2018 |
| CN | 107988229 A | 5/2018 |
| CN | 107988246 A | 5/2018 |
| CN | 107988256 A | 5/2018 |
| CN | 107988268 A | 5/2018 |
| CN | 108018316 A | 5/2018 |
| CN | 108034656 A | 5/2018 |
| CN | 108048466 A | 5/2018 |
| CN | 108102940 A | 6/2018 |
| CN | 108103092 A | 6/2018 |
| CN | 108103098 A | 6/2018 |
| CN | 108103586 A | 6/2018 |
| CN | 108148835 A | 6/2018 |
| CN | 108148837 A | 6/2018 |
| CN | 108148873 A | 6/2018 |
| CN | 108192956 A | 6/2018 |
| CN | 108251423 A | 7/2018 |
| CN | 108251451 A | 7/2018 |
| CN | 108251452 A | 7/2018 |
| CN | 108342480 A | 7/2018 |
| CN | 108359691 A | 8/2018 |
| CN | 108359712 A | 8/2018 |
| CN | 108384784 A | 8/2018 |
| CN | 108396027 A | 8/2018 |
| CN | 108410877 A | 8/2018 |
| CN | 108410906 A | 8/2018 |
| CN | 108410907 A | 8/2018 |
| CN | 108410911 A | 8/2018 |
| CN | 108424931 A | 8/2018 |
| CN | 108441519 A | 8/2018 |
| CN | 108441520 A | 8/2018 |
| CN | 108486108 A | 9/2018 |
| CN | 108486111 A | 9/2018 |
| CN | 108486145 A | 9/2018 |
| CN | 108486146 A | 9/2018 |
| CN | 108486154 A | 9/2018 |
| CN | 108486159 A | 9/2018 |
| CN | 108486234 A | 9/2018 |
| CN | 108504657 A | 9/2018 |
| CN | 108504685 A | 9/2018 |
| CN | 108504693 A | 9/2018 |
| CN | 108546712 A | 9/2018 |
| CN | 108546717 A | 9/2018 |
| CN | 108546718 A | 9/2018 |
| CN | 108559730 A | 9/2018 |
| CN | 108559732 A | 9/2018 |
| CN | 108559745 A | 9/2018 |
| CN | 108559760 A | 9/2018 |
| CN | 108570479 A | 9/2018 |
| CN | 108588071 A | 9/2018 |
| CN | 108588123 A | 9/2018 |
| CN | 108588128 A | 9/2018 |
| CN | 108588182 A | 9/2018 |
| CN | 108610399 A | 10/2018 |
| CN | 108611364 A | 10/2018 |
| CN | 108624622 A | 10/2018 |
| CN | 108642053 A | 10/2018 |
| CN | 108642055 A | 10/2018 |
| CN | 108642077 A | 10/2018 |
| CN | 108642078 A | 10/2018 |
| CN | 108642090 A | 10/2018 |
| CN | 108690844 A | 10/2018 |
| CN | 108707604 A | 10/2018 |
| CN | 108707620 A | 10/2018 |
| CN | 108707621 A | 10/2018 |
| CN | 108707628 A | 10/2018 |
| CN | 108707629 A | 10/2018 |
| CN | 108715850 A | 10/2018 |
| CN | 108728476 A | 11/2018 |
| CN | 108728486 A | 11/2018 |
| CN | 108753772 A | 11/2018 |
| CN | 108753783 A | 11/2018 |
| CN | 108753813 A | 11/2018 |
| CN | 108753817 A | 11/2018 |
| CN | 108753832 A | 11/2018 |
| CN | 108753835 A | 11/2018 |
| CN | 108753836 A | 11/2018 |
| CN | 108795902 A | 11/2018 |
| CN | 108822217 A | 11/2018 |
| CN | 108823248 A | 11/2018 |
| CN | 108823249 A | 11/2018 |
| CN | 108823291 A | 11/2018 |
| CN | 108841845 A | 11/2018 |
| CN | 108853133 A | 11/2018 |
| CN | 108866093 A | 11/2018 |
| CN | 108893529 A | 11/2018 |
| CN | 108913664 A | 11/2018 |
| CN | 108913691 A | 11/2018 |
| CN | 108913714 A | 11/2018 |
| CN | 108913717 A | 11/2018 |
| CN | 208034188 A | 11/2018 |
| CN | 109517841 A | 3/2019 |
| EP | 0264166 A1 | 4/1988 |
| EP | 2604255 A1 | 6/2013 |
| EP | 2840140 A1 | 2/2015 |
| EP | 2966170 A1 | 1/2016 |
| EP | 3009511 A2 | 4/2016 |
| EP | 3031921 A1 | 6/2016 |
| EP | 3045537 A1 | 7/2016 |
| EP | 3 115 457 A | 1/2017 |
| EP | 3144390 A1 | 3/2017 |
| EP | 3199632 A1 | 8/2017 |
| EP | 3216867 A1 | 9/2017 |
| EP | 3252160 A1 | 12/2017 |
| EP | 3450553 B1 | 12/2019 |
| ES | 2740248 T3 | 2/2020 |
| GB | 2528177 A | 1/2016 |
| GB | 2531454 A | 4/2016 |
| GB | 2542653 A | 3/2017 |
| HK | 1208045 A1 | 2/2016 |
| JP | 2007-501626 A | 2/2007 |
| JP | 2008-515405 A | 5/2008 |
| JP | 2010-033344 A | 2/2010 |
| JP | 2010-539929 A | 12/2010 |
| JP | 2011-081011 A | 4/2011 |
| JP | 2011-523353 A | 8/2011 |
| JP | 2012-525146 A | 10/2012 |
| JP | 2012-531909 A | 12/2012 |
| KR | 101584933 B1 | 1/2016 |
| KR | 20160133380 A | 11/2016 |
| KR | 20170037025 A | 4/2017 |
| KR | 20170037028 A | 4/2017 |
| KR | 101748575 B1 | 6/2017 |
| KR | 2018-0022465 A | 3/2018 |
| RU | 2016104674 A | 8/2017 |
| RU | 2634395 C1 | 10/2017 |
| RU | 2652899 C1 | 5/2018 |
| RU | 2015128057 A | 3/2019 |
| RU | 2015128098 A | 3/2019 |
| RU | 2687451 C1 | 5/2019 |
| RU | 2019112514 A | 6/2019 |
| RU | 2019127300 A | 9/2019 |
| RU | 2701850 C2 | 10/2019 |
| TW | I608100 B | 12/2017 |
| TW | 2018-29773 A | 8/2018 |
| WO | WO 90/02809 | 3/1990 |
| WO | WO 91/16024 A1 | 10/1991 |
| WO | WO 91/17271 A1 | 11/1991 |
| WO | WO 91/17424 A1 | 11/1991 |
| WO | WO 92/06188 A2 | 4/1992 |
| WO | WO 92/06200 A1 | 4/1992 |
| WO | WO 93/24641 A2 | 12/1993 |
| WO | WO 94/18316 A2 | 8/1994 |

(56) References Cited

FOREIGN PATENT DOCUMENTS

| | | |
|---|---|---|
| WO | WO 94/026877 A1 | 11/1994 |
| WO | WO 96/04403 A1 | 2/1996 |
| WO | WO 96/10640 A1 | 4/1996 |
| WO | WO 98/32845 A1 | 7/1998 |
| WO | WO 2001/036452 A2 | 5/2001 |
| WO | WO 2001/038547 A2 | 5/2001 |
| WO | WO 2002/059296 A2 | 8/2002 |
| WO | WO 2002/068676 A2 | 9/2002 |
| WO | WO 2002/103028 A2 | 12/2002 |
| WO | WO 2004/007684 A2 | 1/2004 |
| WO | WO 2005/014791 A2 | 2/2005 |
| WO | WO 2005/019415 A2 | 3/2005 |
| WO | WO 2006/002547 A1 | 1/2006 |
| WO | WO 2006/042112 A2 | 4/2006 |
| WO | WO 2007/025097 A2 | 3/2007 |
| WO | WO 2007/066923 A1 | 6/2007 |
| WO | WO 2007/136815 A2 | 11/2007 |
| WO | WO 2007/143574 A1 | 12/2007 |
| WO | WO 2008/005529 A2 | 1/2008 |
| WO | WO 2008/108989 A2 | 9/2008 |
| WO | WO 2009/098290 A1 | 8/2009 |
| WO | WO 2009/134808 A2 | 11/2009 |
| WO | WO 2010/011961 A2 | 1/2010 |
| WO | WO 2010/028347 A2 | 3/2010 |
| WO | WO 2010/054108 A2 | 5/2010 |
| WO | WO 2010/054154 A2 | 5/2010 |
| WO | WO 2010/068289 A2 | 6/2010 |
| WO | WO 2010/075424 A2 | 7/2010 |
| WO | WO 2010/102257 A2 | 9/2010 |
| WO | WO 2010/129019 A2 | 11/2010 |
| WO | WO 2010/129023 A2 | 11/2010 |
| WO | WO 2010/132092 A2 | 11/2010 |
| WO | WO 2010/144150 A2 | 12/2010 |
| WO | WO 2011/002503 A1 | 1/2011 |
| WO | WO 2011/017293 A2 | 2/2011 |
| WO | WO 2011/053868 A1 | 5/2011 |
| WO | WO 2011/053982 A2 | 5/2011 |
| WO | WO 2011/068810 A1 | 6/2011 |
| WO | WO 2011/075627 A1 | 6/2011 |
| WO | WO 2011/091311 A2 | 7/2011 |
| WO | WO 2011/109031 A1 | 9/2011 |
| WO | WO 2011/143124 A2 | 11/2011 |
| WO | WO 2011/147590 A2 | 12/2011 |
| WO | WO 2011/159369 A1 | 12/2011 |
| WO | WO 2012/054726 A1 | 4/2012 |
| WO | WO 2012/065043 A2 | 5/2012 |
| WO | WO 2012/088381 A2 | 6/2012 |
| WO | WO 2012/125445 A2 | 9/2012 |
| WO | WO 2012/138927 A2 | 10/2012 |
| WO | WO 2012/149470 A1 | 11/2012 |
| WO | WO 2012/158985 A2 | 11/2012 |
| WO | WO 2012/158986 A2 | 11/2012 |
| WO | WO 2012/164565 A1 | 12/2012 |
| WO | WO 2012/170930 A1 | 12/2012 |
| WO | WO 2013/012674 A1 | 1/2013 |
| WO | WO 2013/013105 A2 | 1/2013 |
| WO | WO 2013/039857 A1 | 3/2013 |
| WO | WO 2013/039861 A2 | 3/2013 |
| WO | WO 2013/045632 A1 | 4/2013 |
| WO | WO 2013/047844 A1 | 4/2013 |
| WO | WO 2013/066438 A2 | 5/2013 |
| WO | WO 2013/086441 A2 | 6/2013 |
| WO | WO 2013/086444 A2 | 6/2013 |
| WO | WO 2013/098244 A1 | 7/2013 |
| WO | WO 2013/119602 A1 | 8/2013 |
| WO | WO 2013/126794 A1 | 8/2013 |
| WO | WO 2013/130824 A1 | 9/2013 |
| WO | WO 2013/141680 A1 | 9/2013 |
| WO | WO 2013/142578 A1 | 9/2013 |
| WO | WO 2013/152359 A1 | 10/2013 |
| WO | WO 2013/160230 A1 | 10/2013 |
| WO | WO 2013/166315 A1 | 11/2013 |
| WO | WO 2013/169398 A2 | 11/2013 |
| WO | WO 2013/169802 A1 | 11/2013 |
| WO | WO 2013/176772 A1 | 11/2013 |
| WO | WO 2013/176915 A1 | 11/2013 |
| WO | WO 2013/176916 A1 | 11/2013 |
| WO | WO 2013/181440 A1 | 12/2013 |
| WO | WO 2013/186754 A2 | 12/2013 |
| WO | WO 2013/188037 A2 | 12/2013 |
| WO | WO 2013/188522 A2 | 12/2013 |
| WO | WO 2013/188638 A2 | 12/2013 |
| WO | WO 2013/192278 A1 | 12/2013 |
| WO | WO 2013/142378 A9 | 1/2014 |
| WO | WO 2014/004336 A2 | 1/2014 |
| WO | WO 2014/005042 A2 | 1/2014 |
| WO | WO 2014/011237 A1 | 1/2014 |
| WO | WO 2014/011901 A2 | 1/2014 |
| WO | WO 2014/018423 A2 | 1/2014 |
| WO | WO 2014/020608 A1 | 2/2014 |
| WO | WO 2014/022120 A1 | 2/2014 |
| WO | WO 2014/022702 A2 | 2/2014 |
| WO | WO 2014/036219 A2 | 3/2014 |
| WO | WO 2014/039513 A2 | 3/2014 |
| WO | WO 2014/039523 A1 | 3/2014 |
| WO | WO 2014/039585 A2 | 3/2014 |
| WO | WO 2014/039684 A1 | 3/2014 |
| WO | WO 2014/039692 A2 | 3/2014 |
| WO | WO 2014/039702 A2 | 3/2014 |
| WO | WO 2014/039872 A1 | 3/2014 |
| WO | WO 2014/039970 A1 | 3/2014 |
| WO | WO 2014/041327 A1 | 3/2014 |
| WO | WO 2014/043143 A1 | 3/2014 |
| WO | WO 2014/047103 A2 | 3/2014 |
| WO | WO 2014/055782 A1 | 4/2014 |
| WO | WO 2014/059173 A2 | 4/2014 |
| WO | WO 2014/059255 A1 | 4/2014 |
| WO | WO 2014/065596 A1 | 5/2014 |
| WO | WO 2014/066505 A1 | 5/2014 |
| WO | WO 2014/068346 A2 | 5/2014 |
| WO | WO 2014/070887 A1 | 5/2014 |
| WO | WO 2014/071006 A1 | 5/2014 |
| WO | WO 2014/071219 A1 | 5/2014 |
| WO | WO 2014/071235 A1 | 5/2014 |
| WO | WO 2014/072941 A1 | 5/2014 |
| WO | WO 2014/081729 A1 | 5/2014 |
| WO | WO 2014/081730 A1 | 5/2014 |
| WO | WO 2014/081855 A1 | 5/2014 |
| WO | WO 2014/082644 A1 | 6/2014 |
| WO | WO 2014/085261 A1 | 6/2014 |
| WO | WO 2014/085593 A1 | 6/2014 |
| WO | WO 2014/085830 A2 | 6/2014 |
| WO | WO 2014/089212 A1 | 6/2014 |
| WO | WO 2014/089290 A1 | 6/2014 |
| WO | WO 2014/089348 A1 | 6/2014 |
| WO | WO 2014/089513 A1 | 6/2014 |
| WO | WO 2014/089533 A2 | 6/2014 |
| WO | WO 2014/089541 A2 | 6/2014 |
| WO | WO 2014/093479 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/093736 A1 | 6/2014 |
| WO | WO 2014/093768 A1 | 6/2014 |
| WO | WO 2014/093852 A1 | 6/2014 |
| WO | WO 2014/096972 A2 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2014/110006 A1 | 7/2014 |
| WO | WO 2014/110552 A1 | 7/2014 |
| WO | WO 2014/113493 A1 | 7/2014 |
| WO | WO 2014/123967 A2 | 8/2014 |
| WO | WO 2014/124226 A1 | 8/2014 |
| WO | WO 2014/125668 A1 | 8/2014 |
| WO | WO 2014/127287 A1 | 8/2014 |
| WO | WO 2014/128324 A1 | 8/2014 |

(56) References Cited

FOREIGN PATENT DOCUMENTS

| | | |
|---|---|---|
| WO | WO 2014/128659 A1 | 8/2014 |
| WO | WO 2014/130706 A1 | 8/2014 |
| WO | WO 2014/130955 A1 | 8/2014 |
| WO | WO 2014/131833 A1 | 9/2014 |
| WO | WO 2014/138379 A1 | 9/2014 |
| WO | WO 2014/143381 A1 | 9/2014 |
| WO | WO 2014/144094 A1 | 9/2014 |
| WO | WO 2014/144155 A1 | 9/2014 |
| WO | WO 2014/144288 A1 | 9/2014 |
| WO | WO 2014/144592 A2 | 9/2014 |
| WO | WO 2014/144761 A2 | 9/2014 |
| WO | WO 2014/144951 A1 | 9/2014 |
| WO | WO 2014/145599 A2 | 9/2014 |
| WO | WO 2014/145736 A2 | 9/2014 |
| WO | WO 2014/150624 A1 | 9/2014 |
| WO | WO 2014/152432 A2 | 9/2014 |
| WO | WO 2014/152940 A1 | 9/2014 |
| WO | WO 2014/153118 A1 | 9/2014 |
| WO | WO 2014/153470 A2 | 9/2014 |
| WO | WO 2014/158593 A1 | 10/2014 |
| WO | WO 2014/161821 A1 | 10/2014 |
| WO | WO 2014/164466 A1 | 10/2014 |
| WO | WO 2014/165177 A1 | 10/2014 |
| WO | WO 2014/165349 A1 | 10/2014 |
| WO | WO 2014/165612 A2 | 10/2014 |
| WO | WO 2014/165707 A2 | 10/2014 |
| WO | WO 2014/165825 A2 | 10/2014 |
| WO | WO 2014/172458 A1 | 10/2014 |
| WO | WO 2014/172470 A2 | 10/2014 |
| WO | WO 2014/172489 A2 | 10/2014 |
| WO | WO 2014/173955 A1 | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A1 | 12/2014 |
| WO | WO 2014/191527 A1 | 12/2014 |
| WO | WO 2014/193583 A2 | 12/2014 |
| WO | WO 2014/194190 A1 | 12/2014 |
| WO | WO 2014/197568 A2 | 12/2014 |
| WO | WO 2014/197748 A2 | 12/2014 |
| WO | WO 2014/199358 A1 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2014/205192 A2 | 12/2014 |
| WO | WO 2014/207043 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006437 A1 | 1/2015 |
| WO | WO 2015/006498 A2 | 1/2015 |
| WO | WO 2015/006747 A2 | 1/2015 |
| WO | WO 2015/007194 A1 | 1/2015 |
| WO | WO 2015/010114 A1 | 1/2015 |
| WO | WO 2015/011483 A1 | 1/2015 |
| WO | WO 2015/013583 A2 | 1/2015 |
| WO | WO 2015/017866 A1 | 2/2015 |
| WO | WO 2015/018503 A1 | 2/2015 |
| WO | WO 2015/021353 A1 | 2/2015 |
| WO | WO 2015/021426 A1 | 2/2015 |
| WO | WO 2015/021990 A1 | 2/2015 |
| WO | WO 2015/024017 A2 | 2/2015 |
| WO | WO 2015/024986 A1 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |
| WO | WO 2015/028969 A2 | 3/2015 |
| WO | WO 2015/030881 A1 | 3/2015 |
| WO | WO 2015/031619 A1 | 3/2015 |
| WO | WO 2015/031775 A1 | 3/2015 |
| WO | WO 2015/032494 A2 | 3/2015 |
| WO | WO 2015/033293 A1 | 3/2015 |
| WO | WO 2015/034872 A2 | 3/2015 |
| WO | WO 2015/034885 A1 | 3/2015 |
| WO | WO 2015/035136 A2 | 3/2015 |
| WO | WO 2015/035139 A2 | 3/2015 |
| WO | WO 2015/035162 A2 | 3/2015 |
| WO | WO 2015/040075 A1 | 3/2015 |
| WO | WO 2015/040402 A1 | 3/2015 |
| WO | WO 2015/042585 A1 | 3/2015 |
| WO | WO 2015/048577 A2 | 4/2015 |
| WO | WO 2015/048690 A1 | 4/2015 |
| WO | WO 2015/048707 A2 | 4/2015 |
| WO | WO 2015/048801 A2 | 4/2015 |
| WO | WO 2015/049897 A1 | 4/2015 |
| WO | WO 2015/051191 A1 | 4/2015 |
| WO | WO 2015/052133 A1 | 4/2015 |
| WO | WO 2015/052231 A2 | 4/2015 |
| WO | WO 2015/052335 A1 | 4/2015 |
| WO | WO 2015/053995 A1 | 4/2015 |
| WO | WO 2015/054253 A1 | 4/2015 |
| WO | WO 2015/054315 A1 | 4/2015 |
| WO | WO 2015/057671 A1 | 4/2015 |
| WO | WO 2015/057834 A1 | 4/2015 |
| WO | WO 2015/057852 A1 | 4/2015 |
| WO | WO 2015/057976 A1 | 4/2015 |
| WO | WO 2015/057980 A1 | 4/2015 |
| WO | WO 2015/059265 A1 | 4/2015 |
| WO | WO 2015/065964 A1 | 5/2015 |
| WO | WO 2015/066119 A1 | 5/2015 |
| WO | WO 2015/066634 A2 | 5/2015 |
| WO | WO 2015/066636 A2 | 5/2015 |
| WO | WO 2015/066637 A1 | 5/2015 |
| WO | WO 2015/066638 A2 | 5/2015 |
| WO | WO 2015/066643 A1 | 5/2015 |
| WO | WO 2015/069682 A2 | 5/2015 |
| WO | WO 2015/070083 A1 | 5/2015 |
| WO | WO 2015/070193 A1 | 5/2015 |
| WO | WO 2015/070212 A1 | 5/2015 |
| WO | WO 2015/071474 A2 | 5/2015 |
| WO | WO 2015/073683 A2 | 5/2015 |
| WO | WO 2015/073867 A1 | 5/2015 |
| WO | WO 2015/073990 A1 | 5/2015 |
| WO | WO 2015/075056 A1 | 5/2015 |
| WO | WO 2015/075154 A2 | 5/2015 |
| WO | WO 2015/075175 A1 | 5/2015 |
| WO | WO 2015/075195 A1 | 5/2015 |
| WO | WO 2015/075557 A2 | 5/2015 |
| WO | WO 2015/077058 A2 | 5/2015 |
| WO | WO 2015/077290 A2 | 5/2015 |
| WO | WO 2015/077318 A1 | 5/2015 |
| WO | WO 2015/079056 A1 | 6/2015 |
| WO | WO 2015/079057 A2 | 6/2015 |
| WO | WO 2015/086795 A1 | 6/2015 |
| WO | WO 2015/086798 A2 | 6/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/089277 A1 | 6/2015 |
| WO | WO 2015/089351 A1 | 6/2015 |
| WO | WO 2015/089354 A1 | 6/2015 |
| WO | WO 2015/089364 A1 | 6/2015 |
| WO | WO 2015/089406 A1 | 6/2015 |
| WO | WO 2015/089419 A2 | 6/2015 |
| WO | WO 2015/089427 A1 | 6/2015 |
| WO | WO 2015/089462 A1 | 6/2015 |

(56) References Cited

FOREIGN PATENT DOCUMENTS

| | | |
|---|---|---|
| WO | WO 2015/089465 A1 | 6/2015 |
| WO | WO 2015/089473 A1 | 6/2015 |
| WO | WO 2015/089486 A2 | 6/2015 |
| WO | WO 2015/095804 A1 | 6/2015 |
| WO | WO 2015/099850 A1 | 7/2015 |
| WO | WO 2015/100929 A1 | 7/2015 |
| WO | WO 2015/103057 A1 | 7/2015 |
| WO | WO 2015/103153 A1 | 7/2015 |
| WO | WO 2015/105928 A1 | 7/2015 |
| WO | WO 2015/108993 A1 | 7/2015 |
| WO | WO 2015/109752 A1 | 7/2015 |
| WO | WO 2015/110474 A1 | 7/2015 |
| WO | WO 2015/112790 A2 | 7/2015 |
| WO | WO 2015/112896 A2 | 7/2015 |
| WO | WO 2015/113063 A1 | 7/2015 |
| WO | WO 2015/114365 A1 | 8/2015 |
| WO | WO 2015/115903 A1 | 8/2015 |
| WO | WO 2015/116686 A1 | 8/2015 |
| WO | WO 2015/116969 A2 | 8/2015 |
| WO | WO 2015/117021 A1 | 8/2015 |
| WO | WO 2015/117041 A1 | 8/2015 |
| WO | WO 2015/117081 A2 | 8/2015 |
| WO | WO 2015/118156 A1 | 8/2015 |
| WO | WO 2015/119941 A2 | 8/2015 |
| WO | WO 2015/121454 A1 | 8/2015 |
| WO | WO 2015/122967 A1 | 8/2015 |
| WO | WO 2015/123339 A1 | 8/2015 |
| WO | WO 2015/124715 A1 | 8/2015 |
| WO | WO 2015/124718 A1 | 8/2015 |
| WO | WO 2015/126927 A2 | 8/2015 |
| WO | WO 2015/127428 A1 | 8/2015 |
| WO | WO 2015/127439 A1 | 8/2015 |
| WO | WO 2015/129686 A1 | 9/2015 |
| WO | WO 2015/131101 A1 | 9/2015 |
| WO | WO 2015/133554 A1 | 9/2015 |
| WO | WO 2015/134121 A2 | 9/2015 |
| WO | WO 2015/134812 A1 | 9/2015 |
| WO | WO 2015/136001 A1 | 9/2015 |
| WO | WO 2015/138510 A1 | 9/2015 |
| WO | WO 2015/138739 A2 | 9/2015 |
| WO | WO 2015/138855 A1 | 9/2015 |
| WO | WO 2015/138870 A2 | 9/2015 |
| WO | WO 2015/139008 A1 | 9/2015 |
| WO | WO 2015/139139 A1 | 9/2015 |
| WO | WO 2015/143046 A2 | 9/2015 |
| WO | WO 2015/143177 A1 | 9/2015 |
| WO | WO 2015/145417 A1 | 10/2015 |
| WO | WO 2015/148431 A1 | 10/2015 |
| WO | WO 2015/148670 A1 | 10/2015 |
| WO | WO 2015/148680 A1 | 10/2015 |
| WO | WO 2015/148761 A1 | 10/2015 |
| WO | WO 2015/148860 A1 | 10/2015 |
| WO | WO 2015/148863 A2 | 10/2015 |
| WO | WO 2015/153760 A2 | 10/2015 |
| WO | WO 2015/153780 A1 | 10/2015 |
| WO | WO 2015/153789 A1 | 10/2015 |
| WO | WO 2015/153791 A1 | 10/2015 |
| WO | WO 2015/153889 A2 | 10/2015 |
| WO | WO 2015/153940 A1 | 10/2015 |
| WO | WO 2015/155341 A1 | 10/2015 |
| WO | WO 2015/155686 A2 | 10/2015 |
| WO | WO 2015/157070 A2 | 10/2015 |
| WO | WO 2015/157534 A1 | 10/2015 |
| WO | WO 2015/159068 A1 | 10/2015 |
| WO | WO 2015/159086 A1 | 10/2015 |
| WO | WO 2015/159087 A1 | 10/2015 |
| WO | WO 2015/160683 A1 | 10/2015 |
| WO | WO 2015/161276 A2 | 10/2015 |
| WO | WO 2015/163733 A1 | 10/2015 |
| WO | WO 2015/164740 A1 | 10/2015 |
| WO | WO 2015/164748 A1 | 10/2015 |
| WO | WO 2015/165274 A1 | 11/2015 |
| WO | WO 2015/165275 A1 | 11/2015 |
| WO | WO 2015/165276 A1 | 11/2015 |
| WO | WO 2015/166272 A2 | 11/2015 |
| WO | WO 2015/167766 A1 | 11/2015 |
| WO | WO 2015/167956 A1 | 11/2015 |
| WO | WO 2015/168125 A1 | 11/2015 |
| WO | WO 2015/168158 A1 | 11/2015 |
| WO | WO 2015/168404 A1 | 11/2015 |
| WO | WO 2015/168547 A2 | 11/2015 |
| WO | WO 2015/168800 A1 | 11/2015 |
| WO | WO 2015/171603 A1 | 11/2015 |
| WO | WO 2015/171894 A1 | 11/2015 |
| WO | WO 2015/171932 A1 | 11/2015 |
| WO | WO 2015/172128 A1 | 11/2015 |
| WO | WO 2015/173436 A1 | 11/2015 |
| WO | WO 2015/175642 A2 | 11/2015 |
| WO | WO 2015/179540 A1 | 11/2015 |
| WO | WO 2015/183025 A1 | 12/2015 |
| WO | WO 2015/183026 A1 | 12/2015 |
| WO | WO 2015/183885 A1 | 12/2015 |
| WO | WO 2015/184259 A1 | 12/2015 |
| WO | WO 2015/184262 A1 | 12/2015 |
| WO | WO 2015/184268 A1 | 12/2015 |
| WO | WO 2015/188056 A1 | 12/2015 |
| WO | WO 2015/188065 A1 | 12/2015 |
| WO | WO 2015/188094 A1 | 12/2015 |
| WO | WO 2015/188109 A1 | 12/2015 |
| WO | WO 2015/188132 A1 | 12/2015 |
| WO | WO 2015/188135 A1 | 12/2015 |
| WO | WO 2015/188191 A1 | 12/2015 |
| WO | WO 2015/189693 A1 | 12/2015 |
| WO | WO 2015/191693 A2 | 12/2015 |
| WO | WO 2015/191899 A1 | 12/2015 |
| WO | WO 2015/191911 A2 | 12/2015 |
| WO | WO 2015/193858 A1 | 12/2015 |
| WO | WO 2015/195547 A1 | 12/2015 |
| WO | WO 2015/195621 A1 | 12/2015 |
| WO | WO 2015/195798 A1 | 12/2015 |
| WO | WO 2015/198020 A1 | 12/2015 |
| WO | WO 2015/200334 A1 | 12/2015 |
| WO | WO 2015/200378 A1 | 12/2015 |
| WO | WO 2015/200555 A2 | 12/2015 |
| WO | WO 2015/200805 A2 | 12/2015 |
| WO | WO 2016/001978 A1 | 1/2016 |
| WO | WO 2016/004010 A1 | 1/2016 |
| WO | WO 2016/004318 A1 | 1/2016 |
| WO | WO 2016/007347 A1 | 1/2016 |
| WO | WO 2016/007604 A1 | 1/2016 |
| WO | WO 2016/007948 A1 | 1/2016 |
| WO | WO 2016/011080 A2 | 1/2016 |
| WO | WO 2016/011210 A2 | 1/2016 |
| WO | WO 2016/011428 A1 | 1/2016 |
| WO | WO 2016/012544 A2 | 1/2016 |
| WO | WO 2016/012552 A1 | 1/2016 |
| WO | WO 2016/014409 A1 | 1/2016 |
| WO | WO 2016/014565 A2 | 1/2016 |
| WO | WO 2016/014794 A1 | 1/2016 |
| WO | WO 2016/014837 A1 | 1/2016 |
| WO | WO 2016/016119 A1 | 2/2016 |
| WO | WO 2016/016358 A1 | 2/2016 |
| WO | WO 2016/019144 A2 | 2/2016 |
| WO | WO 2016/020399 A1 | 2/2016 |
| WO | WO 2016/021972 A1 | 2/2016 |
| WO | WO 2016/021973 A1 | 2/2016 |
| WO | WO 2016/022363 A2 | 2/2016 |
| WO | WO 2016/022866 A1 | 2/2016 |
| WO | WO 2016/022931 A1 | 2/2016 |
| WO | WO 2016/025131 A1 | 2/2016 |
| WO | WO 2016/025469 A1 | 2/2016 |
| WO | WO 2016/025759 A1 | 2/2016 |
| WO | WO 2016/026444 A1 | 2/2016 |
| WO | WO 2016/028682 A1 | 2/2016 |
| WO | WO 2016/028843 A2 | 2/2016 |
| WO | WO 2016/028887 A1 | 2/2016 |
| WO | WO 2016/033088 A1 | 3/2016 |
| WO | WO 2016/033230 A1 | 3/2016 |
| WO | WO 2016/033246 A1 | 3/2016 |
| WO | WO 2016/033298 A1 | 3/2016 |
| WO | WO 2016/035044 A1 | 3/2016 |
| WO | WO 2016/036754 A1 | 3/2016 |
| WO | WO 2016/037157 A2 | 3/2016 |
| WO | WO 2016/040030 A1 | 3/2016 |

(56) References Cited

FOREIGN PATENT DOCUMENTS

| | | |
|---|---|---|
| WO | WO 2016/040594 A1 | 3/2016 |
| WO | WO 2016/044182 A1 | 3/2016 |
| WO | WO 2016/044416 A1 | 3/2016 |
| WO | WO 2016/046635 A1 | 3/2016 |
| WO | WO 2016/049024 A2 | 3/2016 |
| WO | WO 2016/049163 A2 | 3/2016 |
| WO | WO 2016/049230 A1 | 3/2016 |
| WO | WO 2016/049251 A1 | 3/2016 |
| WO | WO 2016/049258 A2 | 3/2016 |
| WO | WO 2016/053397 A2 | 4/2016 |
| WO | WO 2016/054326 A1 | 4/2016 |
| WO | WO 2016/057061 A2 | 4/2016 |
| WO | WO 2016/057821 A2 | 4/2016 |
| WO | WO 2016/057835 A2 | 4/2016 |
| WO | WO 2016/057850 A1 | 4/2016 |
| WO | WO 2016/057951 A2 | 4/2016 |
| WO | WO 2016/057961 A1 | 4/2016 |
| WO | WO 2016/061073 A1 | 4/2016 |
| WO | WO 2016/061374 A1 | 4/2016 |
| WO | WO 2016/061481 A1 | 4/2016 |
| WO | WO 2016/061523 A1 | 4/2016 |
| WO | WO 2016/064894 A2 | 4/2016 |
| WO | WO 2016/069282 A1 | 5/2016 |
| WO | WO 2016/069283 A1 | 5/2016 |
| WO | WO 2016/069591 A2 | 5/2016 |
| WO | WO 2016/069774 A1 | 5/2016 |
| WO | WO 2016/069910 A1 | 5/2016 |
| WO | WO 2016/069912 A1 | 5/2016 |
| WO | WO 2016/070037 A2 | 5/2016 |
| WO | WO 2016/070070 A1 | 5/2016 |
| WO | WO 2016/070129 A1 | 5/2016 |
| WO | WO 2016/072399 A1 | 5/2016 |
| WO | WO 2016/072936 A1 | 5/2016 |
| WO | WO 2016/073433 A1 | 5/2016 |
| WO | WO 2016/073559 A1 | 5/2016 |
| WO | WO 2016/073990 A2 | 5/2016 |
| WO | WO 2016/075662 A2 | 5/2016 |
| WO | WO 2016/076672 A1 | 5/2016 |
| WO | WO 2016/077273 A1 | 5/2016 |
| WO | WO 2016/077350 A1 | 5/2016 |
| WO | WO 2016/080097 A1 | 5/2016 |
| WO | WO 2016/080795 A1 | 5/2016 |
| WO | WO 2016/081923 A2 | 5/2016 |
| WO | WO 2016/081924 A1 | 5/2016 |
| WO | WO 2016/082135 A1 | 6/2016 |
| WO | WO 2016/083811 A1 | 6/2016 |
| WO | WO 2016/084084 A1 | 6/2016 |
| WO | WO 2016/084088 A1 | 6/2016 |
| WO | WO 2016/086177 A2 | 6/2016 |
| WO | WO 2016/089433 A1 | 6/2016 |
| WO | WO 2016/089866 A1 | 6/2016 |
| WO | WO 2016/089883 A1 | 6/2016 |
| WO | WO 2016/090385 A1 | 6/2016 |
| WO | WO 2016/094679 A1 | 6/2016 |
| WO | WO 2016/094845 A2 | 6/2016 |
| WO | WO 2016/094867 A1 | 6/2016 |
| WO | WO 2016/094872 A1 | 6/2016 |
| WO | WO 2016/094874 A1 | 6/2016 |
| WO | WO 2016/094880 A1 | 6/2016 |
| WO | WO 2016/094888 A1 | 6/2016 |
| WO | WO 2016/097212 A1 | 6/2016 |
| WO | WO 2016/097231 A2 | 6/2016 |
| WO | WO 2016/097751 A1 | 6/2016 |
| WO | WO 2016/099887 A1 | 6/2016 |
| WO | WO 2016/100272 A1 | 6/2016 |
| WO | WO 2016/100389 A1 | 6/2016 |
| WO | WO 2016/100568 A1 | 6/2016 |
| WO | WO 2016/100571 A1 | 6/2016 |
| WO | WO 2016/100951 A2 | 6/2016 |
| WO | WO 2016/100955 A2 | 6/2016 |
| WO | WO 2016/100974 A1 | 6/2016 |
| WO | WO 2016/103233 A2 | 6/2016 |
| WO | WO 2016/104716 A1 | 6/2016 |
| WO | WO 2016/106236 A1 | 6/2016 |
| WO | WO 2016/106239 A1 | 6/2016 |
| WO | WO 2016/106244 A1 | 6/2016 |
| WO | WO 2016/106338 A2 | 6/2016 |
| WO | WO 2016/108926 A1 | 7/2016 |
| WO | WO 2016/109255 A1 | 7/2016 |
| WO | WO 2016/109840 A2 | 7/2016 |
| WO | WO 2016/110214 A1 | 7/2016 |
| WO | WO 2016/110453 A1 | 7/2016 |
| WO | WO 2016/110511 A1 | 7/2016 |
| WO | WO 2016/110512 A1 | 7/2016 |
| WO | WO 2016/111546 A2 | 7/2016 |
| WO | WO 2016/112242 A1 | 7/2016 |
| WO | WO 2016/112351 A1 | 7/2016 |
| WO | WO 2016/112963 A1 | 7/2016 |
| WO | WO 2016/113357 A1 | 7/2016 |
| WO | WO 2016/114972 A1 | 7/2016 |
| WO | WO 2016/115179 A1 | 7/2016 |
| WO | WO 2016/115326 A1 | 7/2016 |
| WO | WO 2016/115355 A1 | 7/2016 |
| WO | WO 2016/116032 A1 | 7/2016 |
| WO | WO 2016/120480 A1 | 8/2016 |
| WO | WO 2016/123071 A1 | 8/2016 |
| WO | WO 2016/123230 A1 | 8/2016 |
| WO | WO 2016/123243 A1 | 8/2016 |
| WO | WO 2016/123578 A1 | 8/2016 |
| WO | WO 2016/126747 A1 | 8/2016 |
| WO | WO 2016/130600 A2 | 8/2016 |
| WO | WO 2016/130697 A1 | 8/2016 |
| WO | WO 2016/131009 A1 | 8/2016 |
| WO | WO 2016/132122 A1 | 8/2016 |
| WO | WO 2016/133165 A1 | 8/2016 |
| WO | WO 2016/135507 A1 | 9/2016 |
| WO | WO 2016/135557 A2 | 9/2016 |
| WO | WO 2016/135558 A2 | 9/2016 |
| WO | WO 2016/135559 A2 | 9/2016 |
| WO | WO 2016/137774 A1 | 9/2016 |
| WO | WO 2016/137949 A1 | 9/2016 |
| WO | WO 2016/141224 A1 | 9/2016 |
| WO | WO 2016/141893 A1 | 9/2016 |
| WO | WO 2016/142719 A1 | 9/2016 |
| WO | WO 2016/145150 A2 | 9/2016 |
| WO | WO 2016/148994 A1 | 9/2016 |
| WO | WO 2016/149484 A2 | 9/2016 |
| WO | WO 2016/149547 A1 | 9/2016 |
| WO | WO 2016/150336 A1 | 9/2016 |
| WO | WO 2016/150855 A1 | 9/2016 |
| WO | WO 2016/154016 A2 | 9/2016 |
| WO | WO 2016/154579 A2 | 9/2016 |
| WO | WO 2016/154596 A1 | 9/2016 |
| WO | WO 2016/155482 A1 | 10/2016 |
| WO | WO 2016/161004 A1 | 10/2016 |
| WO | WO 2016/161207 A1 | 10/2016 |
| WO | WO 2016/161260 A1 | 10/2016 |
| WO | WO 2016/161380 A1 | 10/2016 |
| WO | WO 2016/161446 A1 | 10/2016 |
| WO | WO 2016/164356 A1 | 10/2016 |
| WO | WO 2016/164797 A1 | 10/2016 |
| WO | WO 2016/166340 A1 | 10/2016 |
| WO | WO 2016/167300 A1 | 10/2016 |
| WO | WO 2016/168631 A1 | 10/2016 |
| WO | WO 2016/170484 A1 | 10/2016 |
| WO | WO 2016/172359 A2 | 10/2016 |
| WO | WO 2016/172727 A1 | 10/2016 |
| WO | WO 2016/174056 A1 | 11/2016 |
| WO | WO 2016/174151 A1 | 11/2016 |
| WO | WO 2016/174250 A1 | 11/2016 |
| WO | WO 2016/176191 A1 | 11/2016 |
| WO | WO 2016/176404 A1 | 11/2016 |
| WO | WO 2016/176690 A2 | 11/2016 |
| WO | WO 2016/177682 A1 | 11/2016 |
| WO | WO 2016/178207 A1 | 11/2016 |
| WO | WO 2016/179038 A1 | 11/2016 |
| WO | WO 2016/179112 A1 | 11/2016 |
| WO | WO 2016/181357 A1 | 11/2016 |
| WO | WO 2016/182893 A1 | 11/2016 |
| WO | WO 2016/182917 A1 | 11/2016 |
| WO | WO 2016/182959 A1 | 11/2016 |
| WO | WO 2016/183236 A1 | 11/2016 |
| WO | WO 2016/183298 A2 | 11/2016 |
| WO | WO 2016/183345 A1 | 11/2016 |

(56) References Cited

FOREIGN PATENT DOCUMENTS

| | | |
|---|---|---|
| WO | WO 2016/183402 A2 | 11/2016 |
| WO | WO 2016/183438 A1 | 11/2016 |
| WO | WO 2016/183448 A1 | 11/2016 |
| WO | WO 2016/184955 A2 | 11/2016 |
| WO | WO 2016/184989 A1 | 11/2016 |
| WO | WO 2016/185411 A1 | 11/2016 |
| WO | WO 2016/186745 A1 | 11/2016 |
| WO | WO 2016/186772 A2 | 11/2016 |
| WO | WO 2016/186946 A1 | 11/2016 |
| WO | WO 2016/186953 A1 | 11/2016 |
| WO | WO 2016/187717 A1 | 12/2016 |
| WO | WO 2016/187904 A1 | 12/2016 |
| WO | WO 2016/191684 A1 | 12/2016 |
| WO | WO 2016/191869 A1 | 12/2016 |
| WO | WO 2016/196273 A1 | 12/2016 |
| WO | WO 2016/196282 A1 | 12/2016 |
| WO | WO 2016/196308 A1 | 12/2016 |
| WO | WO 2016/196361 A1 | 12/2016 |
| WO | WO 2016/196499 A1 | 12/2016 |
| WO | WO 2016/196539 A2 | 12/2016 |
| WO | WO 2016/196655 A1 | 12/2016 |
| WO | WO 2016/196805 A1 | 12/2016 |
| WO | WO 2016/196887 A1 | 12/2016 |
| WO | WO 2016/197132 A1 | 12/2016 |
| WO | WO 2016/197133 A1 | 12/2016 |
| WO | WO 2016/197354 A1 | 12/2016 |
| WO | WO 2016/197355 A1 | 12/2016 |
| WO | WO 2016/197356 A1 | 12/2016 |
| WO | WO 2016/197357 A1 | 12/2016 |
| WO | WO 2016/197358 A1 | 12/2016 |
| WO | WO 2016/197359 A1 | 12/2016 |
| WO | WO 2016/197360 A1 | 12/2016 |
| WO | WO 2016/197361 A1 | 12/2016 |
| WO | WO 2016/197362 A1 | 12/2016 |
| WO | WO 2016/198361 A1 | 12/2016 |
| WO | WO 2016/198500 A1 | 12/2016 |
| WO | WO 2016/200263 A1 | 12/2016 |
| WO | WO 2016/201047 A1 | 12/2016 |
| WO | WO 2016/201138 A1 | 12/2016 |
| WO | WO 2016/201152 A1 | 12/2016 |
| WO | WO 2016/201153 A1 | 12/2016 |
| WO | WO 2016/201155 A1 | 12/2016 |
| WO | WO 2016/205276 A1 | 12/2016 |
| WO | WO 2016/205613 A1 | 12/2016 |
| WO | WO 2016/205623 A1 | 12/2016 |
| WO | WO 2016/205680 A1 | 12/2016 |
| WO | WO 2016/205688 A2 | 12/2016 |
| WO | WO 2016/205703 A1 | 12/2016 |
| WO | WO 2016/205711 A1 | 12/2016 |
| WO | WO 2016/205728 A1 | 12/2016 |
| WO | WO 2016/205745 A2 | 12/2016 |
| WO | WO 2016/205749 A1 | 12/2016 |
| WO | WO 2016/205759 A1 | 12/2016 |
| WO | WO 2016/205764 A1 | 12/2016 |
| WO | WO 2017/001572 A1 | 1/2017 |
| WO | WO 2017/001988 A1 | 1/2017 |
| WO | WO 2017/004261 A1 | 1/2017 |
| WO | WO 2017/004279 A2 | 1/2017 |
| WO | WO 2017/004616 A1 | 1/2017 |
| WO | WO 2017/005807 A1 | 1/2017 |
| WO | WO 2017/009399 A1 | 1/2017 |
| WO | WO 2017/010556 A1 | 1/2017 |
| WO | WO 2017/011519 A1 | 1/2017 |
| WO | WO 2017/011721 A1 | 1/2017 |
| WO | WO 2017/011804 A1 | 1/2017 |
| WO | WO 2017/015015 A1 | 1/2017 |
| WO | WO 2017/015101 A1 | 1/2017 |
| WO | WO 2017/015545 A1 | 1/2017 |
| WO | WO 2017/015567 A1 | 1/2017 |
| WO | WO 2017/015637 A1 | 1/2017 |
| WO | WO 2017/017016 A1 | 2/2017 |
| WO | WO 2017/019867 A1 | 2/2017 |
| WO | WO 2017/019895 A1 | 2/2017 |
| WO | WO 2017/023803 A1 | 2/2017 |
| WO | WO 2017/023974 A1 | 2/2017 |
| WO | WO 2017/024047 A1 | 2/2017 |
| WO | WO 2017/024319 A1 | 2/2017 |
| WO | WO 2017/024343 A1 | 2/2017 |
| WO | WO 2017/024602 A1 | 2/2017 |
| WO | WO 2017/025323 A1 | 2/2017 |
| WO | WO 2017/027423 A1 | 2/2017 |
| WO | WO 2017/028768 A1 | 2/2017 |
| WO | WO 2017/029664 A1 | 2/2017 |
| WO | WO 2017/031360 A1 | 2/2017 |
| WO | WO 2017/031483 A1 | 2/2017 |
| WO | WO 2017/035416 A2 | 3/2017 |
| WO | WO 2017/040348 A1 | 3/2017 |
| WO | WO 2017/040511 A1 | 3/2017 |
| WO | WO 2017/040709 A1 | 3/2017 |
| WO | WO 2017/040786 A1 | 3/2017 |
| WO | WO 2017/040793 A1 | 3/2017 |
| WO | WO 2017/040813 A2 | 3/2017 |
| WO | WO 2017/043573 A1 | 3/2017 |
| WO | WO 2017/043656 A1 | 3/2017 |
| WO | WO 2017/044419 A1 | 3/2017 |
| WO | WO 2017/044776 A1 | 3/2017 |
| WO | WO 2017/044857 A2 | 3/2017 |
| WO | WO 2017/048390 A1 | 3/2017 |
| WO | WO 2017/049129 A2 | 3/2017 |
| WO | WO 2017/050963 A1 | 3/2017 |
| WO | WO 2017/053312 A1 | 3/2017 |
| WO | WO 2017/053431 A2 | 3/2017 |
| WO | WO 2017/053713 A1 | 3/2017 |
| WO | WO 2017/053729 A1 | 3/2017 |
| WO | WO 2017/053753 A1 | 3/2017 |
| WO | WO 2017/053762 A1 | 3/2017 |
| WO | WO 2017/053879 A1 | 3/2017 |
| WO | WO 2017/054721 A1 | 4/2017 |
| WO | WO 2017/058658 A2 | 4/2017 |
| WO | WO 2017/059241 A1 | 4/2017 |
| WO | WO 2017/062605 A1 | 4/2017 |
| WO | WO 2017/062723 A1 | 4/2017 |
| WO | WO 2017/062754 A1 | 4/2017 |
| WO | WO 2017/062855 A1 | 4/2017 |
| WO | WO 2017/062886 A1 | 4/2017 |
| WO | WO 2017/062983 A1 | 4/2017 |
| WO | WO 2017/064439 A1 | 4/2017 |
| WO | WO 2017/064546 A1 | 4/2017 |
| WO | WO 2017/064566 A2 | 4/2017 |
| WO | WO 2017/066175 A1 | 4/2017 |
| WO | WO 2017/066497 A2 | 4/2017 |
| WO | WO 2017/066588 A2 | 4/2017 |
| WO | WO 2017/066707 A1 | 4/2017 |
| WO | WO 2017/066781 A1 | 4/2017 |
| WO | WO 2017/068077 A1 | 4/2017 |
| WO | WO 2017/068377 A1 | 4/2017 |
| WO | WO 2017/069829 A2 | 4/2017 |
| WO | WO 2017/070029 A1 | 4/2017 |
| WO | WO 2017/070032 A1 | 4/2017 |
| WO | WO 2017/070169 A1 | 4/2017 |
| WO | WO 2017/070284 A1 | 4/2017 |
| WO | WO 2017/070598 A1 | 4/2017 |
| WO | WO 2017/070605 A1 | 4/2017 |
| WO | WO 2017/070632 A2 | 4/2017 |
| WO | WO 2017/070633 A2 | 4/2017 |
| WO | WO 2017/072590 A1 | 5/2017 |
| WO | WO 2017/074526 A1 | 5/2017 |
| WO | WO 2017/074962 A1 | 5/2017 |
| WO | WO 2017/075261 A1 | 5/2017 |
| WO | WO 2017/075335 A1 | 5/2017 |
| WO | WO 2017/075475 A1 | 5/2017 |
| WO | WO 2017/077135 A1 | 5/2017 |
| WO | WO 2017/077329 A2 | 5/2017 |
| WO | WO 2017/078751 A1 | 5/2017 |
| WO | WO 2017/079400 A1 | 5/2017 |
| WO | WO 2017/079428 A1 | 5/2017 |
| WO | WO 2017/079673 A1 | 5/2017 |
| WO | WO 2017/079724 A1 | 5/2017 |
| WO | WO 2017/081097 A1 | 5/2017 |
| WO | WO 2017/081288 A1 | 5/2017 |
| WO | WO 2017/083368 A1 | 5/2017 |
| WO | WO 2017/083722 A1 | 5/2017 |
| WO | WO 2017/083766 A1 | 5/2017 |
| WO | WO 2017/087395 A1 | 5/2017 |

(56) References Cited

FOREIGN PATENT DOCUMENTS

| | | |
|---|---|---|
| WO | WO 2017/090724 A1 | 6/2017 |
| WO | WO 2017/091510 A1 | 6/2017 |
| WO | WO 2017/091630 A1 | 6/2017 |
| WO | WO 2017/092201 A1 | 6/2017 |
| WO | WO 2017/093370 A1 | 6/2017 |
| WO | WO 2017/093969 A1 | 6/2017 |
| WO | WO 2017/095111 A1 | 6/2017 |
| WO | WO 2017/096041 A1 | 6/2017 |
| WO | WO 2017/096237 A1 | 6/2017 |
| WO | WO 2017/100158 A1 | 6/2017 |
| WO | WO 2017/100431 A2 | 6/2017 |
| WO | WO 2017/104404 A1 | 6/2017 |
| WO | WO 2017/105251 A1 | 6/2017 |
| WO | WO 2017/105350 A1 | 6/2017 |
| WO | WO 2017/105991 A1 | 6/2017 |
| WO | WO 2017/106414 A1 | 6/2017 |
| WO | WO 2017/106528 A2 | 6/2017 |
| WO | WO 2017/106537 A2 | 6/2017 |
| WO | WO 2017/106569 A1 | 6/2017 |
| WO | WO 2017/106616 A1 | 6/2017 |
| WO | WO 2017/106657 A1 | 6/2017 |
| WO | WO 2017/106767 A1 | 6/2017 |
| WO | WO 2017/109134 A1 | 6/2017 |
| WO | WO 2017/109757 A1 | 6/2017 |
| WO | WO 2017/112620 A1 | 6/2017 |
| WO | WO 2017/115268 A1 | 7/2017 |
| WO | WO 2017/117395 A1 | 7/2017 |
| WO | WO 2017/118598 A1 | 7/2017 |
| WO | WO 2017/118720 A1 | 7/2017 |
| WO | WO 2017/123609 A1 | 7/2017 |
| WO | WO 2017/123910 A1 | 7/2017 |
| WO | WO 2017/124086 A1 | 7/2017 |
| WO | WO 2017/124100 A1 | 7/2017 |
| WO | WO 2017/124652 A1 | 7/2017 |
| WO | WO 2017/126987 A1 | 7/2017 |
| WO | WO 2017/127807 A1 | 7/2017 |
| WO | WO 2017/131237 A1 | 8/2017 |
| WO | WO 2017/132112 A1 | 8/2017 |
| WO | WO 2017/132580 A2 | 8/2017 |
| WO | WO 2017/136520 A1 | 8/2017 |
| WO | WO 2017/136629 A1 | 8/2017 |
| WO | WO 2017/136794 A1 | 8/2017 |
| WO | WO 2017/139264 A1 | 8/2017 |
| WO | WO 2017/139505 A2 | 8/2017 |
| WO | WO 2017/141173 A2 | 8/2017 |
| WO | WO 2017/142835 A1 | 8/2017 |
| WO | WO 2017/142999 A2 | 8/2017 |
| WO | WO 2017/143042 A2 | 8/2017 |
| WO | WO 2017/147278 A1 | 8/2017 |
| WO | WO 2017/147432 A1 | 8/2017 |
| WO | WO 2017/147446 A1 | 8/2017 |
| WO | WO 2017/147555 A1 | 8/2017 |
| WO | WO 2017/151444 A1 | 9/2017 |
| WO | WO 2017/151719 A1 | 9/2017 |
| WO | WO 2017/152015 A1 | 9/2017 |
| WO | WO 2017/155717 A1 | 9/2017 |
| WO | WO 2017/157422 A1 | 9/2017 |
| WO | WO 2017/158153 A1 | 9/2017 |
| WO | WO 2017/160689 A1 | 9/2017 |
| WO | WO 2017/160752 A1 | 9/2017 |
| WO | WO 2017/160890 A1 | 9/2017 |
| WO | WO 2017/161068 A1 | 9/2017 |
| WO | WO 2017/165826 A1 | 9/2017 |
| WO | WO 2017/165862 A1 | 9/2017 |
| WO | WO 2017/172644 A2 | 10/2017 |
| WO | WO 2017/172645 A2 | 10/2017 |
| WO | WO 2017/172860 A1 | 10/2017 |
| WO | WO 2017/173004 A1 | 10/2017 |
| WO | WO 2017/173054 A1 | 10/2017 |
| WO | WO 2017/173092 A1 | 10/2017 |
| WO | WO 2017/174329 A1 | 10/2017 |
| WO | WO 2017/176529 A1 | 10/2017 |
| WO | WO 2017/176806 A1 | 10/2017 |
| WO | WO 2017/178590 A1 | 10/2017 |
| WO | WO 2017/180694 A1 | 10/2017 |
| WO | WO 2017/180711 A1 | 10/2017 |
| WO | WO 2017/180915 A2 | 10/2017 |
| WO | WO 2017/180926 A1 | 10/2017 |
| WO | WO 2017/181107 A2 | 10/2017 |
| WO | WO 2017/181735 A2 | 10/2017 |
| WO | WO 2017/182468 A1 | 10/2017 |
| WO | WO 2017/184334 A1 | 10/2017 |
| WO | WO 2017/184768 A1 | 10/2017 |
| WO | WO 2017/184786 A1 | 10/2017 |
| WO | WO 2017/186550 A1 | 11/2017 |
| WO | WO 2017/189308 A1 | 11/2017 |
| WO | WO 2017/189336 A1 | 11/2017 |
| WO | WO 2017/190041 A1 | 11/2017 |
| WO | WO 2017/190257 A1 | 11/2017 |
| WO | WO 2017/190664 A1 | 11/2017 |
| WO | WO 2017/191210 A1 | 11/2017 |
| WO | WO 2017/191274 A2 | 11/2017 |
| WO | WO 2017/192172 A1 | 11/2017 |
| WO | WO 2017/192512 A2 | 11/2017 |
| WO | WO 2017/192544 A1 | 11/2017 |
| WO | WO 2017/192573 A1 | 11/2017 |
| WO | WO 2017/193029 A2 | 11/2017 |
| WO | WO 2017/193053 A1 | 11/2017 |
| WO | WO 2017/196768 A1 | 11/2017 |
| WO | WO 2017/197038 A1 | 11/2017 |
| WO | WO 2017/197238 A1 | 11/2017 |
| WO | WO 2017/197301 A1 | 11/2017 |
| WO | WO 2017/201476 A1 | 11/2017 |
| WO | WO 2017/205290 A1 | 11/2017 |
| WO | WO 2017/205423 A1 | 11/2017 |
| WO | WO 2017/207589 A1 | 12/2017 |
| WO | WO 2017/208247 A1 | 12/2017 |
| WO | WO 2017/209809 A1 | 12/2017 |
| WO | WO 2017/213896 A1 | 12/2017 |
| WO | WO 2017/213898 A2 | 12/2017 |
| WO | WO 2017/214460 A1 | 12/2017 |
| WO | WO 2017/216392 A1 | 12/2017 |
| WO | WO 2017/216771 A2 | 12/2017 |
| WO | WO 2017/218185 A1 | 12/2017 |
| WO | WO 2017/219027 A1 | 12/2017 |
| WO | WO 2017/219033 A1 | 12/2017 |
| WO | WO 2017/220751 A1 | 12/2017 |
| WO | WO 2017/222370 A1 | 12/2017 |
| WO | WO 2017/222773 A1 | 12/2017 |
| WO | WO 2017/222834 A1 | 12/2017 |
| WO | WO 2017/223107 A1 | 12/2017 |
| WO | WO 2017/223330 A1 | 12/2017 |
| WO | WO 2018/000657 A1 | 1/2018 |
| WO | WO 2018/002719 A1 | 1/2018 |
| WO | WO 2018/005117 A1 | 1/2018 |
| WO | WO 2018/005289 A2 | 1/2018 |
| WO | WO 2018/005691 A1 | 1/2018 |
| WO | WO 2018/005782 A1 | 1/2018 |
| WO | WO 2018/005873 A1 | 1/2018 |
| WO | WO 2018/06693 A1 | 1/2018 |
| WO | WO 2018/009520 A1 | 1/2018 |
| WO | WO 2018/009562 A1 | 1/2018 |
| WO | WO 2018/009822 A1 | 1/2018 |
| WO | WO 2018/013821 A1 | 1/2018 |
| WO | WO 2018/013932 A1 | 1/2018 |
| WO | WO 2018/013990 A1 | 1/2018 |
| WO | WO 2018/014384 A1 | 1/2018 |
| WO | WO 2018/015444 A1 | 1/2018 |
| WO | WO 2018/015936 A2 | 1/2018 |
| WO | WO 2018/017754 A1 | 1/2018 |
| WO | WO 2018/018979 A1 | 2/2018 |
| WO | WO 2018/020248 A1 | 2/2018 |
| WO | WO 2018/021878 A1 | 2/2018 |
| WO | WO 2018/022480 A1 | 2/2018 |
| WO | WO 2018/022634 A1 | 2/2018 |
| WO | WO 2018/025206 A1 | 2/2018 |
| WO | WO 2018/026723 A1 | 2/2018 |
| WO | WO 2018/026976 A1 | 2/2018 |
| WO | WO 2018/027078 A1 | 2/2018 |
| WO | WO 2018/030608 A1 | 2/2018 |
| WO | WO 2018/031683 A1 | 2/2018 |
| WO | WO 2018/035250 A1 | 2/2018 |
| WO | WO 2018/035300 A1 | 2/2018 |
| WO | WO 2018/035423 A1 | 2/2018 |

(56) References Cited

FOREIGN PATENT DOCUMENTS

| | | |
|---|---|---|
| WO | WO 2018/035503 A1 | 2/2018 |
| WO | WO 2018/039145 A1 | 3/2018 |
| WO | WO 2018/039438 A1 | 3/2018 |
| WO | WO 2018/039440 A1 | 3/2018 |
| WO | WO 2018/039448 A1 | 3/2018 |
| WO | WO 2018/045630 A1 | 3/2018 |
| WO | WO 2018/048827 A1 | 3/2018 |
| WO | WO 2018/049073 A1 | 3/2018 |
| WO | WO 2018/049168 A1 | 3/2018 |
| WO | WO 2018/051347 A1 | 3/2018 |
| WO | WO 2018/058064 A1 | 3/2018 |
| WO | WO 2018/062866 A2 | 4/2018 |
| WO | WO 2018/064352 A1 | 4/2018 |
| WO | WO 2018/064371 A1 | 4/2018 |
| WO | WO 2018/064516 A1 | 4/2018 |
| WO | WO 2018/067546 A1 | 4/2018 |
| WO | WO 2018/067846 A1 | 4/2018 |
| WO | WO 2018/068053 A2 | 4/2018 |
| WO | WO 2018/069474 A1 | 4/2018 |
| WO | WO 2018/071623 A2 | 4/2018 |
| WO | WO 2018/071663 A1 | 4/2018 |
| WO | WO 2018/071868 A1 | 4/2018 |
| WO | WO 2018/071892 A1 | 4/2018 |
| WO | WO 2018/074979 A1 | 4/2018 |
| WO | WO 2018/079134 A1 | 5/2018 |
| WO | WO 2018/080573 A1 | 5/2018 |
| WO | WO 2018/081504 A1 | 5/2018 |
| WO | WO 2018/081535 A2 | 5/2018 |
| WO | WO 2018/081728 A1 | 5/2018 |
| WO | WO 2018/083128 A2 | 5/2018 |
| WO | WO 2018/083606 A1 | 5/2018 |
| WO | WO 2018/085288 A1 | 5/2018 |
| WO | WO 2018/086623 A1 | 5/2018 |
| WO | WO 2018/089664 A1 | 5/2018 |
| WO | WO 2018/093990 A1 | 5/2018 |
| WO | WO 2018/098383 A1 | 5/2018 |
| WO | WO 2018/098480 A1 | 5/2018 |
| WO | WO 2018/098587 A1 | 6/2018 |
| WO | WO 2018/099256 A1 | 6/2018 |
| WO | WO 2018/103686 A1 | 6/2018 |
| WO | WO 2018/106268 A1 | 6/2018 |
| WO | WO 2018/107028 A1 | 6/2018 |
| WO | WO 2018/107103 A1 | 6/2018 |
| WO | WO 2018/107129 A1 | 6/2018 |
| WO | WO 2018/108272 A1 | 6/2018 |
| WO | WO 2018/109101 A1 | 6/2018 |
| WO | WO 2018/111946 A1 | 6/2018 |
| WO | WO 2018/111947 A1 | 6/2018 |
| WO | WO 2018/112336 A1 | 6/2018 |
| WO | WO 2018/112446 A2 | 6/2018 |
| WO | WO 2018/119354 A1 | 6/2018 |
| WO | WO 2018/119359 A1 | 6/2018 |
| WO | WO 2018/120283 A1 | 7/2018 |
| WO | WO 2018/130830 A1 | 7/2018 |
| WO | WO 2018/135838 A2 | 7/2018 |
| WO | WO 2018/136396 A2 | 7/2018 |
| WO | WO 2018/138385 A1 | 8/2018 |
| WO | WO 2018/142364 A1 | 8/2018 |
| WO | WO 2018/148246 A1 | 8/2018 |
| WO | WO 2018/148256 A1 | 8/2018 |
| WO | WO 2018/148647 A2 | 8/2018 |
| WO | WO 2018/149418 A1 | 8/2018 |
| WO | WO 2018/149888 A1 | 8/2018 |
| WO | WO 2018/149915 A1 | 8/2018 |
| WO | WO 2018/152197 A1 | 8/2018 |
| WO | WO 2018/152418 A1 | 8/2018 |
| WO | WO 2018/154380 A1 | 8/2018 |
| WO | WO 2018/154387 A1 | 8/2018 |
| WO | WO 2018/154412 A1 | 8/2018 |
| WO | WO 2018/154413 A1 | 8/2018 |
| WO | WO 2018/154418 A1 | 8/2018 |
| WO | WO 2018/154439 A1 | 8/2018 |
| WO | WO 2018/154459 A1 | 8/2018 |
| WO | WO 2018/154462 A2 | 8/2018 |
| WO | WO 2018/156372 A1 | 8/2018 |
| WO | WO 2018/161009 A1 | 9/2018 |
| WO | WO 2018/165504 A1 | 9/2018 |
| WO | WO 2018/165629 A1 | 9/2018 |
| WO | WO 2018/170015 A1 | 9/2018 |
| WO | WO 2018/170340 A1 | 9/2018 |
| WO | WO 2018/175502 A2 | 9/2018 |
| WO | WO 2018/176009 A1 | 9/2018 |
| WO | WO 2018/177351 A1 | 10/2018 |
| WO | WO 2018/179578 A1 | 10/2018 |
| WO | WO 2018/183403 A1 | 10/2018 |
| WO | WO 2018/189184 A1 | 10/2018 |
| WO | WO 2018/191388 A1 | 10/2018 |
| WO | WO 2018/195402 A1 | 10/2018 |
| WO | WO 2018/195545 A2 | 10/2018 |
| WO | WO 2018/195555 A1 | 10/2018 |
| WO | WO 2018/197020 A1 | 11/2018 |
| WO | WO 2018/197495 A1 | 11/2018 |
| WO | WO 2018/202800 A1 | 11/2018 |
| WO | WO 2018/204493 A1 | 11/2018 |
| WO | WO 2018/208755 A1 | 11/2018 |
| WO | WO 2018/208998 A1 | 11/2018 |
| WO | WO 2018/209158 A2 | 11/2018 |
| WO | WO 2018/209320 A1 | 11/2018 |
| WO | WO 2018/213351 A1 | 11/2018 |
| WO | WO 2018/213708 A1 | 11/2018 |
| WO | WO 2018/213726 A1 | 11/2018 |
| WO | WO 2018/213771 A1 | 11/2018 |
| WO | WO 2018/213791 A1 | 11/2018 |
| WO | WO 2018/217852 A1 | 11/2018 |
| WO | WO 2018/217981 A1 | 11/2018 |
| WO | WO 2018/218166 A1 | 11/2018 |
| WO | WO 2018/218188 A2 | 11/2018 |
| WO | WO 2018/218206 A1 | 11/2018 |
| WO | WO 2019/005886 A1 | 1/2019 |
| WO | WO 2019/010384 A1 | 1/2019 |
| WO | WO 2019/023680 A1 | 1/2019 |
| WO | WO 2019/051097 A1 | 3/2019 |
| WO | WO 2019/079347 A1 | 4/2019 |
| WO | WO 2019/084062 A1 | 5/2019 |
| WO | WO 2019/118949 A1 | 6/2019 |
| WO | WO 2019/139645 A2 | 7/2019 |
| WO | WO 2019/139951 A1 | 7/2019 |
| WO | WO 2019/147014 A1 | 8/2019 |
| WO | WO 2019/226953 A1 | 11/2019 |
| WO | WO 2020/014261 A1 | 1/2020 |
| WO | WO 2020/041751 A1 | 2/2020 |
| WO | WO 2020/047124 A1 | 3/2020 |
| WO | WO 2020/051360 A1 | 3/2020 |
| WO | WO 2020/086908 A1 | 4/2020 |
| WO | WO 2020/092453 A1 | 5/2020 |
| WO | WO 2020/102659 A1 | 5/2020 |
| WO | WO 2020/154500 A1 | 7/2020 |
| WO | WO 2020/181178 A1 | 9/2020 |
| WO | WO 2020/181180 A1 | 9/2020 |
| WO | WO 2020/181193 A1 | 9/2020 |
| WO | WO 2020/181195 A1 | 9/2020 |
| WO | WO 2020/181202 A1 | 9/2020 |
| WO | WO 2020/191153 A1 | 9/2020 |
| WO | WO 2020/191171 A1 | 9/2020 |
| WO | WO 2020/191233 A1 | 9/2020 |
| WO | WO 2020/191234 A1 | 9/2020 |
| WO | WO 2020/191239 A1 | 9/2020 |
| WO | WO 2020/191241 A1 | 9/2020 |
| WO | WO 2020/191242 A1 | 9/2020 |
| WO | WO 2020/191243 A1 | 9/2020 |
| WO | WO 2020/191245 A1 | 9/2020 |
| WO | WO 2020/191246 A1 | 9/2020 |
| WO | WO 2020/191248 A1 | 9/2020 |
| WO | WO 2020/191249 A1 | 9/2020 |
| WO | WO 2020/210751 A1 | 10/2020 |
| WO | WO 2020/214842 A1 | 10/2020 |

OTHER PUBLICATIONS

U.S. Appl. No. 16/266,937, filed Feb. 4, 2019, Liu et al.
U.S. Appl. No. 14/320,370, filed Jun. 30, 2014, Liu et al.
U.S. Appl. No. 14/320,413, filed Jun. 30, 2014, Liu et al.
U.S. Appl. No. 14/874,123, filed Oct. 2, 2015, Liu et al.

(56) References Cited

OTHER PUBLICATIONS

U.S. Appl. No. 14/911,117, filed Feb. 9, 2016, Liu et al.
U.S. Appl. No. 17/160,329, filed Jan. 27, 2021, Liu et al.
U.S. Appl. No. 14/462,163, filed Aug. 18, 2014, Liu et al.
U.S. Appl. No. 14/462,189, filed Aug. 18, 2014, Liu et al.
U.S. Appl. No. 14/916,679, filed Mar. 4, 2016, Liu et al.
U.S. Appl. No. 16/860,639, filed Apr. 28, 2020, Liu et al.
U.S. Appl. No. 14/320,498, filed Jun. 30, 2014, Liu et al.
U.S. Appl. No. 14/320,467, filed Jun. 30, 2014, Liu et al.
U.S. Appl. No. 14/916,681, filed Mar. 4, 2016, Liu et al.
U.S. Appl. No. 17/103,233, filed Nov. 24, 2020, Liu et al.
U.S. Appl. No. 14/326,329, filed Jul. 8, 2014, Liu et al.
U.S. Appl. No. 14/326,340, filed Jul. 8, 2014, Liu et al.
U.S. Appl. No. 14/326,361, filed Jul. 8, 2014, Liu et al.
U.S. Appl. No. 14/916,683, filed Mar. 4, 2016, Liu et al.
U.S. Appl. No. 16/796,323, filed Feb. 20, 2020, Liu et al.
U.S. Appl. No. 14/325,815, filed Jul. 8, 2014, Liu et al.
U.S. Appl. No. 14/326,109, filed Jul. 8, 2014, Liu et al.
U.S. Appl. No. 14/326,140, filed Jul. 8, 2014, Liu et al.
U.S. Appl. No. 14/326,269, filed Jul. 8, 2014, Liu et al.
U.S. Appl. No. 14/326,290, filed Jul. 8, 2014, Liu et al.
U.S. Appl. No. 14/326,318, filed Jul. 8, 2014, Liu et al.
U.S. Appl. No. 14/326,303, filed Jul. 8, 2014, Liu et al.
U.S. Appl. No. 15/103,608, filed Jun. 10, 2016, Liu et al.
U.S. Appl. No. 16/374,634, filed Apr. 3, 2019, Liu et al.
U.S. Appl. No. 15/329,925, filed Jan. 27, 2017, Liu et al.
U.S. Appl. No. 16/132,276, filed Sep. 14, 2018, Liu et al.
U.S. Appl. No. 16/888,646, filed May 29, 2020, Liu et al.
U.S. Appl. No. 14/529,010, filed Oct. 30, 2014, Liu et al.
U.S. Appl. No. 15/958,721, filed Apr. 20, 2018, Liu et al.
U.S. Appl. No. 17/130,812, filed Dec. 22, 2020, Liu et al.
U.S. Appl. No. 15/331,852, filed Oct. 22, 2016, Liu et al.
U.S. Appl. No. 15/960,171, filed Apr. 23, 2018, Liu et al.
U.S. Appl. No. 15/770,076, filed Apr. 20, 2018, Liu et al.
U.S. Appl. No. 16/327,744, filed Feb. 22, 2019, Maianti et al.
U.S. Appl. No. 15/852,891, filed Dec. 22, 2017, Maianti et al.
U.S. Appl. No. 16/926,436, filed Jul. 10, 2020, Maianti et al.
U.S. Appl. No. 15/852,526, filed Dec. 22, 2017, Maianti et al.
U.S. Appl. No. 16/492,534, filed Sep. 9, 2019, Liu et al.
U.S. Appl. No. 16/324,476, filed Feb. 8, 2019, Liu et al.
U.S. Appl. No. 15/791,085, filed Oct. 23, 2017, Liu et al.
U.S. Appl. No. 16/143,370, filed Sep. 26, 2018, Liu et al.
U.S. Appl. No. 16/492,548, filed Sep. 9, 2019, Maianti et al.
U.S. Appl. No. 15/784,033, filed Oct. 13, 2017, Liu et al.
U.S. Appl. No. 16/492,553, filed Sep. 9, 2019, Liu et al.
U.S. Appl. No. 15/934,945, filed Mar. 23, 2018, Liu et al.
U.S. Appl. No. 16/643,376, filed Feb. 28, 2020, Liu et al.
U.S. Appl. No. 16/612,988, filed Nov. 12, 2019, Liu et al.
U.S. Appl. No. 16/634,405, filed Jan. 27, 2020, Liu et al.
U.S. Appl. No. 16/976,047, filed Aug. 26, 2020, Liu et al.
U.S. Appl. No. 17/289,665, filed Apr. 28, 2021, Liu et al.
U.S. Appl. No. 16/756,432, filed Apr. 15, 2020, Liu et al.
U.S. Appl. No. 16/772,747, filed Jun. 12, 2020, Shen et al.
U.S. Appl. No. 17/057,398, filed Nov. 20, 2020, Liu et al.
U.S. Appl. No. 17/259,147, filed Jan. 8, 2021, Liu et al.
U.S. Appl. No. 17/270,396, filed Feb. 22, 2021, Liu et al.
U.S. Appl. No. 17/273,688, filed Mar. 4, 2021, Liu et al.
U.S. Appl. No. 17/288,504, filed Apr. 23, 2021, Liu et al.
U.S. Appl. No. 17/219,590, filed Mar. 31, 2021, Liu et al.
U.S. Appl. No. 17/219,635, filed Mar. 31, 2021, Liu et al.
Mar. 31, 2021, Liu et al.
EP 123845790.0, Mar. 18, 2015, Partial Supplementary European Search Report.
EP 123845790.0, Oct. 12, 2015, Supplementary European Search Report.
EP 19187331.4, Dec. 19, 2019 Partial European Search Report.
PCT/US2012/047778, May 30, 2013, International Search Report and Written Opinion.
PCT/US2012/047778, Feb. 6, 2014, International Preliminary Report on Patentability.
PCT/US2014/052231, Dec. 4, 2014, International Search Report and Written Opinion.
PCT/US2014/052231, Jan. 30, 2015, International Search Report and Written Opinion (Corrected Version).
PCT/US2014/052231, Mar. 3, 2016, International Preliminary Report on Patentability.
EP 18199195.1, Feb. 12, 2019, Extended European Search Report.
PCT/US2014/050283, Nov. 6, 2014, International Search Report and Written Opinion.
PCT/US2014/050283, Feb. 18, 2016, International Preliminary Report on Patentability.
PCT/US2014/054247, Mar. 27, 2015, International Search Report and Written Opinion.
PCT/US2014/054247, Mar. 17, 2016, International Preliminary Report on Patentability.
PCT/US2014/054291, Dec. 18, 2014, Invitation to Pay Additional Fees.
PCT/US2014/054291, Mar. 27, 2015, International Search Report and Written Opinion.
PCT/US2014/054291, Mar. 17, 2016, International Preliminary Report on Patentability.
PCT/US2014/054252, Mar. 5, 2015, International Search Report and Written Opinion.
PCT/US2014/054252, Mar. 17, 2016, International Preliminary Report on Patentability.
EP 19181479.7, Oct. 31, 2019, Extended European Search Report.
PCT/US2014/070038, Apr. 14, 2015, International Search Report and Written Opinion.
PCT/US2014/070038, Jun. 23, 2016, International Preliminary Report on Patentability.
EP 15830407.1, Mar. 2, 2018, Extended European Search Report.
PCT/US2015/042770, Feb. 23, 2016, International Search Report and Written Opinion.
PCT/US2015/042770, Dec. 19, 2016, International Preliminary Report on Patentability.
PCT/US2015/058479, Feb. 11, 2016, International Search Report and Written Opinion.
PCT/US2015/058479, May 11, 2017, International Preliminary Report on Patentability.
PCT/US2016/044546, Dec. 28, 2016, International Search Report and Written Opinion.
PCT/US2016/058344, Mar. 1, 2017, Invitation to Pay Additional Fees.
PCT/US2016/058344, Apr. 20, 2017, International Search Report and Written Opinion.
PCT/US2016/058344, May 3, 2018, International Preliminary Report on Patentability.
PCT/US2018/025887, Jun. 21, 2018, International Search Report and Written Opinion.
PCT/US2017/48390, Nov. 7, 2017, Invitation to Pay Additional Fees.
PCT/US2017/48390, Jan. 9, 2018, International Search Report and Written Opinion.
PCT/US2014/048390, Mar. 7, 2019, International Preliminary Report on Patentability.
PCT/US2017/068114, Mar. 20, 2018, International Search Report and Written Opinion.
PCT/US2017/068105, Apr. 4, 2018, International Search Report and Written Opinion.
PCT/US2017/068114, Jul. 4, 2019, International Preliminary Report on Patentability.
PCT/US2018/021880, Jun. 20, 2018, International Search Report and Written Opinion.
PCT/US2018/021880, Sep. 19, 2019, International Preliminary Report on Patentability.
PCT/US2017/046144, Oct. 10, 2017, International Search Report and Written Opinion.
PCT/US2017/046144, Feb. 21, 2019, International Preliminary Report on Patentability.
SG 11201900907Y, Jul. 20, 2020, Search Report and Written Opinion.
PCT/US2017/045381, Oct. 26, 2017, International Search Report and Written Opinion.

(56) References Cited

OTHER PUBLICATIONS

PCT/US2017/046144, Feb. 14, 2019, International Preliminary Report on Patentability.
PCT/US2018/021664, Jun. 21, 2018, International Search Report and Written Opinion.
PCT/US2018/021664, Sep. 19, 2019, International Preliminary Report on Patentability.
PCT/US2017/056671, Dec. 21, 2017, Invitation to Pay Additional Fees.
PCT/US2017/056671, Feb. 20, 2018, International Search Report and Written Opinion.
PCT/US2017/056671, Apr. 25, 2019, International Preliminary Report on Patentability.
PCT/US2018/021878, Jun. 8, 2018, Invitation to Pay Additional Fees.
PCT/US2018/021878, Aug. 20, 2018, International Search Report and Written Opinion.
PCT/US2018/021878, Sep. 19, 2019, International Preliminary Report on Patentability.
PCT/US2018/024208, Aug. 23, 2018, International Search Report and Written Opinion.
PCT/US2018/024208, Oct. 3, 2019, International Preliminary Report on Patentability.
PCT/US2018/048969, Jul. 31, 2019, International Search Report and Written Opinion.
PCT/US2018/032460, Jul. 11, 2018, International Search Report and Written Opinion.
PCT/US2018/032460, Nov. 21, 2019, International Preliminary Report on Patentability.
U.S. Appl. No. 61/874,746, filed Sep. 6, 2013, Liu et al.
U.S. Appl. No. 61/874,682, filed Sep. 6, 2013, Liu et al.
U.S. Appl. No. 61/838,178, filed Jun. 21, 2013, Joung et al.
U.S. Appl. No. 61/837,481, filed Jun. 20, 2013, Cho et al.
U.S. Appl. No. 61/803,599, filed Mar. 20, 2013, Kim et al.
U.S. Appl. No. 61/794,422, filed Mar. 15, 2013, Knight et al.
U.S. Appl. No. 61/761,046, filed Feb. 5, 2013, Knight et al.
U.S. Appl. No. 61/758,624, filed Jan. 30, 2013, Chen et al.
U.S. Appl. No. 61/734,256, filed Dec. 6, 2012, Chen et al.
U.S. Appl. No. 61/717,324, filed Oct. 23, 2012, Cho et al.
U.S. Appl. No. 61/716,256, filed Oct. 19, 2012, Jinek et al.
U.S. Appl. No. 62/357,332, filed Jun. 30, 2016, Liu et al.
U.S. Appl. No. 62/288,661, filed Jan. 29, 2016, Muir et al.
[No Author Listed] "FokI" from New England Biolabs Inc. Last accessed online via https://www.neb.com/products/r0109-foki#Product%20Information on Mar. 19, 2021. 1 page.
[No Author Listed] "Human genome." Encyclopedia Britannica. Encyclopedia Brittanica, Inc. Published Feb. 15, 2019. Last accessed online via https://www.britannica.com/science/human-genome on Mar. 19, 2021. 2 pages.
[No Author Listed] "Nucleic Acids Sizes and Molecular Weights." Printed Mar. 19, 2021. 2 pages.
[No Author Listed] "Zinc Finger Nuclease" from Wikipedia. Retrieved from https://en.wikipedia.org/w/index.php?title=Zinc_finger_nuclease&oldid=1007053318. Page last edited Feb. 16, 2021. Printed on Mar. 19, 2021.
[No Author Listed] Beast2: Bayesian evolutionary analysis by sampling trees. http://www.beast2.org/ Last accessed Apr. 28, 2021.
[No Author Listed] HyPhy—Hypothesis testing using Phylogenies. Last modified Apr. 21, 2017. Accessed online via http://hyphy.org/w/index.php/Main_Page on Apr. 28, 2021.
[No Author Listed] NCBI Accession No. XP_015843220.1. C ->U editing enzyme APOBEC-1 [Peromyscus maniculatus bairdii], XP002793540.
[No Author Listed] NCBI Accession No. XP_021505673.1. C ->U editing enzyme APOBEC-1 [Meriones unguiculatus], XP002793541.
[No Author Listed] Score result for SEQ 355 to W02017032580. Muir et al. 2016.
[No Author Listed] Theoretical Biochemistry Group. Institute for Theoretical Chemistry. The ViennaRNA Package. Universitat Wien. https://www.tbi.univie.ac.at/RNA/. Last accessed Apr. 28, 2021.

[No Author Listed], EMBL Accession No. Q99ZW2. Nov. 2012. 2 pages.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.
[No Author Listed], Thermo Fisher Scientific—How Cationic Lipid Mediated Transfection Works, retrieved from the internet Aug. 27, 2015. 2 pages.
Abremski et al., Bacteriophage P1 site-specific recombination. Purification and properties of the Cre recombinase protein. J Biol Chem. Feb. 10, 1984;259(3):1509-14.
Abudayyeh et al., C2c2 is a single-component programmable RNA-guided RNA-targeting CRISPR effector. Science Aug. 2016;353(6299):aaf5573. DOI: 10.1126/science.aaf5573.
Abudayyeh et al., A cytosine deaminase for programmable single-base RNA editing. Science. Jul. 26, 2019;365(6451):382-386. doi: 10.1126/science.aax7063. Epub Jul. 11, 2019.
Abudayyeh et al., RNA targeting with CRISPR-Cas13. Nature. Oct. 12, 2017;550(7675):280-284. doi: 10.1038/nature24049. Epub Oct. 4, 2017.
Ada et al., Carbohydrate-protein conjugate vaccines. Clin Microbiol Infect. Feb. 2003;9(2):79-85. doi: 10.1046/j.1469-0691.2003.00530.x.
Adamala et al., Programmable RNA-binding protein composed of repeats of a single modular unit. Proc Natl Acad Sci U S A. May 10, 2016;113(19):E2579-88. doi: 10.1073/pnas.1519368113. Epub Apr. 26, 2016.
Adams et al., New biarsenical ligands and tetracysteine motifs for protein labeling in vitro and in vivo: synthesis and biological applications. J Am Chem Soc. May 29, 2002;124(21):6063-76. doi: 10.1021/ja017687n.
Addgene Plasmid # 44246. pdCas9-humanized, 2017, Stanley Qi.
Addgene Plasmid # 73021. PCMV-BE3, 2017, David Liu.
Addgene Plasmid # 79620. pcDNA3.1_pCMV-nCas-PmCDA1-ugi pH1-gRNA(HPRT), 2017, Akihiko Kondo.
Adli, The CRISPR tool kit for genome editing and beyond. Nat Commun. May 15, 2018;9(1):1911. doi: 10.1038/s41467-018-04252-2.
Aguilo et al., Coordination of m(6)a mRNA Methylation and Gene Transcription by ZFP217 Regulates Pluripotency and Reprogramming. Cell Stem Cell. Dec. 3, 2015;17(6):689-704. doi: 10.1016/j.stem.2015.09.005. Epub Oct. 29, 2015.
Ahmad et al., Antibody-mediated specific binding and cytotoxicity of liposome-entrapped doxorubicin to lung cancer cells in vitro. Cancer Res. Sep. 1, 1992;52(17):4817-20.
Aihara et al., A conformational switch controls the DNA cleavage activity of lambda integrase. Mol Cell. Jul. 2003;12(1):187-98.
Aik et al., Structure of human RNA N?-methyladenine demethylase Alkbh5 provides insights into its mechanisms of nucleic acid recognition and demethylation. Nucleic Acids Res. Apr. 2014;42(7):4741-54. doi: 10.1093/nar/gku085. Epub Jan. 30, 2014.
Aird et al., Increasing Cas9-mediated homology-directed repair efficiency through covalent tethering of DNA repair template. Commun Biol. May 31, 2018;1:54. doi: 10.1038/s42003-0180054-2.
Akcakaya et al., In vivo CRISPR editing with no detectable genome-wide off-target mutations. Nature. Sep. 2018;561(7723):416-419. doi: 10.1038/s41586-018-0500-9. Epub Sep. 12, 2018. PMID: 30209390; PMCID: PMC6194229.
Akins et al., Mitochondrial plasmids of Neurospora: integration into mitochondrial DNA and evidence for reverse transcription in mitochondria. Cell. Nov. 21, 1986;47(4):505-16. doi: 10.1016/0092-8674(86)90615-x.
Akinsheye et al., Fetal hemoglobin in sickle cell anemia. Blood. Jul. 7, 2011;118(1):19-27. doi: 10.1182/blood-2011-03-325258. Epub Apr. 13, 2011.
Alarcón et al., HNRNPA2B1 Is a Mediator of m(6)A—Dependent Nuclear RNA Processing Events. Cell. Sep. 10, 2015;162(6):1299-308. doi: 10.1016/j.cell.2015.08.011. Epub Aug. 27, 2015.

(56) References Cited

OTHER PUBLICATIONS

Alarcón et al., N6-methyladenosine marks primary microRNAs for processing. Nature. Mar. 26, 2015;519(7544):482-5. doi: 10.1038/nature14281. Epub Mar. 18, 2015.

Alexander, HFE-associated hereditary hemochromatosis. Genet Med. May 2009;11(5):307-13. doi: 10.1097/GIM.0b013e31819d30f2.

Alexandrov et al., Signatures of mutational processes in human cancer. Nature. Aug. 22, 2013;500(7463):415-21. doi: 10.1038/nature12477. Epub Aug. 14, 2013.

Ali et al., Novel genetic abnormalities in Bernard-Soulier syndrome in India. Ann Hematol. Mar. 2014;93(3):381-4. doi: 10.1007/s00277-013-1895-x. Epub Sep. 1, 2013.

Altschul et al., Basic local alignment search tool. J Mol Biol. Oct. 5, 1990;215(3):403-10. doi: 10.1016/S0022-2836(05)80360-2.

Amato et al., Interpreting elevated fetal hemoglobin in pathology and health at the basic laboratory level: new and known ?—gene mutations associated with hereditary persistence of fetal hemoglobin. Int J Lab Hematol. Feb. 2014;36(1):13-9. doi: 10.1111/ijlh.12094. Epub Apr. 29, 2013.

Ames et al., A eubacterial riboswitch class that senses the coenzyme tetrahydrofolate. Chem Biol. Jul. 30, 2010;17(7):681-5. doi: 10.1016/j.chembiol.2010.05.020.

Amrann et al., Tightly regulated tac promoter vectors useful for the expression of unfused and fused proteins in *Escherichia coli*. Gene. Sep. 30, 1988;69(2):301-15.

Anders et al., Chapter One: In Vitro Enzymology of Cas9. in Methods in Enzymology, eds Doudna et al. 2014: 546:1-20.

Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.

Anderson, Human gene therapy. Science. May 8, 1992;256(5058):808-13. doi: 10.1126/science.1589762.

Anzalone et al., Reprogramming eukaryotic translation with ligand-responsive synthetic RNA switches. Nat Methods. May 2016;13(5):453-8. doi: 10.1038/nmeth.3807. Epub Mar. 21, 2016.

Anzalone et al., Search-and-replace genome editing without double-strand breaks or donor DNA. Nature. Dec. 2019;576(7785):149-157. doi: 10.1038/s41586-019-1711-4. Epub Oct. 21, 2019.

Aplan, Causes of oncogenic chromosomal translocation. Trends Genet. Jan. 2006;22(1):46-55. doi: 10.1016/j.tig.2005.10.002. Epub Oct. 28, 2005.

Arakawa et al., A method to convert mRNA into a gRNA library for CRISPR/Cas9 editing of any organism. Sci Adv. Aug. 24, 2016;2(8):e1600699. doi: 10.1126/sciadv.1600699.

Araki et al., Comparative analysis of right element mutant lox sites on recombination efficiency in embryonic stem cells. BMC Biotechnol. Mar. 31, 2010;10:29. doi: 10.1186/14726750-10-29.

Araki et al., Site-specific recombinase, R, encoded by yeast plasmid pSR1. J Mol Biol. May 5, 1992;225(1):25-37. doi: 10.1016/0022-2836(92)91023-i.

Araki et al., Targeted integration of DNA using mutant lox sites in embryonic stem cells. Nucleic Acids Res. Feb. 15, 1997;25(4):868-72. doi: 10.1093/nar/25.4.868.

Arambula et al., Surface display of a massively variable lipoprotein by a Legionella diversity-generating retroelement. Proc Natl Acad Sci U S A. May 14, 2013;110(20):8212-7. doi: 10.1073/pnas.1301366110. Epub Apr. 30, 2013.

Arazoe et al., Targeted Nucleotide Editing Technologies for Microbial Metabolic Engineering. Biotechnol J. Sep. 2018;13(9):e1700596. doi: 10.1002/biot.201700596. Epub Jun. 19, 2018.

Arbab et al., Cloning-free CRISPR. Stem Cell Reports. Nov. 10, 2015;5(5):908-917. doi: 10.1016/j.stemcr.2015.09.022. Epub Oct. 29, 2015.

Arbab et al., Determinants of Base Editing Outcomes from Target Library Analysis and Machine Learning. Cell. Jul. 23, 2020;182(2):463-480.e30. doi: 10.1016/j.cell.2020.05.037. Epub Jun. 12, 2020.

Arezi et al., Novel mutations in Moloney Murine Leukemia Virus reverse transcriptase increase thermostability through tighter binding to template-primer. Nucleic Acids Res. Feb. 2009;37(2):473-81. doi: 10.1093/nar/gkn952. Epub Dec. 4, 2008.

Arnold et al., Mutants of Tn3 resolvase which do not require accessory binding sites for recombination activity. Embo J. Mar. 1, 1999;18(5):1407-14.

Asante et al., a naturally occurring variant of the human prion protein completely prevents prion disease. Nature. Jun. 25, 2015;522(7557):478-81. doi: 10.1038/nature14510. Epub Jun. 10, 2015.

Atkins et al., Ribosomal frameshifting and transcriptional slippage: From genetic steganography and cryptography to adventitious use. Nucleic Acids Res. Sep. 6, 2016;44(15):7007-78. doi: 10.1093/nar/gkw530. Epub Jul. 19, 2016.

Auer et al., Highly efficient CRISPR/Cas9-mediated knock-in in zebrafish by homology-independent DNA repair. Genome Res. Jan. 2014;24(1):142-53. doi: 10.1101/gr.161638.113. Epub Oct. 31, 2013.

Autieri et al., IRT-1, a novel interferon-gamma-responsive transcript encoding a growth-suppressing basic leucine zipper protein. J Biol Chem. Jun. 12, 1998;273(24):14731-7. doi: 10.1074/jbc.273.24.14731.

Avidan et al., The processivity and fidelity of DNA synthesis exhibited by the reverse transcriptase of bovine leukemia virus. Eur J Biochem. Feb. 2002;269(3):859-67. doi: 10.1046/j.0014-2956.2001.02719.x.

Babacic et al., CRISPR-cas gene-editing as plausible treatment of neuromuscular and nucleotide-repeat-expansion diseases: A systematic review. PLoS One. Feb. 22, 2019;14(2):e0212198. doi: 10.1371/journal.pone.0212198.

Bacman et al., Specific elimination of mutant mitochondrial genomes in patient-derived cells by mitoTALENs. Nat Med. Sep. 2013;19(9):1111-3. doi: 10.1038/nm.3261. Epub Aug. 4, 2013.

Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Bae et al., Microhomology-based choice of Cas9 nuclease target sites. Nat Methods. Jul. 2014;11(7):705-6. doi: 10.1038/nmeth.3015.
Bagyinszky et al., Characterization of mutations in PRNP (prion) gene and their possible roles in neurodegenerative diseases. Neuropsychiatr Dis Treat. Aug. 14, 2018;14:2067-2085. doi: 10.2147/NDT.S165445.
Balakrishnan et al., Flap endonuclease 1. Annu Rev Biochem. 2013;82:119-38. doi: 10.1146/annurev-biochem-072511-122603. Epub Feb. 28, 2013.
Baldari et al., A novel leader peptide which allows efficient secretion of a fragment of human interleukin 1 beta in *Saccharomyces cerevisiae*. EMBO J. Jan. 1987;6(1):229-34.
Banerjee et al., Cadmium inhibits mismatch repair by blocking the ATPase activity of the MSH2-MSH6 complex [published correction appears in Nucleic Acids Res. 2005;33(5):1738]. Nucleic Acids Res. 2005;33(4):1410-1419. Published Mar. 3, 2005. doi:10.1093/nar/gki291.
Banerji et al., A lymphocyte-specific cellular enhancer is located downstream of the joining region in immunoglobulin heavy chain genes. Cell. Jul. 1983;33(3):729-40. doi: 10.1016/0092-8674(83)90015-6.
Bannert et al., Retroelements and the human genome: new perspectives on an old relation. Proc Natl Acad Sci U S A. Oct. 5, 2004;101 Suppl 2(Suppl 2):14572-9. doi: 10.1073/pnas.0404838101. Epub Aug. 13, 2004.
Baranauskas et al., Generation and characterization of new highly thermostable and processive M-MuLV reverse transcriptase variants. Protein Eng Des Sel. Oct. 2012;25(10):657-68. doi: 10.1093/protein/gzs034. Epub Jun. 12, 2012.
Barnes et al., Repair and genetic consequences of endogenous DNA base damage in mammalian cells. Annu Rev Genet. 2004;38:445-76.
Barnes et al., The fidelity of Taq polymerase catalyzing PCR is improved by an N-terminal deletion. Gene. Mar. 1, 1992;112(1):29-35. doi: 10.1016/0378-1119(92)90299-5.

(56) References Cited

OTHER PUBLICATIONS

Barrangou et al., CRISPR provides acquired resistance against viruses in prokaryotes. Science. Mar. 23, 2007;315(5819):1709-12.
Barrangou, RNA-mediated programmable DNA cleavage. Nat Biotechnol. Sep. 2012;30(9):836-8. doi: 10.1038/nbt.2357.
Bartlett et al., Efficient expression of protein coding genes from the murine U1 small nuclear RNA promoters. Proc Natl Acad Sci U S A. Aug. 20, 1996;93(17):8852-7. doi: 10.1073/pnas.93.17.8852.
Bartosovic et al., N6-methyladenosine demethylase FTO targets pre-mRNAs and regulates alternative splicing and 3'-end processing. Nucleic Acids Res. Nov. 2, 2017;45(19):11356-11370. doi: 10.1093/nar/gkx778.
Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.
Basturea et al., Substrate specificity and properties of the *Escherichia coli* 16S rRNA methyltransferase, RsmE. RNA. Nov. 2007;13(11):1969-76. doi: 10.1261/rna.700507. Epub Sep. 13, 2007.
Batey et al., Structure of a natural guanine-responsive riboswitch complexed with the metabolite hypoxanthine. Nature. Nov. 18, 2004;432(7015):411-5.
Beale et al., Comparison of the differential context-dependence of DNA deamination by Apobec enzymes: correlation with mutation spectra in vivo. J Mol Biol. Mar. 26, 2004;337(3):585-96.
Bebenek et al., Error-prone polymerization by HIV-1 reverse transcriptase. Contribution of template-primer misalignment, miscoding, and termination probability to mutational hot spots. J Biol Chem. May 15, 1993;268(14):10324-34.
Bedell et al., In vivo genome editing using a high-efficiency TALEN system. Nature. Nov. 1, 2012;491(7422):114-8. Doi: 10.1038/nature11537. Epub Sep. 23, 2012.
Begley, Scientists unveil the 'most clever CRISPR gadget' so far. STAT, Apr. 20, 2016. haps://www.statnews.com/2016/04/20/clever-crispr-advance-unveiled/.
Behr, Gene transfer with synthetic cationic amphiphiles: prospects for gene therapy. Bioconjug Chem. Sep.-Oct. 1994;5(5):382-9. doi: 10.1021/bc00029a002.
Belshaw et al., Controlling programmed cell death with a cyclophilin-cyclosporin-based chemical inducer of dimerization. Chem Biol. Sep. 1996;3(9):731-8. doi: 10.1016/s1074-5521(96)90249-5.
Belshaw et al., Controlling protein association and subcellular localization with a synthetic ligand that induces heterodimerization of proteins. Proc Natl Acad Sci U S A. May 14, 1996;93(10):4604-7. doi: 10.1073/pnas.93.10.4604.
Bennett et al., Painful and painless channelopathies. Lancet Neurol. Jun. 2014;13(6):587-99. doi: 10.1016/S1474-4422(14)70024-9. Epub May 6, 2014.
Berger et al., Reverse transcriptase and its associated ribonuclease H: interplay of two enzyme activities controls the yield of single-stranded complementary deoxyribonucleic acid. Biochemistry. May 10, 1983;22(10):2365-72. doi: 10.1021/bi00279a010.
Berkhout et al., Identification of an active reverse transcriptase enzyme encoded by a human endogenous HERV-K retrovirus. J Virol. Mar. 1999;73(3):2365-75. doi: 10.1128/JVI.73.3.2365-2375. 1999.
Bernhart et al., Local RNA base pairing probabilities in large sequences. Bioinformatics. Mar. 1, 2006;22(5):614-5. doi: 10.1093/bioinformatics/btk014. Epub Dec. 20, 2005.
Bernstein et al., Role for a bidentate ribonuclease in the initiation step of RNA interference. Nature. Jan. 18, 2001;409(6818):363-6. doi: 10.1038/35053110.
Bershtein et al., Advances in laboratory evolution of enzymes. Curr Opin; Chem Biol. Apr. 2008;12(2):151-8. doi: 10.1016/j.cbpa.2008. 01.027. Epub Mar. 7, 2008. Review.
Bertolotti et al., Toward genosafe endonuclease-boosted gene targeting using breakthrough CRISP/Cas9 for next generation stem cell gene therapy culminating in efficient ex Vivo in Vivo gene repair/genomic editing. Molecular Therapy. May 2015;23(Suppl1):S139.
Abstract 350. 18th Ann Meeting of the American Society of Gene and Cell Therapy. ASGCT 2015. New Orleans, LA. May 13, 2015-May 16, 2015.
Bertrand et al., Localization of ASH1 mRNA particles in living yeast. Mol Cell. Oct. 1998;2(4):437-45. doi: 10.1016/s1097-2765(00)80143-4.
Beumer et al., Efficient gene targeting in *Drosophila* with zinc-finger nucleases. Genetics. Apr. 2006;172(4):2391-403. Epub Feb. 1, 2006.
Bi et al., Pseudo attP sites in favor of transgene integration and expression in cultured porcine cells identified by Streptomyces phage phiC31 integrase. BMC Mol Biol. Sep. 8, 2013;14:20. doi: 10.1186/1471-2199-14-20.
Bibb et al., Integration and excision by the large serine recombinase phiRv1 integrase. Mol Microbiol. Mar. 2005;55(6):1896-910. doi: 10.1111/j.1365-2958.2005.04517.x.
Biehs et al., DNA Double-Strand Break Resection Occurs during Non-homologous End Joining in G1 but Is Distinct from Resection during Homologous Recombination. Mol Cell. Feb. 16, 2017;65(4):671-684.e5. doi: 10.1016/j.molcel.2016.12.016. Epub Jan. 26, 2017.
Billon et al., CRISPR-Mediated Base Editing Enables Efficient Disruption of Eukaryotic Genes through Induction of STOP Codons. Mol Cell. Sep. 21, 2017;67(6):1068-1079.e4. doi: 10.1016/j.molcel. 2017.08.008. Epub Sep. 7, 2017.
Birling et al., Site-specific recombinases for manipulation of the mouse genome. Methods Mol Biol. 2009;561:245-63. doi: 10.1007/978-1-60327-019-9_16.
Biswas et al., A structural basis for allosteric control of DNA recombination by lambda integrase. Nature. Jun. 23, 2005;435(7045):1059-66. doi: 10.1038/nature03657.
Bitinaite et al., FokI dimerization is required for DNA cleavage. Proc Natl Acad Sci U S A. Sep. 1, 1998;95(18):10570-5.
Blaese et al., Vectors in cancer therapy: how will they deliver? Cancer Gene Ther. Dec. 1995;2(4):291-7.
Blain et al., Nuclease activities of Moloney murine leukemia virus reverse transcriptase. Mutants with altered substrate specificities. J Biol Chem. Nov. 5, 1993;268(31):23585-92.
Blaisonneau et al., A circular plasmid from the yeast *Torulaspora delbrueckii*. Plasmid. 1997;38(3):202-9. doi: 10.1006/plas.1997. 1315.
Blau et al., A proliferation switch for genetically?modified?cells. PNAS Apr. 1, 1997 94 (7) 3076-3081; https://doi.org/10.1073/pnas. 94.7.3076.
Bloom et al., Evolving strategies for enzyme engineering. Curr Opin Struct Biol. Aug. 2005;15(4):447-52.
Boch, TALEs of genome targeting. Nat Biotechnol. Feb. 2011;29(2):135-6. Doi: 10.1038/nbt.1767.
Böck et al., Selenocysteine: the 21st amino acid. Mol Microbiol. Mar. 1991;5(3):515-20.
Bodi et al., Yeast m6A Methylated mRNAs Are Enriched on Translating Ribosomes during Meiosis, and under Rapamycin Treatment. PLoS One. Jul. 17, 2015;10(7):e0132090. doi: 10.1371/journal. pone.0132090.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Boersma et al., Selection strategies for improved biocatalysts. FEBS J. May 2007;274(9):2181-95.
Bogdanove et al., Engineering altered protein-DNA recognition specificity. Nucleic Acids Res. Jun. 1, 2018;46(10):4845-4871. doi: 10.1093/nar/gky289.
Bogdanove et al., TAL effectors: customizable proteins for DNA targeting. Science. Sep. 30, 2011;333(6051):1843-6. doi: 10.1126/science.1204094.
Bohlke et al., Sense codon emancipation for proteome-wide incorporation of noncanonical amino acids: rare isoleucine codon AUA as a target for genetic code expansion. FEMS Microbiol Lett. Feb. 2014;351(2):133-44. doi: 10.1111/1574-6968.12371. Epub Jan. 27, 2014.
Bolotin et al., Clustered regularly interspaced short palindrome repeats (CRISPRs) have spacers of extrachromosomal origin. Microbiology. Aug. 2005;151(Pt 8):2551-61.

(56) References Cited

OTHER PUBLICATIONS

Bolusani et al., Evolution of variants of yeast site-specific recombinase Flp that utilize native genomic sequences as recombination target sites. Nucleic Acids Res. 2006;34(18):5259-69. Epub Sep. 26, 2006.
Bondeson et al., Inversion of the IDS gene resulting from recombination with IDS-related sequences is a common cause of the Hunter syndrome. Hum Mol Genet. Apr. 1995;4(4):615-21. doi: 10.1093/hmg/4.4.615.
Borchardt et al., Controlling mRNA stability and translation with the CRISPR endoribonuclease Csy4. RNA. Nov. 2015;21(11):1921-30. doi: 10.1261/rna.051227.115. Epub Sep. 9, 2015.
Borman, Improved route to single-base genome editing. Chemical & Engineering News, Apr. 25, 2016;94(17)p5. http://cen.acs.org/articles/94/i17/Improved-route-single-base-genome.html.
Boutabout et al., DNA synthesis fidelity by the reverse transcriptase of the yeast retrotransposon Ty1. Nucleic Acids Res. Jun. 1, 2001;29(11):2217-22. doi: 10.1093/nar/29.11.2217.
Box et al., A multi-domain protein system based on the HC fragment of tetanus toxin for targeting DNA to neuronal cells. J Drug Target. Jul. 2003;11(6):333-43. doi: 10.1080/10611863100016346677.
Branden and Tooze, Introduction to Protein Structure. 1999; 2nd edition. Garland Science Publisher: Mar. 2012.
Braun et al., Immunogenic duplex nucleic acids are nuclease resistant. J Immunol. Sep. 15, 1988;141(6):2084-9.
Briner et al., Guide RNA functional modules direct Cas9 activity and orthogonality. Mol Cell. Oct. 23, 2014;56(2):333-339. doi: 10.1016/j.molcel.2014.09.019.
Britt et al., Re-engineering plant gene targeting. Trends Plant Sci. Feb. 2003;8(2):90-5.
Brouns et al., Small CRISPR RNAs guide antiviral defense in prokaryotes. Science. Aug. 15, 2008;321(5891):960-4. doi: 10.1126/science.1159689.
Brown et al., Serine recombinases as tools for genome engineering. Methods. Apr. 2011;53(4):372-9. doi: 10.1016/j.ymeth.2010.12.031. Epub Dec. 30, 2010.
Brown et al., A mammalian protein targeted by G1-arresting rapamycin-receptor complex. Nature. Jun. 30, 1994;369(6483):756-8. doi: 10.1038/369756a0.
Brown et al., Characterization of the genetic elements required for site-specific integration of plasmid pSE211 in *Saccharopolyspora erythraea*. J Bacteriol. Apr. 1990;172(4):1877-88. doi: 10.1128/jb.172.4.1877-1888.1990.
Brown et al., Structural insights into the stabilization of MALAT1 noncoding RNA by a bipartite triple helix. Nat Struct Mol Biol. Jul. 2014;21(7):633-40. doi: 10.1038/nsmb.2844. Epub Jun. 22, 2014.
Brusse et al., Spinocerebellar ataxia associated with a mutation in the fibroblast growth factor 14 gene (SCA27): A new phenotype. Mov Disord. Mar. 2006;21(3):396-401.
Brzezicha et al., Identification of human tRNA:m5C methyltransferase catalysing intron-dependent m5C formation in the first position of the anticodon of the pre-tRNA Leu (CAA). Nucleic Acids Res. 2006;34(20):6034-43. doi: 10.1093/nar/gk1765. Epub Oct. 27, 2006.
Buchholz et al., Alteration of Cre recombinase site specificity by substrate-linked protein evolution. Nat Biotechnol. Nov. 2001;19(11):1047-52.
Buchschacher et al., Human immunodeficiency virus vectors for inducible expression of foreign genes. J Virol. May 1992;66(5):2731-9. doi: 10.1128/JVI.66.5.2731-2739.1992.
Buchwald et al., Long-term, continuous intravenous heparin administration by an implantable infusion pump in ambulatory patients with recurrent venous thrombosis. Surgery. Oct. 1980;88(4):507-16.
Buckley et al., Targeting the von Hippel-Lindau E3 ubiquitin ligase using small molecules to disrupt the VHL/HIF-1? interaction. J Am Chem Soc. Mar. 14, 2012;134(10):4465-8. doi: 10.1021/ja209924v. Epub Feb. 27, 2012.
Budisa et al., Residue-specific bioincorporation of non-natural, biologically active amino acids into proteins as possible drug carriers: structure and stability of the per-thiaproline mutant of annexin V. Proc Natl Acad Sci U S A. Jan. 20, 1998;95(2):455-9.

Budker et al., Protein/amphipathic polyamine complexes enable highly efficient transfection with minimal toxicity. Biotechniques. Jul. 1997;23(1):139, 142-7. doi: 10.2144/97231rr02.
Budworth et al., A brief history of triplet repeat diseases. Methods Mol Biol. 2013;1010:3-17. doi: 10.1007/978-1-62703-411-1_1.
Bulow et al., Multienzyme systems obtained by gene fusion. Trends Biotechnol. Jul. 1991;9(7):226-31.
Burke et al., RNA Aptamers to the Adenosine Moiety of S-adenosyl Methionine: Structural Inferences From Variations on a Theme and the Reproducibility of SELEX. Nucleic Acids Res. May 15, 1997;25(10):2020-4. doi: 10.1093/nar/25.10.2020.
Burstein et al., New CRISPR-Cas systems from uncultivated microbes. Nature Feb. 2017;542(7640):237-240.
Buskirk et al., Directed evolution of ligand dependence: small-molecule-activated protein splicing. Proc Natl Acad Sci U S A. Jul. 20, 2004;101(29):10505-10. Epub Jul. 9, 2004.
Byrne et al., Multiplex gene regulation: a two-tiered approach to transgene regulation in transgenic mice. Proc Natl Acad Sci U S A. Jul. 1989;86(14):5473-7. doi: 10.1073/pnas.86.14.5473.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Cadwell et al., Randomization of genes by PCR mutagenesis. PCR Methods Appl. Aug. 1992;2(1):28-33. doi: 10.1101/gr.2.1.28.
Cai et al., Reconstruction of ancestral protein sequences and its applications. BMC Evol Biol. Sep. 17, 2004;4:33. doi: 10.1186/1471-2148-4-33.
Calame et al., Transcriptional controlling elements in the immunoglobulin and T cell receptor loci. Adv Immunol. 1988;43:235-75. doi: 10.1016/s0065-2776(08)60367-3.
Caldecott et al., Single-strand break repair and genetic disease. Nat Rev Genet. Aug. 2008;9(8):619-31. doi: 10.1038/nrg2380.
Camarero et al., Biosynthesis of a Head-to-Tail Cyclized Protein with Improved Biological Activity. J. Am. Chem. Soc. May 29, 1999; 121(23):5597-5598. https://doi.org/10.1021/ja990929n.
Cameron, Recent advances in transgenic technology. Mol Biotechnol. Jun. 1997;7(3):253-65.
Camper et al., Postnatal repression of the alpha-fetoprotein gene is enhancer independent. Genes Dev. Apr. 1989;3(4):537-46. doi: 10.1101/gad.3.4.537.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Canchaya et al., Genome analysis of an inducible prophage and prophage remnants integrated in the *Streptococcus pyogenes* strain SF370. Virology. Oct. 25, 2002;302(2):245-58. doi: 10.1006/viro.2002.1570.
Canver et al., Customizing the genome as therapy for the ?-hemoglobinopathies. Blood. May 26, 2016;127(21):2536-45. doi: 10.1182/blood-2016-01-678128. Epub Apr. 6, 2016.
Cargill et al.,Characterization of single-nucleotide polymorphisms in coding regions of human genes. Nat Genet. Jul. 1999;22(3):231-8.
Carlier et al., Burkholderia cenocepacia H111 Rhy-family protein. Apr. 16, 2015. Retrieved from the Internet via https://www.ebi.ac.uk/ena/browser/api/embl/CDN65395.1?lineLimit=1000. Last retrieved Apr. 26, 2021.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Caron et al., Intracellular delivery of a Tat-eGFP fusion protein into muscle cells. Mol Ther. Mar. 2001;3(3):310-8.
Carr et al., Genome engineering. Nat Biotechnol. Dec. 2009;27(12):1151-62. doi: 10.1038/nbt.1590.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.

(56) References Cited

OTHER PUBLICATIONS

Carroll, A CRISPR approach to gene targeting. Mol Ther. Sep. 2012;20(9):1658-60. doi: 10.1038/mt.2012.171.

Carroll, Genome engineering with zinc-finger nucleases. Genetics. Aug. 2011;188(4):773-82. doi: 10.1534/genetics.111.131433. Review.

Carvalho et al., Evolution in health and medicine Sackler colloquium: Genomic disorders: a window into human gene and genome evolution. Proc Natl Acad Sci U S A. Jan. 26, 2010;107 Suppl 1(Suppl 1):1765-71. doi: 10.1073/pnas.0906222107. Epub Jan. 13, 2010.

Caspi et al., Distribution of split DnaE inteins in cyanobacteria. Mol Microbiol. Dec. 2003;50(5):1569-77. doi: 10.1046/j.1365-2958.2003.03825.x.

Cattaneo et al., SEL1L affects human pancreatic cancer cell cycle and invasiveness through modulation of PTEN and genes related to cell-matrix interactions. Neoplasia. 2005;7(11):1030-1038.

Ceccaldi et al., Repair Pathway Choices and Consequences at the Double-Strand Break. Trends Cell Biol. Jan. 2016;26(1):52-64. doi: 10.1016/j.tcb.2015.07.009. Epub Oct. 1, 2015.

Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.

Chadalavada et al., Wild-type is the optimal sequence of the HDV ribozyme under cotranscriptional conditions. RNA. Dec. 2007;13(12):2189-201. doi: 10.1261/rna.778107. Epub Oct. 23, 2007.

Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117.309881. Epub Jul. 27, 2017.

Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.

Chalberg et al., Integration specificity of phage phiC31 integrase in the human genome. J Mol Biol. Mar. 17, 2006;357(1):28-48. doi: 10.1016/j.jmb.2005.11.098. Epub Dec. 22, 2005.

Chalberg et al., phiC31 integrase confers genomic integration and long-term transgene expression in rat retina. Invest Ophthalmol Vis Sci. Jun. 2005;46(6):2140-6. doi: 10.1167/iovs.04-1252.

Chan et al., Molecular recording of mammalian embryogenesis. Nature. Jun. 2019;570(7759):77-82. doi: 10.1038/s41586-019-1184-5. Epub May 13, 2019.

Chapman et al., Playing the end game: DNA double-strand break repair pathway choice. Mol Cell. Aug. 24, 2012;47(4):497-510. doi: 10.1016/j.molcel.2012.07.029.

Charpentier et al., Biotechnology: Rewriting a genome. Nature. Mar. 7, 2013;495(7439):50-1. doi: 10.1038/495050a.

Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.

Chavez et al., Highly efficient Cas9-mediated transcriptional programming. Nat Methods. Apr. 2015;12(4):326-8. doi: 10.1038/nmeth.3312. Epub Mar. 2, 2015.

Chavez et al., Precise Cas9 targeting enables genomic mutation prevention. bioRxiv. Jun. 14, 2016; http://dx/doi.oreg/10.1101/058974. 6 pages.

Chavez et al., Precise Cas9 targeting enables genomic mutation prevention. Jun. 14, 2016. doi:https://doi.org/10.1101/058974. [Preprint].

Chavez et al., Precise Cas9 targeting enables genomic mutation prevention. Proc Natl Acad Sci U S A. Apr. 3, 2018;115(14):3669-3673. doi: 10.1073/pnas.1718148115. Epub Mar. 19, 2018.

Chavez et al., Therapeutic applications of the PhiC31 integrase system. Curr Gene Ther. Oct. 2011;11(5):375-81. Review.

Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 13, 2009.

Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.

Chen et al., Enhanced proofreading governs CRISPR-Cas9 targeting accuracy. Nature. Oct. 19, 2017;550(7676):407-410. doi: 10.1038/nature24268. Epub Sep. 20, 2017.

Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.

Chen et al., Highly Efficient Mouse Genome Editing by CRISPR Ribonucleoprotein Electroporation of Zygotes. J Biol Chem. Jul. 8, 2016;291(28):14457-67. doi: 10.1074/jbc.M116.733154. Epub May 5, 2016.

Chen et al., m(6)a RNA methylation is regulated by microRNAs and promotes reprogramming to pluripotency. Cell Stem Cell. Mar. 5, 2015;16(3):289-301. doi: 10.1016/j.stem.2015.01.016. Epub Feb. 12, 2015.

Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.

Chesnoy et al., Structure and function of lipid-DNA complexes for gene delivery. Annu Rev Biophys Biomol Struct. 2000;29:27-47.

Chew et al., A multifunctional AAV-CRISPR-Cas9 and its host response. Nat Methods. Oct. 2016;13(10):868-74. doi: 10.1038/nmeth.3993. Epub Sep. 5, 2016.

Chew et al., A multifunctional AAV-CRISPR-Cas9 and its host response. Nat Methods. Oct. 2016;13(10):868-74. doi: 10.1038/nmeth.3993. Epub Sep. 5, 2016. Supplementary Information.

Chichili et al., Linkers in the structural biology of protein-protein interactions. Protein Science. 2013;22:153-67.

Chin, Expanding and reprogramming the genetic code of cells and animals. Annu Rev Biochem. 2014;83:379-408. doi: 10.1146/annurev-biochem-060713-035737. Epub Feb. 2014.

Chipev et al., A leucine—proline mutation in the H1 subdomain of keratin 1 causes epidermolytic hyperkeratosis. Cell. Sep. 4, 1992;70(5):821-8.

Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.

Cho et al., Site-specific recombination of bacteriophage P22 does not require integration host factor. J Bacteriol. Jul. 1999;181(14):4245-9. doi: 10.1128/JB.181.14.4245-4249.1999.

Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.

Choe et al., Forging Ahead through Darkness: PCNA, Still the Principal Conductor at the Replication Fork. Mol Cell. Feb. 2, 2017;65(3):380-392. doi: 10.1016/j.molcel.2016.12.020.

Choi et al., N(6)-methyladenosine in mRNA disrupts tRNA selection and translation-elongation dynamics. Nat Struct Mol Biol. Feb. 2016;23(2):110-5. doi: 10.1038/nsmb.3148. Epub Jan. 2016.

Choi et al., Protein trans-splicing and characterization of a split family B-type DNA polymerase from the hyperthermophilic archaeal parasite Nanoarchaeum equitans. J Mol Biol. Mar. 10, 2006;356(5):1093-106. doi: 10.1016/j.jmb.2005.12.036. Epub Dec. 27, 2005.

Chong et al., Modulation of protein splicing of the *Saccharomyces cerevisiae* vacuolar membrane ATPase intein. J Biol Chem. Apr. 24, 1998;273(17):10567-77. doi: 10.1074/jbc.273.17.10567.

Chong et al., Utilizing the C-terminal cleavage activity of a protein splicing element to purify recombinant proteins in a single chromatographic step. Nucleic Acids Res. Nov. 15, 1998;26(22):5109-15. doi: 10.1093/nar/26.22.5109.

Chong et al., Protein splicing involving the *Saccharomyces cerevisiae* VMA intein. The steps in the splicing pathway, side reactions leading to protein cleavage, and establishment of an in vitro splicing system. J Biol Chem. Sep. 6, 1996;271(36):22159-68. doi: 10.1074/jbc.271.36.22159.

(56) References Cited

OTHER PUBLICATIONS

Chong et al., Protein splicing of the *Saccharomyces cerevisiae* VMA intein without the endonuclease motifs. J Biol Chem. Jun. 20, 1997;272(25):15587-90. doi: 10.1074/jbc.272.25.15587.
Chong et al., Single-column purification of free recombinant proteins using a self-cleavable affinity tag derived from a protein splicing element. Gene. Jun. 19, 1997;192(2):271-81. doi: 10.1016/s0378-1119(97)00105-4.
Choudhury et al., Engineering RNA endonucleases with customized sequence specificities. Nat Commun. 2012;3:1147. doi: 10.1038/ncomms2154.
Choulika et al., Induction of homologous recombination in mammalian chromosomes by using the I-SceI system of *Saccharomyces cerevisiae*. Mol Cell Biol. Apr. 1995;15(4):1968-73. doi: 10.1128/MCB.15.4.1968.
Christian et al, Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.
Christian et al., Targeting DNA double-strand breaks with TAL effector nucleases. Genetics. Oct. 2010;186(2):757-61. Doi: 10.1534/genetics.110.120717. Epub Jul. 26, 2010.
Christiansen et al., Characterization of the lactococcal temperate phage TP901-1 and its site-specific integration. J Bacteriol. Feb. 1994;176(4):1069-76. doi: 10.1128/jb.176.4.1069-1076.1994.
Chu et al., Increasing the efficiency of homology-directed repair for CRISPR-Cas9-induced precise gene editing in mammalian cells. Nat Biotech. Feb. 13, 2015;33:543-8.
Chuai et al., DeepCRISPR: optimized CRISPR guide RNA design by deep learning. Genome Biol. Jun. 26, 2018;19(1):80. doi: 10.1186/s13059-018-1459-4.
Chuai et al., In Silico Meets in Vivo: Towards Computational CRISPR-Based sgRNA Design. Trends Biotechnol. Jan. 2017;35(1):12-21. doi: 10.1016/j.tibtech.2016.06.008. Epub Jul. 11, 2016.
Chuang et al., Novel Heterotypic Rox Sites for Combinatorial Dre Recombination Strategies. G3 (Bethesda). Dec. 29, 2015;6(3):559-71. doi: 10.1534/g3.115.025841.
Chujo et al, Trmt61B is a methyltransferase responsible for 1-methyladenosine at position 58 of human mitochondrial tRNAs. RNA. Dec. 2012;18(12):2269-76. doi: 10.1261/rna.035600.112. Epub Oct. 24, 2012.
Chung-Il et al., Artificial control of gene expression in mammalian cells by modulating RNA interference through aptamer-small molecule interaction. RNA. May 2006;12(5):710-6. Epub Apr. 10, 2006.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Clackson et al., Redesigning an FKBP-ligand interface to generate chemical dimerizers with novel specificity. Proc Natl Acad Sci U S A. Sep. 1, 1998;95(18):10437-42. doi: 10.1073/pnas.95.18.10437.
Clement et al., CRISPResso2 provides accurate and rapid genome editing sequence analysis. Nat Biotechnol. Mar. 2019;37(3):224-226. doi: 10.1038/s41587-019-0032-3.
Cobb et al., Directed evolution as a powerful synthetic biology tool. Methods. Mar. 15, 2013;60(1):81-90. doi: 10.1016/j.ymeth.2012.03.009. Epub Mar. 23, 2012.
Cokol et al., Finding nuclear localization signals. EMBO Rep. Nov. 2000;1(5):411-5. doi: 10.1093/embo-reports/kvd092.
Cole et al., Reconstructing evolutionary adaptive paths for protein engineering. Methods Mol Biol. 2013;978:115-25. doi: 10.1007/978-1-62703-293-3_8.
Cole-Strauss et al., Correction of the mutation responsible for sickle cell anemia by an RNA-DNA oligonucleotide. Science. Sep. 6, 1996;273(5280):1386-9.
Collinge, Prion diseases of humans and animals: their causes and molecular basis. Annu Rev Neurosci. 2001;24:519-50. doi: 10.1146/annurev.neuro.24.1.519.

Cong et al., Multiplex genome engineering using CRISPR/Cas systems. Science. Feb. 15, 2013;339(6121):819-23. doi: 10.1126/science.1231143. Epub Jan. 3, 2013.
Conrad et al., A Kaposi's sarcoma virus RNA element that increases the nuclear abundance of intronless transcripts. EMBO J. May 18, 2005;24(10):1831-41. doi: 10.1038/sj.emboj.7600662. Epub Apr. 28, 2005.
Conticello, The AID/APOBEC family of nucleic acid mutators. Genome Biol. 2008;9(6):229. doi: 10.1186/gb-2008-9-6-229. Epub Jun. 17, 2008.
Cornu et al., Refining strategies to translate genome editing to the clinic. Nat Med. Apr. 3, 2017;23(4):415-423. doi: 10.1038/nm.4313.
Costa et al., Frequent use of the same tertiary motif by self-folding RNAs. EMBO J. Mar. 15, 1995;14(6):1276-85.
Cotton et al., Insertion of a Synthetic Peptide into a Recombinant Protein Framework:? A Protein Biosensor. J. Am. Chem. Soc. Jan. 22, 1999; 121(5):1100-1. https://doi.org/10.1021/ja983804b.
Covino et al., The CCL2/CCR2 Axis in the Pathogenesis of HIV-1 Infection: A New Cellular Target for Therapy? Current Drug Targets Dec. 2016;17(1):76-110. DOI: 10.2174/1389450117011512171109 17.
Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.
Cox et al., RNA editing with CRISPR-Cas13. Science. Nov. 24, 2017;358(6366):1019-1027. doi: 10.1126/science.aaq0180. Epub Oct. 25, 2017.
Cox et al., Therapeutic genome editing: prospects and challenges. Nat Med. Feb. 2015;21(2):121-31. doi: 10.1038/nm.3793.
Cox, Proteins pinpoint double strand breaks. Elife. Oct. 29, 2013;2:e01561. doi: 10.7554/eLife.01561.
Crabtree et al., Three-part inventions: intracellular signaling and induced proximity. Trends Biochem Sci. Nov. 1996;21(11):418-22. doi: 10.1016/s0968-0004(96)20027-1.
Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.
Cradick et al., ZFN-site searches genomes for zinc finger nuclease target sites and off-target sites. BMC Bioinformatics. May 13, 2011;12:152. doi: 10.1186/1471-2105-12-152.
Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.
Crick, On protein synthesis. Symp Soc Exp Biol. 1958;12:138-63.
Crystal, Transfer of genes to humans: early lessons and obstacles to success. Science. Oct. 20, 1995;270(5235):404-10. doi: 10.1126/science.270.5235.404.
Cui et al., Consequences of Cas9 cleavage in the chromosome of *Escherichia coli*. Nucleic Acids Res. May 19, 2016;44(9):4243-51. doi: 10.1093/nar/gkw223. Epub Apr. 8, 2016.
Cui et al., m6A RNA Methylation Regulates the Self-Renewal and Tumorigenesis of Glioblastoma Stem Cells. Cell Rep. Mar. 14, 2017;18(11):2622-2634. doi: 10.1016/j.celrep.2017.02.059.
Cui et al., Review of CRISPR/Cas9 sgRNA Design Tools. Interdiscip Sci. Jun. 2018;10(2):455-465. doi: 10.1007/s12539-018-0298-z. Epub Apr. 11, 2018.
Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.
Cunningham et al., Ensembl 2015. Nucleic Acids Res. Jan. 2015;43(Database issue):D662-9. doi: 10.1093/nar/gku1010. Epub Oct. 28, 2014.
Cupples et al., A set of lacZ mutations in *Escherichia coli* that allow rapid detection of each of the six base substitutions. Proc Natl Acad Sci U S A. Jul. 1989;86(14):5345-9.
D'Adda di Fagagna et al., The Gam protein of bacteriophage Mu is an orthologue of eukaryotic Ku. EMBO Rep. Jan. 2003;4(1):47-52.
Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.

(56) References Cited

OTHER PUBLICATIONS

Dahlgren et al., A novel mutation in ribosomal protein S4 that affects the function of a mutated RF1. Biochimie. Aug. 2000;82(8):683-91.

Dahlman et al., Orthogonal gene knockout and activation with a catalytically active Cas9 nuclease. Nat Biotechnol. Nov. 2015;33(11):1159-61. doi: 10.1038/nbt.3390.

Dandage et al., beditor: A Computational Workflow for Designing Libraries of Guide RNAs for CRISPR-Mediated Base Editing. Genetics. Jun. 2019;212(2):377-385. doi: 10.1534/genetics.119.302089. Epub Apr. 1, 2019.

Dang et al., Optimizing sgRNA structure to improve CRISPR-Cas9 knockout efficiency. Genome Biol. Dec. 15, 2015;16:280. doi: 10.1186/s13059-015-0846-3.

Das et al.,The crystal structure of the monomeric reverse transcriptase from Moloney murine leukemia virus. Structure. May 2004;12(5):819-29. doi: 10.1016/j.str.2004.02.032.

Dassa et al., Fractured genes: a novel genomic arrangement involving new split inteins and a new homing endonuclease family. Nucleic Acids Res. May 2009;37(8):2560-73. doi: 10.1093/nar/gkp095. Epub Mar. 5, 2009.

Dassa et al., Trans protein splicing of cyanobacterial split inteins in endogenous and exogenous combinations. Biochemistry. Jan. 9, 2007;46(1):322-30. doi: 10.1021/bi0611762.

Datsenko et al., One-step inactivation of chromosomal genes in *Escherichia coli* K-12 using PCR products. Proc Natl Acad Sci U S A. Jun. 6, 2000;97(12):6640-5.

Davis et al., DNA double strand break repair via non-homologous end-joining. Transl Cancer Res. Jun. 2013;2(3):130-143.

Davis et al., Small molecule-triggered Cas9 protein with improved genome-editing specificity. Nat Chem Biol. May 2015;11(5):316-8. doi: 10.1038/nchembio.1793. Epub Apr. 6, 2015.

De Felipe et al., Co-translational, intraribosomal cleavage of polypeptides by the foot-and-mouth disease virus 2A peptide. J Biol Chem. Mar. 28, 2003;278(13):11441-8. doi: 10.1074/jbc.M211644200. Epub Jan. 8, 2003.

De Souza, Primer: genome editing with engineered nucleases. Nat Methods. Jan. 2012;9(1):27.

De Wit et al., the Human CD4+ T Cell Response against Mumps Virus Targets a Broadly Recognized Nucleoprotein Epitope. J Virol. Mar. 5, 2019;93(6):e01883-18. doi: 10.1128/JVI.01883-18.

Dean et al., Genetic restriction of HIV-1 infection and progression to AIDS by a deletion allele of the CKR5 structural gene. Hemophilia Growth and Development Study, Multicenter AIDS Cohort Study, Multicenter Hemophilia Cohort Study, San Francisco City Cohort, ALIVE Study. Science. Sep. 27, 1996;273(5283):1856-62. doi: 10.1126/science.273.5283.1856.

DeKosky et al., Large-scale sequence and structural comparisons of human naive and antigen-experienced antibody repertoires. Proc Natl Acad Sci U S A. May 10, 2016;113(19):E2636-45. doi: 10.1073/pnas.1525510113. Epub Apr. 25, 2016.

Delebecque et al., Organization of intracellular reactions with rationally designed RNA assemblies. Science. Jul. 22, 2011;333(6041):470-4. doi: 10.1126/science.1206938. Epub Jun. 23, 2011.

Deltcheva et al., CRISPR RNA maturation by trans-encoded small RNA and host factor RNase III. Nature. Mar. 31, 2011;471(7340):602-7. doi: 10.1038/nature09886.

Deng et al., Widespread occurrence of N6-methyladenosine in bacterial mRNA. Nucleic Acids Res. Jul. 27, 2015;43(13):6557-67. doi: 10.1093/nar/gkv596. Epub Jun. 11, 2015.

Deriano et al., Modernizing the nonhomologous end-joining repertoire: alternative and classical NHEJ share the stage. Annu Rev Genet. 2013;47:433-55. doi: 10.1146/annurev-genet-110711-155540. Epub Sep. 11, 2013.

Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.

Dever et al., CRISPR/Cas9 ?-globin gene targeting in human haematopoietic stem cells. Nature. Nov. 17, 2016;539(7629):384-389. doi: 10.1038/nature20134. Epub Nov. 7, 2016.

Dicarlo et al., Genome engineering in *Saccharomyces cerevisiae* using CRISPR-Cas systems. Nucleic Acids Research Apr. 2013;41(7):4336-43.

Dicarlo et al., Safeguarding CRISPR-Cas9 gene drives in yeast. Nat Biotechnol. Dec. 2015;33(12):1250-1255. doi: 10.1038/nbt.3412. Epub Nov. 16, 2015.

Dickey et al., Single-stranded DNA-binding proteins: multiple domains for multiple functions. Structure. Jul. 2, 2013;21(7):1074-84. doi: 10.1016/j.str.2013.05.013.

Dickinson et al., Experimental interrogation of the path dependence and stochasticity of protein evolution using phage-assisted continuous evolution. Proc Natl Acad Sci USA. May 2013;110(22):9007-12.

Dillon, Regulating gene expression in gene therapy. Trends Biotechnol. May 1993;11(5):167-73. doi: 10.1016/0167-7799(93)90109-M.

Ding et al., A TALEN genome-editing system for generating human stem cell-based disease models. Cell Stem Cell. Feb. 7, 2013;12(2):238-51. Doi: 10.1016/j.stem.2012.11.011. Epub Dec. 13, 2012.

Ding et al., Permanent alteration of PCSK9 with in vivo CRISPR-Cas9 genome editing. Circ Res. Aug. 15, 2014;115(5):488-92. doi: 10.1161/CIRCRESAHA.115.304351. Epub Jun. 10, 2014.

Dingwall et al., Nuclear targeting sequences—a consensus? Trends Biochem Sci. Dec. 1991;16(12):478-81. doi: 10.1016/0968-0004(91)90184-w.

Diver et al., Single-Step Synthesis of Cell-Permeable Protein Dimerizers That Activate Signal Transduction and Gene Expression. J. Am. Chem. Soc. Jun. 4, 1997;119(22):5106-5109. https://doi.org/10.1021/ja963891c.

Dixon et al., Reengineering orthogonally selective riboswitches. Proc Natl Acad Sci U S A. Feb. 16, 2010;107(7):2830-5. doi: 10.1073/pnas.0911209107. Epub Jan. 26, 2010.

Doench et al., Optimized sgRNA design to maximize activity and minimize off-target effects of CRISPR-Cas9. Nat Biotechnol. Feb. 2016;34(2):184-191. doi: 10.1038/nbt.3437.

Doman et al., Evaluation and minimization of Cas9-independent off-target DNA editing by cytosine base editors. Nat Biotechnol. May 2020;38(5):620-628. doi: 10.1038/s41587-020-0414-6. Epub Feb. 10, 2020.

Dominissini et al., Topology of the human and mouse m6A RNA methylomes revealed by m6A-seq. Nature. Apr. 29, 2012;485(7397):201-6. doi: 10.1038/nature11112.

Dorgan et al., An enzyme-coupled continuous spectrophotometric assay for S-adenosylmethionine-dependent methyltransferases. Anal Biochem. Mar. 15, 2006;350(2):249-55. doi: 10.1016/j.ab.2006.01.004. Epub Feb. 7, 2006.

Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.

Doudna et al., Genome editing. The new frontier of genome engineering with CRISPR-Cas9. Science. Nov. 28, 2014;346(6213):1258096. doi: 10.1126/science.1258096.

Dove et al., Conversion of the omega subunit of *Escherichia coli* RNA polymerase into a transcriptional activator or an activation target. Genes Dev. Mar. 1, 1998;12(5):745-54.

Doyon et al., Directed evolution and substrate specificity profile of homing endonuclease I-SceI. J Am Chem Soc. Feb. 22, 2006;128(7):2477-84.

Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.

Drake, A constant rate of spontaneous mutation in DNA-based microbes. Proc Natl Acad Sci U S A. Aug. 15, 1991;88(16):7160-4.

Dubois et al., Retroviral RNA Dimerization: From Structure to Functions. Front Microbiol. Mar. 22, 2018;9:527. doi: 10.3389/fmicb.2018.00527.

Dumas et al., Designing logical codon reassignment—Expanding the chemistry in biology. Chem Sci. Jan. 1, 2015;6(1):50-69. doi: 10.1039/c4sc01534g. Epub Jul. 14, 2014. Review.

(56) References Cited

OTHER PUBLICATIONS

Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.
Dunbar et al., Gene therapy comes of age. Science. Jan. 12, 2018;359(6372):eaan4672. doi: 10.1126/science.aan4672.
Dupuy et al., Le syndrome de De La Chapelle [De La Chapelle syndrome]. Presse Med. Mar. 3, 2001;30(8):369-72. French.
Durai et al., A bacterial one-hybrid selection system for interrogating zinc finger-DNA interactions. Comb Chem High Throughput Screen. May 2006;9(4):301-11.
Durai et al., Zinc finger nucleases: custom-designed molecular scissors for genome engineering of plant and mammalian cells. Nucleic Acids Res. Oct. 26, 2005;33(18):5978-90. doi: 10.1093/nar/gki912.
During et al., Controlled release of dopamine from a polymeric brain implant: in vivo characterization. Ann Neurol. Apr. 1989;25(4):351-6.
East-Seletsky et al., Two distinct RNase activities of CRISPR-C2c2 enable guide-RNA processing and RNA detection. Nature Oct. 2016;538(7624):270-3.
Edlund et al., Cell-specific expression of the rat insulin gene: evidence for role of two distinct 5' flanking elements. Science. Nov. 22, 1985;230(4728):912-6. doi: 10.1126/science.3904002.
Edwards et al., An *Escherichia coli* tyrosine transfer RNA is a leucine-specific transfer RNA in the yeast *Saccharomyces cerevisiae*. Proc Natl Acad Sci U S A. Feb. 15, 1991;88(4):1153-6.
Edwards et al., Crystal structures of the thi-box riboswitch bound to thiamine pyrophosphate analogs reveal adaptive RNA-small molecule recognition. Structure. Sep. 2006;14(9):1459-68.
Eick et al., Robustness of Reconstructed Ancestral Protein Functions to Statistical Uncertainty. Mol Biol Evol. Feb. 1, 2017;34(2):247-261. doi: 10.1093/molbev/msw223.
Eiler et al., Structural Basis for the Fast Self-Cleavage Reaction Catalyzed by the Twister Ribozyme. Proc Natl Acad Sci U S A. Sep. 9, 2014;111(36):13028-33. doi: 10.1073/pnas.1414571111. Epub Aug. 25, 2014.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Endo et al., Toward establishing an efficient and versatile gene targeting system in higher plants. Biocatalysis and Agricultural Biotechnology 2014;3,(1):2-6.
Engel et al., The emerging role of mRNA methylation in normal and pathological behavior. Genes Brain Behav. Mar. 2018;17(3):e12428. doi: 10.1111/gbb.12428. Epub Nov. 17, 2017.
Engelward et al., Base excision repair deficient mice lacking the Aag alkyladenine DNA glycosylase. Proc Natl Acad Sci U S A. Nov. 25, 1997;94(24):13087-92.
England, Unnatural amino acid mutagenesis: a precise tool for probing; protein structure and function. Biochemistry. Sep. 21, 2004;43(37):11623-9.
Enyeart et al., Biotechnological applications of mobile group II introns and their reverse transcriptases: gene targeting, RNA-seq, and non-coding RNA analysis. Mobile DNA 5, 2 (2014). https://doi.org/10.1186/1759-8753-5-2. https://doi.org/10.1186/1759-8753-5-2.
Eriksson et al., Recurrent de novo point mutations in lamin A cause Hutchinson-Gilford progeria syndrome. Nature. May 15, 2003;423(6937):293-8. doi: 10.1038/nature01629. Epub Apr. 25, 2003. PMID: 12714972.
Esvelt et al., A system for the continuous directed evolution of biomolecules. Nature. Apr. 28, 2011;472(7344):499-503. doi: 10.1038/nature09929. Epub Apr. 10, 2011.
Esvelt et al., Genome-scale engineering for systems and synthetic biology. Mol Syst Biol. 2013;9:641. doi: 10.1038/msb.2012.66.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.

Evans et al., Protein trans-splicing and cyclization by a naturally split intein from the dnaE. gene of *Synechocystis* species PCC6803. J Biol Chem. Mar. 31, 2000;275(13):9091-4. doi: 10.1074/jbc.275.13.9091.
Evans et al., Semisynthesis of cytotoxic proteins using a modified protein splicing element. Protein Sci. Nov. 1998;7(11):2256-64. doi: 10.1002/pro.5560071103.
Evans et al., The cyclization and polymerization of bacterially expressed proteins using modified self-splicing inteins. J Biol Chem. Jun. 25, 1999;274(26):18359-63. doi: 10.1074/jbc.274.26.18359.
Evans et al., The in vitro ligation of bacterially expressed proteins using an intein from Methanobacterium thermoautotrophicum. J Biol Chem. Feb. 12, 1999;274(7):3923-6. doi: 10.1074/jbc.274.7.3923.
Evers et al., CRISPR knockout screening outperforms shRNA and CRISPRi in identifying essential genes. Nat Biotechnol. Jun. 2016;34(6):631-3. doi: 10.1038/nbt.3536. Epub Apr. 25, 2016.
Extended European Search Report for EP 15830407.1, dated Mar. 2, 2018.
Fagerlund et al., The Cpf1 CRISPR-Cas protein expands genome-editing tools. Genome Biology Nov. 17, 2015;16:251. https://doi.org/10.1186/s13059-015-0824-9.
Falnes et al., DNA repair by bacterial AlkB proteins. Res Microbiol. Oct. 2003;154(8):531-8. doi: 10.1016/S0923-2508(03)00150-5.
Falnes et al., Repair of methyl lesions in DNA and RNA by oxidative demethylation. Neuroscience. Apr. 14, 2007;145(4):1222-32. doi: 10.1016/j.neuroscience.2006.11.018. Epub Dec. 18, 2006.
Fang et al., Synthetic Studies Towards Halichondrins: Synthesis of the Left Halves of Norhalichondrins and Homohalichondrins. Tetrahedron Letters 1992;33(12):1557-1560.
Farhood et al., Codelivery to mammalian cells of a transcriptional factor with cis-acting element using cationic liposomes. Anal Biochem. Feb. 10, 1995;225(1):89-93.
Fawcett et al., Transposable elements controlling I-R hybrid dysgenesis in *D. melanogaster* are similar to mammalian LINEs. Cell. Dec. 26, 1986;47(6):1007-15. doi: 10.1016/0092-8674(86)90815-9.
Feldstein et al., Two sequences participating in the autolytic processing of satellite tobacco ringspot virus complementary Rna. Gene. Oct. 15, 1989;82(1):53-61. doi: 10.1016/0378-1119(89)90029-2.
Felletti et al., Twister Ribozymes as Highly Versatile Expression Platforms for Artificial Riboswitches. Nat Commun. Sep. 27, 2016;7:12834. doi: 10.1038/ncomms12834.
Feng et al., Crystal structures of the human RNA demethylase Alkbh5 reveal basis for substrate recognition. J Biol Chem. Apr. 25, 2014;289(17):11571-11583. doi: 10.1074/jbc.M113.546168. Epub Mar. 10, 2014.
Feng et al., Human L1 retrotransposon encodes a conserved endonuclease required for retrotransposition. Cell. Nov. 29, 1996;87(5):905-16. doi: 10.1016/s0092-8674(00)81997-2.
Ferry et al., Rational design of inducible CRISPR guide RNAs for de novo assembly of transcriptional programs. Nat Commun. Mar. 3, 2017;8:14633. doi: 10.1038/ncomms14633.
Feuk, Inversion variants in the human genome: role in disease and genome architecture. Genome Med. Feb. 12, 2010;2(2):11. doi: 10.1186/gm132.
Filippov et al., A novel type of RNase III family proteins in eukaryotes. Gene. Mar. 7, 2000;245(1):213-21. doi: 10.1016/s0378-1119(99)00571-5.
Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.
Fire et al., Potent and specific genetic interference by double-stranded RNA in Caenorhabditis elegans. Nature. Feb. 19, 1998;391(6669):806-11. doi: 10.1038/35888.
Fischer et al., Cryptic epitopes induce high-titer humoral immune response in patients with cancer. J Immunol. Sep. 1, 2010;185(5):3095-102. doi: 10.4049/jimmunol.0902166. Epub Jul. 26, 2010.
Fitzjohn, Diversitree: comparative phylogenetic analyses of diversification in R. Methods in Evology and Evolution. Dec. 2012;3(6):1084-92 .doi: 10.1111/j.2041-210X.2012.00234.x.

(56) References Cited

OTHER PUBLICATIONS

Flajolet et al., Woodchuck hepatitis virus enhancer I and enhancer II are both involved in N-myc2 activation in woodchuck liver tumors. J Virol. Jul. 1998;72(7):6175-80. doi: 10.1128/JVI.72.7.6175-6180.1998.
Flaman et al., A rapid PCR fidelity assay. Nucleic Acids Res. Aug. 11, 1994;22(15):3259-60. doi: 10.1093/nar/22.15.3259.
Fogg et al., New applications for phage integrases. J Mol Biol. Jul. 29, 2014;426(15):2703-16. doi: 10.1016/j.jmb.2014.05.014. Epub May 22, 2014.
Fogg et al., Genome Integration and Excision by a New Streptomyces Bacteriophage, Joe. Appl Environ Microbiol. Feb. 15, 2017;83(5):e02767-16. doi: 10.1128/AEM.02767-16.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013.
Forster et al., Self-cleavage of virusoid RNA is performed by the proposed 55-nucleotide active site. Cell. Jul. 3, 1987;50(1):9-16. doi: 10.1016/0092-8674(87)90657-x.
Fouts et al., Sequencing Bacillus anthracis typing phages gamma and cherry reveals a common ancestry. J Bacteriol. May 2006;188(9):3402-8. doi: 10.1128/JB.188.9.3402-3408.2006.
Freitas et al., Mechanisms and signals for the nuclear import of proteins. Curr Genomics. Dec. 2009;10(8):550-7. doi: 10.2174/138920209789503941.
Freshney, Culture of Animal Cells. A Manual of Basic Technique. Alan R. Liss, Inc. New York. 1983;4.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fu et al., Promises and Pitfalls of Intracellular Delivery of Proteins. Bioconjugate Chemistry. Aug. 2014;25:1602-8.
Fuchs et al., Polyarginine as a multifunctional fusion tag. Protein Sci. Jun. 2005;14(6):1538-44.
Fujisawa et al., Disease-associated mutations in CIAS1 induce cathepsin B-dependent rapid cell death of human THP-1 monocytic cells. Blood. Apr. 1, 2007;109(7):2903-11.
Fukui et al., DNA Mismatch Repair in Eukaryotes and Bacteria. J Nucleic Acids. Jul. 27, 2010;2010. pii: 260512. doi: 10.4061/2010/260512.
Fung et al., Repair at single targeted DNA double-strand breaks in pluripotent and differentiated human cells. PLoS One. 2011;6(5):e20514. doi: 10.1371/journal.pone.0020514. Epub May 25, 2011.
Furukawa et al., In vitro selection of allosteric ribozymes that sense the bacterial second messenger c-di-GMP. Methods Mol Biol. 2014;1111:209-20. doi: 10.1007/978-1-62703-755-6_15.
Gaj et al., 3rd. Genome engineering with custom recombinases. Methods Enzymol. 2014;546:79-91. doi: 10.1016/B978-0-12-801185-0.00004-0.
Gaj et al., A comprehensive approach to zinc-finger recombinase customization enables genomic targeting in human cells. Nucleic Acids Res. Feb. 6, 2013;41(6):3937-46.
Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gajula, Designing an Elusive CoG?GoC CRISPR Base Editor. Trends Biochem Sci. Feb. 2019;44(2):91-94. doi: 10.1016/j.tibs.2018.10.004. Epub Nov. 13, 2018.
Gallo et al., A novel pathogenic PSEN1 mutation in a family with Alzheimer's disease: phenotypical and neuropathological features. J Alzheimers Dis. 2011;25(3):425-31. doi: 10.3233/JAD-2011-110185.
Gao et al., Cationic liposome-mediated gene transfer. Gene Ther. Dec. 1995;2(10):710-22.
Gao et al., DNA-guided genome editing using the Natronobacterium gregoryi Argonaute. Nat Biotechnol. Jul. 2016;34(7):768-73. doi: 10.1038/nbt.3547. Epub May 2, 2016.
Gao et al., Self-processing of ribozyme-flanked RNAs into guide RNAs in vitro and in vivo for CRISPR-mediated genome editing. J Integr Plant Biol. Apr. 2014;56(4):343-9. doi: 10.1111/jipb.12152. Epub Mar. 6, 2014.
Gao et al., Treatment of autosomal dominant hearing loss by in vivo delivery of genome editing agents. Nature. Jan. 11, 2018;553(7687):217-221. doi: 10.1038/nature25164. Epub Dec. 20, 2017.
Garcia et al., Transglycosylation: a mechanism for RNA modification (and editing?). Bioorg Chem. Jun. 2005;33(3):229-51. doi: 10.1016/j.bioorg.2005.01.001. Epub Feb. 23, 2005.
Gardlik et al., Vectors and delivery systems in gene therapy. Med Sci Monit. Apr. 2005;11(4):RA110-21. Epub Mar. 24, 2005.
Garibyan et al., Use of the rpoB gene to determine the specificity of base substitution mutations on the *Escherichia coli* chromosome. DNA Repair (Amst). May 13, 2003;2(5):593-608.
Garneau et al., The CRISPR/Cas bacterial immune system cleaves bacteriophage and plasmid DNA. Nature. Nov. 4, 2010;468(7320):67-71. doi: 10.1038/nature09523.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Gaudelli et al., Programmable base editing of AoT to GoC in genomic DNA without DNA cleavage. Nature. Nov. 23, 2017;551(7681):464-471. doi: 10.1038/nature24644. Epub Oct. 25, 2017. Erratum in: Nature. May 2, 2018.
Gehrke et al., An APOBEC3A-Cas9 base editor with minimized bystander and off-target activities. Nat Biotechnol. Nov. 2018;36(10):977-982. doi: 10.1038/nbt.4199. Epub Jul. 30, 2018.
GenBank Accession No. J01600.1. Brooks et al., *E.coli* dam gene coding for DNA adenine methylase. Apr. 26, 1993.
GenBank Accession No. U07651.1. Lu, *Escherichia coli* K12 negative regulator of replication initiation (seqA) gene, complete cds. Jul. 19, 1994.
Genbank Submission; NIH/NCBI Accession No. NM_001319224.2. Umar et al., Apr. 21, 2021. 7 pages.
Genbank Submission; NIH/NCBI Accession No. NM_006027.4. Umar et al., Apr. 10, 2021. 7 pages.
Genbank Submission; NIH/NCBI, Accession No. AAA66622.1. Martinelli et al., May 18, 1995. 2 pages.
Genbank Submission; NIH/NCBI, Accession No. AGT42196. Farzadfar et al., Nov. 2, 2013. 2 pages.
Genbank Submission; NIH/NCBI, Accession No. APG80656.1. Burstein et al., Dec. 10, 2016. 1 pages.
Genbank Submission; NIH/NCBI, Accession No. AYD60528.1. Ram et al., Oct. 2, 2018. 1 page.
Genbank Submission; NIH/NCBI, Accession No. J04623. Kita et al., Apr. 26, 1993. 2 pages.
Genbank Submission; NIH/NCBI, Accession No. KR710351.1. Sahni et al., Jun. 1, 2015. 2 pages.
Genbank Submission; NIH/NCBI, Accession No. NC_002737.2. Nasser et al., Feb. 7, 2021. 2 pages.
Genbank Submission; NIH/NCBI, Accession No. NC_002737.1. Ferretti et al., Jun. 27, 2013. 1 page.
Genbank Submission; NIH/NCBI, Accession No. NC_015683.1. Trost et al., Jul. 6, 2013. 1 page.
Genbank Submission; NIH/NCBI, Accession No. NC_016782.1. Trost et al., Jun. 11, 2013. 1 page.
Genbank Submission; NIH/NCBI, Accession No. NC_016786.1. Trost et al., Aug. 28, 2013. 1 page.

(56) References Cited

OTHER PUBLICATIONS

Genbank Submission; NIH/NCBI, Accession No. NC_017053.1. Fittipaldi et al., Jul. 6, 2013. 1 page.
Genbank Submission; NIH/NCBI, Accession No. NC_017317.1. Trost et al., Jun. 11, 2013. 1 page.
Genbank Submission; NIH/NCBI, Accession No. NC_017861.1. Heidelberg et al., Jun. 11, 2013. 1 page.
Genbank Submission; NIH/NCBI, Accession No. NC_018010.1. Lucas et al., Jun. 11, 2013. 2 pages.
Genbank Submission; NIH/NCBI, Accession No. NC_018721.1. Feng et al., Jun. 11, 2013. 1 pages.
Genbank Submission; NIH/NCBI, Accession No. NC_021284.1. Ku et al., Jul. 12, 2013. 1 page.
Genbank Submission; NIH/NCBI, Accession No. NC_021314.1. Zhang et al., Jul. 15, 2013. 1 page.
Genbank Submission; NIH/NCBI, Accession No. NC_021846.1. Lo et al., Jul. 22, 2013. 1 page.
Genbank Submission; NIH/NCBI, Accession No. NM_000311.5. Alves et al., Mar. 7, 2021. 5 pages.
Genbank Submission; NIH/NCBI, Accession No. NM_001319224. Umar et al., Apr. 21, 2021. 7 pages.
Genbank Submission; NIH/NCBI, Accession No. NM_003686. Umar et al., Apr. 9, 2021. 7 pages.
Genbank Submission; NIH/NCBI, Accession No. NM_003686.4. Umar et al., Apr. 9, 2021. 7 pages.
Genbank Submission; NIH/NCBI, Accession No. NM_006027. Umar et al., Apr. 10, 2021. 7 pages.
Genbank Submission; NIH/NCBI, Accession No. NM_174936. Guo et al., Oct. 28, 2015. 6 pages.
Genbank Submission; NIH/NCBI, Accession No. NP_000302.1. Alves et al., Mar. 7, 2021. 4 pages.
Genbank Submission; NIH/NCBI, Accession No. NP_472073.1. Glaser et al., Jun. 27, 2013. 2 pages.
Genbank Submission; NIH/NCBI, Accession No. NP_955579.1. Chen et al., Aug. 13, 2018. 5 pages.
Genbank Submission; NIH/NCBI, Accession No. P42212. Prasher et al., Mar. 19, 2014. 7 pages.
Genbank Submission; NIH/NCBI, Accession No. QBJ66766. Duan et al. Aug. 12, 2020. 2 pages.
Genbank Submission; NIH/NCBI, Accession No. RFF81513.1. Zhou et al., Aug. 21, 2018. 2 pages.
Genbank Submission; NIH/NCBI, Accession No. SNX31424.1. Weckx, S., Feb. 16, 2018. 2 pages.
Genbank Submission; NIH/NCBI, Accession No. TGH57013. Xu et al., Apr. 9, 2019. 2 pages.
Genbank Submission; NIH/NCBI, Accession No. WP_016631044.1. Haft et al., Sep. 22, 2020. 1 page.
Genbank Submission; NIH/NCBI, Accession No. WP_031386437. No Author Listed., Sep. 23, 2019. 1 page.
Genbank Submission; NIH/NCBI, Accession No. WP_031589969.1. Haft et al., Oct. 9, 2019. 2 pages.
Genbank Submission; NIH/NCBI, Accession No. WP_044924278.1. Haft et al., Oct. 9, 2019. 2 pages.
Genbank Submission; NIH/NCBI, Accession No. WP_047338501.1. Haft et al., Oct. 9, 2019. 2 pages.
Genbank Submission; NIH/NCBI, Accession No. WP_060798984.1. Haft et al., Oct. 9, 2019. 2 pages.
Genbank Submission; NIH/NCBI, Accession No. WP_062913273.1. Haft et al., Oct. 9, 2019, 2 pages.
Genbank Submission; NIH/NCBI, Accession No. WP_072754838. No Author Listed., Sep. 23, 2019. 1 page.
Genbank Submission; NIH/NCBI, Accession No. WP_095142515.1. No Author Listed., Sep. 23, 2019. 1 page.
Genbank Submission; NIH/NCBI, Accession No. WP_118538418.1. No Author Listed., Oct. 13, 2019. 1 page.
Genbank Submission; NIH/NCBI, Accession No. WP_119223642.1. No Author Listed., Oct. 13, 2019. 1 page.
Genbank Submission; NIH/NCBI, Accession No. WP_119227726.1. No Author Listed., Oct. 13, 2019. 1 page.
Genbank Submission; NIH/NCBI, Accession No. WP_119623382.1. No Author Listed., Oct. 13, 2019. 1 page.
Genbank Submission; NIH/NCBI, Accession No. WP_132221894.1. No Author Listed., Sep. 23, 2019. 1 page.
Genbank Submission; NIH/NCBI, Accession No. WP_133478044.1. Haft et al., Oct. 9, 2019. 2 pages.
Genbank Submission; NIH/NCBI, Accession No. YP_002342100.1. Bernardini et al., Jun. 10, 2013. 2 pages.
Genbank Submission; NIH/NCBI, Accession No. YP_002344900.1. Gundogdu et al., Mar. 19, 2014. 2 pages.
Genbank Submission; NIH/NCBI, Accession No. YP_009283008.1. Bernardini et al., Sep. 23, 2016. 2 pages.
Genbank Submission; NIH/NCBI, Accession No. YP_820832.1. Makarova et al., Aug. 27, 2013. 2 pages.
George et al., Adenosine deaminases acting on RNA, RNA editing, and interferon action. J Interferon Cytokine Res. Jan. 2011;31(1):99-117. doi: 10.1089/jir.2010.0097. Epub Dec. 23, 2010. PMID: 21182352; PMCID: PMC3034097.
Gerard et al., Influence on stability in *Escherichia coli* of the carboxy-terminal structure of cloned Moloney murine leukemia virus reverse transcriptase. DNA. Aug. 1986;5(4):271-9. doi: 10.1089/dna.1986.5.271.
Gerard et al., Purification and characterization of the DNA polymerase and RNase H activities in Moloney murine sarcoma-leukemia virus. J Virol. Apr. 1975;15(4):785-97. doi: 10.1128/JVI.15.4.785-797.1975.
Gerard et al., The role of template-primer in protection of reverse transcriptase from thermal inactivation. Nucleic Acids Res. Jul. 15, 2002;30(14):3118-29. doi: 10.1093/nar/gkf417.
Gerber et al., An adenosine deaminase that generates inosine at the wobble position of tRNAs. Science. Nov. 5, 1999;286(5442):1146-9. doi: 10.1126/science.286.5442.1146.
Gerber et al., RNA editing by base deamination: more enzymes, more targets, new mysteries. Trends Biochem Sci. Jun. 2001;26(6):376-84.
Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.
Gersbach et al., Targeted plasmid integration into the human genome by an engineered zinc-finger recombinase. Nucleic Acids Res. Sep. 1, 2011;39(17):7868-78. doi: 10.1093/nar/gkr421. Epub Jun. 7, 2011.
Ghahfarokhi et al., Blastocyst Formation Rate and Transgene Expression are Associated with Gene Insertion into Safe and Non-Safe Harbors in the Cattle Genome. Sci Rep. Nov. 13, 2017;7(1):15432. doi: 10.1038/s41598-017-15648-3.
Gibson et al., Enzymatic assembly of DNA molecules up to several hundred kilobases. Nat Methods. May 2009;6(5):343-5. doi: 10.1038/nmeth.1318. Epub Apr. 12, 2009.
Gil, Position-dependent sequence elements downstream of AAUAAA are required for efficient rabbit beta-globin mRNA 3' end formation. Cell. May 8, 1987;49(3):399-406. doi: 10.1016/0092-8674(87)90292-3.
Gilbert et al., CRISPR-mediated modular RNA-guided regulation of transcription in eukaryotes. Cell. 2013 154(2):442-51.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Glasgow et al., DNA-binding properties of the Hin recombinase. J Biol Chem. Jun. 15, 1989;264(17):10072-82.
Glassner et al., Generation of a strong mutator phenotype in yeast by imbalanced base excision repair. Proc Natl Acad Sci U S A. Aug. 18, 1998;95(17):9997-10002.
Goldberg et al., Epigenetics: a landscape takes shape. Cell. Feb. 23, 2007;128(4):635-8. doi: 10.1016/j.cell.2007.02.006.
Gong et al., Active DNA demethylation by oxidation and repair. Cell Res. Dec. 2011;21(12):1649-51. doi: 10.1038/cr.2011.140. Epub Aug. 23, 2011.
Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.

(56) References Cited

OTHER PUBLICATIONS

Goodnough et al., Development of a delivery vehicle for intracellular transport of botulinum neurotoxin antagonists. FEBS Lett. Feb. 27, 2002;513(2-3):163-8.
Gou et al., Designing single guide RNA for CIRSPR-Cas9 base editor by deep learning. Peer reviewed Thesis/Dissertation. UCLA Electronic Theses and Dissertations. Jan. 1, 2019. Retrieved from the Internet via https://escholarship.org/uc/item/7vf9z54t. Last accessed on Apr. 29, 2021.
Grainge et al., The integrase family of recombinase: organization and function of the active site. Mol Microbiol. Aug. 1999;33(3):449-56.
Gregory et al., Integration site for Streptomyces phage phiBT1 and development of site-specific integrating vectors. J Bacteriol. Sep. 2003;185(17):5320-3. doi: 10.1128/jb.185.17.5320-5323.2003.
Griffiths, Endogenous retroviruses in the human genome sequence. Genome Biol. 2001;2(6):REVIEWS1017. doi: 10.1186/gb-2001-2-6-reviews1017. Epub Jun. 5, 2001.
Grishok et al., Genes and Mechanisms Related to RNA Interference Regulate Expression of the Small Temporal RNAs that Control C. elegans Developmental Timing. Jul. 13, 2001:106(1):P23-4.
Groth et al., Construction of transgenic *Drosophila* by using the site-specific integrase from phage phiC31. Genetics. Apr. 2004;166(4):1775-82. doi: 10.1534/genetics.166.4.1775.
Gruber et al., Strategies for measuring evolutionary conservation of RNA secondary structures. BMC Bioinformatics. Feb. 26, 2008;9:122. doi: 10.1186/1471-2105-9-122.
Grunebaum et al., Recent advances in understanding and managing adenosine deaminase and purine nucleoside phosphorylase deficiencies. Curr Opin Allergy Clin Immunol. Dec. 2013;13(6):630-8. doi: 10.1097/ACI.0000000000000006.
Grünewald et al., Transcriptome-wide off-target RNA editing induced by CRISPR-guided DNA base editors. Nature. May 2019;569(7756):433-437. doi: 10.1038/s41586-019-1161-z. Epub Apr. 17, 2019.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Gumulya et al., Exploring the past and the future of protein evolution with ancestral sequence reconstruction: the 'retro' approach to protein engineering. Biochem J. Jan. 1, 2017;474(1):1-19. doi: 10.1042/BCJ20160507.
Guo et al., Facile functionalization of FK506 for biological studies by the thiol—ene 'click' reaction. RSC Advances. 2014;22:11400-3.
Guo et al., Protein tolerance to random amino acid change. Proc Natl Acad Sci U S A. Jun. 22, 2004;101(25):9205-10. Epub Jun. 14, 2004.
Gupta et al., Cross-talk between cognate and noncognate RpoE sigma factors and Zn(2+)-binding anti-sigma factors regulates photooxidative stress response in Azospirillum brasilense. Antioxid Redox Signal. Jan. 1, 2014;20(1):42-59. doi: 10.1089/ars.2013.5314. Epub Jul. 19, 2013.
Gupta et al., Sequences in attB that affect the ability of phiC31 integrase to synapse and to activate DNA cleavage. Nucleic Acids Res. 2007;35(10):3407-19. doi: 10.1093/nar/gkm206. Epub May 3, 2007.
Guzman et al., Tight regulation, modulation, and high-level expression by vectors containing the arabinose PBAD promoter. J Bacteriol. 1995;177(14):4121-4130.
Haapaniemi et al., CRISPR-Cas9 genome editing induces a p53-mediated DNA damage response. Nat Med. Jul. 2018;24(7):927-930. doi: 10.1038/s41591-018-0049-z. Epub Jun. 11, 2018.
Haddada et al., Gene therapy using adenovirus vectors. Curr Top Microbiol Immunol. 1995;199 ( Pt 3):297-306. doi: 10.1007/978-3-642-79586-2_14.
Haeussler et al., Evaluation of off-target and on-target scoring algorithms and integration into the guide RNA selection tool CRISPOR. Genome Biol. Jul. 5, 2016;17(1):148. doi: 10.1186/s13059-016-1012-2.
Hale et al., RNA-guided RNA cleavage by a CRISPR RNA-Cas protein complex. Cell. Nov. 25, 2009;139(5):945-56. doi: 10.1016/j.cell.2009.07.040.
Halmai et al., Targeted CRIPSR/dCas9-mediated reactivation of epigenetically silenced genes suggests limited escape from the inactive X chromosome. 2nd Intl Conf on Epigenetics and Bioengineering. Oct. 4, 2018; Retrieved from the Internet: https://aiche.confex.com/aiche/epibio18/webprogram/paper544785.html. Retrieved Jun. 29, 2020.
Halperin et al., CRISPR-guided DNA polymerases enable diversification of all nucleotides in a tunable window. Nature. Aug. 2018;560(7717):248-252. doi: 10.1038/s41586-018-0384-8. Epub Aug. 1, 2018.
Halvas et al., Role of murine leukemia virus reverse transcriptase deoxyribonucleoside triphosphate-binding site in retroviral replication and in vivo fidelity. J Virol. Nov. 2000;74(22):10349-58. doi: 10.1128/jvi.74.22.10349-10358.2000.
Hamano-Takaku et al., a mutant *Escherichia coli* tyrosyl-tRNA synthetase utilizes the unnatural amino acid azatyrosine more efficiently than tyrosine. J Biol Chem. Dec. 22, 2000;275(51):40324-8.
Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.
Handa et al., Template-assisted synthesis of adenine-mutagenized cDNA by a retroelement protein complex. Nucleic Acids Res. Oct. 12, 2018;46(18):9711-9725. doi: 10.1093/nar/gky620.
Hanson et al., Codon optimality, bias and usage in translation and mRNA decay. Nat Rev Mol Cell Biol. Jan. 2018;19(1):20-30. doi: 10.1038/nrm.2017.91. Epub Oct. 11, 2017.
Harms et al., Evolutionary biochemistry: revealing the historical and physical causes of protein properties. Nat Rev Genet. Aug. 2013;14(8):559-71. doi: 10.1038/nrg3540.
Harrington et al., A thermostable Cas9 with increased lifetime in human plasma. Nat Commun. Nov. 10, 2017;8(1):1424. doi: 10.1038/s41467-017-01408-4.
Harris et al., RNA Editing Enzyme APOBEC1 and Some of Its Homologs Can Act as DNA Mutators. Mol Cell. Nov. 2002;10(5):1247-53.
Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Hasegawa et al., Spontaneous mutagenesis associated with nucleotide excision repair in *Escherichia coli*. Genes Cells. May 2008;13(5):459-69. doi: 10.1111/j.1365-2443.2008.01185.x.
Hayes et al., Stop codons preceded by rare arginine codons are efficient determinants of SsrA tagging in *Escherichia coli*. Proc Natl Acad Sci U S A. Mar. 19, 2002;99(6):3440-5. Epub Mar. 12, 2002.
Hector et al., CDKL5 variants: Improving our understanding of a rare neurologic disorder. Neurol Genet. Dec. 15, 2017;3(6):e200. doi: 10.1212/NXG.0000000000000200.
Heidenreich et al., Non-homologous end joining as an important mutagenic process in cell cycle-arrested cells. EMBO J. May 1, 2003;22(9):2274-83. doi: 10.1093/emboj/cdg203.
Heitz et al., Twenty years of cell-penetrating peptides: from molecular mechanisms to therapeutics. Br J Pharmacol. May 2009;157(2):195-206. doi: 10.1111/j.1476-5381.2009.00057.x. Epub Mar. 20, 2009.
Held et al., In vivo correction of murine hereditary tyrosinemia type I by phiC31 integrase-mediated gene delivery. Mol Ther. Mar. 2005;11(3):399-408. doi: 10.1016/j.ymthe.2004.11.001.
Heller et al., Replisome assembly and the direct restart of stalled replication forks. Nat Rev Mol Cell Biol. Dec. 2006;7(12):932-43. Epub Nov. 8, 2006.

(56) References Cited

OTHER PUBLICATIONS

Hendricks et al., The *S. cerevisiae* Mag1 3-methyladenine DNA glycosylase modulates susceptibility to homologous recombination. DNA Repair (Amst). 2002;1(8):645-659.
Hermonat et al., Use of adeno-associated virus as a mammalian DNA cloning vector: transduction of neomycin resistance into mammalian tissue culture cells. Proc Natl Acad Sci U S A. Oct. 1984;81(20):6466-70. doi: 10.1073/pnas.81.20.6466.
Herschhorn et al., Retroviral reverse transcriptases. Cell Mol Life Sci. Aug. 2010;67(16):2717-47. doi: 10.1007/s00018-010-0346-2. Epub Apr. 1, 2010.
Herzig et al., A Novel Leu92 Mutant of HIV-1 Reverse Transcriptase with a Selective Deficiency in Strand Transfer Causes a Loss of Viral Replication. J Virol. Aug. 2015;89(16):8119-29. doi: 10.1128/JVI.00809-15. Epub May 20, 2015.
Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.
Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.
Hida et al., Directed evolution for drug and nucleic acid; delivery. Adv Drug Deliv Rev. Dec. 22, 2007;59(15):1562-78. Epub Aug. 28, 2007.; Review.
Hill et al., Functional analysis of conserved histidines in ADP-glucose pyrophosphorylase from *Escherichia coli*.Biochem Biophys Res Commun. Mar. 17, 1998;244(2):573-7.
Hille et al., The Biology of CRISPR-Cas: Backward and Forward. Cell. Mar. 8, 2018;172(6):1239-1259. doi: 10.1016/j.cell.2017.11.032.
Hilton et al., Enabling functional genomics with genome engineering. Genome Res. Oct. 2015;25(10):1442-55. doi: 10.1101/gr.190124.115.
Hirano et al., Structural Basis for the Altered PAM Specificities of Engineered CRISPR-Cas9. Mol Cell. Mar. 17, 2016;61(6):886-94. doi: 10.1016/j.molcel.2016.02.018.
Hoang et al., UFBoot2: Improving the Ultrafast Bootstrap Approximation. Mol Biol Evol. Feb. 1, 2018;35(2):518-522. doi: 10.1093/molbev/msx281.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Hockemeyer et al., Genetic engineering of human pluripotent cells using TALE nucleases. Nat Biotechnol. Jul. 7, 2011;29(8):731-4. doi: 10.1038/nbt.1927.
Hoernes et al., Translating the epitranscriptome. Wiley Interdiscip Rev RNA. Jan. 2017;8(1):e1375. doi: 10.1002/wrna.1375. Epub Jun. 27, 2016.
Holden et al., Crystal structure of the anti-viral APOBEC3G catalytic domain and functional implications. Nature. Nov. 6, 2008;456(7218):121-4. doi: 10.1038/nature07357. Epub Oct. 12, 2008.
Hollis et al., Phage integrases for the construction and manipulation of transgenic mammals. Reprod Biol Endocrinol. Nov. 7, 2003;1:79. doi: 10.1186/1477-7827-1-79.
Holsinger et al., Signal transduction in T lymphocytes using a conditional allele of Sos. Proc Natl Acad Sci U S A. Oct. 10, 1995;92(21):9810-4. doi: 10.1073/pnas.92.21.9810.
Hondares et al., Peroxisome Proliferator-activated Receptor α (PPARα) Induces PPARγ Co activator 1α (PGC-1α) Gene Expression and Contributes to Thermogenic Activation of Brown Fat. J Biol. Chem Oct. 2011; 286(50):43112-22. doi: 10.1074/jbc.M111.252775.
Hoogenboom et al., Natural and designer binding sites made by phage display technology. Immunol Today. Aug. 2000;21(8):371-8.
Horvath et al., CRISPR/Cas, the immune system of bacteria and archaea. Science. Jan. 8, 2010;327(5962):167-70. doi: 10.1126/science.1179555.

Horvath et al., Diversity, Activity, and Evolution of CRISPR Loci in *Streptococcus thermophilus*. J Bacteriol. Feb. 2008;190(4):1401-12. doi: 10.1128/JB.01415-07. Epub Dec. 7, 2007.
Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.
Houdebine, The methods to generate transgenic animals and to control transgene expression. J Biotechnol. Sep. 25, 2002;98(2-3):145-60.
Howard et al., Intracerebral drug delivery in rats with lesion-induced memory deficits. J Neurosurg. Jul. 1989;71(1):105-12.
Hower et al., Shape-based peak identification for ChIP-Seq. BMC Bioinformatics. Jan. 12, 2011;12:15. doi: 10.1186/1471-2105-12-15.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013. Supplementary Information. 27 pages.
Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol.2015.12.009.
Hu et al., Evolved Cas9 variants with broad PAM compatibility and high DNA specificity. Nature. Apr. 5, 2018;556(7699):57-63. doi: 10.1038/nature26155. Epub Feb. 28, 2018.
Huang et al., Circularly permuted and PAM-modified Cas9 variants broaden the targeting scope of base editors. Nat Biotechnol. Jun. 2019;37(6):626-631. doi: 10.1038/s41587-019-0134-y. Epub May 20, 2019. Including Supplementary Information.
Huang et al., Heritable gene targeting in zebrafish using customized TALENs. Nat Biotechnol. Aug. 5, 2011;29(8):699-700. doi: 10.1038/nbt.1939.
Huggins et al., Flap endonuclease 1 efficiently cleaves base excision repair and DNA replication intermediates assembled into nucleosomes. Mol Cell. Nov. 2002;10(5):1201-11. doi: 10.1016/s1097-2765(02)00736-0.
Humbert et al., Targeted gene therapies: tools, applications, optimization. Crit Rev Biochem Mol Biol. May-Jun. 2012;47(3):264-81. doi: 10.3109/10409238.2012.658112.
Hung et al., Protein localization in disease and therapy. J Cell Sci. Oct. 15, 2011;124(Pt 20):3381-92. doi: 10.1242/jcs.089110.
Hurt et al., Highly specific zinc finger proteins obtained by directed domain shuffling and cellbased selection. Proc Natl Acad Sci U S A. Oct. 14, 2003;100(21):12271-6. Epub Oct. 3, 2003.
Husimi, Selection and evolution of bacteriophages in cellstat. Adv Biophys. ; 1989;25:1-43. Review.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Hwang et al., Efficient In Vivo Genome Editing Using RNA-Guided Nucleases. Nat Biotechnol. Mar. 2013; 31(3): 227-229. doi: 10.1038/nbt.2501. Epub Jan. 29, 2013.
Hwang et al., Web-based design and analysis tools for CRISPR base editing. Bmc Bioinformatics. Dec. 27, 2018;19(1):542. doi: 10.1186/s12859-018-2585-4.
Ibba et al., Relaxing the substrate specificity of an aminoacyl-tRNA; synthetase allows in vitro and in vivo synthesis of proteins containing unnatural amino acids. FEBS Lett. May 15, 1995;364(3):272-5.
Ibba et al., Substrate specificity is determined by amino acid binding pocket size in *Escherichia coli* phenylalanyl-tRNA synthetase. Biochemistry. Jun. 14, 1994;33(23):7107-12.
Ihry et al., p53 inhibits CRISPR-Cas9 engineering in human pluripotent stem cells. Nat Med. Jul. 2018;24(7):939-946. doi: 10.1038/s41591 018-0050-6. Epub Jun. 11, 2018.
Iida et al., A site-specific, conservative recombination system carried by bacteriophage P1. Mapping the recombinase gene cin and the cross-over sites cix for the inversion of the C segment. EMBO J. 1982;1(11):1445-53.

(56) References Cited

OTHER PUBLICATIONS

Iida et al., The Min DNA inversion enzyme of plasmid p15B of *Escherichia coli* 15T-: a new member of the Din family of site-specific recombinases. Mol Microbiol. Jun. 1990;4(6):991-7. doi: 10.1111/j.1365-2958.1990.tb00671.x.
Ikediobi et al., Mutation analysis of 24 known cancer genes in the NCI-60 cell line set. Mol Cancer Ther. Nov. 2006;5(11):2606-12. Epub Nov. 6, 2006.
Imanishi et al., Detection of N6-methyladenosine based on the methyl-sensitivity of MazF RNA endonuclease. Chem Commun (Camb). Nov. 30, 2017;53(96):12930-12933. doi: 10.1039/c7cc07699a.
Imburgio et al., Studies of promoter recognition and start site selection by T7 RNA polymerase using a comprehensive collection of promoter variants. Biochemistry. Aug. 29, 2000;39(34):10419-30.
Ingram, A specific chemical difference between the globins of normal human and sickle-cell anaemia haemoglobin. Nature. Oct. 13, 1956;178(4537):792-4. doi: 10.1038/178792a0.
International Preliminary Report on Patentability for PCT/US2016/058344, dated May 3, 2018.
International Preliminary Report on Patentability for PCT/US2017/045381, dated Feb. 14, 2019.
International Preliminary Report on Patentability for PCT/US2012/047778, dated Feb. 6, 2014.
International Preliminary Report on patentability for PCT/US2014/050283, dated Feb. 18, 2016.
International Preliminary Report on Patentability for PCT/US2014/052231, dated Mar. 3, 2016.
International Preliminary Report on Patentability for PCT/US2014/054247, dated Mar. 17, 2016.
International Preliminary Report on Patentability for PCT/US2014/054291, dated Mar. 17, 2016.
International Preliminary Report on Patentability for PCT/US2014/070038, dated Jun. 23, 2016.
International Preliminary Report on Patentability for PCT/US2015/042770, dated Dec. 19, 2016.
International Preliminary Report on Patentability for PCT/US2015/058479, dated May 11, 2017.
International Preliminary Report on Patentability or PCT/US2014/054252, dated Mar. 17, 2016.
International Search Report and Written Opinion for PCT/US2012/047778, dated May 30, 2013.
International Search Report and Written Opinion for PCT/US2014/050283, dated Nov. 6, 2014.
International Search Report and Written Opinion for PCT/US2014/052231, dated Dec. 4, 2014.
International Search Report and Written Opinion for PCT/US2014/052231, dated Jan. 30, 2015 (Corrected Version).
International Search Report and Written Opinion for PCT/US2014/054247, dated Mar. 27, 2015.
International Search Report and Written Opinion for PCT/US2014/054252, dated Mar. 5, 2015.
International Search Report and Written Opinion for PCT/US2014/054291, dated Mar. 27, 2015.
International Search Report and Written Opinion for PCT/US2014/070038, dated Apr. 14, 2015.
International Search Report and Written Opinion for PCT/US2015/042770, dated Feb. 23, 2016.
International Search Report and Written Opinion for PCT/US2015/058479, dated Feb. 11, 2016.
International Search Report and Written Opinion for PCT/US2016/044546, dated Dec. 28, 2016.
International Search Report and Written Opinion for PCT/US2016/058344, dated Apr. 20, 2017.
International Search Report and Written Opinion for PCT/US2017/045381, dated Oct. 26, 2017.
International Search Report and Written Opinion for PCT/US2017/046144, dated Oct. 10, 2017.
International Search Report and Written Opinion for PCT/US2017/056671, dated Feb. 20, 2018.
International Search Report and Written Opinion for PCT/US2017/068105, dated Apr. 4, 2018.
International Search Report and Written Opinion for PCT/US2017/068114, dated Mar. 20, 2018.
International Search Report and Written Opinion for PCT/US2017/48390, dated Jan. 9, 2018.
International Search Report for PCT/US2013/032589, dated Jul. 26, 2013.
International Search Report for PCT/US2018/021664, dated Jun. 21, 2018.
International Search Report for PCT/US2018/021878, dated Aug. 20, 2018.
International Search Report for PCT/US2018/021880, dated Jun. 20, 2018.
International Search Report for PCT/US2018/024208, dated Aug. 23, 2018.
International Search Report for PCT/US2018/025887, dated Jun. 21, 2018.
International Search Report for PCT/US2018/032460, dated Jul. 11, 2018.
Invitation to Pay Additional Fees for PCT/US2014/054291, dated Dec. 18, 2014.
Invitation to Pay Additional Fees for PCT/US2016/058344, dated Mar. 1, 2017.
Invitation to Pay Additional Fees for PCT/US2017/056671, dated Dec. 21, 2017.
Invitation to Pay Additional Fees for PCT/US2017/48390, dated Nov. 7, 2017.
Invitation to Pay Additional Fees for PCT/US2018/021878, dated Jun. 8, 2018.
Irion et al., Identification and targeting of the ROSA26 locus in human embryonic stem cells. Nat Biotechnol. Dec. 2007;25(12):1477-82. doi: 10.1038/nbt1362. Epub Nov. 25, 2007.
Irrthum et al., Congenital hereditary lymphedema caused by a mutation that inactivates VEGFR3 tyrosine kinase. Am J Hum Genet. Aug. 2000;67(2):295-301. Epub Jun. 9, 2000.
Ishino et al., Nucleotide sequence of the iap gene, responsible for alkaline phosphatase isozyme conversion in *Escherichia coli*, and identification of the gene product. J Bacteriol. Dec. 1987;169(12):5429-33.
Iwai et al., Circular beta-lactamase: stability enhancement by cyclizing the backbone. FEBS Lett. Oct. 8, 1999;459(2):166-72. doi: 10.1016/s0014-5793(99)01220-x.
Iwai et al., Highly efficient protein trans-splicing by a naturally split DnaE intein from Nostoc punctiforme. FEBS Lett. Mar. 20, 2006;580(7):1853-8. doi: 10.1016/j.febslet.2006.02.045. Epub Feb. 24, 2006.
Jaffrey et al., Emerging links between m6A and misregulated mRNA methylation in cancer. Genome Med. Jan. 12, 2017;9(1):2. doi: 10.1186/s13073-016-0395-8.
Jamieson et al., Drug discovery with engineered zinc-finger proteins. Nat Rev Drug Discov. May 2003;2(5):361-8.
Jansen et al., Backbone and nucleobase contacts to glucosamine-6-phosphate in the glmS ribozyme. Nat Struct Mol Biol. Jun. 2006;13(6):517-23. Epub May 14, 2006.
Jansen et al., Identification of genes that are associated with DNA repeats in prokaryotes. Mol Microbiol. Mar. 2002;43(6):1565-75.
Jardine et al., HIV-1 VACCINES. Priming a broadly neutralizing antibody response to HIV-1 using a germline-targeting immunogen. Science. Jul. 10, 2015;349(6244):156-61. doi: 10.1126/science.aac5894. Epub Jun. 18, 2015.
Jasin et al., Repair of strand breaks by homologous recombination. Cold Spring Harb Perspect Biol. Nov. 1, 2013;5(11):a012740. doi: 10.1101/cshperspect.a012740.
Jeggo, DNA breakage and repair. Adv Genet. 1998;38:185-218. doi: 10.1016/s0065-2660(08)60144-3.
Jemielity et al., Novel "anti-reverse" cap analogs with superior translational properties. RNA. Sep. 2003;9(9):1108-22. doi: 10.1261/rna.5430403.
Jenkins et al., Comparison of a preQ1 riboswitch aptamer in metabolite-bound and free states with implications for gene regu-

(56) References Cited

OTHER PUBLICATIONS lation. J Biol Chem. Jul. 15, 2011;286(28):24626-37. doi: 10.1074/jbc.M111.230375. Epub May 18, 2011.

Jiang et al., CRISPR-Cas9 Structures and Mechanisms. Annu Rev Biophys. May 22, 2017;46:505-529. doi: 10.1146/annurev-biophys-062215-010822. Epub Mar. 30, 2017.

Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.

Jiang et al., Structural Biology. A Cas9-guide RNA Complex Preorganized for Target DNA Recognition. Science. Jun. 26, 2015;348(6242):1477-81. doi: 10.1126/science.aab1452.

Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.

Jin et al., Cytosine, but not adenine, base editors induce genome-wide off-target mutations in rice. Science. Apr. 19, 2019;364(6437):292-295. doi: 10.1126/science.aaw7166. Epub Feb. 28, 2019.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Jinek et al., RNA-programmed genome editing in human cells. Elife. Jan. 29, 2013;2:e00471. doi: 10.7554/eLife.00471.

Jinek et al., Structures of Cas9 endonucleases reveal RNA-mediated conformational activation. Science. Mar. 14, 2014;343(6176):1247997. doi: 10.1126/science.1247997. Epub Feb. 6, 2014.

Johann et al., GLVR1, a receptor for gibbon ape leukemia virus, is homologous to a phosphate permease of Neurospora crassa and is expressed at high levels in the brain and thymus. J Virol. Mar. 1992;66(3):1635-40. doi: 10.1128/JVI.66.3.1635-1640.1992.

Johansson et al., RNA Recognition by the MS2 Phage Coat Protein. Seminars in Virology. 1997;8(3):176-85. https://doi.org/10.1006/smvy.1997.0120.

Johansson et al., Selenocysteine in proteins-properties and biotechnological use. Biochim Biophys Acta. Oct. 30, 2005;1726(1):1-13. Epub Jun. 1, 2005.

Johns et al., The promise and peril of continuous in vitro evolution. J Mol Evol. Aug. 2005;61(2):253-63. Epub Jun. 27, 2005.

Joho et al., Identification of a region of the bacteriophage T3 and T7 RNA polymerases that determines promoter specificity. J Mol Biol. Sep. 5, 1990;215(1):31-9.

Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.

Joung et al., TALENs: a widely applicable technology for targeted genome editing. Nat Rev Mol Cell Biol. Jan. 2013;14(1):49-55. doi: 10.1038/nrm3486. Epub Nov. 21, 2012.

Joyce et al., Amplification, mutation and selection of catalytic RNA. Gene. Oct. 15, 1989;82(1):83-7. doi: 10.1016/0378-1119(89)90033-4.

Judge et al., Design of noninflammatory synthetic siRNA mediating potent gene silencing in vivo. Mol Ther. Mar. 2006;13(3):494-505. Epub Dec. 15, 2005.

Jusiak et al., Comparison of Integrases Identifies Bxb1-GA Mutant as the Most Efficient Site-Specific Integrase System in Mammalian Cells. ACS Synth Biol. Jan. 18, 2019;8(1):16-24. doi: 10.1021/acssynbio.8b00089. Epub Jan. 9, 2019.

Jyothy et al., Translocation Down syndrome. Indian J Med Sci. Mar. 2002;56(3):122-6.

Kacian et al., Purification of the DNA polymerase of avian myeloblastosis virus. Biochim Biophys Acta. Sep. 24, 1971;246(3):365-83. doi: 10.1016/0005-2787(71)90773-8.

Kaczmarczyk et al., Manipulating the Prion Protein Gene Sequence and Expression Levels with CRISPR/Cas9. PLoS One. Apr. 29, 2016;11(4):e0154604. doi: 10.1371/journal.pone.0154604.

Kadoch et al., Reversible disruption of mSWI/SNF (BAF) complexes by the SS18-SSX oncogenic fusion in synovial sarcoma. Cell. Mar. 28, 2013;153(1):71-85. doi: 10.1016/j.cell.2013.02.036.

Kahmann et al., G inversion in bacteriophage Mu DNA is stimulated by a site within the invertase gene and a host factor. Cell. Jul. 1985;41(3):771-80. doi: 10.1016/s0092-8674(85)80058-1.

Kaiser et al., Gene therapy. Putting the fingers on gene repair. Science. Dec. 23, 2005;310(5756):1894-6.

Kakiyama et al., A peptide release system using a photo-cleavable linker in a cell array format for cell-toxicity analysis. Polymer J. Feb. 27, 2013;45:535-9.

Kalyaanamoorthy et al., ModelFinder: fast model selection for accurate phylogenetic estimates. Nat Methods. Jun. 2017;14(6):587-589. doi: 10.1038/nmeth.4285. Epub May 8, 2017.

Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.

Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.

Kao et al., Cleavage specificity of *Saccharomyces cerevisiae* flap endonuclease 1 suggests a double-flap structure as the cellular substrate. J Biol Chem. Apr. 26, 2002;277(17):14379-89. doi: 10.1074/jbc.M110662200. Epub Feb. 1, 2002.

Kappel et al., Regulating gene expression in transgenic animals. Curr Opin Biotechnol. Oct. 1992;3(5):548-53.

Karimova et al., Discovery of Nigri/nox and Panto/pox site-specific recombinase systems facilitates advanced genome engineering. Sci Rep. Jul. 22, 2016;6:30130. doi: 10.1038/srep30130.

Karimova et al., Vika/vox, a novel efficient and specific Cre/loxP-like site-specific recombination system. Nucleic Acids Res. Jan. 2013;41(2):e37. doi: 10.1093/nar/gks1037. Epub Nov. 9, 2012.

Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012. Review.

Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.

Kato et al., Improved purification and enzymatic properties of three forms of reverse transcriptase from avian myeloblastosis virus. J Virol Methods. Dec. 1984;9(4):325-39. doi: 10.1016/0166-0934(84)90058-2.

Katoh et al., MAFFT multiple sequence alignment software version 7: improvements in performance and usability. Mol Biol Evol. Apr. 2013;30(4):772-80. doi: 10.1093/molbev/mst010. Epub Jan. 16, 2013.

Kaufman et al., Translational efficiency of polycistronic mRNAs and their utilization to express heterologous genes in mammalian cells. EMBO J. Jan. 1987;6(1):187-93.

Kawarasaki et al., Enhanced crossover SCRATCHY: construction and high-throughput screening of a combinatorial library containing multiple non-homologous crossovers. Nucleic Acids Res. Nov. 1, 2003;31(21):e126.

Kaya et al., A bacterial Argonaute with noncanonical guide RNA specificity. Proc. Natl. Acad. Sci. USA Apr. 2016;113(15):4057-62.

Keijzers et al., Human exonuclease 1 (EXO1) activity characterization and its function on flap structures. Biosci Rep. Apr. 25, 2015;35(3):e00206. doi: 10.1042/BSR20150058.

Kellendonk et al., Regulation of Cre recombinase activity by the synthetic steroid RU 486. Nucleic Acids Res. Apr. 15, 1996;24(8):1404-11.

Kelman, PCNA: structure, functions and interactions. Oncogene. Feb. 13, 1997;14(6):629-40. doi: 10.1038/sj.onc.1200886.

Keravala et al., A diversity of serine phage integrases mediate site-specific recombination in mammalian cells. Mol Genet Genomics. Aug. 2006;276(2):135-46. doi: 10.1007/s00438-006-0129-5. Epub May 13, 2006.

Kessel et al., Murine developmental control genes. Science. Jul. 27, 1990;249(4967):374-9. doi: 10.1126/science.1974085.

(56) References Cited

OTHER PUBLICATIONS

Kessler et al., Gene delivery to skeletal muscle results in sustained expression and systemic delivery of a therapeutic protein. Proc Natl Acad Sci U S A. Nov. 26, 1996;93(24):14082-7. doi: 10.1073/pnas.93.24.14082.
Kiga et al., An engineered *Escherichia coli* tyrosyl-tRNA synthetase for site-specific incorporation of an unnatural amino acid into proteins in eukaryotic translation and its application in a wheat germ cell-free system. Proc Natl Acad Sci U S A. Jul. 23, 2002;99(15):9715-20. Epub Jul. 3, 2002.
Kilcher et al., Brochothrix thermosphacta bacteriophages feature heterogeneous and highly mosaic genomes and utilize unique prophage insertion sites. J Bacteriol. Oct. 2010;192(20):5441-53. doi: 10.1128/JB.00709-10. Epub Aug. 13, 2010.
Kim et al., DJ-1, a novel regulator of the tumor suppressor PTEN. Cancer Cell. 2005;7(3):263-273.
Kim et al., Genome-wide target specificity of CRISPR RNA-guided adenine base editors. Nat Biotechnol. Apr. 2019;37(4):430-435. doi: 10.1038/s41587-019-0050-1. Epub Mar. 4, 2019.
Kim et al., A library of TAL effector nucleases spanning the human genome. Nat Biotechnol. Mar. 2013;31(3):251-8. Doi: 10.1038/nbt.2517. Epub Feb. 17, 2013.
Kim et al., Evaluating and Enhancing Target Specificity of Gene-Editing Nucleases and Deaminases. Annu Rev Biochem. Jun. 20, 2019;88:191-220. doi: 10.1146/annurev-biochem-013118-111730. Epub Mar. 18, 2019.
Kim et al., Genome-wide target specificities of CRISPR RNA-guided programmable deaminases. Nat Biotechnol. May 2017;35(5):475-480. doi: 10.1038/nbt.3852. Epub Apr. 10, 2017.
Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.
Kim et al., Highly efficient RNA-guided base editing in mouse embryos. Nat Biotechnol. May 2017;35(5):435-437. doi: 10.1038/nbt.3816. Epub Feb. 27, 2017.
Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.
Kim et al., In vivo high-throughput profiling of CRISPR-Cpf1 activity. Nat Methods. Feb. 2017;14(2):153-159. doi: 10.1038/nmeth.4104. Epub Dec. 19, 2016.
Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.
Kim et al., Mycobacteriophage Bxb1 integrates into the *Mycobacterium smegmatis* groEL1 gene. Mol Microbiol. Oct. 2003;50(2):463-73. doi: 10.1046/j.1365-2958.2003.03723.x.
Kim et al., Rescue of high-specificity Cas9 variants using sgRNAs with matched 5' nucleotides. Genome Biol. Nov. 15, 2017;18(1):218. doi: 10.1186/s13059-017-1355-3.
Kim et al., Structural and kinetic characterization of *Escherichia coli* TadA, the wobble-specific tRNA deaminase. Biochemistry. May 23, 2006;45(20):6407-16. doi: 10.1021/bi0522394. PMID: 16700551.
Kim et al., TALENs and ZFNs are associated with different mutationsignatures. Nat Methods. Mar. 2013;10(3):185. doi: 10.1038/nmeth.2364. Epub Feb. 10, 2013.
Kim et al., Targeted genome editing in human cells with zinc finger nucleases constructed via modular assembly. Genome Res. Jul. 2009;19(7):1279-88. doi: 10.1101/gr.089417.108. Epub May 21, 2009.
Kim et al., The role of apolipoprotein E in Alzheimer's disease. Neuron. Aug. 13, 2009;63(3):287-303. doi: 10.1016/j.neuron.2009.06.026.
Kim et al., Transcriptional repression by zinc finger peptides. Exploring the potential for applications in gene therapy. J Biol Chem. Nov. 21, 1997;272(47):29795-800.
Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat.1003361. Epub May 16, 2013.
Klapacz et al., Frameshift mutagenesis and microsatellite instability induced by human alkyladenine DNA glycosylase. Mol Cell. Mar. 26, 2010;37(6):843-53. doi: 10.1016/j.molcel.2010.01.038.
Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.
Klein et al., Cocrystal structure of a class I preQ1 riboswitch reveals a pseudoknot recognizing an essential hypermodified nucleobase. Nat Struct Mol Biol. Mar. 2009;16(3):343-4. doi: 10.1038/nsmb.1563.Epub Feb. 22, 2009.
Kleiner et al., In vitro selection of a DNA-templated small-molecule library reveals a class of macrocyclic kinase inhibitors. J Am Chem Soc. Aug. 25, 2010;132(33):11779-91. doi: 10.1021/ja104903x.
Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.
Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.
Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.
Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.
Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.
Klippel et al., Isolation and characterization of unusual gin mutants. EMBO J. Dec. 1, 1988;7(12):3983-9.
Klippel et al., The DNA invertase Gin of phage Mu: formation of a covalent complex with DNA via a phosphoserine at amino acid position 9. EMBO J. Apr. 1988;7(4):1229-37.
Klompe et al., Transposon-encoded CRISPR-Cas systems direct RNA-guided DNA integration. Nature. Jul. 2019;571(7764):219-225. doi: 10.1038/s41586-019-1323-z. Epub Jun. 12, 2019.
Knott et al., Guide-bound structures of an RNA-targeting A-cleaving CRISPR-Cas13a enzyme. Nat Struct Mol Biol. Oct. 2017;24(10):825-833. doi: 10.1038/nsmb.3466. Epub Sep. 11, 2017.
Koblan et al., Improving cytidine and adenine base editors by expression optimization and ancestral reconstruction. Nat Biotechnol. Oct. 2018;36(9):843-846. doi: 10.1038/nbt.4172. Epub May 29, 2018.
Kobori et al., Deep Sequencing Analysis of Aptazyme Variants Based on a Pistol Ribozyme. Acs Synth Biol. Jul. 21, 2017;6(7):1283-1288. doi: 10.1021/acssynbio.7b00057. Epub Apr. 14, 2017.
Kohli et al., A portable hot spot recognition loop transfers sequence preferences from APOBEC family members to activation-induced cytidine deaminase. J Biol Chem. Aug. 21, 2009;284(34):22898-904. doi: 10.1074/jbc.M109.025536. Epub Jun. 26, 2009.
Kohli et al., Local sequence targeting in the AID/APOBEC family differentially impacts retroviral restriction and antibody diversification. J Biol Chem. Dec. 24, 2010;285(52):40956-64. doi: 10.1074/jbc.M110.177402. Epub Oct. 6, 2010.
Köhrer et al., A possible approach to site-specific insertion of two different unnatural amino acids into proteins in mammalian cells via nonsense suppression. Chem Biol. Nov. 2003;10(11):1095-102.
Köhrer et al., Complete set of orthogonal 21st aminoacyl-tRNA synthetase-amber, ochre and opal suppressor tRNA pairs: concomitant suppression of three different termination codons in an mRNA in mammalian cells. Nucleic Acids Res. Dec. 1, 2004;32(21):6200-11. Print 2004.

(56) References Cited

OTHER PUBLICATIONS

Koike-Yusa et al., Genome-wide recessive genetic screening in mammalian cells with a lentiviral CRISPR-guide RNA library. Nat Biotechnol. Mar. 2014;32(3):267-73. doi: 10.1038/nbt.2800. Epub Dec. 23, 2013.

Kolot et al., Site promiscuity of coliphage HK022 integrase as a tool for gene therapy. Gene Ther. Jul. 2015;22(7):521-7. doi: 10.1038/gt.2015.9. Epub Mar. 12, 2015.

Kolot et al., Site-specific recombination in mammalian cells expressing the Int recombinase of bacteriophage HK022. Mol Biol Rep. Aug. 1999;26(3):207-13. doi: 10.1023/a:1007096701720.

Komor et al., CRISPR-Based Technologies for the Manipulation of Eukaryotic Genomes. Cell. Jan. 12, 2017;168(1-2):20-36. doi: 10.1016/j.cell.2016.10.044.

Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.

Komor et al., Programmable editing of a target base in genomic DNA without double-stranded DNA cleavage. Nature. Apr. 20, 2016;533(7603):420-4. doi: 10.1038/nature17946.

Komor, Editing the Genome Without Double-Stranded DNA Breaks. ACS Chem Biol. Feb. 16, 2018;13(2):383-388. doi: 10.1021/acschembio.7b00710. Epub Oct. 9, 2017.

Konermann et al., Genome-scale transcriptional activation by an engineered CRISPR-Cas9 complex. Nature. Jan. 29, 2015;517(7536):583-8. doi: 10.1038/nature14136. Epub Dec. 10, 2014.

Koonin et al., Diversity, classification and evolution of CRISPR-Cas systems. Curr Opin Microbiol. 2017;37:67?78. doi:10.1016/j.mib.2017.05.008.

Kosicki et al., Repair of double-strand breaks induced by CRISPR-Cas9 leads to large deletions and complex rearrangements. Nat Biotechnol. Sep. 2018;36(8):765-771. doi: 10.1038/nbt.4192. Epub Jul. 16, 2018.

Kotewicz et al., Cloning and overexpression of Moloney murine leukemia virus reverse transcriptase in *Escherichia coli*. Gene. 1985;35(3):249-58. doi: 10.1016/0378-1119(85)90003-4.

Kotewicz et al., Isolation of cloned Moloney murine leukemia virus reverse transcriptase lacking ribonuclease H activity. Nucleic Acids Res. Jan. 11, 1988;16(1):265-77. doi: 10.1093/nar/16.1.265.

Kotin, Prospects for the use of adeno-associated virus as a vector for human gene therapy. Hum Gene Ther. Jul. 1994;5(7):793-801. doi: 10.1089/hum.1994.5.7-793.

Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.

Kowal et al., Exploiting unassigned codons in Micrococcus luteus for tRNA-based amino acid mutagenesis. Nucleic Acids Res. Nov. 15, 1997;25(22):4685-9.

Kowalski et al., Delivering the Messenger: Advances in Technologies for Therapeutic mRNA Delivery. Mol Ther. Apr. 10, 2019;27(4):710-728. doi: 10.1016/j.ymthe.2019.02.012. Epub Feb. 19, 2019.

Kozak, An analysis of 5'-noncoding sequences from 699 vertebrate messenger RNAs. Nucleic Acids Res. Oct. 26, 1987;15(20):8125-48. doi: 10.1093/nar/15.20.8125.

Kraft et al., Deletions, Inversions, Duplications: Engineering of Structural Variants using CRISPR/Cas in Mice. Cell Rep. Feb. 10, 2015;10(5):833-839. doi: 10.1016/j.celrep.2015.01.016. Epub Feb. 7, 2015.

Kremer et al., Adenovirus and adeno-associated virus mediated gene transfer. Br Med Bull. Jan. 1995;51(1):31-44. doi: 10.1093/oxfordjournals.bmb.a072951.

Krokan et al, Uracil in DNA—occurrence, consequences and repair. Oncogene. Dec. 16, 2002;21(58):8935-48. doi: 10.1038/sj.onc.1205996.

Krokan et al., Base excision repair. Cold Spring Harb Perspect Biol. Apr. 1, 2013;5(4):a012583. doi: 10.1101/cshperspect.a012583.

Krzywkowski et al., Limited reverse transcriptase activity of phi29 DNA polymerase. Nucleic Acids Res. Apr. 20, 2018;46(7):3625-3632. doi: 10.1093/nar/gky190.

Kügler et al., Human synapsin 1 gene promoter confers highly neuron-specific long-term transgene expression from an adenoviral vector in the adult rat brain depending on the transduced area. Gene Ther. Feb. 2003;10(4):337-47. doi: 10.1038/sj.gt.3301905.

Kumar et al., Structural and functional consequences of the mutation of a conserved arginine residue in alphaA and alphaB crystallins. J Biol Chem. Aug. 20, 1999;274(34):24137-41.

Kundu et al., Leucine to proline substitution by SNP at position 197 in Caspase-9 gene expression leads to neuroblastoma: a bioinformatics analysis. 3 Biotech. 2013; 3:225-34.

Kunkel et al., Eukaryotic Mismatch Repair in Relation to DNA Replication. Annu Rev Genet. 2015;49:291-313. doi: 10.1146/annurev-genet-112414-054722.

Kunz et al., DNA Repair in mammalian cells: Mismatched repair: variations on a theme. Cell Mol Life Sci. Mar. 2009;66(6):1021-38. doi: 10.1007/s00018-009-8739-9.

Kurjan et al., Structure of a yeast pheromone gene (MF alpha): a putative alpha-factor precursor contains four tandem copies of mature alpha-factor. Cell. Oct. 1982;30(3):933-43. doi: 10.1016/0092-8674(82)90298-7.

Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.

Kuscu et al., CRISPR-Cas9-AID base editor is a powerful gain-of-function screening tool. Nat Methods. Nov. 29, 2016;13(12):983-984. doi: 10.1038/nmeth.4076.

Kuscu et al., CRISPR-STOP: gene silencing through base-editing-induced nonsense mutations. Nat Methods. Jul. 2017;14(7):710-712. doi: 10.1038/nmeth.4327. Epub Jun. 5, 2017.

Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.

Kwart et al., Precise and efficient scarless genome editing in stem cells using CORRECT. Nat Protoc. Feb. 2017;12(2):329-354. doi: 10.1038/nprot.2016.171. Epub Jan. 19, 2017.

Kweon et al., Fusion guide RNAs for orthogonal gene manipulation with Cas9 and Cpf1. Nat Commun. Nov. 23, 2017;8(1):1723. doi: 10.1038/s41467-017-01650-w. Erratum in: Nat Commun. Jan. 16, 2018;9(1):303.

Kwon et al., Chemical basis of glycine riboswitch cooperativity. RNA. Jan. 2008;14(1):25-34. Epub Nov. 27, 2008.

Lada et al., Mutator effects and mutation signatures of editing deaminases produced in bacteria and yeast. Biochemistry (Mosc). Jan. 2011;76(1):131-46.

Lakich et al., Inversions disrupting the factor VIII gene are a common cause of severe haemophilia A. Nat Genet. Nov. 1993;5(3):236-41. doi: 10.1038/ng1193-236.

Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.

Landrum et al., ClinVar: public archive of relationships among sequence variation and human phenotype. Nucleic Acids Res. Jan. 2014;42(Database issue):D980-5. doi: 10.1093/nar/gkt1113. Epub Nov. 14, 2013.

Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.

Langer et al., New methods of drug delivery. Science. Sep. 28, 1990;249(4976):1527-33.

Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.

Lau et al., Molecular basis for discriminating between normal and damaged bases by the human alkyladenine glycosylase, AAG. Proc Natl Acad Sci U S A. Dec. 5, 2000;97(25):13573-8.

(56) References Cited

OTHER PUBLICATIONS

Lauer et al., Construction, characterization, and use of two Listeria monocytogenes site-specific phage integration vectors. J Bacteriol. Aug. 2002;184(15):4177-86. doi: 10.1128/jb.184.15.4177-4186. 2002.

Lavergne et al., Defects in type IIA von Willebrand disease: a cysteine 509 to arginine substitution in the mature von Willebrand factor disrupts a disulphide loop involved in the interaction with platelet glycoprotein Ib-IX. Br J Haematol. Sep. 1992;82(1):66-72.

Lawrence et al., Supercharging proteins can impart unusual resilience. J Am Chem Soc. Aug. 22, 2007;129(33):10110-2. Epub Aug. 1, 2007.

Lawyer et al., High-level expression, purification, and enzymatic characterization of full-length Thermus aquaticus DNA polymerase and a truncated form deficient in 5' to 3' exonuclease activity. PCR Methods Appl. May 1993;2(4):275-87. doi: 10.1101/gr.2.4.275.

Lazar et al., Transforming growth factor alpha: mutation of aspartic acid 47 and leucine 48 results in different biological activities. Mol Cell Biol. Mar. 1988;8(3):1247-52.

Lazarevic et al., Nucleotide sequence of the Bacillus subtilis temperate bacteriophage SPbetac2. Microbiology (Reading). May 1999;145 ( Pt 5):1055-1067. doi: 10.1099/13500872-145-5-1055.

Le Grice et al., Purification and characterization of recombinant equine infectious anemia virus reverse transcriptase. J Virol. Dec. 1991;65(12):7004-7. doi: 10.1128/JVI.65.12.7004-7007.1991.

Leaver-Fay et al., ROSETTA3: an object-oriented software suite for the simulation and design of macromolecules. Methods Enzymol. 2011;487:545-74. doi: 10.1016/B978-0-12-381270-4.00019-6.

Leconte et al., A population-based experimental model for protein evolution: effects of mutation rate and selection stringency on evolutionary outcomes. Biochemistry. Feb. 26, 2013;52(8):1490-9. doi: 10.1021/bi3016185. Epub Feb. 14, 2013.

Ledford, Gene-editing hack yields pinpoint precision. Nature, Apr. 20, 2016. http://www.nature.com/news/gene-editing-hack-yields-pinpoint-precision-1.19773.

Lee et al., A chimeric thyroid hormone receptor constitutively bound to DNA requires retinoid X receptor for hormone-dependent transcriptional activation in yeast. Mol Endocrinol. Sep. 1994;8(9):1245-52.

Lee et al., An allosteric self-splicing ribozyme triggered by a bacterial second messenger. Science. Aug. 13, 2010;329(5993):845-8. doi: 10.1126/science.1190713.

Lee et al., Failure to detect DNA-guided genome editing using Natronobacterium gregoryi Argonaute. Nat Biotechnol. Nov. 28, 2016;35(1):17-18. doi: 10.1038/nbt.3753.

Lee et al., Group I Intron-Based Therapeutics Through Trans-Splicing Reaction. Prog Mol Biol Transl Sci. 2018;159:79-100. doi: 10.1016/bs.pmbts.2018.07.001. Epub Aug. 9, 2018.

Lee et al., PIK3CA gene is frequently mutated in breast carcinomas and hepatocellular carcinomas. Oncogene. Feb. 17, 2005;24(8):1477-80.

Lee et al., Recognition of liposomes by cells: in vitro binding and endocytosis mediated by specific lipid headgroups and surface charge density. Biochim Biophys Acta. Jan. 31, 1992;1103(2):185-97.

Lee et al., Ribozyme Mediated gRNA Generation for In Vitro and In Vivo CRISPR/Cas9 Mutagenesis. PLoS One. Nov. 10, 2016;11(11):e0166020. doi: 10.1371/journal.pone.0166020. eCollection 2016.

Lee et al., Site-specific integration of mycobacteriophage L5: integration-proficient vectors for *Mycobacterium smegmatis*, *Mycobacterium tuberculosis*, and bacille Calmette-Guérin. Proc Natl Acad Sci U S A. Apr. 15, 1991;88(8):3111-5. doi: 10.1073/pnas.88.8.3111.

Lee et al., Synthetically modified guide RNA and donor DNA are a versatile platform for CRISPR-Cas9 engineering. Elife. May 2, 2017;6:e25312. doi: 10.7554/eLife.25312.

Lee et al., Targeted chromosomal deletions in human cells using zinc finger nucleases. Genome Res. Jan. 2010 20: 81-89; Published in Advance Dec. 1, 2009, doi:10.1101/gr.099747.109.

Lee et al., Transcriptional regulation and its misregulation in disease. Cell. Mar. 14, 2013;152(6):1237-51. doi: 10.1016/j.cell. 2013.02.014.

Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.

Lei et al., Site-specificity of serine integrase demonstrated by the attB sequence preference of ?BT1 integrase. FEBS Lett. Apr. 2018;592(8):1389-1399. doi: 10.1002/1873-3468.13023. Epub Mar. 25, 2018.

Lemos et al., CRISPR/Cas9 cleavages in budding yeast reveal templated insertions and strand-specific insertion/deletion profiles. Proc Natl Acad Sci U S A. Feb. 27, 2018;115(9):E2040-E2047. doi: 10.1073/pnas.1716855115. Epub Feb. 13, 2018.

Lenk et al., Pathogenic mechanism of the FIG4 mutation responsible for Charcot-Marie-Tooth disease CMT4J. PLoS Genet. Jun. 2011;7(6):e1002104. doi: 10.1371/journal.pgen.1002104. Epub Jun. 2, 2011.

Levy et al., Cytosine and adenine base editing of the brain, liver, retina, heart and skeletal muscle of mice via adeno-associated viruses. Nat Biomed Eng. 2020;4(1):97-110. doi:10.1038/s41551-019-0501-5.

Levy et al., Inhibition of calcification of bioprosthetic heart valves by local controlled-release diphosphonate. Science. Apr. 12, 1985;228(4696):190-2.

Levy et al., Membrane-associated guanylate kinase dynamics reveal regional and developmental specificity of synapse stability. J Physiol. Mar. 1, 2017;595(5):1699-1709. doi: 10.1113/JP273147. Epub Jan. 18, 2017.

Lew et al., Protein splicing in vitro with a semisynthetic two-component minimal intein. J Biol Chem. Jun. 26, 1998;273(26):15887-90. doi: 10.1074/jbc.273.26.15887.

Lewis et al., A serum-resistant cytofectin for cellular delivery of antisense oligodeoxynucleotides and plasmid DNA. Proc Natl Acad Sci U S A. Apr. 16, 1996;93(8):3176-81.

Lewis et al., Building the Class 2 CRISPR-Cas Arsenal. Mol Cell 2017;65(3);377-379.

Lewis et al., Codon 129 polymorphism of the human prion protein influences the kinetics of amyloid formation. J Gen Virol. Aug. 2006;87(Pt 8):2443-9.

Lewis et al., Cytosine deamination and the precipitous decline of spontaneous mutation during Earth's history. Proc Natl Acad Sci U S A. Jul. 19, 2016;113(29):8194-9. doi: 10.1073/pnas.1607580113. Epub Jul. 5, 2016.

Lewis et al., RNA modifications and structures cooperate to guide RNA-protein interactions. Nat Rev Mol Cell Biol. Mar. 2017;18(3):202-210. doi: 10.1038/nrm.2016.163. Epub Feb. 1, 2017.

Li et al., A Radioactivity-Based Assay for Screening Human m6A-RNA Methyltransferase, METTL3-METTL14 Complex, and Demethylase ALKBH5. J Biomol Screen. Mar. 2016;21(3):290-7. doi: 10.1177/1087057115623264. Epub Dec. 23, 2015.

Li et al., Base editing with a Cpf1-cytidine deaminase fusion. Nat Biotechnol. Apr. 2018;36(4):324-327. doi: 10.1038/nbt.4102. Epub Mar. 19, 2018.

Li et al., Current approaches for engineering proteins with diverse biological properties. Adv Exp Med Biol. 2007;620:18-33.

Li et al., Disruption of splicing-regulatory elements using CRISPR/Cas9 to rescue spinal muscular atrophy in human iPSCs and mice. National Science Review. Jan. 1, 2020:92-101. DOI: 10.1093/nsr/nwz131. Retrieved from the Internet via https://academic.oup.com/nsr/article-pdf/7/1/92/33321439/nwz131.pdf. Last accessed Apr. 28, 2021.

Li et al., Fast and accurate short read alignment with Burrows-Wheeler transform. Bioinformatics. Jul. 15, 2009;25(14):1754-60. doi: 10.1093/bioinformatics/btp324. Epub May 18, 2009.

Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.

Li et al., Highly efficient and precise base editing in discarded human tripronuclear embryos. Protein Cell. Aug. 19, 2017. doi: 10.1007/s13238-017-0458-7. [Epub ahead of print].

(56) References Cited

OTHER PUBLICATIONS

Li et al., Lagging strand DNA synthesis at the eukaryotic replication fork involves binding and stimulation of FEN-1 by proliferating cell nuclear antigen. J Biol Chem. Sep. 22, 1995;270(38):22109-12. doi: 10.1074/jbc.270.38.22109.

Li et al., Loss of post-translational modification sites in disease. Pac Symp Biocomput. 2010:337-47. doi: 10.1142/9789814295291_0036.

Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.

Li et al., Multiplex and homologous recombination-mediated genome editing in *Arabidopsis* and Nicotiana benthamiana using guide RNA and Cas9. Nat Biotechnol. Aug. 2013;31(8):688-91. doi: 10.1038/nbt.2654.

Li et al., Protein trans-splicing as a means for viral vector-mediated in vivo gene therapy. Hum Gene Ther. Sep. 2008;19(9):958-64. doi: 10.1089/hum.2008.009.

Li et al., RSEM: accurate transcript quantification from RNA-Seq data with or without a reference genome. BMC Bioinformatics. Aug. 4, 2011;12:323. doi: 10.1186/1471-2105-12-323.

Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.

Liang et al., Correction of ?-thalassemia mutant by base editor in human embryos. Protein Cell. Nov. 2017;8(11):811-822. doi: 10.1007/s13238-017-0475-6. Epub Sep. 23, 2017.

Liang et al., Homology-directed repair is a major double-strand break repair pathway in mammalian cells. Proc Natl Acad Sci U S A. Apr. 28, 1998;95(9):5172-7. doi: 10.1073/pnas.95.9.5172.

Liang et al., Rapid and highly efficient mammalian cell engineering via Cas9 protein transfection. Send to; J Biotechnol. Aug. 20, 2015;208:44-53. doi: 10.1016/j.jbiotec.2015.04.024.

Lieber et al., Mechanism and regulation of human non-homologous DNA end-joining. Nat Rev Mol Cell Biol. Sep. 2003;4(9):712-20.

Lienert et al., Two- and three-input TALE-based and logic computation in embryonic stem cells. Nucleic Acids Res. Nov. 2013;41(21):9967-75. doi: 10.1093/nar/gkt758. Epub Aug. 27, 2013.

Lilley, D.M. The Varkud Satellite Ribozyme. RNA. Feb. 2004;10(2):151-8.doi: 10.1261/rna.5217104.

Lim et al., Crystal structure of the moloney murine leukemia virus RNase H domain. J Virol. Sep. 2006;80(17):8379-89. doi: 10.1128/JVI.00750-06.

Lin et al., Enhanced homology-directed human genome engineering by controlled timing of CRISPR/Cas9 delivery. Elife. Dec. 15, 2014;3:e04766. doi: 10.7554/eLife.04766.

Link et al., Engineering ligand-responsive gene-control elements: lessons learned from natural riboswitches. Gene Ther. Oct. 2009;16(10):1189-201. doi: 10.1038/gt.2009.81. Epub Jul. 9, 2009. Review.

Liu et al., C2c1-sgRNA Complex Structure Reveals RNA-Guided DNA Cleavage Mechanism. Molecular Cell Jan. 2017;65(2):310-22.

Liu et al., Split dnaE genes encoding multiple novel inteins in Trichodesmium erythraeum. J Biol Chem. Jul. 18, 2003;278(29):26315-8. doi: 10.1074/jbc.C300202200. Epub May 24, 2003.

Liu et al., A METTL3-METTL14 complex mediates mammalian nuclear RNA N6-adenosine methylation. Nat Chem Biol. Feb. 2014;10(2):93-5. doi: 10.1038/nchembio.1432. Epub Dec. 6, 2013.

Liu et al., Adding new chemistries to the genetic code. Annu Rev Biochem. 2010;79:413-44. doi: 10.1146/annurev.biochem.052308.105824.

Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.

Liu et al., Balancing AID and DNA repair during somatic hypermutation. Trends Immunol. Apr. 2009;30(4):173-81. doi: 10.1016/j.it.2009.01.007.

Liu et al., Calcineurin is a common target of cyclophilin-cyclosporin A and FKBP-FK506 complexes. Cell. Aug. 23, 1991;66(4):807-15. doi: 10.1016/0092-8674(91)90124-h.

Liu et al., CasX enzymes comprise a distinct family of RNA-guided genome editors. Nature. Feb. 2019;566(7743):218-223. doi: 10.1038/s41586-019-0908-x. Epub Feb. 4, 2019. Author manuscript entitled CRISPR-CasX is an RNA-dominated enzyme active for human genome editing.

Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.

Liu et al., Design of polydactyl zinc-finger proteins for unique addressing within complex genomes. Proc Natl Acad Sci U S A. May 27, 1997;94(11):5525-30.

Liu et al., Direct Promoter Repression by BCL11A Controls the Fetal to Adult Hemoglobin Switch. Cell. Apr. 5, 2018;173(2):430-442.e17. doi: 10.1016/j.cell.2018.03.016. Epub Mar. 29, 2018.

Liu et al., Distance determination by GIY-YIG intron endonucleases: discrimination between repression and cleavage functions. Nucleic Acids Res. Mar. 31, 2006;34(6):1755-64. Print 2006.

Liu et al., Editing DNA Methylation in the Mammalian Genome. Cell. Sep. 22, 2016;167(1):233-247.e17. doi: 10.1016/j.cell.2016.08.056.

Liu et al., Engineering a tRNA and aminoacyl-tRNA synthetase for the site-specific incorporation of unnatural amino acids into proteins in vivo. Proc Natl Acad Sci U S A. Sep. 16, 1997;94(19):10092-7.

Liu et al., Fast Colorimetric Sensing of Adenosine and Cocaine Based on a General Sensor Design Involving Aptamers and Nanoparticles. Angew Chem. Dec. 16, 2006;45(1):90-4. DOI: 10.1002/anie.200502589.

Liu et al., Fast Colorimetric Sensing of Adenosine and Cocaine Based on a General Sensor Design Involving Aptamers and Nanoparticles. Angew Chem. 2006;118(1):96-100.

Liu et al., Flap endonuclease 1: a central component of DNA metabolism. Annu Rev Biochem. 2004;73:589-615. doi:10.1146/annurev.biochem.73.012803.092453.

Liu et al., Functional Nucleic Acid Sensors. Chem Rev. May 2009;109(5):1948-98. doi: 10.1021/cr030183i.

Liu et al., Genetic incorporation of unnatural amino acids into proteins in mammalian cells. Nat Methods. Mar. 2007;4(3):239-44. Epub Feb. 25, 2007.

Liu et al., Highly efficient RNA-guided base editing in rabbit. Nat Commun. Jul. 13, 2018;9(1):2717. doi: 10.1038/s41467-018-05232-2.

Liu et al., N(6)-methyladenosine-dependent RNA structural switches regulate RNA-protein interactions. Nature. Feb. 26, 2015;518(7540):560-4. doi: 10.1038/nature14234.

Liu et al., Probing N6-methyladenosine RNA modification status at single nucleotide resolution in mRNA and long noncoding RNA. RNA. Dec. 2013;19(12):1848-56. doi: 10.1261/rna.041178.113. Epub Oct. 18, 2013.

Liu et al., Reverse transcriptase of foamy virus. Purification of the enzymes and immunological identification. Arch Virol. 1977;55(3):187-200. doi: 10.1007/BF01319905.

Liu et al., Reverse transcriptase-mediated tropism switching in Bordetella bacteriophage. Science. Mar. 15, 2002;295(5562):2091-4. doi: 10.1126/science.1067467.

Liu et al., *Saccharomyces cerevisiae* flap endonuclease 1 uses flap equilibration to maintain triplet repeat stability. Mol Cell Biol. May 2004;24(9):4049-64. doi: 10.1128/MCB.24.9.4049-4064.2004.

Liu et al., The Molecular Architecture for RNA-Guided RNA Cleavage by Cas13a. Cell. Aug. 10, 2017;170(4):714-726.e10. doi: 10.1016/j.cell.2017.06.050. Epub Jul. 27, 2017.

Loessner et al., Complete nucleotide sequence, molecular analysis and genome structure of bacteriophage A118 of Listeria monocytogenes: implications for phage evolution. Mol Microbiol. Jan. 2000;35(2):324-40. doi: 10.1046/j.1365-2958.2000.01720.x.

Lombardo et al., Gene editing in human stem cells using zinc finger nucleases and integrase-defective lentiviral vector delivery. Nat Biotechnol. Nov. 2007;25(11):1298-306. Epub Oct. 28, 2007.

(56) References Cited

OTHER PUBLICATIONS

Long et al., Postnatal genome editing partially restores dystrophin expression in a mouse model of muscular dystrophy. Science. Jan. 22, 2016;351(6271):400-3. doi: 10.1126/science.aad5725. Epub Dec. 31, 2015.

Lopez-Girona et al., Cereblon is a direct protein target for immunomodulatory and antiproliferative activities of lenalidomide and pomalidomide. Leukemia. Nov. 2012;26(11):2326-35. doi: 10.1038/leu.2012.119. Epub May 3, 2012.

Lorenz et al., ViennaRNA Package 2.0. Algorithms Mol Biol. Nov. 24, 2011;6:26. doi: 10.1186/1748-7188-6-26.

Losey et al., Crystal structure of *Staphylococcus sureus* tRNA adenosine deaminase tadA in complex with RNA. Nature Struct. Mol. Biol. Feb. 2006;13(2):153-9.

Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.

Luan et al., Reverse transcription of R2Bm RNA is primed by a nick at the chromosomal target site: a mechanism for non-LTR retrotransposition. Cell. Feb. 26, 1993;72(4):595-605. doi: 10.1016/0092-8674(93)90078-5.

Luckow et al., High level expression of nonfused foreign genes with Autographa californica nuclear polyhedrosis virus expression vectors. Virology. May 1989;170(1):31-9. doi: 10.1016/0042-6822(89)90348-6.

Lukacsovich et al., Repair of a specific double-strand break generated within a mammalian chromosome by yeast endonuclease I-SceI. Nucleic Acids Res. Dec. 25, 1994;22(25):5649-57. doi: 10.1093/nar/22.25.5649.

Lüke et al., Partial purification and characterization of the reverse transcriptase of the simian immunodeficiency virus TYO-7 isolated from an African green monkey. Biochemistry. Feb. 20, 1990;29(7):1764-9. doi: 10.1021/bi00459a015.

Lundberg et al., Delivery of short interfering RNA using endosomolytic cell-penetrating peptides. FASEB J. Sep. 2007;21(11):2664-71. Epub Apr. 26, 2007.

Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.

Lynch, Evolution of the mutation rate. Trends Genet. Aug. 2010;26(8):345-52. doi: 10.1016/j.tig.2010.05.003. Epub Jun. 30, 2010.

Lyons et al., Efficient Recognition of an Unpaired Lesion by a DNA Repair Glycosylase. J. Am. Chem. Soc., 2009;131(49):17742-3. DOI: 10.1021/ja908378y.

Ma et al., Identification of pseudo attP sites for phage phiC31 integrase in bovine genome. Biochem Biophys Res Commun. Jul. 7, 2006;345(3):984-8. doi: 10.1016/j.bbrc.2006.04.145. Epub May 3, 2006.

Ma et al., In vitro protein engineering using synthetic tRNA(Ala) with different anticodons. Biochemistry. Aug. 10, 1993;32(31):7939-45.

Ma et al., PhiC31 integrase induces efficient site-specific recombination in the Capra hircus genome. DNA Cell Biol. Aug. 2014;33(8):484-91. doi: 10.1089/dna.2013.2124. Epub Apr. 22, 2014.

Ma et al., Single-Stranded DNA Cleavage by Divergent CRISPR-Cas9 Enzymes. Mol Cell. Nov. 5, 2015;60(3):398-407. doi: 10.1016/j.molcel.2015.10.030.

Ma et al., Targeted AID-mediated mutagenesis (TAM) enables efficient genomic diversification in mammalian cells. Nature Methods. Oct. 2016;13:1029-35. doi:10.1038/nmeth.4027.

Maas et al., Identification and characterization of a human tRNA-specific adenosine deaminase related to the ADAR family of pre-mRNA editing enzymes. Proc Natl Acad Sci U S A. Aug. 3, 1999;96(16):8895-900. doi: 10.1073/pnas.96.16.8895.

Macbeth et al., Inositol hexakisphosphate is bound in the ADAR2 core and required for RNA editing. Science. Sep. 2, 2005;309(5740):1534-9. doi: 10.1126/science.1113150.

Macrae et al., Ribonuclease revisited: structural insights into ribonuclease III family enzymes. Curr Opin Struct Biol. Feb. 2007;17(1):138-45. doi: 10.1016/j.sbi.2006.12.002. Epub Dec. 27, 2006.

Maeder et al., CRISPR RNA-guided activation of endogenous human genes. Nat Methods. Oct. 2013;10(10):977-9. doi: 10.1038/nmeth.2598. Epub Jul. 25, 2013.

Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.

Maeder et al., Robust, synergistic regulation of human gene expression using TALE activators. Nat Methods. Mar. 2013;10(3):243-5. doi: 10.1038/nmeth.2366. Epub Feb. 10, 2013.

Magin et al., Corf, the Rev/Rex homologue of HTDV/HERV-K, encodes an arginine-rich nuclear localization signal that exerts a trans-dominant phenotype when mutated. Virology. Aug. 15, 2000;274(1):11-6. doi: 10.1006/viro.2000.0438.

Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.

Makarova et al., Prokaryotic homologs of Argonaute proteins are predicted to function as key components of a novel system of defense against mobile genetic elements. Biology Direct 2009;4:29.

Makarova et al., An updated evolutionary classification of CRISPR-Cas systems. Nat Rev Microbiol. Nov. 2015;13(11):722-36. doi: 10.1038/nrmicro3569. Epub Sep. 28, 2015.

Makarova et al., Classification and Nomenclature of CRISPR-Cas Systems: Where from Here? CRISPR J. Oct. 2018;1(5):325-336. doi: 10.1089/crispr.2018.0033.

Makarova et al., Evolution and classification of the CRISPR-Cas systems. Nat Rev Microbiol. Jun. 2011;9(6):467-77. doi: 10.1038/nrmicro2577. Epub May 9, 2011.

Makeyev et al., Evolutionary potential of an RNA virus. J Virol. Feb. 2004;78(4):2114-20.

Malashkevich et al., Crystal structure of tRNA adenosine deaminase TadA from *Escherichia coli*. Deposited: Mar. 10, 2005 Released: Feb. 21, 2006 doi:10.2210/pdb1z3a/pdb (2006).

Mali et al., Cas9 as a versatile tool for engineering biology. Nat Methods. Oct. 2013;10(10):957-63. doi: 10.1038/nmeth.2649.

Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.

Mali et al., RNA-guided human genome engineering via Cas9. Science. Feb. 15, 2013;339(6121):823-6. doi: 10.1126/science.1232033. Epub Jan. 3, 2013.

Malito et al., Structural basis for lack of toxicity of the diphtheria toxin mutant CRM197. Proc Natl Acad Sci U S A. Apr. 3, 2012;109(14):5229-34. doi: 10.1073/pnas.1201964109. Epub Mar. 19, 2012.

Mandal et al., Efficient ablation of genes in human hematopoietic stem and effector cells using CRISPR/Cas9. Cell Stem Cell. Nov. 6, 2014;15(5):643-52. doi: 10.1016/j.stem.2014.10.004. Epub Nov. 6, 2014.

Mandal et al., Riboswitches Control Fundamental Biochemical Pathways in Bacillus Subtilis and Other Bacteria. Cell. May 30, 2003;113(5):577-86. doi: 10.1016/s0092-8674(03)00391-x.

Mani et al., Design, engineering, and characterization of zinc finger nucleases. Biochem Biophys Res Commun. Sep. 23, 2005;335(2):447-57.

Marceau, Functions of single-strand DNA-binding proteins in DNA replication, recombination, and repair. Methods Mol Biol. 2012;922:1-21. doi: 10.1007/978-1-62703-032-8_1.

Maresca et al., Obligate ligation-gated recombination (ObLiGaRe): custom-designed nuclease-mediated targeted integration through nonhomologous end joining. Genome Res. Mar. 2013;23(3):539-46. Doi: 10.1101/gr.145441.112. Epub Nov. 14, 2012.

Marioni et al., DNA methylation age of blood predicts all-cause mortality in later life. Genome Biol. Jan. 30, 2015;16:25. doi: 10.1186/s13059-015-0584-6.

(56) References Cited

OTHER PUBLICATIONS

Marquart et al., Predicting base editing outcomes with an attention-based deep learning algorithm trained on high-throughput target library screeen. bioRxiv. Jul. 5, 2020. DOI:10.1101/2020.07.05.186544. Retrieved from the Internet via https://www.biorxiv.org/content/10.1101/2020.07.05.186544v1.full.pdf lased accessed on Apr. 28, 2021.

Marraffini et al., CRISPR interference limits horizontal gene transfer in staphylococci by targeting DNA. Science. Dec. 19, 2008;322(5909):1843-5. doi: 10.1126/science.1165771.

Martinez et al., Hypermutagenesis of RNA using human immunodeficiency virus type 1 reverse transcriptase and biased dNTP concentrations. Proc Natl Acad Sci U S A. Dec. 6, 1994;91(25):11787-91. doi: 10.1073/pnas.91.25.11787.

Martsolf et al., Complete trisomy 17p a relatively new syndrome. Ann Genet. 1988;31(3):172-4.

Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.

Mascola et al., HIV-1 neutralizing antibodies: understanding nature's pathways Immunol Rev. Jul. 2013;254(1):225-44. doi: 10.1111/imr.12075.

Mathys et al., Characterization of a self-splicing mini-intein and its conversion into autocatalytic N- and C-terminal cleavage elements: facile production of protein building blocks for protein ligation. Gene. Apr. 29, 1999;231(1-2):1-13. doi: 10.1016/s0378-1119(99)00103-1.

Matsuura et al., A gene essential for the site-specific excision of actinophage r4 prophage genome from the chromosome of a lysogen. J Gen Appl Microbiol. 1995;41(1):53-61.

Matthews, Structures of human ADAR2 bound to dsRNA reveal base-flipping mechanism and basis for site selectivity. Nat Struct Mol Biol. May 2016;23(5):426-33. doi: 10.1038/nsmb.3203. Epub Apr. 11, 2016.

May et al., Emergent lineages of mumps virus suggest the need for a polyvalent vaccine. Int J Infect Dis. Jan. 2018;66:1-4. doi: 10.1016/j.ijid.2017.09.024. Epub Oct. 4, 2017.

McCarroll et al., Copy-number variation and association studies of human disease. Nat Genet. Jul. 2007;39(7 Suppl):537-42. doi: 10.1038/ng2080.

McDonald et al., Characterization of mutations at the mouse phenylalanine hydroxylase locus. Genomics. Feb. 1, 1997;39(3):402-5. doi: 10.1006/geno.1996.4508.

McInerney et al., Error Rate Comparison during Polymerase Chain Reaction by DNA Polymerase. Mol Biol Int. 2014;2014:287430. doi: 10.1155/2014/287430. Epub Aug. 17, 2014.

McKenna et al., Recording development with single cell dynamic lineage tracing. Development. Jun. 27, 2019;146(12):dev169730. doi: 10.1242/dev.169730.

McKenna et al., Whole-organism lineage tracing by combinatorial and cumulative genome editing. Science. Jul. 29, 2016;353(6298):aaf7907. doi: 10.1126/science.aaf7907. Epub May 26, 2016.

McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.

McVey et al., MMEJ repair of double-strand breaks (director's cut): deleted sequences and alternative endings. Trends Genet. Nov. 2008;24(11):529-38. doi: 10.1016/j.tig.2008.08.007. Epub Sep. 21, 2008.

Mead et al., A novel protective prion protein variant that colocalizes with kuru exposure. N Engl J Med. Nov. 19, 2009;361(21):2056-65. doi: 10.1056/NEJMoa0809716.

Meckler et al., Quantitative analysis of TALE-DNA interactions suggests polarity effects. Nucleic Acids Res. Apr. 2013;41(7):4118-28. doi: 10.1093/nar/gkt085. Epub Feb. 13, 2013.

Mei et al., Recent Progress in CRISPR/Cas9 Technology. J Genet Genomics. Feb. 20, 2016;43(2):63-75. doi: 10.1016/j.jgg.2016.01.001. Epub Jan. 18, 2016.

Meinke et al., Cre Recombinase and Other Tyrosine Recombinases. Chem Rev. Oct. 26, 2016;116(20):12785-12820. doi: 10.1021/acs.chemrev.6b00077. Epub May 10, 2016.

Menéndez-Arias, Mutation rates and intrinsic fidelity of retroviral reverse transcriptases. Viruses. Dec. 2009;1(3):1137-65. doi: 10.3390/v1031137. Epub Dec. 4, 2009.

Meng et al., Targeted gene inactivation in zebrafish using engineered zinc-finger nucleases. Nat Biotechnol. Jun. 2008;26(6):695-701. doi: 10.1038/nbt1398. Epub May 25, 2008.

Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.

Mertens et al., Site-specific recombination in bacteriophage Mu: characterization of binding sites for the DNA invertase Gin. EMBO J. Apr. 1988;7(4):1219-27.

Meyer et al., Breathing life into polycations: functionalization with pH-responsive endosomolytic peptides and polyethylene glycol enables siRNA delivery. J Am Chem Soc. Mar. 19, 2008;130(11):3272-3. doi: 10.1021/ja710344v. Epub Feb. 21, 2008.

Meyer et al., Comprehensive analysis of mRNA methylation reveals enrichment in 3' UTRs and near stop codons. Cell. Jun. 22, 2012;149(7):1635-46. doi: 10.1016/j.cell.2012.05.003. Epub May 17, 2012.

Meyer et al., Confirmation of a second natural preQ1 aptamer class in Streptococcaceae bacteria. RNA. Apr. 2008;14(4):685-95. doi: 10.1261/rna.937308. Epub Feb. 27, 2008.

Meyer et al., Library generation by gene shuffling. Curr Protoc Mol Biol. Jan. 6, 2014;105:Unit 15.12.. doi: 10.1002/0471142727.mb1512s105.

Meyer et al., The dynamic epitranscriptome: N6-methyladenosine and gene expression control. Nat Rev Mol Cell Biol. May 2014;15(5):313-26. doi: 10.1038/nrm3785. Epub Apr. 9, 2014.

Michel et al., Mitochondrial class II introns encode proteins related to the reverse transcriptases of retroviruses. Nature. Aug. 15-21, 1985;316(6029):641-3. doi: 10.1038/316641a0.

Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.1476-5381.2009.00288.x.

Mihai et al., PTEN inhibition improves wound healing in lung epithelia through changes in cellular mechanics that enhance migration. Am J Physiol Lung Cell Mol Physiol. 2012;302(3):L287-L299.

Mijakovic et al., Bacterial single-stranded DNA-binding proteins are phosphorylated on tyrosine. Nucleic Acids Res. Mar. 20, 2006;34(5):1588-96. doi: 10.1093/nar/gkj514.

Miller et al., A TALE nuclease architecture for efficient genome editing. Nat Biotechnol. Feb. 2011;29(2):143-8. doi:10.1038/nbt.1755. Epub Dec. 22, 2010.

Miller et al., An improved zinc-finger nuclease architecture for highly specific genome editing. Nat Biotechnol. Jul. 2007;25(7):778-85. Epub Jul. 1, 2007.

Miller et al., Construction and properties of retrovirus packaging cells based on gibbon ape leukemia virus. J Virol. May 1991;65(5):2220-4. doi: 10.1128/JVI.65.5.2220-2224.1991.

Miller, Human gene therapy comes of age. Nature. Jun. 11, 1992;357(6378):455-60. doi: 10.1038/357455a0.

Mills et al., Protein splicing in trans by purified N- and C-terminal fragments of the *Mycobacterium tuberculosis* RecA intein. Proc Natl Acad Sci U S A. Mar. 31, 1998;95(7):3543-8. doi: 10.1073/pnas.95.7.3543.

Minoche et al., Evaluation of genomic high-throughput sequencing data generated on Illumina HiSeq and genome analyzer systems. Genome Biol. Nov. 8, 2011;12(11):R112. doi: 10.1186/gb-2011-12-11-r112.

Minoretti et al., A W148R mutation in the human FOXD4 gene segregating with dilated cardiomyopathy, obsessive-compulsive disorder, and suicidality. Int J Mol Med. Mar. 2007;19(3):369-72.

Mir et al., Two Active Site Divalent Ions in the Crystal Structure of the Hammerhead Ribozyme Bound to a Transition State Analogue.

(56) References Cited

OTHER PUBLICATIONS

Biochemistry . . . Feb. 2, 2016;55(4):633-6. doi: 10.1021/acs.biochem.5b01139. Epub Jan. 19, 2016.

Mishina et al., Conditional gene targeting on the pure C57BL/6 genetic background. Neurosci Res. Jun. 2007;58(2):105-12. doi: 10.1016/j.neures.2007.01.004. Epub Jan. 18, 2007.

Mitani et al., Delivering therapeutic genes—matching approach and application. Trends Biotechnol. May 1993;11(5):162-6. doi: 10.1016/0167-7799(93)90108-L.

Mitton-Fry et al., Poly(A) tail recognition by a viral RNA element through assembly of a triple helix. Science. Nov. 26, 2010;330(6008):1244-7. doi: 10.1126/science.1195858.

Miyaoka et al., Systematic quantification of HDR and NHEJ reveals effects of locus, nuclease, and cell type on genome-editing. Sci Rep. Mar. 31, 2016;6:23549. doi: 10.1038/srep23549.

Moede et al., Identification of a nuclear localization signal, RRMKWKK, in the homeodomain transcription factor PDX-1. FEBS Lett. Nov. 19, 1999;461(3):229-34. doi: 10.1016/s0014-5793(99)01446-5.

Mohr et al., A Reverse Transcriptase-Cas1 Fusion Protein Contains a Cas6 Domain Required for Both CRISPR RNA Biogenesis and RNA Spacer Acquisition. Mol Cell. Nov. 15, 2018;72(4):700-714.e8. doi: 10.1016/j.molcel.2018.09.013. Epub Oct. 18, 2018.

Mohr et al., Thermostable group II intron reverse transcriptase fusion proteins and their use in cDNA synthesis and next-generation RNA sequencing. RNA. Jul. 2013;19(7):958-70. doi: 10.1261/rna.039743.113. Epub May 22, 2013.

Mojica et al., Intervening sequences of regularly spaced prokaryotic repeats derive from foreign genetic elements. J Mol Evol. Feb. 2005;60(2):174-82.

Mok et al., A bacterial cytidine deaminase toxin enables CRISPR-free mitochondrial base editing. Nature. Jul. 2020;583(7817):631-637. doi: 10.1038/s41586-020-2477-4. Epub Jul. 8, 2020.

Mol et al., Crystal structure of human uracil-DNA glycosylase in complex with a protein inhibitor: protein mimicry of DNA. Cell. Sep. 8, 1995;82(5):701-8.

Molla et al., CRISPR/Cas-Mediated Base Editing: Technical Considerations and Practical Applications. Trends Biotechnol. Oct. 2019;37(10):1121-1142. doi: 10.1016/j.tibtech.2019.03.008. Epub Apr. 14, 2019.

Monahan et al., Site-specific incorporation of unnatural amino acids into receptors expressed in Mammalian cells. Chem Biol. Jun. 2003;10(6):573-80.

Monot et al., The specificity and flexibility of l1 reverse transcription priming at imperfect T-tracts. PLoS Genet. May 2013;9(5):e1003499. doi: 10.1371/journal.pgen.1003499. Epub May 9, 2013.

Montange et al., Structure of the S-adenosylmethionine riboswitch regulatory mRNA element. Nature. Jun. 29, 2006;441(7097):1172-5.

Moore et al., Improved somatic mutagenesis in zebrafish using transcription activator-like effector nucleases (TALENs). PloS One. 2012;7(5):e37877. Doi: 10.1371/journal.pone.0037877. Epub May 24, 2012.

Mootz et al., Conditional protein splicing: a new tool to control protein structure and function in vitro and in vivo. J Am Chem Soc. Sep. 3, 2003;125(35):10561-9.

Mootz et al., Protein splicing triggered by a small molecule. J Am Chem Soc. Aug. 7, 2002;124(31):9044-5.

Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.

Morita et al., The site-specific recombination system of actinophage TG1. FEMS Microbiol Lett. Aug. 2009;297(2):234-40. doi: 10.1111/j.1574-6968.2009.01683.x.

Morris et al., A peptide carrier for the delivery of biologically active proteins into mammalian cells. Nat Biotechnol. Dec. 2001;19(12):1173-6.

Moscou et al., A simple cipher governs DNA recognition by TAL effectors. Science. Dec. 11, 2009;326(5959):1501. doi: 10.1126/science.1178817.

Muir et al., Expressed protein ligation: a general method for protein engineering. Proc Natl Acad Sci U S A. Jun. 9, 1998;95(12):6705-10. doi: 10.1073/pnas.95.12.6705.

Muller et al., Nucleotide exchange and excision technology (NExT) DNA shuffling: a robust method for DNA fragmentation and directed evolution. Nucleic Acids Res. Aug. 1, 2005;33(13):e117. doi: 10.1093/nar/gni116. PMID: 16061932; PMCID: PMC1182171.

Mullins et al., Transgenesis in nonmurine species. Hypertension. Oct. 1993;22(4):630-3.

Mumtsidu et al., Structural features of the single-stranded DNA-binding protein of Epstein-Barr virus. J Struct Biol. Feb. 2008;161(2):172-87. doi: 10.1016/j.jsb.2007.10.014. Epub Nov. 1, 2007.

Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

Muzyczka et al., Adeno-associated virus (AAV) vectors: will they work? J Clin Invest. Oct. 1994;94(4):1351. doi: 10.1172/JCI117468.

Myerowitz et al., the major defect in Ashkenazi Jews with Tay-Sachs disease is an insertion in the gene for the alpha-chain of beta-hexosaminidase. J Biol Chem. Dec. 15, 1988;263(35):18587-9.

Myers et al., Insulin signal transduction and the IRS proteins. Annu Rev Pharmacol Toxicol. 1996;36:615-58. doi: 10.1146/annurev.pa.36.040196.003151.

Nabel et al., Direct gene transfer for immunotherapy and immunization. Trends Biotechnol. May 1993;11(5):211-5. doi: 10.1016/0167-7799(93)90117-R.

Nahar et al., A G-quadruplex motif at the 3' end of sgRNAs improves CRISPR-Cas9 based genome editing efficiency. Chem Commun (Camb). Mar. 7, 2018;54(19):2377-2380. doi: 10.1039/c7cc08893k. Epub Feb. 16, 2018.

Nahvi et al., Coenzyme B12 riboswitches are widespread genetic control elements in prokaryotes. Nucleic Acids Res. Jan. 2, 2004;32(1):143-50.

Nakade et al., Microhomology-mediated end-joining-dependent integration of donor DNA in cells and animals using TALENs and CRISPR/Cas9. Nat Commun. Nov. 20, 2014;5:5560. doi: 10.1038/ncomms6560.

Nakamura et al., Codon usage tabulated from international DNA sequence databases: status for the year 2000. Nucleic Acids Res. Jan. 1, 2000;28(1):292. doi: 10.1093/nar/28.1.292.

Naorem et al., DGR mutagenic transposition occurs via hypermutagenic reverse transcription primed by nicked template Rna. Proc Natl Acad Sci U S A. Nov. 21, 2017;114(47):E10187-E10195. doi: 10.1073/pnas.1715952114. Epub Nov. 6, 2017.

Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.

Navaratnam et al., An overview of cytidine deaminases. Int J Hematol. Apr. 2006;83(3):195-200.

NCBI Reference Sequence: NM_002427.3. Wu et al., May 3, 2014. 5 pages.

Neel et al., Riboswitches: Classification, function and in silico approach, International Journal of Pharma Sciences and Research. 2010;1(9):409-420.

Nelson et al., Filamentous phage DNA cloning vectors: a noninfective mutant with a nonpolar deletion in gene III. Virology. 1981;108(2): 338-50.

Nern et al., Multiple new site-specific recombinases for use in manipulating animal genomes. Proc Natl Acad Sci USA. Aug. 23, 2011;108(34):14198-203. doi: 10.1073/pnas.1111704108. Epub Aug. 9, 2011.

Newby et al., Base editing of haematopoietic stem cells rescues sickle cell disease in mice. Nature. Jun. 2, 2021. doi: 10.1038/s41586-021-03609-w. Epub ahead of print.

(56) References Cited

OTHER PUBLICATIONS

Nguyen et al., Evolutionary drivers of thermoadaptation in enzyme catalysis. Science. Jan. 20, 2017;355(6322):289-294. doi: 10.1126/science.aah3717. Epub Dec. 22, 2016.

Nguyen et al., IQ-TREE: a fast and effective stochastic algorithm for estimating maximum-likelihood phylogenies. Mol Biol Evol. Jan. 2015;32(1):268-74. doi: 10.1093/molbev/msu300. Epub Nov. 3, 2014.

Ni et al., A PCSK9-binding antibody that structurally mimics the EGF(A) domain of LDL-receptor reduces LDL cholesterol in vivo. J Lipid Res. 2011;52:76-86.

Ni et al., Nucleic acid aptamers: clinical applications and promising new horizons. Curr Med Chem. 2011;18(27):4206-14. Review.

Nishida et al., Targeted nucleotide editing using hybrid prokaryotic and vertebrate adaptive immune systems. Science. Sep. 16, 2016;353(6305):1248. pii: aaf8729. doi: 10.1126/science.aaf8729. Epub Aug. 4, 2016.

Nishikura, Functions and regulation of RNA editing by ADAR deaminases. Annu Rev Biochem. 2010;79:321-349. doi:10.1146/annurev-biochem-060208-105251.

Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.

Nishimasu et al., Crystal Structure of *Staphylococcus Aureus* Cas9. Cell. Aug. 27, 2015;162(5):1113-26. doi: 10.1016/j.cell.2015.08.007.

Nishimasu et al., Engineered CRISPR-Cas9 nuclease with expanded targeting space. Science. Sep. 21, 2018;361(6408):1259-1262. doi: 10.1126/science.aas9129. Epub Aug. 30, 2018.

Nomura et al., Controlling Mammalian Gene Expression by Allosteric Hepatitis Delta Virus Ribozymes. ACS Synth Biol. Dec. 20, 2013;2(12):684-9. doi: 10.1021/sb400037a. Epub May 22, 2013.

Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.

Noris et al., A phenylalanine-55 to serine amino-acid substitution in the human glycoprotein IX leucine-rich repeat is associated with Bernard-Soulier syndrome. Br J Haematol. May 1997;97(2):312-20.

Nottingham et al., RNA-seq of human reference RNA samples using a thermostable group II intron reverse transcriptase. RNA. Apr. 2016;22(4):597-613. doi: 10.1261/rna.055558.115. Epub Jan. 29, 2016.

Nowak et al., Characterization of single-stranded DNA-binding proteins from the psychrophilic bacteria Desulfotalea psychrophila, Flavobacterium psychrophilum, Psychrobacter arcticus, Psychrobacter cryohalolentis, Psychromonas ingrahamii, Psychroflexus torquis, and Photobacterium profundum. BMC Microbiol. Apr. 14, 2014;14:91. doi: 10.1186/1471-2180-14-91.

Nowak et al., Guide RNA Engineering for Versatile Cas9 Functionality. Nucleic Acids Res. Nov. 16, 2016;44(20):9555-9564. doi: 10.1093/nar/gkw908. Epub Oct. 12, 2016.

Nowak et al., Structural analysis of monomeric retroviral reverse transcriptase in complex with an RNA/DNA hybrid. Nucleic Acids Res. Apr. 1, 2013;41(6):3874-87. doi: 10.1093/nar/gkt053. Epub Feb. 4, 2013.

Numrych et al., A comparison of the effects of single-base and triple-base changes in the integrase arm-type binding sites on the site-specific recombination of bacteriophage lambda. Nucleic Acids Res. Jul. 11, 1990;18(13):3953-9. doi: 10.1093/nar/18.13.3953.

Nyerges et al., A highly precise and portable genome engineering method allows comparison of mutational effects across bacterial species. Proc Natl Acad Sci U S A. Mar. 1, 2016;113(9):2502-7. doi: 10.1073/pnas.1520040113. Epub Feb. 16, 2016.

Oakes et al., CRISPR-Cas9 Circular Permutants as Programmable Scaffolds for Genome Modification. Cell. Jan. 10, 2019;176(1-2):254-267.e16. doi: 10.1016/j.cell.2018.11.052.

Oakes et al., Profiling of engineering hotspots identifies an allosteric CRISPR-Cas9 switch. Nat Biotechnol. Jun. 2016;34(6):646-51. doi: 10.1038/nbt.3528. Epub May 2, 2016.

Oakes et al., Protein engineering of Cas9 for enhanced function. Methods Enzymol. 2014;546:491-511.

O'Connell et al., Programmable RNA recognition and cleavage by CRISPR/Cas9. Nature. Dec. 11, 2014;516(7530):263-6. doi: 10.1038/nature13769. Epub Sep. 28, 2014.

Odsbu et al., Specific N-terminal interactions of the *Escherichia coli* SeqA protein are required to form multimers that restrain negative supercoils and form foci. Genes Cells. Nov. 2005;10(11):1039-49.

Oeemig et al., Solution structure of DnaE intein from Nostoc punctiforme: structural basis for the design of a new split intein suitable for site-specific chemical modification. FEBS Lett. May 6, 2009;583(9):1451-6.

Offord, Advances in Genome Editing. The Scientist, Apr. 20, 2016. http://www.the-scientist.com/?articles.view/articleNo/45903/title/Advances-in-Genome-Editing/.

Oh et al., Positional cloning of a gene for Hermansky-Pudlak syndrome, a disorder of cytoplasmic organelles. Nat Genet. Nov. 1996;14(3):300-6. doi: 10.1038/ng1196-300.

Ohe et al., Purification and properties of xanthine dehydrogenase from Streptomyces cyanogenus. J Biochem. Jul. 1979;86(1):45-53.

Olivares et al., Site-specific genomic integration produces therapeutic Factor IX levels in mice. Nat Biotechnol. Nov. 2002;20(11):1124-8. doi: 10.1038/nbt753. Epub Oct. 15, 2002.

Olorunniji et al., Purification and In Vitro Characterization of Zinc Finger Recombinases. Methods Mol Biol. 2017;1642:229-245. doi: 10.1007/978-1-4939-7169-5_15.

Olorunniji et al., Site-specific recombinases: molecular machines for the Genetic Revolution. Biochem J. Mar. 15, 2016;473(6):673-84. doi: 10.1042/BJ20151112.

O'Maille et al., Structure-based combinatorial protein engineering (SCOPE). J Mol Biol. Aug. 23, 2002;321(4):677-91.

Orlando et al., Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.

Orthwein et al., A mechanism for the suppression of homologous recombination in G1 cells. Nature. Dec. 17, 2015;528(7582):422-6. doi: 10.1038/nature16142. Epub Dec. 9, 2015.

Ortiz-Urda et al., Stable nonviral genetic correction of inherited human skin disease. Nat Med. Oct. 2002;8(10):1166-70. doi: 10.1038/nm766. Epub Sep. 16, 2002. Erratum in: Nat Med. Feb. 2003;9(2):237.

Osborn et al., TALEN-based gene correction for epidermolysis bullosa. Mol Ther. Jun. 2013;21(6):1151-9. doi: 10.1038/mt.2013.56. Epub Apr. 2, 2013.

Ostermeier et al., A combinatorial approach to hybrid enzymes independent of DNA homology. Nat Biotechnol. Dec. 1999;17(12):1205-9.

Ostertag et al., Biology of mammalian L1 retrotransposons. Annu Rev Genet. 2001;35:501-38. doi: 10.1146/annurev.genet.35.102401.091032.

Otomo et al., Improved segmental isotope labeling of proteins and application to a larger protein. J Biomol NMR. Jun. 1999;14(2):105-14. doi: 10.1023/a:1008308128050.

Otomo et al., NMR observation of selected segments in a larger protein: central-segment isotope labeling through intein-mediated ligation. Biochemistry. Dec. 7, 1999;38(49):16040-4. doi: 10.1021/bi991902j.

Otto et al., The probability of fixation in populations of changing size. Genetics. Jun. 1997;146(2):723-33.

Paige et al., RNA mimics of green fluorescent protein. Science. Jul. 29, 2011;333(6042):642-6. doi:10.1126/science.1207339.

Paiva et al., Targeted protein degradation: elements of PROTAC design. Curr Opin Chem Biol. Jun. 2019;50:111-119. doi: 10.1016/j.cbpa.2019.02.022. Epub Apr. 17, 2019.

Pan et al., Biological and biomedical applications of engineered nucleases. Mol Biotechnol. Sep. 2013;55(1):54-62. doi: 10.1007/s12033-012-9613-9.

Paquet et al., Efficient introduction of specific homozygous and heterozygous mutations using CRISPR/Cas9. Nature. May 5, 2016;533(7601):125-9. doi: 10.1038/nature17664. Epub Apr. 27, 2016.

(56) References Cited

OTHER PUBLICATIONS

Park et al., Digenome-seq web tool for profiling CRISPR specificity. Nat Methods. May 30, 2017;14(6):548-549. doi: 10.1038/nmeth. 4262.
Park et al., Highly efficient editing of the ?-globin gene in patient-derived hematopoietic stem and progenitor cells to treat sickle cell disease. Nucleic Acids Res. Sep. 5, 2019;47(15):7955-7972. doi: 10.1093/nar/gkz475.
Park et al., Sendai virus, an RNA virus with no risk of genomic integration, delivers CRISPR/Cas9 for efficient gene editing. Mol Ther Methods Clin Dev. Aug. 24, 2016;3:16057. doi: 10.1038/mtm. 2016.57.
Parker et al., Admixture mapping identifies a quantitative trait locus associated with PEV1/FVC in the COPDGene Study. Genet Epidemiol. Nov. 2014;38(7):652-9. doi: 10.1002/gepi.21847. Epub Aug. 11, 2014.
Partial Supplementary European Search Report for Application No. EP 12845790.0, dated Mar. 18, 2015.
Patel et al., Flap endonucleases pass 5'-flaps through a flexible arch using a disorder-thread-order mechanism to confer specificity for free 5'-ends. Nucleic Acids Res. May 2012;40(10):4507-19. doi: 10.1093/nar/gks051. Epub Feb. 8, 2012.
Pattanayak et al., Determining the specificities of TALENs, Cas9, and other genome-editing enzymes. Methods Enzymol. 2014;546:47-78. doi: 10.1016/B978-0-12-801185-0.00003-9.
Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.
Pattanayak et al., Revealing off-target cleavage specificities of zinc-finger nucleases by in vitro selection. Nat Methods. Aug. 7, 2011;8(9):765-70. doi: 10.1038/nmeth.1670.
Pavletich et al., Zinc finger-DNA recognition: crystal structure of a Zif268-DNA complex at 2.1 A. Science. May 10, 1991;252(5007):809-17.
Pawson et al., Protein phosphorylation in signaling—50 years and counting. Trends Biochem Sci. Jun. 2005;30(6):286-90. doi: 10.1016/j.tibs.2005.04.013.
Pearl, Structure and function in the uracil-DNA glycosylase superfamily. Mutat Res. Aug. 30, 2000;460(3-4):165-81.
Peck et al., Directed evolution of a small-molecule-triggered intein with improved splicing properties in mammalian cells. Chem Biol. May 27, 2011;18(5):619-30. doi: 10.1016/j.chembiol.2011.02.014.
Pellenz et al., New human chromosomal safe harbor sites for genome engineering with CRISPR/Cas9, TAL effector and homing endonucleases. Aug. 20, 2018. bioRxiv doi: https://doi.org/10.1101/396390.
Pelletier, CRISPR-Cas systems for the study of the immune function. Nov. 15, 2016. https://doi.org/10.1002/9780470015902.a0026896.
Pennisi et al., The CRISPR craze. Science. Aug. 23, 2013;341(6148):833-6. doi: 10.1126/science.341.6148.833.
Pennisi et al., The Tale of the TALEs. Science. Dec. 14, 2012;338(6113):1408-11. doi: 10.1126/science.338.6113.1408.
Perach et al., Catalytic features of the recombinant reverse transcriptase of bovine leukemia virus expressed in bacteria. Virology. Jun. 20, 1999;259(1):176-89. doi: 10.1006/viro.1999.9761.
Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.
Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.
Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.
Perler et al., Protein splicing and autoproteolysis mechanisms. Curr Opin Chem Biol. Oct. 1997;1(3):292-9. doi: 10.1016/s1367-5931(97)80065-8.
Perler et al., Protein splicing elements: inteins and exteins—a definition of terms and recommended nomenclature. Nucleic Acids Res. Apr. 11, 1994;22(7):1125-7. doi: 10.1093/nar/22.7.1125.
Perler, InBase, the New England Biolabs Intein Database. Nucleic Acids Res. Jan. 1, 1999;27(1):346-7. doi: 10.1093/nar/27.1.346.
Perler, Protein splicing of inteins and hedgehog autoproteolysis: structure, function, and evolution. Cell. Jan. 9, 1998;92(1):1-4. doi: 10.1016/s0092-8674(00)80892-2.
Petek et al., Frequent endonuclease cleavage at off-target locations in vivo. Mol Ther. May 2010;18(5):983-6. Doi: 10.1038/mt.2010. 35. Epub Mar. 9, 2010.
Petersen-Mahrt et al., AID mutates *E. coli* suggesting a DNA deamination mechanism for antibody diversification. Nature. Jul. 4, 2002;418(6893):99-103.
Petolino et al., Editing Plant Genomes: a new era of crop improvement. Plant Biotechnol J. Feb. 2016;14(2):435-6. doi: 10.1111/pbi. 12542.
Peyrottes et al., Oligodeoxynucleoside phosphoramidates (P-NH2): synthesis and thermal stability of duplexes with DNA and RNA targets. Nucleic Acids Res. May 15, 1996;24(10):1841-8.
Pfeiffer et al., Mechanisms of DNA double-strand break repair and their potential to induce chromosomal aberrations. Mutagenesis. Jul. 2000;15(4):289-302. doi: 10.1093/mutage/15.4.289.
Phillips, The challenge of gene therapy and DNA delivery. J Pharm Pharmacol. Sep. 2001;53(9):1169-74.
Pickart et al., Ubiquitin: structures, functions, mechanisms. Biochim Biophys Acta. Nov. 29, 2004;1695(1-3):55-72. doi: 10.1016/j.bbamcr. 2004.09.019.
Pinkert et al., An albumin enhancer located 10 kb upstream functions along with its promoter to direct efficient, liver-specific expression in transgenic mice. Genes Dev. May 1987;1(3):268-76. doi: 10.1101/gad.1.3.268.
Pirakitikulr et al., PCRless library mutagenesis via oligonucleotide recombination in yeast. Protein Sci. Dec. 2010;19(12):2336-46. doi: 10.1002/pro.513.
Plasterk et al., DNA inversions in the chromosome of *Escherichia coli* and in bacteriophage Mu: relationship to other site-specific recombination systems. Proc Natl Acad Sci U S A. Sep. 1983;80(17):5355-8.
Plosky et al., CRISPR-Mediated Base Editing without DNA Double-Strand Breaks. Mol Cell. May 19, 2016;62(4):477-8. doi: 10.1016/j.molcel.2016.05.006.
Pluciennik et al., PCNA function in the activation and strand direction of MutLα endonuclease in mismatch repair. Proc Natl Acad Sci U S A. Sep. 14, 2010;107(37):16066-71. doi: 10.1073/pnas.1010662107. Epub Aug. 16, 2010.
Poller et al., A leucine-to-proline substitution causes a defective alpha 1-antichymotrypsin allele associated with familial obstructive lung disease. Genomics. Sep. 1993;17(3):740-3.
Popp et al., Sortagging: a versatile method for protein labeling. Nat Chem Biol. Nov. 2007;3(11):707-8. doi: 10.1038/nchembio.2007. 31. Epub Sep. 23, 2007.
Porteus, Design and testing of zinc finger nucleases for use in mammalian cells. Methods Mol Biol. 2008;435:47-61. doi: 10.1007/978-1-59745-232-8_4.
Posnick et al., Imbalanced base excision repair increases spontaneous mutation and alkylation sensitivity in *Escherichia coli*. J Bacteriol. Nov. 1999;181(21):6763-71.
Pospíšilová et al., Hydrolytic cleavage of N6-substituted adenine derivatives by eukaryotic adenine and adenosine deaminases. Biosci Rep. 2008;28(6):335-347. doi:10.1042/BSR20080081.
Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.
Prashant et al., CAS9 transcriptional activators for target specificity screening and paired nickases for cooperative genome engineering. Nature Biotechnology 2013;31(9):833-8.
Prorocic et al., Zinc-finger recombinase activities in vitro. Nucleic Acids Res. Nov. 2011;39(21):9316-28. doi: 10.1093/nar/gkr652. Epub Aug. 17, 2011.

(56) References Cited

OTHER PUBLICATIONS

Proudfoot et al., Zinc finger recombinases with adaptable DNA sequence specificity. PLoS One. Apr. 29, 2011;6(4):e19537. doi: 10.1371/journal.pone.0019537.

Pruschy et al., Mechanistic studies of a signaling pathway activated by the organic dimerizer FK1012. Chem Biol. Nov. 1994;1(3):163-72. doi: 10.1016/1074-5521(94)90006-x.

Prykhozhij et al., CRISPR multitargeter: a web tool to find common and unique CRISPR single guide RNA targets in a set of similar sequences. PLoS One. Mar. 5, 2015;10(3):e0119372. doi: 10.1371/journal.pone.0119372. eCollection 2015.

Pu et al., Evolution of a split RNA polymerase as a versatile biosensor platform. Nat Chem Biol. Apr. 2017;13(4):432-438. doi: 10.1038/nchembio.2299. Epub Feb. 13, 2017.

Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.

Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.

Qi et al., Repurposing CRISPR as an RNA-guided platform for sequence-specific control of gene expression. Cell. Feb. 28, 2013;152(5):1173-83. doi: 10.1016/j.cell.2013.02.022.

Qu et al., Global mapping of binding sites for phic31 integrase in transgenic maden-darby bovine kidney cells using ChIP-seq. Hereditas. Jan. 14, 2019;156:3. doi: 10.1186/s41065-018-0079-z.

Queen et al., Immunoglobulin gene transcription is activated by downstream sequence elements. Cell. Jul. 1983;33(3):741-8. doi: 10.1016/0092-8674(83)90016-8.

Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.

Raina et al., PROTAC-induced BET protein degradation as a therapy for castration-resistant prostate cancer. Proc Natl Acad Sci U S A. Jun. 28, 2016;113(26):7124-9. doi: 10.1073/pnas.1521738113. Epub Jun. 6, 2016.

Rakonjac et al., Roles of PIII in filamentous phage assembly. J Mol Biol. 1998; 282(1)25-41.

Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.

Ramamurthy et al., Identification of immunogenic B-cell epitope peptides of rubella virus E1 glycoprotein towards development of highly specific immunoassays and/or vaccine. Conference Abstract. 2019.

Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.

Ramirez et al., Unexpected failure rates for modular assembly of engineered zinc fingers. Nat Methods. May 2008;5(5):374-5. Doi: 10.1038/nmeth0508-374.

Ran et al., Double Nicking by RNA-guided CRISPR Cas9 for Enhanced Genome Editing Specificity. Cell. Sep. 12, 2013;154(6):1380-9. doi: 10.1016/j.cell.2013.08.021. Epub Aug. 29, 2013.

Ran et al., Genome engineering using the CRISPR-Cas9 system. Nat Protoc. Nov. 2013;8(11):2281-308. doi: 10.1038/nprot.2013.143. Epub Oct. 24, 2013.

Ran et al., In vivo genome editing using *Staphylococcus aureus* Cas9. Nature. Apr. 9, 2015;520(7546):186-91. doi: 10.1038/nature14299. Epub Apr. 1, 2015.

Ranzau et al., Genome, Epigenome, and Transcriptome Editing via Chemical Modification of Nucleobases in Living Cells. Biochemistry. Feb. 5, 2019;58(5):330-335. doi: 10.1021/acs.biochem.8b00958. Epub Dec. 12, 2018.

Rashel et al., A novel site-specific recombination system derived from bacteriophage phiMR11. Biochem Biophys Res Commun. Apr. 4, 2008;368(2):192-8. doi: 10.1016/j.bbrc.2008.01.045. Epub Jan. 22, 2008.

Rasila et al., Critical evaluation of random mutagenesis by error-prone polymerase chain reaction protocols, *Escherichia coli* mutator strain, and hydroxylamine treatment. Anal Biochem. May 1, 2009;388(1):71-80. doi: 10.1016/j.ab.2009.02.008. Epub Feb. 10, 2009.

Raskin et al., Substitution of a single bacteriophage T3 residue in bacteriophage T7 RNA polymerase at position 748 results in a switch in promoter specificity. J Mol Biol. Nov. 20, 1992;228(2):506-15.

Raskin et al., T7 RNA polymerase mutants with altered promoter specificities. Proc Natl Acad Sci U S A. Apr. 15, 1993;90(8):3147-51.

Rath et al., Fidelity of end joining in mammalian episomes and the impact of Metnase on joint processing. BMC Mol Biol. Mar. 22, 2014;15:6. doi: 10.1186/1471-2199-15-6.

Rauch et al., Programmable RNA Binding Proteins for Imaging and Therapeutics. Biochemistry. Jan. 30, 2018;57(4):363-364. doi: 10.1021/acs.biochem.7b01101. Epub Nov. 17, 2017.

Ravishankar et al., X-ray analysis of a complex of *Escherichia coli* uracil DNA glycosylase (EcUDG) with a proteinaceous inhibitor. The structure elucidation of a prokaryotic UDG. Nuclei Acids Res. 26 (21): 4880-4887 (1998).

Ray et al., A compendium of RNA-binding motifs for decoding gene regulation. Nature. Jul. 11, 2013;499(7457):172-7. doi: 10.1038/nature12311.

Ray et al., Homologous recombination: ends as the means. Trends Plant Sci. Oct. 2002;7(10):435-40.

Rebar et al., Phage display methods for selecting zinc finger proteins with novel DNA-binding specificities. Methods Enzymol. 1996;267:129-49.

Rebuzzini et al., New mammalian cellular systems to study mutations introduced at the break site by non-homologous end-joining. DNA Repair (Amst). May 2, 2005;4(5):546-55.

Rees et al., Analysis and minimization of cellular RNA editing by DNA adenine base editors. Sci Adv. May 8, 2019;5(5):eaax5717. doi: 10.1126/sciadv.aax5717.

Rees et al., Base editing: precision chemistry on the genome and transcriptome of living cells. Nat Rev Genet. Dec. 2018;19(12):770-788. doi: 10.1038/s41576-018-0059-1.

Rees et al., Development of hRad51-Cas9 nickase fusions that mediate Hdr without double-stranded breaks. Nat Commun. May 17, 2019;10(1):2212. doi: 10.1038/s41467-019-09983-4.

Rees et al., Improving the DNA specificity and applicability of base editing through protein engineering and protein delivery. Nat Commun. Jun. 6, 2017;8:15790. doi: 10.1038/ncomms15790.

Relph et al., Recent developments and current status of gene therapy using viral vectors in the United Kingdom. BMJ. 2004;329(7470):839-842. doi:10.1136/bmj.329.7470.839.

Remy et al., Gene transfer with a series of lipophilic DNA-binding molecules. Bioconjug Chem. Nov.-Dec. 1994;5(6):647-54. doi: 10.1021/bc00030a021.

Ren et al., In-line Alignment and $Mg^{2+}$ Coordination at the Cleavage Site of the env22 Twister Ribozyme. Nat Commun. Nov. 20, 2014;5:5534. doi: 10.1038/ncomms6534.

Ren et al., Pistol Ribozyme Adopts a Pseudoknot Fold Facilitating Site-Specific In-Line Cleavage. Nat Chem Biol. Sep. 2016;12(9):702-8. doi: 10.1038/nchembio.2125. Epub Jul. 11, 2016.

Reyon et al., Flash assembly of TALENs for high-throughput genome editing. Nat Biotechnol. May 2012;30(5):460-5. doi: 10.1038/nbt.2170.

Ribeiro et al., Protein Engineering Strategies to Expand CRISPR-Cas9 Applications. Int J Genomics. Aug. 2, 2018;2018:1652567. doi: 10.1155/2018/1652567.

Richardson et al., Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016.

(56) References Cited

OTHER PUBLICATIONS

Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.

Riechmann et al.,. The C-terminal domain of TolA is the coreceptor for filamentous phage infection of *E. coli*. Cell. 1997; 90(2):351-60. PMID:9244308.

Ringrose et al., The Kw recombinase, an integrase from Kluyveromyces waltii. Eur J Biochem. Sep. 15, 1997;248(3):903-12. doi: 10.1111/j.1432-1033.1997.00903.x.

Risso et al., Hyperstability and substrate promiscuity in laboratory resurrections of Precambrian ?-lactamases. J Am Chem Soc. Feb. 27, 2013;135(8):2899-902. doi: 10.1021/ja311630a. Epub Feb. 14, 2013.

Ritchie et al., limma powers differential expression analyses for RNA-sequencing and microarray studies. Nucleic Acids Res. Apr. 20, 2015;43(7):e47. doi: 10.1093/nar/gkv007. Epub Jan. 20, 2015.

Robinson et al., The protein tyrosine kinase family of the human genome. Oncogene. Nov. 20, 2000;19(49):5548-57. doi: 10.1038/sj.onc.1203957.

Rogozin et al., Evolution and diversification of lamprey antigen receptors: evidence for involvement of an AID-APOBEC family cytosine deaminase. Nat Immunol. Jun. 2007;8(6):647-56. doi: 10.1038/ni1463. Epub Apr. 29, 2007.

Rong et al., Homologous recombination in human embryonic stem cells using CRISPR/Cas9 nickase and a long DNA donor template. Protein Cell. Apr. 2014;5(4):258-60. doi: 10.1007/s13238-014-0032-5.

Roth et al., A widespread self-cleaving ribozyme class is revealed by bioinformatics. Nat Chem Biol. Jan. 2014;10(1):56-60. doi: 10.1038/nchembio.1386. Epub Nov. 17, 2013.

Roth et al., Purification and characterization of murine retroviral reverse transcriptase expressed in *Escherichia coli*. J Biol Chem. Aug. 5, 1985;260(16):9326-35.

Rouet et al., Expression of a site-specific endonuclease stimulates homologous recombination in mammalian cells. Proc Natl Acad Sci U S A. Jun. 21, 1994;91(13):6064-8. doi: 10.1073/pnas.91.13.6064.

Rouet et al., Introduction of double-strand breaks into the genome of mouse cells by expression of a rare-cutting endonuclease. Mol Cell Biol. Dec. 1994;14(12):8096-106. doi: 10.1128/mcb.14.12.8096.

Rouet et al., Receptor-Mediated Delivery of CRISPR-Cas9 Endonuclease for Cell-Type-Specific Gene Editing. J Am Chem Soc. May 30, 2018;140(21):6596-6603. doi: 10.1021/jacs.8b01551. Epub May 18, 2018.

Roundtree et al.,YTHDC1 mediates nuclear export of N6-methyladenosine methylated mRNAs. Elife. Oct. 6, 2017;6:e31311. doi: 10.7554/eLife.31311.

Rowland et al., Regulatory mutations in Sin recombinase support a structure-based model of the synaptosome. Mol Microbiol. Oct. 2009;74(2):282-98. doi: 10.1111/j.1365-2958.2009.06756.x. Epub Jun. 8, 2009.

Rowland et al., Sin recombinase from *Staphylococcus aureus*: synaptic complex architecture and transposon targeting. Mol Microbiol. May 2002;44(3):607-19. doi: 10.1046/j.1365-2958.2002.02897.x.

Rowley, Chromosome translocations: dangerous liaisons revisited. Nat Rev Cancer. Dec. 2001;1(3):245-50. doi: 10.1038/35106108.

Rubio et al., An adenosine-to-inosine tRNA-editing enzyme that can perform C-to-U deamination of DNA. Proc Natl Acad Sci U S A. May 8, 2007;104(19):7821-6. doi: 10.1073/pnas.0702394104. Epub May 1, 2007. PMID: 17483465; PMCID: PMC1876531.

Rubio et al., Transfer RNA travels from the cytoplasm to organelles. Wiley Interdiscip Rev RNA. Nov.-Dec. 2011;2(6):802-17. doi: 10.1002/wrna.93. Epub Jul. 11, 2011.

Rudolph et al., Synthetic riboswitches for the conditional control of gene expression in Streptomyces coelicolor. Microbiology. Jul. 2013;159(Pt 7):1416-22. doi: 10.1099/mic.0.067322-0. Epub May 15, 2013.

Rüfer et al., Non-contact positions impose site selectivity on Cre recombinase. Nucleic Acids Res. Jul. 1, 2002;30(13):2764-71. doi: 10.1093/nar/gkf399.

Rutherford et al., Attachment site recognition and regulation of directionality by the serine integrases. Nucleic Acids Res. Sep. 2013;41(17):8341-56. doi: 10.1093/nar/gkt580. Epub Jul. 2, 2013.

Ryu et al., Adenine base editing in mouse embryos and an adult mouse model of Duchenne muscular dystrophy. Nat Biotechnol. Jul. 2018;36(6):536-539. doi: 10.1038/nbt.4148. Epub Apr. 27, 2018.

Sadelain et al., Safe harbours for the integration of new DNA in the human genome. Nat Rev Cancer. Dec. 1, 2011;12(1):51-8. doi: 10.1038/nrc3179.

Sadowski, The Flp recombinase of the 2-microns plasmid of *Saccharomyces cerevisiae*. Prog Nucleic Acid Res Mol Biol. 1995;51:53-91.

Sage et al., Proliferation of functional hair cells in vivo in the absence of the retinoblastoma protein. Science. Feb. 18, 2005;307(5712):1114-8. Epub Jan. 13, 2005.

Sakuma et al., MMEJ-assisted gene knock-in using TALENs and CRISPR-Cas9 with the PITCh systems. Nat Protoc. Jan. 2016;11(1):118-33. doi: 10.1038/nprot.2015.140. Epub Dec. 17, 2015.

Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.

Samal et al., Cationic polymers and their therapeutic potential. Chem Soc Rev. Nov. 7, 2012;41(21):7147-94. doi: 10.1039/c2cs35094g. Epub Aug. 10, 2012.

Samulski et al., Helper-free stocks of recombinant adeno-associated viruses: normal integration does not require viral gene expression. J Virol. Sep. 1989;63(9):3822-8. doi: 10.1128/JVI.63.9.3822-3828.1989.

Sander et al., CRISPR-Cas systems for editing, regulating and targeting genomes. Nat Biotechnol. Apr. 2014;32(4):347-55. doi: 10.1038/nbt.2842. Epub Mar. 2, 2014.

Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Epub Aug. 14, 2013.

Sander et al., Targeted gene disruption in somatic zebrafish cells using engineered TALENs. Nat Biotechnol. Aug. 5, 2011;29(8):697-8. doi: 10.1038/nbt.1934.

Sang, Prospects for transgenesis in the chick. Mech Dev. Sep. 2004;121(9):1179-86.

Sanjana et al., A transcription activator-like effector toolbox for genome engineering. Nat Protoc. Jan. 5, 2012;7(1):171-92. doi: 10.1038/nprot.2011.431.

Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.

Santoro et al., Directed evolution of the site specificity of Cre recombinase. Proc Natl Acad Sci U S A. Apr. 2, 2002;99(7):4185-90. Epub Mar. 19, 2002.

Saparbaev et al., Excision of hypoxanthine from DNA containing dIMP residues by the *Escherichia coli*, yeast, rat, and human alkylpurine DNA glycosylases. Proc Natl Acad Sci U S A. Jun. 21, 1994;91(13):5873-7. doi: 10.1073/pnas.91.13.5873.

Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.

Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.

Sarkar et al., HIV-1 proviral DNA excision using an evolved recombinase. Science. Jun. 29, 2007;316(5833):1912-5. doi: 10.1126/science.1141453.

Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

(56) References Cited

OTHER PUBLICATIONS

Sasidharan et al., The selection of acceptable protein mutations. PNAS; Jun. 12, 2007;104(24):10080-5. www.pnas.org/cgi/doi/10.1073.pnas.0703737104.

Satomura et al., Precise genome-wide base editing by the CRISPR Nickase system in yeast. Sci Rep. May 18, 2017;7(1):2095. doi: 10.1038/s41598-017-02013-7.

Saudek et al., A preliminary trial of the programmable implantable medication system for insulin delivery. N Engl J Med. Aug. 31, 1989;321(9):574-9.

Sauer et al., DNA recombination with a heterospecific Cre homolog identified from comparison of the pac-c1 regions of P1-related phages. Nucleic Acids Res. Nov. 18, 2004;32(20):6086-95. doi: 10.1093/nar/gkh941.

Savic et al., Covalent linkage of the DNA repair template to the CRISPR-Cas9 nuclease enhances homology-directed repair. Elife. May 29, 2018;7:e33761. doi: 10.7554/eLife.33761.

Saville et al., A site-specific self-cleavage reaction performed by a novel RNA in Neurospora mitochondria. Cell. May 18, 1990;61(4):685-96. doi: 10.1016/0092-8674(90)90480-3.

Schaaper et al., Base selection, proofreading, and mismatch repair during DNA replication in *Escherichia coli*. J Biol Chem. Nov. 15, 1993;268(32):23762-5.

Schaaper et al., Spectra of spontaneous mutations in *Escherichia coli* strains defective in mismatch correction: the nature of in vivo DNA replication errors. Proc Natl Acad Sci U S A. Sep. 1987;84(17):6220-4.

Schaefer et al., Understanding RNA modifications: the promises and technological bottlenecks of the 'epitranscriptome'. Open Biol. May 2017;7(5):170077. doi: 10.1098/rsob.170077.

Schechner et al., Multiplexable, locus-specific targeting of long RNAs with CRISPR-Display. Nat Methods. Jul. 2015;12(7):664-70. doi: 10.1038/nmeth.3433. Epub Jun. 1, 2015. Author manuscript entitled CRISPR Display: A modular method for locus-specific targeting of long noncoding RNAs and synthetic RNA devices in vivo.

Schek et al., Definition of the upstream efficiency element of the simian virus 40 late polyadenylation signal by using in vitro analyses. Mol Cell Biol. Dec. 1992;12(12):5386-93. doi: 10.1128/mcb.12.12.5386.

Schenk et al., MPDU1 mutations underlie a novel human congenital disorder of glycosylation, designated type If. J Clin Invest. Dec. 2001;108(11):1687-95. doi: 10.1172/JCI13419.

Schmitz et al., Behavioral abnormalities in prion protein knockout mice and the potential relevance of PrP(C) for the cytoskeleton. Prion. 2014;8(6):381-6. doi: 10.4161/19336896.2014.983746.

Schöller et al., Interactions, localization, and phosphorylation of the m6A generating METTL3-METTL14-WTAP complex. RNA. Apr. 2018;24(4):499-512. doi: 10.1261/rna.064063.117. Epub Jan. 18, 2018.

Schriefer et al., Low pressure DNA shearing: a method for random DNA sequence analysis. Nucleic Acids Res. Dec. 25, 1990;18(24):7455-6.

Schultz et al., Expression and secretion in yeast of a 400-kDa envelope glycoprotein derived from Epstein-Barr virus. Gene. 1987;54(1):113-23. doi: 10.1016/0378-1119(87)90353-2.

Schultz et al., Oligo-2'-fluoro-2'-deoxynucleotide N3'-->P5' phosphoramidates: synthesis and properties. Nucleic Acids Res. Aug. 1, 1996;24(15):2966-73.

Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.

Schwartz et al., Post-translational enzyme activation in an animal via optimized conditional protein splicing. Nat Chem Biol. Jan. 2007;3(1):50-4. Epub Nov. 26, 2006.

Schwarze et al., In vivo protein transduction: delivery of a biologically active protein into the mouse. Science. Sep. 3, 1999;285(5433):1569-72.

Sclimenti et al., Directed evolution of a recombinase for improved genomic integration at a native human sequence. Nucleic Acids Res. Dec. 15, 2001;29(24):5044-51.

Scott et al., Production of cyclic peptides and proteins in vivo. Proc Natl Acad Sci U S A. Nov. 23, 1999;96(24):13638-43. doi: 10.1073/pnas.96.24.13638.

Search Report and Written Opinion for SG 11201900907Y, dated Jul. 20, 2020.

Sebastián-Martín et al., Transcriptional inaccuracy threshold attenuates differences in RNA-dependent DNA synthesis fidelity between retroviral reverse transcriptases. Sci Rep. Jan. 12, 2018;8(1):627. doi: 10.1038/s41598-017-18974-8.

Seed, An LFA-3 cDNA encodes a phospholipid-linked membrane protein homologous to its receptor CD2. Nature. Oct. 29-Nov. 4, 1987;329(6142):840-2. doi: 10.1038/329840a0.

Sefton et al., Implantable pumps. Crit Rev Biomed Eng. 1987;14(3):201-40.

Segal et al., Evaluation of a modular strategy for the construction of novel polydactyl zinc finger DNA-binding proteins. Biochemistry. Feb. 25, 2003;42(7):2137-48.

Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.

Sells et al., Delivery of protein into cells using polycationic liposomes. Biotechniques. Jul. 1995;19(1):72-6, 78.

Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.

Semple et al., Rational design of cationic lipids for siRNA delivery. Nat Biotechnol. Feb. 2010;28(2):172-6. doi: 10.1038/nbt.1602. Epub Jan. 17, 2010.

Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.

Serganov et al., Structural basis for discriminative regulation of gene expression by adenine- and guanine-sensing mRNAs. Chem Biol. Dec. 2004;11(12):1729-41.

Serganov et al., Structural basis for gene regulation by a thiamine pyrophosphate-sensing riboswitch. Nature. Jun. 29, 2006;441(7097):1167-71. Epub May 21, 2006.

Seripa et al., The missing ApoE allele. Ann Hum Genet. Jul. 2007;71(Pt 4):496-500. Epub Jan. 22, 2007.

Serrano-Heras et al., Protein p56 from the Bacillus subtilis phage phi29 inhibits DNA-binding ability of uracil-DNA glycosylase. Nucleic Acids Res. 2007;35(16):5393-401. Epub Aug. 13, 2007.

Setten et al., The current state and future directions of RNAi-based therapeutics. Nat Rev Drug Discov. Jun. 2019;18(6):421-446. doi: 10.1038/s41573-019-0017-4.

Severinov et al., Expressed protein ligation, a novel method for studying protein-protein interactions in transcription. J Biol Chem. Jun. 26, 1998;273(26):16205-9. doi: 10.1074/jbc.273.26.16205.

Sha et al., Monobodies and other synthetic binding proteins for expanding protein science. Protein Sci. May 2017;26(5):910-924. doi: 10.1002/pro.3148. Epub Mar. 24, 2017.

Shah et al., Inteins: nature's gift to protein chemists. Chem Sci. 2014;5(1):446-461.

Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.

Shah et al., Protospacer recognition motifs: mixed identities and functional diversity. RNA Biol. May 2013;10(5):891-9. doi: 10.4161/rna.23764. Epub Feb. 12, 2013.

Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.

Shalem et al., High-throughput functional genomics using CRISPR-Cas9. Nat Rev Genet. May 2015;16(5):299-311. doi: 10.1038/nrg3899. Epub Apr. 9, 2015.

(56) References Cited

OTHER PUBLICATIONS

Shalem et al., Genome-scale CRISPR-Cas9 knockout screening in human cells. Science. Jan. 3, 2014;343(6166):84-7. doi: 10.1126/science.1247005. Epub Dec. 12, 2013.
Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.
Sharer et al., The ARF-like 2 (ARL2)-binding protein, BART. Purification, cloning, and initial characterization. J Biol Chem. Sep. 24, 1999;274(39):27553-61. doi: 10.1074/jbc.274.39.27553.
Sharma et al., Efficient introduction of aryl bromide functionality into proteins in vivo. FEBS Lett. Feb. 4, 2000;467(1):37-40.
Sharon et al., Functional Genetic Variants Revealed by Massively Parallel Precise Genome Editing. Cell. Oct. 4, 2018;175(2):544-557.e16. doi: 10.1016/j.cell.2018.08.057. Epub Sep. 20, 2018.
Shaw et al., Implications of human genome architecture for rearrangement-based disorders: the genomic basis of disease. Hum Mol Genet. Apr. 1, 2004;13 Spec No. 1:R57-64. doi: 10.1093/hmg/ddh073. Epub Feb. 5, 2004.
Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.
Shee et al., Engineered proteins detect spontaneous DNA breakage in human and bacterial cells. Elife. Oct. 29, 2013;2:e01222. doi: 10.7554/eLife.01222.
Shen et al., Predictable and precise template-free CRISPR editing of pathogenic variants. Nature. Nov. 2018;563(7733):646-651. doi: 10.1038/s41586-018-0686-x. Epub Nov. 7, 2018.
Sheridan, First CRISPR-Cas patent opens race to stake out intellectual property. Nat Biotechnol. 2014;32(7):599-601.
Sheridan, Gene therapy finds its niche. Nat Biotechnol. Feb. 2011;29(2):121-8. doi: 10.1038/nbt.1769.
Sherwood et al., Discovery of directional and nondirectional pioneer transcription factors by modeling DNase profile magnitude and shape. Nat Biotechnol. Feb. 2014;32(2):171-178. doi: 10.1038/nbt.2798. Epub Jan. 19, 2014.
Shi et al., Structural basis for targeted DNA cytosine deamination and mutagenesis by APOBEC3A and APOBEC3B. Nat Struct Mol Biol. Feb. 2017;24(2):131-139. doi: 10.1038/nsmb.3344. Epub Dec. 19, 2016.
Shi et al., YTHDF3 facilitates translation and decay of N6-methyladenosine-modified RNA. Cell Res. Mar. 2017;27(3):315-328. doi: 10.1038/cr.2017.15. Epub Jan. 20, 2017.
Shimantani et al., Targeted base editing in rice and tomato using a CRISPR-Cas9 cytidine deaminase fusion. Nat Biotechnol. May 2017;35(5):441-443. doi: 10.1038/nbt.3833. Epub Mar. 27, 2017.
Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi: 10.1016/j.braindev.2011.04.014. Epub May 19, 2011.
Shin et al., CRISPR/Cas9 targeting events cause complex deletions and insertions at 17 sites in the mouse genome. Nat Commun. May 31, 2017;8:15464. doi: 10.1038/ncomms15464.
Shindo et al., A Comparison of Two Single-Stranded DNA Binding Models by Mutational Analysis of APOBEC3G. Biology (Basel). Aug. 2, 2012;1(2):260-76. doi: 10.3390/biology1020260.
Shingledecker et al., Molecular dissection of the *Mycobacterium tuberculosis* RecA intein: design of a minimal intein and of a trans-splicing system involving two intein fragments. Gene. Jan. 30, 1998;207(2):187-95. doi: 10.1016/s0378-1119(97)00624-0.
Shmakov et al., Discovery and Functional Characterization of Diverse Class 2 CRISPR Cas Systems. Molecular Cell Nov. 2015;60(3):385-97.
Shmakov et al., Diversity and evolution of class 2 CRISPR-Cas systems. Nat Rev Microbiol. Mar. 2017;15(3):169-182. doi: 10.1038/nrmicro.2016.184. Epub Jan. 23, 2017.
Shultz et al., A genome-wide analysis of FRT-like sequences in the human genome. PLoS One. Mar. 23, 2011;6(3):e18077. doi: 10.1371/journal.pone.0018077.
Siebert et al., An improved PCR method for walking in uncloned genomic DNA. Nucleic Acids Res. Mar. 25, 1995;23(6):1087-8.
Silas et al., Direct CRISPR spacer acquisition from RNA by a natural reverse transcriptase-Cas1 fusion protein. Science. Feb. 26, 2016;351(6276):aad4234. doi: 10.1126/science.aad4234.
Silva et al., Selective disruption of the DNA polymerase III $\alpha$-$\beta$ complex by the umuD gene products. Nucleic Acids Res. Jul. 2012;40(12):5511-22. doi: 10.1093/nar/gks229. Epub Mar. 9, 2012.
Simonelli et al., Base excision repair intermediates are mutagenic in mammalian cells. Nucleic Acids Res. Aug. 2, 2005;33(14):4404-11. Print 2005.
Singh et al., Cross-talk between diverse serine integrases. J Mol Biol. Jan. 23, 2014;426(2):318-31. doi: 10.1016/j.jmb.2013.10.013. Epub Oct. 22, 2013.
Singh et al., Real-time observation of DNA recognition and rejection by the RNA-guided endonuclease Cas9. Nat Commun. Sep. 14, 2016;7:12778. doi: 10.1038/ncomms12778.
Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.
Sivalingam et al., Biosafety assessment of site-directed transgene integration in human umbilical cord-lining cells. Mol Ther. Jul. 2010;18(7):1346-56. doi: 10.1038/mt.2010.61. Epub Apr. 27, 2010.
Sjoblom et al., The consensus coding sequences of human breast and colorectal cancers. Science. Oct. 13, 2006;314(5797):268-74. Epub Sep. 7, 2006.
Skretas et al., Regulation of protein activity with small-molecule-controlled inteins. Protein Sci. Feb. 2005;14(2):523-32. Epub Jan. 4, 2005.
Slaymaker et al., Rationally engineered Cas9 nucleases with improved specificity. Science. Jan. 1, 2016;351(6268):84-8. doi: 10.1126/science.aad5227. Epub Dec. 1, 2015.
Sledz et al., Structural insights into the molecular mechanism of the m(6)A writer complex. Elife. Sep. 14, 2016;5:e18434. doi: 10.7554/eLife.18434.
Smargon et al., Cas13b Is a Type VI-B CRISPR-Associated RNA-Guided RNase Differentially Regulated by Accessory Proteins Csx27 and Csx28. Mol Cell. Feb. 16, 2017;65(4):618-630.e7. doi: 10.1016/j.molcel.2016.12.023. Epub Jan. 5, 2017.
Smith et al., Expression of a dominant negative retinoic acid receptor $\gamma$ in Xenopus embryos leads to partial resistance to retinoic acid. Roux Arch Dev Biol. Mar. 1994;203(5):254-265. doi: 10.1007/BF00360521.
Smith et al., Production of human beta interferon in insect cells infected with a baculovirus expression vector. Mol Cell Biol. Dec. 1983;3(12):2156-65. doi: 10.1128/mcb.3.12.2156.
Smith et al., Single-step purification of polypeptides expressed in *Escherichia coli* as fusions with glutathione S-transferase. Gene. Jul. 15, 1988;67(1):31-40. doi: 10.1016/0378-1119(88)90005-4.
Smith, Filamentous fusion phage: novel expression vectors that display cloned antigens on the virion surface. Science. Jun. 14, 1985;228(4705):1315-7.
Smith, Phage-encoded Serine Integrases and Other Large Serine Recombinases. Microbiol Spectr. Aug. 2015;3(4). doi: 10.1128/microbiolspec.MDNA3-0059-2014.
Sommerfelt et al., Receptor interference groups of 20 retroviruses plating on human cells. Virology. May 1990;176(1):58-69. doi: 10.1016/0042-6822(90)90230-o.
Southworth et al., Control of protein splicing by intein fragment reassembly. EMBO J. Feb. 16, 1998;17(4):918-26. doi: 10.1093/emboj/17.4.918.
Southworth et al., Purification of proteins fused to either the amino or carboxy terminus of the *Mycobacterium xenopi* gyrase A intein. Biotechniques. Jul. 1999;27(1):110-4, 116, 118-20. doi: 10.2144/99271st04.
Spencer et al., A general strategy for producing conditional alleles of Src-like tyrosine kinases. Proc Natl Acad Sci U S A. Oct. 10, 1995;92(21):9805-9. doi: 10.1073/pnas.92.21.9805.

(56) References Cited

OTHER PUBLICATIONS

Spencer et al., Controlling signal transduction with synthetic ligands. Science. Nov. 12, 1993;262(5136):1019-24. doi: 10.1126/science.7694365.

Spencer et al., Functional analysis of Fas signaling in vivo using synthetic inducers of dimerization. Curr Biol. Jul. 1, 1996;6(7):839-47. doi: 10.1016/s0960-9822(02)00607-3.

Srivastava et al., An inhibitor of nonhomologous end-joining abrogates double-strand break repair and impedes cancer progression. Cell. Dec. 21, 2012;151(7):1474-87. doi: 10.1016/j.cell.2012.11.054.

Stadtman, Selenocysteine. Annu Rev Biochem. 1996;65:83-100.

Stamos et al., Structure of a Thermostable Group II Intron Reverse Transcriptase with Template-Primer and Its Functional and Evolutionary Implications. Mol Cell. Dec. 7, 2017;68(5):926-939.e4. doi: 10.1016/j.molcel.2017.10.024. Epub Nov. 16, 2017.

Steele et al., The prion protein knockout mouse: a phenotype under challenge. Prion. Apr.-Jun. 2007;1(2):83-93. doi: 10.4161/pri.1.2.4346. Epub Apr. 25, 2007.

Stella et al., Structure of the Cpf1 endonuclease R-loop complex after target DNA cleavage. Nature. Jun. 22, 2017;546(7659):559-563. doi: 10.1038/nature22398. Epub May 31, 2017.

Stenglein et al., APOBEC3 proteins mediate the clearance of foreign DNA from human cells. Nat Struct Mol Biol. Feb. 2010;17(2):222-9. doi: 10.1038/nsmb.1744. Epub Jan. 10, 2010.

Stenson et al., The Human Gene Mutation Database: towards a comprehensive repository of inherited mutation data for medical research, genetic diagnosis and next-generation sequencing studies. Hum Genet. Jun. 2017;136(6):665-677. doi: 10.1007/s00439-017-1779-6. Epub Mar. 27, 2017.

Stephens et al., The landscape of cancer genes and mutational processes in breast cancer. Nature Jun. 2012;486:400-404. doi:10.1038/nature11017.

Sternberg et al., Conformational control of DNA target cleavage by CRISPR-Cas9. Nature. Nov. 5, 2015;527(7576):110-3. doi: 10.1038/nature15544. Epub Oct. 28, 2015.

Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.

Sterne-Weiler et al., Exon identity crisis: disease-causing mutations that disrupt the splicing code. Genome Biol. Jan. 23, 2014;15(1):201. doi: 10.1186/gb4150.

Stevens et al., Design of a Split Intein with Exceptional Protein-Splicing Activity. J Am Chem Soc. Feb. 24, 2016;138(7):2162-5. doi: 10.1021/jacs.5b13528. Epub Feb. 8, 2016.

Stevens et al., A promiscuous split intein with expanded protein engineering applications. Proc Natl Acad Sci U S A. Aug. 8, 2017;114(32):8538-8543. doi: 10.1073/pnas.1701083114. Epub Jul. 24, 2017.

Stockwell et al., Probing the role of homomeric and heteromeric receptor interactions in TGF-beta signaling using small molecule dimerizers. Curr Biol. Jun. 18, 1998;8(13):761-70. doi: 10.1016/s0960-9822(98)70299-4.

Strecker et al., RNA-guided DNA insertion with CRISPR-associated transposases. Science. Jul. 5, 2019;365(6448):48-53. doi: 10.1126/science.aax9181. Epub Jun. 6, 2019.

Strutt et al., RNA-dependent RNA targeting by CRISPR-Cas9. Elife. Jan. 5, 2018;7:e32724. doi: 10.7554/eLife.32724.

Su et al., Human DNA polymerase ? has reverse transcriptase activity in cellular environments. J Biol Chem. Apr. 12, 2019;294(15):6073-6081. doi: 10.1074/jbc.RA119.007925. Epub Mar. 6, 2019.

Sudarsan et al., An mRNA structure in bacteria that controls gene expression by binding lysine. Genes Dev. Nov. 1, 2003;17(21):2688-97.

Sudarsan et al., Riboswitches in eubacteria sense the second messenger cyclic di-GMP. Science. Jul. 18, 2008;321(5887):411-3. doi: 10.1126/science.1159519.

Suess et al., A theophylline responsive riboswitch based on helix slipping controls gene expression in vivo. Nucleic Acids Res. Mar. 5, 2004;32(4):1610-4.

Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.

Sun et al., The CRISPR/Cas9 system for gene editing and its potential application in pain research. Transl Periop & Pain Med. Aug. 3, 2016;1(3):22-33.

Supplementary European Search Report for Application No. EP 12845790.0, dated Oct. 12, 2015.

Surun et al., High Efficiency Gene Correction in Hematopoietic Cells by Donor-Template-Free CRISPR/Cas9 Genome Editing. Mol Ther Nucleic Acids. Mar. 2, 2018;10:1-8. doi: 10.1016/j.omtn.2017.11.001. Epub Nov. 10, 2017.

Suzuki et al., In vivo genome editing via CRISPR/Cas9 mediated homology-independent targeted integration. Nature. Dec. 1, 2016;540(7631):144-149. doi: 10.1038/nature20565. Epub Nov. 16, 2016.

Suzuki et al., VCre/VIoxP and SCre/SIoxP: new site-specific recombination systems for genome engineering. Nucleic Acids Res. Apr. 2011;39(8):e49. doi: 10.1093/nar/gkq1280. Epub Feb. 1, 2011.

Swarts et al., Argonaute of the archaeon Pyrococcus furiosus is a DNA-guided nuclease that targets cognate DNA. Nucleic Acids Res. May 26, 2015;43(10):5120-9. doi: 10.1093/nar/gkv415. Epub Apr. 29, 2015.

Swarts et al., DNA-guided DNA interference by a prokaryotic Argonaute. Nature. Mar. 13, 2014;507(7491):258-61. doi: 10.1038/nature12971. Epub Feb. 16, 2014.

Swarts et al., The evolutionary journey of Argonaute proteins. Nat Struct Mol Biol. Sep. 2014;21(9):743-53. doi: 10.1038/nsmb.2879.

Szczepek et al., Structure-based redesign of the dimerization interface reduces the toxicity of zinc-finger nucleases. Nat Biotechnol. Jul. 2007;25(7):786-93. Epub Jul. 1, 2007.

Tabebordbar et al., In vivo gene editing in dystrophic mouse muscle and muscle stem cells. Science. Jan. 22, 2016;351(6271):407-411. doi: 10.1126/science.aad5177. Epub Dec 31, 2015.

Tagalakis et al., Lack of RNA-DNA oligonucleotide (chimeraplast) mutagenic activity in mouse embryos. Mol Reprod Dev. Jun. 2005;71(2):140-4.

Tahara et al., Potent and Selective Inhibitors of 8-Oxoguanine DNA Glycosylase. J Am Chem Soc. Feb. 14, 2018;140(6):2105-2114. doi: 10.1021/jacs.7b09316. Epub Feb. 5, 2018.

Tajiri et al., Functional cooperation of MutT, MutM and MutY proteins in preventing mutations caused by spontaneous oxidation of guanine nucleotide in *Escherichia coli*. Mutat Res. May 1995;336(3):257-67. doi: 10.1016/0921-8777(94)00062-b.

Takimoto et al., Stereochemical basis for engineered; pyrrolysyl-tRNA synthetase and the efficient in vivo incorporation of; structurally divergent non-native amino acids. ACS Chem Biol. Jul. 2011; 15;6(7):733-43. doi: 10.1021/cb200057a. Epub May 5, 2011.

Tambunan et al., Vaccine Design for H5N1 Based on B- and T-cell Epitope Predictions. Bioinform Biol Insights. Apr. 28, 2016;10:27-35. doi: 10.4137/BBI.S38378.

Tanenbaum et al., A protein-tagging system for signal amplification in gene expression and fluorescence imaging. Cell. Oct. 23, 2014;159(3):635-46. doi: 10.1016/j.cell.2014.09.039. Epub Oct. 9, 2014.

Tanese et al., Expression of enzymatically active reverse transcriptase in *Escherichia coli*. Proc Natl Acad Sci U S A. Aug. 1985;82(15):4944-8. doi: 10.1073/pnas.82.15.4944.

Tang et al., Aptazyme-embedded guide RNAs enable ligand-responsive genome editing and transcriptional activation. Nat Commun. Jun. 28, 2017;8:15939. doi: 10.1038/ncomms15939.

Tang et al., Evaluation of Bioinformatic Programmes for the Analysis of Variants within Splice Site Consensus Regions. Adv Bioinformatics. 2016;2016:5614058. doi: 10.1155/2016/5614058. Epub May 24, 2016.

Tang et al., Rewritable multi-event analog recording in bacterial and mammalian cells. Science. Apr. 13, 2018;360(6385):eaap8992. doi: 10.1126/science.aap8992. Epub Feb. 15, 2018.

(56) References Cited

OTHER PUBLICATIONS

Tassabehji, Williams-Beuren syndrome: a challenge for genotype-phenotype correlations. Hum Mol Genet. Oct. 15, 2003;12 Spec No. 2:R229-37. doi: 10.1093/hmg/ddg299. Epub Sep. 2, 2003.
Taube et al., Reverse transcriptase of mouse mammary tumour virus: expression in bacteria, purification and biochemical characterization. Biochem J. Feb. 1, 1998;329 ( Pt 3)(Pt 3):579-87. doi: 10.1042/bj3290579. Erratum in: Biochem J Jun. 15, 1998;332(Pt 3):808.
Tebas et al., Gene editing of CCR5 in autologous CD4 T cells of persons infected with HIV. N Engl J Med. Mar. 6, 2014;370(10):901-10. doi: 10.1056/NEJMoa1300662.
Tee et al., Polishing the craft of genetic diversity creation in directed evolution. Biotechnol Adv. Dec. 2013;31(8):1707-21. doi: 10.1016/j.biotechadv.2013.08.021. Epub Sep. 6, 2013.
Telenti et al., The *Mycobacterium xenopi* GyrA protein splicing element: characterization of a minimal intein. J Bacteriol. Oct. 1997;179(20):6378-82. doi: 10.1128/jb.179.20.6378-6382.1997.
Telesnitsky et al., RNase H domain mutations affect the interaction between Moloney murine leukemia virus reverse transcriptase and its primer-template. Proc Natl Acad Sci U S A. Feb. 15, 1993;90(4):1276-80. doi: 10.1073/pnas.90.4.1276.
Tessarollo et al., Targeted mutation in the neurotrophin-3 gene results in loss of muscle sensory neurons. Proc Natl Acad Sci U S A. Dec. 6, 1994;91(25):11844-8.
Tesson et al., Knockout rats generated by embryo microinjection of TALENs. Nat Biotechnol. Aug. 5, 2011;29(8):695-6. doi: 10.1038/nbt.1940.
Thompson et al., Cellular uptake mechanisms and endosomal trafficking of supercharged proteins. Chem Biol. Jul. 27, 2012;19(7):831-43. doi: 10.1016/j.chembiol.2012.06.014.
Thompson et al., Engineering and identifying supercharged proteins for macromolecule delivery into mammalian cells. Methods Enzymol. 2012;503:293-319. doi: 10.1016/B978-0-12-396962-0.00012-4.
Thomson et al., Mutational analysis of loxP sites for efficient Cre-mediated insertion into genomic DNA. Genesis. Jul. 2003;36(3):162-7. doi: 10.1002/gene.10211.
Thorpe et al., Functional correction of episomal mutations with short DNA fragments and RNA-DNA oligonucleotides. J Gene Med. Mar.-Apr. 2002;4(2):195-204.
Thuronyi et al., Continuous evolution of base editors with expanded target compatibility and improved activity. Nat Biotechnol. Sep. 2019;37(9):1070-1079. doi: 10.1038/s41587-019-0193-0. Epub Jul. 22, 2019.
Thyagarajan et al., Creation of engineered human embryonic stem cell lines using phiC31 integrase. Stem Cells. Jan. 2008;26(1):119-26. doi: 10.1634/stemcells.2007-0283. Epub Oct. 25, 2007.
Thyagarajan et al., Mammalian genomes contain active recombinase recognition sites. Gene. Feb. 22, 2000;244(1-2):47-54.
Thyagarajan et al., Site-specific genomic integration in mammalian cells mediated by phage phiC31 integrase. Mol Cell Biol. Jun. 2001;21(12):3926-34.
Tinland et al., The T-DNA-linked VirD2 protein contains two distinct functional nuclear localization signals. Proc Natl Acad Sci U S A. Aug. 15, 1992;89(16):7442-6. doi: 10.1073/pnas.89.16.7442.
Tirumalai et al., Recognition of core-type DNA sites by lambda integrase. J Mol Biol. Jun. 12, 1998;279(3):513-27.
Tom et al., Mechanism whereby proliferating cell nuclear antigen stimulates flap endonuclease 1. J Biol Chem. Apr. 7, 2000;275(14):10498-505. doi: 10.1074/jbc.275.14.10498.
Tone et al., Single-stranded DNA binding protein Gp5 of Bacillus subtilis phage ?29 is required for viral DNA replication in growth-temperature dependent fashion. Biosci Biotechnol Biochem. 2012;76(12):2351-3. doi: 10.1271/bbb.120587. Epub Dec. 7, 2012.
Toor et al., Crystal structure of a self-spliced group II intron. Science. Apr. 4, 2008;320(5872):77-82. doi: 10.1126/science.1153803.
Toro et al., On the Origin and Evolutionary Relationships of the Reverse Transcriptases Associated With Type III CRISPR-Cas Systems. Front Microbiol. Jun. 15, 2018;9:1317. doi: 10.3389/fmicb.2018.01317.
Toro et al., The Reverse Transcriptases Associated with CRISPR-Cas Systems. Sci Rep. Aug. 2, 2017;7(1):7089. doi: 10.1038/s41598-017-07828-y.
Torres et al., Non-integrative lentivirus drives high-frequency cre-mediated cassette exchange in human cells. PLoS One. 2011;6(5):e19794. doi: 10.1371/journal.pone.0019794. Epub May 23, 2011.
Tourdot et al., A general strategy to enhance immunogenicity of low-affinity HLA-A2. 1-associated peptides: implication in the identification of cryptic tumor epitopes. Eur J Immunol. Dec. 2000;30(12):3411-21.
Townsend et al., Role of HFE in iron metabolism, hereditary haemochromatosis, anaemia of chronic disease, and secondary iron overload. Lancet. Mar. 2, 2002;359(9308):786-90. doi: 10.1016/S0140-6736(02)07885-6.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tratschin et al., A human parvovirus, adeno-associated virus, as a eucaryotic vector: transient expression and encapsidation of the procaryotic gene for chloramphenicol acetyltransferase. Mol Cell Biol. Oct. 1984;4(10):2072-81. doi: 10.1128/mcb.4.10.2072.
Tratschin et al., Adeno-associated virus vector for high-frequency integration, expression, and rescue of genes in mammalian cells. Mol Cell Biol. Nov. 1985;5(11):3251-60. doi: 10.1128/mcb.5.11.3251.
Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.
Traxler et al., A genome-editing strategy to treat ?-hemoglobinopathies that recapitulates a mutation associated with a benign genetic condition. Nat Med. Sep. 2016;22(9):987-90. doi: 10.1038/nm.4170. Epub Aug. 15, 2016.
Trouet et al., A covalent linkage between daunorubicin and proteins that is stable in serum and reversible by lysosomal hydrolases, as required for a lysosomotropic drug-carrier conjugate: in vitro and in vivo studies.
Trudeau et al., On the Potential Origins of the High Stability of Reconstructed Ancestral Proteins. Mol Biol Evol. Oct. 2016;33(10):2633-41. doi: 10.1093/molbev/msw138. Epub Jul. 12, 2016.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015. With Supplementary Data.
Tsai et al., CIRCLE-seq: a highly sensitive in vitro screen for genome-wide CRISPR-Cas9 nuclease off-targets. Nat Methods. Jun. 2017;14(6):607-614. doi: 10.1038/nmeth.4278. Epub May 1, 2017.
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Tsai et al., Guide-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.
Tsang et al., Specialization of the DNA-cleaving activity of a group I ribozyme through in vitro evolution. J Mol Biol. Sep. 13, 1996;262(1):31-42. doi: 10.1006/jmbi.1996.0496.
Tsutakawa et al., Human flap endonuclease structures, DNA double-base flipping, and a unified understanding of the FEN1 superfamily. Cell. Apr. 15, 2011;145(2):198-211. doi: 10.1016/j.cell.2011.03.004.

(56) References Cited

OTHER PUBLICATIONS

Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.11.016. Epub Nov. 29, 2012.
Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.
Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011. Review.
Tycko et al., Pairwise library screen systematically interrogates *Staphylococcus aureus* Cas9 specificity in human cells. bioRxiv. doi: https://doi.org/10.1101/269399 Posted Feb. 22, 2018.
Uniprot Consortium, UniProt: the universal protein knowledgebase. Nucleic Acids Res. Mar. 16, 2018;46(5):2699. doi: 10.1093/nar/gky092.
Uniprot Submission; UniProt, Accession No. P01011. Last modified Jun. 11, 2014, version 2. 15 pages.
Uniprot Submission; UniProt, Accession No. P01011. Last modified Sep. 18, 2013, version 2. 15 pages.
Uniprot Submission; UniProt, Accession No. P04264. Last modified Jun. 11, 2014, version 6. 15 pages.
Uniprot Submission; UniProt, Accession No. P04275. Last modified Jul. 9, 2014, version 107. 29 pages.
UniProtein A0A1V6. Dec. 11, 2019.
Uniprotkb Submission; Accession No. F0NH53. May 3, 2011. 4 pages.
Uniprotkb Submission; Accession No. F0NN87. May 3, 2011. 4 pages.
Uniprotkb Submission; Accession No. G3ECR1.2. No Author Listed., Aug. 12, 2020, 8 pages.
Uniprotkb Submission; Accession No. P04264. No Author Listed., Apr. 7, 2021. 12 pages.
Uniprotkb Submission; Accession No. T0D7A2. Oct. 16, 2013. 10 pages.
Uniprotkb Submission; Accession No. U2UMQ6. No Author Listed., Apr. 7, 2021, 11 pages.
Urasaki et al., Functional dissection of the To12 transposable element identified the minimal cis-sequence and a highly repetitive sequence in the subterminal region essential for transposition. Genetics. Oct. 2006;174(2):639-49. doi: 10.1534/genetics.106.060244. Epub Sep. 7, 2006.
Urnov et al., Genome editing with engineered zinc finger nucleases. Nat Rev Genet. Sep. 2010;11(9):636-46. doi: 10.1038/nrg2842.
Urnov et al., Highly efficient endogenous human gene correction using designed zinc-finger nucleases. Nature. Jun. 2, 2005;435(7042):646-51. Epub Apr. 3, 2005.
Vagner et al., Efficiency of homologous DNA recombination varies along the Bacillus subtilis chromosome. J Bacteriol. Sep. 1988;170(9):3978-82.
Van Brunt et al., Genetically Encoded Azide Containing Amino Acid in Mammalian Cells Enables Site-Specific Antibody-Drug Conjugates Using Click Cycloaddition Chemistry. Bioconjug Chem. Nov. 18, 2015;26(11):2249-60. doi: 10.1021/acs.bioconjchem.5b00359. Epub Sep. 11, 2015.
Van Brunt et al., Molecular Farming: Transgenic Animals as Bioreactors. Biotechnology (N Y). 1988;6(10):1149-1154. doi: 10.1038/nbt1088-1149.
Van Duyne et al., Teaching Cre to follow directions. Proc Natl Acad Sci U S A. Jan. 6, 2009;106(1):4-5. doi: 10.1073/pnas.0811624106. Epub Dec. 31, 2008.
Van Overbeek et al., DNA Repair Profiling Reveals Nonrandom Outcomes at Cas9-Mediated Breaks. Mol Cell. Aug. 18, 2016;63(4):633-646. doi: 10.1016/j.molcel.2016.06.037. Epub Aug. 4, 2016.
Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.
Vanamee et al., FokI requires two specific DNA sites for cleavage. J Mol Biol. May 25, 2001;309(1):69-78.
Varga et al., Progressive vascular smooth muscle cell defects in a mouse model of Hutchinson-Gilford progeria syndrome. Proc Natl Acad Sci U S A. Feb. 28, 2006;103(9):3250-5. doi: 10.1073/pnas.0600012103. Epub Feb. 21, 2006.
Vellore et al., A group II intron-type open reading frame from the thermophile Bacillus (Geobacillus) stearothermophilus encodes a heat-stable reverse transcriptase. Appl Environ Microbiol. Dec. 2004;70(12):7140-7. doi: 10.1128/AEM.70.12.7140-7147.2004.
Verma, The reverse transcriptase. Biochim Biophys Acta. Mar. 21, 1977;473(1):1-38. doi: 10.1016/0304-419x(77)90005-1.
Vigne et al., Third-generation adenovectors for gene therapy. Restor Neurol Neurosci. Jan. 1, 1995;8(1):35-6. doi: 10.3233/RNN-1995-81208.
Vik et al., Endonuclease V cleaves at inosines in RNA. Nat Commun. 2013;4:2271. doi: 10.1038/ncomms3271.
Vilenchik et al., Endogenous DNA double-strand breaks: production, fidelity of repair, and induction of cancer. Proc Natl Acad Sci U S A. Oct. 28, 2003;100(22):12871-6. doi: 10.1073/pnas.2135498100. Epub Oct. 17, 2003.
Vitreschak et al., Regulation of the vitamin B12 metabolism and transport in bacteria by a conserved RNA structural element. RNA. Sep. 2003;9(9):1084-97.
Voigt et al., Rational evolutionary design: the theory of in vitro protein evolution. Adv Protein Chem. 2000;55:79-160.
Wacey et al., Disentangling the perturbational effects of amino acid substitutions in the DNA-binding domain of p53. Hum Genet. Jan. 1999;104(1):15-22.
Wadia et al., Modulation of cellular function by TAT mediated transduction of full length proteins. Curr Protein Pept Sci. Apr. 2003;4(2):97-104.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Wah et al., Structure of FokI has implications for DNA cleavage. Proc Natl Acad Sci U S A. Sep. 1, 1998;95(18):10564-9.
Wals et al., Unnatural amino acid incorporation in *E. coli*: current and future applications in the design of therapeutic proteins. Front Chem. Apr. 1, 2014;2:15. doi: 10.3389/fchem.2014.00015. eCollection 2014.
Wang et al. CRISPR-Cas9 and CRISPR-Assisted Cytidine Deaminase Enable Precise and Efficient Genome Editing in Klebsiella pneumoniae. Appl Environ Microbiol. 2018;84(23):e01834-18. Published Nov. 15, 2018. doi:10.1128/AEM.01834-18.
Wang et al., AID upmutants isolated using a high-throughput screen highlight the immunity/cancer balance limiting DNA deaminase activity. Nat Struct Mol Biol. Jul. 2009;16(7):769-76. doi: 10.1038/nsmb.1623. Epub Jun. 21, 2009.
Wang et al., Continuous directed evolutions of proteins with improved soluble expression. Nature Chemical Biology. Nat Publishing Group. Aug. 20, 2018; 14(10):972-980.
Wang et al., CRISPR-Cas9 Targeting of PCSK9 in Human Hepatocytes in Vivo-Brief Report. Arterioscler Thromb Vasc Biol. May 2016;36(5):783-6. doi: 10.1161/ATVBAHA.116.307227. Epub Mar. 3, 2016.
Wang et al., Efficient delivery of genome-editing proteins using bioreducible lipid nanoparticles. Proc Natl Acad Sci U S A. Feb. 29, 2016. pii: 201520244. [Epub ahead of print].
Wang et al., Enhanced base editing by co-expression of free uracil DNA glycosylase inhibitor. Cell Res. Oct. 2017;27(1):1289-92. doi: 10.1038/cr.2017.111. Epub Aug. 29, 2017.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Expanding the genetic code. Annu Rev Biophys Biomol; Struct. 2006;35:225-49. Review.

(56) References Cited

OTHER PUBLICATIONS

Wang et al., Genetic screens in human cells using the CRISPR-Cas9 system. Science. Jan. 3, 2014;343(6166):80-4. doi: 10.1126/science. 1246981. Epub Dec. 12, 2013.
Wang et al., Highly efficient CRISPR/HDR-mediated knock-in for mouse embryonic stem cells and zygotes. Biotechniques. 2015:59,201-2;204;206-8.
Wang et al., N(6)-methyladenosine Modulates Messenger RNA Translation Efficiency. Cell. Jun. 4, 2015;161(6):1388-99. doi: 10.1016/j.cell.2015.05.014.
Wang et al., N6-methyladenosine-dependent regulation of messenger RNA stability. Nature. Jan. 2, 2014;505(7481):117-20. doi: 10.1038/nature12730. Epub Nov. 27, 2013.
Wang et al., Nucleation, propagation and cleavage of target RNAs in Ago silencing complexes. Nature. Oct. 8, 2009;461(7265):754-61. doi: 10.1038/nature08434.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang et al., Programming cells by multiplex genome engineering and accelerated evolution. Nature. Aug. 13, 2009;460(7257):894-8. Epub Jul. 26, 2009.
Wang et al., Reading RNA methylation codes through methyl-specific binding proteins. RNA Biol. 2014;11(6):669-72. doi: 10.4161/rna.28829. Epub Apr. 24, 2014.
Wang et al., Recombinase technology: applications and possibilities. Plant Cell Rep. Mar. 2011;30(3):267-85. doi: 10.1007/s00299-010-0938-1. Epub Oct. 24, 2010.
Wang et al., Riboswitches that sense S-adenosylhomocysteine and activate genes involved in coenzyme recycling. Mol Cell. Mar. 28, 2008;29(6):691-702. doi: 10.1016/j.molcel.2008.01.012.
Wang et al., *Staphylococcus aureus* protein SAUGI acts as a uracil-DNA glycosylase inhibitor. Nucleic Acids Res. Jan. 2014;42(2):1354-64. doi: 10.1093/nar/gkt964. Epub Oct. 22, 2013.
Wang et al., Structural basis of N(6)-adenosine methylation by the METTL3-METTL14 complex. Nature. Jun. 23, 2016;534(7608):575-8. doi: 10.1038/nature18298. Epub May 25, 2016.
Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Wang et al., Uracil-DNA glycosylase inhibitor gene of bacteriophage PBS2 encodes a binding protein specific for uracil-DNA glycosylase. J Biol Chem. Jan. 15, 1989;264(2):1163-71.
Warren et al., A chimeric Cre recombinase with regulated directionality. Proc Natl Acad Sci U S A. Nov. 25, 2008;105(47):18278-83. doi: 10.1073/pnas.0809949105. Epub Nov. 14, 2008.
Warren et al., Mutations in the amino-terminal domain of lambda-integrase have differential effects on integrative and excisive recombination. Mol Microbiol. Feb. 2005;55(4):1104-12.
Watowich, The erythropoietin receptor: molecular structure and hematopoietic signaling pathways. J Investig Med. Oct. 2011;59(7):1067-72. doi: 10.2310/JIM.0b013e31820fb28c.
Waxman et al., Regulating excitability of peripheral afferents: emerging ion channel targets. Nat Neurosci. Feb. 2014;17(2):153-63. doi: 10.1038/nn.3602. Epub Jan. 28, 2014.
Weber et al., Assembly of designer TAL effectors by Golden Gate cloning. PLoS One. 2011;6(5):e19722. doi:10.1371/journal.pone. 0019722. Epub May 19, 2011.
Weinberg et al., New Classes of Self-Cleaving Ribozymes Revealed by Comparative Genomics Analysis. Nat Chem Biol. Aug. 2015;11(8):606-10. doi: 10.1038/nchembio.1846. Epub Jul. 13, 2015.
Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.
Weinberger et al., Disease-causing mutations C277R and C277Y modify gating of human C1C-1 chloride channels in myotonia congenita. J Physiol. Aug. 1, 2012;590(Pt 15):3449-64. doi: 0.1113/jphysiol.2012.232785. Epub May 28, 2012.
Weinert et al., Unbiased detection of CRISPR off-targets in vivo using DISCOVER-Seq. Science. Apr. 19, 2019;364(6437):286-289. doi: 10.1126/science.aav9023. Epub Apr. 18, 2019.
Wen et al., Inclusion of a universal tetanus toxoid CD4(+) T cell epitope P2 significantly enhanced the immunogenicity of recombinant rotavirus ?VP8* subunit parenteral vaccines. Vaccine. Jul. 31, 2014;32(35):4420-4427. doi: 10.1016/j.vaccine.2014.06.060. Epub Jun. 21, 2014.
West et al., Gene expression in adeno-associated virus vectors: the effects of chimeric mRNA structure, helper virus, and adenovirus VA1 RNA. Virology. Sep. 1987;160(1):38-47. doi: 10.1016/0042-6822(87)90041-9.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wheeler et al., The thermostability and specificity of ancient proteins. Curr Opin Struct Biol. Jun. 2016;38:37-43. doi: 10.1016/j.sbi.2016.05.015. Epub Jun. 9, 2016.
Wiedenheft et al., RNA-guided genetic silencing systems in bacteria and archaea. Nature. Feb. 15, 2012;482(7385):331-8. doi: 10.1038/nature10886. Review.
Wienert et al., KLF1 drives the expression of fetal hemoglobin in British HPFH. Blood. Aug. 10, 2017;130(6):803-807. doi: 10.1182/blood-2017-02-767400. Epub Jun. 28, 2017.
Wijesinghe et al., Efficient deamination of 5-methylcytosines in DNA by human APOBEC3A, but not by AID or APOBEC3G. Nucleic Acids Res. Oct. 2012;40(18):9206-17. doi: 10.1093/nar/gks685. Epub Jul. 13, 2012.
Wijnker et al., Managing meiotic recombination in plant breeding. Trends Plant Sci. Dec. 2008;13(12):640-6. doi: 10.1016/j.tplants. 2008.09.004. Epub Oct. 22, 2008.
Williams et al., Assessing the accuracy of ancestral protein reconstruction methods. PLoS Comput Biol. Jun. 23, 2006;2(6):e69. doi: 10.1371/journal.pcbi.0020069. Epub Jun. 23, 2006.
Wilson et al., Assessing annotation transfer for genomics: quantifying the relations between protein sequence, structure and function through traditional and probabilistic scores. J Mol Biol 2000;297:233-49.
Wilson et al., Formation of infectious hybrid virions with gibbon ape leukemia virus and human T-cell leukemia virus retroviral envelope glycoproteins and the gag and pol proteins of Moloney murine leukemia virus. J Virol. May 1989;63(5):2374-8. doi: 10.1128/JVI.63.5.2374-2378.1989.
Wilson et al., In Vitro Selection of Functional Nucleic Acids. Annu Rev Biochem. 1999;68:611-47. doi: 10.1146/annurev.biochem.68. 1.611.
Wilson et al., Kinase dynamics. Using ancient protein kinases to unravel a modern cancer drug's mechanism. Science. Feb. 20, 2015;347(6224):882-6. doi: 10.1126/science.aaa1823.
Winkler et al., An mRNA structure that controls gene expression by binding FMN. Proc Natl Acad Sci U S A. Dec. 10, 2002;99(25):15908-13. Epub Nov. 27, 2002.
Winkler et al., Control of gene expression by a natural metabolite-responsive ribozyme. Nature. Mar. 18, 2004;428(6980):281-6.
Winkler et al., Thiamine derivatives bind messenger RNAs directly to regulate bacterial gene expression. Nature. Oct. 31, 2002;419(6910):952-6. Epub Oct. 16, 2002.
Winoto et al., A novel, inducible and T cell-specific enhancer located at the 3' end of the T cell receptor alpha locus. EMBO J. Mar. 1989;8(3):729-33.
Winter et al., Drug Development. Phthalimide conjugation as a strategy for in vivo target protein degradation. Science. Jun. 19, 2015;348(6241):1376-81. doi:; 10.1126/science.aab1433. Epub May 21, 2015.
Winter et al., Targeted exon skipping with AAV-mediated split adenine base editors. Cell Discov. Aug. 20, 2019;5:41. doi: 10.1038/s41421-019-0109-7.

(56) References Cited

OTHER PUBLICATIONS

Wold, Replication protein A: a heterotrimeric, single-stranded DNA-binding protein required for eukaryotic DNA metabolism. Annu Rev Biochem. 1997;66:61-92. doi: 10.1146/annurev.biochem.66.1.61.

Wolf et al., tadA, an essential tRNA-specific adenosine deaminase from *Escherichia coli*. EMBO J. Jul. 15, 2002;21(14):3841-51.

Wolfe et al., Analysis of zinc fingers optimized via phage display: evaluating the utility of a recognition code. J Mol Biol. Feb. 5, 1999;285(5):1917-34.

Wong et al., A statistical analysis of random mutagenesis methods used for directed protein evolution. J Mol Biol. Jan. 27, 2006;355(4):858-71. Epub Nov. 17, 2005.

Wong et al., The Diversity Challenge in Directed Protein Evolution. Comb Chem High Throughput Screen. May 2006;9(4):271-88.

Wood et al., A genetic system yields self-cleaving inteins for bioseparations. Nat Biotechnol. Sep. 1999;17(9):889-92. doi: 10.1038/12879.

Wood et al., Targeted genome editing across species using ZFNs and TALENs. Science. Jul. 15, 2011;333(6040):307. doi: 10.1126/science.1207773. Epub Jun. 23, 2011.

Wright et al., Continuous in vitro evolution of catalytic function. Science. Apr. 25, 1997;276(5312):614-7.

Wright et al., Rational design of a split-Cas9 enzyme complex. Proc Natl Acad Sci U S A. Mar. 10, 2015;112(10):2984-9. doi: 10.1073/pnas.1501698112. Epub Feb. 23, 2015.

Wu et al., Correction of a genetic disease in mouse via use of CRISPR-Cas9. Cell Stem Cell. Dec. 5, 2013;13(6):659-62. doi: 10.1016/j.stem.2013.10.016.

Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.

Wu et al., Human single-stranded DNA binding proteins: guardians of genome stability. Acta Biochim Biophys Sin (Shanghai). Jul. 2016;48(7):671-7. doi: 10.1093/abbs/gmw044. Epub May 23, 2016.

Wu et al., Protein trans-splicing and functional mini-inteins of a cyanobacterial dnaB intein. Biochim Biophys Acta. Sep. 8, 1998;1387(1-2):422-32. doi: 10.1016/s0167-4838(98)00157-5.

Wu et al., Protein trans-splicing by a split intein encoded in a split DnaE gene of *Synechocystis* sp. PCC6803. Proc Natl Acad Sci U S A. Aug. 4, 1998;95(16):9226-31. doi: 10.1073/pnas.95.16.9226.

Wu et al., Readers, writers and erasers of N6-methylated adenosine modification. Curr Opin Struct Biol. Dec. 2017;47:67-76. doi: 10.1016/j.sbi.2017.05.011. Epub Jun. 16, 2017.

Xiang et al., RNA m6A methylation regulates the ultraviolet-induced DNA damage response. Nature. Mar. 23, 2017;543(7646):573-576. doi: 10.1038/nature21671. Epub Mar. 15, 2017.

Xiao et al., Genetic incorporation of multiple unnatural amino acids into proteins in mammalian cells. Angew Chem Int Ed Engl. Dec. 23, 2013;52(52):14080-3. doi: 10.1002/anie.201308137. Epub Nov. 8, 2013.

Xiao et al., Nuclear m(6)a Reader YTHDC1 Regulates mRNA Splicing. Mol Cell. Feb. 18, 2016;61(4):507-519. doi: 10.1016/j.molcel.2016.01.012. Epub Feb. 11, 2016.

Xie et al., Adjusting the attB site in donor plasmid improves the efficiency of ?C31 integrase system. DNA Cell Biol. Jul. 2012;31(7):1335-40. doi: 10.1089/dna.2011.1590. Epub Apr. 10, 2012.

Xiong et al., Origin and evolution of retroelements based upon their reverse transcriptase sequences. EMBO J. Oct. 1990;9(10):3353-62.

Xu et al., Chemical ligation of folded recombinant proteins: segmental isotopic labeling of domains for NMR studies. Proc Natl Acad Sci U S A. Jan. 19, 1999;96(2):388-93. doi: 10.1073/pnas.96.2.388.

Xu et al., Accuracy and efficiency define Bxb1 integrase as the best of fifteen candidate serine recombinases for the integration of DNA into the human genome. BMC Biotechnol. Oct. 20, 2013;13:87. doi: 10.1186/1472-6750-13-87.

Xu et al., Protein splicing: an analysis of the branched intermediate and its resolution by succinimide formation. EMBO J. Dec. 1, 1994;13(23):5517-22.

Xu et al., PTMD: A Database of Human Disease-associated Post-translational Modifications. Genomics Proteomics Bioinformatics. Aug. 2018;16(4):244-251. doi: 10.1016/j.gpb.2018.06.004. Epub Sep. 21, 2018.

Xu et al., Sequence determinants of improved CRISPR sgRNA design. Genome Res. Aug. 2015;25(8):1147-57. doi: 10.1101/gr.191452.115. Epub Jun. 10, 2015.

Xu et al., Structures of human ALKBH5 demethylase reveal a unique binding mode for specific single-stranded N6-methyladenosine RNA demethylation. J Biol Chem. Jun. 20, 2014;289(25):17299-311. doi: 10.1074/jbc.M114.550350. Epub Apr. 28, 2014.

Xu et al., The mechanism of protein splicing and its modulation by mutation. EMBO J. Oct. 1, 1996;15(19):5146-53.

Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.

Yamamoto et al., The ons and offs of inducible transgenic technology: a review. Neurobiol Dis. Dec. 2001;8(6):923-32.

Yamamoto et al., Virological and immunological bases for HIV-1 vaccine design. Uirusu 2007;57(2):133-139. https://doi.org/10.2222/jsv.57.133.

Yamano et al., Crystal Structure of Cpf1 in Complex with Guide RNA and Target DNA. Cell May 2016;165(4)949-62.

Yamazaki et al., Segmental Isotope Labeling for Protein NMR Using Peptide Splicing. J. Am. Chem. Soc. May 22, 1998; 120(22):5591-2. https://doi.org/10.1021/ja980776o.

Yan et al., Cas13d Is a Compact RNA-Targeting Type VI CRISPR Effector Positively Modulated by a WYL-Domain-Containing Accessory Protein. Mol Cell. Apr. 19, 2018;70(2):327-339.e5. doi: 10.1016/j.molcel.2018.02.028. Epub Mar. 15, 2018.

Yang et al., APOBEC: From mutator to editor. J Genet Genomics. Sep. 20, 2017;44(9):423-437. doi: 10.1016/j.jgg.2017.04.009. Epub Aug. 7, 2017.

Yang et al., Construction of an integration-proficient vector based on the site-specific recombination mechanism of enterococcal temperate phage phiFC1. J Bacteriol. Apr. 2002;184(7):1859-64. doi: 10.1128/jb.184.7.1859-1864.2002.

Yang et al., Engineering and optimising deaminase fusions for genome editing. Nat Commun. Nov. 2, 2016;7:13330. doi: 10.1038/ncomms13330.

Yang et al., Genome editing with targeted deaminases. BioRxiv. Preprint. First posted online Jul. 28, 2016.

Yang et al., Increasing targeting scope of adenosine base editors in mouse and rat embryos through fusion of TadA deaminase with Cas9 variants. Protein Cell. Sep. 2018;9(9):814-819. doi: 10.1007/s13238-018-0568-x.

Yang et al., New CRISPR-Cas systems discovered. Cell Res. Mar. 2017;27(3):313-314. doi: 10.1038/cr.2017.21. Epub Feb. 21, 2017.

Yang et al., One-step generation of mice carrying reporter and conditional alleles by CRISPR/Cas-mediated genome engineering. Cell. Sep. 12, 2013;154(6):1370-9. doi: 10.1016/j.cell.2013.08.022. Epub Aug. 29, 2013.

Yang et al., PAM-dependent Target DNA Recognition and Cleavage by C2C1 CRISPR-Cas endonuclease. Cell Dec. 2016;167(7):1814-28.

Yang et al., Permanent genetic memory with >1-byte capacity. Nat Methods. Dec. 2014;11(12):1261-6. doi: 10.1038/nmeth.3147. Epub Oct. 26, 2014.

Yang et al., Preparation of RNA-directed DNA polymerase from spleens of Balb-c mice infected with Rauscher leukemia virus. Biochem Biophys Res Commun. Apr. 28, 1972;47(2):505-11. doi: 10.1016/0006-291x(72)90743-7.

Yang et al., Small-molecule control of insulin and PDGF receptor signaling and the role of membrane attachment. Curr Biol. Jan. 1, 1998;8(1):11-8. doi: 10.1016/s0960-9822(98)70015-6.

Yang, PAML 4: phylogenetic analysis by maximum likelihood. Mol Biol Evol. Aug. 2007;24(8):1586-91. doi: 10.1093/molbev/msm088. Epub May 4, 2007.

(56) References Cited

OTHER PUBLICATIONS

Yang, Phylogenetic Analysis by Maximum Likelihood (PAML). //abacus.gene.ucl.ac.uk/software/paml.html Last accessed Apr. 28, 2021.
Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.
Yasui et al., Miscoding Properties of 2'-Deoxyinosine, a Nitric Oxide-Derived DNA Adduct, during Translesion Synthesis Catalyzed by Human DNA Polymerases. J Molec Biol. Apr. 4, 2008;377(4):1015-23.
Yasukawa et al., Characterization of Moloney murine leukaemia virus/avian myeloblastosis virus chimeric reverse transcriptases. J Biochem. Mar. 2009;145(3):315-24. doi: 10.1093/jb/mvn166. Epub Dec. 6, 2008.
Yazaki et al., Hereditary systemic amyloidosis associated with a new apolipoprotein AII stop codon mutation Stop78Arg. Kidney Int. Jul. 2003;64(1):11-6.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Yokoe et al., Spatial dynamics of GFP-tagged proteins investigated by local fluorescence enhancement. Nat Biotechnol. Oct. 1996;14(10):1252-6. doi: 10.1038/nbt1096-1252.
Young et al., Beyond the canonical 20 amino acids: expanding the genetic lexicon. J Biol Chem. Apr. 9, 2010;285(15):11039-44. doi: 10.1074/jbc.R109.091306. Epub Feb. 10, 2010.
Yu et al., Circular permutation: a different way to engineer enzyme structure and function. Trends Biotechnol. Jan. 2011;29(1):18-25. doi: 10.1016/j.tibtech.2010.10.004. Epub Nov. 2010.
Yu et al., Liposome-mediated in vivo E1A gene transfer suppressed dissemination of ovarian cancer cells that overexpress HER-2/neu. Oncogene. Oct. 5, 1995;11(7):1383-8.
Yu et al., Progress towards gene therapy for Hiv infection. Gene Ther. Jan. 1994;1(1):13-26.
Yu et al., Small molecules enhance CRISPR genome editing in pluripotent stem cells. Cell Stem Cell. Feb. 5, 2015;16(2):142-7. doi: 10.1016/j.stem.2015.01.003.
Yu et al., Synthesis-dependent microhomology-mediated end joining accounts for multiple types of repair junctions. Nucleic Acids Res. Sep. 2010;38(17):5706-17. doi: 10.1093/nar/gkq379. Epub May 11, 2010.
Yuan et al., Laboratory-directed protein evolution. Microbiol Mol Biol Rev. 2005; 69(3):373-92. PMID: 16148303.
Yuan et al., Tetrameric structure of a serine integrase catalytic domain. Structure. Aug. 6, 2008;16(8):1275-86. doi: 10.1016/j.str.2008.04.018.
Yuen et al., Control of transcription factor activity and osteoblast differentiation in mammalian cells using an evolved small-molecule-dependent intein. J Am Chem Soc. Jul. 12, 2006;128(27):8939-46.
Zakas et al., Enhancing the pharmaceutical properties of protein drugs by ancestral sequence reconstruction. Nat Biotechnol. Jan. 2017;35(1):35-37. doi: 10.1038/nbt.3677. Epub Sep. 26, 2016.
Zalatan et al., Engineering complex synthetic transcriptional programs with CRISPR RNA scaffolds. Cell. Jan. 15, 2015;160(1-2):339-50. doi: 10.1016/j.cell.2014.11.052. Epub Dec. 2014.
Zelphati et al., Intracellular delivery of proteins with a new lipid-mediated delivery system. J Biol Chem. Sep. 14, 2001;276(37):35103-10. Epub Jul. 10, 2001.
Zetsche et al., A split-Cas9 architecture for inducible genome editing and transcription modulation. Nat Biotechnol. Feb. 2015;33(2):139-42. doi: 10.1038/nbt.3149.
Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.
Zettler et al., The naturally split Npu DnaE intein exhibits an extraordinarily high rate in the protein trans-splicing reaction. FEBS Lett. Mar. 4, 2009;583(5):909-14. doi: 10.1016/j.febslet.2009.02.003. Epub Feb. 10, 2009.
Zhang et al., II-Clamp-mediated cysteine conjugation. Nat Chem. Feb. 2016;8(2):120-8. doi: 10.1038/nchem.2413. Epub Dec. 21, 2015.
Zhang et al., A new strategy for the site-specific modification of proteins in vivo. Biochemistry. Jun. 10, 2003;42(22):6735-46.
Zhang et al., Circular intronic long noncoding RNAs. Mol Cell. Sep. 26, 2013;51(6):792-806. doi: 10.1016/j.molcel.2013.08.017. Epub Sep. 12, 2013.
Zhang et al., Comparison of non-canonical PAMs for CRISPR/Cas9-mediated Dna cleavage in human cells. Sci Rep. Jun. 2014;4:5405.
Zhang et al., Conditional gene manipulation: Cre-ating a new biological era. J Zhejiang Univ Sci B. Jul. 2012;13(7):511-24. doi: 10.1631/jzus.B1200042. Review.
Zhang et al., Copy number variation in human health, disease, and evolution. Annu Rev Genomics Hum Genet. 2009;10:451-81. doi: 10.1146/annurev.genom.9.081307.164217.
Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
Zhang et al., Myoediting: Toward Prevention of Muscular Dystrophy by Therapeutic Genome Editing. Physiol Rev. Jul. 1, 2018;98(3):1205-1240. doi: 10.1152/physrev.00046.2017.
Zhang et al., Programmable base editing of zebrafish genome using a modified CRISPR-Cas9 system. Nat Commun. Jul. 25, 2017;8(1):118. doi: 10.1038/s41467-017-00175-6.
Zhang et al., Ribozymes and Riboswitches: Modulation of RNA Function by Small Molecules. Biochemistry. Nov. 2, 2010;49(43):9123-31. doi: 10.1021/bi1012645.
Zhang et al., Stabilized plasmid-lipid particles for regional gene therapy: formulation and transfection properties. Gene Ther. Aug. 1999;6(8):1438-47.
Zhao et al., An ultraprocessive, accurate reverse transcriptase encoded by a metazoan group II intron. RNA. Feb. 2018;24(2):183-195. doi: 10.1261/rna.063479.117. Epub Nov. 6, 2017.
Zhao et al., Crystal structures of a group II intron maturase reveal a missing link in spliceosome evolution. Nat Struct Mol Biol. Jun. 2016;23(6):558-65. doi: 10.1038/nsmb.3224. Epub May 2, 2016.
Zhao et al., Post-transcriptional gene regulation by mRNA modifications. Nat Rev Mol Cell Biol. Jan. 2017;18(1):31-42. doi: 10.1038/nrm.2016.132. Epub Nov. 3, 2016.
Zheng et al., ALKBH5 is a mammalian RNA demethylase that impacts RNA metabolism and mouse fertility. Mol Cell. Jan. 10, 2013;49(1):18-29. doi: 10.1016/j.molcel.2012.10.015. Epub Nov. 21, 2012.
Zheng et al., DNA editing in DNA/RNA hybrids by adenosine deaminases that act on RNA. Nucleic Acids Res. Apr. 7, 2017;45(6):3369-3377. doi: 10.1093/nar/gkx050.
Zheng et al., Highly efficient base editing in bacteria using a Cas9-cytidine deaminase fusion. Commun Biol. Apr. 19, 2018;1:32. doi: 10.1038/s42003-018-0035-5.
Zheng et al., Structural basis for the complete resistance of the human prion protein mutant G127V to prion disease. Sci Rep. Sep. 4, 2018;8(1):13211. doi: 10.1038/s41598-018-31394-6.
Zhong et al., Rational Design of Aptazyme Riboswitches for Efficient Control of Gene Expression in Mammalian Cells. Elife. Nov. 2, 2016;5:e18858. doi: 10.7554/eLife.18858.
Zhou et al., Dynamic m(6)A mRNA methylation directs translational control of heat shock response. Nature. Oct. 22, 2015;526(7574):591-4. doi: 10.1038/nature15377. Epub Oct. 12, 2015.
Zhou et al., Off-target RNA mutation induced by DNA base editing and its elimination by mutagenesis. Nature. Jul. 2019;571(7764):275-278. doi: 10.1038/s41586-019-1314-0. Epub Jun. 10, 2019.
Zhou et al., Protective V127 prion variant prevents prion disease by interrupting the formation of dimer and fibril from molecular dynamics simulations. Sci Rep. Feb. 24, 2016;6:21804. doi: 10.1038/srep21804.
Zhou et al., Seamless Genetic Conversion of SMN2 to SMN1 via CRISPR/Cpf1 and Single-Stranded Oligodeoxynucleotides in Spinal Muscular Atrophy Patient-Specific Induced Pluripotent Stem

(56) References Cited

OTHER PUBLICATIONS

Cells. Hum Gene Ther. Nov. 2018;29(11):1252-1263. doi: 10.1089/hum.2017.255. Epub May 9, 2018.

Zielenski, Genotype and phenotype in cystic fibrosis. Respiration. 2000;67(2):117-33. doi: 10.1159/000029497.

Zimmerly et al., An Unexplored Diversity of Reverse Transcriptases in Bacteria. Microbiol Spectr. Apr. 2015;3(2):MDNA3-0058-2014. doi: 10.1128/microbiolspec.MDNA3-0058-2014.

Zimmerly et al., Group II intron mobility occurs by target DNA-primed reverse transcription. Cell. Aug. 25, 1995;82(4):545-54. doi: 10.1016/0092-8674(95)90027-6.

Zimmermann et al., Molecular interactions and metal binding in the theophylline-binding core of an RNA aptamer. RNA. May 2000;6(5):659-67.

Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.

Zorko et al., Cell-penetrating peptides: mechanism and kinetics of cargo delivery. Adv Drug Deliv Rev. Feb. 28, 2005;57(4):529-45. Epub Jan. 22, 2005.

Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.

Zufferey et al., Woodchuck hepatitis virus posttranscriptional regulatory element enhances expression of transgenes delivered by retroviral vectors. J Virol. Apr. 1999;73(4):2886-92. doi: 10.1128/JVI.73.4.2886-2892.1999.

Zuker et al., Optimal computer folding of large RNA sequences using thermodynamics and auxiliary information. Nucleic Acids Res. Jan. 10, 1981;9(1):133-48. doi: 10.1093/nar/9.1.133.

Zuo et al., Cytosine base editor generates substantial off-target single-nucleotide variants in mouse embryos. Science. Apr. 19, 2019;364(6437):289-292. doi: 10.1126/science.aav9973. Epub Feb. 28, 2019.

Zuris et al., Cationic lipid-mediated delivery of proteins enables efficient protein-based genome editing in vitro and in vivo. Nat Biotechnol. 2015;33:73-80.

| construct | clone | position: | 8 | 17 | 18 | 23 | 34 | 45 | 51 | 56 | 59 | 85 | 94 | 95 | 102 | 104 | 106 | 107 | 108 | 110 | 118 | 127 | 138 | 149 | 151 | 153 | 154 | 156 | 157 |
|---|---|---|---|---|---|---|---|---|---|---|---|---|---|---|---|---|---|---|---|---|---|---|---|---|---|---|---|---|---|
| | | wt res: | His | Thr | Leu | Trp | Leu | Trp | Arg | Ala | Glu | Glu | Met | Ile | Val | Phe | Ala | Arg | Asp | Lys | Met | Asn | Ala | Phe | Met | Arg | Gln | Ile | Lys |
| 1 | 2 | | Tyr | | | | | | | | | | | | | | | | | | | | | | | | | | |
| 2 | 3 | | | | | | | | | | | | | | | | | | | | | | | | | | | | Arg |
| 3 | 5 | | | | | | | | | | | | | | | | Val | Cys | | | | | | | | | | | |
| 4 | 7 | | | | | | | | | | | | | | | | | | | | | Ser | | Tyr | | | | | |
| 5 | 10 | | | | | | | | | Glu | | | | | | | | Asn | | | | | | | | | | | |
| 6 | 11 | | | | | | | Leu | | | | | | | | Leu | | Asn | | | | | | | | | | Asp | |
| 7 | 13 | | | Ser | | | Ser | | | | | | | | | | | | | | | | | | | | | | |
| 8 | 16 | | | | | | | | | | | Lys | | | | | | Cys/His | Gln | | | | | Tyr | | | | | |
| 9 | 18 | | | | | Leu | | | | Glu | Glu | Gln | | | | | | | | | | | | | | | | | |
| 10 | 19 | | | | | | | | | | | | | | | | | | | Ile | | | | | | | | | |
| 11 | 21 | | | | | | | | | | | | | | | | | Asn | Val | | | | Val | | Val | Cys | | Asp | |
| 12 | 23 | | | | | | | | His | Ser | | Lys | | Ile | | | | Pro | Ala | | Lys | | | Tyr | | | | | |
| 13 | 25 | | | | Glu | | | | | | | | | | | | | | | | | | | | | | | | |
| 14 | 28 | | | | | Leu | | | | | | | Leu | | Ala | | | | Tyr | | | | | | | | | | |
| 15 | 29 | | | | | | | | | | | | | | | | | | Leu | | | | | | | | Leu | | |
| 16 | 32 | | | | | | | | | | | | | | | | | Cys | Asn | | | | | | | | | | |

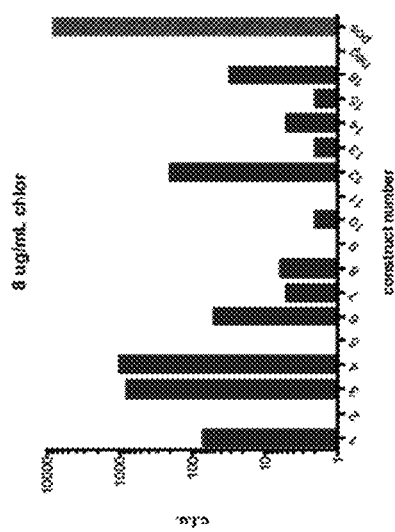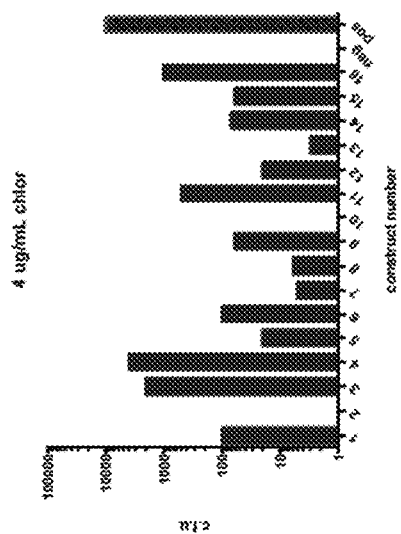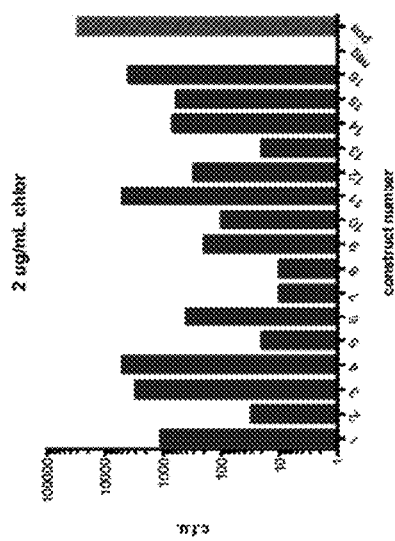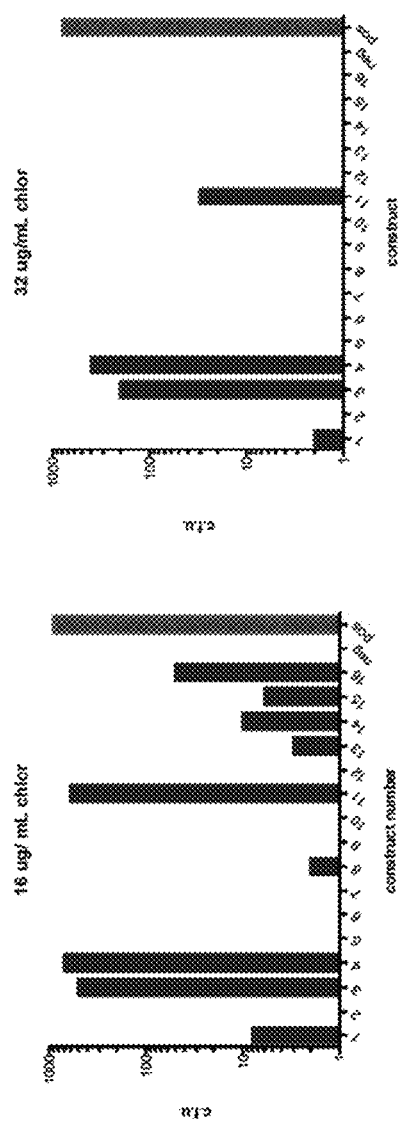
FIGURE 12

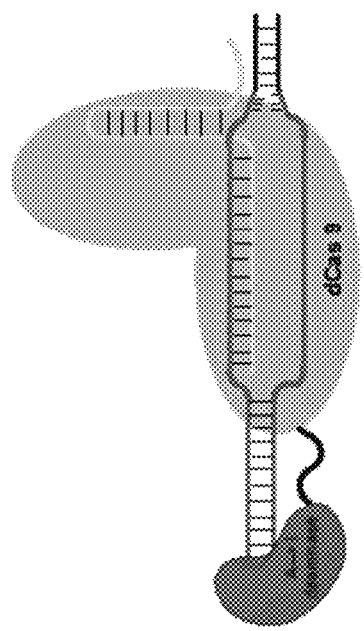
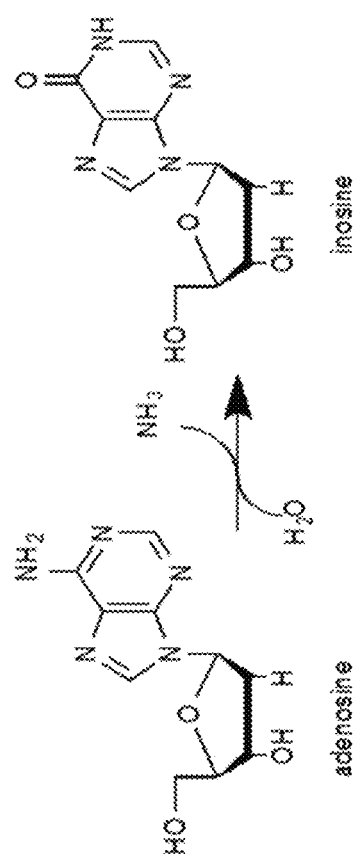
FIGURE 15

| position: | 8 | 26 | 61 | 68 | 70 | 106 | 107 | 108 | 109 | 127 | 147 | 152 | 154 | 155 | 161 | 163 | 166 | wt residue |
|---|---|---|---|---|---|---|---|---|---|---|---|---|---|---|---|---|---|---|
| | His | Arg | Met | Leu | Met | Ala | Arg | Asp | Ala | Asn | Asn | Arg | Gln | Ile | Lys | Gln | Thr | |
| 1 pNMG-149 | Tyr | | | | | | | Asn | | Ser | | | | | | | | |
| 2 pNMG-150 | Tyr | | Ile | | Val | | | Asn | | Ser | Tyr | Cys | His | Gly | | His | | |
| 3 pNMG-151 | Tyr | | | | | | | Asn | | Ser | | | Arg | Val | | | Pro | |
| 4 pNMG-152 | Tyr | | | | | Thr | | Asn | | Ser | | | | Asp | Gln | | | |
| 5 pNMG-153 | Tyr | Trp | | Gln | | | | Asn | | Ser | Tyr | | | Val | | | | |
| 6 pNMG-154 | Tyr | | | | | | | Asn | Thr | Ser | | | | Gly | | | | |

FIGURE 46
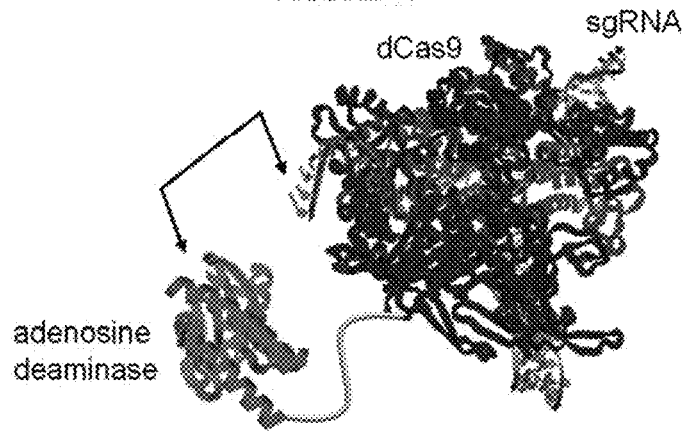
FIGURE 47
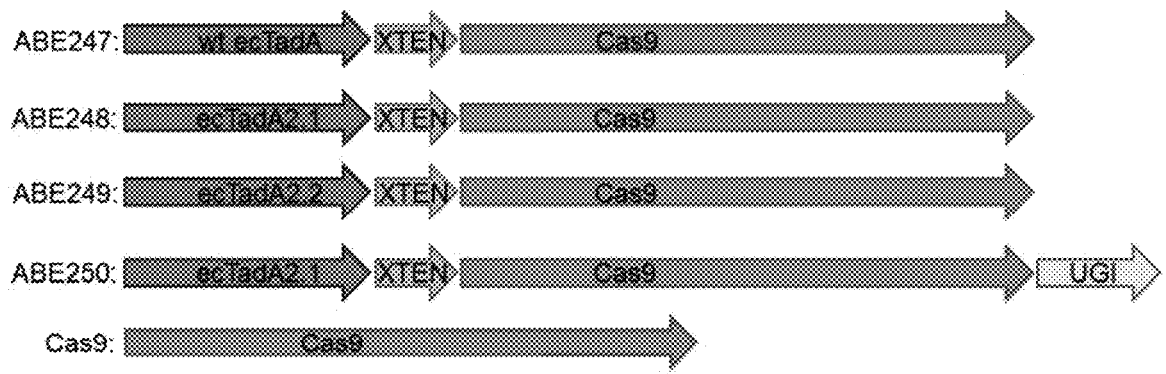
FIGURE 48
|        | EMX1  | FANCF | HEK2  | HEK3  | HEK4  | RNF2  |
|--------|-------|-------|-------|-------|-------|-------|
| wtCas9 | 35.4% | 37.0% | 32.9% | 56.8% | 23.8% | 33.8% |
| ABE247 | 25.5% | 30.2% | 45.7% | 76.3% | 36.5% | 26.8% |
| ABE248 | 24.8% | 26.6% | 39.8% | 64.2% | 35.1% | 26.5% |
| ABE249 | 30.2% | 28.6% | 42.0% | 66.7% | 40.0% | 27.1% |
| ABE250 | 25.0% | 25.2% | 31.3% | 56.3% | 36.4% | 25.2% |
FIGURE 49
     protospacer    PAM
EMX1:    GA$_2$GTCCGA$_8$GCAGAAGAAGAAGGG
FANCF:    GGA$_3$A$_4$TCCCTTCTGCAGCACCTGG
HEK293 site 2: GA$_2$A$_3$CA$_5$CA$_7$A$_8$A$_9$GCATAGACTGCGGG
HEK293 site 3: GGCCCA$_6$GA$_8$CTGAGCACGTGATGG
HEK293 site 4: GGCA$_4$CTGCGGCTGGAGGTCCGGG
RNF2:    GTCA$_4$TCTTA$_9$GTCATTACCTGAGG

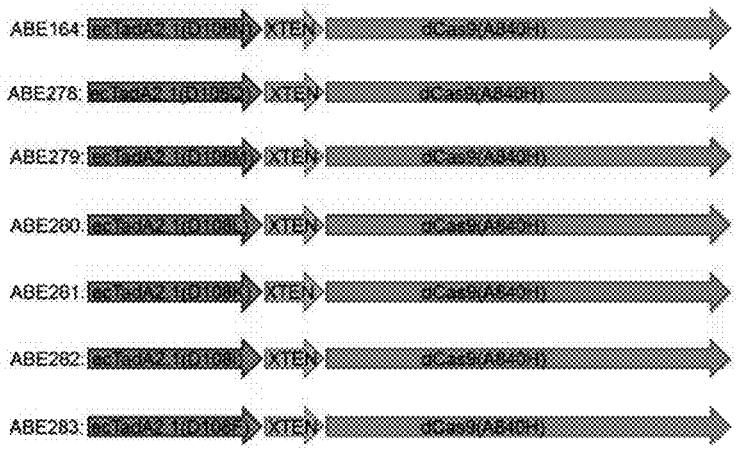

HEK293 site 2:   GA$_2$A$_3$CA$_5$CA$_7$A$_8$A$_9$GCATAGACTGCGGG   (see high editing at A-5)

EMX1:            GA$_2$GTCCGA$_8$GCAGAAGAAGAAGGG   (see no editing)

HEK293 site 3:   GGCCCA$_6$GA$_8$CTGAGCACGTGATGG   (see low editing)

FIGURE 52

| HEK2 | | A$_2$ | A$_3$ | A$_5$ | A$_7$ | A$_8$ | A$_9$ |
|---|---|---|---|---|---|---|---|
| untreated | A | 100.0 | 100.0 | 100.0 | 100.0 | 100.0 | 100.0 |
| | C | 0.0 | 0.0 | 0.0 | 0.0 | 0.0 | 0.0 |
| | G | 0.0 | 0.0 | 0.0 | 0.0 | 0.0 | 0.0 |
| | T | 0.0 | 0.0 | 0.0 | 0.0 | 0.0 | 0.0 |

| D108N (pNMG-164, pCMV_ecTadA_XTEN_nCas9_GGS_NLS) | A | 100.0 | 99.8 | 90.6 | 100.0 | 100.0 | 100.0 |
|---|---|---|---|---|---|---|---|
| | C | 0.0 | 0.0 | 0.0 | 0.0 | 0.0 | 0.0 |
| | G | 0.0 | 0.2 | 9.4 | 0.0 | 0.0 | 0.0 |
| | T | 0.0 | 0.0 | 0.0 | 0.0 | 0.0 | 0.0 |

| D108G (pNMG-278; pCMV_ecTadA_XTEN_nCas9_GGS_NLS) | A | 100.0 | 100.0 | 97.1 | 100.0 | 100.0 | 100.0 |
|---|---|---|---|---|---|---|---|
| | C | 0.0 | 0.0 | 0.0 | 0.0 | 0.0 | 0.0 |
| | G | 0.0 | 0.0 | 2.8 | 0.0 | 0.0 | 0.0 |
| | T | 0.0 | 0.0 | 0.0 | 0.0 | 0.0 | 0.0 |

| D108M (pNMG-279; pCMV_ecTadA_XTEN_nCas9_GGS_NLS) | A | 100.0 | 99.8 | 81.3 | 99.9 | 100.0 | 100.0 |
|---|---|---|---|---|---|---|---|
| | C | 0.0 | 0.0 | 0.0 | 0.0 | 0.0 | 0.0 |
| | G | 0.0 | 0.2 | 18.7 | 0.1 | 0.0 | 0.0 |
| | T | 0.0 | 0.0 | 0.0 | 0.0 | 0.0 | 0.0 |

| D108L (pNMG-280; pCMV_ecTadA_XTEN_nCas9_GGS_NLS) | A | 100.0 | 99.9 | 96.8 | 100.0 | 100.0 | 100.0 |
|---|---|---|---|---|---|---|---|
| | C | 0.0 | 0.0 | 0.0 | 0.0 | 0.0 | 0.0 |
| | G | 0.0 | 0.1 | 3.2 | 0.0 | 0.0 | 0.0 |
| | T | 0.0 | 0.0 | 0.0 | 0.0 | 0.0 | 0.0 |

| D108K (pNMG-281; pCMV_ecTadA_XTEN_nCas9_GGS_NLS) | A | 100.0 | 99.9 | 97.1 | 99.9 | 100.0 | 100.0 |
|---|---|---|---|---|---|---|---|
| | C | 0.0 | 0.0 | 0.0 | 0.0 | 0.0 | 0.0 |
| | G | 0.0 | 0.1 | 2.9 | 0.1 | 0.0 | 0.0 |
| | T | 0.0 | 0.0 | 0.0 | 0.0 | 0.0 | 0.0 |

| D108I (pNMG-282; pCMV_ecTadA_XTEN_nCas9_GGS_NLS) | A | 100.0 | 100.0 | 99.3 | 100.0 | 100.0 | 100.0 |
|---|---|---|---|---|---|---|---|
| | C | 0.0 | 0.0 | 0.0 | 0.0 | 0.0 | 0.0 |
| | G | 0.0 | 0.0 | 0.7 | 0.0 | 0.0 | 0.0 |
| | T | 0.0 | 0.0 | 0.0 | 0.0 | 0.0 | 0.0 |

| D108F (pNMG-283; pCMV_ecTadA_XTEN_nCas9_GGS_NLS) | A | 100.0 | 100.0 | 98.1 | 100.0 | 100.0 | 100.0 |
|---|---|---|---|---|---|---|---|
| | C | 0.0 | 0.0 | 0.0 | 0.0 | 0.0 | 0.0 |
| | G | 0.0 | 0.0 | 1.9 | 0.0 | 0.0 | 0.0 |
| | T | 0.0 | 0.0 | 0.0 | 0.0 | 0.0 | 0.0 |

HEK293 site 2: GA$_2$A$_3$CA$_5$CA$_7$A$_9$A$_0$GCATAGACTGCGGG

RNF2 multi-A: A$_1$GA$_3$A$_4$A$_5$A$_6$A$_7$CA$_9$A$_{10}$TTTTAGTATTTGG

HEK3 multi-A: GCA$_3$GA$_5$A$_6$A$_7$TA$_9$GA$_{11}$CTAATTGCATGG

FIGURE 59

| HEK2 | | A$_2$ | A$_3$ | A$_5$ | A$_7$ | A$_8$ | A$_9$ |
|---|---|---|---|---|---|---|---|
| untreated | A | 100 | 100 | 100 | 100 | 100 | 100 |
| | C | 0 | 0 | 0 | 0 | 0 | 0 |
| | G | 0 | 0 | 0 | 0 | 0 | 0 |
| | T | 0 | 0 | 0 | 0 | 0 | 0 |
| XTEN | A | 100 | 99.8 | 90.6 | 100 | 100 | 100 |
| | C | 0 | 0 | 0 | 0 | 0 | 0 |
| | G | 0 | 0.2 | 9.4 | 0 | 0 | 0 |
| | T | 0 | 0 | 0 | 0 | 0 | 0 |
| GGS | A | 100 | 99.9 | 87.7 | 100 | 100 | 100 |
| | C | 0 | 0 | 0 | 0 | 0 | 0 |
| | G | 0 | 0.1 | 12.3 | 0 | 0 | 0 |
| | T | 0 | 0 | 0 | 0 | 0 | 0 |
| (GGS)$_2$XTEN(GGS)$_2$ | A | 100 | 99.9 | 77.6 | 100 | 100 | 100 |
| | C | 0 | 0 | 0 | 0 | 0 | 0 |
| | G | 0 | 0.1 | 22.4 | 0 | 0 | 0 |
| | T | 0 | 0 | 0 | 0 | 0 | 0 |

FIGURE 60

| | | EMX1 A$_2$ | A$_6$ | FANCF A$_3$ | A$_4$ | HEK3 A$_5$ | A$_8$ | HEK4 A$_4$ | RNF2 A$_4$ | A$_4$ |
|---|---|---|---|---|---|---|---|---|---|---|
| untreated | A | 100.0 | 100.0 | 100.0 | 100.0 | 100.0 | 100.0 | 100 | 100.0 | 100.0 |
| | C | 0.0 | 0.0 | 0.0 | 0.0 | 0.0 | 0.0 | 0 | 0.0 | 0.0 |
| | G | 0.0 | 0.0 | 0.0 | 0.0 | 0.0 | 0.0 | 0 | 0.0 | 0.0 |
| | T | 0.0 | 0.0 | 0.0 | 0.0 | 0.0 | 0.0 | 0 | 0.0 | 0.0 |
| XTEN | A | 100.0 | 100.0 | 100.0 | 100.0 | 99.8 | 99.4 | 99.7 | 99.9 | 99.9 |
| | C | 0.0 | 0.0 | 0.0 | 0.0 | 0.0 | 0.0 | 0.0 | 0.0 | 0.0 |
| | G | 0.0 | 0.0 | 0.0 | 0.0 | 0.2 | 0.6 | 0.3 | 0.0 | 0.1 |
| | T | 0.0 | 0.0 | 0.0 | 0.0 | 0.0 | 0.0 | 0.0 | 0.0 | 0.0 |
| GGS | A | 100.0 | 100.0 | 100.0 | 99.8 | 99.7 | 99.8 | 99.5 | 99.9 | 100.0 |
| | C | 0.0 | 0.0 | 0.0 | 0.0 | 0.0 | 0.0 | 0.0 | 0.0 | 0.0 |
| | G | 0.0 | 0.0 | 0.0 | 0.2 | 0.2 | 0.2 | 0.4 | 0.0 | 0.0 |
| | T | 0.0 | 0.0 | 0.0 | 0.0 | 0.0 | 0.0 | 0.0 | 0.0 | 0.0 |
| (GGS)$_2$XTEN(GGS)$_2$ | A | 100.0 | 99.8 | 100.0 | 99.9 | 99.8 | 99.0 | 99.4 | 99.9 | 99.9 |
| | C | 0.0 | 0.0 | 0.0 | 0.0 | 0.0 | 0.0 | 0.0 | 0.0 | 0.0 |
| | G | 0.0 | 0.2 | 0.0 | 0.1 | 0.2 | 1.0 | 0.6 | 0.1 | 0.1 |
| | T | 0.0 | 0.0 | 0.0 | 0.0 | 0.0 | 0.0 | 0.0 | 0.0 | 0.0 |

HEK293 site 2: GA$_1$A$_2$CA$_3$CA$_4$A$_5$A$_6$GCATAGACTGCGG
(showing as T to C)

FANCF: GGA₃A₄TCCCTTCTGCAGCACCTGG

Run # 2:

FIGURE 75

| | parental | | | out | | | out | |
|---|---|---|---|---|---|---|---|---|
| 142 (pCMV_ecTadA_XTEN_Cas9n_GGS_NLS; wild-type) | A₃ | A₄ | 142 (pCMV_ecTadA_XTEN_Cas9n_GGS_NLS; wild-type) | A₃ | A₄ | 142 (pCMV_ecTadA_XTEN_Cas9n_GGS_NLS; wild-type) | A₃ | A₄ |
| A | 100.0 | 100.0 | A | 100.0 | 100.0 | A | 100.0 | 100.0 |
| C | 0.0 | 0.0 | C | 0.0 | 0.0 | C | 0.0 | 0.0 |
| G | 0.0 | 0.0 | G | 0.0 | 0.0 | G | 0.0 | 0.0 |
| T | 0.0 | 0.0 | T | 0.0 | 0.0 | T | 0.0 | 0.0 |
| 177 (pCMV_ecTadA_XTEN_Cas9n_GGS_NLS; A106V_D108N_D147Y_E155V) | | | 177 (pCMV_ecTadA_XTEN_Cas9n_GGS_NLS; A106V_D108N_D147Y_E155V) | | | 177 (pCMV_ecTadA_XTEN_Cas9n_GGS_NLS; A106V_D108N_D147Y_E155V) | | |
| A | 100.0 | 99.7 | A | 100.0 | 99.8 | A | 99.9 | 99.6 |
| C | 0.0 | 0.0 | C | 0.0 | 0.0 | C | 0.0 | 0.0 |
| G | 0.0 | 0.3 | G | 0.0 | 0.2 | G | 0.1 | 0.2 |
| T | 0.0 | 0.0 | T | 0.0 | 0.0 | T | 0.0 | 0.0 |
| 179 (pCMV_ecTadA_XTEN_Cas9n_GGS_AAG*(E125Q)_GGS_NLS; A106V_D108N_D147Y_E155V) | | | 179 (pCMV_ecTadA_XTEN_Cas9n_GGS_AAG*(E125Q)_GGS_NLS; A106V_D108N_D147Y_E155V) | | | 179 (pCMV_ecTadA_XTEN_Cas9n_GGS_AAG*(E125Q)_GGS_NLS; A106V_D108N_D147Y_E155V) | | |
| A | 100.0 | 100.0 | A | 100.0 | 99.8 | A | 100.0 | 99.9 |
| C | 0.0 | 0.0 | C | 0.0 | 0.0 | C | 0.0 | 0.0 |
| G | 0.0 | 0.0 | G | 0.0 | 0.1 | G | 0.0 | 0.0 |
| T | 0.0 | 0.0 | T | 0.0 | 0.0 | T | 0.0 | 0.0 |
| 180 (pCMV_ecTadA_XTEN_Cas9n_GGS_UGI_GGS_NLS; A106V_D108N_D147Y_E155V) | | | 180 (pCMV_ecTadA_XTEN_Cas9n_GGS_UGI_GGS_NLS; A106V_D108N_D147Y_E155V) | | | 180 (pCMV_ecTadA_XTEN_Cas9n_GGS_UGI_GGS_NLS; A106V_D108N_D147Y_E155V) | | |
| A | 100.0 | 99.8 | A | 100.0 | 100.0 | A | 100.0 | 99.8 |
| C | 0.0 | 0.0 | C | 0.0 | 0.0 | C | 0.0 | 0.0 |
| G | 0.0 | 0.2 | G | 0.0 | 0.0 | G | 0.0 | 0.1 |
| T | 0.0 | 0.0 | T | 0.0 | 0.0 | T | 0.0 | 0.0 |

| HEK2 | | $A_2$ | $A_3$ | $A_5$ | $A_7$ | $A_8$ | $A_9$ |
|---|---|---|---|---|---|---|---|
| 177 (pCMV_ecTadA_XTEN_Cas9n_GGS_NLS; A106V_D108N_D147Y_E155V) | A | 100.0 | 96.7 | 74.1 | 100.0 | 99.9 | 100.0 |
| | C | 0.0 | 0.0 | 0.0 | 0.0 | 0.0 | 0.0 |
| | G | 0.0 | 0.3 | 25.9 | 0.0 | 0.1 | 0.0 |
| | T | 0.0 | 0.0 | 0.0 | 0.0 | 0.0 | 0.0 |
| 238 (pCMV_AAG*(E125A)_XTEN_ecTadA_XTEN_Cas9n_GGS_NLS; A106V_D108N_D147Y_E15 | A | 100.0 | 96.9 | 74.8 | 99.9 | 100.0 | 100.0 |
| | C | 0.0 | 0.0 | 0.0 | 0.0 | 0.0 | 0.0 |
| | G | 0.0 | 0.1 | 25.2 | 0.1 | 0.0 | 0.0 |
| | T | 0.0 | 0.0 | 0.0 | 0.0 | 0.0 | 0.0 |
| 239 (pCMV_AAG*(wt)_XTEN_ecTadA_XTEN_Cas9n_GGS_NLS; A106V_D108N_D147Y_E15 | A | 100.0 | 96.8 | 69.0 | 99.9 | 99.9 | 100.0 |
| | C | 0.0 | 0.0 | 0.1 | 0.0 | 0.0 | 0.0 |
| | G | 0.0 | 0.2 | 30.9 | 0.1 | 0.1 | 0.0 |
| | T | 0.0 | 0.0 | 0.0 | 0.0 | 0.0 | 0.0 |

FIGURE 86
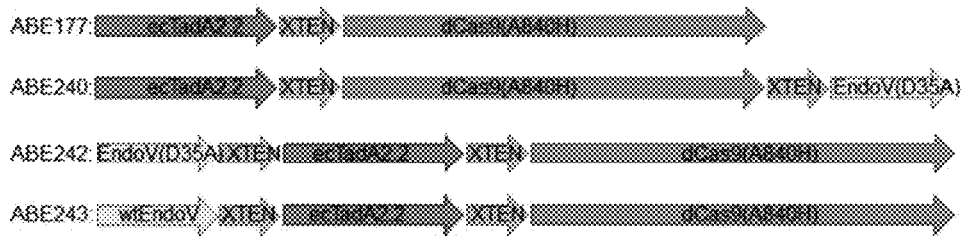
FIGURE 87
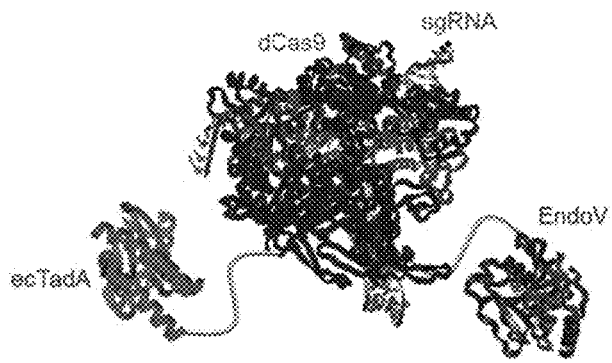
FIGURE 88
| HEK2 | | $A_3$ | $A_5$ | $A_6$ | $A_7$ | $A_8$ | $A_9$ |
|---|---|---|---|---|---|---|---|
| 177 (pCMV_ecTadA_XTEN_Cas9n_GGS_NLS; A106V_D108N_D147Y_E155V) | A | 100.0 | 99.7 | 74.1 | 100.0 | 99.9 | 100.0 |
| | C | 0.0 | 0.0 | 0.0 | 0.0 | 0.0 | 0.0 |
| | G | 0.0 | 0.3 | 25.9 | 0.0 | 0.1 | 0.0 |
| | T | 0.0 | 0.0 | 0.0 | 0.0 | 0.0 | 0.0 |
| 240 (pCMV_ecTadA_XTEN_Cas9n_XTEN_EndoV*(D35A)_GGS_NLS; A106V_D108N_D147Y_E155V) | A | 100.0 | 99.7 | 64.6 | 99.9 | 99.8 | 99.9 |
| | C | 0.0 | 0.0 | 0.0 | 0.0 | 0.0 | 0.0 |
| | G | 0.0 | 0.3 | 35.2 | 0.1 | 0.1 | 0.1 |
| | T | 0.0 | 0.0 | 0.0 | 0.0 | 0.0 | 0.0 |
| 242 (pCMV_EndoV*(D35A)_XTEN_ecTadA_XTEN_Cas9n_GGS_NLS; A106V_D108N_D147Y_E155V) | A | 100.0 | 99.8 | 53.6 | 100.0 | 99.9 | 100.0 |
| | C | 0.0 | 0.0 | 0.0 | 0.0 | 0.0 | 0.0 |
| | G | 0.0 | 0.1 | 46.2 | 0.0 | 0.1 | 0.0 |
| | T | 0.0 | 0.0 | 0.0 | 0.0 | 0.0 | 0.0 |
| 243 (pCMV_EndoV*(wt)_XTEN_ecTadA_XTEN_Cas9n_GGS_NLS; A106V_D108N_D147Y_E155V) | A | 100.0 | 99.9 | 67.9 | 99.9 | 99.9 | 100.0 |
| | C | 0.0 | 0.0 | 0.0 | 0.0 | 0.1 | 0.0 |
| | G | 0.0 | 0.1 | 32.0 | 0.0 | 0.0 | 0.0 |
| | T | 0.0 | 0.0 | 0.0 | 0.0 | 0.0 | 0.0 |

| wt res | S2 | H8 | I49 | L84 | A106 | D108 | H123 | N127 | D147 | E155 | I156 | K160 |
|---|---|---|---|---|---|---|---|---|---|---|---|---|
| clone 1 | Ala | | | Phe | Val | Arg | Tyr | | Tyr | Val | Phe | |
| clone 2 | | | Phe | Val | Arg | | | Tyr | Val | | |
| clone 3 | | Tyr | | | Thr | Arg | | Ser | Asp | Glu | | Ser |

| HEK2 | G | A | A | C | A | C | A | A | A | G |
|---|---|---|---|---|---|---|---|---|---|---|
| 339 | | 0.1% | 5.0% | | 56.6% | | 1.6% | 1.9% | 0.9% | |
| 340 | | 0.1% | 2.6% | | 51.2% | | 0.5% | 1.1% | 0.6% | |
| 341 | | 0.1% | 6.0% | | 57.2% | | 1.7% | 1.6% | 1.1% | |

| HEK2 | G | G | A | A | C | A | C | A | A | A |
|---|---|---|---|---|---|---|---|---|---|---|
| 339 | | | 2.2% | 56.7% | | 59.0% | | 6.6% | 23.3% | 2.1% |
| 340 | | | 1.4% | 31.0% | | 36.0% | | 2.6% | 19.6% | 1.5% |
| 341 | | | 1.9% | 57.1% | | 61.2% | | 5.7% | 18.1% | 2.0% |

| HEK2-3 | G | T | A | A | A | C | A | A | A | G |
|---|---|---|---|---|---|---|---|---|---|---|
| 339 | | | 0.5% | 1.0% | 19.3% | | 0.6% | 1.5% | 0.7% | |
| 340 | | | 0.2% | 0.4% | 17.2% | | 0.2% | 0.7% | 0.3% | |
| 341 | | | 0.5% | 1.0% | 19.5% | | 0.6% | 1.3% | 0.5% | |

| HEK2-6 | G | A | A | G | A | C | C | A | A | G |
|---|---|---|---|---|---|---|---|---|---|---|
| 339 | | 0.0% | 0.1% | | 7.2% | | | 0.4% | 0.3% | |
| 340 | | 0.0% | 0.0% | | 6.1% | | | 0.2% | 0.1% | |
| 341 | | 0.0% | 0.0% | | 6.6% | | | 0.4% | 0.3% | |

| HEK2-7 | G | A | A | A | A | C | A | A | A | T |
|---|---|---|---|---|---|---|---|---|---|---|
| 339 | | 0.0% | 0.0% | 0.0% | 0.6% | | 0.0% | 0.0% | 0.0% | |
| 340 | | 0.0% | 0.0% | 0.0% | 0.3% | | 0.0% | 0.0% | 0.0% | |
| 341 | | 0.0% | 0.0% | 0.0% | 0.4% | | 0.1% | 0.0% | 0.0% | |

| HEK2-8 | G | A | T | C | A | C | A | A | A | G |
|---|---|---|---|---|---|---|---|---|---|---|
| 339 | | 0.2% | | | 23.9% | | 0.5% | 0.5% | 0.3% | |
| 340 | | 0.1% | | | 26.0% | | 0.2% | 0.2% | 0.1% | |
| 341 | | 0.2% | | | 27.5% | | 0.5% | 0.4% | 0.3% | |

Hek-2 site: 5'-GA$_2$A$_3$CA$_5$CA$_7$A$_8$A$_9$GCA$_{12}$TA$_{14}$GA$_{16}$CTGCGGG-3'

| HEK2 pNMG-369 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #3 | A | 99.93% | 97.44% | 99.96% | 99.03% | 99.17% | 99.59% | 99.96% | 99.97% | 100.0% |
| | C | 0.00% | 0.00% | 0.01% | 0.00% | 0.00% | 0.00% | 0.00% | 0.00% | 0.0% |
| | G | 0.07% | 2.56% | 99.01% | 0.96% | 0.83% | 0.41% | 0.03% | 0.02% | 0.0% |
| | T | 0.00% | 0.01% | 0.02% | 0.01% | 0.00% | 0.00% | 0.01% | 0.00% | 0.0% |

| HEK2 pNMG-370 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #3 | A | 99.94% | 98.55% | 97.72% | 99.71% | 99.40% | 99.80% | 99.96% | 99.97% | 100.0% |
| | C | 0.00% | 0.00% | 0.00% | 0.00% | 0.00% | 0.00% | 0.00% | 0.00% | 0.0% |
| | G | 0.05% | 1.44% | 42.26% | 0.29% | 0.59% | 0.20% | 0.03% | 0.02% | 0.0% |
| | T | 0.01% | 0.01% | 0.02% | 0.00% | 0.00% | 0.00% | 0.01% | 0.00% | 0.0% |

| HEK2 pNMG-371 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #3 | A | 99.91% | 96.97% | 44.22% | 99.11% | 99.06% | 99.41% | 99.96% | 99.98% | 100.0% |
| | C | 0.00% | 0.00% | 0.00% | 0.00% | 0.00% | 0.00% | 0.00% | 0.00% | 0.0% |
| | G | 0.09% | 3.02% | 55.76% | 0.89% | 0.93% | 0.59% | 0.03% | 0.01% | 0.0% |
| | T | 0.00% | 0.00% | 0.01% | 0.00% | 0.00% | 0.00% | 0.01% | 0.00% | 0.0% |

| HEK2 pNMG-360 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #4 | A | 99.92% | 98.69% | 72.23% | 99.68% | 99.71% | 99.92% | 99.95% | 99.97% | 100.0% |
| | C | 0.00% | 0.00% | 0.01% | 0.00% | 0.00% | 0.00% | 0.00% | 0.00% | 0.0% |
| | G | 0.07% | 1.30% | 27.76% | 0.32% | 0.28% | 0.07% | 0.04% | 0.02% | 0.0% |
| | T | 0.01% | 0.00% | 0.01% | 0.00% | 0.01% | 0.00% | 0.00% | 0.00% | 0.0% |

| HEK2 pNMG-361 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #4 | A | 99.94% | 98.96% | 89.63% | 99.81% | 99.68% | 99.92% | 99.96% | 99.97% | 100.0% |
| | C | 0.00% | 0.00% | 0.01% | 0.00% | 0.00% | 0.00% | 0.00% | 0.00% | 0.0% |
| | G | 0.05% | 1.04% | 10.36% | 0.18% | 0.31% | 0.08% | 0.01% | 0.02% | 0.0% |
| | T | 0.00% | 0.00% | 0.00% | 0.00% | 0.00% | 0.00% | 0.00% | 0.00% | 0.0% |

| HEK2 pNMG-362 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #4 | A | 99.96% | 99.14% | 82.24% | 99.78% | 99.79% | 99.86% | 99.91% | 99.98% | 100.0% |
| | C | 0.00% | 0.00% | 0.00% | 0.00% | 0.00% | 0.00% | 0.00% | 0.00% | 0.0% |
| | G | 0.04% | 0.86% | 17.75% | 0.21% | 0.20% | 0.14% | 0.08% | 0.01% | 0.0% |
| | T | 0.00% | 0.01% | 0.01% | 0.00% | 0.00% | 0.00% | 0.01% | 0.00% | 0.0% |

FIGURE 108 (Continued)

Hek-2 site: 5'-GA$_2$A$_3$CA$_5$CA$_7$A$_8$A$_9$GCA$_{12}$TA$_{14}$GA$_{16}$CTGCGGG-3'

| HEK2 pNMG-363 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #4 | A | 99.92% | 98.69% | 72.28% | 99.68% | 99.71% | 99.92% | 99.95% | 99.97% | 100.0% |
| | C | 0.00% | 0.00% | 0.01% | 0.00% | 0.00% | 0.00% | 0.00% | 0.00% | 0.0% |
| | G | 0.07% | 1.30% | 27.70% | 0.32% | 0.28% | 0.07% | 0.04% | 0.02% | 0.0% |
| | T | 0.01% | 0.00% | 0.01% | 0.00% | 0.01% | 0.00% | 0.00% | 0.00% | 0.0% |

| HEK2 pNMG-364 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #4 | A | 99.97% | 99.01% | 65.98% | 99.68% | 99.78% | 99.90% | 99.95% | 99.97% | 100.0% |
| | C | 0.00% | 0.00% | 0.00% | 0.00% | 0.00% | 0.00% | 0.00% | 0.00% | 0.0% |
| | G | 0.03% | 0.98% | 34.00% | 0.32% | 0.21% | 0.10% | 0.04% | 0.02% | 0.0% |
| | T | 0.00% | 0.00% | 0.02% | 0.00% | 0.01% | 0.01% | 0.01% | 0.00% | 0.0% |

| HEK2 pNMG-365 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #4 | A | 99.97% | 99.08% | 72.04% | 99.81% | 99.78% | 99.90% | 99.95% | 99.98% | 100.0% |
| | C | 0.00% | 0.00% | 0.00% | 0.00% | 0.00% | 0.00% | 0.00% | 0.00% | 0.0% |
| | G | 0.03% | 0.91% | 27.94% | 0.18% | 0.21% | 0.10% | 0.04% | 0.01% | 0.0% |
| | T | 0.00% | 0.00% | 0.01% | 0.00% | 0.01% | 0.00% | 0.01% | 0.00% | 0.0% |

| HEK2 pNMG-366 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #4 | A | 99.90% | 98.23% | 71.10% | 99.59% | 99.73% | 99.85% | 99.93% | 99.97% | 100.0% |
| | C | 0.00% | 0.00% | 0.00% | 0.00% | 0.00% | 0.00% | 0.00% | 0.00% | 0.0% |
| | G | 0.10% | 1.76% | 28.89% | 0.41% | 0.26% | 0.15% | 0.06% | 0.02% | 0.0% |
| | T | 0.00% | 0.00% | 0.01% | 0.00% | 0.00% | 0.00% | 0.01% | 0.00% | 0.0% |

| HEK2 pNMG-367 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #4 | A | 99.92% | 98.73% | 66.94% | 99.68% | 99.78% | 99.90% | 99.95% | 99.97% | 100.0% |
| | C | 0.00% | 0.00% | 0.01% | 0.00% | 0.00% | 0.00% | 0.00% | 0.00% | 0.0% |
| | G | 0.08% | 1.26% | 33.04% | 0.32% | 0.21% | 0.10% | 0.04% | 0.02% | 0.0% |
| | T | 0.00% | 0.01% | 0.01% | 0.00% | 0.01% | 0.01% | 0.01% | 0.00% | 0.0% |

| HEK2 pNMG-368 | | 2 | 3 | 5 | 7 | 8 | 9 | 12 | 14 | 16 |
|---|---|---|---|---|---|---|---|---|---|---|
| | | A | A | A | A | A | A | A | A | A |
| Evo #4 | A | 99.97% | 99.72% | 99.32% | 99.95% | 99.92% | 99.96% | 99.97% | 99.98% | 100.0% |
| | C | 0.00% | 0.00% | 0.00% | 0.00% | 0.00% | 0.00% | 0.00% | 0.00% | 0.0% |
| | G | 0.02% | 0.27% | 0.67% | 0.05% | 0.08% | 0.03% | 0.02% | 0.01% | 0.0% |
| | T | 0.00% | 0.00% | 0.01% | 0.00% | 0.00% | 0.00% | 0.01% | 0.00% | 0.0% |

FIGURE 109

HEK2-3 site: 5'-GTA$_3$A$_4$A$_5$CA$_7$A$_8$A$_9$GCA$_{12}$TA$_{14}$GA$_{16}$CTGAGGG-3'

| HEK2-3 pNMG-369 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.73% | 99.58% | 93.69% | 99.53% | 99.15% | 99.93% | 99.96% | 99.98% | 100.00% |
| | C | 0.01% | 0.00% | 0.01% | 0.01% | 0.00% | 0.00% | 0.01% | 0.00% | 0.00% |
| | G | 0.25% | 0.41% | 6.30% | 0.44% | 0.85% | 0.07% | 0.02% | 0.01% | 0.00% |
| | T | 0.01% | 0.01% | 0.00% | 0.00% | 0.00% | 0.00% | 0.01% | 0.00% | 0.00% |

| HEK2-3 pNMG-370 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.93% | 99.89% | 94.96% | 99.92% | 99.74% | 99.98% | 99.99% | 99.99% | 99.99% |
| | C | 0.01% | 0.00% | 0.01% | 0.01% | 0.00% | 0.00% | 0.00% | 0.00% | 0.00% |
| | G | 0.06% | 0.11% | 5.03% | 0.07% | 0.25% | 0.02% | 0.00% | 0.01% | 0.00% |
| | T | 0.01% | 0.00% | 0.00% | 0.00% | 0.01% | 0.00% | 0.00% | 0.00% | 0.01% |

| HEK2-3 pNMG-371 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.69% | 99.59% | 93.55% | 99.75% | 99.46% | 99.94% | 99.96% | 99.98% | 99.98% |
| | C | 0.01% | 0.01% | 0.01% | 0.02% | 0.02% | 0.01% | 0.02% | 0.01% | 0.01% |
| | G | 0.30% | 0.40% | 6.45% | 0.23% | 0.52% | 0.05% | 0.01% | 0.01% | 0.01% |
| | T | 0.00% | 0.00% | 0.00% | 0.00% | 0.00% | 0.00% | 0.01% | 0.00% | 0.00% |

| HEK2-3 pNMG-360 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.87% | 99.89% | 98.74% | 99.90% | 99.92% | 99.98% | 99.98% | 99.98% | 99.99% |
| | C | 0.00% | 0.00% | 0.01% | 0.02% | 0.02% | 0.01% | 0.00% | 0.00% | 0.00% |
| | G | 0.18% | 0.10% | 1.25% | 0.08% | 0.06% | 0.01% | 0.01% | 0.01% | 0.01% |
| | T | 0.00% | 0.00% | 0.00% | 0.00% | 0.00% | 0.00% | 0.01% | 0.00% | 0.00% |

| HEK2-3 pNMG-361 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.97% | 99.98% | 99.54% | 99.97% | 99.98% | 99.99% | 99.98% | 99.99% | 99.99% |
| | C | 0.00% | 0.00% | 0.01% | 0.01% | 0.00% | 0.00% | 0.00% | 0.00% | 0.00% |
| | G | 0.03% | 0.02% | 0.44% | 0.02% | 0.01% | 0.00% | 0.01% | 0.00% | 0.01% |
| | T | 0.00% | 0.00% | 0.00% | 0.00% | 0.00% | 0.00% | 0.01% | 0.01% | 0.00% |

| HEK2-3 pNMG-362 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.91% | 99.94% | 98.06% | 99.93% | 99.89% | 99.96% | 99.98% | 99.98% | 99.99% |
| | C | 0.01% | 0.00% | 0.00% | 0.01% | 0.00% | 0.00% | 0.00% | 0.00% | 0.00% |
| | G | 0.09% | 0.06% | 1.93% | 0.06% | 0.10% | 0.04% | 0.02% | 0.02% | 0.00% |
| | T | 0.00% | 0.00% | 0.00% | 0.00% | 0.00% | 0.00% | 0.00% | 0.00% | 0.01% |

FIGURE 109 (Continued)

HEK2-3 site: 5'-GTA A A CA A A GCA TA GA CTGAGGG-3'
         3 4 5   7 8 9    12 14 16

| HEK2-3 pNMG-363 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.80% | 99.91% | 97.58% | 99.90% | 99.89% | 99.97% | 99.96% | 99.99% | 99.99% |
| | C | 0.00% | 0.00% | 0.01% | 0.00% | 0.01% | 0.00% | 0.01% | 0.00% | 0.00% |
| | G | 0.19% | 0.09% | 2.40% | 0.09% | 0.10% | 0.03% | 0.02% | 0.01% | 0.00% |
| | T | 0.00% | 0.00% | 0.00% | 0.00% | 0.01% | 0.00% | 0.02% | 0.00% | 0.00% |

| HEK2-3 pNMG-364 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.96% | 99.97% | 99.47% | 99.96% | 99.98% | 100.00% | 99.99% | 99.98% | 100.00% |
| | C | 0.01% | 0.00% | 0.01% | 0.01% | 0.00% | 0.00% | 0.00% | 0.00% | 0.00% |
| | G | 0.03% | 0.02% | 0.51% | 0.04% | 0.01% | 0.00% | 0.00% | 0.01% | 0.00% |
| | T | 0.01% | 0.00% | 0.01% | 0.00% | 0.00% | 0.00% | 0.00% | 0.01% | 0.00% |

| HEK2-3 pNMG-365 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.91% | 99.97% | 98.49% | 99.95% | 99.92% | 99.97% | 99.92% | 99.98% | 100.00% |
| | C | 0.00% | 0.00% | 0.00% | 0.01% | 0.01% | 0.00% | 0.00% | 0.00% | 0.00% |
| | G | 0.09% | 0.02% | 1.51% | 0.04% | 0.07% | 0.02% | 0.07% | 0.01% | 0.00% |
| | T | 0.00% | 0.00% | 0.00% | 0.00% | 0.00% | 0.00% | 0.01% | 0.00% | 0.00% |

| HEK2-3 pNMG-366 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.70% | 99.86% | 97.73% | 99.68% | 99.77% | 99.97% | 99.98% | 99.99% | 99.99% |
| | C | 0.00% | 0.00% | 0.00% | 0.01% | 0.01% | 0.01% | 0.00% | 0.00% | 0.00% |
| | G | 0.29% | 0.14% | 2.27% | 0.30% | 0.22% | 0.02% | 0.02% | 0.00% | 0.00% |
| | T | 0.00% | 0.00% | 0.00% | 0.00% | 0.00% | 0.00% | 0.00% | 0.00% | 0.01% |

| HEK2-3 pNMG-367 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.87% | 99.89% | 97.80% | 99.87% | 99.91% | 99.97% | 99.92% | 99.96% | 99.99% |
| | C | 0.00% | 0.00% | 0.00% | 0.01% | 0.01% | 0.00% | 0.01% | 0.00% | 0.00% |
| | G | 0.12% | 0.10% | 2.19% | 0.11% | 0.08% | 0.02% | 0.05% | 0.02% | 0.01% |
| | T | 0.01% | 0.00% | 0.00% | 0.00% | 0.00% | 0.00% | 0.01% | 0.01% | 0.00% |

| HEK2-3 pNMG-368 | | 3 | 4 | 5 | 7 | 8 | 9 | 12 | 14 | 16 |
|---|---|---|---|---|---|---|---|---|---|---|
| | | A | A | A | A | A | A | A | A | A |
| | A | 99.97% | 100.00% | 100.00% | 99.99% | 99.98% | 100.00% | 99.98% | 99.98% | 100.00% |
| | C | 0.00% | 0.00% | 0.00% | 0.01% | 0.01% | 0.00% | 0.00% | 0.01% | 0.00% |
| | G | 0.02% | 0.00% | 0.00% | 0.00% | 0.00% | 0.00% | 0.01% | 0.01% | 0.00% |
| | T | 0.00% | 0.00% | 0.00% | 0.00% | 0.01% | 0.00% | 0.01% | 0.00% | 0.00% |

FIGURE 110

HEK2-6: 5'-GA₂A₃GA₅CCA₈A₉GGA₁₂TA₁₄GACTGCTGG-3'

| HEK2-6 pNMG-369 | | 2 A | 3 A | 5 A | 8 A | 9 A | 12 A | 14 A |
|---|---|---|---|---|---|---|---|---|
| | A | 99.80% | 99.94% | 95.27% | 99.70% | 99.74% | 99.94% | 99.94% |
| | C | 0.07% | 0.06% | 0.00% | 0.00% | 0.00% | 0.00% | 0.00% |
| | G | 0.13% | 0.00% | 4.67% | 0.30% | 0.26% | 0.06% | 0.06% |
| | T | 0.00% | 0.00% | 0.06% | 0.00% | 0.00% | 0.00% | 0.00% |

| HEK2-6 pNMG-370 | | 2 A | 3 A | 5 A | 8 A | 9 A | 12 A | 14 A |
|---|---|---|---|---|---|---|---|---|
| | A | 99.97% | 99.98% | 96.45% | 99.77% | 99.92% | 99.98% | 99.98% |
| | C | 0.03% | 0.02% | 0.00% | 0.00% | 0.03% | 0.00% | 0.00% |
| | G | 0.00% | 0.00% | 3.50% | 0.23% | 0.03% | 0.02% | 0.02% |
| | T | 0.00% | 0.00% | 0.05% | 0.00% | 0.03% | 0.00% | 0.00% |

| HEK2-6 pNMG-371 | | 2 A | 3 A | 5 A | 8 A | 9 A | 12 A | 14 A |
|---|---|---|---|---|---|---|---|---|
| | A | 99.97% | 99.94% | 96.33% | 99.80% | 99.78% | 100.00% | 100.00% |
| | C | 0.00% | 0.03% | 0.00% | 0.00% | 0.00% | 0.00% | 0.00% |
| | G | 0.03% | 0.00% | 3.67% | 0.20% | 0.19% | 0.00% | 0.00% |
| | T | 0.00% | 0.03% | 0.00% | 0.00% | 0.03% | 0.00% | 0.00% |

| HEK2-6 pNMG-360 | | 2 A | 3 A | 5 A | 8 A | 9 A | 12 A | 14 A |
|---|---|---|---|---|---|---|---|---|
| | A | 100.00% | 99.96% | 99.03% | 99.96% | 99.91% | 99.96% | 100.00% |
| | C | 0.00% | 0.04% | 0.00% | 0.00% | 0.09% | 0.00% | 0.00% |
| | G | 0.00% | 0.00% | 0.97% | 0.04% | 0.00% | 0.04% | 0.00% |
| | T | 0.00% | 0.00% | 0.00% | 0.00% | 0.00% | 0.00% | 0.00% |

| HEK2-6 361 | | 2 A | 3 A | 5 A | 8 A | 9 A | 12 A | 14 A |
|---|---|---|---|---|---|---|---|---|
| | A | 99.97% | 99.97% | 99.67% | 00.00% | 99.97% | 99.97% | 100.00% |
| | C | 0.00% | 0.00% | 0.00% | 0.00% | 0.00% | 0.00% | 0.00% |
| | G | 0.03% | 0.03% | 0.30% | 0.00% | 0.00% | 0.03% | 0.00% |
| | T | 0.00% | 0.00% | 0.03% | 0.00% | 0.03% | 0.00% | 0.00% |

| HEK2-6 362 | | 2 A | 3 A | 5 A | 8 A | 9 A | 12 A | 14 A |
|---|---|---|---|---|---|---|---|---|
| | A | 99.96% | 99.92% | 98.65% | 99.94% | 99.98% | 99.94% | 99.98% |
| | C | 0.02% | 0.08% | 0.00% | 0.00% | 0.00% | 0.00% | 0.00% |
| | G | 0.02% | 0.00% | 1.35% | 0.04% | 0.02% | 0.04% | 0.02% |
| | T | 0.00% | 0.00% | 0.00% | 0.02% | 0.00% | 0.02% | 0.00% |

FIGURE 110 (Continued)

HEK2-6: 5'-GA$_2$A$_3$GA$_5$CCA$_8$A$_9$GGA$_{12}$TA$_{14}$GACTGCTGG-3'

| HEK2-6 363 | | 2 A | 3 A | 5 A | 8 A | 9 A | 12 A | 14 A |
|---|---|---|---|---|---|---|---|---|
| | A | 99.97% | 99.97% | 95.64% | 99.93% | 99.99% | 99.99% | 99.99% |
| | C | 0.00% | 0.00% | 0.00% | 0.00% | 0.00% | 0.00% | 0.00% |
| | G | 0.03% | 0.03% | 4.36% | 0.05% | 0.01% | 0.00% | 0.00% |
| | T | 0.00% | 0.00% | 0.00% | 0.01% | 0.00% | 0.01% | 0.01% |

| HEK2-6 364 | | 2 A | 3 A | 5 A | 8 A | 9 A | 12 A | 14 A |
|---|---|---|---|---|---|---|---|---|
| | A | 99.98% | 99.98% | 99.59% | 99.98% | 99.90% | 99.98% | 100.00% |
| | C | 0.00% | 0.00% | 0.00% | 0.00% | 0.02% | 0.00% | 0.00% |
| | G | 0.00% | 0.02% | 0.39% | 0.02% | 0.06% | 0.02% | 0.00% |
| | T | 0.02% | 0.00% | 0.02% | 0.00% | 0.02% | 0.00% | 0.00% |

| HEK2-6 365 | | 2 A | 3 A | 5 A | 8 A | 9 A | 12 A | 14 A |
|---|---|---|---|---|---|---|---|---|
| | A | 99.95% | 100.00% | 97.12% | 99.95% | 99.82% | 99.85% | 100.00% |
| | C | 0.00% | 0.00% | 0.00% | 0.00% | 0.00% | 0.03% | 0.00% |
| | G | 0.03% | 0.00% | 2.86% | 0.02% | 0.18% | 0.10% | 0.00% |
| | T | 0.03% | 0.00% | 0.02% | 0.02% | 0.00% | 0.03% | 0.00% |

| HEK2-6 366 | | 2 A | 3 A | 5 A | 8 A | 9 A | 12 A | 14 A |
|---|---|---|---|---|---|---|---|---|
| | A | 99.90% | 99.96% | 97.54% | 99.82% | 99.98% | 99.88% | 99.98% |
| | C | 0.04% | 0.00% | 0.00% | 0.00% | 0.02% | 0.00% | 0.00% |
| | G | 0.02% | 0.04% | 2.46% | 0.15% | 0.00% | 0.08% | 0.02% |
| | T | 0.04% | 0.00% | 0.00% | 0.04% | 0.00% | 0.04% | 0.00% |

| HEK2-6 367 | | 2 A | 3 A | 5 A | 8 A | 9 A | 12 A | 14 A |
|---|---|---|---|---|---|---|---|---|
| | A | 99.89% | 99.99% | 97.00% | 99.93% | 99.94% | 99.96% | 99.99% |
| | C | 0.03% | 0.00% | 0.01% | 0.01% | 0.01% | 0.01% | 0.00% |
| | G | 0.06% | 0.01% | 2.97% | 0.04% | 0.03% | 0.00% | 0.00% |
| | T | 0.02% | 0.00% | 0.01% | 0.01% | 0.01% | 0.03% | 0.01% |

| HEK2-6 368 | | 2 A | 3 A | 5 A | 8 A | 9 A | 12 A | 14 A |
|---|---|---|---|---|---|---|---|---|
| | A | 99.92% | 99.96% | 99.96% | 99.99% | 99.99% | 99.98% | 100.00% |
| | C | 0.02% | 0.02% | 0.00% | 0.00% | 0.01% | 0.00% | 0.00% |
| | G | 0.04% | 0.02% | 0.01% | 0.01% | 0.00% | 0.01% | 0.00% |
| | T | 0.02% | 0.00% | 0.03% | 0.00% | 0.00% | 0.01% | 0.00% |

FIGURE 111

HEK2-7: 3'-CCTGCAGT CAAT GAT T T GT T T T G-5'
                      16    12   9 8 7  5 4 3 2

| HEK2-7 pNMG-369 |   | 16 | 12 | 9 | 8 | 7 | 5 | 4 | 3 | 2 |
|---|---|---|---|---|---|---|---|---|---|---|
|   |   | T | T | T | T | T | T | T | T | T |
|   | A | 0.00% | 0.01% | 0.00% | 0.01% | 0.00% | 0.00% | 0.00% | 0.00% | 0.00% |
|   | C | 0.01% | 0.01% | 0.08% | 0.09% | 0.05% | 0.83% | 0.06% | 0.03% | 0.02% |
|   | G | 0.00% | 0.00% | 0.00% | 0.00% | 0.00% | 0.00% | 0.00% | 0.00% | 0.00% |
|   | T | 99.98% | 99.98% | 99.91% | 99.91% | 99.95% | 99.16% | 99.93% | 99.96% | 99.98% |

| HEK2-7 pNMG-370 |   | 16 | 12 | 9 | 8 | 7 | 5 | 4 | 3 | 2 |
|---|---|---|---|---|---|---|---|---|---|---|
|   |   | T | T | T | T | T | T | T | T | T |
|   | A | 0.01% | 0.01% | 0.00% | 0.01% | 0.00% | 0.00% | 0.01% | 0.01% | 0.01% |
|   | C | 0.00% | 0.00% | 0.01% | 0.00% | 0.01% | 0.24% | 0.01% | 0.01% | 0.01% |
|   | G | 0.01% | 0.00% | 0.00% | 0.00% | 0.01% | 0.01% | 0.01% | 0.00% | 0.00% |
|   | T | 99.99% | 99.99% | 99.99% | 99.99% | 99.98% | 99.75% | 99.98% | 99.98% | 99.98% |

| HEK2-7 pNMG-371 |   | 16 | 12 | 9 | 8 | 7 | 5 | 4 | 3 | 2 |
|---|---|---|---|---|---|---|---|---|---|---|
|   |   | T | T | T | T | T | T | T | T | T |
|   | A | 0.00% | 0.00% | 0.00% | 0.00% | 0.00% | 0.01% | 0.00% | 0.00% | 0.00% |
|   | C | 0.00% | 0.01% | 0.06% | 0.04% | 0.10% | 0.35% | 0.02% | 0.01% | 0.00% |
|   | G | 0.00% | 0.00% | 0.00% | 0.00% | 0.00% | 0.00% | 0.00% | 0.00% | 0.03% |
|   | T | 100.00% | 99.99% | 99.94% | 99.96% | 99.90% | 99.63% | 99.98% | 99.99% | 99.97% |

| HEK2-7 pNMG-360 |   | 16 | 12 | 9 | 8 | 7 | 5 | 4 | 3 | 2 |
|---|---|---|---|---|---|---|---|---|---|---|
|   |   | T | T | T | T | T | T | T | T | T |
|   | A | 0.00% | 0.00% | 0.00% | 0.01% | 0.01% | 0.01% | 0.00% | 0.00% | 0.01% |
|   | C | 0.01% | 0.00% | 0.01% | 0.03% | 0.00% | 0.09% | 0.03% | 0.02% | 0.02% |
|   | G | 0.00% | 0.00% | 0.01% | 0.00% | 0.00% | 0.00% | 0.00% | 0.00% | 0.01% |
|   | T | 99.99% | 100.00% | 99.98% | 99.96% | 99.99% | 99.89% | 99.97% | 99.98% | 99.95% |

| HEK2-7 pNMG-361 |   | 16 | 12 | 9 | 8 | 7 | 5 | 4 | 3 | 2 |
|---|---|---|---|---|---|---|---|---|---|---|
|   |   | T | T | T | T | T | T | T | T | T |
|   | A | 0.02% | 0.02% | 0.00% | 0.00% | 0.00% | 0.00% | 0.00% | 0.00% | 0.00% |
|   | C | 0.02% | 0.04% | 0.00% | 0.00% | 0.02% | 0.06% | 0.02% | 0.00% | 0.02% |
|   | G | 0.00% | 0.00% | 0.00% | 0.00% | 0.00% | 0.00% | 0.00% | 0.00% | 0.00% |
|   | T | 99.96% | 99.94% | 100.00% | 100.00% | 99.98% | 99.94% | 99.98% | 100.00% | 99.98% |

| HEK2-7 pNMG-362 |   | 16 | 12 | 9 | 8 | 7 | 5 | 4 | 3 | 2 |
|---|---|---|---|---|---|---|---|---|---|---|
|   |   | T | T | T | T | T | T | T | T | T |
|   | A | 0.02% | 0.00% | 0.00% | 0.00% | 0.00% | 0.00% | 0.00% | 0.00% | 0.02% |
|   | C | 0.00% | 0.00% | 0.00% | 0.05% | 0.00% | 0.10% | 0.00% | 0.05% | 0.02% |
|   | G | 0.00% | 0.00% | 0.00% | 0.00% | 0.00% | 0.00% | 0.00% | 0.00% | 0.00% |
|   | T | 99.98% | 100.00% | 100.00% | 99.95% | 100.00% | 99.90% | 100.00% | 99.95% | 99.95% |

FIGURE 111 (Continued)

HEK2-7: 3'-CCTGCAGT CAAT GAT T T GT T T T G-5'
           16      12   9 8 7  5 4 3 2

| HEK2-7 pNMG-363 | | 16 T | 12 T | 9 T | 8 T | 7 T | 5 T | 4 T | 3 T | 2 T |
|---|---|---|---|---|---|---|---|---|---|---|
| | A | 0.00% | 0.00% | 0.00% | 0.03% | 0.00% | 0.00% | 0.00% | 0.00% | 0.00% |
| | C | 0.00% | 0.03% | 0.00% | 0.00% | 0.00% | 0.16% | 0.00% | 0.00% | 0.00% |
| | G | 0.00% | 0.00% | 0.00% | 0.00% | 0.00% | 0.00% | 0.00% | 0.00% | 0.00% |
| | T | 100.00% | 99.97% | 100.00% | 99.97% | 100.00% | 99.84% | 100.00% | 100.00% | 100.00% |

| HEK2-7 pNMG-364 | | 16 T | 12 T | 9 T | 8 T | 7 T | 5 T | 4 T | 3 T | 2 T |
|---|---|---|---|---|---|---|---|---|---|---|
| | A | 0.00% | 0.00% | 0.00% | 0.02% | 0.00% | 0.00% | 0.00% | 0.00% | 0.00% |
| | C | 0.02% | 0.02% | 0.00% | 0.00% | 0.00% | 0.02% | 0.02% | 0.02% | 0.04% |
| | G | 0.00% | 0.00% | 0.00% | 0.00% | 0.00% | 0.00% | 0.00% | 0.00% | 0.00% |
| | T | 99.98% | 99.98% | 100.00% | 99.98% | 100.00% | 99.98% | 99.98% | 99.98% | 99.96% |

| HEK2-7 pNMG-365 | | 16 T | 12 T | 9 T | 8 T | 7 T | 5 T | 4 T | 3 T | 2 T |
|---|---|---|---|---|---|---|---|---|---|---|
| | A | 0.01% | 0.00% | 0.00% | 0.00% | 0.00% | 0.00% | 0.00% | 0.00% | 0.01% |
| | C | 0.01% | 0.01% | 0.04% | 0.01% | 0.01% | 0.07% | 0.01% | 0.01% | 0.00% |
| | G | 0.00% | 0.00% | 0.00% | 0.00% | 0.00% | 0.00% | 0.00% | 0.00% | 0.01% |
| | T | 99.98% | 99.99% | 99.96% | 99.98% | 99.99% | 99.93% | 99.99% | 99.99% | 99.97% |

| HEK2-7 pNMG-366 | | 16 T | 12 T | 9 T | 8 T | 7 T | 5 T | 4 T | 3 T | 2 T |
|---|---|---|---|---|---|---|---|---|---|---|
| | A | 0.01% | 0.01% | 0.01% | 0.00% | 0.01% | 0.00% | 0.00% | 0.01% | 0.00% |
| | C | 0.02% | 0.02% | 0.02% | 0.04% | 0.03% | 0.07% | 0.00% | 0.02% | 0.01% |
| | G | 0.00% | 0.00% | 0.00% | 0.01% | 0.00% | 0.01% | 0.00% | 0.00% | 0.00% |
| | T | 99.98% | 99.98% | 99.97% | 99.96% | 99.97% | 99.92% | 100.00% | 99.98% | 99.99% |

| HEK2-7 pNMG-367 | | 16 T | 12 T | 9 T | 8 T | 7 T | 5 T | 4 T | 3 T | 2 T |
|---|---|---|---|---|---|---|---|---|---|---|
| | A | 0.00% | 0.01% | 0.00% | 0.00% | 0.00% | 0.00% | 0.00% | 0.00% | 0.00% |
| | C | 0.01% | 0.03% | 0.01% | 0.01% | 0.00% | 0.07% | 0.01% | 0.02% | 0.00% |
| | G | 0.00% | 0.00% | 0.00% | 0.00% | 0.00% | 0.01% | 0.00% | 0.00% | 0.00% |
| | T | 99.99% | 99.96% | 99.99% | 99.99% | 100.00% | 99.92% | 99.99% | 99.98% | 99.99% |

| HEK2-7 pNMG-368 | | 16 T | 12 T | 9 T | 8 T | 7 T | 5 T | 4 T | 3 T | 2 T |
|---|---|---|---|---|---|---|---|---|---|---|
| | A | 0.01% | 0.00% | 0.00% | 0.01% | 0.01% | 0.00% | 0.00% | 0.00% | 0.01% |
| | C | 0.00% | 0.00% | 0.00% | 0.01% | 0.01% | 0.00% | 0.00% | 0.02% | 0.01% |
| | G | 0.00% | 0.00% | 0.00% | 0.01% | 0.00% | 0.02% | 0.00% | 0.00% | 0.00% |
| | T | 99.99% | 100.00% | 99.99% | 99.97% | 99.97% | 99.97% | 100.00% | 99.97% | 99.98% |

FIGURE 112

HEK2-10: 3'-CCATCAT T C T AT T CT T T AT GT T C-5'
            17 16  14  12 11  9 8  7 5  3 2

| HEK2-10 pNMG-369 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.01% | 0.04% | 0.00% | 0.00% | 0.00% | 0.00% | 0.00% | 0.00% | 0.01% | 0.01% | 0.00% |
| | C | 0.02% | 0.01% | 0.01% | 0.14% | 0.38% | 0.31% | 0.88% | 1.20% | 7.43% | 1.02% | 0.27% |
| | G | 0.01% | 0.00% | 0.00% | 0.00% | 0.01% | 0.00% | 0.00% | 0.01% | 0.00% | 0.00% | 0.00% |
| | T | 99.97% | 99.96% | 99.98% | 99.86% | 99.62% | 99.68% | 99.11% | 98.79% | 92.56% | 98.97% | 99.73% |

| HEK2-10 pNMG-370 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.01% | 0.05% | 0.00% | 0.01% | 0.01% | 0.01% | 0.00% | 0.00% | 0.01% | 0.00% | 0.01% |
| | C | 0.01% | 0.01% | 0.02% | 0.29% | 0.10% | 0.08% | 0.60% | 0.43% | 3.51% | 0.30% | 0.30% |
| | G | 0.00% | 0.00% | 0.00% | 0.00% | 0.00% | 0.00% | 0.01% | 0.00% | 0.00% | 0.00% | 0.00% |
| | T | 99.98% | 99.94% | 99.97% | 99.70% | 99.89% | 99.91% | 99.39% | 99.57% | 96.48% | 99.70% | 99.69% |

| HEK2-10 pNMG-371 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.01% | 0.10% | 0.01% | 0.01% | 0.00% | 0.00% | 0.00% | 0.01% | 0.01% | 0.00% | 0.00% |
| | C | 0.01% | 0.01% | 0.01% | 0.47% | 0.20% | 0.30% | 1.12% | 1.35% | 7.27% | 0.70% | 0.54% |
| | G | 0.00% | 0.00% | 0.00% | 0.00% | 0.01% | 0.00% | 0.00% | 0.00% | 0.00% | 0.00% | 0.00% |
| | T | 99.98% | 99.89% | 99.98% | 99.52% | 99.79% | 99.70% | 98.88% | 98.64% | 92.72% | 99.30% | 99.46% |

| HEK2-10 pNMG-360 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.01% | 0.09% | 0.00% | 0.00% | 0.01% | 0.01% | 0.00% | 0.01% | 0.00% | 0.01% | 0.00% |
| | C | 0.01% | 0.01% | 0.03% | 0.60% | 0.24% | 0.03% | 0.66% | 0.14% | 1.20% | 0.17% | 0.62% |
| | G | 0.01% | 0.00% | 0.00% | 0.00% | 0.02% | 0.00% | 0.02% | 0.01% | 0.00% | 0.00% | 0.00% |
| | T | 99.96% | 99.91% | 99.97% | 99.40% | 99.56% | 99.96% | 99.38% | 99.84% | 98.80% | 99.83% | 99.38% |

| HEK2-10 pNMG-361 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.00% | 0.16% | 0.00% | 0.00% | 0.04% | 0.03% | 0.00% | 0.01% | 0.01% | 0.01% | 0.01% |
| | C | 0.01% | 0.00% | 0.06% | 0.52% | 0.12% | 0.01% | 0.58% | 0.11% | 0.21% | 0.04% | 0.42% |
| | G | 0.01% | 0.00% | 0.00% | 0.00% | 0.02% | 0.00% | 0.02% | 0.03% | 0.00% | 0.00% | 0.00% |
| | T | 99.96% | 99.84% | 99.95% | 99.47% | 99.36% | 99.45% | 99.85% | 99.78% | 99.25% | 99.57% | 99.57% |

| HEK2-10 pNMG-362 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.00% | 0.07% | 0.01% | 0.00% | 0.00% | 0.00% | 0.01% | 0.00% | 0.00% | 0.01% | 0.01% |
| | C | 0.01% | 0.01% | 0.01% | 0.26% | 1.06% | 0.11% | 0.40% | 0.26% | 1.37% | 0.17% | 0.28% |
| | G | 0.01% | 0.00% | 0.00% | 0.00% | 0.01% | 0.00% | 0.00% | 0.00% | 0.00% | 0.00% | 0.00% |
| | T | 99.97% | 99.92% | 99.98% | 99.73% | 98.93% | 99.88% | 99.59% | 99.73% | 98.62% | 99.81% | 99.72% |

FIGURE 112 (Continued)

HEK2-10: 3'-CCATCAT T C T AT T CT T T AT GT T C-5'
              17 16  14 12 11 9 8 7 5 3 2

| HEK2-10 pNMG-363 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.01% | 0.02% | 0.00% | 0.01% | 0.01% | 0.00% | 0.00% | 0.01% | 0.01% | 0.00% | 0.01% |
| | C | 0.02% | 0.01% | 0.01% | 0.15% | 1.24% | 0.13% | 0.30% | 0.35% | 3.03% | 0.41% | 0.23% |
| | G | 0.01% | 0.00% | 0.00% | 0.00% | 0.01% | 0.00% | 0.00% | 0.00% | 0.01% | 0.00% | 0.00% |
| | T | 99.97% | 99.97% | 99.99% | 99.85% | 98.74% | 99.87% | 99.69% | 99.64% | 96.96% | 99.59% | 99.76% |

| HEK2-10 pNMG-364 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.00% | 0.07% | 0.01% | 0.00% | 0.00% | 0.00% | 0.01% | 0.00% | 0.00% | 0.00% | 0.00% |
| | C | 0.02% | 0.01% | 0.01% | 0.38% | 0.04% | 0.01% | 0.39% | 0.04% | 0.49% | 0.14% | 0.36% |
| | G | 0.01% | 0.00% | 0.00% | 0.00% | 0.01% | 0.00% | 0.00% | 0.00% | 0.00% | 0.00% | 0.00% |
| | T | 99.97% | 99.92% | 99.98% | 99.61% | 99.95% | 99.99% | 99.60% | 99.96% | 99.51% | 99.86% | 99.64% |

| HEK2-10 pNMG-365 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.00% | 0.12% | 0.00% | 0.00% | 0.00% | 0.00% | 0.00% | 0.00% | 0.01% | 0.01% | 0.01% |
| | C | 0.01% | 0.01% | 0.02% | 0.40% | 1.68% | 0.06% | 0.48% | 0.13% | 1.51% | 0.24% | 0.40% |
| | G | 0.00% | 0.00% | 0.00% | 0.00% | 0.00% | 0.00% | 0.01% | 0.00% | 0.00% | 0.00% | 0.00% |
| | T | 99.99% | 99.87% | 99.97% | 99.60% | 98.31% | 99.94% | 99.51% | 99.86% | 98.47% | 99.75% | 99.59% |

| HEK2-10 pNMG-366 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.00% | 0.02% | 0.01% | 0.01% | 0.00% | 0.00% | 0.01% | 0.00% | 0.00% | 0.01% | 0.00% |
| | C | 0.01% | 0.01% | 0.01% | 0.08% | 0.28% | 0.15% | 0.35% | 0.66% | 2.82% | 0.61% | 0.31% |
| | G | 0.00% | 0.00% | 0.00% | 0.00% | 0.00% | 0.00% | 0.00% | 0.00% | 0.00% | 0.00% | 0.00% |
| | T | 99.98% | 99.97% | 99.98% | 99.91% | 99.71% | 99.85% | 99.64% | 99.33% | 97.17% | 99.36% | 99.68% |

| HEK2-10 pNMG-367 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.01% | 0.07% | 0.01% | 0.01% | 0.00% | 0.00% | 0.00% | 0.00% | 0.00% | 0.01% | 0.01% |
| | C | 0.01% | 0.01% | 0.01% | 0.38% | 0.84% | 0.11% | 0.52% | 0.26% | 2.27% | 0.27% | 0.51% |
| | G | 0.00% | 0.00% | 0.00% | 0.00% | 0.01% | 0.00% | 0.00% | 0.00% | 0.00% | 0.00% | 0.00% |
| | T | 99.98% | 99.92% | 99.98% | 99.61% | 99.15% | 99.89% | 99.47% | 99.74% | 97.73% | 99.72% | 99.48% |

| HEK2-10 pNMG-368 | | 17 | 16 | 14 | 12 | 11 | 9 | 8 | 7 | 5 | 3 | 2 |
|---|---|---|---|---|---|---|---|---|---|---|---|---|
| | | T | T | T | T | T | T | T | T | T | T | T |
| | A | 0.01% | 0.05% | 0.01% | 0.00% | 0.01% | 0.00% | 0.00% | 0.00% | 0.01% | 0.00% | 0.01% |
| | C | 0.02% | 0.01% | 0.01% | 0.22% | 0.01% | 0.01% | 0.21% | 0.01% | 0.02% | 0.01% | 0.19% |
| | G | 0.01% | 0.00% | 0.00% | 0.00% | 0.01% | 0.00% | 0.00% | 0.01% | 0.00% | 0.00% | 0.00% |
| | T | 99.97% | 99.94% | 99.98% | 99.78% | 99.96% | 99.98% | 99.78% | 99.98% | 99.97% | 99.98% | 99.79% |

FIGURE 113

Hek3- 5'-GGCCCA GA CTGA GCA CGTGATGG-3'

FIGURE 114

FANCF-5'-GGA$_3$A'TCCCTTCTGCA$_{15}$GCA$_{18}$CCTGG-3'

FIGURE 115

Hek-2 site: 3'-CCCGCAGT$_{16}$CT$_{14}$AT$_{12}$GCT$_9$T$_8$T$_7$G T$_5$GT$_3$T$_2$C-5'

| HEK2 pNMG-370/299 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.02% | 0.00% | 0.01% | 0.00% | 0.04% | 0.01% | 0.00% |
| | C | 0.01% | 0.03% | 0.01% | 0.34% | 0.67% | 0.44% | | 1.20% | 0.10% |
| | G | 0.00% | 0.00% | 0.00% | 0.00% | 0.00% | 0.00% | 0.03% | 0.00% | 0.00% |
| | T | 99.98% | 99.96% | 99.97% | 99.65% | 99.32% | 99.56% | | 98.79% | 99.89% |

| HEK2 pNMG-371/299 | | 16 T | 14 T | 12 T | 9 T | 8 T | 7 T | 5 T | 3 T | 2 T |
|---|---|---|---|---|---|---|---|---|---|---|
| | A | 0.00% | 0.01% | 0.01% | 0.00% | 0.01% | 0.00% | 0.01% | 0.01% | 0.00% |
| | C | 0.01% | 0.02% | 0.05% | 0.73% | 1.20% | 1.46% | | 3.91% | 0.11% |
| | G | 0.01% | 0.00% | 0.00% | 0.00% | 0.01% | 0.00% | 0.01% | 0.00% | 0.00% |
| | T | 99.98% | 99.97% | 99.94% | 99.26% | 98.73% | 98.53% | | 96.07% | 99.89% |

| HEK2 pNMG-382/299 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.01% | 0.00% | 0.01% | 0.00% | 0.00% | 0.00% | 0.00% |
| | C | 0.01% | 0.01% | 0.03% | 0.02% | 0.23% | 0.31% | | 0.55% | 0.06% |
| | G | 0.01% | 0.00% | 0.00% | 0.00% | 0.00% | 0.00% | 0.02% | 0.00% | 0.00% |
| | T | 99.97% | 99.98% | 99.96% | 99.98% | 99.76% | 99.69% | | 99.45% | 99.93% |

| HEK2 pNMG-383/299 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.01% | 0.00% | 0.01% | 0.00% | 0.02% | 0.01% | 0.00% |
| | C | 0.01% | 0.02% | 0.02% | 0.10% | 0.07% | 0.13% | | 0.29% | 0.05% |
| | G | 0.01% | 0.00% | 0.00% | 0.00% | 0.01% | 0.00% | 0.01% | 0.00% | 0.00% |
| | T | 99.98% | 99.98% | 99.97% | 99.89% | 99.91% | 99.87% | | 99.69% | 99.94% |

| HEK2 pNMG-384/299 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.00% | 0.00% | 0.01% | 0.00% | 0.01% | 0.00% | 0.01% |
| | C | 0.02% | 0.03% | 0.03% | 0.04% | 0.05% | 0.11% | | 0.12% | 0.03% |
| | G | 0.01% | 0.00% | 0.00% | 0.00% | 0.00% | 0.00% | 0.00% | 0.00% | 0.00% |
| | T | 99.97% | 99.97% | 99.97% | 99.95% | 99.94% | 99.89% | | 99.88% | 99.97% |

| HEK2 pNMG-385/299 | | 16 T | 14 T | 12 T | 9 T | 8 T | 7 T | 5 T | 3 T | 2 T |
|---|---|---|---|---|---|---|---|---|---|---|
| | A | 0.00% | 0.01% | 0.01% | 0.00% | 0.01% | 0.00% | 0.01% | 0.00% | 0.00% |
| | C | 0.01% | 0.02% | 0.02% | 0.01% | 0.06% | 0.09% | | 0.12% | 0.05% |
| | G | 0.01% | 0.00% | 0.00% | 0.00% | 0.01% | 0.00% | 0.01% | 0.00% | 0.00% |
| | T | 99.99% | 99.98% | 99.98% | 99.99% | 99.92% | 99.91% | | 99.88% | 99.95% |

| HEK2 pNMG-386/299 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.01% | 0.00% | 0.01% | 0.00% | 0.01% | 0.00% | 0.00% |
| | C | 0.01% | 0.02% | 0.01% | 0.07% | 0.44% | 0.13% | | 0.80% | 0.04% |
| | G | 0.01% | 0.00% | 0.00% | 0.00% | 0.01% | 0.00% | 0.01% | 0.00% | 0.00% |
| | T | 99.97% | 99.98% | 99.98% | 99.93% | 99.54% | 99.87% | | 99.20% | 99.95% |

FIGURE 115 (Continued)

Hek-2 site: 3'-CCCGCAGT$_{16}$CT$_{14}$AT$_{12}$GCT$_9$T$_8$T$_7$G T$_5$GT$_3$T$_2$C-5'

| HEK2 pNMG-387/299 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.01% | 0.00% | 0.02% | 0.00% | 0.01% | 0.00% | 0.00% |
| | C | 0.01% | 0.02% | 0.02% | 0.05% | 0.18% | 0.13% | — | 0.63% | 0.02% |
| | G | 0.00% | 0.00% | 0.00% | 0.00% | 0.01% | 0.00% | 0.01% | 0.00% | 0.00% |
| | T | 99.98% | 99.97% | 99.97% | 99.94% | 99.79% | 99.86% | — | 99.37% | 99.98% |

| HEK2 pNMG-388/299 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.01% | 0.00% | 0.00% | 0.00% | 0.01% | 0.00% | 0.00% |
| | C | 0.01% | 0.02% | 0.01% | 0.04% | 0.18% | 0.13% | — | 0.55% | 0.07% |
| | G | 0.00% | 0.00% | 0.00% | 0.00% | 0.01% | 0.00% | 0.01% | 0.00% | 0.00% |
| | T | 99.99% | 99.97% | 99.98% | 99.95% | 99.81% | 99.87% | — | 99.44% | 99.93% |

| HEK2 pNMG-389/299 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.00% | 0.01% | 0.02% | 0.00% | 0.02% | 0.00% | 0.00% |
| | C | 0.02% | 0.01% | 0.01% | 0.09% | 0.19% | 0.22% | — | 0.40% | 0.07% |
| | G | 0.00% | 0.00% | 0.00% | 0.00% | 0.00% | 0.01% | 0.01% | 0.00% | 0.00% |
| | T | 99.98% | 99.98% | 99.99% | 99.89% | 99.79% | 99.77% | — | 99.60% | 99.92% |

| HEK2 pNMG-370/301 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.01% | 0.00% | 0.01% | 0.01% | 0.03% | 0.01% | 0.01% |
| | C | 0.01% | 0.02% | 0.01% | 0.90% | 10.56% | 1.26% | — | — | 0.73% |
| | G | 0.01% | 0.00% | 0.00% | 0.00% | 0.05% | 0.00% | 0.00% | 0.00% | 0.00% |
| | T | 99.98% | 99.97% | 99.98% | 99.09% | 89.38% | 98.73% | — | — | 99.26% |

| HEK2 pNMG-371/301 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.01% | 0.00% | 0.05% | 0.02% | 0.02% | 0.03% | 0.00% |
| | C | 0.01% | 0.02% | 0.04% | 1.52% | — | 4.44% | — | — | 1.66% |
| | G | 0.01% | 0.00% | 0.00% | 0.00% | 0.03% | 0.00% | 0.03% | 0.00% | 0.00% |
| | T | 99.98% | 99.98% | 99.95% | 98.48% | — | 95.54% | — | — | 98.33% |

| HEK2 pNMG-382/301 | | 16 T | 14 T | 12 T | 9 T | 8 T | 7 T | 5 T | 3 T | 2 T |
|---|---|---|---|---|---|---|---|---|---|---|
| | A | 0.00% | 0.01% | 0.01% | 0.00% | 0.01% | 0.00% | 0.00% | 0.00% | 0.00% |
| | C | 0.01% | 0.01% | 0.02% | 0.13% | 6.00% | 0.73% | — | — | 0.80% |
| | G | 0.01% | 0.00% | 0.00% | 0.00% | 0.05% | 0.00% | 0.00% | 0.03% | 0.00% |
| | T | 99.98% | 99.98% | 99.97% | 99.87% | 93.94% | 99.27% | — | — | 99.20% |

| HEK2 pNMG-383/301 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.01% | 0.00% | 0.01% | 0.01% | 0.01% | 0.01% | 0.00% |
| | C | 0.01% | 0.02% | 0.01% | 0.51% | 3.02% | 0.62% | — | — | 0.30% |
| | G | 0.00% | 0.00% | 0.00% | 0.00% | 0.01% | 0.00% | 0.00% | 0.00% | 0.00% |
| | T | 99.99% | 99.98% | 99.98% | 99.49% | 96.97% | 99.37% | — | — | 99.69% |

FIGURE 115 (Continued)

Hek-2 site: 3'-CCCGCAGT$_{16}$CT$_{14}$AT$_{12}$GCT$_9$T$_8$T$_7$G T$_5$GT$_3$T$_2$C-5'

| HEK2 pNMG-384/301 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.02% | 0.01% | 0.00% | 0.00% | 0.01% | 0.00% | 0.00% |
| | C | 0.01% | 0.02% | 0.01% | 0.42% | 2.72% | 0.18% | 13.40% | 6.88% | 0.12% |
| | G | 0.01% | 0.00% | 0.00% | 0.00% | 0.03% | 0.00% | 0.00% | 0.00% | 0.00% |
| | T | 99.98% | 99.98% | 99.97% | 99.58% | 97.25% | 99.87% | 86.59% | 93.11% | 99.87% |

| HEK2 pNMG-385/301 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.00% | 0.00% | 0.01% | 0.00% | 0.00% | 0.00% | 0.01% |
| | C | 0.00% | 0.02% | 0.01% | 0.06% | 0.43% | 0.06% | 8.73% | 2.84% | 0.11% |
| | G | 0.01% | 0.00% | 0.00% | 0.00% | 0.01% | 0.00% | 0.00% | 0.00% | 0.00% |
| | T | 99.99% | 99.98% | 99.98% | 99.93% | 99.56% | 99.94% | 91.27% | 97.16% | 99.88% |

| HEK2 pNMG-386/301 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.01% | 0.00% | 0.01% | 0.00% | 0.01% | 0.00% | 0.00% |
| | C | 0.01% | 0.02% | 0.01% | 0.64% | 2.94% | 0.28% | | 7.73% | 0.23% |
| | G | 0.05% | 0.00% | 0.00% | 0.00% | 0.01% | 0.00% | 0.00% | 0.01% | 0.00% |
| | T | 99.94% | 99.98% | 99.98% | 99.35% | 97.04% | 99.72% | | 92.26% | 99.76% |

| HEK2 pNMG-387/301 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.01% | 0.00% | 0.01% | 0.00% | 0.01% | 0.00% | 0.00% |
| | C | 0.01% | 0.01% | 0.04% | 0.13% | 3.90% | 0.44% | | 10.17% | 0.57% |
| | G | 0.00% | 0.00% | 0.00% | 0.00% | 0.01% | 0.00% | 0.01% | 0.00% | 0.00% |
| | T | 99.99% | 99.98% | 99.95% | 99.86% | 96.08% | 99.56% | | 89.78% | 99.43% |

| HEK2 pNMG-388/301 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.00% | 0.00% | 0.01% | 0.00% | 0.01% | 0.00% | 0.01% |
| | C | 0.00% | 0.01% | 0.02% | 0.12% | 4.98% | 0.61% | | 12.33% | 0.70% |
| | G | 0.00% | 0.00% | 0.00% | 0.00% | 0.01% | 0.00% | 0.00% | 0.00% | 0.00% |
| | T | 99.99% | 99.98% | 99.97% | 99.80% | 95.00% | 99.39% | | 87.67% | 99.29% |

| HEK2 pNMG-389/301 | | 16 T | 14 T | 12 T | 9 T | 8 T | 7 T | 5 T | 3 T | 2 T |
|---|---|---|---|---|---|---|---|---|---|---|
| | A | 0.00% | 0.00% | 0.01% | 0.00% | 0.02% | 0.01% | 0.01% | 0.01% | 0.01% |
| | C | 0.01% | 0.02% | 0.01% | 0.27% | 9.95% | 0.60% | 17.48% | 9.82% | 0.86% |
| | G | 0.01% | 0.00% | 0.00% | 0.00% | 0.01% | 0.01% | 0.00% | 0.00% | 0.00% |
| | T | 99.98% | 99.98% | 99.98% | 99.73% | 90.02% | 99.39% | 82.50% | 90.17% | 99.13% |

FIGURE 116

Hek2-2 site: 5'-GA₂A₃TA₅CTA₅A₉GCA₁₂TA₁₄GA₁₆CTCCAGG-3'

| HEK2-2 pNMG-370 | | 2 A | 3 A | 5 A | 8 A | 9 A | 12 A | 14 A | 16 A |
|---|---|---|---|---|---|---|---|---|---|
| | A | 99.81% | 99.80% | 78.88% | 99.53% | 99.93% | 99.97% | 99.99% | 99.99% |
| | C | 0.02% | 0.01% | 0.01% | 0.01% | 0.01% | 0.01% | 0.01% | 0.00% |
| | G | 0.14% | 0.19% | 29.09% | 0.46% | 0.06% | 0.01% | 0.00% | 0.01% |
| | T | 0.02% | 0.01% | 0.01% | 0.00% | 0.00% | 0.01% | 0.01% | 0.00% |

| HEK2-2 pNMG-371 | | 2 A | 3 A | 5 A | 8 A | 9 A | 12 A | 14 A | 16 A |
|---|---|---|---|---|---|---|---|---|---|
| | A | 99.47% | 99.28% | 49.97% | 99.33% | 99.65% | 99.98% | 99.99% | 100.00% |
| | C | 0.02% | 0.00% | 0.00% | 0.00% | 0.00% | 0.00% | 0.00% | 0.00% |
| | G | 0.50% | 0.71% | 50.03% | 0.66% | 0.35% | 0.01% | 0.01% | 0.00% |
| | T | 0.01% | 0.01% | 0.01% | 0.00% | 0.00% | 0.01% | 0.00% | 0.00% |

| HEK2-2 pNMG-382 | | 2 A | 3 A | 5 A | 8 A | 9 A | 12 A | 14 A | 16 A |
|---|---|---|---|---|---|---|---|---|---|
| | A | 99.91% | 99.88% | 75.50% | 99.85% | 99.97% | 99.97% | 99.95% | 99.97% |
| | C | 0.03% | 0.01% | 0.01% | 0.03% | 0.02% | 0.02% | 0.04% | 0.01% |
| | G | 0.05% | 0.10% | 24.48% | 0.12% | 0.01% | 0.01% | 0.01% | 0.00% |
| | T | 0.01% | 0.00% | 0.01% | 0.00% | 0.01% | 0.01% | 0.00% | 0.02% |

| HEK2-2 pNMG-383 | | 2 A | 3 A | 5 A | 8 A | 9 A | 12 A | 14 A | 16 A |
|---|---|---|---|---|---|---|---|---|---|
| | A | 99.91% | 99.97% | 76.15% | 99.93% | 99.95% | 99.98% | 99.99% | 99.98% |
| | C | 0.01% | 0.00% | 0.00% | 0.00% | 0.00% | 0.00% | 0.00% | 0.00% |
| | G | 0.07% | 0.03% | 23.84% | 0.07% | 0.04% | 0.01% | 0.01% | 0.01% |
| | T | 0.00% | 0.00% | 0.01% | 0.00% | 0.00% | 0.01% | 0.01% | 0.00% |

| HEK2-2 pNMG-384 | | 2 A | 3 A | 5 A | 8 A | 9 A | 12 A | 14 A | 16 A |
|---|---|---|---|---|---|---|---|---|---|
| | A | 99.92% | 99.99% | 78.15% | 99.96% | 99.95% | 99.97% | 99.97% | 99.99% |
| | C | 0.02% | 0.01% | 0.01% | 0.01% | 0.01% | 0.01% | 0.01% | 0.01% |
| | G | 0.05% | 0.00% | 21.83% | 0.03% | 0.04% | 0.01% | 0.01% | 0.00% |
| | T | 0.01% | 0.00% | 0.01% | 0.00% | 0.00% | 0.01% | 0.00% | 0.00% |

FIGURE 116 (Continued)

Hek2-2 site: 5'-GA$_2$A$_3$TA$_5$CTA$_8$A$_9$GCA$_{12}$TA$_{14}$GA$_{16}$CTCCAGG-3'

| HEK2-2 pNMG-385 | | 2<br>A | 3<br>A | 5<br>A | 8<br>A | 9<br>A | 12<br>A | 14<br>A | 16<br>A |
|---|---|---|---|---|---|---|---|---|---|
| | A | 99.95% | 99.99% | 88.71% | 99.96% | 99.99% | 99.99% | 99.99% | 99.99% |
| | C | 0.01% | 0.00% | 0.00% | 0.00% | 0.00% | 0.00% | 0.00% | 0.00% |
| | G | 0.04% | 0.01% | 11.29% | 0.03% | 0.01% | 0.00% | 0.01% | 0.00% |
| | T | 0.00% | 0.00% | 0.01% | 0.00% | 0.00% | 0.00% | 0.00% | 0.00% |

| HEK2-2 pNMG-386 | | 2<br>A | 3<br>A | 5<br>A | 8<br>A | 9<br>A | 12<br>A | 14<br>A | 16<br>A |
|---|---|---|---|---|---|---|---|---|---|
| | A | 99.92% | 99.95% | 79.44% | 99.88% | 99.96% | 99.95% | 99.97% | 99.98% |
| | C | 0.04% | 0.02% | 0.02% | 0.04% | 0.03% | 0.04% | 0.02% | 0.02% |
| | G | 0.03% | 0.02% | 20.54% | 0.08% | 0.00% | 0.00% | 0.01% | 0.00% |
| | T | 0.01% | 0.01% | 0.01% | 0.00% | 0.00% | 0.01% | 0.00% | 0.00% |

| HEK2-2 pNMG-387 | | 2<br>A | 3<br>A | 5<br>A | 8<br>A | 9<br>A | 12<br>A | 14<br>A | 16<br>A |
|---|---|---|---|---|---|---|---|---|---|
| | A | 99.86% | 99.93% | 78.43% | 99.82% | 99.94% | 99.98% | 99.99% | 99.99% |
| | C | 0.02% | 0.00% | 0.00% | 0.00% | 0.00% | 0.00% | 0.00% | 0.00% |
| | G | 0.11% | 0.06% | 21.56% | 0.17% | 0.05% | 0.01% | 0.01% | 0.01% |
| | T | 0.00% | 0.00% | 0.01% | 0.00% | 0.01% | 0.01% | 0.00% | 0.01% |

| HEK2-2 pNMG-388 | | 2<br>A | 3<br>A | 5<br>A | 8<br>A | 9<br>A | 12<br>A | 14<br>A | 16<br>A |
|---|---|---|---|---|---|---|---|---|---|
| | A | 99.87% | 99.88% | 76.48% | 99.90% | 99.98% | 99.98% | 99.98% | 99.98% |
| | C | 0.01% | 0.00% | 0.01% | 0.00% | 0.00% | 0.00% | 0.02% | 0.00% |
| | G | 0.12% | 0.12% | 23.64% | 0.09% | 0.01% | 0.01% | 0.00% | 0.00% |
| | T | 0.01% | 0.00% | 0.01% | 0.00% | 0.01% | 0.01% | 0.00% | 0.02% |

| HEK2-2 pNMG-389 | | 2<br>A | 3<br>A | 5<br>A | 8<br>A | 9<br>A | 12<br>A | 14<br>A | 16<br>A |
|---|---|---|---|---|---|---|---|---|---|
| | A | 99.82% | 99.95% | 76.62% | 99.90% | 99.97% | 99.99% | 99.98% | 99.99% |
| | C | 0.01% | 0.00% | 0.00% | 0.00% | 0.00% | 0.00% | 0.00% | 0.00% |
| | G | 0.16% | 0.04% | 23.37% | 0.10% | 0.02% | 0.01% | 0.01% | 0.00% |
| | T | 0.00% | 0.01% | 0.01% | 0.00% | 0.00% | 0.01% | 0.00% | 0.01% |

FIGURE 117

Hek 2-3 site: 5'-GTA$_3$A$_4$A$_5$CA$_7$A$_8$A$_9$GCA$_{12}$TA$_{14}$GA$_{16}$CTGAGGG -3'

| HEK2-3 pNMG-370 | | 3 A | 4 A | 5 A | 7 A | 8 A | 9 A | 12 A | 14 A | 16 A |
|---|---|---|---|---|---|---|---|---|---|---|
| | A | 99.86% | 99.81% | 89.58% | 99.89% | 99.50% | 99.67% | 99.97% | 99.97% | 99.99% |
| | C | 0.00% | 0.01% | 0.01% | 0.01% | 0.01% | 0.14% | 0.01% | 0.02% | 0.00% |
| | G | 0.12% | 0.17% | 10.39% | 0.10% | 0.48% | 0.19% | 0.02% | 0.01% | 0.00% |
| | T | 0.01% | 0.01% | 0.01% | 0.01% | 0.01% | 0.00% | 0.01% | 0.00% | 0.01% |

| HEK2-3 pNMG-371 | | 3 A | 4 A | 5 A | 7 A | 8 A | 9 A | 12 A | 14 A | 16 A |
|---|---|---|---|---|---|---|---|---|---|---|
| | A | 99.61% | 98.90% | 79.92% | 99.00% | 98.38% | 99.18% | 99.94% | 99.97% | 99.99% |
| | C | 0.00% | 0.01% | 0.00% | 0.00% | 0.00% | 0.13% | 0.00% | 0.01% | 0.00% |
| | G | 0.39% | 1.08% | 20.07% | 1.00% | 1.60% | 0.69% | 0.04% | 0.02% | 0.00% |
| | T | 0.00% | 0.01% | 0.01% | 0.00% | 0.01% | 0.00% | 0.02% | 0.00% | 0.01% |

| HEK2-3 pNMG-382 | | 3 A | 4 A | 5 A | 7 A | 8 A | 9 A | 12 A | 14 A | 16 A |
|---|---|---|---|---|---|---|---|---|---|---|
| | A | 0.00% | 0.00% | 0.01% | 0.00% | 0.01% | 0.00% | 0.00% | 0.00% | 0.00% |
| | C | 0.01% | 0.01% | 0.03% | 0.02% | 0.23% | 0.31% | 46.97% | 0.55% | 0.06% |
| | G | 0.01% | 0.00% | 0.00% | 0.00% | 0.00% | 0.00% | 0.02% | 0.00% | 0.00% |
| | T | 99.97% | 99.98% | 99.96% | 99.98% | 99.76% | 99.69% | 53.01% | 99.45% | 99.93% |

| HEK2-3 pNMG-383 | | 3 A | 4 A | 5 A | 7 A | 8 A | 9 A | 12 A | 14 A | 16 A |
|---|---|---|---|---|---|---|---|---|---|---|
| | A | 0.00% | 0.00% | 0.01% | 0.00% | 0.01% | 0.00% | 0.02% | 0.01% | 0.00% |
| | C | 0.01% | 0.02% | 0.02% | 0.10% | 0.07% | 0.13% | 52.87% | 0.29% | 0.05% |
| | G | 0.01% | 0.00% | 0.00% | 0.00% | 0.01% | 0.00% | 0.01% | 0.00% | 0.00% |
| | T | 99.98% | 99.98% | 99.97% | 99.89% | 99.91% | 99.87% | 47.10% | 99.69% | 99.94% |

| HEK2-3 pNMG-384 | | 3 A | 4 A | 5 A | 7 A | 8 A | 9 A | 12 A | 14 A | 16 A |
|---|---|---|---|---|---|---|---|---|---|---|
| | A | 0.00% | 0.00% | 0.00% | 0.00% | 0.01% | 0.00% | 0.01% | 0.00% | 0.01% |
| | C | 0.02% | 0.03% | 0.03% | 0.04% | 0.05% | 0.11% | 44.46% | 0.12% | 0.03% |
| | G | 0.01% | 0.00% | 0.00% | 0.00% | 0.00% | 0.00% | 0.00% | 0.00% | 0.00% |
| | T | 99.97% | 99.97% | 99.97% | 99.95% | 99.94% | 99.89% | 55.53% | 99.88% | 99.97% |

| HEK2-3 pNMG-385 | | 3 A | 4 A | 5 A | 7 A | 8 A | 9 A | 12 A | 14 A | 16 A |
|---|---|---|---|---|---|---|---|---|---|---|
| | A | 0.00% | 0.01% | 0.01% | 0.00% | 0.01% | 0.00% | 0.01% | 0.00% | 0.00% |
| | C | 0.01% | 0.02% | 0.02% | 0.01% | 0.06% | 0.09% | 40.31% | 0.12% | 0.05% |
| | G | 0.01% | 0.00% | 0.00% | 0.00% | 0.01% | 0.00% | 0.01% | 0.00% | 0.00% |
| | T | 99.98% | 99.98% | 99.98% | 99.99% | 99.92% | 99.91% | 59.67% | 99.88% | 99.95% |

FIGURE 117 (Continued)

Hek 2-3 site: 5'-GTA$_3$A$_4$A$_5$CA$_7$A$_8$A$_9$GCA$_{12}$TA$_{14}$GA$_{16}$CTGAGGG -3'

| HEK2-3 pNMG-386 | | 3 A | 4 A | 5 A | 7 A | 8 A | 9 A | 12 A | 14 A | 16 A |
|---|---|---|---|---|---|---|---|---|---|---|
| | A | 0.00% | 0.00% | 0.01% | 0.00% | 0.01% | 0.00% | 0.01% | 0.00% | 0.00% |
| | C | 0.01% | 0.02% | 0.01% | 0.07% | 0.44% | 0.13% | | 0.80% | 0.04% |
| | G | 0.01% | 0.00% | 0.00% | 0.00% | 0.01% | 0.00% | 0.01% | 0.00% | 0.00% |
| | T | 99.97% | 99.98% | 99.98% | 99.93% | 99.54% | 99.87% | | 99.20% | 99.96% |

| HEK2-3 pNMG-387 | | 3 A | 4 A | 5 A | 7 A | 8 A | 9 A | 12 A | 14 A | 16 A |
|---|---|---|---|---|---|---|---|---|---|---|
| | A | 0.00% | 0.00% | 0.01% | 0.00% | 0.02% | 0.00% | 0.01% | 0.00% | 0.00% |
| | C | 0.01% | 0.02% | 0.02% | 0.05% | 0.18% | 0.13% | | 0.63% | 0.02% |
| | G | 0.00% | 0.00% | 0.00% | 0.00% | 0.01% | 0.00% | 0.01% | 0.00% | 0.00% |
| | T | 99.98% | 99.97% | 99.97% | 99.94% | 99.79% | 99.86% | | 99.37% | 99.98% |

| HEK2-3 pNMG-388 | | 3 A | 4 A | 5 A | 7 A | 8 A | 9 A | 12 A | 14 A | 16 A |
|---|---|---|---|---|---|---|---|---|---|---|
| | A | 0.00% | 0.00% | 0.01% | 0.00% | 0.00% | 0.00% | 0.01% | 0.00% | 0.00% |
| | C | 0.01% | 0.02% | 0.01% | 0.04% | 0.18% | 0.13% | | 0.55% | 0.07% |
| | G | 0.00% | 0.00% | 0.00% | 0.00% | 0.01% | 0.00% | 0.01% | 0.00% | 0.00% |
| | T | 99.99% | 99.97% | 99.98% | 99.95% | 99.81% | 99.87% | | 99.44% | 99.93% |

| HEK2-3 pNMG-389 | | 3 A | 4 A | 5 A | 7 A | 8 A | 9 A | 12 A | 14 A | 16 A |
|---|---|---|---|---|---|---|---|---|---|---|
| | A | 0.00% | 0.00% | 0.00% | 0.01% | 0.02% | 0.00% | 0.02% | 0.00% | 0.00% |
| | C | 0.02% | 0.01% | 0.01% | 0.09% | 0.19% | 0.22% | | 0.40% | 0.07% |
| | G | 0.00% | 0.00% | 0.00% | 0.00% | 0.00% | 0.01% | 0.01% | 0.00% | 0.00% |
| | T | 99.98% | 99.98% | 99.99% | 99.89% | 99.79% | 99.77% | | 99.60% | 99.92% |

FIGURE 118

HEK2-6- 5'-GA₂A₃GA₅CCA₈A₉GGA₁₂TA₁₄GA₁₆CTGCTGG-3'

| HEK2-6 pNMG-370 | | 2 | 3 | 5 | 8 | 9 | 12 | 14 | 16 |
|---|---|---|---|---|---|---|---|---|---|
| | | A | A | A | A | A | A | A | A |
| | A | 99.96% | 99.94% | 95.58% | 99.77% | 99.84% | 99.96% | 99.98% | 99.97% |
| | C | 0.00% | 0.01% | 0.01% | 0.01% | 0.01% | 0.01% | 0.00% | 0.02% |
| | G | 0.03% | 0.04% | 4.40% | 0.21% | 0.14% | 0.02% | 0.02% | 0.01% |
| | T | 0.01% | 0.01% | 0.01% | 0.01% | 0.02% | 0.01% | 0.01% | 0.01% |

| HEK2-6 pNMG-371 | | 2 | 3 | 5 | 8 | 9 | 12 | 14 | 16 |
|---|---|---|---|---|---|---|---|---|---|
| | | A | A | A | A | A | A | A | A |
| | A | 99.95% | 99.91% | 92.37% | 99.60% | 99.63% | 99.98% | 99.99% | 99.99% |
| | C | 0.00% | 0.00% | 0.00% | 0.00% | 0.00% | 0.00% | 0.00% | 0.01% |
| | G | 0.04% | 0.08% | 7.61% | 0.39% | 0.35% | 0.01% | 0.01% | 0.00% |
| | T | 0.01% | 0.01% | 0.02% | 0.01% | 0.01% | 0.00% | 0.01% | 0.00% |

| HEK2-6 pNMG-382 | | 2 | 3 | 5 | 8 | 9 | 12 | 14 | 16 |
|---|---|---|---|---|---|---|---|---|---|
| | | A | A | A | A | A | A | A | A |
| | A | 99.97% | 99.97% | 95.39% | 99.88% | 99.90% | 99.99% | 99.99% | 99.96% |
| | C | 0.00% | 0.01% | 0.01% | 0.01% | 0.01% | 0.00% | 0.00% | 0.01% |
| | G | 0.03% | 0.01% | 4.59% | 0.10% | 0.08% | 0.01% | 0.00% | 0.02% |
| | T | 0.01% | 0.01% | 0.01% | 0.01% | 0.01% | 0.00% | 0.01% | 0.01% |

| HEK2-6 pNMG-383 | | 2 | 3 | 5 | 8 | 9 | 12 | 14 | 16 |
|---|---|---|---|---|---|---|---|---|---|
| | | A | A | A | A | A | A | A | A |
| | A | 99.97% | 99.97% | 94.48% | 99.97% | 99.90% | 99.94% | 99.97% | 99.98% |
| | C | 0.00% | 0.01% | 0.00% | 0.00% | 0.01% | 0.00% | 0.01% | 0.01% |
| | G | 0.02% | 0.01% | 5.50% | 0.03% | 0.07% | 0.04% | 0.01% | 0.00% |
| | T | 0.00% | 0.01% | 0.02% | 0.00% | 0.02% | 0.01% | 0.01% | 0.01% |

| HEK2-6 pNMG-384 | | 2 | 3 | 5 | 8 | 9 | 12 | 14 | 16 |
|---|---|---|---|---|---|---|---|---|---|
| | | A | A | A | A | A | A | A | A |
| | A | 99.96% | 99.97% | 97.20% | 99.98% | 99.94% | 99.97% | 99.98% | 99.97% |
| | C | 0.00% | 0.01% | 0.00% | 0.00% | 0.01% | 0.01% | 0.00% | 0.01% |
| | G | 0.03% | 0.01% | 2.79% | 0.01% | 0.04% | 0.01% | 0.01% | 0.01% |
| | T | 0.00% | 0.01% | 0.01% | 0.00% | 0.02% | 0.01% | 0.01% | 0.00% |

FIGURE 118 (Continued)

HEK2-6- 5'-GA₂A₃GA₅CCA₈A₉GGA₁₂TA₁₄GA₁₆CTGCTGG-3'

| HEK2-6 pNMG-385 | | 2 | 3 | 5 | 8 | 9 | 12 | 14 | 16 |
|---|---|---|---|---|---|---|---|---|---|
| | | A | A | A | A | A | A | A | A |
| | A | 99.96% | 99.97% | 98.54% | 99.98% | 99.97% | 99.97% | 99.95% | 99.98% |
| | C | 0.00% | 0.01% | 0.01% | 0.00% | 0.01% | 0.00% | 0.01% | 0.00% |
| | G | 0.02% | 0.01% | 1.45% | 0.01% | 0.02% | 0.01% | 0.03% | 0.01% |
| | T | 0.01% | 0.01% | 0.01% | 0.01% | 0.00% | 0.02% | 0.01% | 0.01% |

| HEK2-6 pNMG-386 | | 2 | 3 | 5 | 8 | 9 | 12 | 14 | 16 |
|---|---|---|---|---|---|---|---|---|---|
| | | A | A | A | A | A | A | A | A |
| | A | 99.98% | 99.97% | 97.56% | 99.95% | 99.93% | 99.95% | 99.96% | 99.97% |
| | C | 0.01% | 0.01% | 0.01% | 0.02% | 0.02% | 0.01% | 0.01% | 0.02% |
| | G | 0.01% | 0.01% | 2.41% | 0.02% | 0.04% | 0.03% | 0.02% | 0.00% |
| | T | 0.00% | 0.01% | 0.01% | 0.01% | 0.01% | 0.00% | 0.02% | 0.00% |

| HEK2-6 pNMG-387 | | 2 | 3 | 5 | 8 | 9 | 12 | 14 | 16 |
|---|---|---|---|---|---|---|---|---|---|
| | | A | A | A | A | A | A | A | A |
| | A | 99.93% | 99.97% | 97.46% | 99.94% | 99.97% | 99.98% | 99.97% | 99.98% |
| | C | 0.01% | 0.01% | 0.00% | 0.01% | 0.01% | 0.00% | 0.00% | 0.01% |
| | G | 0.05% | 0.01% | 2.53% | 0.05% | 0.02% | 0.01% | 0.01% | 0.01% |
| | T | 0.01% | 0.01% | 0.01% | 0.00% | 0.01% | 0.01% | 0.01% | 0.00% |

| HEK2-6 pNMG-388 | | 2 | 3 | 5 | 8 | 9 | 12 | 14 | 16 |
|---|---|---|---|---|---|---|---|---|---|
| | | A | A | A | A | A | A | A | A |
| | A | 99.97% | 99.98% | 96.81% | 99.94% | 99.90% | 99.94% | 99.99% | 99.99% |
| | C | 0.00% | 0.01% | 0.01% | 0.00% | 0.00% | 0.00% | 0.00% | 0.00% |
| | G | 0.02% | 0.01% | 3.18% | 0.06% | 0.08% | 0.06% | 0.00% | 0.00% |
| | T | 0.01% | 0.01% | 0.00% | 0.00% | 0.01% | 0.01% | 0.01% | 0.00% |

| HEK2-6 pNMG-389 | | 2 | 3 | 5 | 8 | 9 | 12 | 14 | 16 |
|---|---|---|---|---|---|---|---|---|---|
| | | A | A | A | A | A | A | A | A |
| | A | 99.97% | 99.96% | 97.46% | 99.97% | 99.85% | 99.89% | 99.97% | 99.97% |
| | C | 0.00% | 0.01% | 0.00% | 0.00% | 0.02% | 0.00% | 0.00% | 0.02% |
| | G | 0.02% | 0.02% | 2.51% | 0.03% | 0.13% | 0.10% | 0.01% | 0.01% |
| | T | 0.01% | 0.02% | 0.03% | 0.00% | 0.01% | 0.01% | 0.02% | 0.00% |

FIGURE 119

HEK2-7- 3'-CCTGCAGT CAAT GAT T T GT T T T G-5'

| HEK2-7 pNMG-370 | | 16 T | 12 T | 9 T | 8 T | 7 T | 5 T | 4 T | 3 T | 2 T |
|---|---|---|---|---|---|---|---|---|---|---|
| | A | 0.00% | 0.00% | 0.00% | 0.01% | 0.01% | 0.01% | 0.00% | 0.00% | 0.01% |
| | C | 0.02% | 0.01% | 0.04% | 0.02% | 0.01% | 0.30% | 0.01% | 0.01% | 0.01% |
| | G | 0.00% | 0.00% | 0.00% | 0.00% | 0.00% | 0.00% | 0.00% | 0.00% | 0.00% |
| | T | 99.98% | 99.99% | 99.96% | 99.98% | 99.99% | 99.69% | 99.99% | 99.99% | 99.99% |

| HEK2-7 pNMG-371 | | 16 T | 12 T | 9 T | 8 T | 7 T | 5 T | 4 T | 3 T | 2 T |
|---|---|---|---|---|---|---|---|---|---|---|
| | A | 0.00% | 0.00% | 0.00% | 0.00% | 0.00% | 0.00% | 0.00% | 0.00% | 0.00% |
| | C | 0.02% | 0.01% | 0.07% | 0.05% | 0.05% | 0.75% | 0.04% | 0.02% | 0.01% |
| | G | 0.00% | 0.00% | 0.00% | 0.00% | 0.00% | 0.00% | 0.00% | 0.00% | 0.00% |
| | T | 99.98% | 99.98% | 99.92% | 99.95% | 99.94% | 99.24% | 99.96% | 99.98% | 99.99% |

| HEK2-7 pNMG-382 | | 16 T | 12 T | 9 T | 8 T | 7 T | 5 T | 4 T | 3 T | 2 T |
|---|---|---|---|---|---|---|---|---|---|---|
| | A | 0.00% | 0.00% | 0.00% | 0.00% | 0.01% | 0.01% | 0.00% | 0.00% | 0.00% |
| | C | 0.01% | 0.01% | 0.01% | 0.01% | 0.00% | 0.26% | 0.01% | 0.01% | 0.01% |
| | G | 0.00% | 0.00% | 0.00% | 0.00% | 0.00% | 0.00% | 0.00% | 0.00% | 0.00% |
| | T | 99.99% | 99.98% | 99.99% | 99.99% | 99.99% | 99.74% | 99.99% | 99.99% | 99.98% |

| HEK2-7 pNMG-383 | | 16 T | 12 T | 9 T | 8 T | 7 T | 5 T | 4 T | 3 T | 2 T |
|---|---|---|---|---|---|---|---|---|---|---|
| | A | 0.00% | 0.00% | 0.00% | 0.00% | 0.00% | 0.01% | 0.00% | 0.00% | 0.00% |
| | C | 0.01% | 0.01% | 0.01% | 0.02% | 0.01% | 0.23% | 0.01% | 0.01% | 0.00% |
| | G | 0.00% | 0.01% | 0.00% | 0.00% | 0.00% | 0.01% | 0.00% | 0.00% | 0.00% |
| | T | 99.99% | 99.98% | 99.99% | 99.98% | 99.99% | 99.76% | 99.99% | 99.99% | 99.99% |

| HEK2-7 pNMG-384 | | 16 T | 12 T | 9 T | 8 T | 7 T | 5 T | 4 T | 3 T | 2 T |
|---|---|---|---|---|---|---|---|---|---|---|
| | A | 0.00% | 0.01% | 0.00% | 0.00% | 0.00% | 0.01% | 0.00% | 0.00% | 0.00% |
| | C | 0.01% | 0.01% | 0.02% | 0.00% | 0.01% | 0.10% | 0.01% | 0.02% | 0.01% |
| | G | 0.00% | 0.00% | 0.00% | 0.00% | 0.00% | 0.01% | 0.00% | 0.00% | 0.00% |
| | T | 99.99% | 99.98% | 99.98% | 99.99% | 99.99% | 99.89% | 99.99% | 99.98% | 99.99% |

FIGURE 119 (Continued)

HEK2-7- 3'-CCTGCAGT₁₆CAAT₁₂GAT₉T₈T₇GT₅T₄T₃T₂G-5'

| HEK2-7 pNMG-385 | | 16<br>T | 12<br>T | 9<br>T | 8<br>T | 7<br>T | 5<br>T | 4<br>T | 3<br>T | 2<br>T |
|---|---|---|---|---|---|---|---|---|---|---|
| | A | 0.01% | 0.00% | 0.00% | 0.01% | 0.00% | 0.00% | 0.00% | 0.00% | 0.00% |
| | C | 0.01% | 0.01% | 0.01% | 0.02% | 0.00% | 0.09% | 0.02% | 0.01% | 0.01% |
| | G | 0.00% | 0.01% | 0.00% | 0.00% | 0.00% | 0.01% | 0.00% | 0.00% | 0.00% |
| | T | 99.99% | 99.97% | 99.99% | 99.97% | 100.00% | 99.91% | 99.98% | 99.99% | 99.98% |

| HEK2-7 pNMG-386 | | 16<br>T | 12<br>T | 9<br>T | 8<br>T | 7<br>T | 5<br>T | 4<br>T | 3<br>T | 2<br>T |
|---|---|---|---|---|---|---|---|---|---|---|
| | A | 0.00% | 0.00% | 0.00% | 0.00% | 0.00% | 0.01% | 0.00% | 0.00% | 0.00% |
| | C | 0.01% | 0.01% | 0.02% | 0.01% | 0.01% | 0.14% | 0.01% | 0.01% | 0.00% |
| | G | 0.00% | 0.00% | 0.00% | 0.00% | 0.00% | 0.00% | 0.00% | 0.00% | 0.00% |
| | T | 99.98% | 99.99% | 99.98% | 99.99% | 99.98% | 99.85% | 99.99% | 99.99% | 99.99% |

| HEK2-7 pNMG-387 | | 16<br>T | 12<br>T | 9<br>T | 8<br>T | 7<br>T | 5<br>T | 4<br>T | 3<br>T | 2<br>T |
|---|---|---|---|---|---|---|---|---|---|---|
| | A | 0.01% | 0.00% | 0.00% | 0.00% | 0.01% | 0.00% | 0.01% | 0.00% | 0.00% |
| | C | 0.01% | 0.01% | 0.02% | 0.02% | 0.01% | 0.14% | 0.01% | 0.02% | 0.01% |
| | G | 0.00% | 0.01% | 0.00% | 0.00% | 0.00% | 0.01% | 0.00% | 0.00% | 0.00% |
| | T | 99.98% | 99.98% | 99.98% | 99.98% | 99.98% | 99.85% | 99.98% | 99.97% | 99.99% |

| HEK2-7 pNMG-388 | | 16<br>T | 12<br>T | 9<br>T | 8<br>T | 7<br>T | 5<br>T | 4<br>T | 3<br>T | 2<br>T |
|---|---|---|---|---|---|---|---|---|---|---|
| | A | 0.00% | 0.00% | 0.00% | 0.00% | 0.00% | 0.00% | 0.00% | 0.00% | 0.00% |
| | C | 0.02% | 0.02% | 0.00% | 0.02% | 0.02% | 0.38% | 0.05% | 0.00% | 0.03% |
| | G | 0.00% | 0.00% | 0.00% | 0.00% | 0.00% | 0.00% | 0.00% | 0.01% | 0.02% |
| | T | 99.99% | 99.97% | 99.99% | 99.98% | 99.98% | 99.62% | 99.95% | 99.99% | 99.95% |

| HEK2-7 pNMG-389 | | 16<br>T | 12<br>T | 9<br>T | 8<br>T | 7<br>T | 5<br>T | 4<br>T | 3<br>T | 2<br>T |
|---|---|---|---|---|---|---|---|---|---|---|
| | A | 0.01% | 0.00% | 0.00% | 0.00% | 0.00% | 0.00% | 0.00% | 0.00% | 0.01% |
| | C | 0.02% | 0.01% | 0.02% | 0.02% | 0.01% | 0.27% | 0.02% | 0.01% | 0.01% |
| | G | 0.00% | 0.01% | 0.00% | 0.00% | 0.01% | 0.00% | 0.00% | 0.00% | 0.00% |
| | T | 99.98% | 99.98% | 99.98% | 99.97% | 99.98% | 99.73% | 99.98% | 99.99% | 99.99% |

FIGURE 120

Hek2-10 site: 3'-CCATCAT₁₇T₁₆CT₁₄AT₁₂T₁₁CT₉T₈T₇AT₅GT₃T₂C-5'

| HEK2-10 pNMG-370 | | 17 T | 16 T | 14 T | 12 T | 11 T | 9 T | 8 T | 7 T | 5 T | 3 T | 2 T |
|---|---|---|---|---|---|---|---|---|---|---|---|---|
| | A | 0.00% | 0.05% | 0.01% | 0.00% | 0.00% | 0.00% | 0.00% | 0.01% | 0.01% | 0.00% | 0.01% |
| | C | 0.01% | 0.01% | 0.02% | 0.19% | 0.22% | 0.19% | 0.57% | 0.94% | 6.27% | 0.53% | 0.26% |
| | G | 0.02% | 0.00% | 0.00% | 0.00% | 0.02% | 0.00% | 0.00% | 0.00% | 0.00% | 0.00% | 0.00% |
| | T | | | | | | | | | | | |

| HEK2-10 pNMG-371 | | 17 T | 16 T | 14 T | 12 T | 11 T | 9 T | 8 T | 7 T | 5 T | 3 T | 2 T |
|---|---|---|---|---|---|---|---|---|---|---|---|---|
| | A | 0.00% | 0.01% | 0.01% | 0.00% | 0.00% | 0.01% | 0.00% | 0.01% | 0.01% | 0.00% | 0.00% |
| | C | 0.01% | 0.01% | 0.01% | 0.09% | 0.69% | 0.73% | 2.06% | 4.06% | | 2.52% | 0.53% |
| | G | 0.02% | 0.00% | 0.01% | 0.00% | 0.02% | 0.00% | 0.00% | 0.00% | 0.01% | 0.00% | 0.00% |
| | T | | | | | | | | | | | |

| HEK2-10 pNMG-382 | | 17 T | 16 T | 14 T | 12 T | 11 T | 9 T | 8 T | 7 T | 5 T | 3 T | 2 T |
|---|---|---|---|---|---|---|---|---|---|---|---|---|
| | A | 0.00% | 0.07% | 0.00% | 0.01% | 0.01% | 0.00% | 0.00% | 0.01% | 0.00% | 0.01% | 0.00% |
| | C | 0.01% | 0.01% | 0.01% | 0.23% | 0.18% | 0.03% | 0.33% | 0.23% | 3.62% | 0.29% | 0.31% |
| | G | 0.02% | 0.00% | 0.01% | 0.00% | 0.02% | 0.00% | 0.00% | 0.00% | 0.00% | 0.00% | 0.00% |
| | T | | | | | | | | | | | |

| HEK2-10 pNMG-383 | | 17 T | 16 T | 14 T | 12 T | 11 T | 9 T | 8 T | 7 T | 5 T | 3 T | 2 T |
|---|---|---|---|---|---|---|---|---|---|---|---|---|
| | A | 0.00% | 0.01% | 0.01% | 0.01% | 0.00% | 0.01% | 0.00% | 0.00% | 0.00% | 0.01% | 0.01% |
| | C | 0.01% | 0.01% | 0.01% | 0.05% | 0.75% | 0.08% | 0.15% | 0.20% | 3.71% | 0.19% | 0.12% |
| | G | 0.02% | 0.00% | 0.00% | 0.00% | 0.02% | 0.00% | 0.00% | 0.00% | 0.00% | 0.00% | 0.00% |
| | T | | | | | | | | | | | |

| HEK2-10 pNMG-384 | | 17 T | 16 T | 14 T | 12 T | 11 T | 9 T | 8 T | 7 T | 5 T | 3 T | 2 T |
|---|---|---|---|---|---|---|---|---|---|---|---|---|
| | A | 0.00% | 0.02% | 0.01% | 0.01% | 0.01% | 0.01% | 0.00% | 0.00% | 0.01% | 0.01% | 0.01% |
| | C | 0.01% | 0.01% | 0.01% | 0.11% | 0.83% | 0.04% | 0.13% | 0.11% | 3.14% | 0.12% | 0.14% |
| | G | 0.02% | 0.00% | 0.00% | 0.00% | 0.02% | 0.00% | 0.00% | 0.00% | 0.00% | 0.00% | 0.00% |
| | T | | | | | | | | | | | |

FIGURE 120 (Continued)

Hek2-10 site: 3'-CCATCAT₁₇T₁₆CT₁₄AT₁₂T₁₁CT₉T₈T₇AT₅GT₃T₂C-5'

| HEK2-10 pNMG-385 | | 17 T | 16 T | 14 T | 12 T | 11 T | 9 T | 8 T | 7 T | 5 T | 3 T | 2 T |
|---|---|---|---|---|---|---|---|---|---|---|---|---|
| | A | 0.00% | 0.02% | 0.00% | 0.00% | 0.00% | 0.01% | 0.00% | 0.00% | 0.01% | 0.01% | 0.00% |
| | C | 0.01% | 0.01% | 0.01% | 0.06% | 0.28% | 0.03% | 0.09% | 0.10% | 1.52% | 0.05% | 0.11% |
| | G | 0.02% | 0.00% | 0.00% | 0.00% | 0.02% | 0.00% | 0.00% | 0.00% | 0.00% | 0.00% | 0.00% |
| | T | 99.97% | 99.97% | 99.99% | 99.94% | 99.69% | 99.97% | 99.91% | 99.90% | 98.47% | 99.94% | 99.88% |

| HEK2-10 pNMG-386 | | 17 T | 16 T | 14 T | 12 T | 11 T | 9 T | 8 T | 7 T | 5 T | 3 T | 2 T |
|---|---|---|---|---|---|---|---|---|---|---|---|---|
| | A | 0.00% | 0.07% | 0.01% | 0.00% | 0.01% | 0.01% | 0.01% | 0.00% | 0.01% | 0.01% | 0.01% |
| | C | 0.01% | 0.01% | 0.01% | 0.24% | 0.70% | 0.05% | 0.27% | 0.19% | 2.78% | 0.11% | 0.23% |
| | G | 0.01% | 0.00% | 0.01% | 0.00% | 0.01% | 0.00% | 0.00% | 0.00% | 0.00% | 0.00% | 0.00% |
| | T | 99.97% | 99.93% | 99.98% | 99.76% | 99.28% | 99.94% | 99.73% | 99.80% | 97.21% | 99.88% | 99.76% |

| HEK2-10 pNMG-387 | | 17 T | 16 T | 14 T | 12 T | 11 T | 9 T | 8 T | 7 T | 5 T | 3 T | 2 T |
|---|---|---|---|---|---|---|---|---|---|---|---|---|
| | A | 0.01% | 0.05% | 0.00% | 0.01% | 0.00% | 0.00% | 0.00% | 0.00% | 0.01% | 0.01% | 0.00% |
| | C | 0.01% | 0.01% | 0.01% | 0.26% | 0.18% | 0.08% | 0.38% | 0.19% | 3.15% | 0.21% | 0.39% |
| | G | 0.01% | 0.00% | 0.01% | 0.00% | 0.02% | 0.00% | 0.00% | 0.01% | 0.00% | 0.00% | 0.00% |
| | T | 99.97% | 99.95% | 99.98% | 99.74% | 99.80% | 99.92% | 99.62% | 99.80% | 96.83% | 99.79% | 99.61% |

| HEK2-10 pNMG-388 | | 17 T | 16 T | 14 T | 12 T | 11 T | 9 T | 8 T | 7 T | 5 T | 3 T | 2 T |
|---|---|---|---|---|---|---|---|---|---|---|---|---|
| | A | 0.00% | 0.03% | 0.00% | 0.00% | 0.00% | 0.00% | 0.00% | 0.00% | 0.01% | 0.01% | 0.01% |
| | C | 0.01% | 0.01% | 0.01% | 0.13% | 0.16% | 0.05% | 0.25% | 0.24% | 4.14% | 0.22% | 0.22% |
| | G | 0.01% | 0.00% | 0.00% | 0.00% | 0.01% | 0.00% | 0.00% | 0.00% | 0.00% | 0.00% | 0.00% |
| | T | 99.97% | 99.96% | 99.99% | 99.87% | 99.83% | 99.94% | 99.75% | 99.75% | 95.85% | 99.77% | 99.77% |

| HEK2-10 pNMG-389 | | 17 T | 16 T | 14 T | 12 T | 11 T | 9 T | 8 T | 7 T | 5 T | 3 T | 2 T |
|---|---|---|---|---|---|---|---|---|---|---|---|---|
| | A | 0.00% | 0.02% | 0.01% | 0.00% | 0.00% | 0.01% | 0.00% | 0.00% | 0.00% | 0.00% | 0.01% |
| | C | 0.01% | 0.01% | 0.01% | 0.09% | 0.23% | 0.06% | 0.18% | 0.23% | 3.10% | 0.15% | 0.21% |
| | G | 0.01% | 0.00% | 0.00% | 0.00% | 0.01% | 0.00% | 0.00% | 0.00% | 0.00% | 0.00% | 0.00% |
| | T | 99.97% | 99.97% | 99.98% | 99.91% | 99.76% | 99.93% | 99.82% | 99.77% | 96.90% | 99.84% | 99.78% |

FIGURE 121

Hek3- 5'-GGCCCA GA CTGA GCA CGTGATGG-3'
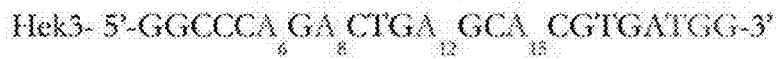

| HEK3 pNMG-370 | | 6 A | 8 A | 12 A | 15 A |
|---|---|---|---|---|---|
| | A | 98.94% | 97.52% | 99.94% | 99.97% |
| | C | 0.01% | 0.01% | 0.01% | 0.02% |
| | G | 1.04% | 2.46% | 0.04% | 0.01% |
| | T | 0.00% | 0.01% | 0.00% | 0.00% |

| HEK3 pNMG-371 | | 6 A | 8 A | 12 A | 15 A |
|---|---|---|---|---|---|
| | A | 98.05% | 95.74% | 99.97% | 99.99% |
| | C | 0.00% | 0.00% | 0.00% | 0.00% |
| | G | 1.95% | 4.25% | 0.03% | 0.01% |
| | T | 0.00% | 0.00% | 0.00% | 0.00% |

| HEK3 pNMG-382 | | 6 A | 8 A | 12 A | 15 A |
|---|---|---|---|---|---|
| | A | 99.39% | 97.01% | 99.93% | 99.99% |
| | C | 0.01% | 0.01% | 0.01% | 0.01% |
| | G | 0.60% | 2.98% | 0.05% | 0.00% |
| | T | 0.00% | 0.00% | 0.00% | 0.00% |

| HEK3 pNMG-383 | | 6 A | 8 A | 12 A | 15 A |
|---|---|---|---|---|---|
| | A | 99.49% | 97.31% | 99.95% | 99.99% |
| | C | 0.00% | 0.00% | 0.00% | 0.00% |
| | G | 0.50% | 2.68% | 0.04% | 0.01% |
| | T | 0.01% | 0.00% | 0.00% | 0.00% |

| HEK3 pNMG-384 | | 6 A | 8 A | 12 A | 15 A |
|---|---|---|---|---|---|
| | A | 99.70% | 98.13% | 99.96% | 99.98% |
| | C | 0.01% | 0.01% | 0.01% | 0.01% |
| | G | 0.28% | 1.83% | 0.03% | 0.01% |
| | T | 0.01% | 0.01% | 0.00% | 0.00% |

| HEK3 pNMG-385 | | 6 A | 8 A | 12 A | 15 A |
|---|---|---|---|---|---|
| | A | 99.75% | 98.93% | 99.96% | 99.99% |
| | C | 0.00% | 0.00% | 0.00% | 0.00% |
| | G | 0.25% | 1.06% | 0.02% | 0.01% |
| | T | 0.01% | 0.01% | 0.00% | 0.00% |

| HEK3 pNMG-385 | | 6 A | 8 A | 12 A | 15 A |
|---|---|---|---|---|---|
| | A | 99.75% | 98.93% | 99.96% | 99.99% |
| | C | 0.00% | 0.00% | 0.00% | 0.00% |
| | G | 0.25% | 1.06% | 0.02% | 0.01% |
| | T | 0.01% | 0.01% | 0.00% | 0.00% |

| HEK3 pNMG-386 | | 6 A | 8 A | 12 A | 15 A |
|---|---|---|---|---|---|
| | A | 99.55% | 97.94% | 99.94% | 99.96% |
| | C | 0.03% | 0.02% | 0.03% | 0.03% |
| | G | 0.41% | 2.04% | 0.03% | 0.01% |
| | T | 0.00% | 0.00% | 0.00% | 0.01% |

| HEK3 pNMG-387 | | 6 A | 8 A | 12 A | 15 A |
|---|---|---|---|---|---|
| | A | 99.64% | 97.14% | 99.95% | 99.98% |
| | C | 0.00% | 0.00% | 0.01% | 0.00% |
| | G | 0.36% | 2.86% | 0.04% | 0.01% |
| | T | 0.00% | 0.01% | 0.00% | 0.01% |

| HEK3 pNMG-388 | | 6 A | 8 A | 12 A | 15 A |
|---|---|---|---|---|---|
| | A | 99.39% | 97.54% | 99.94% | 99.98% |
| | C | 0.00% | 0.00% | 0.00% | 0.00% |
| | G | 0.59% | 2.45% | 0.05% | 0.01% |
| | T | 0.01% | 0.01% | 0.00% | 0.01% |

| HEK3 pNMG-389 | | 6 A | 8 A | 12 A | 15 A |
|---|---|---|---|---|---|
| | A | 99.53% | 97.35% | 99.96% | 99.98% |
| | C | 0.01% | 0.00% | 0.00% | 0.00% |
| | G | 0.46% | 2.63% | 0.03% | 0.01% |
| | T | 0.01% | 0.01% | 0.00% | 0.01% |

FIGURE 122

FANCF- 5'-GGA$_3$ A$_4$ TCCCTTCTGCA$_{15}$ GCA$_{18}$ CCTGG-3'

| FANCF pNMG-370 | | 3 A | 4 A | 15 A | 18 A |
|---|---|---|---|---|---|
| | A | 99.93% | 99.40% | 99.98% | 99.98% |
| | C | 0.00% | 0.00% | 0.00% | 0.00% |
| | G | 0.06% | 0.60% | 0.01% | 0.01% |
| | T | 0.01% | 0.00% | 0.00% | 0.00% |

| FANCF pNMG-371 | | 3 A | 4 A | 15 A | 18 A |
|---|---|---|---|---|---|
| | A | 99.67% | 97.88% | 99.98% | 99.98% |
| | C | 0.00% | 0.00% | 0.00% | 0.00% |
| | G | 0.32% | 2.11% | 0.01% | 0.01% |
| | T | 0.01% | 0.00% | 0.00% | 0.01% |

| FANCF pNMG-382 | | 3 A | 4 A | 15 A | 18 A |
|---|---|---|---|---|---|
| | A | 99.93% | 99.69% | 99.98% | 99.98% |
| | C | 0.00% | 0.00% | 0.00% | 0.00% |
| | G | 0.06% | 0.30% | 0.01% | 0.00% |
| | T | 0.00% | 0.01% | 0.00% | 0.01% |

| FANCF pNMG-383 | | 3 A | 4 A | 15 A | 18 A |
|---|---|---|---|---|---|
| | A | 99.94% | 99.76% | 99.98% | 99.98% |
| | C | 0.00% | 0.00% | 0.00% | 0.00% |
| | G | 0.05% | 0.23% | 0.02% | 0.01% |
| | T | 0.00% | 0.00% | 0.00% | 0.01% |

| FANCF pNMG-384 | | 3 A | 4 A | 15 A | 18 A |
|---|---|---|---|---|---|
| | A | 99.93% | 99.83% | 99.98% | 99.98% |
| | C | 0.00% | 0.00% | 0.00% | 0.00% |
| | G | 0.06% | 0.16% | 0.01% | 0.00% |
| | T | 0.01% | 0.01% | 0.00% | 0.01% |

| FANCF pNMG-385 | | 3 A | 4 A | 15 A | 18 A |
|---|---|---|---|---|---|
| | A | 99.94% | 99.82% | 99.99% | 99.98% |
| | C | 0.00% | 0.00% | 0.00% | 0.00% |
| | G | 0.04% | 0.17% | 0.00% | 0.00% |
| | T | 0.02% | 0.01% | 0.00% | 0.01% |

| FANCF pNMG-386 | | 3 A | 4 A | 15 A | 18 A |
|---|---|---|---|---|---|
| | A | 99.94% | 99.82% | 99.98% | 99.98% |
| | C | 0.00% | 0.00% | 0.00% | 0.00% |
| | G | 0.05% | 0.17% | 0.01% | 0.00% |
| | T | 0.01% | 0.01% | 0.00% | 0.01% |

| FANCF pNMG-387 | | 3 A | 4 A | 15 A | 18 A |
|---|---|---|---|---|---|
| | A | 99.94% | 99.74% | 99.98% | 99.98% |
| | C | 0.00% | 0.00% | 0.00% | 0.00% |
| | G | 0.05% | 0.25% | 0.01% | 0.01% |
| | T | 0.01% | 0.00% | 0.00% | 0.00% |

| FANCF pNMG-388 | | 3 A | 4 A | 15 A | 18 A |
|---|---|---|---|---|---|
| | A | 99.98% | 99.69% | 99.98% | 99.98% |
| | C | 0.00% | 0.00% | 0.00% | 0.00% |
| | G | 0.05% | 0.31% | 0.01% | 0.01% |
| | T | 0.01% | 0.00% | 0.00% | 0.01% |

| FANCF pNMG-389 | | 3 A | 4 A | 15 A | 18 A |
|---|---|---|---|---|---|
| | A | 99.92% | 99.85% | 99.98% | 99.98% |
| | C | 0.00% | 0.00% | 0.00% | 0.00% |
| | G | 0.08% | 0.14% | 0.01% | 0.00% |
| | T | 0.00% | 0.00% | 0.00% | 0.01% |

| Site | Protospacer and PAM sequence | pNMG370 | pNMG371 | pNMG382-389 | | | | | | |
|---|---|---|---|---|---|---|---|---|---|---|
| HEK2 | GAACACAAAGCATAGACTGCTGG | 54.0 | 65.4 | 48.4 | 52.9 | 44.6 | 40.3 | 41.0 | 44.8 | 43.6 | 40.6 |
| HEK2-2 | GAATACTAAGCATAGACTCCAGG | 29.1 | 50.1 | 24.5 | 23.8 | 21.8 | 11.3 | 20.5 | 21.6 | 23.6 | 23.4 |
| HEK2-3 | GTAAACAAAGCATAGACTGAGGG | 10.4 | 20.1 | 8.2 | 11.0 | 4.7 | 3.5 | 8.0 | 4.2 | 8.5 | 6.2 |
| HEK2-6 | GAAGACCAAGGATAGACTGCTGG | 4.4 | 7.6 | 4.6 | 5.5 | 2.8 | 1.4 | 2.4 | 2.5 | 3.2 | 2.5 |
| HEK2-7 | GAAAACAAATCATTGACTGCAGG | 0.3 | 0.7 | 0.3 | 0.2 | 0.1 | 0.1 | 0.1 | 0.1 | 0.4 | 0.3 |
| HEK2-10 | GAACATAAAGAATAGAATGATGG | 6.3 | 21.4 | 3.6 | 6.3 | 4.6 | 2.0 | 4.2 | 4.1 | 5.5 | 4.0 |

FIGURE 126C 128 ug/mL chloramphenicol (7h):

| position: | 36 | 37 | 47 | 48 | 49 | 51 | 69 | 70 | 72 | 77 | 84 | 106 | 108 | 123 | 134 | 146 | 147 | 154 | 155 | 156 | 157 | 159 | 160 | 161 | 163 |
|---|---|---|---|---|---|---|---|---|---|---|---|---|---|---|---|---|---|---|---|---|---|---|---|---|---|
| wt res: | His | Asn | Arg | Pro | Ile | Arg | Val | Met | Asn | Asp | Leu | Ala | Asp | His | Glu | Ser | Asp | Gln | Glu | Ile | Lys | Ala | Lys | Lys | Gln |
| 1 | | | | | | Leu | | | | | Phe | Val | Asn | Tyr | | | Tyr | | Val | Phe | | | | | |
| 2 | | Thr | | | | | | | | | Phe | Val | Asn | Tyr | | | Tyr | | Val | Phe | | | | | |
| 3 | | | | Thr | Val | | | Leu | | | Phe | Val | Asn | Tyr | | Arg | Tyr | | Val | Phe | | | | | |
| 4 | | | | Thr | Val | | | Leu | | | Phe | Val | Asn | Tyr | | Cys | Tyr | | Val | Phe | | | | | |
| 5 | | | | | | | | | | | Phe | Val | Asn | Tyr | | Arg | Tyr | | Val | Phe | | | | | |
| 2 | | | | | | Leu | | | | | Phe | Val | Asn | Tyr | | | Tyr | | Val | Phe | | | | Thr | |
| 3 | | | | | | | | | | Gly | Phe | Val | Asn | Tyr | | | | His | Val | Phe | | | | | | evolution #1
evolution #2
evolution #3

FIGURE 126D 128 ug/mL chloramphenicol + 128 ug/mL spectinomycin (overnight):

| position: | 36 | 37 | 47 | 48 | 49 | 51 | 69 | 70 | 72 | 77 | 84 | 106 | 108 | 123 | 134 | 146 | 147 | 154 | 155 | 156 | 157 | 159 | 160 | 161 | 163 |
|---|---|---|---|---|---|---|---|---|---|---|---|---|---|---|---|---|---|---|---|---|---|---|---|---|---|
| wt res: | His | Asn | Arg | Pro | Ile | Arg | Val | Met | Asn | Asp | Leu | Ala | Asp | His | Glu | Ser | Asp | Gln | Glu | Ile | Lys | Ala | Lys | Lys | Gln |
| 1 | | | | | | | | | | | Phe | Val | Asn | Tyr | | | Tyr | | Val | Phe | | | | | |
| 2 | | | | | | | | Thr | | | Phe | Val | Asn | Tyr | | | Tyr | | Val | Phe | | | | | | evolution #1
evolution #2
evolution #3

| position | 36 | 37 | 47 | 48 | 49 | 51 | 70 | 72 | 77 | 84 | 106 | 108 | 123 | 134 | 145 | 147 | 154 | 155 | 156 | 157 | 161 | position | # | mammalian vector | bacterial vector |
|---|---|---|---|---|---|---|---|---|---|---|---|---|---|---|---|---|---|---|---|---|---|---|---|---|---|
| w.res. | His | Asn | Arg | Pro | Ile | Arg | Met | Asn | Asp | Leu | Ala | Asp | His | Glu | Ser | Asp | Gln | Glu | Ile | Lys | Lys | | | | |
| 1 | | | | | | | | | | | | | | | | | | | | | | | | | |
| 2 | | Phe | | Thr | Val | | Leu | | | Phe | Val | Asn | Thr | | | | | | Phe | | | plate 1, E11 | 85 | pNMG-392 | pNMG-413 |
| 3 | | Phe | | Leu | | | | | | Phe | Val | Asn | Thr | | Ala | | | | Phe | | Thr | plate 1, B11 | 82 | pNMG-393 | pNMG-414 |
| 4 | | | | | | | | Ser | | Phe | Val | Asn | Tyr | | | His | | Val | Phe | | | plate 1, H5 | 40 | pNMG-394 | pNMG-415 |
| 5 | | | | Leu | | | | | | Phe | Val | Asn | Tyr | Gly | | | | | Phe | | | plate 1, G10 | 79 | pNMG-395 | pNMG-416 |
| 6 | | Phe | | | | | | | | Phe | Val | Asn | Thr | | | Thr | | Val | Phe | Asn | | plate 2, H11 | 88 | pNMG-396 | n/a |
| 7 | | | | | | His | | | | Phe | Val | Asn | Thr | | | | | | Phe | | | plate 1, G1 | 7 | pNMG-397 | pNMG-417 |
| 8 | | | | | | Ile | | | | Phe | Val | Asn | Thr | | Gly | Thr | | | Phe | | | plate 1, H3 | 24 | pNMG-398 | pNMG-418 |
| 9 | | Phe | | | | | | | Gly | Phe | Val | Asn | Tyr | | | Thr | | Val | Phe | | Thr | plate 1, G3 | 23 | pNMG-399 | pNMG-419 |
| 10 | | | | | | | | | | Phe | Val | Asn | Tyr | | | Thr | | Val | Phe | Asn | | plate 1, D2 | 12 | pNMG-400 | pNMG-420 |
| 11 | | Phe | | | | | | | | Phe | Val | Asn | Tyr | Gly | | Thr | | Val | Phe | Asn | | plate 1, F3 | 22 | pNMG-401 | pNMG-421 |
| | | | | | | | | | | | | | | | | | | | | | | plate 2, G10 | 79 | n/a | pNMG-422 | evolution #1
evolution #2
evolution #3
evolution #5

FIGURE 129

Hek-2 site: 5'-GA$_2$A$_3$CA$_5$CA$_7$A$_8$A$_9$GCA$_{12}$TA$_{14}$GA$_{16}$CTGCGGG-3'

| HEK2 pNMG-339 | | 2 | 3 | 5 | 7 | 8 | 9 | 12 | 14 | 16 |
|---|---|---|---|---|---|---|---|---|---|---|
| | | A | A | A | A | A | A | A | A | A |
| | A | 99.8% | 95.9% | 34.1% | 98.4% | 98.5% | 99.3% | 99.9% | 100.0% | 100.0% |
| | C | 0.0% | 0.0% | 0.0% | 0.0% | 0.0% | 0.0% | 0.0% | 0.0% | 0.0% |
| | G | 0.2% | 4.1% | 65.9% | 1.6% | 1.5% | 0.7% | 0.0% | 0.0% | 0.0% |
| | T | 0.0% | 0.0% | 0.0% | 0.0% | 0.0% | 0.0% | 0.0% | 0.0% | 0.0% |

| HEK2 pNMG-340 | | 2 | 3 | 5 | 7 | 8 | 9 | 12 | 14 | 16 |
|---|---|---|---|---|---|---|---|---|---|---|
| | | A | A | A | A | A | A | A | A | A |
| | A | 99.89% | 97.88% | 34.81% | 99.43% | 98.98% | 99.54% | 99.98% | 99.99% | 99.99% |
| | C | 0.00% | 0.00% | 0.00% | 0.00% | 0.00% | 0.00% | 0.00% | 0.00% | 0.00% |
| | G | 0.10% | 2.12% | 65.18% | 0.56% | 1.02% | 0.45% | 0.01% | 0.01% | 0.01% |
| | T | 0.00% | 0.00% | 0.01% | 0.00% | 0.01% | 0.00% | 0.00% | 0.00% | 0.00% |

| HEK2 pNMG-341 | | 2 | 3 | 5 | 7 | 8 | 9 | 12 | 14 | 16 |
|---|---|---|---|---|---|---|---|---|---|---|
| | | A | A | A | A | A | A | A | A | A |
| | A | 99.80% | 94.79% | 29.76% | 98.16% | 98.08% | 99.02% | 99.92% | 99.98% | 99.99% |
| | C | 0.00% | 0.01% | 0.00% | 0.00% | 0.00% | 0.00% | 0.00% | 0.00% | 0.00% |
| | G | 0.19% | 5.19% | 70.23% | 1.84% | 1.91% | 0.98% | 0.07% | 0.02% | 0.01% |
| | T | 0.00% | 0.01% | 0.01% | 0.00% | 0.00% | 0.00% | 0.00% | 0.01% | 0.00% |

| HEK2 pNMG-346 | | 2 | 3 | 5 | 7 | 8 | 9 | 12 | 14 | 16 |
|---|---|---|---|---|---|---|---|---|---|---|
| | | A | A | A | A | A | A | A | A | A |
| | A | 99.97% | 99.89% | 93.08% | 99.94% | 99.98% | 99.89% | 99.99% | 99.98% | 99.99% |
| | C | 0.00% | 0.01% | 0.00% | 0.00% | 0.00% | 0.00% | 0.00% | 0.00% | 0.00% |
| | G | 0.02% | 0.10% | 6.91% | 0.04% | 0.01% | 0.10% | 0.01% | 0.01% | 0.01% |
| | T | 0.00% | 0.00% | 0.01% | 0.02% | 0.01% | 0.00% | 0.01% | 0.00% | 0.00% |

| HEK2 pNMG-347 | | 2 | 3 | 5 | 7 | 8 | 9 | 12 | 14 | 16 |
|---|---|---|---|---|---|---|---|---|---|---|
| | | A | A | A | A | A | A | A | A | A |
| | A | 99.97% | 99.68% | 87.50% | 99.89% | 99.86% | 99.74% | 99.99% | 99.99% | 99.99% |
| | C | 0.00% | 0.01% | 0.00% | 0.00% | 0.00% | 0.00% | 0.00% | 0.00% | 0.00% |
| | G | 0.03% | 0.31% | 12.49% | 0.11% | 0.13% | 0.26% | 0.01% | 0.01% | 0.01% |
| | T | 0.01% | 0.00% | 0.01% | 0.00% | 0.00% | 0.00% | 0.01% | 0.00% | 0.00% |

| HEK2 pNMG-348 | | 2 | 3 | 5 | 7 | 8 | 9 | 12 | 14 | 16 |
|---|---|---|---|---|---|---|---|---|---|---|
| | | A | A | A | A | A | A | A | A | A |
| | A | 99.98% | 99.72% | 84.68% | 99.93% | 99.93% | 99.90% | 99.92% | 99.96% | 99.99% |
| | C | 0.00% | 0.00% | 0.00% | 0.00% | 0.00% | 0.00% | 0.00% | 0.00% | 0.00% |
| | G | 0.01% | 0.27% | 15.31% | 0.06% | 0.06% | 0.10% | 0.07% | 0.02% | 0.01% |
| | T | 0.00% | 0.01% | 0.01% | 0.00% | 0.00% | 0.00% | 0.00% | 0.01% | 0.00% |

| HEK2 pNMG-349 | | 2 | 3 | 5 | 7 | 8 | 9 | 12 | 14 | 16 |
|---|---|---|---|---|---|---|---|---|---|---|
| | | A | A | A | A | A | A | A | A | A |
| | A | 99.98% | 99.71% | 85.59% | 99.94% | 99.84% | 99.92% | 99.97% | 99.97% | 99.99% |
| | C | 0.00% | 0.00% | 0.00% | 0.00% | 0.00% | 0.00% | 0.00% | 0.00% | 0.00% |
| | G | 0.02% | 0.28% | 14.40% | 0.05% | 0.15% | 0.07% | 0.02% | 0.02% | 0.01% |
| | T | 0.00% | 0.00% | 0.01% | 0.00% | 0.01% | 0.00% | 0.01% | 0.01% | 0.00% |

FIGURE 130

Hek 2-1 site: 5'-GA$_2$A$_3$A$_4$A$_5$A$_6$A$_7$A$_8$A$_9$GCA$_{12}$GA$_{14}$GACTGCTGG-3'

| HEK2-1 pNMG-339 | | 2 | 3 | 4 | 5 | 6 | 7 | 8 | 9 | 12 | 14 |
|---|---|---|---|---|---|---|---|---|---|---|---|
| | | A | A | A | A | A | A | A | A | A | A |
| | A | 99.99% | 99.99% | 99.97% | 99.90% | 99.97% | 99.98% | 99.98% | 99.97% | 99.97% | 99.99% |
| | C | 0.00% | 0.00% | 0.00% | 0.00% | 0.00% | 0.00% | 0.00% | 0.00% | 0.00% | 0.00% |
| | G | 0.01% | 0.01% | 0.03% | 0.10% | 0.03% | 0.01% | 0.01% | 0.02% | 0.02% | 0.01% |
| | T | 0.00% | 0.00% | 0.00% | 0.00% | 0.00% | 0.00% | 0.01% | 0.00% | 0.01% | 0.01% |

| HEK2-1 pNMG-340 | | 2 | 3 | 4 | 5 | 6 | 7 | 8 | 9 | 12 | 14 |
|---|---|---|---|---|---|---|---|---|---|---|---|
| | | A | A | A | A | A | A | A | A | A | A |
| | A | 99.99% | 99.99% | 99.98% | 99.88% | 99.96% | 99.99% | 99.99% | 99.97% | 99.98% | 99.99% |
| | C | 0.00% | 0.00% | 0.00% | 0.00% | 0.00% | 0.00% | 0.00% | 0.00% | 0.00% | 0.00% |
| | G | 0.01% | 0.01% | 0.01% | 0.11% | 0.02% | 0.01% | 0.01% | 0.03% | 0.01% | 0.01% |
| | T | 0.00% | 0.00% | 0.00% | 0.00% | 0.00% | 0.00% | 0.01% | 0.00% | 0.01% | 0.01% |

| HEK2-1 pNMG-341 | | 2 | 3 | 4 | 5 | 6 | 7 | 8 | 9 | 12 | 14 |
|---|---|---|---|---|---|---|---|---|---|---|---|
| | | A | A | A | A | A | A | A | A | A | A |
| | A | 99.98% | 99.99% | 99.94% | 99.78% | 99.93% | 99.98% | 99.98% | 99.98% | 99.98% | 99.99% |
| | C | 0.00% | 0.00% | 0.00% | 0.00% | 0.00% | 0.00% | 0.00% | 0.00% | 0.00% | 0.00% |
| | G | 0.01% | 0.01% | 0.05% | 0.22% | 0.07% | 0.01% | 0.01% | 0.02% | 0.01% | 0.01% |
| | T | 0.01% | 0.00% | 0.00% | 0.00% | 0.00% | 0.00% | 0.00% | 0.00% | 0.01% | 0.01% |

| HEK2-1 pNMG-346 | | 2 | 3 | 4 | 5 | 6 | 7 | 8 | 9 | 12 | 14 |
|---|---|---|---|---|---|---|---|---|---|---|---|
| | | A | A | A | A | A | A | A | A | A | A |
| | A | 99.99% | 99.99% | 99.99% | 99.99% | 99.99% | 99.99% | 99.97% | 99.98% | 99.98% | 99.99% |
| | C | 0.00% | 0.00% | 0.00% | 0.00% | 0.00% | 0.00% | 0.00% | 0.00% | 0.00% | 0.00% |
| | G | 0.01% | 0.01% | 0.00% | 0.01% | 0.01% | 0.01% | 0.01% | 0.02% | 0.01% | 0.01% |
| | T | 0.00% | 0.00% | 0.00% | 0.00% | 0.00% | 0.00% | 0.01% | 0.00% | 0.01% | 0.01% |

| HEK2-1 pNMG-347 | | 2 | 3 | 4 | 5 | 6 | 7 | 8 | 9 | 12 | 14 |
|---|---|---|---|---|---|---|---|---|---|---|---|
| | | A | A | A | A | A | A | A | A | A | A |
| | A | 99.99% | 99.99% | 99.99% | 99.98% | 99.99% | 99.99% | 99.99% | 99.98% | 99.97% | 99.99% |
| | C | 0.00% | 0.00% | 0.00% | 0.00% | 0.00% | 0.00% | 0.00% | 0.00% | 0.00% | 0.00% |
| | G | 0.01% | 0.00% | 0.01% | 0.02% | 0.01% | 0.00% | 0.01% | 0.02% | 0.02% | 0.01% |
| | T | 0.00% | 0.00% | 0.00% | 0.00% | 0.00% | 0.00% | 0.00% | 0.00% | 0.01% | 0.01% |

| HEK2-1 pNMG-348 | | 2 | 3 | 4 | 5 | 6 | 7 | 8 | 9 | 12 | 14 |
|---|---|---|---|---|---|---|---|---|---|---|---|
| | | A | A | A | A | A | A | A | A | A | A |
| | A | 99.99% | 99.99% | 99.99% | 99.99% | 99.99% | 99.99% | 99.99% | 99.98% | 99.98% | 99.99% |
| | C | 0.00% | 0.00% | 0.00% | 0.00% | 0.00% | 0.00% | 0.00% | 0.00% | 0.00% | 0.00% |
| | G | 0.00% | 0.01% | 0.01% | 0.01% | 0.00% | 0.01% | 0.01% | 0.02% | 0.01% | 0.01% |
| | T | 0.00% | 0.00% | 0.00% | 0.00% | 0.00% | 0.00% | 0.00% | 0.00% | 0.01% | 0.01% |

| HEK2-1 pNMG-349 | | 2 | 3 | 4 | 5 | 6 | 7 | 8 | 9 | 12 | 14 |
|---|---|---|---|---|---|---|---|---|---|---|---|
| | | A | A | A | A | A | A | A | A | A | A |
| | A | 99.99% | 99.99% | 100.00% | 99.98% | 99.99% | 99.99% | 99.99% | 99.98% | 99.97% | 99.99% |
| | C | 0.00% | 0.00% | 0.00% | 0.00% | 0.00% | 0.00% | 0.00% | 0.00% | 0.00% | 0.00% |
| | G | 0.00% | 0.01% | 0.00% | 0.01% | 0.01% | 0.01% | 0.01% | 0.02% | 0.02% | 0.01% |
| | T | 0.00% | 0.00% | 0.00% | 0.00% | 0.00% | 0.00% | 0.00% | 0.00% | 0.01% | 0.01% |

FIGURE 131

Hek 2-2 site: 5'-GA$_2$A$_3$TA$_5$CTA$_8$A$_9$GCA$_{12}$TA$_{14}$GA$_{16}$CTCCAGG-3'

| HEK2-2 pNMG-339 | | 2 | 3 | 5 | 8 | 9 | 12 | 14 | 16 |
|---|---|---|---|---|---|---|---|---|---|
| | | A | A | A | A | A | A | A | A |
| | A | 99.63% | 99.44% | 56.56% | 99.54% | 99.65% | 99.97% | 99.97% | 99.97% |
| | C | 0.00% | 0.00% | 0.00% | 0.00% | 0.00% | 0.00% | 0.00% | 0.00% |
| | G | 0.36% | 0.55% | 43.44% | 0.45% | 0.35% | 0.01% | 0.01% | 0.01% |
| | T | 0.01% | 0.00% | 0.01% | 0.01% | 0.00% | 0.01% | 0.01% | 0.01% |

| HEK2-2 pNMG-340 | | 2 | 3 | 5 | 8 | 9 | 12 | 14 | 16 |
|---|---|---|---|---|---|---|---|---|---|
| | | A | A | A | A | A | A | A | A |
| | A | 99.84% | 99.83% | 86.30% | 99.59% | 99.91% | 99.98% | 99.97% | 99.97% |
| | C | 0.00% | 0.00% | 0.00% | 0.00% | 0.00% | 0.00% | 0.00% | 0.00% |
| | G | 0.15% | 0.16% | 13.68% | 0.40% | 0.09% | 0.01% | 0.01% | 0.01% |
| | T | 0.00% | 0.01% | 0.02% | 0.00% | 0.00% | 0.01% | 0.01% | 0.01% |

| HEK2-2 pNMG-341 | | 2 | 3 | 5 | 8 | 9 | 12 | 14 | 16 |
|---|---|---|---|---|---|---|---|---|---|
| | | A | A | A | A | A | A | A | A |
| | A | 99.56% | 99.29% | 52.56% | 99.35% | 99.60% | 99.95% | 99.97% | 99.97% |
| | C | 0.00% | 0.00% | 0.00% | 0.00% | 0.00% | 0.00% | 0.00% | 0.00% |
| | G | 0.42% | 0.70% | 47.42% | 0.64% | 0.40% | 0.03% | 0.01% | 0.01% |
| | T | 0.01% | 0.00% | 0.01% | 0.01% | 0.00% | 0.02% | 0.01% | 0.01% |

| HEK2-2 pNMG-346 | | 2 | 3 | 5 | 8 | 9 | 12 | 14 | 16 |
|---|---|---|---|---|---|---|---|---|---|
| | | A | A | A | A | A | A | A | A |
| | A | 99.99% | 99.98% | 90.56% | 99.94% | 99.99% | 99.98% | 99.97% | 99.97% |
| | C | 0.00% | 0.00% | 0.00% | 0.00% | 0.00% | 0.00% | 0.00% | 0.00% |
| | G | 0.00% | 0.02% | 9.40% | 0.05% | 0.02% | 0.01% | 0.01% | 0.01% |
| | T | 0.01% | 0.00% | 0.02% | 0.01% | 0.01% | 0.01% | 0.01% | 0.01% |

| HEK2-2 pNMG-347 | | 2 | 3 | 5 | 8 | 9 | 12 | 14 | 16 |
|---|---|---|---|---|---|---|---|---|---|
| | | A | A | A | A | A | A | A | A |
| | A | 99.99% | 99.96% | 84.82% | 99.93% | 99.97% | 99.97% | 99.97% | 99.97% |
| | C | 0.00% | 0.00% | 0.00% | 0.00% | 0.00% | 0.00% | 0.00% | 0.00% |
| | G | 0.01% | 0.03% | 15.16% | 0.06% | 0.03% | 0.01% | 0.01% | 0.01% |
| | T | 0.01% | 0.00% | 0.01% | 0.00% | 0.00% | 0.02% | 0.01% | 0.01% |

| HEK2-2 pNMG-348 | | 2 | 3 | 5 | 8 | 9 | 12 | 14 | 16 |
|---|---|---|---|---|---|---|---|---|---|
| | | A | A | A | A | A | A | A | A |
| | A | 99.98% | 99.93% | 85.38% | 99.91% | 99.96% | 99.97% | 99.97% | 99.97% |
| | C | 0.00% | 0.00% | 0.00% | 0.00% | 0.00% | 0.00% | 0.00% | 0.00% |
| | G | 0.01% | 0.07% | 14.61% | 0.08% | 0.02% | 0.01% | 0.01% | 0.01% |
| | T | 0.01% | 0.00% | 0.02% | 0.01% | 0.02% | 0.02% | 0.01% | 0.01% |

| HEK2-2 pNMG-349 | | 2 | 3 | 5 | 8 | 9 | 12 | 14 | 16 |
|---|---|---|---|---|---|---|---|---|---|
| | | A | A | A | A | A | A | A | A |
| | A | 99.98% | 99.95% | 86.93% | 99.92% | 99.99% | 99.97% | 99.97% | 99.97% |
| | C | 0.00% | 0.00% | 0.00% | 0.00% | 0.00% | 0.00% | 0.00% | 0.00% |
| | G | 0.01% | 0.05% | 13.06% | 0.07% | 0.01% | 0.01% | 0.01% | 0.01% |
| | T | 0.01% | 0.01% | 0.01% | 0.01% | 0.00% | 0.02% | 0.01% | 0.01% |

FIGURE 132

Hek 2-3 site: 5'-GTA₃A₄A₅CA₇A₈A₉GCA₁₂TA₁₄GA₁₆CTGAGGG-3'

| HEK2-3 pNMG-339 | | 3 A | 4 A | 5 A | 7 A | 8 A | 9 A | 12 A | 14 A | 16 A |
|---|---|---|---|---|---|---|---|---|---|---|
| | A | 99.98% | 99.98% | 99.43% | 99.98% | 99.97% | 99.98% | 99.97% | 99.97% | 99.97% |
| | C | 0.00% | 0.00% | 0.00% | 0.00% | 0.00% | 0.00% | 0.00% | 0.00% | 0.00% |
| | G | 0.01% | 0.02% | 0.56% | 0.01% | 0.01% | 0.01% | 0.01% | 0.01% | 0.01% |
| | T | 0.01% | 0.00% | 0.01% | 0.00% | 0.01% | 0.01% | 0.01% | 0.01% | 0.01% |

| HEK2-3 pNMG-340 | | 3 A | 4 A | 5 A | 7 A | 8 A | 9 A | 12 A | 14 A | 16 A |
|---|---|---|---|---|---|---|---|---|---|---|
| | A | 99.97% | 99.96% | 99.02% | 99.96% | 99.97% | 99.76% | 99.96% | 99.97% | 99.97% |
| | C | 0.00% | 0.00% | 0.00% | 0.00% | 0.00% | 0.19% | 0.00% | 0.00% | 0.00% |
| | G | 0.03% | 0.03% | 0.97% | 0.03% | 0.03% | 0.05% | 0.02% | 0.01% | 0.01% |
| | T | 0.01% | 0.01% | 0.01% | 0.01% | 0.00% | 0.00% | 0.02% | 0.01% | 0.01% |

| HEK2-3 pNMG-341 | | 3 A | 4 A | 5 A | 7 A | 8 A | 9 A | 12 A | 14 A | 16 A |
|---|---|---|---|---|---|---|---|---|---|---|
| | A | 99.97% | 99.95% | 98.56% | 99.97% | 99.97% | 99.79% | 99.96% | 99.97% | 99.97% |
| | C | 0.00% | 0.00% | 0.00% | 0.00% | 0.00% | 0.19% | 0.00% | 0.00% | 0.00% |
| | G | 0.02% | 0.05% | 1.42% | 0.01% | 0.02% | 0.02% | 0.02% | 0.01% | 0.01% |
| | T | 0.01% | 0.01% | 0.01% | 0.01% | 0.01% | 0.00% | 0.02% | 0.01% | 0.01% |

FIGURE 133

Hek 2-4 site: 5'-GGA₃CA₅CA₇A₈A₉GCTTA₁₄GA₁₆CTCCAGG-3'

| HEK2-4 pNMG-339 | | 3 A | 5 A | 7 A | 8 A | 9 A | 14 A | 16 A |
|---|---|---|---|---|---|---|---|---|
| | A | 95.12% | 75.77% | 99.50% | 99.35% | 99.67% | 99.98% | 99.98% |
| | C | 0.00% | 0.01% | 0.00% | 0.00% | 0.00% | 0.00% | 0.00% |
| | G | 4.87% | 24.21% | 0.49% | 0.64% | 0.32% | 0.01% | 0.01% |
| | T | 0.01% | 0.01% | 0.01% | 0.01% | 0.00% | 0.00% | 0.00% |

| HEK2-4 pNMG-340 | | 3 A | 5 A | 7 A | 8 A | 9 A | 14 A | 16 A |
|---|---|---|---|---|---|---|---|---|
| | A | 97.41% | 84.81% | 99.76% | 99.67% | 99.82% | 99.98% | 99.98% |
| | C | 0.00% | 0.00% | 0.00% | 0.00% | 0.00% | 0.00% | 0.00% |
| | G | 2.58% | 15.17% | 0.23% | 0.32% | 0.17% | 0.02% | 0.01% |
| | T | 0.01% | 0.01% | 0.01% | 0.00% | 0.00% | 0.00% | 0.00% |

| HEK2-4 pNMG-341 | | 3 A | 5 A | 7 A | 8 A | 9 A | 14 A | 16 A |
|---|---|---|---|---|---|---|---|---|
| | A | 93.73% | 64.91% | 99.34% | 99.22% | 99.69% | 99.98% | 99.98% |
| | C | 0.00% | 0.02% | 0.00% | 0.00% | 0.00% | 0.00% | 0.00% |
| | G | 6.26% | 35.06% | 0.65% | 0.78% | 0.30% | 0.02% | 0.01% |
| | T | 0.01% | 0.01% | 0.01% | 0.00% | 0.00% | 0.00% | 0.00% |

FIGURE 134

Hek2-6 similar: 5'-GA$_2$A$_3$GA$_5$CCA$_8$A$_9$GGATAGACTGCTGG-3'

| HEK2-6 pNMG-339 | 2 A | 3 A | 5 A | 8 A | 9 A | 12 A | 14 A |
|---|---|---|---|---|---|---|---|
| A | 99.94% | 99.86% | 95.56% | 99.74% | 99.90% | 99.97% | 99.98% |
| C | 0.00% | 0.01% | 0.00% | 0.00% | 0.00% | 0.00% | 0.00% |
| G | 0.04% | 0.12% | 4.43% | 0.24% | 0.08% | 0.01% | 0.01% |
| T | 0.01% | 0.01% | 0.01% | 0.02% | 0.01% | 0.02% | 0.00% |

| HEK2-6 pNMG-340 | 2 A | 3 A | 5 A | 8 A | 9 A | 12 A | 14 A |
|---|---|---|---|---|---|---|---|
| A | 99.97% | 99.97% | 95.74% | 99.81% | 99.90% | 99.98% | 99.98% |
| C | 0.00% | 0.00% | 0.00% | 0.01% | 0.00% | 0.00% | 0.00% |
| G | 0.02% | 0.02% | 4.25% | 0.17% | 0.09% | 0.01% | 0.01% |
| T | 0.01% | 0.00% | 0.02% | 0.01% | 0.01% | 0.01% | 0.00% |

| HEK2-6 pNMG-341 | 2 A | 3 A | 5 A | 8 A | 9 A | 12 A | 14 A |
|---|---|---|---|---|---|---|---|
| A | 99.94% | 99.86% | 95.56% | 99.74% | 99.90% | 99.97% | 99.98% |
| C | 0.00% | 0.01% | 0.00% | 0.00% | 0.00% | 0.00% | 0.00% |
| G | 0.04% | 0.12% | 4.43% | 0.24% | 0.08% | 0.01% | 0.01% |
| T | 0.01% | 0.01% | 0.01% | 0.02% | 0.01% | 0.02% | 0.00% |

| HEK2-6 pNMG-346 | 2 A | 3 A | 5 A | 8 A | 9 A | 12 A | 14 A |
|---|---|---|---|---|---|---|---|
| A | 99.98% | 99.99% | 99.76% | 99.97% | 99.98% | 99.98% | 99.98% |
| C | 0.00% | 0.00% | 0.00% | 0.00% | 0.00% | 0.00% | 0.00% |
| G | 0.01% | 0.00% | 0.23% | 0.02% | 0.01% | 0.00% | 0.01% |
| T | 0.01% | 0.01% | 0.01% | 0.01% | 0.01% | 0.01% | 0.00% |

| HEK2-6 pNMG-347 | 2 A | 3 A | 5 A | 8 A | 9 A | 12 A | 14 A |
|---|---|---|---|---|---|---|---|
| A | 99.95% | 99.97% | 99.62% | 99.97% | 99.95% | 99.97% | 99.98% |
| C | 0.00% | 0.00% | 0.00% | 0.00% | 0.00% | 0.00% | 0.00% |
| G | 0.03% | 0.01% | 0.35% | 0.02% | 0.03% | 0.01% | 0.01% |
| T | 0.02% | 0.01% | 0.02% | 0.00% | 0.02% | 0.02% | 0.00% |

| HEK2-6 pNMG-348 | 2 A | 3 A | 5 A | 8 A | 9 A | 12 A | 14 A |
|---|---|---|---|---|---|---|---|
| A | 99.97% | 99.96% | 99.68% | 99.97% | 99.97% | 99.98% | 99.98% |
| C | 0.00% | 0.00% | 0.00% | 0.00% | 0.00% | 0.00% | 0.00% |
| G | 0.02% | 0.02% | 0.30% | 0.01% | 0.01% | 0.00% | 0.01% |
| T | 0.01% | 0.01% | 0.02% | 0.01% | 0.02% | 0.02% | 0.01% |

| HEK2-6 pNMG-349 | 2 A | 3 A | 5 A | 8 A | 9 A | 12 A | 14 A |
|---|---|---|---|---|---|---|---|
| A | 99.97% | 99.97% | 99.74% | 99.97% | 99.97% | 99.97% | 99.98% |
| C | 0.00% | 0.00% | 0.00% | 0.01% | 0.00% | 0.00% | 0.00% |
| G | 0.02% | 0.01% | 0.25% | 0.01% | 0.02% | 0.01% | 0.01% |
| T | 0.01% | 0.01% | 0.01% | 0.01% | 0.00% | 0.01% | 0.00% |

FIGURE 135

Hek2-9 site: 5'-GA$_2$A$_3$ A$_4$A$_5$CA$_7$A$_8$A$_9$A$_{10}$ CA$_{12}$TA$_{14}$GAGTGCTGG-3'

| HEK2-9 pNMG-339 | | 2 A | 3 A | 4 A | 5 A | 7 A | 8 A | 9 A | 10 A | 12 A | 14 A |
|---|---|---|---|---|---|---|---|---|---|---|---|
| | A | 99.96% | 99.90% | 99.69% | 96.43% | 99.74% | 99.76% | 99.54% | 98.67% | 99.97% | 99.97% |
| | C | 0.00% | 0.00% | 0.03% | 0.00% | 0.01% | 0.00% | 0.00% | 0.00% | 0.00% | 0.01% |
| | G | 0.04% | 0.10% | 0.28% | 3.56% | 0.24% | 0.24% | 0.46% | 1.32% | 0.01% | 0.02% |
| | T | 0.00% | 0.00% | 0.00% | 0.00% | 0.01% | 0.00% | 0.00% | 0.01% | 0.01% | 0.01% |

| HEK2-9 pNMG-340 | | 2 A | 3 A | 4 A | 5 A | 7 A | 8 A | 9 A | 10 A | 12 A | 14 A |
|---|---|---|---|---|---|---|---|---|---|---|---|
| | A | 99.96% | 99.97% | 99.80% | 96.26% | 99.94% | 99.92% | 99.76% | 99.33% | 99.98% | 99.97% |
| | C | 0.00% | 0.00% | 0.03% | 0.01% | 0.00% | 0.00% | 0.00% | 0.01% | 0.00% | 0.01% |
| | G | 0.03% | 0.03% | 0.17% | 3.73% | 0.05% | 0.07% | 0.24% | 0.66% | 0.01% | 0.02% |
| | T | 0.01% | 0.00% | 0.00% | 0.00% | 0.00% | 0.00% | 0.00% | 0.00% | 0.01% | 0.01% |

| HEK2-9 pNMG-341 | | 2 A | 3 A | 4 A | 5 A | 7 A | 8 A | 9 A | 10 A | 12 A | 14 A |
|---|---|---|---|---|---|---|---|---|---|---|---|
| | A | 99.90% | 99.83% | 99.47% | 94.93% | 99.62% | 99.65% | 99.33% | 98.64% | 99.92% | 99.97% |
| | C | 0.00% | 0.00% | 0.02% | 0.01% | 0.00% | 0.00% | 0.00% | 0.00% | 0.00% | 0.01% |
| | G | 0.10% | 0.17% | 0.51% | 5.06% | 0.37% | 0.35% | 0.66% | 1.35% | 0.06% | 0.02% |
| | T | 0.01% | 0.00% | 0.00% | 0.00% | 0.00% | 0.00% | 0.00% | 0.00% | 0.02% | 0.01% |

| HEK2-9 pNMG-346 | | 2 A | 3 A | 4 A | 5 A | 7 A | 8 A | 9 A | 10 A | 12 A | 14 A |
|---|---|---|---|---|---|---|---|---|---|---|---|
| | A | 99.98% | 99.98% | 99.96% | 99.90% | 99.99% | 99.98% | 99.99% | 99.95% | 99.98% | 99.98% |
| | C | 0.00% | 0.00% | 0.03% | 0.01% | 0.00% | 0.00% | 0.00% | 0.00% | 0.00% | 0.00% |
| | G | 0.01% | 0.01% | 0.01% | 0.08% | 0.01% | 0.02% | 0.01% | 0.04% | 0.01% | 0.01% |
| | T | 0.01% | 0.01% | 0.00% | 0.00% | 0.00% | 0.00% | 0.00% | 0.01% | 0.01% | 0.01% |

| HEK2-9 pNMG-347 | | 2 A | 3 A | 4 A | 5 A | 7 A | 8 A | 9 A | 10 A | 12 A | 14 A |
|---|---|---|---|---|---|---|---|---|---|---|---|
| | A | 100.00% | 99.98% | 99.94% | 99.76% | 99.98% | 99.97% | 99.97% | 99.93% | 99.98% | 99.97% |
| | C | 0.00% | 0.00% | 0.04% | 0.00% | 0.00% | 0.00% | 0.00% | 0.00% | 0.00% | 0.01% |
| | G | 0.00% | 0.01% | 0.02% | 0.23% | 0.01% | 0.02% | 0.03% | 0.06% | 0.01% | 0.02% |
| | T | 0.00% | 0.01% | 0.00% | 0.00% | 0.01% | 0.01% | 0.00% | 0.01% | 0.01% | 0.01% |

| HEK2-9 pNMG-348 | | 2 A | 3 A | 4 A | 5 A | 7 A | 8 A | 9 A | 10 A | 12 A | 14 A |
|---|---|---|---|---|---|---|---|---|---|---|---|
| | A | 99.97% | 99.98% | 99.96% | 99.85% | 99.99% | 99.99% | 99.99% | 99.96% | 99.98% | 99.94% |
| | C | 0.00% | 0.00% | 0.02% | 0.00% | 0.00% | 0.00% | 0.00% | 0.00% | 0.00% | 0.01% |
| | G | 0.01% | 0.02% | 0.02% | 0.14% | 0.01% | 0.01% | 0.01% | 0.03% | 0.00% | 0.04% |
| | T | 0.01% | 0.01% | 0.00% | 0.00% | 0.00% | 0.00% | 0.00% | 0.01% | 0.01% | 0.01% |

| HEK2-9 pNMG-349 | | 2 A | 3 A | 4 A | 5 A | 7 A | 8 A | 9 A | 10 A | 12 A | 14 A |
|---|---|---|---|---|---|---|---|---|---|---|---|
| | A | 99.98% | 99.98% | 99.62% | 99.66% | 99.97% | 99.99% | 99.99% | 99.63% | 99.98% | 99.96% |
| | C | 0.00% | 0.00% | 0.35% | 0.00% | 0.00% | 0.00% | 0.00% | 0.00% | 0.00% | 0.01% |
| | G | 0.01% | 0.01% | 0.03% | 0.34% | 0.02% | 0.01% | 0.01% | 0.37% | 0.01% | 0.03% |
| | T | 0.01% | 0.01% | 0.00% | 0.00% | 0.00% | 0.00% | 0.00% | 0.01% | 0.01% | 0.00% |

FIGURE 136

Hek2-10 site: 5'-GA$_2$A$_3$CA$_5$TA$_7$A$_8$A$_9$GA$_{11}$A$_{12}$TA$_{14}$GA$_{16}$ATGATGG-3'

| HEK2-10 pNMG-339 | | 2 A | 3 A | 5 A | 7 A | 8 A | 9 A | 11 A | 12 A | 14 A | 16 A |
|---|---|---|---|---|---|---|---|---|---|---|---|
| | A | 99.71% | 98.22% | 89.98% | 98.35% | 98.78% | 99.52% | 99.46% | 99.96% | 99.98% | 99.98% |
| | C | 0.00% | 0.00% | 0.00% | 0.00% | 0.00% | 0.00% | 0.01% | 0.00% | 0.00% | 0.00% |
| | G | 0.28% | 1.71% | 10.00% | 1.64% | 1.21% | 0.47% | 0.52% | 0.02% | 0.01% | 0.01% |
| | T | 0.01% | 0.01% | 0.01% | 0.01% | 0.01% | 0.00% | 0.01% | 0.01% | 0.01% | 0.01% |

| HEK2-10 pNMG-340 | | 2 A | 3 A | 5 A | 7 A | 8 A | 9 A | 11 A | 12 A | 14 A | 16 A |
|---|---|---|---|---|---|---|---|---|---|---|---|
| | A | 99.87% | 99.47% | 93.87% | 99.11% | 99.59% | 99.79% | 99.75% | 99.96% | 99.97% | 99.98% |
| | C | 0.00% | 0.00% | 0.00% | 0.00% | 0.00% | 0.00% | 0.01% | 0.00% | 0.00% | 0.00% |
| | G | 0.12% | 0.52% | 6.12% | 0.89% | 0.40% | 0.20% | 0.22% | 0.02% | 0.02% | 0.01% |
| | T | 0.01% | 0.01% | 0.01% | 0.00% | 0.01% | 0.01% | 0.01% | 0.01% | 0.01% | 0.01% |

| HEK2-10 pNMG-341 | | 2 A | 3 A | 5 A | 7 A | 8 A | 9 A | 11 A | 12 A | 14 A | 16 A |
|---|---|---|---|---|---|---|---|---|---|---|---|
| | A | 99.61% | 97.98% | 84.58% | 97.03% | 98.45% | 99.40% | 99.47% | 99.97% | 99.98% | 99.98% |
| | C | 0.00% | 0.00% | 0.00% | 0.00% | 0.01% | 0.00% | 0.01% | 0.00% | 0.00% | 0.00% |
| | G | 0.39% | 2.00% | 15.40% | 2.96% | 1.53% | 0.59% | 0.50% | 0.02% | 0.01% | 0.01% |
| | T | 0.01% | 0.01% | 0.01% | 0.01% | 0.01% | 0.00% | 0.01% | 0.00% | 0.01% | 0.01% |

| HEK2-10 pNMG-346 | | 2 A | 3 A | 5 A | 7 A | 8 A | 9 A | 11 A | 12 A | 14 A | 16 A |
|---|---|---|---|---|---|---|---|---|---|---|---|
| | A | 99.96% | 99.96% | 99.67% | 99.71% | 99.96% | 99.95% | 99.97% | 99.99% | 99.98% | 99.98% |
| | C | 0.00% | 0.00% | 0.00% | 0.00% | 0.00% | 0.00% | 0.02% | 0.00% | 0.00% | 0.00% |
| | G | 0.02% | 0.03% | 0.32% | 0.29% | 0.03% | 0.04% | 0.01% | 0.01% | 0.01% | 0.01% |
| | T | 0.01% | 0.01% | 0.01% | 0.00% | 0.01% | 0.01% | 0.01% | 0.01% | 0.01% | 0.01% |

| HEK2-10 pNMG-347 | | 2 A | 3 A | 5 A | 7 A | 8 A | 9 A | 11 A | 12 A | 14 A | 16 A |
|---|---|---|---|---|---|---|---|---|---|---|---|
| | A | 99.98% | 99.91% | 99.06% | 99.56% | 99.93% | 99.96% | 99.97% | 99.99% | 99.97% | 99.98% |
| | C | 0.00% | 0.00% | 0.00% | 0.00% | 0.00% | 0.00% | 0.02% | 0.00% | 0.00% | 0.00% |
| | G | 0.01% | 0.06% | 0.93% | 0.43% | 0.06% | 0.04% | 0.01% | 0.01% | 0.02% | 0.01% |
| | T | 0.01% | 0.01% | 0.01% | 0.01% | 0.01% | 0.01% | 0.01% | 0.01% | 0.01% | 0.01% |

| HEK2-10 pNMG-348 | | 2 A | 3 A | 5 A | 7 A | 8 A | 9 A | 11 A | 12 A | 14 A | 16 A |
|---|---|---|---|---|---|---|---|---|---|---|---|
| | A | 99.96% | 99.94% | 98.39% | 99.50% | 99.92% | 99.97% | 99.97% | 99.99% | 99.98% | 99.98% |
| | C | 0.00% | 0.00% | 0.00% | 0.00% | 0.00% | 0.00% | 0.02% | 0.00% | 0.00% | 0.00% |
| | G | 0.03% | 0.05% | 1.59% | 0.49% | 0.08% | 0.02% | 0.01% | 0.01% | 0.01% | 0.01% |
| | T | 0.01% | 0.01% | 0.01% | 0.01% | 0.00% | 0.00% | 0.01% | 0.01% | 0.01% | 0.01% |

| HEK2-10 pNMG-349 | | 2 A | 3 A | 5 A | 7 A | 8 A | 9 A | 11 A | 12 A | 14 A | 16 A |
|---|---|---|---|---|---|---|---|---|---|---|---|
| | A | 99.96% | 99.94% | 98.75% | 99.54% | 99.93% | 99.96% | 99.96% | 99.99% | 99.98% | 99.98% |
| | C | 0.00% | 0.00% | 0.00% | 0.00% | 0.00% | 0.01% | 0.03% | 0.00% | 0.00% | 0.00% |
| | G | 0.01% | 0.04% | 1.24% | 0.46% | 0.06% | 0.02% | 0.01% | 0.01% | 0.01% | 0.01% |
| | T | 0.01% | 0.01% | 0.01% | 0.01% | 0.00% | 0.01% | 0.01% | 0.00% | 0.01% | 0.01% |

FIGURE 137

Hek3- 5'-GGCCCA GA CTGA GCA CGTGATGG-3'
         6   8    12  15

| HEK3 pNMG-339 | 6 A | 8 A | 12 A | 15 A |
|---|---|---|---|---|
| A |  |  |  |  |
| C | 0.00% | 0.00% | 0.00% | 0.00% |
| G | 2.02% | 5.15% | 0.04% | 0.01% |
| T | 0.01% | 0.01% | 0.00% | 0.01% |

| HEK3 pNMG-340 | 6 A | 8 A | 12 A | 15 A |
|---|---|---|---|---|
| A |  |  |  |  |
| C | 0.00% | 0.00% | 0.00% | 0.00% |
| G | 1.03% | 3.43% | 0.04% | 0.01% |
| T | 0.01% | 0.00% | 0.01% | 0.01% |

| HEK3 pNMG-341 | 6 A | 8 A | 12 A | 15 A |
|---|---|---|---|---|
| A |  |  |  |  |
| C | 0.00% | 0.00% | 0.00% | 0.00% |
| G | 2.25% | 5.30% | 0.03% | 0.01% |
| T | 0.01% | 0.01% | 0.01% | 0.01% |

| HEK3 pNMG-346 | 6 A | 8 A | 12 A | 15 A |
|---|---|---|---|---|
| A |  |  |  |  |
| C | 0.00% | 0.00% | 0.00% | 0.00% |
| G | 0.12% | 0.23% | 0.05% | 0.01% |
| T | 0.01% | 0.01% | 0.00% | 0.01% |

| HEK3 pNMG-347 | 6 A | 8 A | 12 A | 15 A |
|---|---|---|---|---|
| A |  |  |  |  |
| C | 0.00% | 0.00% | 0.00% | 0.00% |
| G | 0.26% | 0.56% | 0.03% | 0.01% |
| T | 0.01% | 0.01% | 0.01% | 0.01% |

| HEK3 pNMG-348 | 6 A | 8 A | 12 A | 15 A |
|---|---|---|---|---|
| A |  |  |  |  |
| C | 0.00% | 0.00% | 0.00% | 0.00% |
| G | 0.23% | 0.37% | 0.04% | 0.00% |
| T | 0.02% | 0.01% | 0.00% | 0.01% |

| HEK3 pNMG-349 | 6 A | 8 A | 12 A | 15 A |
|---|---|---|---|---|
| A |  |  |  |  |
| C | 0.00% | 0.00% | 0.00% | 0.00% |
| G | 0.14% | 0.53% | 0.02% | 0.00% |
| T | 0.01% | 0.01% | 0.00% | 0.01% |

FIGURE 138

RNF2- 5'-GTCA TCTTA GTCA TTA CCTGAGG-3'
         4     9     13   16

| RNF2 pNMG-339 | | 4<br>A | 9<br>A | 13<br>A | 16<br>A |
|---|---|---|---|---|---|
| | A | 99.21% | 98.98% | 99.98% | 99.97% |
| | C | 0.00% | 0.02% | 0.00% | 0.00% |
| | G | 0.78% | 0.99% | 0.01% | 0.02% |
| | T | 0.01% | 0.01% | 0.01% | 0.01% |

| RNF2 pNMG-340 | | 4<br>A | 9<br>A | 13<br>A | 16<br>A |
|---|---|---|---|---|---|
| | A | 99.75% | 99.69% | 99.99% | 99.98% |
| | C | 0.00% | 0.01% | 0.00% | 0.00% |
| | G | 0.24% | 0.29% | 0.01% | 0.01% |
| | T | 0.01% | 0.01% | 0.01% | 0.01% |

| RNF2 pNMG-341 | | 4<br>A | 9<br>A | 13<br>A | 16<br>A |
|---|---|---|---|---|---|
| | A | 98.86% | 98.94% | 99.97% | 99.97% |
| | C | 0.00% | 0.02% | 0.00% | 0.00% |
| | G | 1.12% | 1.03% | 0.01% | 0.02% |
| | T | 0.02% | 0.01% | 0.01% | 0.01% |

| RNF2 pNMG-346 | | 4<br>A | 9<br>A | 13<br>A | 16<br>A |
|---|---|---|---|---|---|
| | A | 99.97% | 99.94% | 99.98% | 99.98% |
| | C | 0.00% | 0.02% | 0.00% | 0.00% |
| | G | 0.02% | 0.04% | 0.01% | 0.01% |
| | T | 0.01% | 0.01% | 0.01% | 0.01% |

| RNF2 pNMG-347 | | 4<br>A | 9<br>A | 13<br>A | 16<br>A |
|---|---|---|---|---|---|
| | A | 99.95% | 99.90% | 99.98% | 99.98% |
| | C | 0.00% | 0.01% | 0.00% | 0.00% |
| | G | 0.04% | 0.08% | 0.01% | 0.01% |
| | T | 0.01% | 0.01% | 0.01% | 0.01% |

| RNF2 pNMG-348 | | 4<br>A | 9<br>A | 13<br>A | 16<br>A |
|---|---|---|---|---|---|
| | A | 99.93% | 99.96% | 99.97% | 99.97% |
| | C | 0.00% | 0.01% | 0.00% | 0.00% |
| | G | 0.06% | 0.02% | 0.01% | 0.02% |
| | T | 0.01% | 0.00% | 0.01% | 0.01% |

| RNF2 pNMG-349 | | 4<br>A | 9<br>A | 13<br>A | 16<br>A |
|---|---|---|---|---|---|
| | A | 99.94% | 99.96% | 99.98% | 99.98% |
| | C | 0.00% | 0.02% | 0.00% | 0.00% |
| | G | 0.05% | 0.02% | 0.01% | 0.01% |
| | T | 0.01% | 0.00% | 0.01% | 0.01% |

FIGURE 139

FANCF- 5'-GGA$_3$A$_4$TCCCTTCTGCA$_{15}$GCA$_{18}$CCTGG-3'

| FancF pNMG-339 | 3 A | 4 A | 15 A | 18 A |
|---|---|---|---|---|
| A | 99.72% | 99.46% | 99.98% | 99.98% |
| C | 0.01% | 0.01% | 0.00% | 0.00% |
| G | 0.26% | 1.52% | 0.02% | 0.01% |
| T | 0.01% | 0.01% | 0.00% | 0.01% |

| FancF pNMG-346 | 3 A | 4 A | 15 A | 18 A |
|---|---|---|---|---|
| A | 99.97% | 99.85% | 99.98% | 99.98% |
| C | 0.01% | 0.01% | 0.00% | 0.00% |
| G | 0.01% | 0.13% | 0.02% | 0.01% |
| T | 0.01% | 0.01% | 0.00% | 0.01% |

| FancF pNMG-340 | 3 A | 4 A | 15 A | 18 A |
|---|---|---|---|---|
| A | 99.95% | 99.50% | 99.98% | 99.99% |
| C | 0.01% | 0.01% | 0.00% | 0.00% |
| G | 0.04% | 0.48% | 0.01% | 0.00% |
| T | 0.01% | 0.00% | 0.00% | 0.01% |

| FancF pNMG-347 | 3 A | 4 A | 15 A | 18 A |
|---|---|---|---|---|
| A | 99.95% | 99.65% | 99.98% | 99.99% |
| C | 0.00% | 0.00% | 0.00% | 0.00% |
| G | 0.04% | 0.34% | 0.02% | 0.00% |
| T | 0.01% | 0.00% | 0.01% | 0.01% |

| FancF pNMG-341 | 3 A | 4 A | 15 A | 18 A |
|---|---|---|---|---|
| A | 99.69% | 98.86% | 99.98% | 99.98% |
| C | 0.01% | 0.01% | 0.00% | 0.00% |
| G | 0.29% | 1.82% | 0.02% | 0.01% |
| T | 0.01% | 0.00% | 0.00% | 0.01% |

| FancF pNMG-348 | 3 A | 4 A | 15 A | 18 A |
|---|---|---|---|---|
| A | 99.94% | 99.08% | 99.98% | 99.98% |
| C | 0.00% | 0.00% | 0.00% | 0.00% |
| G | 0.05% | 0.90% | 0.01% | 0.01% |
| T | 0.01% | 0.01% | 0.00% | 0.01% |

| FancF pNMG-349 | 3 A | 4 A | 15 A | 18 A |
|---|---|---|---|---|
| A | 99.93% | 99.33% | 99.98% | 99.98% |
| C | 0.01% | 0.01% | 0.00% | 0.00% |
| G | 0.05% | 0.65% | 0.01% | 0.01% |
| T | 0.01% | 0.01% | 0.00% | 0.01% |

Figure 141

| sgRNA | site | 107 | 108 | 109 | 142 | 144 | 177 | 335 | 370 | 371 | 492 | 494 | 476 | 477 | 478 | 482 | 484 | 492 | 497 | 498 | 500 | BE3 | BE3B | Cas9 (indel) % |
|---|---|---|---|---|---|---|---|---|---|---|---|---|---|---|---|---|---|---|---|---|---|---|---|---|
| 299 | GAACA_CAAAGCATAGACTGC | 0.2 | 0.2 | 1.0 | 0.3 | 2.9 | 14.8 | 0.4 | 62.5 | 57.7 | 54.0 | 55.8 | 62.9 | 64.0 | 61.0 | 0.7 | 36.2 | 34.1 | 45.5 | 56.5 | 29.5 | | | 28.92 |
| 299 | GAACAC_AAAGCATAGACTGC | | | | | | | | | | | | | | | | | | | | | 38.9 | 46.9 | |
| 502 | GGGGA_CGCGCTGGCTTCCCG | 0.1 | 0.0 | 0.0 | 0.1 | 0.3 | 1.2 | 0.0 | 2.0 | 3.6 | 4.0 | 3.1 | 6.1 | 5.1 | 4.9 | 0.1 | 2.7 | | | | | | | |
| 504 | GCCA_CTTCTAAGCCCTTGAT | 0.0 | 0.0 | 0.0 | 0.0 | 0.3 | 1.3 | 0.0 | 4.3 | 21.9 | 19.2 | 15.8 | 7.2 | 5.6 | 6.0 | 0.0 | 3.6 | 4.6 | 3.3 | 4.4 | 1.3 | | | 31.98 |
| 504 | GCCACTTC_TAAGCCCTTGAT | | | | | | | | | | | | | | | | | | | | | 22.5 | 34.6 | |
| 508 | GATGA_GATAATGATGAGTCA | 0.0 | 0.0 | 0.0 | 0.1 | 0.2 | 2.7 | 0.0 | 2.5 | 3.6 | 4.2 | 3.6 | 13.9 | 13.8 | 12.1 | 0.0 | 5.4 | 8.9 | 10.1 | 12.5 | 2.6 | | | 39.19 |
| 508 | GATGAGA_TAATGATGAGTCA | 0.0 | 0.0 | 0.0 | 0.0 | 0.8 | 0.9 | 0.0 | 1.5 | 4.1 | 4.3 | 5.0 | 5.0 | 4.9 | 4.2 | 0.0 | 5.2 | 7.8 | 3.4 | 4.5 | 1.5 | | | |
| 509 | GCCTA_GGCAGTGGGGGGTGCA | 0.0 | 0.0 | 0.0 | 0.0 | 0.1 | 0.4 | 0.0 | 0.7 | 1.4 | 1.5 | 1.0 | 3.8 | 5.2 | 3.2 | 0.0 | 0.3 | 1.0 | 4.0 | 3.9 | 0.9 | | | 17.16 |
| 509 | GCC_TAGGCAGTGGGGGGTGCA | | | | | | | | | | | | | | | | | | | | | 0.1 | 0.3 | |
| 499 | GAGTA_TGAGGGCATAGACTGC | 0.2 | 0.2 | 0.1 | 0.3 | 0.8 | 5.7 | 0.0 | 7.4 | 26.7 | 28.8 | 30.3 | 37.7 | 42.3 | 0.3 | 0.3 | 5.9 | 13.0 | 30.4 | 32.7 | 11.2 | | | |

Figure 142

| construct | HEK2 | Site 2 | site 4 | site 8 | site 9 |
|---|---|---|---|---|---|
| 107 | 0.00 | 0.01 | 0.01 | 0.06 | 0.06 |
| 108 | 0.53 | 0.18 | 0.02 | 0.02 | 0.10 |
| 109 | 0.01 | 0.03 | 0.04 | 0.05 | 0.00 |
| 142 | 0.05 | 0.01 | 0.03 | 0.13 | 0.10 |
| 144 | 0.00 | 0.07 | 0.01 | 0.02 | 0.02 |
| 177 | 0.12 | 0.12 | 0.08 | 0.03 | 0.04 |
| 335 | 0.04 | 0.03 | 0.04 | 0.00 | 0.04 |
| 370 | 0.32 | 0.09 | 0.09 | 0.01 | 0.03 |
| 371 | 0.36 | 0.17 | 0.23 | 0.09 | 0.03 |
| 402 | 0.26 | 0.16 | 0.33 | 0.00 | 0.01 |
| 404 | 0.13 | 0.17 | 0.12 | 0.11 | 0.02 |
| 476 | 0.01 | 0.14 | 0.05 | 0.00 | 0.10 |
| 477 | 0.05 | 0.10 | 0.07 | 0.09 | 0.06 |
| 478 | 0.03 | 0.20 | 0.07 | 0.03 | 0.02 |
| 482 | 0.03 | 0.16 | 0.02 | 0.09 | 0.16 |
| 494 | 0.00 | 0.11 | 0.11 | 0.08 | 0.01 |
| 492 | 0.43 |  | 0.07 | 0.02 | 0.03 |
| 497 | 0.05 |  | 0.05 | 0.07 | 0.12 |
| 498 | 0.13 |  | 0.08 | 0.05 | 0.14 |
| 500 | 0.01 |  | 0.03 | 0.05 | 0.01 |
| BE3 | 1.05 |  | 1.69 | 0.13 | 0.20 |
| BE3B | 6.34 |  | 6.90 | 0.13 | 0.18 |
| Cas9 | 28.92 |  | 31.98 | 39.19 | 17.16 |

Figure 143

| sgRNA | site | 482 | 476 | 476+274 | 476+275 | 477 | 477+274 | 477+275 | 285b | 285b+274 | 285b+275 | 277 |
|---|---|---|---|---|---|---|---|---|---|---|---|---|
| 299 | GAACACAAAGCATAGACTGC | 1.9 | 67.5 | 59.6 | 51.2 | 72.9 | 63.9 | 60.1 | 30.8 | 31.2 | 27.0 | 45.2 |
| 301 | GGAACACAAAGCATAGACTG | 0.3 | 29.5 | 23.3 | 18.5 | 37.1 | 24.6 | 32.0 | 16.9 | 14.5 | 12.5 | 19.9 |
| 301 | GGAACACAAAGCATAGACTG | 2.8 | 53.0 | 38.3 | 33.7 | 61.0 | 44.3 | 47.6 | 19.7 | 17.1 | 15.4 | 24.4 |
| 502 | GGGGACGGCGCTGGCTTCCGG | 0.0 | 4.1 | 4.7 | 3.6 | 3.5 | 4.1 | 3.1 | 2.7 | 2.0 | 1.3 | 1.0 |
| 505 | GGGAAGACCCAGCATCCGT | 0.0 | 0.1 | 0.2 | 0.2 | 0.2 | 0.1 | 0.8 | 0.6 | 0.0 | 0.0 | 0.0 |
| 505 | GGGAAAGACCCAGCATCCGT | 0.0 | 0.6 | 0.6 | 0.1 | 1.1 | 0.2 | 0.2 | 1.2 | 0.1 | 0.1 | 0.5 |
| 505 | GGGAAAGACCCAGCATCCGT | 0.0 | 1.4 | 0.1 | 0.3 | 0.3 | 1.2 | 0.8 | 0.6 | 0.6 | 0.4 | 0.0 |
| 505 | GGGAAAGACCCAGCATCCGT | 0.7 | 3.1 | 1.3 | 1.2 | 3.2 | 1.4 | 1.9 | 0.5 | 0.1 | 0.2 | 0.6 |
| 507 | GAAACTGGTCCGTTTACAG | 0.0 | 0.5 | 0.2 | 0.1 | 0.5 | 0.5 | 0.3 | 0.5 | 0.5 | 0.2 | 0.3 |
| 509 | GCCTAGGCAGTGGGGGTGCA | 0.0 | 7.7 | 2.0 | 2.0 | 3.8 | 1.7 | 2.0 | 1.3 | 0.1 | 0.7 | 0.7 |

Figure 144

| Site | Protospacer and PAM sequence | 371 | 402 | 404 | 410 | 476 | 477 | 478 | 479 | 475 |
|---|---|---|---|---|---|---|---|---|---|---|
| CAC (HeK2) | GAACACAAAGCATAGACTGCTGG | 46.4 | 48.1 | 41.0 | 46.2 | 51.8 | 39.6 | 46.8 | 35.2 | 47.5 |
| AAA | GAAAAAAAGCAGAGACTGCTGG | 0.1 | 0.1 | 0.0 | 0.1 | 0.2 | 0.3 | 0.2 | 0.0 | |
| TAC | GAATACTAAGCATAGACTCCAGG | 37.7 | 39.9 | 38.5 | 43.4 | 45.1 | 41.4 | 38.3 | 25.7 | |
| AAC | GTAAACAAAGCATAGACTGAGGG | 17.8 | 21.8 | 16.9 | 19.5 | 14.1 | 14.8 | 14.2 | 9.7 | |
| GAC | GAAGACCAAGGATAGACTGCTGG | 7.7 | 6.5 | 4.7 | 11.4 | 7.6 | 9.3 | 7.4 | 2.3 | |
| CAT | GAACATAAAGAATAGAATGATGG | 16.4 | 20.8 | 16.0 | 21.7 | 16.7 | 22.3 | 21.3 | 12.9 | |
| CAG | GGACAGGCAGCATAGACTGTGGG | 9.6 | 16.9 | 9.4 | 13.7 | 24.9 | 22.7 | 29.0 | 26.7 | |
| GAA | GTAGAAAAGTATAGACTGCAGG | 2.9 | 2.8 | 2.5 | 4.8 | 8.7 | 6.4 | 6.0 | 3.7 | 11.1 |
| GAG | GGAGAGAAAGCATAGACTGCTGG | 7.6 | 10.6 | 5.6 | 10.4 | 16.5 | 26.0 | 14.1 | 9.2 | |
| GAT | GAAGATAGAGAATAGACTGCTGG | 2.6 | 4.1 | 2.2 | 6.1 | 7.1 | 7.3 | 5.6 | 3.2 | |
| TAA | GGCTAAAGAACCATAGACTGTGG | 2.3 | 3.7 | 1.8 | 2.8 | 4.2 | 5.6 | 4.1 | 2.2 | 0.5 |
| TAG | GTCTAGAAAGCTTAGACTGCTGG | 10.1 | 14.9 | 8.1 | 9.1 | 24.3 | 28.3 | 20.3 | 13.6 | 9.8 |
| TAT | GAGTATGAGGCATAGACTGCAGG | 21.0 | 38.1 | 18.3 | 32.3 | 37.0 | 43.3 | 40.1 | 28.4 | 31.4 |
| AAG | GTCAAGAGAAGCAGAGACTGCCGG | 6.1 | 6.5 | 5.6 | 10.7 | 11.9 | 12.6 | 9.8 | 7.8 | 11.7 |
| AAT | GGGAATAAATCATAGAATCCTGG | 5.9 | 11.2 | 6.4 | 16.7 | 20.1 | 15.3 | 16.0 | 11.1 | 18.7 |
| CAA | GAGCAAAGAGAATAGACTGTAGG | 2.5 | 5.4 | 2.8 | 3.2 | 7.4 | 13.3 | 6.9 | 6.2 | 0.3 |

Figure 145

| sgRNA | site | ABE2 | ABE3 | ABE4 | ABE5-1 | ABE5-2 | ABE5-3 |
|---|---|---|---|---|---|---|---|
| 299* | GAACA₂CAAAGCATAGACTGC | 13.6 | 58.5 | 54.4 | 77.6 | 69.5 | 57.3 |
| 502 | GGGGA₂CGGGCTGGCTTCCCG | 0.9 | 5.6 | 3.0 | 5.8 | 3.0 | 3.3 |
| 504 | GCCA₄CTTCTAAGCCCTTGAT | 1.0 | 7.4 | 4.2 | 7.6 | 5.1 | 5.4 |
| 505 | GGGA₄AAGACCCAGCATCCGT | 0.1 | 0.2 | 0.7 | 0.3 | 0.1 | 0.3 |
| 505 | GGGA₄AGACCCAGCATCCGT | 0.1 | 0.4 | 0.5 | 0.5 | 0.2 | 1.0 |
| 505 | GGGAAA₆GACCCAGCATCCGT | 0.3 | 0.6 | 0.4 | 0.2 | 0.2 | 0.5 |
| 505 | GGGAAAGA₇CCCAGCATCCGT | 0.6 | 1.5 | 1.5 | 3.0 | 1.3 | 3.6 |
| 507 | GAAA₄CTGGTCCCGTTTACAG | 0.1 | 0.6 | 0.3 | 0.9 | 0.4 | 0.6 |
| 508 | GATGA₅GATAATGATGAGTCA | 1.7 | 11.5 | 0.4 | 15.6 | 8.8 | 6.1 |
| 508 | GATGAGA₇TAATGATGAGTCA | 1.4 | 5.1 | 0.1 | 6.0 | 3.5 | 4.7 |
| 509 | GCCTA₅GGCAGTGGGGTGCA | 0.2 | 3.1 | 0.6 | 5.9 | 2.3 | 1.3 |

Figure 149

DNA Shuffle (NeXT)

1. generated shuffled library including constructs from evo #4, 5a, 5b and evo #2

2. transformed library into S1030 + pNMG-333 selection plasmid 3. induce ABE expression for 7h and plated on selection conditions:
   a. 128 ug/mL chlor
   b. 192 ug/mL chlor
   c. 384 ug/mL spect
   d. 256 ug/mL spect, 64 ug/mL chlor 4. selection plate incubated at 37°C, 48h → surviving colonies sequenced Spect target: 5'–CAATGATGACTTCTACAGCG–3'

Chlor target: 5'–TACGCCGTAGTGCACCTGGA–3' outcome:

- >95% of clones surviving on chlor and chlor + spect plates (200 colonies sequenced total) contained Evo #3 mutations only

- clones sequenced from spect only selection condition, however, had high frequency of mutation at A142 and A143, also high frequency of mutations in C-terminal portion of ecTadA (K157, Q159, K160 and K161) – see chart on next slide

- clones sequenced from spect only selection condition had a low relative frequency of evo #3 mutations only (<10% of total constructs sequenced) – very different outcome than colonies sequenced from chlor only plates.

| genetic locus | sequence | position of target A | target sequence |
|---|---|---|---|
| pNMG-469 | TAT | 5 | GAGTATGAGGCATAGACTGC |
| pNMG-470 | AAG | 5 | GTCAAGAAAGCAGAGACTGC |
| pNMG-472 | CAA | 5 | GGGAATAAATCATAGAATCC |
| pNMG-508 | GAG | 5 | GATGAGATAATGATGAGTCA |
| pNMG-536 | GAC | 7 | GGATTGACCCAGGCCAGGGC |
| pNMG-299 | CAC | 5 | GAACACAAAGCATAGACTGC |

Figure 155

| genetic locus | sequence | position of target A | target site |
|---|---|---|---|
| pNMG-469 | TAT | 5 | GAGTATGAGGCATAGACTGC |
| pNMG-470 | AAG | 5 | GTCAAGAAAGCAGAGACTGC |
| pNMG-472 | CAA | 5 | GGGAATAAATCATAGAATCC |
| pNMG-508 | GAG | 5 | GATGAGATAATGATGAGTCA |
| pNMG-536 | GAC | 7 | GGATTGACCCAGGCCAGGGC |
| pNMG-299 | CAC | 5 | GAACACAAAGCATAGACTGC |

Correction of: 5'-TTCATTA(7)ACTGTGGCCGGCT-3'
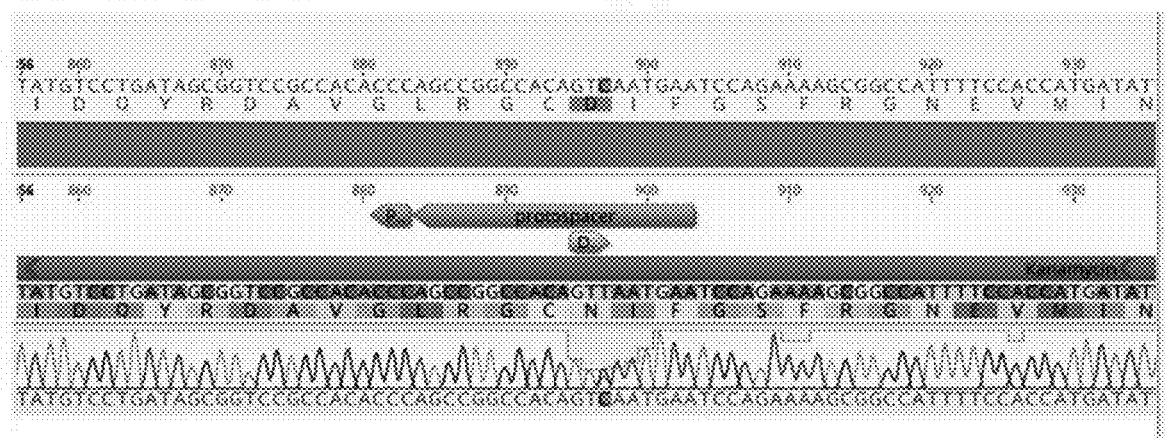
Correction of: 5'-ATCTTA(6)TTCGATCATGCGAA-3'
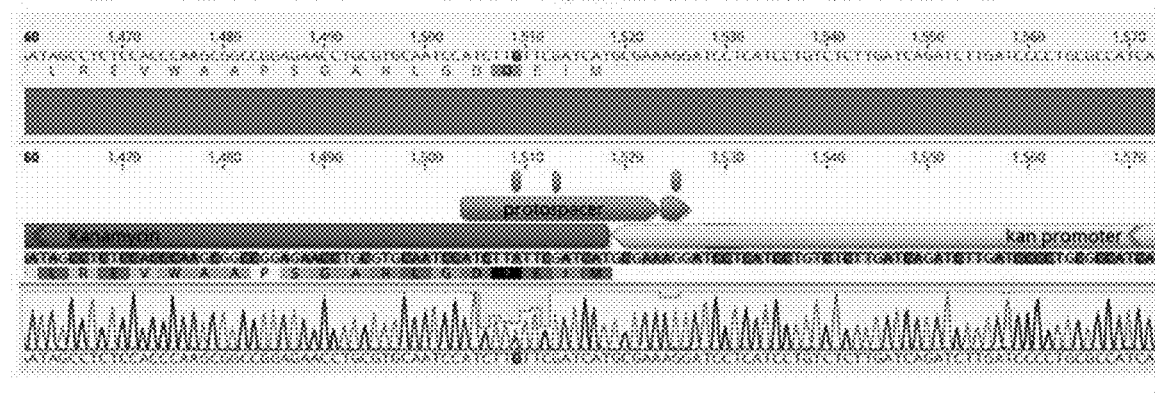
Figure 163

| position: | 17  | 23  | 48  | 111 | 118 | 122 | 123 | 125 | 126 | 147 | 152 | 155 | 156 | 161 | 164 |
|-----------|-----|-----|-----|-----|-----|-----|-----|-----|-----|-----|-----|-----|-----|-----|-----|
| wt res:   | Thr | Trp | Pro | Thr | Met | His | His | Gly | Met | Asp | Arg | Glu | Ile | Lys | Ser |
|           | Ser | Leu | Ala |     |     |     |     |     |     |     |     |     |     |     |     |
|           |     |     | Ala |     |     | Asn |     |     |     |     |     |     |     |     |     |
|           |     |     | Ala | Ser |     |     |     |     |     |     |     |     |     |     |     |
|           | Ser |     | Ala |     |     |     |     |     |     |     |     |     |     | Thr | Tyr |
|           |     |     | Ser |     |     |     |     |     |     |     |     |     |     |     |     |
|           |     |     | Ser |     |     |     |     |     |     |     | Pro |     |     |     |     |
|           |     |     | Ala |     |     |     |     |     | Leu |     |     |     |     | Thr |     |
|           | Ser | Leu | Ser |     |     |     |     |     |     |     |     |     |     | Thr |     |
|           |     |     | Ala |     |     |     |     |     | Leu |     |     |     |     | Thr |     |
|           |     | Leu | Ala |     |     |     |     |     |     |     |     |     |     | Thr |     |
|           |     |     |     |     | Leu |     |     |     |     |     |     |     |     |     |     |
|           | Ser | Leu | Ala |     |     |     |     |     |     |     |     |     |     |     |     |
|           |     |     | Ala |     |     |     |     |     |     |     | His |     |     | Thr |     |
|           |     |     | Ala |     |     |     |     |     |     |     | Pro |     |     |     |     |
|           | Ser | Leu | Ala |     |     |     |     | Ala |     |     |     |     |     | Thr |     |
|           | Ser | Leu | Ala |     |     |     |     |     |     |     |     |     |     | Thr |     |
|           |     |     |     |     |     |     |     |     |     |     | Pro |     |     | Asn |     |
|           |     |     | Ala |     |     |     |     |     |     |     | Pro |     |     |     |     |
|           |     |     | Ala |     |     |     |     |     |     |     |     |     |     |     |     |
|           |     | Arg | Ala |     |     |     |     |     |     |     |     |     |     |     |     |

| sgRNA plasmid | protospacer | %editing | ABE | cell line |
|---|---|---|---|---|
| pNMG-510 | GACTCAGATAAGATGCTGAGG | <0.15% | pNMG-478 | R196* TP53 (Calu-6) |
| pNMG-511 | GCATATGTAACAGTTCCTGCA | <0.80% | pNMG-402 | M237I TP53 (T98G) |
| pNMG-512 | GTGCATGTTTGTGCCTGTCC | <0.13% | pNMG-477 | R273H TP53 (NCI-H1975) |

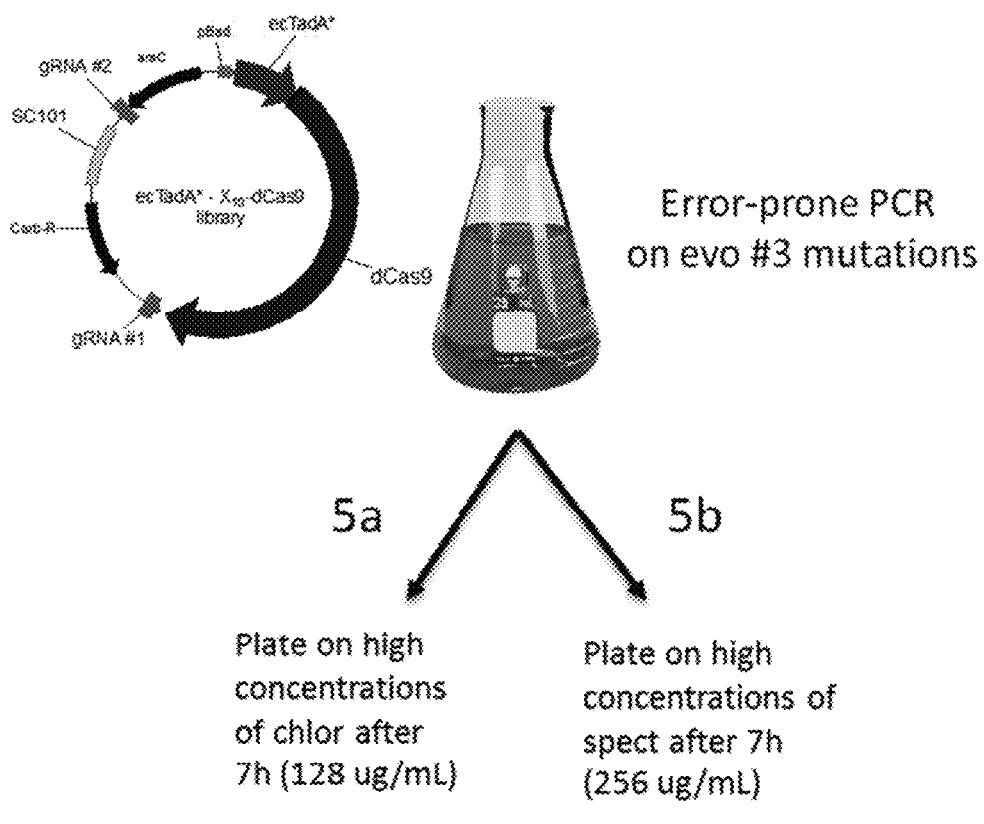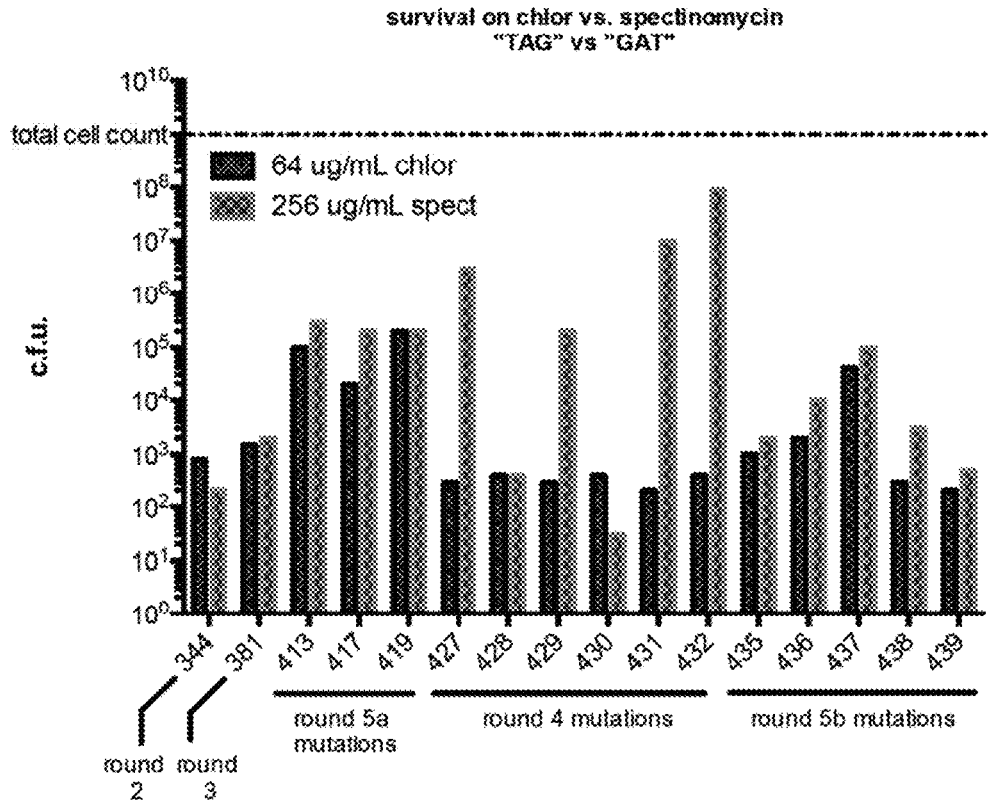
Figure 171

```
HEK2: GAACACAAAGCATAGACTGCGGG          GAG: GGAGAGAGCATAGACTGCTGG
AAA:  GAAAAAAAGCAGAGACTGCTGG          GAT: GAAGATAGAGAATAGACTGCTGG
TAC:  GAATACTAAGCATAGACTCCAGG         GAA: GTAGAAAAGTATAGACTGCAGG
AAC:  GTAAACAAAGCATAGACTGAGGG         AAG: GTCAAGAAAGCAGAGACTGCCGG
GAC:  GAAGACCAAGGATAGACTGCTGG         TAT: GAGTATGAGGCATAGACTGCAGG
CAT:  GAACATAAAGAATAGAATGATGG         TAG: GTCTAGAAAGCTTAGACTGCTGG
                                      CAG: GCACAGGCAGCATAGACTGTGGG
                                      CAA: GAGCAAAGAGAATAGACTGTAGG
                                      TAA: GGCTAAAGACCATAGACTGTGGG
                                      AAT: GGGAATAAATCATAGAATCCTGG
```

Figure 178

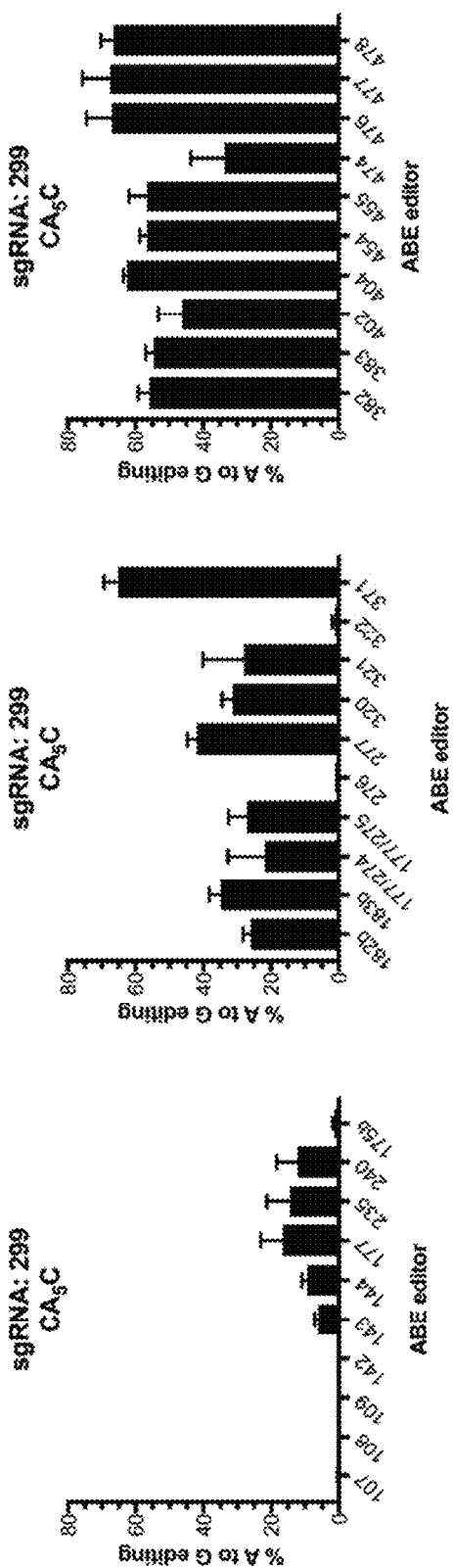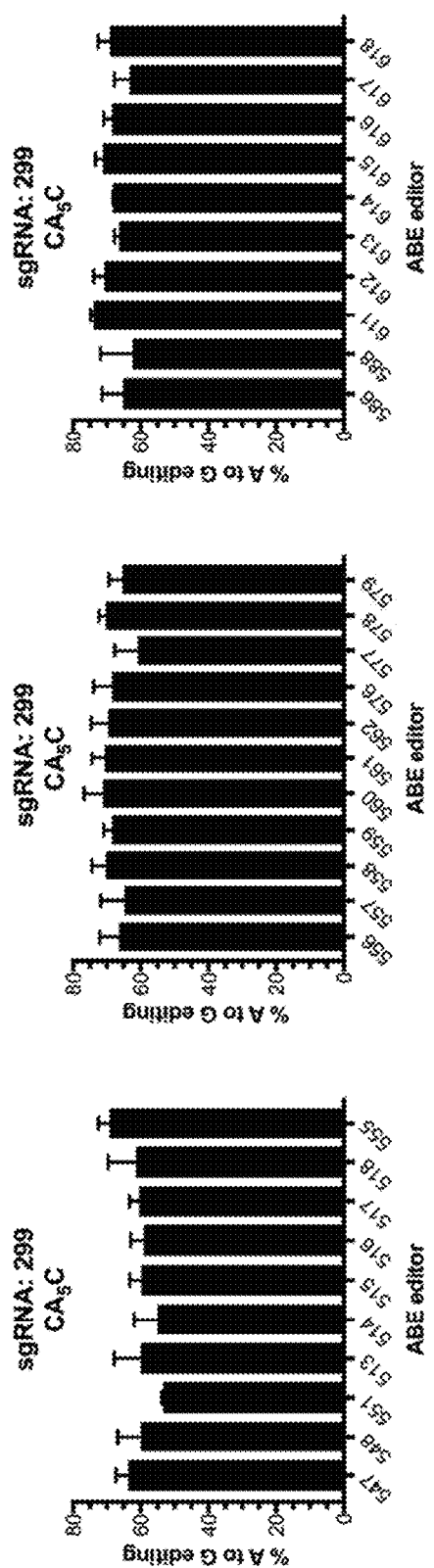
sgRNA 299: 5'-GAACACAAAGCATAGACTGC-3'  Figure 179

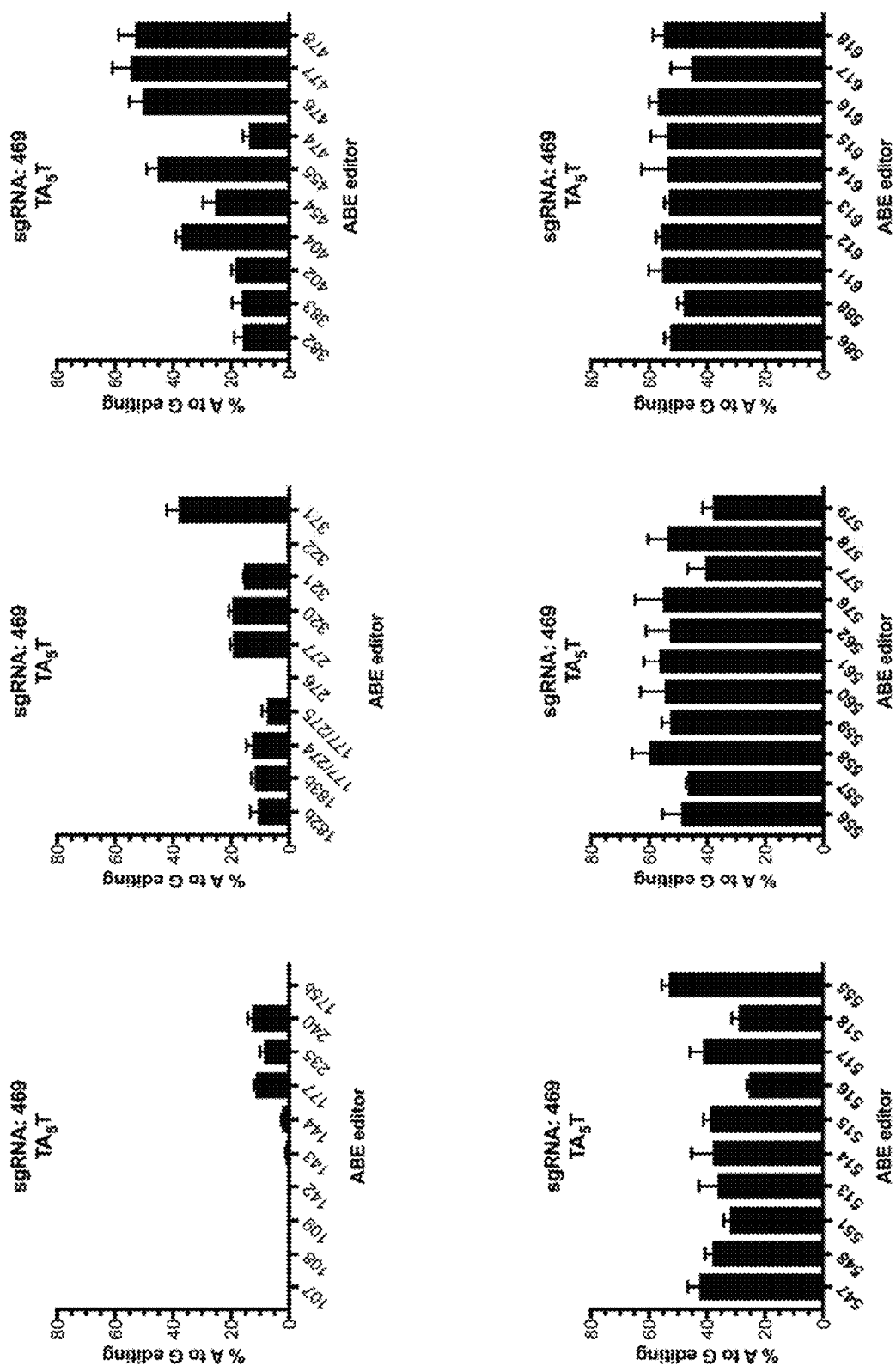
sgRNA 469: 5' - GAGTATGAGGCATAGACTGC-3'   Figure 180

ADENOSINE NUCLEOBASE EDITORS AND USES THEREOF

RELATED APPLICATIONS

This application is a continuation of and claims priority under 35 U.S.C. § 120 to U.S. patent application U.S. Ser. No. 16/143,370, filed Sep. 26, 2018, which is a continuation of and claims priority under 35 U.S.C. § 120 to U.S. patent application U.S. Ser. No. 15/791,085, filed Oct. 23, 2017, which claims priority under 35 U.S.C. § 120 and 365(c) to and is a continuation of international PCT Application, PCT/US2017/045381, filed Aug. 3, 2017, which claims priority under 35 U.S.C. § 119(e) to U.S. Provisional Applications, U.S. Ser. No. 62/473,714, filed Mar. 20, 2017, U.S. Ser. No. 62/454,035, filed Feb. 2, 2017, and U.S. Ser. No. 62/370,684, filed Aug. 3, 2016, each of which is incorporated herein by reference.

BACKGROUND OF THE INVENTION

Targeted editing of nucleic acid sequences, for example, the targeted cleavage or the targeted introduction of a specific modification into genomic DNA, is a highly promising approach for the study of gene function and also has the potential to provide new therapies for human genetic diseases. Since many genetic diseases in principle can be treated by effecting a specific nucleotide change at a specific location in the genome (for example, an A to G or a T to C change in a specific codon of a gene associated with a disease), the development of a programmable way to achieve such precise gene editing represents both a powerful new research tool, as well as a potential new approach to gene editing-based therapeutics.

SUMMARY OF THE INVENTION

Provided herein are compositions, kits, and methods of modifying a polynucleotide (e.g., DNA) using an adenosine deaminase and a nucleic acid programmable DNA binding protein (e.g., Cas9) Some aspects of the disclosure provide nucleobase editing proteins which catalyze hydrolytic deamination of adenosine (forming inosine, which base pairs like guanine (G)) in the context of DNA. There are no known naturally occurring adenosine deaminases that act on DNA. Instead, known adenosine deaminases act on RNA (e.g., tRNA or mRNA). To overcome this drawback, the first deoxyadenosine deaminases were evolved to accept DNA substrates and deaminate deoxyadenosine (dA) to deoxyinosine. The adenosine deaminase acting on tRNA (ADAT) from *Escherichia coli* (TadA, for tRNA adenosine deaminase A), was covalently fused to a dCas9 domain, and libraries of this fusion were assembled containing mutations in the deaminase portion of the construct. It should be appreciated that *E. coli* TadA (ecTadA) deaminases also include truncations of ecTadA. For example, truncations (e.g., N-terminal truncations) of a full length ecTadA (SEQ ID NO: 84), such as the N-terminally truncated ecTadA set forth in SEQ ID NO: 1 are provided herein for use in the present invention. Further, it was found that other adenosine deaminase mutants, such as *S. aureus* TadA mutants, were capable of deaminating adenosine. Without wishing to be bound by any particular theory, truncations of adenosine deaminases (e.g., ecTadA) may have desired solubility and/ or expression properties as compared to their full-length counterparts.

Mutations in the deaminase domain of nucleobase editing proteins were made by evolving adenosine deaminases. Productive variants were identified via selection for A to G reversion at the codon of an active-site His in the acetyl-transferase gene of chloramphenicol (encoded on a co-transformed selection plasmid). A first round of evolution yielded an ecTadA variant, ecTadA D108X (X=G, V, or N), capable of converting A to G in DNA. In some embodiments, the ecTadA variant comprises a D108A mutation in SEQ ID NO: 1, or a corresponding mutation in another adenosine deaminase. The first round of evolution also yielded an ecTadA variant, ecTadA A106V. A subsequent round of evolution resulted in another variant, ecTadA D108N_E155X (X=G, V, or D), which *E. coli* survive in the presence of high concentrations of chloramphenicol. Additional variants were identified by evolving ecTadA. For example, ecTadA variants that are capable of deaminating adenosine in DNA include one or more of the following mutations D108N, A106V, D147, E155V, L84F, H123Y, and I157F of SEQ ID NO: 1. It should be appreciated however, that homologous mutations may be made in other adenosine deaminases to generate variants that are capable of deaminating adenosine in DNA. Additional rounds of evolution provided further ecTadA variants. For example, additional ecTadA variants are shown in FIGS. 11, 16, 97, 104-106, 125-128, 115 and Table 4.

In the examples provided herein, exemplary nucleobase editors having the general structure evolved ecTadA (D108X; X=G, V, or N)-XTEN-nCas9, catalyzed A to G transition mutations in cells such as eukaryotic cells (e.g., Hek293T mammalian cells). In other examples exemplary nucleobase editors contain two ecTadA domains and a nucleic acid programmable DNA binding protein (napD-NAbp). For example, nucleobase editors may have the general structure ecTadA(D108N)-ecTadA(D108N)-nCas9. Additional examples of nucleobase editors containing ecTadA variants provided herein demonstrate an improvement in performance of the nucleobase editors in mammalian cells. For example, certain adenosine base editors include ecTadA having D108X, where X=G, V, or N, and/or E155X, where X=B, V, or D mutations in ecTadA as set forth in SEQ ID NO: 1 or another adenine deaminase. In certain embodiments mutants, nucleobase editors are covalently fused to catalytically dead alkyl adenosine gylcosylase (AAG), which may protect the edited inosine from base excision repair (or other DNA repair systems) until the T on the opposite strand is changed to a C, for example, through mismatch repair (or other DNA repair systems). Once the base opposite the inosine is changed to a C, then the inosine may be changed to a G irreversibly and permanently through cellular DNA repair processes, resulting in a permanent change from an A:T base pair to a G:C base pair.

Without wishing to be bound by any particular theory, the adenosine nucleobase editors described herein work by using ecTadA variants to deaminate A bases in DNA, causing A to G mutations via inosine formation. Inosine preferentially hydrogen bonds with C, resulting in A to G mutation during DNA replication. When covalently tethered to Cas9 (or another nucleic acid programmable DNA binding protein), the adenosine deaminase (e.g., ecTadA) is localized to a gene of interest and catalyzes A to G mutations in the ssDNA substrate. This editor can be used to target and revert single nucleotide polymorphisms (SNPs) in disease-relevant genes, which require A to G reversion. This editor can also be used to target and revert single nucleotide polymorphisms (SNPs) in disease-relevant genes, which require T to C reversion by mutating the A, opposite of the T, to a G. The T may then be replaced with a C, for example by base excision repair mechanisms, or may be changed in subsequent rounds of DNA replication.

Some aspects of the disclosure relate to the discovery that engineered (e.g., evolved) adenosine deaminases are capable of deaminating adenosine in a deoxyribonucleic acid (DNA) substrate. In some embodiments, the disclosure provides such adenosine deaminases. In some embodiments, the adenosine deaminases provided herein are capable of deaminating an adenosine in a DNA molecule. Other aspects of the disclosure provide fusion proteins comprising a Cas9 domain and an adenosine deaminase domain, for example, an engineered deaminase domain capable of deaminating an adenosine in DNA. In some embodiments, the fusion protein comprises one or more of a nuclear localization sequence (NLS), an inhibitor of inosine base excision repair (e.g., dISN), and/or a linker.

In some aspects, the disclosure provides an adenosine deaminase capable of deaminating an adenosine in a deoxyribonucleic acid (DNA) substrate. In some embodiments, the adenosine deaminase is from a bacterium, for example, E. coli or S. aureus. In some embodiments, the adenosine deaminase is a TadA deaminase. In some embodiments, the TadA deaminase is an E. coli TadA deaminase (ecTadA). In some embodiments, the adenosine deaminase comprises a D108X mutation in SEQ ID NO: 1, or a corresponding mutation in another adenosine deaminase, wherein X is any amino acid other than the amino acid found in the wild-type protein. In some embodiments, X is G, N, V, A, or Y.

In some embodiments, the adenosine deaminase comprises a E155X mutation in SEQ ID NO: 1, or a corresponding mutation in another adenosine deaminase, wherein X is any amino acid other than the amino acid found in the wild-type protein. In some embodiments, X is D, G, or V. It should be appreciated that the adenosine deaminases provided herein may contain one or more of the mutations provided herein in any combination.

Some aspects of the disclosure provide a fusion protein comprising: (i) a Cas9 domain, and (ii) an adenosine deaminase, such as any of the adenosine deaminases provided herein. In some embodiments, the Cas9 domain of the fusion protein is a nuclease dead Cas9 (dCas9), a Cas9 nickase (nCas9), or a nuclease active Cas9. In some embodiments, the fusion protein further comprises an inhibitor of inosine base excision repair, for example a dISN or a single stranded DNA binding protein. In some embodiments, the fusion protein comprises one or more linkers used to attach an adenine deaminase (e.g., ecTadA) to a nucleic acid programmable DNA binding protein (e.g., Cas9). In some embodiments, the fusion protein comprises one or more nuclear localization sequences (NLS).

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

FIG. 12 shows the colony forming units (C.F.U.) of various constructs challenged on increasing concentrations of chloramphenicol. The construct numbers correspond to those listed in FIG. 11.

FIG. 15 is a schematic showing the development of ABE.

FIG. 16 is a table showing the results of clones assayed after second round evolution. Columns 1, 8, and 10 represent mutations from the first round evolution. Columns 11 and 14 represent the consensus mutations from second round evolution.

Figure 21:
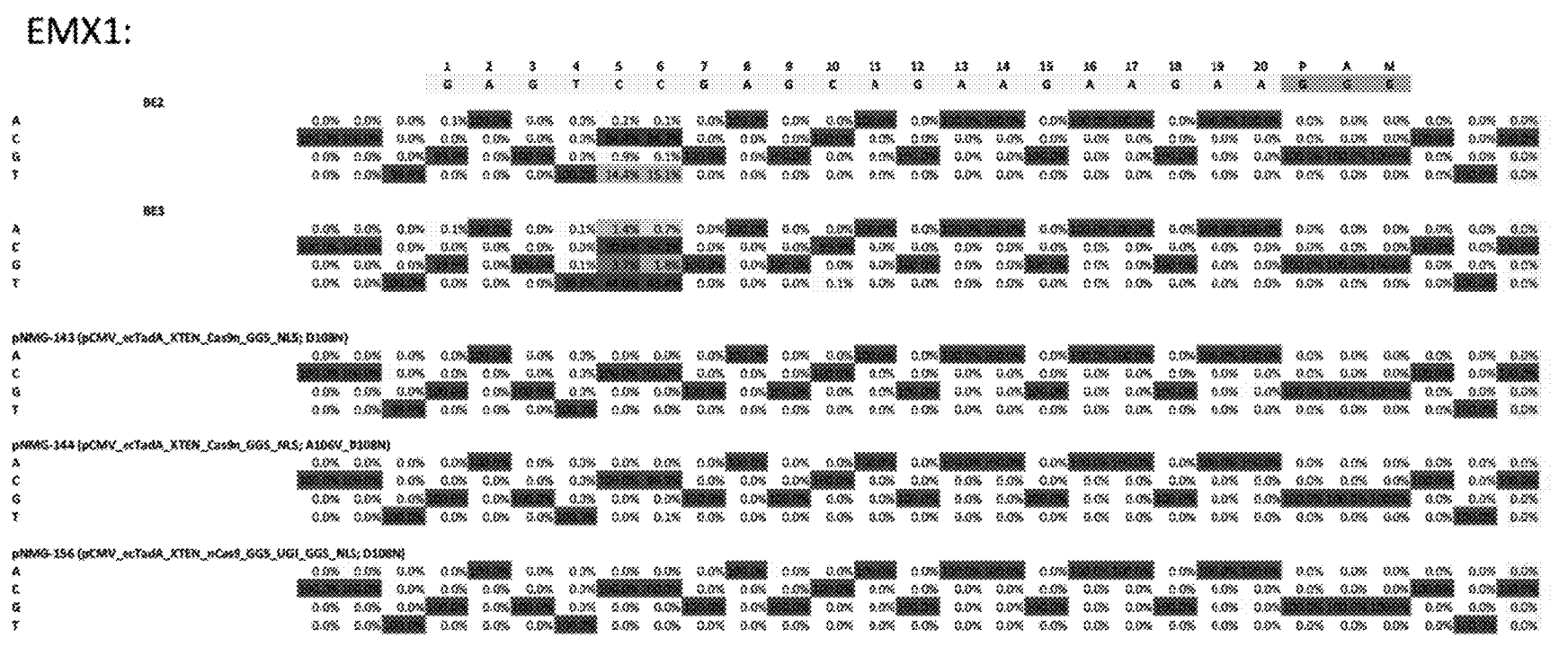

FIG. 21 shows that ABE operates best on 1 of 6 genomic sites tested. The sequence corresponds to SEQ ID NO: 46.

FIG. 24 shows inactive C-terminal Cas9 fusions of ecTadA for pNMG-174 through pNMG-177. The sequence corresponds to SEQ ID NO: 41.

FIG. 25 shows the editing results from ecTadA nucleobase editors (pNMG-143, pNMG-144, pNMG-164, and pNMG-177). The sequence corresponds to SEQ ID NO: 41.

FIG. 26 shows the editing results from ecTadA nucleobase editors (pNMG-164, pNMG-177, pNMG-178, pNMG-179, and pNMG-180). The sequence corresponds to SEQ ID NO: 41.

FIG. 27 shows the results of editing at the Hek-3 site. The sequence corresponds to SEQ ID NO: 42.

Figure 28:
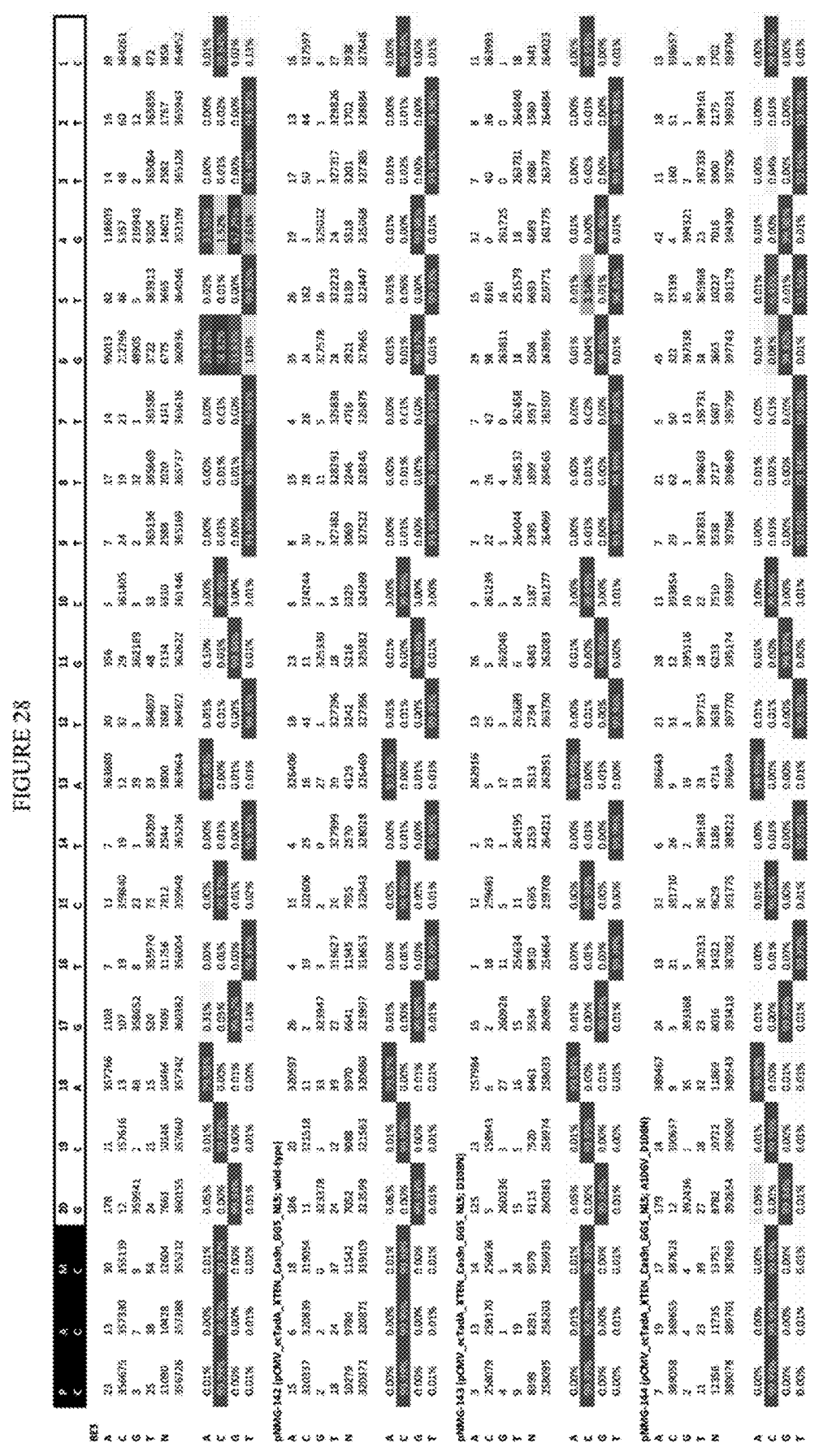
Figure 28:
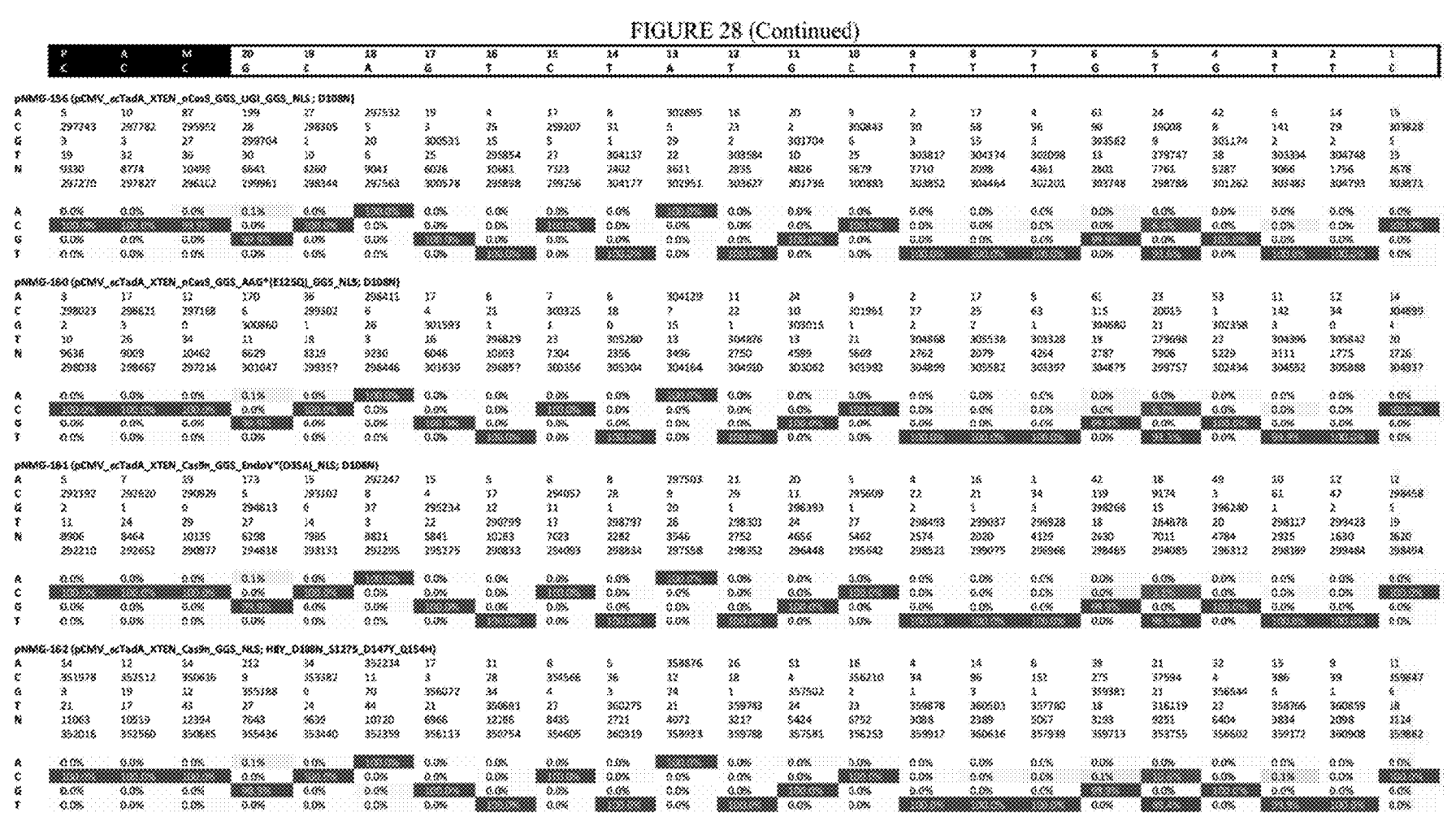
Figure 28:
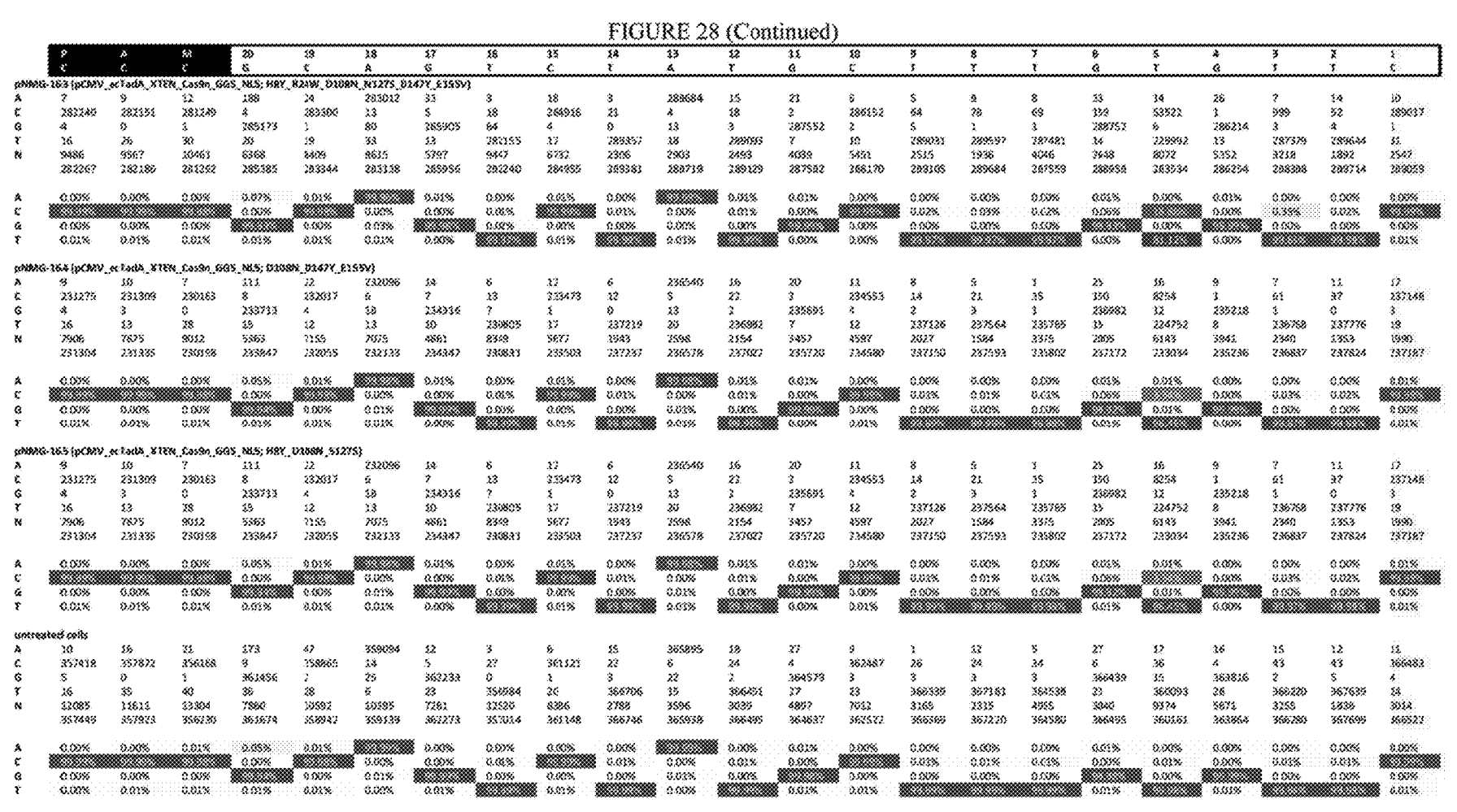

FIG. 28 shows the results of editing at the Hek-2 site. The sequence corresponds to SEQ ID NO: 41.

Figure 29:
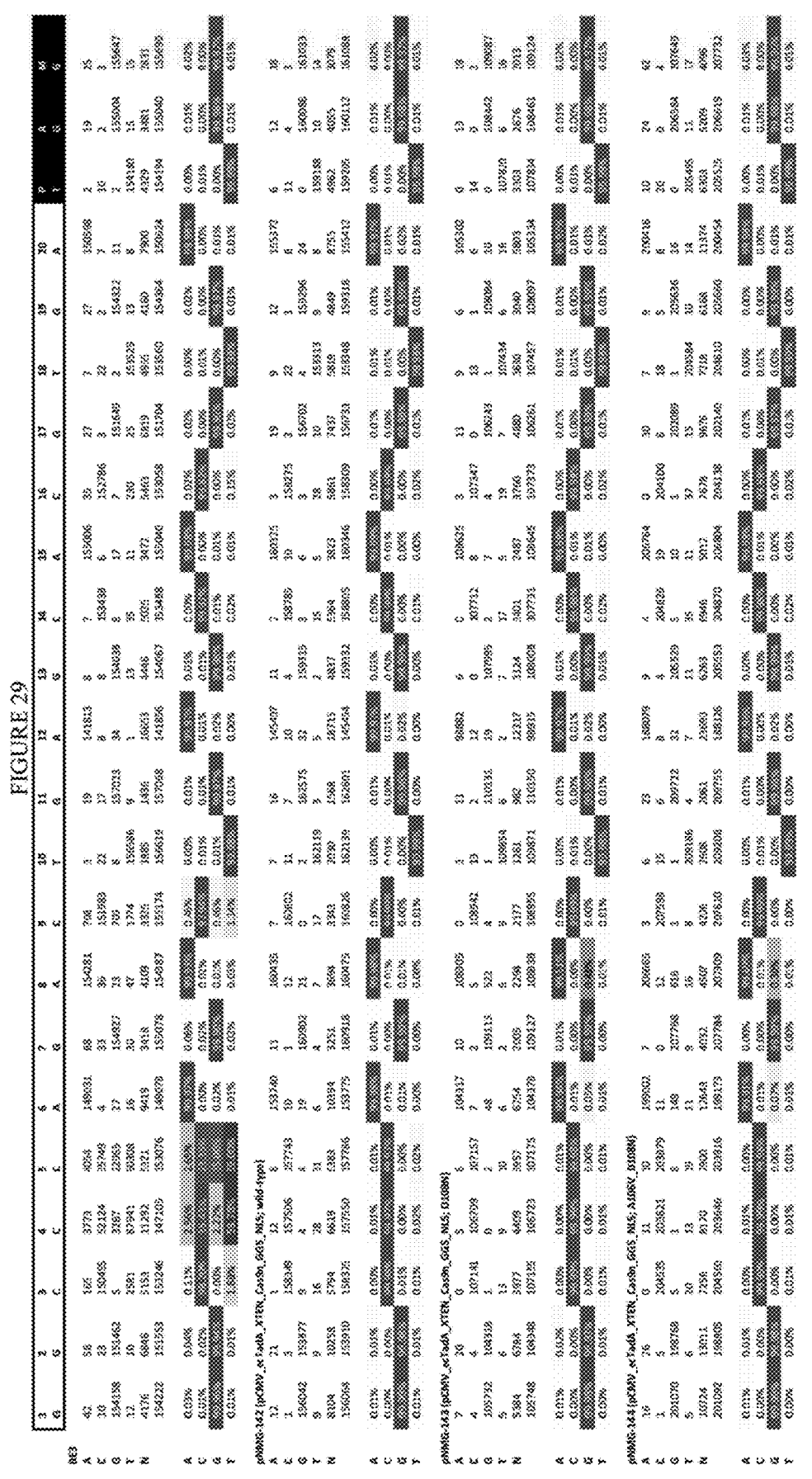
Figure 29:
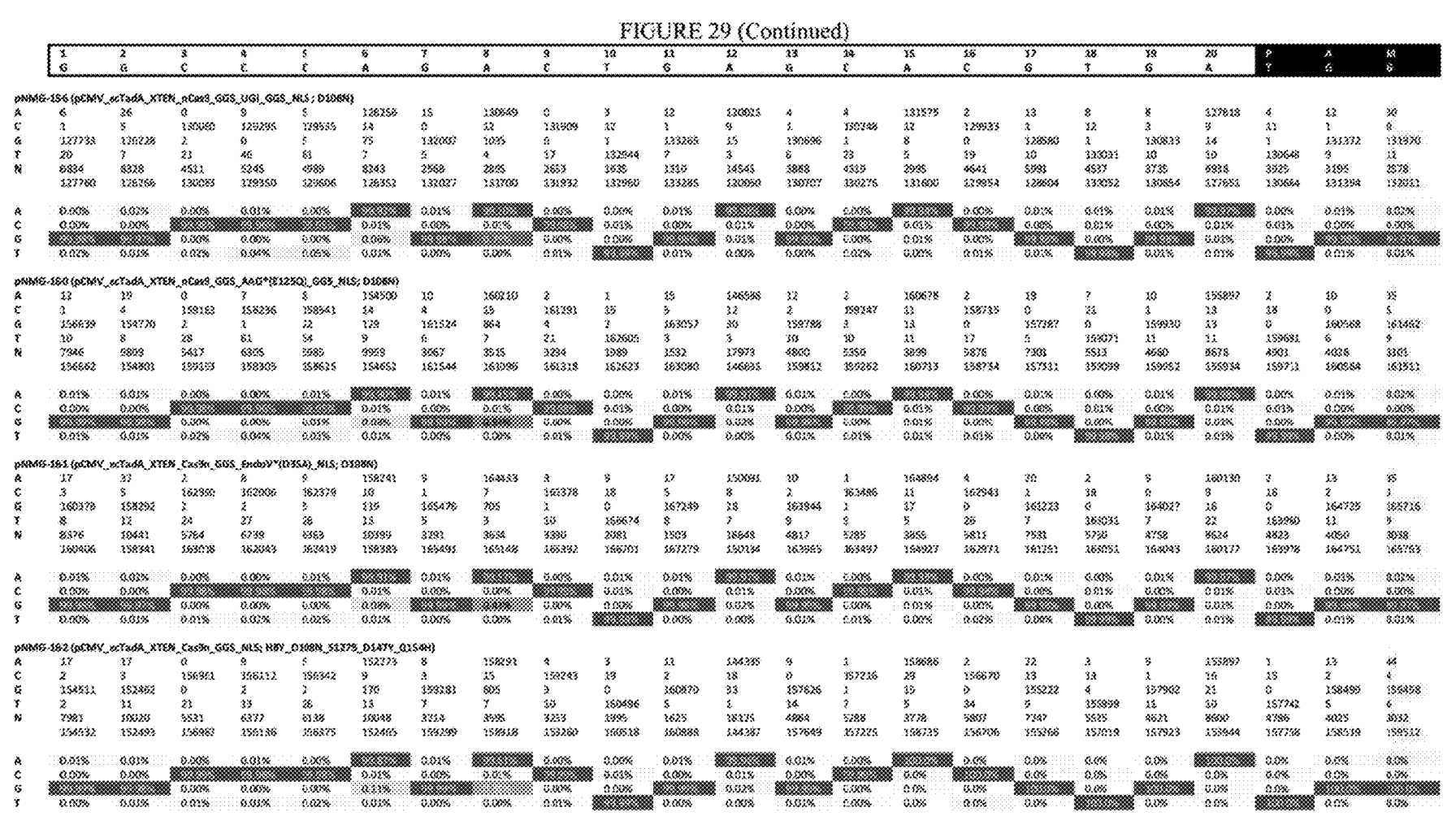
Figure 29:
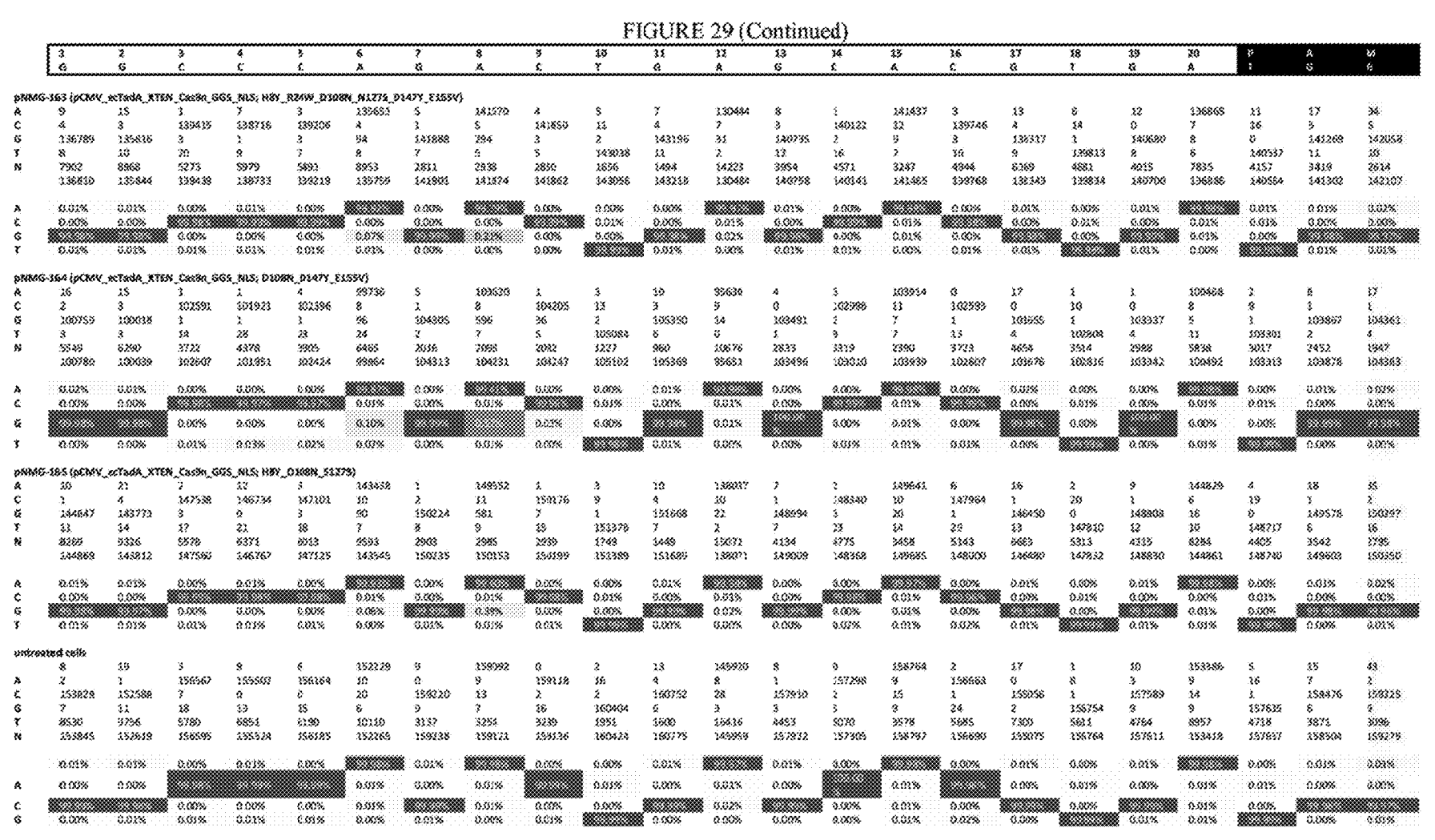

FIG. 29 shows the results of editing at the Hek-3 site. The sequence corresponds to SEQ ID NO: 42.

Figure 30:
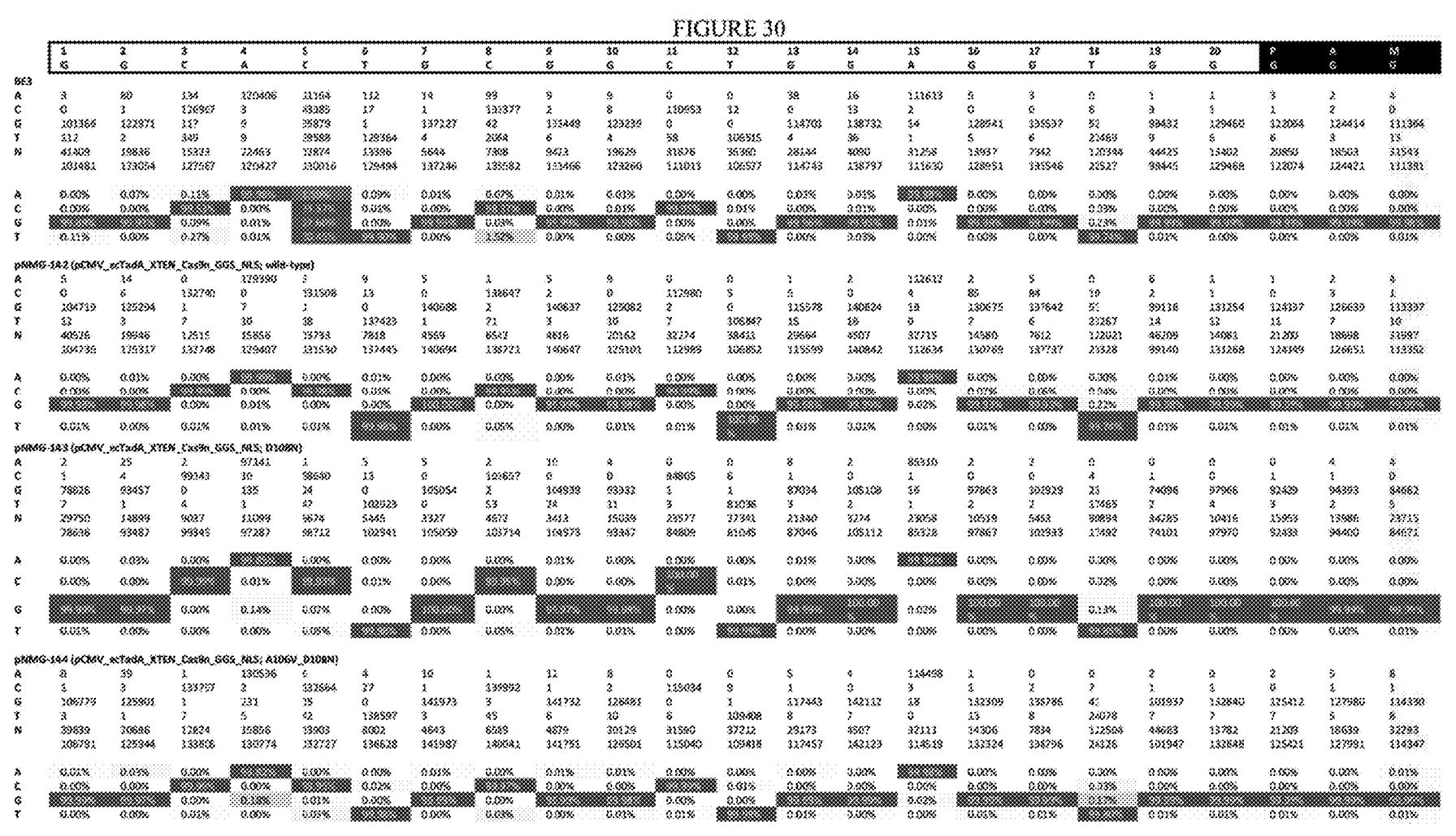
Figure 30:
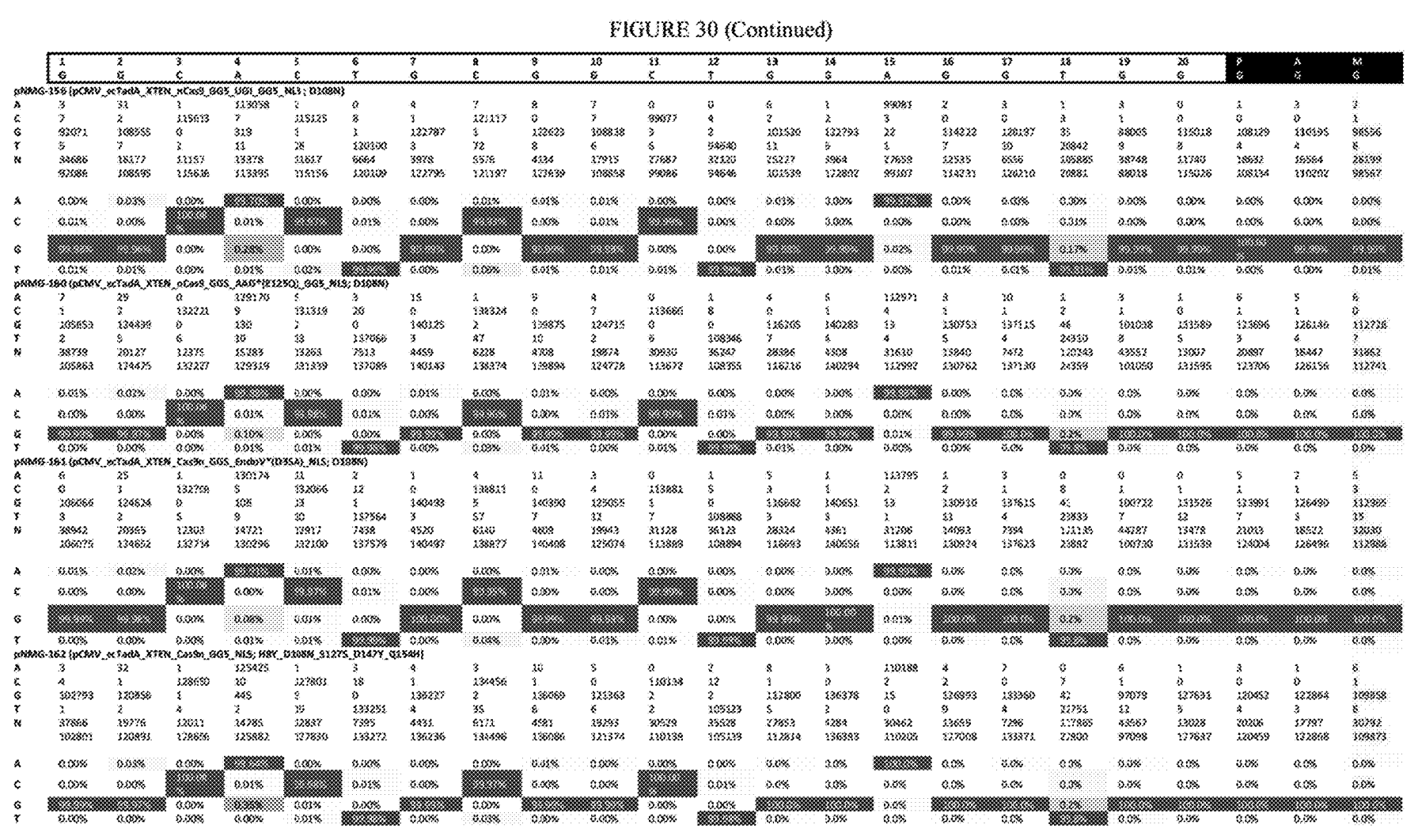
Figure 30:
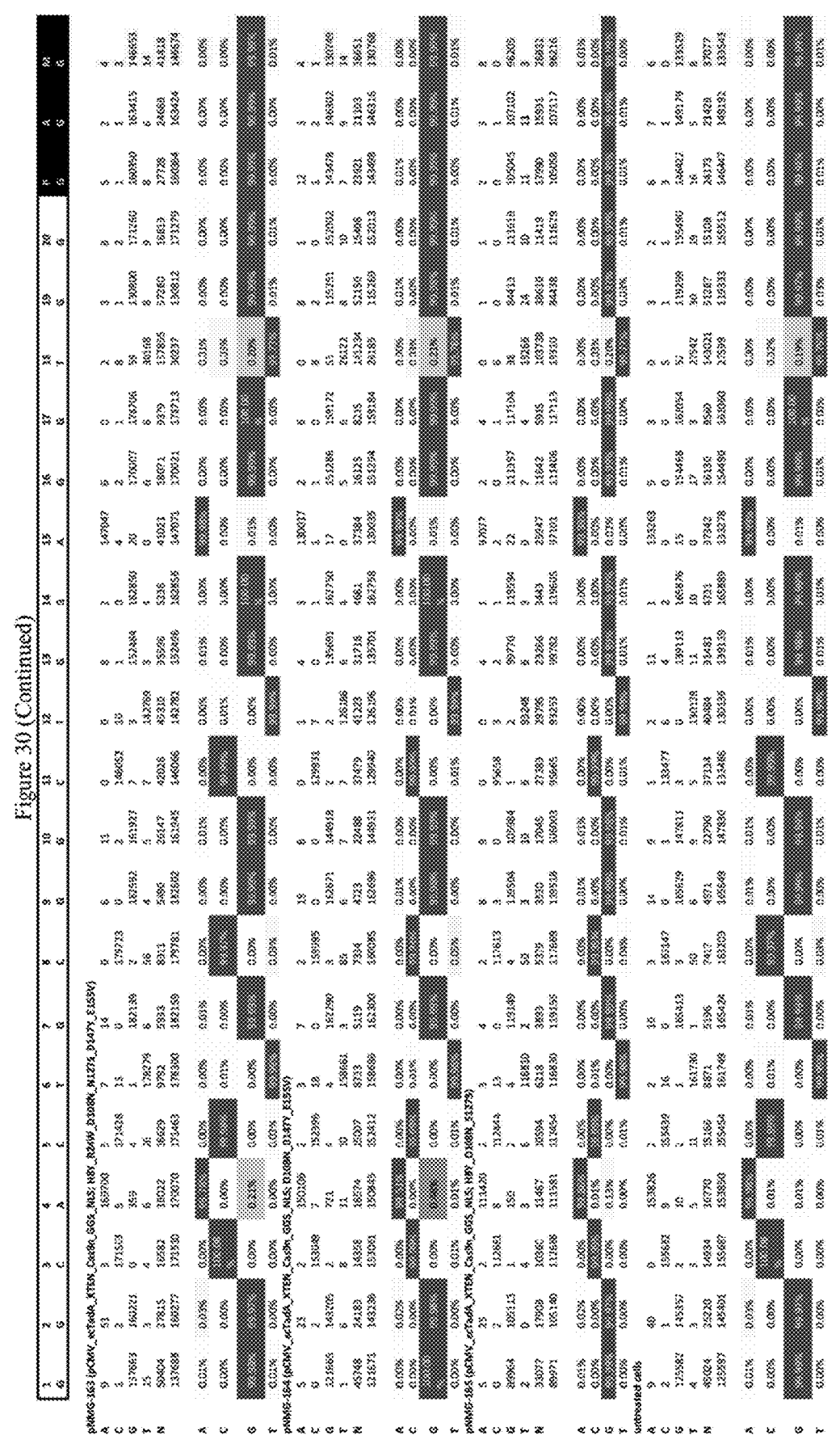

FIG. 30 shows the results of editing at the Hek-4 site. The sequence corresponds to SEQ ID NO: 43.

Figure 31:
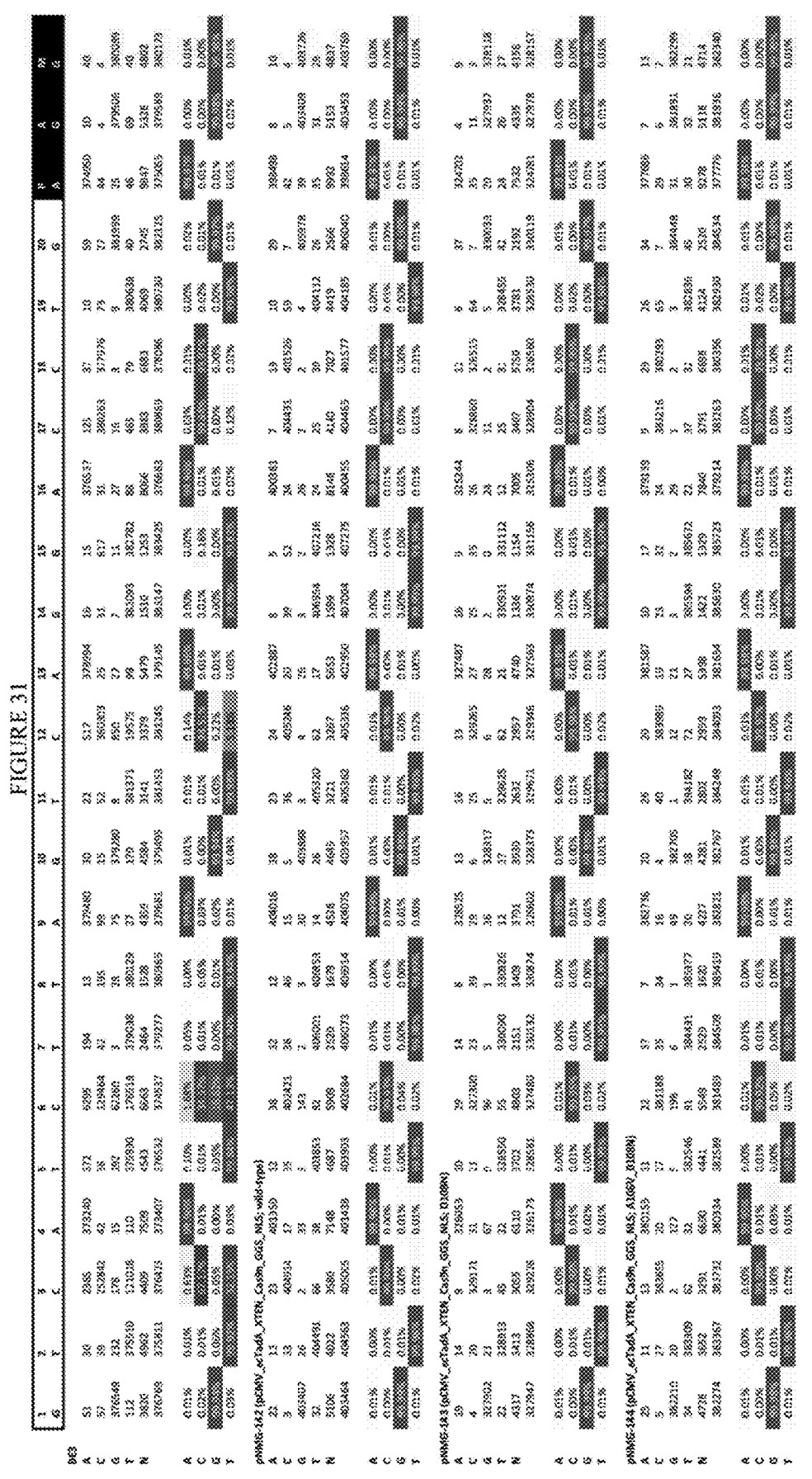
Figure 31:
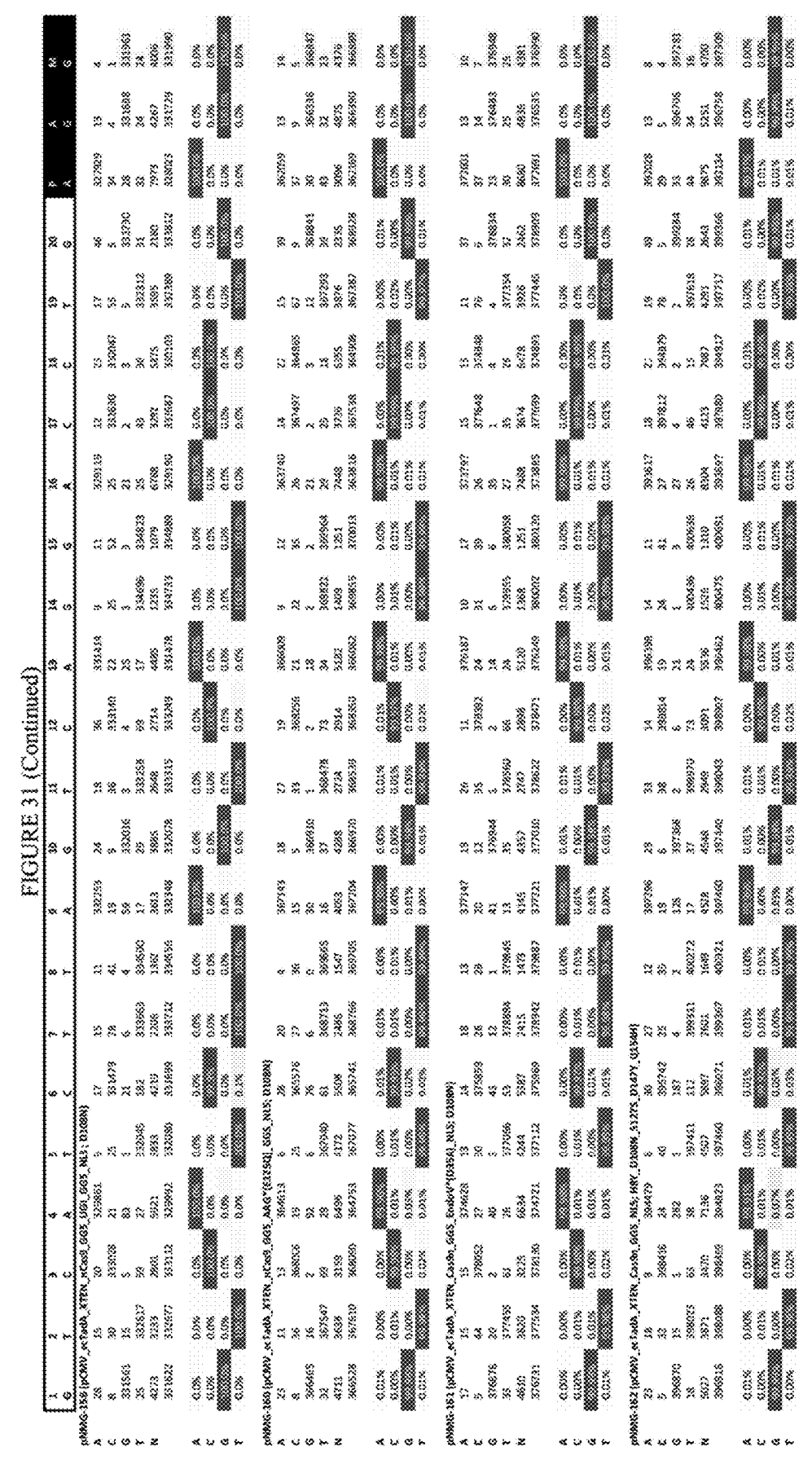
Figure 31:
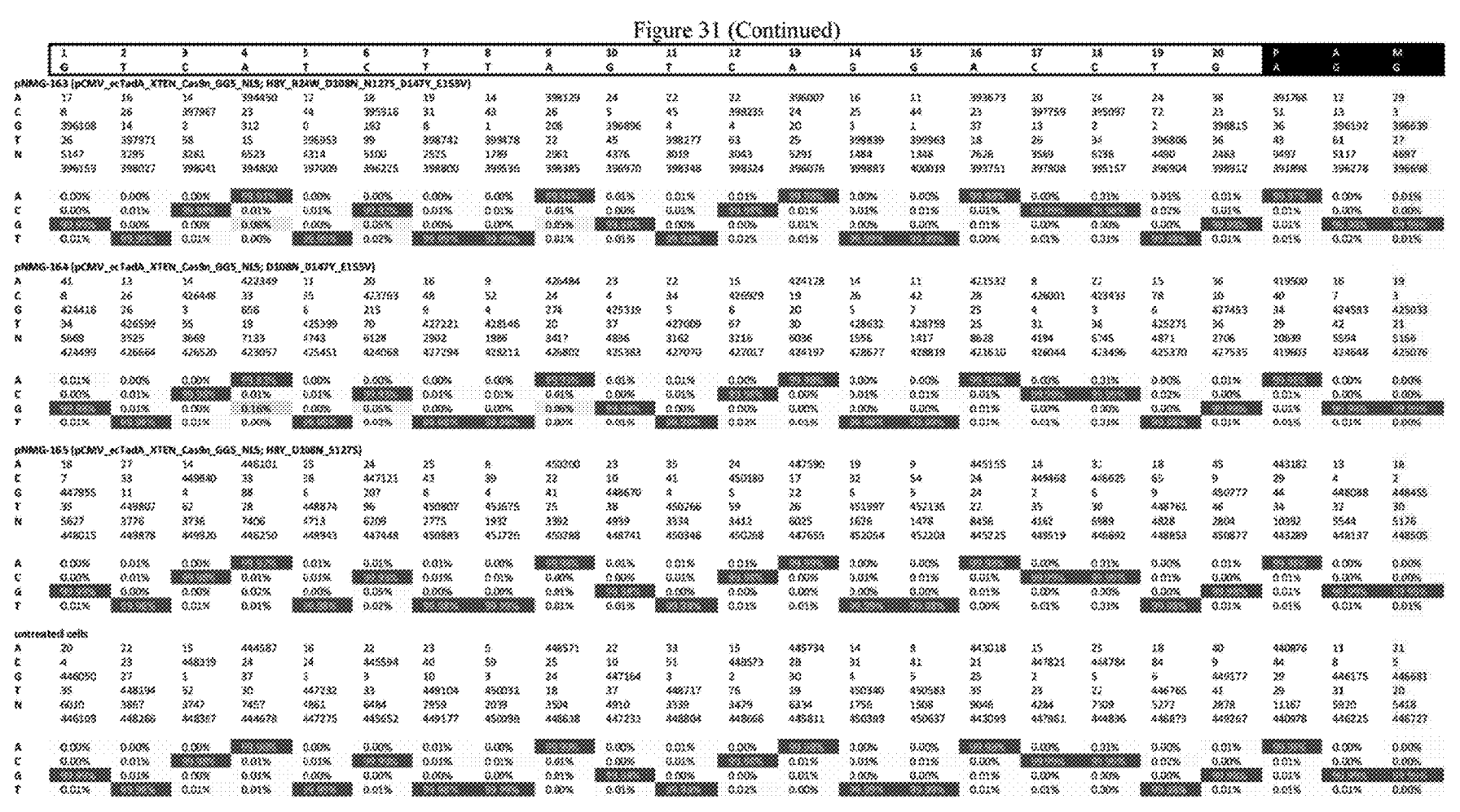

FIG. 31 shows the results of editing at the RNF-2 site. The sequence corresponds to SEQ ID NO: 44.

Figure 32:
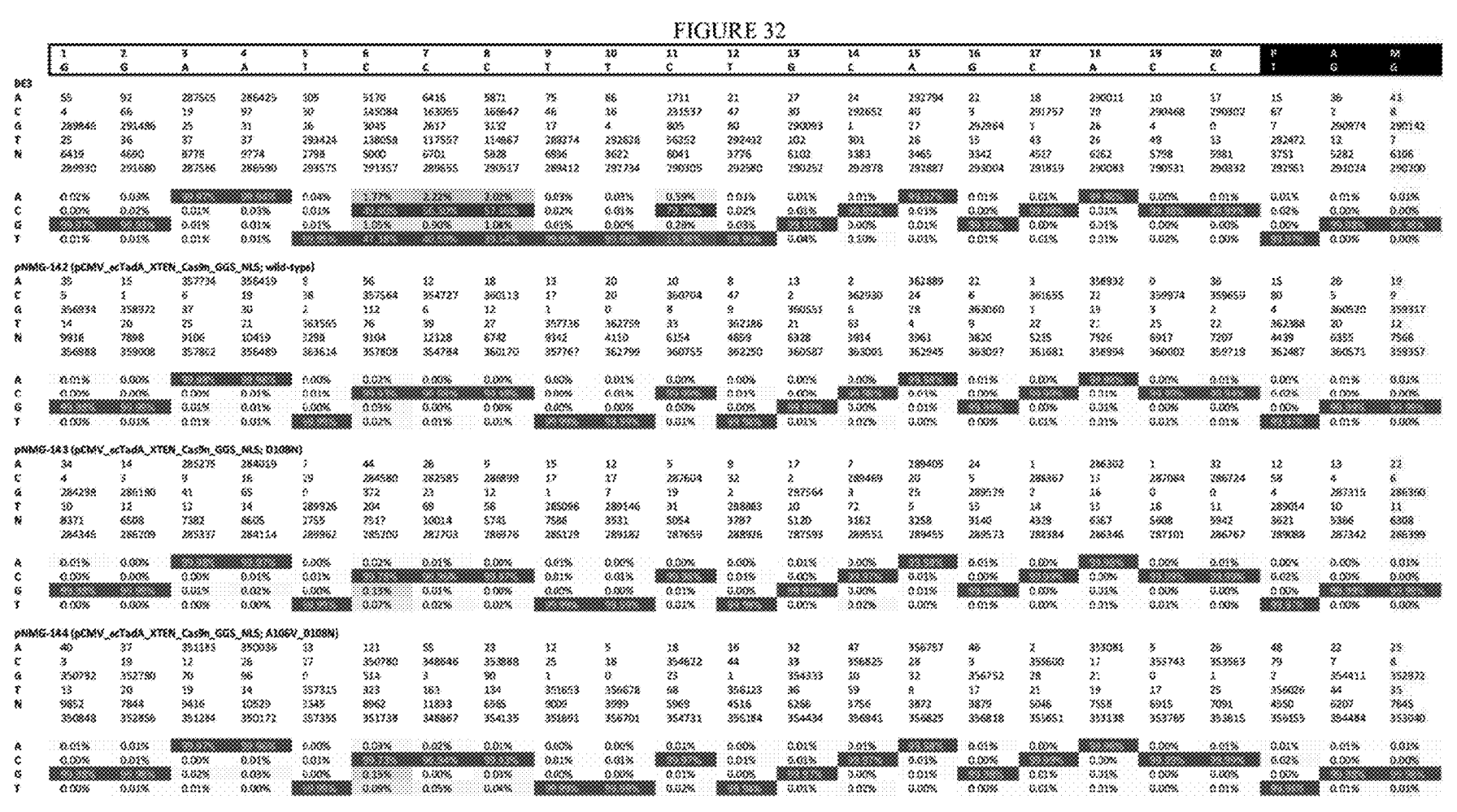
Figure 32:
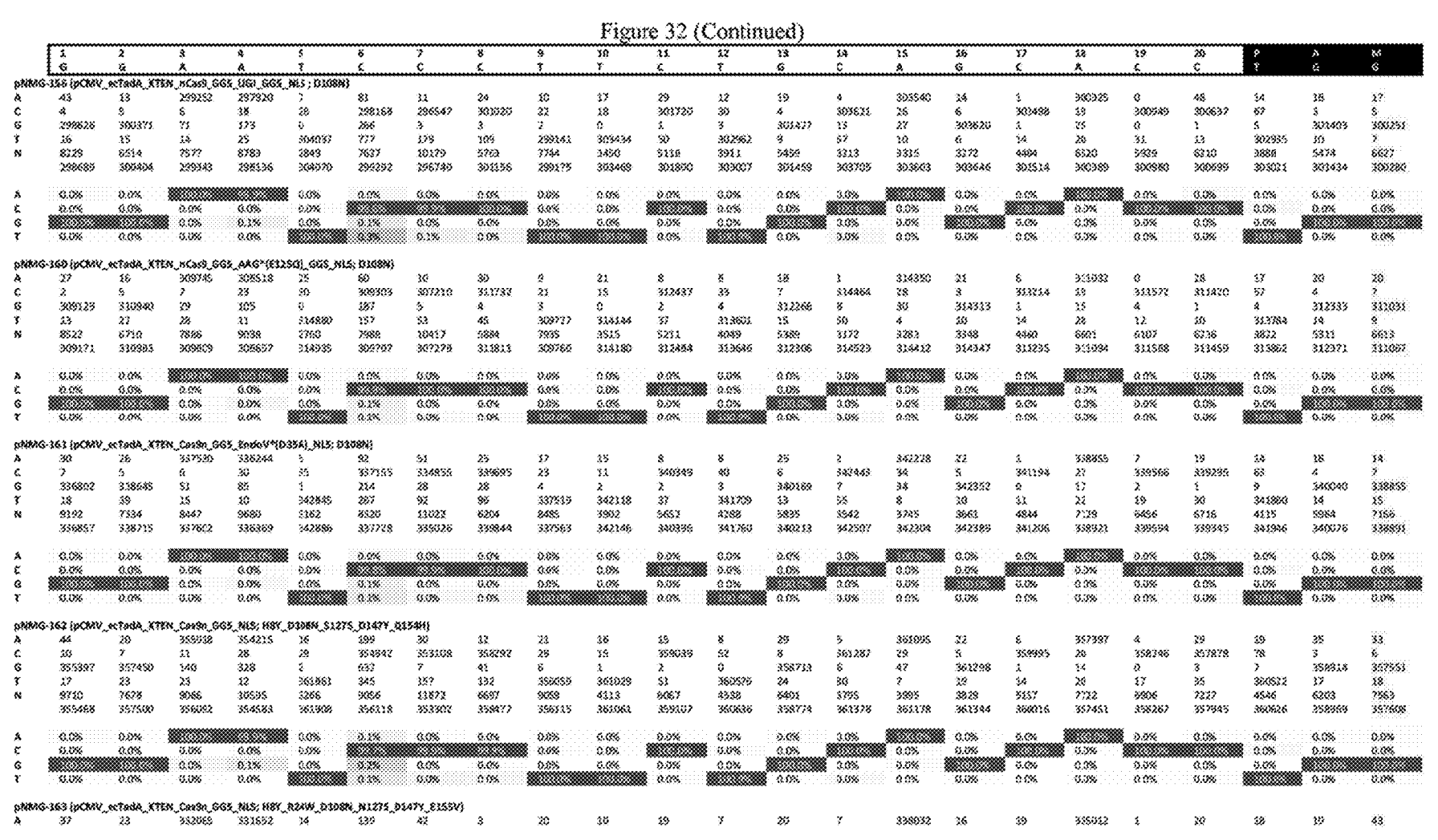
Figure 32:
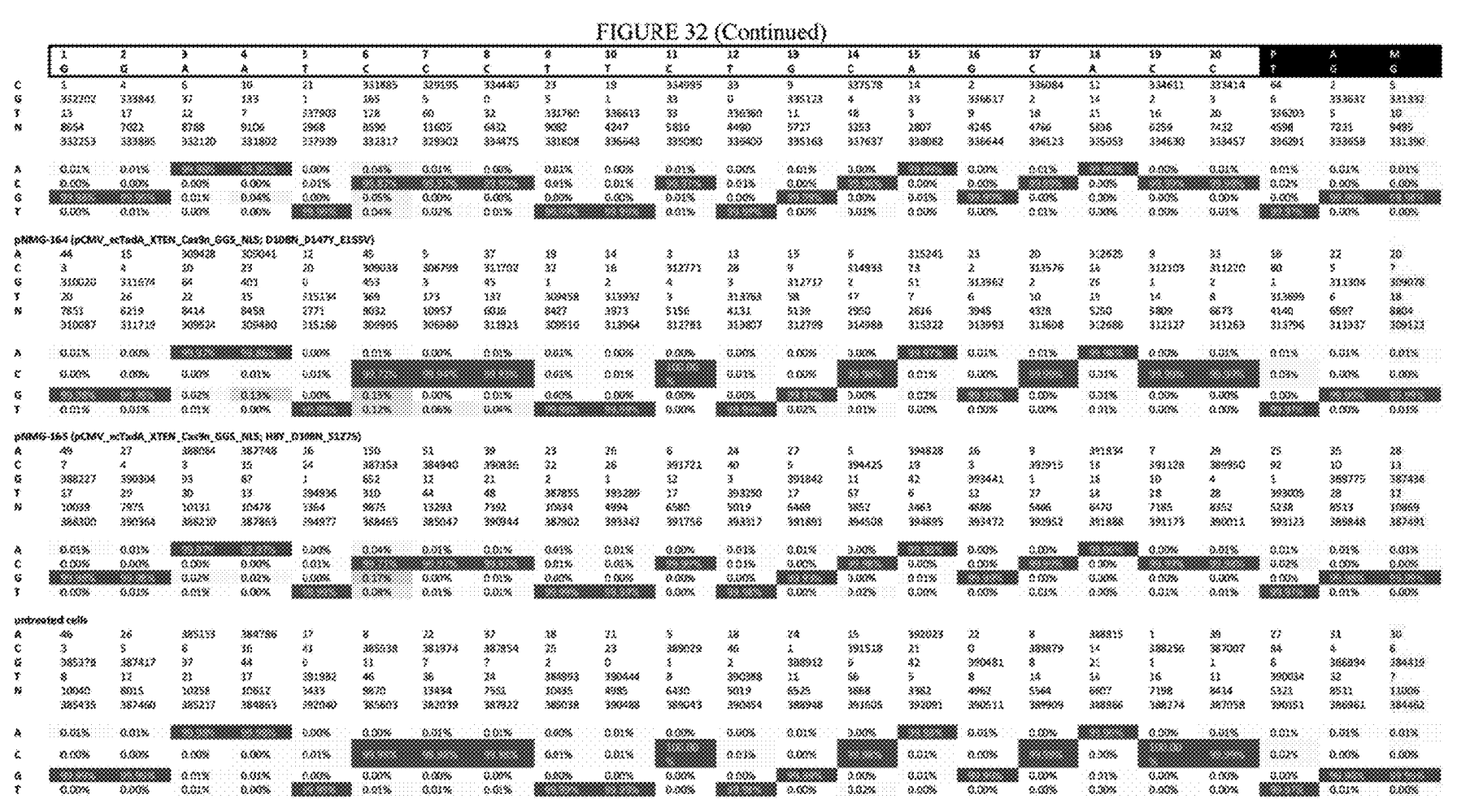

FIG. 32 shows the results of editing at the FANCF site. The sequence corresponds to SEQ ID NO: 45.

Figure 33:
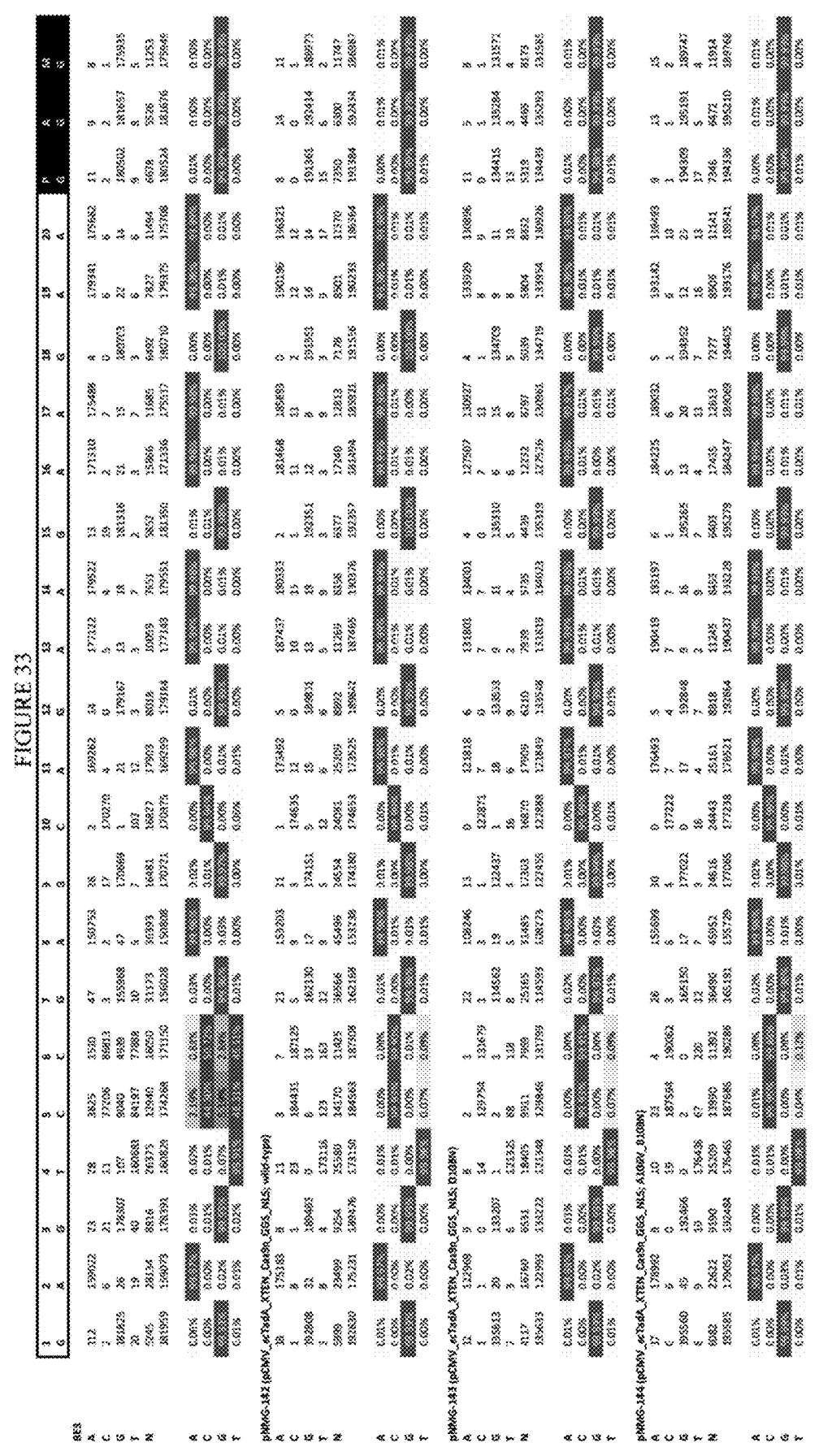
Figure 33:
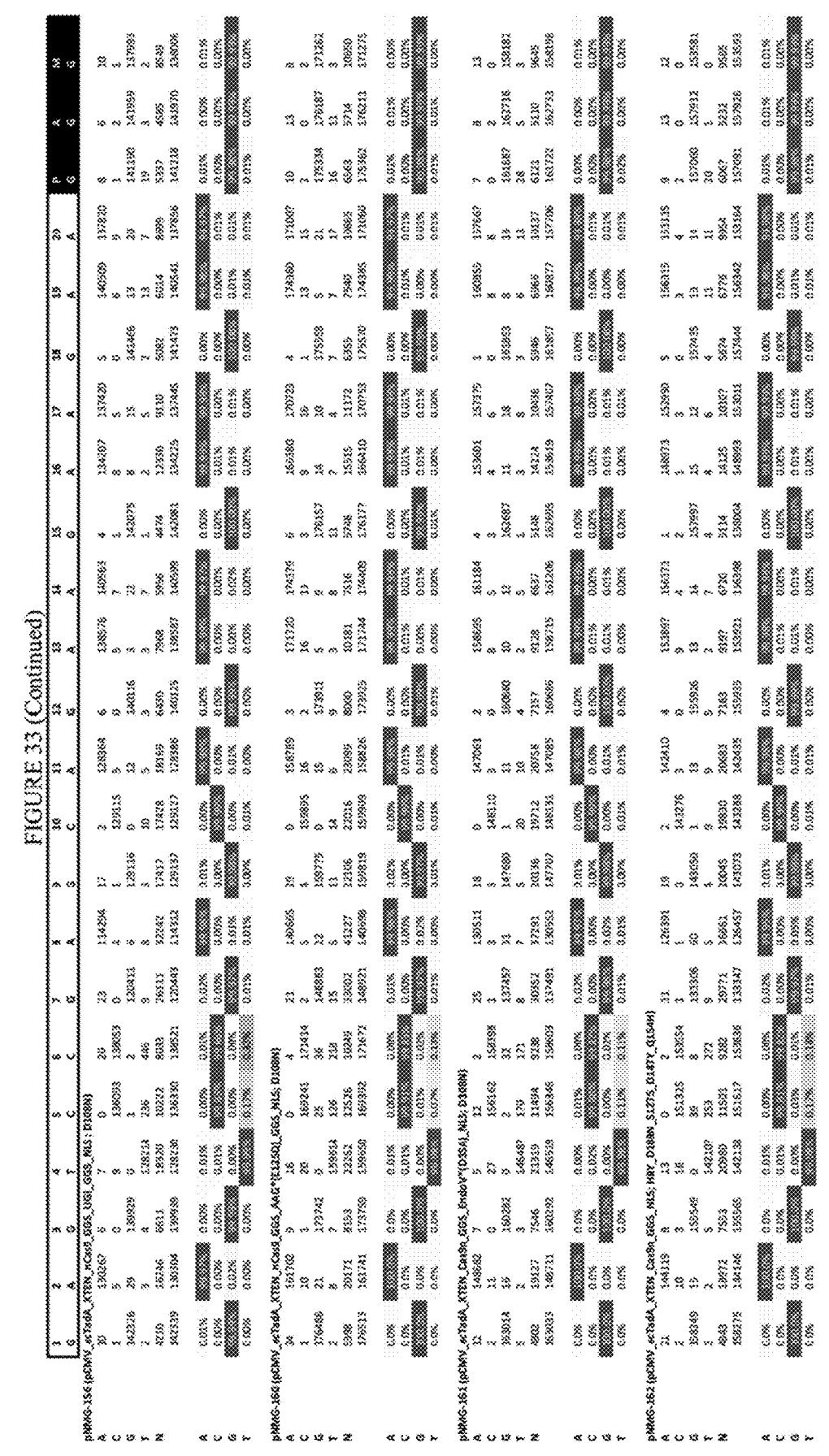
Figure 33:
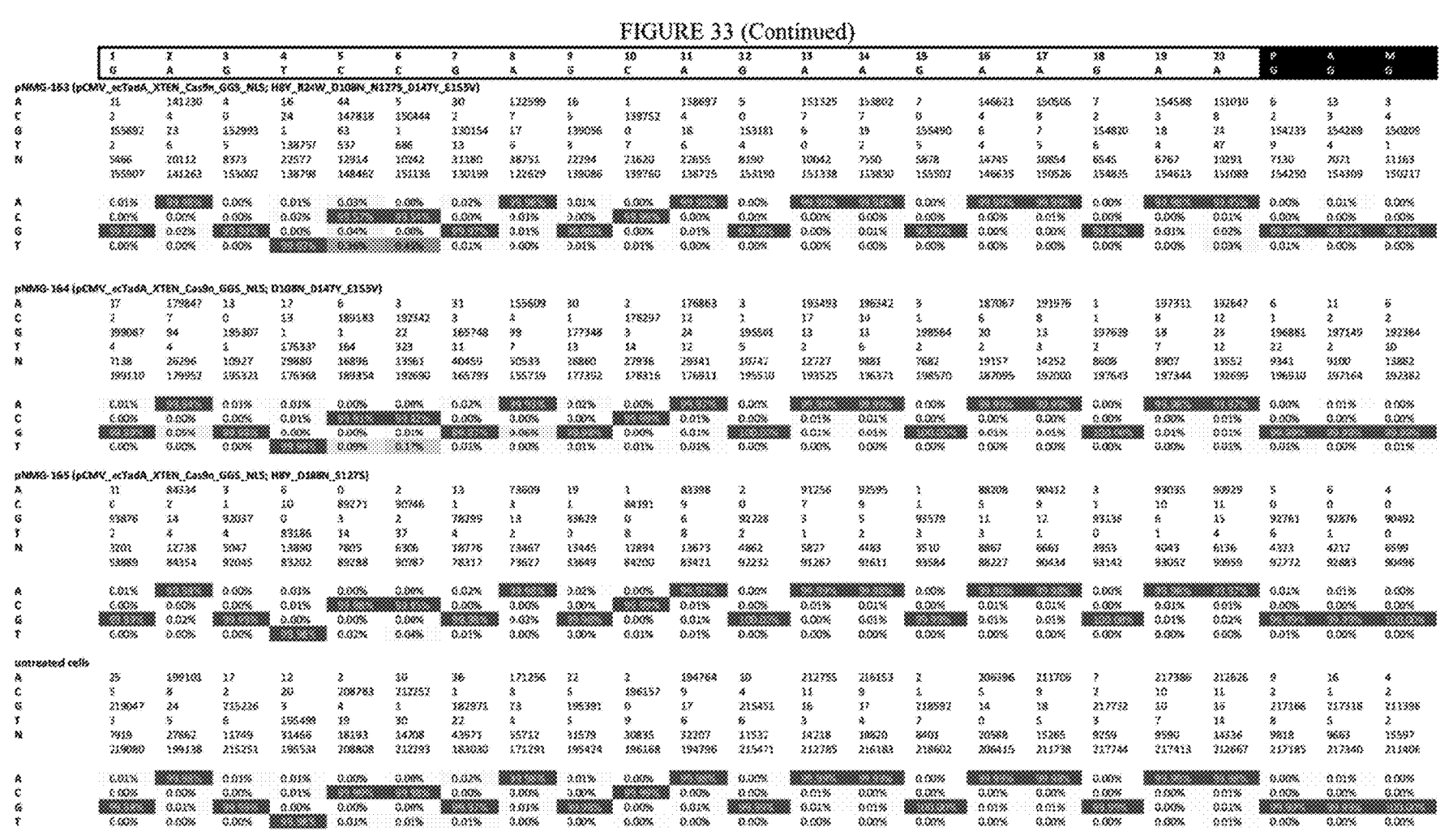

FIG. 33 shows the results of editing at the EMX-1 site. The sequence corresponds to SEQ ID NO: 46.

Figure 34:
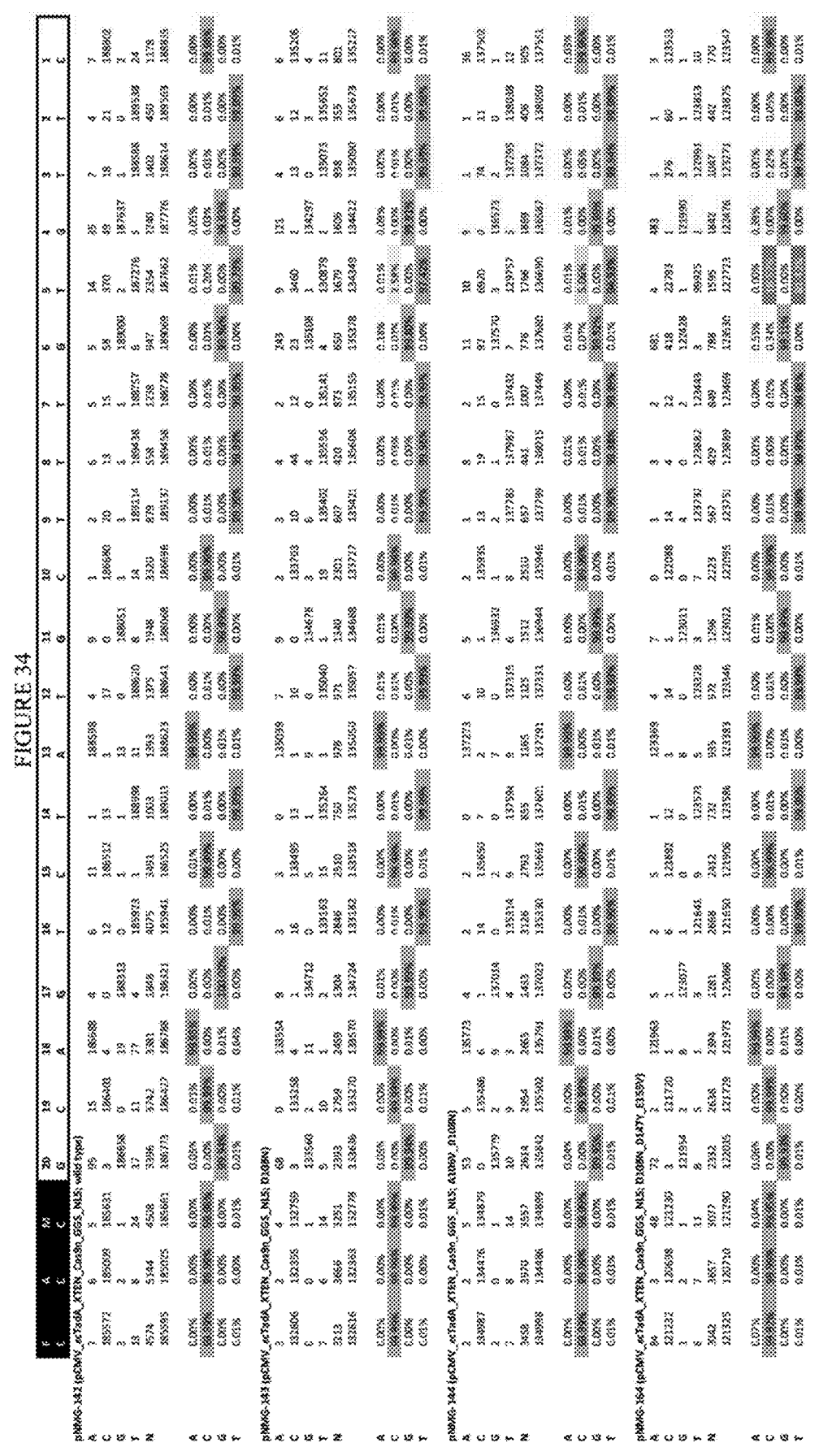
Figure 34:
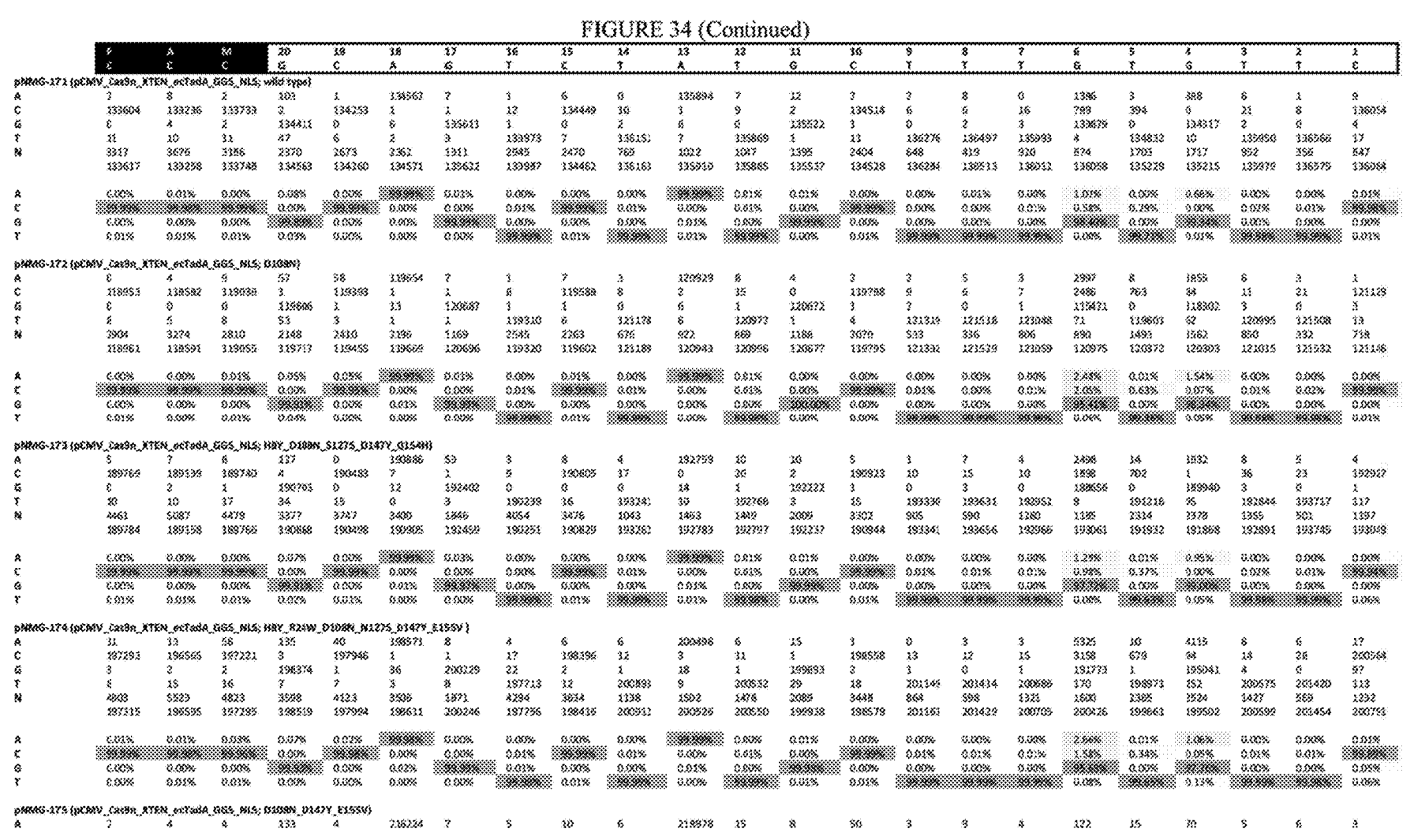
Figure 34:
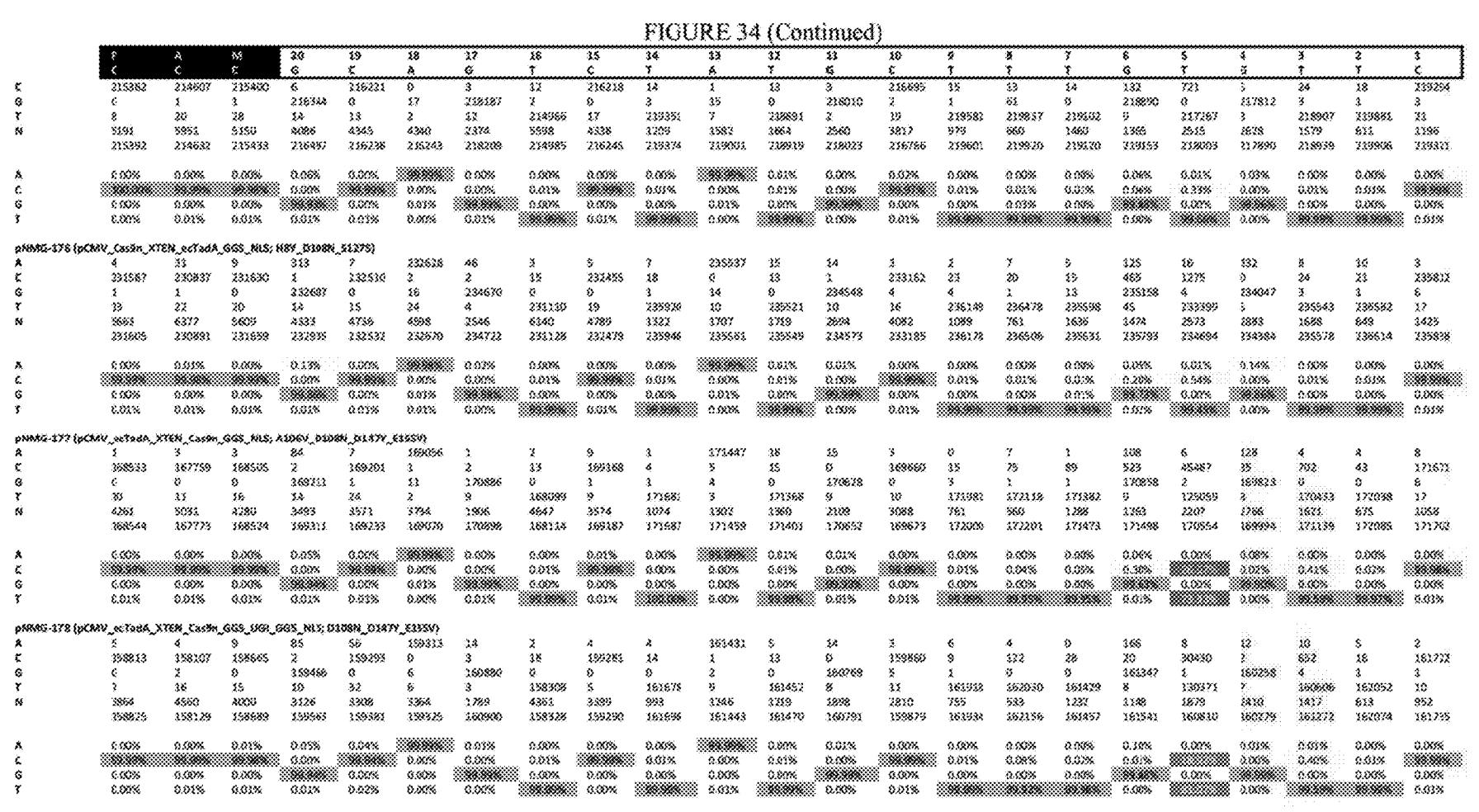
Figure 34:
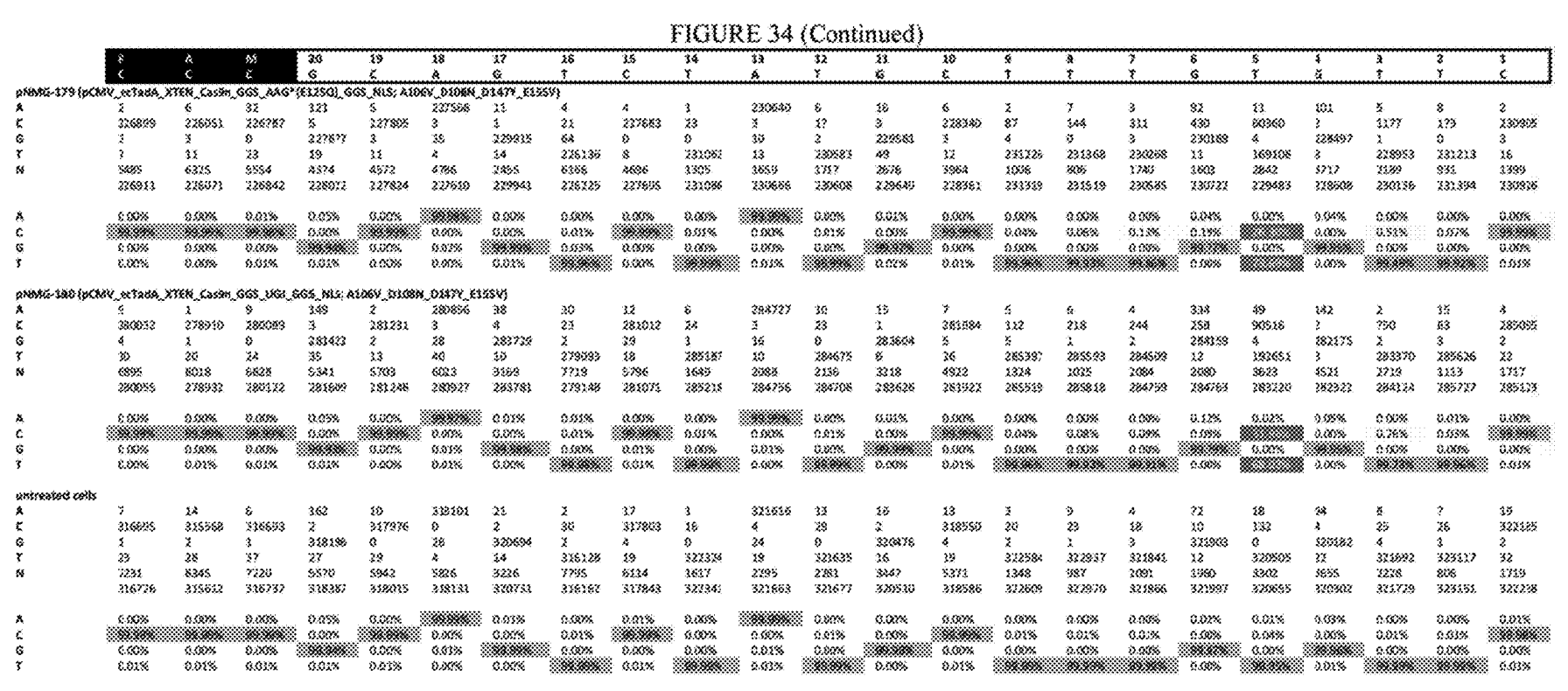

FIG. 34 shows the results of C-terminal fusion at the Hek-2 site. The sequence corresponds to SEQ ID NO: 41.

Figure 35:
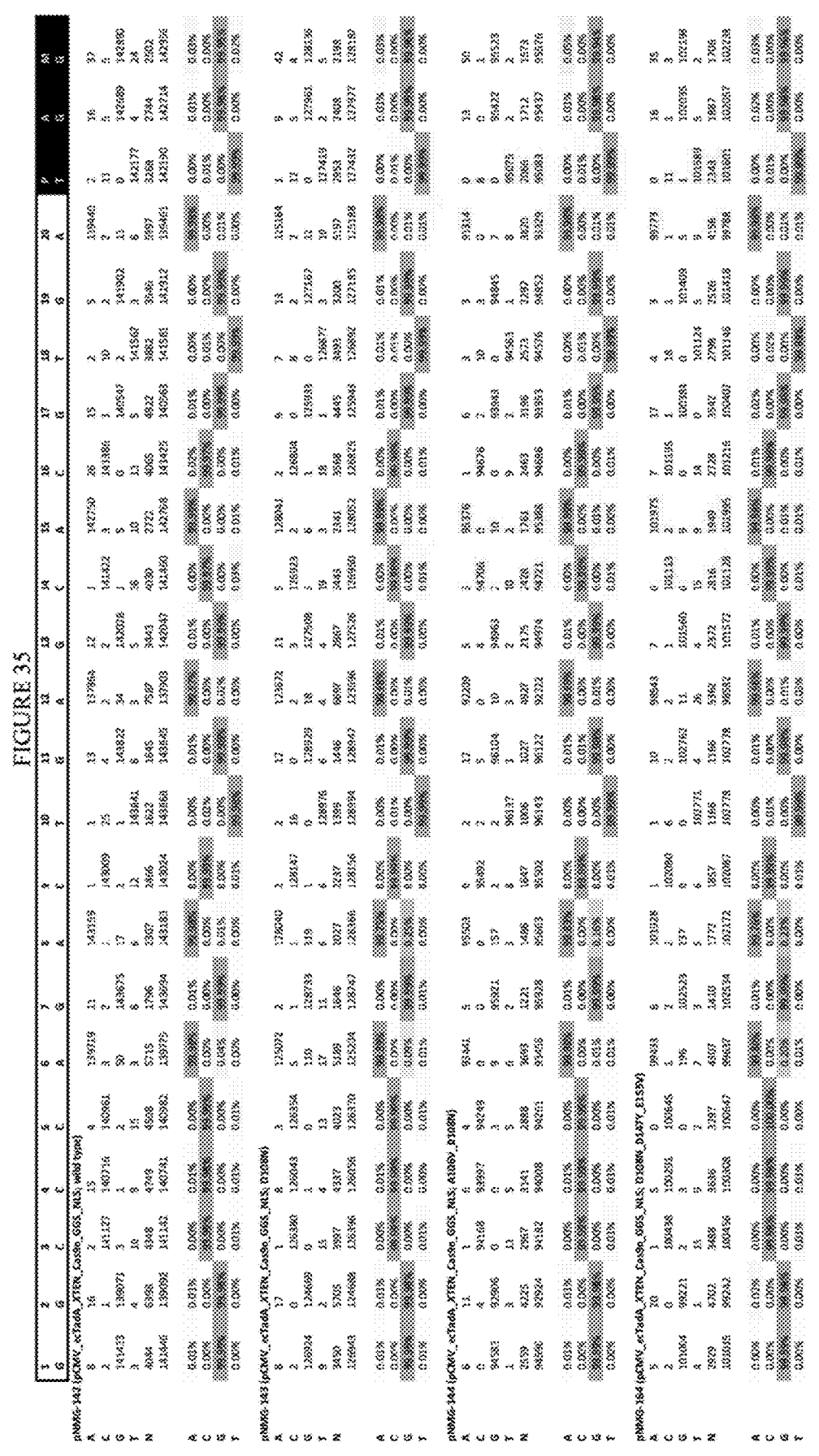
Figure 35:
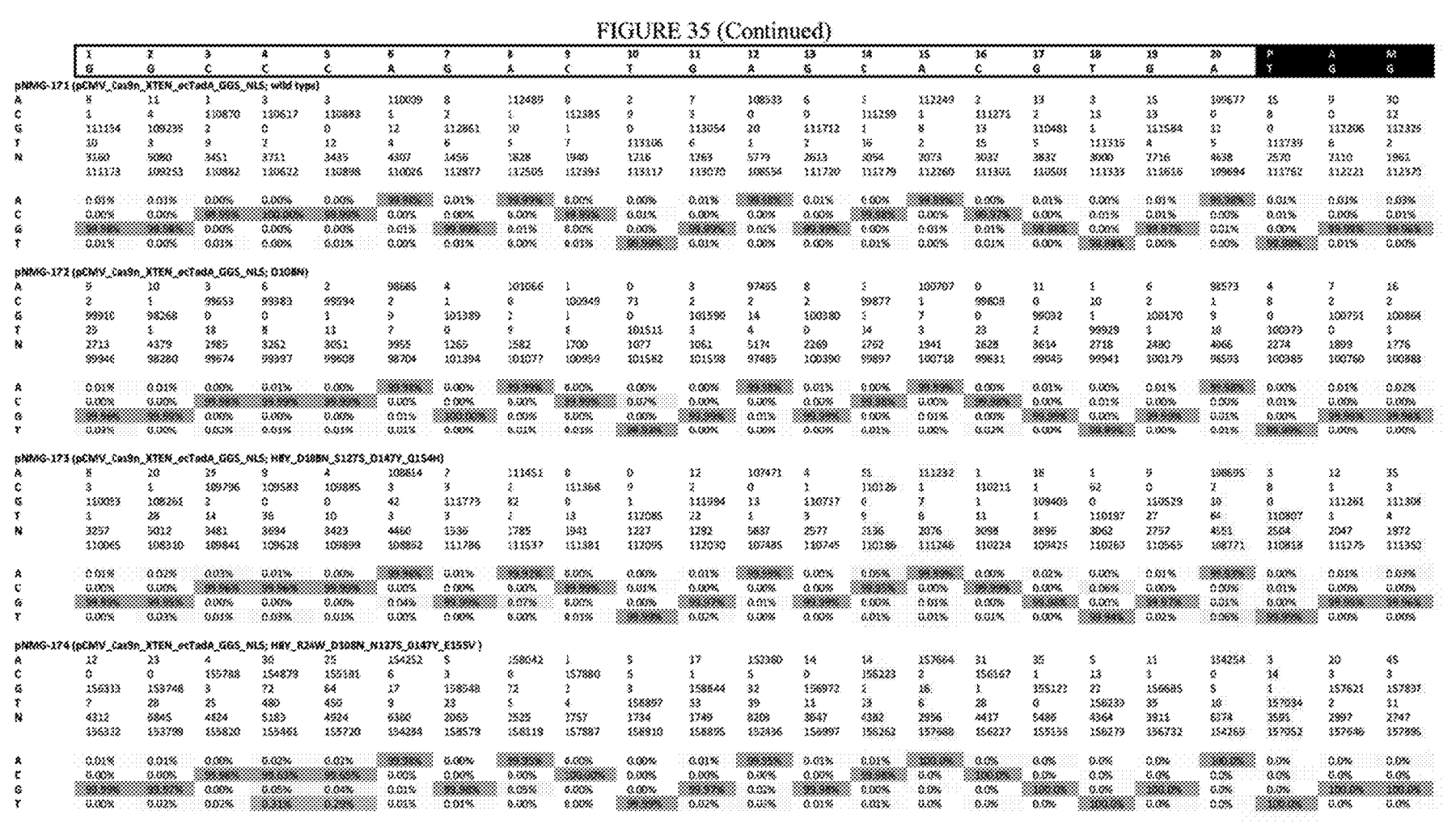
Figure 35:
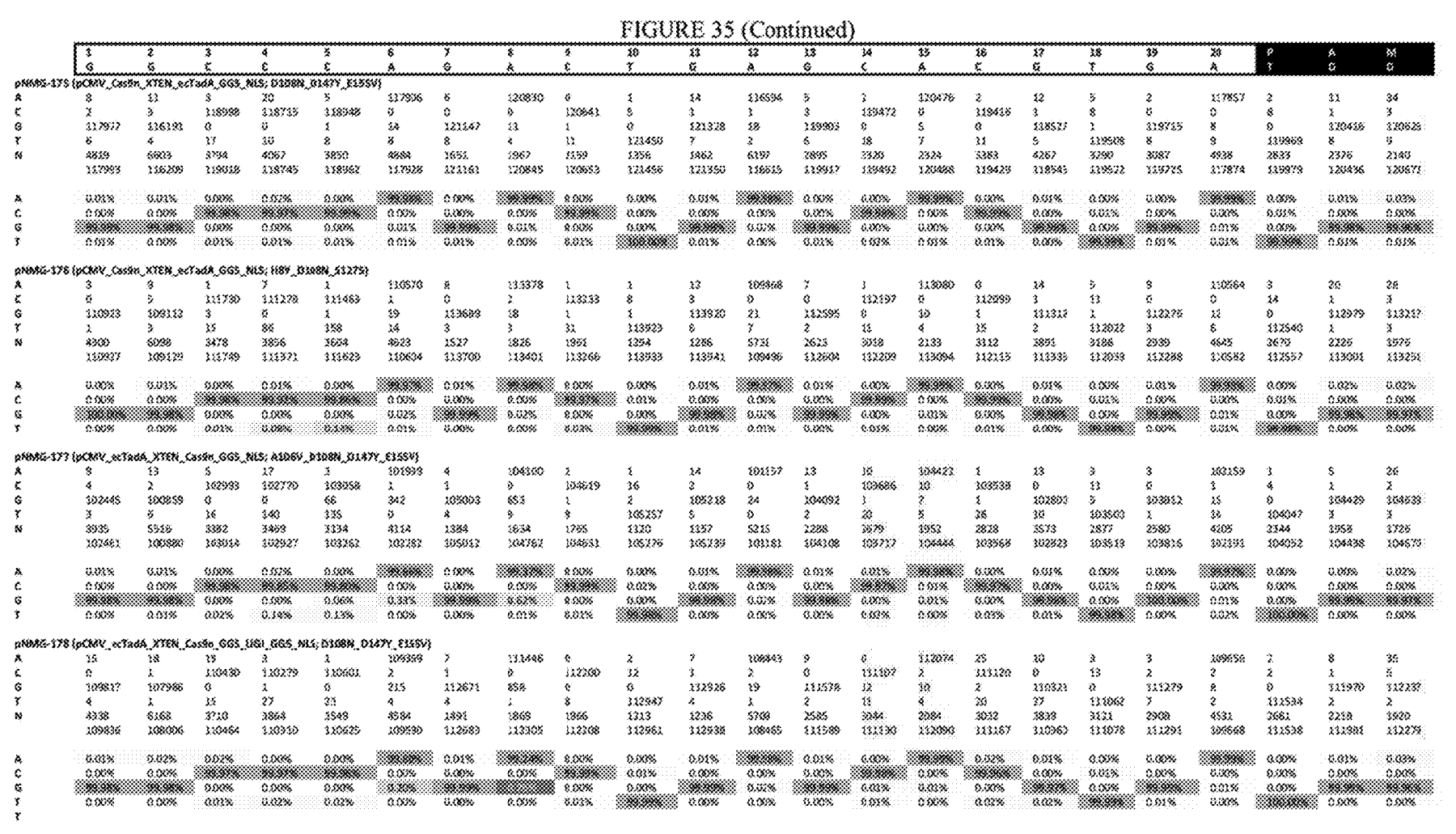
Figure 35:
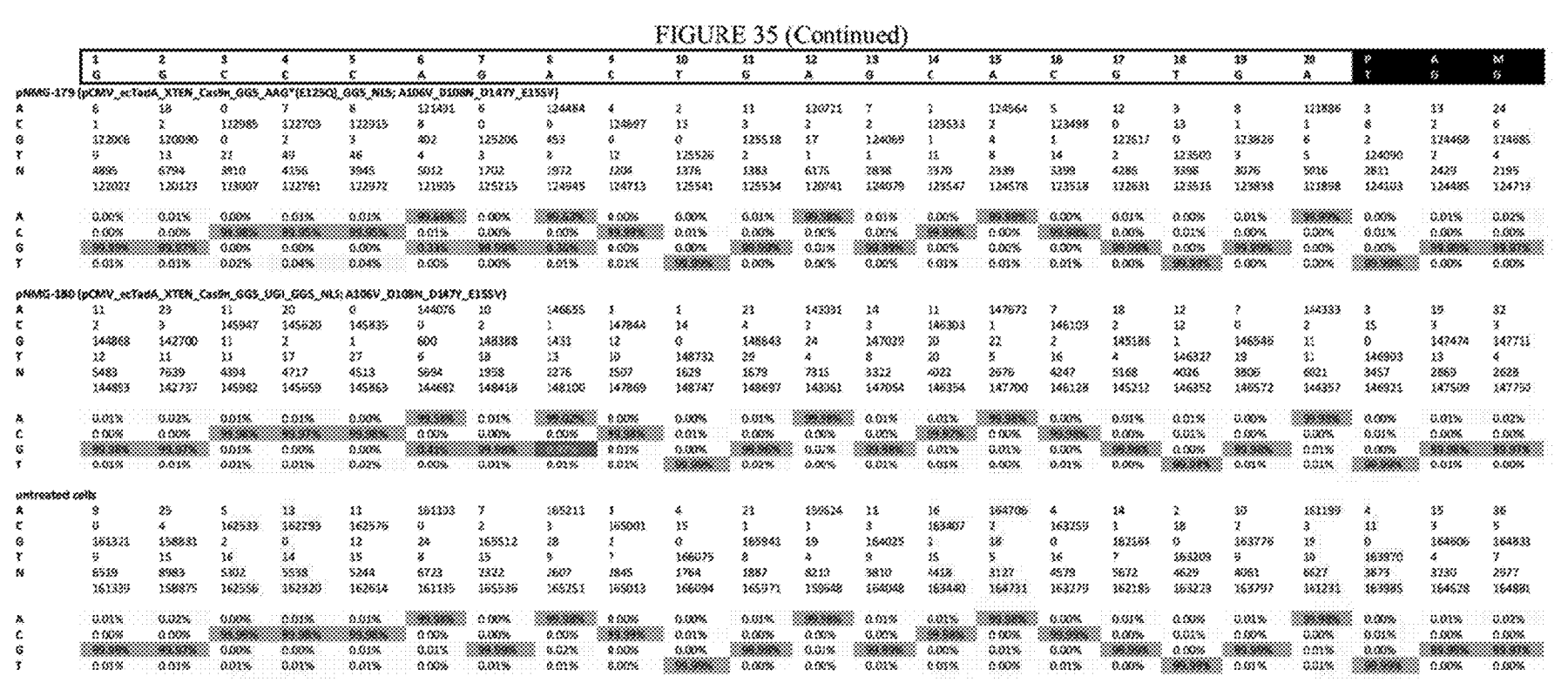

FIG. 35 shows the results of C-terminal fusion at the Hek-3 site. The sequence corresponds to SEQ ID NO: 42.

Figure 36:
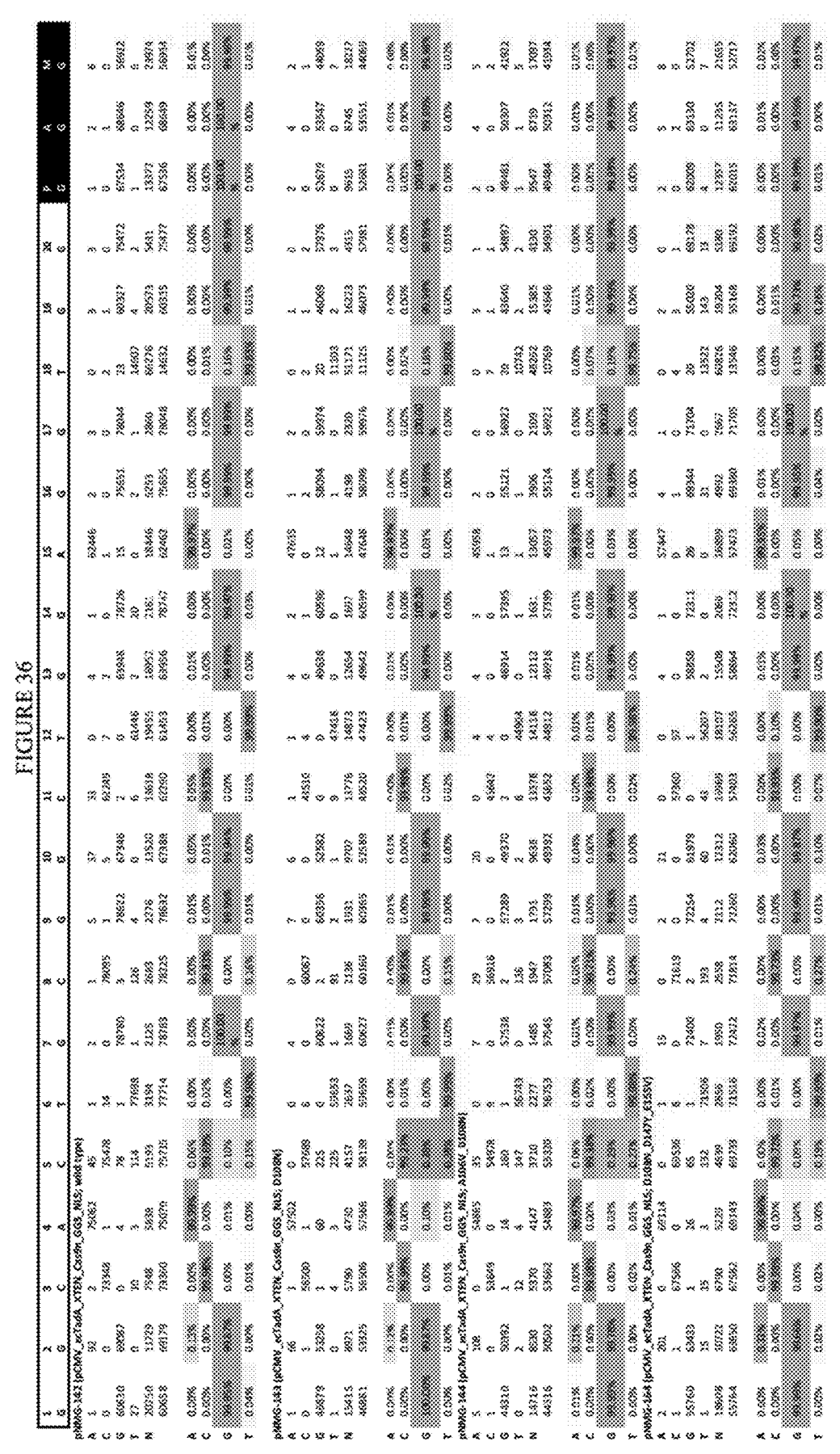
Figure 36:
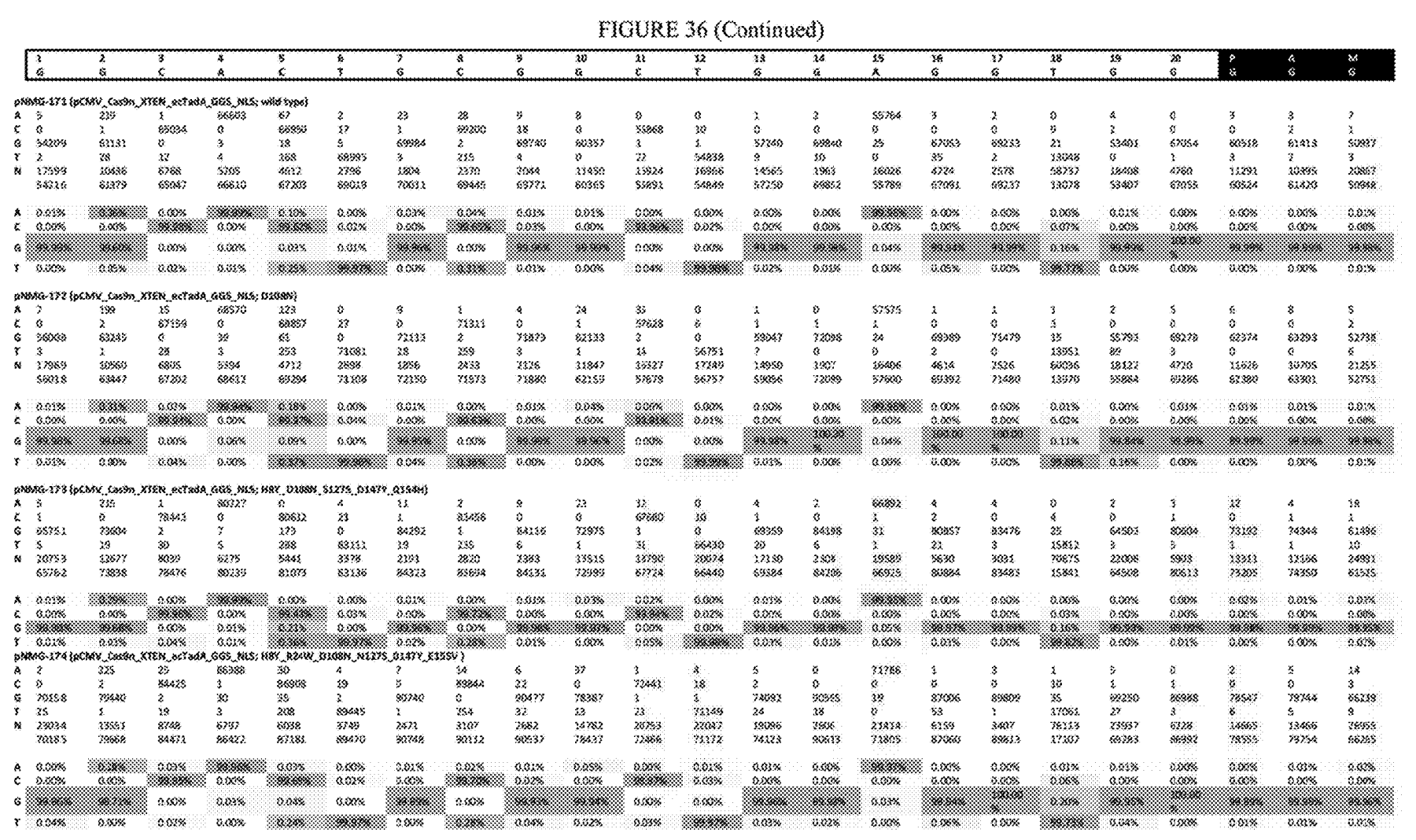
Figure 36:
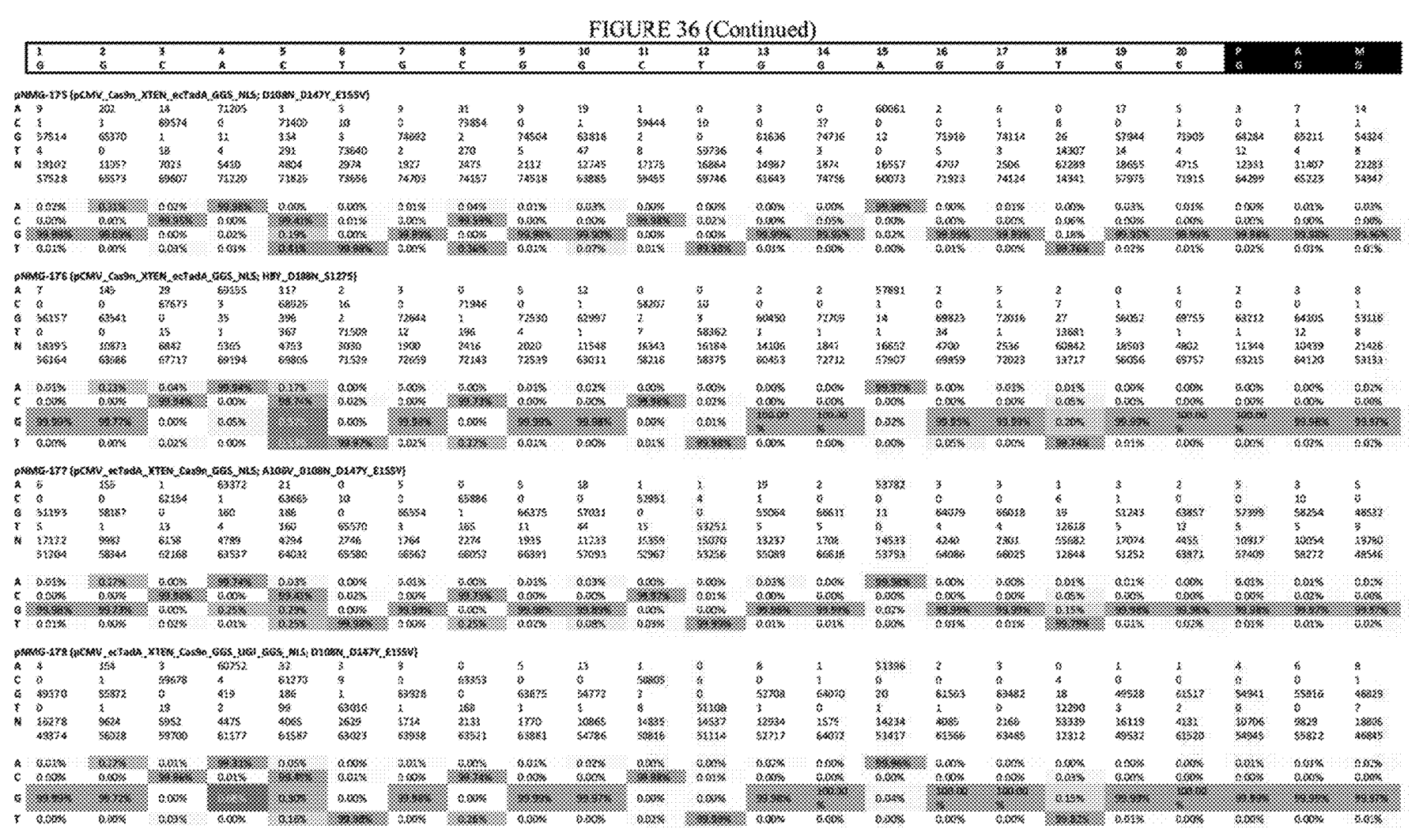
Figure 36:
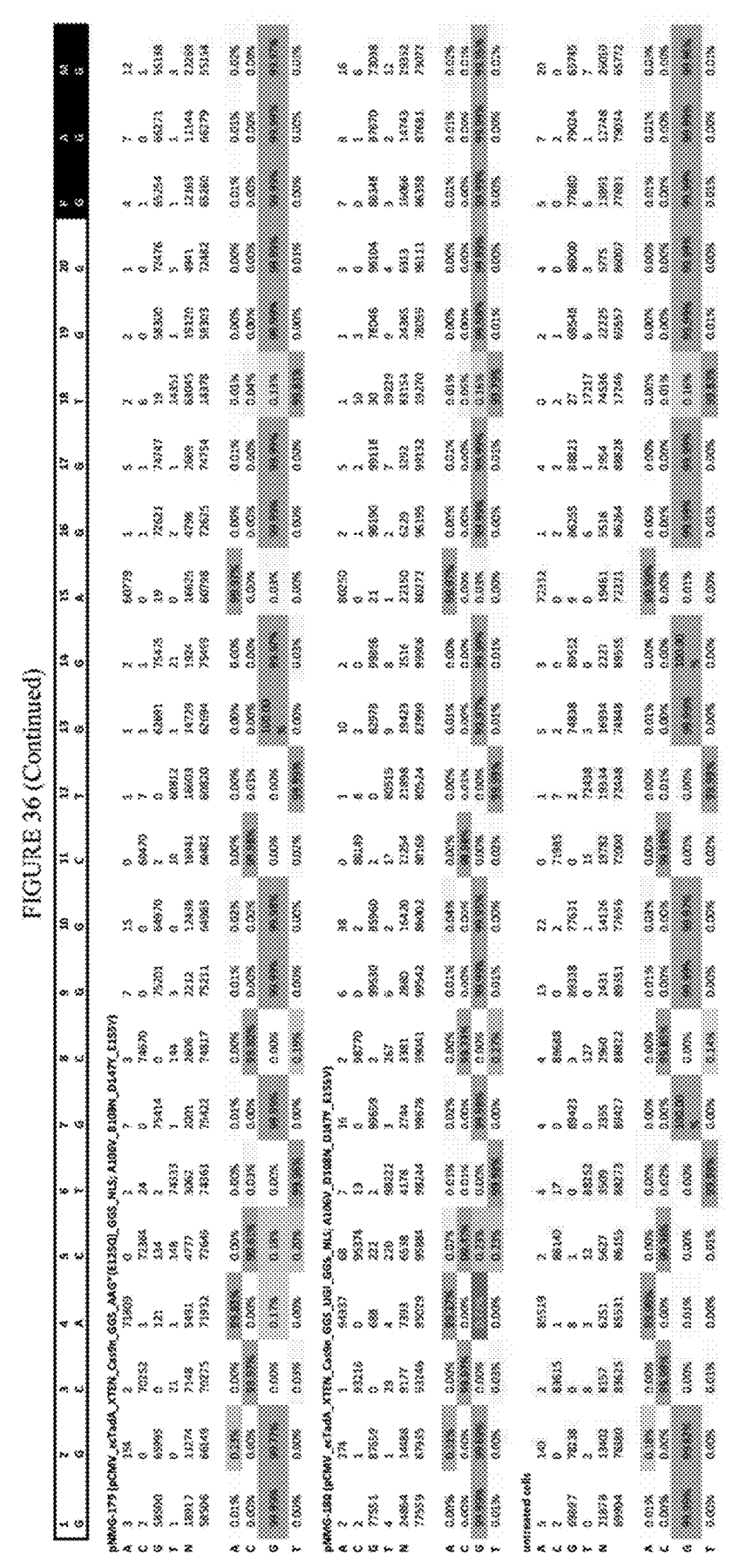

FIG. 36 shows the results of C-terminal fusion at the Hek-4 site. The sequence corresponds to SEQ ID NO: 43.

Figure 37:
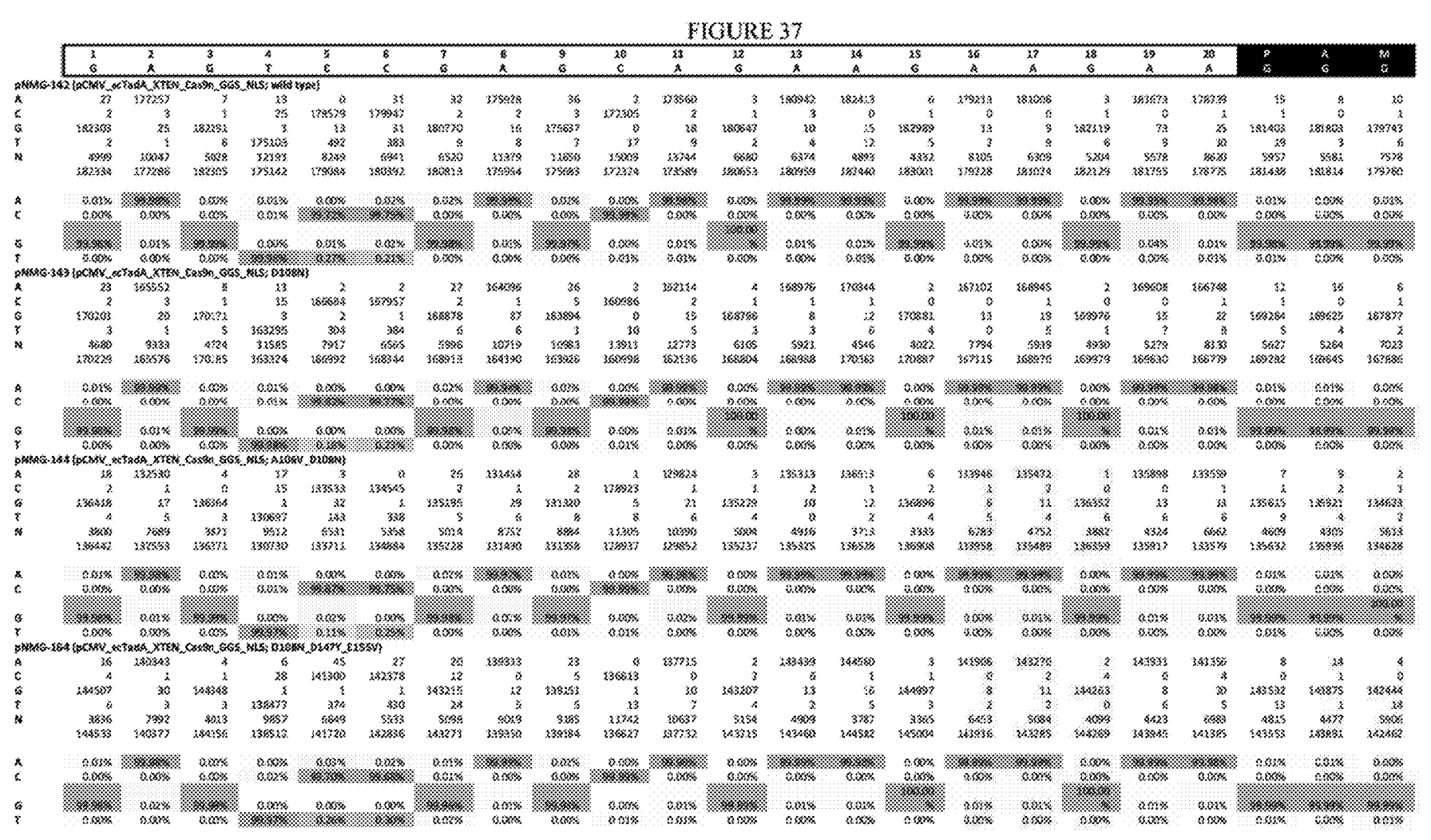
Figure 37:
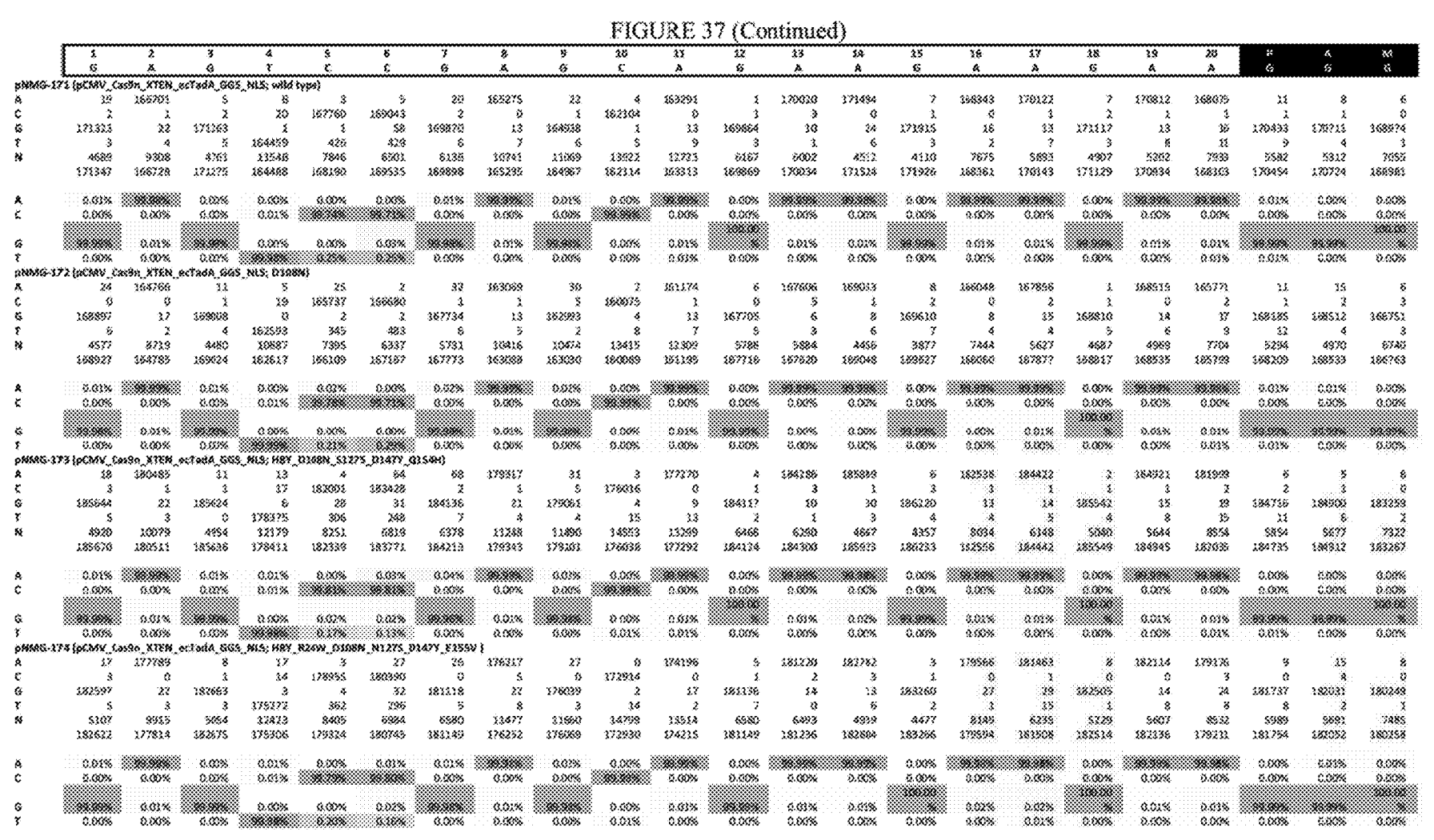
Figure 37:
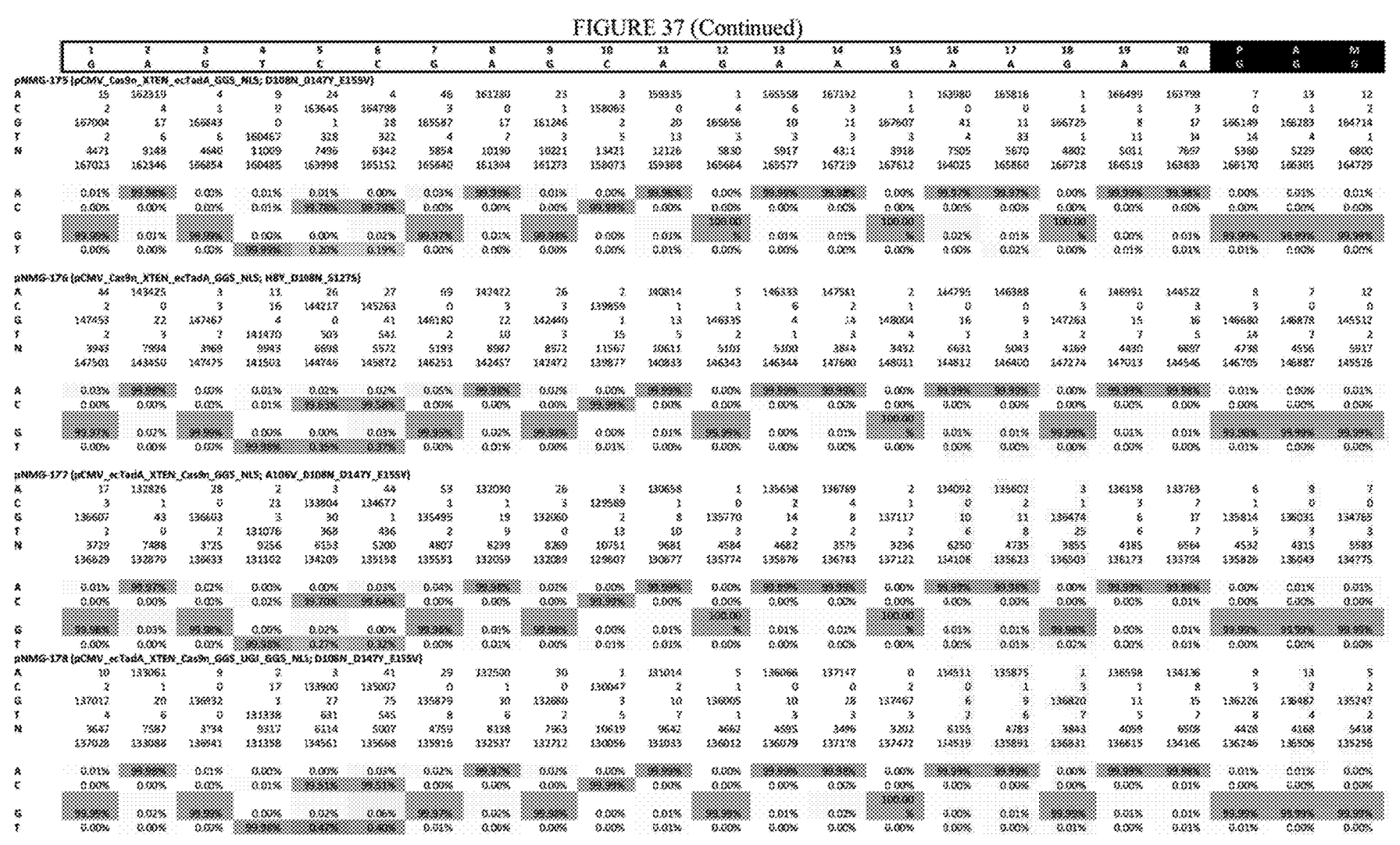
Figure 37:
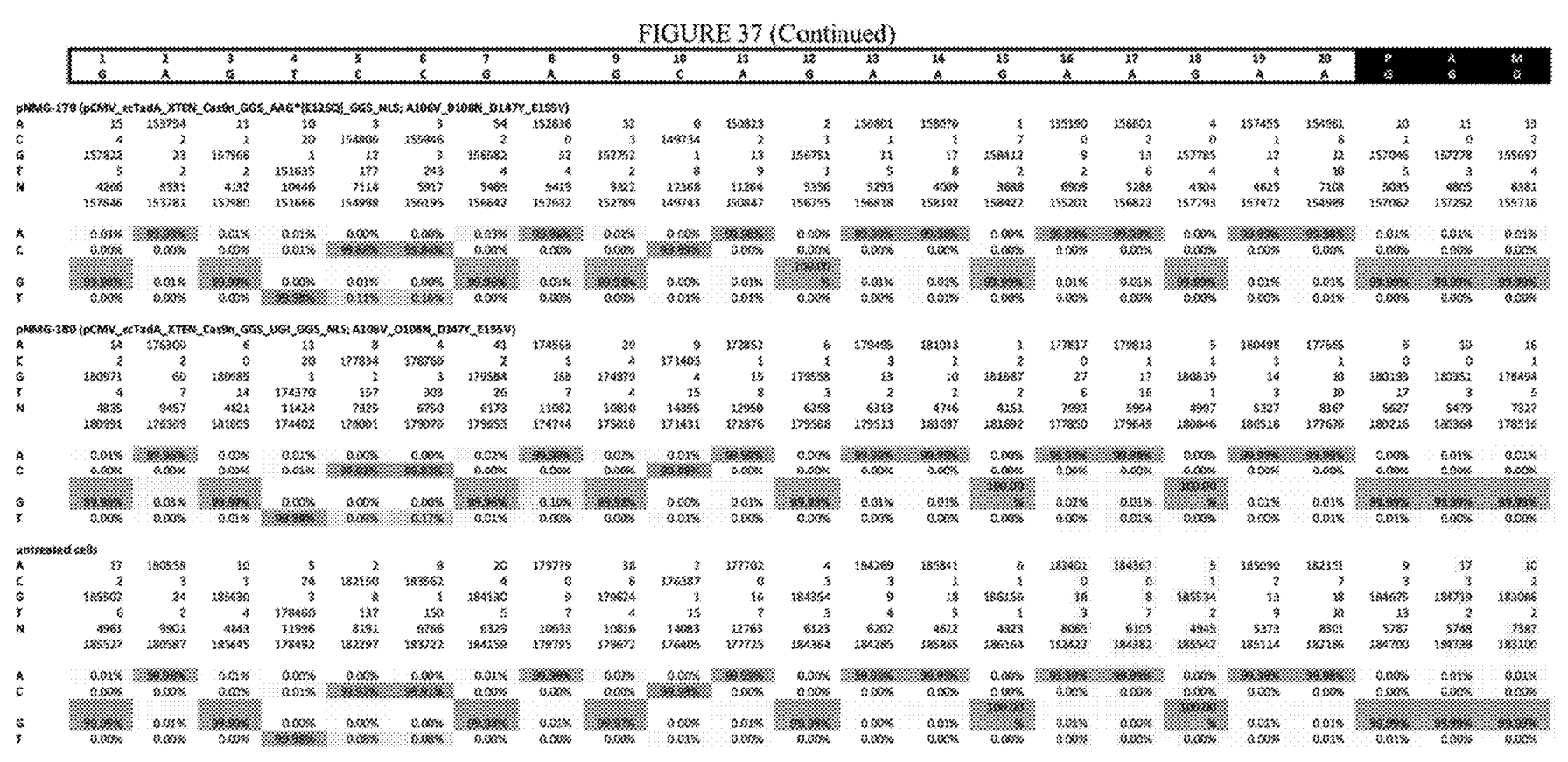

FIG. 37 shows the results of C-terminal fusion at the EMX-1 site. The sequence corresponds to SEQ ID NO: 46.

Figure 38:
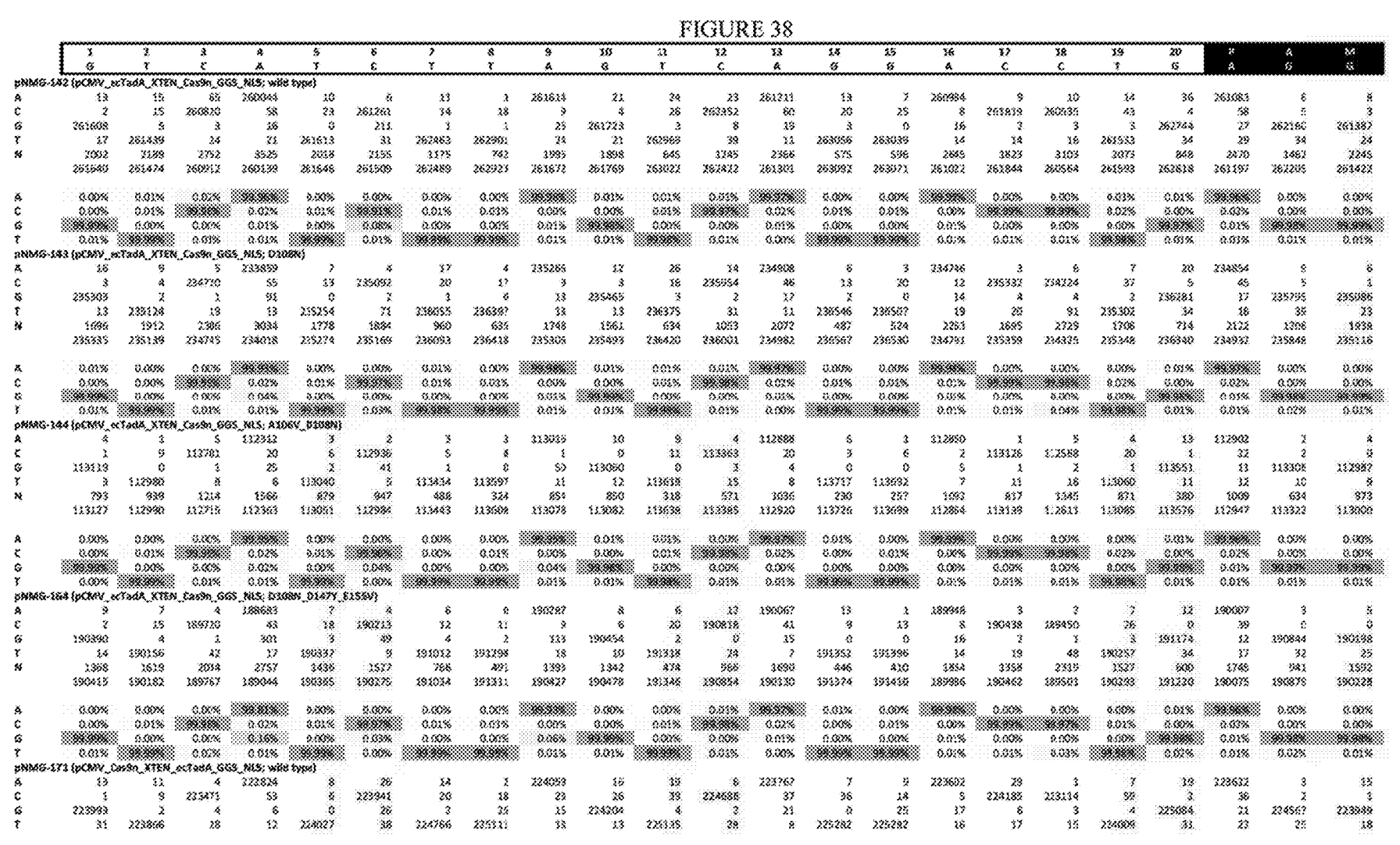
Figure 38:
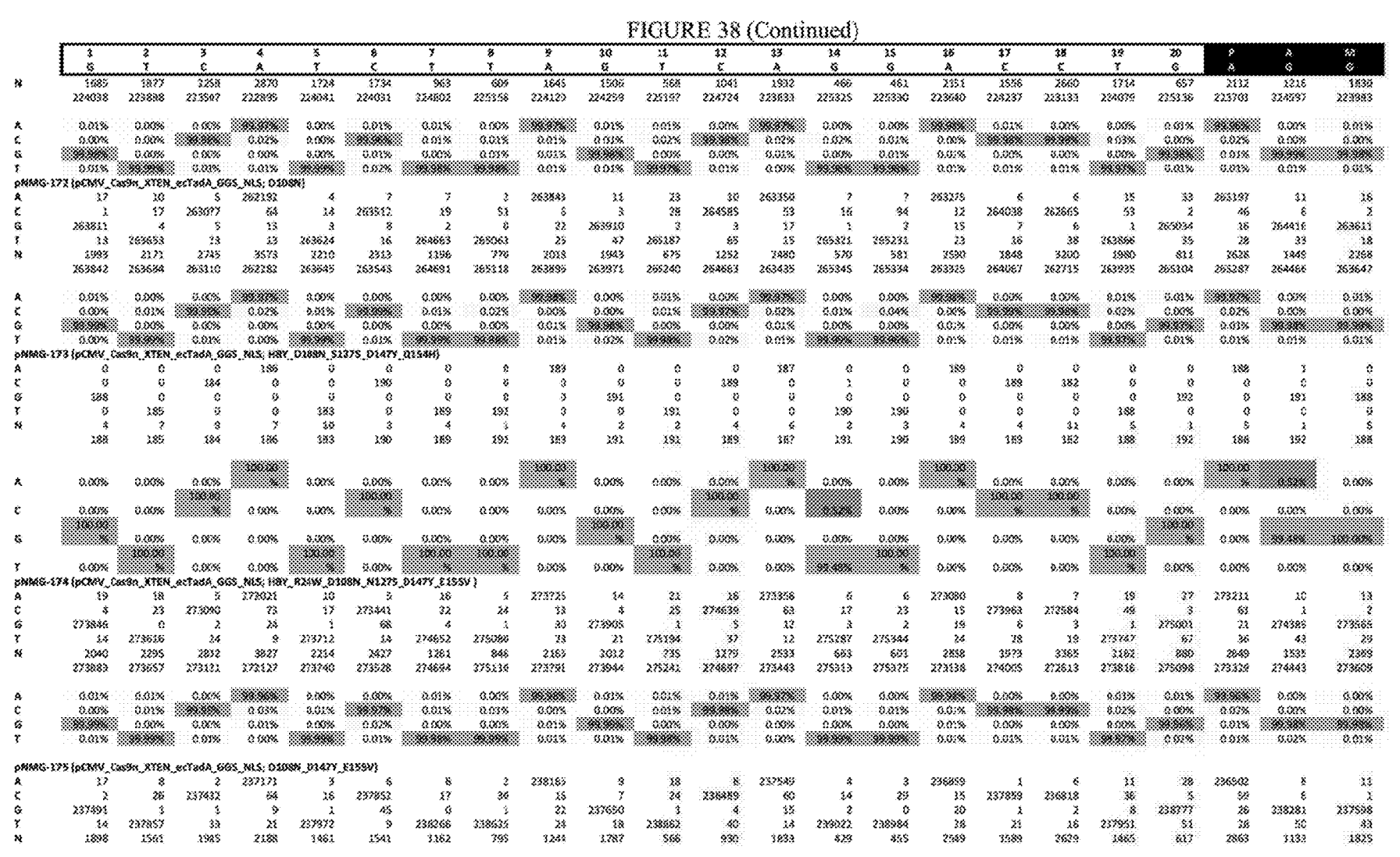
Figure 38:
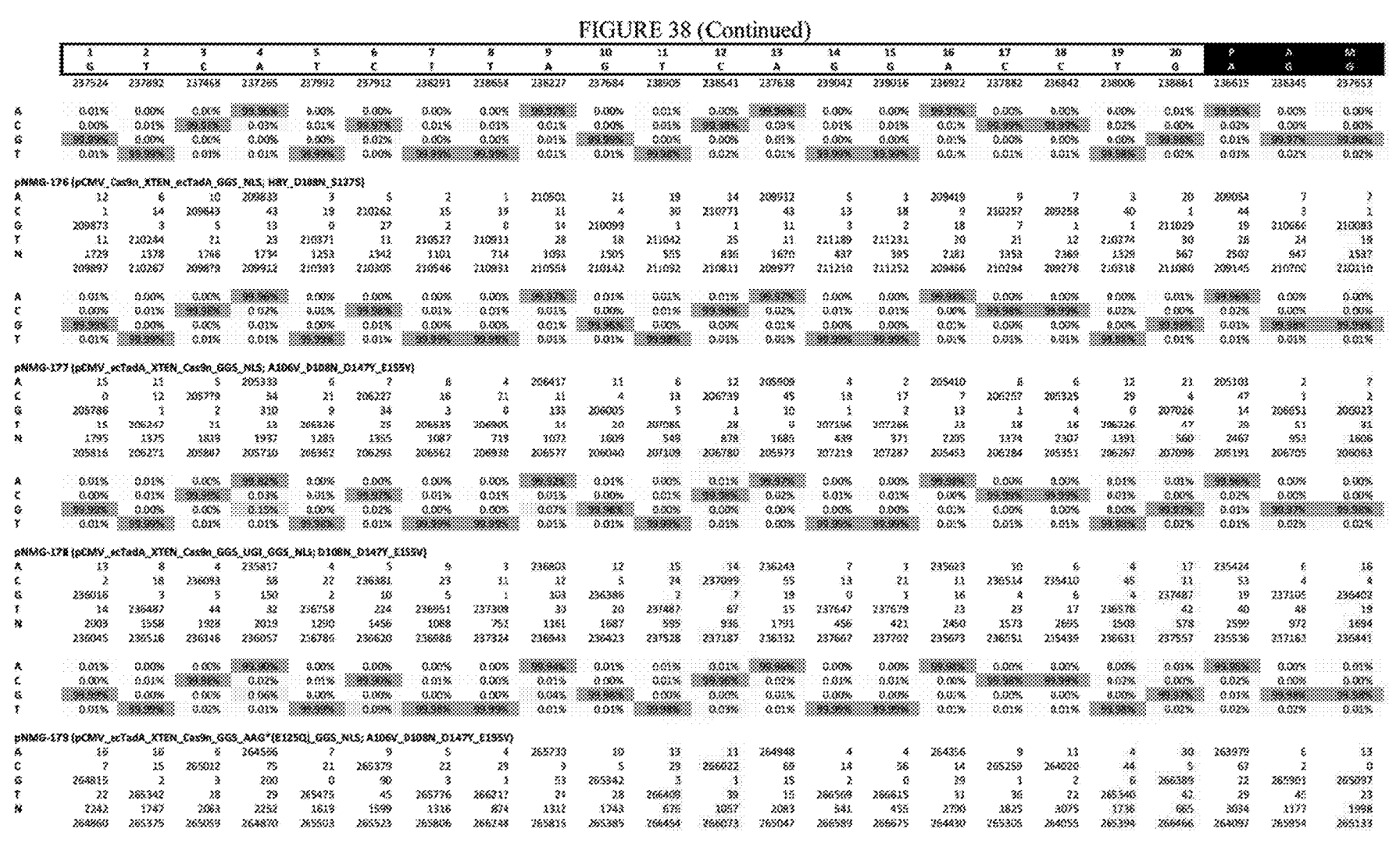
Figure 38:
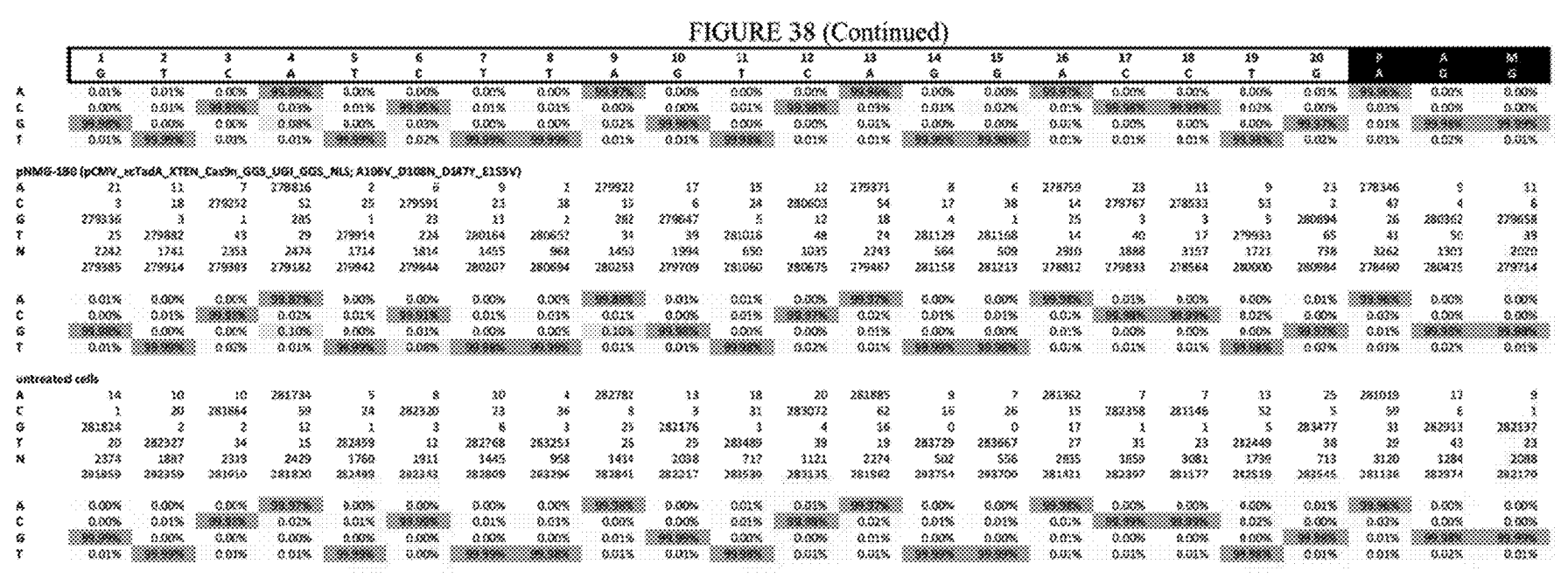

FIG. 38 shows the results of C-terminal fusion at the RNF-2 site. The sequence corresponds to SEQ ID NO: 44.

Figure 39:
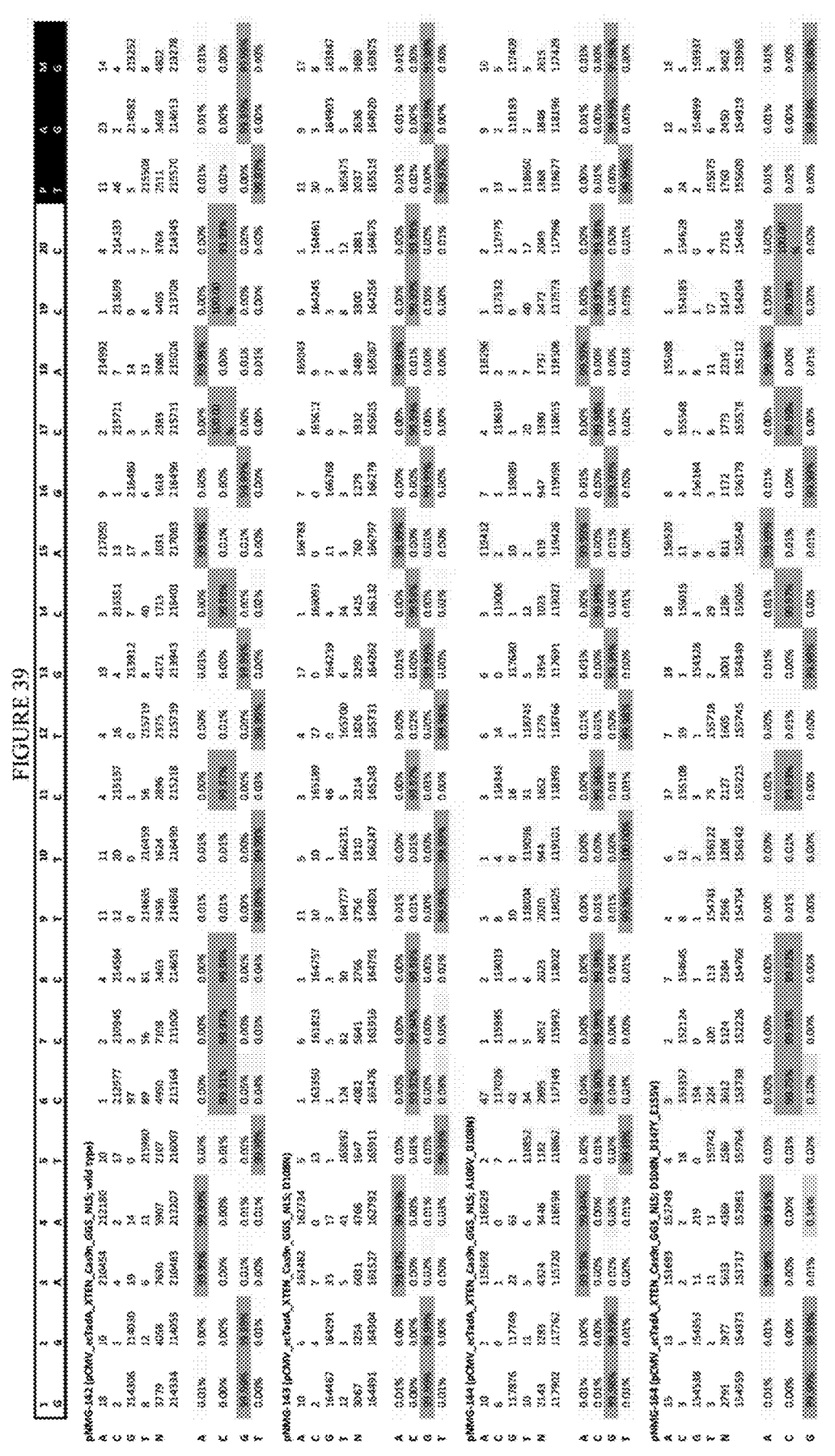
Figure 39:
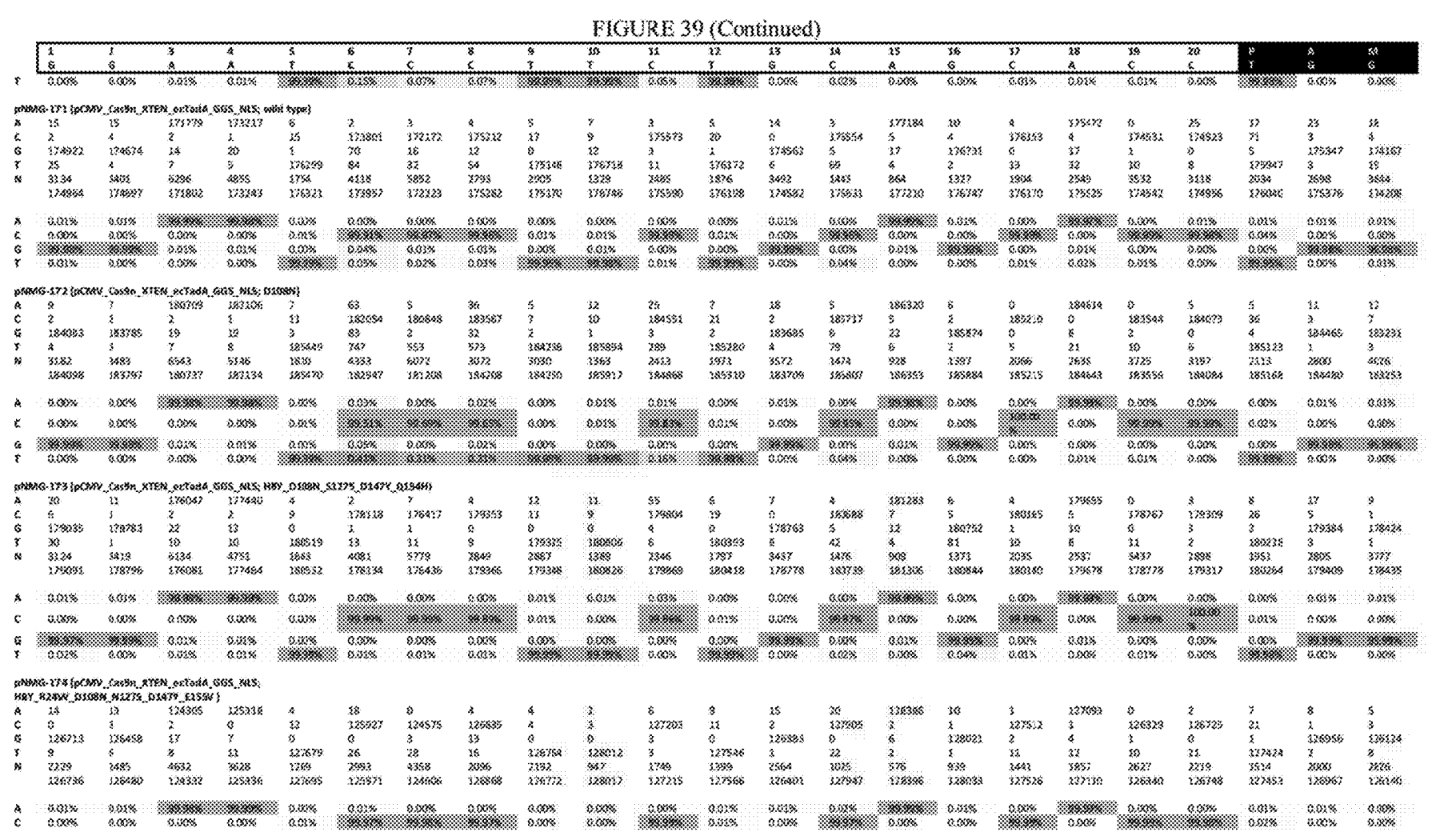
Figure 39:
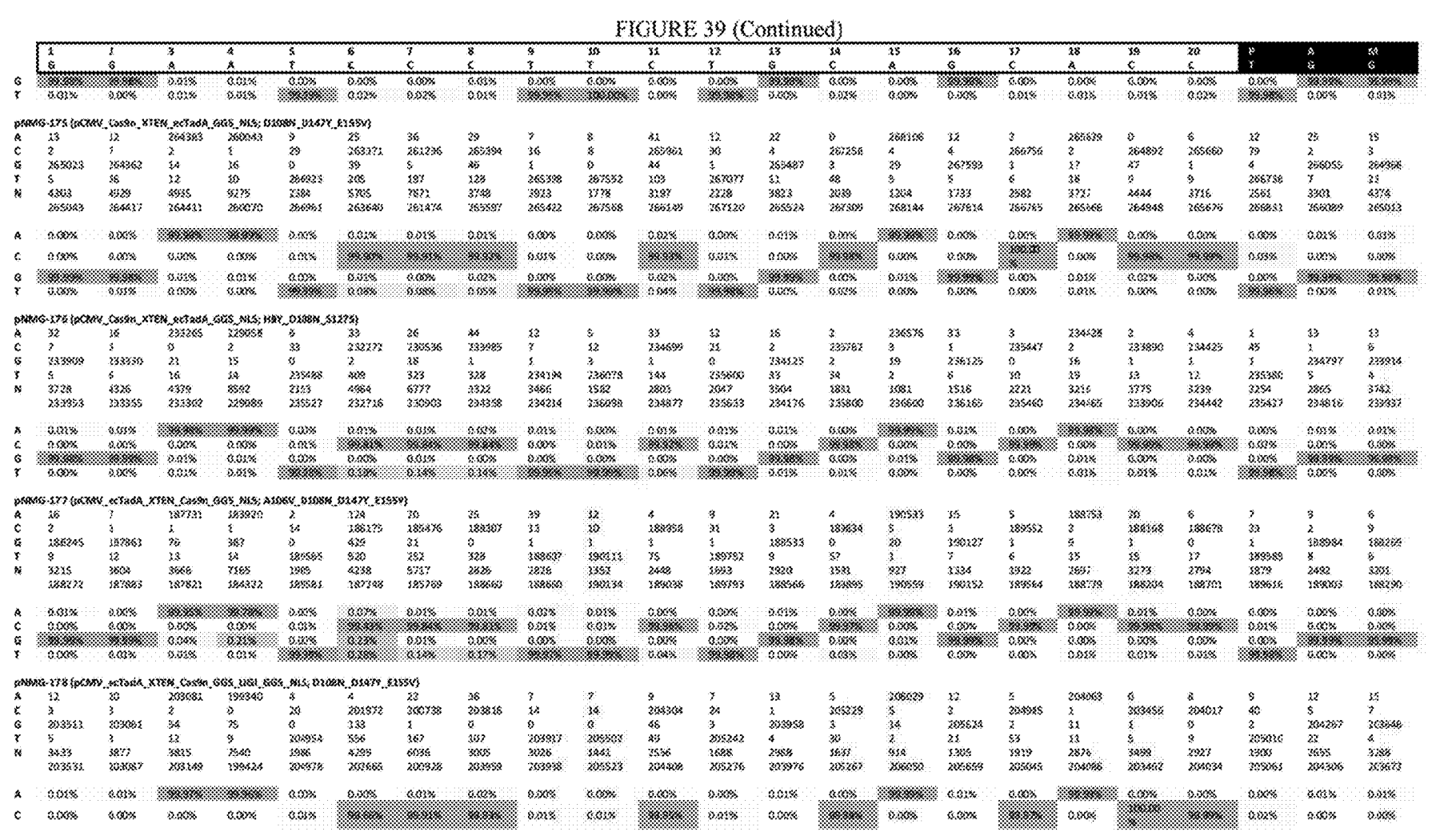
Figure 39:
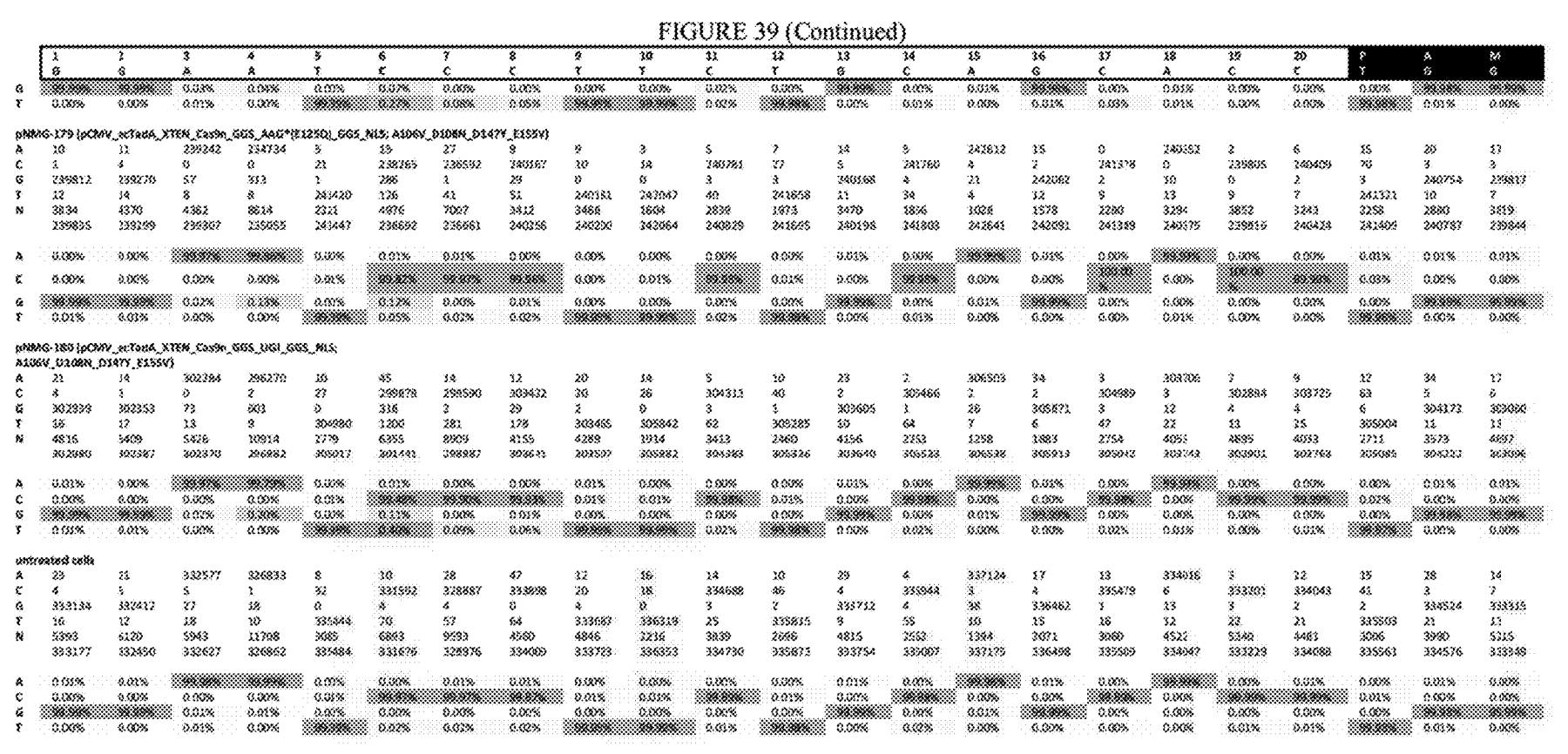

FIG. 39 shows the results of C-terminal fusion at the FANCF site. The sequence corresponds to SEQ ID NO: 45.

FIG. 40 shows the results of transfection at the Hek-2 site. The sequence corresponds to SEQ ID NO: 41.

Figure 41:
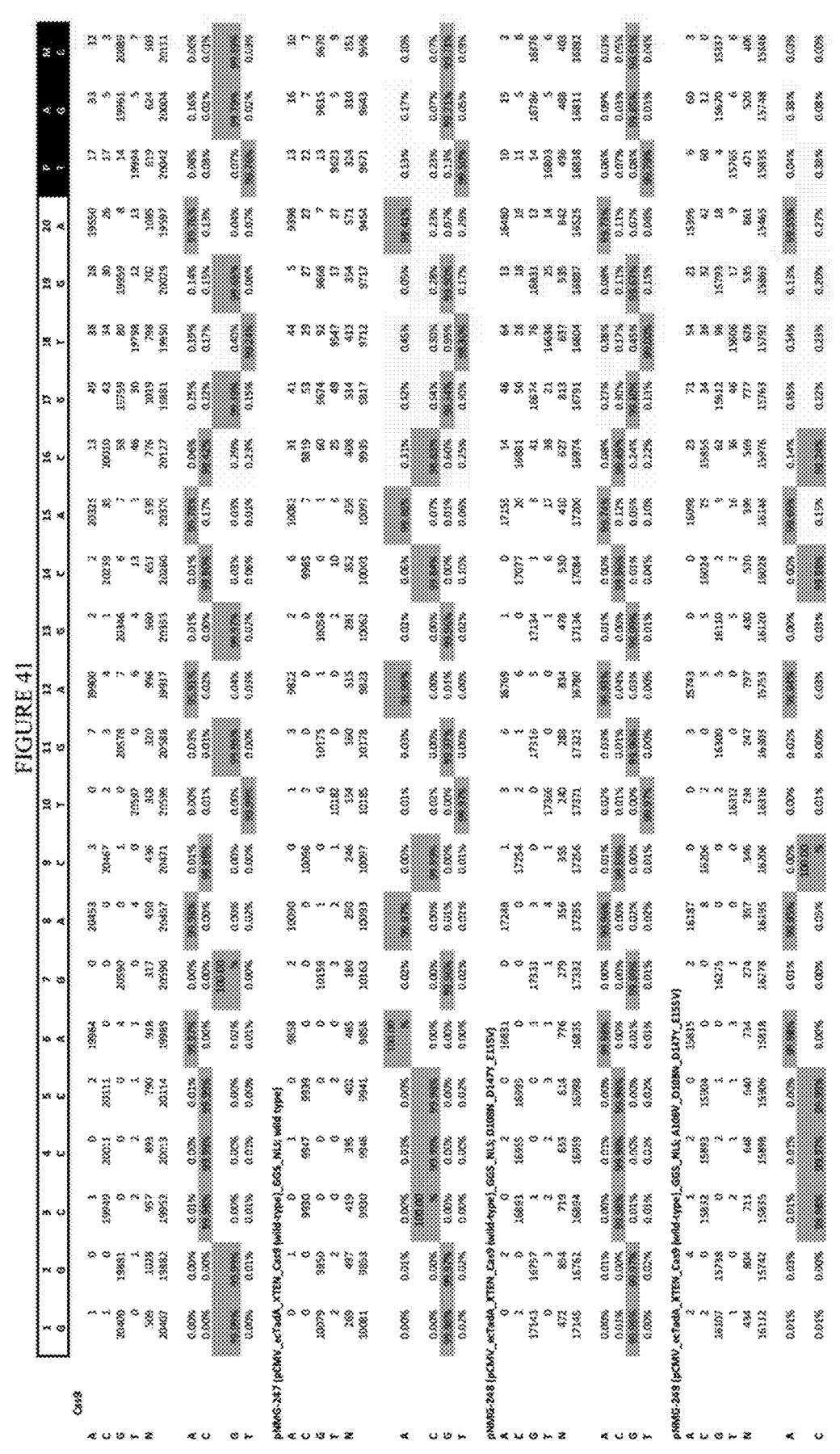
Figure 41:
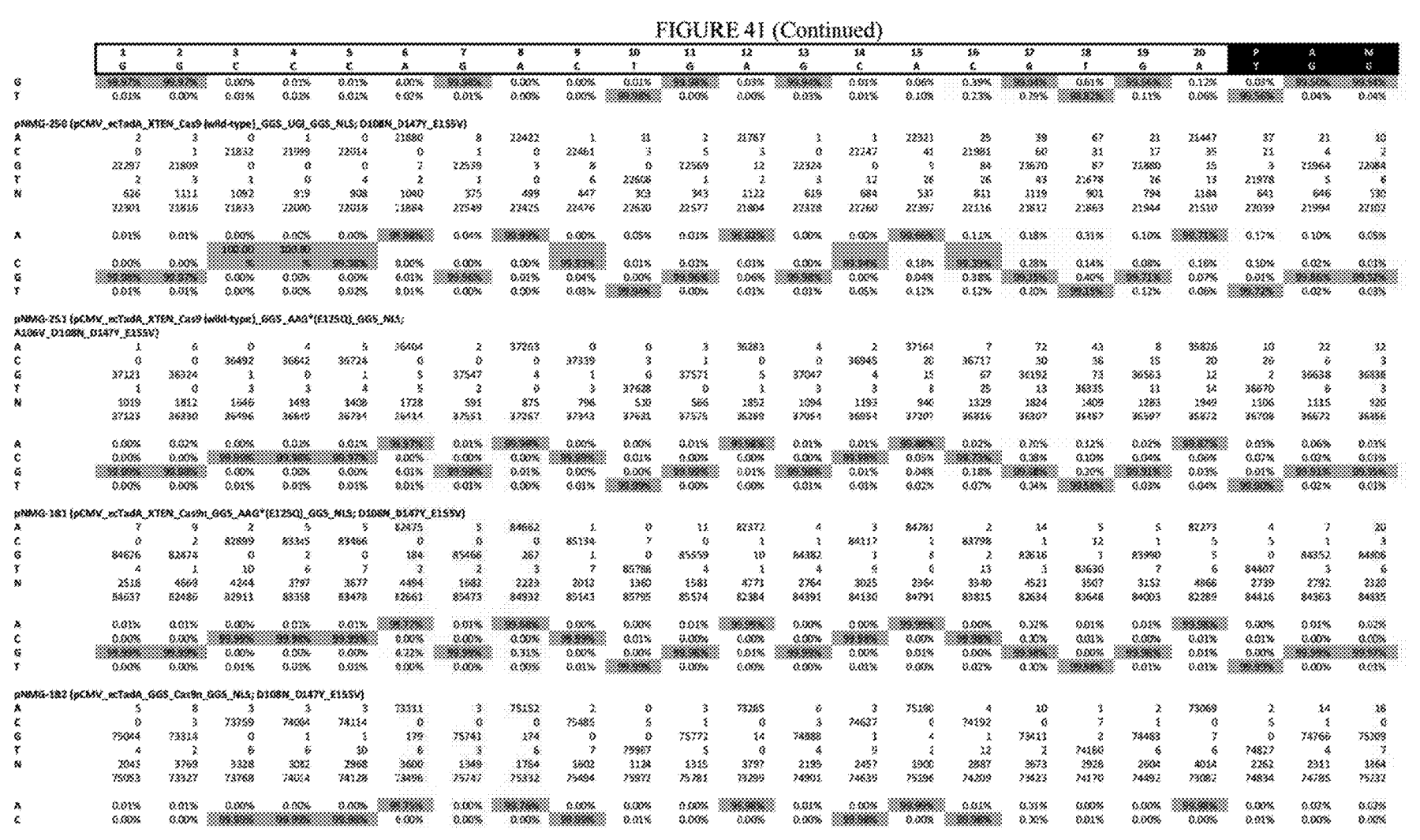
Figure 41:
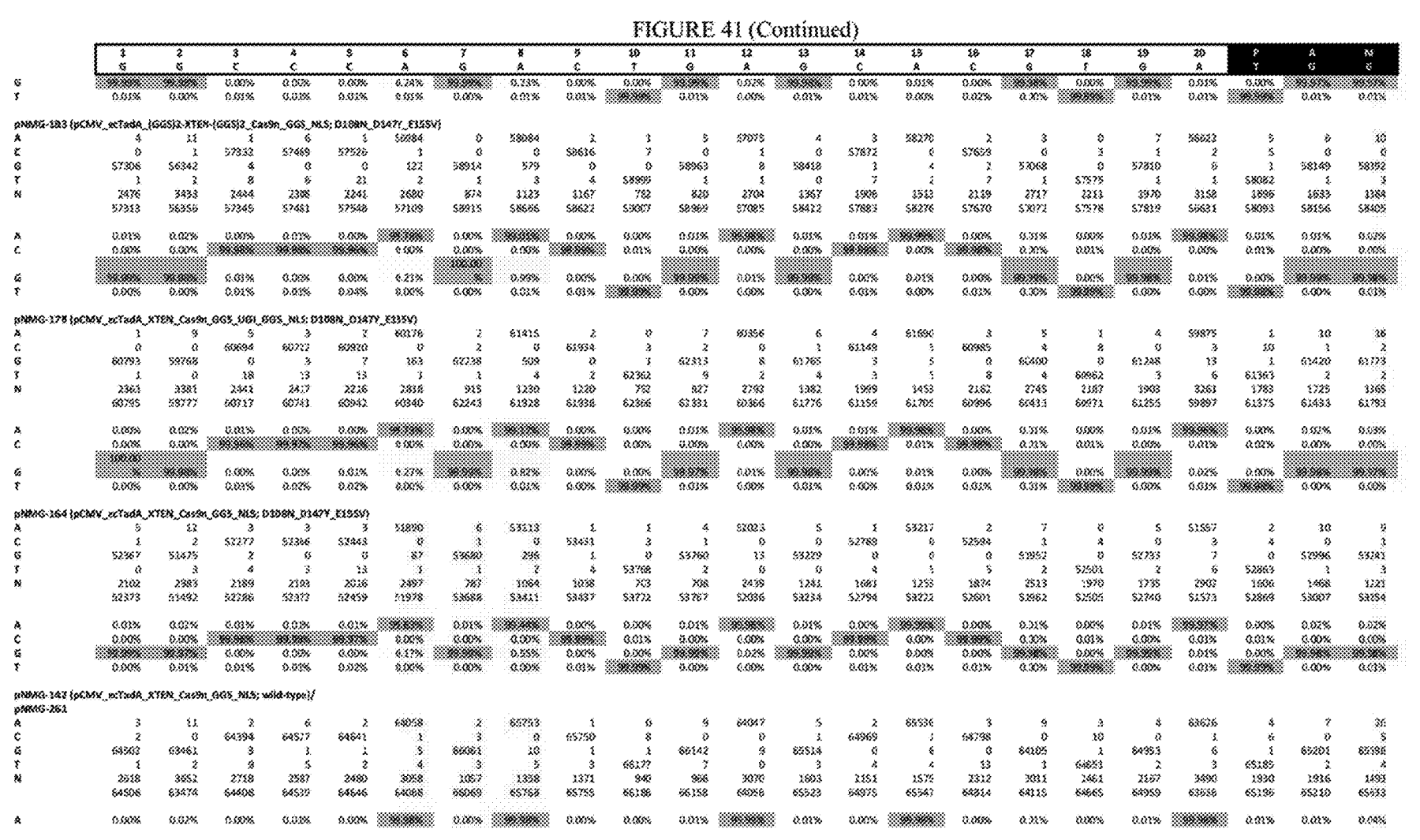
Figure 41:
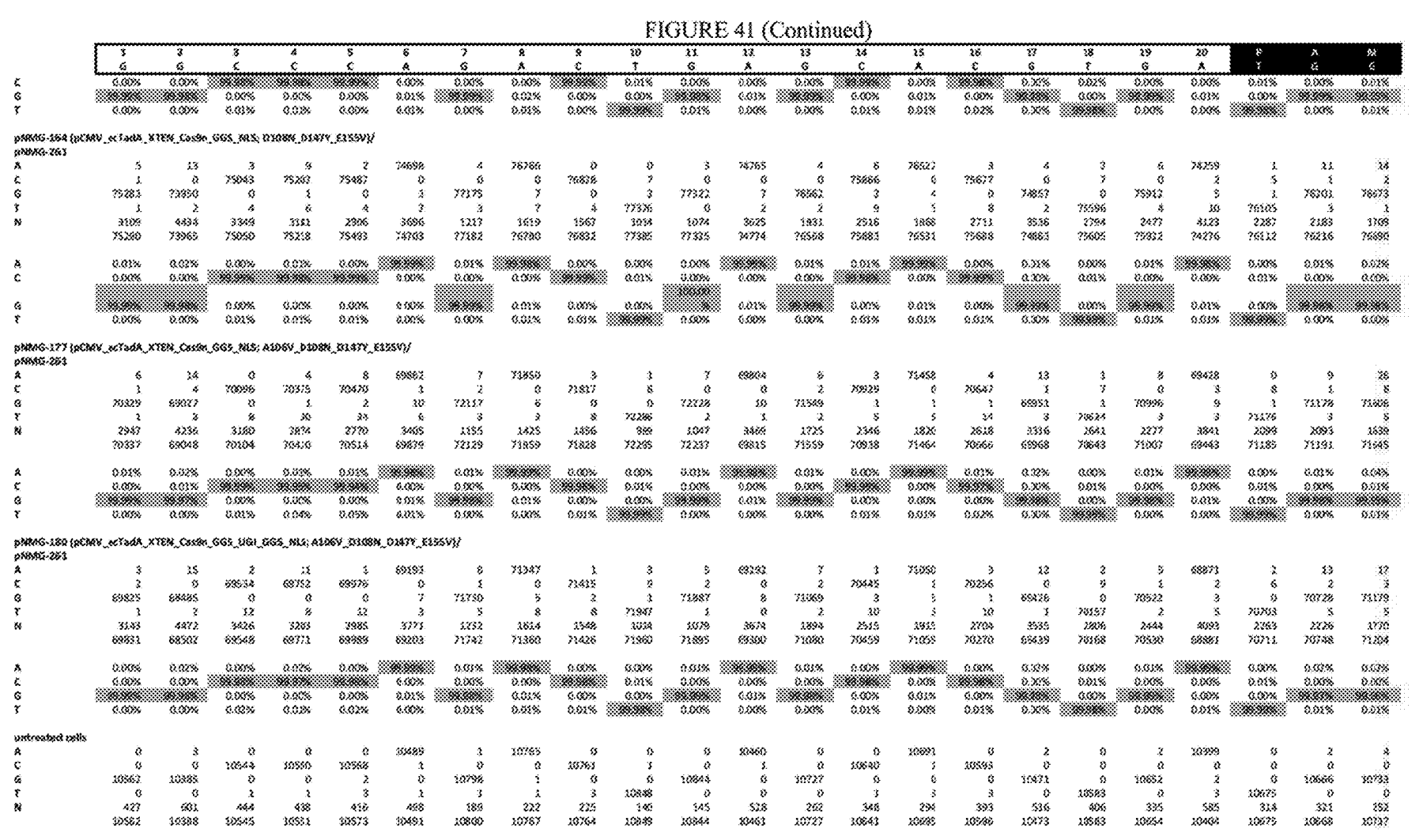
Figure 41:
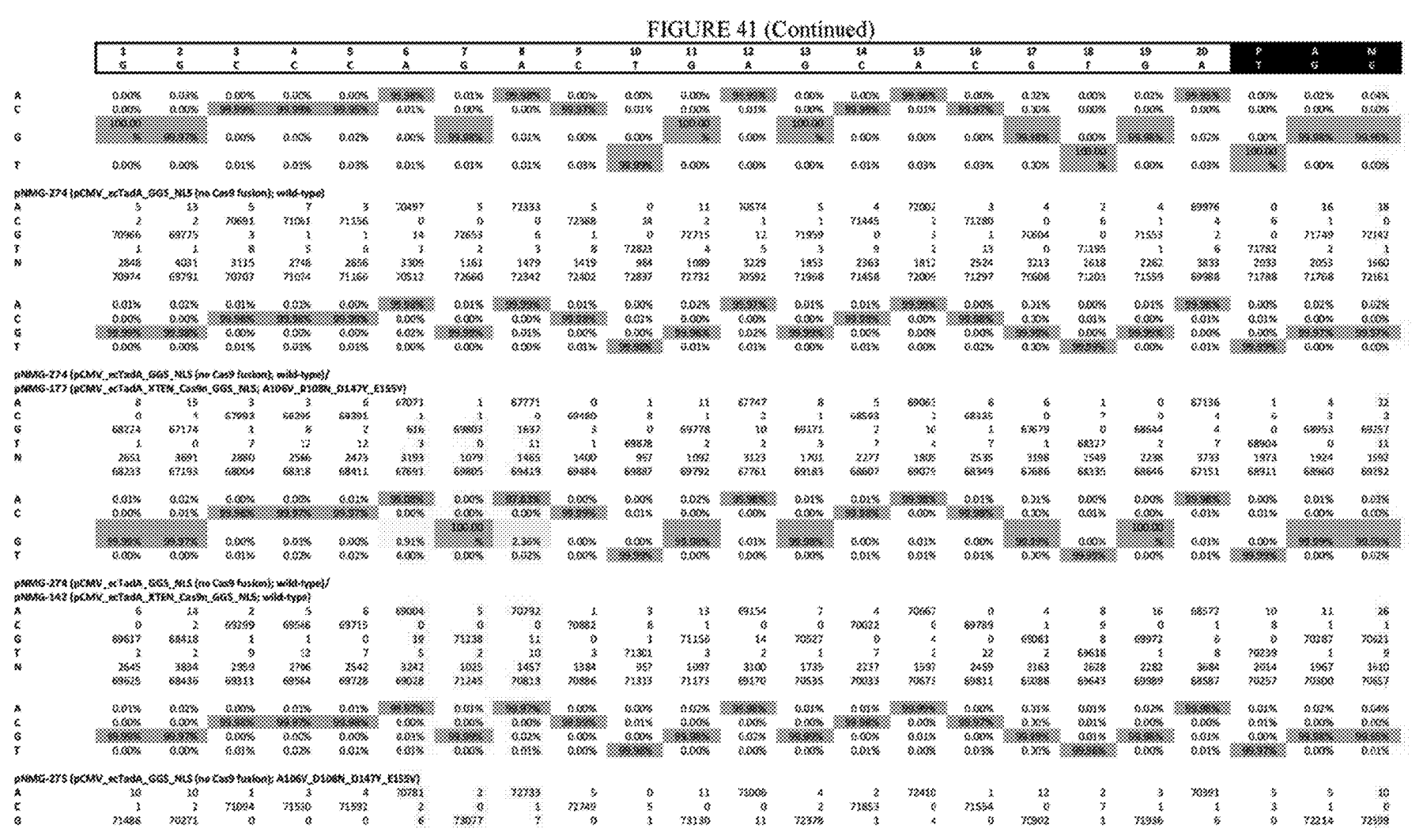
Figure 41:
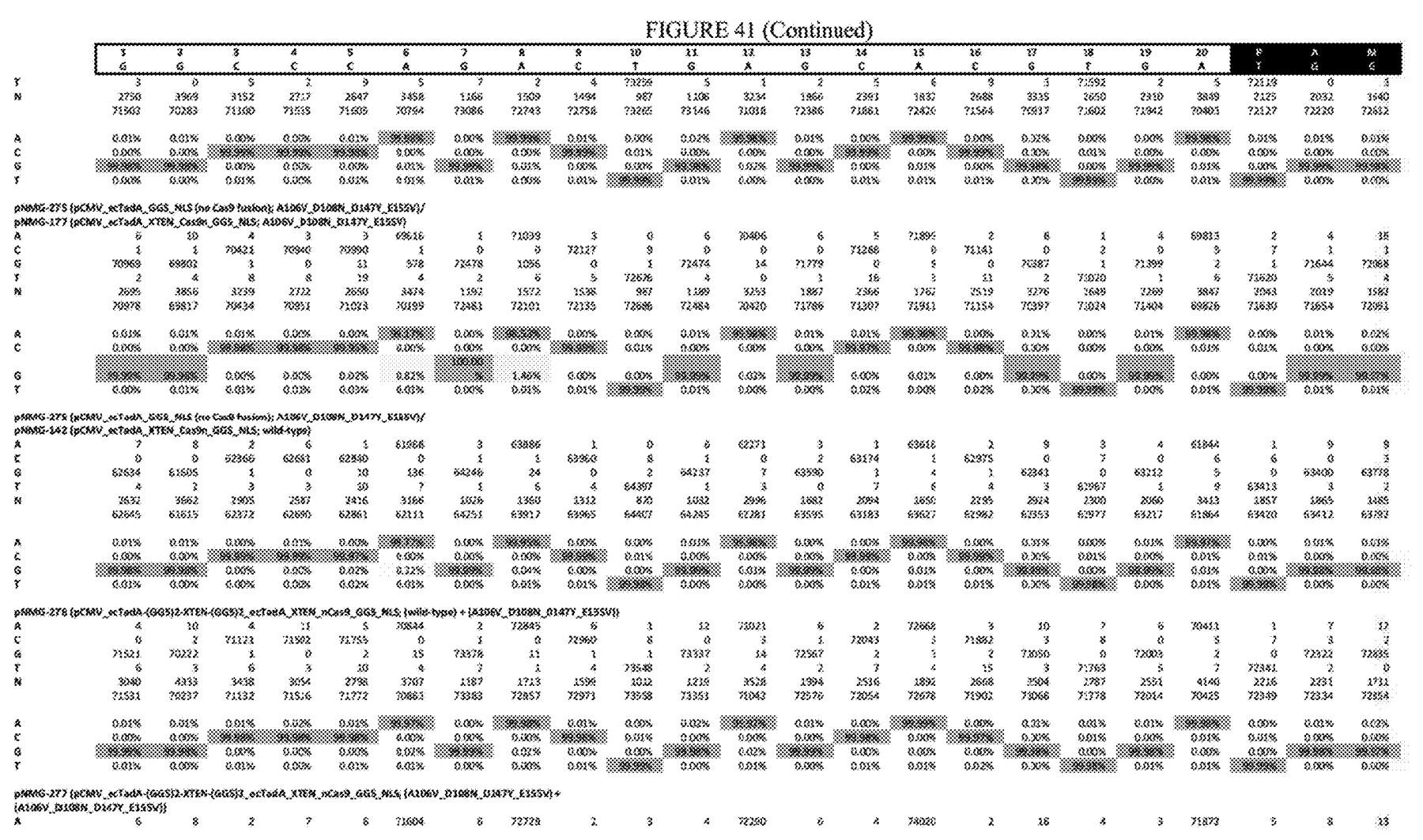
Figure 41:
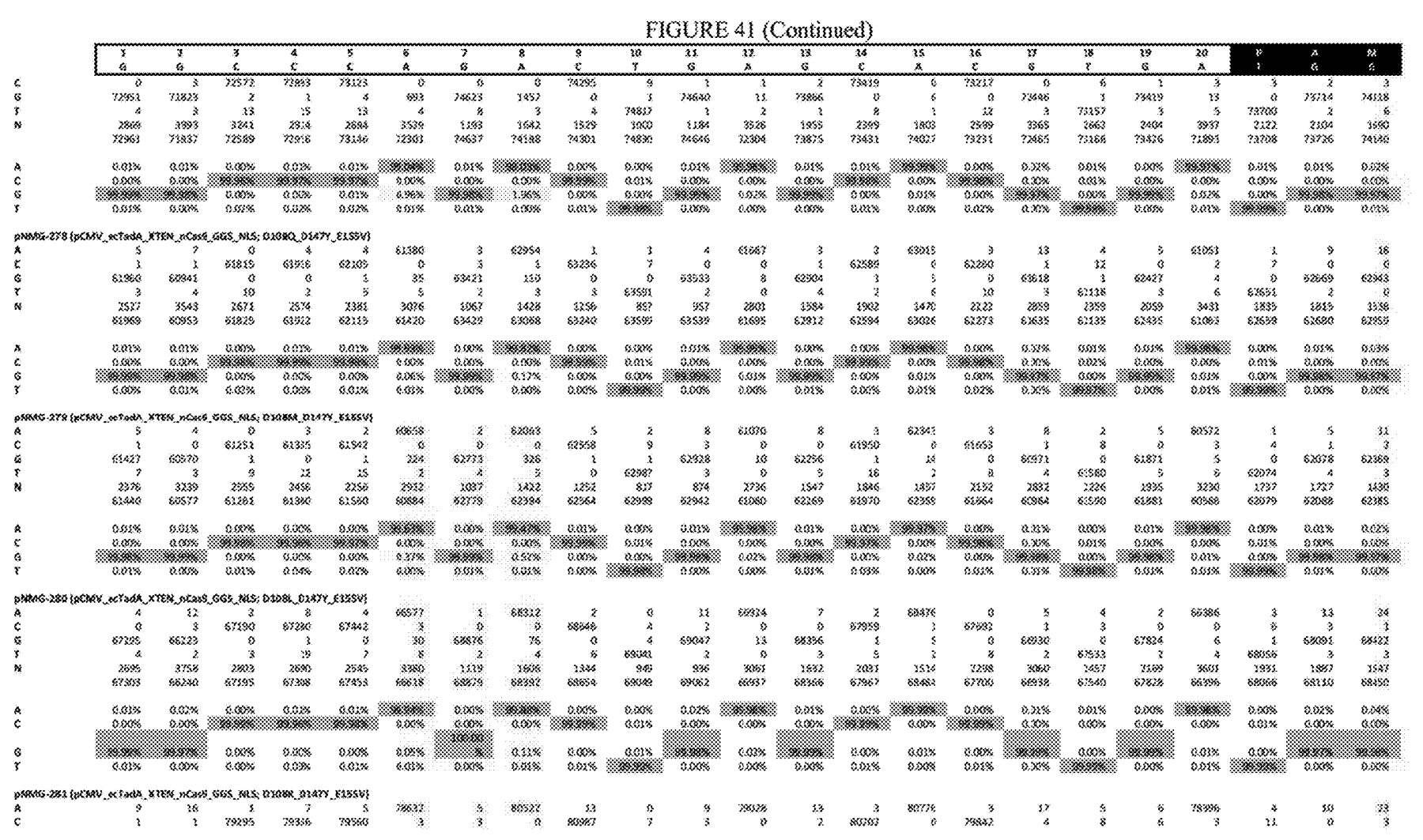
Figure 41:
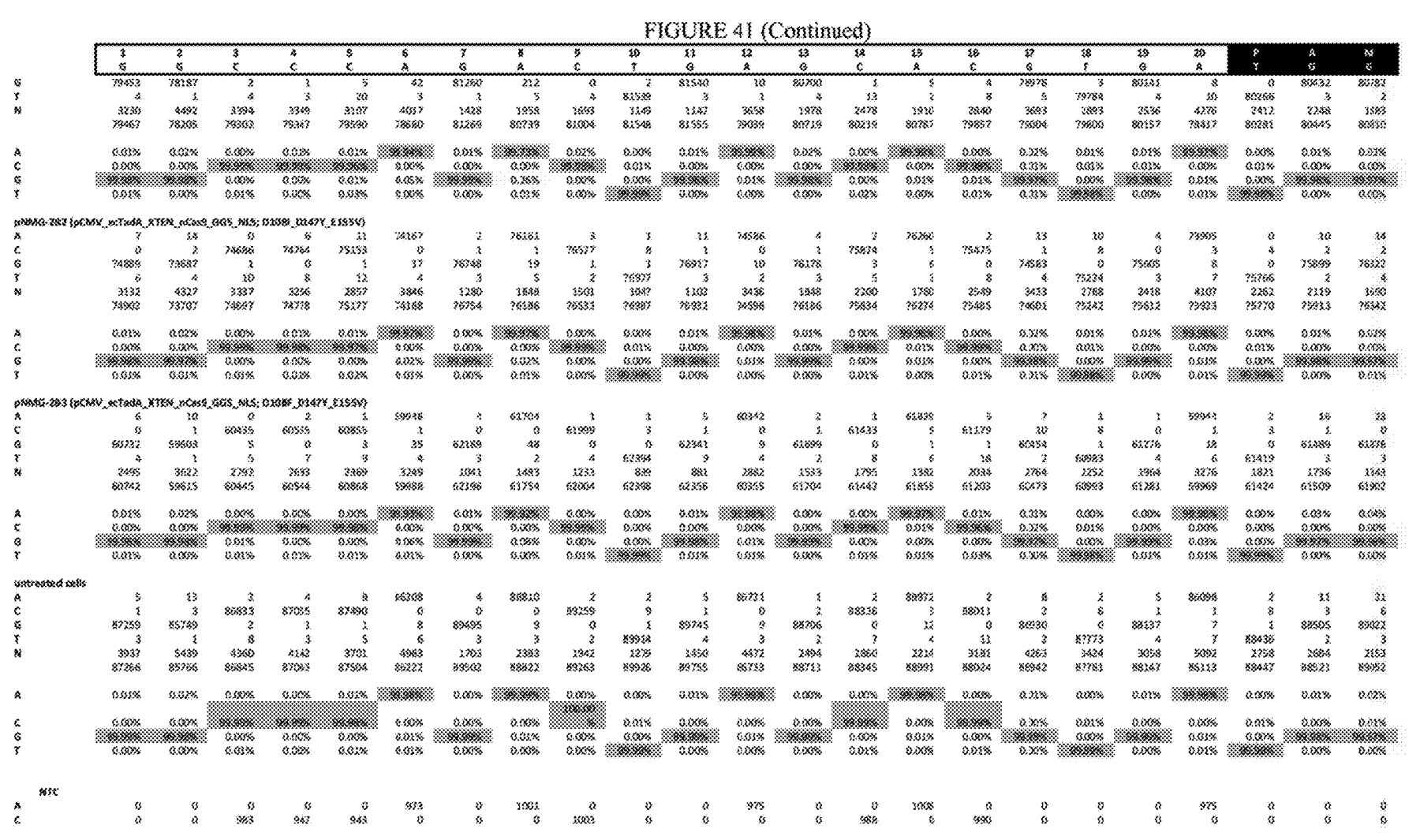
Figure 41:
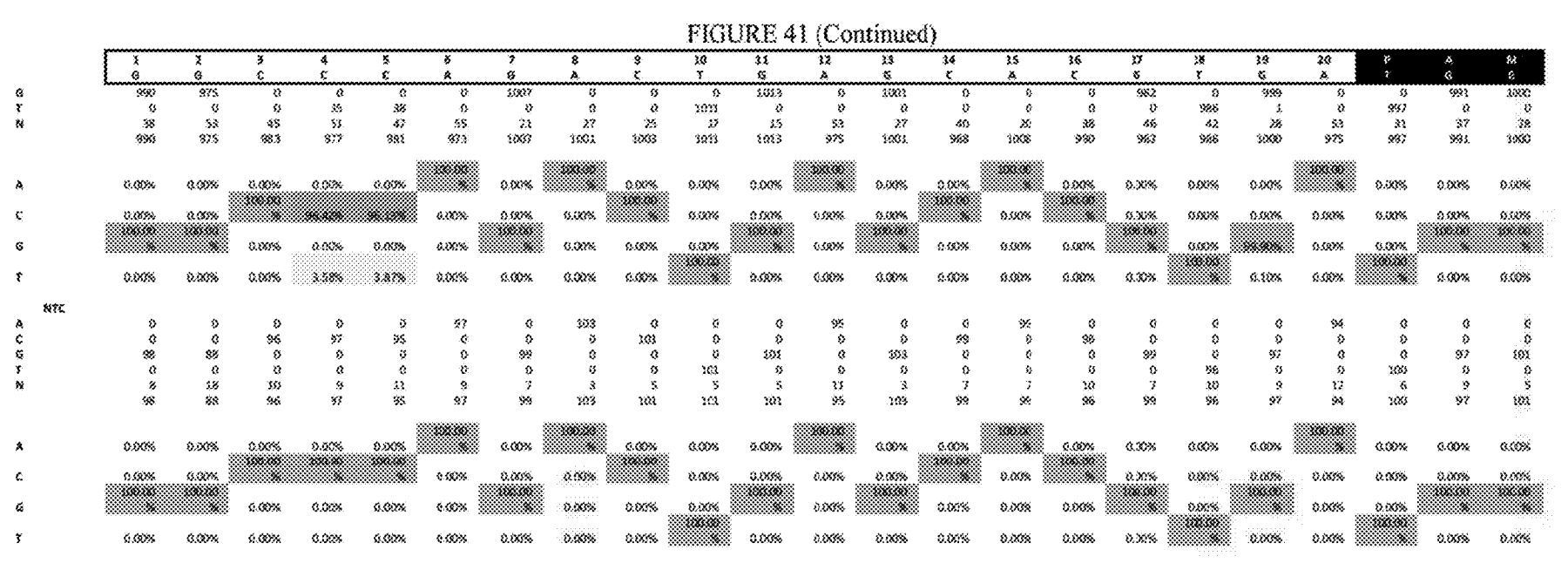

FIG. 41 shows the results of transfection at the Hek-3 site. The sequence corresponds to SEQ ID NO: 42.

Figure 42:
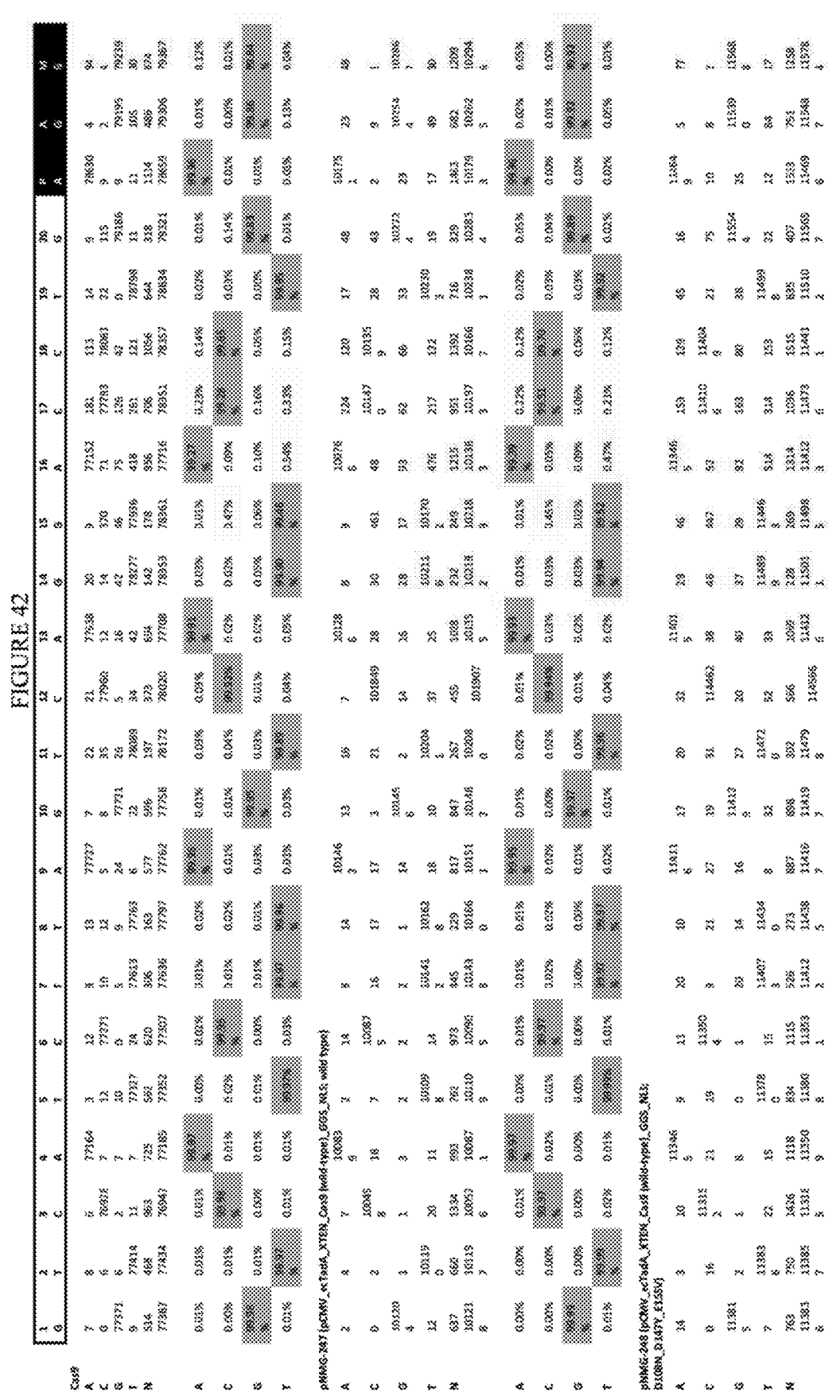
Figure 42:
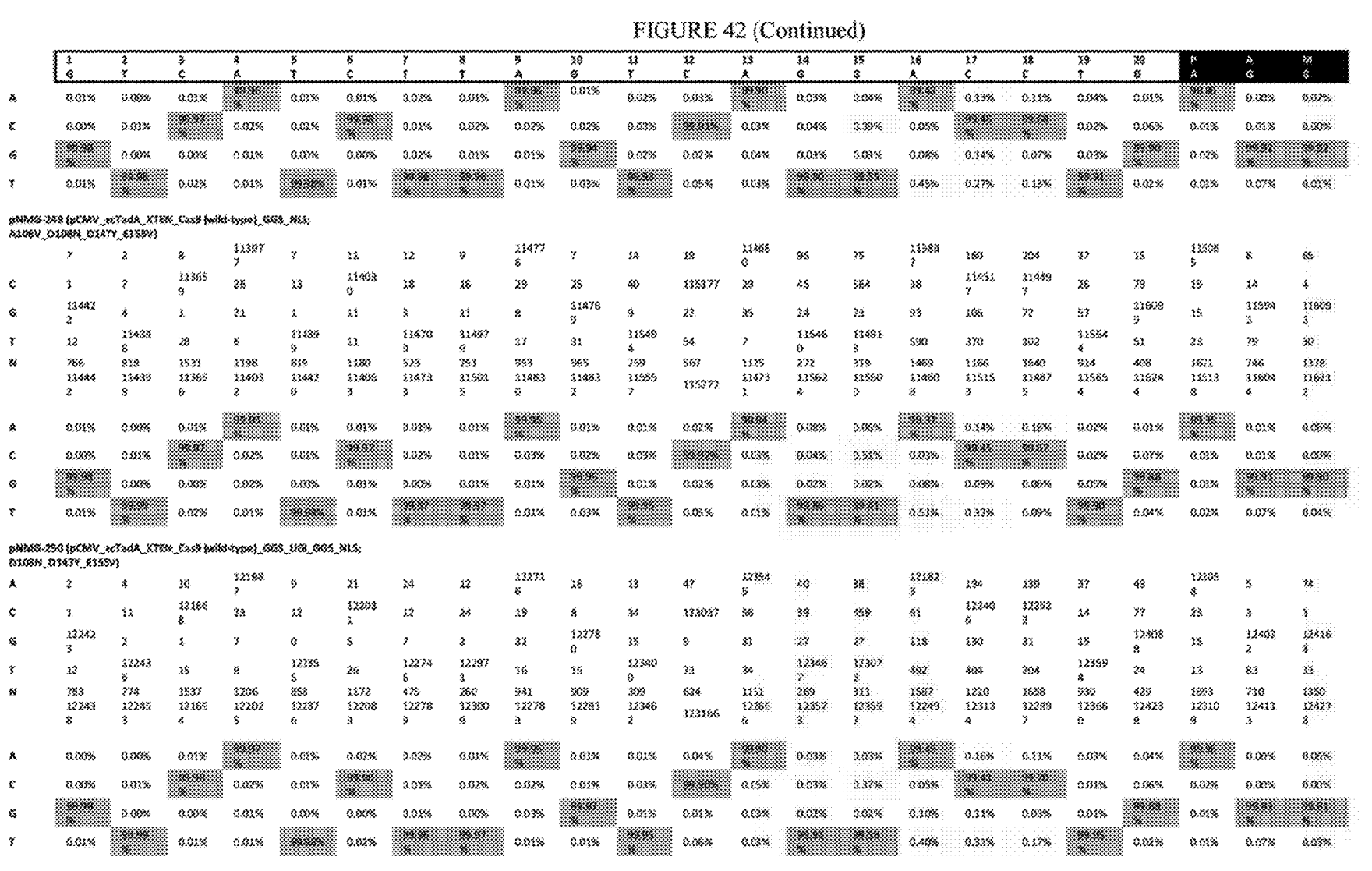
Figure 42:
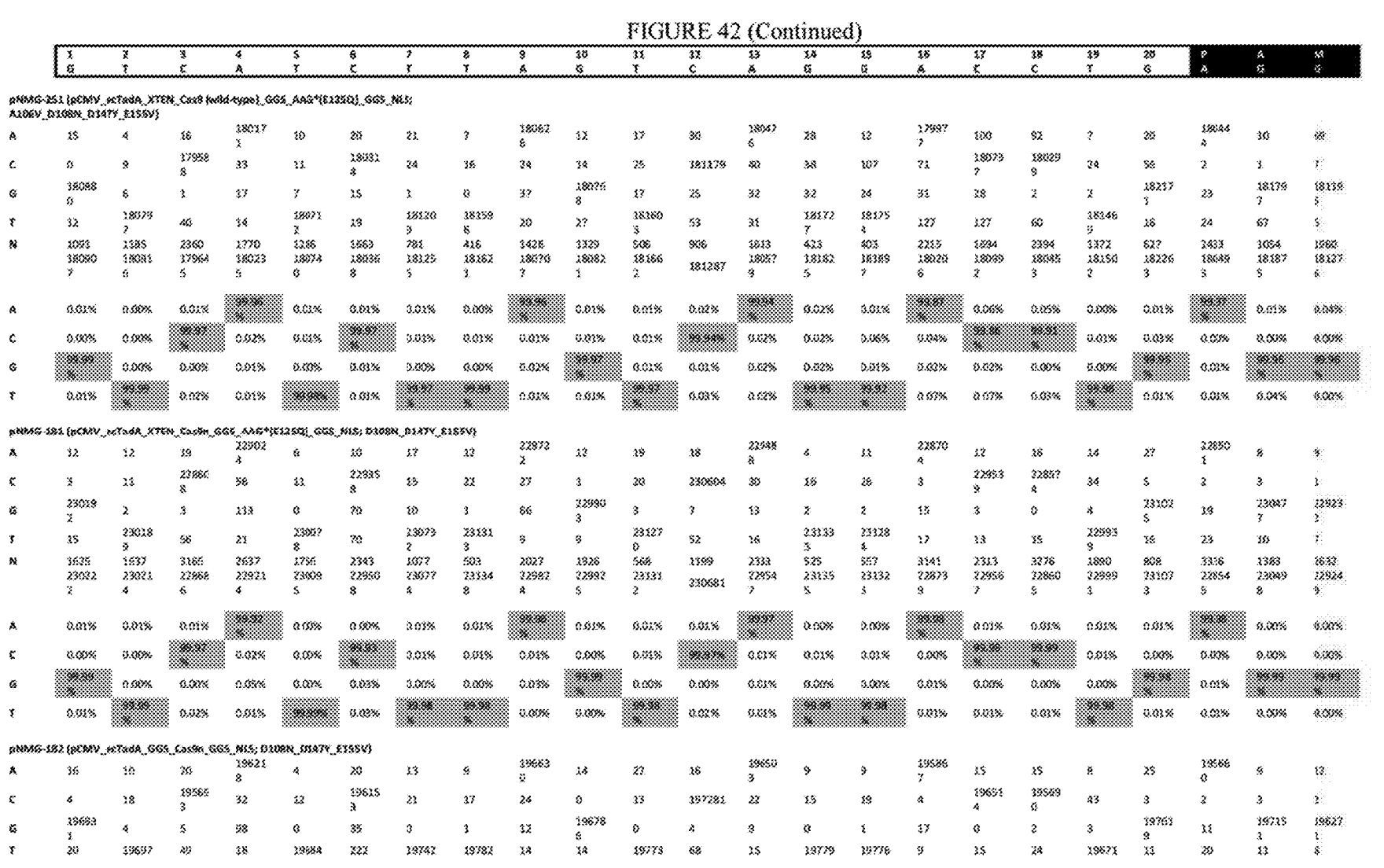
Figure 42:
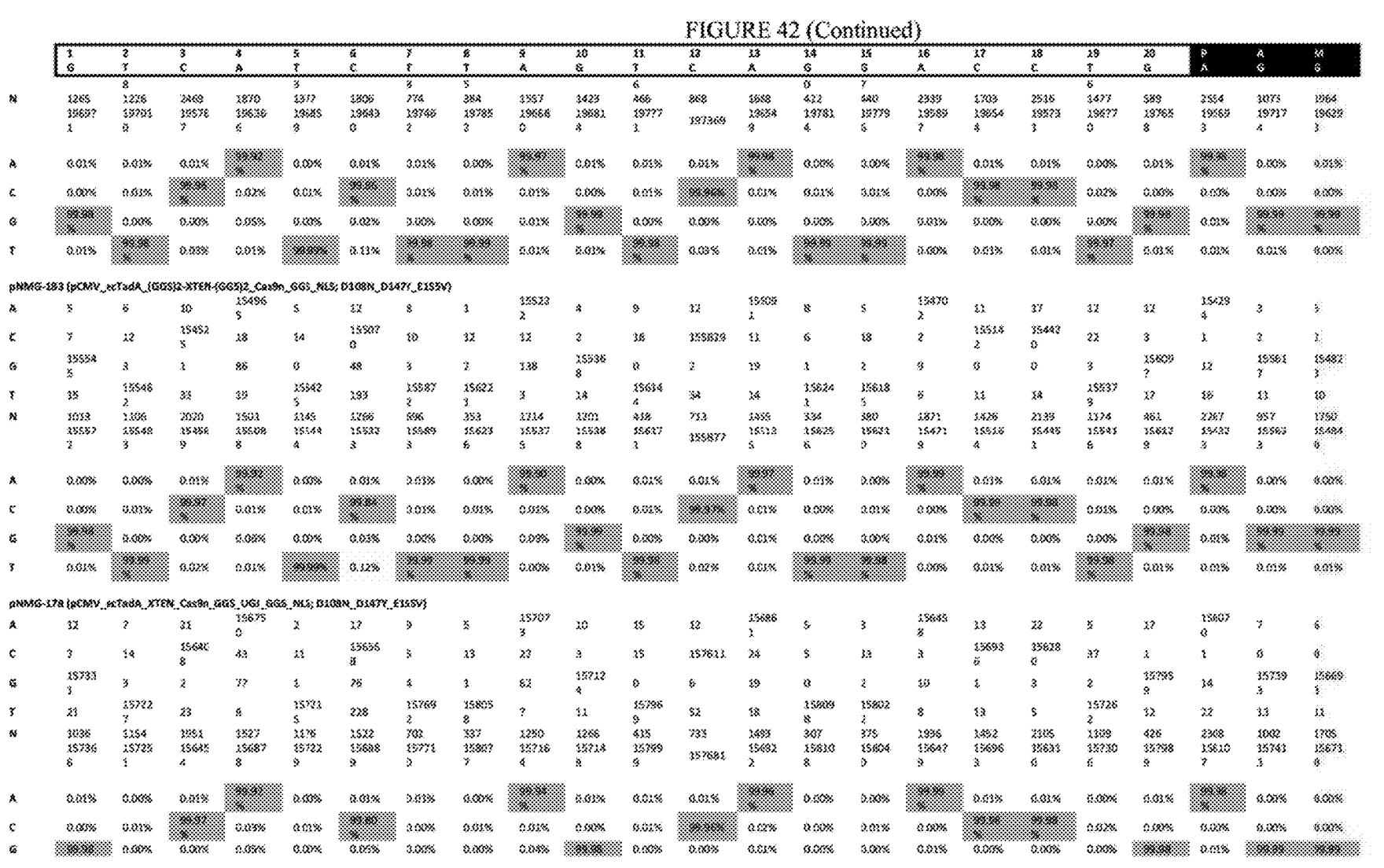
Figure 42:
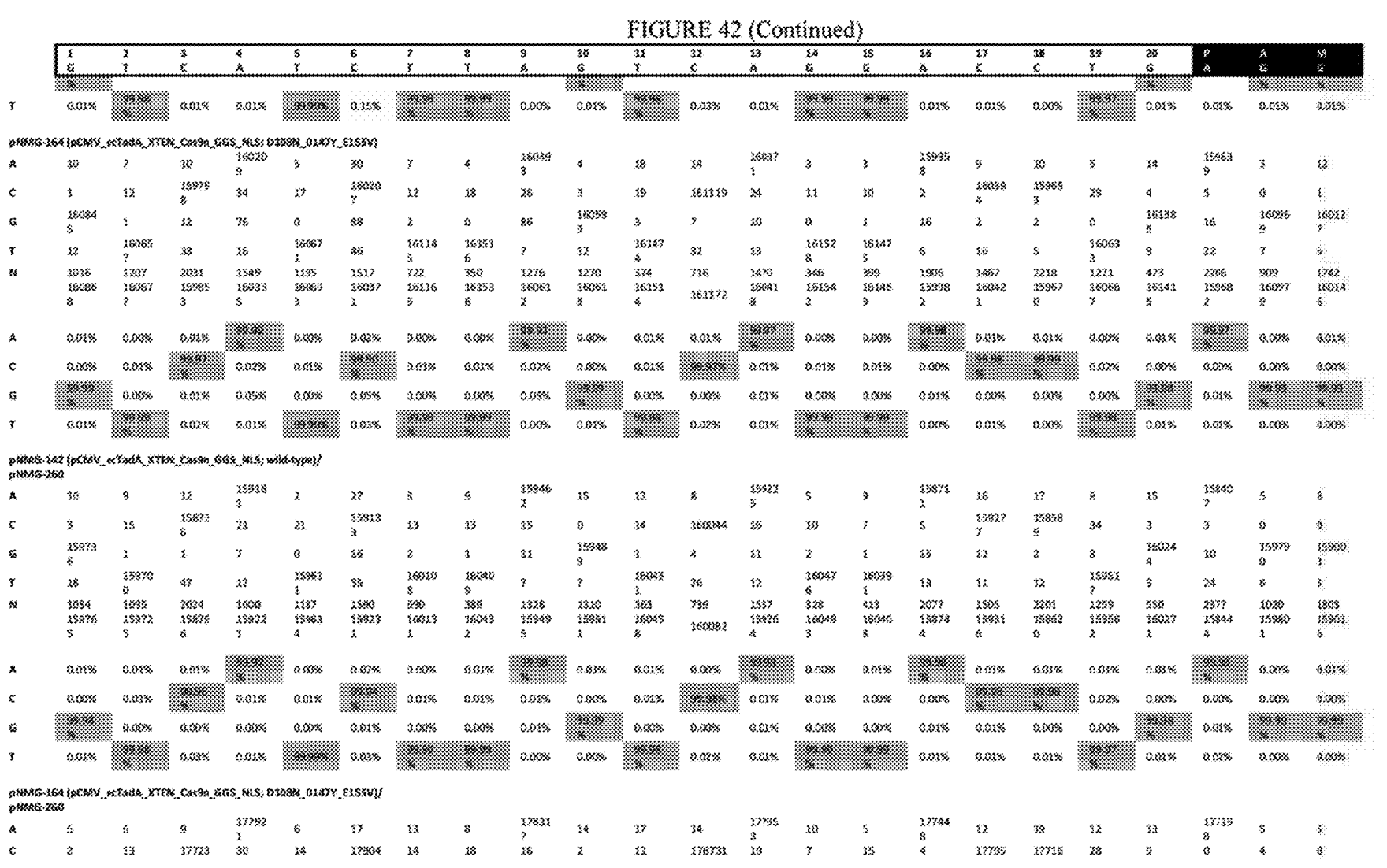
Figure 42:
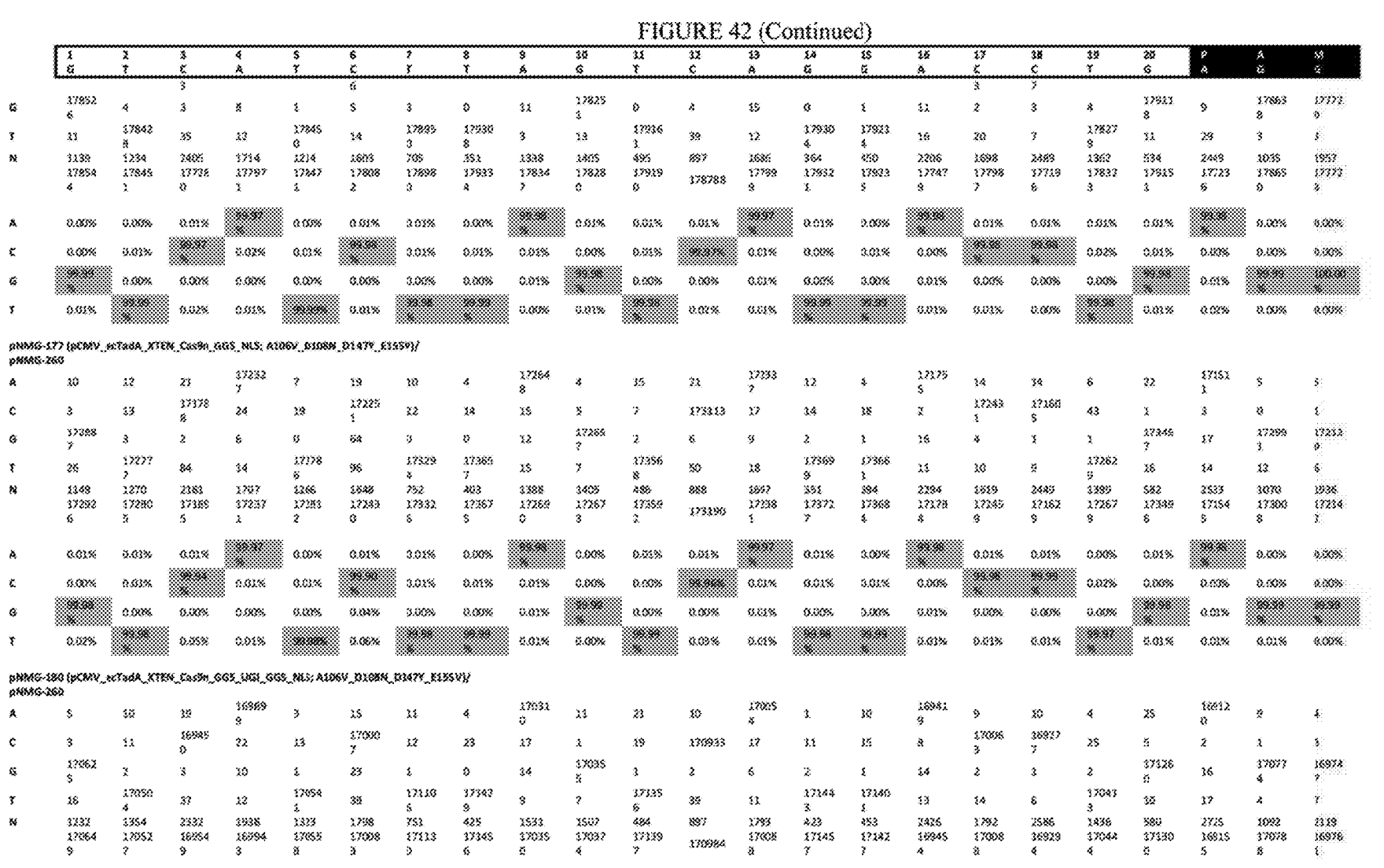
Figure 42:
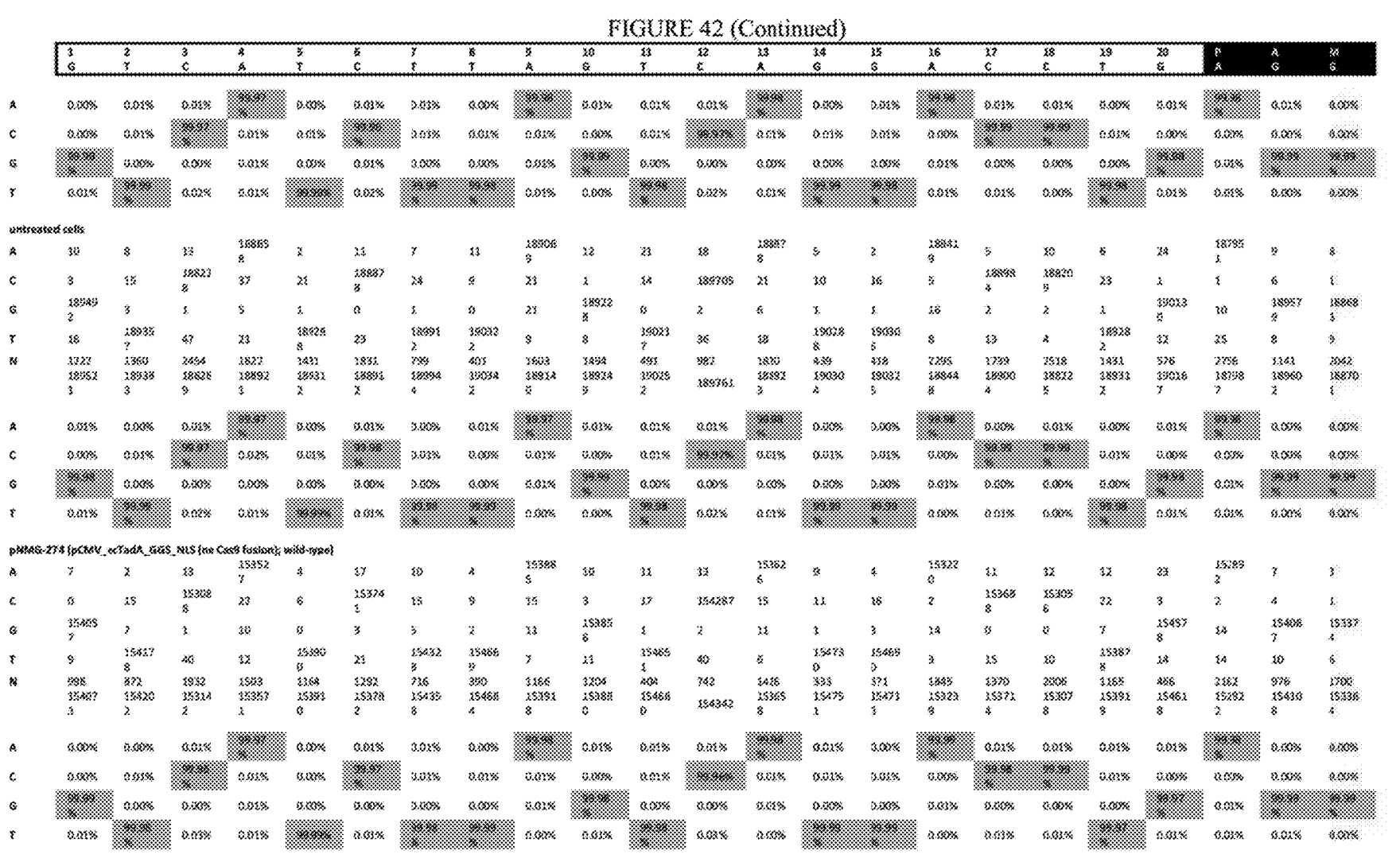
Figure 42:
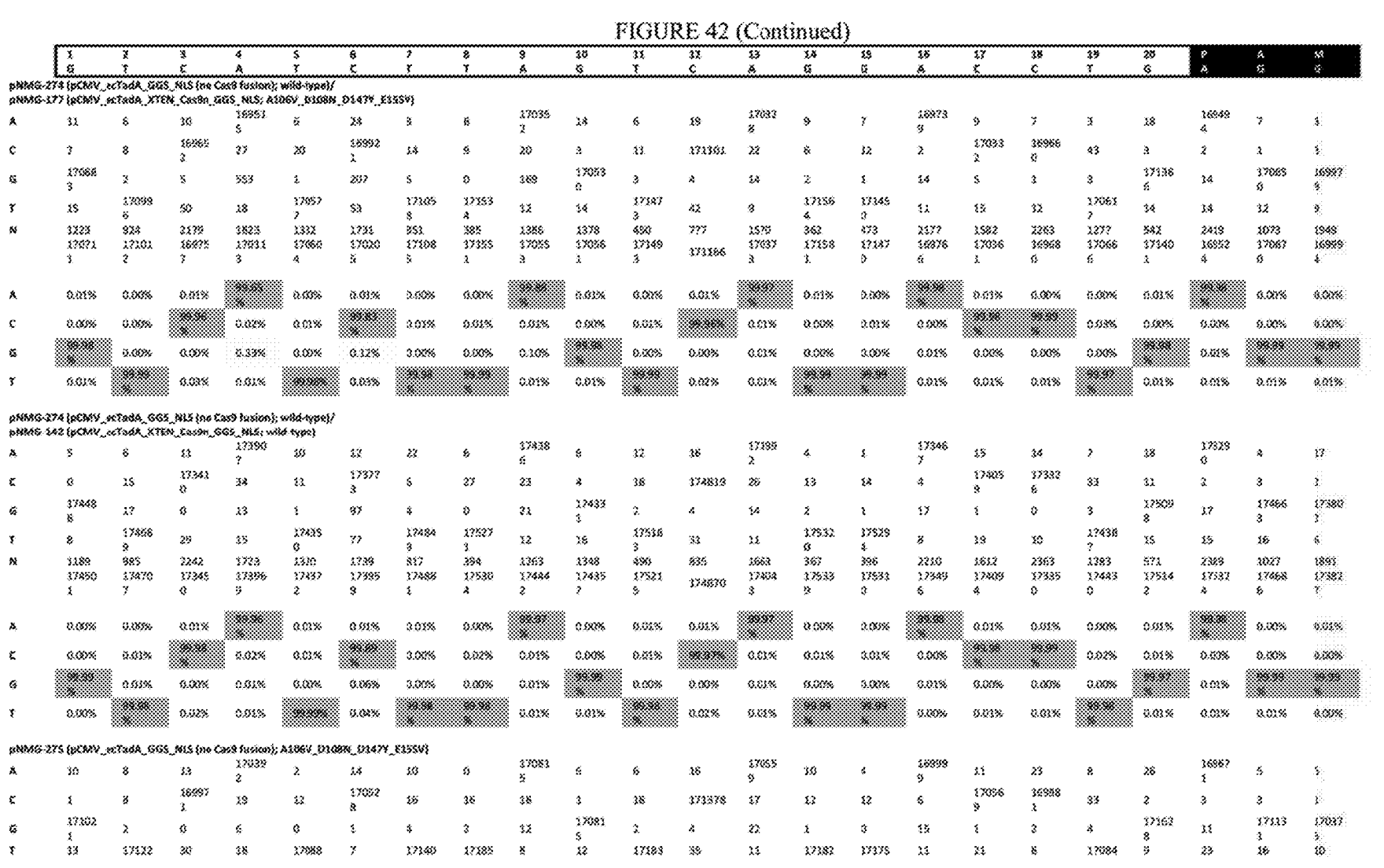
Figure 42:
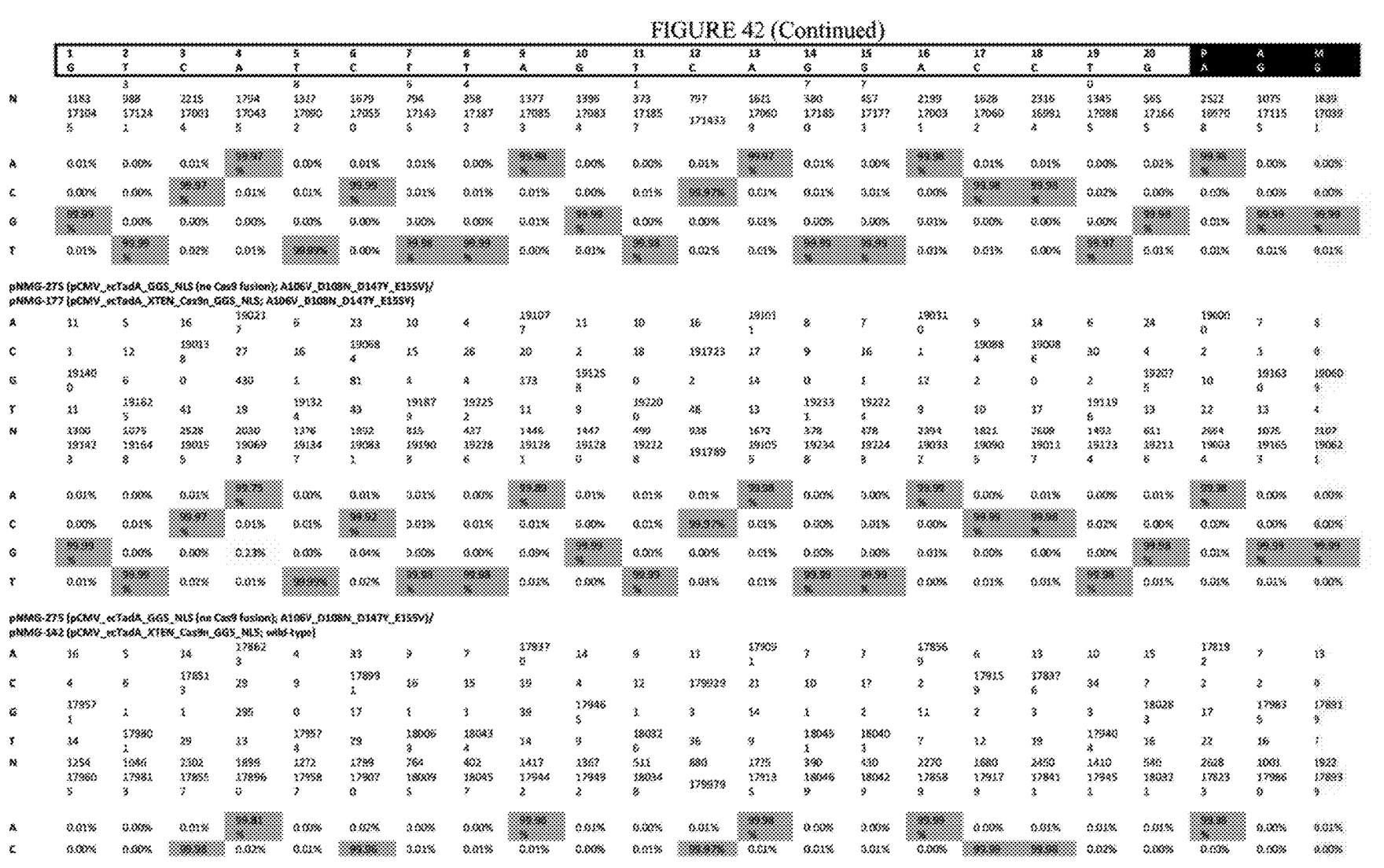
Figure 42:
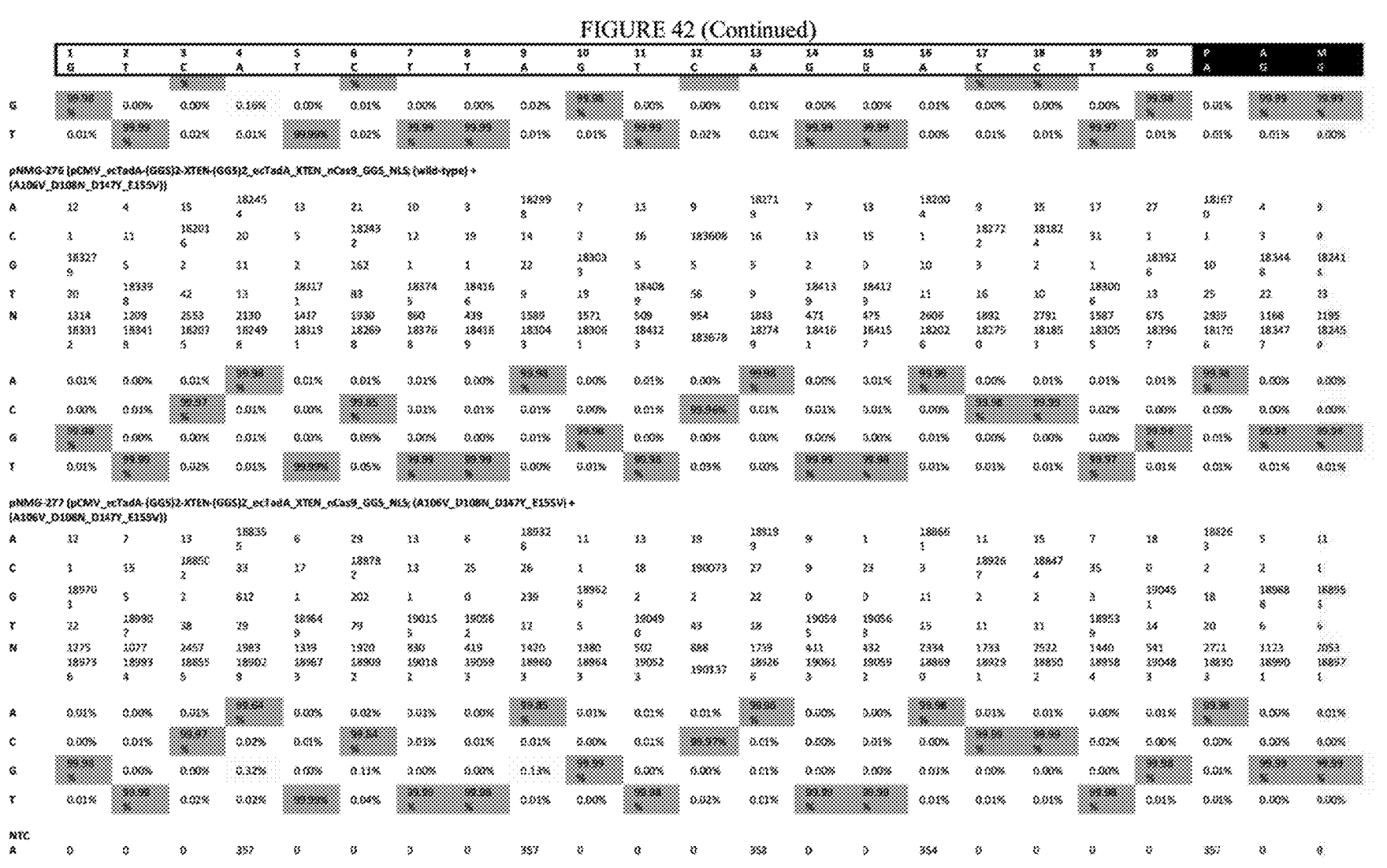
Figure 42:
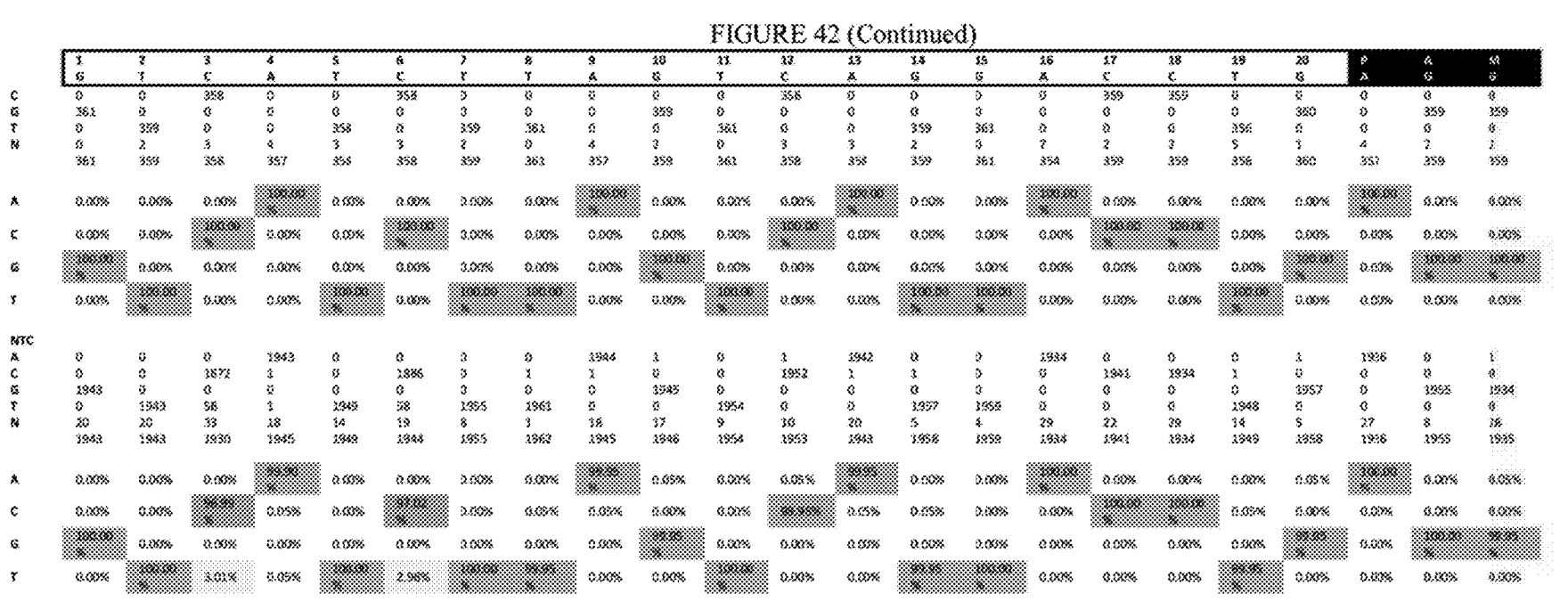

FIG. 42 shows the results of transfection at the RNF-2 site. The sequence corresponds to SEQ ID NO: 44.

Figure 43:
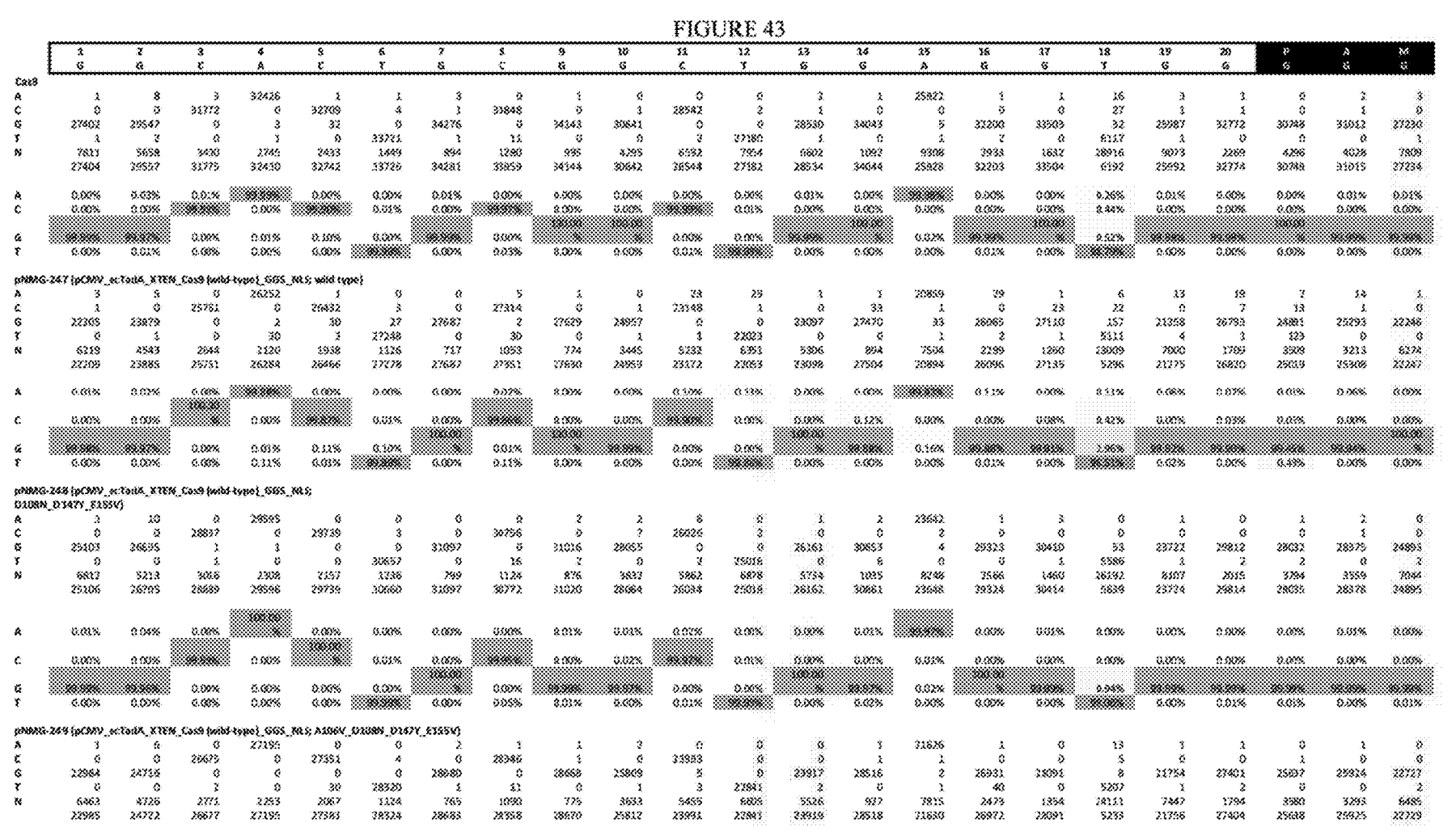
Figure 43:
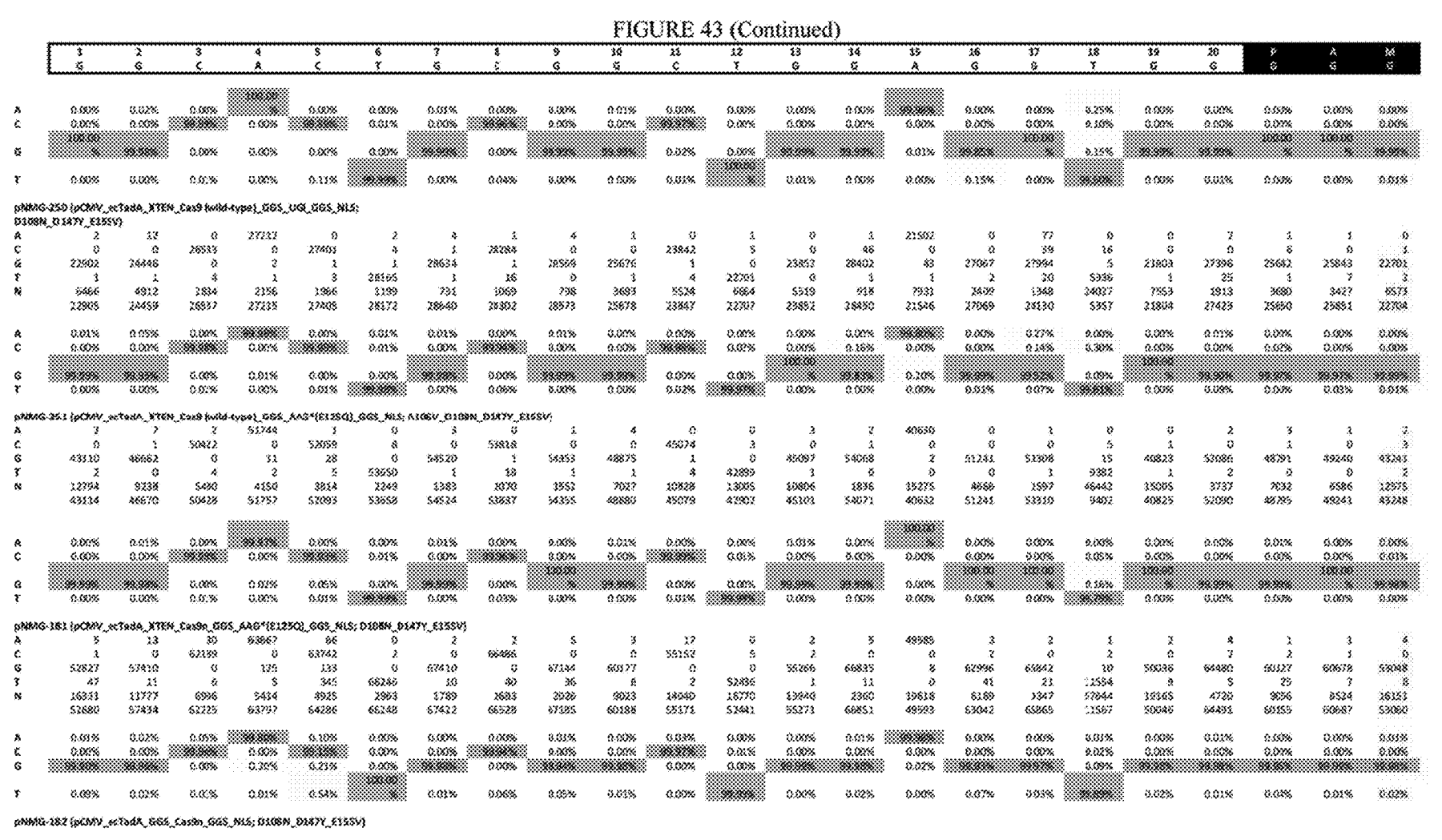
Figure 43:
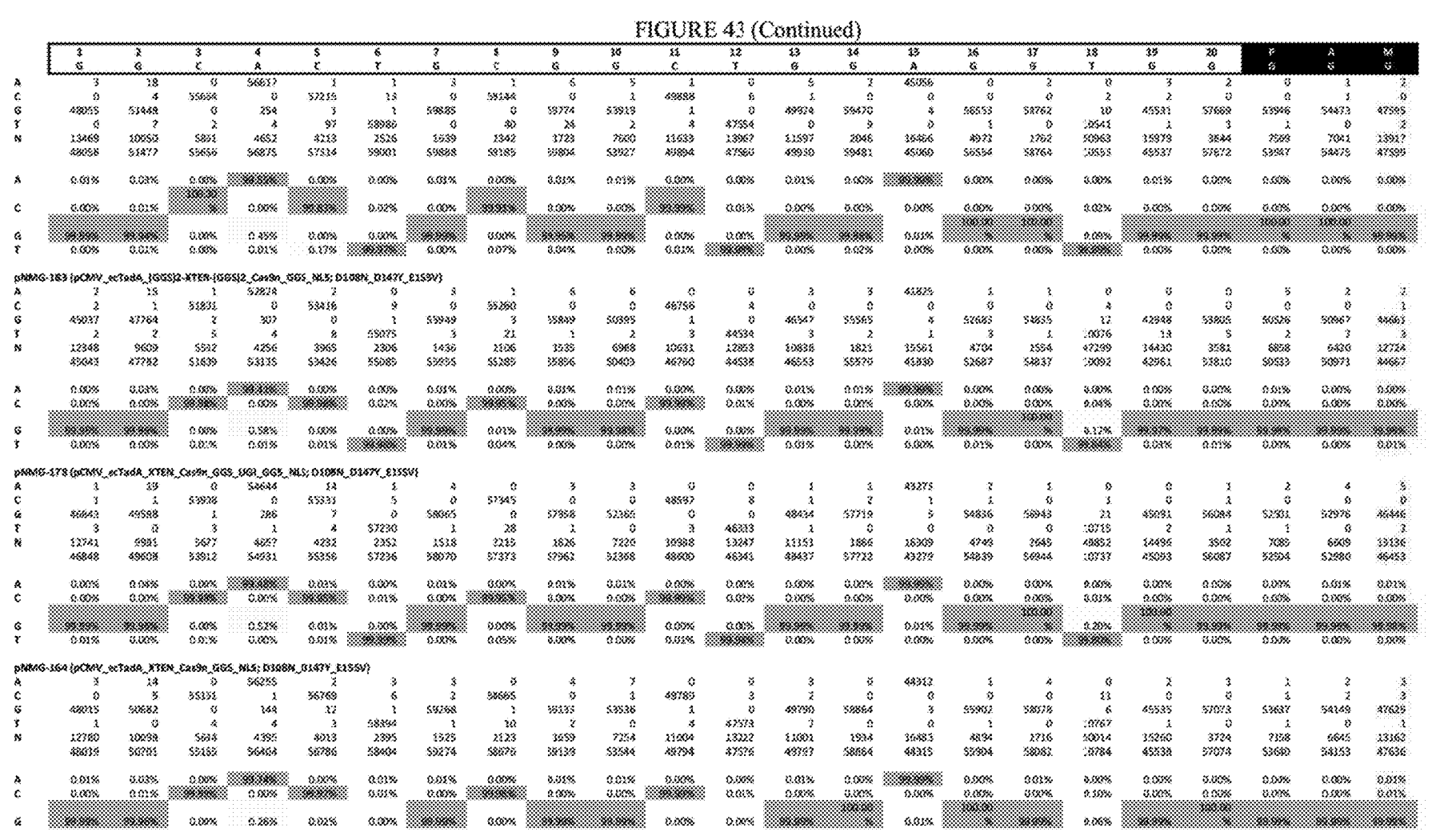
Figure 43:
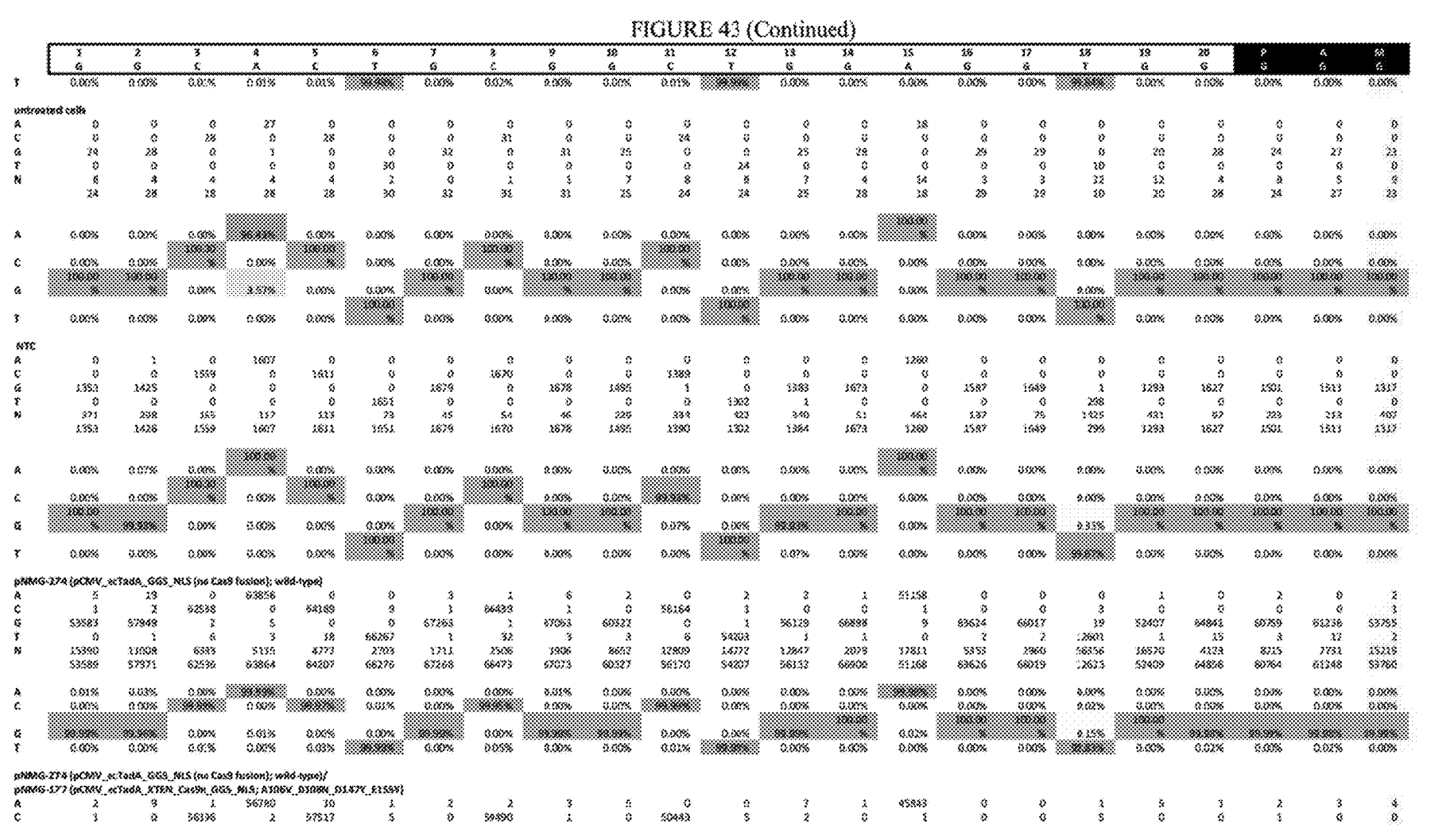
Figure 43:
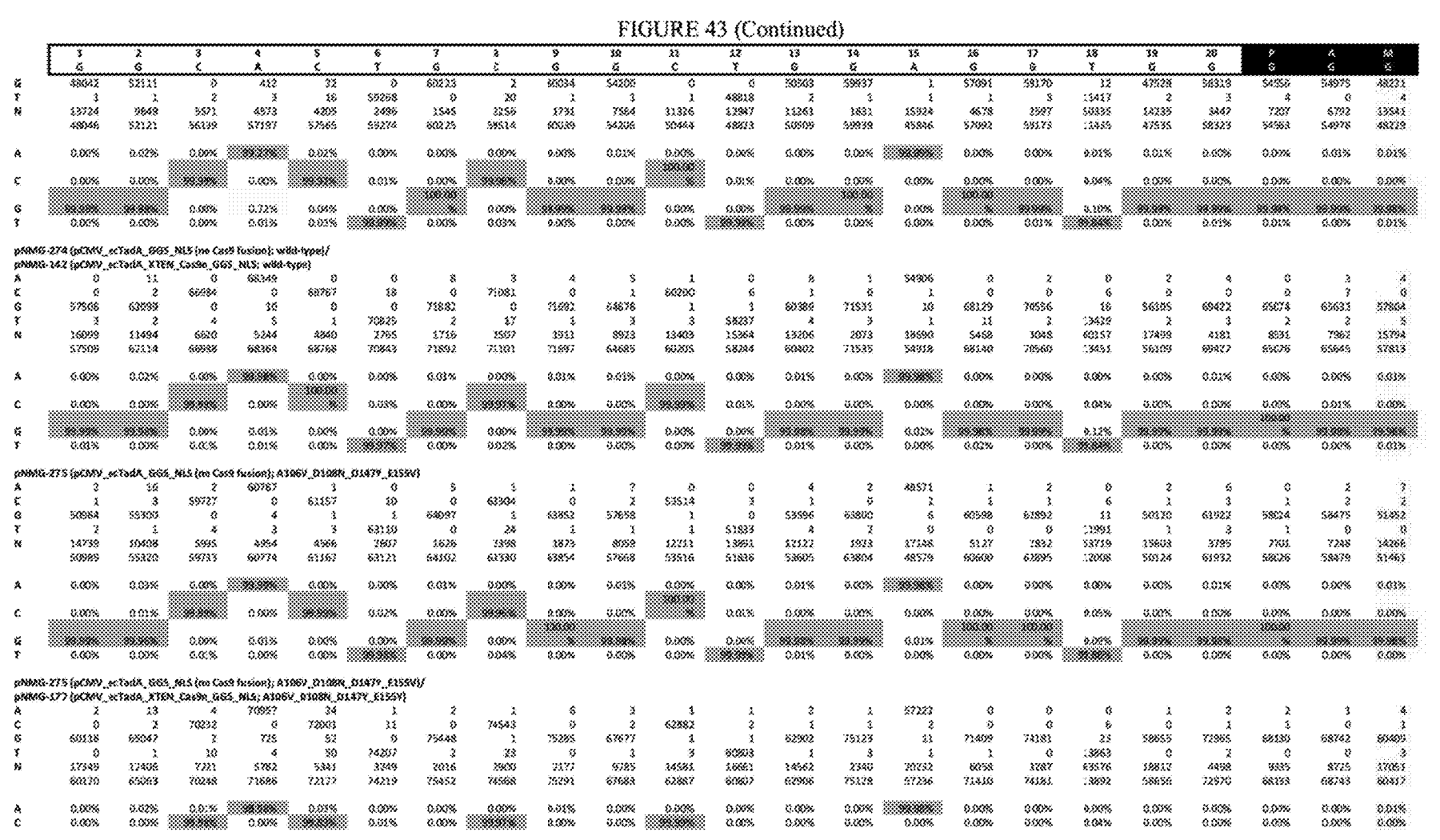
Figure 43:
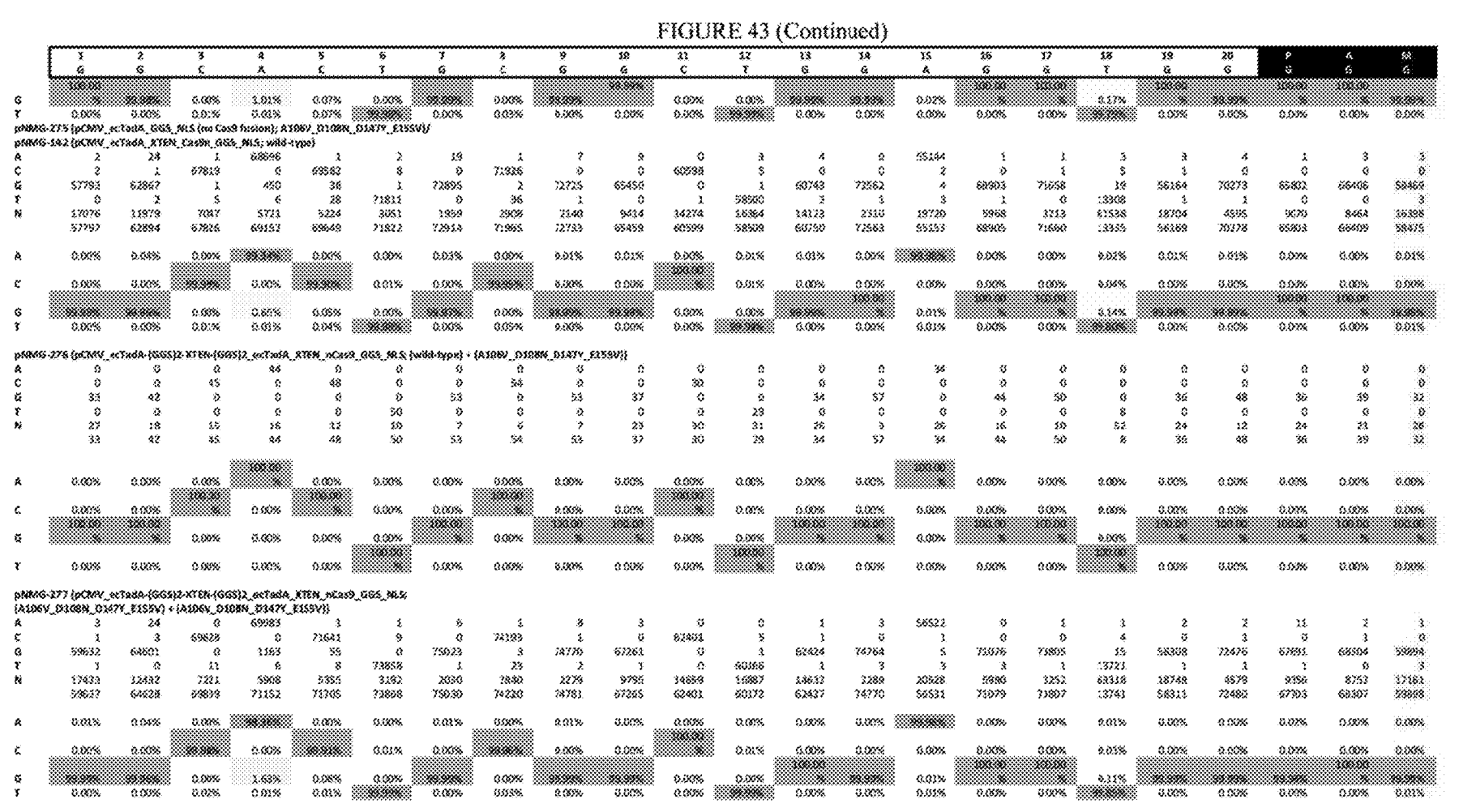

FIG. 43 shows the results of transfection at the Hek-4 site. The sequence corresponds to SEQ ID NO: 43.

Figure 44:
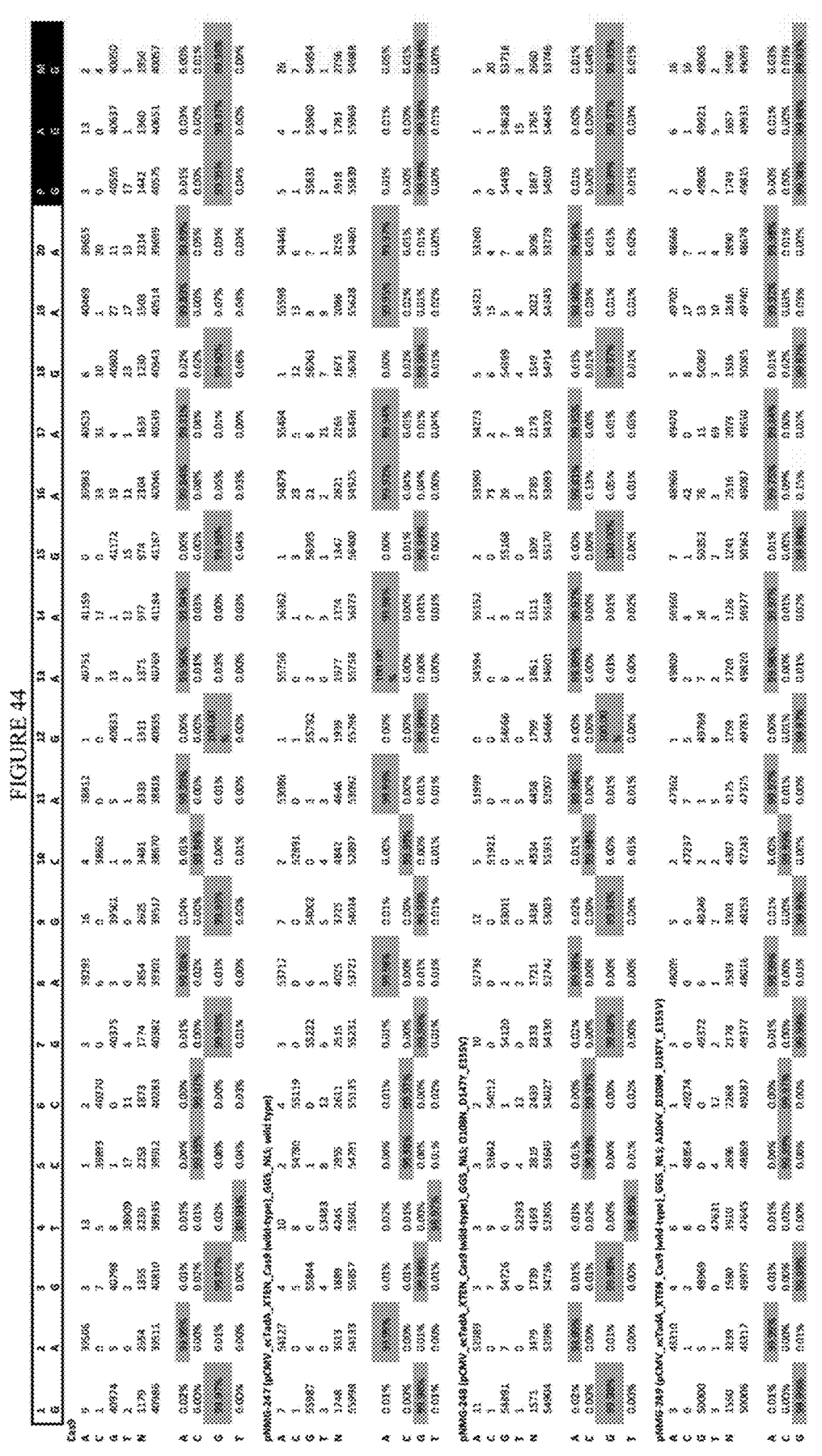
Figure 44:
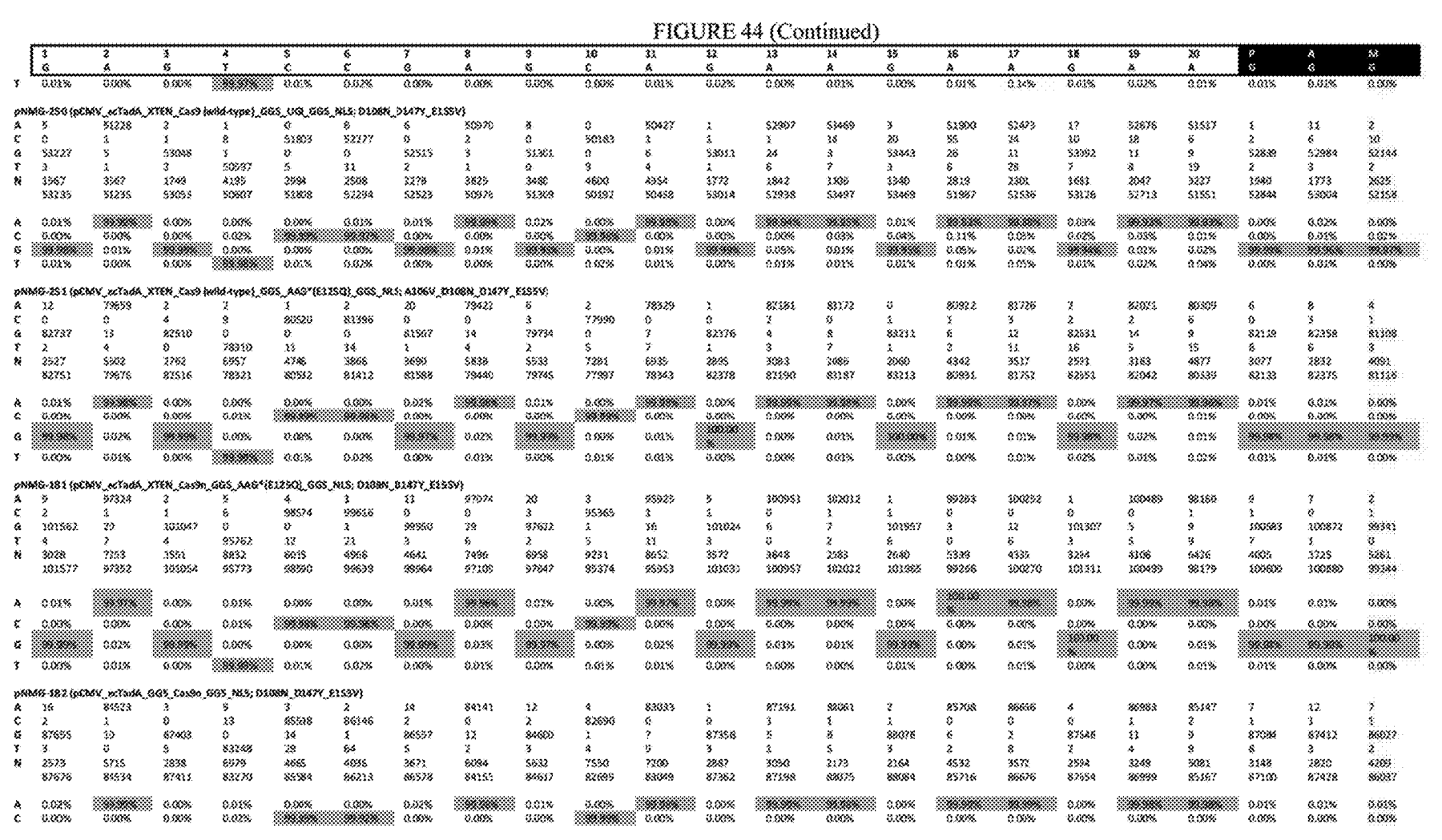
Figure 44:
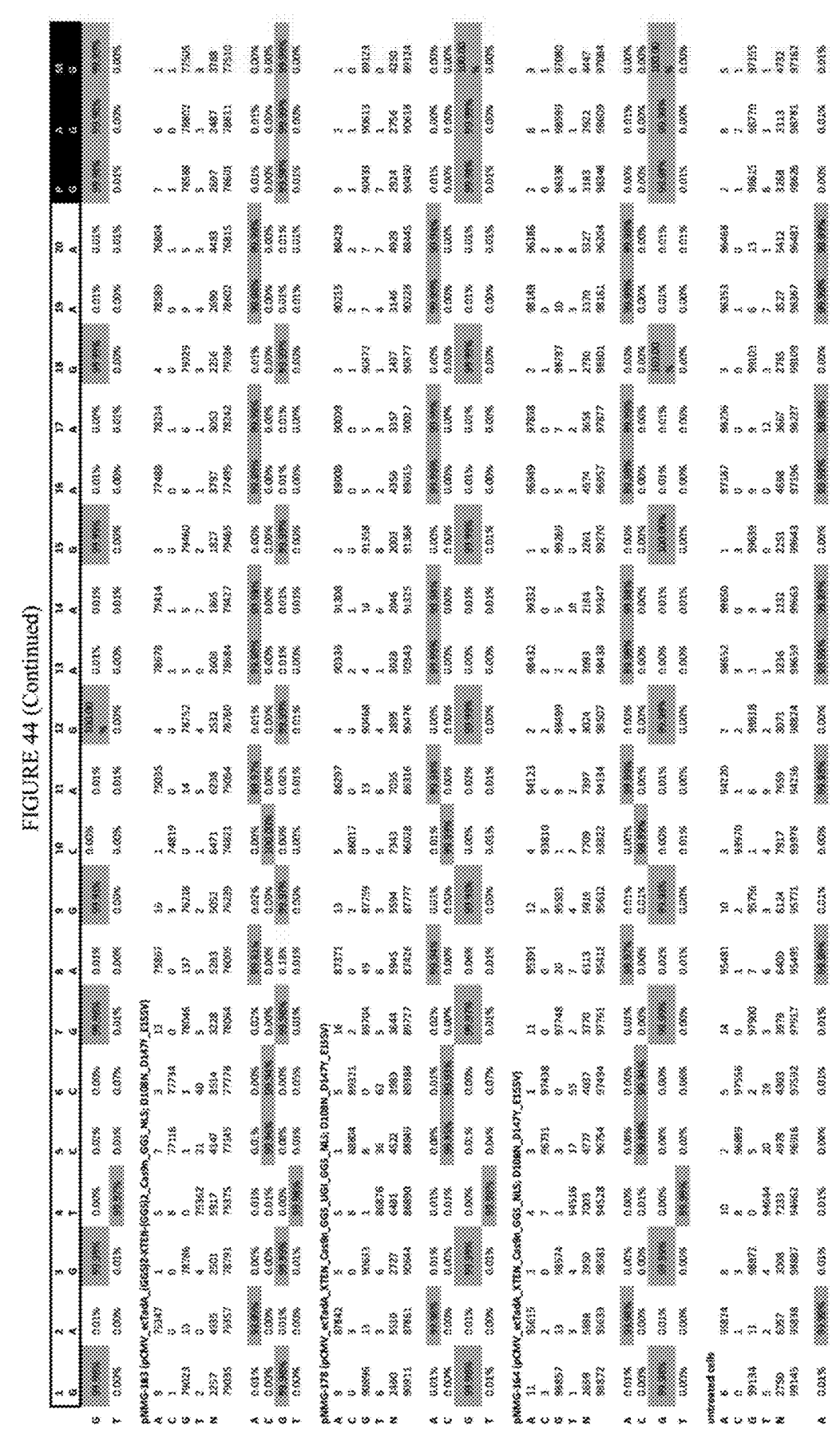
Figure 44:
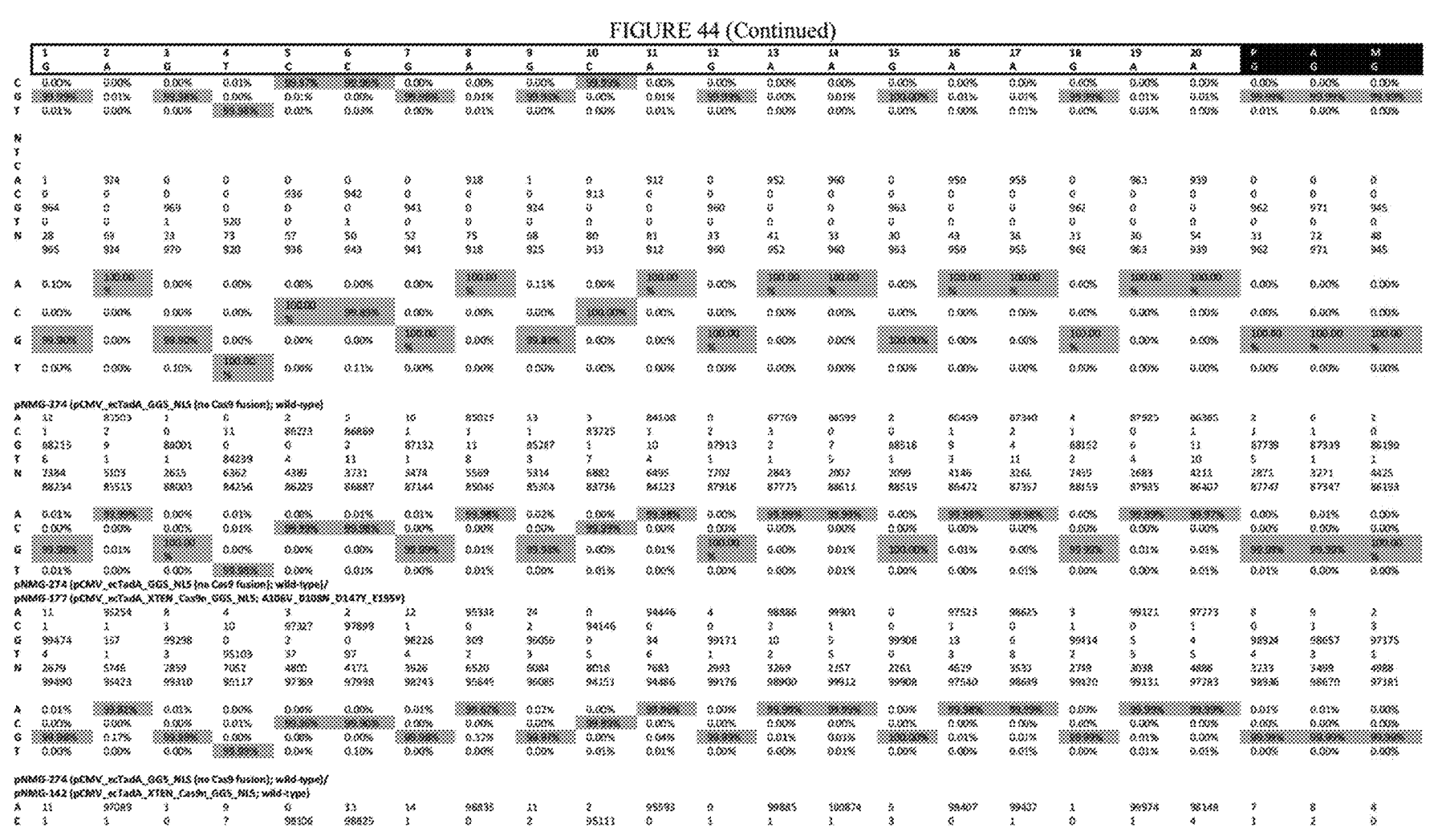
Figure 44:
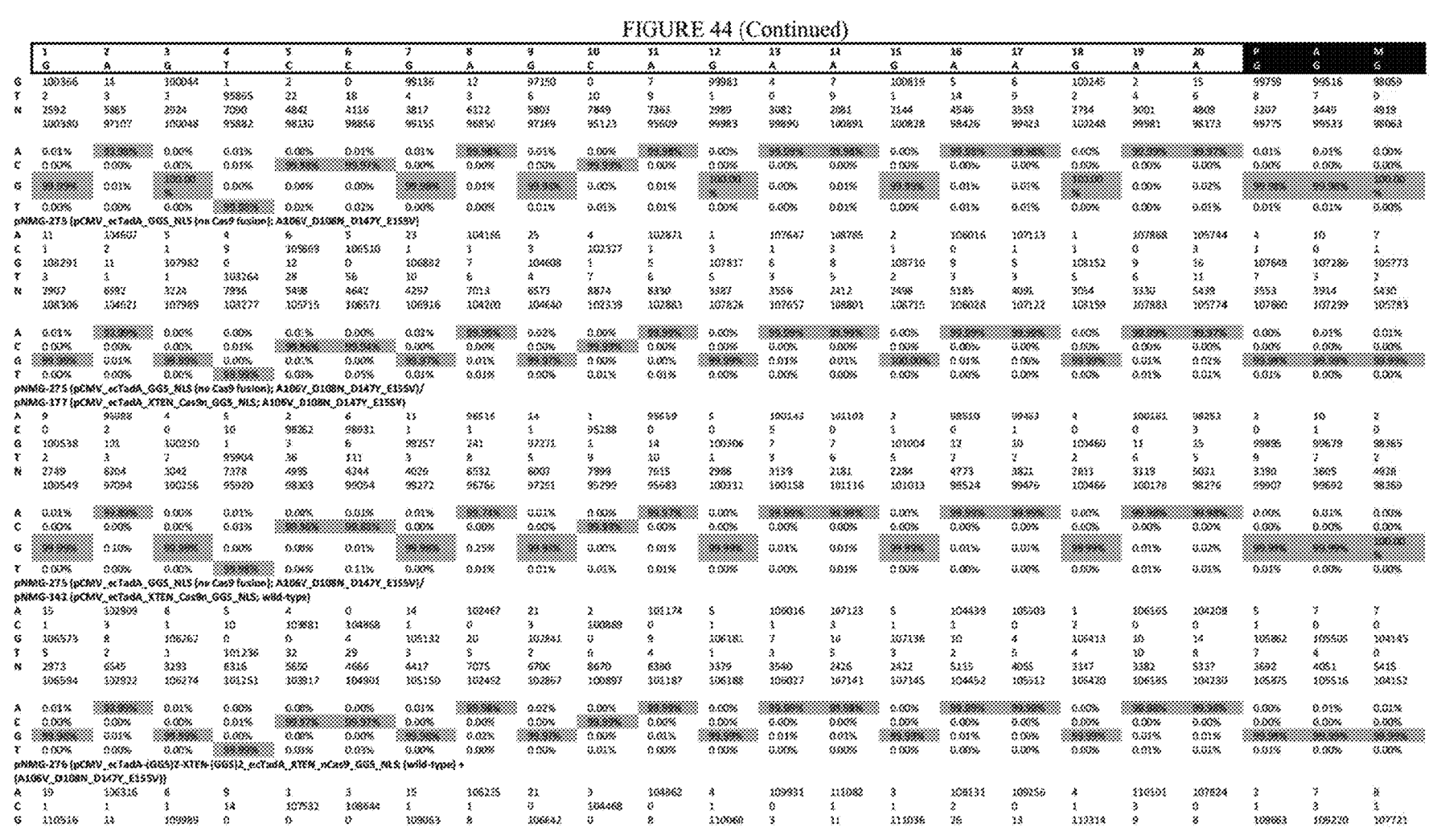
Figure 44:
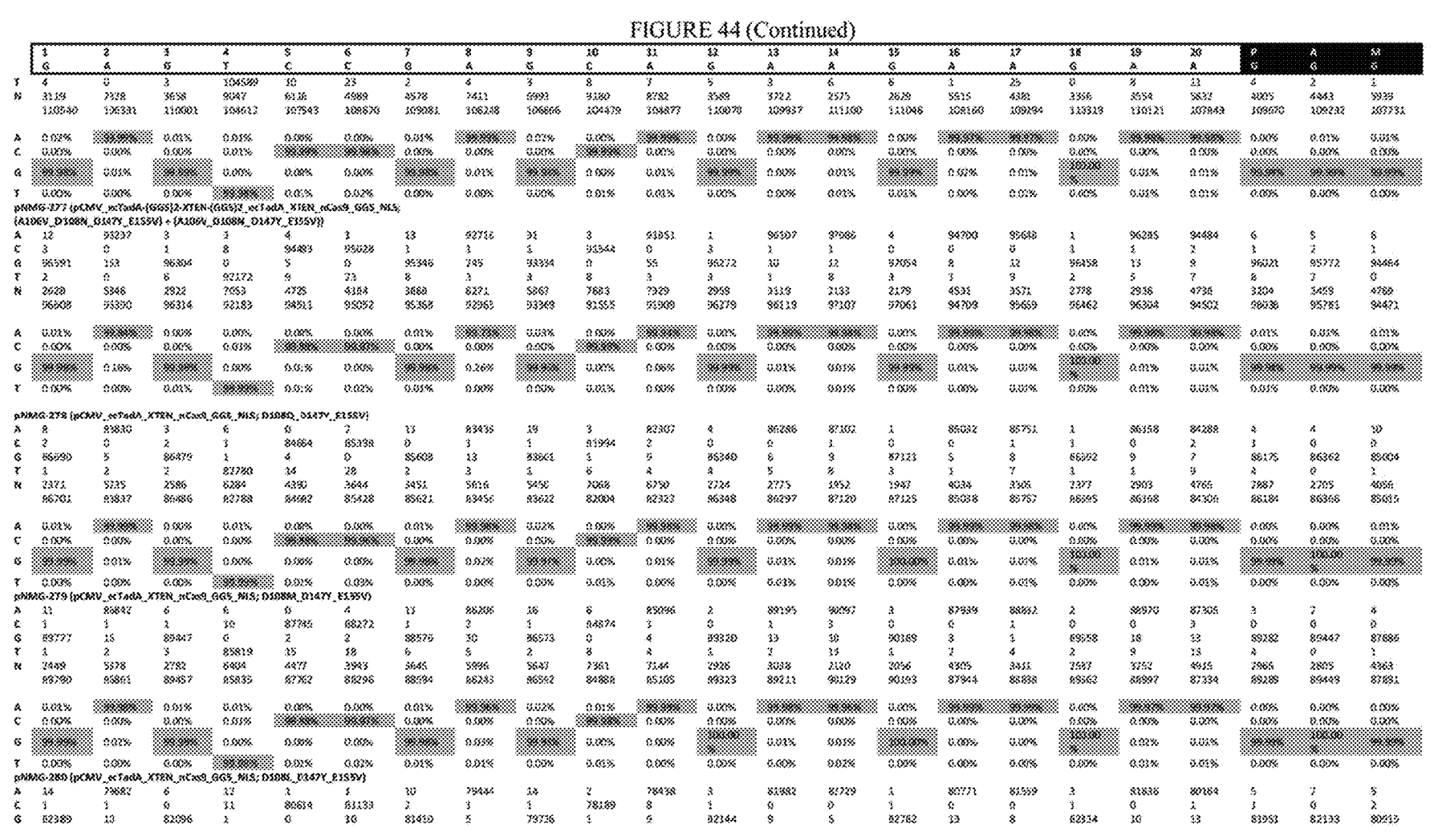
Figure 44:
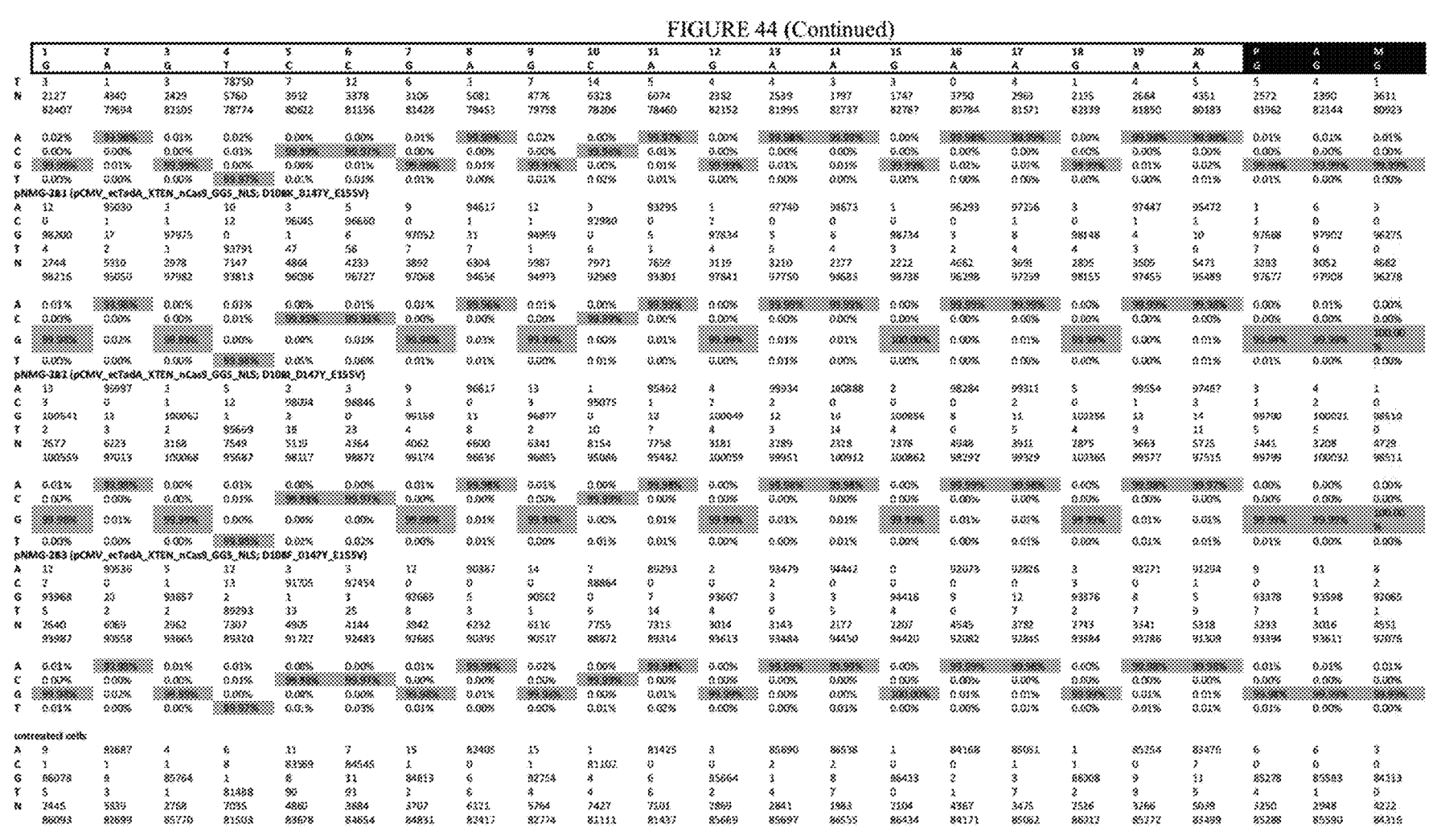
Figure 44:
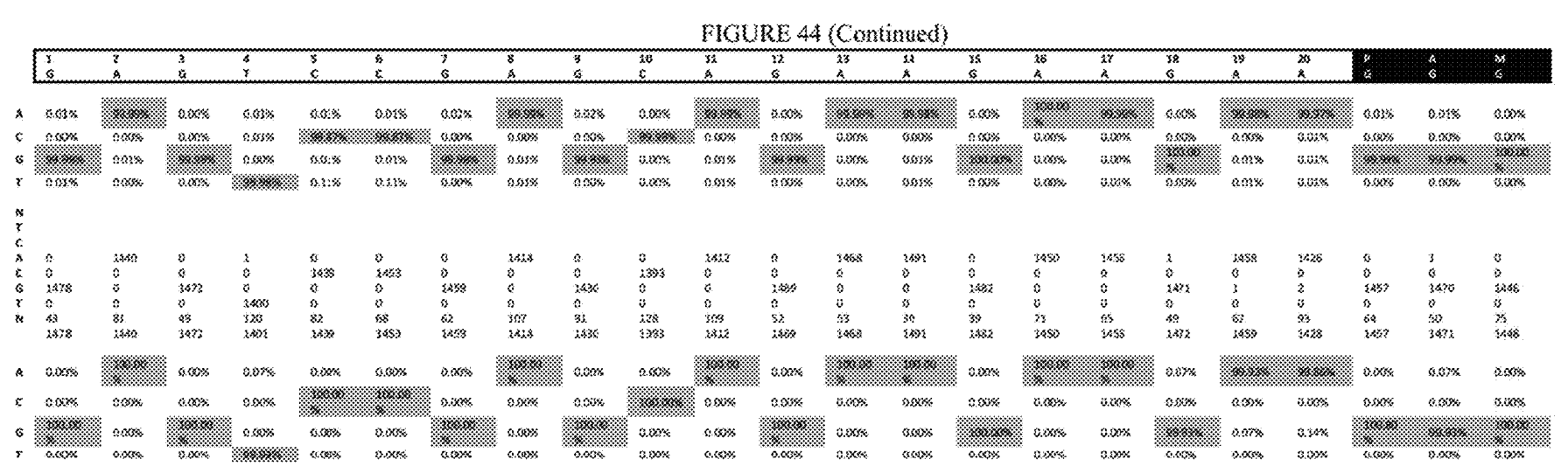

FIG. 44 shows the results of transfection at the EMX-1 site. The sequence corresponds to SEQ ID NO: 46.

Figure 45:
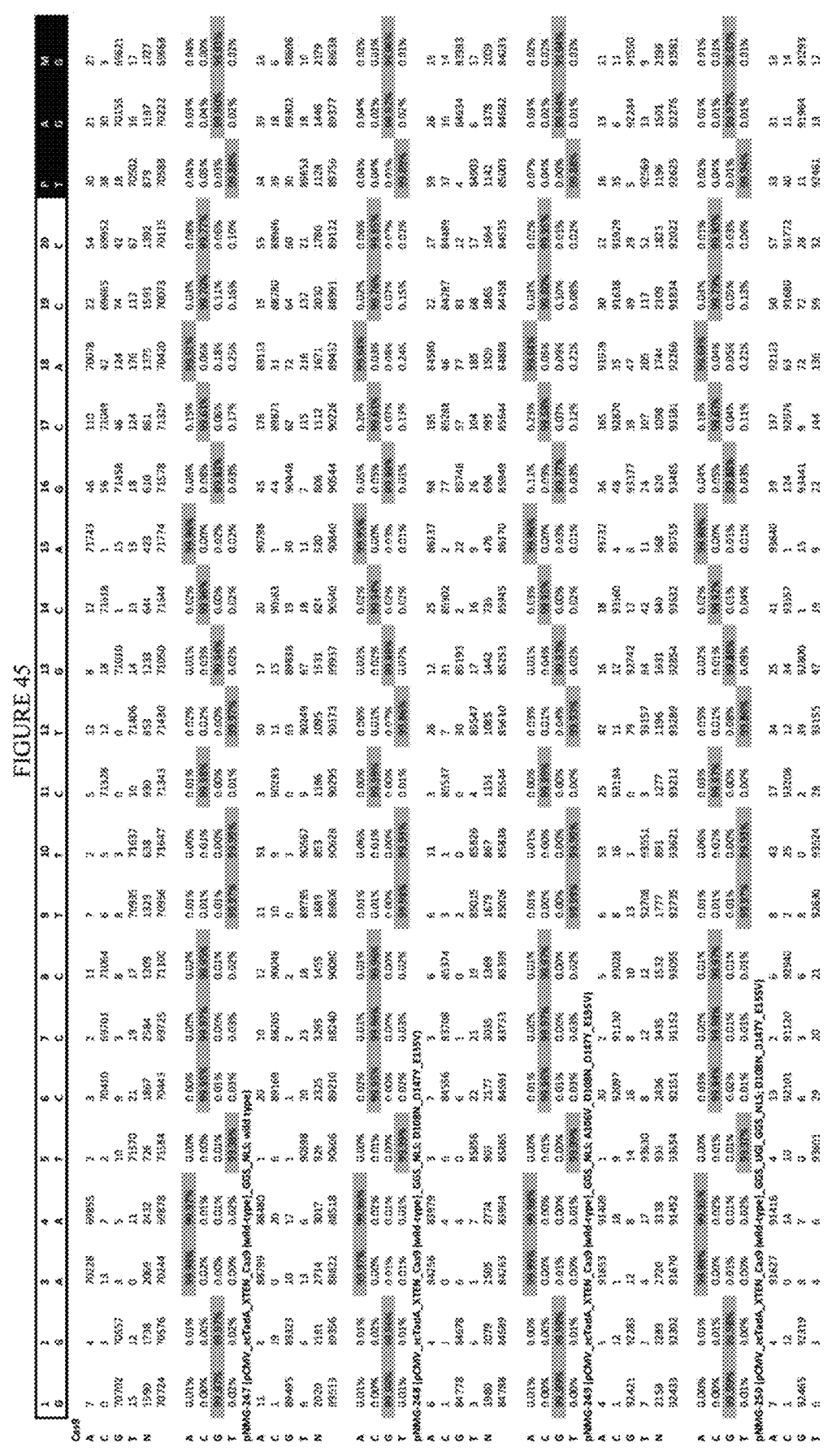
Figure 45:
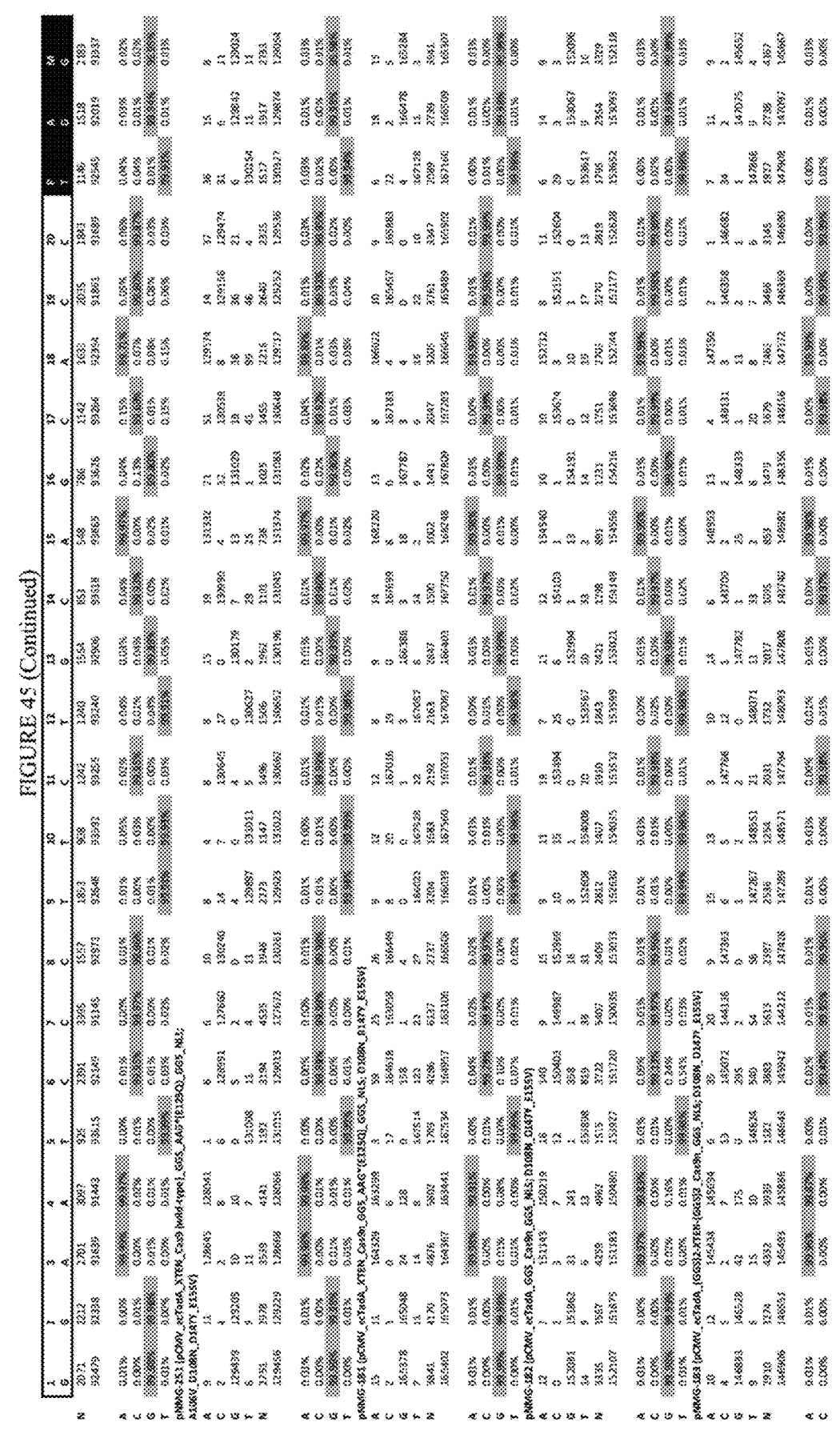
Figure 45:
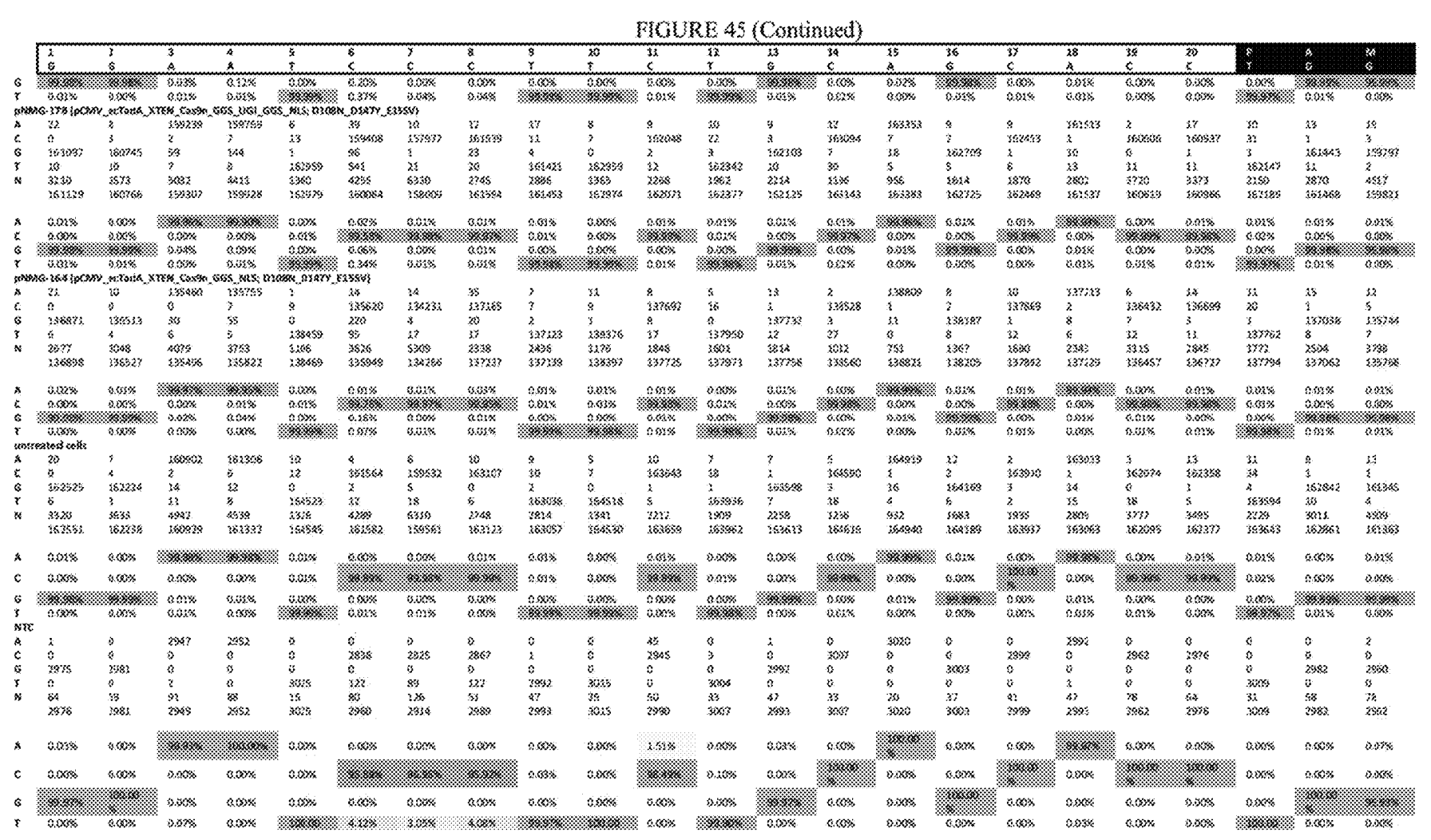
Figure 45:
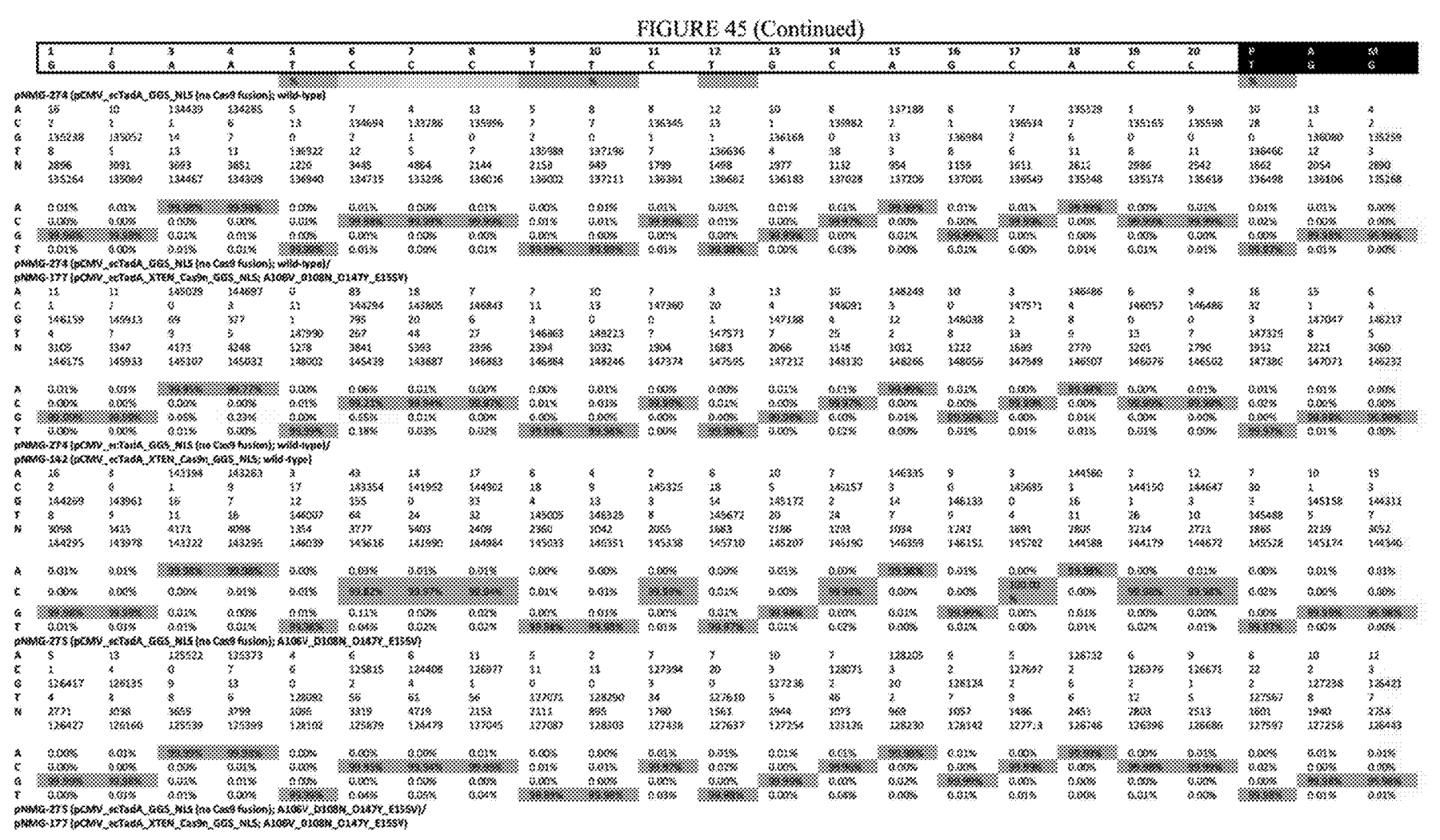
Figure 45:
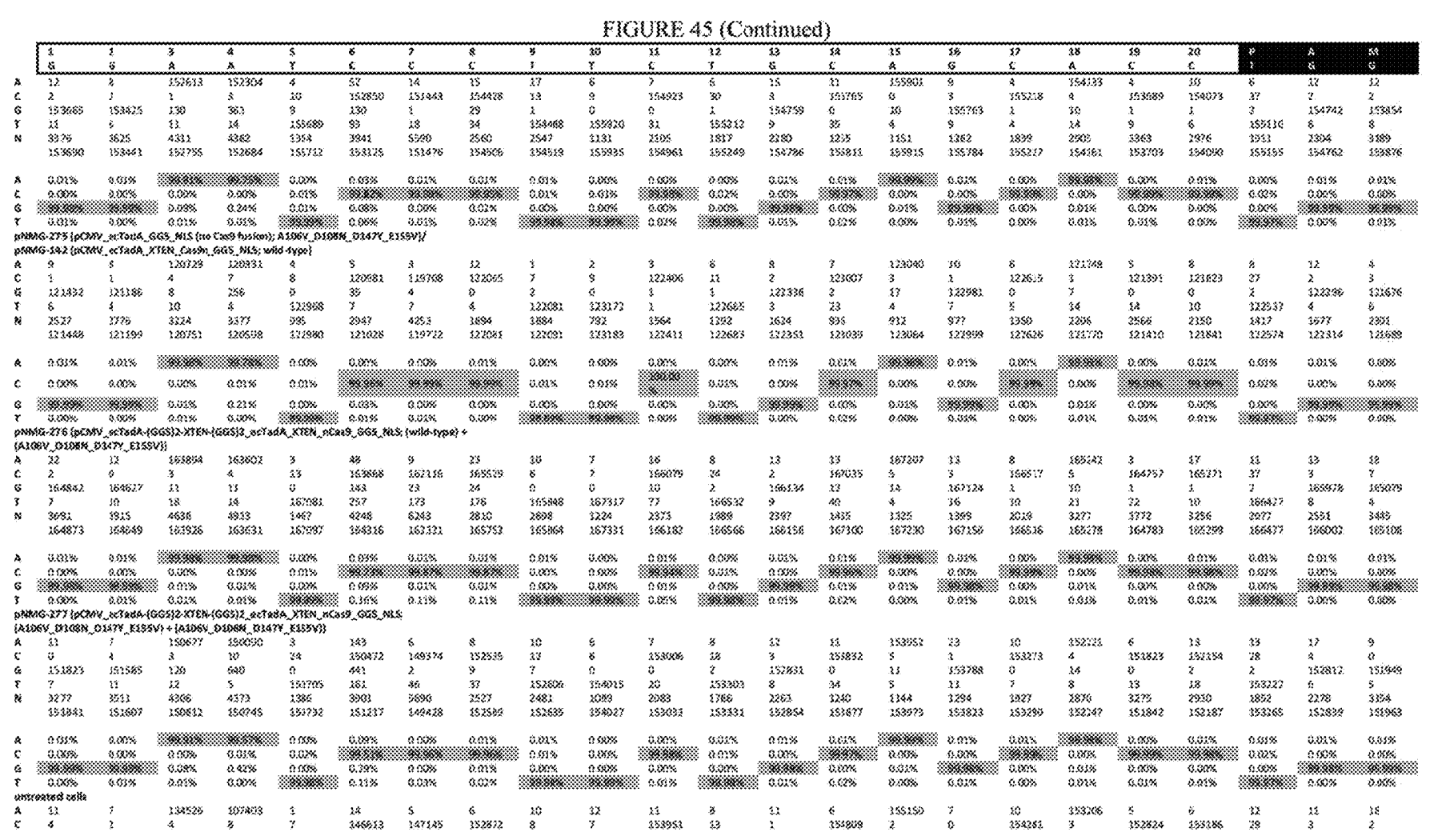
Figure 45:
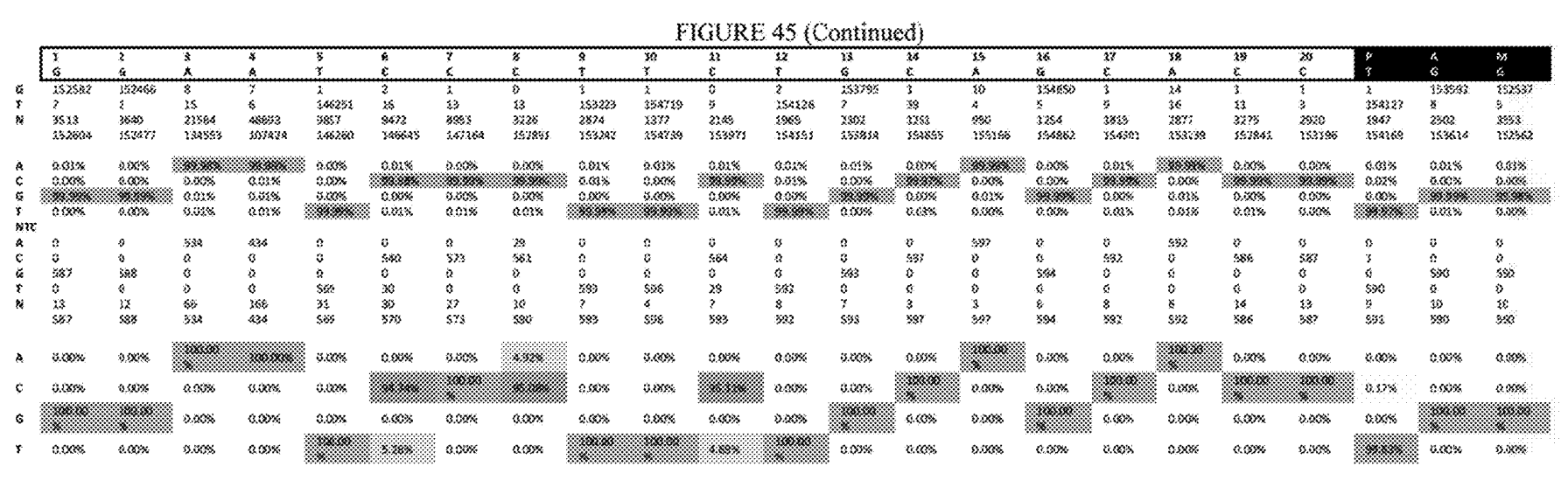

FIG. 45 shows the results of transfection at the FANCF site. The sequence corresponds to SEQ ID NO: 45.

FIG. 46 shows deaminase editing of sgRNA.

FIG. 47 shows constructs developed for fusions at various sites.

FIG. 48 shows indel rates for different fusions at various sites.

FIG. 49 shows the protospacer and PAM sequences of base editing sites set forth in SEQ ID NOs: 46, 45, 6, 42, 43, and 468 from top to bottom, respectively.

FIG. 50 shows constructs developed for fusions at various sites using further mutated D108 residue.

FIG. 51 shows the protospacer and PAM sequences of base editing sites set forth in SEQ ID NOs: 6, 46, and 42 from top to bottom, respectively.

FIG. 52 shows the results of using mutated D108 residues to cause deaminase to reject RNA as a substrate and change the editing outcome.

FIG. 59 shows the importance of linker length on base editing function.

FIG. 60 shows the importance of linker length on base editing function.

FIG. 64 shows dimerization results from base editing.

FIG. 65 shows dimerization results from base editing.

FIG. 71 shows a HEK293 site 2 sequence. The sequence corresponds to SEQ ID NO: 360.

FIG. 72 shows the results of the first run with various edTadA mutations using the sequence of FIG. 71.

Figure 73:
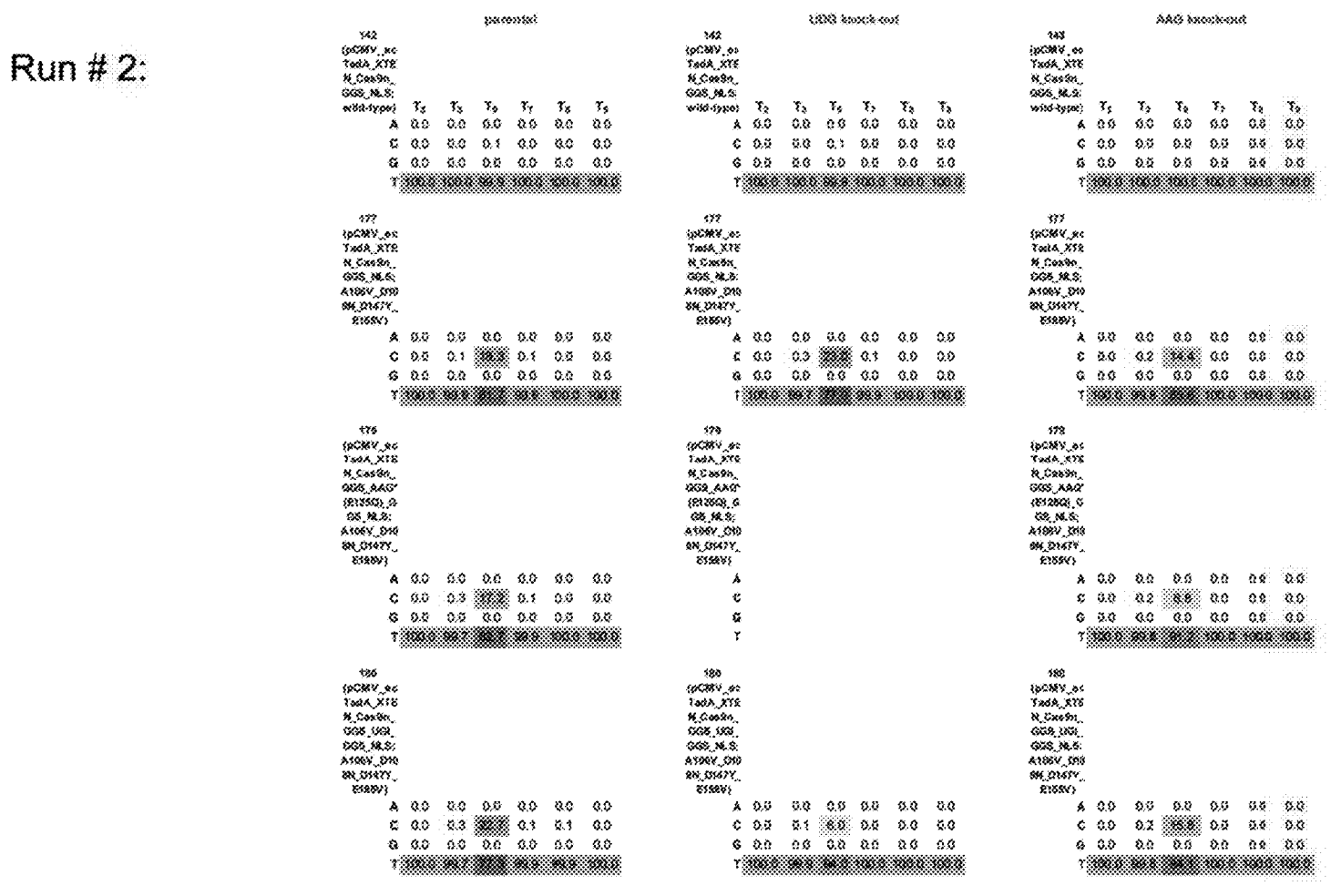

FIG. 73 shows the results of the second run with various edTadA mutations using the sequence of FIG. 71.

FIG. 74 shows a FANCF sequence. The sequence corresponds to SEQ ID NO: 45.

FIG. 75 shows the results of the second run using various edTadA mutations and the sequence of FIG. 74.

Figure 76:
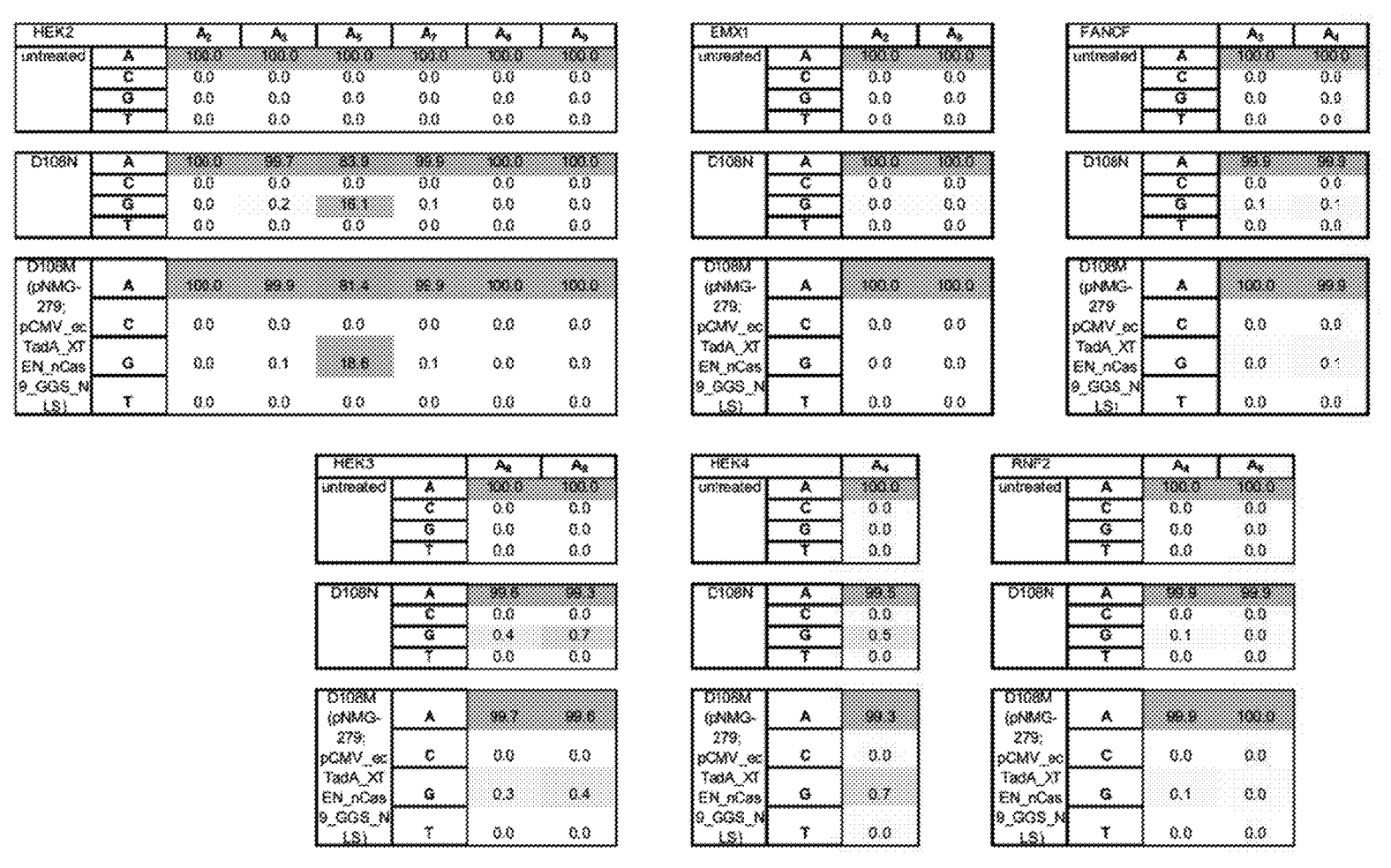

FIG. 76 shows the results of mutated D108 on all sites.

Figure 77:
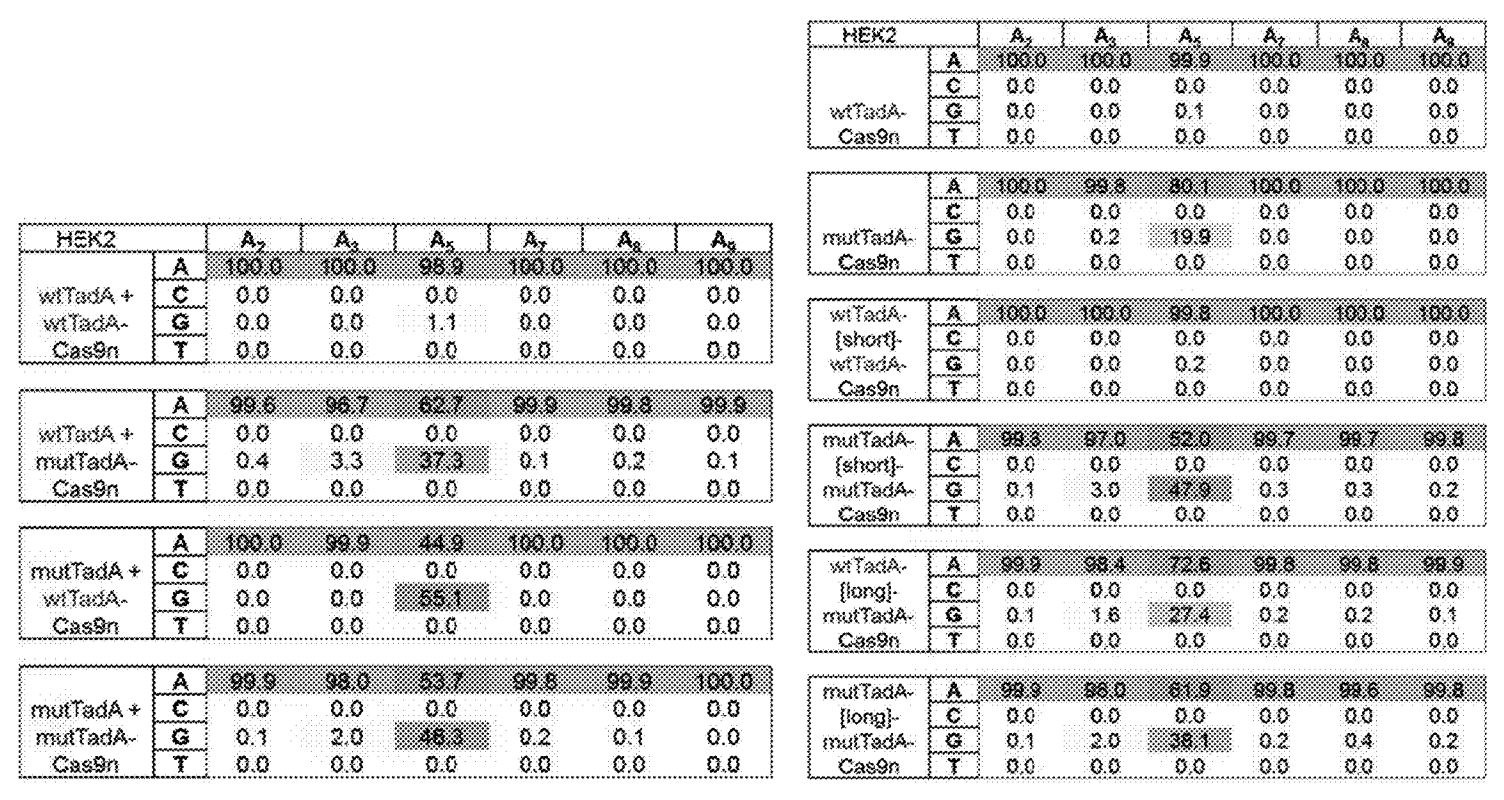

FIG. 77 shows in trans data from previous run (left panel) and the mut-mut fusions hindered by super long linkers.

Figure 78:
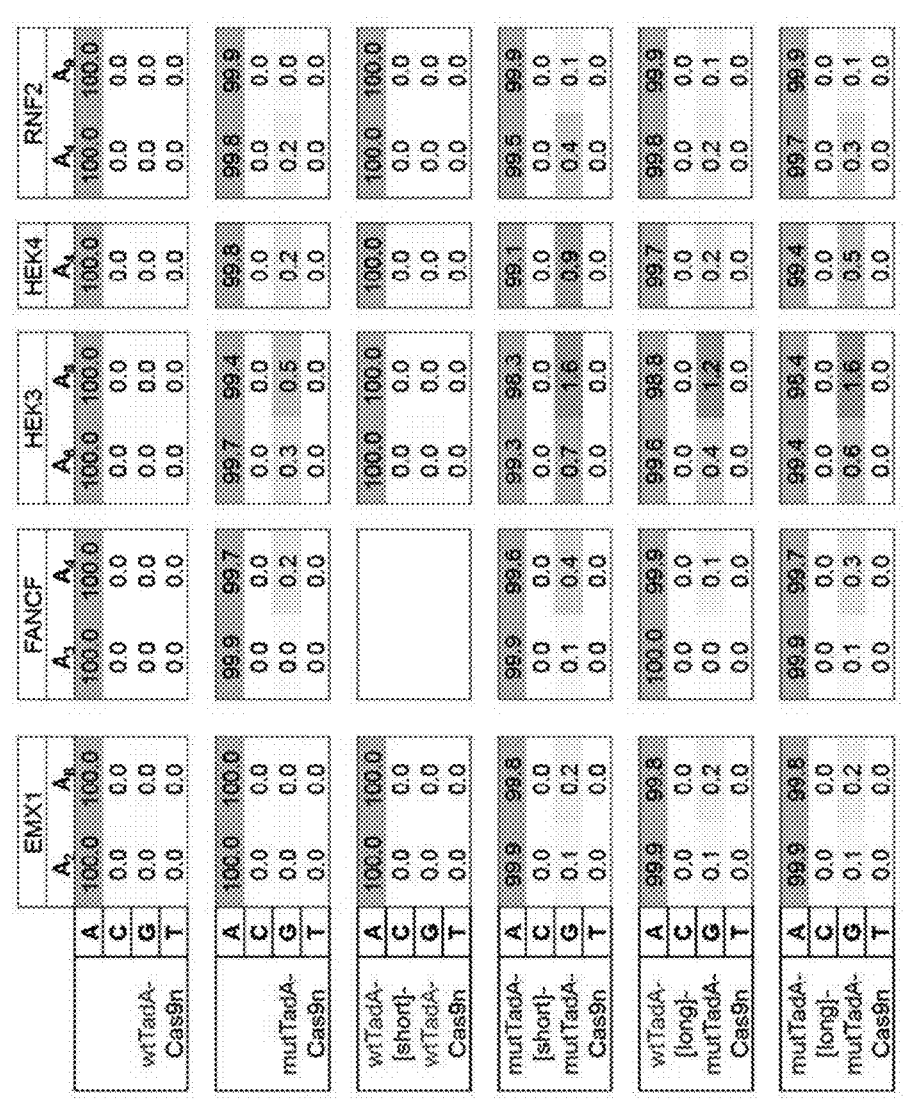

FIG. 78 shows the results of tethering mutTadA to ABE.

FIG. 86 shows the constructs used when tethering EndoV to ABE.

FIG. 87 is a schematic showing the tethering EndoV to ABE.

FIG. 88 shows the results of tethering EndoV to ABE.

FIG. 108 shows a summary of results of editing at the Hek-2 site. The Hek-2 sequence provided in the figure represents the reverse complement of SEQ ID NO: 41, which is the DNA strand where A to G editing takes place. The sequence corresponds to SEQ ID ID: 6.

FIG. 109 shows a summary of results of editing at the Hek2-3 site. The sequence corresponds to SEQ ID NO: 363.

FIG. 110 shows a summary of results of editing at the Hek2-6 site. The sequence corresponds to SEQ ID NO: 364.

FIG. 111 shows a summary of results of editing at the Hek2-7 site. The Hek2-7 sequence provided in the figure represents the reverse complement of the DNA strand where A to G editing takes place. The sequence corresponds to SEQ ID NO: 365.

FIG. 112 shows a summary of results of editing at the Hek2-10 site. The sequence corresponds to SEQ ID NO: 366.

Figure 113:
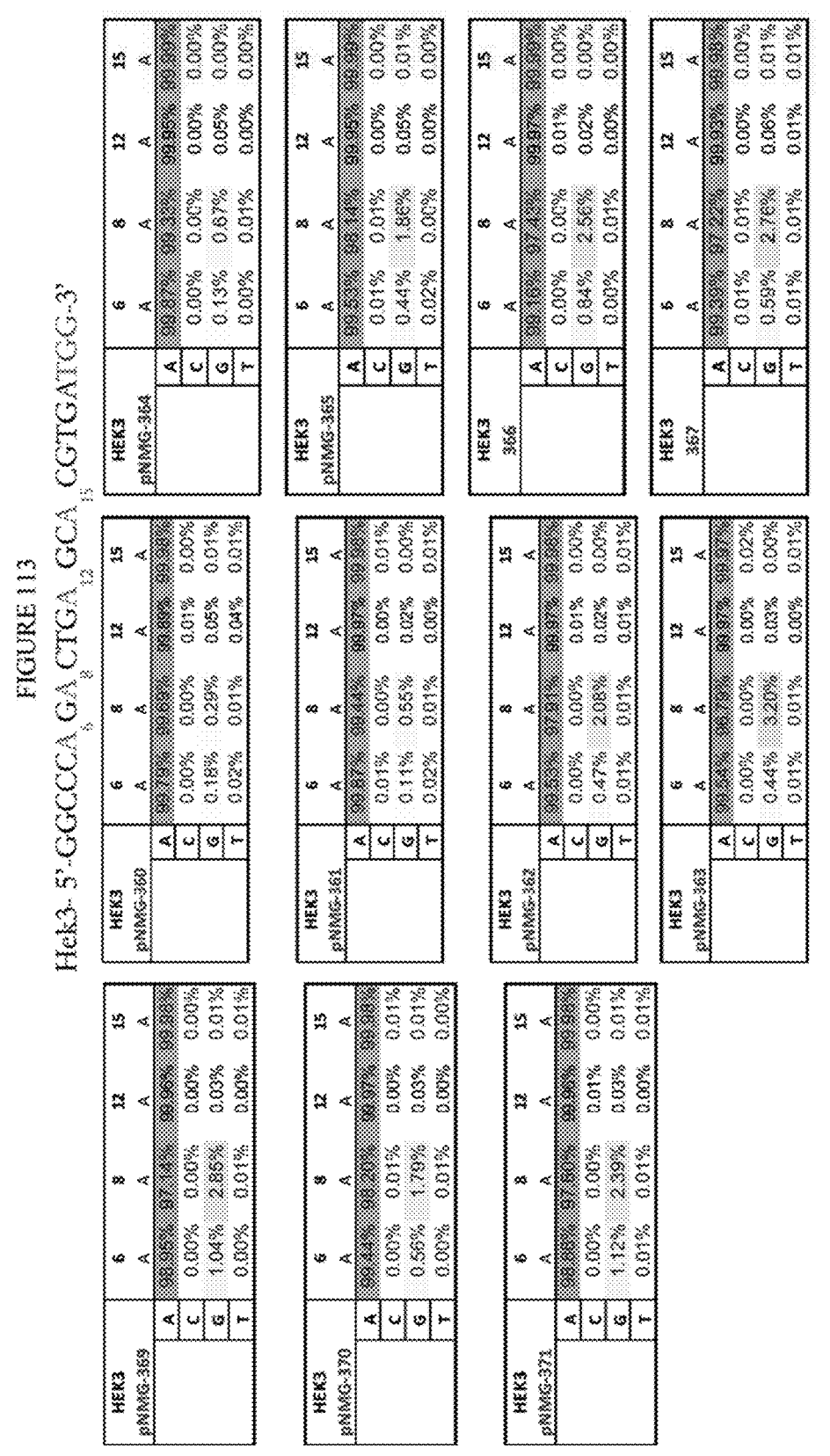

FIG. 113 shows a summary of results of editing at the Hek-3 site. The sequence corresponds to SEQ ID NO: 42.

Figure 114:
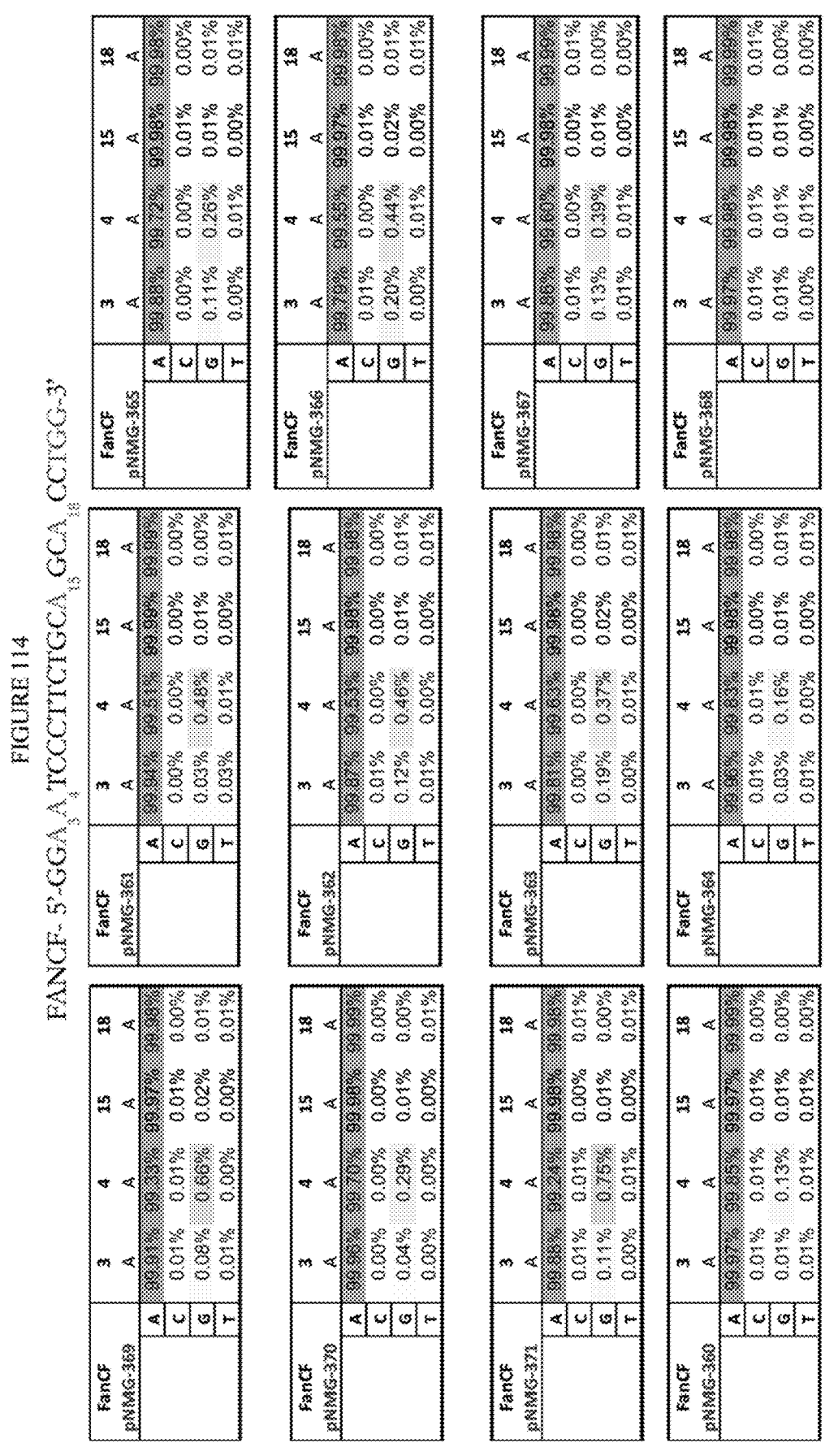

FIG. 114 shows a summary of results of editing at the FANCF site. The sequence corresponds to SEQ ID NO: 45.

FIG. 115 shows a summary of results of editing at the Hek-2 site. The sequence corresponds to SEQ ID NO: 367.

FIG. 116 shows a summary of results of editing at the Hek2-2 site. The sequence corresponds to SEQ ID NO: 368.

FIG. 117 shows a summary of results of editing at the Hek2-3 site. The sequence corresponds to SEQ ID NO: 363.

FIG. 118 shows a summary of results of editing at the Hek2-6 site. The sequence corresponds to SEQ ID NO: 364.

FIG. 119 shows a summary of results of editing at the Hek2-7 site. The sequence corresponds to SEQ ID NO: 365.

FIG. 120 shows a summary of results of editing at the Hek2-10 site. The sequence corresponds to SEQ ID NO: 366.

FIG. 121 shows a summary of results of editing at the Hek-3 site. The sequence corresponds to SEQ ID NO: 42.

FIG. 122 shows a summary of results of editing at the FANCF site. The sequence corresponds to SEQ ID NO: 45.

Figures 123, 124:
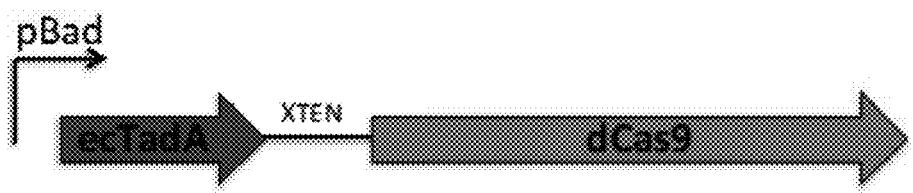

FIG. 123 shows the results of ecTadA evolution (evolution #4) at HEK2, HEK2-2, HEK2-3, HEK2-6, HEK2-7, and HEK2-10 sites. The constructs used were pNMG-370 (evolution #2), pNMG-371 (evolution #3), and pNMG 382-389 (evolution #4). The sequences correspond to SEQ ID NOs: 7, 368, 363, 364, 369, and 370 from top to bottom, respectively.

FIG. 124 shows a schematic of a construct containing ecTadA and dCas9 used for ecTadA evolution (evolution #5).

Figure 125:
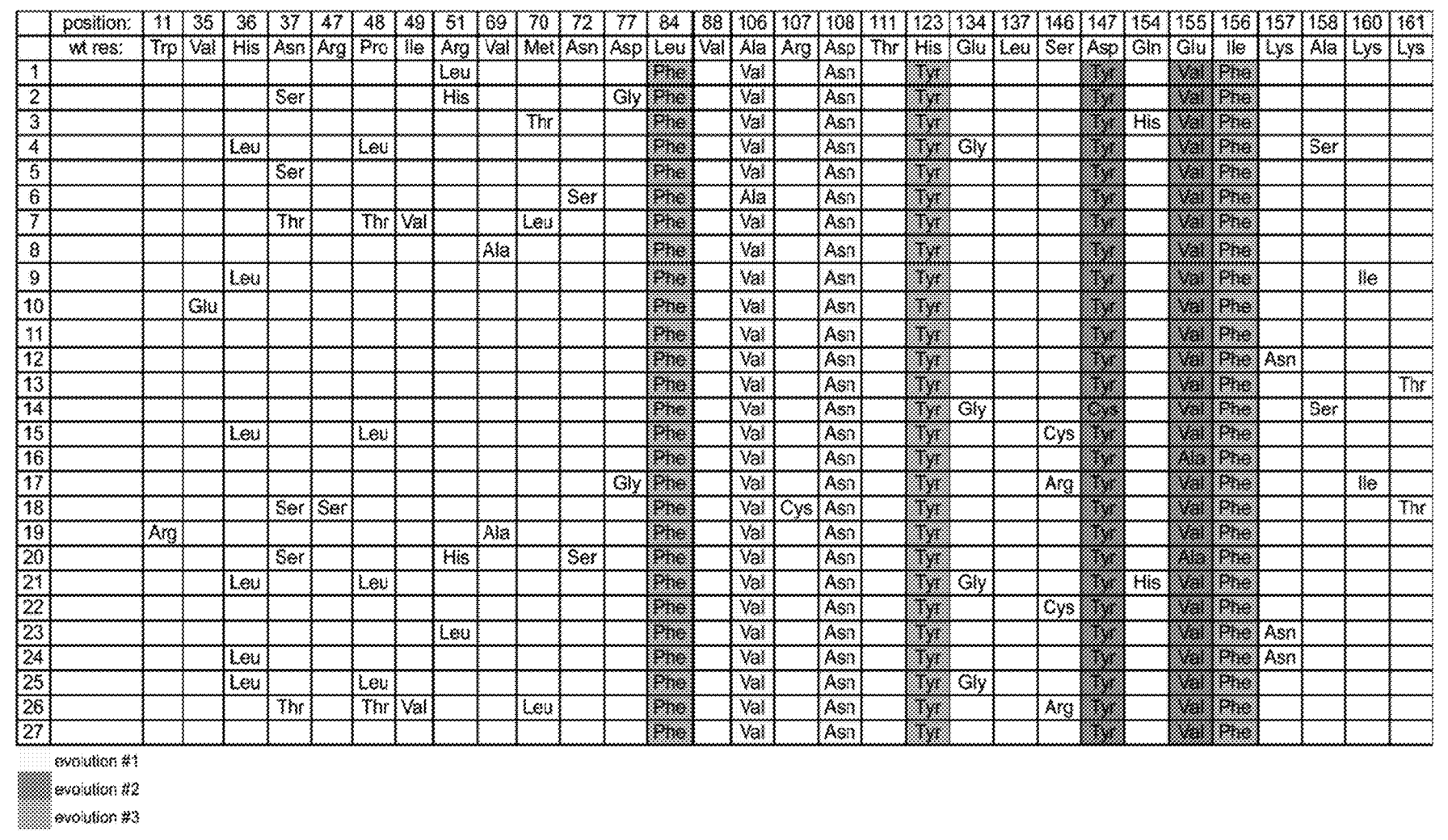

FIG. 125 is a table showing the results of clones assayed after fifth round evolution (128 ug/mL chlor, 7 h).

Figures 126A, 126B:
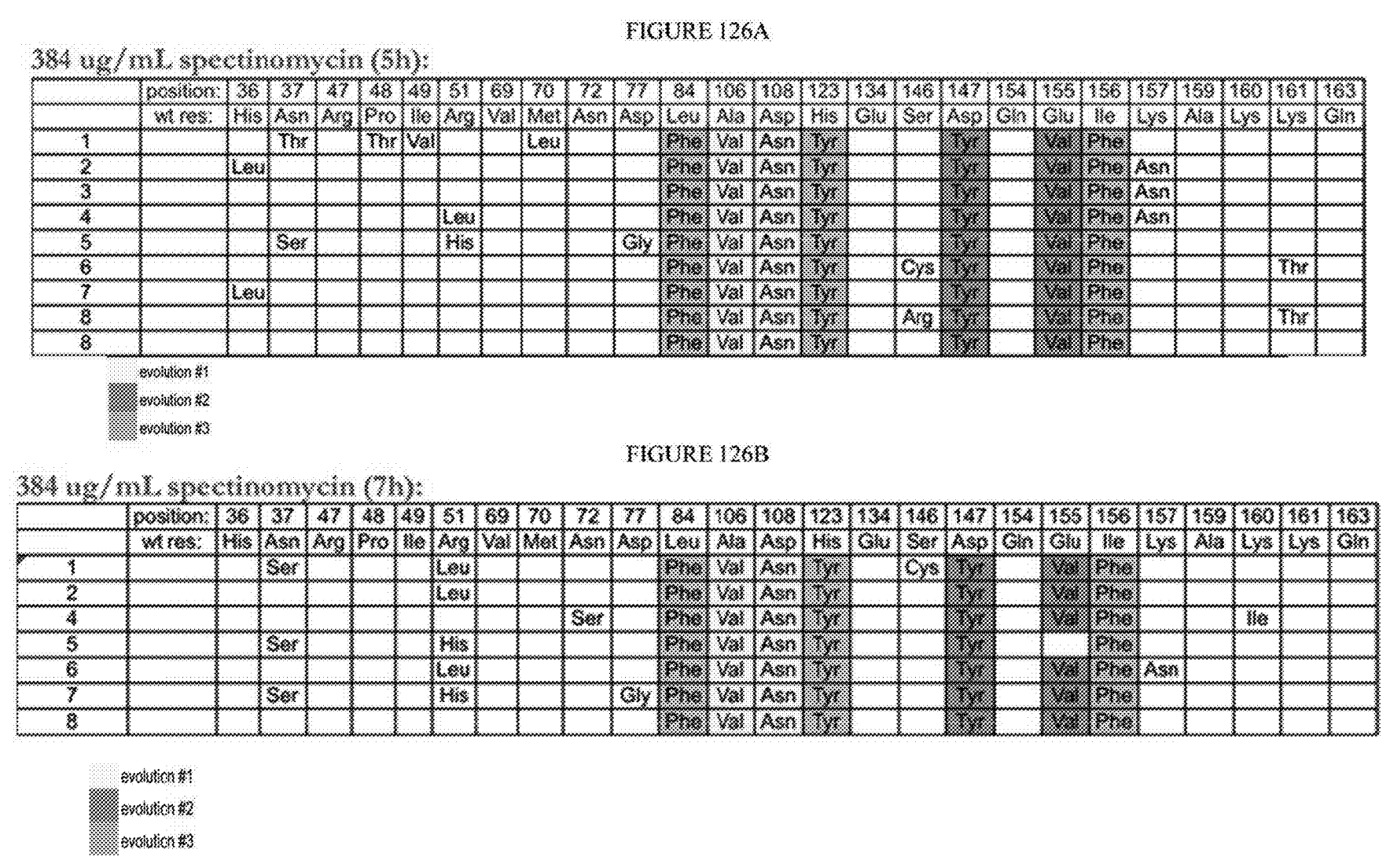

FIGS. 126A to 126E are tables showing the results of sub-cloned and re-transformed clones assayed after fifth round under varying conditions.

Figures 126E, 127:
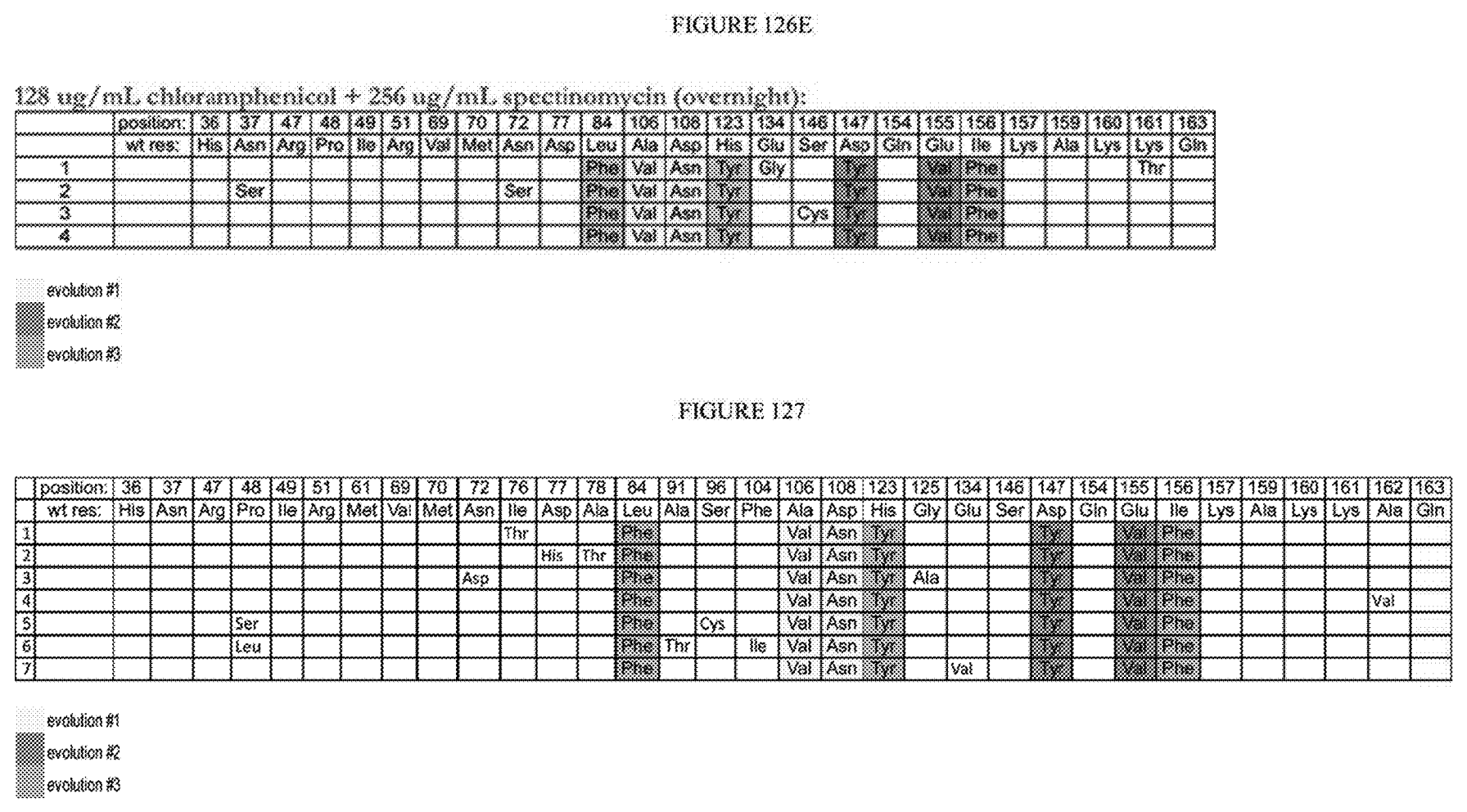

FIG. 127 is a table showing the results of amplicons from spectinomycin selection clones assayed after fifth round evolution.

FIG. 128 is a table showing the results of clones assayed after fifth round evolution.

FIG. 129 shows a summary of results of editing at the Hek-2 site using base editors that contain an engineered *S. aureus* TadA (saTadA), which include pNMG-346-349. As a comparison, results of editors that contain an engineered *E. coli* TadA (ecTadA), which include pNMG-339-341, are shown. The sequence corresponds to SEQ ID NO: 6.

FIG. 130 shows a summary of results of editing at the Hek2-1 site using base editors that contain an engineered *S. aureus* TadA (saTadA), which include pNMG-346-349. As a comparison, results of editors that contain an engineered *E. coli* TadA (ecTadA), which include pNMG-339-341, are shown. The Hek2-1 sequence provided in the figure represents the DNA strand where A to G editing takes place. The sequence corresponds to SEQ ID NO: 465.

FIG. 131 shows a summary of results of editing at the Hek2-2 site using base editors that contain an engineered *S. aureus* TadA (saTadA), which include pNMG-346-349. As a comparison, results of editors that contain an engineered *E. coli* TadA (ecTadA), which include pNMG-339-341, are shown. The sequence corresponds to SEQ ID NO: 368.

FIG. 132 shows a summary of results of editing at the Hek2-3 site using base editors that contain an engineered *S. aureus* TadA (saTadA), which include pNMG-346-349. As a comparison, results of editors that contain an engineered *E. coli* TadA (ecTadA), which include pNMG-339-341, are shown. The sequence corresponds to SEQ ID NO: 363.

FIG. 133 shows a summary of results of editing at the Hek2-4 site using base editors that contain an engineered *S. aureus* TadA (saTadA), which include pNMG-346-349. As a comparison, results of editors that contain an engineered *E. coli* TadA (ecTadA), which include pNMG-339-341, are shown. The Hek2-4 sequence provided in the figure represents the DNA strand where A to G editing takes place. The sequence corresponds to SEQ ID NO: 466.

FIG. 134 shows a summary of results of editing at the Hek2-6 site using base editors that contain an engineered *S. aureus* TadA (saTadA), which include pNMG-346-349. As a comparison, results of editors that contain an engineered *E. coli* TadA (ecTadA), which include pNMG-339-341, are shown. The sequence corresponds to SEQ ID NO: 364.

FIG. 135 shows a summary of results of editing at the Hek2-9 site using base editors that contain an engineered *S. aureus* TadA (saTadA), which include pNMG-346-349. As a comparison, results of editors that contain an engineered *E. coli* TadA (ecTadA), which include pNMG-339-341, are shown. The Hek2-9 sequence provided in the figure represents the DNA strand where A to G editing takes place. The sequence corresponds to SEQ ID NO: 467.

FIG. 136 shows a summary of results of editing at the Hek2-10 site using base editors that contain an engineered *S. aureus* TadA (saTadA), which include pNMG-346-349. As a comparison, results of editors that contain an engineered *E. coli* TadA (ecTadA), which include pNMG-339-341, are shown. The Hek2-10 sequence provided in the figure represents the DNA strand where A to G editing takes place. The sequence corresponds to SEQ ID NO: 370.

FIG. 137 shows a summary of results of editing at the Hek3 site using base editors that contain an engineered *S. aureus* TadA (saTadA), which include pNMG-346-349. As a comparison, results of editors that contain an engineered *E. coli* TadA (ecTadA), which include pNMG-339-341, are shown. The sequence corresponds to SEQ ID NO: 42.

FIG. 138 shows a summary of results of editing at the RNF2 site using base editors that contain an engineered *S. aureus* TadA (saTadA), which include pNMG-346-349. As a comparison, results of editors that contain an engineered *E. coli* TadA (ecTadA), which include pNMG-339-341, are shown. The sequence corresponds to SEQ ID NO: 468.

FIG. 139 shows a summary of results of editing at the FANCF site using base editors that contain an engineered *S. aureus* TadA (saTadA), which include pNMG-346-349. As a comparison, results of editors that contain an engineered *E. coli* TadA (ecTadA), which include pNMG-339-341, are shown. The sequence corresponds to SEQ ID NO: 45.

Figure 140:
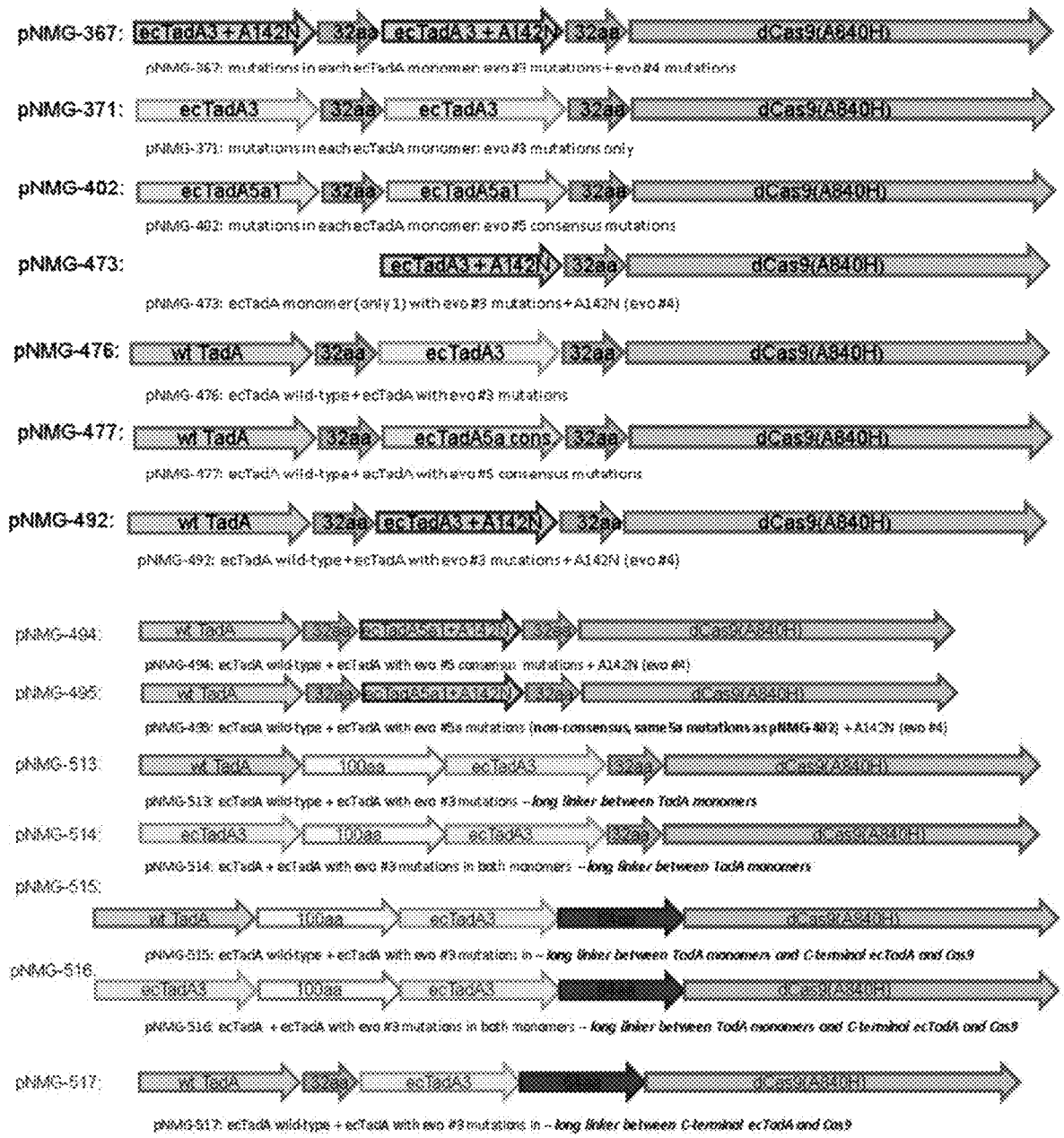
Figure 140:
Figure 140:
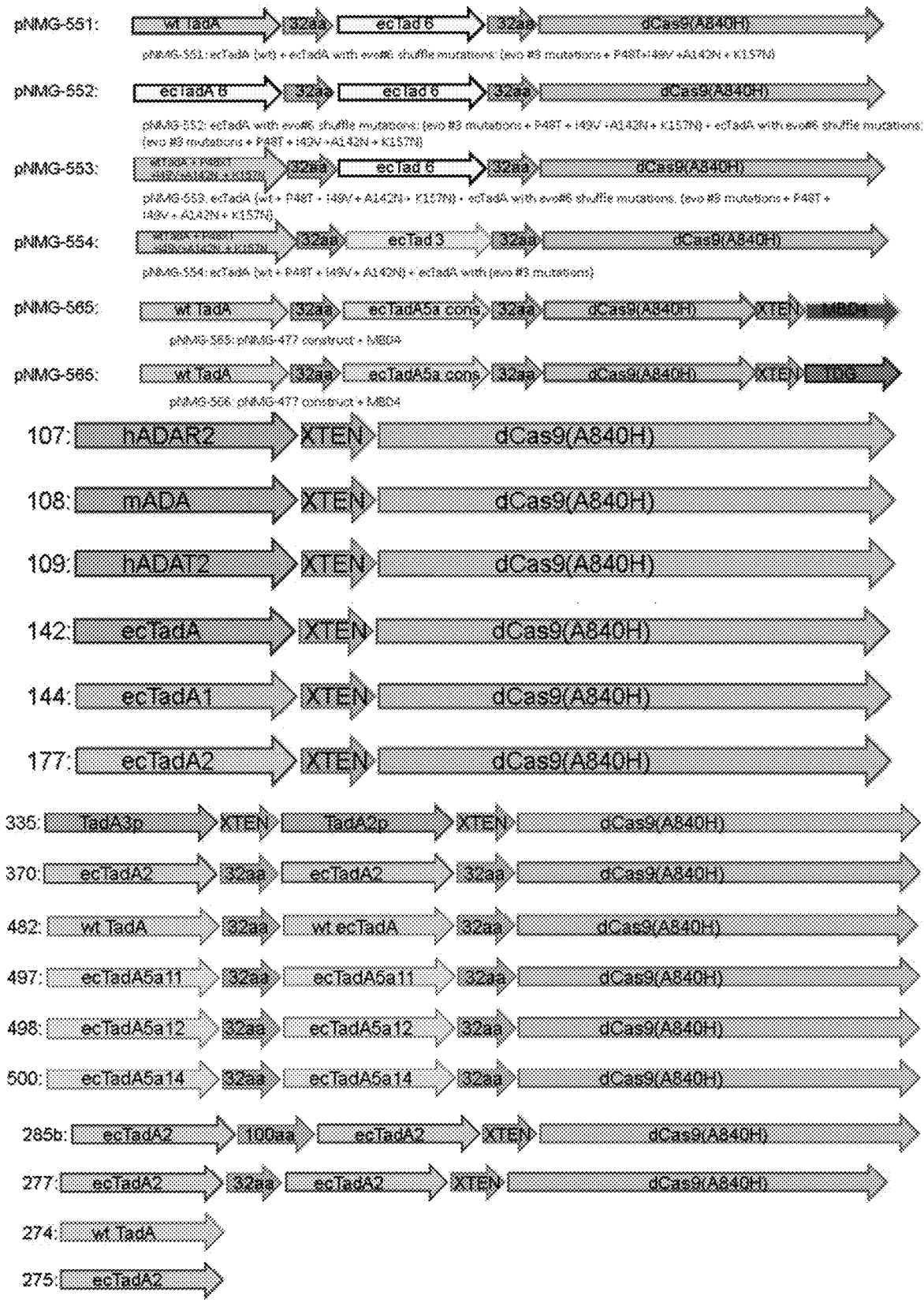
Figure 140:
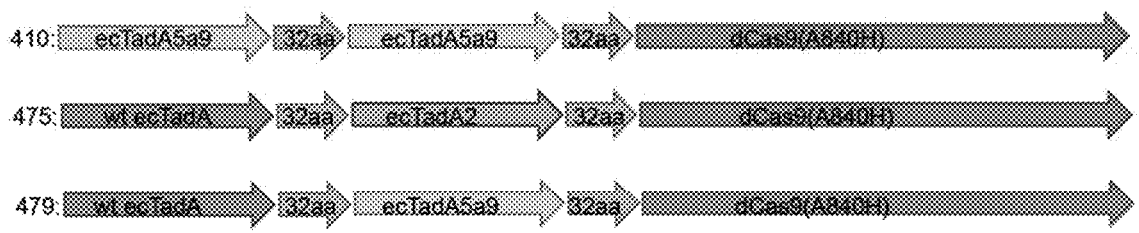

FIG. 140 shows various schematic representations of adenosine base editor (ABE) constructs. The identity of the editors e.g., "pNMG-367" is indicated in Table 4. The following mutations are abbreviated as follows: ecTadA1 (A106V D108N), ecTadA2 (A106V D108N D147Y E155V), ecTadA3 (ecTadA2+L84F H123Y I156F), ecTadA3+(ecTadA3+A142N), ecTadA5a1 (ecTadA3+H36L R51L S146C K157N), ecTadA5a3 (ecTadA3+N37S K161T), ecTadA5a11 (ecTadA3+R51L S146C K157N K161T), ecTadA5a12 (ecTadA3+S146C K161T), ecTadA5a14 (ecTadA3+RS146C K157N K160E), and ecTadA5a1+(ecTadA5a1+A142N), ecTadA5a9 (ecTadA3+S146R K161T). Heterodimers of the top three ABE 5a constructs were made and then tested relative to homodimers. The heterodimer version of the ABE editor typically performs better than the corresponding homodimeric construct. Both homodimeric and heterodimeric constructs are shown in FIG. 140.

Figure 141:
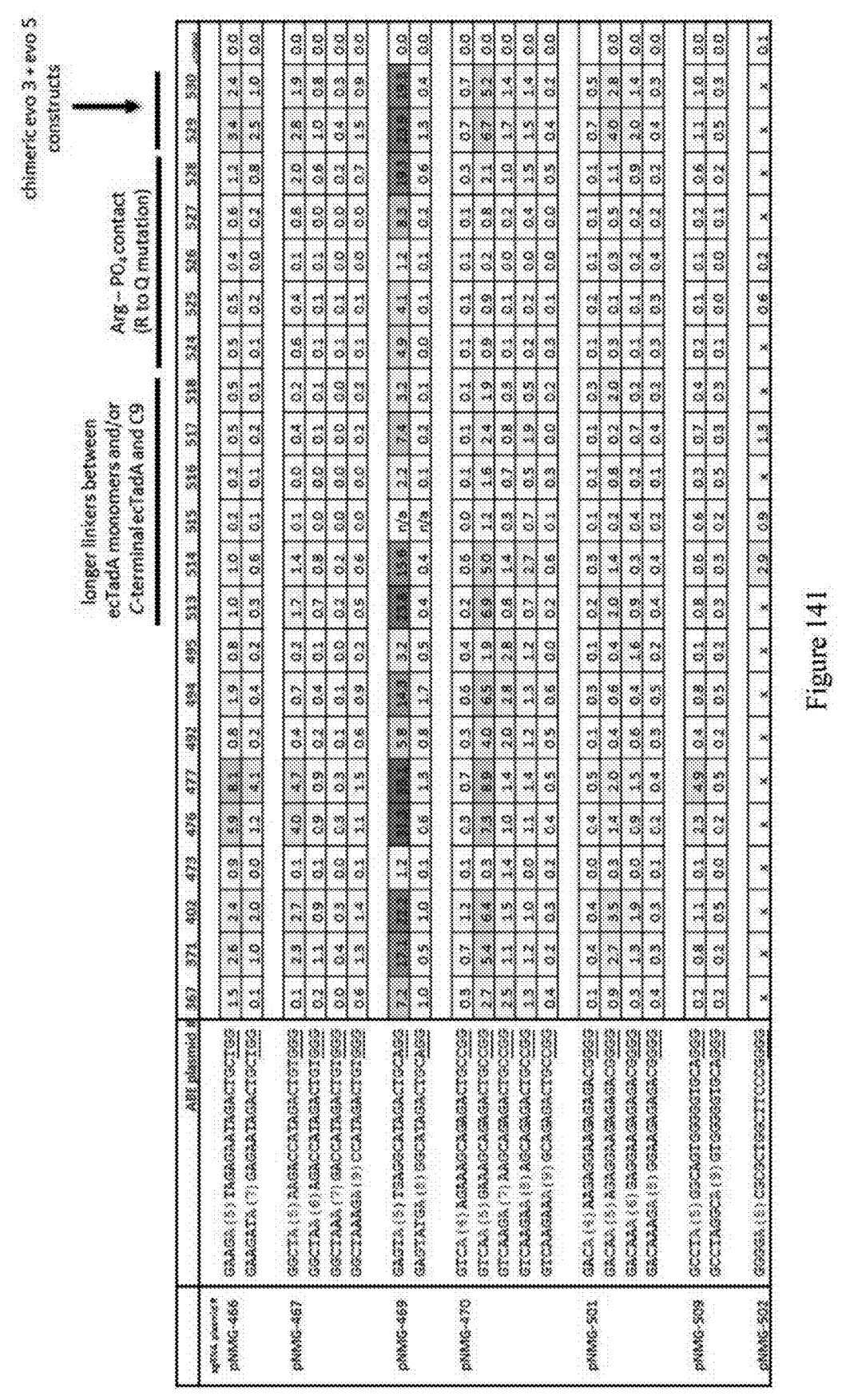

FIG. 141 shows editing results for various ABE constructs. The ABE plasmid #refers to pNMG number as indicated in Table 4. For example, 367 refers to construct pNMG-367 in Table 4. The sequences correspond to SEQ ID NOs: 469 (pNMG-466), 470 (pNMG-467), 471 (pNMG-469), 472 (pNMG-470), 473 (pNMG-501), 474 (pNMG-509), and 475 (pNMG-502) from top to bottom, respectively.

FIG. 142 shows editing results for various ABE constructs at specific sites. The numbers on the top row indicate the pNMG number as indicated in Table 4. For example, 107 refers to construct pNMG-107 in Table 4. In certain contexts, homodimer constructs have been shown to work better than a hetero dimer construct and vice versa (see for example construct 371 which is a homodimer versus construct 476 which is a heterodimer). Schematics for these ABE constructs are shown in FIG. 140, and the construct architecture is shown in Table 4. The sequences correspond to SEQ ID NOs: 478, 478, 514, 516, 516, 520, 520, 521, 521, and 509 from top to bottom, respectively.

FIG. 143 shows the percentage of indels formed for ABE constructs from FIG. 142.

FIG. 144 shows editing results for various ABE constructs at specific sites. The identity of the constructs are shown in the top row and refer to the pNMG reference number of Table 4. The results in FIG. 144 indicate that adding ecTadA monomer to ABE construct may not improve editing. However, adding a long linker between monomers may help editing at some sites (see, for example, the editing results for sgRNA constructs 285b versus 277 at sites 502, 505, 507). The identity of the sgRNA constructs is shown in Table 8 Schematics for these ABE constructs are shown in FIG. 140. The sequences correspond to SEQ ID NOs: 478, 480, 480, 514, 517, 517, 517, 517, 519, and 521 from top to bottom, respectively.

FIG. 145 shows results for ABE constructs at all NAN sites, where the target A is at position 5 of the Protospacer and PAM sequences. The identity of the ABE constructs, shown in the top row refers to the pNMG reference number in Table 4. The number values represent the % of target A residues that were edited (e.g., % editing efficiency). The sequences correspond to SEQ ID NOs: 537-552 from top to bottom, respectively.

Figure 146:
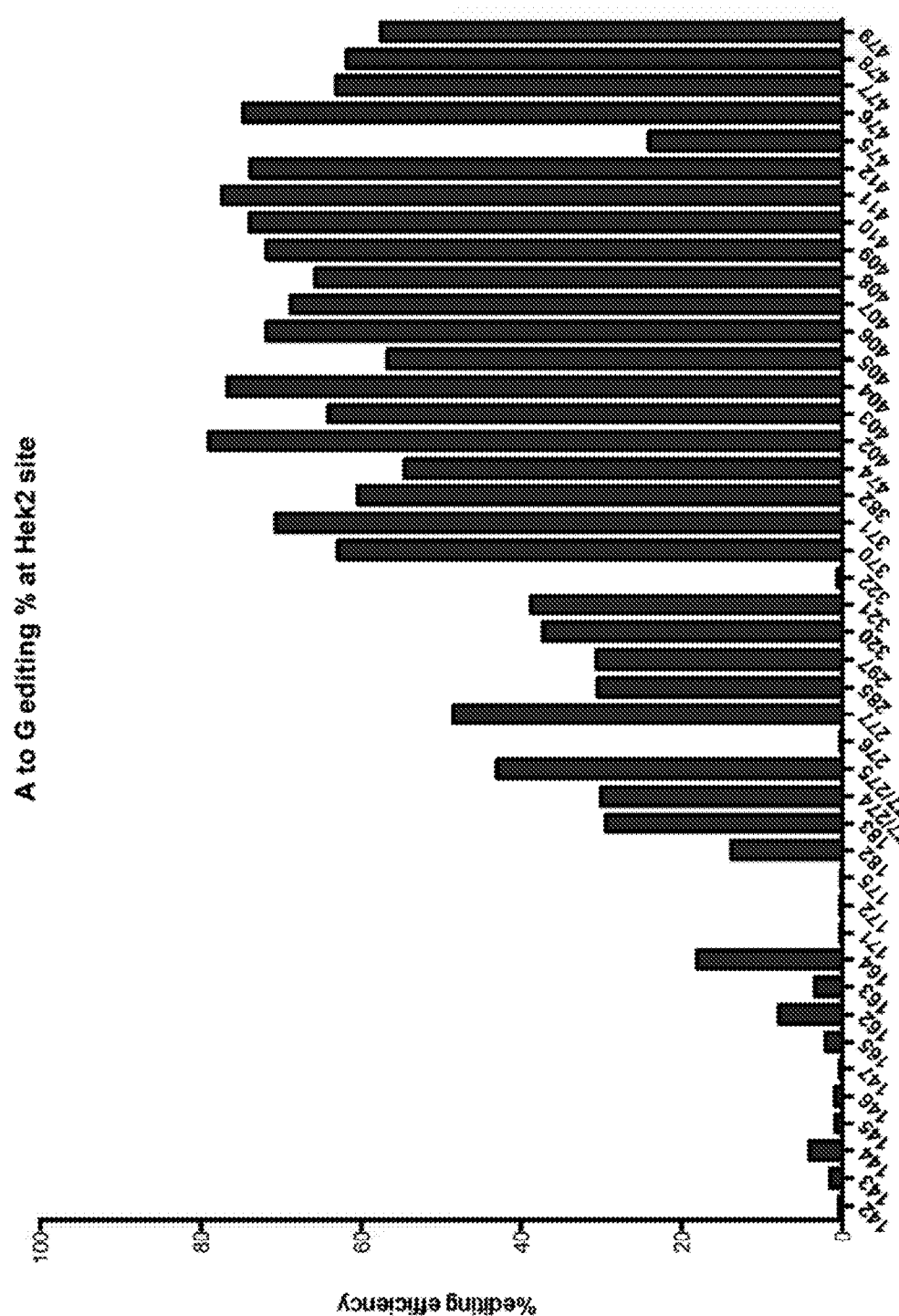

FIG. 146 shows A to G editing percent at the Hek2 site for various ABE constructs as referenced by their reference pNMG number in Table 4.

Figure 147:
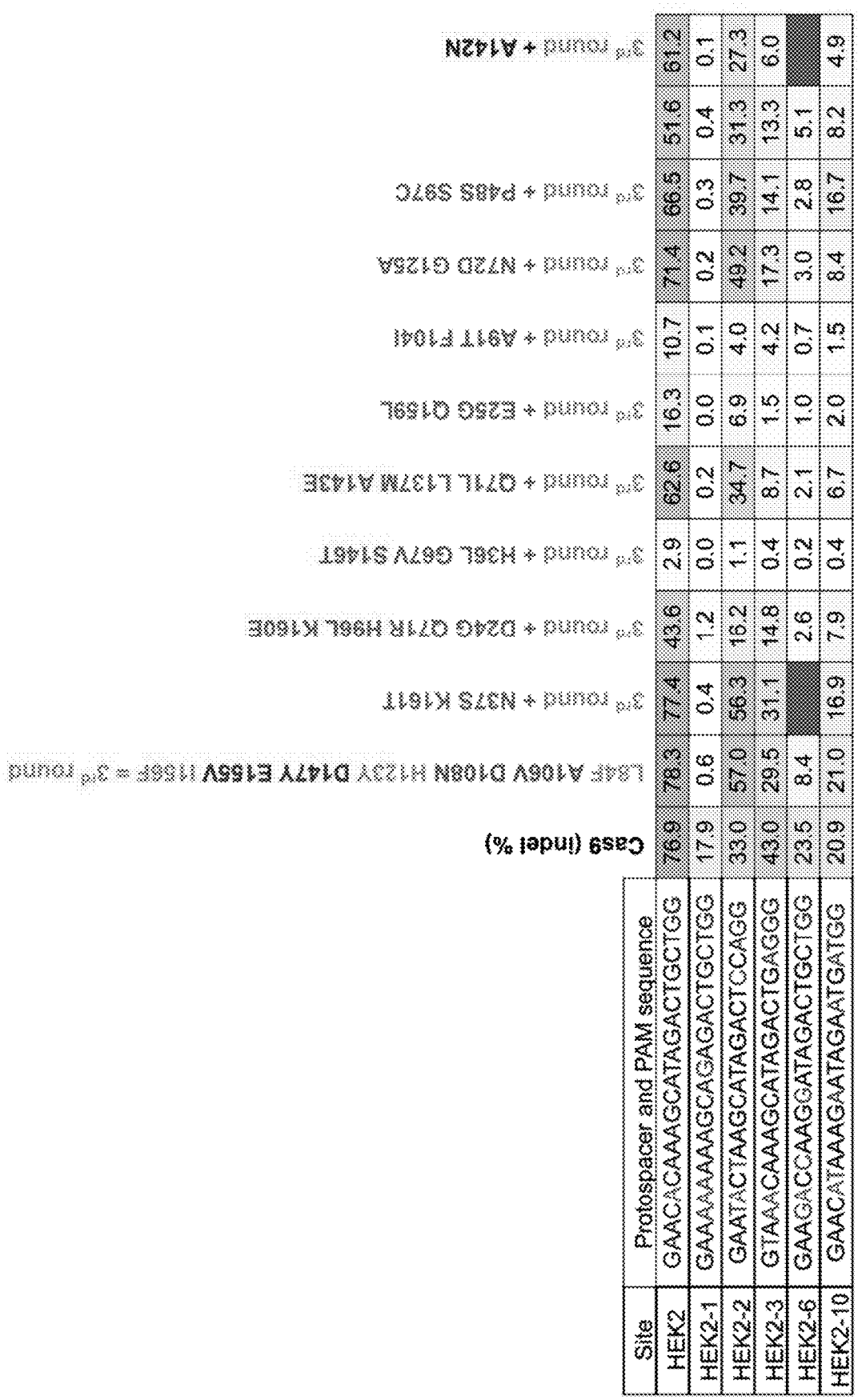

FIG. 147 shows evolution round #5b evolution results. The number values represent the % of A to G editing for the indicated sites. The sequences from top to bottom correspond to SEQ ID NOs: 7, 465, 368, 363, 364, and 370 from top to bottom, respectively.

Figure 148:
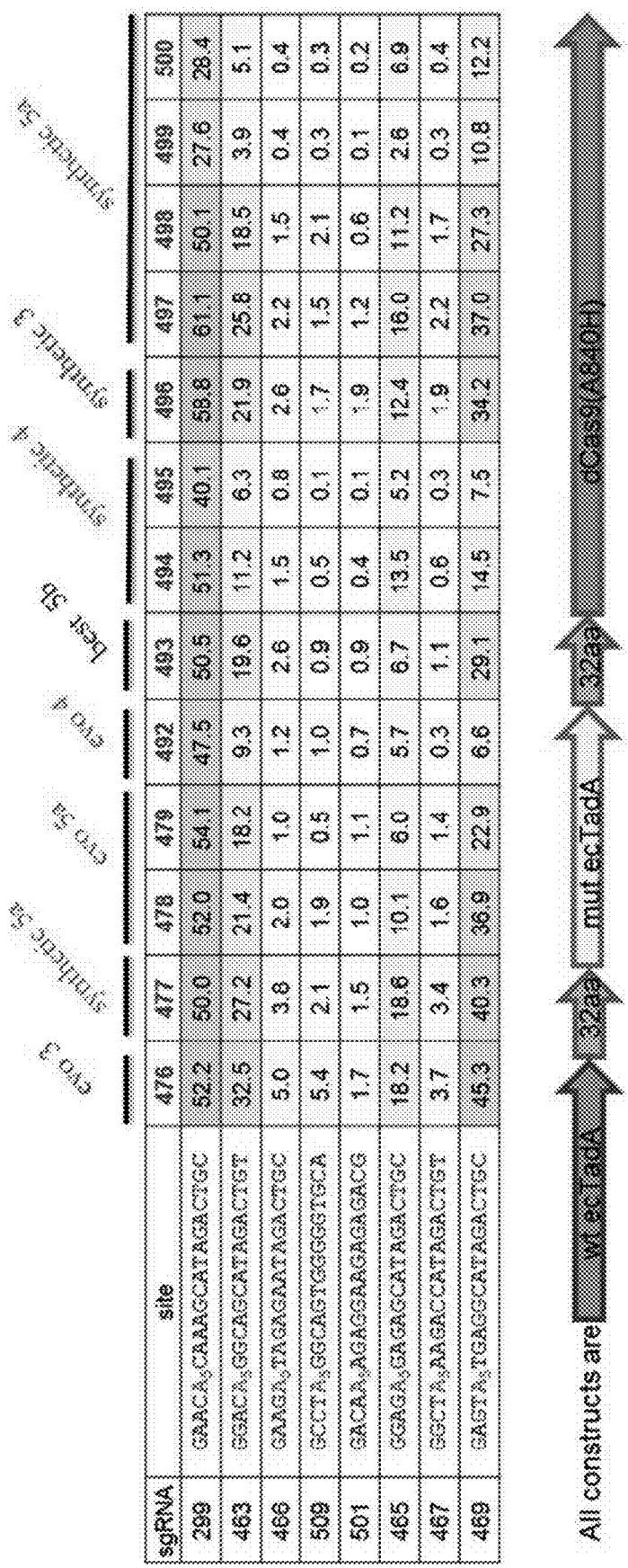

FIG. 148 shows editing results for various ABE constructs which were obtained from different rounds of evolution (e.g., evo3). The generic schematic for the ABE constructs is also shown. The identity of the sgRNA, as indicated in Table 8, and the identity of the base editors (pNMG reference), as indicated in Table 4, are shown. The number values represent the % of A to G editing for the indicated sites. The sequences correspond to SEQ ID NOs: 478, 503, 506, 521, 513, 505, 507, and 509 from top to bottom, respectively.

FIG. 149 shows examination of the ABE constructs at genomic sites other than the Hek-2 sequence. The Hek-2 site (sgRNA 299) is represented by the asterisk. The identity of the sgRNA is indicated in Table 8. The sequences correspond to SEQ ID NOs: 478, 514, 516, 517, 517, 517, 517, 519, 520, 529, 521 from top to bottom, respectively.

Figure 150:
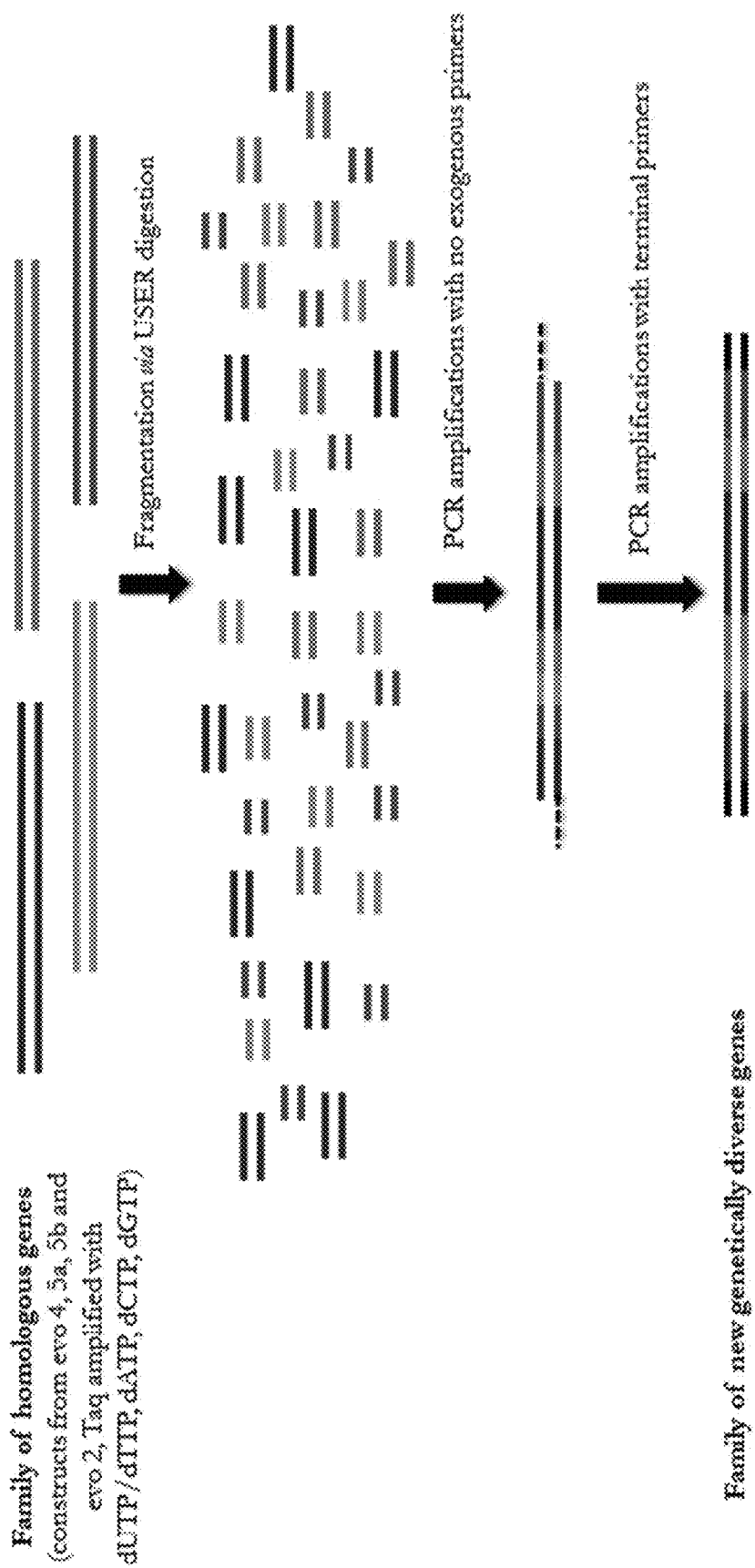

FIG. 150 shows a schematic of the DNA shuffling experiment using nucleotide exchange and excision technology (NExT), which is referred to as ABE evolution #6. The goal of this approach was to assemble a more efficient editor and remove potential epistatic mutations. DNA shuffling of constructs from various evolutions were used to optimize for desired mutations and eliminate mutations that negatively affect editing efficiencies and/or protein stability.

FIG. 151 shows a schematic for DNA Shuffle (NeXT). The spect target sequence is 5'-CAATGATGACTTCTA-CAGCG-3' (SEQ ID NO: 444) and the chlor target sequence is 5'-TACGGCGTAGTGCACCTGGA-3' (SEQ ID NO: 441).

Figure 152:
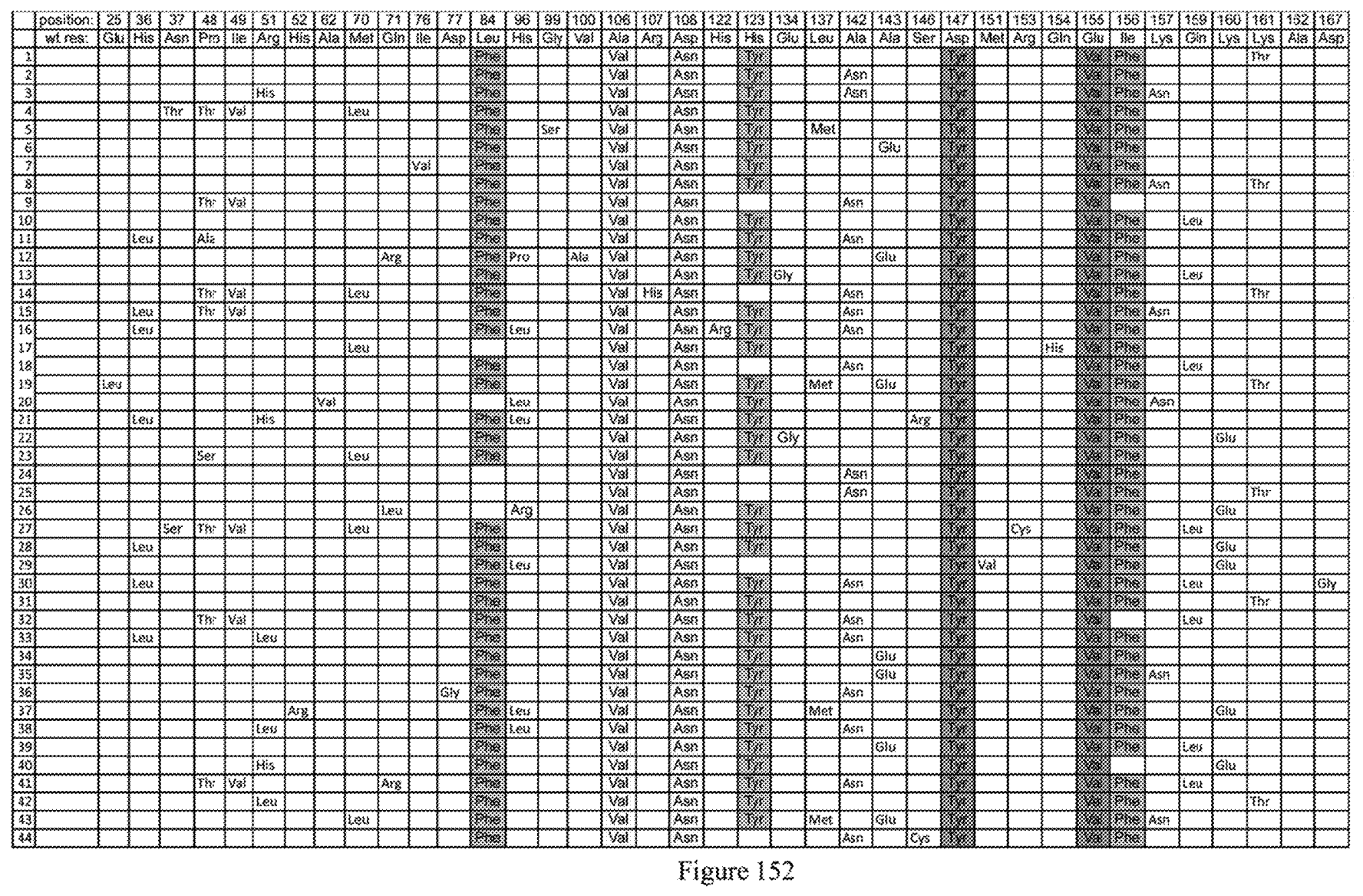

FIG. 152 shows the sequence identity of clones from evolution #6 surviving on spect only (non-YAC target). The mutations indicated are relative to ecTadA (SEQ ID NO: 1).

Figure 153:
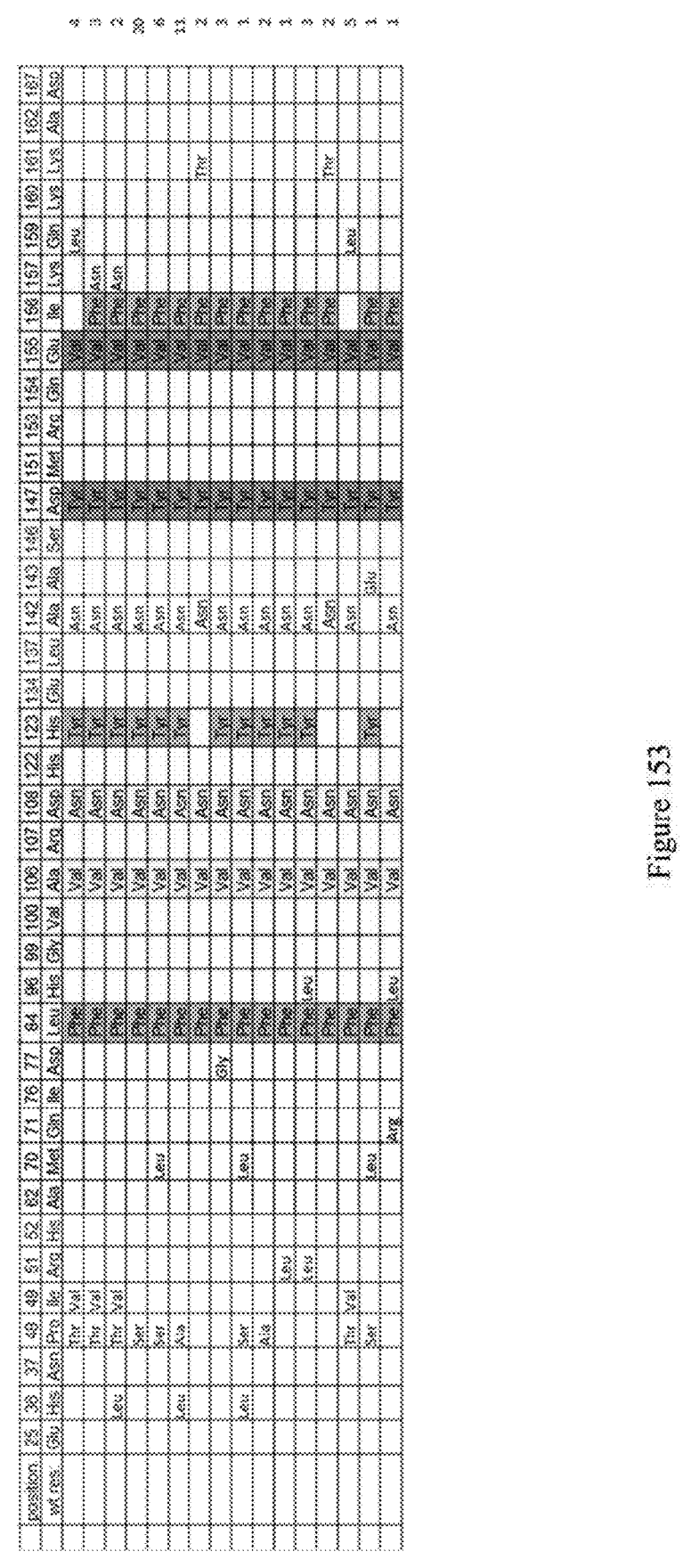

FIG. 153 shows evolution #6.2 which refers to the enrichment of clones from evolution #6. The mutations indicated are relative to ecTadA (SEQ ID NO: 1). A142N is present in almost all clones sequenced and the Pro48 mutation is also abundant. The clones were selected against "GAT" in the spectinomycin site. The selection target sequence was 5'-CAATGATGACTTCTACAGCG-3' (SEQ ID NO: 444).

Figure 154:
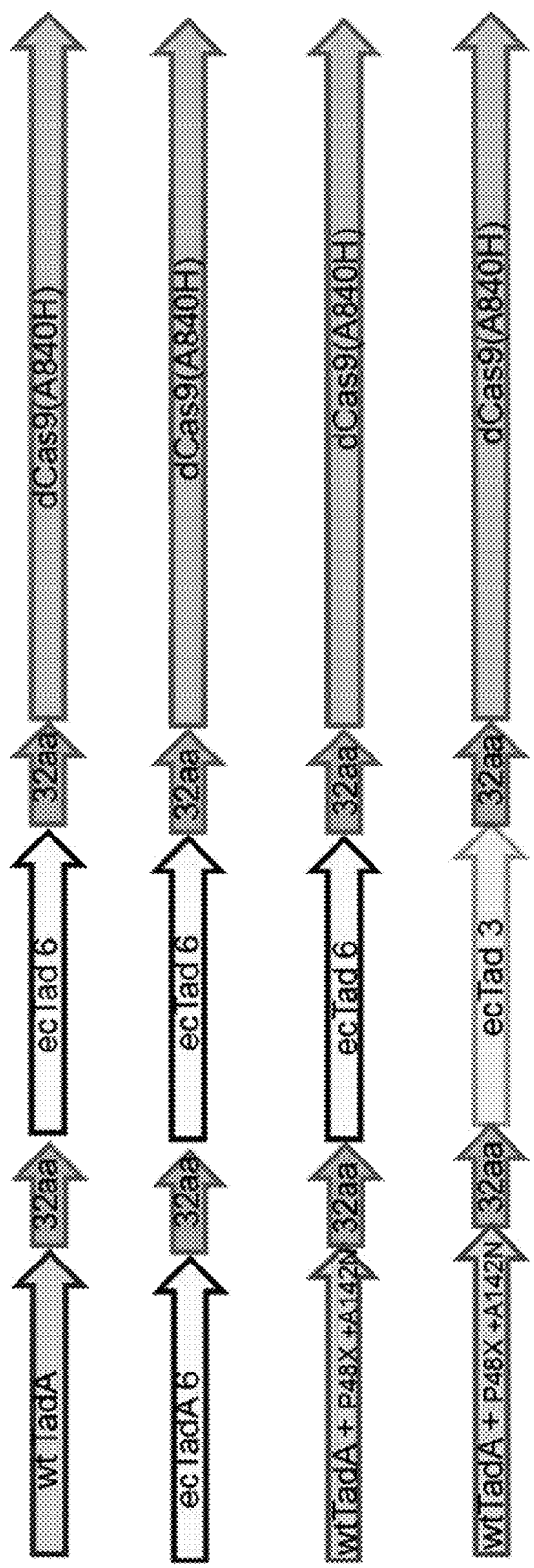

FIG. 154 shows schematic representations of ABE 6 constructs. 8 new constructs in total were developed. Mutations from the top 2 highest frequency amplicons in Evo #6 were used in each of the four architectures.

FIG. 155 shows data harvesting for ABE: step 1—transfection+HTS of key intermediates at 6 genomic sites, n=3. The transfection was performed with 750 ng ABE+250 ng gRNA and incubated for 5 days before the genomic DNA was extracted to perform HTS. The identity of each of the ABE constructs is indicated by the pNMG reference number as shown in Table 4. The sequences correspond to SEQ ID NOs: 509, 510, 512, 520, 530, 478 from top to bottom, respectively.

Figure 156:
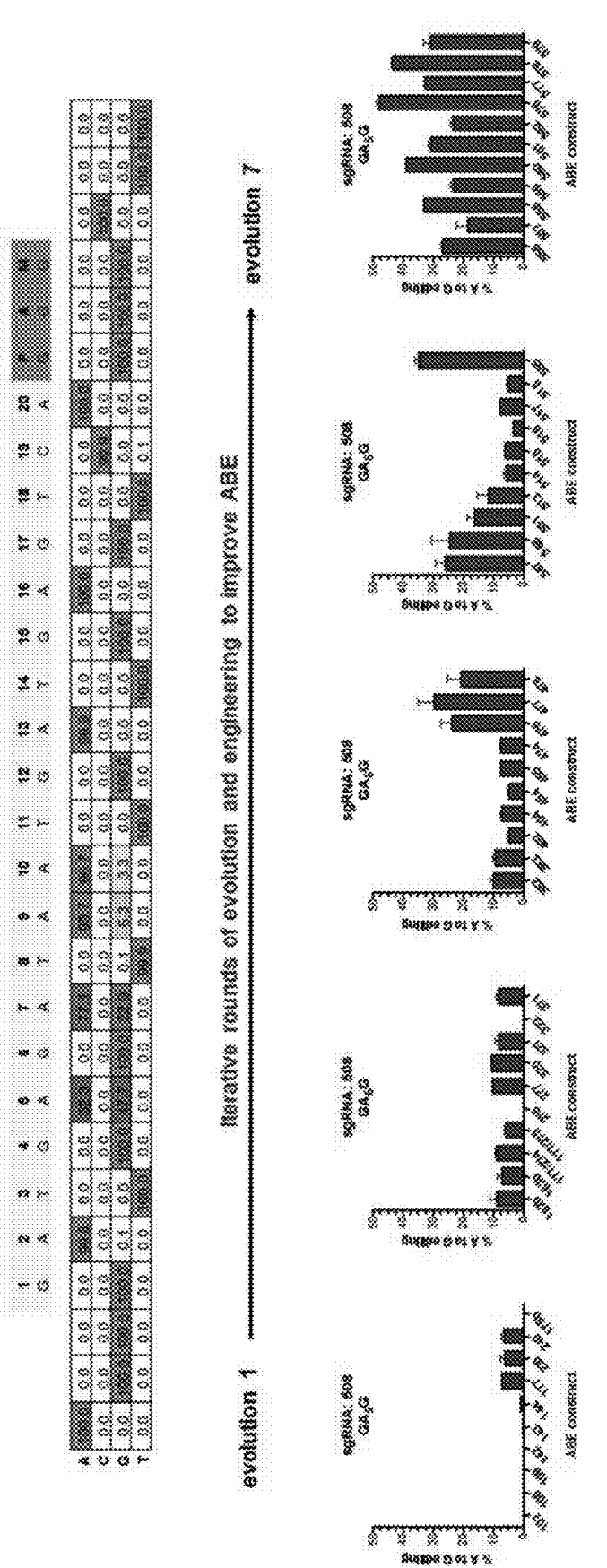

FIG. 156 shows that ABE editing efficiencies improve with iterative rounds of evolution. The top panel shows representative A to G % editing at targeted genetic locus in Hek293T cells using evolved/engineered ABE construct. The sequence corresponds to SEQ ID NO: 561. The bottom panel shows that iterative rounds of evolution and engineering improve ABE. ABE constructs are indicated by their pNMG reference numbers as shown in Table 4. The '508' target sequence corresponds to SEQ ID NO: 520.

Figure 157:
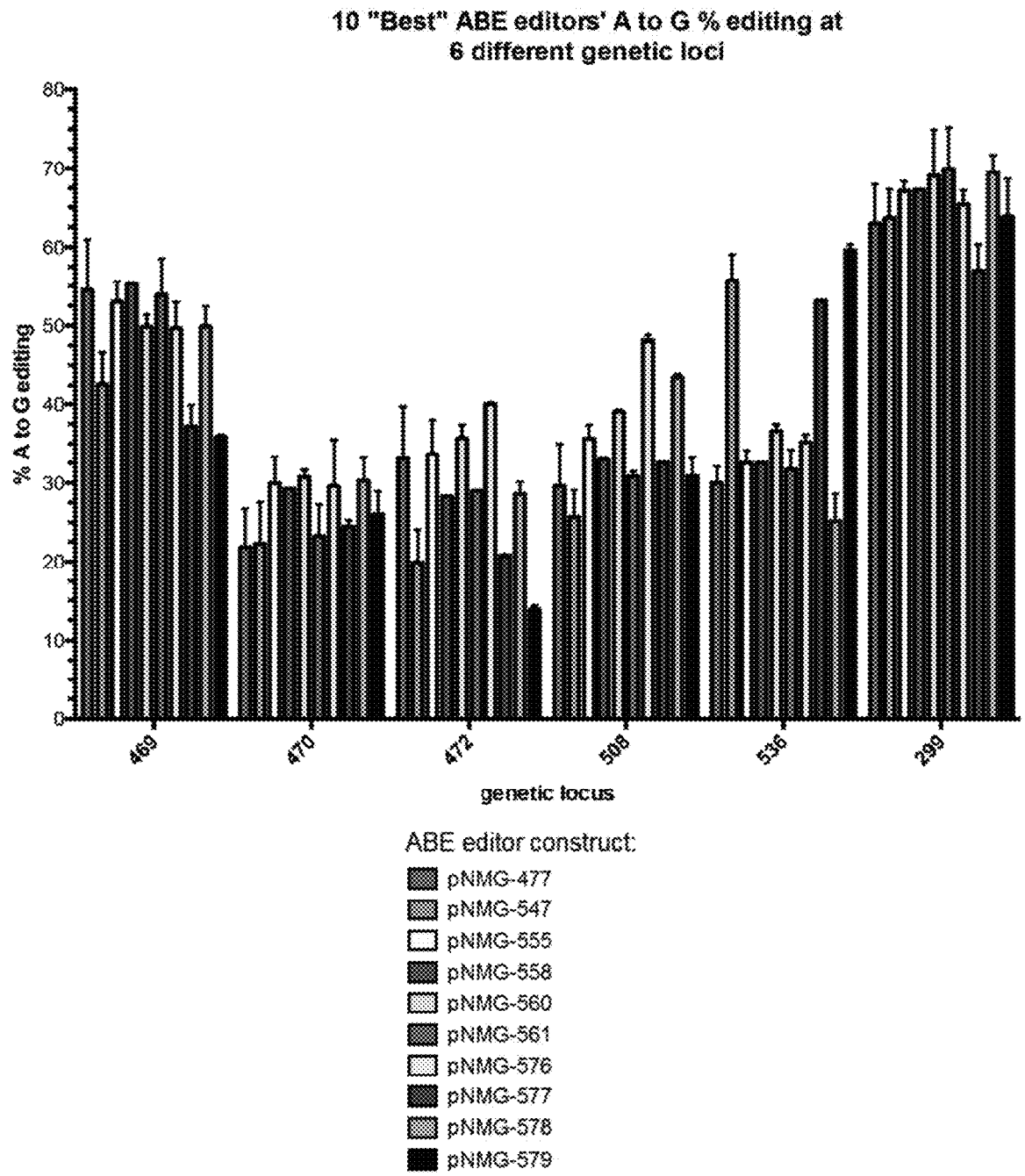

FIG. 157 shows HTS results of core 6 genomic sites from the 10 "Best" ABE. The results indicate that different editors have different local sequence preference (bottom panel). The graph shows the A to G percent editing at 6 different genetic loci. ABE constructs are indicated by their pNMG reference numbers as shown in Table 4. The sequences correspond to SEQ ID NOs: 509, 510, 512, 520, 530, 478 from top to bottom, respectively.

Figure 158:
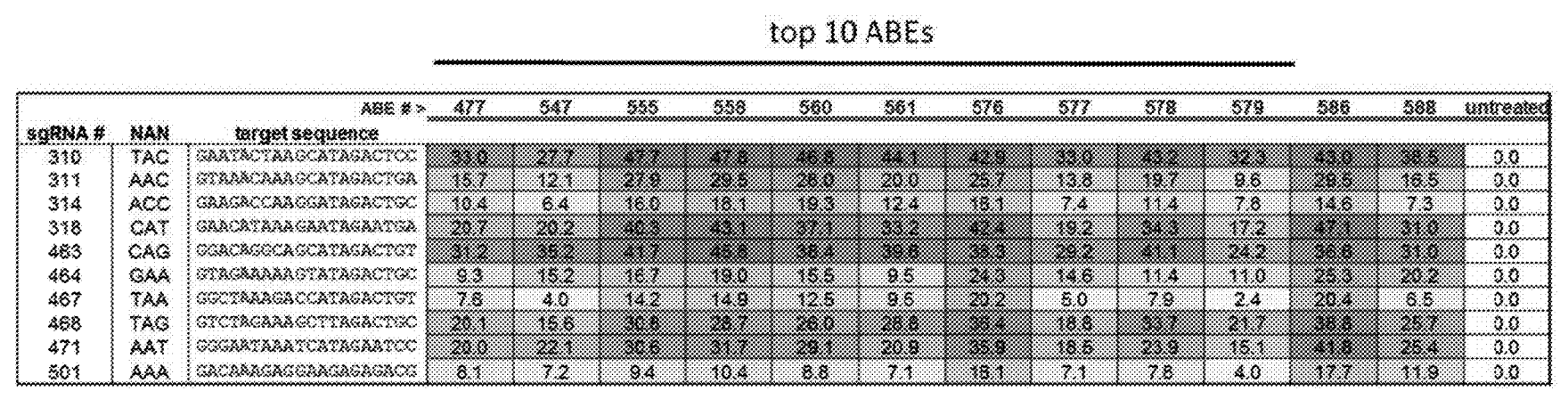

FIG. 158 shows transfection of functioning "top 10" ABEs at all genomic sites covering every combination of NAN sequence. The data represents n=1. The sequences correspond to SEQ ID NOs: 489, 490, 493, 497, 503, 504, 507, 508, 511, and 513 from top to bottom, respectively.

Figure 159:
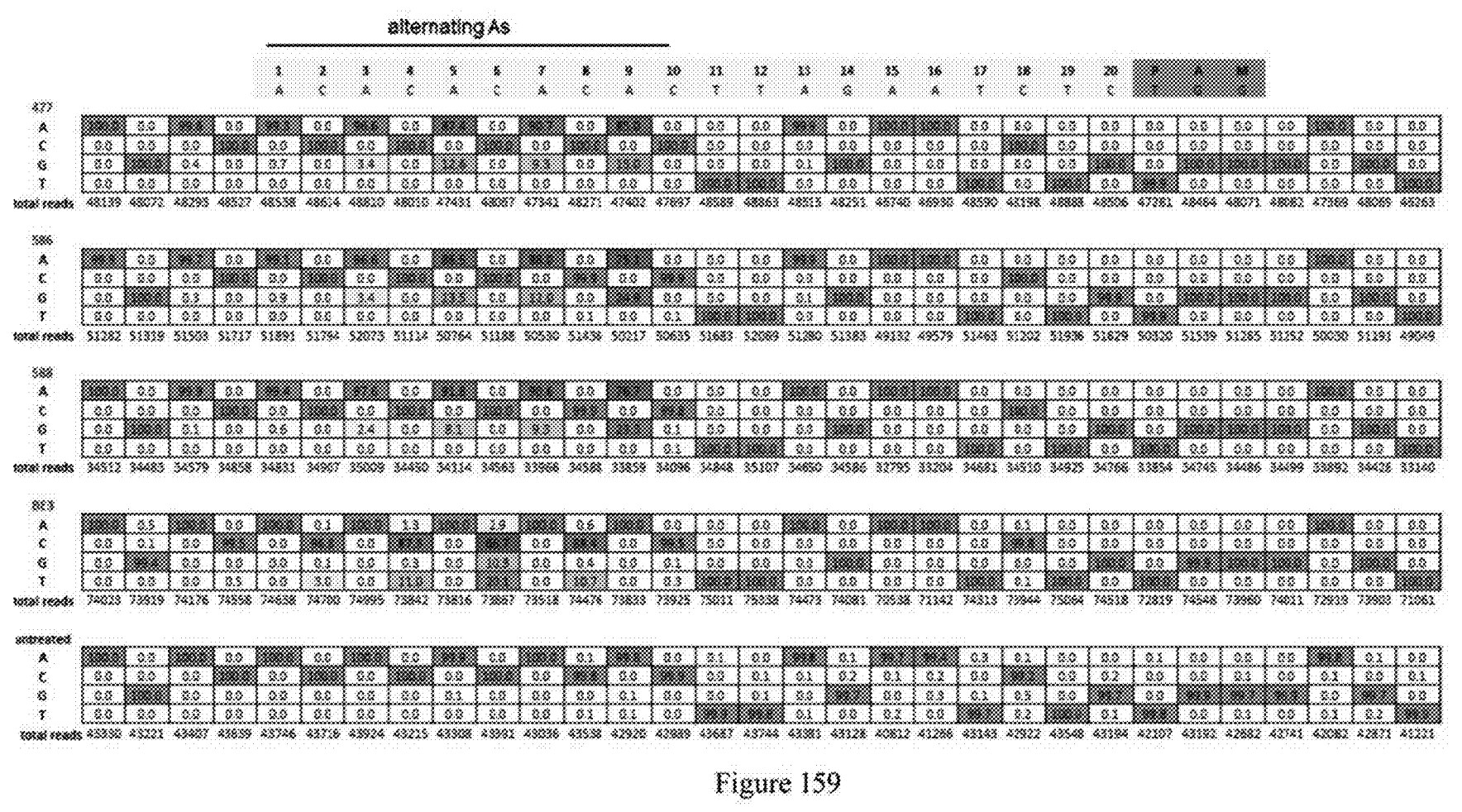

FIG. 159 shows ABE window experiments (A's at odd positions) for identifying which A's are edited. ABEs pNMG-477, pNMG-586, pNMG-588, BE3 and untreated control are shown. The sequence for editing is shown at the top. The sequence corresponds to SEQ ID NO: 562.

Figure 160:
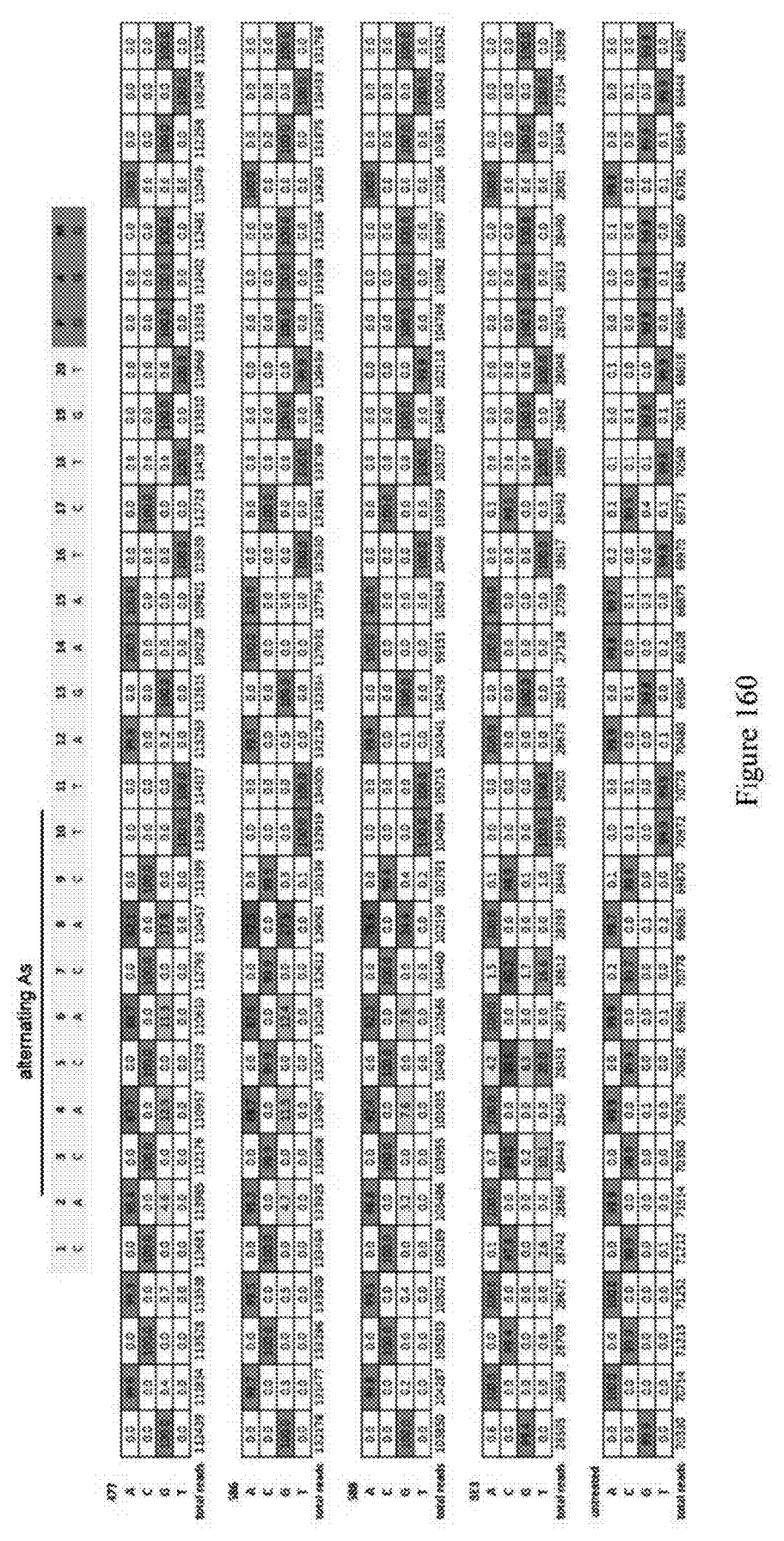

FIG. 160 shows ABE window experiment (A's at even positions) for identifying which A's are edited. ABEs pNMG-477, pNMG-586, pNMG-588, BE3 and untreated control are shown. The sequence for editing is shown at the top. The sequence corresponds to SEQ ID NO: 563.

Figure 161:
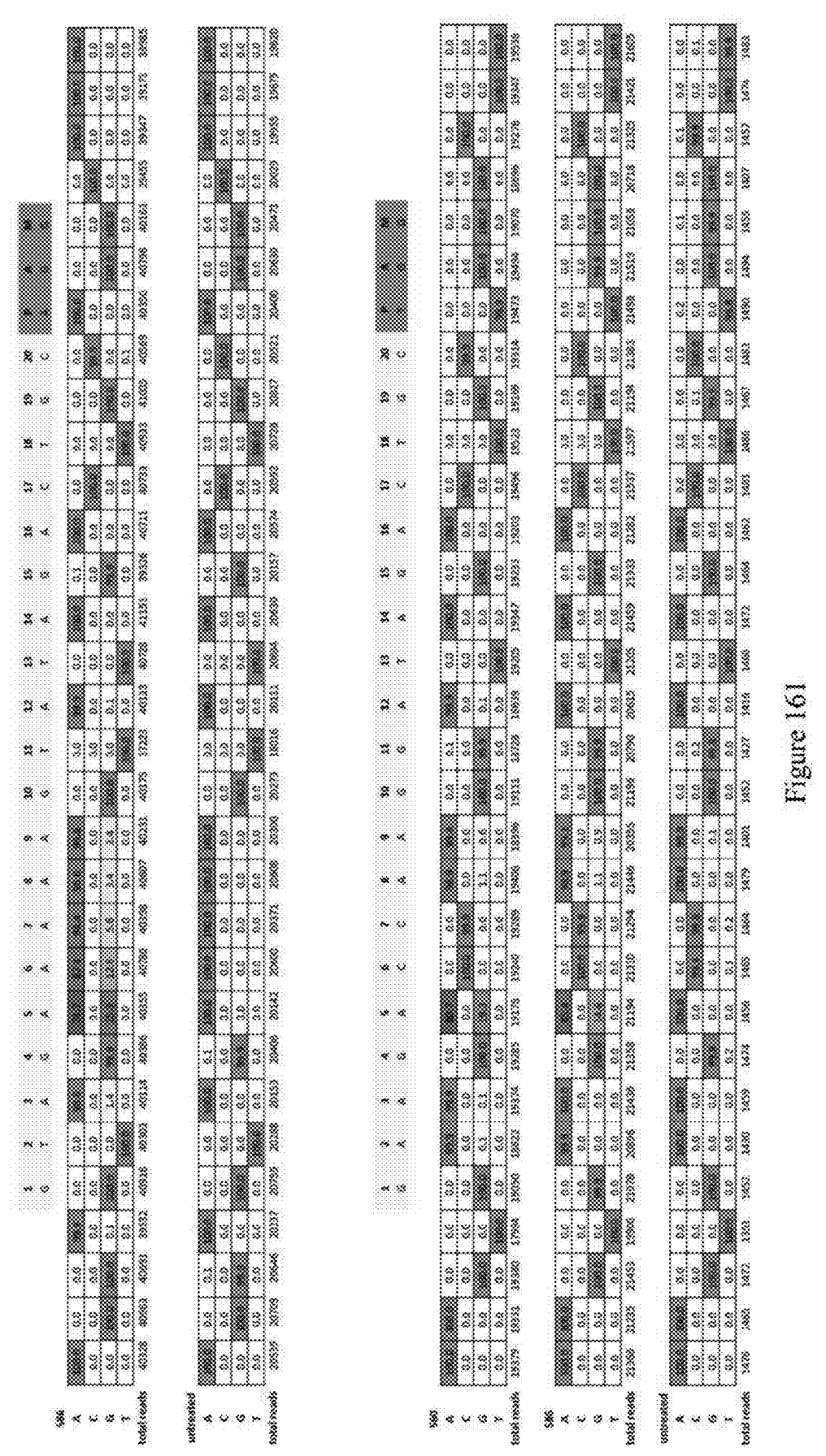

FIG. 161 shows additional ABE window experiments for identifying which A's are edited. ABEs pNMG-586, pNMG-560, and untreated control are shown. The sequence for editing is shown at the top. The sequences correspond to SEQ ID NOs: 544 and 541 from top to bottom, respectively.

Figure 162:
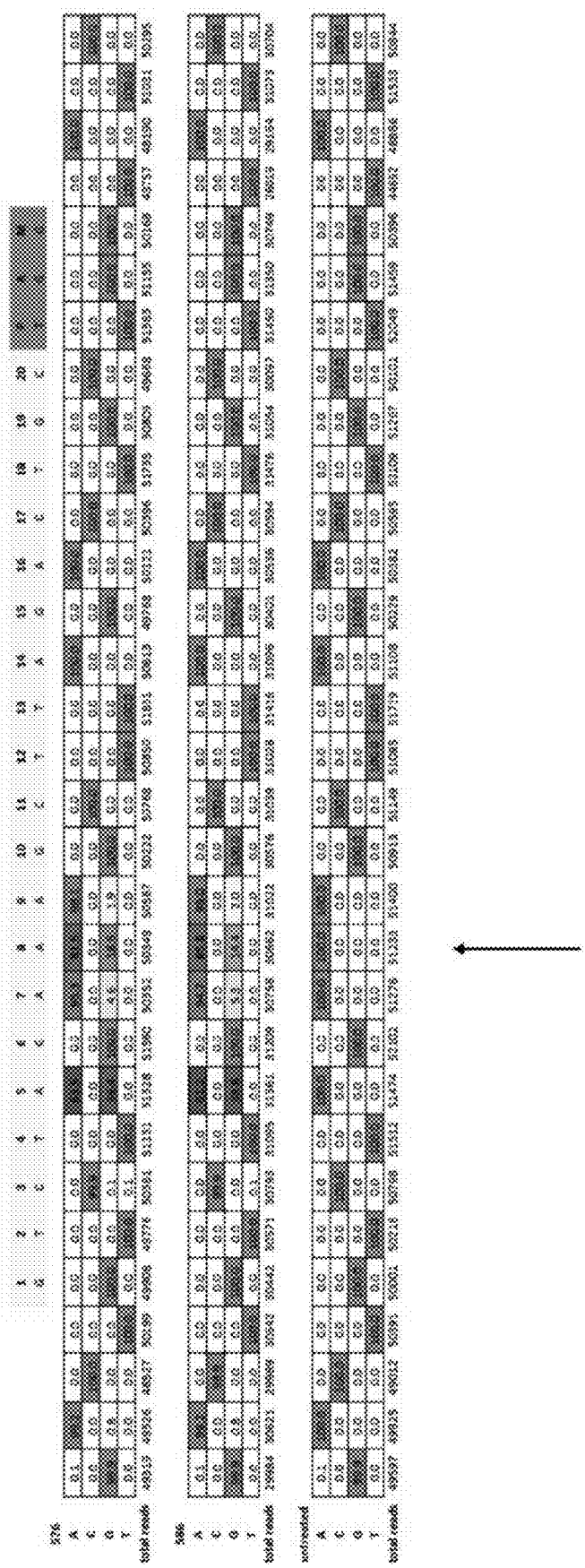

FIG. 162 shows additional ABE window experiments for identifying which A's are edited. ABEs pNMG-576, pNMG-586, and untreated control are shown. The sequence for editing is shown at the top. The sequence corresponds to SEQ ID NO: 564.

FIG. 163 shows evolution #7 an attempt to edit a multi-A site. The evolution selection design was to target 2 point mutations in the same gene using two separate gRNAs: 5'-TTCATTA(7)ACTGTGGCCGGCT-3'(SEQ ID NO: 565) and 5'-ATCTTA(6)TTCGATCATGCGAA-3' (SEQ ID NO: 566) in order to make a D208N reversion mutation in Kan and to revert a stop codon to a Q.

Figure 164:
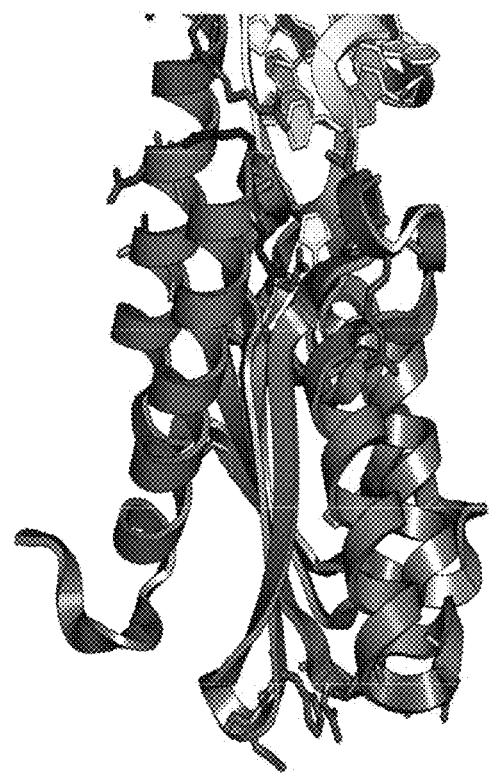

FIG. 164 shows evolution #7 mutations which were evolved to target As within a multi A site, meaning that they are flanked on one or both sides by an A. The identity of mutations, relative to SEQ ID NO: 1 are shown.

Figure 165:
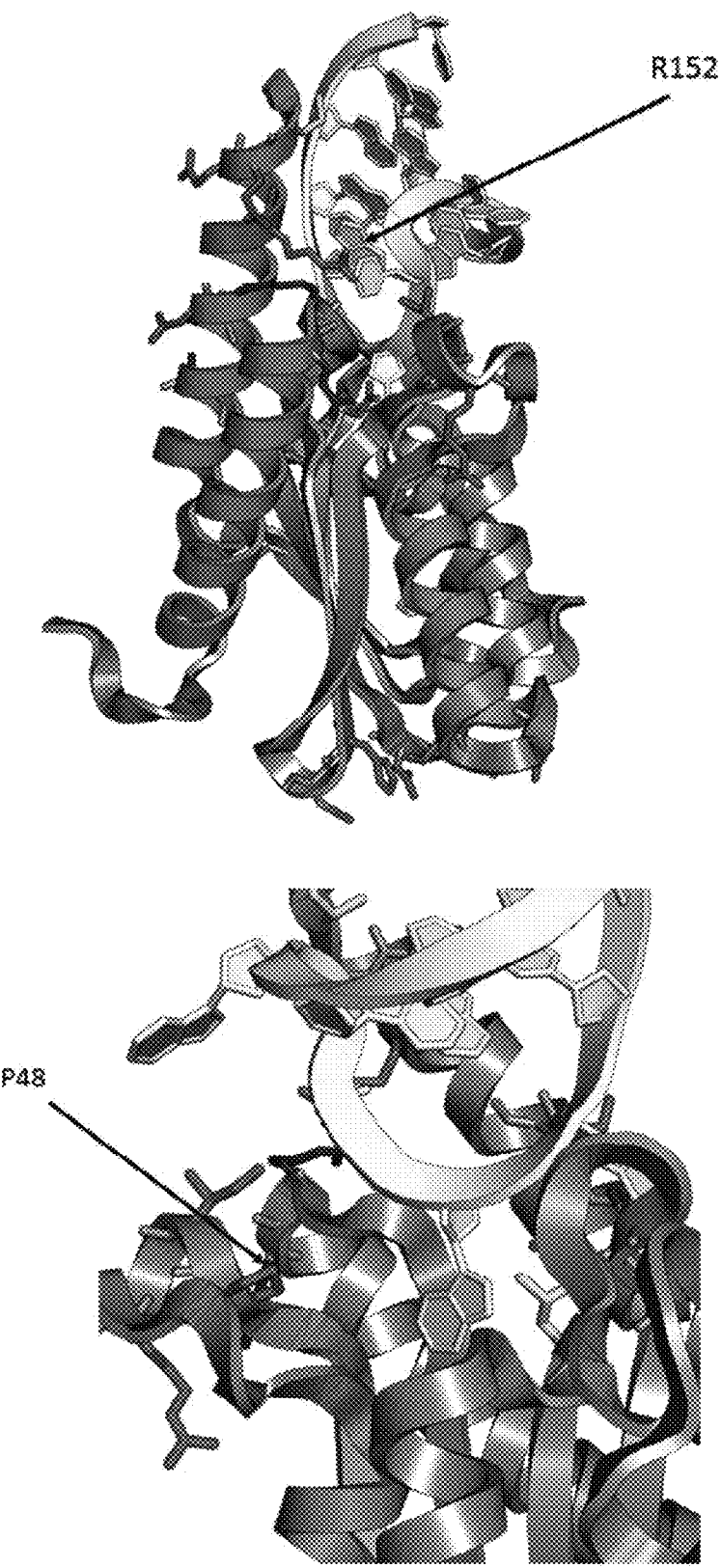

FIG. 165 shows schematics of ecTadA identifying residues R152 and P48.

FIG. 166 shows MiSeq results of ABE editing on disease relevant mutations in alternative cell lines. Nucleofection with Lonza kit was used with 3 different nucleofection solutions×16 different electroporation conditions (48 total conditions/cell line). The sequences correspond to SEQ ID NOs: 522-524 from top to bottom, respectively.

Figure 167:
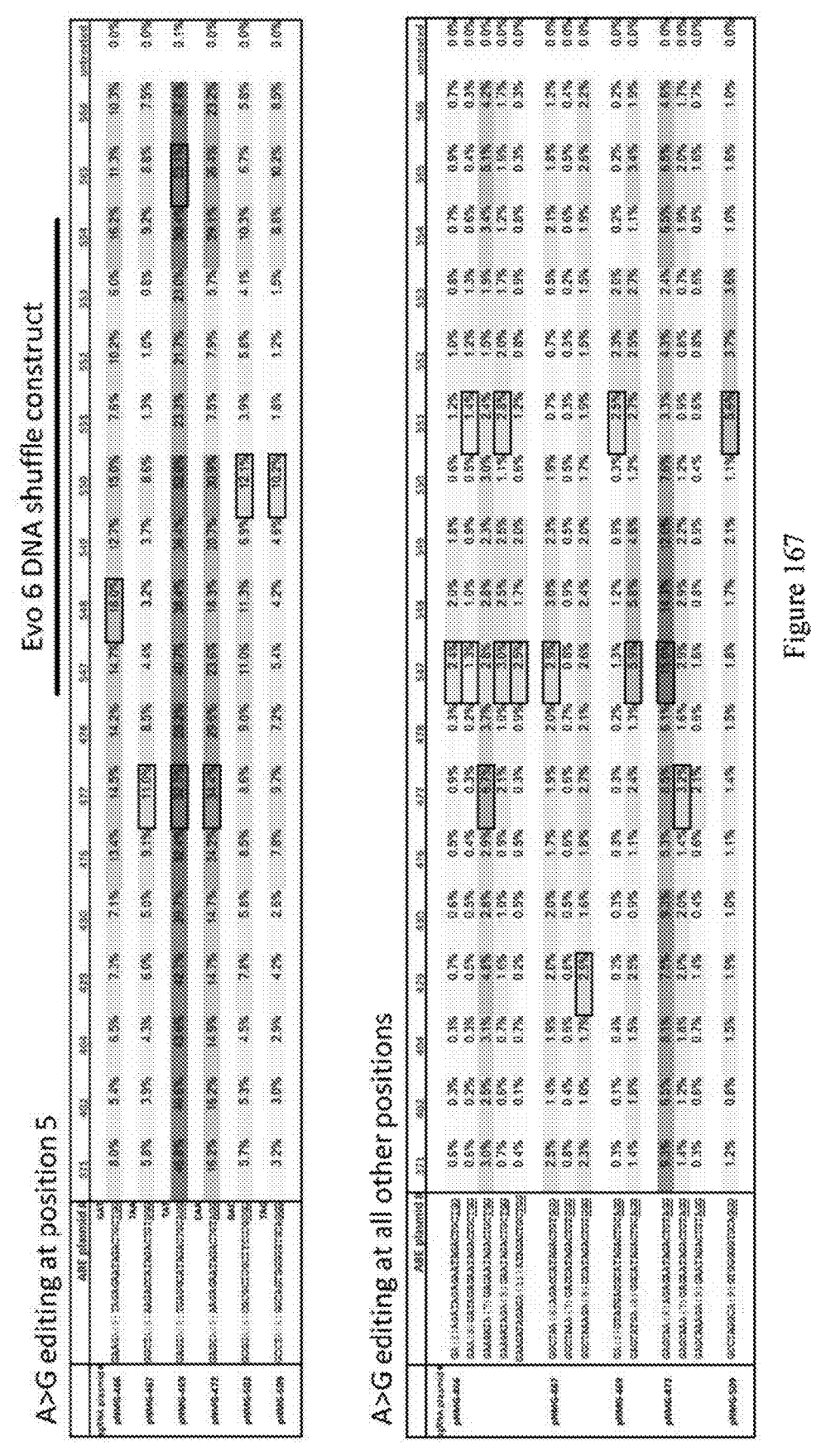

FIG. 167 shows results for A to G editing at multiple positions for various constructs. ABE constructs are indicated by their pNMG reference numbers as shown in Table 4. In the top panel the sequences correspond to SEQ ID NOs: 469-471, 567, 475, and 474 from top to bottom, respectively. In the bottom panel the sequences correspond to SEQ ID NOs: 469 (pNMG-466), 470 (pNMG-467), 471 (pNMG-469), 567 (pNMG-472), and 474 (pNMG-509) from top to bottom, respectively.

Figure 168:
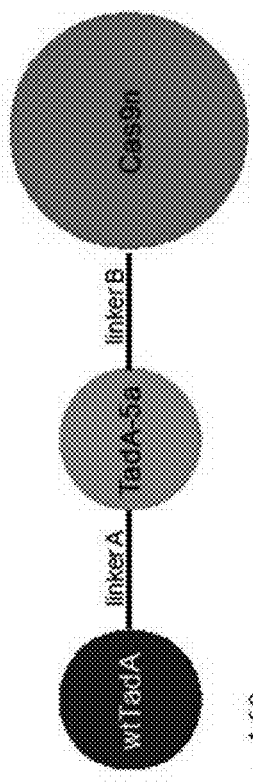

FIG. 168 shows editing results for various constructs using ABEs with different linkers. ABE constructs are indicated by their pNMG reference numbers as shown in Table 4. A schematic of the new linker ABE is also shown. The sequences correspond to SEQ ID NOs: 469 (pNMG-466), 568 (pNMG-468), 471 (pNMG-469), 567 (pNMG-472), 574 (pNGM-509), and 569) (pNMG-539) from top to bottom, respectively.

Figure 169:
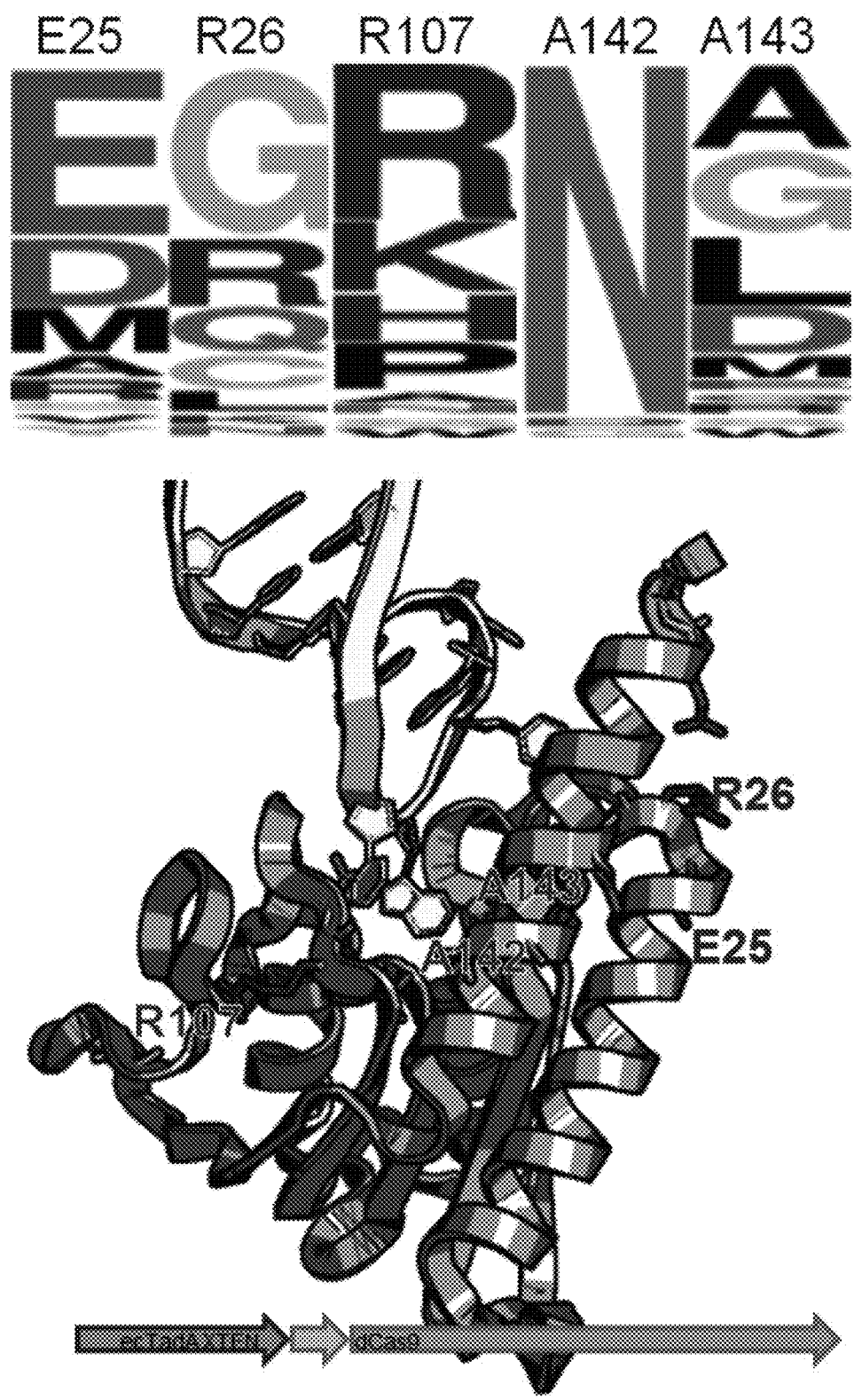

FIG. 169 shows the 4' round evolution. Evolution was done with a monomer construct and endogenous TadA complements TadA-dCas9 fusion.

Figure 170:
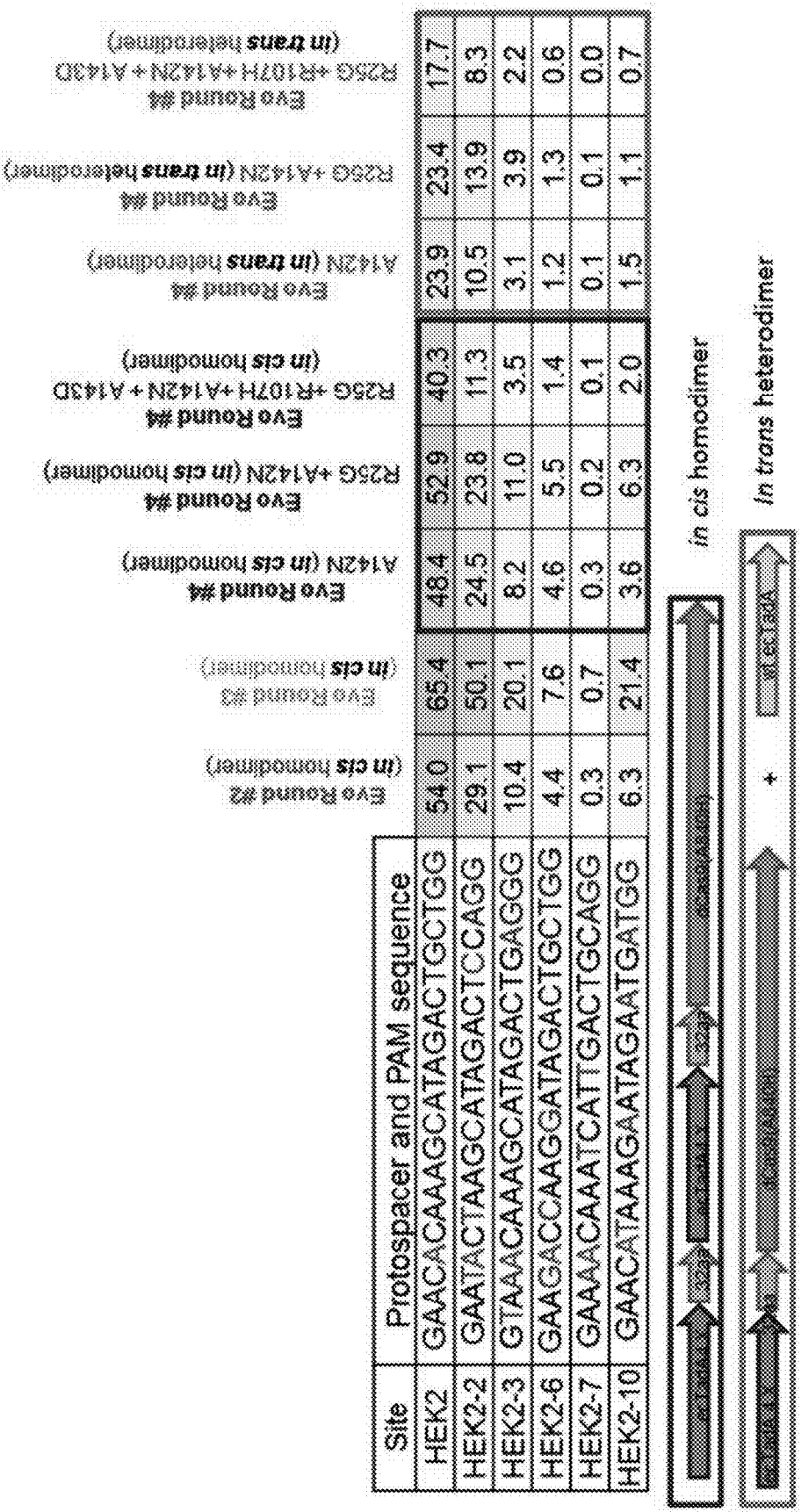

FIG. 170 shows $4^{th}$ round evolution results. The sequences correspond to SEQ ID NOs: 7, 368, 363, 364, 369, and 370 from top to bottom, respectively.

FIG. 171 shows evolution round #5. The plasmid and experimental outline are shown (top panel). The graph illustrates survival on chlor vs. spectinomycin "TAG" vs. "GAT." The chlor target sequence is 5'-TACGGCGT AGTGCACCTGGA-3' (SEQ ID NO: 441) and the spect target sequence is 5'-CAATG ATGACTTCTACAGCG-3'(SEQ ID NO: 444).

Figure 172:
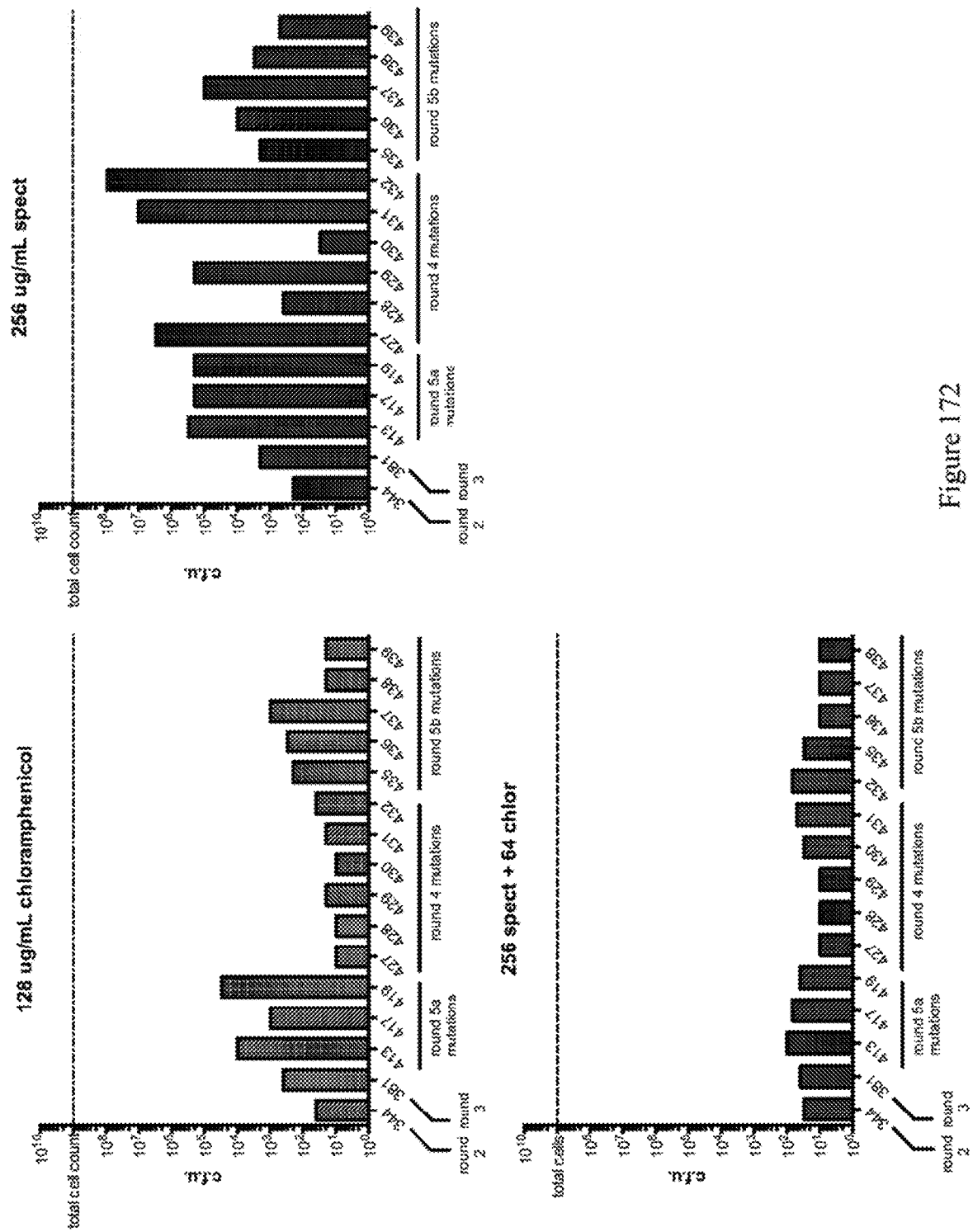

FIG. 172 shows editing results at the chlor and spect sites. Constructs identified from evolution #4 (site saturated/NNK library) appear edit more efficiently on the spect site rather than on the chor site. ABE constructs are indicated by their pNMG reference numbers as shown in Table 4.

Figure 173:
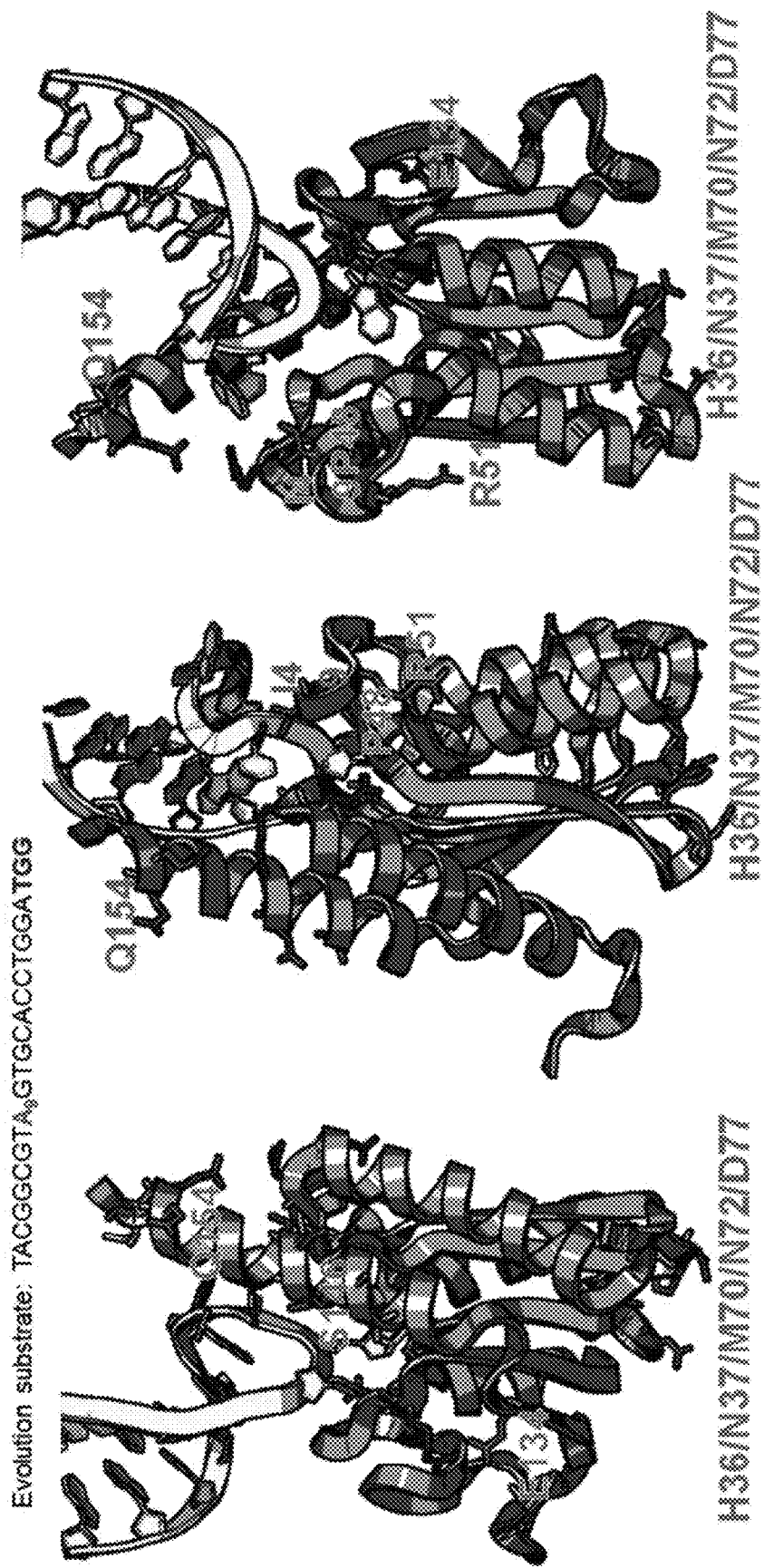

FIG. 173 shows 5th round evolution (part a). The sequence corresponds to SEQ ID NO: 570.

Figure 174:
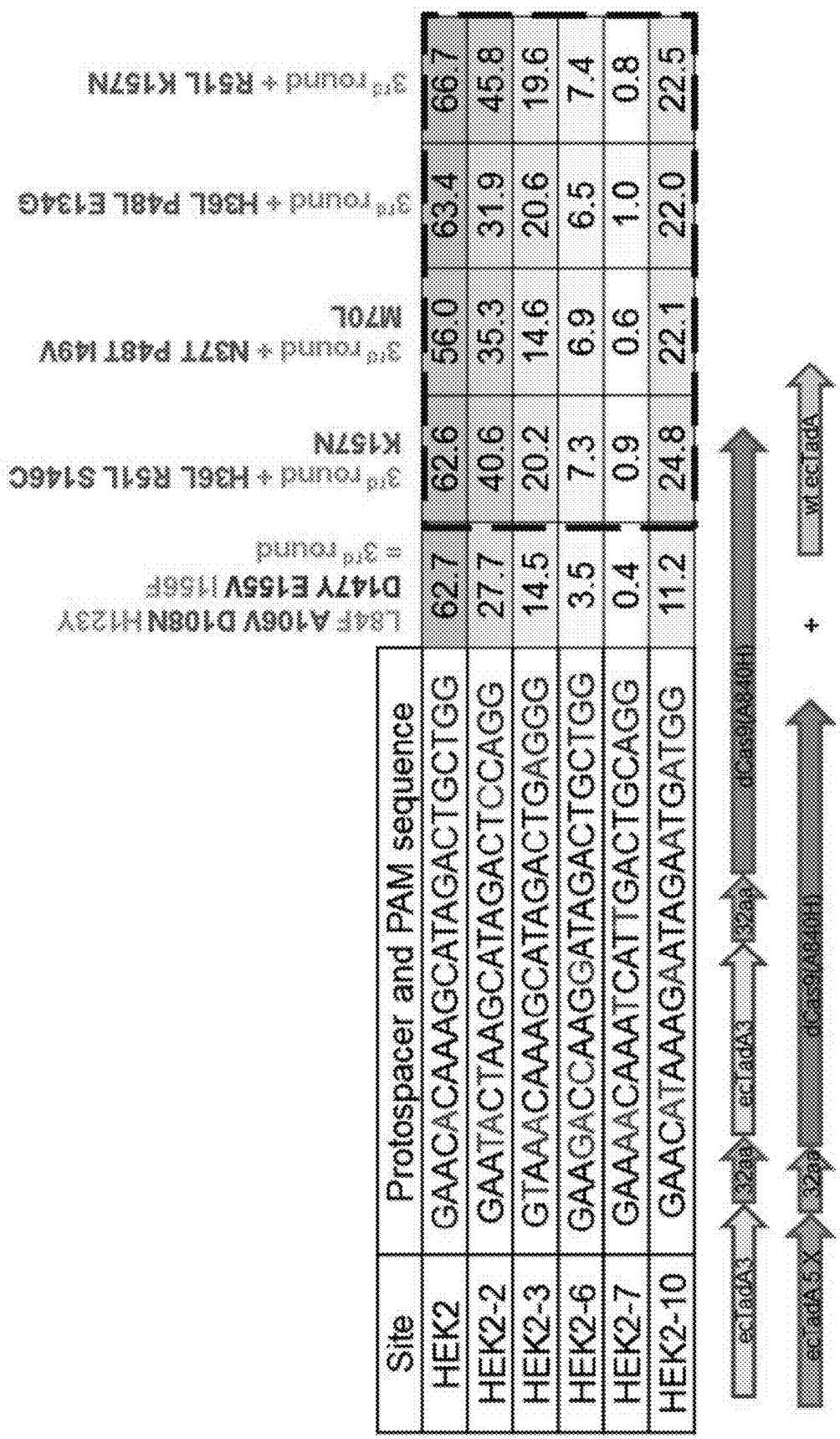

FIG. 174 shows 5th round heterodimer (in trans) results. Round #5a identified mutations improved both editing efficiencies and broadened substrate specificity. The sequences correspond to SEQ ID NOs: 7, 368, and 363, 364, 369, and 370 from top to bottom, respectively.

Figure 175:
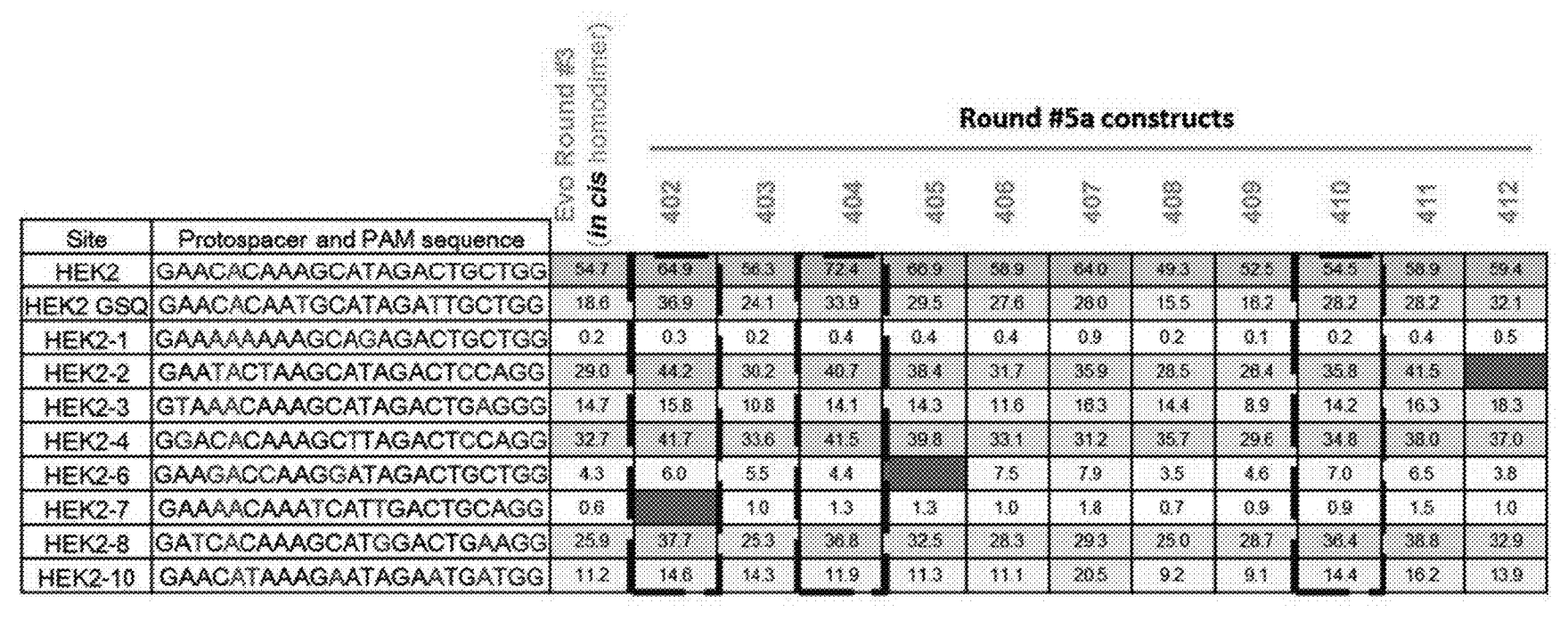

FIG. 175 shows 5th round heterodimer (in cis) results. Round #5a identified mutations improved both editing efficiencies and broadened substrate specificity, but the cis results gave higher editing efficiencies. ABE constructs are indicated by their pNMG reference numbers as shown in Table 4. The sequences correspond to SEQ ID NOs: 7, 571, 465, 368, 363, 466, 364, 369, 572, and 370 from top to bottom, respectively.

Figure 176:
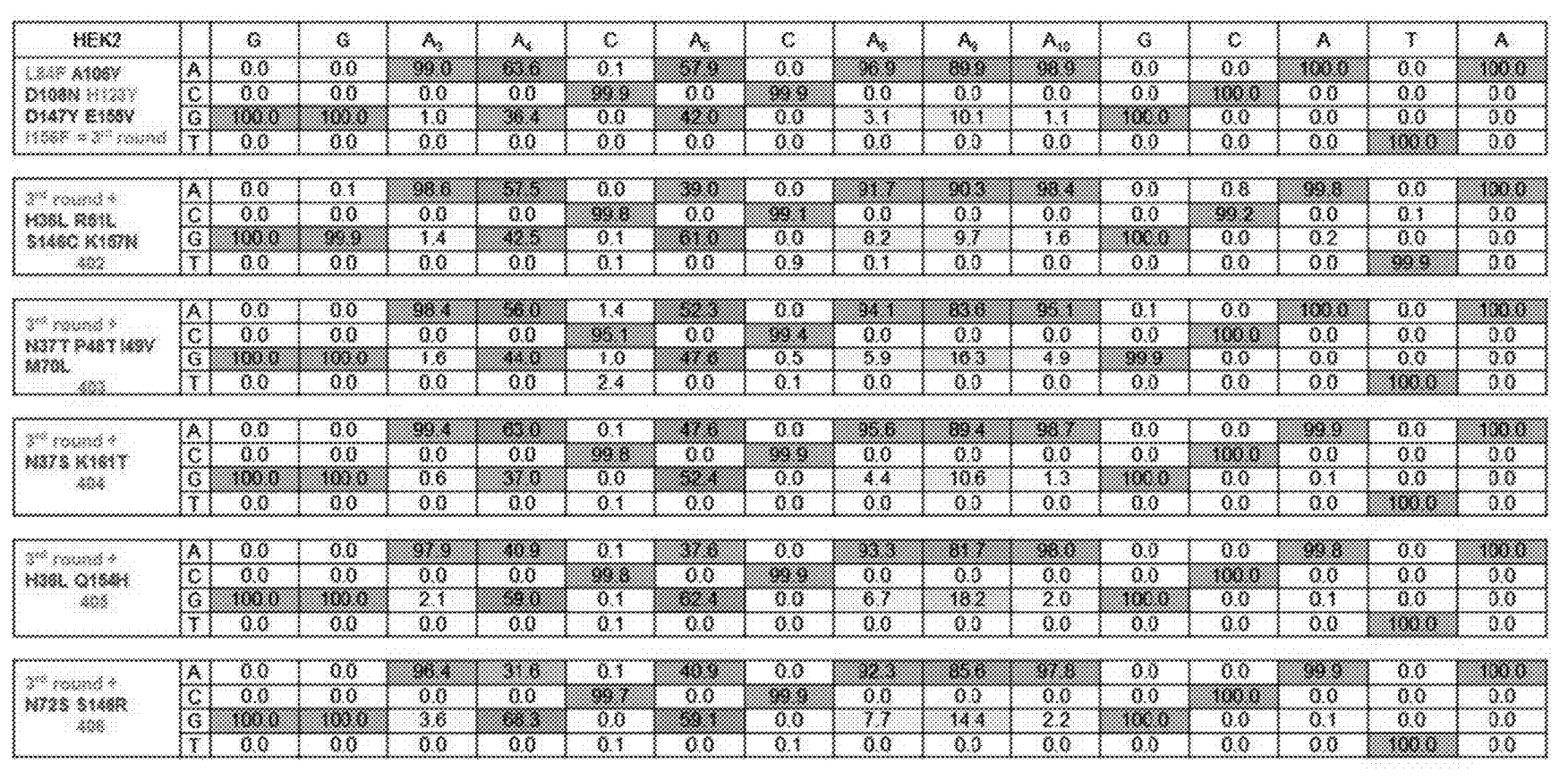

FIG. 176 shows editing results of various constructs for evolution 5.

Figure 177:
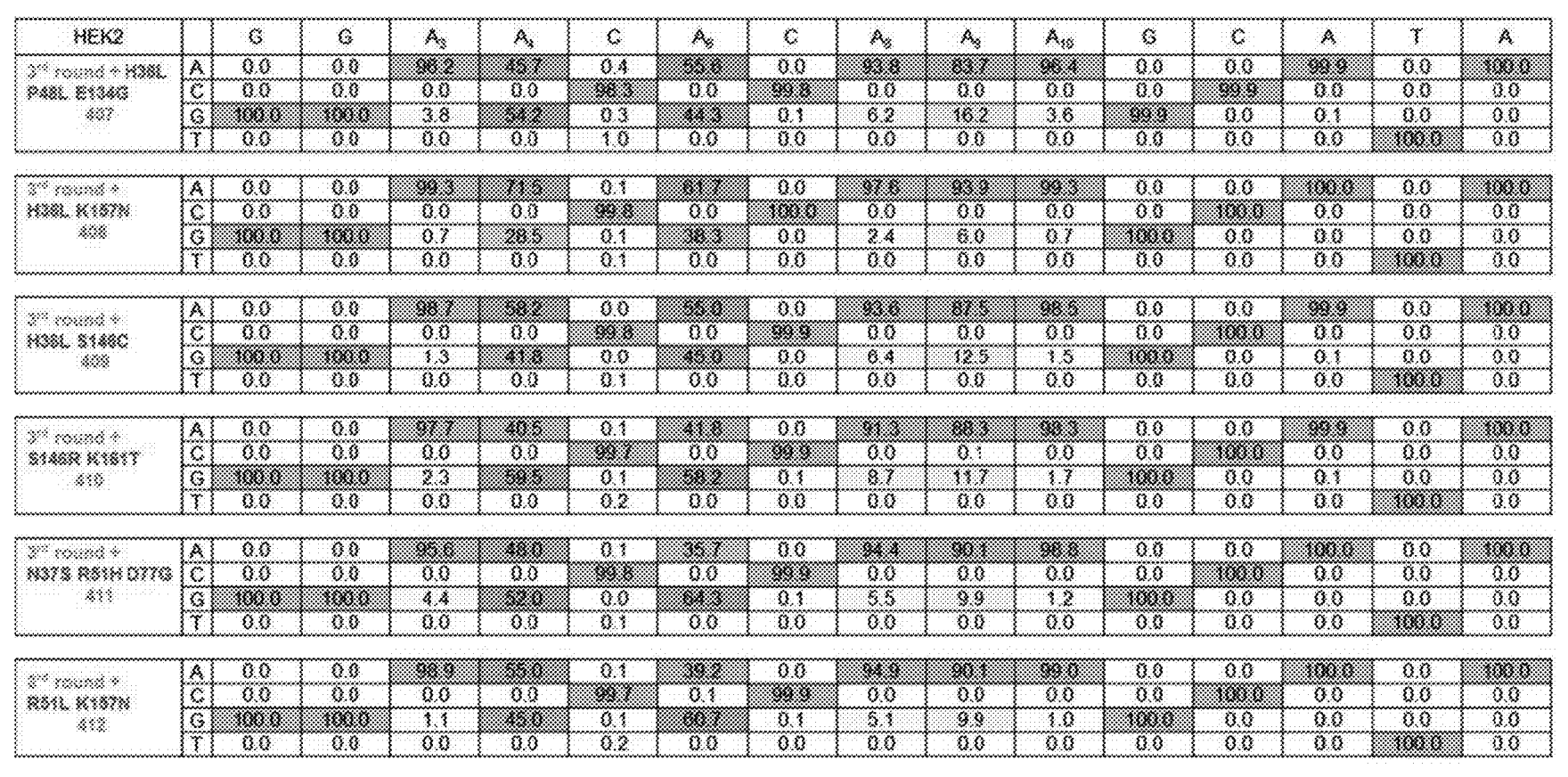

FIG. 177 shows editing results of various constructs for evolution 5.

FIG. 178 shows gRNAs for ABE. 5a constructs are characterized on all 16 NAN sequences A at position 5 in protospacer (left panel). The sequences correspond to SEQ ID NOs: 573-578 from top to bottom, respectively. Additional sequences starting with a "G" in order to minimize variations in yield gRNA synthesis are proposed (right panel). The sequences correspond to SEQ ID NOs: 579-588 from top to bottom, respectively.

FIG. 179 shows % A to G editing of $A_5$ using sgRNA 299 as indicated in Table 8 and the ABE constructs, which are indicated by their pNMG reference numbers as shown in Table 4. The sequence corresponds to SEQ ID NO: 478.

FIG. 180 shows % A to G editing of $A_5$ using sgRNA 469 as indicated in Table 8 and the ABE constructs, which are indicated by their pNMG reference numbers as shown in Table 4. The sequence corresponds to SEQ ID NO: 509.

Figure 181:
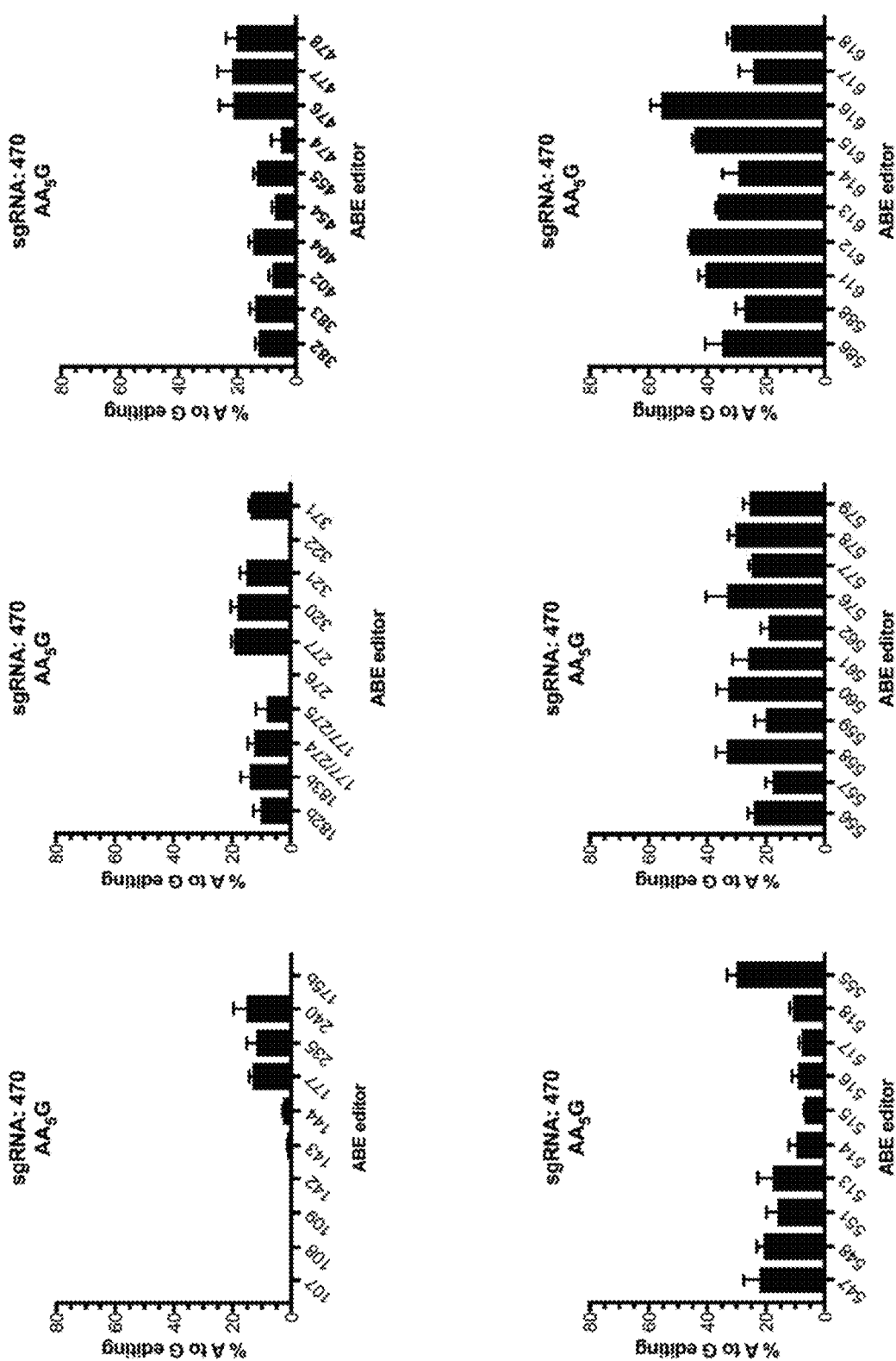

FIG. 181 shows % A to G editing of $A_5$ using sgRNA 470 as indicated in Table 8 and the ABE constructs, which are indicated by their pNMG reference numbers as shown in Table 4. The sequence corresponds to SEQ ID NO: 510.

Figure 182:
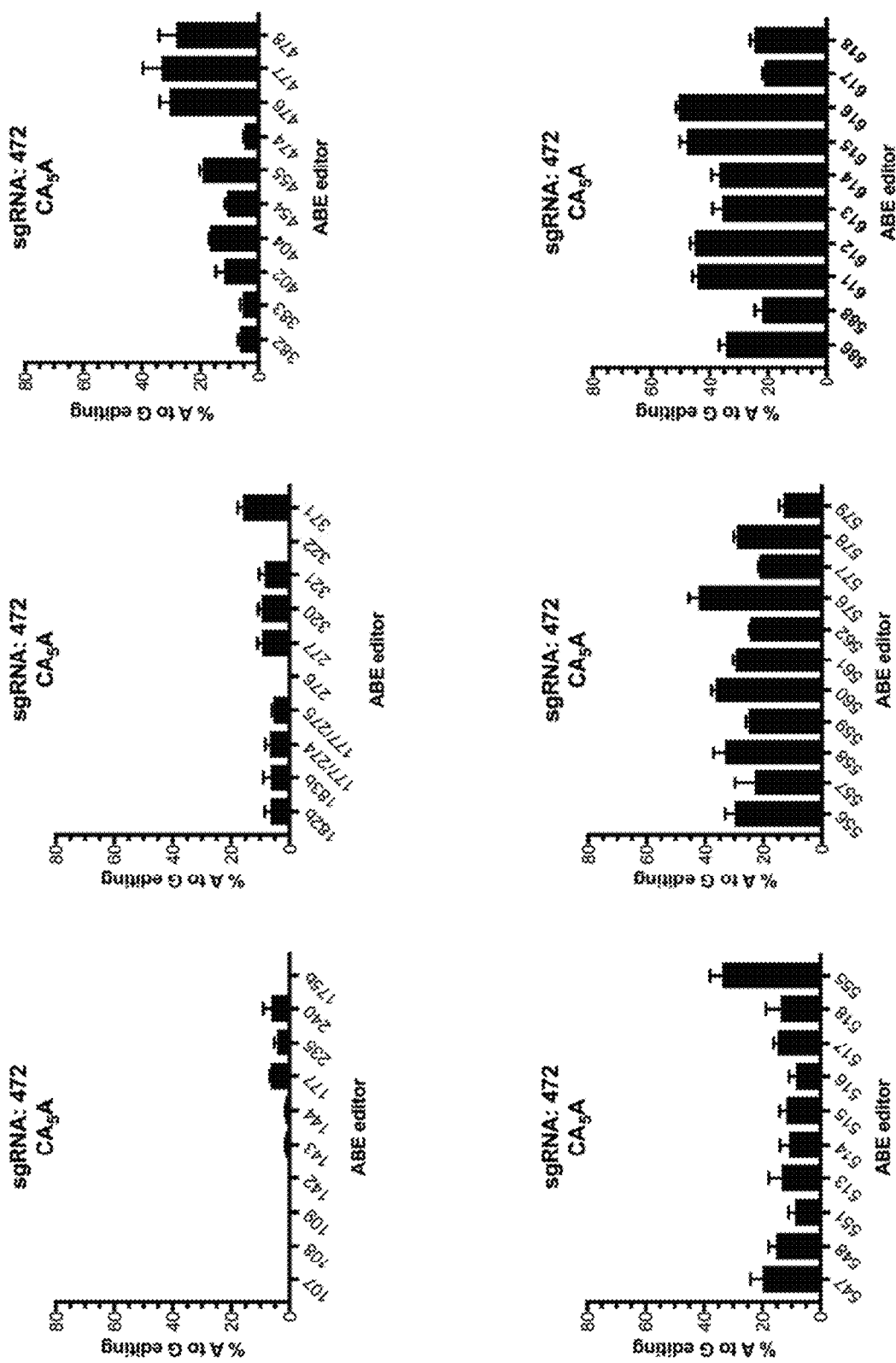

FIG. 182 shows % A to G editing of $A_5$ using sgRNA 472 as indicated in Table 8 and the ABE constructs, which are indicated by their pNMG reference numbers as shown in Table 4. The sequence corresponds to SEQ ID NO: 512.

Figure 183:
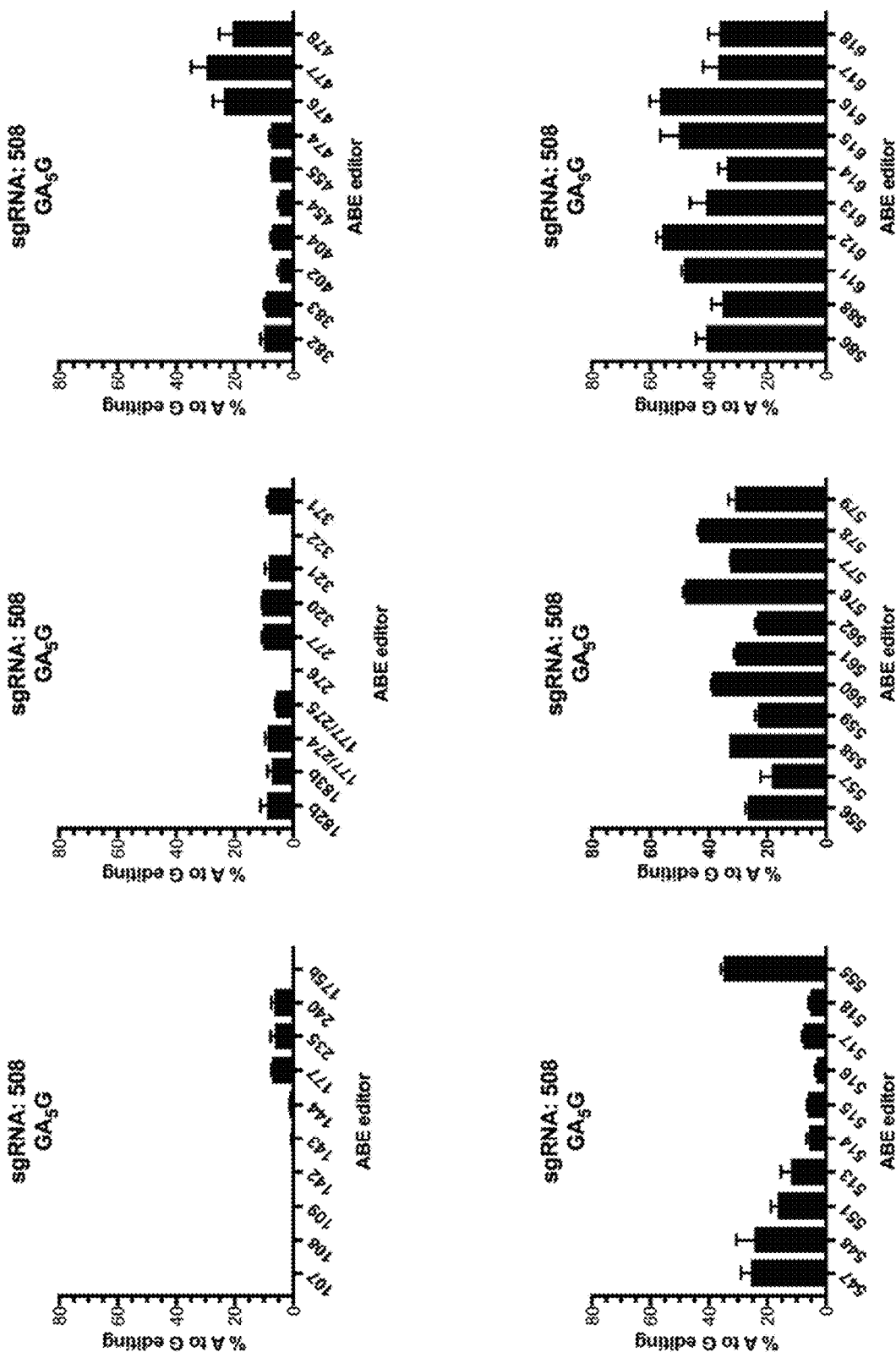

FIG. 183 shows % A to G editing of As using sgRNA 508 as indicated in Table 8 and the ABE constructs, which are indicated by their pNMG reference numbers as shown in Table 4. The sequence corresponds to SEQ ID NO: 520.

Figure 184:
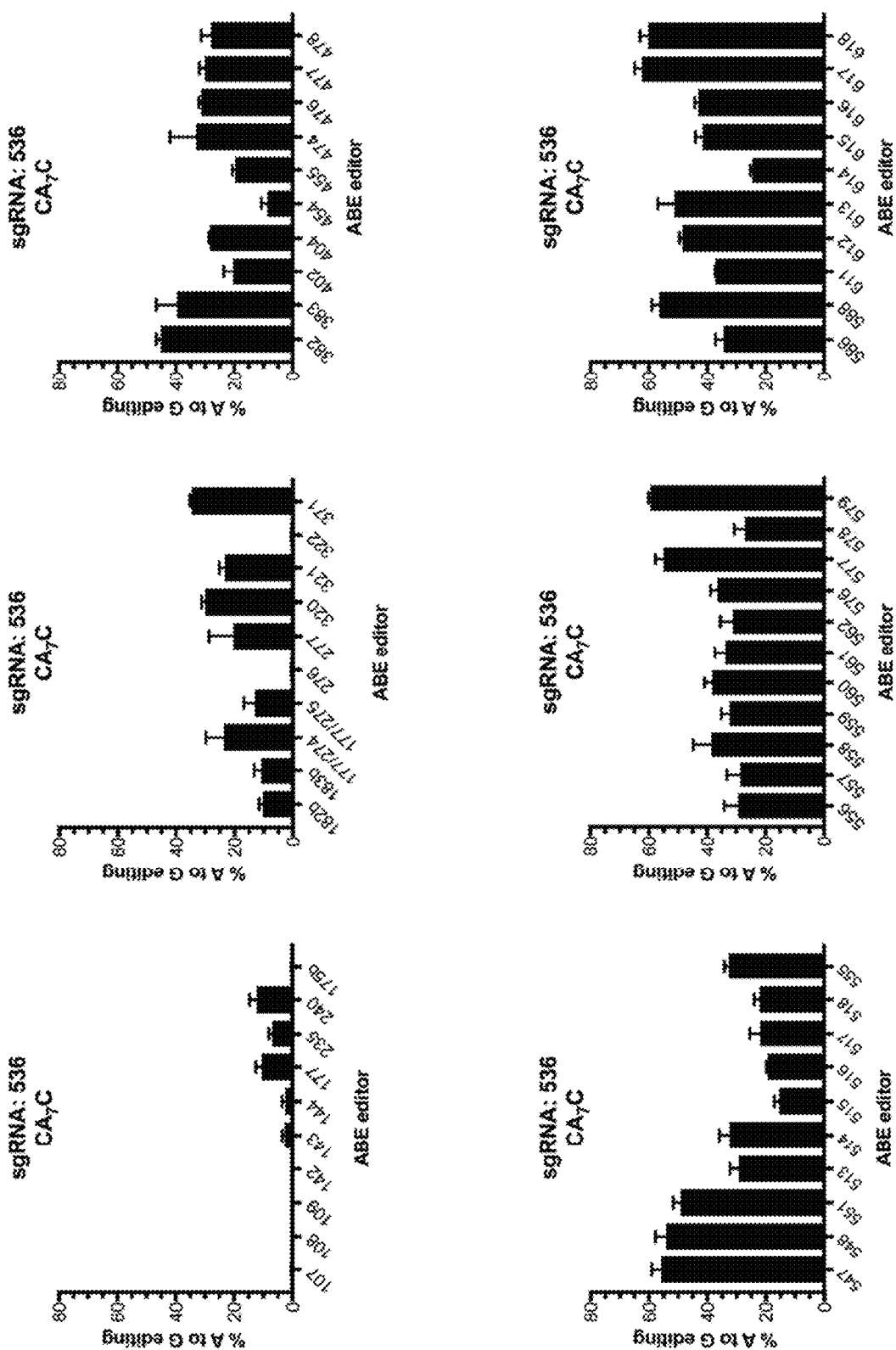

FIG. 184 shows % A to G editing of $A_7$ using sgRNA 536 as indicated in Table 8 and the ABE constructs, which are indicated by their pNMG reference numbers as shown in Table 4. The sequence corresponds to SEQ ID NO: 530.

Figure 185:
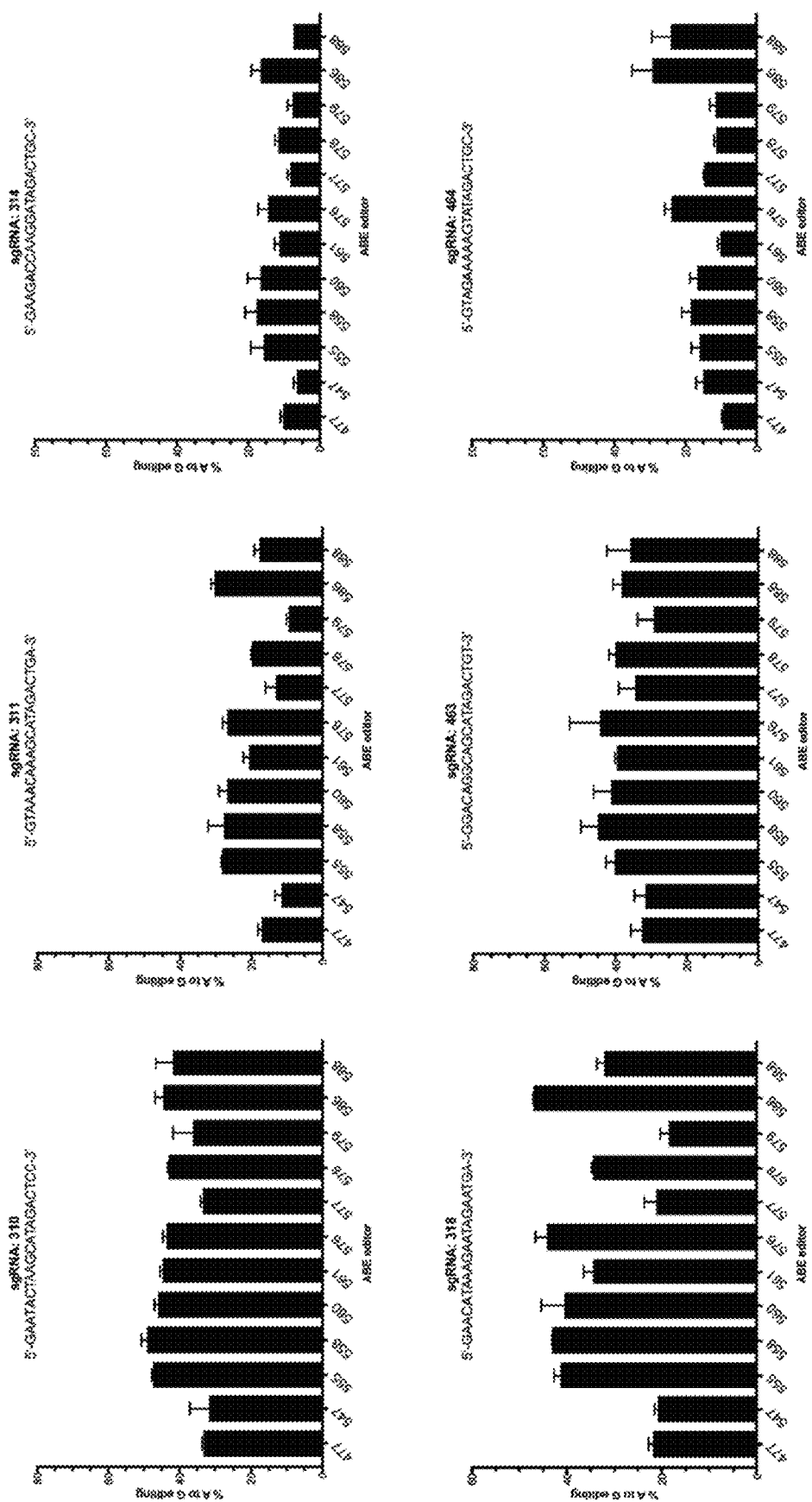

FIG. 185 shows the % of A to G editing of the highlighted A (As) using sgRNA: 310, sgRNA: 311, sgRNA: 314, sgRNA: 318, sgRNA: 463, and sgRNA: 464 for each of the indicated base editors, which are indicated by their pNMG reference numbers as shown in Table 4. The sequences correspond to SEQ ID NOs: 489, 490, 493, 497, 503 and 504 from left to right and top to bottom, respectively.

Figure 186:
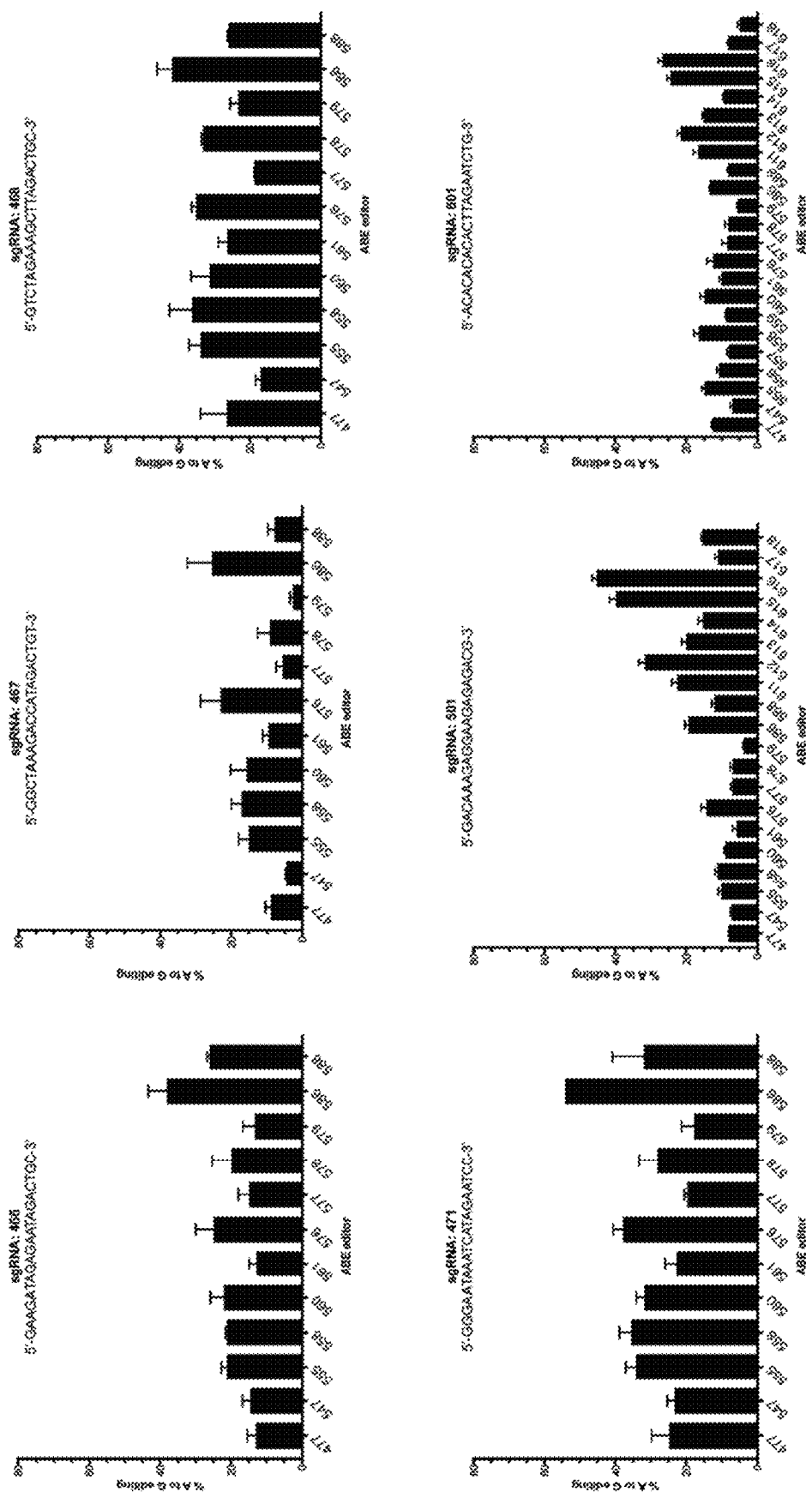

FIG. 186 shows the % of A to G editing of the highlighted A (As) using sgRNA: 466, sgRNA: 467, sgRNA: 468, sgRNA: 471, sgRNA: 501, and sgRNA: 601 for each of the indicated base editors, which are indicated by their pNMG reference numbers as shown in Table 4. The sequences correspond to SEQ ID NOs: 506, 507, 508, 511, 513, and 535 from left to right and top to bottom, respectively.

DEFINITIONS

As used herein and in the claims, the singular forms "a," "an," and "the" include the singular and the plural unless the context clearly indicates otherwise. Thus, for example, a reference to "an agent" includes a single agent and a plurality of such agents.

The term "deaminase" or "deaminase domain" refers to a protein or enzyme that catalyzes a deamination reaction. In some embodiments, the deaminase is an adenosine deaminase, which catalyzes the hydrolytic deamination of adenine or adenosine. In some embodiments, the deaminase or deaminase domain is an adenosine deaminase, catalyzing the hydrolytic deamination of adenosine or deoxyadenosine to inosine or deoxyinosine, respectively. In some embodiments, the adenosine deaminase catalyzes the hydrolytic deamination of adenine or adenosine in deoxyribonucleic acid (DNA). The adenosine deaminases (e.g. engineered adenosine deaminases, evolved adenosine deaminases) provided herein may be from any organism, such as a bacterium. In some embodiments, the deaminase or deaminase domain is a variant of a naturally-occurring deaminase from an organism. In some embodiments, the deaminase or deaminase domain does not occur in nature. For example, in some embodiments, the deaminase or deaminase domain is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to a naturally-occurring deaminase. In some embodiments, the adenosine deaminase is from a bacterium, such as, E. coli, S. aureus, S. typhi, S. putrefaciens, H. influenzae, or C. crescentus. In some embodiments, the adenosine deaminase is a TadA deaminase. In some embodiments, the TadA deaminase is an E. coli TadA deaminase (ecTadA). In some embodiments, the TadA deaminase is a truncated E. coli TadA deaminase. For example, the truncated ecTadA may be missing one or more N-terminal amino acids relative to a full-length ecTadA. In some embodiments, the truncated ecTadA may be missing 1, 2, 3, 4, 5, 6, 7, 8, 9, 10, 11, 12, 13, 14, 15, 6, 17, 18, 19, or 20 N-terminal amino acid residues relative to the full length ecTadA. In some embodiments, the truncated ecTadA may be missing 1, 2, 3, 4, 5, 6, 7, 8, 9, 10, 11, 12, 13, 14, 15, 6, 17, 18, 19, or 20 C-terminal amino acid residues relative to the full length ecTadA. In some embodiments, the ecTadA deaminase does not comprise an N-terminal methionine In some embodiments, the TadA deaminase is an N-terminal truncated TadA. In certain embodiments, the adenosine deaminase comprises the amino acid sequence:

(SEQ ID NO: 1)
MSEVEFSHEYWMRHALTLAKRAWDEREVPVGAVLVHNNRVIGEGWNR

PIGRHDPTAHAEIMALRQGGLVMQNYRLIDATLYVTLEPCVMCAGAM

IHSRIGRVVFGARDAKTGAAGSLMDVLHHPGMNHRVEITEGILADEC

AALLSDFFRMRRQEIKAQKKAQSSTD.

In some embodiments the TadA deaminase is a full-length E. coli TadA deaminase. For example, in certain embodiments, the adenosine deaminase comprises the amino acid sequence:

(SEQ ID NO: 84)
MRRAFITGVFFLSEVEFSHEYWMRHALTLAKRAWDEREVPVGAVLVH

NNRVIGEGWNRPIGRHDPTAHAEIMALRQGGLVMQNYRLIDATLYVT

```
LEPCVMCAGAMIHSRIGRVVFGARDAKTGAAGSLMDVLHHPGMNHRV

EITEGILADECAALLSDFFRMRRQEIKAQKKAQSSTD
```

It should be appreciated, however, that additional adenosine deaminases useful in the present application would be apparent to the skilled artisan and are within the scope of this disclosure. For example, the adenosine deaminase may be a homolog of an ADAT. Exemplary ADAT homologs include, without limitation:

```
Staphylococcus aureus TadA:
                                        (SEQ ID NO: 8)
MGSHMTNDIYFMTLAIEEAKKAAQLGEVPIGAIITKDDEVIARAHNL

RETLQQPTAHAEHIAIERAAKVLGSWRLEGCTLYVTLEPCVMCAGTI

VMSRIPRVVYGADDPKGGCSGSLMNLLQQSNFNHRAIVDKGVLKEAC

STLLTTFFKNLRANKKSTN

Bacillus subtilis TadA:
                                        (SEQ ID NO: 9)
MTQDELYMKEAIKEAKKAEEKGEVPIGAVLVINGEIIARAHNLRETE

QRSIAHAEMLVIDEACKALGTWRLEGATLYVTLEPCPMCAGAVVLSR

VEKVVFGAFDPKGGCSGTLMNLLQEERFNHQAEVVSGVLEEECGGML

SAFFRELRKKKKAARKNLSE

Salmonella typhimurium (S. typhimurium) TadA:
                                        (SEQ ID NO: 371)
MPPAFITGVTSLSDVELDHEYWMRHALTLAKRAWDEREVPVGAVLVH

NHRVIGEGWNRPIGRHDPTAHAEIMALRQGGLVLQNYRLLDTTLYVT

LEPCVMCAGAMVHSRIGRVVFGARDAKTGAAGSLIDVLHHPGMNHRV

EIIEGVLRDECATLLSDFFRMRRQEIKALKKADRAEGAGPAV

Shewanella putrefaciens (S. putrefaciens) TadA:
                                        (SEQ ID NO: 372)
MDEYWMQVAMQMAEKAEAAGEVPVGAVLVKDGQQIATGYNLSISQHD

PTAHAEILCLRSAGKKLENYRLLDATLYITLEPCAMCAGAMVHSRIA

RVVYGARDEKTGAAGTVVNLLQHPAFNHQVEVTSGVLAEACSAQLSR

FFKRRRDEKKALKLAQRAQQGIE

Haemophilus influenzae F3031 (H. influenzae)
TadA:
                                        (SEQ ID NO: 373)
MDAAKVRSEFDEKMMRYALELADKAEALGEIPVGAVLVDDARNIIGE

GWNLSIVQSDPTAHAEIIALRNGAKNIQNYRLLNSTLYVTLEPCTMC

AGAILHSRIKRLVFGASDYKTGAIGSRFHFFDDYKMNHTLEITSGVL

AEECSQKLSTFFQKRREEKKIEKALLKSLSDK

Caulobacter crescentus (C. crescentus) TadA:
                                        (SEQ ID NO: 374)
MRTDESEDQDHRMMRLALDAARAAAEAGETPVGAVILDPSTGEVIAT

AGNGPIAAHDPTAHAEIAAMRAAAAKLGNYRLTDLTLVVTLEPCAMC

AGAISHARIGRVVFGADDPKGGAVVHGPKFFAQPTCHWRPEVTGGVL

ADESADLLRGFFRARRKAKI

Geobacter sulfurreducens (G. sulfurreducens)
TadA:
                                        (SEQ ID NO: 375)
MSSLKKTPIRDDAYWMGKAIREAAKAAARDEVPIGAVIVRDGAVIGR

GHNLREGSNDPSAHAEMIAIRQAARRSANWRLTGATLYVTLEPCLMC

MGAIILARLERVVFGCYDPKGGAAGSLYDLSADPRLNHQVRLSPGVC

QEECGTMLSDFFRDLRRRKKAKATPALFIDERKVPPEP
```

The term "base editor (BE)," or "nucleobase editor (NBE)" refers to an agent comprising a polypeptide that is capable of making a modification to a base (e.g., A, T, C, G, or U) within a nucleic acid sequence (e.g., DNA or RNA). In some embodiments, the base editor is capable of deaminating a base within a nucleic acid. In some embodiments, the base editor is capable of deaminating a base within a DNA molecule. In some embodiments, the base editor is capable of deaminating an adenine (A) in DNA. In some embodiments, the base editor is a fusion protein comprising a nucleic acid programmable DNA binding protein (napDNAbp) fused to an adenosine deaminase. In some embodiments, the base editor is a Cas9 protein fused to an adenosine deaminase. In some embodiments, the base editor is a Cas9 nickase (nCas9) fused to an adenosine deaminase. In some embodiments, the base editor is a nuclease-inactive Cas9 (dCas9) fused to an adenosine deaminase. In some embodiments, the base editor is fused to an inhibitor of base excision repair, for example, a UGI domain, or a dISN domain. In some embodiments, the fusion protein comprises a Cas9 nickase fused to a deaminase and an inhibitor of base excision repair, such as a UGI or dISN domain. In some embodiments, the dCas9 domain of the fusion protein comprises a D10A and a H840A mutation of SEQ ID NO: 52, or a corresponding mutation in any of SEQ ID NOs: 108-357, which inactivates the nuclease activity of the Cas9 protein. In some embodiments, the fusion protein comprises a D10A mutation and comprises a histidine at residue 840 of SEQ ID NO: 52, or a corresponding mutation in any of SEQ ID NOs: 108-357, which renders Cas9 capable of cleaving only one strand of a nucleic acid duplex. An example of a Cas9 nickase is shown in SEQ ID NO: 35.

The term "linker," as used herein, refers to a bond (e.g., covalent bond), chemical group, or a molecule linking two molecules or moieties, e.g., two domains of a fusion protein, such as, for example, a nuclease-inactive Cas9 domain and a nucleic acid-editing domain (e.g., an adenosine deaminase). In some embodiments, a linker joins a gRNA binding domain of an RNA-programmable nuclease, including a Cas9 nuclease domain, and the catalytic domain of a nucleic-acid editing protein. In some embodiments, a linker joins a dCas9 and a nucleic-acid editing protein. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated. In some embodiments, a linker comprises the amino acid sequence SGSETPGTSESATPES (SEQ ID NO: 10), which may also be referred to as the XTEN linker. In some embodiments, a linker comprises the amino acid sequence SGGS (SEQ ID NO: 37). In some embodiments, a linker comprises (SGGS)$_n$ (SEQ ID NO: 37), (GGGS)$_n$ (SEQ ID NO: 38), (GGGGS)$_n$ (SEQ ID NO: 39), (G)$_n$, (EAAAK)$_n$ (SEQ ID NO: 40), (GGS)$_n$, SGSETPGTSESATPES (SEQ ID NO: 10), or (XP)$_n$ motif, or a combination of any of these, wherein n is independently an integer between 1 and 30, and wherein X is any amino acid. In some embodiments, n is 1, 2, 3, 4, 5, 6, 7, 8, 9, 10, 11, 12, 13, 14, or 15.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* (4$^{th}$ ed., Cold Spring Harbor Laboratory Press, Cold Spring Harbor, N.Y. (2012)).

The term "inhibitor of base repair" or "IBR" refers to a protein that is capable in inhibiting the activity of a nucleic acid repair enzyme, for example a base excision repair enzyme. In some embodiments, the IBR is an inhibitor of inosine base excision repair. Exemplary inhibitors of base repair include inhibitors of APE 1, Endo III, Endo IV, Endo V, Endo VIII, Fpg, hOGG1, hNEIL1, T7 EndoI, T4PDG, UDG, hSMUG1, and hAAG. In some embodiments, the IBR is an inhibitor of Endo V or hAAG. In some embodiments, the IBR is a catalytically inactive EndoV or a catalytically inactive hAAG.

The term "uracil glycosylase inhibitor" or "UGI," as used herein, refers to a protein that is capable of inhibiting a uracil-DNA glycosylase base-excision repair enzyme. In some embodiments, a UGI domain comprises a wild-type UGI or a UGI as set forth in SEQ ID NO: 3. In some embodiments, the UGI proteins provided herein include fragments of UGI and proteins homologous to a UGI or a UGI fragment. For example, in some embodiments, a UGI domain comprises a fragment of the amino acid sequence set forth in SEQ ID NO: 3. In some embodiments, a UGI fragment comprises an amino acid sequence that comprises at least 60%, at least 65%, at least 70%, at least 75%, at least 80%, at least 85%, at least 90%, at least 95%, at least 96%, at least 97%, at least 98%, at least 99%, or at least 99.5% of the amino acid sequence as set forth in SEQ ID NO: 3. In some embodiments, a UGI comprises an amino acid sequence homologous to the amino acid sequence set forth in SEQ ID NO: 3, or an amino acid sequence homologous to a fragment of the amino acid sequence set forth in SEQ ID NO: 3. In some embodiments, proteins comprising UGI or fragments of UGI or homologs of UGI or UGI fragments are referred to as "UGI variants." A UGI variant shares homology to UGI, or a fragment thereof. For example a UGI variant is at least 70% identical, at least 75% identical, at least 80% identical, at least 85% identical, at least 90% identical, at least 95% identical, at least 96% identical, at least 97% identical, at least 98% identical, at least 99% identical, at least 99.5% identical, or at least 99.9% identical to a wild type UGI or a UGI as set forth in SEQ ID NO: 3. In some embodiments, the UGI variant comprises a fragment of UGI, such that the fragment is at least 70% identical, at least 80% identical, at least 90% identical, at least 95% identical, at least 96% identical, at least 97% identical, at least 98% identical, at least 99% identical, at least 99.5% identical, or at least 99.9% to the corresponding fragment of wild-type UGI or a UGI as set forth in SEQ ID NO: 3. In some embodiments, the UGI comprises the following amino acid sequence:

```
>sp|P14739|UNGI_BPPB2 Uracil-DNA
glycosylase inhibitor
                                    (SEQ ID NO: 3)
MTNLSDIIEKETGKQLVIQESILMLPEEVEEVIGNKPESDILVHTAY

DESTDENVMLLTSDAPEYKPWALVIQDSNGENKIKML.
```

The term "catalytically inactive inosine-specific nuclease," or "dead inosine-specific nuclease (dISN)," as used herein, refers to a protein that is capable of inhibiting an inosine-specific nuclease. Without wishing to be bound by any particular theory, catalytically inactive inosine glycosylases (e.g., alkyl adenine glycosylase [AAG]) will bind inosine, but will not create an abasic site or remove the inosine, thereby sterically blocking the newly-formed inosine moiety from DNA damage/repair mechanisms. In some embodiments, the catalytically inactive inosine-specific nuclease may be capable of binding an inosine in a nucleic acid but does not cleave the nucleic acid. Exemplary catalytically inactive inosine-specific nucleases include, without limitation, catalytically inactive alkyl adenosine glycosylase (AAG nuclease), for example, from a human, and catalytically inactive endonuclease V (EndoV nuclease), for example, from *E. coli*. In some embodiments, the catalytically inactive AAG nuclease comprises an E125Q mutation as shown in SEQ ID NO: 32, or a corresponding mutation in another AAG nuclease. In some embodiments, the catalytically inactive AAG nuclease comprises the amino acid sequence set forth in SEQ ID NO: 32. In some embodiments, the catalytically inactive EndoV nuclease comprises an D35A mutation as shown in SEQ ID NO 32, or a corresponding mutation in another EndoV nuclease. In some embodiments, the catalytically inactive EndoV nuclease comprises the amino acid sequence set forth in SEQ ID NO: 33. It should be appreciated that other catalytically inactive inosine-specific nucleases (dISNs) would be apparent to the skilled artisan and are within the scope of this disclosure.

```
Truncated AAG (H. sapiens) nuclease (E125Q);
mutated residue underlined in bold.
                                    (SEQ ID NO: 32)
KGHLTRLGLEFFDQPAVPLARAFLGQVLVRRLPNGTELRGRIVETQAY

LGPEDEAAHSRGGRQTPRNRGMFMKPGTLYVYIIYGMYFCMNISSQGD

GACVLLRALEPLEGLETMRQLRSTLRKGTASRVLKDRELCSGPSKLCQ

ALAINKSFDQRDLAQDEAVWLERGPLEPSEPAVVAAARVGVGHAGEWA

RKPLRFYVRGSPWVSVVDRVAEQDTQA

EndoV nuclease (D35A); mutated residue
underlined in bold.
                                    (SEQ ID NO: 33)
DLASLRAQQIELASSVIREDRLDKDPPDLIAGAAVGFEQGGEVTRAAM

VLLKYPSLELVEYKVARIATTMPYIPGFLSFREYPALLAAWEMLSQKP

DLVFVDGHGISHPRRLGVASHFGLLVDVPTIGVAKKRLCGKFEPLSSE

PGALAPLMDKGEQLAWVWRSKARCNPLFIATGHRVSVDSALAWVQRCM

KGYRLPEPTRWADAVASERPAFVRYTANQP
```

The term "nuclear localization sequence" or "NLS" refers to an amino acid sequence that promotes import of a protein into the cell nucleus, for example, by nuclear transport. Nuclear localization sequences are known in the art and would be apparent to the skilled artisan. For example, NLS sequences are described in Plank et al., international PCT application, PCT/EP2000/011690, filed Nov. 23, 2000, published as WO/2001/038547 on May 31, 2001, the contents of which are incorporated herein by reference for their disclosure of exemplary nuclear localization sequences. In some embodiments, a NLS comprises the amino acid sequence PKKKRKV (SEQ ID NO: 4) or MDSLLMNRRKFLY-QFKNVRWAKGRRETYLC (SEQ ID NO: 5).

The term "nucleic acid programmable DNA binding protein" or "napDNAbp" refers to a protein that associates with a nucleic acid (e.g., DNA or RNA), such as a guide nucleic acid, that guides the napDNAbp to a specific nucleic acid sequence. For example, a Cas9 protein can associate with a guide RNA that guides the Cas9 protein to a specific DNA sequence that has complementary to the guide RNA. In some embodiments, the napDNAbp is a class 2 microbial CRISPR-Cas effector. In some embodiments, the napDNAbp is a Cas9 domain, for example a nuclease active Cas9, a Cas9 nickase (nCas9), or a nuclease inactive Cas9 (dCas9). Examples of nucleic acid programmable DNA binding proteins include, without limitation, Cas9 (e.g., dCas9 and nCas9), CasX, CasY, Cpf1, C2c1, C2c2, C2C3, and Argonaute. It should be appreciated, however, that nucleic acid programmable DNAbinding proteins also include nucleic acid programmable proteins that bind RNA. For example, the napDNAbp may be associated with a nucleic acid that guides the napDNAbp to an RNA. Other nucleic acid programmable DNA binding proteins are also within the scope of this disclosure, though they may not be specifically listed in this disclosure.

The term "Cas9" or "Cas9 domain" refers to an RNA-guided nuclease comprising a Cas9 protein, or a fragment thereof (e.g., a protein comprising an active, inactive, or partially active DNA cleavage domain of Cas9, and/or the gRNA binding domain of Cas9). A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. See, e.g., Jinek M., Chylinski K., Fonfara I., Hauer M., Doudna J. A., Charpentier E. *Science* 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain, that is, the Cas9 is a nickase.

A nuclease-inactivated Cas9 protein may interchangeably be referred to as a "dCas9" protein (for nuclease-"dead" Cas9). Methods for generating a Cas9 protein (or a fragment thereof) having an inactive DNA cleavage domain are known (See, e.g., Jinek et al., *Science*. 337:816-821(2012); Qi et al., "Repurposing CRISPR as an RNA-Guided Platform for Sequence-Specific Control of Gene Expression" (2013) *Cell*. 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (Jinek et al., *Science*. 337:816-821(2012); Qi et al., *Cell*. 28; 152(5):1173-83 (2013)). In some embodiments, proteins comprising fragments of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9 or fragments thereof are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to wild type Cas9. In some embodiments, the Cas9 variant may have 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50, or more amino acid changes compared to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the corresponding fragment of wild type Cas9. In some embodiments, the fragment is at least 30%, at least 35%, at least 40%, at least 45%, at least 50%, at least 55%, at least 60%, at least 65%, at least 70%, at least 75%, at least 80%, at least 85%, at least 90%, at least 95% identical, at least 96%, at least 97%, at least 98%, at least 99%, or at least 99.5% of the amino acid length of a corresponding wild type Cas9.

In some embodiments, the fragment is at least 100 amino acids in length. In some embodiments, the fragment is at least 100, 150, 200, 250, 300, 350, 400, 450, 500, 550, 600, 650, 700, 750, 800, 850, 900, 950, 1000, 1050, 1100, 1150, 1200, 1250, or 1300 amino acids in length. In some embodiments, wild type Cas9 corresponds to Cas9 from *Streptococcus pyogenes* (NCBI Reference Sequence: NC_017053.1, SEQ ID NO: 47 (nucleotide); SEQ ID NO: 48 (amino acid)).

(SEQ ID NO: 47)
```
ATGGATAAGAAATACTCAATAGGCTTAGATATCGGCACAAATAGCGTCGGATGG
GCGGTGATCACTGATGATTATAAGGTTCCGTCTAAAAAGTTCAAGGTTCTGGGAA
ATACAGACCGCCACAGTATCAAAAAAAATCTTATAGGGGCTCTTTTATTTGGCAG
TGGAGAGACAGCGGAAGCGACTCGTCTCAAACGGACAGCTCGTAGAAGGTATAC
ACGTCGGAAGAATCGTATTTGTTATCTACAGGAGATTTTTTCAAATGAGATGGCG
AAAGTAGATGATAGTTTCTTTCATCGACTTGAAGAGTCTTTTTTGGTGGAAGAAG
ACAAGAAGCATGAACGTCATCCTATTTTTGGAAATATAGTAGATGAAGTTGCTTA
TCATGAGAAATATCCAACTATCTATCATCTGCGAAAAAAATTGGCAGATTCTACT
GATAAAGCGGATTTGCGCTTAATCTATTTGGCCTTAGCGCATATGATTAAGTTTC
GTGGTCATTTTTTGATTGAGGGAGATTTAAATCCTGATAATAGTGATGTGGACAA
ACTATTTATCCAGTTGGTACAAATCTACAATCAATTATTTGAAGAAAACCCTATT
AACGCAAGTAGAGTAGATGCTAAAGCGATTCTTTCTGCACGATTGAGTAAATCA
AGACGATTAGAAAATCTCATTGCTCAGCTCCCCGGTGAGAAGAGAAATGGCTTG
TTTGGGAATCTCATTGCTTTGTCATTGGGATTGACCCCTAATTTTAAATCAAATTT
TGATTTGGCAGAAGATGCTAAATTACAGCTTTCAAAAGATACTTACGATGATGAT
TTAGATAATTTATTGGCGCAAATTGGAGATCAATATGCTGATTTGTTTTTGGCAG
CTAAGAATTTATCAGATGCTATTTTACTTTCAGATATCCTAAGAGTAAATAGTGA
AATAACTAAGGCTCCCCTATCAGCTTCAATGATTAAGCGCTACGATGAACATCAT
CAAGACTTGACTCTTTTAAAAGCTTTAGTTCGACAACAACTTCCAGAAAAGTATA
AAGAAATCTTTTTTGATCAATCAAAAAACGGATATGCAGGTTATATTGATGGGGG
AGCTAGCCAAGAAGAATTTTATAAATTTATCAAACCAATTTTAGAAAAAATGGAT
GGTACTGAGGAATTATTGGTGAAACTAAATCGTGAAGATTTGCTGCGCAAGCAA
CGGACCTTTGACAACGGCTCTATTCCCCATCAAATTCACTTGGGTGAGCTGCATG
CTATTTTGAGAAGACAAGAAGACTTTTATCCATTTTTAAAAGACAATCGTGAGAA
GATTGAAAAAATCTTGACTTTTCGAATTCCTTATTATGTTGGTCCATTGGCGCGTG
GCAATAGTCGTTTTGCATGGATGACTCGGAAGTCTGAAGAAACAATTACCCCATG
GAATTTTGAAGAAGTTGTCGATAAAGGTGCTTCAGCTCAATCATTTATTGAACGC
ATGACAAACTTTGATAAAAATCTTCCAAATGAAAAAGTACTACCAAAACATAGT
TTGCTTTATGAGTATTTTACGGTTTATAACGAATTGACAAAGGTCAAATATGTTA
CTGAGGGAATGCGAAAACCAGCATTTCTTTCAGGTGAACAGAAGAAAGCCATTG
TTGATTTACTCTTCAAAACAAATCGAAAAGTAACCGTTAAGCAATTAAAAGAAG
ATTATTTCAAAAAAATAGAATGTTTTGATAGTGTTGAAATTTCAGGAGTTGAAGA
```

```
-continued
TAGATTTAATGCTTCATTAGGCGCCTACCATGATTTGCTAAAAATTATTAAAGAT

AAAGATTTTTTGGATAATGAAGAAAATGAAGATATCTTAGAGGATATTGTTTTAA

CATTGACCTTATTTGAAGATAGGGGGATGATTGAGGAAAGACTTAAAACATATG

CTCACCTCTTTGATGATAAGGTGATGAAACAGCTTAAACGTCGCCGTTATACTGG

TTGGGGACGTTTGTCTCGAAAATTGATTAATGGTATTAGGGATAAGCAATCTGGC

AAAACAATATTAGATTTTTTGAAATCAGATGGTTTTGCCAATCGCAATTTTATGC

AGCTGATCCATGATGATAGTTTGACATTTAAAGAAGATATTCAAAAAGCACAGG

TGTCTGGACAAGGCCATAGTTTACATGAACAGATTGCTAACTTAGCTGGCAGTCC

TGCTATTAAAAAAGGTATTTTACAGACTGTAAAAATTGTTGATGAACTGGTCAAA

GTAATGGGGCATAAGCCAGAAAATATCGTTATTGAAATGGCACGTGAAAATCAG

ACAACTCAAAAGGGCCAGAAAAATTCGCGAGAGCGTATGAAACGAATCGAAGA

AGGTATCAAAGAATTAGGAAGTCAGATTCTTAAAGAGCATCCTGTTGAAAATAC

TCAATTGCAAAATGAAAAGCTCTATCTCTATTATCTACAAAATGGAAGAGACATG

TATGTGGACCAAGAATTAGATATTAATCGTTTAAGTGATTATGATGTCGATCACA

TTGTTCCACAAAGTTTCATTAAAGACGATTCAATAGACAATAAGGTACTAACGCG

TTCTGATAAAAATCGTGGTAAATCGGATAACGTTCCAAGTGAAGAAGTAGTCAA

AAAGATGAAAAACTATTGGAGACAACTTCTAAACGCCAAGTTAATCACTCAACG

TAAGTTTGATAATTTAACGAAAGCTGAACGTGGAGGTTTGAGTGAACTTGATAAA

GCTGGTTTTATCAAACGCCAATTGGTTGAAACTCGCCAAATCACTAAGCATGTGG

CACAAATTTTGGATAGTCGCATGAATACTAAATACGATGAAAATGATAAACTTAT

TCGAGAGGTTAAAGTGATTACCTTAAAAATCTAAATTAGTTTCTGACTTCCGAAAA

GATTTCCAATTCTATAAAGTACGTGAGATTAACAATTACCATCATGCCCATGATG

CGTATCTAAATGCCGTCGTTGGAACTGCTTTGATTAAGAAATATCCAAAACTTGA

ATCGGAGTTTGTCTATGGTGATTATAAAGTTTATGATGTTCGTAAAATGATTGCT

AAGTCTGAGCAAGAAATAGGCAAAGCAACCGCAAAATATTTCTTTTACTCTAATA

TCATGAACTTCTTCAAAACAGAAATTACACTTGCAAATGGAGAGATTCGCAAAC

GCCCTCTAATCGAAACTAATGGGAAACTGGAGAAATTGTCTGGGATAAAGGGC

GAGATTTTGCCACAGTGCGCAAAGTATTGTCCATGCCCCAAGTCAATATTGTCAA

GAAAACAGAAGTACAGACAGGCGGATTCTCCAAGGAGTCAATTTTACCAAAAAG

AAATTCGGACAAGCTTATTGCTCGTAAAAAAGACTGGGATCCAAAAAAATATGG

TGGTTTTGATAGTCCAACGGTAGCTTATTCAGTCCTAGTGGTTGCTAAGGTGGAA

AAAGGGAAATCGAAGAAGTTAAAATCCGTTAAAGAGTTACTAGGGATCACAATT

ATGGAAAGAAGTTCCTTTGAAAAAAAATCCGATTGACTTTTTAGAAGCTAAAGGAT

ATAAGGAAGTTAAAAAAGACTTAATCATTAAACTACCTAAATATAGTCTTTTTGA

GTTAGAAAACGGTCGTAAACGGATGCTGGCTAGTGCCGGAGAATTACAAAAAGG

AAATGAGCTGGCTCTGCCAAGCAAATATGTGAATTTTTTATATTTAGCTAGTCAT

TATGAAAAGTTGAAGGGTAGTCCAGAAGATAACGAACAAAAACAATTGTTTGTG

GAGCAGCATAAGCATTATTTAGATGAGATTATTGAGCAAATCAGTGAATTTTCTA

AGCGTGTTATTTTAGCAGATGCCAATTTAGATAAAGTTCTTAGTGCATATAACAA

ACATAGAGACAAACCAATACGTGAACAAGCAGAAAATATTATTCATTTATTTAC

GTTGACGAATCTTGGAGCTCCCGCTGCTTTTAAATATTTTGATACAACAATTGATC
```

-continued

```
GTAAACGATATACGTCTACAAAAGAAGTTTTAGATGCCACTCTTATCCATCAATC

CATCACTGGTCTTTATGAAACACGCATTGATTTGAGTCAGCTAGGAGGTGACTGA
```

(SEQ ID NO: 48)
MDKK<u>YSIGLDIGTNSVGWAVITDDYKVPSKKFKVLGNTDRHSIKKNLIGALLFGSGE
T</u>AEATRLKRTARRRYTRRKNRICYLQEIFSNEMAKVDDSFFHRLEESFLVEEDKKHE

RHPIFGNIVDEVAYHEKYPTIYHLRKKLADSTDKADLRLIYLALAHMIKFRGHFLIEG

DLNPDNSDVDKLFIQLVQIYNQLFEENPINASRVDAKAILSARLSKSRRLENLIAQLPG

EKRNGLFGNLIALSLGLTPNFKSNFDLAEDAKLQLSKDTYDDDLDNLLAQIGDQYAD

LFLAAKNLSDAILLSDILRVNSEITKAPLSASMIKRYDEHHQDLTLLKALVRQQLPEK

YKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFA

WMTRKSEETITPWNFEEVVDKGASAQSFIERMTNFDKNLPNEKVLPKHSLLYEYFTV

YNELTKVKYVTEGMRKPAFLSGEQKKAIVDLLFKTNRKVTVKQLKEDYFKKIECFD

SVEISGVEDRFNASLGAYHDLLKIIKDKDFLDNEENEDILEDIVLTLTLFEDRGMIEER

LKTYAHLFDDKVMKQLKRRRYTGWGRLSRKLINGIRDKQSGKTILDFLKSDGFANR

NFMQLIHDDSLTFKEDIQKAQVSGQG<u>HSLHEQIANLAGSPAIKKGILQTVKIVDELVK
VMGHKPENIVIEMAR</u>ENQTTQKGQKNSRERMKRIEEGIKELGSQILKEHPVENTQLQ

NEKLYLYYLQNGRDMYVDQELDINRLSDYDVDHIVPQSFIKDDSIDNKVLTRSDKNR

GKSDNVPSEEVVKKMKNYWRQLLNAKLITQRKFDNLTKAERGG<u>LSELDKAGFIKRQ
LVETRQITKHVAQILDSRMNTKYDENDKLIREVKVITLKSKLVSDFRKDFQFYKVREI

NNYHHAHDAYLNAVVGTALIKKYPKLESEFVYGDYKVYDVRKMIAKSEQEIGKAT

AKYFFYSNIMNFFKTEITLANGEIRKRPLIETNGETGEIVWDKGRDFATVRKVLSMPQ

VNIVKKTEVQ</u>TGGFSKESILPKRNSDKLIARKKDWDPKKYGGFDSPTVAYSVLVVAK

VEKGKSKKLKSVKELLGITIMERSSFEKNPIDFLEAKGYKEVKKDLIIKLPKYSLFELE

NGRKRMLASAGELQKGNELALPSKYVNFLYLASHYEKLKGSPEDNEQKQLFVEQHK

HYLDEIIEQISEFSKRVILADANLDKVLSAYNKHRDKPIREQAENIIHLFTLTNLGAPA

AFKYFDTTIDRKRYTSTKEVLDATLIHQSITGLYETRIDLSQLGGD (single underline: HNH domain; double underline: RuvC domain)

In some embodiments, wild type Cas9 corresponds to, or comprises SEQ ID NO:49 (nucleotide) and/or SEQ ID NO: 50 (amino acid):

(SEQ ID NO: 49)
```
ATGGATAAAAAGTATTCTATTGGTTTAGACATCGGCACTAATTCCGTTGGATGGG

CTGTCATAACCGATGAATACAAAGTACCTTCAAAGAAATTTAAGGTGTTGGGGA

ACACAGACCGTCATTCGATTAAAAAGAATCTTATCGGTGCCCTCCTATTCGATAG

TGGCGAAACGGCAGAGGCGACTCGCCTGAAACGAACCGCTCGGAGAAGGTATAC

ACGTCGCAAGAACCGAATATGTTACTTACAAGAAATTTTTAGCAATGAGATGGCC

AAAGTTGACGATTCTTTCTTTCACCGTTTGGAAGAGTCCTTCCTTGTCGAAGAGG

ACAAGAAACATGAACGGCACCCCATCTTTGGAAACATAGTAGATGAGGTGGCAT

ATCATGAAAGTACCCAACGATTTATCACCTCAGAAAAAAGCTAGTTGACTCAA

CTGATAAAGCGGACCTGAGGTTAATCTACTTGGCTCTTGCCCATATGATAAAGTT
```

-continued

```
CCGTGGGCACTTTCTCATTGAGGGTGATCTAAATCCGGACAACTCGGATGTCGAC
AAACTGTTCATCCAGTTAGTACAAACCTATAATCAGTTGTTTGAAGAGAACCCTA
TAAATGCAAGTGGCGTGGATGCGAAGGCTATTCTTAGCGCCCGCCTCTCTAAATC
CCGACGGCTAGAAAACCTGATCGCACAATTACCCGGAGAGAAGAAAAATGGGTT
GTTCGGTAACCTTATAGCGCTCTCACTAGGCCTGACACCAAATTTTAAGTCGAAC
TTCGACTTAGCTGAAGATGCCAAATTGCAGCTTAGTAAGGACACGTACGATGAC
GATCTCGACAATCTACTGGCACAAATTGGAGATCAGTATGCGGACTTATTTTTGG
CTGCCAAAAACCTTAGCGATGCAATCCTCCTATCTGACATACTGAGAGTTAATAC
TGAGATTACCAAGGCGCCGTTATCCGCTTCAATGATCAAAAGGTACGATGAACAT
CACCAAGACTTGACACTTCTCAAGGCCCTAGTCCGTCAGCAACTGCCTGAGAAAT
ATAAGGAAATATTCTTTGATCAGTCGAAAACGGGTACGCAGGTTATATTGACG
GCGGAGCGAGTCAAGAGGAATTCTACAAGTTTATCAAACCCATATTAGAGAAGA
TGGATGGGACGGAAGAGTTGCTTGTAAAACTCAATCGCGAAGATCTACTGCGAA
AGCAGCGGACTTTCGACAACGGTAGCATTCCACATCAAATCCACTTAGGCGAATT
GCATGCTATACTTAGAAGGCAGGAGGATTTTTATCCGTTCCTCAAAGACAATCGT
GAAAAGATTGAGAAAATCCTAACCTTTCGCATACCTTACTATGTGGGACCCCTGG
CCCGAGGGAACTCTCGGTTCGCATGGATGACAAGAAAGTCCGAAGAAACGATTA
CTCCATGGAATTTTGAGGAAGTTGTCGATAAAGGTGCGTCAGCTCAATCGTTCAT
CGAGAGGATGACCAACTTTGACAAGAATTTACCGAACGAAAAAGTATTGCCTAA
GCACAGTTTACTTTACGAGTATTTCACAGTGTACAATGAACTCACGAAAGTTAAG
TATGTCACTGAGGGCATGCGTAAACCCGCCTTTCTAAGCGGAGAACAGAAGAAA
GCAATAGTAGATCTGTTATTCAAGACCAACCGCAAAGTGACAGTTAAGCAATTG
AAAGAGGACTACTTTAAGAAAATTGAATGCTTCGATTCTGTCGAGATCTCCGGGG
TAGAAGATCGATTTAATGCGTCACTTGGTACGTATCATGACCTCCTAAAGATAAT
TAAAGATAAGGACTTCCTGGATAACGAAGAGAATGAAGATATCTTAGAAGATAT
AGTGTTGACTCTTACCCTCTTTGAAGATCGGGAAATGATTGAGGAAAGACTAAAA
ACATACGCTCACCTGTTCGACGATAAGGTTATGAAACAGTTAAAGAGGCGTCGCT
ATACGGGCTGGGGACGATTGTCGCGGAAACTTATCAACGGGATAAGAGACAAGC
AAAGTGGTAAAACTATTCTCGATTTTCTAAAGAGCGACGGCTTCGCCAATAGGAA
CTTTATGCAGCTGATCCATGATGACTCTTTAACCTTCAAAGAGGATATACAAAAG
GCACAGGTTTCCGGACAAGGGGACTCATTGCACGAACATATTGCGAATCTTGCTG
GTTCGCCAGCCATCAAAAAGGGCATACTCCAGACAGTCAAAGTAGTGGATGAGC
TAGTTAAGGTCATGGGACGTCACAAACCGGAAAACATTGTAATCGAGATGGCAC
GCGAAAATCAAACGACTCAGAAGGGGCAAAAAAACAGTCGAGAGCGGATGAAG
AGAATAGAAGAGGGTATTAAAGAACTGGGCAGCCAGATCTTAAAGGAGCATCCT
GTGGAAAATACCCAATTGCAGAACGAGAAACTTTACCTCTATTACCTACAAAATG
GAAGGGACATGTATGTTGATCAGGAACTGGACATAAACCGTTTATCTGATTACGA
CGTCGATCACATTGTACCCCAATCCTTTTTGAAGGACGATTCAATCGACAATAAA
GTGCTTACACGCTCGGATAAGAACCGAGGGAAAAGTGACAATGTTCCAAGCGAG
GAAGTCGTAAAGAAAATGAAGAACTATTGGCGGCAGCTCCTAAATGCGAAACTG
```

```
ATAACGCAAAGAAAGTTCGATAACTTAACTAAAGCTGAGAGGGGTGGCTTGTCT

GAACTTGACAAGGCCGGATTTATTAAACGTCAGCTCGTGGAAACCCGCCAAATC

ACAAAGCATGTTGCACAGATACTAGATTCCCGAATGAATACGAAATACGACGAG

AACGATAAGCTGATTCGGGAAGTCAAAGTAATCACTTTAAAGTCAAAATTGGTG

TCGGACTTCAGAAAGGATTTTCAATTCTATAAAGTTAGGGAGATAAATAACTACC

ACCATGCGCACGACGCTTATCTTAATGCCGTCGTAGGGACCGCACTCATTAAGAA

ATACCCGAAGCTAGAAAGTGAGTTTGTGTATGGTGATTACAAAGTTTATGACGTC

CGTAAGATGATCGCGAAAAGCGAACAGGAGATAGGCAAGGCTACAGCCAAATA

CTTCTTTTATTCTAACATTATGAATTTCTTTAAGACGGAAATCACTCTGGCAAACG

GAGAGATACGCAAACGACCTTTAATTGAAACCAATGGGGAGACAGGTGAAATCG

TATGGGATAAGGGCCGGGACTTCGCGACGGTGAGAAAAGTTTTGTCCATGCCCC

AAGTCAACATAGTAAAGAAAACTGAGGTGCAGACCGGAGGGTTTTCAAAGGAAT

CGATTCTTCCAAAAAGGAATAGTGATAAGCTCATCGCTCGTAAAAAGGACTGGG

ACCCGAAAAAGTACGGTGGCTTCGATAGCCCTACAGTTGCCTATTCTGTCCTAGT

AGTGGCAAAAGTTGAGAAGGGAAAATCCAAGAAACTGAAGTCAGTCAAAGAAT

TATTGGGGATAACGATTATGGAGCGCTCGTCTTTTGAAAAGAACCCCATCGACTT

CCTTGAGGCGAAAGGTTACAAGGAAGTAAAAAAGGATCTCATAATTAAACTACC

AAAGTATAGTCTGTTTGAGTTAGAAAATGGCCGAAAACGGATGTTGGCTAGCGC

CGGAGAGCTTCAAAAGGGGAACGAACTCGCACTACCGTCTAAATACGTGAATTT

CCTGTATTTAGCGTCCCATTACGAGAAGTTGAAAGGTTCACCTGAAGATAACGAA

CAGAAGCAACTTTTTGTTGAGCAGCACAAACATTATCTCGACGAAATCATAGAGC

AAATTTCGGAATTCAGTAAGAGAGTCATCCTAGCTGATGCCAATCTGGACAAAGT

ATTAAGCGCATACAACAAGCACAGGGATAAACCCATACGTGAGCAGGCGGAAA

ATATTATCCATTTGTTTACTCTTACCAACCTCGGCGCTCCAGCCGCATTCAAGTAT

TTTGACACAACGATAGATCGCAAACGATACACTTCTACCAAGGAGGTGCTAGAC

GCGACACTGATTCACCAATCCATCACGGGATTATATGAAACTCGGATAGATTTGT

CACAGCTTGGGGGTGACGGATCCCCCAAGAAGAAGAGGAAAGTCTCGAGCGACT

ACAAAGACCATGACGGTGATTATAAAGATCATGACATCGATTACAAGGATGACG

ATGACAAGGCTGCAGGA
```

(SEQ ID NO: 50)
MDKK<u>YSIGLAIGTNSVGWAVITDEYKVPSKKFKVLGNTDRHSIKKNLIGALLFDSGE</u>
<u>T</u>AEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEG

DLNPDNSDVDKLFIQLVQTYNQLFEENPINASGVDAKAILSARLSKSRRLENLIAQLP

GEKKNGLFGNLIALSLGLTPNFKSNFDLAEDAKLQLSKDTYDDDLDNLLAQIGDQYA

DLFLAAKNLSDAILLSDILRVNTEITKAPLSASMIKRYDEHHQDLTLLKALVRQQLPE

KYKEIFFDQSKNGYAGYIDGGASQEEFYKFIKPILEKMDGTEELLVKLNREDLLRKQR

TFDNGSIPHQIHLGELHAILRRQEDFYPFLKDNREKIEKILTFRIPYYVGPLARGNSRFA

WMTRKSEETITPWNFEEVVDKGASAQSFIERMTNFDKNLPNEKVLPKHSLLYEYFTV

YNELTKVKYVTEGMRKPAFLSGEQKKAIVDLLFKTNRKVTVKQLKEDYFKKIECFD

SVEISGVEDRFNASLGTYHDLLKIIKDKDFLDNEENEDILEDIVLTLTLFEDREMIEERL

-continued
```
KTYAHLFDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVK

VMGRHKPENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKVLTRSDK

NRGKSDNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGA

PAAFKYFDTTIDRKRYTSTKEVLDATLIHQSITGLYETRIDLSQLGGD (single underline: HNH domain; double underline: RuvC domain)
```

In some embodiments, wild type Cas9 corresponds to Cas9 from *Streptococcus pyogenes* (NCBI Reference Sequence: NC_002737.2, SEQ ID NO: 51 (nucleotide); and Uniport Reference Sequence: Q99ZW2, SEQ ID NO: 52 (amino acid).

```
                                              (SEQ ID NO: 51)
ATGGATAAGAAATACTCAATAGGCTTAGATATCGGCACAAATAGCGTCGGATGG

GCGGTGATCACTGATGAATATAAGGTTCCGTCTAAAAAGTTCAAGGTTCTGGGAA

ATACAGACCGCCACAGTATCAAAAAAAATCTTATAGGGGCTCTTTTATTTGACAG

TGGAGAGACAGCGGAAGCGACTCGTCTCAAACGGACAGCTCGTAGAAGGTATAC

ACGTCGGAAGAATCGTATTTGTTATCTACAGGAGATTTTTTCAAATGAGATGGCG

AAAGTAGATGATAGTTTCTTTCATCGACTTGAAGAGTCTTTTTTGGTGGAAGAAG

ACAAGAAGCATGAACGTCATCCTATTTTTGGAAATATAGTAGATGAAGTTGCTTA

TCATGAGAAATATCCAACTATCTATCATCTGCGAAAAAAATTGGTAGATTCTACT

GATAAAGCGGATTTGCGCTTAATCTATTTGGCCTTAGCGCATATGATTAAGTTTC

GTGGTCATTTTTTGATTGAGGGAGATTTAAATCCTGATAATAGTGATGTGGACAA

ACTATTTATCCAGTTGGTACAAACCTACAATCAATTATTTGAAGAAAACCCTATT

AACGCAAGTGGAGTAGATGCTAAAGCGATTCTTTCTGCACGATTGAGTAAATCA

AGACGATTAGAAAATCTCATTGCTCAGCTCCCCGGTGAGAAGAAAAATGGCTTA

TTTGGGAATCTCATTGCTTTGTCATTGGGTTTGACCCCTAATTTTAAATCAAATTT

TGATTTGGCAGAAGATGCTAAATTACAGCTTTCAAAAGATACTTACGATGATGAT

TTAGATAATTTATTGGCGCAAATTGGAGATCAATATGCTGATTTGTTTTTGGCAG

CTAAGAATTTATCAGATGCTATTTTACTTTCAGATATCCTAAGAGTAAATACTGA

AATAACTAAGGCTCCCCTATCAGCTTCAATGATTAAACGCTACGATGAACATCAT

CAAGACTTGACTCTTTTAAAAGCTTTAGTTCGACAACAACTTCCAGAAAAGTATA

AAGAAATCTTTTTTGATCAATCAAAAAACGGATATGCAGGTTATATTGATGGGGG

AGCTAGCCAAGAAGAATTTATAAATTTATCAAACCAATTTTAGAAAAAATGGAT

GGTACTGAGGAATTATTGGTGAAACTAAATCGTGAAGATTTGCTGCGCAAGCAA
```

-continued

```
CGGACCTTTGACAACGGCTCTATTCCCCATCAAATTCACTTGGGTGAGCTGCATG

CTATTTTGAGAAGACAAGAAGACTTTTATCCATTTTTAAAAGACAATCGTGAGAA

GATTGAAAAAATCTTGACTTTTCGAATTCCTTATTATGTTGGTCCATTGGCGCGTG

GCAATAGTCGTTTTGCATGGATGACTCGGAAGTCTGAAGAAACAATTACCCCATG

GAATTTTGAAGAAGTTGTCGATAAAGGTGCTTCAGCTCAATCATTTATTGAACGC

ATGACAAACTTTGATAAAAATCTTCCAAATGAAAAGTACTACCAAAACATAGT

TTGCTTTATGAGTATTTTACGGTTTATAACGAATTGACAAAGGTCAAATATGTTA

CTGAAGGAATGCGAAAACCAGCATTTCTTTCAGGTGAACAGAAGAAAGCCATTG

TTGATTTACTCTTCAAAACAAATCGAAAAGTAACCGTTAAGCAATTAAAAGAAG

ATTATTTCAAAAAAATAGAATGTTTTGATAGTGTTGAAATTTCAGGAGTTGAAGA

TAGATTTAATGCTTCATTAGGTACCTACCATGATTTGCTAAAAATTATTAAAGAT

AAAGATTTTTTGGATAATGAAGAAAATGAAGATATCTTAGAGGATATTGTTTTAA

CATTGACCTTATTTGAAGATAGGGAGATGATTGAGGAAAGACTTAAAACATATG

CTCACCTCTTTGATGATAAGGTGATGAAACAGCTTAAACGTCGCCGTTATACTGG

TTGGGGACGTTTGTCTCGAAAATTGATTAATGGTATTAGGGATAAGCAATCTGGC

AAAACAATATTAGATTTTTTGAAATCAGATGGTTTTGCCAATCGCAATTTTATGC

AGCTGATCCATGATGATAGTTTGACATTTAAAGAAGACATTCAAAAAGCACAAG

TGTCTGGACAAGGCGATAGTTTACATGAACATATTGCAAATTTAGCTGGTAGCCC

TGCTATTAAAAAAGGTATTTTACAGACTGTAAAAGTTGTTGATGAATTGGTCAAA

GTAATGGGGCGGCATAAGCCAGAAAAATATCGTTATTGAAATGGCACGTGAAAAT

CAGACAACTCAAAAGGGCCAGAAAAATTCGCGAGAGCGTATGAAACGAATCGA

AGAAGGTATCAAAGAATTAGGAAGTCAGATTCTTAAAGAGCATCCTGTTGAAAA

TACTCAATTGCAAAATGAAAAGCTCTATCTCTATTATCTCCAAAATGGAAGAGAC

ATGTATGTGGACCAAGAATTAGATATTAATCGTTTAAGTGATTATGATGTCGATC

ACATTGTTCCACAAAGTTTCCTTAAAGACGATTCAATAGACAATAAGGTCTTAAC

GCGTTCTGATAAAAATCGTGGTAAATCGGATAACGTTCCAAGTGAAGAAGTAGT

CAAAAAGATGAAAAACTATTGGAGACAACTTCTAAACGCCAAGTTAATCACTCA

ACGTAAGTTTGATAATTTAACGAAAGCTGAACGTGGAGGTTTGAGTGAACTTGAT

AAAGCTGGTTTTATCAAACGCCAATTGGTTGAAACTCGCCAAATCACTAAGCATG

TGGCACAAATTTTGGATAGTCGCATGAATACTAAATACGATGAAAATGATAAAC

TTATTCGAGAGGTTAAAGTGATTACCTTAAAATCTAAATTAGTTTCTGACTTCCG

AAAAGATTTCCAATTCTATAAAGTACGTGAGATTAACAATTACCATCATGCCCAT

GATGCGTATCTAAATGCCGTCGTTGGAACTGCTTTGATTAAGAAATATCCAAAAC

TTGAATCGGAGTTTGTCTATGGTGATTATAAAGTTTATGATGTTCGTAAAATGATT

GCTAAGTCTGAGCAAGAAATAGGCAAAGCAACCGCAAAATATTTCTTTTACTCTA

ATATCATGAACTTCTTCAAAACAGAAATTACACTTGCAAATGGAGAGATTCGCAA

ACGCCCTCTAATCGAAACTAATGGGGAAACTGGAGAAATTGTCTGGGATAAAGG

GCGAGATTTTGCCACAGTGCGCAAAGTATTGTCCATGCCCCAAGTCAATATTGTC

AAGAAAACAGAAGTACAGACAGGCGGATTCTCCAAGGAGTCAATTTTACCAAAA

AGAAATTCGGACAAGCTTATTGCTCGTAAAAAAGACTGGGATCCAAAAAAATAT
```

```
GGTGGTTTTGATAGTCCAACGGTAGCTTATTCAGTCCTAGTGGTTGCTAAGGTGG

AAAAAGGGAAATCGAAGAAGTTAAAATCCGTTAAAGAGTTACTAGGGATCACAA

TTATGGAAAGAAGTTCCTTTGAAAAAAATCCGATTGACTTTTTAGAAGCTAAAGG

ATATAAGGAAGTTAAAAAAGACTTAATCATTAAACTACCTAAATATAGTCTTTTT

GAGTTAGAAAACGGTCGTAAACGGATGCTGGCTAGTGCCGGAGAATTACAAAAA

GGAAATGAGCTGGCTCTGCCAAGCAAATATGTGAATTTTTTATATTTAGCTAGTC

ATTATGAAAAGTTGAAGGGTAGTCCAGAAGATAACGAACAAAAACAATTGTTTG

TGGAGCAGCATAAGCATTATTTAGATGAGATTATTGAGCAAATCAGTGAATTTTC

TAAGCGTGTTATTTTAGCAGATGCCAATTTAGATAAAGTTCTTAGTGCATATAAC

AAACATAGAGACAAACCAATACGTGAACAAGCAGAAAATATTATTCATTTATTT

ACGTTGACGAATCTTGGAGCTCCCGCTGCTTTTAAATATTTTGATACAACAATTG

ATCGTAAACGATATACGTCTACAAAAGAAGTTTTAGATGCCACTCTTATCCATCA

ATCCATCACTGGTCTTTATGAAACACGCATTGATTTGAGTCAGCTAGGAGGTGAC

TGA
```

(SEQ ID NO: 52)
MDKK<u>YSIGLDIGTNSVGWAVITDEYKVPSKKFKVLGNTDRHSIKKNLIGALLFDSGE
T</u>AEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLP
GEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPE
KYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFA
WMTRKSEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRN
FMQLIHDDSLTFKEDIQKAQVSGQG<u>DSLHEHIANLAGSPAIKKGILQTVKVVDELVK</u>
<u>VMGRHKPENIVIEMA</u>RENQTTQKGQKNSRERMKRIEEGIKELGSQILKEHPVENTQL
QNEKLYLYYLQNGRDMYVDQELDINRLSDYDVDHIVPQSFLKDDSIDNKVLTRSDK
NRGKSDNVPSEEVVKKMKNYWRQLLNAKLITQRKFDNLTKAERG<u>GLSELDKAGFIK</u>
<u>RQLVETRQITKHVAQILDSRMNTKYDENDKLIREVKVITLKSKLVSDFRKDFQFYKV</u>
<u>REINNYHHAHDAYLNAVVGTALIKKYPKLESEFVYGDYKVYDVRKMIAKSEQEIGK</u>
<u>ATAKYFFYSNIMNFFKTEITLANGEIRKRPLIETNGETGEIVWDKGRDFATVRKVLSM</u>
<u>PQVNIVKKTEVQT</u>GGFSKESILPKRNSDKLIARKKDWDPKKYGGFDSPTVAYSVLVV
AKVEKGKSKKLKSVKELLGITIMERSSFEKNPIDFLEAKGYKEVKKDLIIKLPKYSLFE
LENGRKRMLASAGELQKGNELALPSKYVNFLYLASHYEKLKGSPEDNEQKQLFVEQ
HKHYLDEIIEQISEFSKRVILADANLDKVLSAYNKHRDKPIREQAENIIHLFTLTNLGA
PAAFKYFDTTIDRKRYTSTKEVLDATLIHQSITGLYETRIDLSQLGGD (single underline: HNH domain; double underline: RuvC domain)

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola*

(NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisl* (NCBI Ref: NC_018721.1); *Streptococcus thermophilus* (NCBI Ref: YP_820832.1), *Listeria innocua* (NCBI Ref: NP_472073.1), *Campylobacter jejuni* (NCBI Ref: YP_002344900.1) or *Neisseria. meningitidis* (NCBI Ref: YP_002342100.1) or to a Cas9 from any other organism.

In some embodiments, dCas9 corresponds to, or comprises in part or in whole, a Cas9 amino acid sequence having one or more mutations that inactivate the Cas9 nuclease activity. For example, in some embodiments, a dCas9 domain comprises D10A and an H840A mutation of SEQ ID NO: 52 or corresponding mutations in another Cas9. In some embodiments, the dCas9 comprises the amino acid sequence of SEQ ID NO: 53 dCas9 (D10A and H840A):

```
                                          (SEQ ID NO: 53)
MDKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRLE

ESFLVEEDKKHERHPIFGNIVDEVAYHEKYPTIYHLRKKLVDSTDKADLRL

IYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSN

FDLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSKN

GYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGN

SRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTV

KQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLS

RKLINGIRDKQSGKTILDFLKSDGFANRNFMQLIHDDSLTFKEDIQKAQVS

GQGDSLHEHIANLAGSPAIKKGILQTVKVVDELVKVMGRHKPENIVIEMAR

ENQTTQKGQKNSRERMKRIEEGIKELGSQILKEHPVENTQLQNEKLYLYYL

QNGRDMYVDQELDINRLSDYDVDAIVPQSFLKDDSIDNKVLTRSDKNRGKS

DNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKD

FQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGE

IVWDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMERSS

FEKNPIDFLEAKGYKEVKKDLIIKLPKYSLFELENGRKRMLASAGELQKGN

ELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKY

FDTTIDRKRYTSTKEVLDATLIHQSITGLYETRIDLSQLGGD
(single underline: HNH domain; double underline:
RuvC domain).
```

Figure 94:
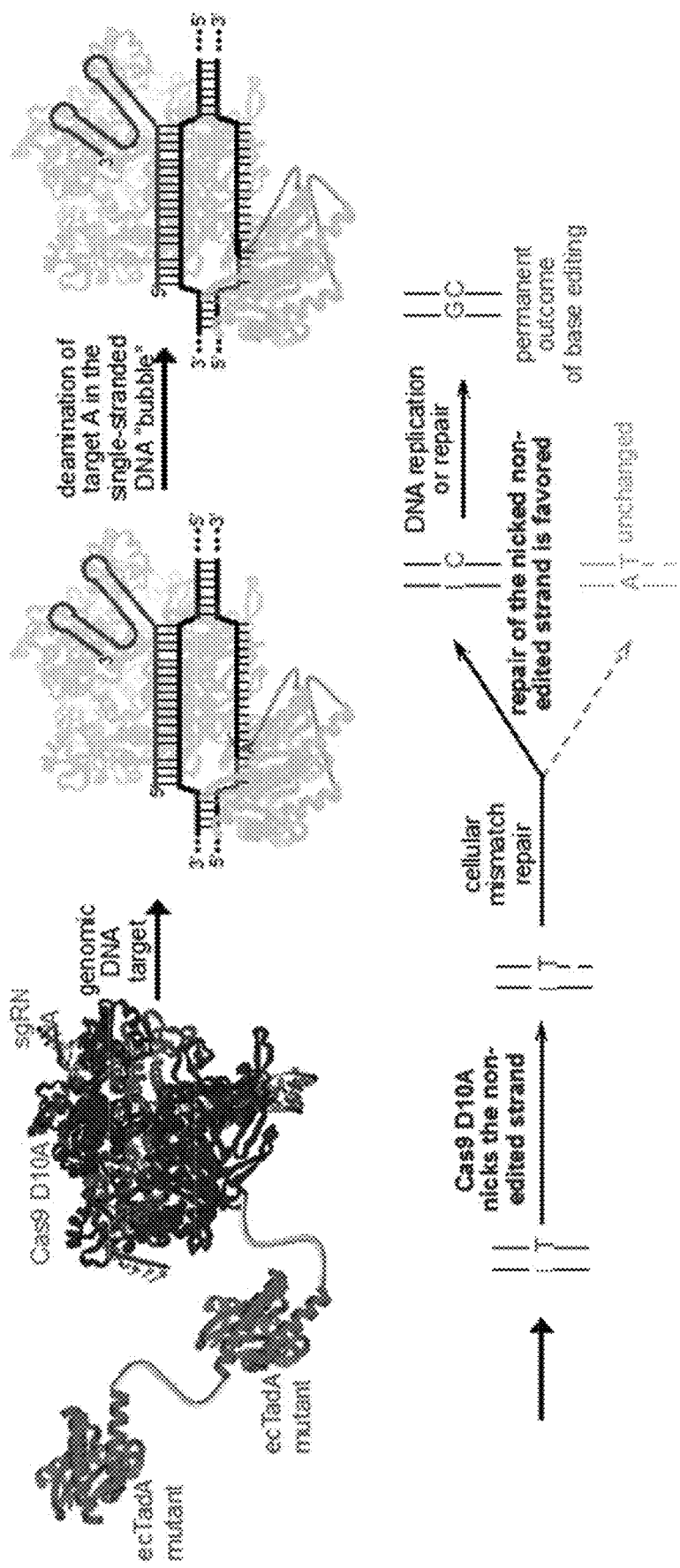
FIG. 94 shows a schematic representation of an exemplary adenosine base editing process.
Figure 95:
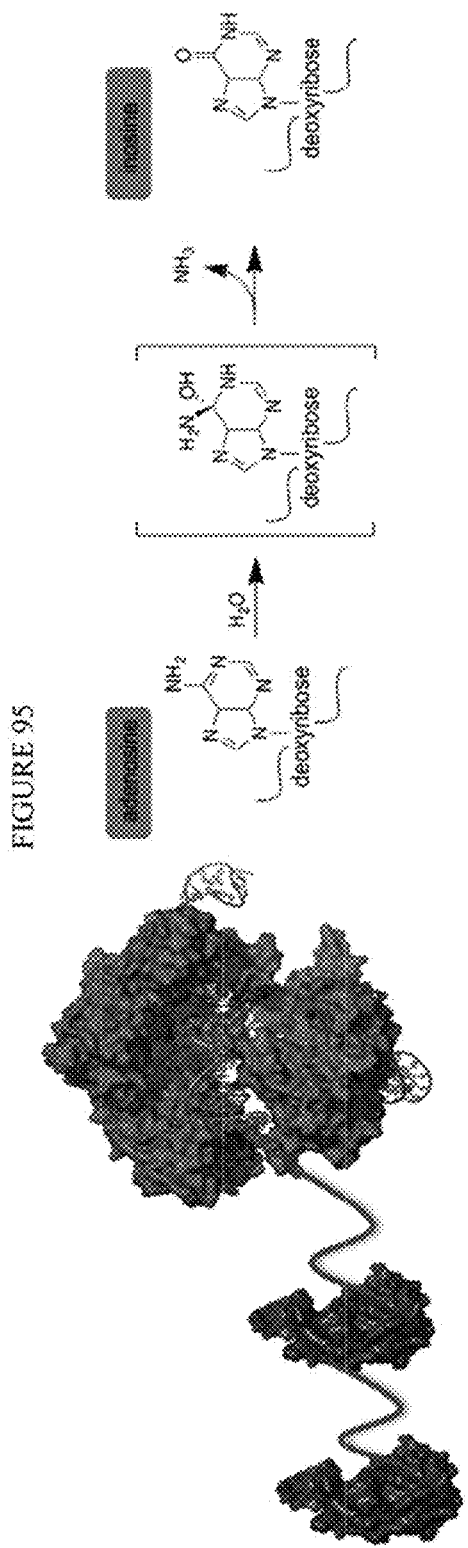
FIG. 95 shows a schematic representation of an exemplary adenosine base editor, which deaminates adenosine to inosine.

In some embodiments, the Cas9 domain comprises a D10A mutation, while the residue at position 840 remains a histidine in the amino acid sequence provided in SEQ ID NO: 52, or at corresponding positions in any of the amino acid sequences provided in SEQ ID NOs: 108-357. Without wishing to be bound by any particular theory, the presence of the catalytic residue H840 maintains the activity of the Cas9 to cleave the non-edited (e.g., non-deaminated) strand containing a T opposite the targeted A. Restoration of H840 (e.g., from A840 of a dCas9) does not result in the cleavage of the target strand containing the A. Such Cas9 variants are able to generate a single-strand DNA break (nick) at a specific location based on the gRNA-defined target sequence, leading to repair of the non-edited strand, ultimately resulting in a T to C change on the non-edited strand. A schematic representation of this process is shown in FIG. 94. Briefly, and without wishing to be bound by any particular theory, the A of a A-T base pair can be deaminated to a inosine (I) by an adenosine deaminase, e.g., an engineered adenosine deaminase that deaminates an adenosine in DNA. Nicking the non-edited strand, having the T, facilitates removal of the T via mismatch repair mechanisms. A UGI domain or a catalytically inactive inosine-specific nuclease (dISN) may inhibit inosine-specific nucleases (e.g., sterically) thereby preventing removal of the inosine (I).

In other embodiments, dCas9 variants having mutations other than D10A and H840A are provided, which, e.g., result in nuclease inactivated Cas9 (dCas9). Such mutations, by way of example, include other amino acid substitutions at D10 and H840, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO: 53) are provided which are at least about 70% identical, at least about 80% identical, at least about 90% identical, at least about 95% identical, at least about 98% identical, at least about 99% identical, at least about 99.5% identical, or at least about 99.9% identical to SEQ ID NO: 10. In some embodiments, variants of dCas9 (e.g., variants of SEQ ID NO: 53) are provided having amino acid sequences which are shorter, or longer than SEQ ID NO: 53, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

In some embodiments, Cas9 fusion proteins as provided herein comprise the full-length amino acid sequence of a Cas9 protein, e.g., one of the Cas9 sequences provided herein. In other embodiments, however, fusion proteins as provided herein do not comprise a full-length Cas9 sequence, but only a fragment thereof. For example, in some embodiments, a Cas9 fusion protein provided herein comprises a Cas9 fragment, wherein the fragment binds crRNA and tracrRNA or sgRNA, but does not comprise a functional nuclease domain, e.g., in that it comprises only a truncated version of a nuclease domain or no nuclease domain at all.

Exemplary amino acid sequences of suitable Cas9 domains and Cas9 fragments are provided herein, and additional suitable sequences of Cas9 domains and fragments will be apparent to those of skill in the art.

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref:

NC_018010.1); *Psychroflexus torquisl* (NCBI Ref: NC_018721.1); *Streptococcus thermophilus* (NCBI Ref: YP_820832.1); *Listeria innocua* (NCBI Ref: NP_472073.1); *Campylobacter jejuni* (NCBI Ref: YP_002344900.1); or *Neisseria. meningitidis* (NCBI Ref: YP_002342100.1).

It should be appreciated that additional Cas9 proteins (e.g., a nuclease dead Cas9 (dCas9), a Cas9 nickase (nCas9), or a nuclease active Cas9), including variants and homologs thereof, are within the scope of this disclosure. Exemplary Cas9 proteins include, without limitation, those provided below. In some embodiments, the Cas9 protein is a nuclease dead Cas9 (dCas9). In some embodiments, the dCas9 comprises the amino acid sequence (SEQ ID NO: 34). In some embodiments, the Cas9 protein is a Cas9 nickase (nCas9). In some embodiments, the nCas9 comprises the amino acid sequence (SEQ ID NO: 35). In some embodiments, the Cas9 protein is a nuclease active Cas9. In some embodiments, the nuclease active Cas9 comprises the amino acid sequence (SEQ ID NO: 36).

```
Exemplary catalytically inactive Cas9 (dCas9):
                                    (SEQ ID NO: 34)
DKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEE

SFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASG

VDAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDILR

VNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGS

IPHQIHLGELHAILRRQEDFYPFLKDNREKIEKILTFRIPYYVGPLARGNS

RFAWMTRKSEETITPWNFEEVVDKGASAQSFIERMTNFDKNLPNEKVLPKH

SLLYEYFTVYNELTKVKYVTEGMRKPAFLSGEQKKAIVDLLFKTNRKVTVK

QLKEDYFKKIECFDSVETSGVEDRFNASLGTYHDLLKIIKDKDFLDNEENE

DILEDIVLTLTLFEDREMIEERLKTYAHLFDDKVMKQLKRRRYTGWGRLSR

KLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARE

NQTTQKGQKNSRERMKRIEEGIKELGSQILKEHPVENTQLQNEKLYLYYLQ

NGRDMYVDQELDINRLSDYDVDAIVPQSFLKDDSIDNKVLTRSDKNRGKSD

NVPSEEVVKKMKNYWRQLLNAKLITQRKFDNLTKAERGGLSELDKAGFIKR

QLVETRQITKHVAQILDSRMNTKYDENDKLIREVKVITLKSKLVSDFRKDF

QFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARK

KDWDPKKYGGFDSPTVAYSVLVVAKVEKGKSKKLKSVKELLGITIMERSSF

EKNPIDFLEAKGYKEVKKDLIIKLPKYSLFELENGRKRMLASAGELQKGNE

LALPSKYVNFLYLASHYEKLKGSPEDNEQKQLFVEQHKYLDEIIEQISEF

SKRVILADANLDKVLSAYNKHRDKPIREQAENIIHLFTLTNLGAPAAFKYF

DTTIDRKRYTSTKEVLDATLIHQSITGLYETRIDLSQLGGD

Exemplary Cas9 nickase (nCas9):
                                    (SEQ ID NO: 35)
DKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEE

SFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASG

VDAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDILR

VNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGS

IPHQIHLGELHAILRRQEDFYPFLKDNREKIEKILTFRIPYYVGPLARGNS

RFAWMTRKSEETITPWNFEEVVDKGASAQSFIERMTNFDKNLPNEKVLPKH

SLLYEYFTVYNELTKVKYVTEGMRKPAFLSGEQKKAIVDLLFKTNRKVTVK

QLKEDYFKKIECFDSVETSGVEDRFNASLGTYHDLLKIIKDKDFLDNEENE

DILEDIVLTLTLFEDREMIEERLKTYAHLFDDKVMKQLKRRRYTGWGRLSR

KLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARE

NQTTQKGQKNSRERMKRIEEGIKELGSQILKEHPVENTQLQNEKLYLYYLQ

NGRDMYVDQELDINRLSDYDVDHIVPQSFLKDDSIDNKVLTRSDKNRGKSD

NVPSEEVVKKMKNYWRQLLNAKLITQRKFDNLTKAERGGLSELDKAGFIKR

QLVETRQITKHVAQILDSRMNTKYDENDKLIREVKVITLKSKLVSDFRKDF

QFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARK

KDWDPKKYGGFDSPTVAYSVLVVAKVEKGKSKKLKSVKELLGITIMERSSF

EKNPIDFLEAKGYKEVKKDLIIKLPKYSLFELENGRKRMLASAGELQKGNE

LALPSKYVNFLYLASHYEKLKGSPEDNEQKQLFVEQHKYLDEIIEQISEF

SKRVILADANLDKVLSAYNKHRDKPIREQAENIIHLFTLTNLGAPAAFKYF

DTTIDRKRYTSTKEVLDATLIHQSITGLYETRIDLSQLGGD

Exemplary catalytically active Cas9:
                                    (SEQ ID NO: 36)
DKKYSIGLDIGTNSVGWAVITDEYKVPSKKFKVLGNTDRHSIKKNLIGALL

FDSGETAEATRLKRTARRRYTRRKNRICYLQEIFSNEMAKVDDSFFHRLEE

SFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASG

VDAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDILR

VNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGS

IPHQIHLGELHAILRRQEDFYPFLKDNREKIEKILTFRIPYYVGPLARGNS

RFAWMTRKSEETITPWNFEEVVDKGASAQSFIERMTNFDKNLPNEKVLPKH

SLLYEYFTVYNELTKVKYVTEGMRKPAFLSGEQKKAIVDLLFKTNRKVTVK
```

```
-continued
QLKEDYFKKIECFDSVETSGVEDRFNASLGTYHDLLKIIKDKDFLDNEENE

DILEDIVLTLTLFEDREMIEERLKTYAHLFDDKVMKQLKRRRYTGWGRLSR

KLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARE

NQTTQKGQKNSRERMKRIEEGIKELGSQILKEHPVENTQLQNEKLYLYYLQ

NGRDMYVDQELDINRLSDYDVDHIVPQSFLKDDSIDNKVLTRSDKNRGKSD

NVPSEEVVKKMKNYWRQLLNAKLITQRKFDNLTKAERGGLSELDKAGFIKR

QLVETRQITKHVAQILDSRMNTKYDENDKLIREVKVITLKSKLVSDFRKDF

QFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARK

KDWDPKKYGGFDSPTVAYSVLVVAKVEKGKSKKLKSVKELLGITIMERSSF

EKNPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYF

DTTIDRKRYTSTKEVLDATLIHQSITGLYETRIDLSQLGGD.
```

In some embodiments, Cas9 refers to a Cas9 from arehaea (e.g. nanoarchaea), which constitute a domain and kingdom of single-celled prokaryotic microbes. In some embodiments, Cas9 refers to CasX or CasY, which have been described in, for example, Burstein et al., "New CRISPR-Cas systems from uncultivated microbes." *Cell Res.* 2017 Feb. 21. doi: 10.1038/cr.2017.21, the entire contents of which is hereby incorporated by reference. Using genome-resolved metagenomics, a number of CRISPR-Cas systems were identified, including the first reported Cas9 in the archaeal domain of life. This divergent Cas9 protein was found in little-studied nanoarchaea as part of an active CRISPR-Cas system. In bacteria, two previously unknown systems were discovered, CRISPR-CasX and CRISPR-CasY, which are among the most compact systems yet discovered. In some embodiments, Cas9 refers to CasX, or a variant of CasX. In some embodiments, Cas9 refers to a CasY, or a variant of CasY. It should be appreciated that other RNA-guided DNA binding proteins may be used as a nucleic acid programmable DNA binding protein (napDNAbp) and are within the scope of this disclosure.

In some embodiments, the nucleic acid programmable DNA binding protein (napDNAbp) of any of the fusion proteins provided herein may be a CasX or CasY protein. In some embodiments, the napDNAbp is a CasX protein. In some embodiments, the napDNAbp is a CasY protein. In some embodiments, the napDNAbp comprises an amino acid sequence that is at least 85%, at least 90%, at least 91%, at least 92%, at least 93%, at least 94%, at least 95%, at least 96%, at least 97%, at least 98%, at least 99%, or at ease 99.5% identical to a naturally-occurring CasX or CasY protein. In some embodiments, the napDNAbp is a naturally-occurring CasX or CasY protein. In some embodiments, the napDNAbp comprises an amino acid sequence that is at least 85%, at least 90%, at least 91%, at least 92%, at least 93%, at least 94%, at least 95%, at least 96%, at least 97%, at least 98%, at least 99%, or at ease 99.5% identical to any one of SEQ ID NOs: 417-419. In some embodiments, the napDNAbp comprises an amino acid sequence of any one SEQ ID NOs: 417-419. It should be appreciated that CasX and CasY from other bacterial species may also be used in accordance with the present disclosure.

```
CasX (uniprot.org/uniprot/F0NN87; uniprot.org/
uniprot/F0NH53)
>tr|F0NN87|F0NN87_SULIH CRISPR-associated Casx
protein OS = Sulfolobus islandicus (strain HVE10/4)
GN = SiH_0402 PE = 4 SV = 1
                                     (SEQ ID NO: 417)
MEVPLYNIFGDNYIIQVATEAENSTIYNNKVEIDDEELRNVLNLAYKIAKN

NEDAAAERRGKAKKKKGEEGETTTSNIILPLSGNDKNPWTETLKCYNFPTT

VALSEVFKNFSQVKECEEVSAPSFVKPEFYEFGRSPGMVERTRRVKLEVEP

HYLIIAAAGWVLTRLGKAKVSEGDYVGVNVFTPTRGILYSLIQNVNGIVPG

IKPETAFGLWIARKVVSSVTNPNVSVVRIYTISDAVGQNPTTINGGFSIDL

TKLLEKRYLLSERLEAIARNALSISSNMRERYIVLANYIYEYLTGSKRLED

LLYFANRDLIMNLNSDDGKVRDLKLISAYVNGELIRGEG

>tr|F0NH53|F0NH53_SULIR CRISPR associated protein,
Casx OS = Sulfolobus islandicus (strain REY15A)
GN = SiRe_0771 PE = 4 SV = 1
                                     (SEQ ID NO: 418)
MEVPLYNIFGDNYIIQVATEAENSTIYNNKVEIDDEELRNVLNLAYKIAKN

NEDAAAERRGKAKKKKGEEGETTTSNIILPLSGNDKNPWTETLKCYNFPTT

VALSEVFKNFSQVKECEEVSAPSFVKPEFYKFGRSPGMVERTRRVKLEVEP

HYLIMAAAGWVLTRLGKAKVSEGDYVGVNVFTPTRGILYSLIQNVNGIVPG

IKPETAFGLWIARKVVSSVTNPNVSVVSIYTISDAVGQNPTTINGGFSIDL

TKLLEKRDLLSERLEAIARNALSISSNMRERYIVLANYIYEYLTGSKRLED

LLYFANRDLIMNLNSDDGKVRDLKLISAYVNGELIRGEG

CasY (ncbi.nlm.nih.gov/protein/APG80656.1)
>APG80656.1 CRISPR-associated protein CasY
[uncultured Parcubacteria group bacterium]
                                     (SEQ ID NO: 419)
MSKRHPRISGVKGYRLHAQRLEYTGKSGAMRTIKYPLYSSPSGGRTVPREI

VSAINDDYVGLYGLSNFDDLYNAEKRNEEKVYSVLDFWYDCVQYGAVFSYT

APGLLKNVAEVRGGSYELTKTLKGSHLYDELQIDKVIKFLNKKEISRANGS

LDKLKKDIIDCFKAEYRERHKDQCNKLADDIKNAKKDAGASLGERQKKLFR

DFFGISEQSENDKPSFTNPLNLTCCLLPFDTVNNNRNRGEVLFNKLKEYAQ

KLDKNEGSLEMWEYIGIGNSGTAFSNFLGEGFLGRLRENKITELKKAMMDI

TDAWRGQEQEEELEKRLRILAALTIKLREPKFDNHWGGYRSDINGKLSSWL

QNYINQTVKIKEDLKGHKKDLKKAKEMINRFGESDTKEEAVVSSLLESIEK

IVPDDSADDEKPDIPAIAIYRRFLSDGRLTLNRFVQREDVQEALIKERLEA

EKKKKPKKRKKKSDAEDEKETIDFKELFPHLAKPLKLVPNFYGDSKRELYK

KYKNAAIYTDALWKAVEKIYKSAFSSSLKNSFFDTDFDKDFFIKRLQKIFS

VYRRFNTDKWKPIVKNSFAPYCDIVSLAENEVLYKPKQSRSRKSAAIDKNR

VRLPSTENIAKAGIALARELSVAGFDWKDLLKKEEHEEYIDLIELHKTALA

LLLAVTETQLDISALDFVENGTVKDFMKTRDGNLVLEGRFLEMFSQSIVFS

ELRGLAGLMSRKEFITRSAIQTMNGKQAELLYIPHEFQSAKITTPKEMSRA

FLDLAPAEFATSLEPESLSEKSLLKLKQMRYYPHYFGYELTRTGQGIDGGV

AENALRLEKSPVKKREIKCKQYKTLGRGQNKIVLYVRSSYYQTQFLEWFLH

RPKNVQTDVAVSGSFLIDEKKVKTRWNYDALTVALEPVSGSERVFVSQPFT
```

```
IFPEKSAEEEGQRYLGIDIGEYGIAYTALEITGDSAKILDQNFISDPQLKT

LREEVKGLKLDQRRGTFAMPSTKIARIRESLVHSLRNRIHHLALKHKAKIV

YELEVSRFEEGKQKIKKVYATLKKADVYSEIDADKNLQTTVWGKLAVASEI

SASYTSQFCGACKKLWRAEMQVDETITTQELIGTVRVIKGGTLIDAIKDFM

RPPIFDENDTPFPKYRDFCDKHHISKKMRGNSCLFICPFCRANADADIQAS

QTIALLRYVKEEKKVEDYFERFRKLKNIKVLGQMKKI
```

The term "effective amount," as used herein, refers to an amount of a biologically active agent that is sufficient to elicit a desired biological response. For example, in some embodiments, an effective amount of a nucleobase editor may refer to the amount of the nucleobase editor that is sufficient to induce mutation of a target site specifically bound mutated by the nucleobase editor. In some embodiments, an effective amount of a fusion protein provided herein, e.g., of a fusion protein comprising a nucleic acid programmable DNA binding protein and a deaminase domain (e.g., an adenosine deaminase domain) may refer to the amount of the fusion protein that is sufficient to induce editing of a target site specifically bound and edited by the fusion protein. As will be appreciated by the skilled artisan, the effective amount of an agent, e.g., a fusion protein, a nucleobase editor, a deaminase, a hybrid protein, a protein dimer, a complex of a protein (or protein dimer) and a polynucleotide, or a polynucleotide, may vary depending on various factors as, for example, on the desired biological response, e.g., on the specific allele, genome, or target site to be edited, on the cell or tissue being targeted, and on the agent being used.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to as cancer.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site) and a nucleic acid cleavage domain or a catalytic domain of a nucleic-acid editing protein. In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* (4$^{th}$ ed., Cold Spring Harbor Laboratory Press, Cold Spring Harbor, N.Y. (2012)), the entire contents of which are incorporated herein by reference.

The term "RNA-programmable nuclease," and "RNA-guided nuclease" are used interchangeably herein and refer to a nuclease that forms a complex with (e.g., binds or associates with) one or more RNA(s) that is not a target for cleavage. In some embodiments, an RNA-programmable nuclease, when in a complex with an RNA, may be referred to as a nuclease: RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. In some embodiments, domain (2) corresponds to a sequence known as a tracrRNA and comprises a stem-loop structure. For example, in some embodiments, domain (2) is identical or homologous to a tracrRNA as provided in Jinek et al., *Science* 337:816-821(2012), the entire contents of which is incorporated herein by reference. Other examples of gRNAs (e.g., those including domain 2) can be found in U.S. Provisional Patent Application, U.S. Ser. No. 61/874,682, filed Sep. 6, 2013, entitled "Switchable Cas9 Nucleases And Uses Thereof," and U.S. Provisional Patent Application, U.S. Ser. No. 61/874,746, filed Sep. 6, 2013, entitled "Delivery System For Functional Nucleases," the entire contents of each are hereby incorporated by reference in their entirety. In some embodiments, a gRNA comprises two or more of domains (1) and (2) and may be referred to as an "extended gRNA." For example, an extended gRNA will, e.g., bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example, Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference.

Because RNA-programmable nucleases (e.g., Cas9) use RNA:DNA hybridization to target DNA cleavage sites, these proteins are able to be targeted, in principle, to any sequence specified by the guide RNA. Methods of using RNA-programmable nucleases, such as Cas9, for site-specific cleavage (e.g., to modify a genome) are known in the art (see e.g., Cong, L. et al., Multiplex genome engineering using CRISPR/Cas systems. *Science* 339, 819-823 (2013); *Mali*, P. et al., RNA-guided human genome engineering via Cas9. *Science* 339, 823-826 (2013); Hwang, W. Y. et al., Efficient genome editing in zebrafish using a CRISPR-Cas system. *Nature biotechnology* 31, 227-229 (2013); Jinek, M. et al., RNA-programmed genome editing in human cells. eLife 2, e00471 (2013); Dicarlo, J. E. et al., Genome engineering in *Saccharomyces cerevisiae* using CRISPR-Cas systems. *Nucleic acids research* (2013); Jiang, W. et al. RNA-guided editing of bacterial genomes using CRISPR-Cas systems. *Nature biotechnology* 31, 233-239 (2013); the entire contents of each of which are incorporated herein by reference).

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The term "target site" refers to a sequence within a nucleic acid molecule that is deaminated by a deaminase or a fusion protein comprising a deaminase, (e.g., a dCas9-adenosine deaminase fusion protein provided herein).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "recombinant" as used herein in the context of proteins or nucleic acids refers to proteins or nucleic acids that do not occur in nature, but are the product of human engineering. For example, in some embodiments, a recombinant protein or nucleic acid molecule comprises an amino acid or nucleotide sequence that comprises at least one, at least two, at least three, at least four, at least five, at least six, or at least seven mutations as compared to any naturally occurring sequence.

DETAILED DESCRIPTION OF THE INVENTION

Some aspects of this disclosure relate to proteins that deaminate the nucleobase adenine. This disclosure provides adenosine deaminase proteins that are capable of deaminating (i.e., removing an amine group) adenine of a deoxyadenosine residue in deoxyribonucleic acid (DNA). For example, the adenosine deaminases provided herein are capable of deaminating adenine of a deoxyadenosine residue of DNA. It should be appreciated that there were no known adenosine deaminases capable of deaminating deoxyadenosine in DNA before the present invention. Other aspects of the disclosure provide fusion proteins that comprise an adenosine deaminase (e.g., an adenosine deaminase that deaminates deoxyadenosine in DNA as described herein) and a domain (e.g., a Cas9 or a Cpf1 protein) capable of binding to a specific nucleotide sequence. The deamination of an adenosine by an adenosine deaminase can lead to a point mutation, this process is referred to herein as nucleic acid editing. For example, the adenosine may be converted to an inosine residue, which typically base pairs with a cytosine residue. Such fusion proteins are useful inter alia for targeted editing of nucleic acid sequences. Such fusion proteins may be used for targeted editing of DNA in vitro, e.g., for the generation of mutant cells or animals; for the introduction of targeted mutations, e.g., for the correction of genetic defects in cells ex vivo, e.g., in cells obtained from a subject that are subsequently re-introduced into the same or another subject; and for the introduction of targeted mutations in vivo, e.g., the correction of genetic defects or the introduction of deactivating mutations in disease-associated genes in a subject. As an example, diseases that can be treated by making an A to G, or a T to C mutation may be treated using the nucleobase editors provided herein. The invention provides deaminases, fusion proteins, nucleic acids, vectors, cells, compositions, methods, kits, systems, etc. that utilize the deaminases and nucleobase editors.

In some embodiments, the nucleobase editors provided herein can be made by fusing together one or more protein domains, thereby generating a fusion protein. In certain embodiments, the fusion proteins provided herein comprise one or more features that improve the base editing activity (e.g., efficiency, selectivity, and specificity) of the fusion proteins. For example, the fusion proteins provided herein may comprise a Cas9 domain that has reduced nuclease activity. In some embodiments, the fusion proteins provided herein may have a Cas9 domain that does not have nuclease activity (dCas9), or a Cas9 domain that cuts one strand of a duplexed DNA molecule, referred to as a Cas9 nickase (nCas9). Without wishing to be bound by any particular theory, the presence of the catalytic residue (e.g., H840) maintains the activity of the Cas9 to cleave the non-edited (e.g., non-deaminated) strand containing a T opposite the targeted A. Mutation of the catalytic residue (e.g., D10 to A10) of Cas9 prevents cleavage of the edited strand containing the targeted A residue. Such Cas9 variants are able to generate a single-strand DNA break (nick) at a specific location based on the gRNA-defined target sequence, leading to repair of the non-edited strand, ultimately resulting in a T to C change on the non-edited strand. In some embodiments, any of the fusion proteins provided herein further comprise an inhibitor of inosine base excision repair, for example, a uracil glycosylase inhibitor (UGI) domain or a catalytically inactive inosine-specific nuclease (dISN). Without wishing to be bound by any particular theory, the UGI domain or dISN may inhibit or prevent base excision repair of a deaminated adenosine residue (e.g., inosine), which may improve the activity or efficiency of the base editor.

Adenosine Deaminases

Some aspects of the disclosure provide adenosine deaminases. In some embodiments, the adenosine deaminases provided herein are capable of deaminating adenine. In some embodiments, the adenosine deaminases provided herein are capable of deaminating adenine in a deoxyadenosine residue of DNA. The adenosine deaminase may be derived from any suitable organism (e.g., *E. coli*). In some embodiments, the adenine deaminase is a naturally-occurring adenosine deaminase that includes one or more mutations corresponding to any of the mutations provided herein (e.g., mutations in ecTadA). One of skill in the art will be able to identify the corresponding residue in any homologous protein and in the respective encoding nucleic acid by methods well known in the art, e.g., by sequence alignment and determination of homologous residues. Accordingly, one of skill in the art would be able to generate mutations in any naturally-occurring adenosine deaminase (e.g., having homology to ecTadA) that corresponds to any of the mutations described herein, e.g., any of the mutations identified in ecTadA. In some embodiments, the adenosine deaminase is from a prokaryote. In some embodiments, the adenosine deaminase is from a bacterium. In some embodiments, the adenosine deaminase is from *Escherichia coli, Staphylococcus aureus, Salmonella typhi, Shewanella putrefaciens, Haemophilus influenzae, Caulobacter crescentus*, or *Bacillus subtilis*. In some embodiments, the adenosine deaminase is from *E. coli*.

Figure 92:
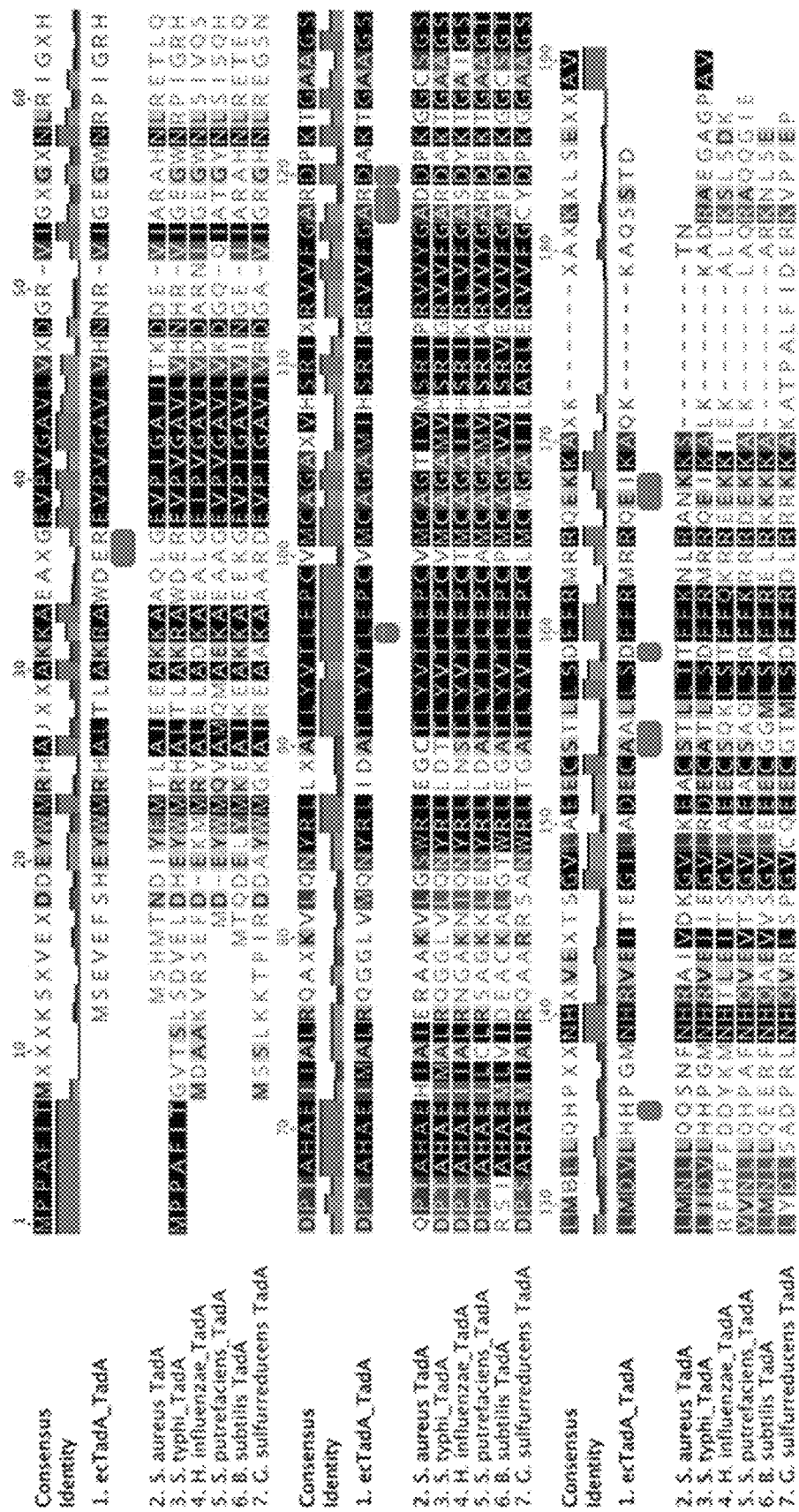
FIG. 92 shows a sequence alignment of prokaryotic TadA amino acid sequences. The sequences correspond to SEQ ID NOs: 634-657 from top to bottom respectively.
Figure 93:
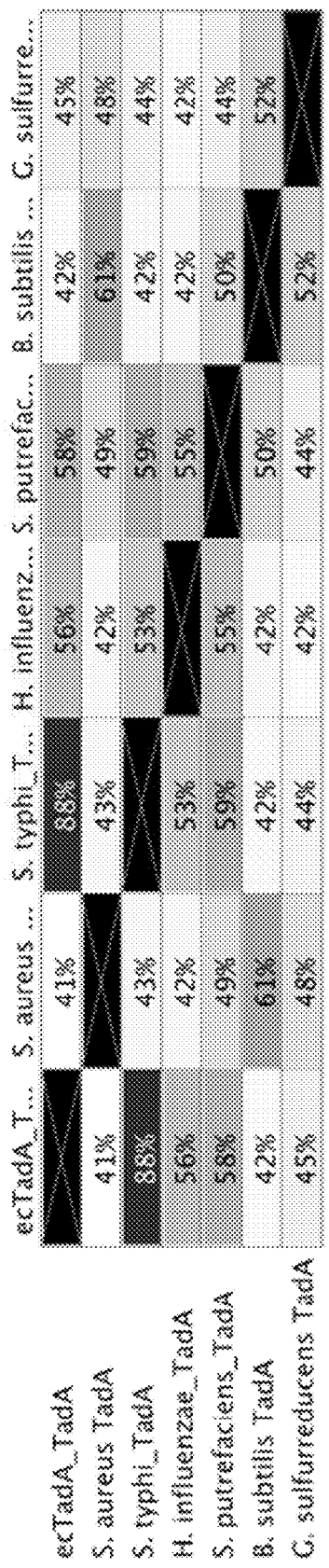
FIG. 93 shows a schematic of the relative sequence identity analysis of TadA amino acid sequences.

Exemplary alignment of prokaryotic TadA proteins is shown in FIG. 92. The residues highlighted in blue are the residues which may be important for catalyzing A to I deamination on ssDNA. Accordingly, it should be appreciated that any of the mutations identified in ecTadA provided herein may be made in any homologous residue in another adenine deaminase, for example, a TadA deaminase from another bacterium. FIG. 93 shows the relative sequence identity analysis (heatmap of sequence identity):

In some embodiments, the adenosine deaminase comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the amino acid sequences set forth in any one of SEQ ID NOs: 1, 64-84, 420-437, 672-684, or to any of the adenosine deaminases provided herein. It should be appreciated that adenosine deaminases provided herein may include one or more mutations (e.g., any of the mutations provided herein). The disclosure provides any deaminase domains with a certain percent identity plus any of the mutations or combinations thereof described herein. In some embodiments, the adenosine deaminase comprises an amino acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50, or more mutations compared to any one of the amino acid sequences set forth in SEQ ID NOs: 1, 64-84, 420-437, 672-684, or any of the adenosine deaminases provided herein. In some embodiments, the adenosine deaminase comprises an amino acid sequence that has at least 5, at least 10, at least 15, at least 20, at least 25, at least 30, at least 35, at least 40, at least 45, at least 50, at least 60, at least 70, at least 80, at least 90, at least 100, at least 110, at least 120, at least 130, at least 140, at least 150, at least 160, or at least 170 identical contiguous amino acid residues as compared to any one of the amino acid sequences set forth in SEQ ID NOs: 1, 64-84, 420-437, 672-684, or any of the adenosine deaminases provided herein.

Evolution #1 and #2 Mutations

In some embodiments, the adenosine deaminase comprises a D108X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises a D108G, D108N, D108V, D108A, or D108Y mutation in SEQ ID NO: 1, or a corresponding mutation in another adenosine deaminase. An exemplary alignment of deaminases is shown in FIG. 92. It should be appreciated, however, that additional deaminases may similarly be aligned to identify homologous amino acid residues that can be mutated as provided herein.

In some embodiments, the adenosine deaminase comprises an A106X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an A106V mutation in SEQ ID NO: 1, or a corresponding mutation in another adenosine deaminase.

In some embodiments, the adenosine deaminase comprises a E155X mutation in SEQ ID NO: 1, or a corresponding mutation in another adenosine deaminase, where the presence of X indicates any amino acid other than the corresponding amino acid in the wild-type adenosine deaminase. In some embodiments, the adenosine deaminase comprises a E155D, E155G, or E155V mutation in SEQ ID NO: 1, or a corresponding mutation in another adenosine deaminase.

In some embodiments, the adenosine deaminase comprises a D147X mutation in SEQ ID NO: 1, or a corresponding mutation in another adenosine deaminase, where the presence of X indicates any amino acid other than the corresponding amino acid in the wild-type adenosine deaminase. In some embodiments, the adenosine deaminase comprises a D147Y, mutation in SEQ ID NO: 1, or a corresponding mutation in another adenosine deaminase.

It should be appreciated that any of the mutations provided herein (e.g., based on the ecTadA amino acid sequence of SEQ ID NO: 1) may be introduced into other adenosine deaminases, such as S. aureus TadA (saTadA), or other adenosine deaminases (e.g., bacterial adenosine deaminases). It would be apparent to the skilled artisan how to identify amino acid residues from other adenosine deaminases that are homologous to the mutated residues in ecTadA. Thus, any of the mutations identified in ecTadA may be made in other adenosine deaminases that have homologous amino acid residues. It should also be appreciated that any of the mutations provided herein may be made individually or in any combination in ecTadA or another adenosine deaminase. For example, an adenosine deaminase may contain a D108N, a A106V, a E155V, and/or a D147Y mutation in ecTadA SEQ ID NO: 1, or a corresponding mutation in another adenosine deaminase. In some embodiments, an adenosine deaminase comprises the following group of mutations (groups of mutations are separated by a ";") in ecTadA SEQ ID NO: 1, or corresponding mutations in another adenosine deaminase:
D108N and A106V; D108N and E155V; D108N and D147Y; A106V and E155V; A106V and D147Y; E155V and D147Y; D108N, A106V, and E55V; D108N, A106V, and D147Y; D108N, E55V, and D147Y; A106V, E55V, and D147Y; and D108N, A106V, E55V, and D147Y. It should be appreciated, however, that any combination of corresponding mutations provided herein may be made in an adenosine deaminase (e.g., ecTadA). In some embodiments, an adenosine deaminase comprises one or more of the mutations shown in Table 4, which identifies individual mutations and combinations of mutations made in ecTadA and saTadA. In some embodiments, an adenosine deaminase comprises a mutation or combination of mutations shown in Table 4.

In some embodiments, the adenosine deaminase comprises one or more of a H8X, T17X, L18X, W23X, L34X, W45X, R51X, A56X, E59X, E85X, M94X, I95X, V102X, F104X, A106X, R107X, D108X, K110X, M118X, N127X, A138X, F149X, M151X, R153X, Q154X, I156X, and/or K157X mutation in SEQ ID NO: 1, or one or more corresponding mutations in another adenosine deaminase, where the presence of X indicates any amino acid other than the corresponding amino acid in the wild-type adenosine deaminase. In some embodiments, the adenosine deaminase comprises one or more of H8Y, T17S, L18E, W23L, L34S, W45L, R51H, A56E, or A56S, E59G, E85K, or E85G, M94L, I95I, V102A, F104L, A106V, R107C, or R107H, or R107P, D108G, or D108N, or D108V, or D108A, or D108Y, K110I, M118K, N127S, A138V, F149Y, M151V, R153C, Q154L, I156D, and/or K157R mutation in SEQ ID NO: 1, or one or more corresponding mutations in another adenosine deaminase. In some embodiments, the adenosine deaminase comprises one or more of the mutations provided in FIG. 11 corresponding to SEQ ID NO: 1, or one or more corresponding mutations in another adenosine deaminase. In some embodiments, the adenosine deaminase comprises the mutation or mutations of any one of constructs 1-16 shown in FIG. 11 or in any one of the constructs shown in Table 4 corresponding to SEQ ID NO: 1, or a corresponding mutation or mutations in another adenosine deaminase.

In some embodiments, the adenosine deaminase comprises one or more of a H8X, D108X, and/or N127X mutation in SEQ ID NO: 1, or one or more corresponding mutations in another adenosine deaminase, where X indicates the presence of any amino acid. In some embodiments, the adenosine deaminase comprises one or more of a H8Y, D108N, and/or N127S mutation in SEQ ID NO: 1, or one or more corresponding mutations in another adenosine deaminase.

In some embodiments, the adenosine deaminase comprises one or more of H8X, R26X, M61X, L68X, M70X, A106X, D108X, A109X, N127X, D147X, R152X, Q154X, E155X, K161X, Q163X, and/or T166X mutation in SEQ ID NO: 1, or one or more corresponding mutations in another adenosine deaminase, where X indicates the presence of any amino acid other than the corresponding amino acid in the wild-type adenosine deaminase. In some embodiments, the adenosine deaminase comprises one or more of H8Y, R26W, M61I, L68Q, M70V, A106T, D108N, A109T, N127S, D147Y, R152C, Q154H or Q154R, E155G or E155V or E155D, K161Q, Q163H, and/or T166P mutation in SEQ ID NO: 1, or one or more corresponding mutations in another adenosine deaminase.

In some embodiments, the adenosine deaminase comprises one, two, three, four, five, or six mutations selected from the group consisting of H8X, D108X, N127X, D147X, R152X, and Q154X in SEQ ID NO: 1, or a corresponding mutation or mutations in another adenosine deaminase, where X indicates the presence of any amino acid other than the corresponding amino acid in the wild-type adenosine deaminase. In some embodiments, the adenosine deaminase comprises one, two, three, four, five, six, seven, or eight mutations selected from the group consisting of H8X, M61X, M70X, D108X, N127X, Q154X, E155X, and Q163X in SEQ ID NO: 1, or a corresponding mutation or mutations in another adenosine deaminase, where X indicates the presence of any amino acid other than the corresponding amino acid in the wild-type adenosine deaminase. In some embodiments, the adenosine deaminase comprises one, two, three, four, or five, mutations selected from the group consisting of H8X, D108X, N127X, E155X, and T166X in SEQ ID NO: 1, or a corresponding mutation or mutations in another adenosine deaminase, where X indicates the presence of any amino acid other than the corresponding amino acid in the wild-type adenosine deaminase. In some embodiments, the adenosine deaminase comprises one, two, three, four, five, or six mutations selected from the group consisting of H8X, A106X, D108X, N127X, E155X, and K161X in SEQ ID NO: 1, or a corresponding mutation or mutations in another adenosine deaminase, where X indicates the presence of any amino acid other than the corresponding amino acid in the wild-type adenosine deaminase. In some embodiments, the adenosine deaminase comprises one, two, three, four, five, six, seven, or eight mutations selected from the group consisting of H8X, R126X, L68X, D108X, N127X, D147X, and E155X in SEQ ID NO: 1, or a corresponding mutation or mutations in another adenosine deaminase, where X indicates the presence of any amino acid other than the corresponding amino acid in the wild-type adenosine deaminase. In some embodiments, the adenosine deaminase comprises one, two, three, four, or five, mutations selected from the group consisting of H8X, D108X, A109X, N127X, and E155X in SEQ ID NO: 1, or a corresponding mutation or mutations in another adenosine deaminase, where X indicates the presence of any amino acid other than the corresponding amino acid in the wild-type adenosine deaminase.

In some embodiments, the adenosine deaminase comprises one, two, three, four, five, or six mutations selected from the group consisting of H8Y, D108N, N127S, D147Y, R152C, and Q154H in SEQ ID NO: 1, or a corresponding mutation or mutations in another adenosine deaminase. In some embodiments, the adenosine deaminase comprises one, two, three, four, five, six, seven, or eight mutations selected from the group consisting of H8Y, M61I, M70V, D108N, N127S, Q154R, E155G and Q163H in SEQ ID NO: 1, or a corresponding mutation or mutations in another adenosine deaminase. In some embodiments, the adenosine deaminase comprises one, two, three, four, or five, mutations selected from the group consisting of H8Y, D108N, N127S, E155V, and T166P in SEQ ID NO: 1, or a corresponding mutation or mutations in another adenosine deaminase. In some embodiments, the adenosine deaminase comprises one, two, three, four, five, or six mutations selected from the group consisting of H8Y, A106T, D108N, N127S, E155D, and K161Q in SEQ ID NO: 1, or a corresponding mutation or mutations in another adenosine deaminase. In some embodiments, the adenosine deaminase comprises one, two, three, four, five, six, seven, or eight mutations selected from the group consisting of H8Y, R126W, L68Q, D108N, N127S, D147Y, and E155V in SEQ ID NO: 1, or a corresponding mutation or mutations in another adenosine deaminase. In some embodiments, the adenosine deaminase comprises one, two, three, four, or five, mutations selected from the group consisting of H8Y, D108N, A109T, N127S, and E155G in SEQ ID NO: 1, or a corresponding mutation or mutations in another adenosine deaminase.

In some embodiments, the adenosine deaminase comprises one or more of the mutations provided in FIG. 16 corresponding to SEQ ID NO: 1, or one or more corresponding mutations in another adenosine deaminase. In some embodiments, the adenosine deaminase comprises the mutations of any one of constructs pNMG-149 to pNMG-154 of FIG. 16, corresponding to SEQ ID NO: 1, or corresponding mutations in another adenosine deaminase. In some embodiments, the adenosine deaminase comprises a D108N, D108G, or D108V mutation in SEQ ID NO: 1, or corresponding mutations in another adenosine deaminase. In some embodiments, the adenosine deaminase comprises a A106V and D108N mutation in SEQ ID NO: 1, or corresponding mutations in another adenosine deaminase. In some embodiments, the adenosine deaminase comprises R107C and D108N mutations in SEQ ID NO: 1, or corresponding mutations in another adenosine deaminase. In some embodiments, the adenosine deaminase comprises a H8Y, D108N, N127S, D147Y, and Q154H mutation in SEQ ID NO: 1, or corresponding mutations in another adenosine deaminase. In some embodiments, the adenosine deaminase comprises a H8Y, R24W, D108N, N127S, D147Y, and E155V mutation in SEQ ID NO: 1, or corresponding mutations in another adenosine deaminase. In some embodiments, the adenosine deaminase comprises a D108N, D147Y, and E155V mutation in SEQ ID NO: 1, or corresponding mutations in another adenosine deaminase. In some embodiments, the adenosine deaminase comprises a H8Y, D108N, and S127S mutation in SEQ ID NO: 1, or corresponding mutations in another adenosine deaminase. In some embodiments, the adenosine deaminase comprises a A106V, D108N, D147Y and E155V mutation in SEQ ID NO: 1, or corresponding mutations in another adenosine deaminase.

Figures 96, 97:
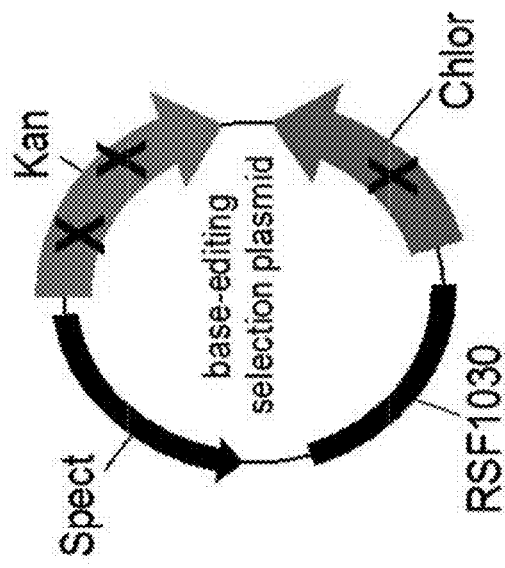
FIG. 96 shows a schematic of an exemplary base-editing selection plasmid.
FIG. 97 shows a list of clones including identified mutations in ecTadA.
Figure 98:
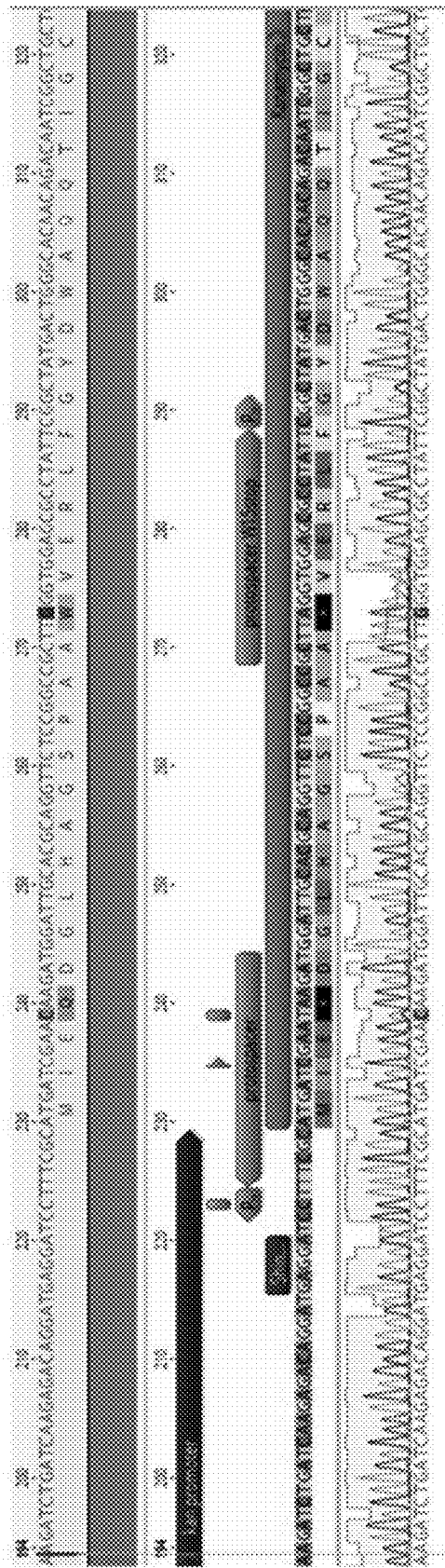
FIG. 98 shows an exemplary sequencing analysis of a selection plasmid from surviving colonies. The sequences correspond to SEQ ID NOs: 658-661, 5529-5530, and 662 from top to bottom and left to right, respectively.
Figures 99, 100:
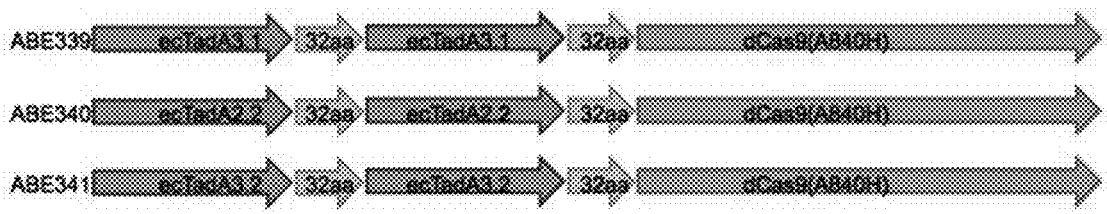
FIG. 99 shows a schematic of exemplary adenosine base editors from a third round of evolution.
FIG. 100 shows the percentage of A to G conversions in Hek293T cells.
Figure 101:
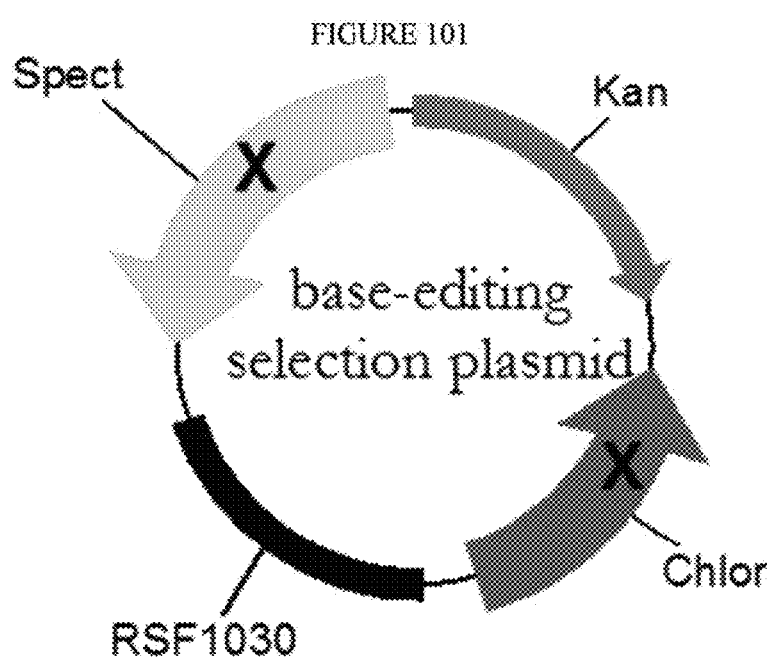
FIG. 101 shows a schematic of an exemplary base-editing selection plasmid.
Figure 102:
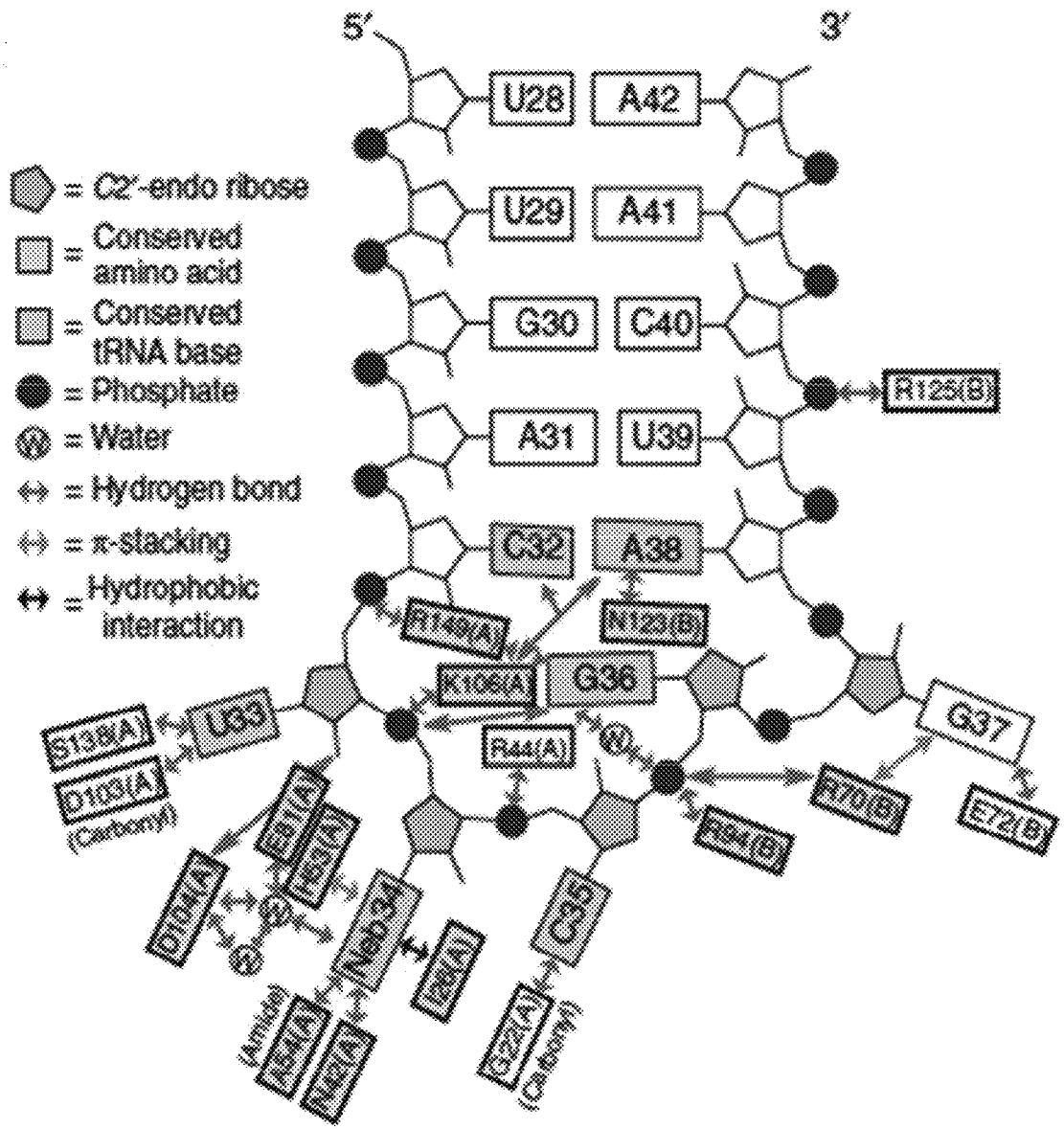
FIG. 102 shows a schematic representation of the verdine crystal structure of *S. aureus* TadA. The *S. aureus* TadA, a homolog of ecTadA, is shown with its tRNA substrate co-crystalized. Red arrows are the H-bond contacts with the various nucleic acids in the tRNA substrate. SeeLosey, H. C., et al., "Crystal structure of *Staphylococcus sureus* tRNA adenosine deaminase tadA in complex with RNA", *Nature Struct. Mol. Biol.* 2, 153-159 (2006).
Figure 103:
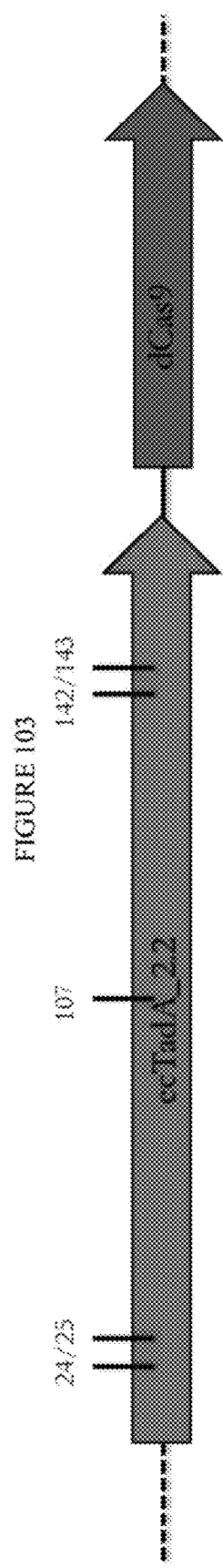
FIG. 103 shows a schematic of a construct containing ecTadA_2.2 and dCas9, identifying mutated ecTadA residues.
Figure 104:
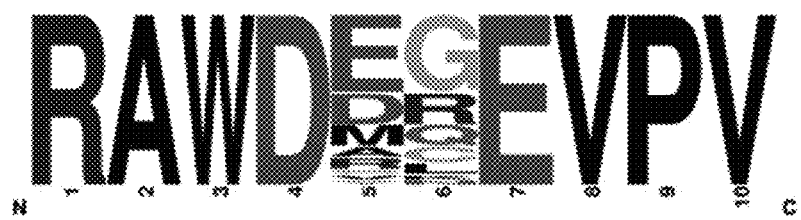
FIG. 104 shows results of ecTadA evolution (evolution #4) at sites E25 and R26.
Figure 105:
FIG. 105 shows results of ecTadA evolution (evolution #4) at site R107.
Figure 106:
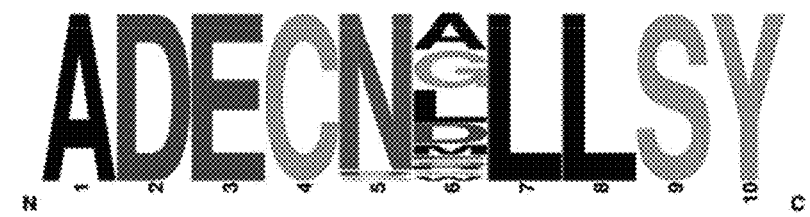
FIG. 106 shows results of ecTadA evolution (evolution #4) at sites A142 and A143.
Figure 107:
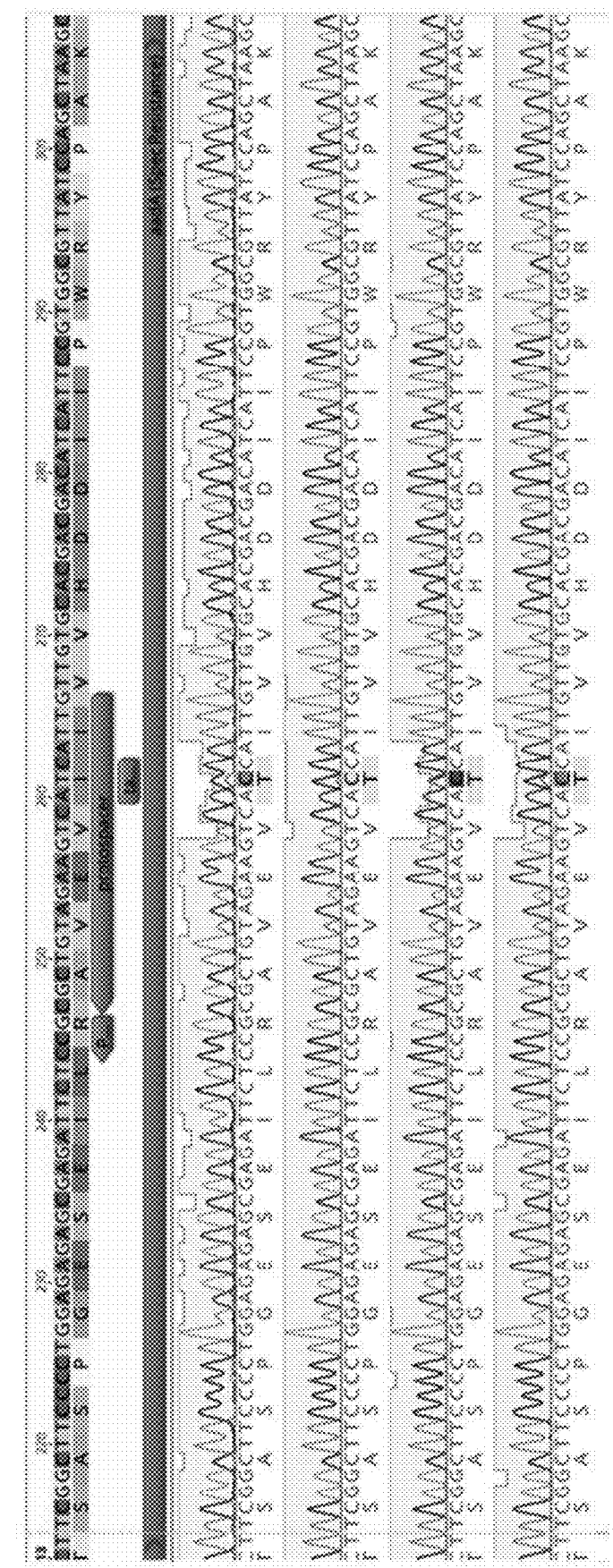
FIG. 107 shows an exemplary sequencing analysis of a selection plasmid from surviving colonies. The sequences correspond to SEQ ID NO: 662-671 from top to bottom respectively.

In some embodiments, the adenosine deaminase comprises one or more of a, S2X, H8X, I49X, L84X, H123X, N127X, I156X and/or K160X mutation in SEQ ID NO: 1, or one or more corresponding mutations in another adenosine deaminase, where the presence of X indicates any amino acid other than the corresponding amino acid in the wild-type adenosine deaminase. In some embodiments, the adenosine deaminase comprises one or more of S2A, H8Y, I49F, L84F, H123Y, N127S, I156F and/or K160S mutation in SEQ ID NO: 1, or one or more corresponding mutations in another adenosine deaminase. In some embodiments, the adenosine deaminase comprises one or more of the mutations provided in FIG. 97 corresponding to SEQ ID NO: 1, or one or more corresponding mutations in another adenosine deaminase. In some embodiments, the adenosine deaminase comprises the mutation or mutations of any one of clones 1-3 shown in FIG. 97 corresponding to SEQ ID NO: 1, or a corresponding mutation or mutations in another adenosine deaminase.

In some embodiments, the adenosine deaminase comprises an L84X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an L84F mutation in SEQ ID NO: 1, or a corresponding mutation in another adenosine deaminase.

In some embodiments, the adenosine deaminase comprises an H123X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an H123Y mutation in SEQ ID NO: 1, or a corresponding mutation in another adenosine deaminase.

In some embodiments, the adenosine deaminase comprises an I157X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an I157F mutation in SEQ ID NO: 1, or a corresponding mutation in another adenosine deaminase.

In some embodiments, the adenosine deaminase comprises one, two, three, four, five, six, or seven mutations selected from the group consisting of L84X, A106X, D108X, H123X, D147X, E155X, and I156X in SEQ ID NO: 1, or a corresponding mutation or mutations in another adenosine deaminase, where X indicates the presence of any amino acid other than the corresponding amino acid in the wild-type adenosine deaminase. In some embodiments, the adenosine deaminase comprises one, two, three, four, five, or six mutations selected from the group consisting of S2X, I49X, A106X, D108X, D147X, and E155X in SEQ ID NO: 1, or a corresponding mutation or mutations in another adenosine deaminase, where X indicates the presence of any amino acid other than the corresponding amino acid in the wild-type adenosine deaminase. In some embodiments, the adenosine deaminase comprises one, two, three, four, or five, mutations selected from the group consisting of H8X, A106X, D108X, N127X, and K160X in SEQ ID NO: 1, or a corresponding mutation or mutations in another adenosine deaminase, where X indicates the presence of any amino acid other than the corresponding amino acid in the wild-type adenosine deaminase.

In some embodiments, the adenosine deaminase comprises one, two, three, four, five, six, or seven mutations selected from the group consisting of L84F, A106V, D108N, H123Y, D147Y, E155V, and I156F in SEQ ID NO: 1, or a corresponding mutation or mutations in another adenosine deaminase. In some embodiments, the adenosine deaminase comprises one, two, three, four, five, or six mutations selected from the group consisting of S2A, I49F, A106V, D108N, D147Y, and E155V in SEQ ID NO: 1, or a corresponding mutation or mutations in another adenosine deaminase. In some embodiments, the adenosine deaminase comprises one, two, three, four, or five, mutations selected from the group consisting of H8Y, A106T, D108N, N127S, and K160S in SEQ ID NO: 1, or a corresponding mutation or mutations in another adenosine deaminase.

In some embodiments, the adenosine deaminase comprises one or more of a, E25X, R26X, R107X, A142X, and/or A143X mutation in SEQ ID NO: 1, or one or more corresponding mutations in another adenosine deaminase, where the presence of X indicates any amino acid other than the corresponding amino acid in the wild-type adenosine deaminase. In some embodiments, the adenosine deaminase comprises one or more of E25M, E25D, E25A, E25R, E25V, E25S, E25Y, R26G, R26N, R26Q, R26C, R26L, R26K, R107P, R07K, R107A, R107N, R107W, R107H, R107S, A142N, A142D, A142G, A143D, A143G, A143E, A143L, A143W, A143M, A143S, A143Q and/or A143R mutation in SEQ ID NO: 1, or one or more corresponding mutations in another adenosine deaminase. In some embodiments, the adenosine deaminase comprises one or more of the mutations provided in Table 7 corresponding to SEQ ID NO: 1, or one or more corresponding mutations in another adenosine deaminase. In some embodiments, the adenosine deaminase comprises the mutation or mutations of any one of clones 1-22 shown in Table 7 corresponding to SEQ ID NO: 1, or a corresponding mutation or mutations in another adenosine deaminase.

In some embodiments, the adenosine deaminase comprises an E25X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an E25M, E25D, E25A, E25R, E25V, E25S, or E25Y mutation in SEQ ID NO: 1, or a corresponding mutation in another adenosine deaminase.

In some embodiments, the adenosine deaminase comprises an R26X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an, R26G, R26N, R26Q, R26C, R26L, or R26K mutation in SEQ ID NO: 1, or a corresponding mutation in another adenosine deaminase.

In some embodiments, the adenosine deaminase comprises an R107X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an R107P, R07K, R107A, R107N, R107W, R107H, or R107S mutation in SEQ ID NO: 1, or a corresponding mutation in another adenosine deaminase.

In some embodiments, the adenosine deaminase comprises an A142X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an A142N, A142D, A142G, mutation in SEQ ID NO: 1, or a corresponding mutation in another adenosine deaminase.

In some embodiments, the adenosine deaminase comprises an A143X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an A143D, A143G, A143E, A143L, A143W, A143M, A143S, A143Q and/or A143R mutation in SEQ ID NO: 1, or a corresponding mutation in another adenosine deaminase.

In some embodiments, the adenosine deaminase comprises one or more of a, H36X, N37X, P48X, I49X, R51X, M70X, N72X, D77X, E134X, S146X, Q154X, K157X, and/or K161X mutation in SEQ ID NO: 1, or one or more corresponding mutations in another adenosine deaminase, where the presence of X indicates any amino acid other than the corresponding amino acid in the wild-type adenosine deaminase. In some embodiments, the adenosine deaminase comprises one or more of H36L, N37T, N37S, P48T, P48L, I49V, R51H, R51L, M70L, N72S, D77G, E134G, S146R, S146C, Q154H, K157N, and/or K161T mutation in SEQ ID NO: 1, or one or more corresponding mutations in another adenosine deaminase. In some embodiments, the adenosine deaminase comprises one or more of the mutations provided in any one of FIGS. 125-128 corresponding to SEQ ID NO: 1, or one or more corresponding mutations in another adenosine deaminase. In some embodiments, the adenosine deaminase comprises the mutation or mutations of any one of clones 1-11 shown in any one of FIGS. 125-128 corresponding to SEQ ID NO: 1, or a corresponding mutation or mutations in another adenosine deaminase.

In some embodiments, the adenosine deaminase comprises an H36X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an H36L mutation in SEQ ID NO: 1, or a corresponding mutation in another adenosine deaminase.

In some embodiments, the adenosine deaminase comprises an N37X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an N37T, or N37S mutation in SEQ ID NO: 1, or a corresponding mutation in another adenosine deaminase.

In some embodiments, the adenosine deaminase comprises an P48X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an P48T, or P48L mutation in SEQ ID NO: 1, or a corresponding mutation in another adenosine deaminase.

In some embodiments, the adenosine deaminase comprises an R51X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an R51H, or R51L mutation in SEQ ID NO: 1, or a corresponding mutation in another adenosine deaminase.

In some embodiments, the adenosine deaminase comprises an S146X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises an S146R, or S146C mutation in SEQ ID NO: 1, or a corresponding mutation in another adenosine deaminase.

In some embodiments, the adenosine deaminase comprises an K157X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises a K157N mutation in SEQ ID NO: 1, or a corresponding mutation in another adenosine deaminase.

In some embodiments, the adenosine deaminase comprises an P48X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises a P48S, P48T, or P48A mutation in SEQ ID NO: 1, or a corresponding mutation in another adenosine deaminase.

In some embodiments, the adenosine deaminase comprises an A142X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises a A142N mutation in SEQ ID NO: 1, or a corresponding mutation in another adenosine deaminase.

In some embodiments, the adenosine deaminase comprises an W23X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises a W23R, or W23L mutation in SEQ ID NO: 1, or a corresponding mutation in another adenosine deaminase.

In some embodiments, the adenosine deaminase comprises an R152X mutation in ecTadA SEQ ID NO: 1, or a corresponding mutation in another adenosine deaminase, where X indicates any amino acid other than the corresponding amino acid in the wild-type adenosine deaminase. In some embodiments, the adenosine deaminase comprises a R152P, or R52H mutation in SEQ ID NO: 1, or a corresponding mutation in another adenosine deaminase.

It should be appreciated that the adenosine deaminase (e.g., a first or second adenosine deaminase) may comprise one or more of the mutations provided in any of the adenosine deaminases (e.g., ecTadA adenosine deaminases) shown in Table 4. In some embodiments, the adenosine deaminase comprises the combination of mutations of any of the adenosine deaminases (e.g., ecTadA adenosine deaminases) shown in Table 4. For example, the adenosine deaminase may comprise the mutations H36L, R51L, L84F, A106V, D108N, H123Y, S146C, D147Y, E155V, I156F, and K157N, which are shown in the second ecTadA (relative to SEQ ID NO: 1) of clone pNMG-477. In some embodiments, the adenosine deaminase comprises the following combination of mutations relative to SEQ ID NO:1, where each mutation of a combination is separated by a "_" and each combination of mutations is between parentheses: (A106V_D108N), (R107C_D108N), (H8Y_D108N_S127S_D147Y_Q154H), (H8Y_R24W_D108N_N127S_D147Y_E155V), (D108N_D147Y_E155V), (H8Y_D108N_S127S), (H8Y_D108N_N127S_D147Y_Q154H), (A106V_D108N_D147Y_E155V), (D108Q_D147Y_E155V), (D108M_D147Y_E155V), (D108L_D147Y_E155V), (D108K_D147Y_E155V), (D108I_D147Y_E155V), (D108F_D147Y_E155V), (A106V_D108N_D147Y), (A106V_D108M_D147Y_E155V), (E59A_A106V_D108N_D147Y_E155V), (E59A cat dead_A106V_D108N_D147Y_E155V), (L84F_A106V_D108N_H123Y_D147Y_E155V_I156Y), (L84F_A106V_D108N_H123Y_D147Y_E155V_I156F), (D103A_D014N), (G22P_D103A_D104N), (G22P_D103A_D104N_S138A), (D103A_D104N_S138A), (R26G_L84F_A106V_R107H_D108N_H123Y_A142N_A143D_D147Y_E155V_I156F), (E25G_R26G_L84F_A106V_R107H_D108N_H123Y_A142N_A143D_D147Y_E155V_I156F), (E25D_R26G_L84F_A106V_R107K_D108N_H123Y_A142N_A143G_D147Y_E155V_I156F), (R26Q_L84F_A106V_D108N_H123Y_A142N_D147Y_E155V_I156F), (E25M_R26G_L84F_A106V_R107P_D108N_H123Y_A142N_A143D_D147Y_E155V_I156F), (R26C_L84F_A106V_R107H_D108N_H123Y_A142N_D147Y_E155V_I156F), (L84F_A106V_D108N_H123Y_A142N_A143L_D147Y_E155V_I156F), (R26G_L84F_A106V_D108N_H123Y_A142N_D147Y_E155V_I156F), (E25A_R26G_L84F_A106V_R107N_D108N_H123Y_A142N_A143E_D147Y_E155V_I156F), (R26G_L84F_A106V_R107H_D108N_H123Y_A142N_A143D_D147Y_E155V_I156F), (A106V_D108N_A142N_D147Y_E155V), (R26G_A106V_D108N_A142N_D147Y_E155V), (E25D_R26G_A106V_R107K_D108N_A142N_A143G_D147Y_E155V), (R26G_A106V_D108N_R107H_A142N_A143D_D147Y_E155V), (E25D_R26G_A106V_D108N_A142N_D147Y_E155V), (A106V_R107K_D108N_A142N_D147Y_E155V), (A106V_D108N_A142N_A143G_D147Y_E155V), (A106V_D108N_A142N_A143L_D147Y_E155V), (H36L_R51L_L84F_A106V_D108N_H123Y_S146C_D147Y_E155V_I156F_K157N), (N37T_P48T_M70L_L84F_A106V_D108N_H123Y_D147Y_I49V_E155V_I156F), (N37S_L84F_A106V_D108N_H123Y_D147Y_E155V_I156F_K161T), (H36L_L84F_A106V_

D108N_H123Y_D147Y_Q154H_E155V_I156F), (N72S_
L84F_A106V_D108N_H123Y_S146R_D147Y_E155V_
I156F), (H36L_P48L_L84F_A106V_D108N_H123Y_
E134G_D147Y_E155V_I156F), (H36L_L84F_A106V_
D108N_H123Y_D147Y_E155V_I156F_K157N), (H36L_
L84F_A106V_D108N_H123Y_S146C_D147Y_E155V_
I156F), (L84F_A106V_D108N_H123Y_S146R_D147Y_
E155V_I156F_K161T), (N37S_R51H_D77G_L84F_
A106V_D108N_H123Y_D147Y_E155V_I156F), (R51L_
L84F_A106V_D108N_H123Y_D147Y_E155V_I156F_
K157N), (D24G_Q71R_L84F_H96L_A106V_D108N_
H123Y_D147Y_E155V_I156F_K160E), (H36L_G67V_
L84F_A106V_D108N_H123Y_S146T_D147Y_E155V_
I156F), (Q71L_L84F_A106V_D108N_H123Y_L137M_
A143E_D147Y_E155V_I156F), (E25G_L84F_A106V_
D108N_H123Y_D147Y_E155V_I156F_Q159L),
(L84F_A91T_F104I_A106V_D108N_H123Y_D147Y_
E155V_I156F), (N72D_L84F_A106V_D108N_H123Y_
G125A_D147Y_E155V_I156F), (P48S_L84F_S97C_
A106V_D108N_H123Y_D147Y_E155V_I156F), (W23G_
L84F_A106V_D108N_H123Y_D147Y_E155V_I156F),
(D24G_P48L_Q71R_L84F_A106V_D108N_H123Y_
D147Y_E155V_I156F_Q159L), (L84F_A106V_D108N_
H123Y_A142N_D147Y_E155V_I156F), (H36L_R51L_
L84F_A106V_ D108N_H123Y_A142N_S146C_D147Y_
E155V_I156F_K157N), (N37S_L84F_A106V_D108N_
H123Y_A142N_D147Y_E155V_I156F_K161T), (L84F_
A106V_D108N_D147Y_E155V_I156F), (R51L_L84F_
A106V_D108N_H123Y_S146C_D147Y_E155V_I156F_
K157N_K161T), (L84F_A106V_D108N_H123Y_S146C_
D147Y_E155V_I156F_K161T), (L84F_A106V_D108N_
H123Y_S146C_D147Y_E155V_I156F_K157N_K160E_
K161T), (L84F_A106V_D108N_H123Y_S146C_D147Y_
E155V_I156F_K157N_K160E), (R74Q_L84F_A106V_
D108N_H123Y_D147Y_E155V_I156F), (R74A_L84F_
A106V_D108N_H123Y_D147Y_E155V_I156F), (L84F_
A106V_D108N_H123Y_D147Y_E155V_I156F), (R74Q_
L84F_A106V_D108N_H123Y_D147Y_E155V_I156F),
(L84F_R98Q_A106V_D108N_H123Y_D147Y_E155V_
I156F), (L84F_A106V_D108N_H123Y_R129Q_D147Y_
E155V_I156F), (P48S_L84F_A106V_D108N_H123Y_
A142N_D147Y_E155V_I156F), (P48S_A142N), (P48T_
I49V_L84F_A106V_D108N_H123Y_A142N_D147Y_
E155V_I156F_L157N), (P48T_I49V_A142N), (H36L_
P48S_R51L_L84F_A106V_D108N_H123Y_S146C_
D147Y_E155V_I156F_K157N), (H36L_P48S_R51L_
L84F_A106V_D108N_H123Y_S146C_A142N_D147Y_
E155V_I156F_K157N), (H36L_P48T_I49V_R51L_
L84F_A106V_D108N_H123Y_S146C_D147Y_E155V_
I156F_K157N), (H36L_P48T_I49V_R51L_L84F_
A106V_D108N_H123Y_A142N_S146C_D147Y_E155V_
I156F_K157N), (H36L_P48A_R51L_L84F_A106V_
D108N_H123Y_S146C_D147Y_E155V_I156F_K157N),
(H36L_P48A_ R51L_L84F_A106V_D108N_H123Y_
A142N_S146C_D147Y_E155V_I156F_K157N), (H36L_
P48A_R51L_L84F_A106V_D108N_H123Y_S146C_
A142N_D147Y_E155V_I156F_K157N), (W23L_H36L_
P48A_R51L_L84F_A106V_D108N_H123Y_S146C_
D147Y_E155V_I156F_K157N), (W23R_H36L_P48A_
R51L_L84F_A106V_D108N_H123Y_S146C_D147Y_
E155V_I156F_K157N), (W23L_H36L_P48A_R51L_
L84F_A106V_D108N_H123Y_S146R_D147Y_E155V_
I156F_K161T), (H36L_P48A_R51L_L84F_A106V_
D108N_H123Y_S146C_D147Y_R152H_E155V_I156F_
K157N), (H36L_ P48A_R51L_L84F_A106V_D108N_
H123Y_S146C_D147Y_R152P_E155V_I156F_K157N),
(W23L_H36L_P48A_R51L_L84F_A106V_D108N_
H123Y_S146C_D147Y_R152P_E155V_I156F_K157N),
(W23L_H36L_P48A_R51L_L84F_A106V_D108N_
H123Y_A142A_ S146C_D147Y_E155 V_I156F_K157N),
(W23L_H36L_P48A_R51L_L84F_A106V_D108N_
H123Y_A142A_S146C_D147Y_R152P_ E155V_I156F_
K157N), (W23L_H36L_P48A_R51L_L84F_A106V_
D108N_H123Y_S146R_D147Y_E155V_I156F_K161T),
(W23R_H36L_P48A_R51L_L84F_A106V_D108N_
H123Y_S146C_D147Y_R152P_E155V_I156F_K157N),
(H36L_P48A_R51L_L84F_A106V_D108N_H123Y_
A142N_S146C_D147Y_R152P_E155V_I156F_K157N).

In some embodiments, the adenosine deaminase comprises an amino acid sequence that is at least 60%, 65%, 70%, 75%, 80%, 85%, 90%, 95, 98%, 99%, or 99.5% identical to any one of SEQ ID NOs: 1, 64-84, 420-437, 672-684, or any of the adenosine deaminases provided herein. In some embodiments, the adenosine deaminase comprises an amino acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more mutations compared to any one of the amino acid sequences set forth in SEQ ID NOs: 1, 64-84, 420-437, 672-684, or any of the adenosine deaminases provided herein. In some embodiments, the adenosine deaminase comprises an amino acid sequence that has at least 5, at least 10, at least 15, at least 20, at least 25, at least 30, at least 35, at least 40, at least 45, at least 50, at least 60, at least 70, at least 80, at least 90, at least 100, at least 110, at least 120, at least 130, at least 140, at least 150, at least 160, or at least 166, identical contiguous amino acid residues as compared to any one of the amino acid sequences set forth in SEQ ID NOs: 1, 64-84, 420-437, 672-684, or any of the adenosine deaminases provided herein. In some embodiments, the adenosine deaminase comprises the amino acid sequence of any one of SEQ ID NOs: 1, 64-84, 420-437, 672-684, or any of the adenosine deaminases provided herein. In some embodiments, the adenosine deaminase consists of the amino acid sequence of any one of SEQ ID NOs: 1, 64-84, 420-437, 672-684, or any of the adenosine deaminases provided herein. The ecTadA sequences provided below are from ecTadA (SEQ ID NO: 1), absent the N-terminal methionine (M). The saTadA sequences provided below are from saTadA (SEQ DI NO: 8), absent the N-terminal methionine (M). For clarity, the amino acid numbering scheme used to identify the various amino acid mutations is derived from ecTadA (SEQ ID NO: 1) for *E. coli* TadA and saTadA (SEQ ID NO: 8) for *S. aureus* TadA. Amino acid mutations, relative to SEQ ID NO: 1 (ecTadA) or SEQ DI NO: 8 (saTadA), are indicated by underlining.

ecTadA
(SEQ ID NO: 64)
SEVEFSHEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGARDAKTGAAGSLMDVLHHPGMNHRVEITEGILADECAALLSDFFRMRRQ

EIKAQKKAQSSTD ecTadA (D108N)
(SEQ ID NO: 65)
SEVEFSHEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGARNAKTGAAGSLMDVLHHPGMNHRVEITEGILADECAALLSDFFRMRRQ

EIKAQKKAQSSTD ecTadA (D108G)

(SEQ ID NO: 66)
SEVEFSHEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGARGAKTGAAGSLMDVLHHPGMNHRVEITEGILADECAALLSDFFRMRRQ

EIKAQKKAQSSTD ecTadA (D108V)

(SEQ ID NO: 67)
SEVEFSHEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGARVAKTGAAGSLMDVLHHPGMNHRVEITEGILADECAALLSDFFRMRRQ

EIKAQKKAQSSTD ecTadA (H8Y, D108N, and N127S)

(SEQ ID NO: 68)
SEVEFSYEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGARNAKTGAAGSLMDVLHHPGMSHRVEITEGILADECAALLSDFFRMRRQ

EIKAQKKAQSSTD ecTadA (H8Y, D108N, N127S, and E155D)

(SEQ ID NO: 69)
SEVEFSYEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGARNAKTGAAGSLMDVLHHPGMSHRVEITEGILADECAALLSDFFRMRRQ

DIKAQKKAQSSTD ecTadA (H8Y, D108N, N127S, and E155G)

(SEQ ID NO: 70)
SEVEFSYEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGARNAKTGAAGSLMDVLHHPGMSHRVEITEGILADECAALLSDFFRMRRQ

GIKAQKKAQSSTD ecTadA (H8Y, D108N, N127S, and E155V)

(SEQ ID NO: 71)
SEVEFSYEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGARNAKTGAAGSLMDVLHHPGMSHRVEITEGILADECAALLSDFFRMRRQ

VIKAQKKAQSSTD ecTadA (A106V, D108N, D147Y, and E155V)

(SEQ ID NO: 72)
SEVEFSHEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGVRNAKTGAAGSLMDVLHHPGMNHRVEITEGILADECAALLSYFFRMRRQ

VIKAQKKAQSSTD ecTadA (L84F, A106V, D108N, H123Y, D147Y, E155V, I156F) - result of evolution #3

(SEQ ID NO: 73)
SEVEFSHEYWMRHALTLAKRAWDEREVPVGAVLVHNNRVIGEGWNRPIGRH

DPTAHAEIMALRQGGLVMQNYRLIDATLYVTFEPCVMCAGAMIHSRIGRVV

FGVRNAKTGAAGSLMDVLHYPGMNHRVEITEGILADECAALLSYFFRMRRQ

VFKAQKKAQSSTD ecTadA (S2A, I49F, A106V, D108N, D147Y, E155V) - result of evolution #3

(SEQ ID NO: 74)
AEVEFSHEYWMRHALTLAKRAWDEREVPVGAVLVHNNRVIGEGWNRPFGRH

DPTAHAEIMALRQGGLVMQNYRLIDATLYVTLEPCVMCAGAMIHSRIGRVV

FGVRNAKTGAAGSLMDVLHHPGMNHRVEITEGILADECAALLSYFFRMRRQ

VIKAQKKAQSSTD ecTadA (H8Y, A106T, D108N, N127S, K160S) - result of evolution #3

(SEQ ID NO: 75)
SEVEFSYEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGTRNAKTGAAGSLMDVLHHPGMSHRVEITEGILADECAALLSDFFRMRRQ

EIKAQSKAQSSTD ecTadA (R26G, L84F, A106V, R107H, D108N, H123Y, A142N, A143D, D147Y, E155V, I156F) - result of evolution #4

(SEQ ID NO: 76)
SEVEFSHEYWMRHALTLAKRAWDEGEVPVGAVLVHNNRVIGEGWNRPIGRH

DPTAHAEIMALRQGGLVMQNYRLIDATLYVTFEPCVMCAGAMIHSRIGRVV

FGVHNAKTGAAGSLMDVLHYPGMNHRVEITEGILADECNDLLSYFFRMRRQ

VFKAQKKAQSSTD ecTadA (E25G, R26G, L84F, A106V, R107H, D108N, H123Y, A142N, A143D, D147Y, E155V, I156F) - result of evolution #4

(SEQ ID NO: 77)
SEVEFSHEYWMRHALTLAKRAWDGGEVPVGAVLVHNNRVIGEGWNRPIGRH

DPTAHAEIMALRQGGLVMQNYRLIDATLYVTFEPCVMCAGAMIHSRIGRVV

FGVHNAKTGAAGSLMDVLHYPGMNHRVEITEGILADECNDLLSYFFRMRRQ

VFKAQKKAQSSTD ecTadA (E25D, R26G, L84F, A106V, R107K, D108N, H123Y, A142N, A143G, D147Y, E155V, I156F) - result of evolution #4

(SEQ ID NO: 78)
SEVEFSHEYWMRHALTLAKRAWDDGEVPVGAVLVHNNRVIGEGWNRPIGRH

DPTAHAEIMALRQGGLVMQNYRLIDATLYVTFEPCVMCAGAMIHSRIGRVV

FGVKNAKTGAAGSLMDVLHYPGMNHRVEITEGILADECNGLLSYFFRMRRQ

VFKAQKKAQSSTD ecTadA (R26Q, L84F, A106V, D108N, H123Y, A142N, D147Y, E155V, I156F) - result of evolution #9

(SEQ ID NO: 79)
SEVEFSHEYWMRHALTLAKRAWDEQEVPVGAVLVHNNRVIGEGWNRPIGRH

DPTAHAEIMALRQGGLVMQNYRLIDATLYVTFEPCVMCAGAMIHSRIGRVV

FGVRNAKTGAAGSLMDVLHYPGMNHRVEITEGILADECNALLSYFFRMRRQ

VFKAQKKAQSSTD ecTadA (E25M, R26G, L84F, A106V, R107P, D108N, H123Y, A142N, A143D, D147Y, E155V, I156F) - result of evolution #4

(SEQ ID NO: 80)
SEVEFSHEYWMRHALTLAKRAWDMGEVPVGAVLVHNNRVIGEGWNRPIGRH

DPTAHAEIMALRQGGLVMQNYRLIDATLYVTFEPCVMCAGAMIHSRIGRVV

FGV<u>P</u>NAKTGAAGSLMDVL<u>H</u>YPGMNHRVEITEGILADEC<u>N</u>DLLS<u>Y</u>FFRMRRQ

V<u>F</u>KAQKKAQSSTD ecTadA (R26C, L84F, A106V, R107H, D108N, H123Y, A142N, D147Y, E155V, I156F) - result of evolution #4
(SEQ ID NO: 81)
SEVEFSHEYWMRHALTLAKRAWDE<u>C</u>EVPVGAVLVHNNRVIGEGWNRPIGRH DPTAHAEIMALRQGGLVMQNYRLIDATLYVT<u>F</u>EPCVMCAGAMIHSRIGRVV FGV<u>H</u>NAKTGAAGSLMDVL<u>H</u>YPGMNHRVEITEGILADEC<u>N</u>ALLS<u>Y</u>FFRMRRQ V<u>F</u>KAQKKAQSSTD ecTadA (L84F, A106V, D108N, H123Y, A142N, A143L, D147Y, E155V, I156F) - result of evolution #4
(SEQ ID NO: 82)
SEVEFSHEYWMRHALTLAKRAWDEREVPVGAVLVHNNRVIGEGWNRPIGRH DPTAHAEIMALRQGGLVMQNYRLIDATLYVT<u>F</u>EPCVMCAGAMIHSRIGRVV FGV<u>R</u>NAKTGAAGSLMDVL<u>H</u>YPGMNHRVEITEGILADEC<u>N</u>LLLS<u>Y</u>FFRMRRQ V<u>F</u>KAQKKAQSSTD ecTadA (R26G, L84F, A106V, D108N, H123Y, A142N, D147Y, E155V, I156F) - result of evolution #4
(SEQ ID NO: 83)
SEVEFSHEYWMRHALTLAKRAWDE<u>G</u>EVPVGAVLVHNNRVIGEGWNRPIGRH DPTAHAEIMALRQGGLVMQNYRLIDATLYVT<u>F</u>EPCVMCAGAMIHSRIGRVV FGV<u>R</u>NAKTGAAGSLMDVL<u>H</u>YPGMNHRVEITEGILADEC<u>N</u>ALLS<u>Y</u>FFRMRRQ V<u>F</u>KAQKKAQSSTD ecTadA (E25A, R26G, L84F, A106V, R107N, D108N, H123Y, A142N, A143E, D147Y, E155V, I156F) - result of evolution #4
(SEQ ID NO: 420)
SEVEFSHEYWMRHALTLAKRAWD<u>A</u>GEVPVGAVLVHNNRVIGEGWNRPIGRH DPTAHAEIMALRQGGLVMQNYRLIDATLYVT<u>F</u>EPCVMCAGAMIHSRIGRVV FGV<u>NN</u>AKTGAAGSLMDVL<u>H</u>YPGMNHRVEITEGILADEC<u>N</u>ELLS<u>Y</u>FFRMRRQ V<u>F</u>KAQKKAQSSTD ecTadA (L84F, A106V, D108N, H123Y, D147Y, E155V, I156F) - mutations from evolution #'s 1-3
(SEQ ID NO: 421)
SEVEFSHEYWMRHALTLAKRAWDEREVPVGAVLVH<u>N</u>NRVIGEGWNRPIGRH DPTAHAEIMALRQGGLVMQNYRLIDATLYVT<u>F</u>EPCVMCAGAMIHSRIGRVV FGV<u>R</u>NAKTGAAGSLMDVL<u>H</u>YPGMNHRVEITEGILADECAALLS<u>Y</u>FFRMRRQ V<u>F</u>KAQKKAQSSTD ecTadA (N37T, P48T, L84F, A106V, D108N, H123Y, D147Y, E155V, I156F) - mutations from evolution #5-1
(SEQ ID NO: 422)
SEVEFSHEYWMRHALTLAKRAWDEREVPVGAVLVH<u>T</u>NRVIGEGWNR<u>T</u>IGRH DPTAHAEIMALRQGGLVMQNYRLIDATLYVT<u>F</u>EPCVMCAGAMIHSRIGRVV FGV<u>R</u>NAKTGAAGSLMDVL<u>H</u>YPGMNHRVEITEGILADECAALLS<u>Y</u>FFRMRRQ V<u>F</u>KAQKKAQSSTD ecTadA (N37S, L84F, A106V, D108N, H123Y, D147Y, E155V, I156F) - mutations from evolution #5-2
(SEQ ID NO: 423)
SEVEFSHEYWMRHALTLAKRAWDEREVPVGAVLVH<u>S</u>NRVIGEGWNRPIGRH DPTAHAEIMALRQGGLVMQNYRLIDATLYVT<u>F</u>EPCVMCAGAMIHSRIGRVV FGV<u>R</u>NAKTGAAGSLMDVL<u>H</u>YPGMNHRVEITEGILADECAALLS<u>Y</u>FFRMRRQ V<u>F</u>KAQKKAQSSTD ecTadA (H36L, L84F, A106V, D108N, H123Y, D147Y, E155V, I156F) - mutations from evolution #5-3
(SEQ ID NO: 424)
SEVEFSHEYWMRHALTLAKRAWDEREVPVGAVLV<u>L</u>NNRVIGEGWNRPIGRH DPTAHAEIMALRQGGLVMQNYRLIDATLYVT<u>F</u>EPCVMCAGAMIHSRIGRVV FGV<u>R</u>NAKTGAAGSLMDVL<u>H</u>YPGMNHRVEITEGILADECAALLS<u>Y</u>FFRMRRQ V<u>F</u>KAQKKAQSSTD ecTadA (L84F, A106V, D108N, H123Y, S146R, D147Y, E155V, I156F) - mutations from evolution # 5-4
(SEQ ID NO: 425)
SEVEFSHEYWMRHALTLAKRAWDEREVPVGAVLVHNNRVIGEGWNRPIGRH DPTAHAEIMALRQGGLVMQNYRLIDATLYVT<u>F</u>EPCVMCAGAMIHSRIGRVV FGV<u>R</u>NAKTGAAGSLMDVL<u>H</u>YPGMNHRVEITEGILADECAALL<u>R</u>Y<u>F</u>FRMRRQ V<u>F</u>KAQKKAQSSTD ecTadA (H36L, P48L, L84F, A106V, D108N, H123Y, D147Y, E155V, I156F) - mutations from evolution # 5-5
(SEQ ID NO: 426)
SEVEFSHEYWMRHALTLAKRAWDEREVPVGAVLV<u>L</u>NNRVIGEGWNR<u>L</u>IGRH DPTAHAEIMALRQGGLVMQNYRLIDATLYVT<u>F</u>EPCVMCAGAMIHSRIGRVV FGV<u>R</u>NAKTGAAGSLMDVL<u>H</u>YPGMNHRVEITEGILADECAALLS<u>Y</u>FFRMRRQ V<u>F</u>KAQKKAQSSTD ecTadA (H36L, L84F, A106V, D108N, H123Y, D147Y, E155V, K57N, I156F) - mutations from evolution #5-6
(SEQ ID NO: 427)
SEVEFSHEYWMRHALTLAKRAWDEREVPVGAVLV<u>L</u>NNRVIGEGWNRPIGRH DPTAHAEIMALRQGGLVMQNYRLIDATLYVT<u>F</u>EPCVMCAGAMIHSRIGRVV FGV<u>R</u>NAKTGAAGSLMDVL<u>H</u>YPGMNHRVEITEGILADECAALLS<u>Y</u>FFRMRRQ V<u>FN</u>AQKKAQSSTD ecTadA (H36L, L84F, A106V, D108N, H123Y, S146C, D147Y, E155V, I156F) - mutations from evolution # 5-7
(SEQ ID NO: 428)
SEVEFSHEYWMRHALTLAKRAWDEREVPVGAVLV<u>L</u>NNRVIGEGWNRPIGRH DPTAHAEIMALRQGGLVMQNYRLIDATLYVT<u>F</u>EPCVMCAGAMIHSRIGRVV FGV<u>R</u>NAKTGAAGSLMDVL<u>H</u>YPGMNHRVEITEGILADECAALL<u>C</u>Y<u>F</u>FRMRRQ V<u>F</u>KAQKKAQSSTD ecTadA (L84F, A106V, D108N, H123Y, S146R, D147Y, E155V, I156F) - mutations from evolution # 5-8
(SEQ ID NO: 429)
SEVEFSHEYWMRHALTLAKRAWDEREVPVGAVLVHNNRVIGEGWNRPIGRH DPTAHAEIMALRQGGLVMQNYRLIDATLYVT<u>F</u>EPCVMCAGAMIHSRIGRVV FGV<u>R</u>NAKTGAAGSLMDVL<u>H</u>YPGMNHRVEITEGILADECAALL<u>R</u>Y<u>F</u>FRMRRQ V<u>F</u>KAQKKAQSSTD ecTadA (N37S, R51H, L84F, A106V, D108N, H123Y, D147Y, E155V, I156F) - mutations from evolution # 5-9
(SEQ ID NO: 430)
SEVEFSHEYWMRHALTLAKRAWDEREVPVGAVLVH<u>S</u>NRVIGEGWNRPIG<u>HH</u>

DPTAHAEIMALRQGGLVMQNYRLIDATLYVT<u>F</u>EPCVMCAGAMIHSRIGRVV

-continued

```
FGVRNAKTGAAGSLMDVLHYPGMNHRVEITEGILADECAALLSYFFRMRRQ

VFKAQKKAQSSTD ecTadA (R51L, L84F, A106V, D108N, H123Y, D147Y,
E155V, I156F, K157N) - mutations from evolution
# 5-10
                                  (SEQ ID NO: 431)
SEVEFSHEYWMRHALTLAKRAWDEREVPVGAVLVHNNRVIGEGWNRPIGLH

DPTAHAEIMALRQGGLVMQNYRLIDATLYVTFEPCVMCAGAMIHSRIGRVV

FGVRNAKTGAAGSLMDVLHYPGMNHRVEITEGILADECAALLSYFFRMRRQ

VFNAQKKAQSSTD ecTadA (R51H, L84F, A106V, D108N, H123Y, D147Y,
E155V, I156F, K157N) - mutations from evolution
# 5-11
                                  (SEQ ID NO: 432)
SEVEFSHEYWMRHALTLAKRAWDEREVPVGAVLVHNNRVIGEGWNRPIGHH

DPTAHAEIMALRQGGLVMQNYRLIDATLYVTFEPCVMCAGAMIHSRIGRVV

FGVRNAKTGAAGSLMDVLHYPGMNHRVEITEGILADECAALLSYFFRMRRQ

VFNAQKKAQSSTD saTadA (wt) - as used in pNMG-345:
                                    (SEQ ID NO: 8)
MGSHMTNDIYFMTLAIEEAKKAAQLGEVPIGAIITKDDEVIARAHNLRETL

QQPTAHAEHIAIERAAKVLGSWRLEGCTLYVTLEPCVMCAGTIVMSRIPRV

VYGADDPKGGCSGSLMNLLQQSNFNHRAIVDKGVLKEACSTLLTTFFKNLR

ANKKSTN saTadA (D108N) - as used in pNMG-346:
                                  (SEQ ID NO: 433)
GSHMTNDIYFMTLAIEEAKKAAQLGEVPIGAIITKDDEVIARAHNLRETLQ

QPTAHAEHIAIERAAKVLGSWRLEGCTLYVTLEPCVMCAGTIVMSRIPRVV

YGADNPKGGCSGSLMNLLQQSNFNHRAIVDKGVLKEACSTLLTTFFKNLRA

NKKSTN saTadA (D107A_D108N) - as used in pNMG-347:
                                  (SEQ ID NO: 434)
GSHMTNDIYFMTLAIEEAKKAAQLGEVPIGAIITKDDEVIARAHNLRETLQ

QPTAHAEHIAIERAAKVLGSWRLEGCTLYVTLEPCVMCAGTIVMSRIPRVV

YGAANPKGGCSGSLMNLLQQSNFNHRAIVDKGVLKEACSTLLTTFFKNLRA

NKKSTN saTadA (G26P_D107A_D108N) - as used in pNMG-348:
                                  (SEQ ID NO: 435)
GSHMTNDIYFMTLAIEEAKKAAQLPEVPIGAIITKDDEVIARAHNLRETLQ

QPTAHAEHIAIERAAKVLGSWRLEGCTLYVTLEPCVMCAGTIVMSRIPRVV

YGAANPKGGCSGSLMNLLQQSNFNHRAIVDKGVLKEACSTLLTTFFKNLRA

NKKSTN saTadA (G26P_D107A_D108N_S142A) - as used in
pNMG-349:
                                  (SEQ ID NO: 436)
GSHMTNDIYFMTLAIEEAKKAAQLPEVPIGAIITKDDEVIARAHNLRETLQ

QPTAHAEHIAIERAAKVLGSWRLEGCTLYVTLEPCVMCAGTIVMSRIPRVV

YGAANPKGGCSGSLMNLLQQSNFNHRAIVDKGVLKEACATLLTTFFKNLRA

NKKSTN saTadA (D107A_D108N_S142A) - as used in pNMG-350:
                                  (SEQ ID NO: 437)
GSHMTNDIYFMTLAIEEAKKAAQLGEVPIGAIITKDDEVIARAHNLRETLQ

QPTAHAEHIAIERAAKVLGSWRLEGCTLYVTLEPCVMCAGTIVMSRIPRVV

YGAANPKGGCSGSLMNLLQQSNFNHRAIVDKGVLKEACATLLTTFFKNLRA

NKKSTN ecTadA (P48S) - mutation from evolution #6
                                  (SEQ ID NO: 672)
SEVEFSHEYWMRHALTLAKRAWDEREVPVGAVLVHNNRVIGEGWNRSIGRH

DPTAHAEIMALRQGGLVMQNYRLIDATLYVTLEPCVMCAGAMIHSRIGRVV

FGARDAKTGAAGSLMDVLHHPGMNHRVEITEGILADECAALLSDFFRMRRQ

EIKAQKKAQSSTD ecTadA (P48T) - mutation from evolution #6
                                  (SEQ ID NO: 673)
SEVEFSHEYWMRHALTLAKRAWDEREVPVGAVLVHNNRVIGEGWNRTIGRH

DPTAHAEIMALRQGGLVMQNYRLIDATLYVTLEPCVMCAGAMIHSRIGRVV

FGARDAKTGAAGSLMDVLHHPGMNHRVEITEGILADECAALLSDFFRMRRQ

EIKAQKKAQSSTD ecTadA (P48A) - mutation from evolution #6
                                  (SEQ ID NO: 674)
SEVEFSHEYWMRHALTLAKRAWDEREVPVGAVLVHNNRVIGEGWNRAIGRH

DPTAHAEIMALRQGGLVMQNYRLIDATLYVTLEPCVMCAGAMIHSRIGRVV

FGARDAKTGAAGSLMDVLHHPGMNHRVEITEGILADECAALLSDFFRMRRQ

EIKAQKKAQSSTD ecTadA (A142N) - mutation from evolution #6
                                  (SEQ ID NO: 675)
SEVEFSHEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGARDAKTGAAGSLMDVLHHPGMNHRVEITEGILADECNALLSDFFRMRRQ

EIKAQKKAQSSTD ecTadA (W23R) - mutation from evolution #7
                                  (SEQ ID NO: 676)
SEVEFSHEYWMRHALTLAKRARDEREVPVGAVLVHNNRVIGEGWNRPIGRH

DPTAHAEIMALRQGGLVMQNYRLIDATLYVTLEPCVMCAGAMIHSRIGRVV

FGARDAKTGAAGSLMDVLHHPGMNHRVEITEGILADECAALLSDFFRMRRQ

EIKAQKKAQSSTD ecTadA (W23L) - mutation from evolution #7
                                  (SEQ ID NO: 677)
SEVEFSHEYWMRHALTLAKRALDEREVPVGAVLVHNNRVIGEGWNRPIGRH

DPTAHAEIMALRQGGLVMQNYRLIDATLYVTLEPCVMCAGAMIHSRIGRVV

FGARDAKTGAAGSLMDVLHHPGMNHRVEITEGILADECAALLSDFFRMRRQ

EIKAQKKAQSSTD ecTadA (R152P) - mutation from evolution #7
                                  (SEQ ID NO: 678)
SEVEFSHEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGARDAKTGAAGSLMDVLHHPGMNHRVEITEGILADECAALLSDFFRMPRQ

EIKAQKKAQSSTD
``` ecTadA (R152H) - mutation from evolution #7
(SEQ ID NO: 679)
SEVEFSHEYWMRHALTLAKRAWDEREVPVGAVLVHNNRVIGEGWNRPIGRH

DPTAHAEIMALRQGGLVMQNYRLIDATLYVTLEPCVMCAGAMIHSRIGRVV

FGARDAKTGAAGSLMDVLHHPGMNHRVEITEGILADECAALLSDFFRMHRQ

EIKAQKKAQSSTD ecTadA (L84F, A106V, D108N, H123Y, D147Y, E155V, I156F) - mutations from pNMG 371
(SEQ ID NO: 680)
SEVEFSHEYWMRHALTLAKRAWDEREVPVGAVLVHNNRVIGEGWNRPIGRH

DPTAHAEIMALRQGGLVMQNYRLIDATLYVTFEPCVMCAGAMIHSRIGRVV

FGVRNAKTGAAGSLMDVLHYPGMNHRVEITEGILADECAALLSYFFRMRRQ

VFKAQKKAQSSTD ecTadA (H36L, R51L, L84F, A106V, D108N, H123Y, S146C, D147Y, E155V, I156F, K157N) - mutations from pNMG 477
(SEQ ID NO: 681)
SEVEFSHEYWMRHALTLAKRAWDEREVPVGAVLVLNNRVIGEGWNRPIGLH

DPTAHAEIMALRQGGLVMQNYRLIDATLYVTFEPCVMCAGAMIHSRIGRVV

FGVRNAKTGAAGSLMDVLHYPGMNHRVEITEGILADECAALLCYFFRMRRQ

VFNAQKKAQSSTD ecTadA (H36L, P48S, R51L, L84F, A106V, D108N, H123Y, S146C, D147Y, E155V, I156F, K157N) - mutations from pNMG 576
(SEQ ID NO: 682)
SEVEFSHEYWMRHALTLAKRAWDEREVPVGAVLVLNNRVIGEGWNRSIGLH

DPTAHAEIMALRQGGLVMQNYRLIDATLYVTFEPCVMCAGAMIHSRIGRVV

FGVRNAKTGAAGSLMDVLHYPGMNHRVEITEGILADECAALLCYFFRMRRQ

VFNAQKKAQSSTD ecTadA (H36L, P48A, R51L, L84F, A106V, D108N, H123Y, S146C, D147Y, E155V, I156F, K157N) - mutations from pNMG 586
(SEQ ID NO: 683)
SEVEFSHEYWMRHALTLAKRAWDEREVPVGAVLVLNNRVIGEGWNRAIGLH

DPTAHAEIMALRQGGLVMQNYRLIDATLYVTFEPCVMCAGAMIHSRIGRVV

FGVRNAKTGAAGSLMDVLHYPGMNHRVEITEGILADECAALLCYFFRMRRQ

VFNAQKKAQSSTD ecTadA (W23L, H36L, P48A, R51L, L84F, A106V, D108N, H123Y, S146C, D147Y, R152P, E155V, I156F, K157N) - mutations from pNMG 616
(SEQ ID NO: 684)
SEVEFSHEYWMRHALTLAKRALDEREVPVGAVLVLNNRVIGEGWNRAIGLH

DPTAHAEIMALRQGGLVMQNYRLIDATLYVTFEPCVMCAGAMIHSRIGRVV

FGVRNAKTGAAGSLMDVLHYPGMNHRVEITEGILADECAALLCYFFRMPRQ

VFNAQKKAQSSTD

Cas9 Domains of Nucleobase Editors

In some aspects, a nucleic acid programmable DNA binding protein (napDNAbp) is a Cas9 domain. Non-limiting, exemplary Cas9 domains are provided herein. The Cas9 domain may be a nuclease active Cas9 domain, a nuclease inactive Cas9 domain, or a Cas9 nickase. In some embodiments, the Cas9 domain is a nuclease active domain. For example, the Cas9 domain may be a Cas9 domain that cuts both strands of a duplexed nucleic acid (e.g., both strands of a duplexed DNA molecule). In some embodiments, the Cas9 domain comprises any one of the amino acid sequences as set forth in SEQ ID NOs: 108-357. In some embodiments the Cas9 domain comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the amino acid sequences set forth in SEQ ID NOs: 108-357. In some embodiments, the Cas9 domain comprises an amino acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more or more mutations compared to any one of the amino acid sequences set forth in SEQ ID NOs: 108-357. In some embodiments, the Cas9 domain comprises an amino acid sequence that has at least 10, at least 15, at least 20, at least 30, at least 40, at least 50, at least 60, at least 70, at least 80, at least 90, at least 100, at least 150, at least 200, at least 250, at least 300, at least 350, at least 400, at least 500, at least 600, at least 700, at least 800, at least 900, at least 1000, at least 1100, or at least 1200 identical contiguous amino acid residues as compared to any one of the amino acid sequences set forth in SEQ ID NOs: 108-357.

In some embodiments, the Cas9 domain is a nuclease-inactive Cas9 domain (dCas9). For example, the dCas9 domain may bind to a duplexed nucleic acid molecule (e.g., via a gRNA molecule) without cleaving either strand of the duplexed nucleic acid molecule. In some embodiments, the nuclease-inactive dCas9 domain comprises a D10X mutation and a H840X mutation of the amino acid sequence set forth in SEQ ID NO: 52, or a corresponding mutation in any of the amino acid sequences provided in SEQ ID NOs: 108-357, wherein X is any amino acid change. In some embodiments, the nuclease-inactive dCas9 domain comprises a D10A mutation and a H840A mutation of the amino acid sequence set forth in SEQ ID NO: 52, or a corresponding mutation in any of the amino acid sequences provided in SEQ ID NOs: 108-357. As one example, a nuclease-inactive Cas9 domain comprises the amino acid sequence set forth in SEQ ID NO: 54 (Cloning vector pPlatTET-gRNA2, Accession No. BAV54124).

MDKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRLE

ESFLVEEDKKHERHPIFGNIVDEVAYHEKYPTIYHLRKKLVDSTDKADLRL

IYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSN

FDLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSKN

GYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGN

SRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTV

KQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLS

RKLINGIRDKQSGKTILDFLKSDGFANRNFMQLIHDDSLTFKEDIQKAQVS

GQGDSLHEHIANLAGSPAIKKGILQTVKVVDELVKVMGRHKPENIVIEMAR

-continued

```
ENQTTQKGQKNSRERMKRIEEGIKELGSQILKEHPVENTQLQNEKLYLYYL

QNGRDMYVDQELDINRLSDYDVDAIVPQSFLKDDSIDNKVLTRSDKNRGKS

DNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKD

FQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGE

IVWDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMERSS

FEKNPIDFLEAKGYKEVKKDLIIKLPKYSLFELENGRKRMLASAGELQKGN

ELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKY

FDTTIDRKRYTSTKEVLDATLIHQSITGLYETRIDLSQLGGD
(SEQ ID NO: 54; see, e.g., Qi et al., "Repurposing
CRISPR as an RNA-guided platform for sequence-
specific control of gene expression." Cell.
2013; 152(5):1173-83, the entire contents of which
are incorporated herein by reference).
```

Additional suitable nuclease-inactive dCas9 domains will be apparent to those of skill in the art based on this disclosure and knowledge in the field, and are within the scope of this disclosure. Such additional exemplary suitable nuclease-inactive Cas9 domains include, but are not limited to, D10A/H840A, D10A/D839A/H840A, and D10A/D839A/H840A/N863A mutant domains (See, e.g., Prashant et al., CAS9 transcriptional activators for target specificity screening and paired nickases for cooperative genome engineering. *Nature Biotechnology*. 2013; 31(9): 833-838, the entire contents of which are incorporated herein by reference). In some embodiments the dCas9 domain comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the dCas9 domains provided herein. In some embodiments, the Cas9 domain comprises an amino acid sequences that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50, or more mutations compared to any one of the amino acid sequences set forth in SEQ ID NOs: 108-357. In some embodiments, the Cas9 domain comprises an amino acid sequence that has at least 10, at least 15, at least 20, at least 30, at least 40, at least 50, at least 60, at least 70, at least 80, at least 90, at least 100, at least 150, at least 200, at least 250, at least 300, at least 350, at least 400, at least 500, at least 600, at least 700, at least 800, at least 900, at least 1000, at least 1100, or at least 1200 identical contiguous amino acid residues as compared to any one of the amino acid sequences set forth in SEQ ID NOs: 108-357.

In some embodiments, the Cas9 domain is a Cas9 nickase. The Cas9 nickase may be a Cas9 protein that is capable of cleaving only one strand of a duplexed nucleic acid molecule (e.g., a duplexed DNA molecule). In some embodiments the Cas9 nickase cleaves the target strand of a duplexed nucleic acid molecule, meaning that the Cas9 nickase cleaves the strand that is base paired to (complementary to) a gRNA (e.g., an sgRNA) that is bound to the Cas9. In some embodiments, a Cas9 nickase comprises a D10A mutation and has a histidine at position 840 of SEQ ID NO: 52, or a mutation in any of SEQ ID NOs: 108-357. As one example, a Cas9 nickase may comprise the amino acid sequence as set forth in SEQ ID NO: 35. In some embodiments, the Cas9 nickase cleaves the non-target, non-base-edited strand of a duplexed nucleic acid molecule, meaning that the Cas9 nickase cleaves the strand that is not base paired to a gRNA (e.g., an sgRNA) that is bound to the Cas9. In some embodiments, a Cas9 nickase comprises an H840A mutation and has an aspartic acid residue at position 10 of SEQ ID NO: 52, or a corresponding mutation in any of SEQ ID NOs: 108-357. In some embodiments the Cas9 nickase comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the Cas9 nickases provided herein. Additional suitable Cas9 nickases will be apparent to those of skill in the art based on this disclosure and knowledge in the field, and are within the scope of this disclosure.

Cas9 Domains with Reduced PAM Exclusivity

Some aspects of the disclosure provide Cas9 domains that have different PAM specificities. Typically, Cas9 proteins, such as Cas9 from *S. pyogenes* (spCas9), require a canonical NGG PAM sequence to bind a particular nucleic acid region, where the "N" in "NGG" is adenine (A), thymine (T), guanine (G), or cytosine (C), and the G is guanine. This may limit the ability to edit desired bases within a genome. In some embodiments, the base editing fusion proteins provided herein need to be positioned at a precise location, for example, where a target base is within a 4 base region (e.g., a "deamination window"), which is approximately 15 bases upstream of the PAM. See Komor, A. C., et al., "Programmable editing of a target base in genomic DNA without double-stranded DNA cleavage" *Nature* 533, 420-424 (2016), the entire contents of which are hereby incorporated by reference. In some embodiments, the deamination window is within a 2, 3, 4, 5, 6, 7, 8, 9, or 10 base region. In some embodiments, the deamination window is 5, 6, 7, 8, 9, 10, 11, 12, 13, 14, 15, 16, 17, 18, 19, 20, 21, 22, 23, 24, or 25 bases upstream of the PAM. Accordingly, in some embodiments, any of the fusion proteins provided herein may contain a Cas9 domain that is capable of binding a nucleotide sequence that does not contain a canonical (e.g., NGG) PAM sequence. Cas9 domains that bind to non-canonical PAM sequences have been described in the art and would be apparent to the skilled artisan. For example, Cas9 domains that bind non-canonical PAM sequences have been described in Kleinstiver, B. P., et al., "Engineered CRISPR-Cas9 nucleases with altered PAM specificities" *Nature* 523, 481-485 (2015); and Kleinstiver, B. P., et al., "Broadening the targeting range of *Staphylococcus aureus* CRISPR-Cas9 by modifying PAM recognition" *Nature Biotechnology* 33, 1293-1298 (2015); the entire contents of each are hereby incorporated by reference.

In some embodiments, the Cas9 domain is a Cas9 domain from *Staphylococcus aureus* (SaCas9). In some embodiments, the SaCas9 domain is a nuclease active SaCas9, a nuclease inactive SaCas9 (SaCas9d), or a SaCas9 nickase (SaCas9n). In some embodiments, the SaCas9 comprises the amino acid sequence SEQ ID NO: 55. In some embodiments, the SaCas9 comprises a N579X mutation of SEQ ID NO: 55, or a corresponding mutation in any of the amino acid sequences provided in SEQ ID NOs: 108-357, wherein X is any amino acid except for N. In some embodiments, the SaCas9 comprises a N579A mutation of SEQ ID NO: 55, or a corresponding mutation in any of the amino acid sequences provided in SEQ ID NOs: 108-357.

In some embodiments, the SaCas9 domain, the SaCas9d domain, or the SaCas9n domain can bind to a nucleic acid sequence having a non-canonical PAM. In some embodiments, the SaCas9 domain, the SaCas9d domain, or the SaCas9n domain can bind to a nucleic acid sequence having a NNGRRT PAM sequence, where N=A, T, C, or G, and R=A or G. In some embodiments, the SaCas9 domain comprises one or more of E781X, N967X, and R1014X mutation of SEQ ID NO: 55, or a corresponding mutation in any of the amino acid sequences provided in SEQ ID NOs: 108-357, wherein X is any amino acid. In some embodiments, the SaCas9 domain comprises one or more of a E781K, a N967K, and a R1014H mutation of SEQ ID NO: 55, or one or more corresponding mutation in any of the amino acid sequences provided in SEQ ID NOs: 108-357. In some embodiments, the SaCas9 domain comprises a E781K, a N967K, or a R1014H mutation of SEQ ID NO: 55, or corresponding mutations in any of the amino acid sequences provided in SEQ ID NOs: 108-357.

In some embodiments, the Cas9 domain of any of the fusion proteins provided herein comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of SEQ ID NOs: 55-57. In some embodiments, the Cas9 domain of any of the fusion proteins provided herein comprises the amino acid sequence of any one of SEQ ID NOs: 55-57. In some embodiments, the Cas9 domain of any of the fusion proteins provided herein consists of the amino acid sequence of any one of SEQ ID NOs: 55-57.

Exemplary SaCas9 sequence
(SEQ ID NO: 55)
KRNYILGLDIGITSVGYGIIDYETRDVIDAGVRLFKEANVENNEGRRSKRG

ARRLKRRRRHRIQRVKKLLFDYNLLTDHSELSGINPYEARVKGLSQKLSEE

EFSAALLHLAKRRGVHNVNEVEEDTGNELSTKEQISRNSKALEEKYVAELQ

LERLKKDGEVRGSINRFKTSDYVKEAKQLLKVQKAYHQLDQSFIDTYIDLL

ETRRTYYEGPGEGSPFGWKDIKEWYEMLMGHCTYFPEELRSVKYAYNADLY

NALNDLNNLVITRDENEKLEYYEKFQIIENVFKQKKKPTLKQIAKEILVNE

EDIKGYRVTSTGKPEFTNLKVYHDIKDITARKEIIENAELLDQIAKILTIY

QSSEDIQEELTNLNSELTQEEIEQISNLKGYTGTHNLSLKAINLILDELWH

TNDNQIAIFNRLKLVPKKVDLSQQKEIPTTLVDDFILSPVVKRSFIQSIKV

INAIIKKYGLPNDIIIELAREKNSKDAQKMINEMQKRNRQTNERIEEIIRT

TGKENAKYLIEKIKLHDMQEGKCLYSLEAIPLEDLLNNPFNYEVDHIIPRS

VSFDNSFNNKVLVKQEENSKKGNRTPFQYLSSSDSKISYETFKKHILNLAK

GKGRISKTKKEYLLEERDINRFSVQKDFINRNLVDTRYATRGLMNLLRSYF

RVNNLDVKVKSINGGFTSFLRRKWKFKKERNKGYKHHAEDALIIANADFIF

KEWKKLDKAKKVMENQMFEEKQAESMPEIETEQEYKEIFITPHQIKHIKDF

KDYKYSHRVDKKPNRELINDTLYSTRKDDKGNTLIVNNLNGLYDKDNDKLK

KLINKSPEKLLMYHHDPQTYQKLKLIMEQYGDEKNPLYKYYEETGNYLTKY

SKKDNGPVIKKIKYYGNKLNAHLDITDDYPNSRNKVVKLSLKPYRFDVYLD

NGVYKFVTVKNLDVIKKENYYEVNSKCYEEAKKLKKISNQAEFIASFYNND

LIKINGELYRVIGVNNDLLNRIEVNMIDITYREYLENMNDKRPPRIIKTIA

SKTQSIKKYSTDILGNLYEVKSKKHPQIIKKG

Residue N579 of SEQ ID NO: 55, which is underlined and in bold, may be mutated (e.g., to a A579) to yield a SaCas9 nickase.

Exemplary SaCas9n sequence
(SEQ ID NO: 56)
KRNYILGLDIGITSVGYGIIDYETRDVIDAGVRLFKEANVENNEGRRSKRG

ARRLKRRRRHRIQRVKKLLFDYNLLTDHSELSGINPYEARVKGLSQKLSEE

EFSAALLHLAKRRGVHNVNEVEEDTGNELSTKEQISRNSKALEEKYVAELQ

LERLKKDGEVRGSINRFKTSDYVKEAKQLLKVQKAYHQLDQSFIDTYIDLL

ETRRTYYEGPGEGSPFGWKDIKEWYEMLMGHCTYFPEELRSVKYAYNADLY

NALNDLNNLVITRDENEKLEYYEKFQIIENVFKQKKKPTLKQIAKEILVNE

EDIKGYRVTSTGKPEFTNLKVYHDIKDITARKEIIENAELLDQIAKILTIY

QSSEDIQEELTNLNSELTQEEIEQISNLKGYTGTHNLSLKAINLILDELWH

TNDNQIAIFNRLKLVPKKVDLSQQKEIPTTLVDDFILSPVVKRSFIQSIKV

INAIIKKYGLPNDIIIELAREKNSKDAQKMINEMQKRNRQTNERIEEIIRT

TGKENAKYLIEKIKLHDMQEGKCLYSLEAIPLEDLLNNPFNYEVDHIIPRS

VSFDNSFNNKVLVKQEEASKKGNRTPFQYLSSSDSKISYETFKKHILNLAK

GKGRISKTKKEYLLEERDINRFSVQKDFINRNLVDTRYATRGLMNLLRSYF

RVNNLDVKVKSINGGFTSFLRRKWKFKKERNKGYKHHAEDALIIANADFIF

KEWKKLDKAKKVMENQMFEEKQAESMPEIETEQEYKEIFITPHQIKHIKDF

KDYKYSHRVDKKPNRELINDTLYSTRKDDKGNTLIVNNLNGLYDKDNDKLK

KLINKSPEKLLMYHHDPQTYQKLKLIMEQYGDEKNPLYKYYEETGNYLTKY

SKKDNGPVIKKIKYYGNKLNAHLDITDDYPNSRNKVVKLSLKPYRFDVYLD

NGVYKFVTVKNLDVIKKENYYEVNSKCYEEAKKLKKISNQAEFIASFYNND

LIKINGELYRVIGVNNDLLNRIEVNMIDITYREYLENMNDKRPPRIIKTIA

SKTQSIKKYSTDILGNLYEVKSKKHPQIIKKG.

Residue A579 of SEQ ID NO: 56, which can be mutated from N579 of SEQ ID NO: 55 to yield a SaCas9 nickase, is underlined and in bold.

Exemplary SaKKH Cas9
(SEQ ID NO: 57)
KRNYILGLDIGITSVGYGIIDYETRDVIDAGVRLFKEANVENNEGRRSKRG

ARRLKRRRRHRIQRVKKLLFDYNLLTDHSELSGINPYEARVKGLSQKLSEE

EFSAALLHLAKRRGVHNVNEVEEDTGNELSTKEQISRNSKALEEKYVAELQ

LERLKKDGEVRGSINTRFKTSDYVKEAKQLLKVQKAYHQLDQSFIDTYIDL

LETRRTYYEGPGEGSPFGWKDIKEWYEMLMGHCTYFPEELRSVKYAYNADL

YNALNDLNNLVITRDENEKLEYYEKFQIIENVFKQKKKPTLKQIAKEILVN

EEDIKGYRVTSTGKPEFTNLKVYHDIKDITARKEIIENAELLDQIAKILTI

YQSSEDIQEELTNLNSELTQEEIEQISNLKGYTGTHNLSLKAINLILDELW

HTNDNQIAIFNRLKLVPKKVDLSQQKEIPTTLVDDFILSPVVKRSFIQSIK

-continued

VINAIIKKYGLPNDIIIELAREKNSKDAQKMINEMQKRNRQTNERIEEIIR

TTGKENAKYLIEKIKLHDMQEGKCLYSLEAIPLEDLLNNPFNYEVDHIIPR

SVSFDNSFNNKVLVKQEEASKKGNRTPFQYLSSSDSKISYETFKKHILNLA

KGKGRISKTKKEYLLEERDINRFSVQKDFINRNLVDTRYATRGLMNLLRSY

FRVNNLDVKVKSINGGFTSFLRRKWKFKKERNKGYKHHAEDALIIANADFI

FKEWKKLDKAKKVMENQMFEEKQAESMPEIETEQEYKEIFITPHQIKHIKD

FKDYKYSHRVDKKPNR*K*LINDTLYSTRKDDKGNTLIVNNLNGLYDKDNDKL

KKLINKSPEKLLMYHHDPQTYQKLKLIMEQYGDEKNPLYKYYEETGNYLTK

YSKKDNGPVIKKIKYYGNKLNAHLDITDDYPNSRNKVVKLSLKPYRFDVYL

DNGVYKFVTVKNLDVIKKENYYEVNSKCYEEAKKLKKISNQAEFIASFYKN

DLIKINGELYRVIGVNNDLLNRIEVNMIDITYREYLENMNDKRPP*H*IIKTI

ASKTQSIKKYSTDILGNLYEVKSKKHPQIIKKG.

Residue A579 of SEQ ID NO: 57, which can be mutated from N579 of SEQ ID NO: 55 to yield a SaCas9 nickase, is underlined and in bold. Residues K781, K967, and H1014 of SEQ ID NO: 57, which can be mutated from E781, N967, and R1014 of SEQ ID NO: 55 to yield a SaKKH Cas9 are underlined and in italics.

In some embodiments, the Cas9 domain is a Cas9 domain from *Streptococcus pyogenes* (SpCas9). In some embodiments, the SpCas9 domain is a nuclease active SpCas9, a nuclease inactive SpCas9 (SpCas9d), or a SpCas9 nickase (SpCas9n). In some embodiments, the SpCas9 comprises the amino acid sequence SEQ ID NO: 58. In some embodiments, the SpCas9 comprises a D9X mutation of SEQ ID NO: 58, or a corresponding mutation in any of the amino acid sequences provided in SEQ ID NOs: 108-357, wherein X is any amino acid except for D. In some embodiments, the SpCas9 comprises a D9A mutation of SEQ ID NO: 58, or a corresponding mutation in any of the amino acid sequences provided in SEQ ID NOs: 108-357. In some embodiments, the SpCas9 domain, the SpCas9d domain, or the SpCas9n domain can bind to a nucleic acid sequence having a non-canonical PAM. In some embodiments, the SpCas9 domain, the SpCas9d domain, or the SpCas9n domain can bind to a nucleic acid sequence having a NGG, a NGA, or a NGCG PAM sequence. In some embodiments, the SpCas9 domain comprises one or more of a D1134X, a R1334X, and a T1336X mutation of SEQ ID NO: 58, or a corresponding mutation in any of the amino acid sequences provided in SEQ ID NOs: 108-35, wherein X is any amino acid. In some embodiments, the SpCas9 domain comprises one or more of a D1134E, R1334Q, and T1336R mutation of SEQ ID NO: 58, or a corresponding mutation in any of the amino acid sequences provided in SEQ ID NOs: 108-35. In some embodiments, the SpCas9 domain comprises a D1134E, a R1334Q, and a T1336R mutation of SEQ ID NO: 58, or corresponding mutations in any of the amino acid sequences provided in SEQ ID NOs: 108-35. In some embodiments, the SpCas9 domain comprises one or more of a D1134X, a R1334X, and a T1336X mutation of SEQ ID NO: 58, or a corresponding mutation in any of the amino acid sequences provided in SEQ ID NOs: 108-35, wherein X is any amino acid. In some embodiments, the SpCas9 domain comprises one or more of a D1134V, a R1334Q, and a T1336R mutation of SEQ ID NO: 58, or a corresponding mutation in any of the amino acid sequences provided in SEQ ID NOs: 108-35. In some embodiments, the SpCas9 domain comprises a D1134V, a R1334Q, and a T1336R mutation of SEQ ID NO: 58, or corresponding mutations in any of the amino acid sequences provided in SEQ ID NOs: 108-35. In some embodiments, the SpCas9 domain comprises one or more of a D1134X, a G1217X, a R1334X, and a T1336X mutation of SEQ ID NO: 58, or a corresponding mutation in any of the amino acid sequences provided in SEQ ID NOs: 108-35, wherein X is any amino acid. In some embodiments, the SpCas9 domain comprises one or more of a D1134V, a G1217R, a R1334Q, and a T1336R mutation of SEQ ID NO: 58, or a corresponding mutation in any of the amino acid sequences provided in SEQ ID NOs: 108-35. In some embodiments, the SpCas9 domain comprises a D1134V, a G1217R, a R1334Q, and a T1336R mutation of SEQ ID NO: 58, or corresponding mutations in any of the amino acid sequences provided in SEQ ID NOs: 108-35.

In some embodiments, the Cas9 domain of any of the fusion proteins provided herein comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of SEQ ID NOs: 58-62. In some embodiments, the Cas9 domain of any of the fusion proteins provided herein comprises the amino acid sequence of any one of SEQ ID NOs: 58-62. In some embodiments, the Cas9 domain of any of the fusion proteins provided herein consists of the amino acid sequence of any one of SEQ ID NOs: 58-62.

Exemplary SpCas9

(SEQ ID NO: 58)
DKKYSIGLDIGTNSVGWAVITDEYKVPSKKFKVLGNTDRHSIKKNLIGALL

FDSGETAEATRLKRTARRRYTRRKNRICYLQEIFSNEMAKVDDSFFHRLEE

SFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASG

VDAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDILR

VNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGS

IPHQIHLGELHAILRRQEDFYPFLKDNREKIEKILTFRIPYYVGPLARGNS

RFAWMTRKSEETITPWNFEEVVDKGASAQSFIERMTNFDKNLPNEKVLPKH

SLLYEYFTVYNELTKVKYVTEGMRKPAFLSGEQKKAIVDLLFKTNRKVTVK

QLKEDYFKKIECFDSVETSGVEDRFNASLGTYHDLLKIIKDKDFLDNEENE

DILEDIVLTLTLFEDREMIEERLKTYAHLFDDKVMKQLKRRRYTGWGRLSR

KLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARE

NQTTQKGQKNSRERMKRIEEGIKELGSQILKEHPVENTQLQNEKLYLYYLQ

NGRDMYVDQELDINRLSDYDVDHIVPQSFLKDDSIDNKVLTRSDKNRGKSD

NVPSEEVVKKMKNYWRQLLNAKLITQRKFDNLTKAERGGLSELDKAGFIKR

QLVETRQITKHVAQILDSRMNTKYDENDKLIREVKVITLKSKLVSDFRKDF

QFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARK

```
KDWDPKKYGGFDSPTVAYSVLVVAKVEKGKSKKLKSVKELLGITIMERSSF

EKNPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYF

DTTIDRKRYTSTKEVLDATLIHQSITGLYETRIDLSQLGGD

Exemplary SpCas9n
                                (SEQ ID NO: 59)
DKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEE

SFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASG

VDAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDILR

VNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGS

IPHQIHLGELHAILRRQEDFYPFLKDNREKIEKILTFRIPYYVGPLARGNS

RFAWMTRKSEETITPWNFEEVVDKGASAQSFIERMTNFDKNLPNEKVLPKH

SLLYEYFTVYNELTKVKYVTEGMRKPAFLSGEQKKAIVDLLFKTNRKVTVK

QLKEDYFKKIECFDSVETSGVEDRFNASLGTYHDLLKIIKDKDFLDNEENE

DILEDIVLTLTLFEDREMIEERLKTYAHLFDDKVMKQLKRRRYTGWGRLSR

KLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARE

NQTTQKGQKNSRERMKRIEEGIKELGSQILKEHPVENTQLQNEKLYLYYLQ

NGRDMYVDQELDINRLSDYDVDHIVPQSFLKDDSIDNKVLTRSDKNRGKSD

NVPSEEVVKKMKNYWRQLLNAKLITQRKFDNLTKAERGGLSELDKAGFIKR

QLVETRQITKHVAQILDSRMNTKYDENDKLIREVKVITLKSKLVSDFRKDF

QFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARK

KDWDPKKYGGFDSPTVAYSVLVVAKVEKGKSKKLKSVKELLGITIMERSSF

EKNPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYF

DTTIDRKRYTSTKEVLDATLIHQSITGLYETRIDLSQLGGD

Exemplary SpEQR Cas9
                                (SEQ ID NO: 60)
DKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEE

SFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASG

VDAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDILR

VNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGS

IPHQIHLGELHAILRRQEDFYPFLKDNREKIEKILTFRIPYYVGPLARGNS

RFAWMTRKSEETITPWNFEEVVDKGASAQSFIERMTNFDKNLPNEKVLPKH

SLLYEYFTVYNELTKVKYVTEGMRKPAFLSGEQKKAIVDLLFKTNRKVTVK

QLKEDYFKKIECFDSVETSGVEDRFNASLGTYHDLLKIIKDKDFLDNEENE

DILEDIVLTLTLFEDREMIEERLKTYAHLFDDKVMKQLKRRRYTGWGRLSR

KLINGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMARE

NQTTQKGQKNSRERMKRIEEGIKELGSQILKEHPVENTQLQNEKLYLYYLQ

NGRDMYVDQELDINRLSDYDVDHIVPQSFLKDDSIDNKVLTRSDKNRGKSD

NVPSEEVVKKMKNYWRQLLNAKLITQRKFDNLTKAERGGLSELDKAGFIKR

QLVETRQITKHVAQILDSRMNTKYDENDKLIREVKVITLKSKLVSDFRKDF

QFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARK

KDWDPKKYGGFESPTVAYSVLVVAKVEKGKSKKLKSVKELLGITIMERSSF

EKNPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYF

DTTIDRKQYR**STKEVLDATLIHQSITGLYETRIDLSQLGGD
```

Residues E1134, Q1334, and R1336 of SEQ ID NO: 60, which can be mutated from D1134, R1334, and T1336 of SEQ ID NO: 58 to yield a SpEQR Cas9, are underlined and in bold.

```
Exemplary SpVQR Cas9
                                (SEQ ID NO: 61)
DKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFH

RLEESFLVEEDKKHERHPIFGNIVDEVAYHEKYPTIYHLRKKLVDSTDK

ADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSL

GLTPNFKSNFDLAEDAKLQLSKDTYDDDLDNLLAQIGDQYADLFLAAKN

LSDAILLSDILRVNTEITKAPLSASMIKRYDEHHQDLTLLKALVRQQLP

EKYKEIFFDQSKNGYAGYIDGGASQEEFYKFIKPILEKMDGTEELLVKL

NREDLLRKQRTFDNGSIPHQIHLGELHAILRRQEDFYPFLKDNREKIEK

ILTFRIPYYVGPLARGNSRFAWMTRKSEETITPWNFEEVVDKGASAQSF

IERMTNFDKNLPNEKVLPKHSLLYEYFTVYNELTKVKYVTEGMRKPAFL

SGEQKKAIVDLLFKTNRKVTVKQLKEDYFKKIECFDSVETSGVEDRFNA

SLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDG

FANRNFMQLIHDDSLTFKEDIQKAQVSGQGDSLHEHIANLAGSPAIKKG
```

```
ILQTVKVVDELVKVMGRHKPENIVIEMARENQTTQKGQKNSRERMKRIE

EGIKELGSQILKEHPVENTQLQNEKLYLYYLQNGRDMYVDQELDINRLS

DYDVDHIVPQSFLKDDSIDNKVLTRSDKNRGKSDNVPSEEVVKKMKNYW

RQLLNAKLITQRKFDNLTKAERGGLSELDKAGFIKRQLVETRQITKHVA

QILDSRMNTKYDENDKLIREVKVITLKSKLVSDFRKDFQFYKVREINNY

HHAHDAYLNAVVGTALIKKYPKLESEFVYGDYKVYDVRKMIAKSEQEIG

KATAKYFFYSNIMNFFKTEITLANGEIRKRPLIETNGETGEIVWDKGRD

FATVRKVLSMPQVNIVKKTEVQTGGFSKESILPKRNSDKLIARKKDWDP

KKYGGFVSPTVAYSVLVVAKVEKGKSKKLKSVKELLGITIMERSSFEKN

PIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAF

KYFDTTIDRKQYRSTKEVLDATLIHQSITGLYETRIDLSQLGGD
```

Residues V1134, Q1334, and R1336 of SEQ ID NO: 61, which can be mutated from D1134, R1334, and T1336 of SEQ ID NO: 58 to yield a SpVQR Cas9, are underlined and in bold.

```
Exemplary SpVRER Cas9
                                        (SEQ ID NO: 62)
DKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFH

RLEESFLVEEDKKHERHPIFGNIVDEVAYHEKYPTIYHLRKKLVDSTDK

ADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSL

GLTPNFKSNFDLAEDAKLQLSKDTYDDDLDNLLAQIGDQYADLFLAAKN

LSDAILLSDILRVNTEITKAPLSASMIKRYDEHHQDLTLLKALVRQQLP

EKYKEIFFDQSKNGYAGYIDGGASQEEFYKFIKPILEKMDGTEELLVKL

NREDLLRKQRTFDNGSIPHQIHLGELHAILRRQEDFYPFLKDNREKIEK

ILTFRIPYYVGPLARGNSRFAWMTRKSEETITPWNFEEVVDKGASAQSF

IERMTNFDKNLPNEKVLPKHSLLYEYFTVYNELTKVKYVTEGMRKPAFL

SGEQKKAIVDLLFKTNRKVTVKQLKEDYFKKIECFDSVETSGVEDRFNA

SLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDG

FANRNFMQLIHDDSLTFKEDIQKAQVSGQGDSLHEHIANLAGSPAIKKG

ILQTVKVVDELVKVMGRHKPENIVIEMARENQTTQKGQKNSRERMKRIE

EGIKELGSQILKEHPVENTQLQNEKLYLYYLQNGRDMYVDQELDINRLS

DYDVDHIVPQSFLKDDSIDNKVLTRSDKNRGKSDNVPSEEVVKKMKNYW

RQLLNAKLITQRKFDNLTKAERGGLSELDKAGFIKRQLVETRQITKHVA

QILDSRMNTKYDENDKLIREVKVITLKSKLVSDFRKDFQFYKVREINNY

HHAHDAYLNAVVGTALIKKYPKLESEFVYGDYKVYDVRKMIAKSEQEIG

KATAKYFFYSNIMNFFKTEITLANGEIRKRPLIETNGETGEIVWDKGRD

FATVRKVLSMPQVNIVKKTEVQTGGFSKESILPKRNSDKLIARKKDWDP

KKYGGFVSPTVAYSVLVVAKVEKGKSKKLKSVKELLGITIMERSSFEKN

PIDFLEAKGYKEVKKDLIIKLPKYSLFELENGRKRMLASARELQKGNEL

ALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAF

KYFDTTIDRKEYRSTKEVLDATLIHQSITGLYETRIDLSQLGGD
```

Residues V1134, R1217, Q1334, and R1336 of SEQ ID NO: 62, which can be mutated from D1134, G1217, R1334, and T1336 of SEQ ID NO: 58 to yield a SpVRER Cas9, are underlined and in bold.

High Fidelity Cas9 Domains

Some aspects of the disclosure provide high fidelity Cas9 domains of the nucleobase editors provided herein. In some embodiments, high fidelity Cas9 domains are engineered Cas9 domains comprising one or more mutations that decrease electrostatic interactions between the Cas9 domain and the sugar-phosphate backbone of DNA, as compared to a corresponding wild-type Cas9 domain. Without wishing to be bound by any particular theory, high fidelity Cas9 domains that have decreased electrostatic interactions with the sugar-phosphate backbone of DNA may have less off-target effects. In some embodiments, the Cas9 domain (e.g., a wild type Cas9 domain) comprises one or more mutations that decreases the association between the Cas9 domain and the sugar-phosphate backbone of DNA. In some embodiments, a Cas9 domain comprises one or more mutations that decreases the association between the Cas9 domain and the sugar-phosphate backbone of DNA by at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, or more.

In some embodiments, any of the Cas9 fusion proteins provided herein comprise one or more of N497X, R661X, Q695X, and/or Q926X mutation of the amino acid sequence provided in SEQ ID NO: 52, or a corresponding mutation in any of the amino acid sequences provided in SEQ ID NOs: 108-357, wherein X is any amino acid. In some embodiments, any of the Cas9 fusion proteins provided herein comprise one or more of N497A, R661A, Q695A, and/or Q926A mutation of the amino acid sequence provided in SEQ ID NO: 52, or a corresponding mutation in any of the amino acid sequences provided in SEQ ID NOs: 108-357. In some embodiments, the Cas9 domain comprises a D10A mutation of the amino acid sequence provided in SEQ ID NO: 52, or a corresponding mutation in any of the amino acid sequences provided in SEQ ID NOs: 108-357. In some embodiments, the Cas9 domain (e.g., of any of the fusion proteins provided herein) comprises the amino acid sequence as set forth in SEQ ID NO: 62. Cas9 domains with high fidelity are known in the art and would be apparent to the skilled artisan. For example, Cas9 domains with high fidelity have been described in Kleinstiver, B. P., et al. "High-fidelity CRISPR-Cas9 nucleases with no detectable genome-wide off-target effects." *Nature* 529, 490-495 (2016); and Slaymaker, I. M., et al. "Rationally engineered Cas9 nucleases with improved specificity." *Science* 351, 84-88 (2015); the entire contents of each are incorporated herein by reference.

It should be appreciated that any of the base editors provided herein, for example, any of the adenosine deaminase base editors provided herein, may be converted into high fidelity base editors by modifying the Cas9 domain as described herein to generate high fidelity base editors, for example, a high fidelity adenosine base editor. In some embodiments, the high fidelity Cas9 domain is a dCas9 domain. In some embodiments, the high fidelity Cas9 domain is a nCas9 domain.

High Fidelity Cas9 domain where mutations relative
to Cas9 of SEQ ID NO: 10 are shown in bold and
underlines
(SEQ ID NO: 63)
DKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFH

RLEESFLVEEDKKHERHPIFGNIVDEVAYHEKYPTIYHLRKKLVDSTDK

ADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSL

GLTPNFKSNFDLAEDAKLQLSKDTYDDDLDNLLAQIGDQYADLFLAAKN

LSDAILLSDILRVNTEITKAPLSASMIKRYDEHHQDLTLLKALVRQQLP

EKYKEIFFDQSKNGYAGYIDGGASQEEFYKFIKPILEKMDGTEELLVKL

NREDLLRKQRTFDNGSIPHQIHLGELHAILRRQEDFYPFLKDNREKIEK

ILTFRIPYYVGPLARGNSRFAWMTRKSEETITPWNFEEVVDKGASAQSF

IERMTAFDKNLPNEKVLPKHSLLYEYFTVYNELTKVKYVTEGMRKPAFL

SGEQKKAIVDLLFKTNRKVTVKQLKEDYFKKIECFDSVEISGVEDRFNA

SLGTYHDLLKIIKDKDFLDNEENEDILEDIVLTLTLFEDREMIEERLKT

YAHLFDDKVMKQLKRRRYTGWGALSRKLINGIRDKQSGKTILDFLKSDG

FANRNFMALIHDDSLTFKEDIQKAQVSGQGDSLHEHIANLAGSPAIKKG

ILQTVKVVDELVKVMGRHKPENIVIEMARENQTTQKGQKNSRERMKRIE

EGIKELGSQILKEHPVENTQLQNEKLYLYYLQNGRDMYVDQELDINRLS

DYDVDHIVPQSFLKDDSIDNKVLTRSDKNRGKSDNVPSEEVVKKMKNYW

RQLLNAKLITQRKFDNLTKAERGGLSELDKAGFIKRQLVETRAITKHVA

QILDSRMNTKYDENDKLIREVKVITLKSKLVSDFRKDFQFYKVREINNY

HHAHDAYLNAVVGTALIKKYPKLESEFVYGDYKVYDVRKMIAKSEQEIG

KATAKYFFYSNIMNFFKTEITLANGEIRKRPLIETNGETGEIVWDKGRD

FATVRKVLSMPQVNIVKKTEVQTGGFSKESILPKRNSDKLIARKKDWDP

KKYGGFDSPTVAYSVLVVAKVEKGKSKKLKSVKELLGITIMERSSFEKN

PIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAF

KYFDTTIDRKRYTSTKEVLDATLIHQSITGLYETRIDLSQLGGD

Nucleic Acid Programmable DNA Binding Proteins

Some aspects of the disclosure provide nucleic acid programmable DNA binding proteins, which may be used to guide a protein, such as a base editor, to a specific nucleic acid (e.g., DNA or RNA) sequence. Nucleic acid programmable DNA binding proteins include, without limitation, Cas9 (e.g., dCas9 and nCas9), CasX, CasY, Cpf1, C2c1, C2c2, C2C3, and Argonaute. One example of an nucleic acid programmable DNA-binding protein that has different PAM specificity than Cas9 is Clustered Regularly Interspaced Short Palindromic Repeats from *Prevotella* and *Francisella* 1 (Cpf1). Similar to Cas9, Cpf1 is also a class 2 CRISPR effector. It has been shown that Cpf1 mediates robust DNA interference with features distinct from Cas9. Cpf1 is a single RNA-guided endonuclease lacking tracrRNA, and it utilizes a T-rich protospacer-adjacent motif (TTN, TTTN, or YTN). Moreover, Cpf1 cleaves DNA via a staggered DNA double-stranded break. Out of 16 Cpf1-family proteins, two enzymes from Acidaminococcus and Lachnospiraceae are shown to have efficient genome-editing activity in human cells. Cpf1 proteins are known in the art and have been described previously, for example Yamano et al., "Crystal structure of Cpf1 in complex with guide RNA and target DNA." Cell (165) 2016, p. 949-962; the entire contents of which is hereby incorporated by reference.

Also useful in the present compositions and methods are nuclease-inactive Cpf1 (dCpf1) variants that may be used as a guide nucleotide sequence-programmable DNA-binding protein domain. The Cpf1 protein has a RuvC-like endonuclease domain that is similar to the RuvC domain of Cas9 but does not have a HNH endonuclease domain, and the N-terminal of Cpf1 does not have the alfa-helical recognition lobe of Cas9. It was shown in Zetsche et al., *Cell,* 163, 759-771, 2015 (which is incorporated herein by reference) that, the RuvC-like domain of Cpf1 is responsible for cleaving both DNA strands and inactivation of the RuvC-like domain inactivates Cpf1 nuclease activity. For example, mutations corresponding to D917A, E1006A, or D1255A in *Francisella novicida* Cpf1 (SEQ ID NO: 382) inactivates Cpf1 nuclease activity. In some embodiments, the dCpf1 of the present disclosure comprises mutations corresponding to D917A, E1006A, D1255A, D917A/E1006A, D917A/D1255A, E1006A/D1255A, or D917A/E1006A/D1255A in SEQ ID NO: 376. It is to be understood that any mutations, e.g., substitution mutations, deletions, or insertions that inactivate the RuvC domain of Cpf1, may be used in accordance with the present disclosure.

In some embodiments, the nucleic acid programmable DNA binding protein (napDNAbp) of any of the fusion proteins provided herein may be a Cpf1 protein. In some embodiments, the Cpf1 protein is a Cpf1 nickase (nCpf1). In some embodiments, the Cpf1 protein is a nuclease inactive Cpf1 (dCpf1). In some embodiments, the Cpf1, the nCpf1, or the dCpf1 comprises an amino acid sequence that is at least 85%, at least 90%, at least 91%, at least 92%, at least 93%, at least 94%, at least 95%, at least 96%, at least 97%, at least 98%, at least 99%, or at ease 99.5% identical to any one of SEQ ID NOs: 376-382. In some embodiments, the dCpf1 comprises an amino acid sequence that is at least 85%, at least 90%, at least 91%, at least 92%, at least 93%, at least 94%, at least 95%, at least 96%, at least 97%, at least 98%, at least 99%, or at ease 99.5% identical to any one of SEQ ID NOs: 376-382, and comprises mutations corresponding to D917A, E1006A, D1255A, D917A/E1006A, D917A/D1255A, E1006A/D1255A, or D917A/E1006A/D1255A in SEQ ID NO: 376. In some embodiments, the dCpf1 comprises an amino acid sequence of any one SEQ ID NOs: 376-382. It should be appreciated that Cpf1 from other bacterial species may also be used in accordance with the present disclosure.

Wild type *Francisella novicida* Cpf1 (SEQ ID NO: 376) (D917, E1006, and D1255 are bolded and underlined)

(SEQ ID NO: 376)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMlFDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIDRGERHLAYYTLVDG

KGNIIKQDTFNIIGNDRMKTNYHDKLAAIEKDRDSARKDWKKINNIKEMKEGYLSQV

VHEIAKLVIEYNAIVVFEDLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDADANGAYHIGLKGLMLLGRI

KNNQEGKKLNLVIKNEEYFEFVQNRNN

*Francisella novicida* Cpf1 D917A (SEQ ID NO: 377) (A917, E1006, and D1255 are bolded and underlined)

(SEQ ID NO: 377)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMEDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

-continued

FTEDKFFFHCPITINFKSSGANKFNDEINLLLKEKANDVHILSIARGERHLAYYTLVDG

KGNIIKQDTFNIIGNDRMKTNYHDKLAAIEKDRDSARKDWKKINNIKEMKEGYLSQV

VHEIAKLVIEYNAIVVFEDLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDADANGAYHIGLKGLMLLGRI

KNNQEGKKLNLVIKNEEYFEFVQNRNN

*Francisella novicida* Cpf1 E1006A (SEQ ID NO: 378) (D917, A1006, and D1255 are bolded and underlined)

(SEQ ID NO: 378)
MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMlFDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIDRGERHLAYYTLVDG

KGNIIKQDTFNIIGNDRMKTNYHDKLAAIEKDRDSARKDWKKINNIKEMKEGYLSQV

VHEIAKLVIEYNAIVVFADLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDADANGAYHIGLKGLMLLGRI

KNNQEGKKLNLVIKNEEYFEFVQNRNN

*Francisella novicida* Cpf1 D1255A (SEQ ID NO: 379) (D917, E1006, and A1255 are bolded and underlined)

(SEQ ID NO: 379)
MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

-continued

```
QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMEDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIDRGERHLAYYTLVDG

KGNIIKQDTFNIIGNDRMKTNYHDKLAAIEKDRDSARKDWKKINNIKEMKEGYLSQV

VHEIAKLVIEYNAIVVFEDLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDAAANGAYHIGLKGLMLLGRI

KNNQEGKKLNLVIKNEEYFEFVQNRNN

Francisella novicida Cpf1 D917A/E1006A (SEQ ID NO: 380) (A917, A1006,
and D1255 are bolded and underlined)
                                                  (SEQ ID NO: 380)
MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMEDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIARGERHLAYYTLVDG

KGNIIKQDTFNIIGNDRMKTNYHDKLAAIEKDRDSARKDWKKINNIKEMKEGYLSQV

VHEIAKLVIEYNAIVVFADLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM
```

-continued

RNSKTGTELDYLISPVADVNGNFFDSRQAPKNMPQDADANGAYHIGLKGLMLLGRI

KNNQEGKKLNLVIKNEEYFEFVQNRNN

*Francisella novicida* Cpf1 D917A/D1255A (SEQ ID NO: 381) (A917, E1006, and A1255 are bolded and underlined)

(SEQ ID NO: 381)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMEDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIARGERHLAYYTLVDG

KGNIIKQDTFNIIGNDRMKTNYHDKLAAIEKDRDSARKDWKKINNIKEMKEGYLSQV

VHEIAKLVIEYNAIVVFEDLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDAAANGAYHIGLKGLMLLGRI

KNNQEGKKLNLVIKNEEYFEFVQNRNN

*Francisella novicida* Cpf1 E1006A/D1255A (SEQ ID NO: 382) (D917, A1006, and A1255 are bolded and underlined)

(SEQ ID NO: 382)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMEDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

```
GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIDRGERHLAYYTLVDG

KGNIIKQDTFNIIGNDRMKTNYHDKLAAIEKDRDSARKDWKKINNIKEMKEGYLSQV

VHEIAKLVIEYNAIVVFADLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDAAANGAYHIGLKGLMLLGRI

KNNQEGKKLNLVIKNEEYFEFVQNRNN
```

*Francisella novicida* Cpf1 D917A/E1006A/D1255A (SEQ ID NO: 383) (A917, A1006, and A1255 are bolded and underlined)

(SEQ ID NO: 383)
```
MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMEDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIARGERHLAYYTLVDG

KGNIIKQDTFNIIGNDRMKTNYHDKLAAIEKDRDSARKDWKKINNIKEMKEGYLSQV

VHEIAKLVIEYNAIVVFADLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDAAANGAYHIGLKGLMLLGRI

KNNQEGKKLNLVIKNEEYFEFVQNRNN
```

In some embodiments, the nucleic acid programmable DNA binding protein (napDNAbp) is a nucleic acid programmable DNA binding protein that does not require a canonical (NGG) PAM sequence. In some embodiments, the napDNAbp is an argonaute protein. One example of such a nucleic acid programmable DNA binding protein is an Argonaute protein from *Natronobacterium gregoryi* (NgAgo). NgAgo is a ssDNA-guided endonuclease. NgAgo binds 5' phosphorylated ssDNA of ~24 nucleotides (gDNA) to guide it to its target site and will make DNA double-strand breaks at the gDNA site. In contrast to Cas9, the NgAgo-gDNA system does not require a protospacer-adjacent motif (PAM). Using a nuclease inactive NgAgo (dNgAgo) can greatly expand the bases that may be targeted. The characterization and use of NgAgo have been described in Gao et al., *Nat Biotechnol.*, 2016 July; 34(7):768-73. PubMed PMID: 27136078; Swarts et al., *Nature.* 507(7491) (2014): 258-61; and Swarts et al., *Nucleic Acids Res.* 43(10) (2015): 5120-9, each of which is incorporated herein by reference. The sequence of *Natronobacterium gregoryi* Argonaute is provided in SEQ ID NO: 416.

```
Wild type Natronobacterium gregoryi Argonaute
(SEQ ID NO: 416)
                                         (SEQ ID NO: 416)
MTVIDLDSTTTADELTSGHTYDISVTLTGVYDNTDEQHPRMSLAFEQD

NGERRYITLWKNTTPKDVFTYDYATGSTYIFTNIDYEVKDGYENLTAT

YQTTVENATAQEVGTTDEDETFAGGEPLDHHLDDALNETPDDAETESD

SGHVMTSFASRDQLPEWTLHTYTLTATDGAKTDTEYARRTLAYTVRQE

LYTDHDAAPVATDGLMLLTPEPLGETPLDLDCGVRVEADETRTLDYTT

AKDRLLARELVEEGLKRSLWDDYLVRGIDEVLSKEPVLTCDEFDLHER

YDLSVEVGHSGRAYLHINFRHRFVPKLTLADIDDDNIYPGLRVKTTYR

PRRGHIVWGLRDECATDSLNTLGNQSVVAYHRNNQTPINTDLLDAIEA

ADRRVVETRRQGHGDDAVSFPQELLAVEPNTHQIKQFASDGFHQQARS

KTRLSASRCSEKAQAFAERLDPVRLNGSTVEFSSEFFTGNNEQQLRLL

YENGESVLTFRDGARGAHPDETFSKGIVNPPESFEVAVVLPEQQADTC

KAQWDTMADLLNQAGAPPTRSETVQYDAFSSPESISLNVAGAIDPSEV

DAAFVVLPPDQEGFADLASPTETYDELKKALANMGIYSQMAYFDRFRD

AKIFYTRNVALGLLAAAGGVAFTTEHAMPGDADMFIGIDVSRSYPEDG

ASGQINIAATATAVYKDGTILGHSSTRPQLGEKLQSTDVRDIMKNAIL

GYQQVTGESPTHIVIHRDGFMNEDLDPATEFLNEQGVEYDIVEIRKQP

QTRLLAVSDVQYDTPVKSIAAINQNEPRATVATFGAPEYLATRDGGGL

PRPIQIERVAGETDIETLTRQVYLLSQSHIQVHNSTARLPITTAYADQ

ASTHATKGYLVQTGAFESNVGFL
```

In some embodiments, the napDNAbp is a prokaryotic homolog of an Argonaute protein. Prokaryotic homologs of Argonaute proteins are known and have been described, for example, in Makarova K., et al., "Prokaryotic homologs of Argonaute proteins are predicted to function as key components of a novel system of defense against mobile genetic elements", *Biol Direct.* 2009 Aug. 25; 4:29. doi: 10.1186/1745-6150-4-29, the entire contents of which is hereby incorporated by reference. In some embodiments, the napDNAbp is a *Marinitoga piezophila* Argunaute (MpAgo) protein. The CRISPR-associated *Marinitoga piezophila* Argunaute (MpAgo) protein cleaves single-stranded target sequences using 5'-phosphorylated guides. The 5' guides are used by all known Argonautes. The crystal structure of an MpAgo-RNA complex shows a guide strand binding site comprising residues that block 5' phosphate interactions. This data suggests the evolution of an Argonaute subclass with noncanonical specificity for a 5'-hydroxylated guide. See, e.g., Kaya et al., "A bacterial Argonaute with noncanonical guide RNA specificity", *Proc Natl Acad Sci USA.* 2016 Apr. 12; 113(15):4057-62, the entire contents of which are hereby incorporated by reference). It should be appreciated that other argonaute proteins may be used, and are within the scope of this disclosure.

In some embodiments, the nucleic acid programmable DNA binding protein (napDNAbp) is a single effector of a microbial CRISPR-Cas system. Single effectors of microbial CRISPR-Cas systems include, without limitation, Cas9, Cpf1, C2c1, C2c2, and C2c3. Typically, microbial CRISPR-Cas systems are divided into Class 1 and Class 2 systems. Class 1 systems have multisubunit effector complexes, while Class 2 systems have a single protein effector. For example, Cas9 and Cpf1 are Class 2 effectors. In addition to Cas9 and Cpf1, three distinct Class 2 CRISPR-Cas systems (C2c1, C2c2, and C2c3) have been described by Shmakov et al., "Discovery and Functional Characterization of Diverse Class 2 CRISPR Cas Systems", *Mol. Cell,* 2015 Nov. 5; 60(3): 385-397, the entire contents of which is hereby incorporated by reference. Effectors of two of the systems, C2c1 and C2c3, contain RuvC-like endonuclease domains related to Cpf1. A third system, C2c2 contains an effector with two predicated HEPN RNase domains. Production of mature CRISPR RNA is tracrRNA-independent, unlike production of CRISPR RNA by C2c1. C2c1 depends on both CRISPR RNA and tracrRNA for DNA cleavage. Bacterial C2c2 has been shown to possess a unique RNase activity for CRISPR RNA maturation distinct from its RNA-activated single-stranded RNA degradation activity. These RNase functions are different from each other and from the CRISPR RNA-processing behavior of Cpf1. See, e.g., East-Seletsky, et al., "Two distinct RNase activities of CRISPR-C2c2 enable guide-RNA processing and RNA detection", *Nature,* 2016 Oct. 13; 538(7624):270-273, the entire contents of which are hereby incorporated by reference. In vitro biochemical analysis of C2c2 in *Leptotrichia shahii* has shown that C2c2 is guided by a single CRISPR RNA and can be programed to cleave ssRNA targets carrying complementary protospacers. Catalytic residues in the two conserved HEPN domains mediate cleavage. Mutations in the catalytic residues generate catalytically inactive RNA-binding proteins. See e.g., Abudayyeh et al., "C2c2 is a single-component programmable RNA-guided RNA-targeting CRISPR effector", *Science,* 2016 Aug. 5; 353(6299), the entire contents of which are hereby incorporated by reference.

The crystal structure of *Alicyclobaccillus acidoterrastris* C2c1 (AacC2c1) has been reported in complex with a chimeric single-molecule guide RNA (sgRNA). See e.g., Liu et al., "C2c1-sgRNA Complex Structure Reveals RNA-Guided DNA Cleavage Mechanism", *Mol. Cell,* 2017 Jan. 19; 65(2):310-322, the entire contents of which are hereby incorporated by reference. The crystal structure has also been reported in *Alicyclobacillus acidoterrestris* C2c1 bound to target DNAs as ternary complexes. See e.g., Yang et al., "PAM-dependent Target DNA Recognition and Cleavage by C2C1 CRISPR-Cas endonuclease", *Cell,* 2016 Dec. 15; 167(7):1814-1828, the entire contents of which are hereby incorporated by reference. Catalytically competent conformations of AacC2c1, both with target and non-target DNA strands, have been captured independently positioned within a single RuvC catalytic pocket, with C2c1-mediated cleavage resulting in a staggered seven-nucleotide break of target DNA. Structural comparisons between C2c1 ternary complexes and previously identified Cas9 and Cpf1 counterparts demonstrate the diversity of mechanisms used by CRISPR-Cas9 systems.

In some embodiments, the nucleic acid programmable DNA binding protein (napDNAbp) of any of the fusion proteins provided herein may be a C2c1, a C2c2, or a C2c3 protein. In some embodiments, the napDNAbp is a C2c1 protein. In some embodiments, the napDNAbp is a C2c2 protein. In some embodiments, the napDNAbp is a C2c3 protein. In some embodiments, the napDNAbp comprises an amino acid sequence that is at least 85%, at least 90%, at least 91%, at least 92%, at least 93%, at least 94%, at least 95%, at least 96%, at least 97%, at least 98%, at least 99%, or at ease 99.5% identical to a naturally-occurring C2c1, C2c2, or C2c3 protein. In some embodiments, the napDNAbp is a naturally-occurring C2c1, C2c2, or C2c3 protein. In some embodiments, the napDNAbp comprises an amino acid sequence that is at least 85%, at least 90%, at least 91%, at least 92%, at least 93%, at least 94%, at least 95%, at least 96%, at least 97%, at least 98%, at least 99%, or at ease 99.5% identical to any one of SEQ ID NOs: 438 or 439. In some embodiments, the napDNAbp comprises an amino acid sequence of any one SEQ ID NOs: 438 or 439. It should be appreciated that C2c1, C2c2, or C2c3 from other bacterial species may also be used in accordance with the present disclosure.

```
C2c1 (uniprot.org/uniprot/T0D7A2#)
sp|T0D7A2|C2C1_ALIAG CRISPR-associated endonuclease C2c1 OS = Alicyclobacillus
acidoterrestris (strain ATCC 49025/DSM 3922/CIP 106132/NCIMB 13137/GD3B)
GN = c2c1 PE = 1 SV = 1
                                                            (SEQ ID NO: 438)
MAVKSIKVKLRLDDMPEIRAGLWKLHKEVNAGVRYYTEWLSLLRQENLYRRSPNG

DGEQECDKTAEECKAELLERLRARQVENGHRGPAGSDDELLQLARQLYELLVPQAI

GAKGDAQQIARKFLSPLADKDAVGGLGIAKAGNKPRWVRMREAGEPGWEEEKEKA

ETRKSADRTADVLRALADFGLKPLMRVYTDSEMSSVEWKPLRKGQAVRTWDRDM

FQQAIERMMSWESWNQRVGQEYAKLVEQKNRFEQKNFVGQEHLVHLVNQLQQDM

KEASPGLESKEQTAHYVTGRALRGSDKVFEKWGKLAPDAPFDLYDAEIKNVQRRNT

RRFGSHDLFAKLAEPEYQALWREDASFLTRYAVYNSILRKLNHAKMFATFTLPDAT

AHPIWTRFDKLGGNLHQYTFLFNEFGERRHAIRFHKLLKVENGVAREVDDVTVPISM

SEQLDNLLPRDPNEPIALYFRDYGAEQHFTGEFGGAKIQCRRDQLAHMHRRRGARD

VYLNVSVRVQSQSEARGERRPPYAAVFRLVGDNHRAFVHFDKLSDYLAEHPDDGKL

GSEGLLSGLRVMSVDLGLRTSASISVFRVARKDELKPNSKGRVPFFFPIKGNDNLVAV

HERSQLLKLPGETESKDLRAIREERQRTLRQLRTQLAYLRLLVRCGSEDVGRRERSW

AKLIEQPVDAANHMTPDWREAFENELQKLKSLHGICSDKEWMDAVYESVRRVWRH

MGKQVRDWRKDVRSGERPKIRGYAKDVVGGNSIEQIEYLERQYKFLKSWSFFGKVS

GQVIRAEKGSRFAITLREHIDHAKEDRLKKLADRIIMEALGYVYALDERGKGKWVA

KYPPCQLILLEELSEYQFNNDRPPSENNQLMQWSHRGVFQELINQAQVHDLLVGTM

YAAFSSRFDARTGAPGIRCRRVPARCTQEHNPEPFPWWLNKFVVEHTLDACPLRAD

DLIPTGEGEIFVSPFSAEEGDFHQIHADLNAAQNLQQRLWSDFDISQIRLRCDWGEVD

GELVLIPRLTGKRTADSYSNKVFYTNTGVTYYERERGKKRRKVFAQEKLSEEEAELL

VEADEAREKSVVLMRDPSGIINRGNWTRQKEFWSMVNQRIEGYLVKQIRSRVPLQD

SACENTGDI

C2c2 (uniprot.org/uniprot/P0DOC6)
>sp|P0DOC6|C2C2_LEPSD CRISPR-associated endoribonuclease C2c2 OS = Leptotrichia
shahii (strain DSM 19757/CCUG 47503/CIP 107916/JCM 16776/LB37) GN = c2c2
PE = 1 SV = 1
                                                            (SEQ ID NO: 439)
MGNLFGHKRWYEVRDKKDFKIKRKVKVKRNYDGNKYILNINENNNKEKIDNNKFIR

KYINYKKNDNILKEFTRKFHAGNILFKLKGKEGIIRIENNDDFLETEEVVLYIEAYGKS

EKLKALGITKKKIIDEAIRQGITKDDKKIEIKRQENEEEIEIDIRDEYTNKTLNDCSIILRI

IENDELETKKSIYEIFKNINMSLYKIIEKIIENETEKVFENRYYEEHLREKLLKDDKIDVI

LTNFMEIREKIKSNLEILGFVKFYLNVGGDKKKSKNKKMLVEKILNINVDLTVEDIAD

FVIKELEFWNITKRIEKVKKVNNEFLEKRRNRTYIKSYVLLDKHEKFKIERENKKDKI

VKFFVENIKNNSIKEKIEKILAEFKIDELIKKLEKELKKGNCDTEIFGIFKKHYKVNFDS

KKFSKKSDEEKELYKIIYRYLKGRIEKILVNEQKVRLKKMEKIEIEKILNESILSEKILK

RVKQYTLEHIMYLGKLRHNDIDMTTVNTDDFSRLHAKEELDLELITFFASTNMELNK

IFSRENINNDENIDFFGGDREKNYVLDKKILNSKIKIIRDLDFIDNKNNITNNFIRKFTKI
```

-continued

```
GTNERNRILHAISKERDLQGTQDDYNKVINIIQNLKISDEEVSKALNLDVVFKDKKNII

TKINDIKISEENNNDIKYLPSFSKVLPEILNLYRNNPKNEPFDTIETEKIVLNALIYVNKE

LYKKLILEDDLEENESKNIFLQELKKTLGNIDEIDENIIENYYKNAQISASKGNNKAIK

KYQKKVIECYIGYLRKNYEELFDFSDFKMNIQEIKKQIKDINDNKTYERITVKTSDKTI

VINDDFEYIISIFALLNSNAVINKIRNRFFATSVWLNTSEYQNIIDILDEIMQLNTLRNEC

ITENWNLNLEEFIQKMKEIEKDFDDFKIQTKKEIFNNYYEDIKNNILTEFKDDINGCDV

LEKKLEKIVIFDDETKFEIDKKSNILQDEQRKLSNINKKDLKKKVDQYIKDKDQEIKS

KILCRIIFNSDFLKKYKKEIDNLIEDMESENENKFQEIYYPKERKNELYIYKKNLFLNIG

NPNFDKIYGLISNDIKMADAKFLFNIDGKNIRKNKISEIDAILKNLNDKLNGYSKEYKE

KYIKKLKENDDFFAKNIQNKNYKSFEKDYNRVSEYKKIRDLVEFNYLNKIESYLIDIN

WKLAIQMARFERDMHYIVNGLRELGIIKLSGYNTGISRAYPKRNGSDGFYTTTAYYK

FFDEESYKKFEKICYGFGIDLSENSEINKPENESIRNYISHFYIVRNPFADYSIAEQIDRV

SNLLSYSTRYNNSTYASVFEVFKKDVNLDYDELKKKFKLIGNNDILERLMKPKKVSV

LELESYNSDYIKNLIIELLTKIENTNDTL
```

Fusion Proteins Comprising a Nuclease Programmable DNA Binding Protein and an Adenosine Deaminase Some aspects of the disclosure provide fusion proteins comprising a nucleic acid programmable DNA binding protein (napDNAbp) and an adenosine deaminase. In some embodiments, any of the fusion proteins provided herein are base editors. In some embodiments, the napDNAbp is a Cas9 domain, a Cpf1 domain, a CasX domain, a CasY domain, a C2c1 domain, a C2c2 domain, aC2c3 domain, or an Argonaute domain. In some embodiments, the napD-NAbp is any napDNAbp provided herein. Some aspects of the disclosure provide fusion proteins comprising a Cas9 domain and an adenosine deaminase. The Cas9 domain may be any of the Cas9 domains or Cas9 proteins (e.g., dCas9 or nCas9) provided herein. In some embodiments, any of the Cas9 domains or Cas9 proteins (e.g., dCas9 or nCas9) provided herein may be fused with any of the adenosine deaminases provided herein. In some embodiments, the fusion protein comprises the structure:
NH$_2$-[adenosine deaminase]-[napDNAbp]-COOH; or
NH$_2$-[napDNAbp]-[adenosine deaminase]-COOH In some embodiments, the fusion proteins comprising an adenosine deaminase and a napDNAbp (e.g., Cas9 domain) do not include a linker sequence. In some embodiments, a linker is present between the adenosine deaminase domain and the napDNAbp. In some embodiments, the "-" used in the general architecture above indicates the presence of an optional linker. In some embodiments, the adenosine deaminase and the napDNAbp are fused via any of the linkers provided herein. For example, in some embodiments the adenosine deaminase and the napDNAbp are fused via any of the linkers provided below in the section entitled "Linkers". In some embodiments, the adenosine deaminase and the napDNAbp are fused via a linker that comprises between 1 and and 200 amino acids. In some embodiments, the adenosine deaminase and the napDNAbp are fused via a linker that comprises from 1 to 5, 1 to 10, 1 to 20, 1 to 30, 1 to 40, 1 to 50, 1 to 60, 1 to 80, 1 to 100, 1 to 150, 1 to 200, 5 to 10, 5 to 20, 5 to 30, 5 to 40, 5 to 60, 5 to 80, 5 to 100, 5 to 150, 5 to 200, 10 to 20, 10 to 30, 10 to 40, 10 to 50, 10 to 60, 10 to 80, 10 to 100, 10 to 150, 10 to 200, 20 to 30, 20 to 40, 20 to 50, 20 to 60, 20 to 80, 20 to 100, 20 to 150, 20 to 200, 30 to 40, 30 to 50, 30 to 60, 30 to 80, 30 to 100, 30 to 150, 30 to 200, 40 to 50, 40 to 60, 40 to 80, 40 to 100, 40 to 150, 40 to 200, 50 to 60 50 to 80, 50 to 100, 50 to 150, 50 to 200, 60 to 80, 60 to 100, 60 to 150, 60 to 200, 80 to 100, 80 to 150, 80 to 200, 100 to 150, 100 to 200, or 150 to 200 amino acids in length. In some embodiments, the adenosine deaminase and the napDNAbp are fused via a linker that comprises 4, 16, 32, or 104 amino acids in length. In some embodiments, the adenosine deaminase and the napDNAbp are fused via a linker that comprises the amino acid sequence of SGSETPGTSESATPES (SEQ ID NO: 10), SGGS (SEQ ID NO: 37), SGGSSGSETPGTSESAT-PESSGGS (SEQ ID NO: 384), SGGSSGGSSGSETPGTS-ESATPESSGGSSGGS (SEQ ID NO: 385), or GGSGGSPGSPAGSPTSTEEGTSESATPESGPGT-STEPSEGSAPGSPAGSPTSTEEGTSTE PSEGSAPGT-STEPSEGSAPGTSESATPESGPGSEPATSGGSGGS (SEQ ID NO: 386). In some embodiments, the adenosine deaminase and the napDNAbp are fused via a linker comprising the amino acid sequence SGSETPGTSESATPES (SEQ ID NO: 10), which may also be referred to as the XTEN linker. In some embodiments, the linker is 24 amino acids in length. In some embodiments, the linker comprises the amino acid sequence SGGSSGGSSGSETPGTSESATPES (SEQ ID NO: 685). In some embodiments, the linker is 40 amino acids in length. In some embodiments, the linker comprises the amino acid sequence SGGSSGGSSGSETPGTSESAT-PESSGGSSGGSSGGSSGGS (SEQ ID NO: 686).

In some embodiments, the linker is 64 amino acids in length. In some embodiments, the linker comprises the amino acid sequence SGGSSGGSSGSETPGTSESAT-PESSGGSSGGSSGGSSGGSSGGSGSETPGTSESAT-PESSGGS SGGS (SEQ ID NO: 687). In some embodiments, the linker is 92 amino acids in length. In some embodiments, the linker comprises the amino acid sequence PGSPAGSPTSTEEGTSESATPESGPGTSTEPSEGSA-PGSPAGSPTSTEEGTSTEPSEGSAP GTSTEPSEGSA-PGTSESATPESGPGSEPATS (SEQ ID NO: 688).

Fusion Proteins Comprising an Inhibitor of Base Repair

Some aspects of the disclosure provide fusion proteins that comprise an inhibitor of base repair (IBR). For example a fusion protein comprising an adenosine deaminase and a nucleic acid programmable DNA binding protein may further comprise an inhibitor of base repair. In some embodiments, the IBR comprises an inhibitor of inosine base repair. In some embodiments, the IBR is an inhibitor of inosine base excision repair. In some embodiments, the inhibitor of inosine base excision repair is a catalytically inactive inosine specific nuclease (dISN).

In some embodiments, the fusion proteins provided herein further comprise a catalytically inactive inosine-specific nuclease (dISN). In some embodiments, any of the fusion proteins provided herein that comprise a napDNAbp (e.g., a nuclease active Cas9 domain, a nuclease inactive dCas9 domain, or a Cas9 nickase) and an adenosine deaminase may be further fused to a catalytically inactive inosine-specific nuclease (dISN) either directly or via a linker. Some aspects of this disclosure provide fusion proteins that comprise an adenosine deaminase (e.g., an engineered adenosine deaminase that deaminates adenosine in a DNA) a napDNAbp (e.g., a dCas9 or nCas9), and a dISN. Without wishing to be bound by any particular theory, cellular DNA-repair response to the presence of I:T heteroduplex DNA may be responsible for the decrease in nucleobase editing efficiency in cells. For example, AAG catalyzes removal of inosine (I) from DNA in cells, which may initiate base excision repair, with reversion of the I:T pair to a A:T pair as the most common outcome. In some embodiments, a catalytically inactive inosine-specific nuclease may be capable of binding an inosine in a nucleic acid, without cleaving the nucleic acid, to prevent removal (e.g., by cellular DNA repair mechanisms) of the inosine residue in the DNA.

In some embodiments, a dISN may inhibit (e.g., by steric hindrance) inosine removing enzymes from excising the inosine residue from DNA. For example, catalytically dead inosine glycosylases (e.g., alkyl adenine glycosylase [AAG]) will bind inosine but will not create an abasic site or remove the inosine, thereby sterically blocking the newly-formed inosine moiety from potential DNA damage/repair mechanisms. Thus, this disclosure contemplates a fusion protein comprising a napDNAbp and an adenosine deaminase further fused to a dISN. This disclosure contemplates a fusion protein comprising any Cas9 domain, for example, a Cas9 nickase (nCas9) domain, a catalytically inactive Cas9 (dCas9) domain, a high fidelity Cas9 domain, or a Cas9 domain with reduced PAM exclusivity. It should be understood that the use of a dISN may increase the editing efficiency of a adenosine deaminase that is capable of catalyzing a A to I change. For example, fusion proteins comprising a dISN domain may be more efficient in deaminating A residues. In some embodiments, the fusion protein comprises the structure:

NH$_2$-[adenosine deaminase]-[napDNAbp]-[dISN]—COOH;
NH$_2$-[adenosine deaminase]-[dISN]-[napDNAbp]-COOH;
NH$_2$-[dISN]-[adenosine deaminase]-[napDNAbp]-COOH;
NH$_2$-[napDNAbp]-[adenosine deaminase]-[dISN]-COOH;
NH$_2$-[napDNAbp]-[dISN]-[adenosine deaminase]-COOH; or
NH$_2$-[dISN]-[napDNAbp]-[adenosine deaminase]-COOH In some embodiments, the fusion proteins provided herein do not comprise a linker. In some embodiments, a linker is present between two domains or proteins (e.g., adenosine deaminase, napDNAbp, or dISN). In some embodiments, the "-" used in the general architecture above indicates the presence of an optional linker sequence. In some embodiments, a dISN comprises an inosine-specific nuclease that has reduced or nuclease activity, or does not have nuclease activity. In some embodiments, a dISN has up to 1%, up to 2%, up to 3%, up to 4%, up to 5%, up to 10%, up to 15%, up to 20%, up to 25%, up to 30%, up to 35%, up to 40%, up to 45%, or up to 50% of the nuclease activity of a corresponding (e.g., the wild-type) inosine-specific nuclease. In some embodiments, the dISN is a wild-type inosine-specific nuclease that comprises one or more mutations that reduces or eliminates the nuclease activity of the wild-type inosine-specific nuclease. Exemplary catalytically inactive inosine-specific nucleases include, without limitation, catalytically inactive AAG nuclease and catalytically inactive EndoV nuclease. In some embodiments, the catalytically inactive AAG nuclease comprises an E125Q mutation as compared to SEQ ID NO: 32, or a corresponding mutation in another AAG nuclease. In some embodiments, the catalytically inactive AAG nuclease comprises the amino acid sequence set forth in SEQ ID NO: 32. In some embodiments, the catalytically inactive EndoV nuclease comprises an D35A mutation as compared to SEQ ID NO 32, or a corresponding mutation in another EndoV nuclease. In some embodiments, the catalytically inactive EndoV nuclease comprises the amino acid sequence set forth in SEQ ID NO: 33. It should be appreciated that other catalytically inactive inosine-specific nucleases (dISNs) would be apparent to the skilled artisan and are within the scope of this disclosure.

In some embodiments, the dISN proteins provided herein include fragments of dISN proteins and proteins homologous to a dISN or a dISN fragment. For example, in some embodiments, a dISN comprises a fragment of the amino acid sequence set forth in SEQ ID NO: 32 or 33. In some embodiments, a dISN fragment comprises an amino acid sequence that comprises at least 60%, at least 65%, at least 70%, at least 75%, at least 80%, at least 85%, at least 90%, at least 95%, at least 96%, at least 97%, at least 98%, at least 99%, or at least 99.5% of the amino acid sequence as set forth in SEQ ID NO: 32 or 33. In some embodiments, a dISN comprises an amino acid sequence homologous to the amino acid sequence set forth in SEQ ID NO: 32 or 33, or an amino acid sequence homologous to a fragment of the amino acid sequence set forth in SEQ ID NO: 32 or 33. In some embodiments, proteins comprising a dISN or fragments of a dISN or homologs of a dISN or a dISN fragment are referred to as "dISN variants." A dISN variant shares homology to a dISN, or a fragment thereof. For example a dISN variant is at least 70% identical, at least 75% identical, at least 80% identical, at least 85% identical, at least 90% identical, at least 95% identical, at least 96% identical, at least 97% identical, at least 98% identical, at least 99% identical, at least 99.5% identical, or at least 99.9% identical to a wild-type dISN or a dISN as set forth in SEQ ID NO: 32 or 33. In some embodiments, the dISN variant comprises a fragment of dISN, such that the fragment is at least 70% identical, at least 80% identical, at least 90% identical, at least 95% identical, at least 96% identical, at least 97% identical, at least 98% identical, at least 99% identical, at least 99.5% identical, or at least 99.9% to the corresponding fragment of wild-type dISN or a dISN as set forth in SEQ ID NO: 32 or 33. In some embodiments, the dISN comprises the following amino acid sequence:

AAG nuclease (E125Q); mutated residue underlined in bold.

(SEQ ID NO: 32)
KGHLTRLGLEFFDQPAVPLARAFLGQVLVRRLPNGTELRGRIVETQAYL

GPEDEAAHSRGGRQTPRNRGMFMKPGTLYVYIIYGMYFCMNISSQGDGA

-continued

CVLLRALEPLEGLETMRQLRSTLRKGTASRVLKDRELCSGPSKLCQALA

INKSFDQRDLAQDEAVWLERGPLEPSEPAVVAAARVGVGHAGEWARKPL

RFYVRGSPWVSVVDRVAEQDTQA

EndoV nuclease (D35A); mutated residue underlined in bold.
(SEQ ID NO: 33)
DLASLRAQQIELASSVIREDRLDKDPPDLIAGAAVGFEQGGEVTRAAMV

LLKYPSLELVEYKVARIATTMPYIPGFLSFREYPALLAAWEMLSQKPDL

VFVDGHGISHPRRLGVASHFGLLVDVPTIGVAKKRLCGKFEPLSSEPGA

LAPLMDKGEQLAWVWRSKARCNPLFIATGHRVSVDSALAWVQRCMKGYR

LPEPTRWADAVASERPAFVRYTANQP

Suitable dISN proteins are provided herein and additional suitable dISN proteins are known to those in the art, and include, for example, AAG, EndoV, and variants thereof. It should be appreciated that additional proteins that block or inhibit base-excision repair, such as base excision of an inosine, are also within the scope of this disclosure. In some embodiments, a protein that binds inosine in DNA is used.

Some aspects of the disclosure relate to fusion proteins that comprise MBD4, or TDG, which may be used as inhibitors of base repair. Thus, this disclosure contemplates a fusion protein comprising a napDNAbp and an adenosine deaminase further fused to MBD4 or TDG. This disclosure contemplates a fusion protein comprising any Cas9 domain, for example, a Cas9 nickase (nCas9) domain, a catalytically inactive Cas9 (dCas9) domain, a high fidelity Cas9 domain, or a Cas9 domain with reduced PAM exclusivity. It should be understood that the use of MBD4 or TDG may increase the editing efficiency of a adenosine deaminase that is capable of catalyzing a A to I change. For example, fusion proteins comprising MBD4 or TDG may be more efficient in deaminating A residues. In some embodiments, the fusion protein comprises the structure:

NH$_2$-[adenosine deaminase]-[napDNAbp]-[MBD4 or TDG]-COOH;

NH$_2$-[adenosine deaminase]-[MBD4 or TDG]-[napDNAbp]-COOH;

NH$_2$-[MBD4 or TDG]-[adenosine deaminase]-[napDNAbp]-COOH;

NH$_2$-[napDNAbp]-[adenosine deaminase]-[MBD4 or TDG]-COOH;

NH$_2$-[napDNAbp]-[MBD4 or TDG]-[adenosine deaminase]-COOH; or

NH$_2$-[MBD4 or TDG]-[napDNAbp]-[adenosine deaminase]-COOH

In some embodiments, the fusion proteins provided herein do not comprise a linker. In some embodiments, a linker is present between two domains or proteins (e.g., adenosine deaminase, napDNAbp, MBD4 or TDG). In some embodiments, the "-" used in the general architecture above indicates the presence of an optional linker sequence. In some embodiments, the MBD4 or TDG is a wild-type MBD4 or TDG. Exemplary, MBD4 and TDG amino acid sequences would be apparent to the skilled artisan and include, without limitation, the MBD4 and TDG amino acid sequences provided below.

Sequence of MBD4:
(SEQ ID NO: 689)
GTTGLESLSLGDRGAAPTVTSSERLVPDPPNDLRKEDVAMELERVGED

EEQMMIKRSSECNPLLQEPIASAQFGATAGTECRKSVPCGWERVVKQR

LFGKTAGRFDVYFISPQGLKFRSKSSLANYLHKNGETSLKPEDFDFTV

LSKRGIKSRYKDCSMAALTSHLQNQSNNSNWNLRTRSKCKKDVFMPPS

SSSELQESRGLSNFTSTHLLLKEDEGVDDVNFRKVRKPKGKVTILKGI

PIKKTKKGCRKSCSGFVQSDSKRESVCNKADAESEPVAQKSQLDRTVC

ISDAGACGETLSVTSEENSLVKKKERSLSSGSNFCSEQKTSGIINKFC

SAKDSEHNEKYEDTFLESEEIGTKVEVVERKEHLHTDILKRGSEMDNN

CSPTRKDFTGEKIFQEDTIPRTQIERRKTSLYFSSKYNKEALSPPRRK

AFKKWTPPRSPFNLVQETLFHDPWKLLIATIFLNRTSGKMAIPVLWKF

LEKYPSAEVARTADWRDVSELLKPLGLYDLRAKTIVKFSDEYLTKQWK

YPIELHGIGKYGNDSYRIFCVNEWKQVHPEDHKLNKYHDWLWENHEKL

SLS

Sequence of TDG:
(SEQ ID NO: 690)
EAENAGSYSLQQAQAFYTFPFQQLMAEAPNMAVVNEQQMPEEVPAPAP

AQEPVQEAPKGRKRKPRTTEPKQPVEPKKPVESKKSGKSAKSKEKQEK

ITDTFKVKRKVDRFNGVSEAELLTKTLPDILTFNLDIVIIGINPGLMA

AYKGHHYPGPGNHFWKCLFMSGLSEVQLNHMDDHTLPGKYGIGFTNMV

ERTTPGSKDLSSKEFREGGRILVQKLQKYQPRIAVFNGKCIYEIFSKE

VFGVKVKNLEFGLQPHKIPDTETLCYVMPSSSARCAQFPRAQDKVHYY

IKLKDLRDQLKGIERNMDVQEVQYTFDLQLAQEDAKKMAVKEEKYDPG

YEAAYGGAYGENPCSSEPCGFSSNGLIESVELRGESAFSGIPNGQWMT

QSFTDQIPSFSNHCGTQEQEEESHA

In some embodiments, the MBD4 or TDG proteins provided herein include fragments of MBD4 or TDG proteins and proteins homologous to a MBD4 or a TDG fragment. For example, in some embodiments, a MBD4 or TDG protein comprises a fragment of the amino acid sequence set forth in SEQ ID NO: 689 or 690. In some embodiments, a MBD4 or TDG fragment comprises an amino acid sequence that comprises at least 60%, at least 65%, at least 70%, at least 75%, at least 80%, at least 85%, at least 90%, at least 95%, at least 96%, at least 97%, at least 98%, at least 99%, or at least 99.5% of the amino acid sequence as set forth in SEQ ID NO: 689 or 690. In some embodiments, a MBD4 or TDG protein comprises an amino acid sequence homologous to the amino acid sequence set forth in SEQ ID NO: 689 or 690, or an amino acid sequence homologous to a fragment of the amino acid sequence set forth in SEQ ID NO: 689 or 690. In some embodiments, proteins comprising a MBD4 or TDG or fragments of a MBD4 or TDG or homologs of a MBD4 or TDG fragment are referred to as "MBD4 variants" or "TDG variants." A MBD4 or TDG variant shares homology to a MBD4 or TDG, or a fragment thereof. For example a MBD4 or TDG variant is at least 70% identical, at least 75% identical, at least 80% identical, at least 85% identical, at least 90% identical, at least 95% identical, at least 96% identical, at least 97% identical, at least 98% identical, at least 99% identical, at least 99.5% identical, or at least 99.9% identical to a wild-type MBD4 or TDG or a MBD4 or TDG as set forth in SEQ ID NO: 689 or 690. In some embodiments, the MBD4 or TDG variant comprises a fragment of MBD4 or TDG, such that the fragment is at least 70% identical, at least 80% identical, at least 90% identical, at least 95% identical, at least 96% identical, at least 97% identical, at least 98% identical, at least 99% identical, at least 99.5% identical, or at least 99.9% to the corresponding fragment of wild-type MBD4 or TDG or a MBD4 or TDG as set forth in SEQ ID NO: 689 or 690. In some embodiments, the dISN comprises the following amino acid sequence:

Some aspects of the disclosure relate to fusion proteins that comprise a uracil glycosylase inhibitor (UGI) domain. In some embodiments, any of the fusion proteins provided herein that comprise a napDNAbp (e.g., a nuclease active Cas9 domain, a nuclease inactive dCas9 domain, or a Cas9 nickase), and an adenosine deaminase, may be further fused to a UGI domain either directly or via a linker. Some aspects of this disclosure provide fusion proteins that comprise an adenosine deaminase (e.g., an engineered adenosine deaminase that deaminates deoxyadenosine in a DNA) a napDNAbp (e.g., a dCas9 or nCas9), and a UGI domain. Without wishing to be bound by any particular theory, the cellular DNA-repair response to the presence of I:T heteroduplex DNA may be responsible for the decrease in nucleobase editing efficiency in cells. For example, alkyl adenosine glycosylase (AAG) is involved in inosine (I) associated DNA repair and catalyzes removal of I from DNA in cells. This may initiate base excision repair, with reversion of the I:T pair to a A:T pair as the most common outcome. A UGI domain, may inhibit (e.g., by steric hindrance) inosine removing enzymes from excising the inosine residue from DNA. Thus, this disclosure contemplates a fusion protein comprising a Cas9 domain and an adenosine deaminase domain further fused to a UGI domain. This disclosure contemplates a fusion protein comprising any nucleic acid programmable DNA binding protein, for example, a Cas9 nickase (nCas9) domain, a catalytically inactive Cas9 (dCas9) domain, a high fidelity Cas9 domain, or a Cas9 domain with reduced PAM exclusivity. It should be understood that the use of a UGI domain may increase the editing efficiency of a adenosine deaminase that is capable of catalyzing a A to I change. For example, fusion proteins comprising a UGI domain may be more efficient in deaminating adenosine residues. In some embodiments, the fusion protein comprises the structure:
NH₂-[adenosine deaminase]-[napDNAbp]-[UGI]-COOH;
NH₂-[adenosine deaminase]-[UGI]-[napDNAbp]-COOH;
NH₂-[UGI]-[adenosine deaminase]-[napDNAbp]-COOH;
NH₂-[napDNAbp]-[adenosine deaminase]-[UGI]-COOH;
NH₂-[napDNAbp]-[UGI]-[adenosine deaminase]-COOH; or
NH₂-[UGI]-[napDNAbp]-[adenosine deaminase]-COOH In some embodiments, the fusion proteins provided herein do not comprise a linker. In some embodiments, a linker is present between any of the domains or proteins (e.g., adenosine deaminase, napDNAbp, and/or UGI domains). In some embodiments, the "-" used in the general architecture above indicates the presence of an optional linker.

In some embodiments, a UGI domain comprises a wild-type UGI or a UGI as set forth in SEQ ID NO: 3. In some embodiments, the UGI proteins provided herein include fragments of UGI and proteins homologous to a UGI or a UGI fragment. For example, in some embodiments, a UGI domain comprises a fragment of the amino acid sequence set forth in SEQ ID NO: 3. In some embodiments, a UGI fragment comprises an amino acid sequence that comprises at least 60%, at least 65%, at least 70%, at least 75%, at least 80%, at least 85%, at least 90%, at least 95%, at least 96%, at least 97%, at least 98%, at least 99%, or at least 99.5% of the amino acid sequence as set forth in SEQ ID NO: 3. In some embodiments, a UGI comprises an amino acid sequence homologous to the amino acid sequence set forth in SEQ ID NO: 3 or an amino acid sequence homologous to a fragment of the amino acid sequence set forth in SEQ ID NO: 3. In some embodiments, proteins comprising UGI or fragments of UGI or homologs of UGI or UGI fragments are referred to as "UGI variants." A UGI variant shares homology to UGI, or a fragment thereof. For example a UGI variant is at least 70% identical, at least 75% identical, at least 80% identical, at least 85% identical, at least 90% identical, at least 95% identical, at least 96% identical, at least 97% identical, at least 98% identical, at least 99% identical, at least 99.5% identical, or at least 99.9% identical to a wild type UGI or a UGI as set forth in SEQ ID NO: 3. In some embodiments, the UGI variant comprises a fragment of UGI, such that the fragment is at least 70% identical, at least 80% identical, at least 90% identical, at least 95% identical, at least 96% identical, at least 97% identical, at least 98% identical, at least 99% identical, at least 99.5% identical, or at least 99.9% to the corresponding fragment of wild-type UGI or a UGI as set forth in SEQ ID NO: 3. In some embodiments, the UGI comprises the following amino acid sequence:

```
>sp|P14739|UNGI_BPPB2 Uracil-DNA glycosylase
inhibitor
                                    (SEQ ID NO: 3)
MTNLSDIIEKETGKQLVIQESILMLPEEVEEVIGNKPESDILVHTAY

DESTDENVMLLTSDAPEYKPWALVIQDSNGENKIKML
```

Suitable UGI protein and nucleotide sequences are provided herein and additional suitable UGI sequences are known to those in the art, and include, for example, those published in Wang et al., Uracil-DNA glycosylase inhibitor gene of bacteriophage PBS2 encodes a binding protein specific for uracil-DNA glycosylase. *J. Biol. Chem.* 264: 1163-1171(1989); Lundquist et al., Site-directed mutagenesis and characterization of uracil-DNA glycosylase inhibitor protein. Role of specific carboxylic amino acids in complex formation with *Escherichia coli* uracil-DNA glycosylase. *J. Biol. Chem.* 272:21408-21419(1997); Ravishankar et al., X-ray analysis of a complex of *Escherichia coli* uracil DNA glycosylase (EcUDG) with a proteinaceous inhibitor. The structure elucidation of a prokaryotic UDG. *Nucleic Acids Res.* 26:4880-4887(1998); and Putnam et al., Protein mimicry of DNA from crystal structures of the uracil-DNA glycosylase inhibitor protein and its complex with *Escherichia coli* uracil-DNA glycosylase. *J. Mol. Biol.* 287:331-346(1999), the entire contents of each are incorporated herein by reference.

It should be appreciated that additional proteins that block or inhibit base-excision repair, such as base excision of an inosine, are also within the scope of this disclosure. In some embodiments, a protein that binds DNA is used. In another embodiment, a substitute for UGI is used. In some embodiments, a uracil glycosylase inhibitor is a protein that binds single-stranded DNA. For example, a uracil glycosylase inhibitor may be a *Erwinia tasmaniensis* single-stranded binding protein. In some embodiments, the single-stranded binding protein comprises the amino acid sequence (SEQ ID NO: 29). In some embodiments, a uracil glycosylase inhibitor is a protein that binds uracil. In some embodiments, a uracil glycosylase inhibitor is a protein that binds uracil in DNA. In some embodiments, a uracil glycosylase inhibitor is a catalytically inactive uracil DNA-glycosylase protein. In some embodiments, a uracil glycosylase inhibitor is a catalytically inactive uracil DNA-glycosylase protein that does not excise uracil from the DNA. For example, a uracil glycosylase inhibitor is a UdgX. In some embodiments, the UdgX comprises the amino acid sequence (SEQ ID NO: 30). As another example, a uracil glycosylase inhibitor is a catalytically inactive UDG. In some embodiments, a catalytically inactive UDG comprises the amino acid sequence (SEQ ID NO: 31). It should be appreciated that other uracil glycosylase inhibitors would be apparent to the skilled artisan and are within the scope of this disclosure. In some embodiments, a uracil glycosylase inhibitor is a protein that is homologous to any one of SEQ ID NOs: 29-31. In some embodiments, a uracil glycosylase inhibitor is a protein that is at least 50% identical, at least 55% identical, at least 60% identical, at least 65% identical, at least 70% identical, at least 75% identical, at least 80% identical at least 85% identical, at least 90% identical, at least 95% identical, at least 96% identical, at least 98% identical, at least 99% identical, or at least 99.5% identical to any one of SEQ ID NOs: 29-31.

```
Erwinia tasmaniensis SSB (themostable single-
stranded DNA binding protein)
                                    (SEQ ID NO: 29)
MASRGVNKVILVGNLGQDPEVRYMPNGGAVANITLATSESWRDKQTGE

TKEKTEWHRVVLFGKLAEVAGEYLRKGSQVYIEGALQTRKWTDQAGVE

KYTTEVVVNVGGTMQMLGGRSQGGGASAGGQNGGSNNGWGQPQQPQGG

NQFSGGAQQQARPQQQPQQNNAPANNEPPIDFDDDIP

UdgX (binds to Uracil in DNA but does not excise)
                                    (SEQ ID NO: 30)
MAGAQDFVPHTADLAELAAAAGECRGCGLYRDATQAVFGAGGRSAREV

IMIGEQPGDKEDLAGLPFVGPAGRLLDRALEAADIDRDALYVTNAVKH

FKFTRAAGGKRRIHKTPSRTEVVACRPWLIAEMTSVEPDVVVLLGATA

AKALLGNDFRVTQHRGEVLHVDDVPGDPALVATVHPSSLLRGPKEERE

SAFAGLVDDLRVAADVRP

UDG (catalytically inactive human UDG, binds to
Uracil in DNA but does not excise)
                                    (SEQ ID NO: 31)
MIGQKTLYSFFSPSPARKRHAPSPEPAVQGTGVAGVPEESGDAAAIPA

KKAPAGQEEPGTPPSSPLSAEQLDRIQRNKAAALLRLAARNVPVGFGE

SWKKHLSGEFGKPYFIKLMGFVAEERKHYTVYPPPHQVFTWTQMCDIK

DVKVVILGQEPYHGPNQAHGLCFSVQRPVPPPSLENIYKELSTDIED

FVHPGHGDLSGWAKQGVLLLNAVLTVRAHQANSHKERGWEQFTDAVVS

WLNQNSNGLVFLLWGSYAQKKGSAIDRKRHHVLQTAHPSPLSVYRGFF

GCRHFSKTNELLQKSGKKPIDWKEL
```

Fusion Proteins Comprising a Nuclear Localization Sequence (NLS)

In some embodiments, the fusion proteins provided herein further comprise one or more nuclear targeting sequences, for example, a nuclear localization sequence (NLS). In some embodiments, a NLS comprises an amino acid sequence that facilitates the importation of a protein, that comprises an NLS, into the cell nucleus (e.g., by nuclear transport). In some embodiments, any of the fusion proteins provided herein further comprise a nuclear localization sequence (NLS). In some embodiments, the NLS is fused to the N-terminus of the fusion protein. In some embodiments, the NLS is fused to the C-terminus of the fusion protein. In some embodiments, the NLS is fused to the N-terminus of the IBR (e.g., dISN). In some embodiments, the NLS is fused to the C-terminus of the IBR (e.g., dISN). In some embodiments, the NLS is fused to the N-terminus of the napDNAbp. In some embodiments, the NLS is fused to the C-terminus of the napDNAbp. In some embodiments, the NLS is fused to the N-terminus of the adenosine deaminase. In some embodiments, the NLS is fused to the C-terminus of the adenosine deaminase. In some embodiments, the NLS is fused to the fusion protein via one or more linkers. In some embodiments, the NLS is fused to the fusion protein without a linker. In some embodiments, the NLS comprises an amino acid sequence of any one of the NLS sequences provided or referenced herein. In some embodiments, the NLS comprises an amino acid sequence as set forth in SEQ ID NO: 4 or SEQ ID NO: 5. Additional nuclear localization sequences are known in the art and would be apparent to the skilled artisan. For example, NLS sequences are described in Plank et al., PCT/EP2000/011690, the contents of which are incorporated herein by reference for their disclosure of exemplary nuclear localization sequences. In some embodiments, a NLS comprises the amino acid sequence PKKKRKV (SEQ ID NO: 4) or MDSLLMNRRKFLY-QFKNVRWAKGRRETYLC (SEQ ID NO: 5).

In some embodiments, the general architecture of exemplary fusion proteins with an adenosine deaminase and a napDNAbp comprises any one of the following structures, where NLS is a nuclear localization sequence (e.g., any NLS provided herein), $NH_2$ is the N-terminus of the fusion protein, and COOH is the C-terminus of the fusion protein.

Fusion proteins comprising an adenosine deaminase, a napDNAbp, and a NLS.
$NH_2$-[NLS]-[adenosine deaminase]-[napDNAbp]-COOH;
$NH_2$-[adenosine deaminase]-[NLS]-[napDNAbp]-COOH;
$NH_2$-[adenosine deaminase]-[napDNAbp]-[NLS]-COOH;
$NH_2$-[NLS]-[napDNAbp]-[adenosine deaminase]-COOH;
$NH_2$-[napDNAbp]-[NLS]-[adenosine deaminase]-COOH;
$NH_2$-[napDNAbp]-[adenosine deaminase]-[NLS]-COOH;

In some embodiments, the fusion proteins provided herein do not comprise a linker. In some embodiments, a linker is present between one or more of the domains or proteins (e.g., adenosine deaminase, napDNAbp, and/or NLS). In some embodiments, the "-" used in the general architecture above indicates the presence of an optional linker.

Fusion proteins comprising an adenosine deaminase, a napDNAbp, and an inhibitor of base repair (IBR).
$NH_2$-[IBR]-[adenosine deaminase]-[napDNAbp]-COOH;
$NH_2$-[adenosine deaminase]-[IBR]-[napDNAbp]-COOH;
$NH_2$-[adenosine deaminase]-[napDNAbp]-[IBR]-COOH;
$NH_2$-[IBR]-[napDNAbp]-[adenosine deaminase]-COOH;
$NH_2$-[napDNAbp]-[IBR]-[adenosine deaminase]-COOH;
$NH_2$-[napDNAbp]-[adenosine deaminase]-[IBR]-COOH;

In some embodiments, the fusion proteins provided herein do not comprise a linker. In some embodiments, a linker is present between one or more of the domains or proteins (e.g., adenosine deaminase, napDNAbp, and/or IBR). In some embodiments, the "-" used in the general architecture above indicates the presence of an optional linker.

Fusion proteins comprising an adenosine deaminase, a napDNAbp, an inhibitor of base repair (IBR) and a NLS.
$NH_2$-[IBR]-[NLS]-[adenosine deaminase]-[napDNAbp]-COOH;
$NH_2$-[NLS]-[IBR]-[adenosine deaminase]-[napDNAbp]-COOH;

NH$_2$-[NLS]-[adenosine deaminase]-[IBR]-[napDNAbp]-COOH;
NH$_2$-[NLS]-[adenosine deaminase]-[napDNAbp]-[IBR]-COOH;
NH$_2$-[IBR]-[adenosine deaminase]-[NLS]-[napDNAbp]-COOH;
NH$_2$-[adenosine deaminase]-[IBR]-[NLS]-[napDNAbp]-COOH;
NH$_2$-[adenosine deaminase]-[NLS]-[IBR]-[napDNAbp]-COOH;
NH$_2$-[adenosine deaminase]-[NLS]-[napDNAbp]-[IBR]-COOH;
NH$_2$-[IBR]-[adenosine deaminase]-[napDNAbp]-[NLS]-COOH;
NH$_2$-[adenosine deaminase]-[IBR]-[napDNAbp]-[NLS]-COOH;
NH$_2$-[adenosine deaminase]-[napDNAbp]-[IBR]-[NLS]-COOH;
NH$_2$-[adenosine deaminase]-[napDNAbp]-[NLS]-[IBR]-COOH;
NH$_2$-[IBR]-[NLS]-[napDNAbp]-[adenosine deaminase]-COOH;
NH$_2$-[NLS]-[IBR]-[napDNAbp]-[adenosine deaminase]-COOH;
NH$_2$-[NLS]-[napDNAbp]-[IBR]-[adenosine deaminase]-COOH;
NH$_2$-[NLS]-[napDNAbp]-[adenosine deaminase]-[IBR]-COOH;
NH$_2$-[IBR]-[napDNAbp]-[NLS]-[adenosine deaminase]-COOH;
NH$_2$-[napDNAbp]-[IBR]-[NLS]-[adenosine deaminase]-COOH;
NH$_2$-[napDNAbp]-[NLS]-[IBR]-[adenosine deaminase]-COOH;
NH$_2$-[napDNAbp]-[NLS]-[adenosine deaminase]-[IBR]-COOH;
NH$_2$-[IBR]-[napDNAbp]-[adenosine deaminase]-[NLS]-COOH;
NH$_2$-[napDNAbp]-[IBR]-[adenosine deaminase]-[NLS]-COOH;
NH$_2$-[napDNAbp]-[adenosine deaminase]-[IBR]-[NLS]-COOH;
NH$_2$-[napDNAbp]-[adenosine deaminase]-[NLS]-[IBR]-COOH;

In some embodiments, the fusion proteins provided herein do not comprise a linker. In some embodiments, a linker is present between one or more of the domains or proteins (e.g., adenosine deaminase, napDNAbp, NLS, and/or IBR). In some embodiments, the "-" used in the general architecture above indicates the presence of an optional linker.

Some aspects of the disclosure provide fusion proteins that comprise a nucleic acid programmable DNA binding protein (napDNAbp) and at least two adenosine deaminase domains. Without wishing to be bound by any particular theory, dimerization of adenosine deaminases (e.g., in cis or in trans) may improve the ability (e.g., efficiency) of the fusion protein to modify a nucleic acid base, for example to deaminate adenine. In some embodiments, any of the fusion proteins may comprise 2, 3, 4 or 5 adenosine deaminase domains. In some embodiments, any of the fusion proteins provided herein comprise two adenosine deaminases. In some embodiments, any of the fusion proteins provided herein contain only two adenosine deaminases. In some embodiments, the adenosine deaminases are the same. In some embodiments, the adenosine deaminases are any of the adenosine deaminases provided herein. In some embodiments, the adenosine deaminases are different. In some embodiments, the first adenosine deaminase is any of the adenosine deaminases provided herein, and the second adenosine is any of the adenosine deaminases provided herein, but is not identical to the first adenosine deaminase. As one example, the fusion protein may comprise a first adenosine deaminase and a second adenosine deaminase that both comprise the amino acid sequence of SEQ ID NO: 72, which contains a A106V, D108N, D147Y, and E155V mutation from ecTadA (SEQ ID NO: 1). As another example, the fusion protein may comprise a first adenosine deaminase domain that comprises the amino amino acid sequence of SEQ ID NO: 72, which contains a A106V, D108N, D147Y, and E155V mutation from ecTadA (SEQ ID NO: 1), and a second adenosine deaminase that comprises the amino acid sequence of SEQ ID NO: 421, which contains a L84F, A106V, D108N, H123Y, D147Y, E155V, and I156F mutation from ecTadA (SEQ ID NO: 1).

In some embodiments, the fusion protein comprises two adenosine deaminases (e.g., a first adenosine deaminase and a second adenosine deaminase). In some embodiments, the fusion protein comprises a first adenosine deaminase and a second adenosine deaminase. In some embodiments, the first adenosine deaminase is N-terminal to the second adenosine deaminase in the fusion protein. In some embodiments, the first adenosine deaminase is C-terminal to the second adenosine deaminase in the fusion protein. In some embodiments, the first adenosine deaminase and the second deaminase are fused directly or via a linker. In some embodiments, the linker is any of the linkers provided herein, for example, any of the linkers described in the "Linkers" section. In some embodiments, the linker comprises the amino acid sequence of any one of SEQ ID NOs: 10, 37-40, 384-386, or 685-688. In some embodiments, the first adenosine deaminase is the same as the second adenosine deaminase. In some embodiments, the first adenosine deaminase and the second adenosine deaminase are any of the adenosine deaminases described herein. In some embodiments, the first adenosine deaminase and the second adenosine deaminase are different. In some embodiments, the first adenosine deaminase is any of the adenosine deaminases provided herein. In some embodiments, the second adenosine deaminase is any of the adenosine deaminases provided herein but is not identical to the first adenosine deaminase. In some embodiments, the first adenosine deaminase is an ecTadA adenosine deaminase. In some embodiments, the first adenosine deaminase comprises an amino acid sequence that is at least least 60%, at least 65%, at least 70%, at least 75%, at least 80%, at least 85%, at least 90%, at least 95%, at least 96%, at least 97%, at least 98%, at least 99%, or at least 99.5% identical to any one of the amino acid sequences set forth in any one of SEQ ID NOs: 1, 64-84, 420-437, 672-684, or to any of the adenosine deaminases provided herein. In some embodiments, the first adenosine deaminase comprises the amino acid sequence of SEQ ID NO: 1. In some embodiments, the second adenosine deaminase comprises an amino acid sequence that is at least least 60%, at least 65%, at least 70%, at least 75%, at least 80%, at least 85%, at least 90%, at least 95%, at least 96%, at least 97%, at least 98%, at least 99%, or at least 99.5% identical to any one of the amino acid sequences set forth in any one of SEQ ID NOs: 1, 64-84, 420-437, 672-684, or to any of the adenosine deaminases provided herein. In some embodiments, the second adenosine deaminase comprises the amino acid sequence of SEQ ID NO: 1. In some embodiments, the first adenosine deaminase and the second adenosine deaminase of the fusion protein comprise the mutations in ecTadA (SEQ ID NO: 1), or corresponding mutations in another adenosine deaminase, as shown in any one of the constructs provided in Table 4 (e.g., pNMG-371, pNMG-477, pNMG-576, pNMG-586, and pNMG-616). In some embodiments, the fusion protein comprises the two adenosine deaminases (e.g., a first adenosine deaminase and a second adenosine deaminase) of any one of the constructs (e.g., pNMG-371, pNMG-477, pNMG-576, pNMG-586, and pNMG-616) in Table 4.

In some embodiments, the general architecture of exemplary fusion proteins with a first adenosine deaminase, a second adenosine deaminase, and a napDNAbp comprises any one of the following structures, where NLS is a nuclear localization sequence (e.g., any NLS provided herein), $NH_2$ is the N-terminus of the fusion protein, and COOH is the C-terminus of the fusion protein.

Fusion proteins comprising a first adenosine deaminase, a second adenosine deaminase, and a napDNAbp.
$NH_2$-[first adenosine deaminase]-[second adenosine deaminase]-[napDNAbp]-COOH;
$NH_2$-[first adenosine deaminase]-[napDNAbp]-[second adenosine deaminase]-COOH;
$NH_2$-[napDNAbp]-[first adenosine deaminase]-[second adenosine deaminase]-COOH;
$NH_2$-[second adenosine deaminase]-[first adenosine deaminase]-[napDNAbp]-COOH;
$NH_2$-[second adenosine deaminase]-[napDNAbp]-[first adenosine deaminase]-COOH;
$NH_2$-[napDNAbp]-[second adenosine deaminase]-[first adenosine deaminase]-COOH;

In some embodiments, the fusion proteins provided herein do not comprise a linker. In some embodiments, a linker is present between one or more of the domains or proteins (e.g., first adenosine deaminase, second adenosine deaminase, and/or napDNAbp). In some embodiments, the "-" used in the general architecture above indicates the presence of an optional linker.

Fusion proteins comprising a first adenosine deaminase, a second adenosine deaminase, a napDNAbp, and an NLS.
$NH_2$-[NLS]-[first adenosine deaminase]-[second adenosine deaminase]-[napDNAbp]-COOH;
$NH_2$-[first adenosine deaminase]-[NLS]-[second adenosine deaminase]-[napDNAbp]-COOH;
$NH_2$-[first adenosine deaminase]-[second adenosine deaminase]-[NLS]-[napDNAbp]-COOH;
$NH_2$-[first adenosine deaminase]-[second adenosine deaminase]-[napDNAbp]-[NLS]-COOH;
$NH_2$-[NLS]-[first adenosine deaminase]-[napDNAbp]-[second adenosine deaminase]-COOH;
$NH_2$-[first adenosine deaminase]-[NLS]-[napDNAbp]-[second adenosine deaminase]-COOH;
$NH_2$-[first adenosine deaminase]-[napDNAbp]-[NLS]-[second adenosine deaminase]-COOH;
$NH_2$-[first adenosine deaminase]-[napDNAbp]-[second adenosine deaminase]-[NLS]-COOH;
$NH_2$-[NLS]-[napDNAbp]-[first adenosine deaminase]-[second adenosine deaminase]-COOH;
$NH_2$-[napDNAbp]-[NLS]-[first adenosine deaminase]-[second adenosine deaminase]-COOH;
$NH_2$-[napDNAbp]-[first adenosine deaminase]-[NLS]-[second adenosine deaminase]-COOH;
$NH_2$-[napDNAbp]-[first adenosine deaminase]-[second adenosine deaminase]-[NLS]-COOH;
$NH_2$-[NLS]-[second adenosine deaminase]-[first adenosine deaminase]-[napDNAbp]-COOH;
$NH_2$-[second adenosine deaminase]-[NLS]-[first adenosine deaminase]-[napDNAbp]-COOH;
$NH_2$-[second adenosine deaminase]-[first adenosine deaminase]-[NLS]-[napDNAbp]-COOH;
$NH_2$-[second adenosine deaminase]-[first adenosine deaminase]-[napDNAbp]-[NLS]-COOH;
$NH_2$-[NLS]-[second adenosine deaminase]-[napDNAbp]-[first adenosine deaminase]-COOH;
$NH_2$-[second adenosine deaminase]-[NLS]-[napDNAbp]-[first adenosine deaminase]-COOH;
$NH_2$-[second adenosine deaminase]-[napDNAbp]-[NLS]-[first adenosine deaminase]-COOH;
$NH_2$-[second adenosine deaminase]-[napDNAbp]-[first adenosine deaminase]-[NLS]-COOH;
$NH_2$-[NLS]-[napDNAbp]-[second adenosine deaminase]-[first adenosine deaminase]-COOH;
$NH_2$-[napDNAbp]-[NLS]-[second adenosine deaminase]-[first adenosine deaminase]-COOH;
$NH_2$-[napDNAbp]-[second adenosine deaminase]-[NLS]-[first adenosine deaminase]-COOH;
$NH_2$-[napDNAbp]-[second adenosine deaminase]-[first adenosine deaminase]-[NLS]-COOH;

In some embodiments, the fusion proteins provided herein do not comprise a linker. In some embodiments, a linker is present between one or more of the domains or proteins (e.g., first adenosine deaminase, second adenosine deaminase, napDNAbp, and/or NLS). In some embodiments, the "-" used in the general architecture above indicates the presence of an optional linker.

It should be appreciated that the fusion proteins of the present disclosure may comprise one or more additional features. For example, in some embodiments, the fusion protein may comprise cytoplasmic localization sequences, export sequences, such as nuclear export sequences, or other localization sequences, as well as sequence tags that are useful for solubilization, purification, or detection of the fusion proteins. Suitable protein tags provided herein include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. Additional suitable sequences will be apparent to those of skill in the art. In some embodiments, the fusion protein comprises one or more His tags.

Linkers

In certain embodiments, linkers may be used to link any of the protein or protein domains described herein. The linker may be as simple as a covalent bond, or it may be a polymeric linker many atoms in length. In certain embodiments, the linker is a polypeptide or based on amino acids. In other embodiments, the linker is not peptide-like. In certain embodiments, the linker is a covalent bond (e.g., a carbon-carbon bond, disulfide bond, carbon-heteroatom bond, etc.). In certain embodiments, the linker is a carbon-nitrogen bond of an amide linkage. In certain embodiments, the linker is a cyclic or acyclic, substituted or unsubstituted, branched or unbranched aliphatic or heteroaliphatic linker. In certain embodiments, the linker is polymeric (e.g., polyethylene, polyethylene glycol, polyamide, polyester, etc.). In certain embodiments, the linker comprises a monomer, dimer, or polymer of aminoalkanoic acid. In certain embodiments, the linker comprises an aminoalkanoic acid (e.g., glycine, ethanoic acid, alanine, beta-alanine, 3-aminopropanoic acid, 4-aminobutanoic acid, 5-pentanoic acid, etc.). In certain embodiments, the linker comprises a monomer, dimer, or polymer of aminohexanoic acid (Ahx). In certain embodiments, the linker is based on a carbocyclic moiety (e.g., cyclopentane, cyclohexane). In other embodiments, the linker comprises a polyethylene glycol moiety (PEG). In other embodiments, the linker comprises amino acids. In certain embodiments, the linker comprises a peptide. In certain embodiments, the linker comprises an aryl or heteroaryl moiety. In certain embodiments, the linker is based on a phenyl ring. The linker may include functionalized moieties to facilitate attachment of a nucleophile (e.g., thiol, amino) from the peptide to the linker. Any electrophile may be used as part of the linker. Exemplary electrophiles include, but are not limited to, activated esters, activated amides, Michael acceptors, alkyl halides, aryl halides, acyl halides, and isothiocyanates.

In some embodiments, the linker is an amino acid or a plurality of amino acids (e.g., a peptide or protein). In some embodiments, the linker is a bond (e.g., a covalent bond), an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-110, 110-120, 120-130, 130-140, 140-150, or 150-210 amino acids in length. Longer or shorter linkers are also contemplated. In some embodiments, a linker comprises the amino acid sequence SGSETPGTSESATPES (SEQ ID NO: 10), which may also be referred to as the XTEN linker. In some embodiments, a linker comprises the amino acid sequence SGGS (SEQ ID NO: 37). In some embodiments, a linker comprises (SGGS)$_n$ (SEQ ID NO: 37), (GGGS)n (SEQ ID NO: 38), (GGGGS)n (SEQ ID NO: 39), (G)n, (EAAAK)n (SEQ ID NO: 40), (GGS)$_n$, SGSETPGTSESATPES (SEQ ID NO: 10), or (XP)$_n$ motif, or a combination of any of these, wherein n is independently an integer between 1 and 30, and wherein X is any amino acid. In some embodiments, n is 1, 2, 3, 4, 5, 6, 7, 8, 9, 10, 11, 12, 13, 14, or 15. In some embodiments, a linker comprises SGSETPGTSESATPES (SEQ ID NO: 10), and SGGS (SEQ ID NO: 37). In some embodiments, a linker comprises SGGSSGSETPGTSESATPESSGGS (SEQ ID NO: 384). In some embodiments, a linker comprises SGGSSGGSSGSETPGTSESATPESSGGSSGGS (SEQ ID NO: 385). In some embodiments, a linker comprises GGSGGSPGSPAGSPTSTEEGTSESATPESGPGTSTEPSEGSAPGSPAGSPTSTEEGTSTE PSEGSAPGTSTEPSEGSAPGTSESATPESGPGSEPATSGGSGGS (SEQ ID NO: 386). In some embodiments, the linker is 24 amino acids in length. In some embodiments, the linker comprises the amino acid sequence SGGSSGGSSGSETPGTSESATPES (SEQ ID NO: 685). In some embodiments, the linker is 40 amino acids in length. In some embodiments, the linker comprises the amino acid sequence SGGSSGGSSGSETPGTSESATPESSGGSSGGSSGGSSGGS (SEQ ID NO: 686). In some embodiments, the linker is 64 amino acids in length. In some embodiments, the linker comprises the amino acid sequence SGGSSGGSSGSETPGTSESATPESSGGSSGGSSGGSSGGSSGGSSGSETPGTSESATPESSGGS SGGS (SEQ ID NO: 687). In some embodiments, the linker is 92 amino acids in length. In some embodiments, the linker comprises the amino acid sequence PGSPAGSPTSTEEGTSESATPESGPGTSTEPSEGSAPGSPAGSPTSTEEGTSTEPSEGSAP GTSTEPSEGSAPGTSESATPESGPGSEPATS (SEQ ID NO: 688). It should be appreciated that any of the linkers provided herein may be used to link a first adenosine deaminase and a second adenosine deaminase; an adenosine deaminase (e.g., a first or a second adenosine deaminase) and a napDNAbp; a napDNAbp and an NLS; or an adenosine deaminase (e.g., a first or a second adenosine deaminase) and an NLS.

In some embodiments, any of the fusion proteins provided herein, comprise an adenosine deaminase and a napDNAbp that are fused to each other via a linker. In some embodiments, any of the fusion proteins provided herein, comprise a first adenosine deaminase and a second adenosine deaminase that are fused to each other via a linker. In some embodiments, any of the fusion proteins provided herein, comprise an NLS, which may be fused to an adenosine deaminase (e.g., a first and/or a second adenosine deaminase), a nucleic acid programmable DNA binding protein (napDNAbp), and or an inhibitor of base repair (IBR). Various linker lengths and flexibilities between an adenosine deaminase (e.g., an engineered ecTadA) and a napDNAbp (e.g., a Cas9 domain), and/or between a first adenosine deaminase and a second adenosine deaminase can be employed (e.g., ranging from very flexible linkers of the form (GGGGS)n (SEQ ID NO: 38), (GGGGS)n (SEQ ID NO: 39), and (G)n to more rigid linkers of the form (EAAAK)n (SEQ ID NO: 40), (SGGS)n (SEQ ID NO: 37), SGSETPGTSESATPES (SEQ ID NO: 10) (see, e.g., Guilinger J P, Thompson D B, Liu D R. Fusion of catalytically inactive Cas9 to FokI nuclease improves the specificity of genome modification. *Nat. Biotechnol.* 2014; 32(6): 577-82; the entire contents are incorporated herein by reference) and (XP)$_n$) in order to achieve the optimal length for deaminase activity for the specific application. In some embodiments, n is 1, 2, 3, 4, 5, 6, 7, 8, 9, 10, 11, 12, 13, 14, or 15. In some embodiments, the linker comprises a (GGS)$_n$ motif, wherein n is 1, 3, or 7. In some embodiments, the adenosine deaminase and the napDNAbp, and/or the first adenosine deaminase and the second adenosine deaminase of any of the fusion proteins provided herein are fused via a linker comprising the amino acid sequence SGSETPGTSESATPES (SEQ ID NO: 10), SGGS (SEQ ID NO: 37), SGGSSGSETPGTSESATPESSGGS (SEQ ID NO: 384), SGGSSGGSSGSETPGTSESATPESSGGSSGGS (SEQ ID NO: 385), or GGSGGSPGSPAGSPTSTEEGTSESATPESGPGTSTEPSEGSAPGSPAGSPTSTEEGTSTE PSEGSAPGTSTEPSEGSAPGTSESATPESGPGSEPATSGGSGGS (SEQ ID NO: 386). In some embodiments, the linker is 24 amino acids in length. In some embodiments, the linker comprises the amino acid sequence SGGSSGGSSGSETPGTSESATPES (SEQ ID NO: 685). In some embodiments, the linker is 40 amino acids in length. In some embodiments, the linker comprises the amino acid sequence SGGSSGGSSGSETPGTSESATPESSGGSSGGSSGGSSGGS (SEQ ID NO: 686). In some embodiments, the linker is 64 amino acids in length. In some embodiments, the linker comprises the amino acid sequence SGGSSGGSSGSETPGTSESATPESSGGSSGGSSGGSSGGSSGSETPGTSESATPESSGGS SGGS (SEQ ID NO: 687). In some embodiments, the linker is 92 amino acids in length. In some embodiments, the linker comprises the amino acid sequence PGSPAGSPTSTEEGTSESATPESGPGTSTEPSEGSAPGSPAGSPTSTEEGTSTEPSEGSAP GTSTEPSEGSAPGTSESATPESGPGSEPATS (SEQ ID NO: 688).

Some aspects of the disclosure provide fusion proteins comprising a Cas9 domain and an adenosine deaminase. Exemplary fusion proteins include, without limitation, the following fusion proteins (for the purposes of clarity, the adenosine deaminase domain is shown in Bold; mutations of the ecTadA deaminase domain are shown in Bold underlining; the XTEN linker is shown in italics; the UGI/AAG/EndoV domains are shown in Bold italics; and NLS is shown in underlined italics):

ecTadA(wt)-XTEN-nCas9-NLS:

(SEQ ID NO: 11)

MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARDAKTGAAGSLMDVLHHPGMNHRVEITEGILADECAALLSDFFRMRRQEIKAQKKAQSSTDSGSETPGTS
ESATPESDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQLPGEKKNGLFGNLIALSLGLTPNFKSNFDL
AEDAKLQLSKDTYDDDLDNLLAQIGDQYADLFLAAKNLSDAILLSDILRVNTEITKAPLSASMIKRYDEHHQDLTLLKALVRQQLPEK
YKEIFFDQSKNGYAGYIDGGASQEEFYKFIKPILEKMDGTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDKGASAQSFIERMTNFDKNLPNEKVLPKHSLLYEYFTVYN
ELTKVKYVTEGMRKPAFLSGEQKKAIVDLLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDVDHIVPQSFLKDDSIDNKVLTRSDKNRGKSDNVPSEE
VVKKMKNYWRQLLNAKLITQRKFDNLTKAERGGLSELDKAGFIKRQLVETRQITKHVAQILDSRMNTKYDENDKLIREVKVITLKSKL
VSDFRKDFQFYKVREINNYHHAHDAYLNAVVGTALIKKYPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEVQTGGFSKESILPKRNSDKLIARKKDWDPKKYGGFDSPT
VAYSVLVVAKVEKGKSKKLKSVKELLGITIMERSSFEKNPIDFLEAKGYKEVKKDLIIKLPKYSLFELENGRKRMLASAGELQKGNEL
ALPSKYVNFLYLASHYEKLKGSPEDNEQKQLFVEQHKHYLDEIIEQISEFSKRVILADANLDKVLSAYNKHRDKPIREQAENIIHLFT
LTNLGAPAAFKYFDTTIDRKRYTSTKEVLDATLIHQSITGLYETRIDLSQLGGD*SGGS**PKKKRKV* ecTadA(D108N)-XTEN-nCas9-NLS: (mammalian construct, active on DNA, A to G editing):

(SEQ ID NO: 12)

MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARNAKTGAAGSLMDVLHHPGMNHRVEITEGILADECAALLSDFFRMRRQEIKAQKKAQSSTDSGSETPGTS
ESATPESDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQLPGEKKNGLFGNLIALSLGLTPNFKSNFDL
AEDAKLQLSKDTYDDDLDNLLAQIGDQYADLFLAAKNLSDAILLSDILRVNTEITKAPLSASMIKRYDEHHQDLTLLKALVRQQLPEK
YKEIFFDQSKNGYAGYIDGGASQEEFYKFIKPILEKMDGTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDKGASAQSFIERMTNFDKNLPNEKVLPKHSLLYEYFTVYN
ELTKVKYVTEGMRKPAFLSGEQKKAIVDLLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDVDHIVPQSFLKDDSIDNKVLTRSDKNRGKSDNVPSEE
VVKKMKNYWRQLLNAKLITQRKFDNLTKAERGGLSELDKAGFIKRQLVETRQITKHVAQILDSRMNTKYDENDKLIREVKVITLKSKL
VSDFRKDFQFYKVREINNYHHAHDAYLNAVVGTALIKKYPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEVQTGGFSKESILPKRNSDKLIARKKDWDPKKYGGFDSPT
VAYSVLVVAKVEKGKSKKLKSVKELLGITIMERSSFEKNPIDFLEAKGYKEVKKDLIIKLPKYSLFELENGRKRMLASAGELQKGNEL
ALPSKYVNFLYLASHYEKLKGSPEDNEQKQLFVEQHKHYLDEIIEQISEFSKRVILADANLDKVLSAYNKHRDKPIREQAENIIHLFT
LTNLGAPAAFKYFDTTIDRKRYTSTKEVLDATLIHQSITGLYETRIDLSQLGGD*SGGS**PKKKRKV*

-continued ecTadA(D108G)-XTEN-nCas9-NLS: (mammalian construct, active on DNA, A to G editing):
(SEQ ID NO: 13)
MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARGAKTGAAGSLMDVLHHPGMNHRVEITEGILADECAALLSDFFRMRRQEIKAQKKAQSSTD_SGSETPGTS_
_ESATPES_DKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADKAILSARLSKSRRLENLIAQ
LPGEKKNGLFGNLIALSLGLTPNFKSNFDLAEDAKLQLSKDTYDDDLDNLLAQIGDQYADLFLAAKNLSDAILLSDILRVNTEITKAP
LSASMIKRYMDGTEELLVKLNREDLLRKQRTFDNGSIPHQIHLGELHAILRRQEDFYPFLKDNREKIEKILTFRIPYYVGPLARGNSR
FAWMTRKSEETITPWNFEEVVDKGASAQSFIERMTNFDKNLPNEKVLPKHSLLYEYFTVYNELTKVKYVTEGMRKPAFLSGEQKKAIV
DLLFKTNRKVTVKQLKEDYFKKIECFDSVEISGVEDRFNASLGTYHDLLKIIKDKDFLDNEENEDILEDIVLTLTLFEDREMIEERLK
TYAHLFDDKVMKQLKRRRYTGWGRLSRKLINGIRDKQSGKTILDFLKSDGFANRNFMQLIHDDSLTFKEDIQKAQVSGQGDSLHEHIA NLAGSPAIKKGILQTVKVVDELVKVMGRHKPENIVIEMARENQTTQKGQKNSRERMKRIEEGIKELGSQILKEHPVENTQLQNEKLYL
YYLQNGRDMYVDQELDINRLSDYDVDHIVPQSFLKDDSIDNKVLTRSDKNRGKSDNVPSEEVVKKMKNYWRQLLNAKLITQRKFDNLT
KAERGGLSELDKAGFIKRQLVETRQITKHVAQILDSRMNTKYDENDKLIREVKVITLKSKLVSDFRKDFQFYKVREINNYHHAHDAYL
NAVVGTALIKKYPKLESEFVYGDYKVYDVRKMIAKSEQEIGKATAKYFFYSNIMNFFKTEITLANGEIRKRPLIETNGETGEIVWDKG
RDFATVRKVLSMPQVNIVKKTEVQTGGFSKESILPKRNSDKLIARKKDWDPKKYGGFDSPTVAYSVLVVAKVEKGKSKKLKSVKELLG
ITIMERSSFEKNPIDFLEAKGYKEVKKDLIIKLPKYSLFELENGRKRMLASAGELQKGNELALPSKYVNFLYLASHYEKLKGSPEDNE
QKQLFVEQHKHYLDEIIEQISEFSKRVILADANLDKVLSAYNKHRDKPIREQAENIIHLFTLTNLGAPAAFKYFDTTIDRKRYTSTKE
VLDATLIHQSITGLYETRIDLSQLGGDSGGS_PKKKRKV_ ecTadA(D108V)-XTEN-nCas9-NLS: (mammalian construct, active on DNA, A to G editing):
(SEQ ID NO: 14)
MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARVAKTGAAGSLMDVLHHPGMNHRVEITEGILADECAALLSDFFRMRRQEIKAQKKAQSSTD_SGSETPGTS_
_ESATPES_DKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQLPGEKKNGLFGNLIALSLGLTPNFKSNFDL
AEDAKLQLSKDTYDDDLDNLLAQIGDQYADLFLAAKNLSDAILLSDILRVNTEITKAPLSASMIKRYDEHHQDLTLLKALVRQQLPEK
YKEIFFDQSKNGYAGYIDGGASQEEFYKFIKPILEKMDGTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDKGASAQSFIERMTNFDKNLPNEKVLPKHSLLYEYFTVYN
ELTKVKYVTEGMRKPAFLSGEQKKAIVDLLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDVDHIVPQSFLKDDSIDNKVLTRSDKNRGKSDNVPSEE
VVKKMKNYWRQLLNAKLITQRKFDNLTKAERGGLSELDKAGFIKRQLVETRQITKHVAQILDSRMNTKYDENDKLIREVKVITLKSKL
VSDFRKDFQFYKVREINNYHHAHDAYLNAVVGTALIKKYPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEVQTGGFSKESILPKRNSDKLIARKKDWDPKKYGGFDSPT
VAYSVLVVAKVEKGKSKKLKSVKELLGITIMERSSFEKNPIDFLEAKGYKEVKKDLIIKLPKYSLFELENGRKRMLASAGELQKGNEL
ALPSKYVNFLYLASHYEKLKGSPEDNEQKQLFVEQHKHYLDEIIEQISEFSKRVILADANLDKVLSAYNKHRDKPIREQAENIIHLFT
LTNLGAPAAFKYFDTTIDRKRYTSTKEVLDATLIHQSITGLYETRIDLSQLGGDSGGS_PKKKRKV_ ecTadA(D108N)-XTEN-nCas9-UGI-NLS (BE3 analog of A to G editor):
(SEQ ID NO: 15)
MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARNAKTGAAGSLMDVLHHPGMNHRVEITEGILADECAALLSDFFRMRRQEIKAQKKAQSSTD_SGSETPGTS_

-continued

*ESATPES*DKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQLPGEKKNGLFGNLIALSLGLTPNFKSNFDL
AEDAKLQLSKDTYDDDLDNLLAQIGDQYADLFLAAKNLSDAILLSDILRVNTEITKAPLSASMIKRYDEHHQDLTLLKALVRQQLPEK
YKEIFFDQSKNGYAGYIDGGASQEEFYKFIKPILEKMDGTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDKGASAQSFIERMTNFDKNLPNEKVLPKHSLLYEYFTVYN
ELTKVKYVTEGMRKPAFLSGEQKKAIVDLLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDVDHIVPQSFLKDDSIDNKVLTRSDKNRGKSDNVPSEE
VVKKMKNYWRQLLNAKLITQRKFDNLTKAERGGLSELDKAGFIKRQLVETRQITKHVAQILDSRMNTKYDENDKLIREVKVITLKSKL
VSDFRKDFQFYKVREINNYHHAHDAYLNAVVGTALIKKYPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEVQTGGFSKESILPKRNSDKLIARKKDWDPKKYGGFDSPT
VAYSVLVVAKVEKGKSKKLKSVKELLGITIMERSSFEKNPIDFLEAKGYKEVKKDLIIKLPKYSLFELENGRKRMLASAGELQKGNEL
ALPSKYVNFLYLASHYEKLKGSPEDNEQKQLFVEQHKHYLDEIIEQISEFSKRVILADANLDKVLSAYNKHRDKPIREQAENIIHLFT
LTNLGAPAAFKYFDTTIDRKRYTSTKEVLDATLIHQSITGLYETRIDLSQLGGD*SGGS**TNLSDIIEKETGKQLVIQESILML*
*PEEVEEVIGNKPESDILVHTAYDESTDENVMLLTSDAPEYKP**WALVIQDSNGENKIKML*SGGS *PKKKRKV* ecTadA(D108G)-XTEN-nCas9-UGI-NLS (BE3 analog of A to G editor):
(SEQ ID NO: 16)
MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARGAKTGAAGSLMDVLHHPGMNHRVEITEGILADECAALLSDFFRMRRQEIKAQKKAQSSTD*SGSETPGTS*
*ESATPES*DKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQLPGEKKNGLFGNLIALSLGLTPNFKSNFDL
AEDAKLQLSKDTYDDDLDNLLAQIGDQYADLFLAAKNLSDAILLSDILRVNTEITKAPLSASMIKRYDEHHQDLTLLKALVRQQLPEK
YKEIFFDQSKNGYAGYIDGGASQEEFYKFIKPILEKMDGTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDKGASAQSFIERMTNFDKNLPNEKVLPKHSLLYEYFTVYN
ELTKVKYVTEGMRKPAFLSGEQKKAIVDLLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDVDHIVPQSFLKDDSIDNKVLTRSDKNRGKSDNVPSEE
VVKKMKNYWRQLLNAKLITQRKFDNLTKAERGGLSELDKAGFIKRQLVETRQITKHVAQILDSRMNTKYDENDKLIREVKVITLKSKL
VSDFRKDFQFYKVREINNYHHAHDAYLNAVVGTALIKKYPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEVQTGGFSKESILPKRNSDKLIARKKDWDPKKYGGFDSPT
VAYSVLVVAKVEKGKSKKLKSVKELLGITIMERSSFEKNPIDFLEAKGYKEVKKDLIIKLPKYSLFELENGRKRMLASAGELQKGNEL
ALPSKYVNFLYLASHYEKLKGSPEDNEQKQLFVEQHKHYLDEIIEQISEFSKRVILADANLDKVLSAYNKHRDKPIREQAENIIHLFT
LTNLGAPAAFKYFDTTIDRKRYTSTKEVLDATLIHQSITGLYETRIDLSQLGGD*SGGS**TNLSDIIEKETGKQLVIQESILML*
*PEEVEEVIGNKPESDILVHTAYDESTDENVMLLTSDAPEYKP**WALVIQDSNGENKIKML*SGGS *PKKKRKV* ecTadA(D108V)-XTEN-nCas9-UGI-NLS (BE3 analog of A to G editor):
(SEQ ID NO: 17)
MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARVAKTGAAGSLMDVLHHPGMNHRVEITEGILADECAALLSDFFRMRRQEIKAQKKAQSSTD*SGSETPGTS*

*ESATPES*DKKYSIGLAIGTNSVGWAVITDEYKVPSKKFKVLGNTDRHSIKKNLIGALLFDSGETAEATRLKRTARRRYTRRKNRICYL

QEIFSNEMAKVDDSFFHRLEESFLVEEDKKHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQDLTLLKALVRQQLPEK

YKEIFFDQSKNGYAGYIDGGASQEEFYKFIKPILEKMDGTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEISGVEDRFNASLGTYHDLLKIIKDKDFLDNE

ENEDILEDIVLTLTLFEDREMIEERLKTYAHLFDDKVMKQLKRRRYTGWGRLSRKLINGIAGSPAIKKGILQTVKVVDELVKVMGRHK

PENIVIEMARENQTTQKGQKNSRERMKRIEEGIKELGSQILKEHPVENTQLQNEKLYLYYLQNGRDMYVDQELDINRLSDYDVDHIVP

QSFLKDDSIDNKVLTRSDKNRGKSDNVPSEEVVKKMKNYWRQLLNAKLITQRKFDNLTKAERGGLSELDKAGFIKRQLVETRQITKHV

AQILDSRMNTKYDENDKLIREVKVITLKSKLVSDFRKDFQFYKVREINNYHHAHDAYLNAVVGTALIKKYPKLESEFVYGDYKVYDVR

KMIAKSEQEIGKATAKYFFYSNIMNFFKTEITLANGEIRKRPLIETNGETGEIVWDKGRDFATVRKVLSMPQVNIVKKTEVQTGGFSK

ESILPKRNSDKLIARKKDWDPKKYGGFDSPTVAYSVLVVAKVEKGKSKKLKSVKELLGITIMERSSFEKNPIDFLEAKGYKEVKKDLI

IKLPKYSLFELENGRKRMLASAGELQKGNELALPSKYVNFLYLASHYEKLKGSPEDNEQKQLFVEQHKHYLDEIIEQISEFSKRVILA

DANLDKVLSAYNKHRDKPIREQAENIIHLFTLTNLGAPAAFKYFDTTIDRKRYTSTKEVLDATLIHQSITGLYETRIDLSQLGGDSGG

S*TNLSDIIEKETGKQLVIQESIL*MLPEEVEEVIGNKPESDILVHTAYDESTDENVMLLTSDAP*EYKPWALVIQDSNGENKIKML*

SGGS <u>PKKKRKV</u> ecTadA(D108N)-XTEN-dCas9-UGI-NLS (mammalian cells, BE2 analog of A to G editor):
(SEQ ID NO: 18)
MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGAR<u>N</u>AKTGAAGSLMDVLHHPGMNHRVEITEGILADECAALLSDFFRMRRQEIKAQKKAQSSTD*SGSETPGTS*

*ESATPES*DKKYSIGLAIGTNSVGWAVITDEYKVPSKKFKVLGNTDRHSIKKNLIGALLFDSGETAEATRLKRTARRRYTRRKNRICYL

QEIFSNEMAKVDDSFFHRLEESFLVEEDKKHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQDLTLLKALVRQQLPEK

YKEIFFDQSKNGYAGYIDGGASQEEFYKFIKPILEKMDGTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEISGVEDRFNASLGTYHDLLKIIKDKDFLDNE

ENEDILEDIVLTLTLFEDREMIEERLKTYAHLFDDKVMKQLKRRRYTGWGRLSRKLINGIRDKQSGKTILDFLKSDGFANRNFMQLIH

DDSLTFKEDIQKAQVSGQGDSLHEHIANLAGSPAIKKGILQTVKVVDELVKVMGRHKPENIVIEMARENQTTQKGQKNSRERMKRIEE

GIKELGSQILKEHPVENTQLQNEKLYLYYLQNGRDMYVDQELDINRLSDYDVDAIVPQSFLKDDSIDNKVLTRSDKNRGKSDNVPSEE

VVKKMKNYWRQLLNAKLITQRKFDNLTKAERGGLSELDKAGFIKRQLVETRQITKHVAQILDSRMNTKYDENDKLIREVKVITLKSKL

VSDFRKDFQFYKVREINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISEFSKRVILADANLDKVLSAYNKHRDKPIREQAENIIHLFT

LTNLGAPAAFKYFDTTIDRKRYTSTKEVLDATLIHQSITGLYETRIDLSQLGGDSGGS*TNLSDIIEKETGKQLVIQESILML*

*PEEVEEVIGNKPESDILVHTAYDESTDENVMLLTSDA*P*EYKPWALVIQDSNGENKIKML***SGGS<u>PKKKRKV</u> ecTadA(D108G)-XTEN-dCas9-UGI-NLS (mammalian cells, BE2 analog of A to G editor):
(SEQ ID NO: 19)
MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARGAKTGAAGSLMDVLHHPGMNHRVEITEGILADECAALLSDFFRMRRQEIKAQKKAQSSTD*SGSETPGTS*

*ESATPES*DKKYSIGLAIGTNSVGWAVITDEYKVPSKKFKVLGNTDRHSIKKNLIGALLFDSGETAEATRLKRTARRRYTRRKNRICYL

-continued

QEIFSNEMAKVDDSFFHRLEESFLVEEDKKHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQDLTLLKALVRQQLPEK

YKEIFFDQSKNGYAGYIDGGASQEEFYKFIKPILEKMDGTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEISGVEDRFNASLGTYHDLLKIIKDKDFLDNE

ENEDILEDIVLTLTLFEDREMIEERLKTYAHLFDDKVMKQLKRRRYTGWGRLSRKLINGIRDKQSGKTILDFLKSDGFANRNFMQLIH

DDSLTFKEDIQKAQVSGQGDSLHEHIANLAGSPAIKKGILQTVKVVDELVKVMGRHKPENIVIEMARENQTTQKGQKNSRERMKRIEE

GIKELGSQILKEHPVENTQLQNEKLYLYYLQNGRDMYVDQELDINRLSDYDVDAIVPQSFLKDDSIDNKVLTRSDKNRGKSDNVPSEE

VVKKMKNYWRQLLNAKLITQRKFDNLTKAERGGLSELDKAGFIKRQLVETRQITKHVAQILDSRMNTKYDENDKLIREVKVITLKSKL

VSDFRKDFQFYKVREINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISEFSKRVILADANLDKVLSAYNKHRDKPIREQAENIIHLFT

LTNLGAPAAFKYFDTTIDRKRYTSTKEVLDATLIHQSITGLYETRIDLSQLGGD*SGGS**TNLSDIIEKETGKQLVIQESIL*

*MILPEEVEEVIGNKPESDILVHTAYDESTDENVMLLTSDAPEYK**PWALVIQDSNGENKIKML*SGGS PKKKRKV ecTadA(D108V)-XTEN-dCas9-UGI-NLS (mammalian cells, BE2 analog of A to G editor):

(SEQ ID NO: 20)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARVAKTGAAGSLMDVLHHPGMNHRVEITEGILADECAALLSDFFRMRRQEIKAQKKAQSSTD*SGSETPGTS*

*ESATPES*DKKYSIGLAIGTNSVGWAVITDEYKVPSKKFKVLGNTDRHSIKKNLIGALLFDSGETAEATRLKRTARRRYTRRKNRICYL

QEIFSNEMAKVDDSFFHRLEESFLVEEDKKHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQDLTLLKALVRQQLPEK

YKEIFFDQSKNGYAGYIDGGASQEEFYKFIKPILEKMDGTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEISGVEDRFNASLGTYHDLLKIIKDKDFLDNE

ENEDILEDIVLTLTLFEDREMIEERLKTYAHLFDDKVMKQLKRRRYTGWGRLSRKLINGIRDKQSGKTILDFLKSDGFANRNFMQLIH

DDSLTFKEDIQKAQVSGQGDSLHEHIANLAGSPAIKKGILQTVKVVDELVKVMGRHKPENIVIEMARENQTTQKGQKNSRERMKRIEE

GIKELGSQILKEHPVENTQLQNEKLYLYYLQNGRDMYVDQELDINRLSDYDVDAIVPQSFLKDDSIDNKVLTRSDKNRGKSDNVPSEE

VVKKMKNYWRQLLNAKLITQRKFDNLTKAERGGLSELDKAGFIKRQLVETRQITKHVAQILDSRMNTKYDENDKLIREVKVITLKSKL

VSDFRKDFQFYKVREINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISEFSKRVILADANLDKVLSAYNKHRDKPIREQAENIIHLFT

LTNLGAPAAFKYFDTTIDRKRYTSTKEVLDATLIHQSITGLYETRIDLSQLGGD*SGGS**TNLSDIIEKETGKQLVIQESIL*

*MLPEEVEEVIGNKPESDILVHT**AYDESTDENVMLLTSDAPEYKKPWALVIQDSNGENKIKML*SGGS PKKKRKV ecTadA(D108N)-XTEN-nCas9-AAG(E125Q)-NLS-cat. alkyladenosine glycosylase:

(SEQ ID NO: 21)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARNAKTGAAGSLMDVLHHPGMNHRVEITEGILADECAALLSDFFRMRRQEIKAQKKAQSSTDSGSETPGTS

ESATPESDKKYSIGLAIGTNSVGWAVITDEYKVPSKKFKVLGNTDRHSIKKNLIGALLFDSGETAEATRLKRTARRRYTRRKNRICYL

-continued

QEIFSNEMAKVDDSFFHRLEESFLVEEDKKHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQLPGEKKNGLFGNLIALSLGLTPNFKSNFDL
AEDAKLQLSKDTYDDDLDNLLAQIGDQYADLFLAAKNLSDAILLSDILRVNTEITKAPLSASMIKRYDEHHQDLTLLKALVRQQLPEK
YKEIFFDQSKNGYAGYIDGGASQEEFYKFIKPILEKMDGTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDKGASAQSFIERMTNFDKNLPNEKVLPKHSLLYEYFTVYN
ELTKVKYVTEGMRKPAFLSGEQKKAIVDLLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDVDHIVPQSFLKDDSIDNKVLTRSDKNRGKSDNVPSEE
VVKKMKNYWRQLLNAKLITQRKFDNLTKAERGGLSELDKAGFIKRQLVETRQITKHVAQILDSRMNTKYDENDKLIREVKVITLKSKL
VSDFRKDFQFYKVREINNYHHAHDAYLNAVVGTALIKKYPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEVQTGGFSKESILPKRNSDKLIARKKDWDPKKYGGFDSPT
VAYSVLVVAKVEKGKSKKLKSVKELLGITIMERSSFEKNPIDFLEAKGYKEVKKDLIIKLPKYSLFELENGRKRMLASAGELQKGNEL
ALPSKYVNFLYLASHYEKLKGSPEDNEQKQLFVEQHKHYLDEIIEQISEFSKRVILADANLDKVLSAYNKHRDKPIREQAENIIHLFT
LTNLGAPAAFKYFDTTIDRKRYTSTKEVLDATLIHQSITGLYETRIDLSQLGGDSGGS*KGHLTRLGLEFFDQPAVPLARAF*
*LGQVLVRRLPNGTELRGRIVETQAYLGPEDEAAHSRGGRQ*TPRNRGMFMKPGTLYVYI*IYGMYFCMNISSQGDGA*CVLLRALEPLEGLETMRQLRST*
*LRKGTASRVLKDRELCSG*PSKLCQALAINKSFDQRDLAQDEAVWLERGPLEPSEPAV*VAAARVGVHAGEWARK*PLRFYVRGSPWVSVVD*
*RVAEQDTQA*SGGS PKKKRV ecTadA(D108G)-XTEN-nCas9-AAG(E125Q)-NLS-cat. alkyladenosine glycosylase:
(SEQ ID NO: 22)
MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARGAKTGAAGSLMDVLHHPGMNHRVEITEGILADECAALLSDFFRMRRQEIKAQKKAQSSTD*SGSETPGTS*
*ESATPES*DKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQLPGEKKNGLFGNLIALSLGLTPNFKSNFDL
AEDAKLQLSKDTYDDDLDNLLAQIGDQYADLFLAAKNLSDAILLSDILRVNTEITKAPLSASMIKRYDEHHQDLTLLKALVRQQLPEK
YKEIFFDQSKNGYAGYIDGGASQEEFYKFIKPILEKMDGTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDKGASAQSFIERMTNFDKNLPNEKVLPKHSLLYEYFTVYN
ELTKVKYVTEGMRKPAFLSGEQKKAIVDLLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDVDHIVPQSFLKDDSIDNKVLTRSDKNRGKSDNVPSEE
VVKKMKNYWRQLLNAKLITQRKFDNLTKAERGGLSELDKAGFIKRQLVETRQITKHVAQILDSRMNTKYDENDKLIREVKVITLKSKL
VSDFRKDFQFYKVREINNYHHAHDAYLNAVVGTALIKKYPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEVQTGGFSKESILPKRNSDKLIARKKDWDPKKYGGFDSPT
VAYSVLVVAKVEKGKSKKLKSVKELLGITIMERSSFEKNPIDFLEAKGYKEVKKDLIIKLPKYSLFELENGRKRMLASAGELQKGNEL
ALPSKYVNFLYLASHYEKLKGSPEDNEQKQLFVEQHKHYLDEIIEQISEFSKRVILADANLDKVLSAYNKHRDKPIREQAENIIHLFT
LTNLGAPAAFKYFDTTIDRKRYTSTKEVLDATLIHQSITGLYETRIDLSQLGGDSGGS*KGHLTRLGLEFFDQPAVPLARA*
*FLGQVLVRRLPNGTELRGRIVETQAYLGPEDEAAHSRGGRQ*TPRNRGMFMKPGTLYVYI*IYGMYFCMNISSQGDGA*
*CVLLRALEPLEGLETMRQLRSTL*RKGTASRVLKDRELCSGP*SKLCQALAINKSFDQRDLAQDEAVWLERGPLEPSEPA*
*VVAAARVGVHAGEWARKPLRFYVRGSPWVSVVD*RVAEQDTQA*SGGS PKKKRV ecTadA(D108V)-XTEN-nCas9-AAG(E125Q)-NLS-cat. alkyladenosine glycosylase:

(SEQ ID NO: 23)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARVAKTGAAGSLMDVLHHPGMNHRVEITEGILADECAALLSDFFRMRRQEIKAQKKAQSSTD*SGSETPGTS*

*ESATPES*DKKYSIGLAIGTNSVGWAVITDEYKVPSKKFKVLGNTDRHSIKKNLIGALLFDSGETAEATRLKRTARRRYTRRKNRICYL

QEIFSNEMAKVDDSFFHRLEESFLVEEDKKHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQDLTLLKALVRQQLPEK

YKEIFFDQSKNGYAGYIDGGASQEEFYKFIKPILEKMDGTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEISGVEDRFNASLGTYHDLLKIIKDKDFLDNE

ENEDILEDIVLTLTLFEDREMIEERLKTYAHLFDDKVMKQLKRRRYTGWGRLSRKLINGIRDKQSGKTILDFLKSDGFANRNFMQLIH

DDSLTFKEDIQKAQVSGQGDSLHEHIANLAGSPAIKKGILQTVKVVDELVKVMGRHKPENIVIEMARENQTTQKGQKNSRERMKRIEE

GIKELGSQILKEHPVENTQLQNEKLYLYYLQNGRDMYVDQELDINRLSDYDVDHIVPQSFLKDDSIDNKVLTRSDKNRGKSDNVPSEE

VVKKMKNYWRQLLNAKLITQRKFDNLTKAERGGLSELDKAGFIKRQLVETRQITKHVAQILDSRMNTKYDENDKLIREVKVITLKSKL

VSDFRKDFQFYKVREINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISEFSKRVILADANLDKVLSAYNKHRDKPIREQAENIIHLFT

LTNLGAPAAFKYFDTTIDRKRYTSTKEVLDATLIHQSITGLYETRIDLSQLGGD*SGGS**KGHLTRLGLEFFDQPAVPLARA*

*FLGQVLVRRLPNGTELRGRIVETQAYLGPEDEAAHSRGGRQ**PRNRGMFMKPGTLYVYII*YGMYFCMNISSQGDGACVLLRALEPLEGLETMRQLRST*

*LRKGTASRVLKDRELCSGPSKLCQALAINKSFDQRDLAQDEAVWLERGPLEPSEPAVVAAARVGVGHAGEWA*RKPLRFYVRGSPWVSVVD

RVAEQDTQASGGS *PKKKRKV* ecTadA(D108N)-XTEN-nCas9-EndoV(D35A)-NLS: contains cat. endonuclease V:

(SEQ ID NO: 24)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARNAKTGAAGSLMDVLHHPGMNHRVEITEGILADECAALLSDFFRMRRQEIKAQKKAQSSTD*SGSETPGTS*

*ESATPES*DKKYSIGLAIGTNSVGWAVITDEYKVPSKKFKVLGNTDRHSIKKNLIGALLFDSGETAEATRLKRTARRRYTRRKNRICYL

QEIFSNEMAKVDDSFFHRLEESFLVEEDKKHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQDLTLLKALVRQQLPEK

YKEIFFDQSKNGYAGYIDGGASQEEFYKFIKPILEKMDGTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEISGVEDRFNASLGTYHDLLKIIKDKDFLDNE

ENEDILEDIVLTLTLFEDREMIEERLKTYAHLFDDKVMKQLKRRRYTGWGRLSRKLINGIRDKQSGKTILDFLKSDGFANRNFMQLIH

DDSLTFKEDIQKAQVSGQGDSLHEHIANLAGSPAIKKGILQTVKVVDELVKVMGRHKPENIVIEMARENQTTQKGQKNSRERMKRIEE

GIKELGSQILKEHPVENTQLQNEKLYLYYLQNGRDMYVDQELDINRLSDYDVDHIVPQSFLKDDSIDNKVLTRSDKNRGKSDNVPSEE

VVKKMKNYWRQLLNAKLITQRKFDNLTKAERGGLSELDKAGFIKRQLVETRQITKHVAQILDSRMNTKYDENDKLIREVKVITLKSKL

VSDFRKDFQFYKVREINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISEFSKRVILADANLDKVLSAYNKHRDKPIREQAENIIHLFT

-continued

LTNLGAPAAFKYFDTTIDRKRYTSTKEVLDATLIHQSITGLYETRIDLSQLGGD SGGS *DLASLRAQQIELASSVIREDRLLDK*

*DPPDLIAGAAVGFEQGGEV* TRAAMVLLKYPSLELVEYKVARIATTMPYIPGFLSFREYPA *L* LAAWEMLSQKPDLVF *VDGHGISHPRRLGVASHFGLL*

*VDVPTIGVAKKRLCGKFEPI* SSEPGALAPLMDKGEQ *LAWVWRSKARCNPLFIATGH* RVSVDSALAWVQRCMKGYR *LPEPTRWADAVASERPA*

*FVRYTANQP* SGGS PKKKRKV ecTadA(D108G)-XTEN-nCas9-EndoV (D35A)-NLS: contains cat. endonuclease V:
(SEQ ID NO: 25)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARGAKTGAAGSLMDVLHHPGMNHRVEITEGILADECAALLSDFFRMRRQEIKAQKKAQSSTD *SGSETPGTS*

*ESATPES* DKKYSIGLAIGTNSVGWAVITDEYKVPSKKFKVLGNTDRHSIKKNLIGALLFDSGETAEATRLKRTARRRYTRRKNRICYL

QEIFSNEMAKVDDSFFHRLEESFLVEEDKKHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQDLTLLKALVRQQLPEK

YKEIFFDQSKNGYAGYIDGGASQEEFYKFIKPILEKMDGTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEISGVEDRFNASLGTYHDLLKIIKDKDFLDNE

ENEDILEDIVLTLTLFEDREMIEERLKTYAHLFDDKVMKQLKRRRYTGWGRLSRKLINGIRDKQSGKTILDFLKSDGFANRNFMQLIH

DDSLTFKEDIQKAQVSGQGDSLHEHIANLAGSPAIKKGILQTVKVVDELVKVMGRHKPENIVIEMARENQTTQKGQKNSRERMKRIEE

GIKELGSQILKEHPVENTQLQNEKLYLYYLQNGRDMYVDQELDINRLSDYDVDHIVPQSFLKDDSIDNKVLTRSDKNRGKSDNVPSEE

VVKKMKNYWRQLLNAKLITQRKFDNLTKAERGGLSELDKAGFIKRQLVETRQITKHVAQILDSRMNTKYDENDKLIREVKVITLKSKL

VSDFRKDFQFYKVREINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISEFSKRVILADANLDKVLSAYNKHRDKPIREQAENIIHLFT

LTNLGAPAAFKYFDTTIDRKRYTSTKEVLDATLIHQSITGLYETRIDLSQLGGDSGGS *DLASLRAQQIELASSVIREDR*

*LDKDPPDLIAGAAVGFEQGGE* TRAAMVLLKYPSLELVEYKVARIATTMPYIPGFLSFREYPA *L* LAAWEMLSQKPDLVF *VDGHGISHPRRLGVASHFGLL*

*VDVPTIGVAKKRLCGKFEP* LSSEPGALAPLMDKGEQ *LAWVWRSKARCNPLFIATGHRVSVDSALAWVQRCMKG*

*YRLPEPTRWADAVASERPA* FVRYTANQP SGGS PKKKRKV ecTadA(D108V)-XTEN-nCas9-EndoV(D35A)-NLS: contains cat. endonuclease V:
(SEQ ID NO: 26)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARVAKTGAAGSLMDVLHHPGMNHRVEITEGILADECAALLSDFFRMRRQEIKAQKKAQSSTD *SGSETPGTS*

*ESATPES* DKKYSIGLAIGTNSVGWAVITDEYKVPSKKFKVLGNTDRHSIKKNLIGALLFDSGETAEATRLKRTARRRYTRRKNRICYL

QEIFSNEMAKVDDSFFHRLEESFLVEEDKKHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQDLTLLKALVRQQLPEK

YKEIFFDQSKNGYAGYIDGGASQEEFYKFIKPILEKMDGTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEISGVEDRFNASLGTYHDLLKIIKDKDFLDNE

ENEDILEDIVLTLTLFEDREMIEERLKTYAHLFDDKVMKQLKRRRYTGWGRLSRKLINGIRDKQSGKTILDFLKSDGFANRNFMQLIH

DDSLTFKEDIQKAQVSGQGDSLHEHIANLAGSPAIKKGILQTVKVVDELVKVMGRHKPENIVIEMARENQTTQKGQKNSRERMKRIEE

GIKELGSQILKEHPVENTQLQNEKLYLYYLQNGRDMYVDQELDINRLSDYDVDHIVPQSFLKDDSIDNKVLTRSDKNRGKSDNVPSEE

VVKKMKNYWRQLLNAKLITQRKFDNLTKAERGGLSELDKAGFIKRQLVETRQITKHVAQILDSRMNTKYDENDKLIREVKVITLKSKL

-continued

VSDFRKDFQFYKVREINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISEFSKRVILADANLDKVLSAYNKHRDKPIREQAENIIHLFT

LTNLGAPAAFKYFDTTIDRKRYTSTKEVLDATLIHQSITGLYETRIDLSQLGGDSGGS*DLASLRAQQIELASSVIREDRLD*

*KDPPDLIAGAAVGFEQGGEV*TRAAMVLLKYPSLELVEYKVARIATTMPYIPGFLSFREYPA*LLAAWEMLSQKPDLVF*

*VDGHGISHPRRLGVASHFGLLVDVPTIGVAKKRLCGKFEPLS*SEPGALAP*LMDKGEQ*LAWVWRSKARCNPLFIATGH

*RVSVDSALAWVQRCMKGYR*LPEPTRWADAVASERPA*FVRYTANQP*SGGS PKKKRKV

Variant resulting from first round of evolution (in bacteria) ecTadA(H8Y_D108N_N127S)-XTEN-dCas9:

(SEQ ID NO: 27)

MSEVEFSYEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARNAKTGAAGSLMDVLHHPGMSHRVEITEGILADECAALLSDFFRMRRQEIKAQKKAQSSTDSGSETPGTS

ESATPESDKKYSIGLAIGTNSVGWAVITDEYKVPSKKFKVLGNTDRHSIKKNLIGALLFDSGETAEATRLKRTARRRYTRRKNRICYL

QEIFSNEMAKVDDSFFHRLEESFLVEEDKKHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQDLTLLKALVRQQLPEK

YKEIFFDQSKNGYAGYIDGGASQEEFYKFIKPILEKMDGTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEISGVEDRFNASLGTYHDLLKIIKDKDFLDNE

ENEDILEDIVLTLTLFEDREMIEERLKTYAHLFDDKVMKQLKRRRYTGWGRLSRKLINGIRDKQSGKTILDFLKSDGFANRNFMQLIH

DDSLTFKEDIQKAQVSGQGDSLHEHIANLAGSPAIKKGILQTVKVVDELVKVMGRHKPENIVIEMARENQTTQKGQKNSRERMKRIEE

GIKELGSQILKEHPVENTQLQNEKLYLYYLQNGRDMYVDQELDINRLSDYDVDAIVPQSFLKDDSIDNKVLTRSDKNRGKSDNVPSEE

VVKKMKNYWRQLLNAKLITQRKFDNLTKAERGGLSELDKAGFIKRQLVETRQITKHVAQILDSRMNTKYDENDKLIREVKVITLKSKL

VSDFRKDFQFYKVREINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISEFSKRVILADANLDKVLSAYNKHRDKPIREQAENIIHLFT

LTNLGAPAAFKYFDTTIDRKRYTSTKEVLDATLIHQSITGLYETRIDLSQLGGD

Enriched variants from second round of evolution (in bacteria) ecTadA
(H8Y_D108N_N127S_E155X)-XTEN-dCas9; X = D, G or V:

(SEQ ID NO: 28)

MSEVEFSYEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARNAKTGAAGSLMDVLHHPGMSHRVEITEGILADECAALLSDFFRMRRQXIKAQKKAQSSTDSGSETPGTS

ESATPESDKKYSIGLAIGTNSVGWAVITDEYKVPSKKFKVLGNTDRHSIKKNLIGALLFDSGETAEATRLKRTARRRYTRRKNRICYL

QEIFSNEMAKVDDSFFHRLEESFLVEEDKKHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQDLTLLKALVRQQLPEK

YKEIFFDQSKNGYAGYIDGGASQEEFYKFIKPILEKMDGTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEISGVEDRFNASLGTYHDLLKIIKDKDFLDNE

ENEDILEDIVLTLTLFEDREMIEERLKTYAHLFDDKVMKQLKRRRYTGWGRLSRKLINGIRDKQSGKTILDFLKSDGFANRNFMQLIH

DDSLTFKEDIQKAQVSGQGDSLHEHIANLAGSPAIKKGILQTVKVVDELVKVMGRHKPENIVIEMARENQTTQKGQKNSRERMKRIEE

GIKELGSQILKEHPVENTQLQNEKLYLYYLQNGRDMYVDQELDINRLSDYDVDAIVPQSFLKDDSIDNKVLTRSDKNRGKSDNVPSEE

-continued

VVKKMKNYWRQLLNAKLITQRKFDNLTKAERGGLSELDKAGFIKRQLVETRQITKHVAQILDSRMNTKYDENDKLIREVKVITLKSKL
VSDFRKDFQFYKVREINNYHHAHDAYLNAVVGTALIKKYPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEVQTGGFSKESILPKRNSDKLIARKKDWDPKKYGGFDSPT
VAYSVLVVAKVEKGKSKKLKSVKELLGITIMERSSFEKNPIDFLEAKGYKEVKKDLIIKLPKYSLFELENGRKRMLASAGELQKGNEL
ALPSKYVNFLYLASHYEKLKGSPEDNEQKQLFVEQHKHYLDEIIEQISEFSKRVILADANLDKVLSAYNKHRDKPIREQAENIIHLFT
LTNLGAPAAFKYFDTTIDRKRYTSTKEVLDATLIHQSITGLYETRIDLSQLGGD ecTadA\*-XTEN-nCas9-GGS-DNA repair inhibitor-GGS-NLS (Inhibitor = UGI, AAG\*E125Q or
EndoV\*D35A) pNMG-160: ecTadA(D108N)-XTEN-nCas9-GGS-***AAG\*(E125Q)***-GGS-NLS
(SEQ ID NO: 387)

MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARNAKTGAAGSLMDVLHHPGMNHRVEITEGILADECAALLSDFFRMRRQEIKAQKKAQSSTDSGSETPGTS
ESATPESDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQLPGEKKNGLFGNLIALSLGLTPNFKSNFDL
AEDAKLQLSKDTYDDDLDNLLAQIGDQYADLFLAAKNLSDAILLSDILRVNTEITKAPLSASMIKRYDEHHQDLTLLKALVRQQLPEK
YKEIFFDQSKNGYAGYIDGGASQEEFYKFIKPILEKMDGTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDKGASAQSFIERMTNFDKNLPNEKVLPKHSLLYEYFTVYN
ELTKVKYVTEGMRKPAFLSGEQKKAIVDLLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDVDHIVPQSFLKDDSIDNKVLTRSDKNRGKSDNVPSEE
VVKKMKNYWRQLLNAKLITQRKFDNLTKAERGGLSELDKAGFIKRQLVETRQITKHVAQILDSRMNTKYDENDKLIREVKVITLKSKL
VSDFRKDFQFYKVREINNYHHAHDAYLNAVVGTALIKKYPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEVQTGGFSKESILPKRNSDKLIARKKDWDPKKYGGFDSPT
VAYSVLVVAKVEKGKSKKLKSVKELLGITIMERSSFEKNPIDFLEAKGYKEVKKDLIIKLPKYSLFELENGRKRMLASAGELQKGNEL
ALPSKYVNFLYLASHYEKLKGSPEDNEQKQLFVEQHKHYLDEIIEQISEFSKRVILADANLDKVLSAYNKHRDKPIREQAENIIHLFT
LTNLGAPAAFKYFDTTIDRKRYTSTKEVLDATLIHQSITGLYETRIDLSQLGGDGGS*KGHLTRLGLEFFDQPAVPLAR*
*FLGQVLVRRLPNGTELRGRIVETQAYLGPEDEAAHSRGGRQ*TPRNRGMFMKPGTLYVYII*YGMYFCMNISSQGDGAC*
*VLLRALEPLEGLETMRQLRS*TLRKGTASRVLKDRELCSGPS*KLCQALAINKSFDQRDLAQDEAVWLERGPLEPSEPA*
*VVAAARVGVGHAGEWARKPLRFYVRGSPWVSVVDR*VAEQDTQAGGS PKKKRKV pNMG-161: ecTadA(D108N)-XTEN-nCas9-GGS-***EndoV\*(D35A)***-GGS-NLS
(SEQ ID NO: 388)

MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARNAKTGAAGSLMDVLHHPGMNHRVEITEGILADECAALLSDFFRMRRQEIKAQKKAQSSTDSGSETPGTS
ESATPESDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQLPGEKKNGLFGNLIALSLGLTPNFKSNFDL
AEDAKLQLSKDTYDDDLDNLLAQIGDQYADLFLAAKNLSDAILLSDILRVNTEITKAPLSASMIKRYDEHHQDLTLLKALVRQQLPEK
YKEIFFDQSKNGYAGYIDGGASQEEFYKFIKPILEKMDGTEELLVKLNREDLLRKQRTFDNGSIPHQIHLGELHAILRRQEDFYPFLK
DNREKIEKILTFRIPYYVGPLARGNSRFAWMTRKSEETITPWNFEEVVDKGASAQSFIERMTNFDKNLPNEKVLPKHSLLYEYFTVYN
ELTKVKYVTEGMRKPAFLSGEQKKAIVDLLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEMARENQTTQKGQKNSRERMKRIEE

-continued

GIKELGSQILKEHPVENTQLQNEKLYLYYLQNGRDMYVDQELDINRLSDYDVDHIVPQSFLKDDSIDNKVLTRSDKNRGKSDNVPSEE

VVKKMKNYWRQLLNAKLITQRKFDNLTKAERGGLSELDKAGFIKRQLVETRQITKHVAQILDSRMNTKYDENDKLIREVKVITLKSKL

VSDFRKDFQFYKVREINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISEFSKRVILADANLDKVLSAYNKHRDKPIREQAENIIHLFT

LTNLGAPAAFKYFDTTIDRKRYTSTKEVLDATLIHQSITGLYETRIDLSQLGGDGGS*DLASLRAQQIELASSVIR*

*EDRLDKDPPDLIAGAAVGFEQGGEVTRAAMVLLKYPSLELVEYKVARIATTMPYIPGFLSFREYPALLAAWEMLSQKPDLVFV*

*DGHGISHPRRLGVASHFGLIVDVPTIGVAKKRLCGKFEPLSSEPGALAPLMDKGEQIAWVWRSKARCNPLFIATGH*

*RVSVDSALAWVQRCMKGYRLPEPTRWADAVASERPAFVRYTANQP*GGS PKKKRKV pNMG-371: ecTadA(L84F_A106V_D108N_H123Y_D147Y_E155V_I156F)-SGGS-SGGS-*XTEN*-SGGS-SGGS-
ecTadA(L84F_A106V_D108N_H123Y_D147Y_E155V_I156F)-SGGS-SGGS-*XTEN*-SGGS-SGGS-nCas9-SGGS-NLS
(SEQ ID NO: 440)

SEVEFSHEYWMRHALTLAKRAWDEREVPVGAVLVHNNRVIGEGWNRPIGRHDPTAHAEIMALRQGGLVMQNYRLIDATLYVTFEPCVM

CAGAMIHSRIGRVVFGVRNAKTGAAGSLMDVLHYPGMNHRVEITEGILADECAALLSYFFRMRRQVFKAQKKAQSSTDSGGSSGGS*SG*

*SETPGTSESATPESS*SGGSSGGSSEVEFSHEYWMRHALTLAKRAWDEREVPVGAVLVHNNRVIGEGWNRPIGRHDPTAHAEIMALRQGG

LVMQNYRLIDATLYVTFEPCVMCAGAMIHSRIGRVVFGVRNAKTGAAGSLMDVLHYPGMNHRVEITEGILADECAALLSYFFRMRRQV

FKAQKKAQSSTDSGGSSGGS*SGSETPGTSESATPESS*SGGSSGGSDKKYSIGLAIGTNSVGWAVITDEYKVPSKKFKVLGNTDRHSIKK

NLIGALLFDSGETAEATRLKRTARRRYTRRKNRICYLQEIFSNEMAKVDDSFFHRLEESFLVEEDKKHERHPIFGNIVDEVAYHEKYP

TIYHLRKKLVDSTDKADLRLIYLALAHMIKFRGHFLIEGDLNPDNSDVDKLFIQLVQTYNQLFEENPINASGVDAKAILSARLSKSRR

LENLIAQLPGEKKNGLFGNLIALSLGLTPNFKSNFDLAEDAKLQLSKDTYDDDLDNLLAQIGDQYADLFLAAKNLSDAILLSDILRVN

TEITKAPLSASMIKRYDEHHQDLTLLKALVRQQLPEKYKEIFFDQSKNGYAGYIDGGASQEEFYKFIKPILEKMDGTEELLVKLNRED

LLRKQRTFDNGSIPHQIHLGELHAILRRQEDFYPFLKDNREKIEKILTFRIPYYVGPLARGNSRFAWMTRKSEETITPWNFEEVVDKG

ASAQSFIERMTNFDKNLPNEKVLPKHSLLYEYFTVYNELTKVKYVTEGMRKPAFLSGEQKKAIVDLLFKTNRKVTVKQLKEDYFKKIE

CFDSVEISGVEDRFNASLGTYHDLLKIIKDKDFLDNEENEDILEDIVLTLTLFEDREMIEERLKTYAHLFDDKVMKQLKRRRYTGWGR

LSRKLINGIRDKQSGKTILDFLKSDGFANRNFMQLIHDDSLTFKEDIQKAQVSGQGDSLHEHIANLAGSPAIKKGILQTVKVVDELVK

VMGRHKPENIVIEMARENQTTQKGQKNSRERMKRIEEGIKELGSQILKEHPVENTQLQNEKLYLYYLQNGRDMYVDQELDINRLSDYD

VDHIVPQSFLKDDSIDNKVLTRSDKNRGKSDNVPSEEVVKKMKNYWRQLLNAKLITQRKFDNLTKAERGGLSELDKAGFIKRQLVETR

QITKHVAQILDSRMNTKYDENDKLIREVKVITLKSKLVSDFRKDFQFYKVREINNYHHAHDAYLNAVVGTALIKKYPKLESEFVYGDY

KVYDVRKMIAKSEQEIGKATAKYFFYSNIMNFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLKSVKELLGITIMERSSFEKNPIDFLEAKGYKE

VKKDLIIKLPKYSLFELENGRKRMLASAGELQKGNELALPSKYVNFLYLASHYEKLKGSPEDNEQKQLFVEQHKHYLDEIIEQISEFS

KRVILADANLDKVLSAYNKHRDKPIREQAENIIHLFTLTNLGAPAAFKYFDTTIDRKRYTSTKEVLDATLIHQSITGLYETRIDLSQL

GGDSGGS*PKKKRKV* pNMG-616 amino acid sequence: ecTadA(wild type)-(SGGS)2-*XTEN*-(SGGS)2-**ecTadA
(W23L_H36L_P48A_R51L_L84F_A106V_D108N_H123Y_S146C_D147Y_R152P_E155V_I156F_K157N)**-
(SGGS)2-*XTEN*-(SGGS)2_nCas9_SGGS_NLS
(SEQ ID NO: 691)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTDSGGSSGGS*S*

*GSETPGTSESATPESS*SGGSSGGSSEVEFSHEYWMRHALTLAKRALDEREVPVGAVLVLNNRVIGEGWNRAIGLHDPTAHAEIMALRQG

GLVMQNYRLIDATLYVTFEPCVMCAGAMIHSRIGRVVFGVRNAKTGAAGSLMDVLHYPGMNHRVEITEGILADECAALLCYFFRMPRQ

VFNAQKKAQSSTDSGGSSGGS*SGSETPGTSESATPESS*SGGSSGGSDKKYSIGLAIGTNSVGWAVITDEYKVPSKKFKVLGNTDRHSIK

KNLIGALLFDSGETAEATRLKRTARRRYTRRKNRICYLQEIFSNEMAKVDDSFFHRLEESFLVEEDKKHERHPIFGNIVDEVAYHEKY

PTIYHLRKKLVDSTDKADLRLIYLALAHMIKFRGHFLIEGDLNPDNSDVDKLFIQLVQTYNQLFEENPINASGVDAKAILSARLSKSR

RLENLIAQLPGEKKNGLFGNLIALSLGLTPNFKSNFDLAEDAKLQLSKDTYDDDLDNLLAQIGDQYADLFLAAKNLSDAILLSDILRV

NTEITKAPLSASMIKRYDEHHQDLTLLKALVRQQLPEKYKEIFFDQSKNGYAGYIDGGASQEEFYKFIKPILEKMDGTEELLVKLNRE

DLLRKQRTFDNGSIPHQIHLGELHAILRRQEDFYPFLKDNREKIEKILTFRIPYYVGPLARGNSRFAWMTRKSEETITPWNFEEVVDK

GASAQSFIERMTNFDKNLPNEKVLPKHSLLYEYFTVYNELTKVKYVTEGMRKPAFLSGEQKKAIVDLLFKTNRKVTVKQLKEDYFKKI

ECFDSVEISGVEDRFNASLGTYHDLLKIIKDKDFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQGDSLHEHIANLAGSPAIKKGILQTVKVVDELV

KVMGRHKPENIVIEMARENQTTQKGQKNSRERMKRIEEGIKELGSQILKEHPVENTQLQNEKLYLYYLQNGRDMYVDQELDINRLSDY

DVDHIVPQSFLKDDSIDNKVLTRSDKNRGKSDNVPSEEVVKKMKNYWRQLLNAKLITQRKFDNLTKAERGGLSELDKAGFIKRQLVET

RQITKHVAQILDSRMNTKYDENDKLIREVKVITLKSKLVSDFRKDFQFYKVREINNYHHAHDAYLNAVVGTALIKKYPKLESEFVYGD

YKVYDVRKMIAKSEQEIGKATAKYFFYSNIMNFFKTEITLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVEGKSKKLKSVKELLGITIMERSSFEKNPIDFLEAKGYK

EVKKDLIIKLPKYSLFELENGRKRMLASAGELQKGNELALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYFDTTIDRKRYTSTKEVLDATLIHQSITGLYETRIDLSQ

LGGDSGGS*PKKKRKV* pNMG-624 amino acid sequence: ecTadA(wild type)-*32 a.a. linker*-**ecTadA
(W23R_H36L_P48A_R51L_L84F_A106V_D108N_H123Y_S146C_D147Y_R152P_E155V_I156F_K157N)**-
*24 a.a.linker*_nCas9_SGGS_*NLS*

(SEQ ID NO: 692)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTD*SGGSSGGSS*

*GSETPGTSESATPESSGGSSGGSS*SEVEFSHEYWMRHALTLAKRARDEREVPVGAVLVLNNRVIGEGWNRAIGLHDPTAHAEIMALRQG

GLVMQNYRLIDATLYVTFEPCVMCAGAMIHSRIGRVVFGVRNAKTGAAGSLMDVLHYPGMNHRVEITEGILADECAALLCYFFRMPRQ

VFNAQKKAQSSTD*SGGSSGGSSGSETPGTSESATPES*DKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEESFLVEEDKKHERHPIFGNIVDEVAYHEKYPTIYHLRK

KLVDSTDKADLRLIYLALAHMIKFRGHFLIEGDLNPDNSDVDKLFIQLVQTYNQLFEENPINASGVDAKAILSARLSKSRRLENLIAQ

LPGEKKNGLFGNLIALSLGLTPNFKSNFDLAEDAKLQLSKDTYDDDLDNLLAQIGDQYADLFLAAKNLSDAILLSDILRVNTEITKAP

LSASMIKRYDEHHQDLTLLKALVRQQLPEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKAIVDLLFKTNRKVTVKQLKEDYFKKIECFDSVET

SGVEDRFNASLGTYHDLLKIIKDKDFLDNEENEDILEDIVLTLTLFEDREMIEERLKTYAHLFDDKVMKQLKRRRYTGWGRLSRKLIN

GIRDKQSGKTILDFLKSDGFANRNFMQLIHDDSLTFKEDIQKAQVSGQGDSLHEHIANLAGSPAIKKGILQTVKVVDELVKVMGRHKP

ENIVIEMARENQTTQKGQKNSRERMKRIEEGIKELGSQILKEHPVENTQLQNEKLYLYYLQNGRDMYVDQELDINRLSDYDVDHIVPQ

SFLKDDSIDNKVLTRSDKNRGKSDNVPSEEVVKKMKNYWRQLLNAKLITQRKFDNLTKAERGGLSELDKAGFIKRQLVETRQITKHVA

QILDSRMNTKYDENDKLIREVKVITLKSKLVSDFRKDFQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGEIVWDKGRDFATVRKVLSMPQVNIVKKTEVQTGGFSKE

SILPKRNSDKLIARKKDWDPKKYGGFDSPTVAYSVLVVAKVEGKSKKLKSVKELLGITHVIERSSFEKNPIDFLEAKGYKEVKKDLI

IKLPKYSLFELENGRKRMLASAGELQKGNELALPSKYVNFLYLASHYEKLKGSPEDNEQKQLFVEQHKHYLDEIIEQISEFSKRVILA

DANLDKVLSAYNKHRDKPIREQAENIIHLFTLTNLGAPAAFKYFDTTIDRKRYTSTKEVLDATLIHQSITGLYETRIDLSQLGGDSGG

*SPKKKRKV*

-continued pNMG-476 amino acid sequence (evolution #3 hetero dimer, wt TadA + TadA evo
3 mutations): ecTadA (wild-type)-(SGGS)2-*XTEN*-(SGGS)2-ecTadA
(L84F_A106V_D108N_H123Y_D147Y_E155V_I156F)-(SGGS)2-*XTEN*-(SGGS)2_nCas9_SGGS_<u>NLS</u>

(SEQ ID NO: 693)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTDSGGSSGGS*S*

*GSETPGTSESATPESS*GGSSGGSSEVEFSHEYWMRHALTLAKRAWDEREVPVGAVLVHNNRVIGEGWNRPIGRHDPTAHAEIMALRQG

GLVMQNYRLIDATLYVTFEPCVMCAGAMIHSRIGRVVFGVRNAKTGAAGSLMDVLHYPGMNHRVEITEGILADECAALLSYFFRMRRQ

VFKAQKKAQSSTDSGGSSGGS*SGSETPGTSESATPESS*GGSSGGS<u>DKKYSIGLAIGTNSVGWAVITDEYKVPSKKFKVLGNTDRHSIK</u>

<u>KNLIGALLFDSGETAEATRLKRTARRRYTRRKNRICYLQEIFSNEMAKVDDSFFHRLEESFLVEEDKKHERHPIFGNIVDEVAYHEKY</u>

<u>PTIYHLRKKLVDSTDKADLRLIYLALAHMIKFRGHFLIEGDLNPDNSDVDKLFIQLVQTYNQLFEENPINASGVDAKAILSARLSKSR</u>

<u>RLENLIAQLPGEKKNGLFGNLIALSLGLTPNFKSNFDLAEDAKLQLSKDTYDDDLDNLLAQIGDQYADLFLAAKNLSDAILLSDILRV</u>

<u>NTEITKAPLSASMIKRYDEHHQDLTLLKALVRQQLPEKYKEIFFDQSKNGYAGYIDGGASQEEFYKFIKPILEKMDGTEELLVKLNRE</u>

<u>DLLRKQRTFDNGSIPHQIHLGELHAILRRQEDFYPFLKDNREKIEKILTFRIPYYVGPLARGNSRFAWMTRKSEETITPWNFEEVVDK</u>

<u>GASAQSFIERMTNFDKNLPNEKVLPKHSLLYEYFTVYNELTKVKYVTEGMRKPAFLSGEQKKAIVDLLFKTNRKVTVKQLKEDYFKKI</u>

<u>ECFDSVEISGVEDRFNASLGTYHDLLKIIKDKDFLDNEENEDILEDIVLTLTLFEDREMIEERLKTYAHLFDDKVMKQLKRRRYTGWG</u>

<u>RLSRKLINGIRDKQSGKTILDFLKSDGFANRNFMQLIHDDSLTFKEDIQKAQVSGQGDSLHEHIANLAGSPAIKKGILQTVKVVDELV</u>

<u>KVMGRHKPENIVIEMARENQTTQKGQKNSRERMKRIEEGIKELGSQILKEHPVENTQLQNEKLYLYYLQNGRDMYVDQELDINRLSDY</u>

<u>DVDHIVPQSFLKDDSIDNKVLTRSDKNRGKSDNVPSEEVVKKMKNYWRQLLNAKLITQRKFDNLTKAERGGLSELDKAGFIKRQLVET</u>

<u>RQITKHVAQILDSRMNTKYDENDKLIREVKVITLKSKLVSDFRKDFQFYKVREINNYHHAHDAYLNAVVGTALIKKYPKLESEFVYGD</u>

<u>YKVYDVRKMIAKSEQEIGKATAKYFFYSNIMNFFKTEITLANGEIRKRPLIETNGETGEIVWDKGRDFATVRKVLSMPQVNIVKKTEV</u>

<u>QTGGFSKESILPKRNSDKLIARKKDWDPKKYGGFDSPTVAYSVLVVAKVEKGKSKKLKSVKELLGITIMERSSFEKNPIDFLEAKGYK</u>

<u>EVKKDLIIKLPKYSLFELENGRKRMLASAGELQKGNELALPSKYVNFLYLASHYEKLKGSPEDNEQKQLFVEQHKHYLDEIIEQISEF</u>

<u>SKRVILADANLDKVLSAYNKHRDKPIREQAENIIHLFTLTNLGAPAAFKYFDTTIDRKRYTSTKEVLDATLIHQSITGLYETRIDLSQ</u>

<u>LGGD</u>SGGS<u>PKKKRKV</u> pNMG-477 amino acid sequence: ecTadA(wild-type)-(SGGS)2-*XTEN*-(SGGS)2-
ecTadA(H36L_R51L_L84F_A106V_D108N_H123Y_S146C_D147Y_E155V_I156F_K157N)-
(SGGS)2-*XTEN*-(SGGS)2_nCas9_SGGS_<u>NLS</u>

(SEQ ID NO: 694)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTDSGGSSGGS*S*

*GSETPGTSESATPESS*GGSSGGSSEVEFSHEYWMRHALTLAKRAWDEREVPVGAVLVLNNRVIGEGWNRPIGLHDPTAHAEIMALRQG

GLVMQNYRLIDATLYVTFEPCVMCAGAMIHSRIGRVVFGVRNAKTGAAGSLMDVLHYPGMNHRVEITEGILADECAALLCYFFRMRRQ

VFNAQKKAQSSTDSGGSSGGS*SGSETPGTSESATPESS*GGSSGGS<u>DKKYSIGLAIGTNSVGWAVITDEYKVPSKKFKVLGNTDRHSIK</u>

<u>KNLIGALLFDSGETAEATRLKRTARRRYTRRKNRICYLQEIFSNEMAKVDDSFFHRLEESFLVEEDKKHERHPIFGNIVDEVAYHEKY</u>

<u>PTIYHLRKKLVDSTDKADLRLIYLALAHMIKFRGHFLIEGDLNPDNSDVDKLFIQLVQTYNQLFEENPINASGVDAKAILSARLSKSR</u>

<u>RLENLIAQLPGEKKNGLFGNLIALSLGLTPNFKSNFDLAEDAKLQLSKDTYDDDLDNLLAQIGDQYADLFLAAKNLSDAILLSDILRV</u>

<u>NTEITKAPLSASMIKRYDEHHQDLTLLKALVRQQLPEKYKEIFFDQSKNGYAGYIDGGASQEEFYKFIKPILEKMDGTEELLVKLNRE</u>

<u>DLLRKQRTFDNGSIPHQIHLGELHAILRRQEDFYPFLKDNREKIEKILTFRIPYYVGPLARGNSRFAWMTRKSEETITPWNFEEVVDK</u>

<u>GASAQSFIERMTNFDKNLPNEKVLPKHSLLYEYFTVYNELTKVKYVTEGMRKPAFLSGEQKKAIVDLLFKTNRKVTVKQLKEDYFKKI</u>

<u>ECFDSVEISGVEDRFNASLGTYHDLLKIIKDKDFLDNEENEDILEDIVLTLTLFEDREMIEERLKTYAHLFDDKVMKQLKRRRYTGWG</u>

<u>RLSRKLINTGIRDKQSGKTILDFLKSDGFANRNFMQLIHDDSLTFKEDIQKAQVSGQGDSLHEHIANLAGSPAIKKGILQTVKVVDEL</u>

<u>VKVMGRHKPENIVIEMARENQTTQKGQKNSRERMKRIEEGIKELGSQILKEHPVENTQLQNEKLYLYYLQNGRDMYVDQELDINRLSD</u>

<u>YDVDHIVPQSFLKDDSIDNKVLTRSDKNRGKSDNVPSEEVVKKMKNYWRQLLNAKLITQRKFDNLTKAERGGLSELDKAGFIKRQLVE</u>

-continued

TRQITKHVAQILDSRMNTKYDENDKLIREVKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEIVWDKGRDFATVRKVLSMPQVNIVKKTE

VQTGGFSKESILPKRNSDKLIARKKDWDPKKYGGFDSPTVAYSVLVVAKVEKGKSKKLKSVKELLGITIMERSSFEKNPIDFLEAKGY

KEVKKDLIIKLPKYSLFELENGRKRMLASAGELQKGNELALPSKYVNFLYLASHYEKLKGSPEDNEQKQLFVEQHKYLDEIIEQISE

FSKRVILADANLDKVLSAYNKHRDKPIREQAENIIHLFTLTNLGAPAAFKYFDTTIDRKRYTSTKEVLDATLIHQSITGLYETRIDLS

QLGGDSGGS*PKKKRKV* pNMG-558 amino acid sequence: ecTadA(wild-type)-*32 a.a. linker*-
ecTadA(H36L_R51L_L84F_A106V_D108N_H123Y_S146C_D147Y_E155V_I156F_K157N)-
*24 a.a. linker*_nCas9_SGGS_*NLS*

(SEQ ID NO: 695)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTD*SGGSSGGSS*

*GSETPGTSESATPESSGGSSGGS*SEVEFSHEYWMRHALTLAKRAWDEREVPVGAVLVLNNRVIGEGWNRPIGLHDPTAHAEIMALRQG

GLVMQNYRLIDATLYVTFEPCVMCAGAMIHSRIGRVVFGVRNAKTGAAGSLMDVLHYPGMNHRVEITEGILADECAALLCYFFRMRRQ

VFNAQKKAQSSTD*SGGSSGGSSGSETPGTSESATPES*DKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEESFLVEEDKKHERHPIFGNIVDEVAYHEKYPTIYHLRK

KLVDSTDKADLRLIYLALAHMIKFRGHFLIEGDLNPDNSDVDKLFIQLVQTYNQLFEENPINASGVDAKAILSARLSKSRRLENLIAQ

LPGEKKNGLFGNLIALSLGLTPNFKSNFDLAEDAKLQLSKDTYDDDLDNLLAQIGDQYADLFLAAKNLSDAILLSDILRVNTEITKAP

LSASMIKRYDEHHQDLTLLKALVRQQLPEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKAIVDLLFKTNRKVTVKQLKEDYFKKIECFDSVET

SGVEDRFNASLGTYHDLLKIIKDKDFLDNEENEDILEDIVLTLTLFEDREMIEERLKTYAHLFDDKVMKQLKRRRYTGWGRLSRKLIN

GIRDKQSGKTILDFLKSDGFANRNFMQLIHDDSLTFKEDIQKAQVSGQGDSLHEHIANLAGSPAIKKGILQTVKVVDELVKVMGRHKP

ENIVIEMARENQTTQKGQKNSRERMKRIEEGIKELGSQILKEHPVENTQLQNEKLYLYYLQNGRDMYVDQELDINRLSDYDVDHIVPQ

SFLKDDSIDNKVLTRSDKNRGKSDNVPSEEVVKKMKNYWRQLLNAKLITQRKFDNLTKAERGGLSELDKAGFIKRQLVETRQnKHVAQ

ILDSRMNTKYDENDKLIREVKVITLKSKLVSDFRKDFQFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEIVWDKGRDFATVRKVLSMPQVNIVKKTEVQTGGFSKES

ILPKRNSDKLIARKKDWDPKKYGGFDSPTVAYSVLVVAKVEKGKSKKLKSVKELLGITIIVIERSSFEKNPIDFLEAKGYKEVKKDLI

IKLPKYSLFELENGRKRMLASAGELQKGNELALPSKYVNFLYLASHYEKLKGSPEDNEQKQLFVEQHKYLDEIIEQISEFSKRVILA

DANLDKVLSAYNKHRDKPIREQAENIIHLFTLTNLGAPAAFKYFDTTIDRKRYTSTKEVLDATLIHQSITGLYETRIDLSQLGGDSGG

S*PKKKRKV* pNMG-576 amino acid sequence: ecTadA(wild-type)-*(SGGS)2-XTEN-(SGGS)2*-
ecTadA(H36L_P48S_R51L_L84F_A106V_D108N_H123Y_S146C_D147Y_E155V_I156F_K157N)-
*(SGGS)2-XTEN-(SGGS)2*_nCas9_GGS_*NLS*

(SEQ ID NO: 696)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTD*SGGSSGGSS*

*GSETPGTSESATPESSGGSSGGS*SEVEFSHEYWMRHALTLAKRAWDEREVPVGAVLVLNNRVIGEGWNRSIGLHDPTAHAEIMALRQG

GLVMQNYRLIDATLYVTFEPCVMCAGAMIHSRIGRVVFGVRNAKTGAAGSLMDVLHYPGMNHRVEITEGILADECAALLCYFFRMRRQ

VFNAQKKAQSSTD*SGGSSGGSSGSETPGTSESATPESSGGSSGGS*DKKYSIGLAIGTNSVGWAVITDEYKVPSKKFKVLGNTDRHSIK

KNLIGALLFDSGETAEATRLKRTARRRYTRRKNRICYLQEIFSNEMAKVDDSFFHRLEESFLVEEDKKHERHPIFGNIVDEVAYHEKY

PTIYHLRKKLVDSTDKADLRLIYLALAHMIKFRGHFLIEGDLNPDNSDVDKLFIQLVQTYNQLFEENPINASGVDAKAILSARLSKSR

RLENLIAQLPGEKKNGLFGNLIALSLGLTPNFKSNFDLAEDAKLQLSKDTYDDDLDNLLAQIGDQYADLFLAAKNLSDAILLSDILRV

NTEITKAPLSASMIKRYDEHHQDLTLLKALVRQQLPEKYKEIFFDQSKNGYAGYIDGGASQEEFYKFIKPILEKMDGTEELLVKLNRE

DLLRKQRTFDNGSIPHQIHLGELHAILRRQEDFYPFLKDNREKIEKILTFRIPYYVGPLARGNSRFAWMTRKSEETITPWNFEEVVDK

GASAQSFIERMTNFDKNLPNEKVLPKHSLLYEYFTVYNELTKVKYVTEGMRKPAFLSGEQKKAIVDLLFKTNRKVTVKQLKEDYFKKI

ECFDSVEISGVEDRFNASLGTYHDLLKIIKDKDFLDNEENEDILEDIVLTLTLFEDREMIEERLKTYAHLFDDKVMKQLKRRRYTGWG

RLSRKLINTGIRDKQSGKTILDFLKSDGFANRNFMQLIHDDSLTFKEDIQKAQVSGQGDSLHEHIANLAGSPAIKKGILQTVKVVDEL

VKVMGRHKPENIVIEMARENQTTQKGQKNSRERMKRIEEGIKELGSQILKEHPVENTQLQNEKLYLYYLQNGRDMYVDQELDINRLSD

YDVDHIVPQSFLKDDSIDNKVLTRSDKNRGKSDNVPSEEVVKKMKNYWRQLLNAKLITQRKFDNLTKAERGGLSELDKAGFIKRQLVE

TRQITKHVAQILDSRMNTKYDENDKLIREVKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEIVWDKGRDFATVRKVLSMPQVNIVKKTE

VQTGGFSKESILPKRNSDKLIARKKDWDPKKYGGFDSPTVAYSVLVVAKVEKGKSKKLKSVKELLGITIMERSSFEKNPIDFLEAKGY

KEVKKDLIIKLPKYSLFELENGRKRMLASAGELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRKRYTSTKEVLDATLIHQSITGLYETRIDLS

QLGGD*SGGS*PKKKRKV pNMG-577 amino acid sequence: ecTadA(wild-type)-(SGGS)2-*XTEN*-(SGGS)2-ecTadA
(H36L_P48S_R51L_L84F_A106V_D108N_H123Y_S146C_A142N_D147Y_E155V_I156F_K157N)-
(SGGS)2-*XTEN*-(SGGS)2_nCas9_GGS_*NLS*

(SEQ ID NO: 697)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTD*SGGSSGGSS*

*GSETPGTSESATPESSGGSSGGS*SEVEFSHEYWMRHALTLAKRAWDEREVPVGAVLVLNNRVIGEGWNRSIGLHDPTAHAEIMALRQG

GLVMQNYRLIDATLYVTFEPCVMCAGAMIHSRIGRVVFGVRNAKTGAAGSLMDVLHYPGMNHRVEITEGILADECNALLCYFFRMRRQ

VFNAQKKAQSSTD*SGGSSGGS SGSETPGTSESATPESSGGSSGGS*DKKYSIGLAIGTNSVGWAVITDEYKVPSKKFKVLGNTDRHSIK

KNLIGALLFDSGETAEATRLKRTARRRYTRRKNRICYLQEIFSNEMAKVDDSFFHRLEESFLVEEDKKHERHPIFGNIVDEVAYHEKY

PTIYHLRKKLVDSTDKADLRLIYLALAHMIKFRGHFLIEGDLNPDNSDVDKLFIQLVQTYNQLFEENPINASGVDAKAILSARLSKSR

RLENLIAQLPGEKKNGLFGNLIALSLGLTPNFKSNFDLAEDAKLQLSKDTYDDDLDNLLAQIGDQYADLFLAAKNLSDAILLSDILRV

NTEITKAPLSASMIKRYDEHHQDLTLLKALVRQQLPEKYKEIFFDQSKNGYAGYIDGGASQEEFYKFIKPILEKMDGTEELLVKLNRE

DLLRKQRTFDNGSIPHQIHLGELHAILRRQEDFYPFLKDNREKIEKILTFRIPYYVGPLARGNSRFAWMTRKSEETITPWNFEEVVDK

GASAQSFIERMTNFDKNLPNEKVLPKHSLLYEYFTVYNELTKVKYVTEGMRKPAFLSGEQKKAIVDLLFKTNRKVTVKQLKEDYFKKI

ECFDSVEISGVEDRFNASLGTYHDLLKIIKDKDFLDNEENEDILEDIVLTLTLFEDREMIEERLKTYAHLFDDKVMKQLKRRRYTGWG

RLSRKLINTGIRDKQSGKTILDFLKSDGFANRNFMQLIHDDSLTFKEDIQKAQVSGQGDSLHEHIANLAGSPAIKKGILQTVKVVDEL

VKVMGRHKPENIVIEMARENQTTQKGQKNSRERMKRIEEGIKELGSQILKEHPVENTQLQNEKLYLYYLQNGRDMYVDQELDINRLSD

YDVDHIVPQSFLKDDSIDNKVLTRSDKNRGKSDNVPSEEVVKKMKNYWRQLLNAKLITQRKFDNLTKAERGGLSELDKAGFIKRQLVE

TRQITKHVAQILDSRMNTKYDENDKLIREVKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEIVWDKGRDFATVRKVLSMPQVNIVKKTE

VQTGGFSKESILPKRNSDKLIARKKDWDPKKYGGFDSPTVAYSVLVVAKVEKGKSKKLKSVKELLGITIMERSSFEKNPIDFLEAKGY

KEVKKDLIIKLPKYSLFELENGRKRMLASAGELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRKRYTSTKEVLDATLIHQSITGLYETRIDLS

QLGGD*SGGS*PKKKRKV pNMG-586 amino acid sequence: ecTadA(wild-type)-(SGGS)2-*XTEN*-(SGGS)2-
ecTadA(H36L_P48A_R51L_L84F_A106V_D108N_H123Y_S146C_D147Y_E155V_I156F_K157N)-
(SGGS)2-*XTEN*-(SGGS)2_nCas9_GGS_*NLS*

(SEQ ID NO: 698)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTD*SGGSSGGSS*

*GSETPGTSESATPESSGGSSGGS*SEVEFSHEYWMRHALTLAKRAWDEREVPVGAVLVLNNRVIGEGWNRAIGLHDPTAHAEIMALRQG

GLVMQNYRLIDATLYVTFEPCVMCAGAMIHSRIGRVVFGVRNAKTGAAGSLMDVLHYPGMNHRVEITEGILADECAALLCYFFRMRRQ

-continued

VFNAQKKAQSSTDSGGSSGGS*SGSETPGTSESATPESS*GGSSGGS<u>DKKYSIGLAIGTNSVGWAVITDEYKVPSKKFKVLGNTDRHSIK
KNLIGALLFDSGETAEATRLKRTARRRYTRRKNRICYLQEIFSNEMAKVDDSFFHRLEESFLVEEDKKHERHPIFGNIVDEVAYHEKY
PTIYHLRKKLVDSTDKADLRLIYLALAHMIKFRGHFLIEGDLNPDNSDVDKLFIQLVQTYNQLFEENPINASGVDAKAILSARLSKSR
RLENLIAQLPGEKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDGTEELLVKLNRE
DLLRKQRTFDNGSIPHQIHLGELHAILRRQEDFYPFLKDNREKIEKILTFRIPYYVGPLARGNSRFAWMTRKSEETITPWNFEEVVDK
GASAQSFIERMTNFDKNLPNEKVLPKHSLLYEYFTVYNELTKVKYVTEGMRKPAFLSGEQKKAIVDLLFKTNRKVTVKQLKEDYFKKI
ECFDSVEISGVEDRFNASLGTYHDLLKIIKDKDFLDNEENEDILEDIVLTLTLFEDREMIEERLKTYAHLFDDKVMKQLKRRRYTGWG
RLSRKLINTGIRDKQSGKTILDFLKSDGFANRNFMQLIHDDSLTFKEDIQKAQVSGQGDSLHEHIANLAGSPAIKKGILQTVKVVDEL
VKVMGRHKPENIVIEMARENQTTQKGQKNSRERMKRIEEGIKELGSQILKEHPVENTQLQNEKLYLYYLQNGRDMYVDQELDINRLSD
YDVDHIVPQSFLKDDSIDNKVLTRSDKNRGKSDNVPSEEVVKKMKNYWRQLLNAKLITQRKFDNLTKAERGGLSELDKAGFIKRQLVE
TRQITKHVAQILDSRMNTKYDENDKLIREVKVITLKSKLVSDFRKDFQFYKVREINNYHHAHDAYLNAVVGTALIKKYPKLESEFVYG
DYKVYDVRKMIAKSEQEIGKATAKYFFYSNIMNFFKTEITLANGEIRKRPLIETNGETGEIVWDKGRDFATVRKVLSMPQVNIVKKTE
VQTGGFSKESILPKRNSDKLIARKKDWDPKKYGGFDSPTVAYSVLVVAKVEKGKSKKLKSVKELLGITIMERSSFEKNPIDFLEAKGY
KEVKKDLIIKLPKYSLFELENGRKRMLASAGELQKGNELALPSKYVNFLYLASHYEKLKGSPEDNEQKQLFVEQHKYHLDEIIEQISE
FSKRVILADANLDKVLSAYNKHRDKPIREQAENIIHLFTLTNLGAPAAFKYFDTTIDRKRYTSTKEVLDATLIHQSITGLYETRIDLS
QLGGD</u>SGGS*PKKKRKV* pNMG-5 88 amino acid sequence: ecTadA(wild-type)-(SGGS)2-*XTEN*-(SGGS)2-**ecTadA
(H36L_P48A_R51L_L84F_A106V_D108N_H123Y_S146C_A142N_D147Y_E155V_I156F_K157N)**-
(SGGS)2-*XTEN*-(SGGS)2_<u>nCas9</u>_GGS_*NLS*

(SEQ ID NO: 699)

**MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARDAKTGAAGSLMDVLHHPGMNHRVEITEGILADECAALLSDFFRMRRQEIKAQKKAQSSTD**SGGSSGGS*S
GSETPGTSESATPESS*GGSSGGS**SEVEFSHEYWMRHALTLAKRAWDEREVPVGAVLVLNNRVIGEGWNRAIGLHDPTAHAEIMALRQG
GLVMQNYRLIDATLYVTFEPCVMCAGAMIHSRIGRVVFGVRNAKTGAAGSLMDVLHYPGMNHRVEITEGILADECNALLCYFFRMRRQ
VFNAQKKAQSSTD**SGGSSGGS*SGSETPGTSESATPESS*GGSSGGS<u>DKKYSIGLAIGTNSVGWAVITDEYKVPSKKFKVLGNTDRHSIK
KNLIGALLFDSGETAEATRLKRTARRRYTRRKNRICYLQEIFSNEMAKVDDSFFHRLEESFLVEEDKKHERHPIFGNIVDEVAYHEKY
PTIYHLRKKLVDSTDKADLRLIYLALAHMIKFRGHFLIEGDLNPDNSDVDKLFIQLVQTYNQLFEENPINASGVDAKAILSARLSKSR
RLENLIAQLPGEKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDGTEELLVKLNRE
DLLRKQRTFDNGSIPHQIHLGELHAILRRQEDFYPFLKDNREKIEKILTFRIPYYVGPLARGNSRFAWMTRKSEETITPWNFEEVVDK
GASAQSFIERMTNFDKNLPNEKVLPKHSLLYEYFTVYNELTKVKYVTEGMRKPAFLSGEQKKAIVDLLFKTNRKVTVKQLKEDYFKKI
ECFDSVEISGVEDRFNASLGTYHDLLKIIKDKDFLDNEENEDILEDIVLTLTLFEDREMIEERLKTYAHLFDDKVMKQLKRRRYTGWG
RLSRKLINTGIRDKQSGKTILDFLKSDGFANRNFMQLIHDDSLTFKEDIQKAQVSGQGDSLHEHIANLAGSPAIKKGILQTVKVVDEL
VKVMGRHKPENIVIEMARENQTTQKGQKNSRERMKRIEEGIKELGSQILKEHPVENTQLQNEKLYLYYLQNGRDMYVDQELDINRLSD
YDVDHIVPQSFLKDDSIDNKVLTRSDKNRGKSDNVPSEEVVKKMKNYWRQLLNAKLITQRKFDNLTKAERGGLSELDKAGFIKRQLVE
TRQITKHVAQILDSRMNTKYDENDKLIREVKVITLKSKLVSDFRKDFQFYKVREINNYHHAHDAYLNAVVGTALIKKYPKLESEFVYG
DYKVYDVRKMIAKSEQEIGKATAKYFFYSNIMNFFKTEITLANGEIRKRPLIETNGETGEIVWDKGRDFATVRKVLSMPQVNIVKKTE
VQTGGFSKESILPKRNSDKLIARKKDWDPKKYGGFDSPTVAYSVLVVAKVEKGKSKKLKSVKELLGITIMERSSFEKNPIDFLEAKGY
KEVKKDLIIKLPKYSLFELENGRKRMLASAGELQKGNELALPSKYVNFLYLASHYEKLKGSPEDNEQKQLFVEQHKYHLDEIIEQISE
FSKRVILADANLDKVLSAYNKHRDKPIREQAENIIHLFTLTNLGAPAAFKYFDTTIDRKRYTSTKEVLDATLIHQSITGLYETRIDLS
QLGGD</u>SGGS*PKKKRKV* pNMG-620 amino acid sequence: ecTadA(wild-type)-(SGGS)2-*XTEN*-(SGGS)2-ecTadA
(W23R_H36L_P48A_R51L_L84F_A106V_D108N_H123Y_S146C_D147Y_R152P_E155V_I156F_K157N)-
(SGGS)2-*XTEN*-(SGGS)2_nCas9_GGS_<u>NLS</u>

(SEQ ID NO: 700)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTDSGGSSGGS*S*

*GSETPGTSESATPESS*GGSSGGSSEVEFSHEYWMRHALTLAKRARDEREVPVGAVLVLNNRVIGEGWNRAIGLHDPTAHAEIMALRQG

GLVMQNYRLIDATLYVTFEPCVMCAGAMIHSRIGRVVFGVRNAKTGAAGSLMDVLHYPGMNHRVEITEGILADECAALLCYFFRMPRQ

VFNAQKKAQSSTDSGGSSGGS*SGSETPGTSESATPESS*GGSSGGS<u>DKKYSIGLAIGTNSVGWAVITDEYKVPSKKFKVLGNTDRHSIK</u>

<u>KNLIGALLFDSGETAEATRLKRTARRRYTRRKNRICYLQEIFSNEMAKVDDSFFHRLEESFLVEEDKKHERHPIFGNIVDEVAYHEKY</u>

<u>PTIYHLRKKLVDSTDKADLRLIYLALAHMIKFRGHFLIEGDLNPDNSDVDKLFIQLVQTYNQLFEENPINASGVDAKAILSARLSKSR</u>

<u>RLENLIAQLPGEKKNGLFGNLIALSLGLTPNFKSNFDLAEDAKLQLSKDTYDDDLDNLLAQIGDQYADLFLAAKNLSDAILLSDILRV</u>

<u>NTEITKAPLSASMIKRYDEHHQDLTLLKALVRQQLPEKYKEIFFDQSKNGYAGYIDGGASQEEFYKFIKPILEKMDGTEELLVKLNRE</u>

<u>DLLRKQRTFDNGSIPHQIHLGELHAILRRQEDFYPFLKDNREKIEKILTFRIPYYVGPLARGNSRFAWMTRKSEETITPWNFEEVVDK</u>

<u>GASAQSFIERMTNFDKNLPNEKVLPKHSLLYEYFTVYNELTKVKYVTEGMRKPAFLSGEQKKAIVDLLFKTNRKVTVKQLKEDYFKKI</u>

<u>ECFDSVEISGVEDRFNASLGTYHDLLKIIKDKDFLDNEENEDILEDIVLTLTLFEDREMIEERLKTYAHLFDDKVMKQLKRRRYTGWG</u>

<u>RLSRKLINGIRDKQSGKTILDFLKSDGFANRNFMQLIHDDSLTFKEDIQKAQVSGQGDSLHEHIANLAGSPAIKKGILQTVKVVDEL</u>

<u>VKVMGRHKPENIVIEMARENQTTQKGQKNSRERMKRIEEGIKELGSQILKEHPVENTQLQNEKLYLYYLQNGRDMYVDQELDINRLSD</u>

<u>YDVDHIVPQSFLKDDSIDNKVLTRSDKNRGKSDNVPSEEVVKKMKNYWRQLLNAKLITQRKFDNLTKAERGGLSELDKAGFIKRQLVE</u>

<u>TRQITKHVAQILDSRMNTKYDENDKLIREVKVITLKSKLVSDFRKDFQFYKVREINNYHHAHDAYLNAVVGTALIKKYPKLESEFVYG</u>

<u>DYKVYDVRKMIAKSEQEIGKATAKYFFYSNIMNFFKTEITLANGEIRKRPLIETNGETGEIVWDKGRDFATVRKVLSMPQVNIVKKTE</u>

<u>VQTGGFSKESILPKRNSDKLIARKKDWDPKKYGGFDSPTVAYSVLVVAKVEKGKSKKLKSVKELLGITIMERSSFEKNPIDFLEAKGY</u>

<u>KEVKKDLIIKLPKYSLFELENGRKRMLASAGELQKGNELALPSKYVNFLYLASHYEKLKGSPEDNEQKQLFVEQHKHYLDEIIEQISE</u>

<u>FSKRVILADANLDKVLSAYNKHRDKPIREQAENIIHLFTLTNLGAPAAFKYFDTTIDRKRYTSTKEVLDATLIHQSITGLYETRIDLS</u>

<u>QLGGD</u>SGGS<u>PKKKRKV</u> pNMG-617 amino acid sequence: ecTadA(wild-type)-(SGGS)2-*XTEN*-(SGGS)2-ecTadA
(W23L_H36L_P48A_R51L_L84F_A106V_D108N_H123Y_A142A_S146C_D147Y_E155V_I156F_K157N)-
(SGGS)2-*XTEN*-(SGGS)2_nCas9_GGS_<u>NLS</u>

(SEQ ID NO: 701)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTDSGGSSGGS*S*

*GSETPGTSESATPESS*GGSSGGSSEVEFSHEYWMRHALTLAKRALDEREVPVGAVLVLNNRVIGEGWNRAIGLHDPTAHAEIMALRQG

GLVMQNYRLIDATLYVTFEPCVMCAGAMIHSRIGRVVFGVRNAKTGAAGSLMDVLHYPGMNHRVEITEGILADECNALLCYFFRMRRQ

VFNAQKKAQSSTDSGGSSGGS*SGSETPGTSESATPESS*GGSSGGS<u>DKKYSIGLAIGTNSVGWAVITDEYKVPSKKFKVLGNTDRHSIK</u>

<u>KNLIGALLFDSGETAEATRLKRTARRRYTRRKNRICYLQEIFSNEMAKVDDSFFHRLEESFLVEEDKKHERHPIFGNIVDEVAYHEKY</u>

<u>PTIYHLRKKLVDSTDKADLRLIYLALAHMIKFRGHFLIEGDLNPDNSDVDKLFIQLVQTYNQLFEENPINASGVDAKAILSARLSKSR</u>

<u>RLENLIAQLPGEKKNGLFGNLIALSLGLTPNFKSNFDLAEDAKLQLSKDTYDDDLDNLLAQIGDQYADLFLAAKNLSDAILLSDILRV</u>

<u>NTEITKAPLSASMIKRYDEHHQDLTLLKALVRQQLPEKYKEIFFDQSKNGYAGYIDGGASQEEFYKFIKPILEKMDGTEELLVKLNRE</u>

<u>DLLRKQRTFDNGSIPHQIHLGELHAILRRQEDFYPFLKDNREKIEKILTFRIPYYVGPLARGNSRFAWMTRKSEETITPWNFEEVVDK</u>

<u>GASAQSFIERMTNFDKNLPNEKVLPKHSLLYEYFTVYNELTKVKYVTEGMRKPAFLSGEQKKAIVDLLFKTNRKVTVKQLKEDYFKKI</u>

<u>ECFDSVEISGVEDRFNASLGTYHDLLKIIKDKDFLDNEENEDILEDIVLTLTLFEDREMIEERLKTYAHLFDDKVMKQLKRRRYTGWG</u>

<u>RLSRKLINGIRDKQSGKTILDFLKSDGFANRNFMQLIHDDSLTFKEDIQKAQVSGQGDSLHEHIANLAGSPAIKKGILQTVKVVDELV</u>

<u>KVMGRHKPENIVIEMARENQTTQKGQKNSRERMKRIEEGIKELGSQILKEHPVENTQLQNEKLYLYYLQNGRDMYVDQELDINRLSDY</u>

<u>DVDHIVPQSFLKDDSIDNKVLTRSDKNRGKSDNVPSEEVVKKMKNYWRQLLNAKLITQRKFDNLTKAERGGLSELDKAGFIKRQLVET</u>

RQITKHVAQILDSRMNTKYDENDKLIREVKVITLKSKLVSDFRKDFQFYKVREINNYHHAHDAYLNAVVGTALIKKYPKLESEFVYGD
YKVYDVRKMIAKSEQEIGKATAKYFFYSNIMNFFKTEITLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVEKGKSKKLKSVKELLGITIMERSSFEKNPIDFLEAKGYK
EVKKDLIIKLPKYSLFELENGRKRMLASAGELQKGNELALPSKYVNFLYLASHYEKLKGSPEDNEQKQLFVEQHKHYLDEIIEQISEF
SKRVILADANLDKVLSAYNKHRDKPIREQAENIIHLFTLTNLGAPAAFKYFDTTIDRKRYTSTKEVLDATLIHQSITGLYETRIDLSQ
LGGD*SGGS*<u>PKKKRKV</u> pNMG-618 amino acid sequence: ecTadA(wild-type)-(SGGS)2-*XTEN*-(SGGS)2-**ecTadA
(W23L_H36L_P48A_R51L_L84F_A106V_D108N_H123Y_A142A_S146C_D147Y_R152P_E155V_I156F_K157N)**-
(SGGS)2-*XTEN*-(SGGS)2_<u>nCas9</u>_GGS_<u>NLS</u>

(SEQ ID NO: 702)

**MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARDAKTGAAGSLMDVLHHPGMNHRVEITEGILADECAALLSDFFRMRRQEIKAQKKAQSSTD**SGGS*SGGSS
GSETPGTSESATPESS*SGGS*SGGS***SEVEFSHEYWMRHALTLAKRALDEREVPVGAVLVLNNRVIGEGWNRAIGLHDPTAHAEIMALRQG
GLVMQNYRLIDATLYVTFEPCVMCAGAMIHSRIGRVVFGVRNAKTGAAGSLMDVLHYPGMNHRVEITEGILADECNALLCYFFRMPRQ
VFNAQKKAQSSTD**SGGS*SGGS* *SGSETPGTSESATPESS*SGGS*SGGS*<u>DKKYSIGLAIGTNSVGWAVITDEYKVPSKKFKVLGNTDRHSIK
KNLIGALLFDSGETAEATRLKRTARRRYTRRKNRICYLQEIFSNEMAKVDDSFFHRLEESFLVEEDKKHERHPIFGNIVDEVAYHEKY
PTIYHLRKKLVDSTDKADLRLIYLALAHMIKFRGHFLIEGDLNPDNSDVDKLFIQLVQTYNQLFEENPINASGVDAKAILSARLSKSR
RLENLIAQLPGEKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDGTEELLVKLNRE
DLLRKQRTFDNGSIPHQIHLGELHAILRRQEDFYPFLKDNREKIEKILTFRIPYYVGPLARGNSRFAWMTRKSEETITPWNFEEVVDK
GASAQSFIERMTNFDKNLPNEKVLPKHSLLYEYFTVYNELTKVKYVTEGMRKPAFLSGEQKKAIVDLLFKTNRKVTVKQLKEDYFKKI
ECFDSVEISGVEDRFNASLGTYHDLLKIIKDKDFLDNEENEDILEDIVLTLTLFEDREMIEERLKTYAHLFDDKVMKQLKRRRYTGWG
RLSRKLINGIRDKQSGKTILDFLKSDGFANRNFMQLIHDDSLTFKEDIQKAQVSGQGDSLHEHIANLAGSPAIKKGILQTVKVVDELV
KVMGRHKPENIVIEMARENQTTQKGQKNSRERMKRIEEGIKELGSQILKEHPVENTQLQNEKLYLYYLQNGRDMYVDQELDINRLSDY
DVDHIVPQSFLKDDSIDNKVLTRSDKNRGKSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHHAHDAYLNAVVGTALIKKYPKLESEFVYGD
YKVYDVRKMIAKSEQEIGKATAKYFFYSNIMNFFKTEITLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVEKGKSKKLKSVKELLGITIMERSSFEKNPIDFLEAKGYK
EVKKDLIIKLPKYSLFELENGRKRMLASAGELQKGNELALPSKYVNFLYLASHYEKLKGSPEDNEQKQLFVEQHKHYLDEIIEQISEF
SKRVILADANLDKVLSAYNKHRDKPIREQAENIIHLFTLTNLGAPAAFKYFDTTIDRKRYTSTKEVLDATLIHQSITGLYETRIDLSQ
LGGD*SGGS*<u>PKKKRKV</u></u> pNMG-620 amino acid sequence: ecTadA(wild-type)-(SGGS)2-*XTEN*-(SGGS)2-**ecTadA
(W23R_H36L_P48A_R51L_L84F_A106V_D108N_H123Y_S146C_D147Y_R152P_E155V_I156F_K157N)**-
(SGGS)2-*XTEN*-(SGGS)2_<u>nCas9</u>_GGS_<u>NLS</u>

(SEQ ID NO: 703)

**MSEVEFSHEYWMRHALTLAKRAWDEREVPVGAVLVHNNRVIGEGWNRPIGRHDPTAHAEIMALRQGGLVMQNYRLIDATLYVTLEPCV
MCAGAMIHSRIGRVVFGARDAKTGAAGSLMDVLHHPGMNHRVEITEGILADECAALLSDFFRMRRQEIKAQKKAQSSTD**SGGS*SGGSS
GSETPGTSESATPESS*SGGS*SGGS***SEVEFSHEYWMRHALTLAKRARDEREVPVGAVLVLNNRVIGEGWNRAIGLHDPTAHAEIMALRQG
GLVMQNYRLIDATLYVTFEPCVMCAGAMIHSRIGRVVFGVRNAKTGAAGSLMDVLHYPGMNHRVEITEGILADECAALLCYFFRMPRQ
VFNAQKKAQSSTD**SGGS*SGGS* *SGSETPGTSESATPESS*SGGS*SGGS*<u>DKKYSIGLAIGTNSVGWAVITDEYKVPSKKFKVLGNTDRHSIK
KNLIGALLFDSGETAEATRLKRTARRRYTRRKNRICYLQEIFSNEMAKVDDSFFHRLEESFLVEEDKKHERHPIFGNIVDEVAYHEKY
PTIYHLRKKLVDSTDKADLRLIYLALAHMIKFRGHFLIEGDLNPDNSDVDKLFIQLVQTYNQLFEENPINASGVDAKAILSARLSKSR
RLENLIAQLPGEKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDGTEELLVKLNRE
DLLRKQRTFDNGSIPHQIHLGELHAILRRQEDFYPFLKDNREKIEKILTFRIPYYVGPLARGNSRFAWMTRKSEETITPWNFEEVVDK

-continued

GASAQSFIERMTNFDKNLPNEKVLPKHSLLYEYFTVYNELTKVKYVTEGMRKPAFLSGEQKKAIVDLLFKTNRKVTVKQLKEDYFKKI

ECFDSVEISGVEDRFNASLGTYHDLLKIIKDKDFLDNEENEDILEDIVLTLTLFEDREMIEERLKTYAHLFDDKVMKQLKRRRYTGWG

RLSRKLINTGIRDKQSGKTILDFLKSDGFANRNFMQLIHDDSLTFKEDIQKAQVSGQGDSLHEHIANLAGSPAIKKGILQTVKVVDEL

VKVMGRHKPENIVIEMARENQTTQKGQKNSRERMKRIEEGIKELGSQILKEHPVENTQLQNEKLYLYYLQNGRDMYVDQELDINRLSD

YDVDHIVPQSFLKDDSIDNKVLTRSDKNRGKSDNVPSEEVVKKMKNYWRQLLNAKLITQRKFDNLTKAERGGLSELDKAGFIKRQLVE

TRQITKHVAQILDSRMNTKYDENDKLIREVKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEIVWDKGRDFATVRKVLSMPQVNIVKKTE

VQTGGFSKESILPKRNSDKLIARKKDWDPKKYGGFDSPTVAYSVLVVAKVEKGKSKKLKSVKELLGITIMERSSFEKNPIDFLEAKGY

KEVKKDLIIKLPKYSLFELENGRKRMLASAGELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRKRYTSTKEVLDATLIHQSITGLYETRIDLS

QLGGDSGGS*PKKKRKV* pNMG-621 amino acid sequence: ecTadA(wild-type)-*32 a.a. linker*-ecTadA
(H36L_P48A_R51L_L84F_A106V_D108N_H123Y_S146C_D147Y_R152P_E155V_I156F_K157N)-
*24 a.a. linker*_nCas9_GGS_*NLS*

(SEQ ID NO: 704)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTDSGGSSGGSS

GSETPGTSESATPESSGGSSGGSSEVEFSHEYWMRHALTLAKRAWDEREVPVGAVLVLNNRVIGEGWNRAIGLHDPTAHAEIMALRQG

GLVMQNYRLIDATLYVTFEPCVMCAGAMIHSRIGRVVFGVRNAKTGAAGSLMDVLHYPGMNHRVEITEGILADECAALLCYFFRMPRQ

VFNAQKKAQSSTDSGGSSGGSSGSETPGTSESATPESDKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEESFLVEEDKKHERHPIFGNIVDEVAYHEKYPTIYHLRK

KLVDSTDKADLRLIYLALAHMIKFRGHFLIEGDLNPDNSDVDKLFIQLVQTYNQLFEENPINASGVDAKAILSARLSKSRRLENLIAQ

LPGEKKNGLFGNLIALSLGLTPNFKSNFDLAEDAKLQLSKDTYDDDLDNLLAQIGDQYADLFLAAKNLSDAILLSDILRVNTEITKAP

LSASMIKRYDEHHQDLTLLKALVRQQLPEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKAIVDLLFKTNRKVTVKQLKEDYFKKIECFDSVET

SGVEDRFNASLGTYHDLLKIIKDKDFLDNEENEDILEDIVLTLTLFEDREMIEERLKTYAHLFDDKVMKQLKRRRYTGWGRLSRKLIN

GIRDKQSGKTILDFLKSDGFANRNFMQLIHDDSLTFKEDIQKAQVSGQGDSLHEHIANLAGSPAIKKGILQTVKVVDELVKVMGRHKP

ENIVIEMARENQTTQKGQKNSRERMKRIEEGIKELGSQILKEHPVENTQLQNEKLYLYYLQNGRDMYVDQELDINRLSDYDVDHIVPQ

SFLKDDSIDNKVLTRSDKNRGKSDNVPSEEVVKKMKNYWRQLLNAKLITQRKFDNLTKAERGGLSELDKAGFIKRQLVETRQITKHVA

QILDSRMNTKYDENDKLIREVKVITLKSKLVSDFRKDFQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGEIVWDKGRDFATVRKVLSMPQVNIVKKTEVQTGGFSKE

SILPKRNSDKLIARKKDWDPKKYGGFDSPTVAYSVLVVAKVEKGKSKKLKSVKELLGITIIVIERSSFEKNPIDFLEAKGYKEVKKDL

IIKLPKYSLFELENGRKRMLASAGELQKGNELALPSKYVNFLYLASHYEKLKGSPEDNEQKQLFVEQHKHYLDEIIEQISEFSKRVIL

ADANLDKVLSAYNKHRDKPIREQAENIIHLFTLTNLGAPAAFKYFDTTIDRKRYTSTKEVLDATLIHQSITGLYETRIDLSQLGGDSG

GS*PKKKRKV* pNMG-622 amino acid sequence: ecTadA(wild-type)-*32 a.a. linker*-ecTadA
(H36L_P48A_R51L_L84F_A106V_D108N_H123Y_A142N_S146C_D147Y_R152P_E155V_I156F_K157N)-
*24 a.a. linker*_nCas9_GGS_*NLS*

(SEQ ID NO: 705)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTDSGGSSGGSS

GSETPGTSESATPESSGGSSGGSSEVEFSHEYWMRHALTLAKRAWDEREVPVGAVLVLNNRVIGEGWNRAIGLHDPTAHAEIMALRQG

GLVMQNYRLIDATLYVTFEPCVMCAGAMIHSRIGRVVFGVRNAKTGAAGSLMDVLHYPGMNHRVEITEGILADECNALLCYFFRMPRQ

-continued

VFNAQKKAQSSTD_SGGSSGGSSGSGSETPGTSESATPES_DKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEESFLVEEDKKHERHPIFGNIVDEVAYHEKYPTIYHLRK

KLVDSTDKADLRLIYLALAHMIKFRGHFLIEGDLNPDNSDVDKLFIQLVQTYNQLFEENPINASGVDAKAILSARLSKSRRLENLIAQ

LPGEKKNGLFGNLIALSLGLTPNFKSNFDLAEDAKLQLSKDTYDDDLDNLLAQIGDQYADLFLAAKNLSDAILLSDILRVNTEITKAP

LSASMIKRYDEHHQDLTLLKALVRQQLPEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKAIVDLLFKTNRKVTVKQLKEDYFKKIECFDSVET

SGVEDRFNASLGTYHDLLKIIKDKDFLDNEENEDILEDIVLTLTLFEDREMIEERLKTYAHLFDDKVMKQLKRRRYTGWGRLSRKLIN

GIRDKQSGKTILDFLKSDGFANRNFMQLIHDDSLTFKEDIQKAQVSGQGDSLHEHIANLAGSPAIKKGILQTVKVVDELVKVMGRHKP

ENIVIEMARENQTTQKGQKNSRERMKRIEEGIKELGSQILKEHPVENTQLQNEKLYLYYLQNGRDMYVDQELDINRLSDYDVDHIVPQ

SFLKDDSIDNKVLTRSDKNRGKSDNVPSEEVVKKMKNYWRQLLNAKLITQRKFDNLTKAERGGLSELDKAGFIKRQLVETRQnKHVAQ

ILDSRMNTKYDENDKLIREVKVITLKSKLVSDFRKDFQFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEIVWDKGRDFATVRKVLSMPQVNIVKKTEVQTGGFSKES

ILPKRNSDKLIARKKDWDPKKYGGFDSPTVAYSVLVVAKVEKGKSKKLKSVKELLGITIIVIERSSFEKNPIDFLEAKGYKEVKKDLI

IKLPKYSLFELENGRKRMLASAGELQKGNELALPSKYVNFLYLASHYEKLKGSPEDNEQKQLFVEQHKHYLDEIIEQISEFSKRVILA

DANLDKVLSAYNKHRDKPIREQAENIIHLFTLTNLGAPAAFKYFDTTIDRKRYTSTKEVLDATLIHQSITGLYETRIDLSQLGGDSGG

_S_PKKKRKV pNMG-623 amino acid sequence: ecTadA(wild-type)-_32 a.a. linker_-ecTadA
(W23L_H36L_P48A_R51L_L84F_A106V_D108N_H123Y_S146C_D147Y_R152P_E155V_I156F_K157N)-
_24 a.a. linker_-_nCas9__GGS__NLS_

(SEQ ID NO: 706)

MSEVEFSHEYWMRHALTLAKRAWDEREVPVGAVLVHNNRVIGEGWNRPIGRHDPTAHAEIMALRQGGLVMQNYRLIDATLYVTLEPCV

MCAGAMIHSRIGRVVFGARDAKTGAAGSLMDVLHHPGMNHRVEITEGILADECAALLSDFFRMRRQEIKAQKKAQSSTD_SGGSSGGSS_

_GSETPGTSESATPESS_GGSSGGSSSEVEFSHEYWMRHALTLAKRALDEREVPVGAVLVLNNRVIGEGWNRAIGLHDPTAHAEIMALRQG

GLVMQNYRLIDATLYVTFEPCVMCAGAMIHSRIGRVVFGVRNAKTGAAGSLMDVLHPGMNHRVEITEGILADECAALLCYFFRMPRQ

VFNAQKKAQSSTD_SGGSSGGSSGSETPGTSESATPES_DKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEESFLVEEDKKHERHPIFGNIVDEVAYHEKYPTIYHLRK

KLVDSTDKADLRLIYLALAHMIKFRGHFLIEGDLNPDNSDVDKLFIQLVQTYNQLFEENPINASGVDAKAILSARLSKSRRLENLIAQ

LPGEKKNGLFGNLIALSLGLTPNFKSNFDLAEDAKLQLSKDTYDDDLDNLLAQIGDQYADLFLAAKNLSDAILLSDILRVNTEITKAP

LSASMIKRYDEHHQDLTLLKALVRQQLPEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKAIVDLLFKTNRKVTVKQLKEDYFKKIECFDSVET

SGVEDRFNASLGTYHDLLKIIKDKDFLDNEENEDILEDIVLTLTLFEDREMIEERLKTYAHLFDDKVMKQLKRRRYTGWGRLSRKLIN

GIRDKQSGKTILDFLKSDGFANRNFMQLIHDDSLTFKEDIQKAQVSGQGDSLHEHIANLAGSPAIKKGILQTVKVVDELVKVMGRHKP

ENIVIEMARENQTTQKGQKNSRERMKRIEEGIKELGSQILKEHPVENTQLQNEKLYLYYLQNGRDMYVDQELDINRLSDYDVDHIVPQ

SFLKDDSIDNKVLTRSDKNRGKSDNVPSEEVVKKMKNYWRQLLNAKLITQRKFDNLTKAERGGLSELDKAGFIKRQLVETRQITKHVA

QILDSRMNTKYDENDKLIREVKVITLKSKLVSDFRKDFQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGEIVWDKGRDFATVRKVLSMPQVNIVKKTEVQTGGFSKE

SILPKRNSDKLIARKKDWDPKKYGGFDSPTVAYSVLVVAKVEKGKSKKLKSVKELLGITIIVIERSSFEKNPIDFLEAKGYKEVKKDL

IIKLPKYSLFELENGRKRMLASAGELQKGNELALPSKYVNFLYLASHYEKLKGSPEDNEQKQLFVEQHKHYLDEIIEQISEFSKRVIL

ADANLDKVLSAYNKHRDKPIREQAENIIHLFTLTNLGAPAAFKYFDTTIDRKRYTSTKEVLDATLIHQSITGLYETRIDLSQLGGDSG

_GS_PKKKRKV

In some embodiments, the fusion protein comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the amino acid sequences set forth in any one of SEQ ID NOs: 11-28, 387, 388, 440, 691-706, or to any of the fusion proteins provided herein. In some embodiments, the fusion protein comprises an amino acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50, or more mutations compared to any one of the amino acid sequences set forth in SEQ ID NOs: 11-28, 387, 388, 440, 691-706, or any of the fusion proteins provided herein. In some embodiments, the fusion protein comprises an amino acid sequence that has at least 5, at least 10, at least 15, at least 20, at least 25, at least 30, at least 35, at least 40, at least 45, at least 50, at least 60, at least 70, at least 80, at least 90, at least 100, at least 110, at least 120, at least 130, at least 140, at least 150, at least 160, at least 170, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1750, or at least 1800 identical contiguous amino acid residues as compared to any one of the amino acid sequences set forth in SEQ ID NOs: 11-28, 387, 388, 440, 691-706, or any of the fusion proteins provided herein.

Nucleic Acid Programmable DNA Binding Protein (napDNAbp) Complexes with Guide Nucleic Acids Some aspects of this disclosure provide complexes comprising any of the fusion proteins provided herein, and a guide nucleic acid bound to napDNAbp of the fusion protein. Some aspects of this disclosure provide complexes comprising any of the fusion proteins provided herein, and a guide RNA bound to a Cas9 domain (e.g., a dCas9, a nuclease active Cas9, or a Cas9 nickase) of fusion protein.

In some embodiments, the guide nucleic acid (e.g., guide RNA) is from 15-100 nucleotides long and comprises a sequence of at least 10 contiguous nucleotides that is complementary to a target sequence. In some embodiments, the guide RNA is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. In some embodiments, the guide RNA comprises a sequence of 15, 16, 17, 18, 19, 20, 21, 22, 23, 24, 25, 26, 27, 28, 29, 30, 31, 32, 33, 34, 35, 36, 37, 38, 39, or 40 contiguous nucleotides that is complementary to a target sequence. In some embodiments, the target sequence is a DNA sequence. In some embodiments, the target sequence is an RNA sequence. In some embodiments, the target sequence is a sequence in the genome of a mammal. In some embodiments, the target sequence is a sequence in the genome of a human. In some embodiments, the 3' end of the target sequence is immediately adjacent to a canonical PAM sequence (NGG). In some embodiments, the guide nucleic acid (e.g., guide RNA) is complementary to a sequence associated with a disease or disorder. In some embodiments, the guide nucleic acid (e.g., guide RNA) is complementary to a sequence associated with a disease or disorder having a mutation in a gene selected from the genes disclosed in any one of Tables 1 and 2.

Methods of Using Fusion Proteins Comprising an Adenosine Deaminase and a Nucleic Acid Programmable DNA Binding Protein (napDNAbp) Domain Some aspects of this disclosure provide methods of using the fusion proteins, or complexes comprising a guide nucleic acid (e.g., gRNA) and a nucleobase editor provided herein. For example, some aspects of this disclosure provide methods comprising contacting a DNA, or RNA molecule with any of the fusion proteins provided herein, and with at least one guide nucleic acid (e.g., guide RNA), wherein the guide nucleic acid, (e.g., guide RNA) is about 15-100 nucleotides long and comprises a sequence of at least 10 contiguous nucleotides that is complementary to a target sequence. In some embodiments, the 3' end of the target sequence is immediately adjacent to a canonical PAM sequence (NGG). In some embodiments, the 3' end of the target sequence is not immediately adjacent to a canonical PAM sequence (NGG). In some embodiments, the 3' end of the target sequence is immediately adjacent to an AGC, GAG, TTT, GTG, or CAA sequence.

In some embodiments, the target DNA sequence comprises a sequence associated with a disease or disorder. In some embodiments, the target DNA sequence comprises a point mutation associated with a disease or disorder. In some embodiments, the activity of the fusion protein (e.g., comprising an adenosine deaminase and a Cas9 domain), or the complex, results in a correction of the point mutation. In some embodiments, the target DNA sequence comprises a G→A point mutation associated with a disease or disorder, and wherein the deamination of the mutant A base results in a sequence that is not associated with a disease or disorder. In some embodiments, the target DNA sequence encodes a protein, and the point mutation is in a codon and results in a change in the amino acid encoded by the mutant codon as compared to the wild-type codon. In some embodiments, the deamination of the mutant A results in a change of the amino acid encoded by the mutant codon. In some embodiments, the deamination of the mutant A results in the codon encoding the wild-type amino acid. In some embodiments, the contacting is in vivo in a subject. In some embodiments, the subject has or has been diagnosed with a disease or disorder. In some embodiments, the disease or disorder is phenylketonuria, von Willebrand disease (vWD), a neoplastic disease associated with a mutant PTEN or BRCA1, or Li-Fraumeni syndrome. A list of exemplary diseases and disorders that may be treated using the nucleobase editors provided herein is shown in Table 1. Table 1 includes the target gene, the mutation to be corrected, the related disease and the nucleotide sequence of the associated protospacer and PAM.

TABLE 1

List of exemplary diseases that may be treated using the nucleobase editors provided herein. The A to be edited in the protospacer is indicated by underlining and the PAM is indicated in bold.

| Target Gene | Mutation | ATCC Cell Line | Disease | Protospacer and PAM |
|---|---|---|---|---|
| PTEN | Cy5136Tyr | HTB-12E | Cancer Predisposition | TATATGCATATTTATTACATCGG (SEQ ID NO: 85) |
| PTEN | Arg233Ter | HTB-13 | Cancer Predisposition | CCGTCATGTGGGTCCTGAATTGG (SEQ ID NO: 86) |

TABLE 1-continued

List of exemplary diseases that may be treated using the nucleobase editors provided herein. The A to be edited in the protospacer is indicated by underlining and the PAM is indicated in bold.

| Target Gene | Mutation | ATCC Cell Line | Disease | Protospacer and PAM |
|---|---|---|---|---|
| TP53 | Glu258Lys | HTB-65 | Cancer Predisposition | ACACTGAAAGACTCCAGGTCAGG (SEQ ID NO: 87) |
| BRCA1 | Gly1738Arg | NA | Cancer Predisposition | GTCAGAAGAGATGTGGTCAATGG (SEQ ID NO: 88) |
| BRCA1 | 4097-1.G>A | NA | Cancer Predisposition | TTTAAAGTGAAGCAGCATCTGGG (SEQ ID NO: 89); ATTTAAAGTGAAGCAGCATCTGG (SEQ ID NO: 90) |
| PAH | Thr380Met | NA | Phenylketonuria | ACTCCATGACAGTGTAATTTTGG (SEQ ID NO: 91) |
| VWF | Ser1285Phe | NA | von Willebrand (Hemophilia) | GCCTGGAGAAGCCATCCAGCAGG (SEQ ID NO: 92) |
| VWF | Arg2535Ter | NA | von Wiliebrand (Hemophilia) | CTCAGACACACTCATTGATGAGG (SEQ ID NO: 93) |
| TP53 | Arg175His | HCC1395 | Li-Fraumenl syndrome | GAGGCACTGCCCCCACCATGAGCG (SEG ID NO: 94) |

Some embodiments provide methods for using the DNA editing fusion proteins provided herein. In some embodiments, the fusion protein is used to introduce a point mutation into a nucleic acid by deaminating a target nucleobase, e.g., an A residue. In some embodiments, the deamination of the target nucleobase results in the correction of a genetic defect, e.g., in the correction of a point mutation that leads to a loss of function in a gene product. In some embodiments, the genetic defect is associated with a disease or disorder, e.g., a lysosomal storage disorder or a metabolic disease, such as, for example, type I diabetes. In some embodiments, the methods provided herein are used to introduce a deactivating point mutation into a gene or allele that encodes a gene product that is associated with a disease or disorder. For example, in some embodiments, methods are provided herein that employ a DNA editing fusion protein to introduce a deactivating point mutation into an oncogene (e.g., in the treatment of a proliferative disease). A deactivating mutation may, in some embodiments, generate a premature stop codon in a coding sequence, which results in the expression of a truncated gene product, e.g., a truncated protein lacking the function of the full-length protein.

In some embodiments, the purpose of the methods provided herein is to restore the function of a dysfunctional gene via genome editing. The nucleobase editing proteins provided herein can be validated for gene editing-based human therapeutics in vitro, e.g., by correcting a disease-associated mutation in human cell culture. It will be understood by the skilled artisan that the nucleobase editing proteins provided herein, e.g., the fusion proteins comprising a nucleic acid programmable DNA binding protein (e.g., Cas9) and an adenosine deaminase domain can be used to correct any single point G to A or C to T mutation. In the first case, deamination of the mutant A to I corrects the mutation, and in the latter case, deamination of the A that is base-paired with the mutant T, followed by a round of replication, corrects the mutation. Exemplary point mutations that can be corrected are listed in Tables 1 and 2.

The successful correction of point mutations in disease-associated genes and alleles opens up new strategies for gene correction with applications in therapeutics and basic research. Site-specific single-base modification systems like the disclosed fusions of a nucleic acid programmable DNA binding protein and an adenosine deaminase domain also have applications in "reverse" gene therapy, where certain gene functions are purposely suppressed or abolished. In these cases, site-specifically mutating residues that lead to inactivating mutations in a protein, or mutations that inhibit function of the protein can be used to abolish or inhibit protein function in vitro, ex vivo, or in vivo.

The instant disclosure provides methods for the treatment of a subject diagnosed with a disease associated with or caused by a point mutation that can be corrected by a DNA editing fusion protein provided herein. For example, in some embodiments, a method is provided that comprises administering to a subject having such a disease, e.g., a cancer associated with a point mutation as described above, an effective amount of an adenosine deaminase fusion protein that corrects the point mutation or introduces a deactivating mutation into a disease-associated gene. In some embodiments, the disease is a proliferative disease. In some embodiments, the disease is a genetic disease. In some embodiments, the disease is a neoplastic disease. In some embodiments, the disease is a metabolic disease. In some embodiments, the disease is a lysosomal storage disease. Other diseases that can be treated by correcting a point mutation or introducing a deactivating mutation into a disease-associated gene will be known to those of skill in the art, and the disclosure is not limited in this respect.

The instant disclosure provides methods for the treatment of additional diseases or disorders, e.g., diseases or disorders that are associated or caused by a point mutation that can be corrected by deaminase-mediated gene editing. Some such diseases are described herein, and additional suitable diseases that can be treated with the strategies and fusion proteins provided herein will be apparent to those of skill in the art based on the instant disclosure. Exemplary suitable diseases and disorders are listed below. It will be understood that the numbering of the specific positions or residues in the respective sequences depends on the particular protein and numbering scheme used. Numbering might be different, e.g., in precursors of a mature protein and the mature protein itself, and differences in sequences from species to species may affect numbering. One of skill in the art will be able to identify the respective residue in any homologous protein and in the respective encoding nucleic acid by methods well known in the art, e.g., by sequence alignment and determination of homologous residues. Exemplary suitable diseases and disorders include, without limitation: 2-methyl-3-hydroxybutyric aciduria; 3 beta-Hydroxysteroid dehydrogenase deficiency; 3-Methylglutaconic aciduria; 3-Oxo-5 alpha-steroid delta 4-dehydrogenase deficiency; 46, XY sex reversal, type 1, 3, and 5; 5-Oxoprolinase deficiency; 6-pyruvoyl-tetrahydropterin synthase deficiency; Aarskog syndrome; Aase syndrome; Achondrogenesis type 2; Achromatopsia 2 and 7; Acquired long QT syndrome; Acrocallosal syndrome, Schinzel type; Acrocapitofemoral dysplasia; Acrodysostosis 2, with or without hormone resistance; Acroerythrokeratoderma; Acromicric dysplasia; Acth-independent macronodular adrenal hyperplasia 2; Activated PI3K-delta syndrome; Acute intermittent porphyria; deficiency of Acyl-CoA dehydrogenase family, member 9; Adams-Oliver syndrome 5 and 6; Adenine phosphoribosyltransferase deficiency; Adenylate kinase deficiency; hemolytic anemia due to Adenylosuccinate lyase deficiency; Adolescent nephronophthisis; Renal-hepatic-pancreatic dysplasia; Meckel syndrome type 7; Adrenoleukodystrophy; Adult junctional epidermolysis bullosa; Epidermolysis bullosa, junctional, localisata variant; Adult neuronal ceroid lipofuscinosis; Adult neuronal ceroid lipofuscinosis; Adult onset ataxia with oculomotor apraxia; ADULT syndrome; Afibrinogenemia and congenital Afibrinogenemia; autosomal recessive Agammaglobulinemia 2; Age-related macular degeneration 3, 6, 11, and 12; Aicardi Goutieres syndromes 1, 4, and 5; Chilbain lupus 1; Alagille syndromes 1 and 2; Alexander disease; Alkaptonuria; Allan-Herndon-Dudley syndrome; Alopecia universalis congenita; Alpers encephalopathy; Alpha-1-antitrypsin deficiency; autosomal dominant, autosomal recessive, and X-linked recessive Alport syndromes; Alzheimer disease, familial, 3, with spastic paraparesis and apraxia; Alzheimer disease, types, 1, 3, and 4; hypocalcification type and hypomaturation type, IIA1 Amelogenesis imperfecta; Aminoacylase 1 deficiency; Amish infantile epilepsy syndrome; Amyloidogenic transthyretin amyloidosis; Amyloid Cardiomyopathy, Transthyretin-related; Cardiomyopathy; Amyotrophic lateral sclerosis types 1, 6, 15 (with or without frontotemporal dementia), 22 (with or without frontotemporal dementia), and 10; Frontotemporal dementia with TDP43 inclusions, TAR-DBP-related; Andermann syndrome; Andersen Tawil syndrome; Congenital long QT syndrome; Anemia, nonspherocytic hemolytic, due to G6PD deficiency; Angelman syndrome; Severe neonatal-onset encephalopathy with microcephaly; susceptibility to Autism, X-linked 3; Angiopathy, hereditary, with nephropathy, aneurysms, and muscle cramps; Angiotensin i-converting enzyme, benign serum increase; Aniridia, cerebellar ataxia, and mental retardation; Anonychia; Antithrombin III deficiency; Antley-Bixler syndrome with genital anomalies and disordered steroidogenesis; Aortic aneurysm, familial thoracic 4, 6, and 9; Thoracic aortic aneurysms and aortic dissections; Multisystemic smooth muscle dysfunction syndrome; Moyamoya disease 5; Aplastic anemia; Apparent mineralocorticoid excess; Arginase deficiency; Argininosuccinate lyase deficiency; Aromatase deficiency; Arrhythmogenic right ventricular cardiomyopathy types 5, 8, and 10; Primary familial hypertrophic cardiomyopathy; Arthrogryposis multiplex congenita, distal, X-linked; Arthrogryposis renal dysfunction cholestasis syndrome; Arthrogryposis, renal dysfunction, and cholestasis 2; Asparagine synthetase deficiency; Abnormality of neuronal migration; Ataxia with vitamin E deficiency; Ataxia, sensory, autosomal dominant; Ataxia-telangiectasia syndrome; Hereditary cancer-predisposing syndrome; Atransferrinemia; Atrial fibrillation, familial, 11, 12, 13, and 16; Atrial septal defects 2, 4, and 7 (with or without atrioventricular conduction defects); Atrial standstill 2; Atrioventricular septal defect 4; Atrophia bulborum hereditaria; ATR-X syndrome; Auriculocondylar syndrome 2; Autoimmune disease, multisystem, infantile-onset; Autoimmune lymphoproliferative syndrome, type 1a; Autosomal dominant hypohidrotic ectodermal dysplasia; Autosomal dominant progressive external ophthalmoplegia with mitochondrial DNA deletions 1 and 3; Autosomal dominant torsion dystonia 4; Autosomal recessive centronuclear myopathy; Autosomal recessive congenital ichthyosis 1, 2, 3, 4A, and 4B; Autosomal recessive cutis laxa type IA and 1B; Autosomal recessive hypohidrotic ectodermal dysplasia syndrome; Ectodermal dysplasia 11b; hypohidrotic/hair/tooth type, autosomal recessive; Autosomal recessive hypophosphatemic bone disease; Axenfeld-Rieger syndrome type 3; Bainbridge-Ropers syndrome; Bannayan-Riley-Ruvalcaba syndrome; PTEN hamartoma tumor syndrome; Baraitser-Winter syndromes 1 and 2; Barakat syndrome; Bardet-Biedl syndromes 1, 11, 16, and 19; Bare lymphocyte syndrome type 2, complementation group E; Bartter syndrome antenatal type 2; Bartter syndrome types 3, 3 with hypocalciuria, and 4; Basal ganglia calcification, idiopathic, 4; Beaded hair; Benign familial hematuria; Benign familial neonatal seizures 1 and 2; Seizures, benign familial neonatal, 1, and/or myokymia; Seizures, Early infantile epileptic encephalopathy 7; Benign familial neonatal-infantile seizures; Benign hereditary chorea; Benign scapuloperoneal muscular dystrophy with cardiomyopathy; Bernard-Soulier syndrome, types A1 and A2 (autosomal dominant); Bestrophinopathy, autosomal recessive; beta Thalassemia; Bethlem myopathy and Bethlem myopathy 2; Bietti crystalline corneoretinal dystrophy; Bile acid synthesis defect, congenital, 2; Biotinidase deficiency; Birk Barel mental retardation dysmorphism syndrome; Blepharophimosis, ptosis, and epicanthus inversus; Bloom syndrome; Borjeson-Forssman-Lehmann syndrome; Boucher Neuhauser syndrome; Brachydactyly types A1 and A2; Brachydactyly with hypertension; Brain small vessel disease with hemorrhage; Branched-chain ketoacid dehydrogenase kinase deficiency; Branchiootic syndromes 2 and 3; Breast cancer, early-onset; Breast-ovarian cancer, familial 1, 2, and 4; Brittle cornea syndrome 2; Brody myopathy; Bronchiectasis with or without elevated sweat chloride 3; Brown-Vialetto-Van laere syndrome and Brown-Vialetto-Van Laere syndrome 2; Brugada syndrome; Brugada syndrome 1; Ventricular fibrillation; Paroxysmal familial ventricular fibrillation; Brugada syndrome and Brugada syndrome 4; Long QT syndrome; Sudden cardiac death; Bull eye macular dystrophy; Stargardt disease 4; Cone-rod dystrophy 12; Bullous ichthyosiform erythroderma; Burn-Mckeown syndrome; Candidiasis, familial, 2, 5, 6, and 8; Carbohydrate-deficient glycoprotein syndrome type I and II; Carbonic anhydrase VA deficiency, hyperammonemia due to; Carcinoma of colon; Cardiac arrhythmia; Long QT syndrome, LQT1 subtype; Cardioencephalomyopathy, fatal infantile, due to cytochrome c oxidase deficiency; Cardiofaciocutaneous syndrome; Cardiomyopathy; Danon disease; Hypertrophic cardiomyopathy; Left ventricular noncompaction cardiomyopathy; Carnevale syndrome; Carney complex, type 1; Carnitine acylcarnitine translocase deficiency; Carnitine palmitoyltransferase I, II, II (late onset), and II (infantile) deficiency; Cataract 1, 4, autosomal dominant, autosomal dominant, multiple types, with microcornea, coppock-like, juvenile, with microcornea and glucosuria, and nuclear diffuse nonprogressive; Catecholaminergic polymorphic ventricular tachycardia; Caudal regression syndrome; Cd8 deficiency, familial; Central core disease; Centromeric instability of chromosomes 1,9 and 16 and immunodeficiency; Cerebellar ataxia infantile with progressive external ophthalmoplegi and Cerebellar ataxia, mental retardation, and dysequilibrium syndrome 2; Cerebral amyloid angiopathy, APP-related; Cerebral autosomal dominant and recessive arteriopathy with subcortical infarcts and leukoencephalopathy; Cerebral cavernous malformations 2; Cerebrooculofacioskeletal syndrome 2; Cerebro-oculo-facio-skeletal syndrome; Cerebroretinal microangiopathy with calcifications and cysts; Ceroid lipofuscinosis neuronal 2, 6, 7, and 10; Ch†xc3†xa9diak-Higashi syndrome, Chediak-Higashi syndrome, adult type; Charcot-Marie-Tooth disease types 1B, 2B2, 2C, 2F, 2I, 2U (axonal), 1C (demyelinating), dominant intermediate C, recessive intermediate A, 2A2, 4C, 4D, 4H, IF, IVF, and X; Scapuloperoneal spinal muscular atrophy; Distal spinal muscular atrophy, congenital nonprogressive; Spinal muscular atrophy, distal, autosomal recessive, 5; CHARGE association; Childhood hypophosphatasia; Adult hypophosphatasia; Cholecystitis; Progressive familial intrahepatic cholestasis 3; Cholestasis, intrahepatic, of pregnancy 3; Cholestanol storage disease; Cholesterol monooxygenase (side-chain cleaving) deficiency; Chondrodysplasia Blomstrand type; Chondrodysplasia punctata 1, X-linked recessive and 2 X-linked dominant; CHOPS syndrome; Chronic granulomatous disease, autosomal recessive cytochrome b-positive, types 1 and 2; Chudley-McCullough syndrome; Ciliary dyskinesia, primary, 7, 11, 15, 20 and 22; Citrullinemia type I; Citrullinemia type I and II; Cleidocranial dysostosis; C-like syndrome; Cockayne syndrome type A; Coenzyme Q10 deficiency, primary 1, 4, and 7; Coffin Siris/Intellectual Disability; Coffin-Lowry syndrome; Cohen syndrome; Cold-induced sweating syndrome 1; COLE-CARPENTER SYNDROME 2; Combined cellular and humoral immune defects with granulomas; Combined d-2- and 1-2-hydroxyglutaric aciduria; Combined malonic and methylmalonic aciduria; Combined oxidative phosphorylation deficiencies 1, 3, 4, 12, 15, and 25; Combined partial and complete 17-alpha-hydroxylase/17,20-lyase deficiency; Common variable immunodeficiency 9; Complement component 4, partial deficiency of, due to dysfunctional cl inhibitor; Complement factor B deficiency; Cone monochromatism; Cone-rod dystrophy 2 and 6; Cone-rod dystrophy amelogenesis imperfecta; Congenital adrenal hyperplasia and Congenital adrenal hypoplasia, X-linked; Congenital amegakaryocytic thrombocytopenia; Congenital aniridia; Congenital central hypoventilation; Hirschsprung disease 3; Congenital contractural arachnodactyly; Congenital contractures of the limbs and face, hypotonia, and developmental delay; Congenital disorder of glycosylation types 1B, 1D, 1G, 1H, 1J, 1K, 1N, 1P, 2C, 2J, 2K, IIm; Congenital dyserythropoietic anemia, type I and II; Congenital ectodermal dysplasia of face; Congenital erythropoietic porphyria; Congenital generalized lipodystrophy type 2; Congenital heart disease, multiple types, 2; Congenital heart disease; Interrupted aortic arch; Congenital lipomatous overgrowth, vascular malformations, and epidermal nevi; Non-small cell lung cancer; Neoplasm of ovary; Cardiac conduction defect, nonspecific; Congenital microvillous atrophy; Congenital muscular dystrophy; Congenital muscular dystrophy due to partial LAMA2 deficiency; Congenital muscular dystrophy-dystroglycanopathy with brain and eye anomalies, types A2, A7, A8, A11, and A14; Congenital muscular dystrophy-dystroglycanopathy with mental retardation, types B2, B3, B5, and B15; Congenital muscular dystrophy-dystroglycan-opathy without mental retardation, type B5; Congenital muscular hypertrophy-cerebral syndrome; Congenital myasthenic syndrome, acetazolamide-responsive; Congenital myopathy with fiber type disproportion; Congenital ocular coloboma; Congenital stationary night blindness, type 1A, 1B, 1C, 1E, 1F, and 2A; Coproporphyria; Cornea plana 2; Corneal dystrophy, Fuchs endothelial, 4; Corneal endothelial dystrophy type 2; Corneal fragility keratoglobus, blue sclerae and joint hypermobility; Cornelia de Lange syndromes 1 and 5; Coronary artery disease, autosomal dominant 2; Coronary heart disease; Hyperalphalipoproteinemia 2; Cortical dysplasia, complex, with other brain malformations 5 and 6; Cortical malformations, occipital; Corticosteroid-binding globulin deficiency; Corticosterone methyloxidase type 2 deficiency; Costello syndrome; Cowden syndrome 1; Coxa plana; Craniodiaphyseal dysplasia, autosomal dominant; Craniosynostosis 1 and 4; Craniosynostosis and dental anomalies; Creatine deficiency, X-linked; Crouzon syndrome; Cryptophthalmos syndrome; Cryptorchidism, unilateral or bilateral; Cushing symphalangism; Cutaneous malignant melanoma 1; Cutis laxa with osteodystrophy and with severe pulmonary, gastrointestinal, and urinary abnormalities; Cyanosis, transient neonatal and atypical nephropathic; Cystic fibrosis; Cystinuria; Cytochrome c oxidase i deficiency; Cytochrome-c oxidase deficiency; D-2-hydroxyglutaric aciduria 2; Darier disease, segmental; Deafness with labyrinthine aplasia microtia and microdontia (LAMM); Deafness, autosomal dominant 3a, 4, 12, 13, 15, autosomal dominant nonsyndromic sensorineural 17, 20, and 65; Deafness, autosomal recessive 1A, 2, 3, 6, 8, 9, 12, 15, 16, 18b, 22, 28, 31, 44, 49, 63, 77, 86, and 89; Deafness, cochlear, with myopia and intellectual impairment, without vestibular involvement, autosomal dominant, X-linked 2; Deficiency of 2-methylbutyryl-CoA dehydrogenase; Deficiency of 3-hydroxyacyl-CoA dehydrogenase; Deficiency of alpha-mannosidase; Deficiency of aromatic-L-amino-acid decarboxylase; Deficiency of bisphosphoglycerate mutase; Deficiency of butyryl-CoA dehydrogenase; Deficiency of ferroxidase; Deficiency of galactokinase; Deficiency of guanidinoacetate methyltransferase; Deficiency of hyaluronoglucosaminidase; Deficiency of ribose-5-phosphate isomerase; Deficiency of steroid 11-beta-monooxygenase; Deficiency of UDPglucose-hexose-1-phosphate uridylyltransferase; Deficiency of xanthine oxidase; Dejerine-Sottas disease; Charcot-Marie-Tooth disease, types ID and IVF; Dejerine-Sottas syndrome, autosomal dominant; Dendritic cell, monocyte, B lymphocyte, and natural killer lymphocyte deficiency; Desbuquois dysplasia 2; Desbuquois syndrome; DFNA 2 Nonsyndromic Hearing Loss; Diabetes mellitus and insipidus with optic atrophy and deafness; Diabetes mellitus, type 2, and insulin-dependent, 20; Diamond-Blackfan anemia 1, 5, 8, and 10; Diarrhea 3 (secretory sodium, congenital, syndromic) and 5 (with tufting enteropathy, congenital); Dicarboxylic aminoaciduria; Diffuse palmoplantar keratoderma, Bothnian type; Digitorenocerebral syndrome; Dihydropteridine reductase deficiency; Dilated cardiomyopathy 1A, 1AA, 1C, 1G, 1BB, 1DD, 1FF, 1HH, 1I, 1KK, 1N, 1S, 1Y, and 3B; Left ventricular noncompaction 3; Disordered steroidogenesis due to cytochrome p450 oxidoreductase deficiency; Distal arthrogryposis type 2B; Distal hereditary motor neuronopathy type 2B; Distal myopathy Markesbery-Griggs type; Distal spinal muscular atrophy, X-linked 3; Distichiasis-lymphedema syndrome; Dominant dystrophic epidermolysis bullosa with absence of skin; Dominant hereditary optic atrophy; Donnai Barrow syndrome; Dopamine beta hydroxylase deficiency; Dopamine receptor d2, reduced brain density of; Dowling-degos disease 4; Doyne honeycomb retinal dystrophy; Malattia leventinese; Duane syndrome type 2; Dubin-Johnson syndrome; Duchenne muscular dystrophy; Becker muscular dystrophy; Dysfibrinogenemia; Dyskeratosis congenita autosomal dominant and autosomal dominant, 3; Dyskeratosis congenita, autosomal recessive, 1, 3, 4, and 5; Dyskeratosis congenita X-linked; Dyskinesia, familial, with facial myokymia; Dysplasminogenemia; Dystonia 2 (torsion, autosomal recessive), 3 (torsion, X-linked), 5 (Dopa-responsive type), 10, 12, 16, 25, 26 (Myoclonic); Seizures, benign familial infantile, 2; Early infantile epileptic encephalopathy 2, 4, 7, 9, 10, 11, 13, and 14; Atypical Rett syndrome; Early T cell progenitor acute lymphoblastic leukemia; Ectodermal dysplasia skin fragility syndrome; Ectodermal dysplasia-syndactyly syndrome 1; Ectopia lentis, isolated autosomal recessive and dominant; Ectrodactyly, ectodermal dysplasia, and cleft lip/palate syndrome 3; Ehlers-Danlos syndrome type 7 (autosomal recessive), classic type, type 2 (progeroid), hydroxylysine-deficient, type 4, type 4 variant, and due to tenascin-X deficiency; Eichsfeld type congenital muscular dystrophy; Endocrine-cerebroosteodysplasia; Enhanced s-cone syndrome; Enlarged vestibular aqueduct syndrome; Enterokinase deficiency; Epidermodysplasia verruciformis; Epidermolysa bullosa simplex and limb girdle muscular dystrophy, simplex with mottled pigmentation, simplex with pyloric atresia, simplex, autosomal recessive, and with pyloric atresia; Epidermolytic palmoplantar keratoderma; Familial febrile seizures 8; Epilepsy, childhood absence 2, 12 (idiopathic generalized, susceptibility to) 5 (nocturnal frontal lobe), nocturnal frontal lobe type 1, partial, with variable foci, progressive myoclonic 3, and X-linked, with variable learning disabilities and behavior disorders; Epileptic encephalopathy, childhood-onset, early infantile, 1, 19, 23, 25, 30, and 32; Epiphyseal dysplasia, multiple, with myopia and conductive deafness; Episodic ataxia type 2; Episodic pain syndrome, familial, 3; Epstein syndrome; Fechtner syndrome; Erythropoietic protoporphyria; Estrogen resistance; Exudative vitreoretinopathy 6; Fabry disease and Fabry disease, cardiac variant; Factor H, VII, X, v and factor viii, combined deficiency of 2, xiii, a subunit, deficiency; Familial adenomatous polyposis 1 and 3; Familial amyloid nephropathy with urticaria and deafness; Familial cold urticarial; Familial aplasia of the vermis; Familial benign pemphigus; Familial cancer of breast; Breast cancer, susceptibility to; Osteosarcoma; Pancreatic cancer 3; Familial cardiomyopathy; Familial cold autoinflammatory syndrome 2; Familial colorectal cancer; Familial exudative vitreoretinopathy, X-linked; Familial hemiplegic migraine types 1 and 2; Familial hypercholesterolemia; Familial hypertrophic cardiomyopathy 1, 2, 3, 4, 7, 10, 23 and 24; Familial hypokalemia-hypomagnesemia; Familial hypoplastic, glomerulocystic kidney; Familial infantile myasthenia; Familial juvenile gout; Familial Mediterranean fever and Familial mediterranean fever, autosomal dominant; Familial porencephaly; Familial porphyria cutanea tarda; Familial pulmonary capillary hemangiomatosis; Familial renal glucosuria; Familial renal hypouricemia; Familial restrictive cardiomyopathy 1; Familial type 1 and 3 hyperlipoproteinemia; Fanconi anemia, complementation group E, I, N, and O; Fanconi-Bickel syndrome; Favism, susceptibility to; Febrile seizures, familial, 11; Feingold syndrome 1; Fetal hemoglobin quantitative trait locus 1; FG syndrome and FG syndrome 4; Fibrosis of extraocular muscles, congenital, 1, 2, 3a (with or without extraocular involvement), 3b; Fish-eye disease; Fleck corneal dystrophy; Floating-Harbor syndrome; Focal epilepsy with speech disorder with or without mental retardation; Focal segmental glomerulosclerosis 5; Forebrain defects; Frank Ter Haar syndrome; Borrone Di Rocco Crovato syndrome; Frasier syndrome; Wilms tumor 1; Freeman-Sheldon syndrome; Frontometaphyseal dysplasia land 3; Frontotemporal dementia; Frontotemporal dementia and/or amyotrophic lateral sclerosis 3 and 4; Frontotemporal Dementia Chromosome 3-Linked and Frontotemporal dementia ubiquitin-positive; Fructose-biphosphatase deficiency; Fuhrmann syndrome; Gamma-aminobutyric acid transaminase deficiency; Gamstorp-Wohlfart syndrome; Gaucher disease type 1 and Subacute neuronopathic; Gaze palsy, familial horizontal, with progressive scoliosis; Generalized dominant dystrophic epidermolysis bullosa; Generalized epilepsy with febrile seizures plus 3, type 1, type 2; Epileptic encephalopathy Lennox-Gastaut type; Giant axonal neuropathy; Glanzmann thrombasthenia; Glaucoma 1, open angle, e, F, and G; Glaucoma 3, primary congenital, d; Glaucoma, congenital and Glaucoma, congenital, Coloboma; Glaucoma, primary open angle, juvenile-onset; Glioma susceptibility 1; Glucose transporter type 1 deficiency syndrome; Glucose-6-phosphate transport defect; GLUT1 deficiency syndrome 2; Epilepsy, idiopathic generalized, susceptibility to, 12; Glutamate formiminotransferase deficiency; Glutaric acidemia IIA and IIB; Glutaric aciduria, type 1; Gluthathione synthetase deficiency; Glycogen storage disease 0 (muscle), II (adult form), IXa2, IXc, type 1A; type II, type IV, IV (combined hepatic and myopathic), type V, and type VI; Goldmann-Favre syndrome; Gordon syndrome; Gorlin syndrome; Holoprosencephaly sequence; Holoprosencephaly 7; Granulomatous disease, chronic, X-linked, variant; Granulosa cell tumor of the ovary; Gray platelet syndrome; Griscelli syndrome type 3; Groenouw corneal dystrophy type I; Growth and mental retardation, mandibulofacial dysostosis, microcephaly, and cleft palate; Growth hormone deficiency with pituitary anomalies; Growth hormone insensitivity with immunodeficiency; GTP cyclohydrolase I deficiency; Hajdu-Cheney syndrome; Hand foot uterus syndrome; Hearing impairment; Hemangioma, capillary infantile; Hematologic neoplasm; Hemochromatosis type 1, 2B, and 3; Microvascular complications of diabetes 7; Transferrin serum level quantitative trait locus 2; Hemoglobin H disease, nondeletional; Hemolytic anemia, nonspherocytic, due to glucose phosphate isomerase deficiency; Hemophagocytic lymphohistiocytosis, familial, 2; Hemophagocytic lymphohistiocytosis, familial, 3; Heparin cofactor II deficiency; Hereditary acrodermatitis enteropathica; Hereditary breast and ovarian cancer syndrome; Ataxia-telangiectasia-like disorder; Hereditary diffuse gastric cancer; Hereditary diffuse leukoencephalopathy with spheroids; Hereditary factors II, IX, VIII deficiency disease; Hereditary hemorrhagic telangiectasia type 2; Hereditary insensitivity to pain with anhidrosis; Hereditary lymphedema type I; Hereditary motor and sensory neuropathy with optic atrophy; Hereditary myopathy with early respiratory failure; Hereditary neuralgic amyotrophy; Hereditary Nonpolyposis Colorectal Neoplasms; Lynch syndrome I and II; Hereditary pancreatitis; Pancreatitis, chronic, susceptibility to; Hereditary sensory and autonomic neuropathy type IIB amd IIA; Hereditary sideroblastic anemia; Hermansky-Pudlak syndrome 1, 3, 4, and 6; Heterotaxy, visceral, 2, 4, and 6, autosomal; Heterotaxy, visceral, X-linked; Heterotopia; Histiocytic medullary reticulosis; Histiocytosis-lymphadenopathy plus syndrome; Holocarboxylase synthetase deficiency; Holoprosencephaly 2, 3, 7, and 9; Holt-Oram syndrome; Homocysteinemia due to MTHFR deficiency, CBS deficiency, and Homocystinuria, pyridoxine-responsive; Homocystinuria-Megaloblastic anemia due to defect in cobalamin metabolism, cblE complementation type; Howel-Evans syndrome; Hurler syndrome; Hutchinson-Gilford syndrome; Hydrocephalus; Hyperammonemia, type III; Hypercholesterolaemia and Hypercholesterolemia, autosomal recessive; Hyperekplexia 2 and Hyperekplexia hereditary; Hyperferritinemia cataract syndrome; Hyperglycinuria; Hyperimmunoglobulin D with periodic fever; Mevalonic aciduria; Hyperimmunoglobulin E syndrome; Hyperinsulinemic hypoglycemia familial 3, 4, and 5; Hyperinsulinism-hyperammonemia syndrome; Hyperlysinemia; Hypermanganesemia with dystonia, polycythemia and cirrhosis; Hyperornithinemia-hyperammonemia-homocitrullinuria syndrome; Hyperparathyroidism 1 and 2; Hyperparathyroidism, neonatal severe; Hyperphenylalaninemia, bh4-deficient, a, due to partial pts deficiency, BH4-deficient, D, and non-pku; Hyperphosphatasia with mental retardation syndrome 2, 3, and 4; Hypertrichotic osteochondrodysplasia; Hypobetalipoproteinemia, familial, associated with apob32; Hypocalcemia, autosomal dominant 1; Hypocalciuric hypercalcemia, familial, types 1 and 3; Hypochondrogenesis; Hypochromic microcytic anemia with iron overload; Hypoglycemia with deficiency of glycogen synthetase in the liver; Hypogonadotropic hypogonadism 11 with or without anosmia; Hypohidrotic ectodermal dysplasia with immune deficiency; Hypohidrotic X-linked ectodermal dysplasia; Hypokalemic periodic paralysis 1 and 2; Hypomagnesemia 1, intestinal; Hypomagnesemia, seizures, and mental retardation; Hypomyelinating leukodystrophy 7; Hypoplastic left heart syndrome; Atrioventricular septal defect and common atrioventricular junction; Hypospadias 1 and 2, X-linked; Hypothyroidism, congenital, nongoitrous, 1; Hypotrichosis 8 and 12; Hypotrichosis-lymphedema-telangiectasia syndrome; I blood group system; Ichthyosis bullosa of Siemens; Ichthyosis exfoliativa; Ichthyosis prematurity syndrome; Idiopathic basal ganglia calcification 5; Idiopathic fibrosing alveolitis, chronic form; Dyskeratosis congenita, autosomal dominant, 2 and 5; Idiopathic hypercalcemia of infancy; Immune dysfunction with T-cell inactivation due to calcium entry defect 2; Immunodeficiency 15, 16, 19, 30, 31C, 38, 40, 8, due to defect in cd3-zeta, with hyper IgM type 1 and 2, and X-Linked, with magnesium defect, Epstein-Barr virus infection, and neoplasia; Immunodeficiency-centromeric instability-facial anomalies syndrome 2; Inclusion body myopathy 2 and 3; Nonaka myopathy; Infantile convulsions and paroxysmal choreoathetosis, familial; Infantile cortical hyperostosis; Infantile GM1 gangliosidosis; Infantile hypophosphatasia; Infantile nephronophthisis; Infantile nystagmus, X-linked; Infantile Parkinsonism-dystonia; Infertility associated with multi-tailed spermatozoa and excessive DNA; Insulin resistance; Insulin-resistant diabetes mellitus and acanthosis nigricans; Insulin-dependent diabetes mellitus secretory diarrhea syndrome; Interstitial nephritis, karyomegalic; Intrauterine growth retardation, metaphyseal dysplasia, adrenal hypoplasia congenita, and genital anomalies; Iodotyrosyl coupling defect; IRAK4 deficiency; Iridogoniodysgenesis dominant type and type 1; Iron accumulation in brain; Ischiopatellar dysplasia; Islet cell hyperplasia; Isolated 17,20-lyase deficiency; Isolated lutropin deficiency; Isovaleryl-CoA dehydrogenase deficiency; Jankovic Rivera syndrome; Jervell and Lange-Nielsen syndrome 2; Joubert syndrome 1, 6, 7, 9/15 (digenic), 14, 16, and 17, and Orofaciodigital syndrome xiv; Junctional epidermolysis bullosa gravis of Herlitz; Juvenile GM>1<gangliosidosis; Juvenile polyposis syndrome; Juvenile polyposis/hereditary hemorrhagic telangiectasia syndrome; Juvenile retinoschisis; Kabuki make-up syndrome; Kallmann syndrome 1, 2, and 6; Delayed puberty; Kanzaki disease; Karak syndrome; Kartagener syndrome; Kenny-Caffey syndrome type 2; Keppen-Lubinsky syndrome; Keratoconus 1; Keratosis follicularis; Keratosis palmoplantaris *striata* 1; Kindler syndrome; L-2-hydroxyglutaric aciduria; Larsen syndrome, dominant type; Lattice corneal dystrophy Type III; Leber amaurosis; Zellweger syndrome; Peroxisome biogenesis disorders; Zellweger syndrome spectrum; Leber congenital amaurosis 11, 12, 13, 16, 4, 7, and 9; Leber optic atrophy; Aminoglycoside-induced deafness; Deafness, nonsyndromic sensorineural, mitochondrial; Left ventricular noncompaction 5; Left-right axis malformations; Leigh disease; Mitochondrial short-chain Enoyl-CoA Hydratase 1 deficiency; Leigh syndrome due to mitochondrial complex I deficiency; Leiner disease; Leri Weill dyschondrosteosis; Lethal congenital contracture syndrome 6; Leukocyte adhesion deficiency type I and III; Leukodystrophy, Hypomyelinating, 11 and 6; Leukoencephalopathy with ataxia, with Brainstem and Spinal Cord Involvement and Lactate Elevation, with vanishing white matter, and progressive, with ovarian failure; Leukonychia totalis; Lewy body dementia; Lichtenstein-Knorr Syndrome; Li-Fraumeni syndrome 1; Lig4 syndrome; Limb-girdle muscular dystrophy, type 1B, 2A, 2B, 2D, C1, C5, C9, C14; Congenital muscular dystrophy-dystroglycanopathy with brain and eye anomalies, type A14 and B14; Lipase deficiency combined; Lipid proteinosis; Lipodystrophy, familial partial, type 2 and 3; Lissencephaly 1, 2 (X-linked), 3, 6 (with microcephaly), X-linked; Subcortical laminar heterotopia, X-linked; Liver failure acute infantile; Loeys-Dietz syndrome 1, 2, 3; Long QT syndrome 1, 2, 2/9, 2/5, (digenic), 3, 5 and 5, acquired, susceptibility to; Lung cancer; Lymphedema, hereditary, id; Lymphedema, primary, with myelodysplasia; Lymphoproliferative syndrome 1, 1 (X-linked), and 2; Lysosomal acid lipase deficiency; Macrocephaly, macrosomia, facial dysmorphism syndrome; Macular dystrophy, vitelliform, adult-onset; Malignant hyperthermia susceptibility type 1; Malignant lymphoma, non-Hodgkin; Malignant melanoma; Malignant tumor of prostate; Mandibuloacral dysostosis; Mandibuloacral dysplasia with type A or B lipodystrophy, atypical; Mandibulofacial dysostosis, Treacher Collins type, autosomal recessive; Mannose-binding protein deficiency; Maple syrup urine disease type 1A and type 3; Marden Walker like syndrome; Marfan syndrome; Marinesco-Sj†xc3†xb6gren syndrome; Martsolf syndrome; Maturity-onset diabetes of the young, type 1, type 2, type 11, type 3, and type 9; May-Hegglin anomaly; MYH9 related disorders; Sebastian syndrome; McCune-Albright syndrome; Somatotroph adenoma; Sex cord-stromal tumor; Cushing syndrome; McKusick Kaufman syndrome; McLeod neuroacanthocytosis syndrome; Meckel-Gruber syndrome; Medium-chain acyl-coenzyme A dehydrogenase deficiency; Medulloblastoma; Megalencephalic leukoencephalopathy with subcortical cysts land 2a; Megalencephaly cutis marmorata telangiectatica congenital; PIK3CA Related Overgrowth Spectrum; Megalencephaly-polymicrogyria-polydactyly-hydrocephalus syndrome 2; Megaloblastic anemia, thiamine-responsive, with diabetes mellitus and sensorineural deafness; Meier-Gorlin syndromes land 4; Melnick-Needles syndrome; Meningioma; Mental retardation, X-linked, 3, 21, 30, and 72; Mental retardation and microcephaly with pontine and cerebellar hypoplasia; Mental retardation X-linked syndromic 5; Mental retardation, anterior maxillary protrusion, and strabismus; Mental retardation, autosomal dominant 12, 13, 15, 24, 3, 30, 4, 5, 6, and 9; Mental retardation, autosomal recessive 15, 44, 46, and 5; Mental retardation, stereotypic movements, epilepsy, and/or cerebral malformations; Mental retardation, syndromic, Claes-Jensen type, X-linked; Mental retardation, X-linked, nonspecific, syndromic, Hedera type, and syndromic, wu type; Merosin deficient congenital muscular dystrophy; Metachromatic leukodystrophy juvenile, late infantile, and adult types; Metachromatic leukodystrophy; Metatrophic dysplasia; Methemoglobinemia types I and 2; Methionine adenosyltransferase deficiency, autosomal dominant; Methylmalonic acidemia with homocystinuria; Methylmalonic aciduria cblB type; Methylmalonic aciduria due to methylmalonyl-CoA mutase deficiency; METHYLMALONIC ACIDURIA, mut(0) TYPE; Microcephalic osteodysplastic primordial dwarfism type 2; Microcephaly with or without chorioretinopathy, lymphedema, or mental retardation; Microcephaly, hiatal hernia and nephrotic syndrome; Microcephaly; Hypoplasia of the corpus callosum; Spastic paraplegia 50, autosomal recessive; Global developmental delay; CNS hypomyelination; Brain atrophy; Microcephaly, normal intelligence and immunodeficiency; Microcephaly-capillary malformation syndrome; Microcytic anemia; Microphthalmia syndromic 5, 7, and 9; Microphthalmia, isolated 3, 5, 6, 8, and with coloboma 6; Microspherophakia; Migraine, familial basilar; Miller syndrome; Minicore myopathy with external ophthalmoplegia; Myopathy, congenital with cores; Mitchell-Riley syndrome; mitochondrial 3-hydroxy-3-methylglutaryl-CoA synthase deficiency; Mitochondrial complex I, II, III, III (nuclear type 2, 4, or 8) deficiency; Mitochondrial DNA depletion syndrome 11, 12 (cardiomyopathic type), 2, 4B (MNGIE type), 8B (MNGIE type); Mitochondrial DNA-depletion syndrome 3 and 7, hepatocerebral types, and 13 (encephalomyopathic type); Mitochondrial phosphate carrier and pyruvate carrier deficiency; Mitochondrial trifunctional protein deficiency; Long-chain 3-hydroxyacyl-CoA dehydrogenase deficiency; Miyoshi muscular dystrophy 1; Myopathy, distal, with anterior tibial onset; Mohr-Tranebjaerg syndrome; Molybdenum cofactor deficiency, complementation group A; Mowat-Wilson syndrome; Mucolipidosis III Gamma; Mucopolysaccharidosis type VI, type VI (severe), and type VII; Mucopolysaccharidosis, MPS—I-H/S, MPS-II, MPS-III-A, MPS—III—B, MPS—III—C, MPS-IV-A, MPS—IV-B; Retinitis Pigmentosa 73; Gangliosidosis GM1 type1 (with cardiac involvement) 3; Multicentric osteolysis nephropathy; Multicentric osteolysis, nodulosis and arthropathy; Multiple congenital anomalies; Atrial septal defect 2; Multiple congenital anomalies-hypotonia-seizures syndrome 3; Multiple Cutaneous and Mucosal Venous Malformations; Multiple endocrine neoplasia, types 1and 4; Multiple epiphyseal dysplasia 5 or Dominant; Multiple gastrointestinal atresias; Multiple pterygium syndrome Escobar type; Multiple sulfatase deficiency; Multiple synostoses syndrome 3; Muscle AMP deaminase deficiency; Muscle eye brain disease; Muscular dystrophy, congenital, megaconial type; Myasthenia, familial infantile, 1; Myasthenic Syndrome, Congenital, 11, associated with acetylcholine receptor deficiency; Myasthenic Syndrome, Congenital, 17, 2A (slow-channel), 4B (fast-channel), and without tubular aggregates; Myeloperoxidase deficiency; MYH-associated polyposis; Endometrial carcinoma; Myocardial infarction 1; Myoclonic dystonia; Myoclonic-Atonic Epilepsy; Myoclonus with epilepsy with ragged red fibers; Myofibrillar myopathy 1 and ZASP-related; Myoglobinuria, acute recurrent, autosomal recessive; Myoneural gastrointestinal encephalopathy syndrome; Cerebellar ataxia infantile with progressive external ophthalmoplegia; Mitochondrial DNA depletion syndrome 4B, MNGIE type; Myopathy, centronuclear, 1, congenital, with excess of muscle spindles, distal, 1, lactic acidosis, and sideroblastic anemia 1, mitochondrial progressive with congenital cataract, hearing loss, and developmental delay, and tubular aggregate, 2; Myopia 6; Myosclerosis, autosomal recessive; Myotonia congenital; Congenital myotonia, autosomal dominant and recessive forms; Nail-patella syndrome; Nance-Horan syndrome; Nanophthalmos 2; Navajo neurohepatopathy; Nemaline myopathy 3 and 9; Neonatal hypotonia; Intellectual disability; Seizures; Delayed speech and language development; Mental retardation, autosomal dominant 31; Neonatal intrahepatic cholestasis caused by citrin deficiency; Nephrogenic diabetes insipidus, Nephrogenic diabetes insipidus, X-linked; Nephrolithiasis/osteoporosis, hypophosphatemic, 2; Nephronophthisis 13, 15 and 4; Infertility; Cerebello-oculo-renal syndrome (nephronophthisis, oculomotor apraxia and cerebellar abnormalities); Nephrotic syndrome, type 3, type 5, with or without ocular abnormalities, type 7, and type 9; Nestor-Guillermo progeria syndrome; Neu-Laxova syndrome 1; Neurodegeneration with brain iron accumulation 4 and 6; Neuroferritinopathy; Neurofibromatosis, type 1and type 2; Neurofibrosarcoma; Neurohypophyseal diabetes insipidus; Neuropathy, Hereditary Sensory, Type IC; Neutral 1 amino acid transport defect; Neutral lipid storage disease with myopathy; Neutrophil immunodeficiency syndrome; Nicolaides-Baraitser syndrome; Niemann-Pick disease type C1, C2, type A, and type C1, adult form; Non-ketotic hyperglycinemia; Noonan syndrome 1 and 4, LEOPARD syndrome 1; Noonan syndrome-like disorder with or without juvenile myelomonocytic leukemia; Normokalemic periodic paralysis, potassium-sensitive; Norum disease; Epilepsy, Hearing Loss, And Mental Retardation Syndrome; Mental Retardation, X-Linked 102 and syndromic 13; Obesity; Ocular albinism, type I; Oculocutaneous albinism type 1B, type 3, and type 4; Oculodentodigital dysplasia; Odontohypophosphatasia; Odontotrichomelic syndrome; Oguchi disease; Oligodontia-colorectal cancer syndrome; Opitz G/BBB syndrome; Optic atrophy 9; Oral-facial-digital syndrome; Ornithine aminotransferase deficiency; Orofacial cleft 11 and 7, Cleft lip/palate-ectodermal dysplasia syndrome; Orstavik Lindemann Solberg syndrome; Osteoarthritis with mild chondrodysplasia; Osteochondritis dissecans; Osteogenesis imperfecta type 12, type 5, type 7, type 8, type I, type III, with normal sclerae, dominant form, recessive perinatal lethal; Osteopathia striata with cranial sclerosis; Osteopetrosis autosomal dominant type 1 and 2, recessive 4, recessive 1, recessive 6; Osteoporosis with pseudoglioma; Oto-palato-digital syndrome, types I and II; Ovarian dysgenesis 1; Ovarioleukodystrophy; Pachyonychia congenita 4 and type 2; Paget disease of bone, familial; Pallister-Hall syndrome; Palmoplantar keratoderma, nonepidermolytic, focal or diffuse; Pancreatic agenesis and congenital heart disease; Papillon-LefAxc3xa8vre syndrome; Paragangliomas 3; Paramyotonia congenita of von Eulenburg; Parathyroid carcinoma; Parkinson disease 14, 15, 19 (juvenile-onset), 2, 20 (early-onset), 6, (autosomal recessive early-onset, and 9; Partial albinism; Partial hypoxanthine-guanine phosphoribosyltransferase deficiency; Patterned dystrophy of retinal pigment epithelium; PC-K6a; Pelizaeus-Merzbacher disease; Pendred syndrome; Peripheral demyelinating neuropathy, central dysmyelination; Hirschsprung disease; Permanent neonatal diabetes mellitus; Diabetes mellitus, permanent neonatal, with neurologic features; Neonatal insulin-dependent diabetes mellitus; Maturity-onset diabetes of the young, type 2; Peroxisome biogenesis disorder 14B, 2A, 4A, 5B, 6A, 7A, and 7B; Perrault syndrome 4; Perry syndrome; Persistent hyperinsulinemic hypoglycemia of infancy; familial hyperinsulinism; Phenotypes; Phenylketonuria; Pheochromocytoma; Hereditary Paraganglioma-Pheochromocytoma Syndromes; Paragangliomas 1; Carcinoid tumor of intestine; Cowden syndrome 3; Phosphoglycerate dehydrogenase deficiency; Phosphoglycerate kinase 1 deficiency; Photosensitive trichothiodystrophy; Phytanic acid storage disease; Pick disease; Pierson syndrome; Pigmentary retinal dystrophy; Pigmented nodular adrenocortical disease, primary, 1; Pilomatrixoma; Pitt-Hopkins syndrome; Pituitary dependent hypercortisolism; Pituitary hormone deficiency, combined 1, 2, 3, and 4; Plasminogen activator inhibitor type 1 deficiency; Plasminogen deficiency, type I; Platelet-type bleeding disorder 15 and 8; Poikiloderma, hereditary fibrosing, with tendon contractures, myopathy, and pulmonary fibrosis; Polycystic kidney disease 2, adult type, and infantile type; Polycystic lipomembranous osteodysplasia with sclerosing leukoencephalopathy; Polyglucosan body myopathy 1 with or without immunodeficiency; Polymicrogyria, asymmetric, bilateral frontoparietal; Polyneuropathy, hearing loss, ataxia, retinitis pigmentosa, and cataract; Pontocerebellar hypoplasia type 4; Popliteal pterygium syndrome; Porencephaly 2; Porokeratosis 8, disseminated superficial actinic type; Porphobilinogen synthase deficiency; Porphyria cutanea tarda; Posterior column ataxia with retinitis pigmentosa; Posterior polar cataract type 2; Prader-Willi-like syndrome; Premature ovarian failure 4, 5, 7, and 9; Primary autosomal recessive microcephaly 10, 2, 3, and 5; Primary ciliary dyskinesia 24; Primary dilated cardiomyopathy; Left ventricular noncompaction 6; 4, Left ventricular noncompaction 10; Paroxysmal atrial fibrillation; Primary hyperoxaluria, type I, type, and type III; Primary hypertrophic osteoarthropathy, autosomal recessive 2; Primary hypomagnesemia; Primary open angle glaucoma juvenile onset 1; Primary pulmonary hypertension; Primrose syndrome; Progressive familial heart block type 1B; Progressive familial intrahepatic cholestasis 2 and 3; Progressive intrahepatic cholestasis; Progressive myoclonus epilepsy with ataxia; Progressive pseudorheumatoid dysplasia; Progressive sclerosing poliodystrophy; Prolidase deficiency; Proline dehydrogenase deficiency; Schizophrenia 4; Properdin deficiency, X-linked; Propionic academia; Proprotein convertase ⅓ deficiency; Prostate cancer, hereditary, 2; Protan defect; Proteinuria; Finnish congenital nephrotic syndrome; Proteus syndrome; Breast adenocarcinoma; Pseudoachondroplastic spondyloepiphyseal dysplasia syndrome; Pseudohypoaldosteronism type 1 autosomal dominant and recessive and type 2; Pseudohypoparathyroidism type 1A, Pseudopseudohypoparathyroidism; Pseudoneonatal adrenoleukodystrophy; Pseudoprimary hyperaldosteronism; Pseudoxanthoma elasticum; Generalized arterial calcification of infancy 2; Pseudoxanthoma elasticum-like disorder with multiple coagulation factor deficiency; Psoriasis susceptibility 2; PTEN hamartoma tumor syndrome; Pulmonary arterial hypertension related to hereditary hemorrhagic telangiectasia; Pulmonary Fibrosis And/Or Bone Marrow Failure, Telomere-Related, 1 and 3; Pulmonary hypertension, primary, 1, with hereditary hemorrhagic telangiectasia; Purine-nucleoside phosphorylase deficiency; Pyruvate carboxylase deficiency; Pyruvate dehydrogenase E1-alpha deficiency; Pyruvate kinase deficiency of red cells; Raine syndrome; Rasopathy; Recessive dystrophic epidermolysis bullosa; Nail disorder, nonsyndromic congenital, 8; Reifenstein syndrome; Renal adysplasia; Renal carnitine transport defect; Renal coloboma syndrome; Renal dysplasia; Renal dysplasia, retinal pigmentary dystrophy, cerebellar ataxia and skeletal dysplasia; Renal tubular acidosis, distal, autosomal recessive, with late-onset sensorineural hearing loss, or with hemolytic anemia; Renal tubular acidosis, proximal, with ocular abnormalities and mental retardation; Retinal cone dystrophy 3B; Retinitis pigmentosa; Retinitis pigmentosa 10, 11, 12, 14, 15, 17, and 19; Retinitis pigmentosa 2, 20, 25, 35, 36, 38, 39, 4, 40, 43, 45, 48, 66, 7, 70, 72; Retinoblastoma; Rett disorder; Rhabdoid tumor predisposition syndrome 2; Rhegmatogenous retinal detachment, autosomal dominant; Rhizomelic chondrodysplasia punctata type 2 and type 3; Roberts-SC phocomelia syndrome; Robinow Sorauf syndrome; Robinow syndrome, autosomal recessive, autosomal recessive, with brachy-syn-polydactyly; Rothmund-Thomson syndrome; Rapadilino syndrome; RRM2B-related mitochondrial disease; Rubinstein-Taybi syndrome; Salla disease; Sandhoff disease, adult and infantil types; Sarcoidosis, early-onset; Blau syndrome; Schindler disease, type 1; Schizencephaly; Schizophrenia 15; Schneckenbecken dysplasia; Schwannomatosis 2; Schwartz Jampel syndrome type 1; Sclerocornea, autosomal recessive; Sclerosteosis; Secondary hypothyroidism; Segawa syndrome, autosomal recessive; Senior-Loken syndrome 4 and 5; Sensory ataxic neuropathy, dysarthria, and ophthalmoparesis; Sepiapterin reductase deficiency; SeSAME syndrome; Severe combined immunodeficiency due to ADA deficiency, with microcephaly, growth retardation, and sensitivity to ionizing radiation, atypical, autosomal recessive, T cell-negative, B cell-positive, NK cell-negative of NK-positive; Partial adenosine deaminase deficiency; Severe congenital neutropenia; Severe congenital neutropenia 3, autosomal recessive or dominant; Severe congenital neutropenia and 6, autosomal recessive; Severe myoclonic epilepsy in infancy; Generalized epilepsy with febrile seizures plus, types 1 and 2; Severe X-linked myotubular myopathy; Short QT syndrome 3; Short stature with nonspecific skeletal abnormalities; Short stature, auditory canal atresia, mandibular hypoplasia, skeletal abnormalities; Short stature, onychodysplasia, facial dysmorphism, and hypotrichosis; Primordial dwarfism; Short-rib thoracic dysplasia 11 or 3 with or without polydactyly; Sialidosis type I and II; Silver spastic paraplegia syndrome; Slowed nerve conduction velocity, autosomal dominant; Smith-Lemli-Opitz syndrome; Snyder Robinson syndrome; Somatotroph adenoma; Prolactinoma; familial, Pituitary adenoma predisposition; Sotos syndrome 1 or 2; Spastic ataxia 5, autosomal recessive, Charlevoix-Saguenay type, 1, 10, or 11, autosomal recessive; Amyotrophic lateral sclerosis type 5; Spastic paraplegia 15, 2, 3, 35, 39, 4, autosomal dominant, 55, autosomal recessive, and 5A; Bile acid synthesis defect, congenital, 3; Spermatogenic failure 11, 3, and 8; Spherocytosis types 4 and 5; Spheroid body myopathy; Spinal muscular atrophy, lower extremity predominant 2, autosomal dominant; Spinal muscular atrophy, type II; Spinocerebellar ataxia 14, 21, 35, 40, and 6; Spinocerebellar ataxia autosomal recessive 1 and 16; Splenic hypoplasia; Spondylocarpotarsal synostosis syndrome; Spondylocheirodysplasia, Ehlers-Danlos syndrome-like, with immune dysregulation, Aggrecan type, with congenital joint dislocations, short limb-hand type, Sedaghatian type, with cone-rod dystrophy, and Kozlowski type; Parastremmatic dwarfism; Stargardt disease 1; Cone-rod dystrophy 3; Stickler syndrome type 1; Kniest dysplasia; Stickler syndrome, types 1 (nonsyndromic ocular) and 4; Sting-associated vasculopathy, infantile-onset; Stormorken syndrome; Sturge-Weber syndrome, Capillary malformations, congenital, 1; Succinyl-CoA acetoacetate transferase deficiency; Sucrase-isomaltase deficiency; Sudden infant death syndrome; Sulfite oxidase deficiency, isolated; Supravalvar aortic stenosis; Surfactant metabolism dysfunction, pulmonary, 2 and 3; Symphalangism, proximal, 1b; Syndactyly Cenani Lenz type; Syndactyly type 3; Syndromic X-linked mental retardation 16; Talipes equinovarus; Tangier disease; TARP syndrome; Tay-Sachs disease, B1 variant, Gm2-gangliosidosis (adult), Gm2-gangliosidosis (adult-onset); Temtamy syndrome; Tenorio Syndrome; Terminal osseous dysplasia; Testosterone 17-beta-dehydrogenase deficiency; Tetraamelia, autosomal recessive; Tetralogy of Fallot; Hypoplastic left heart syndrome 2; Truncus arteriosus; Malformation of the heart and great vessels; Ventricular septal defect 1; Thiel-Behnke corneal dystrophy; Thoracic aortic aneurysms and aortic dissections; Marfanoid habitus; Three M syndrome 2; Thrombocytopenia, platelet dysfunction, hemolysis, and imbalanced globin synthesis; Thrombocytopenia, X-linked; Thrombophilia, hereditary, due to protein C deficiency, autosomal dominant and recessive; Thyroid agenesis; Thyroid cancer, follicular; Thyroid hormone metabolism, abnormal; Thyroid hormone resistance, generalized, autosomal dominant; Thyrotoxic periodic paralysis and Thyrotoxic periodic paralysis 2; Thyrotropin-releasing hormone resistance, generalized; Timothy syndrome; TNF receptor-associated periodic fever syndrome (TRAPS); Tooth agenesis, selective, 3 and 4; Torsades de pointes; Townes-Brocks-branchiootorenal-like syndrome; Transient bullous dermolysis of the newborn; Treacher collins syndrome 1; Trichomegaly with mental retardation, dwarfism and pigmentary degeneration of retina; Trichorhinophalangeal dysplasia type I; Trichorhinophalangeal syndrome type 3; Trimethylaminuria; Tuberous sclerosis syndrome; Lymphangiomyomatosis; Tuberous sclerosis 1 and 2; Tyrosinase-negative oculocutaneous albinism; Tyrosinase-positive oculocutaneous albinism; Tyrosinemia type I; UDPglucose-4-epimerase deficiency; Ullrich congenital muscular dystrophy; Ulna and fibula absence of with severe limb deficiency; Upshaw-Schulman syndrome; Urocanate hydratase deficiency; Usher syndrome, types 1, 1B, 1D, 1G, 2A, 2C, and 2D; Retinitis pigmentosa 39; UV-sensitive syndrome; Van der Woude syndrome; Van Maldergem syndrome 2; Hennekam lymphangiectasia-lymphedema syndrome 2; Variegate porphyria; Ventriculomegaly with cystic kidney disease; Verheij syndrome; Very long chain acyl-CoA dehydrogenase deficiency; Vesicoureteral reflux 8; Visceral heterotaxy 5, autosomal; Visceral myopathy; Vitamin D-dependent rickets, types land 2; Vitelliform dystrophy; von Willebrand disease type 2M and type 3; Waardenburg syndrome type 1, 4C, and 2E (with neurologic involvement); Klein-Waardenberg syndrome; Walker-Warburg congenital muscular dystrophy; Warburg micro syndrome 2 and 4; Warts, hypogammaglobulinemia, infections, and myelokathexis; Weaver syndrome; Weill-Marchesani syndrome 1 and 3; Weill-Marchesani-like syndrome; Weissenbacher-Zweymuller syndrome; Werdnig-Hoffmann disease; Charcot-Marie-Tooth disease; Werner syndrome; WFS1-Related Disorders; Wiedemann-Steiner syndrome; Wilson disease; Wolfram-like syndrome, autosomal dominant; Worth disease; Van Buchem disease type 2; Xeroderma pigmentosum, complementation group b, group D, group E, and group G; X-linked agammaglobulinemia; X-linked hereditary motor and sensory neuropathy; X-linked ichthyosis with steryl-sulfatase deficiency; X-linked periventricular heterotopia; Oto-palato-digital syndrome, type I; X-linked severe combined immunodeficiency; Zimmermann-Laband syndrome and Zimmermann-Laband syndrome 2; and Zonular pulverulent cataract 3.

The instant disclosure provides lists of genes comprising pathogenic G to A or C to T mutations. Such pathogenic G to A or C to T mutations may be corrected using the methods and compositions provided herein, for example by mutating the A to a G, and/or the T to a C, thereby restoring gene function. Table 2 includes exemplary mutations that can be corrected using nucleobase editors provided herein. Table 2 includes the gene symbol, the associated phenotype, the mutation to be corrected and exemplary gRNA sequences which may be used to correct the mutations. The gRNA sequences provided in Table 2 are sequences that encode RNA that can direct Cas9, or any of the base editors provided herin, to a target site. For example, the gRNA sequences provided in Table 2 may be cloned into a gRNA expression vector, such as pFYF to encode a gRNA that targets Cas9, or any of the base editors provided herein, to a target site in order to correct a disease-related mutation. It should be appreciated, however, that additional mutations may be corrected to treat additional diseases associated with a G to A or C to T mutation. Furthermore, additional gRNAs may be designed based on the disclosure and the knowledge in the art, which would be appreciated by the skilled artisan.

Lengthy table referenced here

US11702651-20230718-T00001

Please refer to the end of the specification for access instructions.

In some embodiments, a fusion protein recognizes canonical PAMs and therefore can correct the pathogenic G to A or C to T mutations with canonical PAMs, e.g., NGG, respectively, in the flanking sequences. For example, Cas9 proteins that recognize canonical PAMs comprise an amino acid sequence that is at least 80%, 85%, 90%, 95%, 97%, 98%, or 99% identical to the amino acid sequence of *Streptococcus pyogenes* Cas9 as provided by SEQ ID NO: 52, or to a fragment thereof comprising the RuvC and HNH domains of SEQ ID NO: 52.

It will be apparent to those of skill in the art that in order to target any of the fusion proteins comprising a Cas9 domain and an adenosine deaminase, as disclosed herein, to a target site, e.g., a site comprising a point mutation to be edited, it is typically necessary to co-express the fusion protein together with a guide RNA, e.g., an sgRNA. As explained in more detail elsewhere herein, a guide RNA typically comprises a tracrRNA framework allowing for Cas9 binding, and a guide sequence, which confers sequence specificity to the Cas9:nucleic acid editing enzyme/domain fusion protein. In some embodiments, the guide RNA comprises a structure 5'-[guide sequence]-guuuuagagcuagaaauagcaaguuaaaauaaaggcuaguccguuaucaacuugaaaaaguggcaccgagucggugcuu uuu-3' (SEQ ID NO: 389), wherein the guide sequence comprises a sequence that is complementary to the target sequence. In some embodiments, the guide sequence comprises any of the nucleotide sequences provided in Table 2 The guide sequence is typically 20 nucleotides long. The sequences of suitable guide RNAs for targeting Cas9:nucleic acid editing enzyme/domain fusion proteins to specific genomic target sites will be apparent to those of skill in the art based on the instant disclosure. Such suitable guide RNA sequences typically comprise guide sequences that are complementary to a nucleic sequence within 50 nucleotides upstream or downstream of the target nucleotide to be edited. Some exemplary guide RNA sequences suitable for targeting any of the provided fusion proteins to specific target sequences are provided herein. Additional guide sequences are shown below in Table 3, including their locus.

TABLE 3

Additional target sites.

| locus | 5 to 3' |
|---|---|
| other sites within HEK2 locus | GAACACAAAGCATAGACTGCG (SEQ ID NO: 390) |
| other sites within HEK2 locus | GGAACACAAAGCATAGACTG (SEQ ID NO: 391) |
| other sites within HEK2 locus | AACACAAAGCATAGACTGCG (SEQ ID NO: 392) |
| other sites within HEK2 locus | ACAAAGCATAGACTGCGGGG (SEQ ID NO: 393) |
| other sites within HEK2 locus | CAAAGCATAGACTGCGGGGC (SEQ ID NO: 394) |
| other sites within HEK2 locus | GTGGTAATTTTCCAGCCCGC (SEQ ID NO: 395) |
| other sites within HEK2 locus | CCTTTACAGGGCCAGCGGGC (SEQ ID NO: 396) |
| other sites within HEK2 locus | CTGTCACAGTTAGCTCAGCC (SEQ ID NO: 397) |
| other sites within HEK2 locus | GTGTTCCAGTTTCCTTTACA (SEQ ID NO: 398) |
| Hek-2 guideSEQ off-target | GAACACAATGCATAGATTGC (SEQ ID NO: 399) |
| Hek-2 similar site | GAAAAAAAGCAGAGACTGC (SEQ ID NO: 400) |
| Hek-2 similar site | GAATACTAAGCATAGACTCC (SEQ ID NO: 401) |
| Hek-2 similar site | GTAAACAAAGCATAGACTGA (SEQ ID NO: 402) |
| Hek-2 similar site | GGACACAAAGCTTAGACTCC (SEQ ID NO: 403) |
| Hek-2 similar site | CAATACAAAGGATAGACTGC (SEQ ID NO: 404) |
| Hek-2 similar site | GAAGACCAAGGATAGACTGC (SEQ ID NO: 405) |
| Hek-2 similar site | GAAAACAAATCATTGACTGC (SEQ ID NO: 406) |
| Hek-2 similar site | GATCACAAAGCATGGACTGA (SEQ ID NO: 407) |
| Hek-2 similar site | GAAAACAAAACATAGAGTGC (SEQ ID NO: 408) |
| Hek-2 similar site | GAACATAAAGAATAGAATGA (SEQ ID NO: 409) |
| EMX1 | GAGTCCGAGCAGAAGAAGAA (SEQ ID NO: 410) |
| FANCF: | GGAATCCCTTCTGCAGCACC (SEQ ID NO: 411) |
| HEK293 site 2: | GAACACAAAGCATAGACTGC (SEQ ID NO: 412) |
| HEK293 site 3: | GGCCCAGACTGAGCACGTGA (SEQ ID NO: 413) |
| HEK293 site 4: | GGCACTGCGGCTGGAGGTCC (SEQ ID NO: 414) |
| RNF2: | GTCATCTTAGTCATTACCTG (SEQ ID NO: 415) |

Base Editor Efficiency

Some aspects of the disclosure are based on the recognition that any of the base editors provided herein are capable of modifying a specific nucleotide base without generating a significant proportion of indels. An "indel", as used herein, refers to the insertion or deletion of a nucleotide base within a nucleic acid. Such insertions or deletions can lead to frame shift mutations within a coding region of a gene. In some embodiments, it is desirable to generate base editors that efficiently modify (e.g. mutate or deaminate) a specific nucleotide within a nucleic acid, without generating a large number of insertions or deletions (i.e., indels) in the nucleic acid. In certain embodiments, any of the base editors provided herein are capable of generating a greater proportion of intended modifications (e.g., point mutations or deaminations) versus indels. In some embodiments, the base editors provided herein are capable of generating a ratio of intended point mutations to indels that is greater than 1:1. In some embodiments, the base editors provided herein are capable of generating a ratio of intended point mutations to indels that is at least 1.5:1, at least 2:1, at least 2.5:1, at least 3:1, at least 3.5:1, at least 4:1, at least 4.5:1, at least 5:1, at least 5.5:1, at least 6:1, at least 6.5:1, at least 7:1, at least 7.5:1, at least 8:1, at least 10:1, at least 12:1, at least 15:1, at least 20:1, at least 25:1, at least 30:1, at least 40:1, at least 50:1, at least 100:1, at least 200:1, at least 300:1, at least 400:1, at least 500:1, at least 600:1, at least 700:1, at least 800:1, at least 900:1, or at least 1000:1, or more. The number of intended mutations and indels may be determined using any suitable method, for example the methods used in the below Examples. in some embodiments, to calculate indel frequencies, sequencing reads are scanned for exact matches to two 10-bp sequences that flank both sides of a window in which indels might occur. If no exact matches are located, the read is excluded from analysis. If the length of this indel window exactly matches the reference sequence the read is classified as not containing an indel. If the indel window is two or more bases longer or shorter than the reference sequence, then the sequencing read is classified as an insertion or deletion, respectively.

In some embodiments, the base editors provided herein are capable of limiting formation of indels in a region of a nucleic acid. In some embodiments, the region is at a nucleotide targeted by a base editor or a region within 2, 3, 4, 5, 6, 7, 8, 9, or 10 nucleotides of a nucleotide targeted by a base editor. In some embodiments, any of the base editors provided herein are capable of limiting the formation of indels at a region of a nucleic acid to less than 1%, less than 1.5%, less than 2%, less than 2.5%, less than 3%, less than 3.5%, less than 4%, less than 4.5%, less than 5%, less than 6%, less than 7%, less than 8%, less than 9%, less than 10%, less than 12%, less than 15%, or less than 20%. The number of indels formed at a nucleic acid region may depend on the amount of time a nucleic acid (e.g., a nucleic acid within the genome of a cell) is exposed to a base editor. In some embodiments, an number or proportion of indels is determined after at least 1 hour, at least 2 hours, at least 6 hours, at least 12 hours, at least 24 hours, at least 36 hours, at least 48 hours, at least 3 days, at least 4 days, at least 5 days, at least 7 days, at least 10 days, or at least 14 days of exposing a nucleic acid (e.g., a nucleic acid within the genome of a cell) to a base editor.

Some aspects of the disclosure are based on the recognition that any of the base editors provided herein are capable of efficiently generating an intended mutation, such as a point mutation, in a nucleic acid (e.g. a nucleic acid within a genome of a subject) without generating a significant number of unintended mutations, such as unintended point mutations. In some embodiments, a intended mutation is a mutation that is generated by a specific base editor bound to a gRNA, specifically designed to generate the intended mutation. In some embodiments, the intended mutation is a mutation associated with a disease or disorder. In some embodiments, the intended mutation is a adenine (A) to guanine (G) point mutation associated with a disease or disorder. In some embodiments, the intended mutation is a thymine (T) to cytosine (C) point mutation associated with a disease or disorder. In some embodiments, the intended mutation is a adenine (A) to guanine (G) point mutation within the coding region of a gene. In some embodiments, the intended mutation is a thymine (T) to cytosine (C) point mutation within the coding region of a gene. In some embodiments, the intended mutation is a point mutation that generates a stop codon, for example, a premature stop codon within the coding region of a gene. In some embodiments, the intended mutation is a mutation that eliminates a stop codon. In some embodiments, the intended mutation is a mutation that alters the splicing of a gene. In some embodiments, the intended mutation is a mutation that alters the regulatory sequence of a gene (e.g., a gene promotor or gene repressor). In some embodiments, any of the base editors provided herein are capable of generating a ratio of intended mutations to unintended mutations (e.g., intended point mutations:unintended point mutations) that is greater than 1:1. In some embodiments, any of the base editors provided herein are capable of generating a ratio of intended mutations to unintended mutations (e.g., intended point mutations:unintended point mutations) that is at least 1.5:1, at least 2:1, at least 2.5:1, at least 3:1, at least 3.5:1, at least 4:1, at least 4.5:1, at least 5:1, at least 5.5:1, at least 6:1, at least 6.5:1, at least 7:1, at least 7.5:1, at least 8:1, at least 10:1, at least 12:1, at least 15:1, at least 20:1, at least 25:1, at least 30:1, at least 40:1, at least 50:1, at least 100:1, at least 150:1, at least 200:1, at least 250:1, at least 500:1, or at least 1000:1, or more. It should be appreciated that the characteristics of the base editors described in the "Base Editor Efficiency" section, herein, may be applied to any of the fusion proteins, or methods of using the fusion proteins provided herein.

Methods for Editing Nucleic Acids

Some aspects of the disclosure provide methods for editing a nucleic acid. In some embodiments, the method is a method for editing a nucleobase of a nucleic acid (e.g., a base pair of a double-stranded DNA sequence). In some embodiments, the method comprises the steps of: a) contacting a target region of a nucleic acid (e.g., a double-stranded DNA sequence) with a complex comprising a base editor (e.g., a Cas9 domain fused to an adenosine deaminase) and a guide nucleic acid (e.g., gRNA), wherein the target region comprises a targeted nucleobase pair, b) inducing strand separation of said target region, c) converting a first nucleobase of said target nucleobase pair in a single strand of the target region to a second nucleobase, and d) cutting no more than one strand of said target region, where a third nucleobase complementary to the first nucleobase base is replaced by a fourth nucleobase complementary to the second nucleobase. In some embodiments, the method results in less than 20% indel formation in the nucleic acid. It should be appreciated that in some embodiments, step b is omitted. In some embodiments, the first nucleobase is an adenine. In some embodiments, the second nucleobase is a deaminated adenine, or inosine. In some embodiments, the third nucleobase is a thymine. In some embodiments, the fourth nucleobase is a cytosine. In some embodiments, the method results in less than 19%, 18%, 16%, 14%, 12%, 10%, 8%, 6%, 4%, 2%, 1%, 0.5%, 0.2%, or less than 0.1% indel formation. In some embodiments, the method further comprises replacing the second nucleobase with a fifth nucleobase that is complementary to the fourth nucleobase, thereby generating an intended edited base pair (e.g., A:T to G:C). In some embodiments, the fifth nucleobase is a guanine. In some embodiments, at least 5% of the intended base pairs are edited. In some embodiments, at least 10%, 15%, 20%, 25%, 30%, 35%, 40%, 45%, or 50% of the intended base pairs are edited.

In some embodiments, the ratio of intended products to unintended products in the target nucleotide is at least 2:1, 5:1, 10:1, 20:1, 30:1, 40:1, 50:1, 60:1, 70:1, 80:1, 90:1, 100:1, or 200:1, or more. In some embodiments, the ratio of intended point mutation to indel formation is greater than 1:1, 10:1, 50:1, 100:1, 500:1, or 1000:1, or more. In some embodiments, the cut single strand (nicked strand) is hybridized to the guide nucleic acid. In some embodiments, the cut single strand is opposite to the strand comprising the first nucleobase. In some embodiments, the base editor comprises a Cas9 domain. In some embodiments, the first base is adenine, and the second base is not a G, C, A, or T. In some embodiments, the second base is inosine. In some embodiments, the first base is adenine. In some embodiments, the second base is not a G, C, A, or T. In some embodiments, the second base is inosine. In some embodiments, the base editor inhibits base excision repair of the edited strand. In some embodiments, the base editor protects or binds the non-edited strand. In some embodiments, the base editor comprises UGI activity. In some embodiments, the base editor comprises a catalytically inactive inosine-specific nuclease. In some embodiments, the base editor comprises nickase activity. In some embodiments, the intended edited base pair is upstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides upstream of the PAM site. In some embodiments, the intended edited basepairs is downstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides downstream stream of the PAM site. In some embodiments, the method does not require a canonical (e.g., NGG) PAM site. In some embodiments, the nucleobase editor comprises a linker. In some embodiments, the linker is 1-25 amino acids in length. In some embodiments, the linker is 5-20 amino acids in length. In some embodiments, linker is 10, 11, 12, 13, 14, 15, 16, 17, 18, 19, or 20 amino acids in length. In some embodiments, the target region comprises a target window, wherein the target window comprises the target nucleobase pair. In some embodiments, the target window comprises 1-10 nucleotides. In some embodiments, the target window is 1-9, 1-8, 1-7, 1-6, 1-5, 1-4, 1-3, 1-2, or 1 nucleotides in length. In some embodiments, the target window is 1, 2, 3, 4, 5, 6, 7, 8, 9, 10, 11, 12, 13, 14, 15, 16, 17, 18, 19, or 20 nucleotides in length. In some embodiments, the intended edited base pair is within the target window. In some embodiments, the target window comprises the intended edited base pair. In some embodiments, the method is performed using any of the base editors provided herein. In some embodiments, a target window is a deamination window.

In some embodiments, the disclosure provides methods for editing a nucleotide. In some embodiments, the disclosure provides a method for editing a nucleobase pair of a double-stranded DNA sequence. In some embodiments, the method comprises a) contacting a target region of the double-stranded DNA sequence with a complex comprising a base editor and a guide nucleic acid (e.g., gRNA), where the target region comprises a target nucleobase pair, b) inducing strand separation of said target region, c) converting a first nucleobase of said target nucleobase pair in a single strand of the target region to a second nucleobase, d) cutting no more than one strand of said target region, wherein a third nucleobase complementary to the first nucleobase base is replaced by a fourth nucleobase complementary to the second nucleobase, and the second nucleobase is replaced with a fifth nucleobase that is complementary to the fourth nucleobase, thereby generating an intended edited base pair, wherein the efficiency of generating the intended edited base pair is at least 5%. It should be appreciated that in some embodiments, step b is omitted. In some embodiments, at least 5% of the intended base pairs are edited. In some embodiments, at least 10%, 15%, 20%, 25%, 30%, 35%, 40%, 45%, or 50% of the intended base pairs are edited. In some embodiments, the method causes less than 19%, 18%, 16%, 14%, 12%, 10%, 8%, 6%, 4%, 2%, 1%, 0.5%, 0.2%, or less than 0.1% indel formation. In some embodiments, the ratio of intended product to unintended products at the target nucleotide is at least 2:1, 5:1, 10:1, 20:1, 30:1, 40:1, 50:1, 60:1, 70:1, 80:1, 90:1, 100:1, or 200:1, or more. In some embodiments, the ratio of intended point mutation to indel formation is greater than 1:1, 10:1, 50:1, 100:1, 500:1, or 1000:1, or more. In some embodiments, the cut single strand is hybridized to the guide nucleic acid. In some embodiments, the cut single strand is opposite to the strand comprising the first nucleobase. In some embodiments, the first base is adenine. In some embodiments, the second nucleobase is not G, C, A, or T. In some embodiments, the second base is inosine. In some embodiments, the base editor inhibits base excision repair of the edited strand. In some embodiments, the base editor protects (e.g., form base excision repair) or binds the non-edited strand. In some embodiments, the nucleobase editor comprises UGI activity. In some embodiments, the base editor comprises a catalytically inactive inosine-specific nuclease. In some embodiments, the nucleobase editor comprises nickase activity. In some embodiments, the intended edited base pair is upstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides upstream of the PAM site. In some embodiments, the intended edited basepairs is downstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides downstream stream of the PAM site. In some embodiments, the method does not require a canonical (e.g., NGG) PAM site. In some embodiments, the nucleobase editor comprises a linker. In some embodiments, the linker is 1-25 amino acids in length. In some embodiments, the linker is 5-20 amino acids in length. In some embodiments, the linker is 10, 11, 12, 13, 14, 15, 16, 17, 18, 19, or 20 amino acids in length. In some embodiments, the target region comprises a target window, wherein the target window comprises the target nucleobase pair. In some embodiments, the target window comprises 1-10 nucleotides. In some embodiments, the target window is 1-9, 1-8, 1-7, 1-6, 1-5, 1-4, 1-3, 1-2, or 1 nucleotides in length. In some embodiments, the target window is 1, 2, 3, 4, 5, 6, 7, 8, 9, 10, 11, 12, 13, 14, 15, 16, 17, 18, 19, or 20 nucleotides in length. In some embodiments, the intended edited base pair occurs within the target window. In some embodiments, the target window comprises the intended edited base pair. In some embodiments, the nucleobase editor is any one of the base editors provided herein.

Pharmaceutical Compositions

Other aspects of the present disclosure relate to pharmaceutical compositions comprising any of the adenosine deaminases, fusion proteins, or the fusion protein-gRNA complexes described herein. The term "pharmaceutical composition", as used herein, refers to a composition formulated for pharmaceutical use. In some embodiments, the pharmaceutical composition further comprises a pharmaceutically acceptable carrier. In some embodiments, the pharmaceutical composition comprises additional agents (e.g. for specific delivery, increasing half-life, or other therapeutic compounds).

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the compound from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, the pharmaceutical composition is formulated for delivery to a subject, e.g., for gene editing. Suitable routes of administrating the pharmaceutical composition described herein include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration.

In some embodiments, the pharmaceutical composition described herein is administered locally to a diseased site (e.g., tumor site). In some embodiments, the pharmaceutical composition described herein is administered to a subject by injection, by means of a catheter, by means of a suppository, or by means of an implant, the implant being of a porous, non-porous, or gelatinous material, including a membrane, such as a sialastic membrane, or a fiber.

In other embodiments, the pharmaceutical composition described herein is delivered in a controlled release system. In one embodiment, a pump may be used (see, e.g., Langer, 1990, *Science* 249:1527-1533; Sefton, 1989, CRC Crit. Ref. Biomed. Eng. 14:201; Buchwald et al., 1980, *Surgery* 88:507; Saudek et al., 1989, *N. Engl. J. Med.* 321:574). In another embodiment, polymeric materials can be used. (See, e.g., *Medical Applications of Controlled Release* (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, *Macromol. Sci. Rev. Macromol. Chem.* 23:61. See also Levy et al., 1985, Science 228:190; During et al., 1989, *Ann. Neurol.* 25:351; Howard et al., 1989, *J. Neurosurg.* 71:105.) Other controlled release systems are discussed, for example, in Langer, supra.

In some embodiments, the pharmaceutical composition is formulated in accordance with routine procedures as a composition adapted for intravenous or subcutaneous administration to a subject, e.g., a human. In some embodiments, pharmaceutical composition for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical composition is administered by injection, an ampoule of sterile water for injection or saline can be provided so that the ingredients can be mixed prior to administration.

A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated.

The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein. Compounds can be entrapped in "stabilized plasmid-lipid particles" (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., *Gene Ther.* 1999, 6:1438-47). Positively charged lipids such as N-[1-(2,3-dioleoyloxi)propyl]-N,N,N-trimethyl-amoniummethyl-sulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757; each of which is incorporated herein by reference.

The pharmaceutical composition described herein may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

Further, the pharmaceutical composition can be provided as a pharmaceutical kit comprising (a) a container containing a compound of the invention in lyophilized form and (b) a second container containing a pharmaceutically acceptable diluent (e.g., sterile water) for injection. The pharmaceutically acceptable diluent can be used for reconstitution or dilution of the lyophilized compound of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In another aspect, an article of manufacture containing materials useful for the treatment of the diseases described above is included. In some embodiments, the article of manufacture comprises a container and a label. Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is a compound of the invention. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

Kits, Vectors, Cells

Some aspects of this disclosure provide kits comprising a nucleic acid construct comprising a nucleotide sequence encoding an adenosine deaminase capable of deaminating an adenosine in a deoxyribonucleic acid (DNA) molecule. In some embodiments, the nucleotide sequence encodes any of the adenosine deaminases provided herein. In some embodiments, the nucleotide sequence comprises a heterologous promoter that drives expression of the adenosine deaminase.

Some aspects of this disclosure provide kits comprising a nucleic acid construct, comprising (a) a nucleotide sequence encoding a napDNAbp (e.g., a Cas9 domain) fused to an adenosine deaminase, or a fusion protein comprising a napDNAbp (e.g., Cas9 domain) and an adenosine deaminase as provided herein; and (b) a heterologous promoter that drives expression of the sequence of (a). In some embodiments, the kit further comprises an expression construct encoding a guide nucleic acid backbone, (e.g., a guide RNA backbone), wherein the construct comprises a cloning site positioned to allow the cloning of a nucleic acid sequence identical or complementary to a target sequence into the guide nucleic acid (e.g., guide RNA backbone).

Some aspects of this disclosure provide cells comprising any of the adenosine deaminases, fusion proteins, or complexes provided herein. In some embodiments, the cells comprise a nucleotide that encodes any of the adenosine deaminases or fusion proteins provided herein. In some embodiments, the cells comprise any of the nucleotides or vectors provided herein.

The description of exemplary embodiments of the reporter systems above is provided for illustration purposes only and not meant to be limiting. Additional reporter systems, e.g., variations of the exemplary systems described in detail above, are also embraced by this disclosure.

It should be appreciated however, that additional fusion proteins would be apparent to the skilled artisan based on the present disclosure and knowledge in the art.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Data provided in the below examples describe engineering of base editors that are capable of catalyzing hydrolytic deamination of adenosine (forming inosine, which base pairs like guanine (G)) in the context of DNA. There are no known naturally occurring adenosine deaminases that act on DNA. Instead, known adenosine deaminases act on RNA (e.g., tRNA or mRNA). The first deoxyadenosine deaminases were evolved to accept DNA substrates and deaminate deoxyadenosine (dA) to deoxyinosine. As one example, evolution experiments were performed using the adenosine deaminase acting on tRNA (ADAT) from *Escherichia coli* (TadA, for tRNA adenosine deaminase A), to engineer adenosine deaminases that act on DNA. Briefly, ecTadA was covalently fused to a dCas9 domain, and libraries of this fusion were assembled containing mutations in the deaminase portion of the construct. In the evolution experiments described below, several mutations in ecTadA were found to improve the ability of ecTadA to deaminate adenosine in DNA.

Example 1—Evolution of Adenosine Base Editors (Evolution #1)

Evolution of adenosine base editors (ABEs) was achieved by creating librars of an ecTadA-XTEN-dead Cas9 construct (pNMG-104) via error-prone PCR, which was mutagenized in the ecTadA portion of the editor only. Selection of editors capable of catalyzing A to I deamination on DNA (A to G reversion) was selected for using an antibiotic selection platform. For the first round of evolution (Evolution #1), an adenosine base editor (ABE) library was co-expressed with a gRNA that targeted an active site mutation in a chloramphenicol acetyl-transferase gene, which requires an A to G reversion to restore acetyl-transferase activity and subsequent survival on chloramphenicol selection media. The selection plasmid is co-transformed into the S1030 host strain along with the ABE library. Evolution #1 was conducted and mutations D108N and A106V were identified as two mutations which enable A to G reversions on DNA. The D108N mutation more efficiently induced A to G reversions in DNA than A106V. Sequence alignment studies with *S. aureus* TadA revealed that residue D108 participates in H-bond contacts with the 2' OH of the ribose sugar in the wild-type, tRNA substrate. In DNA, this 3' OH is replaced with a 3' H.

Wild-Type Adenosine Deaminases and a to G Deaminases

Figure 1:
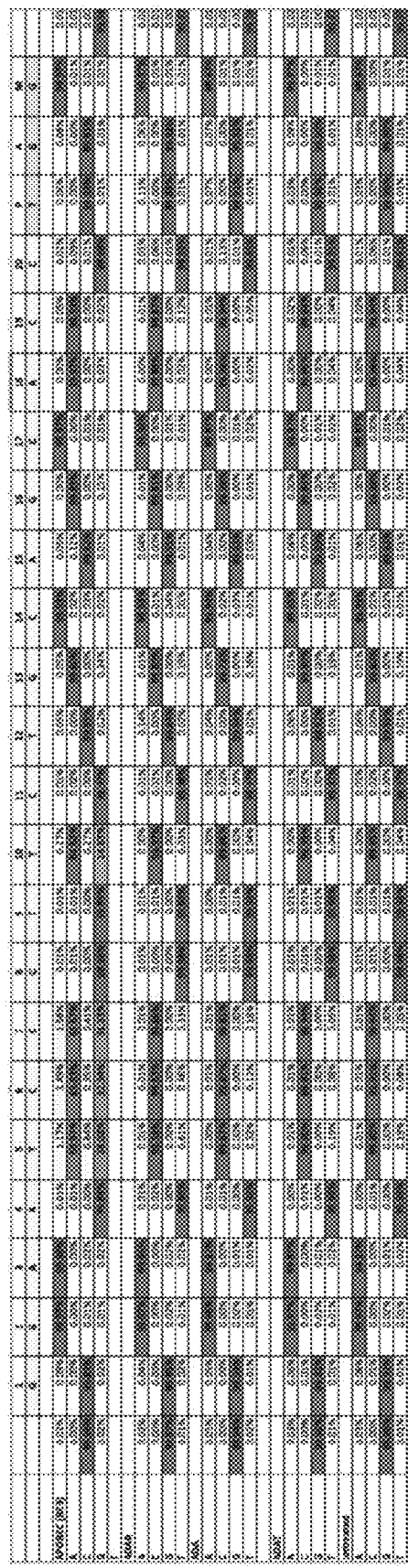
FIG. 1 shows high throughput screen results with various deaminases. APOBEC (BE3) is the positive control; ADAR acts on mRNA, ADA acts on deoxyadenosine, and ADAT acts on tRNA. The untreated group is the negative control. The sequence corresponds to SEQ ID: 45.

Transfection of various A to G deaminase fusions (+XTEN-nCas9) into Hek293T cells did not cause A to G SNP at the targeted sites. Six different sites were targeted, but none of the wild-type adenosine deaminase Cas9 fusions produced observable A to G modifications in DNA. BE3 (rAPOBEC1-XTEN-nCas9-UGI-NLS) was used as positive control. The following wild-type deaminase-nCas9 fusions were tested: ADAR (acts on mRNA), ADA (acts on deoxyadenosine), and ADAT (acts on tRNA) (FIG. 1).

Figure 2:
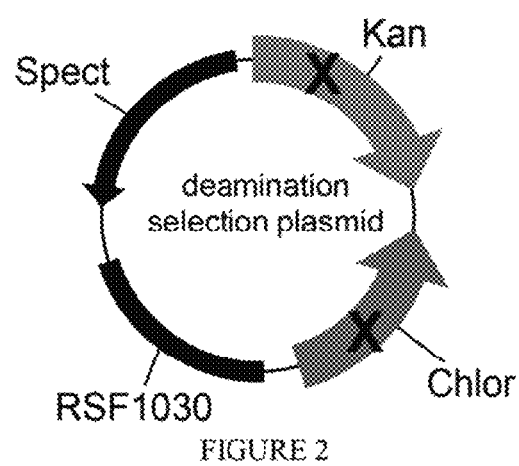
FIG. 2 is a schematic of a deamination selection plasmid.

A to G deaminases which act on DNA were developed. First, an antibiotic selection plasmid was developed, in which restoration of the active site residue in the antibiotic-resistant gene (A to G reversion) resulted in the host's resistance to antibiotic challenges. A high copy plasmid (RSF1030), was constructed. It required either a STOP reversion to a wild-type amino acid (Kan) or an active site residue restoration (Chlor). Specifically, on the template strand, the STOP needed to revert to glutamic acid (Kan) or tyrosine needed to revert to histidine (a cationic residue) (Chlor) (FIG. 2).

Figure 3:
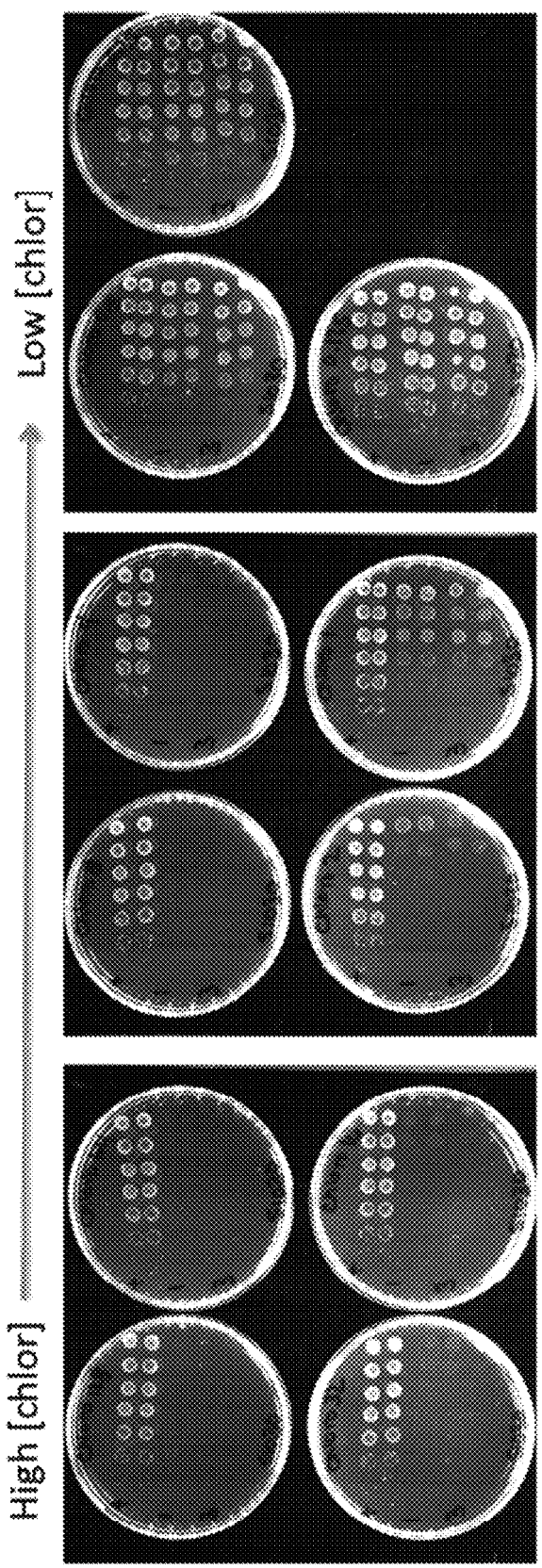
FIG. 3 shows a serial dilution of the selection plasmid in S1030 cells plated on increasing concentrations of chloramphenicol.

The minimum inhibitory concentration (MIC) was determined by the selection plasmid. The A to I selection plasmid was grown in S1030, and plated on varying concentrations of chloramphenicol. The MIC was found to be approximately 1 µg/mL. A serial dilution of the selection plasmid in S1030 cells (the host strain) plated on increasing concentrations of chlor (FIG. 3). Cells harboring library members which survive on concentrations of chlor above 1 µg/mL were considered to be possible hits.

Figure 4:
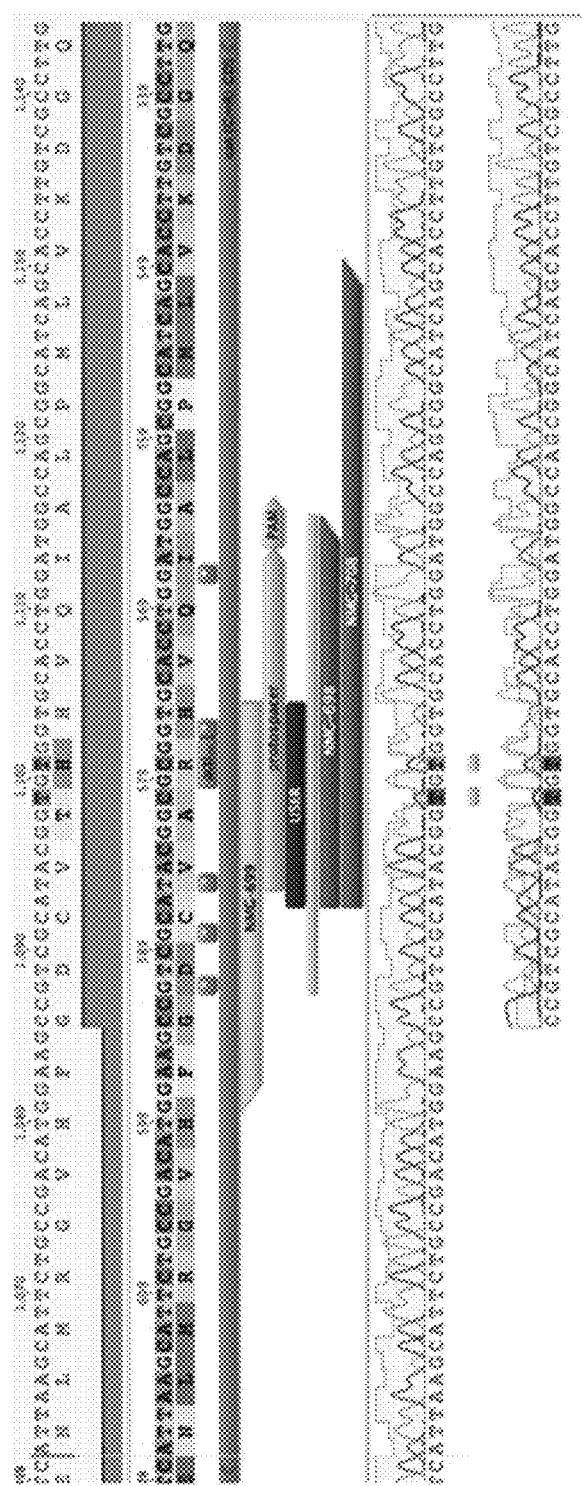
FIG. 4 shows the validation of chloramphenicol selection with a rAPOBEC1-XTEN-dCas9 construct as a positive control. The sequences from top to bottom correspond to SEQ ID NOs: 95 (the nucleotide sequence), 96 (the amino acid sequence), 97 (the nucleotide sequence), 98 (the amino acid sequence), 95 (the nucleotide sequence) and 99 (the truncated nucleotide sequence).

The chloramphenicol (Chlor) selection was further validated using rAPOBEC1-XTEN-dCas9 construct as a positive control. Colonies that survived at 8 µg/mL chlor were then sequenced, and the C to T reversion was observed in DNA (FIG. 4). The assay was performed by growing cells with the selection plasmid and deaminase fusion to $OD_{600nm}$ ~0.3 and then inducing fusion expression overnight. The resulting culture was then plated on increasing concentrations of chloramphenicol and the desired DNA reversion was screened.

An A to I deaminase library was then generated. Optimized assembly/library generation conditions, including PreCR vs. USER, electroporation vs. chemical composition, nucleofection vs. electroporation, outgrowth time, SOC vx. DRM, and sub-cloning vs. direct transformation, were examined. After the library assembly/electroporation conditions were optimized the following two libraries were made: APOBEC-XTEN-dCas9 and ADAT-XTEN-dCas9. The average library size was $2-4\times10^6$ based on the calculated colony-forming unit (CFU). The APOBEC-XTEN-dCas9 library produced no useful hits. The ADAT-XTEN-dCas9 library produced successful. The ADAT used was TadA (truncated) in *E. coli*.

Architecture of the Deaminase Library

Figure 5:
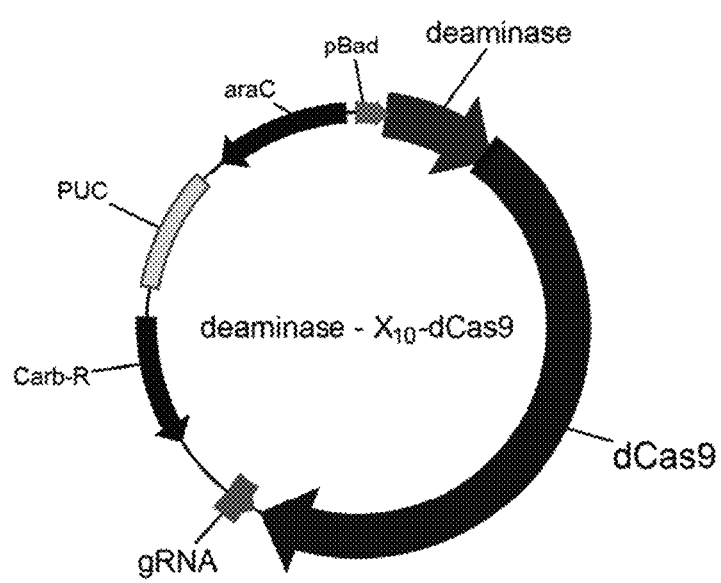
FIG. 5 is a schematic of a deaminase-XTEN-dCas9 construct.

The deaminase-XTEN-dCas9 fusion includes a SC101 backbone and a gRNA (lac promoter) to target the chloroamphernicol site (FIG. 5). Only deaminase is subjected to error-prone PCR, and the assembly is two-piece PreCR (a modified USER protocol). The gRNA is driven by the lac promoter; it targets the Chlor active site. A to G reversion is needed at position 9 of the protospacer to restore the His active site (a tyrosine to histidine reversion). Repair is needed and targeted on the template strand. APOBEC/CDA was used as a positive control. A to I constructs included the following: mADA, ADAR1, and ADAT2.

Figure 6:
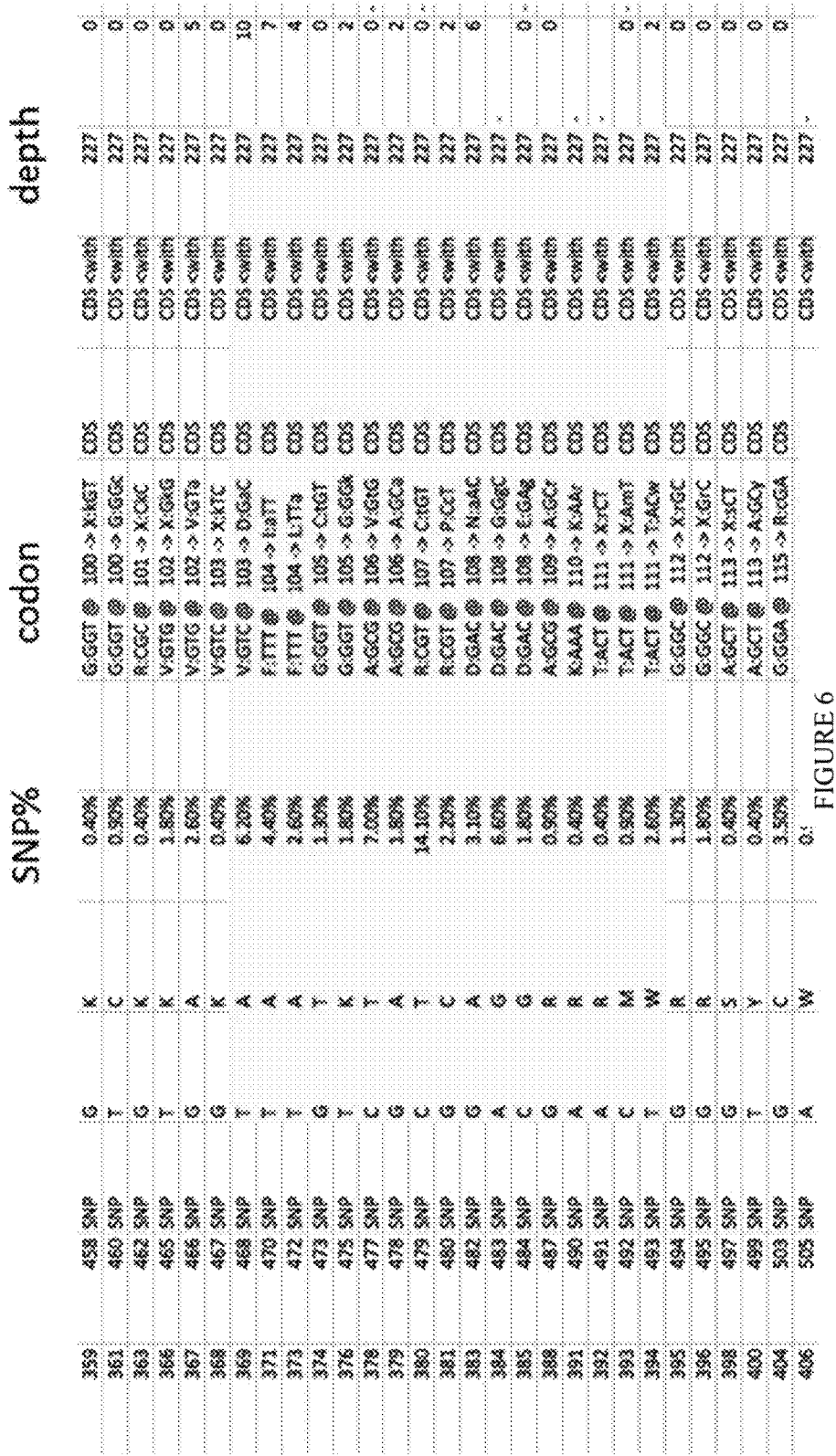
FIG. 6 shows the sequencing results from the first round of the TadA-XTEN-dCas9 library.
Figure 7:
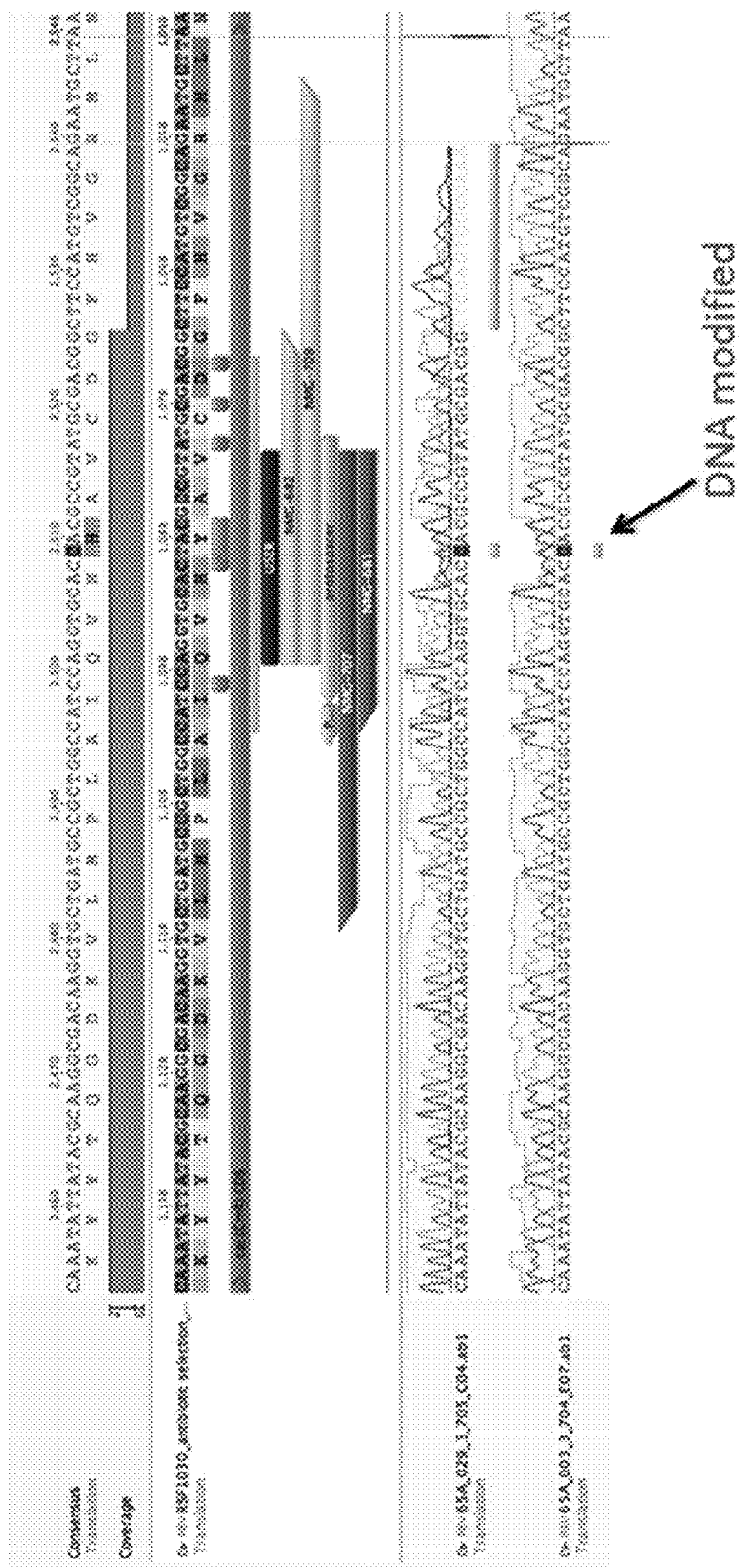
FIG. 7 shows the sequence of a selection plasmid; an A to G reversion was observed. The sequences from top to bottom correspond to SEQ ID NOs: 100 (the nucleotide sequence), 101 (the amino acid sequence), 102 (the nucleotide sequence), 103 (the amino acid sequence), 104 (the nucleotide sequence), and 100 (the nucleotide sequence).

A TadA-XTEN-dCas9 library was also constructed. Error Prone PCR on TadA enzyme only was used. The optimized protocol was used and resulting constructs were subcloned. S1030 cells (with the selection plasmid) were transformed with a TadA*-XTEN-dCas9 randomized library. Protein expression was induced after a recovery phase. The library was then plated the next day on increasing concentrations of chloramphenicol (0.5, 1, 2, and 4 µg/mL) onto separate 24×24 cm plates and incubated overnight. TadA(wt)-XTEN-dCas9 was used as a negative control. Colonies grew on all four places, and as concentrations increased, fewer colonies were observed. The negative control had far fewer colonies than the plates with library members. Eight selection plasmids were sequenced and all plasmids contained the A to G reversion at the targeted site. In all, 120 colonies were PCR-amplified and then sequenced. The results of the first round of sequencing are shown in FIG. 6. An exemplary sequence of a selection plasmid with the A to G reversion is given in FIG. 7. The target is the template strand's A to G (observed as T to C in coding). The example shows about 50% reversion in the Sanger trace (Y to H).

Figure 8:
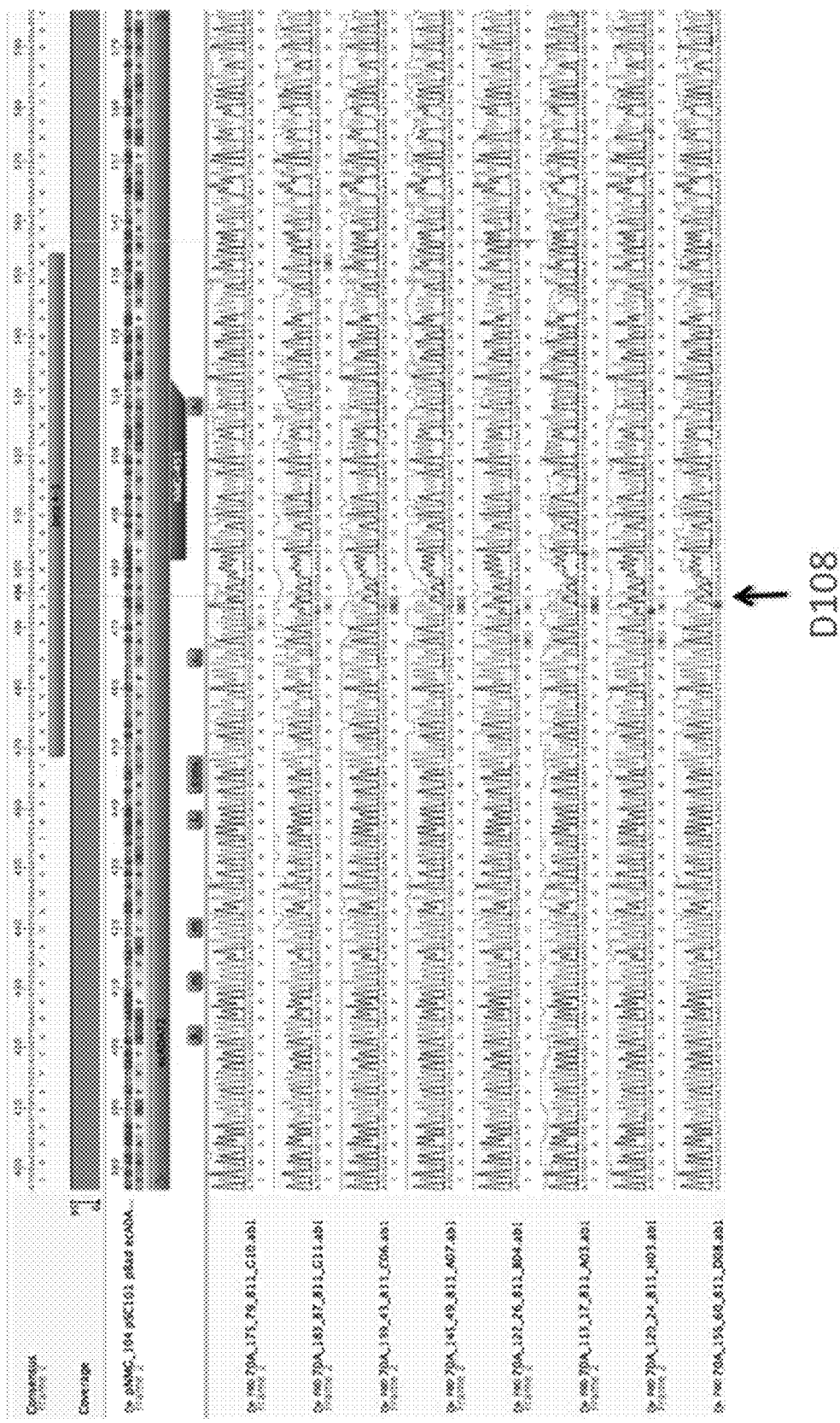
FIG. 8 shows the results of deaminase sequencing, illustrating the convergence at residue D108. The sequences correspond to SEQ ID NOs: 589-607 from top to bottom.
Figure 9:
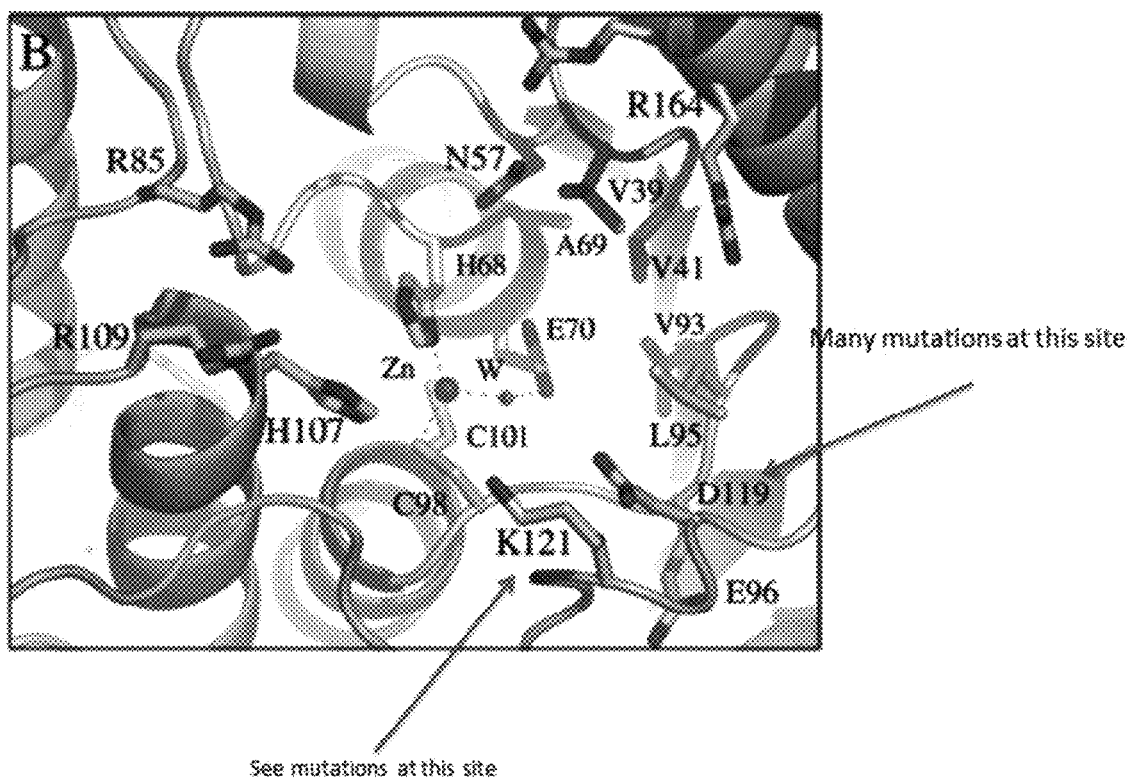
FIG. 9 shows the E. coli TadA crystal structure. Note that D119 in the figure corresponds to D108, as the residue numbering is offset in the figure.
Figure 10:
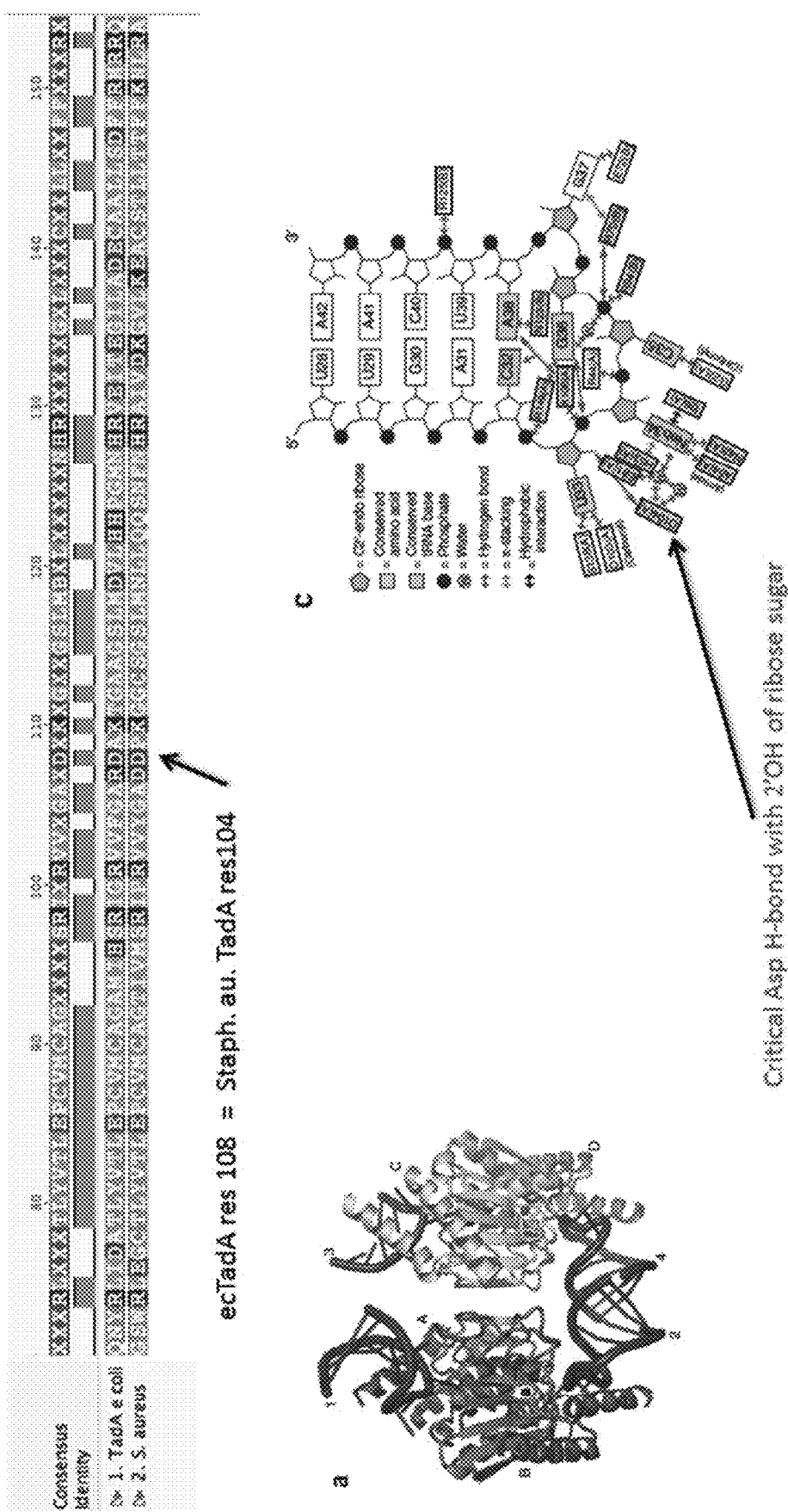
FIG. 10 shows the crystal structure of TadA (in S. aureus) tRNA and an alignment of with TadA from E. coli. The sequences from top to bottom correspond to SEQ ID NOs: 105-107.

A convergence at residue D108 was observed (FIG. 8). The crystal show of *E. coli* TadA is shown in FIG. 9. D119 in the figure is D108, as the residue numbers are offset. Many mutations were found to occur in that residue. FIG. 10 shows the crystal structure of Tad A (*S. aureus*) and aligns the sequences with that of *E. coli*. ecTadA residue 108 is equivalent to *S. aureus* TadA residue 104, which is part of a critical asparagine hydrogen bond with 2'OH of a ribose sugar.

Selection plasmids used in the evolution experiments contain mutations in various antibiotic resistance genes, which are targeted by adenosine base editors. Below are target sequences of the various antibiotic resistance genes (SEQ ID NOs: 441-444), where the targeted adenine required to restore resistance to its respective antibiotic is shown in bold and underlined. The plasmids used were high-copy plasmids with a RSF1030 origin.

```
Chloramphenicol target (H193Y):
                                (SEQ ID NO: 441)
5'-TACGGCGTAGTGCACCTGGA-3'

Kanamycin target 1 (Q4Term):
                                (SEQ ID NO: 442)
5'-ATCTTATTCGATCATGCGAA-3'

Kanamycing target 2 (W15Term):
                                (SEQ ID NO: 443)
5'-GCTTAGGTGGAGCGCCTATT-3'

Spectinomycin target (T89I):
                                (SEQ ID NO: 444)
5'-CAATGATGACTTCTACAGCG-3'
```

Mammalian codon optimized constructs were made by ordering a mammalian codon optimized version of ecTadA from Integrated Dna Technologies (IDT) as a gene block. This gene block was used to make pNMG-142, which served as a template for all subsequent mammalian codon-optimized constructs. See Table 4. After mutations were identified from the various rounds of evolution, primers were designed and ordered to introduce desired mutation(s) into the mammalian construct.

ecTadA Evolution and Challenge

Figure 11:
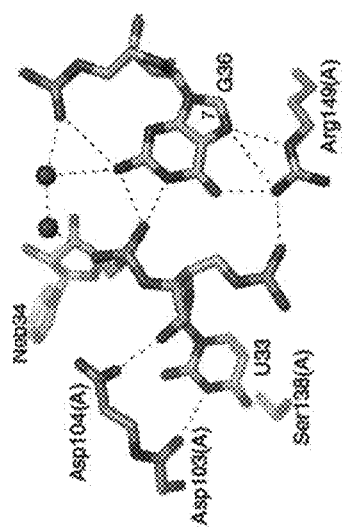
FIG. 11 shows results from the isolation and challenge of individual constructs from ecTadA evolution.

Individual constructs from the ecTadA evolution were isolated and challenged. Sixteen clones were sub-cloned, resulting in the first round of evolution. Each of the 16 clones were transformed in S1030 cells with selection plasmid and challenged with increasing doses of chloramphenicol. rAPOBEC1-XTEN-dCas9, which has a C to T reversion at the same site, was used as a control. The results are shown in FIGS. 11 and 12. FIG. 12 shows the C.F.U. of various constructs challenged on increasing concentrations of chloramphenicol. Constructs 3 and 4 performed the best under the assay's conditions. D108N is a key mutation.

Figure 19:
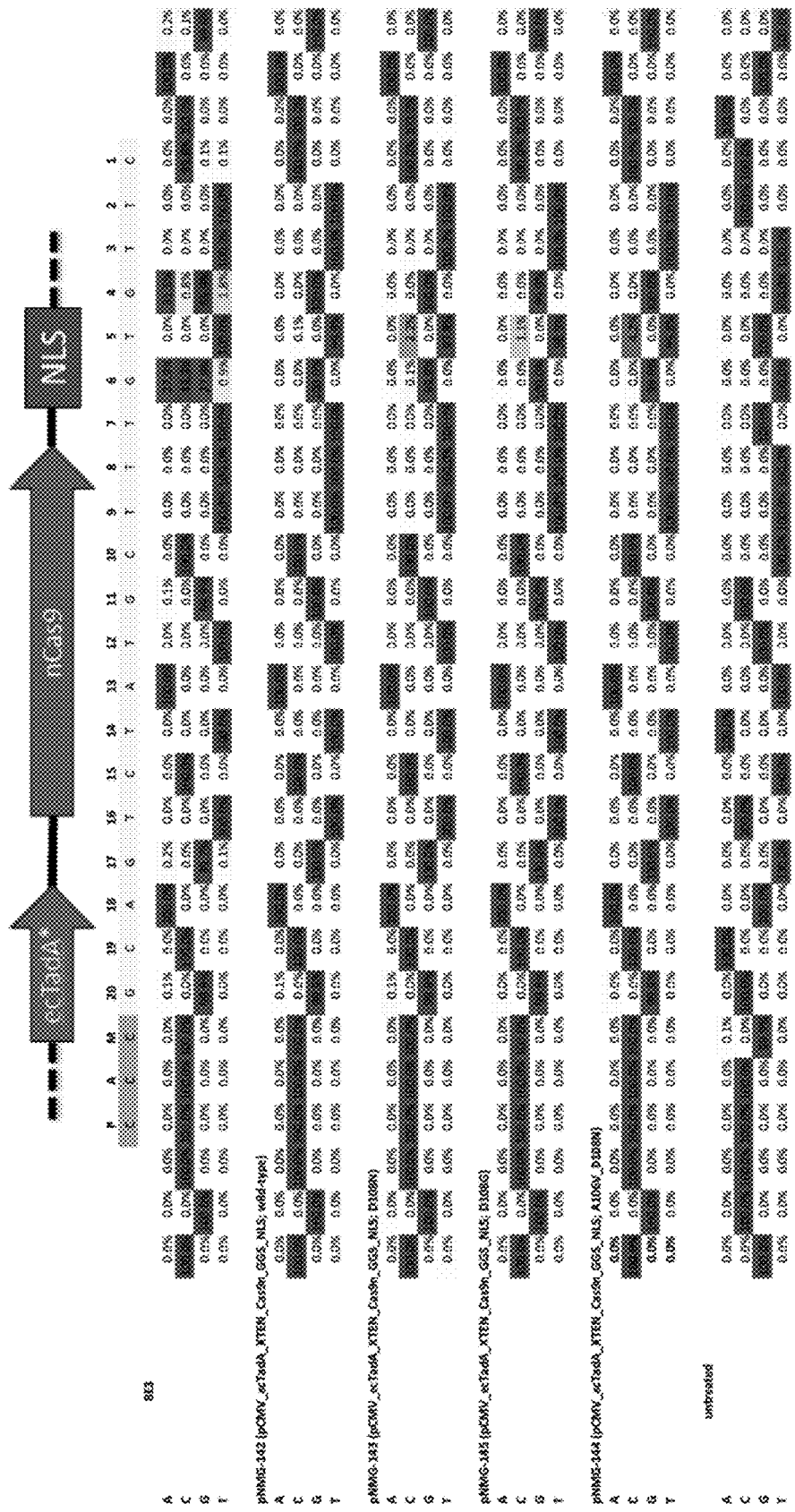
FIG. 19 shows the transfection of constructs into mammalian cells containing single or double mutations in ecTadA. The sequence corresponds to SEQ ID NO: 41.
Figure 20:
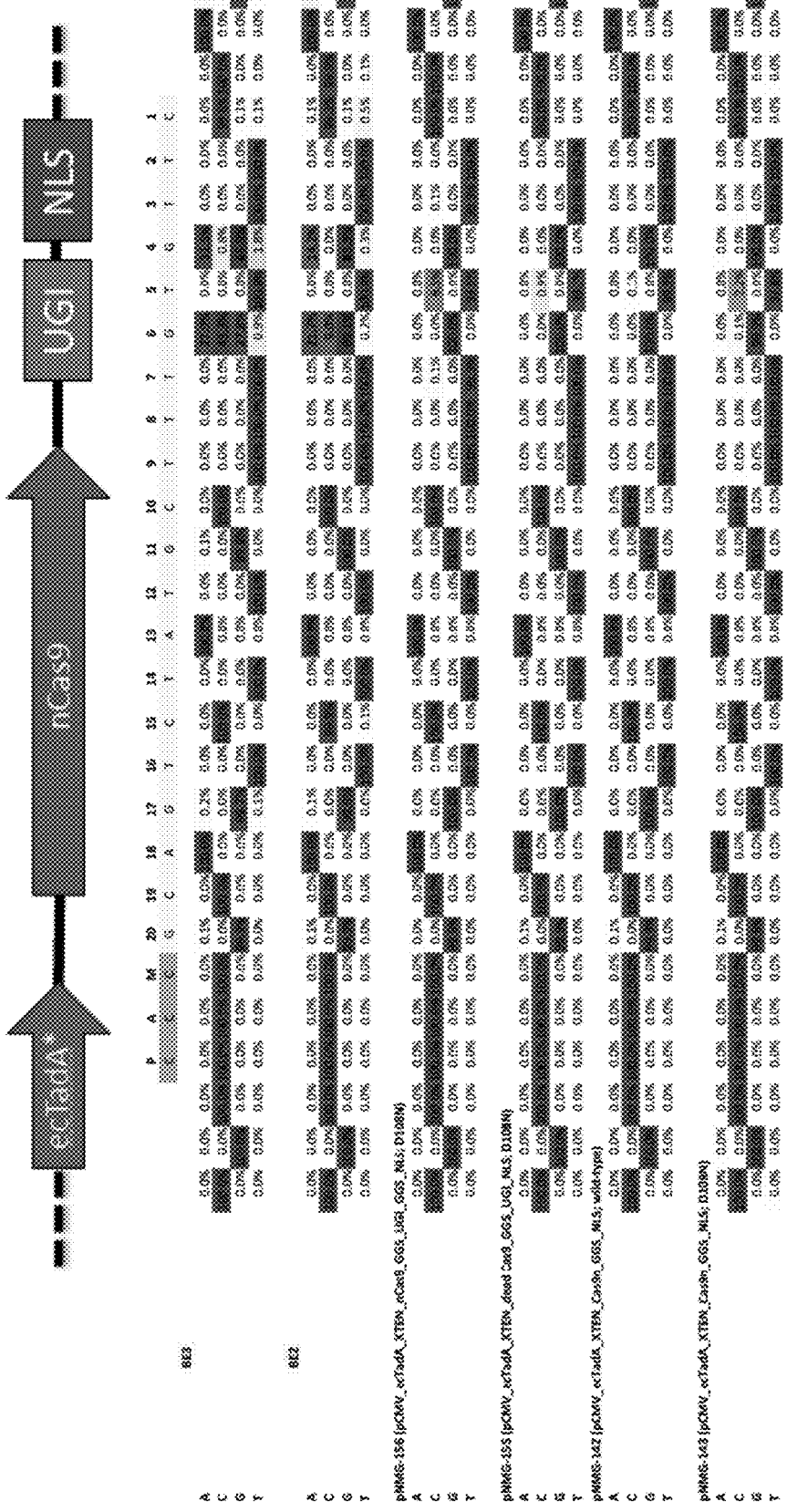
FIG. 20 shows the transfection of constructs with the addition of UGI to adenosine nucleobase editor (ABE) (D108N). The sequence corresponds to SEQ ID NO: 41.
Figure 22:
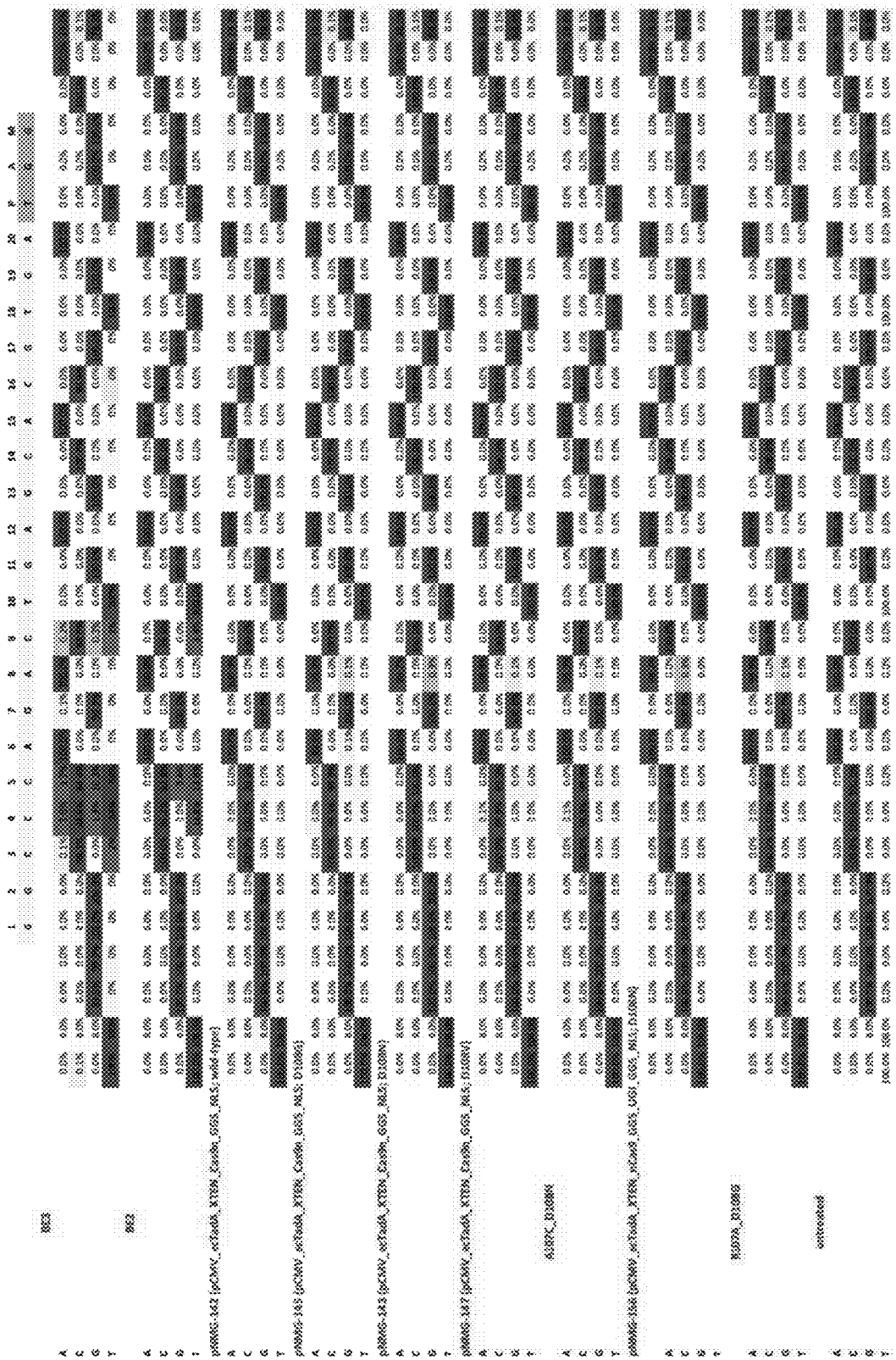
FIG. 22 shows that the Hek-3 site also has lower editing relative to the Hek-2 site editing at position 8 of the protospacer. The sequence corresponds to SEQ ID NO: 42.

Base editors, having mutations at residue D108 of ecTadA are capable of generating an adenine to guanine mutation in DNA via hydrolytic deamination of adenine, which results in inosine formation at the adenine site. Inosine is the read as guanine by DNA polymerase. See FIGS. 18-22, and 129-139, which show the ability of various base editors to generate an adenine to guanine mutation in DNA in various target DNA sequences, such as Hek2 (FIGS. 19, 20, and 129), Hek 2-1 (FIG. 130), Hek 2-2 (FIG. 131), Hek 2-3 (FIG. 132), Hek 2-4 (FIG. 133), Hek 2-6 (FIG. 134), Hek 2-9 (FIG. 135), Hek 2-10 (FIG. 136), RNF2 (FIG. 138), FANCF (FIG. 139), EMX1 (FIG. 21), and Hek3 (FIGS. 22 and 137). In these experiments the D108N mutation as most efficient for generating an A to G mutation, with the addition of an A106V mutation improving efficiency further. Additionally, base editors more efficiently generated A to G mutations at the Hek2 site than any other site tested. In the figures, BE3 and BE2 refer to base editors that induce C to G mutations and act as a positive control for C to G base editing.

Figure 13:
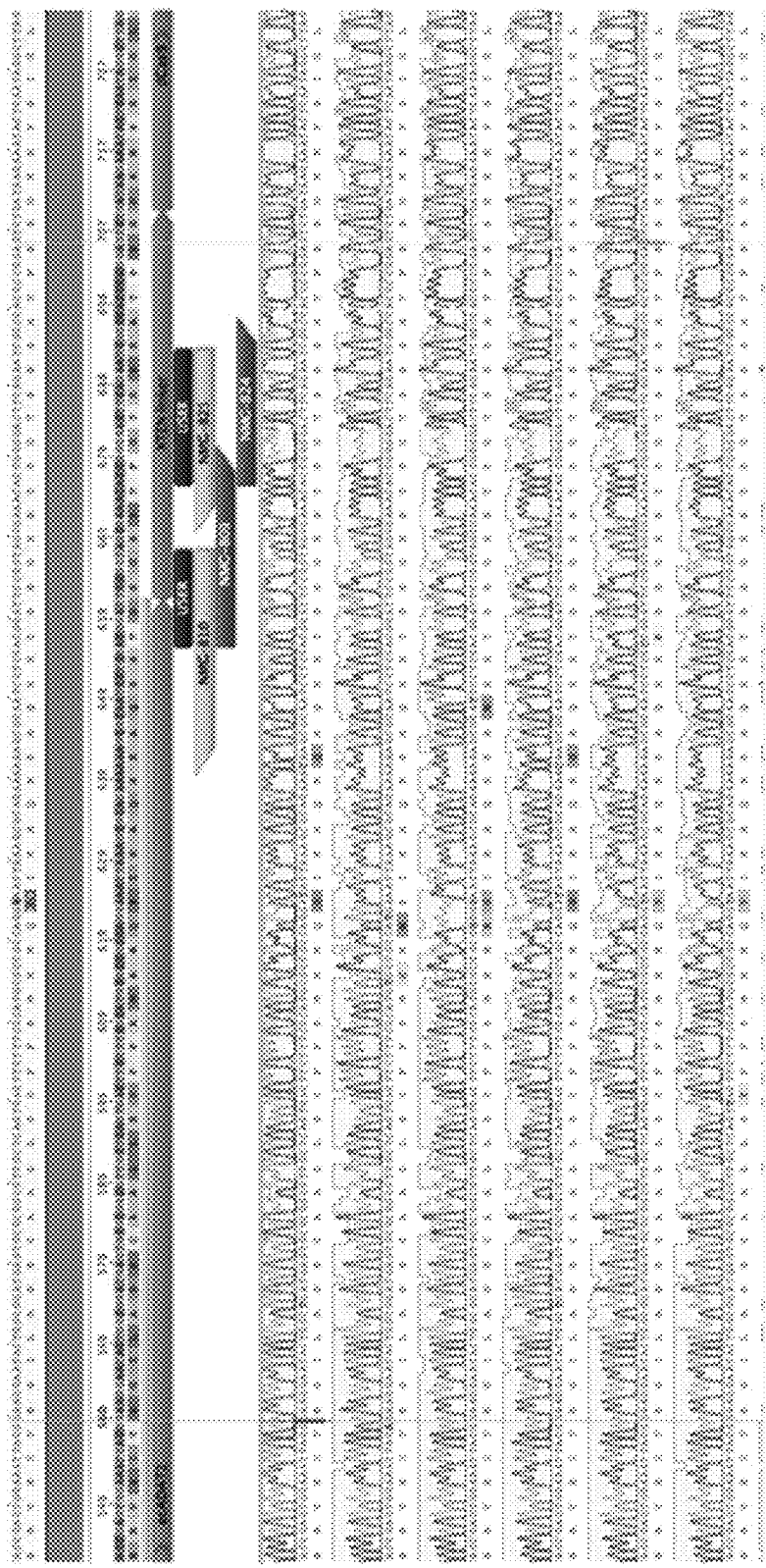
FIG. 13 shows data from the second round of evolution from the constructs containing the D108N mutation. The sequences from top to bottom correspond to SEQ ID NOs: 608-623.

A second round of evolution, described in greater detail below, was performed. Constructs containing the D108N mutation were randomized (plasmid NMG-128). The selection assay was repeated, and the clones were challenged with high concentrations of chloramphenicol. The resulting material was sub-cloned, and the selection assay was repeated. The resulting colonies that survived on high concentrations of chloramphenicol were then sequenced. An enrichment of mutations at position E155 was observed (FIG. 13).

A to G Editing in Mammalian Cells

Figure 14:
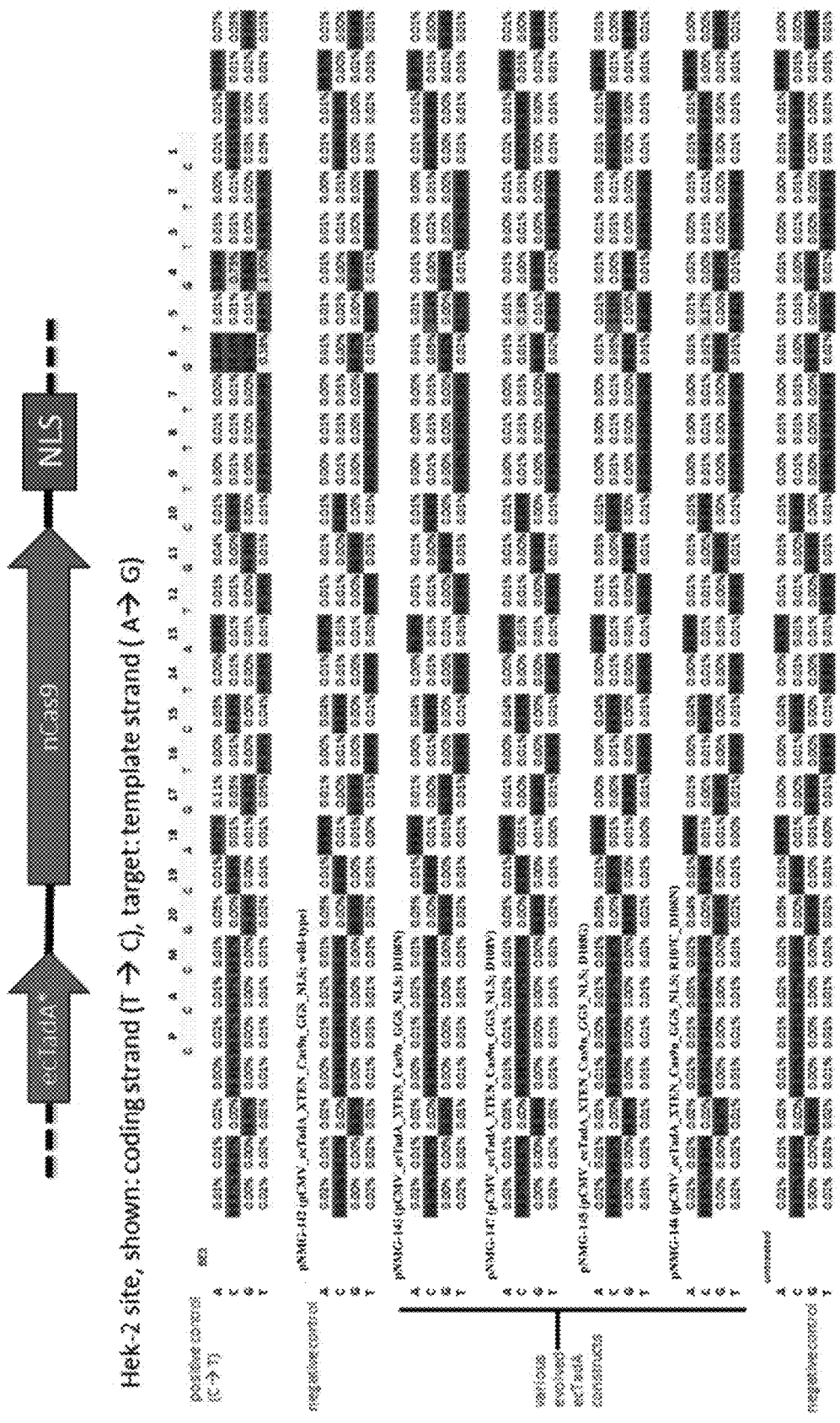
FIG. 14 shows A to G editing in mammalian cells. The sequence corresponds to SEQ ID NO: 41.

A to G editing in was examined in mammalian (Hek293T) cells. As shown in FIG. 14, the editing (from A to G) occurred in the various evolved ecTadA constructs, while it did not occur in the negative controls. The constructs used in the experiments described herein (e.g., Evolution #1-#7) are shown in Table 4. Table 4 includes the construct name, the construct architecture, and the ecTadA mutations. In table 4, pCMV refers to the expression vector comprising the construct. ecTadA refers to the ecTadA of SEQ ID NO: 1, however, for constructs comprising two ecTadA sequences, the second (C-terminal to the first ecTadA) ecTadA sequence does not comprise an N-terminal methionine. Table 4 also lists the mutations in ecTadA relative to SEQ ID NO: 1. Wild-type ecTadA refers to SEQ ID NO: 1. When two ecTadA domains are present the mutations in both ecTadA domains are indicated with the N-terminal ecTadA being indicated first. The 24 a.a linker refers to the amino acid sequence SGGSSGGSSGSETPGTSESATPES (SEQ ID NO: 685), the 32 a.a linker refers to the amino acid sequence SGGSSGGSSGSETPGTSESATPESSGGSSGGS (SEQ ID NO: 385), the 40 a.a linker refers to the amino acid sequence SGGSSGGSSGSETPGTSESATPESSGGSSGGSSGGSSGGS (SEQ ID NO: 686), the 64 a.a linker refers to the amino acid sequence SGGSSGGSSG-SETPGTSESATPESSGGSSGGSSGGSSGGSSGSETPGT-SESATPESSGGS SGGS (SEQ ID NO: 687), and the 92 a.a.

linker refers to the amino acid sequence PGSPAGSPTSTEEGTSESATPESGPGTSTEPSEGSAPGSPAGSPTSTEEGTSTEPSEGSAP GTSTEPSEGSAPGTSESATPESGPGSEPATS (SEQ ID NO: 688).

TABLE 4

| Name | Construct Architecture | Plasmid Identity Key Mutations in TadA |
|---|---|---|
| pNMG-142 | pCMV_ecTadA_XTEN_Cas9n_SGGS_NLS | wild-type |
| pNMG-143 | pCMV_ecTadA_XTEN_Cas9n_SGGS_NLS | D108N |
| pNMG-144 | pCMV_ecTadA_XTEN_Cas9n_SGGS_NLS | A106V_D108N |
| pNMG-145 | pCMV_ecTadA_XTEN_Cas9n_SGGS_NLS | D108G |
| pNMG-146 | pCMV_ecTadA_XTEN_Cas9n_SGGS_NLS | R107C_D108N |
| pNMG-147 | pCMV_ecTadA_XTEN_Cas9n_SGGS_NLS | D108V |
| pNMG-155 | pCMV_ecTadA_XTEN_dead Cas9_SGGS_UGI_NLS | D108N |
| pNMG-156 | pCMV_ecTadA_XTEN_nCas9_SGGS_UGI_SGGS_NLS | D108N |
| pNMG-157 | pCMV_ecTadA_XTEN_dead Cas9_SGGS_UGI_SGGS_NLS | D108G |
| pNMG-158 | pCMV_ecTadA_XTEN_nCas9_SGGS_UGI_SGGS_NLS | D108G |
| pNMG-160 | pCMV_ecTadA_XTEN_nCas9_SGGS_AAG*(E125Q)_SGGS_NLS | D108N |
| pNMG-161 | pCMV_ecTadA_XTEN_Cas9n_SGGS_EndoV*(D35A)_NLS | D108N |
| pNMG-162 | pCMV_ecTadA_XTEN_Cas9n_SGGS_NLS | H8Y_D108N_S127S_D147Y_Q154H |
| pNMG-163 | pCMV_ecTadA_XTEN_Cas9n_SGGS_NLS | H8Y_R24W_D108N_N127S_D147Y_E155V |
| pNMG-164 | pCMV_ecTadA_XTEN_Cas9n_SGGS_NLS | D108N_D147Y_E155V |
| pNMG-165 | pCMV_ecTadA_XTEN_Cas9n_SGGS_NLS | H8Y_D108N_S127S |
| pNMG-171 | pCMV_Cas9n_XTEN_ecTadA_SGGS_NLS | wild-type |
| pNMG-172 | pCMV_Cas9n_XTEN_ecTadA_SGGS_NLS | D108N |
| pNMG-173 | pCMV_Cas9n_XTEN_ecTadA_SGGS_NLS | H8Y_D108N_N127S_D147Y_Q154H |
| pNMG-174 | pCMV_Cas9n_XTEN_ecTadA_SGGS_NLS | H8Y_R24W_D108N_N127S_D147Y_E155V |
| pNMG-175 | pCMV_Cas9n_XTEN_ecTadA_SGGS_NLS | D108N_D147Y_E155V |
| pNMG-176 | pCMV_Cas9n_XTEN_ecTadA_SGGS_NLS | H8Y_D108N_S127S |
| pNMG-177 | pCMV_ecTadA_XTEN_Cas9n_SGGS_NLS | A106V_D108N_D147Y_E155V |
| pNMG-178 | pCMV_ecTadA_XTEN_Cas9n_SGGS_UGI_SGGS_NLS | D108N_D147Y_E155V |
| pNMG-179 | pCMV_ecTadA_XTEN_Cas9n_SGGS_AAG*(E125Q)_SGGS_NLS | A106V_D108N_D147Y_E155V |
| pNMG-180 | pCMV_ecTadA_XTEN_Cas9n_SGGS_UGI_SGGS_NLS | A106V_D108N_D147Y_E155V |
| pNMG-181 | pCMV_ecTadA_XTEN_Cas9n_SGGS_AAG*(E125Q)_SGGS_NLS | D108N_D147Y_E155V |
| pNMG-182 | pCMV_ecTadA_SGGS_nCas9_SGGS_NLS | D108N_D147Y_E155V |
| pNMG-183 | pCMV_ecTadA_(SGGS)2-XTEN-(SGGS)2_nCas9_SGGS_NLS | D108N_D147Y_E155V |
| pNMG-235 | pCMV_ecTadA_XTEN_Cas9n_XTEN_AAG*(E125A)_SGGS_NLS | A106V_D108N_D147Y_E155V |
| pNMG-236 | pCMV_ecTadA_XTEN_Cas9n_XTEN_AAG*(E125Q)_SGGS_NLS | A106V_D108N_D147Y_E155V |
| pNMG-237 | pCMV_ecTadA_XTEN_Cas9n_XTEN_AAG*(wt)_SGGS_NLS | A106V_D108N_D147Y_E155V |
| pNMG-238 | pCMV_AAG*(E125A)_XTEN_ecTadA_XTEN_Cas9n_SGGS_NLS | A106V_D108N_D147Y_E155V |
| pNMG-239 | pCMV_AAG*(wt)_XTEN_ecTadA_XTEN_Cas9n_SGGS_NLS | A106V_D108N_D147Y_E155V |
| pNMG-240 | pCMV_ecTadA_XTEN_Cas9n_XTEN_EndoV*(D35A)_SGG-S_NLS | A106V_D108N_D147Y_E155V |
| pNMG-241 | pCMV_ecTadA_XTEN_Cas9n_XTEN_EndoV*(wt)_SGGS_NLS | A106V_D108N_D147Y_E155V |
| pNMG-242 | pCMV_EndoV*(D35A)_XTEN_ecTadA_XTEN_Cas9n_SGGS_NLS | A106V_D108N_D147Y_E155V |
| pNMG-243 | pCMV_EndoV*(wt)_XTEN_ecTadA_XTEN_Cas9n_SGGS_NLS | A106V_D108N_D147Y_E155V |
| pNMG-247 | pCMV_ecTadA_XTEN_Cas9 (wild-type)_SGGS_NLS | wild-type |
| pNMG-248 | pCMV_ecTadA_XTEN_Cas9 (wild-type)_SGGS_NLS | D108N_D147Y_E155V |
| pNMG-249 | pCMV_ecTadA_XTEN_Cas9 (wild-type)_SGGS_NLS | A106V_D108N_D147Y_E155V |
| pNMG-250 | pCMV_ecTadA_XTEN_Cas9 (wild-type)_SGGS_UGI_SGGS_NLS | D108N_D147Y_E155V |
| pNMG-251 | pCMV_ecTadA_AAG*(E125Q)_SGGS_NLS | A106V_D108N_D147Y_E155V |

TABLE 4-continued

| Name | Construct Architecture | Mutations in TadA |
|---|---|---|
| pNMG-274 | pCMV_ecTadA_SGGS_NLS (no Cas9 fusion) | wild-type |
| pNMG-275 | pCMV_ecTadA_SGGS_NLS (no Cas9 fusion) | A106V_D108N_D147Y_E155V |
| pNMG-276 | pCMV_ecTadA-(SGGS)2-XTEN-(SGGS)2_ecTadA_XTEN_nCas9_SGGS_NLS | (wild-type) + (wild-type) |
| pNMG-277 | pCMV_ecTadA-(SGGS)2-XTEN-(SGGS)2_ecTadA_XTEN_nCas9_SGGS_NLS | (A106V_D108N_D147Y_E155V) + (A106V_D108N_D147Y_E155V) |
| pNMG-278 | pCMV_ecTadA_XTEN_nCas9_SGGS_NLS | D108Q_D147Y_E155V |
| pNMG-279 | pCMV_ecTadA_XTEN_nCas9_SGGS_NLS | D108M_D147Y_E155V |
| pNMG-280 | pCMV_ecTadA_XTEN_nCas9_SGGS_NLS | D108L_D147Y_E155V |
| pNMG-281 | pCMV_ecTadA_XTEN_nCas9_SGGS_NLS | D108I_D147Y_E155V |
| pNMG-282 | pCMV_ecTadA_XTEN_nCas9_SGGS_NLS | D108K_D147Y_E155V |
| pNMG-283 | pCMV_ecTadA_XTEN_nCas9_SGGS_NLS | D108F_D147Y_E155V |
| pNMG-284 | pCMV_ecTadA_LONGER LINKER (92 a.a.)_ecTadA_XTEN_nCas9_SGGS_NLS | (wild-type) + (A106V_D108N_D147Y_E155V) |
| pNMG-285 | pCMV_ecTadA_LONGER LINKER (92 a.a.)_ecTadA_XTEN_nCas9_SGGS_NLS | (A106V_D108N_D147Y_E155V) + (A106V_D108N_D147Y) |
| pNMG-285b | pCMV_ecTadA_XTEN_nCas9_SGGS_NLS | (A106V_D108N_D147Y_E155V) + (A106V_D108N_D147Y_E155V) |
| pNMG-286 | pCMV_ecTadA_XTEN_nCas9_SGGS_NLS | A106V_D108N_D147Y_E155V |
| pNMG-287 | pCMV_ecTadA-(SGGS)2-XTEN-(SGGS)2_ecTadA_XTEN-nCas9 (S. aureus) SGGS_NLS | (A106V_D108N_D147Y_E155V) + (A106V_D108N_D147Y_E155V) |
| pNMG-289 | pCMV_ecTadA-(SGGS)2-XTEN-(SGGS)2_ecTadA_XTEN_nCas9_SGGS_UGI_NLS | (A106V_D108N_D147Y_E155V) + (A106V_D108N_D147Y_E155V) |
| pNMG-290 | pCMV_ecTadA-(SGGS)2-XTEN-(SGGS)2_ecTadA_XTEN-(SGGS)2-XTEN-(SGGS)2_nCas9_SGGS_UGI_NLS | (A106V_D108N_D147Y_E155V) + (A106V_D108N_D147Y_E155V) |
| pNMG-293 | pCMV_ecTadA_XTEN_Cas9n_SGGS_NLS | E59A_A106V_D108N_D147Y_E155V |
| pNMG-294 | pCMV_ecTadA_XTEN_Cas9n_SGGS_NLS | E59A |
| pNMG-295 | pCMV_ecTadA_SGGS_NLS (no Cas9 fusion) | E59A |
| pNMG-296 | pCMV_ecTadA_SGGS_NLS (no Cas9 fusion) | E59A cat dead_A106V_D108N_D147Y_E155V |
| pNMG-297 | pCMV_ecTadA-(SGGS)2-XTEN-(SGGS)2_ecTadA_XTEN_nCas9_SGGS_NLS | (A106V_D108N_D147Y_E155V) + (wild-type) |
| pNMG-298 | pCMV_ecTadA-(SGGS)2-XTEN-(SGGS)2_ecTadA_XTEN_nCas9_SGGS_NLS | (D108M_D147Y_E155V) + (D108M_D147Y_E155V) |
| pNMG-320 | pCMV_ecTadA-(SGGS)2-XTEN-(SGGS)2_ecTadA_XTEN_nCas9_SGGS_NLS | (wild-type) + (A106V_D108N_D147Y_E155V) |
| pNMG-321 | pCMV_ecTadA-(SGGS)2-XTEN-(SGGS)2_ecTadA_XTEN_nCas9_SGGS_NLS | (E59A_A106V_D108N_D147Y_E155V) + (A106V_D108N_D147Y_E155V) |
| pNMG-322 | pCMV_ecTadA-(SGGS)2-XTEN-(SGGS)2_ecTadA_XTEN_nCas9_SGGS_NLS | (A106V_D108N_D147Y_E155V) + (E59A_A106V_D108N_D147Y_E155V) |
| pNMG-335 | pCMV_TadA3p-XTEN-TadA2p-XTEN-nCas9-NLS | wild-type |
| pNMG-336 | pCMV_ecTadA_(SGGS)2-XTEN-(SGGS)2_nCas9_SGGS_UGI_SGGS_NLS | L84F_A106V_D108N_H123Y_D147Y_E155V_I156Y |
| pNMG-337 | pCMV_ecTadA_(SGGS)2-XTEN-(SGGS)2_nCas9_SGGS_UGI_SGGS_NLS | A106V_D108N_D147Y_E155V |
| pNMG-338 | pCMV_ecTadA_(SGGS)2-XTEN-(SGGS)2_nCas9_SGGS_UGI_SGGS_NLS | L84F_A106V_D108N_H123Y_D147Y_E155V_I156F |
| pNMG-339 | pCMV_ecTadA-(SGGS)2-XTEN-(SGGS)2_ecTadA_(SGGS)2-XTEN-(SGGS)2_nCas9_SGGS_UGI_SGGS_NLS | (L84F_A106V_D108N_H123Y_D147Y_E155V_I156Y) + (L84F_A106V_D108N_H123Y_D147Y_E155V_I156Y) |

TABLE 4-continued

| Name | Construct Architecture | Mutations in TadA |
|---|---|---|
| pNMG-340 | pCMV_ecTadA-(SGGS)2-XTEN-(SGGS)2_ecTadA_(SGGS)2-XTEN-(SGGS)2_nCas9_SGGS_UGI_SGGS_NLS | (A106V_D108N_D147Y_E155V) + (A106V_D108N_D147Y_E155V) |
| pNMG-341 | pCMV_ecTadA-(SGGS)2-XTEN-(SGGS)2_ecTadA_(SGGS)2-XTEN-(SGGS)2_nCas9_SGGS_UGI_SGGS_NLS | (L84F_A106V_D108N_H123Y_D147Y_E155V_I156F) + (L84F_A106V_D108N_H123Y_D147Y_E155V_I156F) |
| pNMG-345 | pCMV_S. aureusTadA-(SGGS)2-XTEN-(SGGS)2-S. aureusTadA-(SGGS)2-XTEN-(SGGS)2-nCas9_SGGS_NLS | wild-type |
| pNMG-346 | pCMV_S. aureusTadA-(SGGS)2-XTEN-(SGGS)2-S. aureusTadA-(SGGS)2-XTEN-(SGGS)2-nCas9_SGGS_NLS | (D108N) + (D108N) |
| pNMG-347 | pCMV_S. aureusTadA-(SGGS)2-XTEN-(SGGS)2-S. aureusTadA-(SGGS)2-XTEN-(SGGS)2-nCas9_SGGS_NLS | (D107A_D018N) + (D107A_D108N) |
| pNMG-348 | pCMV_S. aureusTadA-(SGGS)2-XTEN-(SGGS)2-S. aureusTadA-(SGGS)2-XTEN-(SGGS)2-nCas9_SGGS_NLS | (G26P_D107A_D108N) + (G26P_D107A_D108N) |
| pNMG-349 | pCMV_S. aureusTadA-(SGGS)2-XTEN-(SGGS)2-S. aureusTadA-(SGGS)2-XTEN-(SGGS)2-nCas9_sGGS_NLS | (G26P_D107A_D108N_S142A) + (G26P_D107A_D108N_S142A) |
| pNMG-350 | pCMV_S. aureusTadA-(SGGS)2-XTEN-(SGGS)2-S. aureusTadA-(SGGS)2-XTEN-(SGGS)2-nCas9_SGGS_NLS | (D104A_D108N_S142A) + (D107A_D108N_S142A) |
| pNMG-351 | pCMV_ecTadA_(SGGS)2-XTEN-(SGGS)2_nCas9_SGGS_NLS | (R26G_L84F_A106V_R107H_D108N_H123Y_A142N_A143D_D147Y_E155V_I156F) |
| pNMG-352 | pCMV_ecTadA_(SGGS)2-XTEN-(SGGS)2_nCas9_SGGS_NLS | (E25G_R26G_L84F_A106V_R107K_D108N_H123Y_A142N_A143D_D147Y_E155V_I156F) |
| pNMG-353 | pCMV_ecTadA_(SGGS)2-XTEN-(SGGS)2_nCas9_SGGS_NLS | (E25D_R26G_L84F_A106V_R107K_D108N_H123Y_A142N_A143G_D147Y_E155V_I156F) |
| pNMG-354 | pCMV_ecTadA_(SGGS)2-XTEN-(SGGS)2_nCas9_SGGS_NLS | (R26Q_L84F_A106V_D108N_H123Y_A106V_D108N_H123Y_A142N_D147Y_E155V_I156F) |
| pNMG-355 | pCMV_ecTadA_(SGGS)2-XTEN-(SGGS)2_nCas9_SGGS_NLS | (E25M_R26G_L84F_A106V_R107P_D108N_H123Y_A142N_A143D_D147Y_E155V_I156F) |
| pNMG-356 | pCMV_ecTadA_(SGGS)2-XTEN-(SGGS)2_nCas9_SGGS_NLS | (R26C_L84F_A106V_R107H_D108N_H123Y_A142N_A143L_D147Y_E155V_I156F) |
| pNMG-357 | pCMV_ecTadA_(SGGS)2-XTEN-(SGGS)2_nCas9_SGGS_NLS | (L84F_A106V_D108N_H123Y_A142N_A143L_D147Y_E155V_I156F) |
| pNMG-358 | pCMV_ecTadA_(SGGS)2-XTEN-(SGGS)2_nCas9_SGGS_NLS | (R26G_L84F_A106V_D108N_H123Y_A142N_D147Y_E155V_I156F) |
| pNMG-359 | pCMV_ecTadA_(SGGS)2-XTEN-(SGGS)2_nCas9_SGGS_NLS | (E25A_R26G_L84F_A106V_R107N_D108N_H123Y_A142N_A143E_D147Y_E155V_I156F) |
| pNMG-360 | pCMV_ecTadA-(SGGS)2-XTEN-(SGGS)2-ecTadA-(SGGS)2-XTEN-(SGGS)2_nCas9_SGGS_NLS | (R26G_L84F_A106V_R107H_D108N_H123Y_A142N_A143D_D147Y_E155V_I156F) + (R26G_L84F_A106V_R107H_D108N_H123Y_A142N_A143D_D147Y_E155V_I156F) |
| pNMG-361 | pCMV_ecTadA-(SGGS)2-XTEN-(SGGS)2-ecTadA-(SGGS)2-XTEN-(SGGS)2_nCas9_SGGS_NLS | (E25G_R26G_L84F_A106V_R107H_D108N_H123Y_A142N_A143D_D147Y_E155V_I156F) × 2 |
| pNMG-362 | pCMV_ecTadA-(SGGS)2-XTEN-(SGGS)2-ecTadA-(SGGS)2-XTEN-(SGGS)2-ecTadA-(SGGS)2-XTEN-(SGGS)2_nCas9_SGGS_NLS | (E25D_R26G_L84F_A106V_R107K_D108N_H123Y_A142N_A143G_D147Y_E155V_I156F) × 2 |
| pNMG-363 | pCMV_ecTadA-(SGGS)2-XTEN-(SGGS)2-ecTadA-(SGGS)2-XTEN-(SGGS)2_nCas9_SGGS_NLS | (R26Q_L84F_A106V_D108N_H123Y_A142N_D147Y_E155V_I156F) × 2 |
| pNMG-364 | pCMV_ecTadA-(SGGS)2-XTEN-(SGGS)2-ecTadA-(SGGS)2-XTEN-(SGGS)2_nCas9_SGGS_NLS | (E25M_R26G_L84F_A106V_R107P_D108N_H123Y_A142N_A143D_D147Y_E155V_I156F) × 2 |
| pNMG-365 | pCMV_ecTadA-(SGGS)2-XTEN-(SGGS)2-ecTadA-(SGGS)2-XTEN-(SGGS)2_nCas9_SGGS_NLS | (R26C_L84F_A106V_R107H_D108N_H123Y_A142N_D147Y_E155V_I156F) × 2 |
| pNMG-366 | pCMV_ecTadA-(SGGS)2-XTEN-(SGGS)2-ecTadA-(SGGS)2-XTEN-(SGGS)2_nCas9_SGGS_NLS | (L84F_A106V_D108N_H123Y_A142N_A143L_D147Y_E155V_I156F) × 2 |
| pNMG-367 | pCMV_ecTadA-(SGGS)2-XTEN-(SGGS)2-ecTadA-(SGGS)2-XTEN-(SGGS)2_nCas9_SGGS_NLS | (R26G_L84F_A106V_D108N_H123Y_A142N_D147Y_E155V_I156F) × 2 |
| pNMG-368 | pCMV_ecTadA-(SGGS)2-XTEN-(SGGS)2-ecTadA-(SGGS)2-XTEN-(SGGS)2_nCas9_SGGS_NLS | (E25A_R26G_L84F_A106V_R107N_D108N_H123Y_A142N_A143E_D147Y_E155V_I156F) × 2 |
| pNMG-369 | pCMV_ecTadA-(SGGS)2-XTEN-(SGGS)2-ecTadA-(SGGS)2-XTEN-(SGGS)2_nCas9_SGGS_NLS | (L84F_A106V_D108N_H123Y_D147Y_E155V_I156Y) + (L84F_A106V_D108N_H123Y_D147Y_E155V_I156Y) |
| pNMG-370 | pCMV_ecTadA-(SGGS)2-XTEN-(SGGS)2-ecTadA-(SGGS)2-XTEN-(SGGS)2_nCas9_SGGS_NLS | (A106V_D108N_D147Y_E155V) + (A106V_D108N_D147Y_E155V) |
| pNMG-371 | pCMV_ecTadA-(SGGS)2-XTEN-(SGGS)2-ecTadA-(SGGS)2-XTEN-(SGGS)2_nCas9_SGGS_NLS | (L84F_A106_D108N_H123Y_D147Y_E155V_I156F) + (L84F_A106V_D108N_H123Y_D147Y_E155V_I156F) |

TABLE 4-continued

| Name | Construct Architecture | Mutations in TadA |
|---|---|---|
| pNMG-372 | pCMV_ecTadA_(SGGS)2-XTEN-(SGGS)2_Cas9n_SGGS_NLS | A106V_D108N_A142N_D147Y_E155V |
| pNMG-373 | pCMV_ecTadA_(SGGS)2-XTEN-(SGGS)2_Cas9n_SGGS_NLS | R26G_A106V_D108N_A142N_D147Y_E155V |
| pNMG-374 | pCMV_ecTadA_(SGGS)2-XTEN-(SGGS)2_Cas9n_SGGS_NLS | E25D_R26G_A106V_R107K_D108N_A142N_A143G_D147Y_E155V |
| pNMG-375 | pCMV_ecTadA_(SGGS)2-XTEN-(SGGS)2_Cas9n_SGGS_NLS | R26G_A106V_D108N_R107H_A142N_A143D_D147Y_E155V |
| pNMG-376 | pCMV_ecTadA_(SGGS)2-XTEN-(SGGS)2_Cas9n_SGGS_NLS | E25D_R26G_A106V_D108N_A142N_D147Y_E155V |
| pNMG-377 | pCMV_ecTadA_(SGGS)2-XTEN-(SGGS)2_Cas9n_SGGS_NLS | A106V_R107K_D108N_A142 N_D147Y_E155V |
| pNMG-378 | pCMV_ecTadA_(SGGS)2-XTEN-(SGGS)2_Cas9n_SGGS_NLS | A106V_D108N_A142N_A143G_D147Y_E155V |
| pNMG-379 | pCMV_ecTadA_(SGGS)2-XTEN-(SGGS)2_Cas9n_SGGS_NLS | A106V_D108N_A142N_A143L_D147Y_E155V |
| pNMG-382 | pCMV_ecTadA-(SGGS)2-XTEN-(SGGS)2-ecTadA-(SGGS)2-XTEN-(SGGS)2_SGGS_NLS | A106V_D108N_A142N_D147Y_E155V × 2 |
| pNMG-383 | pCMV_ecTadA-(SGGS)2-XTEN-(SGGS)2-ecTadA-(SGGS)2_nCas9_SGGS_NLS | R26G_A106V_D108N_A142N_D147Y_E155V × 2 |
| pNMG-384 | pCMV_ecTadA-(SGGS)2-XTEN-(SGGS)2-ecTadA-(SGGS)2_nCas9_SGGS_NLS | E25D_R26G_A106V_R107K_D108N_A142N_A143G_D147Y_E155V × 2 |
| pNMG-385 | pCMV_ecTadA-(SGGS)2-XTEN-(SGGS)2-ecTadA-(SGGS)2_nCas9_SGGS_NLS | R26G_A106V_D108N_R107H_A142N_A143D_D147Y_E155V × 2 |
| pNMG-386 | pCMV_ecTadA-(SGGS)2-XTEN-(SGGS)2-ecTadA-(SGGS)2_nCas9_SGGS_NLS | E25D_R26G_A106V_D108N_A142N_D147Y_E155V × 2 |
| pNMG-387 | pCMV_ecTadA-(SGGS)2-XTEN-(SGGS)2-ecTadA-(SGGS)2_nCas9_SGGS_NLS | A106V_R107K_D108N_A142N_D147Y_E155V × 2 |
| pNMG-388 | pCMV_ecTadA-(SGGS)2-XTEN-(SGGS)2-ecTadA-(SGGS)2_nCas9_SGGS_NLS | A106V_D108N_A142N_A143G_D147Y_E155V × 2 |
| pNMG-389 | pCMV_ecTadA-(SGGS)2-XTEN-(SGGS)2-ecTadA-(SGGS)2_nCas9_SGGS_NLS | A106V_D108N_A142N_A143L_D147Y_E155V × 2 |
| pNMG-391 | pCMV_ecTadA_(SGGS)2-XTEN-(SGGS)2_Cas9n_SGGS_UGL_SGGS_NLS | H36L_R51L_L84F_A106V_D108N_H123Y_S146C_D147Y_E155V_I156F_K157N |
| pNMG-392 | pCMV_ecTadA_(SGGS)2-XTEN-(SGGS)2_Cas9n_SGGS_UGL_SGGS_NLS | N37T_P48T_M70L_L84F_A106V_D108N_H123Y_D147Y_I49V_E155V_I156F |
| pNMG-393 | pCMV_ecTadA_(SGGS)2-XTEN-(SGGS)2_Cas9n_SGGS_UGL_SGGS_NLS | N37S_L84F_A106V_D108N_H123Y_D147Y_Q154H_E155V_I156F_K161T |
| pNMG-394 | pCMV_ecTadA_(SGGS)2-XTEN-(SGGS)2_Cas9n_SGGS_UGL_SGGS_NLS | H36L_L84F_A106V_D108N_H123Y_D147Y_S146R_D147Y_E155V_I156F |
| pNMG-395 | pCMV_ecTadA_(SGGS)2-XTEN-(SGGS)2_Cas9n_SGGS_UGL_SGGS_NLS | N72S_L84F_A106V_D108N_H123Y_S146R_D147Y_E155V_I156F |
| pNMG-396 | pCMV_ecTadA_(SGGS)2-XTEN-(SGGS)2_Cas9n_SGGS_UGL_SGGS_NLS | H36L_P48L_L84F_A106V_D108N_H123Y_E134G_D147Y_E155V_I156F |
| pNMG-397 | pCMV_ecTadA_(SGGS)2-XTEN-(SGGS)2_Cas9n_SGGS_UGL_SGGS_NLS | H36L_L84F_A106V_D108N_H123Y_D147Y_E155V_I156F_K157N |
| pNMG-398 | pCMV_ecTadA_(SGGS)2-XTEN-(SGGS)2_Cas9n_SGGS_UGL_SGGS_NLS | H36L_L84F_A106V_D108N_H123Y_S146C_D147Y_E155V_I156F |
| pNMG-399 | pCMV_ecTadA_(SGGS)2-XTEN-(SGGS)2_Cas9n_SGGS_UGL_SGGS_NLS | L84F_A106V_D108N_H123Y_S146R_D147Y_E155V_I156F_K161T |
| pNMG-400 | pCMV_ecTadA_(SGGS)2-XTEN-(SGGS)2_Cas9n_SGGS_UGL_SGGS_NLS | N37S_R51H_D77G_L84F_A106V_D108N_H123Y_D147Y_E155V_I156F |
| pNMG-401 | pCMV_ecTadA_(SGGS)2-XTEN-(SGGS)2_Cas9n_SGGS_UGL_SGGS_NLS | R51L_L84F_A106V_D108N_H123Y_D147Y_E155V_I156F_K157N |
| pNMG-402 | pCMV_ecTadA-(SGGS)2-XTEN-(SGGS)2-ecTadA-(SGGS)2-XTEN-(SGGS)2_SGGS_NLS | (H36L_R51L_L84F_A106V_D108N_H123Y_S146C_D147Y_E155V_I156F_K157N) × 2 |

TABLE 4-continued

Plasmid Identity Key

| Name | Construct Architecture | Mutations in TadA |
|---|---|---|
| pNMG-403 | pCMV_ecTadA-(SGGS)2-XTEN-(SGGS)2_nCas9-ecTadA-(SGGS)2-XTEN-(SGGS)2_nCas9_SGGS_NLS | (N37T_P48T_M70L_L84F_A106V_D108N_H123Y_D147Y_I49V_E155V_I156F) x 2 |
| pNMG-404 | pCMV_ecTadA-(SGGS)2-XTEN-(SGGS)2_nCas9-ecTadA-(SGGS)2-XTEN-(SGGS)2_nCas9_SGGS_NLS | (N37S_L84F_A106V_D108N_H123Y_D147Y_E155V_I156F_K161T) x 2 |
| pNMG-405 | pCMV_ecTadA-(SGGS)2-XTEN-(SGGS)2_nCas9-ecTadA-(SGGS)2-XTEN-(SGGS)2_nCas9_SGGS_NLS | (H36L_L84F_A106V_D108N_H123Y_D147Y_Q154H_E155V_I156F) x 2 |
| pNMG-406 | pCMV_ecTadA-(SGGS)2-XTEN-(SGGS)2_nCas9-ecTadA-(SGGS)2-XTEN-(SGGS)2_nCas9_SGGS_NLS | (N72S_L84F_A106V_D108N_H123Y_S146R_D147Y_E155V_I156F) x 2 |
| pNMG-407 | pCMV_ecTadA-(SGGS)2-XTEN-(SGGS)2_nCas9-ecTadA-(SGGS)2-XTEN-(SGGS)2_nCas9_SGGS_NLS | (H36L_P48L_L84F_A106V_D108N_H123Y_E134G_D147Y_E155V_I156F) x 2 |
| pNMG-408 | pCMV_ecTadA-(SGGS)2-XTEN-(SGGS)2_nCas9-ecTadA-(SGGS)2-XTEN-(SGGS)2_nCas9_SGGS_NLS | (H36L_L84F_A106V_D108N_H123Y_D147Y_E155V_I156F_K157N) x 2 |
| pNMG-409 | pCMV_ecTadA-(SGGS)2-XTEN-(SGGS)2_nCas9-ecTadA-(SGGS)2-XTEN-(SGGS)2_nCas9_SGGS_NLS | (H36L_L84F_A106V_D108N_H123Y_S146C_D147Y_E155V_I156F) x 2 |
| pNMG-410 | pCMV_ecTadA-(SGGS)2-XTEN-(SGGS)2_nCas9-ecTadA-(SGGS)2-XTEN-(SGGS)2_nCas9_SGGS_NLS | (L84F_A106V_D108N_H123Y_S146R_D147Y_E155V_I156F_K161T) x 2 |
| pNMG-411 | pCMV_ecTadA-(SGGS)2-XTEN-(SGGS)2_nCas9-ecTadA-(SGGS)2-XTEN-(SGGS)2_nCas9_SGGS_NLS | (N37S_R51H_D77G_L84F_A106V_D108N_H123Y_D147Y_E155V_I156F) x 2 |
| pNMG-412 | pCMV_ecTadA-(SGGS)2-XTEN-(SGGS)2_nCas9-ecTadA-(SGGS)2-XTEN-(SGGS)2_nCas9_SGGS_NLS | (R51L_L84F_A106V_D108N_H123Y_D147Y_E155V_I156F_K157N) x 2 |
| pNMG-440 | pCMV_ecTadA-(SGGS)2-XTEN-(SGGS)2_Cas9n_SGGS_UGI_SGGS_NLS | D24G_Q71R_L84F_A106V_D108N_H123Y_D147Y_E155V_1156F_K160E |
| pNMG-441 | pCMV_ecTadA-(SGGS)2-XTEN-(SGGS)2_Cas9n_SGGS_UGI_SGGS_NLS | H36L_G67V_L84F_A106V_D108N_H123Y_S146T_D147Y_E155V_I156F |
| pNMG-442 | pCMV_ecTadA-(SGGS)2-XTEN-(SGGS)2_Cas9n_SGGS_UGI_SGGS_NLS | Q71L_L84F_A106V_D108N_H123Y_L137M_A143E_D147Y_E155V_I156F |
| pNMG-443 | pCMV_ecTadA-(SGGS)2-XTEN-(SGGS)2_Cas9n_SGGS_UGI_SGGS_NLS | E25G_L84F_A106V_D108N_H123Y_D147_E155V_I156F_Q159L |
| pNMG-444 | pCMV_ecTadA-(SGGS)2-XTEN-(SGGS)2_Cas9n_SGGS_UGI_SGGS_NLS | L84F_A91T_F104I_A106V_D108N_H123Y_D147Y_E155V_I156F |
| pNMG-445 | pCMV_ecTadA-(SGGS)2-XTEN-(SGGS)2_Cas9n_SGGS_UGI_SGGS_NLS | N72D_L84F_A106V_D108N_H123Y_G125A_D147Y_E155V_I156F |
| pNMG-446 | pCMV_ecTadA-(SGGS)2-XTEN-(SGGS)2_Cas9n_SGGS_UGI_SGGS_NLS | P48S_L84F_S97C_A106V_D108N_H123Y_D147Y_E155V_I156F |
| pNMG-447 | pCMV_ecTadA-(SGGS)2-XTEN-(SGGS)2_Cas9n_SGGS_UGI_SGGS_NLS | W23G_L84F_A106V_D108N_H123Y_D147Y_E155V_I156F |
| pNMG-448 | pCMV_ecTadA-(SGGS)2-XTEN-(SGGS)2_Cas9n_SGGS_UGI_SGGS_NLS | D24G_P48L_Q71R_L84F_A106V_D108N_H123Y_D147Y_E155V_I156F_Q159L |
| pNMG-449 | pCMV_ecTadA-(SGGS)2-XTEN-(SGGS)2_nCas9_SGGS_NLS | (D24G_Q71R_L84F_H96L_A106V_D108N_H123Y_D147Y_E155V_I156F_K16OE) x 2 |
| pNMG-450 | pCMV_ecTadA-(SGGS)2-XTEN-(SGGS)2_nCas9_SGGS_NLS | (H36L_G67V_L84F_A106V_D108N_H123Y_S146T_D147Y_E155V_I156F) x 2 |
| pNMG-451 | pCMV_ecTadA-(SGGS)2-XTEN-(SGGS)2_nCas9_SGGS_NLS | (Q71L_L84F_A106V_D108N_H123Y_L137M_A143E_D147Y_E155V_I156F) x 2 |
| pNMG-452 | pCMV_ecTadA-(SGGS)2-XTEN-(SGGS)2_nCas9_SGGS_NLS | (E25G_L84F_A106V_D108N_H123Y_D147Y_E155V_I156F_Q159L) x 2 |
| pNMG-453 | pCMV_ecTadA-(SGGS)2-XTEN-(SGGS)2_nCas9_SGGS_NLS | (L84F_A91T_F104I_A106V_D108N_H123Y_D147Y_E155V_I156F) x 2 |

TABLE 4-continued

| Name | Construct Architecture | Mutations in TadA |
|---|---|---|
| pNMG-454 | pCMV_ecTadA-(SGGS)2-XTEN-(SGGS)2-ecTadA-(SGGS)2-XTEN-(SGGS)2_nCas9_SGGS_NLS | (N72D_L84F_A106V_D108N_H123Y_G125A_D147Y_E155V_I156F) x 2 |
| pNMG-455 | pCMV_ecTadA-(SGGS)2-XTEN-(SGGS)2-ecTadA-(SGGS)2-XTEN-(SGGS)2_nCas9_SGGS_NLS | (P48S_L84F_S97C_A106V_D108N_H123Y_D147Y_E155V_I156F) x 2 |
| pNMG-456 | pCMV_ecTadA-(SGGS)2-XTEN-(SGGS)2-ecTadA-(SGGS)2-XTEN-(SGGS)2_nCas9_SGGS_NLS | (W23G_L84F_A106V_D108N_H123Y_D147Y_E155V_I156F) x 2 |
| pNMG-457 | pCMV_ecTadA-(SGGS)2-XTEN-(SGGS)2-ecTadA-(SGGS)2-XTEN-(SGGS)2_nCas9_SGGS_NLS | (D24G_P48L_Q71R_L84F_A106V_D108N_H123Y_D147Y_E155V_I156F_Q159L) x 2 |
| pNMG-473 | pCMV_ecTadA-(SGGS)2-XTEN-(SGGS)2_Cas9n_SGGS_UGI_SGGS_NLS | L84F_A106V_D108N_H123Y_A142N_D147Y_E155V_I156F |
| pNMG-474 | pCMV_ecTadA-(SGGS)2-XTEN-(SGGS)2-ecTadA-(SGGS)2-XTEN-(SGGS)2_nCas9_SGGS_NLS | (L84F_A106V_D108N_H123Y_A142N_D147Y_E155V_I156F) x 2 |
| pNMG-475 | pCMV_ecTadA-(SGGS)2-XTEN-(SGGS)2-ecTadA-(SGGS)2-XTEN-(SGGS)2_nCas9_SGGS_NLS | (wild-type) + (A106V_D108N_D147Y_E155V) |
| pNMG-476 | pCMV_ecTadA-(SGGS)2-XTEN-(SGGS)2-ecTadA-(SGGS)2-XTEN-(SGGS)2_nCas9_SGGS_NLS | (wild-type) + (L84F_A106V_D108N_H123Y_D147Y_E155V_I156F) |
| pNMG-477 | pCMV_ecTadA-(SGGS)2-XTEN-(SGGS)2-ecTadA-(SGGS)2-XTEN-(SGGS)2_nCas9_SGGS_NLS | (wild-type) + (H36L_R51L_L84F_A106V_D108N_H123Y_S146C_D147Y_E155V_I156F_K157N) |
| pNMG-478 | pCMV_ecTadA-(SGGS)2-XTEN-(SGGS)2-ecTadA-(SGGS)2-XTEN-(SGGS)2_nCas9_SGGS_NLS | (wild-type) + (N37S_L84F_A106V_D108N_H123Y_D147Y_E155V_I156F_K161T) |
| pNMG-479 | pCMV_ecTadA-(SGGS)2-XTEN-(SGGS)2-ecTadA-(SGGS)2-XTEN-(SGGS)2_nCas9_SGGS_NLS | (wild-type) + (L84F_A106V_D108N_H123Y_S146R_D147Y_E155V_I156F_K161T) |
| pNMG-480 | pCMV_ecTadA-(SGGS)2-XTEN-(SGGS)2_Cas9n_SGGS_NLS | wild-type |
| pNMG-481 | pCMV_ecTadA-(SGGS)2-XTEN-(SGGS)2_Cas9n_SGGS_NLS | A106V_D108N |
| pNMG-482 | pCMV_ecTadA-(SGGS)2-XTEN-(SGGS)2-ecTadA-(SGGS)2-XTEN-(SGGS)2_nCas9_SGGS_NLS | wild-type + wild-type |
| pNMG-483 | pCMV_ecTadA-(SGGS)2-XTEN-(SGGS)2-ecTadA-(SGGS)2-XTEN-(SGGS)2_nCas9_SGGS_NLS | (A106V_D108N) x 2 |
| pNMG-484 | pCMV_ecTadA-(SGGS)2-XTEN-(SGGS)2-ecTadA-(SGGS)2-XTEN-(SGGS)2_nCas9_SGGS_NLS | (wild-type) + (A106V_D108N) |
| pNMG-485 | pCMV_ecTadA-(SGGS)2-XTEN-(SGGS)2_Cas9n_SGGS_UGI_SGGS_NLS | H36L_R51L_L84F_A106V_D108N_H123Y_A142N_S146C_D147Y_E155V_I156F_K157N |
| pNMG-486 | pCMV_ecTadA-(SGGS)2-XTEN-(SGGS)2_Cas9n_SGGS_UGI_SGGS_NLS | N37S_L84F_A106V_D108N_H123Y_A142N_D147Y_E155V_I156F_K161T |
| pNMG-487 | pCMV_ecTadA-(SGGS)2-XTEN-(SGGS)2_Cas9n_SGGS_UGI_SGGS_NLS | L84F_A106V_D108N_H123Y_D147Y_E155V_I156F |
| pNMG-488 | pCMV_ecTadA-(SGGS)2-XTEN-(SGGS)2_Cas9n_SGGS_UGI_SGGS_NLS | R51L_L84F_A106V_D108N_H123Y_S146C_D147Y_E155V_I156F_K161T |
| pNMG-489 | pCMV_ecTadA-(SGGS)2-XTEN-(SGGS)2_Cas9n_SGGS_UGI_SGGS_NLS | L84F_A106V_D108N_H123Y_S146C_D147Y_E155V_I156F_K161T |
| pNMG-490 | pCMV_ecTadA-(SGGS)2-XTEN-(SGGS)2_Cas9n_SGGS_UGI_SGGS_NLS | L84F_A106V_D108N_H123Y_S146C_D147Y_E155V_I156F_K157N_K160E_K161T |
| pNMG-491 | pCMV_ecTadA-(SGGS)2-XTEN-(SGGS)2_Cas9n_SGGS_UGI_SGGS_NLS | L84F_A106V_D108N_H123Y_S146C_D147Y_E155V_I156F_K157N_K160E |
| pNMG-492 | pCMV_ecTadA-(SGGS)2-XTEN-(SGGS)2-ecTadA-(SGGS)2-XTEN-(SGGS)2_nCas9_SGGS_NLS | (wt) + (L84F_A106V_D108N_H123Y_A142N_D147Y_E155V_I156F) |
| pNMG-493 | pCMV_ecTadA-(SGGS)2-XTEN-(SGGS)2-ecTadA-(SGGS)2-XTEN-(SGGS)2_nCas9_SGGS_NLS | (wt) + (D24G_Q71R_L84F_H96L_A106V_D108N_H123Y_D147Y_E155V_I156F_K160E) |

TABLE 4-continued

| Name | Construct Architecture | Mutations in TadA |
|---|---|---|
| pNMG-494 | pCMV_ecTadA-(SGGS)2-XTEN-(SGGS)2-ecTadA-(SGGS)2-XTEN-(SGGS)2_nCas9_SGGS_NLS | (wt) + (H36L_R51L_L84F_A106V_D108N_H123Y_A142N_S146C_D147Y_E155V_I156F_K157N) |
| pNMG-495 | pCMV_ecTadA-(SGGS)2-XTEN-(SGGS)2-ecTadA-(SGGS)2-XTEN-(SGGS)2_nCas9_SGGS_NLS | (wt) + (N37S_L84F_A106V_D108N_H123Y_A142N_D147Y_E155V_I156F_K161T) |
| pNMG-496 | pCMV_ecTadA-(SGGS)2-XTEN-(SGGS)2-ecTadA-(SGGS)2-XTEN-(SGGS)2_nCas9_SGGS_NLS | (wt) + (L84F_A106V_D108N_D147Y_E155V_I156F) |
| pNMG-497 | pCMV_ecTadA-(SGGS)2-XTEN-(SGGS)2-ecTadA-(SGGS)2-XTEN-(SGGS)2_nCas9_SGGS_NLS | (wt) + (R51L_L84F_A106V_D108N_H123Y_S146C_D147Y_E155V_I156F_K157N_K161T) |
| pNMG-498 | pCMV_ecTadA-(SGGS)2-XTEN-(SGGS)2-ecTadA-(SGGS)2-XTEN-(SGGS)2_nCas9_SGGS_NLS | (wt) + (L84F_A106V_D108N_H123Y_S146C_D147Y_E155V_I156F_K161T) |
| pNMG-499 | pCMV_ecTadA-(SGGS)2-XTEN-(SGGS)2-ecTadA-(SGGS)2-XTEN-(SGGS)2_nCas9_SGGS_NLS | (wt) + (L84F_A106V_D108N_H123Y_S146C_D147Y_E155V_I156F_K161T) |
| pNMG-500 | pCMV_ecTadA-(SGGS)2-XTEN-(SGGS)2-ecTadA-(SGGS)2-XTEN-(SGGS)2_nCas9_SGGS_NLS | (wt) + (L84F_A106V_D108N_H123Y_D147Y_E155V_I156F_K157N_K160E_K161T) |
| pNMG-513 | pCMV_ecTadA-92 a.a.-ecTadA-32 a.a._nCas9_SGGS_NLS | (wt) + (L84F_A106V_D108N_H123Y_D147Y_E155V_I156F_K157N_K160E) |
| pNMG-514 | pCMV_ecTadA-92 a.a.-ecTadA-32 a.a._nCas9_SGGS_NLS | (wt) + (L84F_A106V_D108N_H123Y_D147Y_E155V_I156F) + (L84F_A106V_D108N_H123Y_D147Y_E155V_I156F) |
| pNMG-515 | pCMV_ecTadA-92 a.a.-ecTadA-32 a.a._nCas9_SGGS_NLS | (wt) + (L84F_A106V_D108N_H123Y_D147Y_E155V_I156F) |
| pNMG-516 | pCMV_ecTadA-92 a.a.-ecTadA-64 a.a._nCas9_SGGS_NLS | (wt) + (L84F_A106V_D108N_H123Y_D147Y_E155V_I156F) + (L84F_A106V_D108N_H123Y_D147Y_E155V_I156F) |
| pNMG-517 | pCMV_ecTadA-92 a.a.-ecTadA-64 a.a._nCas9_SGGS_NLS | (wt) + (L84F_A106V_D108N_H123Y_D147Y_E155V_I156F) |
| pNMG-518 | pCMV_ecTadA-92 a.a.-ecTadA-64 a.a._nCas9_SGGS_NLS | (wt) + (L84F_A106V_D108N_H123Y_D147Y_E155V_I156F) + (L84F_A106V_D108N_H123Y_D147Y_E155V_I156F) |
| pNMG-519 | pCMV_ecTadA-32 a.a._nCas9_SGGS_NLS | R74Q |
| pNMG-520 | pCMV_ecTadA-32 a.a._nCas9_SGGS_NLS | R74Q |
| pNMG-521 | pCMV_ecTadA-32 a.a._nCas9_SGGS_NLS | L84F_A106V_D108N_H123Y_D147Y_E155V_I156F |
| pNMG-522 | pCMV_ecTadA-32 a.a._nCas9_SGGS_NLS | R74A_L84F_A106V_D108N_H123Y_D147Y_E155V_I156F |
| pNMG-523 | pCMV_ecTadA-32 a.a._nCas9_SGGS_NLS | R98Q |
| pNMG-524 | pCMV_ecTadA-(SGGS)2-XTEN-(SGGS)2-ecTadA-(SGGS)2-XTEN-(SGGS)2_nCas9_SGGS_NLS | R129Q |
| pNMG-525 | pCMV_ecTadA-(SGGS)2-XTEN-(SGGS)2-ecTadA-(SGGS)2-XTEN-(SGGS)2_nCas9_SGGS_NLS | (wt + R74Q) + (L84F_A106V_D108N_H123Y_D147Y_E155V_I156F) |
| pNMG-526 | pCMV_ecTadA-(SGGS)2-XTEN-(SGGS)2-ecTadA-(SGGS)2-XTEN-(SGGS)2_nCas9_SGGS_NLS | (wt + R74Q) + (R74Q_L84F_A106V_D108N_H123Y_D147Y_E155V_I156F) (R74A_L84F_A106V_D108N_H123Y_D147Y_E155V_I156F) + (R74A_L84F_A106V_D108N_H123Y_D147Y_E155V_I156F) |
| pNMG-527 | pCMV_ecTadA-(SGGS)2-XTEN-(SGGS)2-ecTadA-(SGGS)2-XTEN-(SGGS)2_nCas9_SGGS_NLS | (wt + R98Q) + (L84F_R98Q_A106V_D108N_H123Y_D147Y_E155V_I156F) |
| pNMG-528 | pCMV_ecTadA-(SGGS)2-XTEN-(SGGS)2-ecTadA-(SGGS)2-XTEN-(SGGS)2_nCas9_SGGS_NLS | (wt + R129Q) + (L84F_A106V_D108N_H123Y_R129Q_D147Y_E155V_I156F) |
| pNMG-529 | pCMV_ecTadA-(SGGS)2-XTEN-(SGGS)2-ecTadA-(SGGS)2-XTEN-(SGGS)2_nCas9_SGGS_NLS | (L84F_A106V_D108N_H123Y_A106V_D108N_H123Y_S146C_D147Y_E155V_I156F_K157N) + (H36L_R51L_L84F_A106V_D108N_H123Y_S146C_D147Y_E155V_I156F_K157N) |
| pNMG-530 | pCMV_ecTadA-(SGGS)2-XTEN-(SGGS)2-ecTadA-(SGGS)2-XTEN-(SGGS)2_nCas9_SGGS_NLS | (L84F_A106V_D108N_H123Y_D147Y_E155V_I156F) |
| pNMG-543 | pCMV_ecTadA-(SGGS)2-XTEN-(SGGS)2-ecTadA-(SGGS)2-XTEN-(SGGS)2_nCas9_SGGS_NLS | (P48S_L84F_A106V_D108N_H123Y_A142N_D147Y_E155V_I156F) |
| pNMG-544 | pCMV_ecTadA-(SGGS)2-XTEN-(SGGS)2-ecTadA-(SGGS)2-XTEN-(SGGS)2_nCas9_SGGS_NLS | (P48T_I49V_L84F_A106V_D108N_H123Y_A142N_D147Y_E155V_I156F_L157N) |
| pNMG-545 | pCMV_ecTadA-(SGGS)2-XTEN-(SGGS)2-ecTadA-(SGGS)2-XTEN-(SGGS)2_nCas9_SGGS_NLS | P48S_A142N |
| pNMG-546 | pCMV_ecTadA-(SGGS)2-XTEN-(SGGS)2-ecTadA-(SGGS)2-XTEN-(SGGS)2_nCas9_SGGS_NLS | P48T_I49V_A142N |
| pNMG-547 | pCMV_ecTadA-(SGGS)2-XTEN-(SGGS)2-ecTadA-(SGGS)2-XTEN-(SGGS)2_nCas9_SGGS_NLS | (wt) + (P48S_L84F_A106V_D108N_H123Y_A142N_D147Y_E155V_I156F) |
| pNMG-548 | pCMV_ecTadA-(SGGS)2-XTEN-(SGGS)2-ecTadA-(SGGS)2-XTEN-(SGGS)2_nCas9_SGGS_NLS | (P48S_L84F_A106V_D108N_H123Y_A142N_D147Y_E155V_I156F) + (P48S_L84F_A106V_D108N_H123Y_A142N_D147Y_E155V_I156F)) |

TABLE 4-continued

Plasmid Identity Key

| Name | Construct Architecture | Mutations in TadA |
|---|---|---|
| pNMG-549 | pCMV_ecTadA-(SGGS)2-XTEN-(SGGS)2-ecTadA-(SGGS)2-XTEN-(SGGS)2_nCas9_SGGS_NLS | (P48S_A142N) + |
| pNMG-550 | pCMV_ecTadA-(SGGS)2-XTEN-(SGGS)2-ecTadA-(SGGS)2-XTEN-(SGGS)2_nCas9_SGGS_NLS | (P48S_L84F_A106V_D108N_H123Y_A142N_D147Y_E155V_I156F)) |
| pNMG-551 | pCMV_ecTadA-(SGGS)2-XTEN-(SGGS)2-ecTadA-(SGGS)2-XTEN-(SGGS)2_nCas9_SGGS_NLS | (P48S_A142N) + |
| pNMG-552 | pCMV_ecTadA-(SGGS)2-XTEN-(SGGS)2-ecTadA-(SGGS)2-XTEN-(SGGS)2_nCas9_SGGS_NLS | (L84F_A106V_D108N_H123Y_D147Y_E155V_I156F) |
| pNMG-553 | pCMV_ecTadA-(SGGS)2-XTEN-(SGGS)2-ecTadA-(SGGS)2-XTEN-(SGGS)2_nCas9_SGGS_NLS | (P48T_I49V_L84F_A106V_D108N_H123Y_A142N_D147Y_E155V_I156F_L157N) |
| pNMG-554 | pCMV_ecTadA-(SGGS)2-XTEN-(SGGS)2-ecTadA-(SGGS)2-XTEN-(SGGS)2_nCas9_SGGS_NLS | (P48T_I49V_L84F_A106V_D108N_H123Y_A142N_D147Y_E155V_I156F_L157N) + |
| pNMG-555 | pCMV_ecTadA-24 a.a. linker-ecTadA-24 a.a. linker_nCas9_SGGS_NLS | (P48T_I49V_L84F_A106V_D108N_H123Y_A142N_D147Y_E155V_I156F_L157N) |
| pNMG-556 | pCMV_ecTadA-24 a.a. linker-ecTadA-32 a.a. linker_nCas9_SGGS_NLS | (P48T_I49V_L84F_A106V_D108N_H123Y_A142N_D147Y_E155V_I156F_L157N) + |
| pNMG-557 | pCMV_ecTadA-24 a.a. linker-ecTadA-40 a.a. linker_nCas9_SGGS_NLS | (P48T_I49V_A142N) + |
| pNMG-558 | pCMV_ecTadA-32 a.a. linker-ecTadA-24 a.a. linker_nCas9_SGGS_NLS | (P48T_I49V_A142N) + |
| pNMG-559 | pCMV_ecTadA-32 a.a. linker-ecTadA-32 a.a. linker_nCas9_SGGS_NLS | (L84F_A106V_D108N_H123Y_D147Y_E155V_I156F) |
| pNMG-560 | pCMV_ecTadA-32 a.a. linker-ecTadA-40 a.a. linker_nCas9_SGGS_NLS | (wt) + |
| pNMG-561 | pCMV_ecTadA-40 a.a. linker-ecTadA-24 a.a. linker_nCas9_SGGS_NLS | (H36L_R51L_L84F_A106V_D108N_H123Y_S146C_D147Y_E155V_I156F_K157N) |
| pNMG-562 | pCMV_ecTadA-40 a.a. linker-ecTadA-32 a.a. linker_nCas9_SGGS_NLS | (wt) + |
| pNMG-563 | pCMV_ecTadA-40 a.a. linker-ecTadA-40 a.a. linker_nCas9_SGGS_NLS | (H36L_R51L_L84F_A106V_D108N_H123Y_S146C_D147Y_E155V_I156F_K157N) |
| pNMG-564 | pCMV_ecTadA-24 a.a. linker_nCas9_SGGS_NLS | (wt) + |
| pNMG-565 | pCMV_ecTadA-24 a.a. linker_nCas9_SGGS_NLS | (H36L_R51L_L84F_A106V_D108N_H123Y_S146C_D147Y_E155V_I156F_K157N) |
| pNMG-566 | pCMV_ecTadA-(SGGS)2-XTEN-(SGGS)2-ecTadA-(SGGS)2-XTEN-(SGGS)2_nCas9_XTEN_MBD4_SGGS_NLS | (wt) + |
| pNMG-572 | pCMV_ecTadA-(SGGS)2-XTEN-(SGGS)2-ecTadA-(SGGS)2-XTEN-(SGGS)2_nCas9_XTEN_TDG_SGGS_NLS | wild-type |
| pNMG-573 | pCMV_ecTadA-(SGGS)2-XTEN-(SGGS)2-ecTadA-(SGGS)2-XTEN-(SGGS)2_nCas9_SGGS_NLS | (H36L_R51L_P48S_R51L_L84F_A106V_D108N_H123Y_S146C_D147Y_E155V_I156F_K157N) |
| pNMG-574 | pCMV_ecTadA-(SGGS)2-XTEN-(SGGS)2-ecTadA-(SGGS)2-XTEN-(SGGS)2_nCas9_SGGS_NLS | (H36L_R51L_P48S_R51L_L84F_A106V_D108N_H123Y_S146C_A142N_D147Y_E155V_I156F_K157N) |
| pNMG-575 | pCMV_ecTadA-(SGGS)2-XTEN-(SGGS)2-ecTadA-(SGGS)2-XTEN-(SGGS)2_nCas9_SGGS_NLS | (H36L_P48T_I49V_R51L_L84F_A106V_D108N_H123Y_S146C_D147Y_E155V_I156F_K157N) |
| pNMG-576 | pCMV_ecTadA-(SGGS)2-XTEN-(SGGS)2-ecTadA-(SGGS)2-XTEN-(SGGS)2_nCas9_SGGS_NLS | (H36L_P48T_I49V_R51L_L84F_A106V_D108N_H123Y_A142N_S146C_D147Y_E155V_I156F_K157N) |
| pNMG-577 | pCMV_ecTadA-(SGGS)2-XTEN-(SGGS)2-ecTadA-(SGGS)2-XTEN-(SGGS)2_nCas9_SGGS_NLS | (wt) + |
| pNMG-578 | pCMV_ecTadA-(SGGS)2-XTEN-(SGGS)2-ecTadA-(SGGS)2-XTEN-(SGGS)2_nCas9_SGGS_NLS | (H36L_R51L_P48S_R51L_L84F_A106V_D108N_H123Y_S146C_D147Y_E155V_I156F_K157N) |
| pNMG-579 | pCMV_ecTadA-(SGGS)2-XTEN-(SGGS)2-ecTadA-(SGGS)2-XTEN-(SGGS)2_nCas9_SGGS_NLS | (wt) + |
| pNMG-580 | pCMV_ecTadA-(SGGS)2-XTEN-(SGGS)2-ecTadA-(SGGS)2-XTEN-(SGGS)2_nCas9_SGGS_NLS | (H36L_P48S_R51L_L84F_A106V_D108N_H123Y_S146C_D147Y_E155V_I156F_K157N) + |
| pNMG-581 | pCMV_ecTadA-32 a.a._nCas9_SGGS_NLS | (H36L_P48A_R51L_L84F_A106V_D108N_H123Y_S146C_D147Y_E155V_I156F_K157N) |

TABLE 4-continued

Plasmid Identity Key

| Name | Construct Architecture | Mutations in TadA |
|---|---|---|
| pNMG-583 | pCMV_ecTadA-32 a.a.-_nCas9_SGGS_NLS | (H36L_P48A_R51L_L84F_A106V_D108N_H123Y_A142N_S146C_D147Y_E155V_I156F_K157N) |
| pNMG-586 | pCMV_ecTadA-(SGGS)2-XTEN-(SGGS)2-ecTadA-(SGGS)2-XTEN-(SGGS)2_nCas9_SGGS_NLS | (wt) + (H36L_P48A_R51L_L84F_A106V_D108N_H123Y_S146C_D147Y_E155V_I156F_K157N) |
| pNMG-588 | pCMV_ecTadA-(SGGS)2-XTEN-(SGGS)2-ecTadA-(SGGS)2-XTEN-(SGGS)2_nCas9_SGGS_NLS | (wt) + (H36L_P48A_R51L_L84F_A106V_D108N_H123Y_S146C_A142N_D147Y_E155V_I156F_K157N) |
| pNMG-603 | pCMV_ecTadA-32 a.a.-_nCas9_SGGS_NLS | (W23L_H36L_P48A_R51L_L84F_A106V_D108N_H123Y_S146C_D147Y_E155V_I156F_K157N) |
| pNMG-604 | pCMV_ecTadA-32 a.a.-_nCas9_SGGS_NLS | (W23R_H36L_P48A_R51L_L84F_A106V_D108N_H123Y_S146C_D147Y_E155V_I156F_K157N) |
| pNMG-605 | pCMV_ecTadA-32 a.a.-_nCas9_SGGS_NLS | (W23L_H36L_P48A_R51L_L84F_A106V_D108N_H123Y_S146R_D147Y_E155V_I156F_K161T) |
| pNMG-606 | pCMV_ecTadA-32 a.a.-_nCas9_SGGS_NLS | (W23L_H36L_P48A_R51L_L84F_A106V_D108N_H123Y_S146C_D147Y_R152H_E155V_I156F_K157N) |
| pNMG-607 | pCMV_ecTadA-32 a.a.-_nCas9_SGGS_NLS | (H36L_P48A_R51L_L84F_A106V_D108N_H123Y_S146C_D147Y_R152P_E155V_I156F_K157N) |
| pNMG-608 | pCMV_ecTadA-32 a.a.-_nCas9_SGGS_NLS | (W23L_H36L_P48A_R51L_L84F_A106V_D108N_H123Y_S146C_D147Y_R152P_E155V_I156F_K157N) |
| pNMG-609 | pCMV_ecTadA-32 a.a.-_nCas9_SGGS_NLS | (W23L_H36L_P48A_R51L_L84F_A106V_D108N_H123Y_A142A_S146C_D147Y_E155V_I156F_K157N) |
| pNMG-610 | pCMV_ecTadA-32 a.a.-_nCas9_SGGS_NLS | (W23L_H36L_P48A_R51L_L84F_A106V_D108N_H123Y_A142A_S146C_D147Y_R152P_E155V_I156F_K157N) |
| pNMG-611 | pCMV_ecTadA-(SGGS)2-XTEN-(SGGS)2-ecTadA-(SGGS)2-XTEN-(SGGS)2_nCas9_SGGS_NLS | (wt) + (W23L_H36L_P48A_R51L_L84F_A106V_D108N_H123Y_S146C_D147Y_E155V_I156F_K157N) |
| pNMG-612 | pCMV_ecTadA-(SGGS)2-XTEN-(SGGS)2-ecTadA-(SGGS)2-XTEN-(SGGS)2_nCas9_SGGS_NLS | (wt) + (W23R_H36L_P48A_R51L_L84F_A106V_D108N_H123Y_S146C_D147Y_E155V_I156F_K157N) |
| pNMG-613 | pCMV_ecTadA-(SGGS)2-XTEN-(SGGS)2-ecTadA-(SGGS)2-XTEN-(SGGS)2_nCas9_SGGS_NLS | (wt) + (W23L_H36L_P48A_R51L_L84F_A106V_D108N_H123Y_S146R_D147Y_E155V_I156F_K161T) |
| pNMG-614 | pCMV_ecTadA-(SGGS)2-XTEN-(SGGS)2-ecTadA-(SGGS)2-XTEN-(SGGS)2_nCas9_SGGS_NLS | (wt) + (H36L_P48A_R51L_L84F_A106V_D108N_H123Y_S146C_D147Y_R152H_E155V_I156F_K157N) |
| pNMG-615 | pCMV_ecTadA-(SGGS)2-XTEN-(SGGS)2-ecTadA-(SGGS)2-XTEN-(SGGS)2_nCas9_SGGS_NLS | (wt) + (H36L_P48A_R51L_L84F_A106V_D108N_H123Y_S146C_D147Y_R152P_E155V_I156F_K157N) |
| pNMG-616 | pCMV_ecTadA-(SGGS)2-XTEN-(SGGS)2-ecTadA-(SGGS)2-XTEN-(SGGS)2_nCas9_SGGS_NLS | (wt) + (W23L_H36L_P48A_R51L_L84F_A106V_D108N_H123Y_S146C_D147Y_R152P_E155V_I156F_K157N) |
| pNMG-617 | pCMV_ecTadA-(SGGS)2-XTEN-(SGGS)2-ecTadA-(SGGS)2-XTEN-(SGGS)2_nCas9_SGGS_NLS | (wt) + (W23L_H36L_P48A_R51L_L84F_A106V_D108N_H123Y_A142A_S146C_D147Y_E155V_I156F_K157N) |
| pNMG-618 | pCMV_ecTadA-(SGGS)2-XTEN-(SGGS)2-ecTadA-(SGGS)2-XTEN-(SGGS)2_nCas9_SGGS_NLS | (wt) + (W23L_H36L_P48A_R51L_L84F_A106V_D108N_H123Y_A142A_S146C_D147Y_R152P_E155V_I156F_K157N) |
| pNMG-619 | pCMV_ecTadA-32 a.a.-_nCas9_SGGS_NLS | (W23R_H36L_P48A_R51L_L84F_A106V_D108N_H123Y_S146C_D147Y_R152P_E155V_I156F_K157N) |
| pNMG-620 | pCMV_ecTadA-(SGGS)2-XTEN-(SGGS)2-ecTadA-(SGGS)2-XTEN-(SGGS)2_nCas9_SGGS_NLS | (wt) + (W23R_H36L_P48A_R51L_L84F_A106V_D108N_H123Y_S146C_D147Y_R152P_E155V_I156F_K157N) |
| pNMG-621 | pCMV_ecTadA-32 a.a. linker-ecTadA-24 a.a. linker_nCas9_SGGS_NLS | (H36L_P48A_R51L_L84F_A106V_D108N_H123Y_S146C_D147Y_R152P_E155V_I156F_K157N) |
| pNMG-622 | pCMV_ecTadA-32 a.a. linker-ecTadA-24 a.a. linker_nCas9_SGGS_NLS | (H36L_P48A_R51L_L84F_A106V_D108N_H123Y_A142N_S146C_D147Y_R152P_E155V_I156F_K157N) |
| pNMG-623 | pCMV_ecTadA-32 a.a. linker-ecTadA-24 a.a. linker_nCas9_SGGS_NLS | (W23L_H36L_P48A_R51L_L84F_A106V_D108N_H123Y_S146C_D147Y_R152P_E155V_I156F_K157N) |
| pNMG-624 | pCMV_ecTadA-32 a.a. linker-ecTadA-24 a.a. linker_nCas9_SGGS_NLS | (W23R_H36L_P48A_R51L_L84F_A106V_D108N_H123Y_S146C_D147Y_R152P_E155V_I156F_K157N) |

Example 2—Evolution of Adenosine Base Editor Containing the D108N Mutation of ecTadA (Evolution #2)

An ecTadA construct with a D108N (pNMG-128) mutation was mutagenized via error-prone PCR, as in Evolution #1, and this library was selected against the same chloramphenicol site, except higher concentrations of chloramphenicol was used in the selection media to increase the stringency of the selection. This round of selection produced two new mutations which improved the editing efficiencies of ABE: D147Y and E155V.

In the first round of evolution, error-prone PCR was conducted on the ecTadA deaminase portion of a ecTadA-XTEN-dCas9 fusion construct followed by USER assembly to create a library of ecTadA-XTEN-dCas9 variants (varied only in the deaminase portion). These library members were transformed into S1030 cells containing a selection plasmid, which contained a single G to A point mutation in the active site portion of the chloramphenicol resistance gene. Cells were cultured overnight and plated on concentrations of chloramphenicol which were higher than the MIC of the S1030 cells with the selection plasmid. Surviving colonies were sub-cloned and re-challenged under the selection conditions and then sequenced to identify the genotype of the productive variants. Sanger sequencing analysis revealed that a D108N, a D108V, and a D108G mutation conferred the desired phenotype (A to G transition mutation in DNA). Subsequent studies involving individual clones isolated from this first round of evolution demonstrated that the D108N mutation was the optimal substitution at this site.

Figure 17:
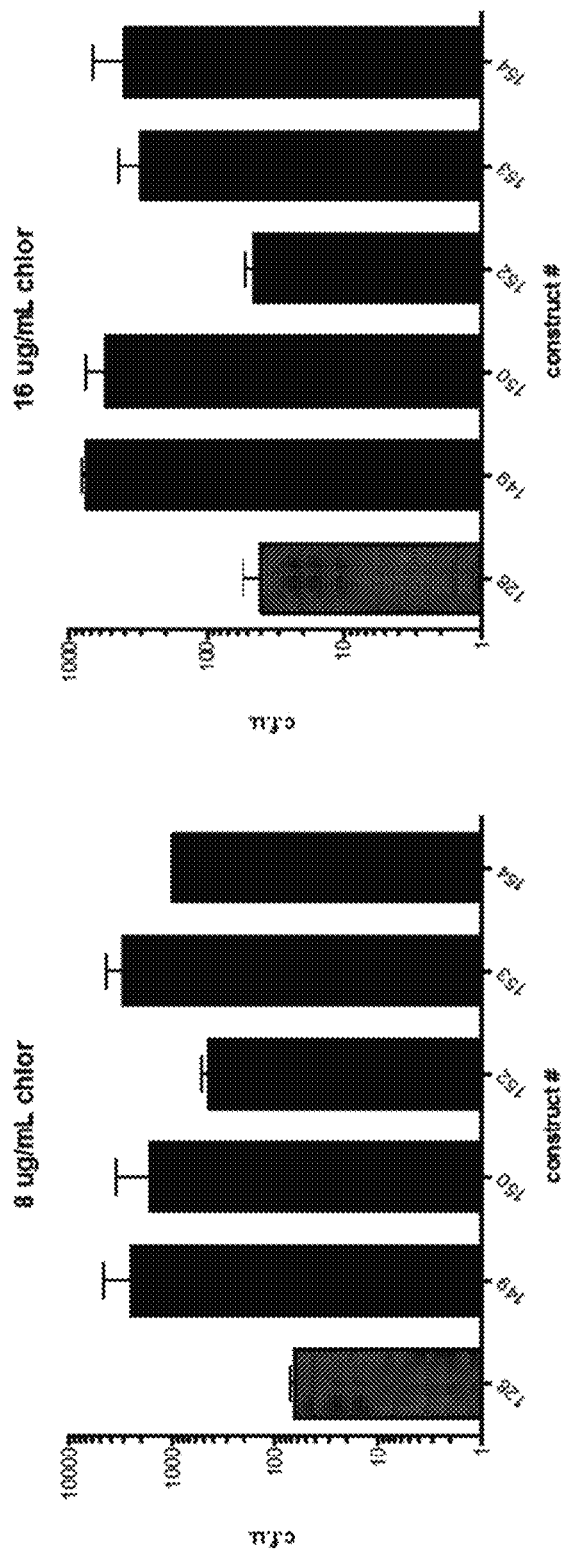
FIG. 17 shows the results of individual clone antibiotic challenge assays. The identity of the construct numbers correspond to the pNMG clone numbers from FIG. 16.
Figure 17:
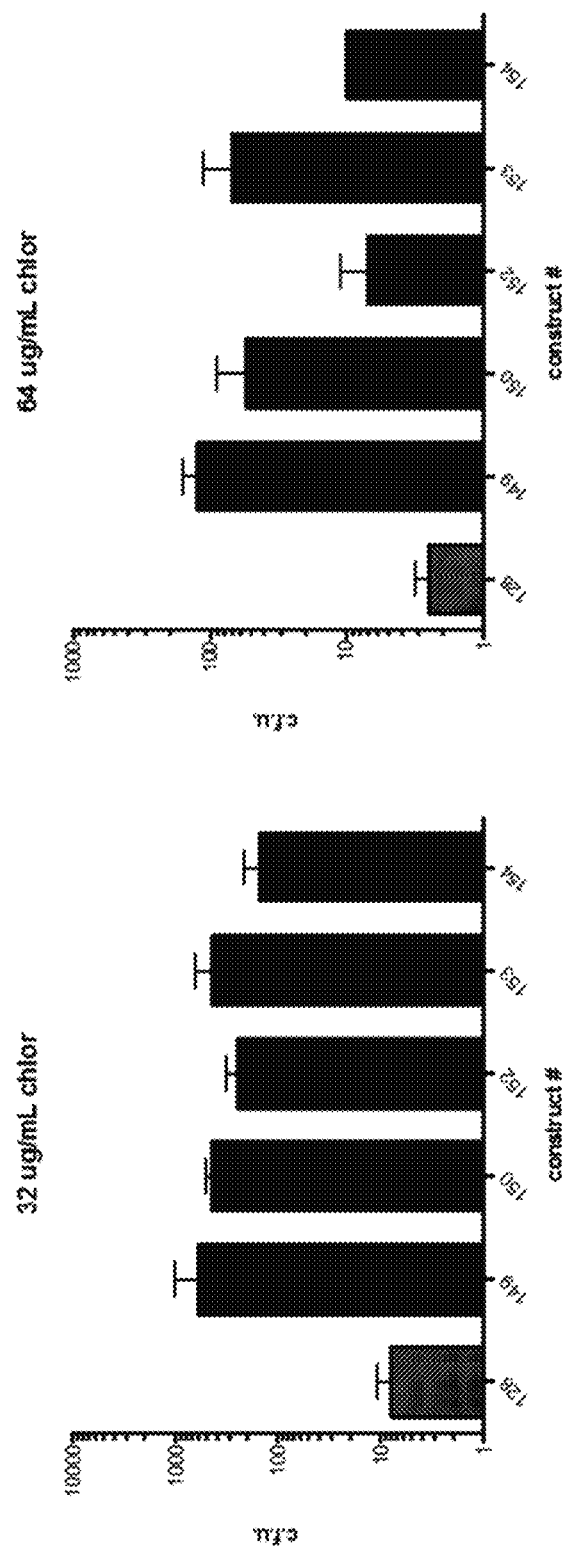
Figure 18:
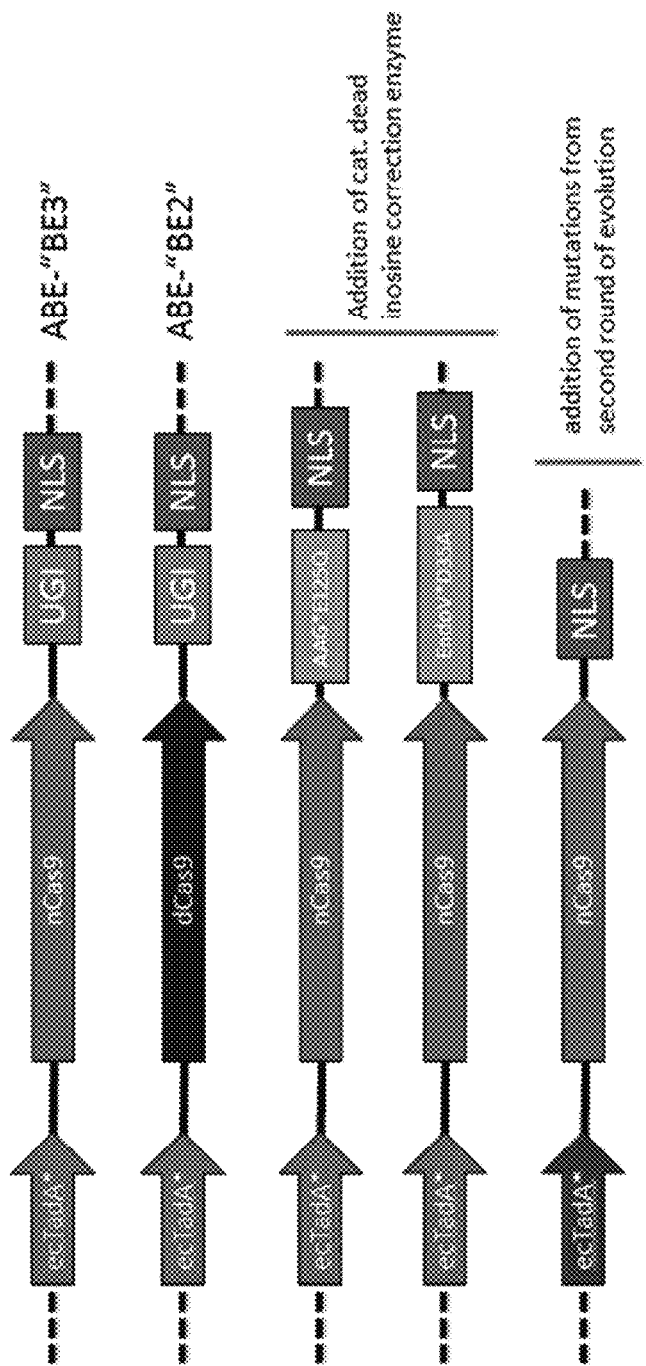
FIG. 18 show schematic representations of new constructs that were developed. New constructs include UGI, AAG*E125Q, and EndoV*D35A domains.

A second round of evolution was performed by evolving ecTadA containing a D108N mutation (see construct 3, clone 5, as listed in FIG. 11 (pNMG-128), which was identified from first round of evolution. pNMG-128 also contains mutations H8Y and N127S, which are "hitch-hiker" mutations. The evolved clones of the resulting library were challenged with 32, 64 and 128 ug/mL chloramphenicol (higher stringency than 1st round evolution of 1, 2 and 4 ug/mL). Clones which survived on 32, 64 and 128 ug/mL chloramphenicol were subcloned and re-plated, individual clones from this enrichment were isolated and assayed. The number of colony forming units (C.F.U) for each construct, pNMG-128 and pNMG 149-154, are shown in FIG. 17 under varying concentrations of chloramphenicol. A second round of evolution with high stringency conditions resulted in a high frequency of mutations at D147 and E155 of ecTadA, which are highlighted in FIG. 16.

Figure 23:
FIG. 23 shows inactive C-terminal Cas9 fusions of ecTadA for constructs pNMG-164 through pNMG-173. The sequence corresponds to SEQ ID NO: 41.
Figure 24:
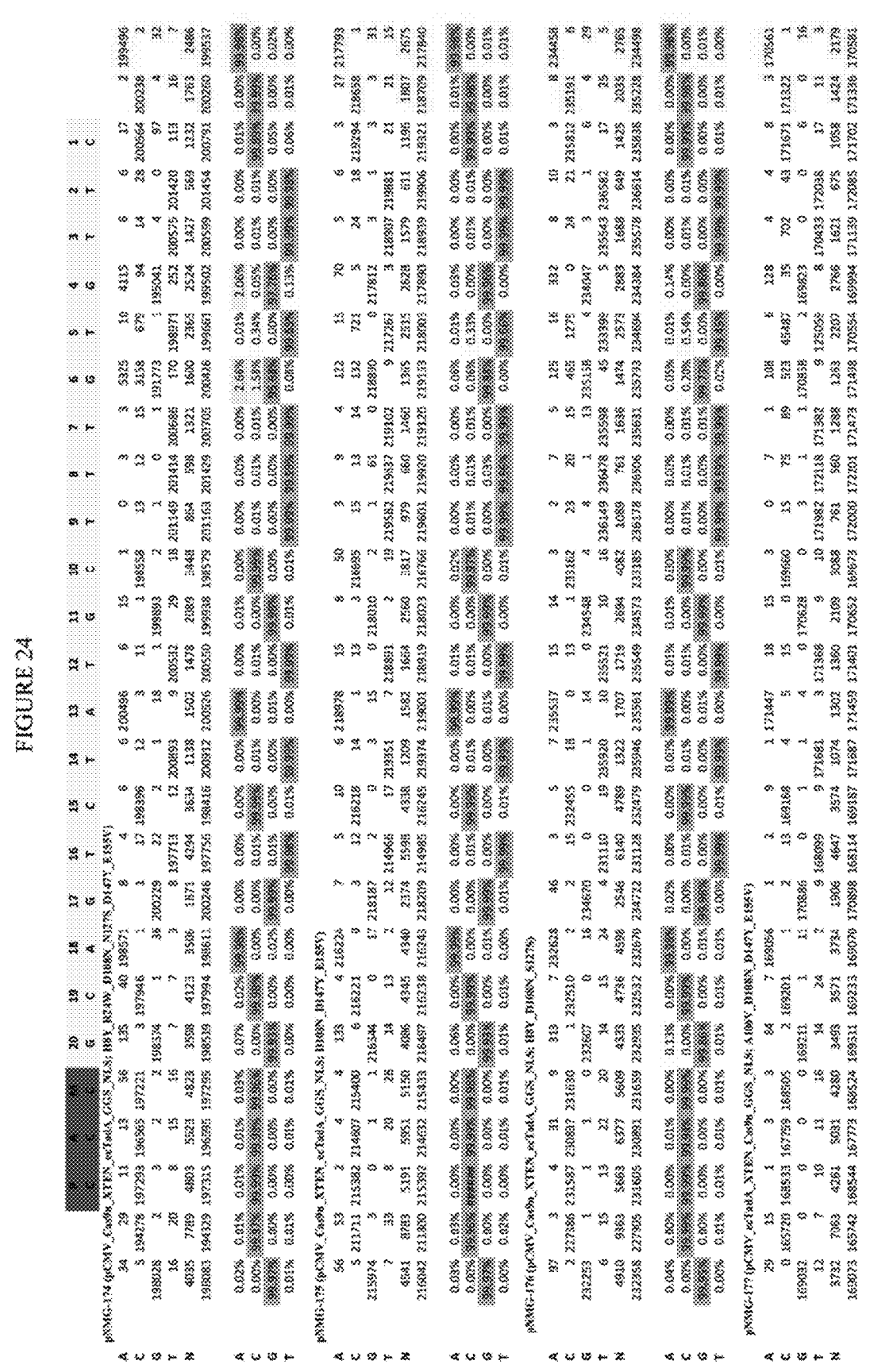
Figure 25:
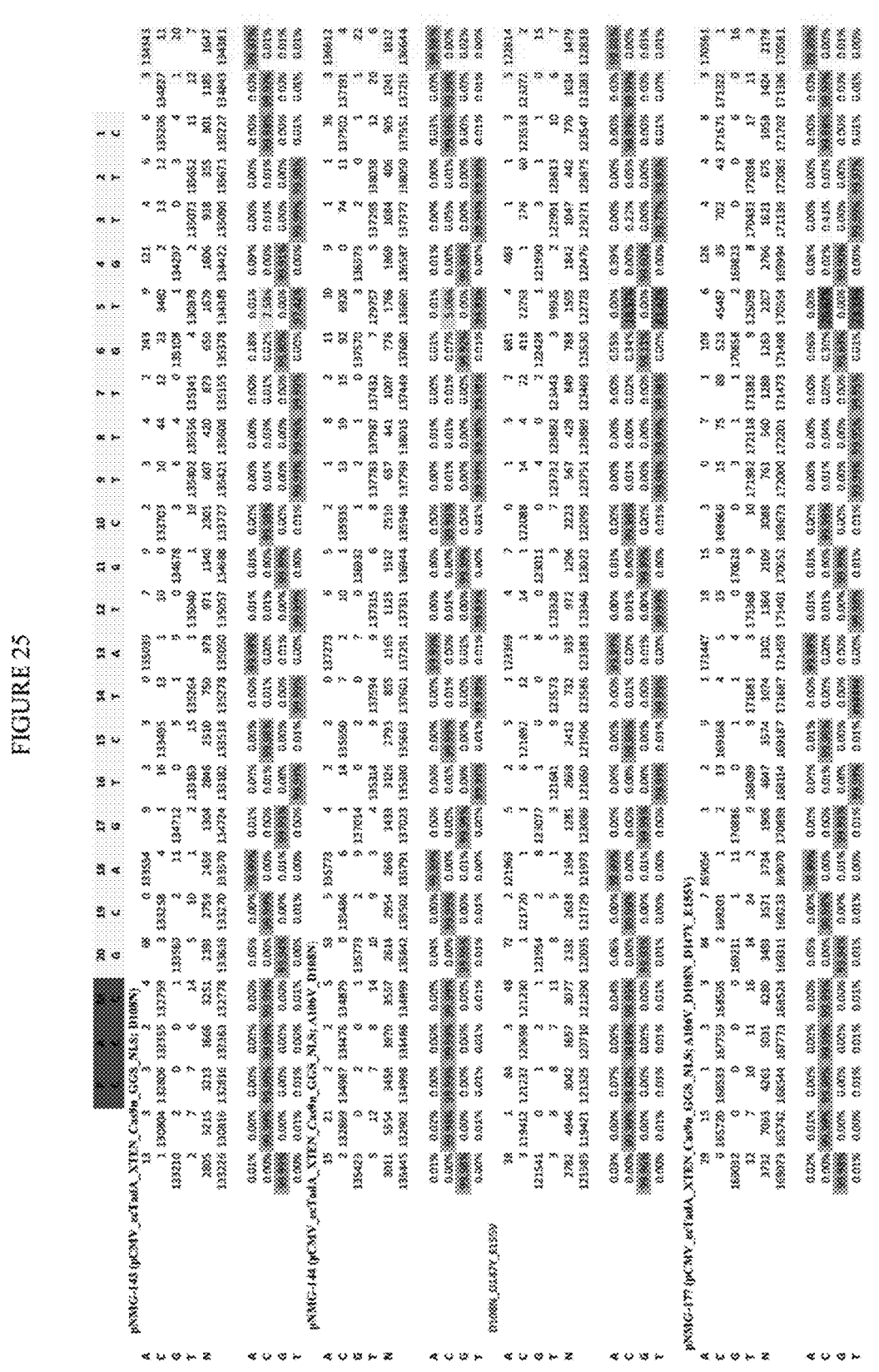
Figure 26:
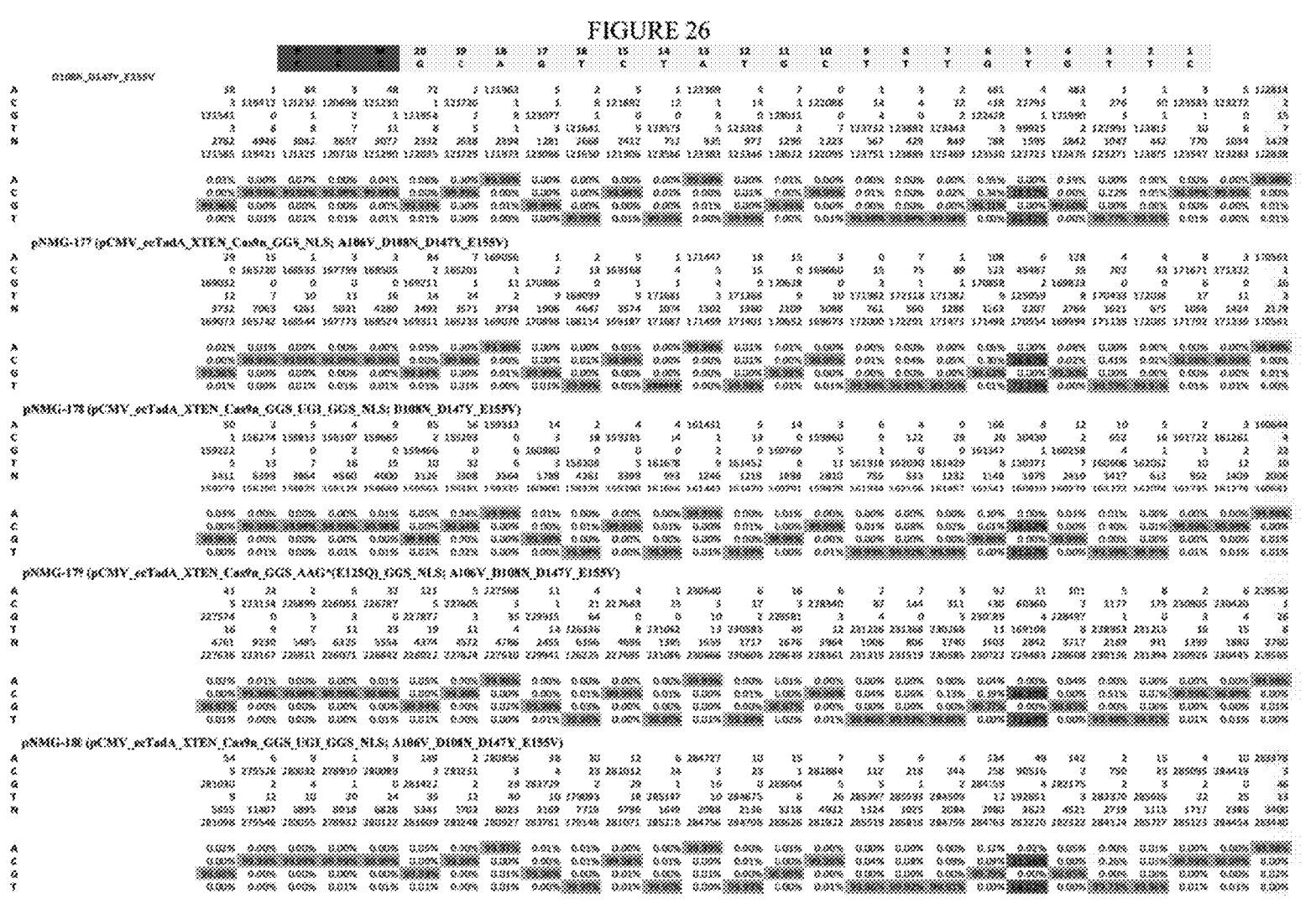
Figure 27:
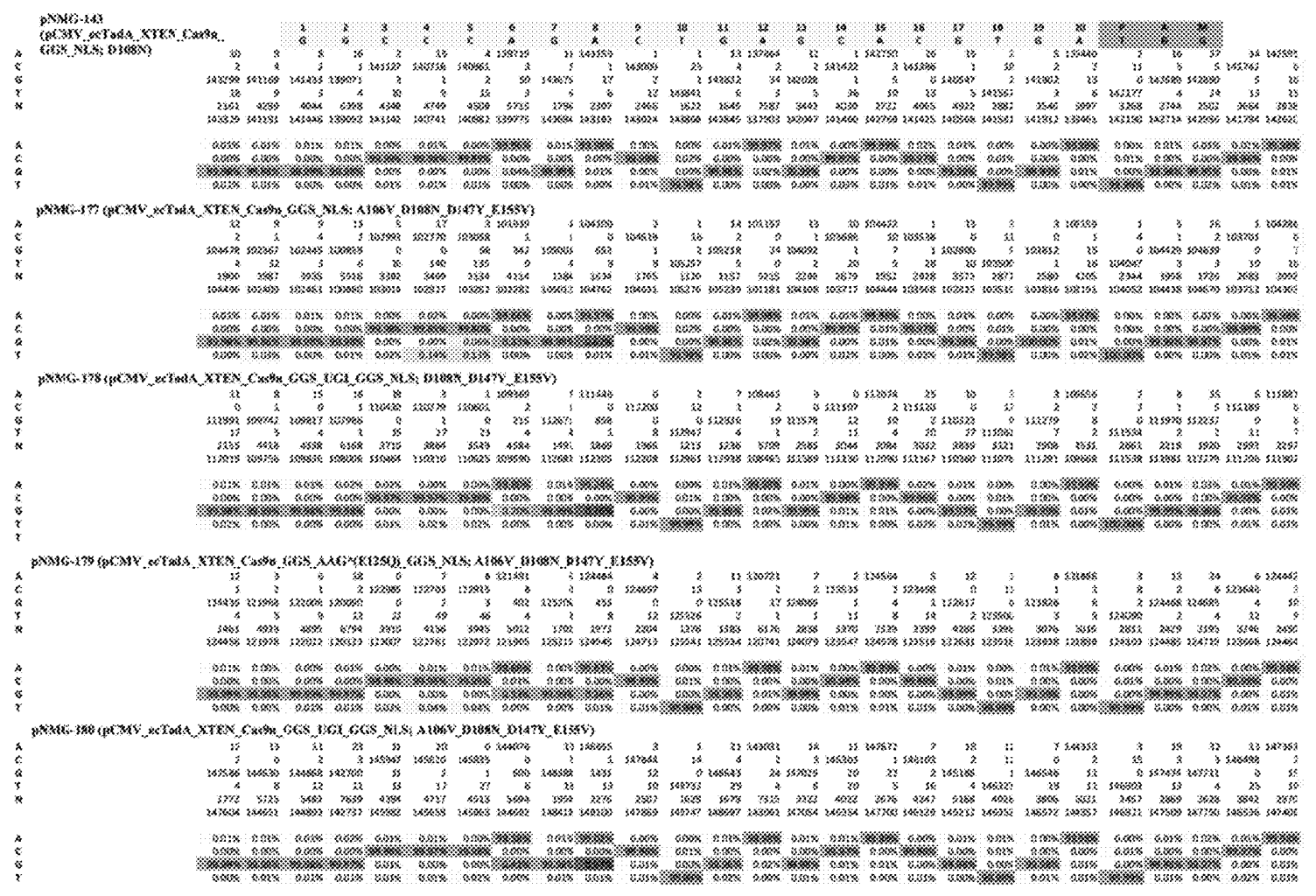
Figures 53, 54, 55:
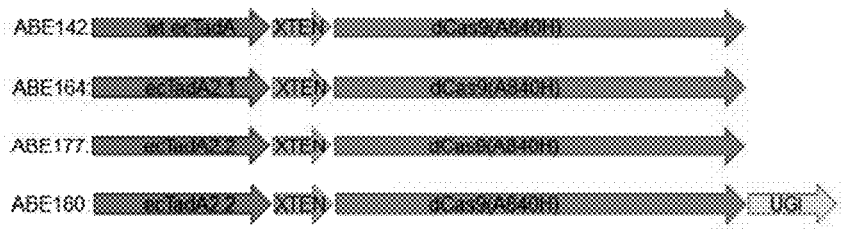
FIG. 53 shows the results of using mutated D108 residues to cause deaminase to reject RNA as a substrate and change the editing outcome.
FIG. 54 shows constructs developed for fusions at various sites.
FIG. 55 shows the protospacer and PAM sequences of base editing sites set forth in SEQ ID NOs: 6, 358, 359 from top to bottom, respectively.

FIGS. 23-27 show the results of transfections of various ABE constructs into Hek293T cells, using a gRNA to direct the editor to the various genetic loci. FIG. 23 shows pNMG-164, 171, 172, and 173 editing on Hek-2. FIG. 24p shows NMG-174-177 editing on Hek-2. FIG. 25 shows pNMG 143, 144, 164, 177 editing on Hek-2. FIG. 26 shows pNMG-164, pNMG-177, pNMG-178, pNMG-179, and pNMG-180 editing on Hek-2. FIG. 27 shows pNMG-164, 177-180 editing on Hek-2.

Regarding FIGS. 28-45, mammalian codon optimized constructs of ecTadA containing mutations at D108, (in some cases the mutations included the following: D108N, D108G, D108V) were used to probe whether D108 mutations identified in the first round of evolution also catalyzed A to G reversion in mammalian cells. Constructs pNMG-142-147 were transfected into Hek293T cells, and showed the greatest amount of A to G editing efficiencies at position #5 of the Hek-2 site, with low to no editing of adenines at any other sites. Exemplary DNA sequences that were targeted are described below as HEk2 (SEQ ID NO: 41), Hek3 (SEQ ID NO: 42), Hek4 (SEQ ID NO: 43), RNF2 (SEQ ID NO: 44), FANCF (SEQ ID NO: 45), and EMX1 (SEQ ID NO: 46). Subsequent experiments and evolutions have increased the editing efficiencies and identified that the editing window generally occurs at positions 4-6 in the protospacer and with a surrounding sequence of "YAC"; where "Y" is a pyrimidine (T or C) base and the underlined nucleotides, in the sequences below, is the PAM sequence. For the Hek2 sequence (SEQ ID NO: 41), shown below, the protospacer positions are indicated as 1-20 going from right to left. Position 5 of the protospacer at the Hek2 site is a T, which is opposite the A that may be edited by any of the adenosine deaminases described herein. For the Hek3, Hek4 RNF2, FANCF and EMX1 sequences (SEQ ID NOs: 42-46), shown below, the protospacer positions are indicated as 1-20 going from left to right. For these sequences one or more of the adenines (As), such as the A at position 6 of the Hek3 site (SEQ ID NO: 41), may be edited by any of the adenosine deaminases described herein. It should be noted that transfection of pNMG-142 (wild-type ecTadA fused to nCas9) produced no observable amounts of editing, underscoring the importance and necessity of implementation of the mutations arising from the directed evolution experiments.

Target sequences used in the Examples are provided below (PAM sequences are underlined in bold):

Hek2:
(SEQ ID NO: 41)
CCCGCAGTCTATGCTTTGTGTTC

Hek3:
(SEQ ID NO: 42)
GGCCCAGACTGAGCACGTGATGG

Hek4:
(SEQ ID NO: 43)
GGCACTGCGGCTGGAGGTGGGGG

RNF2:
(SEQ ID NO: 44)
GTCATCTTAGTCAGGACCTGAGG

FANCF:
(SEQ ID NO: 45)
GGAATCCCTTCTGCAGCACCTGG

EMX1:
(SEQ ID NO: 46)
GAGTCCGAGCAGAAGAAGAAGGG

Engineering Adenosine Base Editors with Domains that Inhibit Reversion of Inosine to Adenine It was hypothesized that blocking inosine reversion to adenine, for example as a result of endogenous hAAG activity, could improve base editing efficiency. Accordingly, experiments were performed to examine the effect of adding a catalytically inactive alkyl adenosine glycosylase to the C-terminal end of ABE editors. Base editor 3 (BE3) in these transfections served as the positive control for C to G base editing, pNMG-142 is the negative control, pNMG-143 is an evolution round #1 construct, pNMG-144 (D108N) is another evolution round #1 construct (A106V_D108N). The mutations in the pNMG-156 construct are all mutations identified from the highest frequency amplicons resulting from the first round of ecTadA bacterial evolution (including "hitch-hicker" mutations). Hitch-hiker mutations refer to mutations that were identified in evolution experiments, but may not have a significant effect on adenosine base editing. A method for identifying hitch-hiker mutations is to do reversion analysis and then re-assay the construct to determine whether the mutation has an effect on base editing. pNMG-156 is the mammalian codon-optimized version of pNMG-128 (the bacterial vector I isolated in the selection) with contains a C-terminal UGI. pNMG-160 is the equivalent of pNMG-143 having a catalytically inactive AAG (E125Q), pNMG-161 is pNMG-143 having a catalytically inactive Endo V (D35A). Mutations E125Q and D35A correspond to the mutations in the catalytically dead AAG and EndoV open reading frame (ORF), respectively. pNMG-162 thas the same construct architecture as pNMG-156, except it does not contain UGI. The ability of these constructs to deaminate adenosine in the target sequences, HEk2 (SEQ ID NO: 41), Hek3 (SEQ ID NO: 42), Hek4 (SEQ ID NO: 43), RNF2 (SEQ ID NO: 44), FANCF (SEQ ID NO: 45), and EMX1 (SEQ ID NO: 46) is shown in FIGS. 28-33, respectively. In general, it was found that, for the constructs tested, incorporation of UGI, AAG(E125Q), or EndoV (D35A)C-terminal to the ecTadA and the Cas9 domain did not provide a significant increase in the efficiency of the base editors to generate an adenosine to guanine mutation.

Arranging the Adenosine Deaminase Domain Relative to the Cas9 Domain

Arrangement of the adenosine deaminase domain (e.g., ecTadA) relative to the Cas9 domain in adenosine base editors was tested. For example, it was tested whether placement of the adenosine deaminase N-terminal or C-terminal relative to a Cas9 domain affected base editing efficiency. Further, experiments including mutations from evolution #1 of ecTadA and evolution #2 of ecTadA were compared. See FIGS. 34-39. In general, the mutations identified in evolution #2 improved the editing efficiencies of the ABE editors identified in evolution #1. Additionally, it was found that adenosine base editors were active (mutated adenine to guanine) when the adenosine deaminase was arranged N-terminal to Cas9. Adenosine base editor constructs where the adenosine deaminase was arranged C-terminal to Cas9 showed little to no observable editing of adenine to guanine.

The following ABE constructs were transfected into Hek293T cells; pNMG-142, which served as a negative control (no mutations in ecTadA); pNMG-143 (where ecTadA has a D108N mutation), pNMG-144 (where ecTadA has a A106V, and a D108N mutation) and pNMG-164 (where ecTadA has a D108N, a D147Y, and a E155V mutation). These constructs were mammalian codon optimized constructs with mutations from evolution #1. Construct pNMG-171 served as a control for the C-terminal TadA fusion constructs of pNMG-172 to pNMG-176, which contain various ecTadA mutations. pNMG-171 contains a C-terminal wild-type ecTadA fusion to nCas9, whereas pNMG-172-176 contain mutations in TadA identified from evolution #1. pNMG-177 and pNMG-178 represent two mammalian codon optimized plasmids with mutations identified from evolution #2, where pNMG-178 contains a UGI domain. pNMG-179 and pNMG-180 are the same as pNMG-177 but with an added C-terminal catalytically inactive AAG (E125Q), and a UGI domain, respectively. The ability of these constructs to deaminate adenosine in the target sequences, HEk2 (SEQ ID NO: 41), Hek3 (SEQ ID NO: 42), Hek4 (SEQ ID NO: 43), RNF2 (SEQ ID NO: 44), FANCF (SEQ ID NO: 45), and EMX1 (SEQ ID NO: 46) is shown in FIGS. 34-39, respectively.

In general, it was found that fusing the adenosine deaminase (ecTadA) N-terminal to the Cas9, as opposed to C-terminal, yielded more efficient base editing of adenine. It was also found that ecTadA containing the mutations A106V, D108N, D147Y, and E155V performed better (e.g., edited adenine more efficiently) than the other ecTadA mutations tested in evolution #1 and evolution #2. Further, it was found that for the constructs tested, incorporation of UGI, or AAG(E125Q), in these constructs did not provide a significant increase in the efficiency of the base editors to generate an adenosine to guanine mutation.

Figure 40:
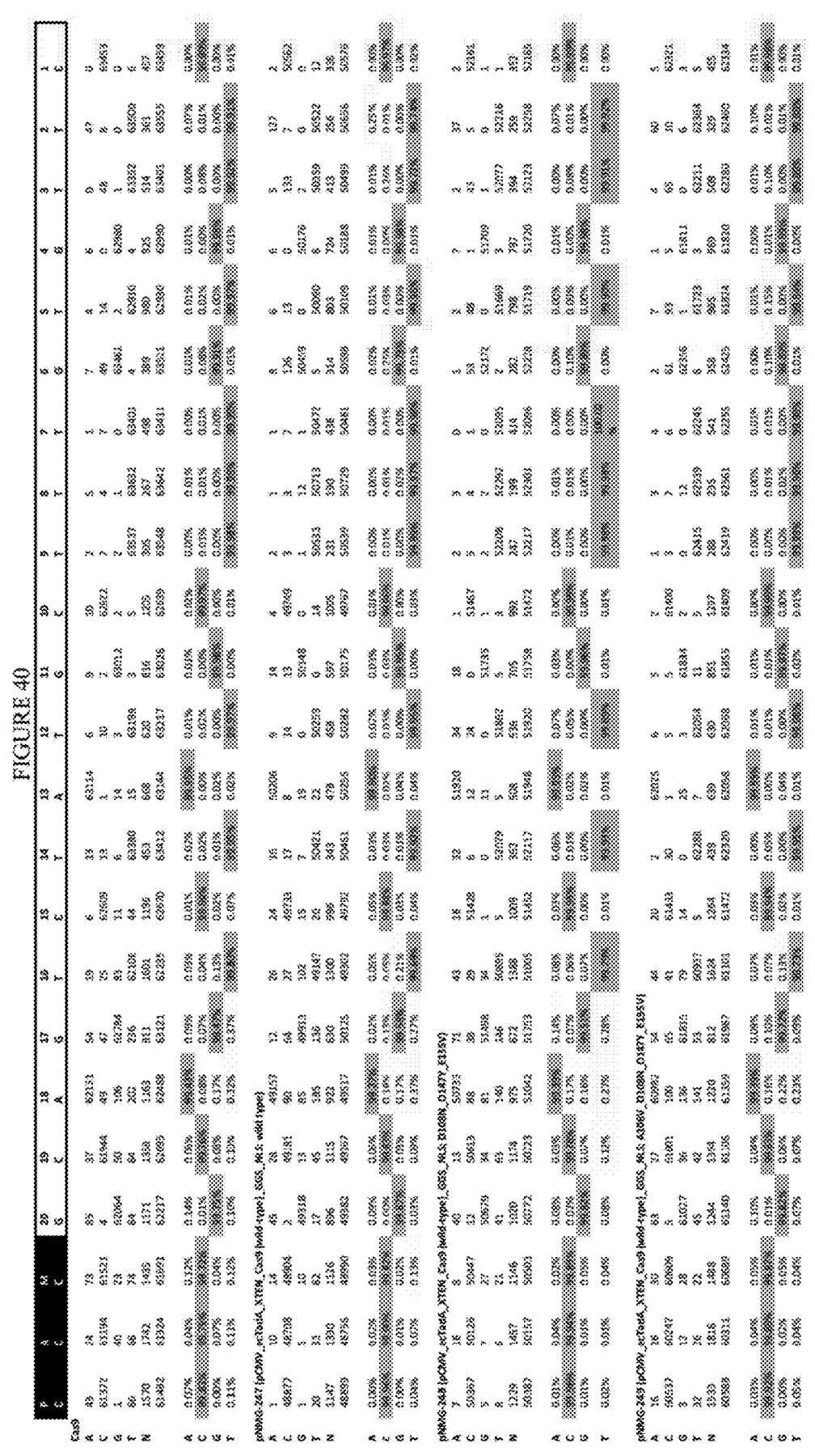
Figure 40:
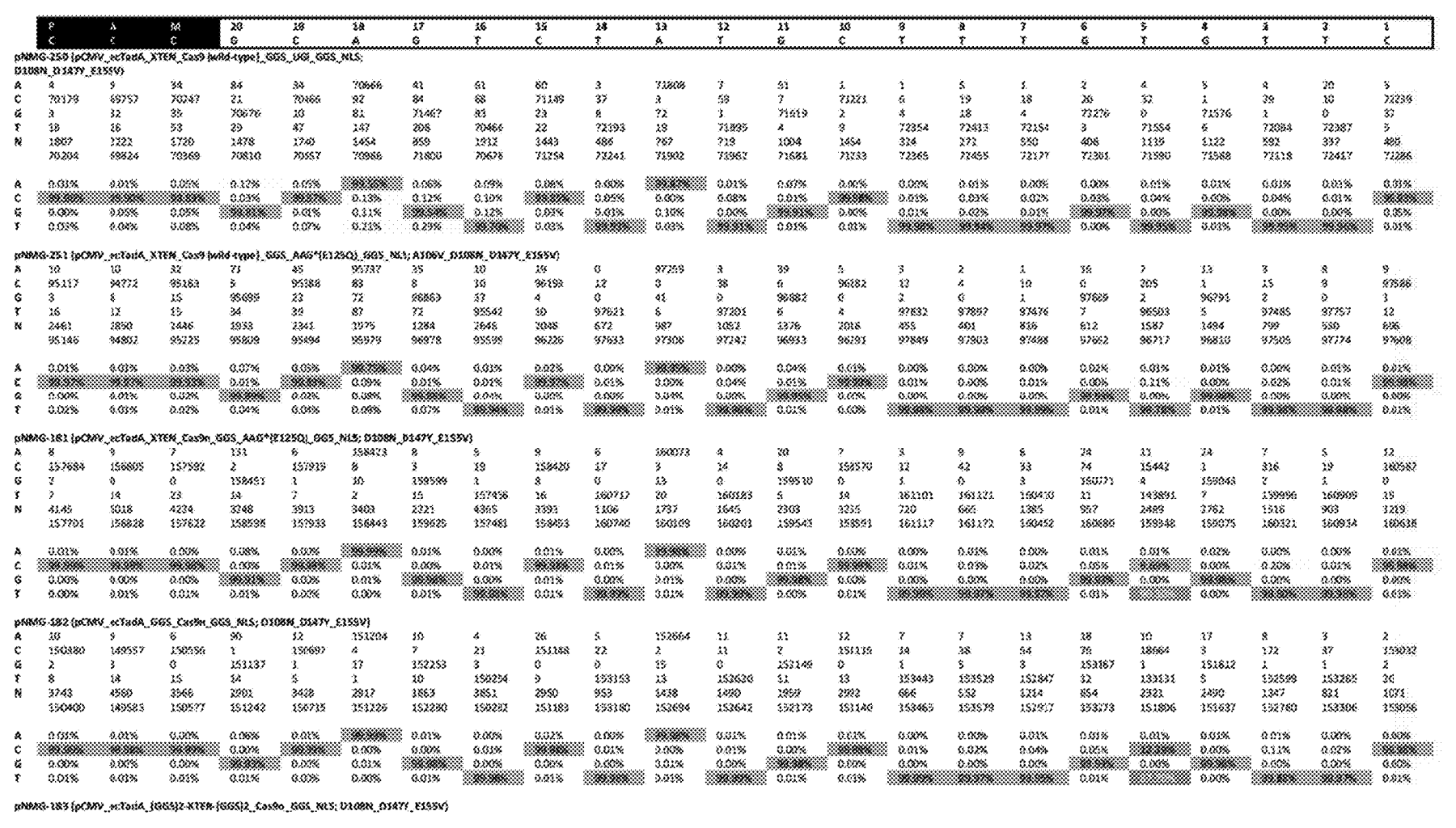
Figure 40:
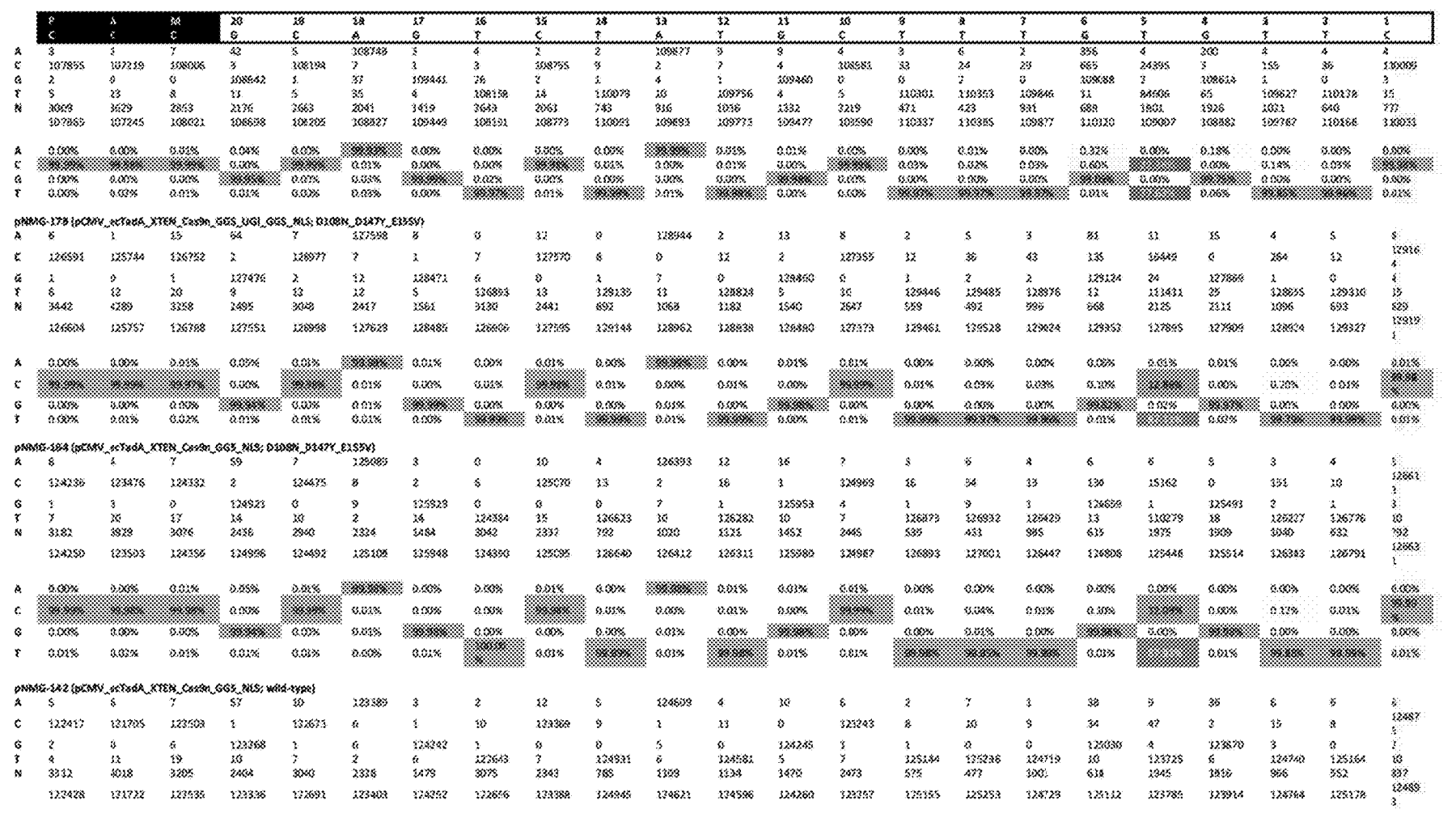
Figure 40:
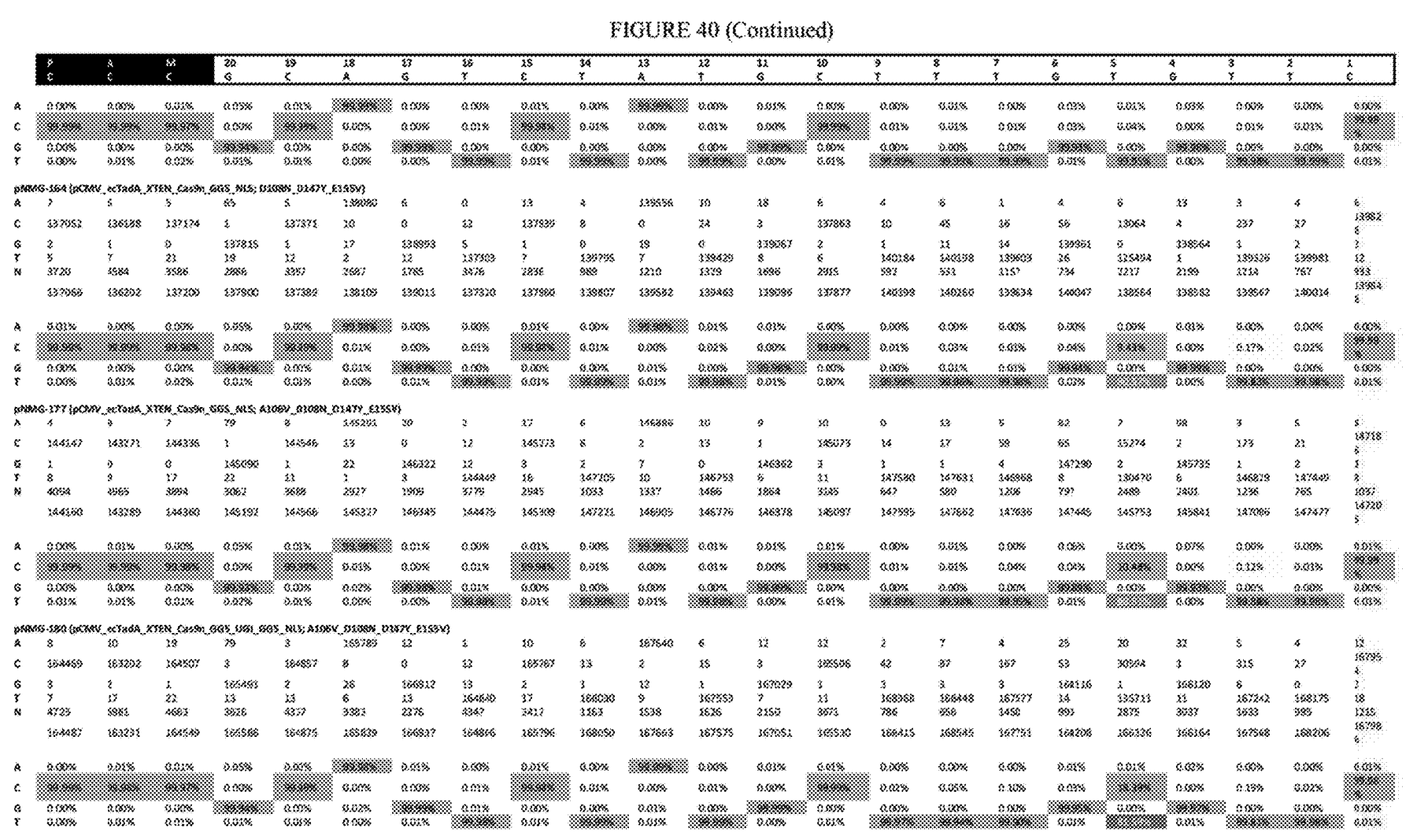
Figure 40:
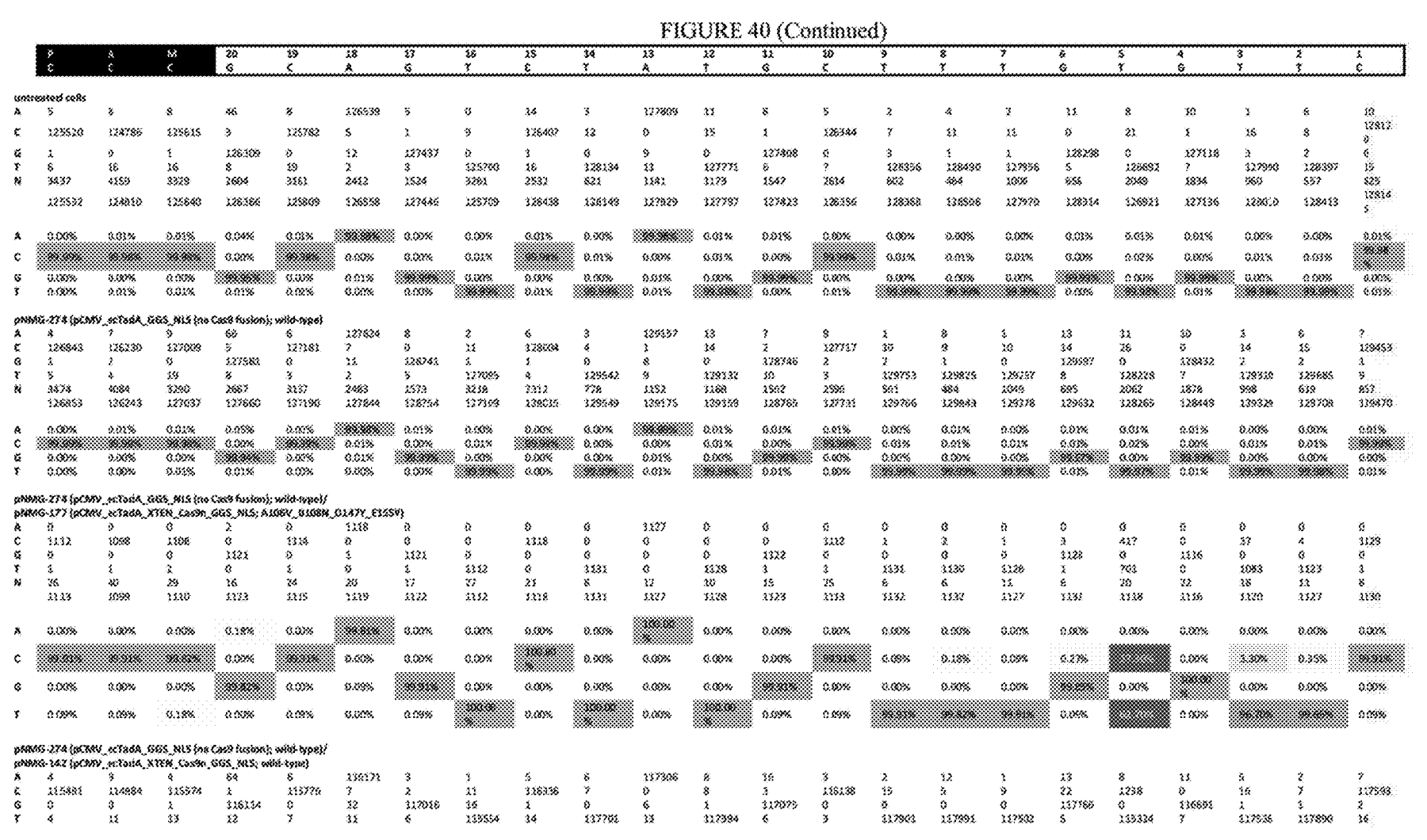
Figure 40:
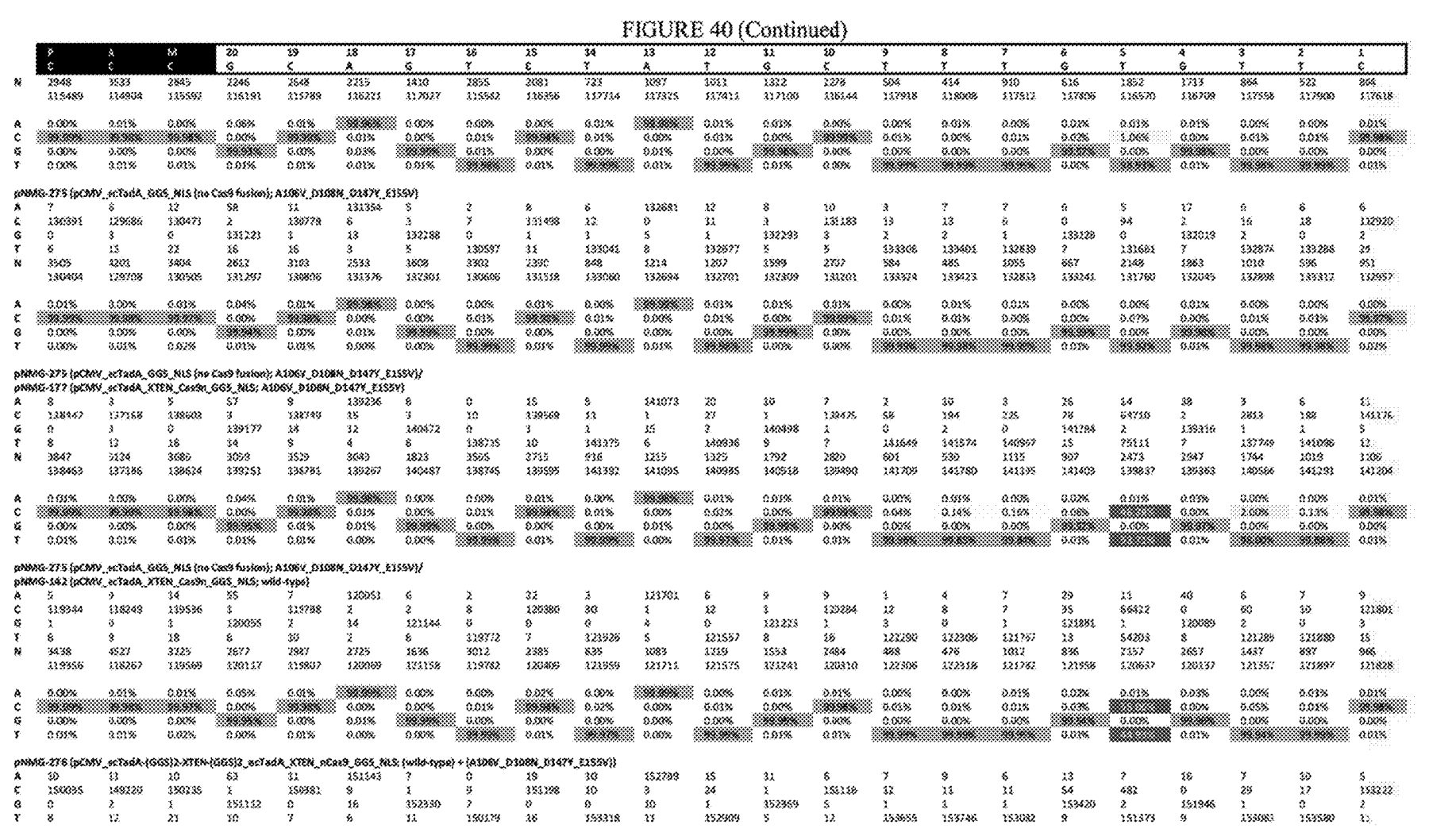
Figure 40:
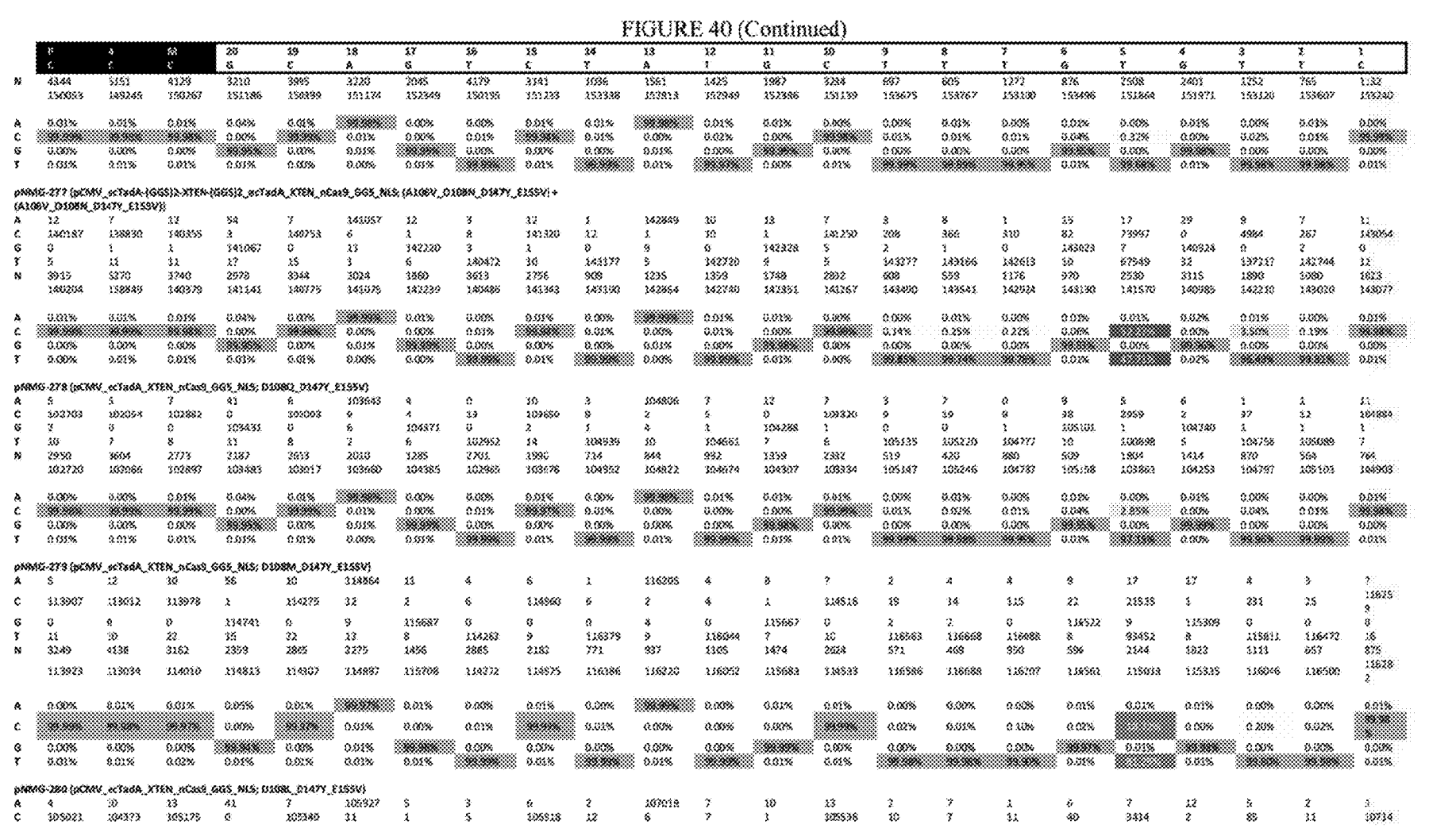
Figure 40:
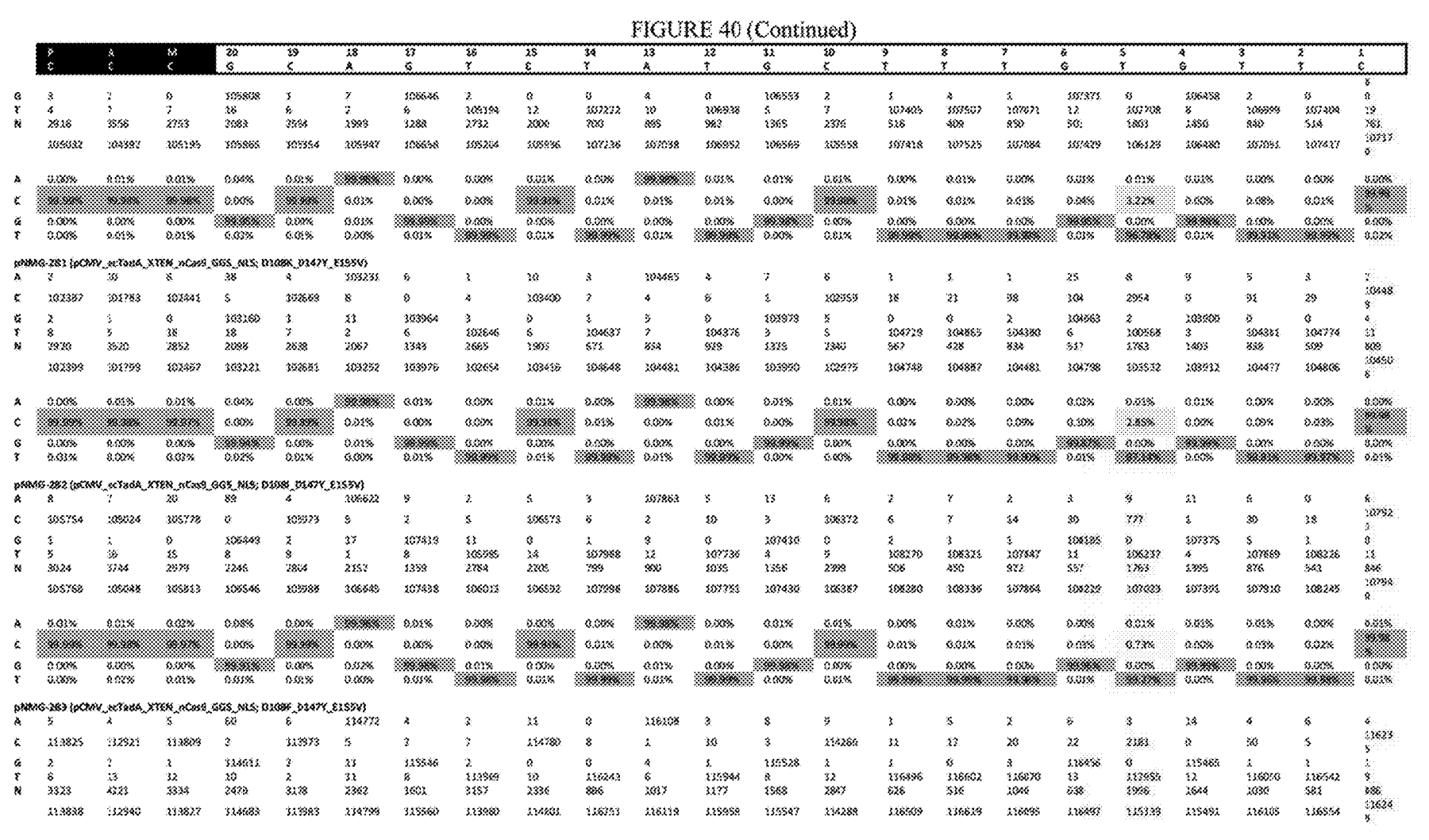
Figure 40:
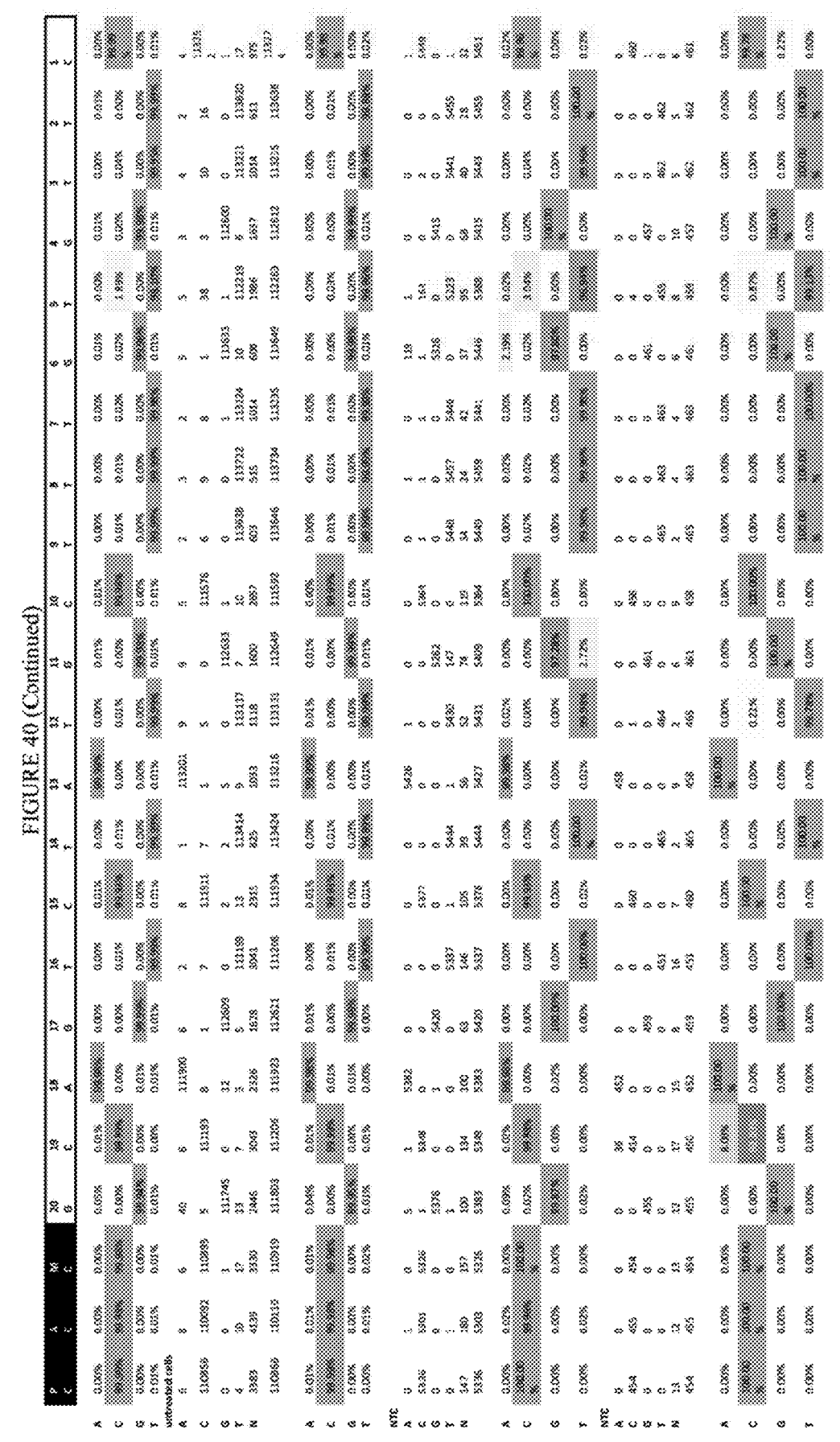

The transfection experiments shown in FIG. 40 were performed to determine four key points: One, whether ecTadA interferes with gRNA/Cas9 binding by deaminating As in the RNA of the guide. Two, whether a short linker (GGS only) or a long linker ((SGGS)$_2$—XTEN-(SGGS)$_2$) ((SGGS)$_2$) corresponds to SEQ ID NO: 2) between the evolved deaminase and Cas9 affects window size and/or overall editing efficiencies of ABE. Three, whether or not dimerization of evolved ecTadA improves ABE editing efficiencies. Four, if other substitutions at the position D108 in TadA could further enhance editing efficiencies. It was found that the ABE editors do not interfere with gRNA/Cas9 binding and that dimerization of ecTadA does improve editing efficiencies. To test whether ABE interferes with gRNA/Cas9 binding nCas9 was replaced with wild-type Cas9 in various evolved ABE constructs (pNMG-247-251) and compared INDEL rates to Cas9 (wt) only INDEL rates (see FIG. 48). A to G editing efficiencies are undetectable in FIG. 40 for pNMG-247-251, likely due to wild-type Cas9 nuclease activity. It was also determined that the long linker between the evolved ecTadA and nCas9 (pNMG-183) yielded higher editing efficiencies relative to XTEN only and GGS only linkers. Most strikingly, dimerization of the ecTadA unit of ABE was tested both in trans by co-transfecting equimolar amounts of ecTadA (with and without mutations from evolution) with ABE editors pNMG-142 (neg control), pNMG-177 (A106V_D108N_D147Y_E155V) and in cis by making editors in which two untis of ecTadA were covalently tethered (with a (SGGS)$_2$—XTEN-(SGGS)$_2$ linker). Monomeric units used for in trans dimerization experiments are pNMG-274 and pNMG-275. Covalent fusions of two untis of ecTadA in the ABE editor are represented in pNMG-276 (negative control, two units of wild-type TadA in the ABE editor) and pNMG-277. Lastly, transfections with plasmids pNMG-278-283, which represent ABE editors that have varying mutations at D108 position in ecTadA (e.g. D108M, D108Q, D108K, etc), showed that the D108N substitution originally identified in round #1 evolution is the best performing mutation at this position.

Example 3—Development of Adenosine Base Editors (Evolution #3)

An ecTadA construct with the consensus mutations A106V, D108N, D147Y (pNMG-184) and E155V was mutagenized with error-pone PCR and the resulting ABE library was targeted with 2 separate gRNAs to two different sites in a kanamycin resistance gene which require two A to G reversions (both in premature stop codons) to conder kanamycin resistance. The 2 gRNA/2 target approach was used to increase the stringency of the selection. This evolution resulted in the identification of the following new mutations: L84F, H123Y and I157F.

Deaminase Editing sgRNA

During the development of ABE, it was questioned whether or not the deaminase was editing the sgRNA and did TadA still have RNA activity. Based on the results shown in FIG. 48, fusions appeared to bind well, but there was no significant difference between ABE and Cas9 indel percentage. This demonstrates that ABE is not interfering or modifying the gRNA strand. Differences between wt Cas9 only and ABE fused to wild-type Cas9 would suggest deaminase interference with the gRNA. This was not the case.

It was also questioned whether or not D108 residue could be further mutated to cause deaminase to reject RNA as a substrate. The sgRNAs encoding sites can be found in FIG. 51. Results have shown that a D108M mutation in ecTadA does not significantly improve editing efficiency of the adenosine base editors.

It was found that tethering an additional unit of the mutant TadA to the ABE results in higher editing efficiencies for deamination of the DNA. Tethering an AAG, a base excision repair enzyme, to ABE did not significantly enhance base editing. Tethering catalytically inactivated EndoV, the E. Coli DNA repair enzyme, to ABE also did not significantly enhance base editing. Furthermore, knock-out cell lines of AAG (which revert inosine back to A) had no better editing efficiencies than the parent strain.

Figures 56, 57, 58:
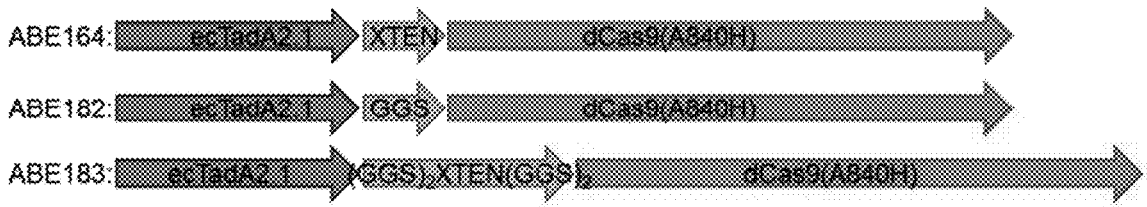
FIG. 56 shows the results of ABE on HEK site 2.
FIG. 57 shows the results of ABE on HEK site 2.
FIG. 58 shows constructs developed for fusions at various sites using various linker lengths.
Figure 61:
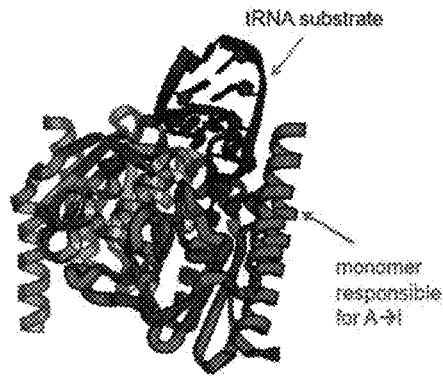
FIG. 61 is a schematic showing the dimerization of deaminase.
Figure 62:
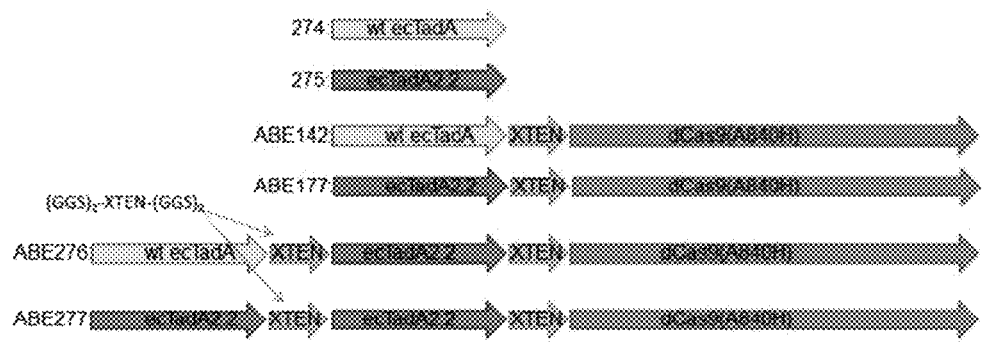
FIG. 62 shows constructs developed for fusions at various sites using various linker lengths.

A next goal was to determine why ABE edit more efficiently on the HEK site 2 than on other sites tested. While adenosine base editors worked well at all sites, they worked optimally at the Hek-2 site. It was theorized that ABE worked best on HEK site 2 due to an abundance of adenine residues. Results shown in FIG. 57 show that this is not the case. Another theory was that linker length could be why ABE only worked on the HEK site 2. Results shown in FIG. 59 and FIG. 60 proved inconclusive. The longest linker to Cas9 between ecTadA and Cas9 enhanced editing efficiencies but did not seem to expand the base editing window. It was also tested whether an ABE efficiently edited Hek-2 similar sites and it was found that there was very efficient editing at Hek-2 similar sites. From this data it was found that the ABEs edited adenines more efficiently when they were part of a "YAC" consensus sequence, where Y is C or T. Also, the tRNA substrate of ecTadA is in the context of "U-A-C" which is YAC.

Figure 63:
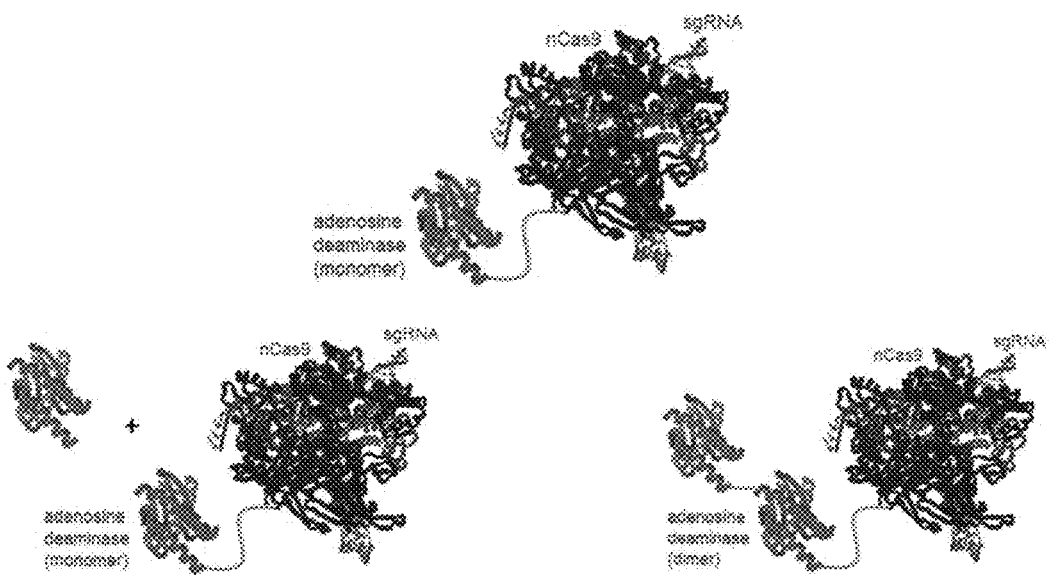
FIG. 63 shows the current editor architecture (top panel), the in trans dimerization (bottom panel, left), and the in cis dimerization (bottom panel, right).
Figures 64, 65:
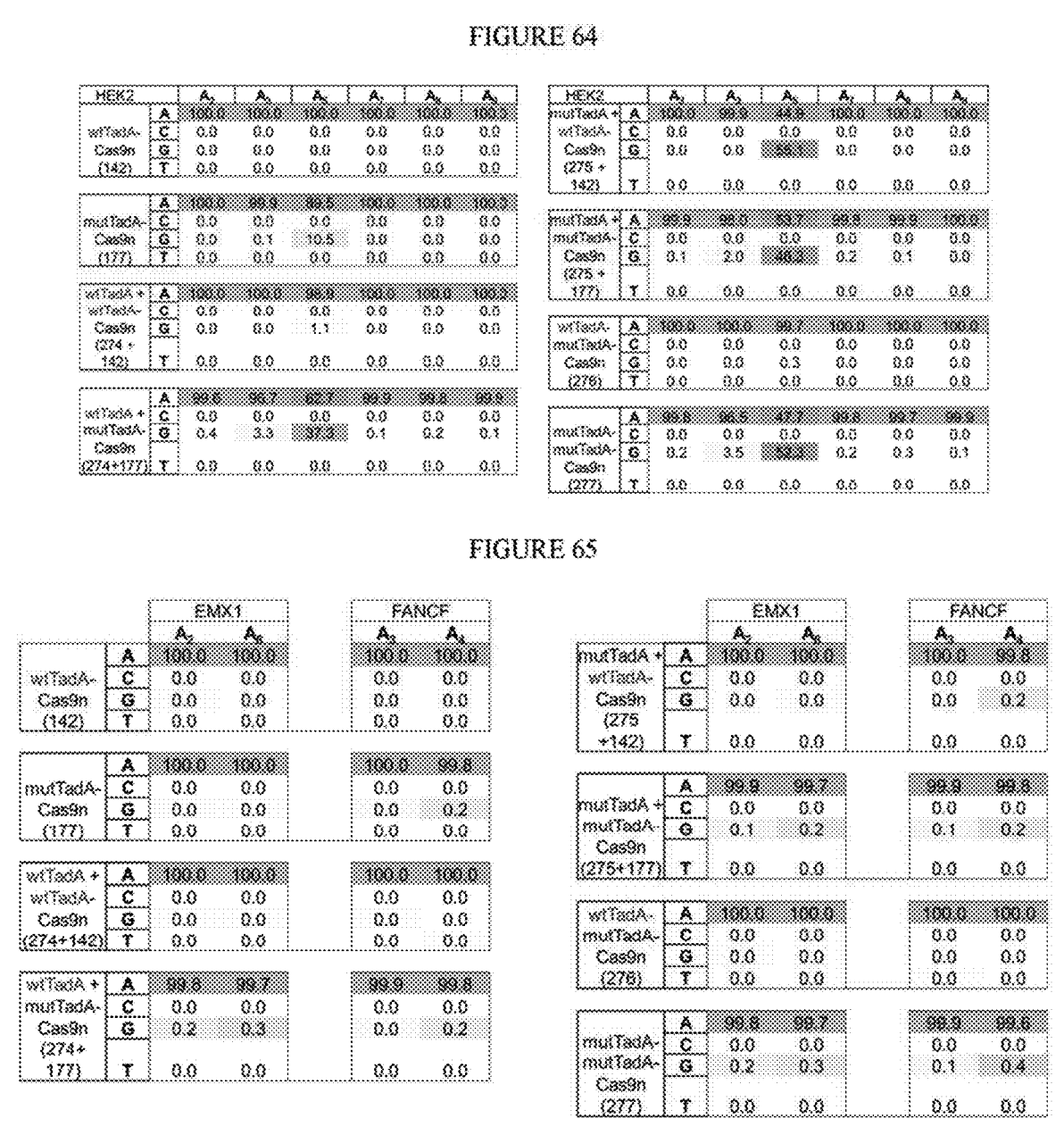
Figures 66, 67:
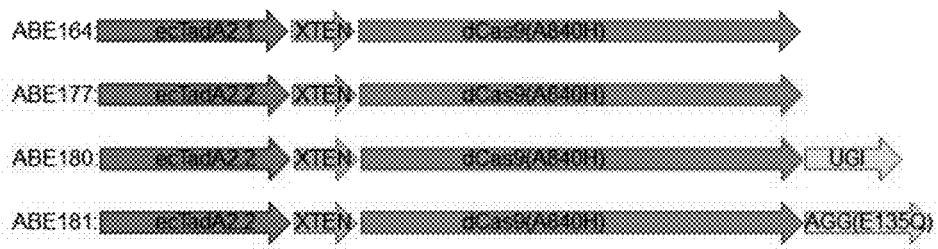
FIG. 66 shows dimerization results from base editing.
FIG. 67 shows constructs developed for fusions at various sgRNA sites.
Figure 68:
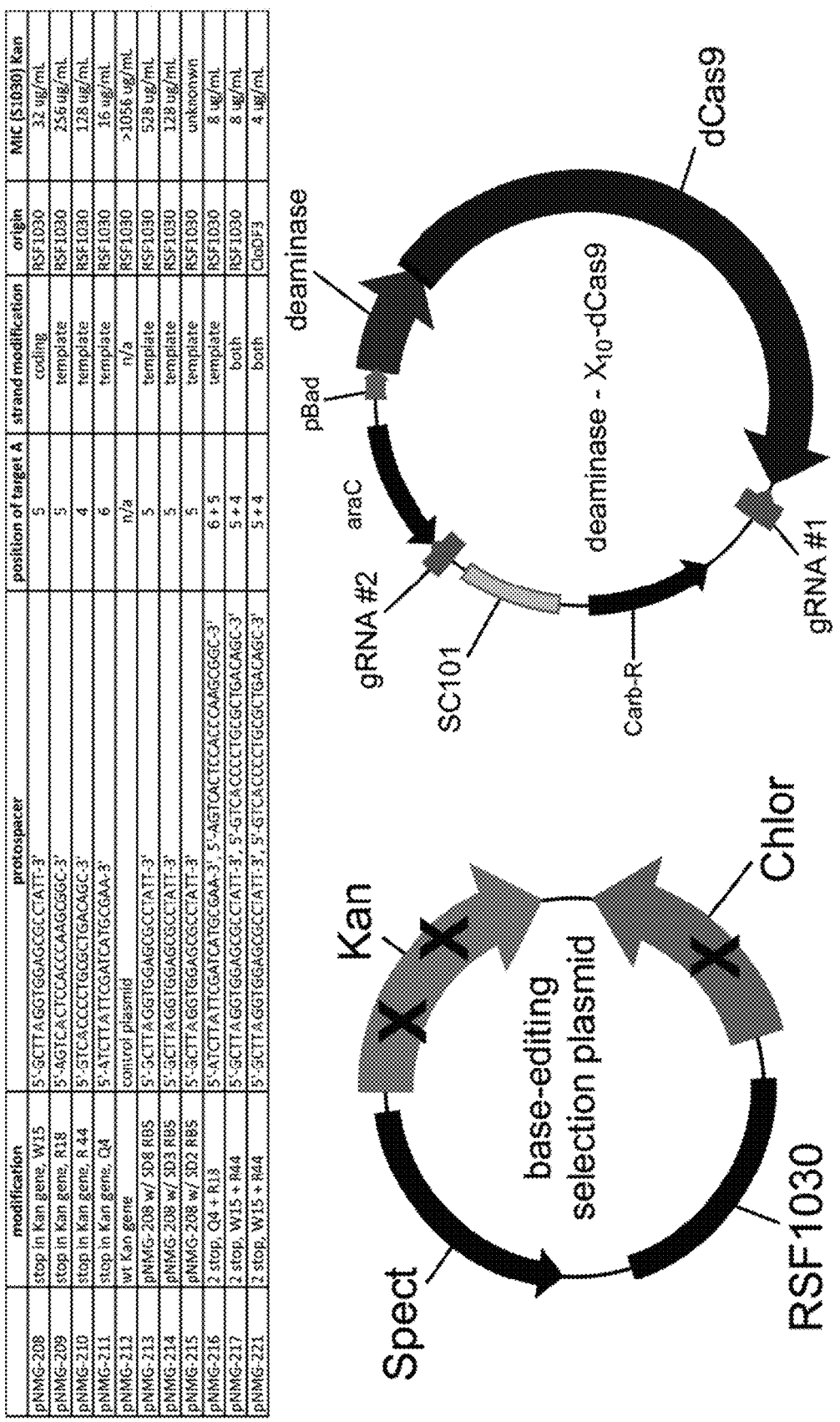
FIG. 68 shows the evolution of ABE editor against new selection sequences. The sequences from top to bottom and left to right correspond to SEQ ID NOs: 707-719, respectively.

It has been suggested that dimerization of the deaminase may improve base editing. The current editor architecture, in trans dimerization, and in cis dimerization are shown in FIG. 63 (top structure, bottom left structure, and bottom right structure). Results shown in FIG. 64 through FIG. 66 show that dimerization of the deaminase improved base editing. With respect to the "YAC" sequence specificity, one hypothesis, supported by the data, is that ABE operates best on As in positions 4-6 of the protospacer and with a surrounding sequence of "YAC"; target A underlined, where Y is C or T.

Evolving ABE Editor Against New Selection Sequences

Figure 69:
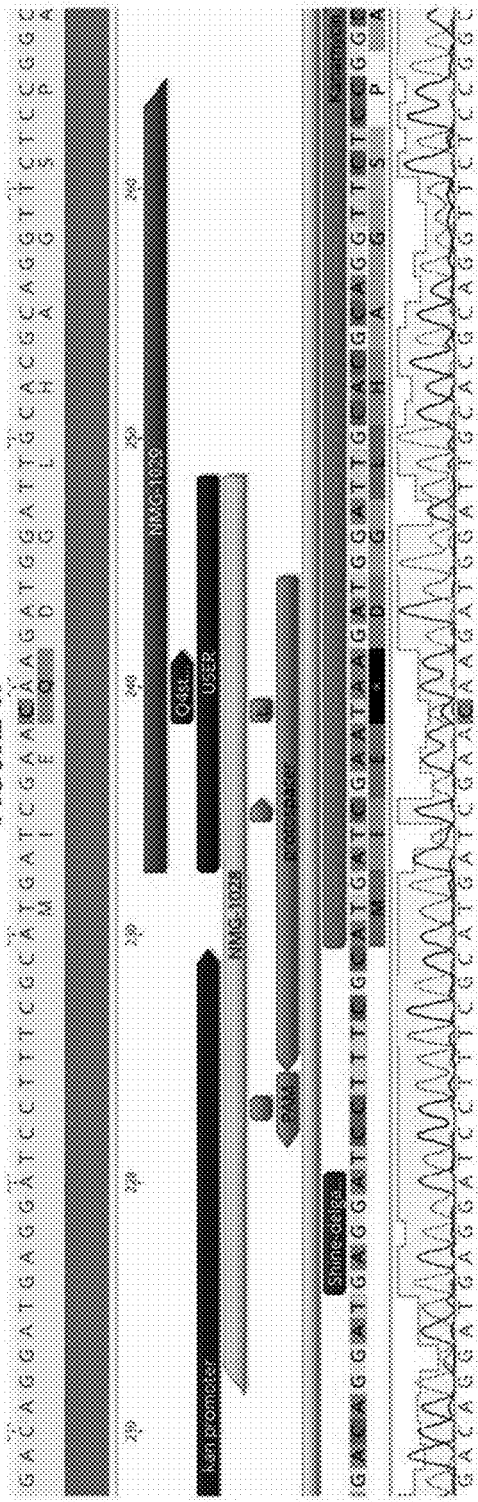
FIG. 69 shows the current editor targeting Q4 stop site. The sequences from top to bottom and left to right correspond to SEQ ID NOs: 624-627, 5527, and 628.
Figure 70:
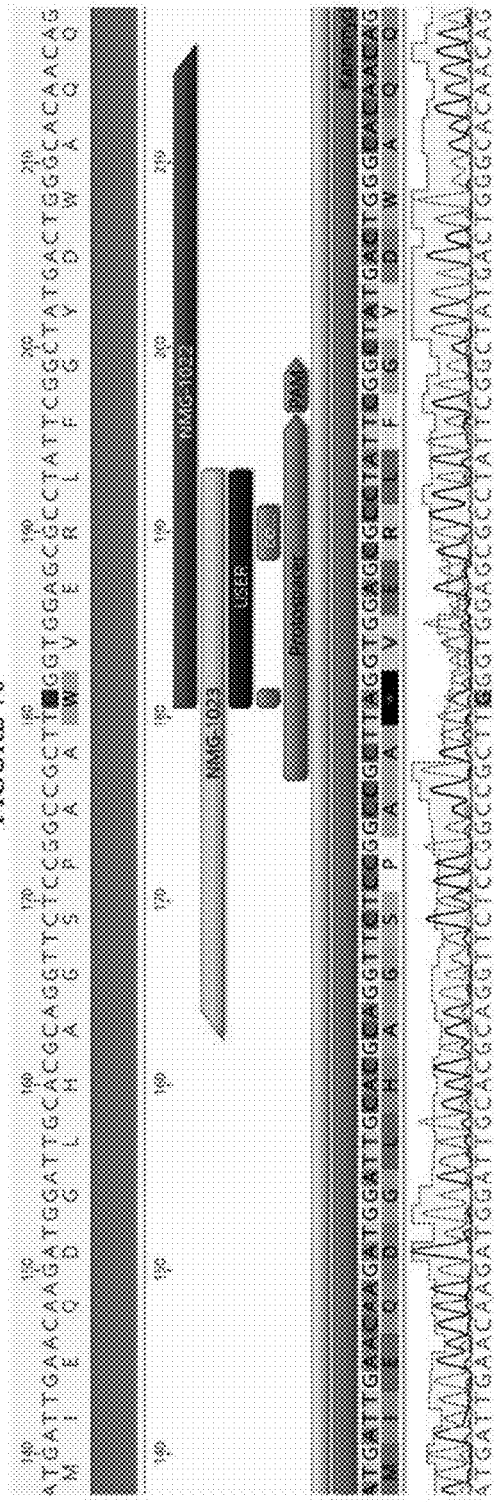
FIG. 70 shows the current editor targeting W15 stop site. The sequences correspond to SEQ ID NOs: 629-632, 5528, and 633 from top to bottom and left to right, respectively.
Figure 79:
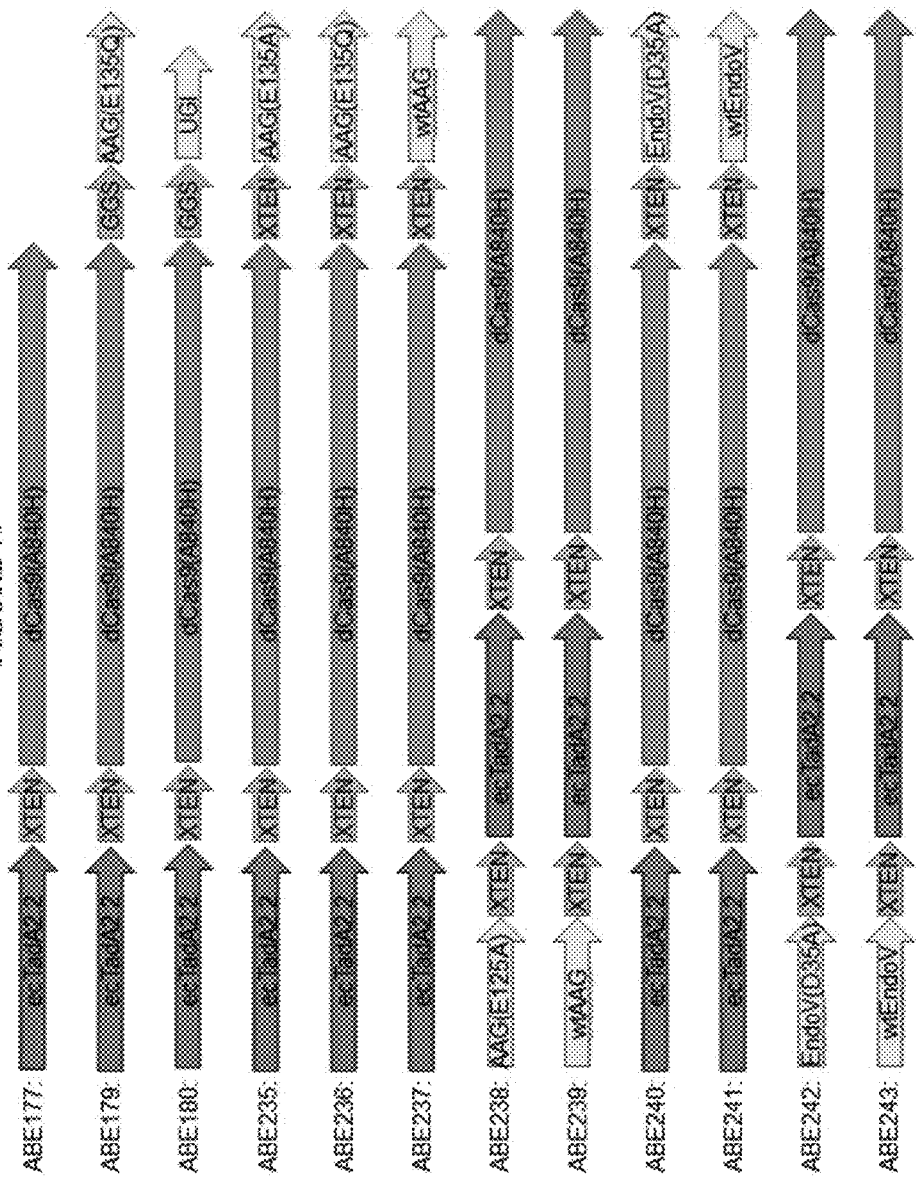
FIG. 79 shows the constructs of all inhibitors tested.
Figures 80, 81:
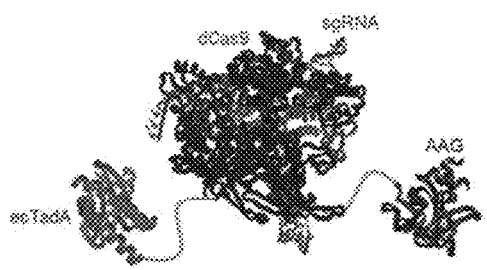
FIG. 80 shows the constructs used when tethering AAG to ABE.
FIG. 81 is a schematic showing the tethering of AAG to ABE.
Figures 82, 83:
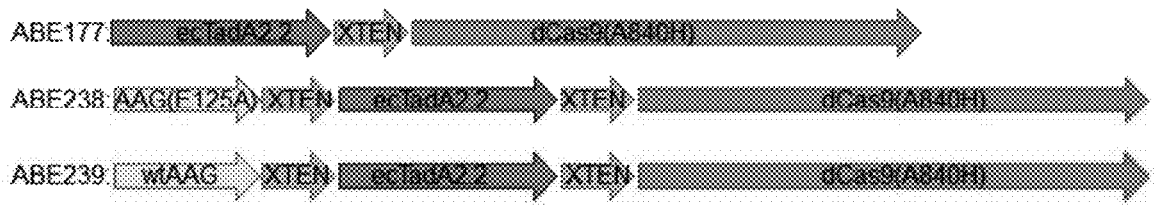
FIG. 82 shows the results of tethering AAG to ABE.
FIG. 83 shows the constructs used when tethering AAG to ABE with an N-terminus of TadA.
Figures 84, 85:
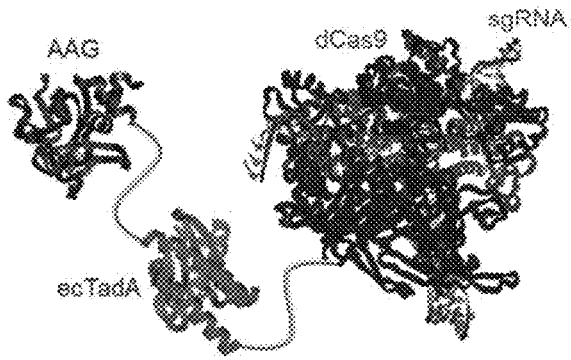
FIG. 84 is a schematic showing the tethering of AAG to ABE with an N-terminus of TadA.
FIG. 85 shows the results of tethering AAG to ABE.
Figures 89, 90:
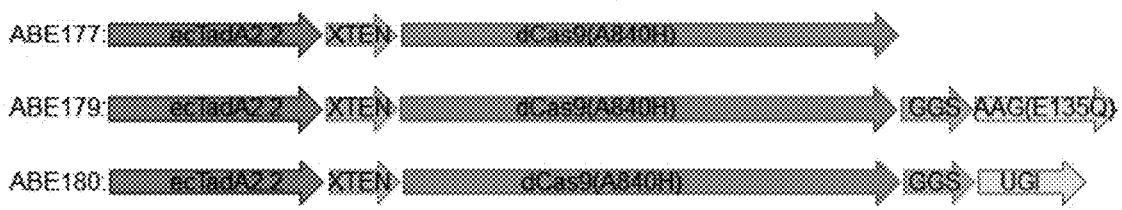
FIG. 89 shows the constructs used when tethering UGI to ABE.
FIG. 90 shows the results of tethering UGI to the end of ABE.
Figure 91:
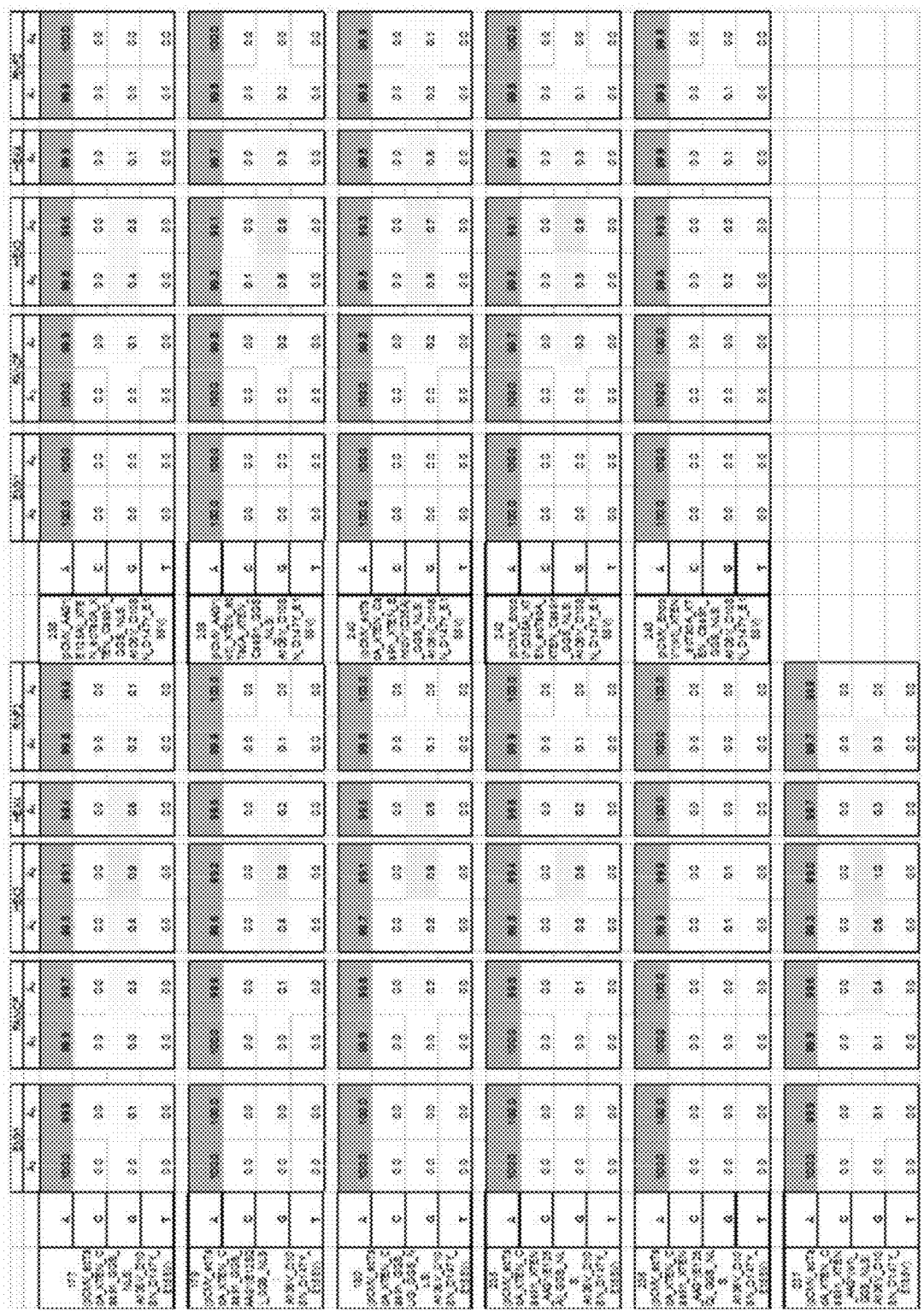
FIG. 91 shows the results of various inhibitors increasing A to G editing.

A next goal was to modify the ABE editor sequence preferences. One ABE targeted the Q4 stop site only and A to G reversion was observed, as shown in FIG. 69. Results also showed that the editor targeted the W15 stop site only and A to G reversion was observed, as shown in FIG. 70. Sequences were different than original evolution target, which was the chloramphenicol active site. New mutations could result in a kinetically faster enzyme. The third round of evolution targeted both Q4 and W15 sites simultaneously in the kanamycin gene. Correction of two sites in the same gene, in addition to targeting sites of with sequence identity dissimilar from the original chloramphenicol gene creates greater selection stringency. The template used for evolution #3 was bacterial plasmid pNMG-288 which contained 2gRNA (targeting Q4 stop and W15 stop in kanamycin). Error-pone PCR was performed on the deaminase portion of pNMG-288 which already contained the following mutations: A106V, D108N, D147Y, E155V.

Upon creating mammalian constructs of the corresponding variants resulting from evolution round #3, it was found that pNMG-341 and pNMG-340 generally out-performed pNMG-290, which was the most highly optimized construct from evolution #2.

TABLE 5

Includes exemplary protospacer and PAM sequences. An RNA sequence complementary to the protospacer sequence in the table would be used in a gRNA to target an ABE to the sequence. The target A with respect to the original Hek-2 site (originally at position 5) is shown in bold, and nucleotides that differ from the original Hek-2 sequence are underlined. The sequences correspond to SEQ ID NOs: 445-464 from top to bottom.

| plasmid name | comment | protospacer sequence | PAM |
|---|---|---|---|
| pNMG-299 | other sites within HEK2 locus | GAACACAAAGCATAGACTGC | GGG |
| pNMG-301 | other sites within HEK2 locus | GGAACACAAAGCATAGACTG | CGG |
| pNMG-302 | other sites within HEK2 locus | AACACAAAGCATAGACTGCG | GGG |
| pNMG-303 | other sites within HEK2 locus | ACAAAGCATAGACTGCGGGG | CGG |
| pNMG-304 | other sites within HEK2 locus | CAAAGCATAGACTGCGGGGC | GGG |
| pNMG-305 | other sites within HEK2 locus | GTGGTAATTTTCCAGCCCGC | TGG |
| pNMG-306 | other sites within HEK2 locus | CCTTTACAGGGCCAGCGGGC | TGG |

TABLE 5-continued

Includes exemplary protospacer and PAM sequences.
An RNA sequence complementary to the protospacer
sequence in the table would be used in a gRNA to
target an ABE to the sequence. The target A with
respect to the original Hek-2 site (originally at
position 5) is shown in bold, and nucleotides that
differ from the original Hek-2 sequence are
underlined. The sequences correspond to SEQ ID
NOs: 445-464 from top to bottom.

| plasmid name | comment | protospacer sequence | PAM |
|---|---|---|---|
| pNMG-307 | other sites within HEK2 locus | CTGTCACAGTTAGCTCAGCC | AGG |
| pNMG-308 | other sites within HEK2 locus | GTGTTCCAGTTTCCTTTACA | GGG |
| pNMG-300 | Hek-2 guideSEQ off-target | GAACACAATGCATAGATTGC | CGG |
| pNMG-309 | Hek-2 similar site | GAAAAAAAGCAGAGACTGC | TGG |
| pNMG-310 | Hek-2 similar site | GAATACTAAGCATAGACTCC | AGG |
| pNMG-311 | Hek-2 similar site | GTAAACAAAGCATAGACTGA | GGG |
| pNMG-312 | Hek-2 similar site | GGACACAAAGCTTAGACTCC | AGG |
| pNMG-313 | Hek-2 similar site | CAATACAAAGGATAGACTGC | AGG |
| pNMG-314 | Hek-2 similar site | GAAGACCAAGGATAGACTGC | TGG |
| pNMG-315 | Hek-2 similar site | GAAAACAAATCATTGACTGC | AGG |
| pNMG-316 | Hek-2 similar site | GATCACAAAGCATGGACTGA | AGG |
| pNMG-317 | Hek-2 similar site | GAAAACAAAACATAGAGTGC | TGG |
| pNMG-318 | Hek-2 similar site | GAACATAAAGAATAGAATGA | TGG |

Example 3—Evolution of Adenosine Base Editor Containing the A106V, D108N, D147Y, and E155V Mutations of ecTadA (Evolution #3)

An ecTadA construct with the consensus mutations A106V, D108N, D147Y (pNMG-184) and E155V was mutagenized with error-pone PCR and the resulting ABE library was targeted with 2 separate gRNAs to two different sites in a kanamycin resistance gene which require two A to G reversions (both in premature stop codons) to confer kanamycin resistance. The 2 gRNA/2 target approach was used to increase the stringency of the selection. See FIGS. 96-99. This evolution resulted in the identification of the following new mutations: L84F, H123Y and I157F.

Evolution #3 was performed analogously as evolution number 1 and 2, except bacterial plasmid pNMG-288 was used as a template, mutations in ecTadA (A106V_D108N_D147Y_E155V) and 2 gRNA expressed to target stop codons in selection plasmid pNMG-27- (Q4term+W15term). Libraries were plated on concentrations of kanamycin above the MIC. The most efficient base editor from evolution #3 was pNMG-371, which contains two ecTadA domains comprising the mutations L84F, A106V, D108N, H123Y, D147Y, E155V, and I156F.

Example 4—Evolution of Adenosine Base Editor ecTadA Residues E25, R26, R107, A142, and A143 to Increase Editing Efficiency of Adenine in Non-YAC Sequences (Evolution #4)

An ecTadA bacterial codon-optimized construct with the consensus mutations from evolution #2, A106V, D108N, D147Y and E155V, which is composed of one unit of ecTadA, an XTEN linker, and catalytically inactive Cas9 (dCas9), was mutagenized using NNK primers that target sites in ecTadA (e.g., E25, R26, R107, A142 and A143) to generate a site-saturated ABE library. Residues E25, R26, R107, A142 and A143 of ecTadA are hypothesized to make contact with the tRNA substrate with the wt ecTadA homodimer. For the NNK primers, N is A, T, C, or G, and K is G or T. The primers contain the mutations and are designed to bind at the 5 regions of interest, and a full-length product is obtained using PCR overlap extension protocol and assembled using USER junctions as used previously in the error-prone library assemblies. The 5 residues of ecTadA that were targeted included E25, R26, R107, A142 and A143. A goal of this evolution was to modify the "YAC" sequence preference of the adenosine base editor. In this round of evolution, the library of ABEs was selected against a spectinomycin resistance gene whose target A was presented in a non-YAC context. See FIGS. 101-123. The results from this round of evolution yielded mutations: R26G and A142N.

The ecTadA_2.2 deaminase construct was mutagenized to target active site residue in spectinomycin (T89). The gRNA targeted region: 5'-CAATGATGACTTCTACAGCG-3' (SEQ ID NO: 444) corresponds to a non "YAC" sequence. The targeted residues and their respective interactions are shown in Table 6.

Table 6—Shows the amino acid residues in saTadA and ecTadA responsible for the specifically listed interactions.

The size of the library used in evolution #4 is $32^5$, which is the size of the library based on codon frequency.

| S. aureus TadA | E. coli TadA | interaction |
|---|---|---|
| G22 | E25/H26 | carbonyl H-bond to 3' C in tRNA substrate |
| D103 | R107 | carbonyl H-bond with 5' U in tRNA substrate |
| S13B | A142/A143 | carbonyl H-bond with 5' U in tRNA substrate |

The NNK library with ecTadA_2.2 deaminase template was generated from approximately 500 colonies total from plates containing 128, 256, 384 and 512 of ug/mL spectinomycin. The editor constructs were sub-cloned, re-transformed into S1030 with uncorrected spectinomycin T89I selection plasmid and re-challenged with increasing concentrations of spectinomycin to clarify the true positive phenotypes from random reversions. The editing results of the evolution #4 variants (NNK library) at sites HEK-2, HEK2-3, HEK2-6, HEK2-7, HEK2-10, HEK3, and FANCF sites are shown in FIGS. 108 through 122. The evolution #4 variants do not perform better than the evolution #3 variants and do not demonstrate a relaxed substrate specificity with respect to the "YAC" sequence.

The results of the evolution #4 mammalian transfection for sites HEK-2, HEK2-2, HEK2-3, HEK2-6, HEK2-7, and HEK2-10 sites are shown in FIG. 123. The ecTadA evolution round #4 mutations neither improve editing efficiencies nor broadened substrate tolerance.

The evolution #4 template for evolution for the target sites in ecTadA (A106V, D108N, D147Y, E155V) is given in Table 7, which identifies individual clones that were identified.

TABLE 7

Mutations identified in Evolution #4. The template for evolution: ecTadA (A106V, D108N, D147Y, and E155V).

| clone: | 25 E | 26 R | 107 R | 142 A | 143 A |
|---|---|---|---|---|---|
| PLATE 1 | | | | | |
| 1 | M | G | P | N | D |
| 2 | D | G | K | N | G |
| 3 | | N | A | N | |
| 4 | | Q | | N | |
| 5 | A | G | N | N | E |
| 6 | | G | W | N | |
| 7 | | | | N | L |
| 8 | A | C | | N | W |
| PLATE 2 | | | | | |
| 9 | D | G | K | N | G |
| 10 | R | | | N | L |
| 11 | | | H | N | M |
| 12 | M | G | P | N | D |
| 13 | | Q | | N | |
| 14 | M | G | | N | D |
| 15 | | L | | N | L |
| 16 | R | | | N | L |
| PLATE 3 | | | | | |
| 17 | | C | H | N | |
| 18 | | G | H | N | G |
| 19 | V | G | S | D | S |
| 20 | | Q | | N | |
| 21 | S | C | | N | Q |
| 22 | Y | K | | G | R |

Example 5—Evolution of Adenosine Base Editor Containing the L84F, A106V, D108N, H123Y, D147Y, E155V, and I157F Mutations of ecTadA (Evolution #5)

An ecTadA construct containing mutations from evolution #3, L84F, A106V, D108N, H123Y, D147Y, E155V, I157F (pNMG-325) was mutagenized with error-prone PCR and the resulting ABE library was targeted with 2 separate gRNAs to two different loci in two different antibiotic resistant genes: chloramphenicol and spectinomycin. Both target sequences contained a target A in a non-YAC context.

The editor plasmid encodes two different gRNA: chlor and spect, both of which are "non-YAC" targets. The chlor target sequence is 5'-TACGGCGTAGTGCACCTGGA-3' (SEQ ID NO: 441) and has a target "A" at position "9." The spect target sequence is 5'-CAATGATGACTTCTACAGCG-3 (SEQ ID NO: 444) and has a target "A" at position "6." A schematic of the construct containing ecTadA and dCas9 used for ecTadA evolution (evolution #5) is shown in FIG. 124.

The library was transformed into S1030+selection plasmid, ABE expressed for 7 hours before plating on selection media: 128 ug/mL chloramphenicol (+kan/carb), 128 ug/mL chloramphenicol, 128 ug/mL spectinomycin (+kan/carb), 128 ug/mL chloramphenicol, 256 ug/mL spectinomycin (+kan/carb), 128 ug/mL chloramphenicol, 384 ug/mL spectinomycin (+kan/carb). The results of the clones assayed after fifth evolution #5 are shown in FIGS. 125 through 128. Surviving colonies are shown. The amplicons from spect selection clones assayed after evolution #5 are shown in FIG. 127. All colonies sequenced from double selection plates did not have any new mutations relative to the starting material.

Example 6—Examination of Mutations Introduced into the S. aureus TadA

Mutations were introduced into the S. aureus TadA (saTadA) based on the published crystal structure in Losey H. C., et al., "Crystal structure of Staphylococcus aureus tRNA adenosine deaminase TadA in complex with RNA," Nature Structural and Molecular Biology, 13, p. 153-159 (2006); the entire contents of which are hereby incorporated by reference. Based on tbe crystal structure of S. aureus TadA bound to its native tRNA substrate, 4 residues were selected for mutagenesis which made H-bond contact with the anticodon loop of the substrate. A first goal was to determine whether or not another version of an ABE editor could be made that could induce A to G mutations in DNA. For example, by using a TadA from another bacterial species (e.g., S. aureus). A second goal was to determine if the sequence specificity of a S. aureus editor was similar or different than the an ecTadA editor. A third goal was to test whether the editing efficiencies of an S. aureus ABE editor are improved as compared to an E. coli ABE editor. Briefly, mutations D104N, D103A, G22P, and S138A were made in saTadA. See constructs pNMG-345-350 in Table 4. The editing results of base editing at sites HEK-2, HEK2-1, HEK2-2, HEK2-3, HEK2-4, HEK2-6, HEK2-9, HEK2-10, HEK3, RNF2, and FANCF sites are shown in FIGS. 129 through 139. These figures show that mutations identified in ecTadA can be made in S. Aureus TadA (saTadA) to confer the ability of saTadA to deaminate adenine in DNA. The figures also show that the YAC sequence preference is similar for saTadA as it is for ecTadA.

Example 7—Testing ecTadA Homodimers vs Heterodimers and Linker Lengths of Adenosine Base Editors Adenosine base editor constructs were generated to test various linker lengths and various combinations of adenosine deaminase (e.g., wild-type ecTadA and/or mutant ecTadA domains) domains. For each construct the efficiency of mutating a target A to a G was tested. For example, constructs pNMG 492-500 and pNMG-513-518 were tested for their ability to generate A to G mutations in the DNA of cells. The identities of constructs pNMG 492-500 and pNMG-513-551 are shown in Table 4. Results of these tests are shown, for example, in FIGS. 141-149. Further, arginine residues within the adenosine deaminase of base editors were mutated to determine whether they had an effect on target sequence specificity, for example, their ability to mutate an A that is not part of a 5'-YAC-3' sequence, where Y is C or T, was tested. Results of these tests are shown, for example, in FIG. 141.

TABLE 8 sgRNA Plasmid key. The plasmid key below contains the protospacer sequence of the sgRNA sequence and identifies the reference plasmid number and site. For the protospacer sequence, the T is a U in the gRNA. In some embodiments, any of the gRNAs provided herein comprise any of the protospacer sequences in Table 8, where T is U.

| plasmid number | site | protospacer | SEQ ID NO: |
|---|---|---|---|
| pNMG-260 | RNF-multiA | AGAAAAACAATTTTAGTATT | 476 |
| pNMG-261 | HEK3-multiA | GCAGAAATAGACTAATTGCA | 477 |
| pNMG-299 | HEK2 | GAACACAAAGCATAGACTGC | 478 |
| pNMG-300 | HEK2 guideseq | GAACACAATGCATAGATTGC | 479 |
| pNMG-301 | HEK2-2 | GGAACACAAAGCATAGACTG | 480 |
| pNMG-302 | HEK2-3 | AACACAAAGCATAGACTGCG | 481 |
| pNMG-303 | HEK2-4 | ACAAAGCATAGACTGCGGGG | 482 |
| pNMG-304 | HEK2-5 | CAAAGCATAGACTGCGGGGC | 483 |
| pNMG-305 | HEK2-6 | GTGGTAATTTTCCAGCCCGC | 484 |
| pNMG-306 | HEK2-7 | CCTTTACAGGGCCAGCGGGC | 485 |
| pNMG-307 | HEK2-8 | CTGTCACAGTTAGCTCAGCC | 486 |
| pNMG-308 | HEK2-9 | GTGTTCCAGTTTCCTTTACA | 487 |
| pNMG-309 | HEK2 similar 1 | GAAAAAAAGCAGAGACTGC | 488 |
| pNMG-310 | TAC (HEK2 similar 2) | GAATACTAAGCATAGACTCC | 489 |
| pNMG-311 | AAC (HEK2 similar 3) | GTAAACAAAGCATAGACTGA | 490 |
| pNMG-312 | HEK2 similar 4 | GGACACAAAGCTTAGACTCC | 491 |
| pNMG-313 | HEK2 similar 5 | CAATACAAAGGATAGACTGC | 492 |
| pNMG-314 | GAC (HEK2 similar 6) | GAAGACCAAGGATAGACTGC | 493 |
| pNMG-315 | HEK2 similar 7 | GAAAACAAATCATTGACTGC | 494 |
| pNMG-316 | HEK2 similar 8 | GATCACAAAGCATGGACTGA | 495 |
| pNMG-317 | HEK2 similar 9 | GAAAACAAAACATAGAGTGC | 496 |
| pNMG-318 | CAT (HEK2 similar 10) | GAACATAAAGAATAGAATGA | 497 |
| pNMG-380 | R1329* SCN1A | AATCAAGATAAGGCTCTTAG | 498 |
| pNMG-423 | R580* SCN1A | GCTCACCCTCTAAAGCTGAAA | 499 |
| pNMG-424 | C136Y PTEN (MDA-MB-415) | GTATATGCATATTTATTACAT | 500 |
| pNMG-425 | Q144* TP53 (NCI-H2171) | GCAGCTACACAGGGCAGGTCT | 501 |

TABLE 8-continued sgRNA Plasmid key. The plasmid key below contains the protospacer sequence of the sgRNA sequence and identifies the reference plasmid number and site. For the protospacer sequence, the T is a U in the gRNA. In some embodiments, any of the gRNAs provided herein comprise any of the protospacer sequences in Table 8, where T is U.

| plasmid number | site | protospacer | SEQ ID NO: |
|---|---|---|---|
| pNMG-426 | R306* TP53 (HCC1937) | GACCTCACTTAGTGCTCCCTG | 502 |
| pNMG-463 | CAG | GGACAGGCAGCATAGACTGT | 503 |
| pNMG-464 | GAA | GTAGAAAAGTATAGACTGC | 504 |
| pNMG-465 | GAG | GGAGAGAGAGCATAGACTGC | 505 |
| pNMG-466 | GAT | GAAGATAGAGAATAGACTGC | 506 |
| pNMG-467 | TAA | GGCTAAAGACCATAGACTGT | 507 |
| pNMG-468 | TAG | GTCTAGAAAGCTTAGACTGC | 508 |
| pNMG-469 | TAT | GAGTATGAGGCATAGACTGC | 509 |
| pNMG-470 | AAG | GTCAAGAAAGCAGAGACTGC | 510 |
| pNMG-471 | AAT | GGGAATAAATCATAGAATCC | 511 |
| pNMG-472 | CAA | GAGCAAAGACAATACACTGT | 512 |
| pNMG-501 | AAA | GACAAAGAGGAAGAGAGACG | 513 |
| pNMG-502 | SITE 2 | GGGGACGCGCTGGCTTCCCG | 514 |
| pNMG-503 | SITE 3 | GGACCGGCTCCCTGGCGGTC | 515 |
| pNMG-504 | SITE 4 | GCCACTTCTAAGCCCTTGAT | 516 |
| pNMG-505 | SITES | GGGAAAGACCCAGCATCCGT | 517 |
| pNMG-506 | SITE 6 | GCGGTACGCCGCTTCAGTGA | 518 |
| pNMG-507 | SITE 7 | GAAACTGGTCCCGTTTACAG | 519 |
| pNMG-508 | SITE 8 | GATGAGATAATGATGAGTCA | 520 |
| pNMG-509 | SITE 9 | GCCTAGGCAGTGGGGGTGCA | 521 |
| pNMG-510 | R196* TP53 (Calu-6) | GACTCAGATAAGATGCTGAGG | 522 |
| pNMG-511 | M237I TP53 (T98G) | GCATATGTAACAGTTCCTGCA | 523 |
| pNMG-512 | R273H TP53 (NCI-H1975) | GTGCATGTTTGTGCCTGTCC | 524 |
| pNMG-531 | EMX1-5 | GGGGATGGCAGGGCAGGAAG | 525 |
| pNMG-532 | EMX1-6 | GGGTTAGGGGCCCCAGGCCG | 526 |
| pNMG-533 | FANCF-7 | GGATGCAGCTCGTTACCACC | 527 |
| pNMG-534 | FANCF-5 | GCGCACGGTGGCGGGGTCCC | 528 |
| pNMG-535 | HEK3-6 | GGGCCAGGTCCCTCCTCTCC | 529 |
| pNMG-536 | HEK3-7 | GGATTGACCCAGGCCAGGGC | 530 |
| pNMG-537 | HEK4-5 | GATGACAGGCAGGGGCACCG | 531 |
| pNMG-538 | HEK4-6 | GGGCCAGTGAAATCACCCTG | 532 |
| pNMG-539 | RNF2-5 | GGGGACTTTGGGAGGTGATC | 533 |
| pNMG-540 | RNF2-6 | GCACCAGCAGATGCAGTGTC | 534 |

TABLE 8-continued sgRNA Plasmid key. The plasmid key below contains
the protospacer sequence of the sgRNA sequence and
identifies the reference plasmid number and site.
For the protospacer sequence, the T is a U in the
gRNA. In some embodiments, any of the gRNAs provided
herein comprise any of the protospacer sequences
in Table 8, where T is U.

| plasmid number | site | protospacer | SEQ ID NO: |
|---|---|---|---|
| pNMG-601 | RNF2-6 | GACACACACACTTAGAATCTG | 535 |
| pNMG-602 | RNF2-6 | GCACACACACTTAGAATCTGT | 536 |

Example 8—DNA Shuffling Using Nucleotide Exchange and Excision Technology (NExT) to Remove Epistatic Mutations, Evolution #6

To generate more efficient adenosine base editors and remove potential epistatic mutations constructs from evolutions 4, 5a, 5b and 2 were subjected to DNA shuffle experiments using Nucleotide Exchange and Excision Technology (NExT). A schematic representation of DNA shuffling is shown in FIGS. 150 and 151. Briefly, a DNA shuffle library was created. NExT shuffle and USER assembly, were transformed into 10B cells. The isolated DNA shuffle library was transformed into S1030 with selection plasmid. Plating was performed using 4 different selection conditions, including, low chlor, high chlor, high spect, and chlor plus spect after 7 hours of adenosine base editor induction. Incubation was performed at 37 C for 48 hours then colony PCR was performed on survivors. See FIGS. 150 and 151.

The sequence identity of the clones obtained from evolution #6 is shown in FIGS. 152 and 153. The mutations are given relative to SEQ ID NO: 1. FIG. 154 contains schematic representations of base editors derived from evolution #6. Evolution #6 identified mutations in P48 (e.g., P48T, P48S and P48A) and A142 (e.g., A142N), relative to SEQ ID NO: 1. These mutations improved the efficiency of base editors to mutate an A residue to a G in DNA. See, for example, the experimental results in FIGS. 155-158.

Example 9—Evolving Adenosine Base Editors to Efficiently Edit Multi a Sites, Evolution #7

To generate base editors that are more efficient at editing an A within a site containing multiple A residues (e.g., a 5'-AAA-3' sequence), base editors capable of editing a multi-A site were evolved. Evolution was performed by identifying evolved base editors that could correct two point mutations that conferred the ability of cells to be antibiotic (kan) resistant. See, for example, FIGS. 163-165. Mutations that improve base editing efficiency and/or the ability to edit an A at a multi-A site are shown in FIG. 164, where mutations are identified relative to SEQ ID NO: 1. Evolution #7 identified mutations in W23 (e.g., W23R, and W23L) and R152 (e.g., R152P, and R152H), relative to SEQ ID NO: 1. A summary of base editing efficiency for selected adenosine base editor constructs on various target sequences is shown in FIGS. 179-186. Tables 9 and 10 contain bacterial selection plasmid data.

TABLE 9

Bacterial selection plasmid data.

| selection plasmid | corresponding editor + gRNA | modification | protospacer (targeted selection) | position of target A | strand modification | origin | MIC (S1030) Kan |
|---|---|---|---|---|---|---|---|
| pNMG-208 | pNMG-255 | stop in Kan gene, W15 | 5'-GCTTAGGTGGAGCGCCTATT-3' (SEQ ID NO: 707) | 5 | coding | RSF1030 | 32 ug/mL |
| pNMG-209 | pNMG-257 | stop in Kan gene, R18 | 5'-AGTCACTCCACCCAAGCGGC-3' (SEQ ID NO: 708) | 5 | template | RSF1030 | 256 ug/mL |
| pNMG-210 | pNMG-259 | stop in Kan gene, R44 | 5'-GTCACCCCTGCGCTGACAGC-3' (SEQ ID NO: 709) | 4 | template | RSF1030 | 128 ug/mL |
| pNMG-211 | pNMG-253 | stop in Kan gene, Q4 | 5'-ATCTTATTCGATCATGCGAA-3' (SEQ ID NO: 710) | 6 | template | RSF1030 | 16 ug/mL |
| pNMG-212 | n/a | wt Kan gene | control plasmid | n/a | n/a | RSF1030 | >1056 ug/mL |
| pNMG-213 | pNMG-255 | pNMG-208 w/ SD8 RBS | 5'-GCTTAGGTGGAGCGCCTATT-3' (SEQ ID NO: 711) | 5 | template | RSF1030 | 528 ug/mL |
| pNMG-214 | pNMG-255 | pNMG-208 w/ SD3 RBS | 5'-GCTTAGGTGGAGCGCCTATT-3' (SEQ ID NO: 712) | 5 | template | RSF1030 | 128 ug/mL |
| pNMG-215 | pNMG-255 | pNMG-208 w/ SD2 RBS | 5'-GCTTAGGTGGAGCGCCTATT-3' (SEQ ID NO: 713) | 5 | template | RSF1030 | unknownwn |

TABLE 9-continued

Bacterial selection plasmid data.

| selection plasmid | corresponding editor + gRNA | modification | protospacer (targeted selection) | position of target A | strand modification | origin | MIC (S1030) Kan |
|---|---|---|---|---|---|---|---|
| pNMG-216 | n/a | 2 stop, Q4 + R18 | 5'-ATCTTATTCGATCATGCG AA-3' (SEQ ID NO: 714), 5'-AGTCACTCCACCCAAGCG GC-3' (SEQ ID NO: 715) | 6 + 5 | template | RSF1030 | 8 ug/mL |
| pNMG-217 | n/a | 2 stop, W15 + R44 | 5'-GCTTAGGTGGAGCGCCTA TT-3' (SEQ ID NO: 716), 5'-GTCACCCCTGCGCTGACA GC-3' (SEQ ID NO: 717) | 5 + 4 | both | RSF1030 | 8 ug/mL |
| pNMG-221 | n/a | 2 stop, W15 + R44 | 5'-GCTTAGGTGGAGCGCCTA TT-3' (SEQ ID NO: 718), 5'-GTCACCCCTGCGCTGACA GC-3' (SEQ ID NO: 719) | 5 + 4 | both | CloDF3 | 4 ug/mL |

TABLE 10

Bacterial selection plasmid data

| selection plasmid | corresponding editor + gRNA | original Chlor selection | 5'-TACGGCGTAGTGCACCTGGA-3' (SEQ ID NO: 441) silent mutations in chlor site in italics, bold is target A: | position of target A | strand modification | origin RSF 1030 | MIC (S1030) Chlor 1 ug/mL | SEQ ID NO: |
|---|---|---|---|---|---|---|---|---|
| pNMG-186 | pNMG-197 | original chlor site (H193Y) | 5'-TAC*TGTGTA*ATG*TA*TCTGGA-3' | 9 | template | RSF 1030 | 1 ug/mL | 720 |
| pNMG-187 | pNMG-198 | original chlor site (H193Y) | 5'-TAC*TG*CGTAGTGCACCTGGA-3' | 9 | template | RSF 1030 | 1 ug/mL | 721 |
| pNMG-188 | pNMG-199 | original chlor site (H193Y) | 5'-TAC*C*GCGTAGTGCACCTGGA-3' | 9 | template | RSF 1030 | 1 ug/mL | 722 |
| pNMG-189 | pNMG-200 | original chlor site (H193Y) | 5'-TAC*AG*CGTAGTGCACCTGGA-3' | 9 | template | RSF 1030 | 1 ug/mL | 723 |
| pNMG-190 | pNMG-200 | original chlor site (H193Y) | 5'-TACGGCGTA*A*TGCACCTGGA-3' | 9 | template | RSF 1030 | 1 ug/mL | 724 |
| pNMG-191 | pNMG-201 | original chlor site (H193Y) | 5'-TACGG*CA*TAGTGCACCTGGA-3' | 9 | template | RSF 1030 | 1 ug/mL | 725 |
| pNMG-192 | pNMG-202 | original chlor site (H193Y) | 5'-TACGGCGTAGTG*T*ACCTGGA-3' | 9 | template | RSF 1030 | 1 ug/mL | 726 |
| pNMG-193 | pNMG-203 | original chlor site (H193Y) | 5'-TACGGCGTAGTG*G*ACCTGGA-3' | 9 | template | RSF 1030 | 1 ug/mL | 727 |
| pNMG-194 | pNMG-204 | original chlor site (H193Y) | 5'-TACGGCGTAGTGA*ACCTGGA-3' | 9 | template | RSF 1030 | 1 ug/mL | 728 |
| pNMG-195 | pNMG-205 | original chlor site (H193Y) | 5'-TACGGCGTAGTGCACT*TGGA-3' | 9 | template | RSF 1030 | 1 ug/mL | 729 |
| pNMG-196 | pNMG-206 | original chlor site (H193Y) | 5'-CGT*AGTGCACCTGGAT*GGCC-3' | 4 | template | RSF 1030 | 1 ug/mL | 730 |
|  | pNMG-227 | chlor (1)_H193Y | 5'-TAC*C*GCGTAGTGA*ACTTGGA-3' | 9 |  |  | 1 ug/mL | 731 |
|  | pNMG-228 | chlor (2)_H193Y | 5'-TAC*C*GCA*TAGTGA*ACTTGGA-3' | 7 + 9 |  |  | 1 ug/mL | 732 |

TABLE 10-continued

Bacterial selection plasmid data

| selection plasmid | original Chlor selection | corresponding editor + 2 gRNA target Kan only | 5'-TACGGCGTAGTGCACCTGGA-3' (SEQ ID NO: 441) silent mutations in chlor site in italics, bold is target A: | 9 | template | RSF 1030 | MIC (S1030) Chlor 1 ug/mL | SEQ ID NO: |
|---|---|---|---|---|---|---|---|---|
| pNMG-270 | pNMG-288 | stop in Kan gene, W15STOP | 5'-GCTTAGGTGGAGCGCCTATT-3' | 5 | coding | RSF 1030 | | 733 |
| | | stop in Kan gene, Q4STOP | 5'-ATCTTATTCGATCATGCGAA-3' | 6 | template | | | 734 |
| | | original Chlor selection His193Y | 5'-TACGGCGTAGTGCACCTGGA-3' | 9 | template | | | 735 |
| pNMG-319 | | stop in Kan gene, W15STOP | 5'-GCTTAGGTGGAGCGCCTATT-3' | 5 | coding | RSF 1030 | | 733 |
| | | stop in Kan gene, Q4STOP | 5'-ATCTTATTCGATCATGCGAA-3' | 6 | template | | | 734 |
| | | chlor (2) | 5'-TACCGCATAGTGAACTTGGA-3' | 7 + 9 | template | | | 732 |
| pNMG-333 | round 4, evolve against spect only | spect gene: T89I mutation | 5'-CAATGATGACTTCTACAGCG-3' | 6 | template | RSF 1030 | | 736 |
| | round 5: chlor + spect | chlor gene: H193Y mutation | 5'-TACGGCGTAGTGCACCTGGA-3' | 9 | template | | | 737 |
| | round 6: spect + chlor | | | | | | | |
| pNMG-570 | round 7, evolve against two mutations, same gene kanamycin (Q4sop and D208N reversion needed) | kan gene D208N mutation | 5'-TTCATTAACTGTGGCCGGCT-3' | 7 | coding | RSF 1030 | | 738 |
| | | | 5'-ATCTTATTCGATCATGCGAA-3' | 6 | template | | | 739 |

Example 10—Cas9 Variant Sequences

The disclosure provides Cas9 variants, for example Cas9 proteins from one or more organisms, which may comprise one or more mutations (e.g., to generate dCas9 or Cas9 nickase). In some embodiments, one or more of the amino acid residues, identified below by an asterisk, of a Cas9 protein may be mutated. In some embodiments, the D10 and/or H840 residues of the amino acid sequence provided in SEQ ID NO: 52, or a corresponding mutation in any of the amino acid sequences provided in SEQ ID NOs: 108-357, are mutated. In some embodiments, the D10 residue of the amino acid sequence provided in SEQ ID NO: 52, or a corresponding mutation in any of the amino acid sequences provided in SEQ ID NOs: 108-357, is mutated to any amino acid residue, except for D. In some embodiments, the D10 residue of the amino acid sequence provided in SEQ ID NO: 52, or a corresponding mutation in any of the amino acid sequences provided in SEQ ID NOs: 108-357, is mutated to an A. In some embodiments, the H840 residue of the amino acid sequence provided in SEQ ID NO: 52, or a corresponding residue in any of the amino acid sequences provided in SEQ ID NOs: 108-357, is an H. In some embodiments, the H840 residue of the amino acid sequence provided in SEQ ID NO: 52, or a corresponding mutation in any of the amino acid sequences provided in SEQ ID NOs: 108-357, is mutated to any amino acid residue, except for H. In some embodiments, the H840 residue of the amino acid sequence provided in SEQ ID NO: 52, or a corresponding mutation in any of the amino acid sequences provided in SEQ ID NOs: 108-357, is mutated to an A. In some embodiments, the D10 residue of the amino acid sequence provided in SEQ ID NO: 52, or a corresponding residue in any of the amino acid sequences provided in SEQ ID NOs: 108-357, is a D.

A number of Cas9 sequences from various species were aligned to determine whether corresponding homologous amino acid residues of D10 and H840 of SEQ ID NO: 52 or SEQ ID NO: 108 can be identified in other Cas9 proteins, allowing the generation of Cas9 variants with corresponding mutations of the homologous amino acid residues. The alignment was carried out using the NCBI Constraint-based Multiple Alignment Tool (COBALT(accessible at st-va.ncbi.nlm.nih.gov/tools/cobalt), with the following parameters. Alignment parameters: Gap penalties −11, −1; End-Gap penalties −5, −1. CDD Parameters: Use RPS BLAST on; Blast E-value 0.003; Find Conserved columns and Recompute on. Query Clustering Parameters: Use query clusters on; Word Size 4; Max cluster distance 0.8; Alphabet Regular.

An exemplary alignment of four Cas9 sequences is provided below. The Cas9 sequences in the alignment are: Sequence 1 (S1): SEQ ID NO: 108|WP_0109222511 gi 499224711|type II CRISPR RNA-guided endonuclease Cas9 [*Streptococcus pyogenes*]; Sequence 2 (S2): SEQ ID NO: 109|WP_039695303|gi 746743737|type II CRISPR RNA-guided endonuclease Cas9 [*Streptococcus gallolyticus*]; Sequence 3 (S3): SEQ ID NO: 110|WP_045635197|gi 782887988|type II CRISPR RNA-guided endonuclease Cas9 [*Streptococcus mitis*]; Sequence 4 (S4): SEQ ID NO: 111|5AXW_A|gi 924443546|*Staphylococcus Aureus* Cas9.

The HNH domain (bold and underlined) and the RuvC domain (boxed) are identified for each of the four sequences. Amino acid residues 10 and 840 in S1 and the homologous amino acids in the aligned sequences are identified with an asterisk following the respective amino acid residue.

```
S1    1  --MDKK-YSIGLD*IGTNSVGWAVITDEYKVESKKEKVLGNTDRESIKENLI--GALLEDSG--ETAKATRLKRTARRRYT    73

S2    1  --MTKKNYSIGLD*IGTNSVGWAVITDDYKVPAKKMKVIGNTDKEYIKENLL--GALLEDSG--ETAKATRLKRTARRRYT    74

S3    1  --M-KKGYSIGLD*IGTNSVGFAVITDDYKVESKEMEVLGNTDERFIKENLI--GALLFDEG--TTAKARRLKRTARRRYT    73

S4    1  GSHMKRNYILGLD*IGITSVGYGII--DYET----------------RDVIDAGVRIFKEANVENNEGRRSKRGARRLKR    61

S1   74  RRKNRICYLQEIFSNEMAKVDDSFFHRLEESFLVEEDKKHERHPIFGNIVDEVAYHEKYPTIYHLRKKLVDSTDKADLRL   153

S2   75  RRKNRLRYLQEIFANEIAKVDESFFQRLDESFLTDDDKTEDSHPIFGNKAEEDAYHQKFPTIYHLRKHLADSSEKADLRL   154

S3   74  RRKNRLRYLQEIFSEEMSKVDSSFFHRLDDSFLIPEDKRESKYPIFATLTEEKEYHKQFPTIYHLRKQLADSKEKTDLRL   153

S4   62  RRRHRIQRVKKLL--------------FDYNLLTD-------------------HSELSGINPYEARVKGLSQKLSEEE   107

S1  154  IYLALAHNIKFRGHFLIEGDLNPDNSDVDKLFIQLVQTYNQLFEENPINASGVDAKAILSARLSKSRRLENLIAQLPGEK   233

S2  155  VYLALAHMIKFRGHFLIEGELNAENTDVQKIFADFVGVYNRTFDDSHLSEITVDVASILTEKISKSRRLENLIKYYPTEK   234

S3  154  IYLALAHNIKYRGHFLYEEAFDIKNNDIQKIFNEFISIYDNTFEGSSLSGQNAQVEAIFTDKISKSAKRERVLKLEPDEK   233

S4  108  FSAALLHLAKRRG--------------------VHNVNEVEEDT-----------------------------------   131

S1  234  KNGLFGNLIALSLGLTPNFKSNFDLAEDAKLQLSKDTYDDDLDNLLAQIGDQYADLFLAAKNLSDAILLSDILRVNTEIT   313

S2  235  KNTLFGNLIALALGLQPNFKTNFKLSEDAKLQFSKDTYEEDLEELLGKIGDDYADLFTSAKNLYDAILLSGILTVDDNST   314

S3  234  STGLFSEFLKLIVGNQADFKKHFDLEDKAPLQFSKDTYDEDLENLLGQIGDDFTDLFVSAKKLYDAILLSGILTVTDPST   313

S4  132  -----GNELS------------------TKEQISRN-------------------------------------------   144

S1  314  KAPLSASMIKRYDEHHQDLTLLKALVRQQLPEKYKEIFFDQSKNGYAGYIDGGASQEEFYKFIKPILEKM--DGTEELLV   391

S2  315  KAPLSASMIKRYVEHHEDLEKLKEFIKANKSELYHDIFKDKNKNGYAGYIENGVKQDEFYKYLKNILSKIKIDGSDYFLD   394

S3  314  KAPLSASMIERYENHQNDLAALKQFIKNNLPEKYDEVFSDQSKDGYAGYIDGKTTQETFYKYIKNLLSKF--EGTDYFLD   391

S4  145  ----SKALEEKYVAELQ-----------------------------------------LERLKKDG------   165

S1  392  KLNREDLLRKQRTFDNGSIPHQIHLGELHAILRRQEDFYPFLKDNREKIEKILTFRIPYYVGPLARGNSRFAWMTRKSEE   471

S2  395  KIEREDFLRKQRTFDNGSIPHQIHLQEMHAILRRQGDYYPFLKEKQDRIEKILTFRIPYYVGPLVRKDSRFAWAEYRSDE   474

S3  392  KIEREDFLRKQRTFDNGSIPHQIHLQEMNAILRRQGEYYPFLKDNKEKIEKILTFRIPYYVGPLARGNRDFAWLTRNSDE   471

S4  166  --EVRGSINRFKTSD--------YVKEAKQLLKVQKAYHQLDQSFIDTYIDLLETRRTYYEGP--GEGSPFGW------K   227

S1  472  TITPWNFEEVVDKGASAQSFIERMTNFDKNLPNEKVLPKHSLLYEYFTVYNELTKVKYVTEGMRKPAFLSGEQKKAIVDL   551

S2  475  KITPWNFDKVIDKEKSAEKFITRMTLNDLYLPEEKVLPKHSHVYETYAVYNELTKIKYVNEQGKE-SFFDSNMKQEIFDH   553

S3  472  AIRPWNFEEIVDKASSAEDFINKMTNYDLYLPEEKVLPKHSLLYETFAVYNELTKVKFIAEGLRDYQFLDSGQKKQIVNQ   551

S4  228  DIKEW---------------YEMLMGHCTYFPEELRSVKYAYNADLYNALNDLNNLVITRDENEK---LEYYEKFQIIEN   289

S1  552  LEKTNRKVTVKQLKEDYFKKIECFDSVEISGVEDR---FNASLGTYHDLLKIIKDKDFLDNEENEDILEDIVLTLTLFED   628

S2  554  VFKENRKVTKEKLLNYLNKEFPEYRIKDLIGLDKENKSFNASLGTYHDLKKIL-DKAFLDDKVNEEVIEDIIKTLTLFED   632

S3  552  LFKENRKVTEKDIIHYLHN-VDGYDGIELKGIEKQ---FNASLSTYHDLLKIIKDKEFNDDAKNEAILENIVHTLTIFED   627

S4  290  VFKQKKKPTLKQIAKEILVNEEDIKGYRVTSTGKPEF---TNLKVYHDIKDITARKEII---ENAELLDQIAKILTIYQS   363

S1  629  REMIEERLKTYAHLFDDKVMKQLKR-RRYTGWGRLSRKLINGIRDKQSGKTILDFLKSDGFANRNFMQLIHDDSLTFKED   707

S2  633  KDMIHERLQKYSDIFTANQLKKLER-RHYTGWGRLSYKLINGIRNKENNKTILDYLIDDGSANRNFMQLINDDTLPFKQI   711

S3  628  REMIKQRLAQYDSLFDEKVIKALTR-RHYTGWGKLSAKLINGICDKQTGNTILDYLIDDGKINRNFMQLINDDGLSFKEI   706

S4  364  SEDIQEELTNLNSELTQEEIEQISNLKGYTGTHNLSLKAINLILDE------LWHTNDNQIAIFNRLKLVP---------   428
```

-continued

```
S1   708 IQKAQVSGQGDSLHEHIANLAGSPAIKKGILQTVKVVDELVKVMGRHKPENIVIEMARENQTT------QKGQKNSRERM  781
S2   712 IQKSQVVGDVDDIEAVVHDLPGSPAIKKGILQSVKIVDELVKVMG-GNPDNIVIEMARENQTT------NRGRSQSQQRL  784
S3   707 IQKAQVIGKTDDVKQVVQELSGSPAIKKGILQSIKIVDELVKVMG-HAPESIVIEMARENQTT------ARGKKNSQQRY  779
S4   429 -KKVDLSQQKEIPTTLVDDFILSPVVKRSFIQSIKVINAIIKKYG--LPNDIIIELAREKNSKDAQKMINEMQKRNRQTN  505

S1   782 KRIEEGIKELGSQIL-------KEHPVENTQLQNEKLYLYYLQNGRDMYVDQELDINRLSD----YDVDH*IVPQSFLKDD  850
S2   785 KKLQNSLKELGSNILNEEKPSYIEDKVENSHLQNDQLFYYIQNGKDMYTGDELDIDHLSD----YDIDH*IIPQAFIKDD  860
S3   780 KRIEDSLKILASGL----DSNILKENPTDNNQLQNDRLFLYYLQNGKDMYTGEALDINQLSS----YDIDH*IIPQAFIKDD  852
S4   506 ERIEEIIRTTGK--------------ENAKYLIEKIKLHDMQEGKCLYSLEAIPLEDLLNNPFNYEVDH*IIPRSVSFDN  570

S1   851 SIDNKVLTRSDKNRGKSDNVPSEEVVKKMKNYWRQLLNAKLITQRKFDN-LTKAERGGL-SELD------KAGFIKRQLV  922
S2   861 SIDNRVLTSSAKNRGKSDDVPSLDIVRARKAEWVRLYKSGLISKRKFDN-LTKAERGGL-TEAD------KAGFIKRQLV  932
S3   853 SLDNRVLTSSKDNRGKSDNVPSIEVVQKRKAFWQQLLDSKLISERKFNN-LTKAERGGL-DERD------KVGFIKRQLV  924
S4   571 SFNNKVLVKQEEASKKGNRTPFQYLSSSDSKISYETFKKHILNLAKGKGRISKTKKEYLLEERDINRFSVQKDFINRNLV  650

S1   923 ETRQITKHVAQILDSRMNTKYDENDKLIREVKVITLKSKLVSDFRKDFQFYKVREINNYHHAHDAYLNAVVGTALIKKYP  1002
S2   933 ETRQITKHVAQILDARFNTEHDENDKVIRDVKVITLKSNLVSQFRKDFEFYKVREINDYHHAHDAYLNAVVGTALLKKYP  1012
S3   925 ETRQITKHVAQILDARYNTEVNEKDKKNRTVKIITLKSNLVSNFRKEFRLYKVREINDYHHAHDAYLNAVVAKAILKKYP  1004
S4   651 DTRYATRGLMNLLRSYFRVN-------NLDVKVKSINGGFTSFLRRKWKFKKERNKGYKHHAEDALIIA----------  712

S1   1003 KLESEFVYGDYKVYDVRKMIAKSEQ--EIGKATAYFFYSNIMNFFKTEITLANGEIRKRPLIETNGETGEIVWDKG---  1077
S2   1013 KLASEFVYGEYKKYDIRKFITNSSD-----KATAKYFFYSNLMNFFKTKVKYADGTVFERPIIETNAD-GEIAWNKQ---  1083
S3   1005 KLEPEFVYGEYQKYDLKRYISRSKDPKEVEKATEKYFFYSNLLNFFKEEVHYADGTIVKRENIEYSKDTGEIAWNKE---  1081
S4   713 -NADFIFKEWKKLDKAKKVMENQM------------------------FEEKQAESMPEIETEQEYKEIFITPHQIK  764

S1   1078 -----RDFATVRKVLSMPQVNIVKKTEVQTGGFSKESILPKRNSDKLIARKKD---WDPKKYGGFDSPTVAYSVLVVAKV  1149
S2   1084 -----IDFEKVRKVLSYPQVNIVKKVETQTGGFSKESILPKGDSDKLIPRKTKKVYWDTKKYGGFDSPTVAYSVFVVADV  1158
S3   1082 -----KDFAIIKKVLSLPQVNIVKKREVQTGGFSKESILPKGNSDKLIPRKTKDILLDTTKYGGFDSPVIAYSILLIADI  1156
S4   765 HIKDFKDYKYSHRVDKKPNRELINDTLYSTRKDDKGNTLIVNNLNGLYDKDNDKL----KKLIN-KSP----EKLLMYHH  835

S1   1150 EKGKSKKLKSVKELLGITIMERSSFEKNPI-DFLEAKG-----YKEVKKDLIIKLPKYSLFELENGRKRMLASAGELQKG  1223
S2   1159 EKGKAKKLKTVKELVGISIMERSFFEENPV-EFLENKG-----YHNIREDKLIKLPKYSLFEFEGGRRRLLASASELQKG  1232
S3   1157 EKGKAKKLKTVKTLVGITIMEKAAFEENPI-TFLENKG-----YHNVRKENILCLPKYSLFELENGRRRLLASAKELQKG  1230
S4   836 DPQTYQKLK--------LIMEQYGDEKNPLYKYYEETGNYLTKYSKKDNGPVIKKIKYYGNKLNAHLDITDDYPNSRNKV  907

S1   1224 NELALPSKYVNFLYLASHYEKLKGSPEDNEQKQLFVEQHKHYLDEIIEQISEFSKRVILADANLDKVLSAYNKH------  1297
S2   1233 NEMVLPGYLVELLYHAHRADNF-----NSTEYLNYVSEHKKEFEKVLSCVEDFANLYVDVEKNLSKIRAVADSM------  1301
S3   1231 NEIVLPVYLTTLLYHSKNVHKL-----DEPGHLEYIQKHRNEFKDLLNLVSEFSQKYVLADANLEKIKSLYADN------  1299
S4   908 VKLSLKPYRFD-VYLDNGVYKFV-----TVKNLDVIK--KENYYEVNSKAYEEAKKLKKISNQAEFIASFYNNDLIKING  979

S1   1298 RDKPIREQAENIIHLFTLTNLGAPAAFKYFDTTIDRKRYTSTKEVLDATLIHQSIT--------GLYETRI----DLSQL  1365
S2   1302 DNFSIEEISNSFINLLTLTALGAPADFNFLGEKIPRKRYTSTKECLNATLIHQSIT--------GLYETRI----DLSKL  1369
S3   1300 EQADIEILANSFINLLTFTALGAPAAFKFFGKDIDRKRYTTVSEILNATLIHQSIT--------GLYETWI----DLSKL  1367
S4   980 ELYRVIGVNNDLLNRIEVNMIDITYR-EYLNMNDKRPPRIIKTIASKT---QSIKKYSTDILGNLYEVKSKKHPQIIKK  1055

S1   1366 GGD  1368

S2   1370 GEE  1372
```

```
S3  1368 GED                                                                        1370

S4  1056 G--                                                                        1056
```

The alignment demonstrates that amino acid sequences and amino acid residues that are homologous to a reference Cas9 amino acid sequence or amino acid residue can be identified across Cas9 sequence variants, including, but not limited to Cas9 sequences from different species, by identifying the amino acid sequence or residue that aligns with the reference sequence or the reference residue using alignment programs and algorithms known in the art. This disclosure provides Cas9 variants in which one or more of the amino acid residues identified by an asterisk in SEQ ID NOs: 108-111 (e.g., S1, S2, S3, and S4, respectively) are mutated as described herein. The residues D10 and H840 in Cas9 of SEQ ID NO: 52 that correspond to the residues identified in SEQ ID NOs: 108-111 by an asterisk are referred to herein as "homologous" or "corresponding" residues. Such homologous residues can be identified by sequence alignment, e.g., as described above, and by identifying the sequence or residue that aligns with the reference sequence or residue. Similarly, mutations in Cas9 sequences that correspond to mutations identified in SEQ ID NO: 52 herein, e.g., mutations of residues 10, and 840 in SEQ ID NO: 52, are referred to herein as "homologous" or "corresponding" mutations. For example, the mutations corresponding to the D10A mutation in SEQ ID NO: 52 or S1 (SEQ ID NO: 108) for the four aligned sequences above are D11A for S2, D10A for S3, and D13A for S4; the corresponding mutations for H840A in SEQ ID NO: 52 or S1 (SEQ ID NO: 108) are H850A for S2, H842A for S3, and H560A for S4.

A total of 250 Cas9 sequences (SEQ ID NOs: 108-357) from different species were aligned using the same algorithm and alignment parameters outlined above. Amino acid residues homologous to residues 10, and 840 of SEQ ID NO: 52 were identified in the same manner as outlined above. The alignments are provided below. The HNH domain (bold and underlined) and the RuvC domain (boxed) are identified for each of the four sequences. Single residues corresponding to amino acid residues 10, and 840 in SEQ ID NO: 52 are boxed in SEQ ID NO: 108 in the alignments, allowing for the identification of the corresponding amino acid residues in the aligned sequences.

| Accession | Description | SEQ ID NO |
|---|---|---|
| WP_010922251.1 | type II CRISPR RNA-guided endonuclease Cas9 [Streptococcus pyogenes] | SEQ ID NO: 108 |
| WP_039695303.1 | type II CRISPR RNA-guided endonuclease Cas9 [Streptococcus gallolyticus] | SEQ ID NO: 109 |
| WP_045635197.1 | type II CRISPR RNA-guided endonuclease Cas9 [Streptococcus mitis] | SEQ ID NO: 110 |
| 5AXW_A | Cas9, Chain A, Crystal Structure [Staphylococcus Aureus] | SEQ ID NO: 111 |
| WP_009880683.1 | type II CRISPR RNA-guided endonuclease Cas9 [Streptococcus pyogenes] | SEQ ID NO: 112 |
| WP_010922251.1 | type II CRISPR RNA-guided endonuclease Cas9 [Streptococcus pyogenes] | SEQ ID NO: 113 |
| WP_011054416.1 | type II CRISPR RNA-guided endonuclease Cas9 [Streptococcus pyogenes] | SEQ ID NO: 114 |
| WP_011284745.1 | type II CRISPR RNA-guided endonuclease Cas9 [Streptococcus pyogenes] | SEQ ID NO: 115 |
| WP_011285506.1 | type II CRISPR RNA-guided endonuclease Cas9 [Streptococcus pyogenes] | SEQ ID NO: 116 |
| WP_011527619.1 | type II CRISPR RNA-guided endonuclease Cas9 [Streptococcus pyogenes] | SEQ ID NO: 117 |
| WP_012560673.1 | type II CRISPR RNA-guided endonuclease Cas9 [Streptococcus pyogenes] | SEQ ID NO: 118 |
| WP_014407541.1 | type II CRISPR RNA-guided endonuclease Cas9 [Streptococcus pyogenes] | SEQ ID NO: 119 |
| WP_020905136.1 | type II CRISPR RNA-guided endonuclease Cas9 [Streptococcus pyogenes] | SEQ ID NO: 120 |
| WP_023080005.1 | type II CRISPR RNA-guided endonuclease Cas9 [Streptococcus pyogenes] | SEQ ID NO: 121 |
| WP_023610282.1 | type II CRISPR RNA-guided endonuclease Cas9 [Streptococcus pyogenes] | SEQ ID NO: 122 |
| WP_030125963.1 | type II CRISPR RNA-guided endonuclease Cas9 [Streptococcus pyogenes] | SEQ ID NO: 123 |
| WP_030126706.1 | type II CRISPR RNA-guided endonuclease Cas9 [Streptococcus pyogenes] | SEQ ID NO: 124 |
| WP_031488318.1 | type II CRISPR RNA-guided endonuclease Cas9 [Streptococcus pyogenes] | SEQ ID NO: 125 |
| WP_032460140.1 | type II CRISPR RNA-guided endonuclease Cas9 [Streptococcus pyogenes] | SEQ ID NO: 126 |
| WP_032461047.1 | type II CRISPR RNA-guided endonuclease Cas9 [Streptococcus pyogenes] | SEQ ID NO: 127 |
| WP_032462016.1 | type II CRISPR RNA-guided endonuclease Cas9 [Streptococcus pyogenes] | SEQ ID NO: 128 |
| WP_032462936.1 | type II CRISPR RNA-guided endonuclease Cas9 [Streptococcus pyogenes] | SEQ ID NO: 129 |
| WP_032464890.1 | type II CRISPR RNA-guided endonuclease Cas9 [Streptococcus pyogenes] | SEQ ID NO: 130 |
| WP_033888930.1 | type II CRISPR RNA-guided endonuclease Cas9 [Streptococcus pyogenes] | SEQ ID NO: 131 |
| WP_038431314.1 | type II CRISPR RNA-guided endonuclease Cas9 [Streptococcus pyogenes] | SEQ ID NO: 132 |
| WP_038432938.1 | type II CRISPR RNA-guided endonuclease Cas9 [Streptococcus pyogenes] | SEQ ID NO: 133 |

| Accession | Description | SEQ ID NO |
|---|---|---|
| WP_038434062.1 | type II CRISPR RNA-guided endonuclease Cas9 [Streptococcus pyogenes] | 134 |
| BAQ51233.1 | CRISPR-associated protein, Csn1 family [Streptococcus pyogenes] | 135 |
| KGE60162.1 | hypothetical protein MGAS2111_0903 [Streptococcus pyogenes MGAS2111] | 136 |
| KGE60856.1 | CRISPR-associated endonuclease protein [Streptococcus pyogenes SS1447] | 137 |
| WP_002989955.1 | MULTISPECIES: type II CRISPR RNA-guided endonuclease Cas9 [Streptococcus] | 138 |
| WP_003030002.1 | MULTISPECIES: type II CRISPR RNA-guided endonuclease Cas9 [Streptococcus] | 139 |
| WP_003065552.1 | MULTISPECIES: type II CRISPR RNA-guided endonuclease Cas9 [Streptococcus] | 140 |
| WP_001040076.1 | type II CRISPR RNA-guided endonuclease Cas9 [Streptococcus agalactiae] | 141 |
| WP_001040078.1 | type II CRISPR RNA-guided endonuclease Cas9 [Streptococcus agalactiae] | 142 |
| WP_001040080.1 | type II CRISPR RNA-guided endonuclease Cas9 [Streptococcus agalactiae] | 143 |
| WP_001040081.1 | type II CRISPR RNA-guided endonuclease Cas9 [Streptococcus agalactiae] | 144 |
| WP_001040083.1 | type II CRISPR RNA-guided endonuclease Cas9 [Streptococcus agalactiae] | 145 |
| WP_001040085.1 | type II CRISPR RNA-guided endonuclease Cas9 [Streptococcus agalactiae] | 146 |
| WP_001040087.1 | type II CRISPR RNA-guided endonuclease Cas9 [Streptococcus agalactiae] | 147 |
| WP_001040088.1 | type II CRISPR RNA-guided endonuclease Cas9 [Streptococcus agalactiae] | 148 |
| WP_001040089.1 | type II CRISPR RNA-guided endonuclease Cas9 [Streptococcus agalactiae] | 149 |
| WP_001040090.1 | type II CRISPR RNA-guided endonuclease Cas9 [Streptococcus agalactiae] | 150 |
| WP_001040091.1 | type II CRISPR RNA-guided endonuclease Cas9 [Streptococcus agalactiae] | 151 |
| WP_001040092.1 | type II CRISPR RNA-guided endonuclease Cas9 [Streptococcus agalactiae] | 152 |
| WP_001040094.1 | type II CRISPR RNA-guided endonuclease Cas9 [Streptococcus agalactiae] | 153 |
| WP_001040095.1 | type II CRISPR RNA-guided endonuclease Cas9 [Streptococcus agalactiae] | 154 |
| WP_001040096.1 | type II CRISPR RNA-guided endonuclease Cas9 [Streptococcus agalactiae] | 155 |
| WP_001040097.1 | type II CRISPR RNA-guided endonuclease Cas9 [Streptococcus agalactiae] | 156 |
| WP_001040098.1 | type II CRISPR RNA-guided endonuclease Cas9 [Streptococcus agalactiae] | 157 |
| WP_001040099.1 | type II CRISPR RNA-guided endonuclease Cas9 [Streptococcus agalactiae] | 158 |
| WP_001040100.1 | type II CRISPR RNA-guided endonuclease Cas9 [Streptococcus agalactiae] | 159 |
| WP_001040104.1 | type II CRISPR RNA-guided endonuclease Cas9 [Streptococcus agalactiae] | 160 |

| Accession | Description |
|---|---|
| WP_001040105.1 | type II CRISPR RNA-guided endonuclease Cas9 [Streptococcus agalactiae] SEQ ID NO: 161 |
| WP_001040106.1 | type II CRISPR RNA-guided endonuclease Cas9 [Streptococcus agalactiae] SEQ ID NO: 162 |
| WP_001040107.1 | type II CRISPR RNA-guided endonuclease Cas9 [Streptococcus agalactiae] SEQ ID NO: 163 |
| WP_001040108.1 | type II CRISPR RNA-guided endonuclease Cas9 [Streptococcus agalactiae] SEQ ID NO: 164 |
| WP_001040109.1 | type II CRISPR RNA-guided endonuclease Cas9 [Streptococcus agalactiae] SEQ ID NO: 165 |
| WP_001040110.1 | type II CRISPR RNA-guided endonuclease Cas9 [Streptococcus agalactiae] SEQ ID NO: 166 |
| WP_015058523.1 | type II CRISPR RNA-guided endonuclease Cas9 [Streptococcus agalactiae] SEQ ID NO: 167 |
| WP_017643650.1 | type II CRISPR RNA-guided endonuclease Cas9 [Streptococcus agalactiae] SEQ ID NO: 168 |
| WP_017647151.1 | type II CRISPR RNA-guided endonuclease Cas9 [Streptococcus agalactiae] SEQ ID NO: 169 |
| WP_017648376.1 | type II CRISPR RNA-guided endonuclease Cas9 [Streptococcus agalactiae] SEQ ID NO: 170 |
| WP_017649527.1 | type II CRISPR RNA-guided endonuclease Cas9 [Streptococcus agalactiae] SEQ ID NO: 171 |
| WP_017771611.1 | type II CRISPR RNA-guided endonuclease Cas9 [Streptococcus agalactiae] SEQ ID NO: 172 |
| WP_017771984.1 | type II CRISPR RNA-guided endonuclease Cas9 [Streptococcus agalactiae] SEQ ID NO: 173 |
| CFQ25032.1 | CRISPR-associated protein [Streptococcus agalactiae] SEQ ID NO: 174 |
| CFV16040.1 | CRISPR-associated protein [Streptococcus agalactiae] SEQ ID NO: 175 |
| KLJ37842.1 | CRISPR-associated protein Csn1 [Streptococcus agalactiae] SEQ ID NO: 176 |
| KLJ72361.1 | CRISPR-associated protein Csn1 [Streptococcus agalactiae] SEQ ID NO: 177 |
| KLL20707.1 | CRISPR-associated protein Csn1 [Streptococcus agalactiae] SEQ ID NO: 178 |
| KLL42645.1 | CRISPR-associated protein Csn1 [Streptococcus agalactiae] SEQ ID NO: 179 |
| WP_047207273.1 | type II CRISPR RNA-guided endonuclease Cas9 [Streptococcus agalactiae] SEQ ID NO: 180 |
| WP_047209694.1 | type II CRISPR RNA-guided endonuclease Cas9 [Streptococcus agalactiae] SEQ ID NO: 181 |
| WP_050198062.1 | type II CRISPR RNA-guided endonuclease Cas9 [Streptococcus agalactiae] SEQ ID NO: 182 |
| WP_050201642.1 | type II CRISPR RNA-guided endonuclease Cas9 [Streptococcus agalactiae] SEQ ID NO: 183 |
| WP_050204027.1 | type II CRISPR RNA-guided endonuclease Cas9 [Streptococcus agalactiae] SEQ ID NO: 184 |
| WP_050881965.1 | type II CRISPR RNA-guided endonuclease Cas9 [Streptococcus agalactiae] SEQ ID NO: 185 |
| WP_050886065.1 | type II CRISPR RNA-guided endonuclease Cas9 [Streptococcus agalactiae] SEQ ID NO: 186 |
| AHN30376.1 | CRISPR-associated protein Csn1 [Streptococcus agalactiae 138P] SEQ ID NO: 187 |

| Accession | Description | SEQ ID NO |
|---|---|---|
| EAO78426.1 | reticulocyte binding protein [Streptococcus agalactiae H36B] | 188 |
| CCW42055.1 | CRISPR-associated protein, SAG0894 family [Streptococcus agalactiae ILRI112] | 189 |
| WP_003041502.1 | type II CRISPR RNA-guided endonuclease Cas9 [Streptococcus anginosus] | 190 |
| WP_037593752.1 | type II CRISPR RNA-guided endonuclease Cas9 [Streptococcus anginosus] | 191 |
| WP_049516684.1 | CRISPR-associated protein Csn1 [Streptococcus anginosus] | 192 |
| GAD46167.1 | hypothetical protein ANG6_0662 [Streptococcus anginosus T5] | 193 |
| WP_018363470.1 | type II CRISPR RNA-guided endonuclease Cas9 [Streptococcus caballi] | 194 |
| WP_003043819.1 | type II CRISPR RNA-guided endonuclease Cas9 [Streptococcus canis] | 195 |
| WP_006269658.1 | type II CRISPR RNA-guided endonuclease Cas9 [Streptococcus constellatus] | 196 |
| WP_048800889.1 | type II CRISPR RNA-guided endonuclease Cas9 [Streptococcus constellatus] | 197 |
| WP_012767106.1 | type II CRISPR RNA-guided endonuclease Cas9 [Streptococcus dysgalactiae] | 198 |
| WP_014612333.1 | type II CRISPR RNA-guided endonuclease Cas9 [Streptococcus dysgalactiae] | 199 |
| WP_015017095.1 | type II CRISPR RNA-guided endonuclease Cas9 [Streptococcus dysgalactiae] | 200 |
| WP_015057649.1 | type II CRISPR RNA-guided endonuclease Cas9 [Streptococcus dysgalactiae] | 201 |
| WP_048327215.1 | type II CRISPR RNA-guided endonuclease Cas9 [Streptococcus dysgalactiae] | 202 |
| WP_049519324.1 | CRISPR-associated protein Csn1 [Streptococcus dysgalactiae] | 203 |
| WP_012515931.1 | type II CRISPR RNA-guided endonuclease Cas9 [Streptococcus equi] | 204 |
| WP_021320964.1 | type II CRISPR RNA-guided endonuclease Cas9 [Streptococcus equi] | 205 |
| WP_037581760.1 | type II CRISPR RNA-guided endonuclease Cas9 [Streptococcus equi] | 206 |
| WP_004232481.1 | type II CRISPR RNA-guided endonuclease Cas9 [Streptococcus equinus] | 207 |
| WP_009854540.1 | type II CRISPR RNA-guided endonuclease Cas9 [Streptococcus gallolyticus] | 208 |
| WP_012962174.1 | type II CRISPR RNA-guided endonuclease Cas9 [Streptococcus gallolyticus] | 209 |
| WP_039695303.1 | type II CRISPR RNA-guided endonuclease Cas9 [Streptococcus gallolyticus] | 210 |
| WP_014334983.1 | type II CRISPR RNA-guided endonuclease Cas9 [Streptococcus infantarius] | 211 |
| WP_003099269.1 | type II CRISPR RNA-guided endonuclease Cas9 [Streptococcus iniae] | 212 |
| AHY15608.1 | CRISPR-associated protein Csn1 [Streptococcus iniae] | 213 |
| AHY17476.1 | CRISPR-associated protein Csn1 [Streptococcus iniae] | 214 |

-continued

| Accession | Description | SEQ ID NO |
|---|---|---|
| ESR09100.1 | hypothetical protein IUSA1_08595 [Streptococcus iniae IUSA1] | 215 |
| AGM98575.1 | CRISPR-associated protein Cas9/Csn1, subtype II/NMEMI [Streptococcus iniae SF1] | 216 |
| ALF27331.1 | CRISPR-associated protein Csn1 [Streptococcus intermedius] | 217 |
| WP_018372492.1 | type II CRISPR RNA-guided endonuclease Cas9 [Streptococcus massiliensis] | 218 |
| WP_045618028.1 | type II CRISPR RNA-guided endonuclease Cas9 [Streptococcus mitis] | 219 |
| WP_045635197.1 | type II CRISPR RNA-guided endonuclease Cas9 [Streptococcus mitis] | 220 |
| WP_002263549.1 | type II CRISPR RNA-guided endonuclease Cas9 [Streptococcus mutans] | 221 |
| WP_002263887.1 | type II CRISPR RNA-guided endonuclease Cas9 [Streptococcus mutans] | 222 |
| WP_002264920.1 | type II CRISPR RNA-guided endonuclease Cas9 [Streptococcus mutans] | 223 |
| WP_002269043.1 | type II CRISPR RNA-guided endonuclease Cas9 [Streptococcus mutans] | 224 |
| WP_002269448.1 | type II CRISPR RNA-guided endonuclease Cas9 [Streptococcus mutans] | 225 |
| WP_002271977.1 | type II CRISPR RNA-guided endonuclease Cas9 [Streptococcus mutans] | 226 |
| WP_002272766.1 | type II CRISPR RNA-guided endonuclease Cas9 [Streptococcus mutans] | 227 |
| WP_002273241.1 | type II CRISPR RNA-guided endonuclease Cas9 [Streptococcus mutans] | 228 |
| WP_002275430.1 | type II CRISPR RNA-guided endonuclease Cas9 [Streptococcus mutans] | 229 |
| WP_002276448.1 | type II CRISPR RNA-guided endonuclease Cas9 [Streptococcus mutans] | 230 |
| WP_002277050.1 | type II CRISPR RNA-guided endonuclease Cas9 [Streptococcus mutans] | 231 |
| WP_002277364.1 | type II CRISPR RNA-guided endonuclease Cas9 [Streptococcus mutans] | 232 |
| WP_002279025.1 | type II CRISPR RNA-guided endonuclease Cas9 [Streptococcus mutans] | 233 |
| WP_002279859.1 | type II CRISPR RNA-guided endonuclease Cas9 [Streptococcus mutans] | 234 |
| WP_002280230.1 | type II CRISPR RNA-guided endonuclease Cas9 [Streptococcus mutans] | 235 |
| WP_002281696.1 | type II CRISPR RNA-guided endonuclease Cas9 [Streptococcus mutans] | 236 |
| WP_002282247.1 | type II CRISPR RNA-guided endonuclease Cas9 [Streptococcus mutans] | 237 |
| WP_002282906.1 | type II CRISPR RNA-guided endonuclease Cas9 [Streptococcus mutans] | 238 |
| WP_002283846.1 | type II CRISPR RNA-guided endonuclease Cas9 [Streptococcus mutans] | 239 |
| WP_002287255.1 | type II CRISPR RNA-guided endonuclease Cas9 [Streptococcus mutans] | 240 |
| WP_002288990.1 | type II CRISPR RNA-guided endonuclease Cas9 [Streptococcus mutans] | 241 |

-continued

| Accession | Description | SEQ ID NO |
|---|---|---|
| WP_002289641.1 | type II CRISPR RNA-guided endonuclease Cas9 [Streptococcus mutans] | SEQ ID NO: 242 |
| WP_002290427.1 | type II CRISPR RNA-guided endonuclease Cas9 [Streptococcus mutans] | SEQ ID NO: 243 |
| WP_002295753.1 | type II CRISPR RNA-guided endonuclease Cas9 [Streptococcus mutans] | SEQ ID NO: 244 |
| WP_002296423.1 | type II CRISPR RNA-guided endonuclease Cas9 [Streptococcus mutans] | SEQ ID NO: 245 |
| WP_002304487.1 | type II CRISPR RNA-guided endonuclease Cas9 [Streptococcus mutans] | SEQ ID NO: 246 |
| WP_002305844.1 | type II CRISPR RNA-guided endonuclease Cas9 [Streptococcus mutans] | SEQ ID NO: 247 |
| WP_002307203.1 | type II CRISPR RNA-guided endonuclease Cas9 [Streptococcus mutans] | SEQ ID NO: 248 |
| WP_002310390.1 | type II CRISPR RNA-guided endonuclease Cas9 [Streptococcus mutans] | SEQ ID NO: 249 |
| WP_002352408.1 | type II CRISPR RNA-guided endonuclease Cas9 [Streptococcus mutans] | SEQ ID NO: 250 |
| WP_012997688.1 | type II CRISPR RNA-guided endonuclease Cas9 [Streptococcus mutans] | SEQ ID NO: 251 |
| WP_014677909.1 | type II CRISPR RNA-guided endonuclease Cas9 [Streptococcus mutans] | SEQ ID NO: 252 |
| WP_019312892.1 | type II CRISPR RNA-guided endonuclease Cas9 [Streptococcus mutans] | SEQ ID NO: 253 |
| WP_019313659.1 | type II CRISPR RNA-guided endonuclease Cas9 [Streptococcus mutans] | SEQ ID NO: 254 |
| WP_019314093.1 | type II CRISPR RNA-guided endonuclease Cas9 [Streptococcus mutans] | SEQ ID NO: 255 |
| WP_019315370.1 | type II CRISPR RNA-guided endonuclease Cas9 [Streptococcus mutans] | SEQ ID NO: 256 |
| WP_019803776.1 | type II CRISPR RNA-guided endonuclease Cas9 [Streptococcus mutans] | SEQ ID NO: 257 |
| WP_019805234.1 | type II CRISPR RNA-guided endonuclease Cas9 [Streptococcus mutans] | SEQ ID NO: 258 |
| WP_024783594.1 | type II CRISPR RNA-guided endonuclease Cas9 [Streptococcus mutans] | SEQ ID NO: 259 |
| WP_024784288.1 | type II CRISPR RNA-guided endonuclease Cas9 [Streptococcus mutans] | SEQ ID NO: 260 |
| WP_024784666.1 | type II CRISPR RNA-guided endonuclease Cas9 [Streptococcus mutans] | SEQ ID NO: 261 |
| WP_024784894.1 | type II CRISPR RNA-guided endonuclease Cas9 [Streptococcus mutans] | SEQ ID NO: 262 |
| WP_024786433.1 | type II CRISPR RNA-guided endonuclease Cas9 [Streptococcus mutans] | SEQ ID NO: 263 |
| WP_049473442.1 | CRISPR-associated protein Csn1 [Streptococcus mutans] | SEQ ID NO: 264 |
| WP_049474547.1 | CRISPR-associated protein Csn1 [Streptococcus mutans] | SEQ ID NO: 265 |
| EMC03581.1 | hypothetical protein SMU69_09359 [Streptococcus mutans NLML4] | SEQ ID NO: 266 |
| WP_000428612.1 | type II CRISPR RNA-guided endonuclease Cas9 [Streptococcus oralis] | SEQ ID NO: 267 |
| WP_000428613.1 | type II CRISPR RNA-guided endonuclease Cas9 [Streptococcus oralis] | SEQ ID NO: 268 |

| | | |
|---|---|---|
| WP_049523028.1 | CRISPR-associated protein Csn1 [Streptococcus parasanguinis] | SEQ ID NO: 269 |
| WP_003107102.1 | type II CRISPR RNA-guided endonuclease Cas9 [Streptococcus parauberis] | SEQ ID NO: 270 |
| WP_054279288.1 | type II CRISPR RNA-guided endonuclease Cas9 [Streptococcus phocae] | SEQ ID NO: 271 |
| WP_049531101.1 | CRISPR-associated protein Csn1 [Streptococcus pseudopneumoniae] | SEQ ID NO: 272 |
| WP_049538452.1 | CRISPR-associated protein Csn1 [Streptococcus pseudopneumoniae] | SEQ ID NO: 273 |
| WP_049549711.1 | CRISPR-associated protein Csn1 [Streptococcus pseudopneumoniae] | SEQ ID NO: 274 |
| WP_007896501.1 | type II CRISPR RNA-guided endonuclease Cas9 [Streptococcus pseudoporcinus] | SEQ ID NO: 275 |
| EFR44625.1 | CRISPR-associated protein, Csn1 family [Streptococcus pseudoporcinus SPIN 20026] | SEQ ID NO: 276 |
| WP_002897477.1 | type II CRISPR RNA-guided endonuclease Cas9 [Streptococcus sanguinis] | SEQ ID NO: 277 |
| WP_002906454.1 | type II CRISPR RNA-guided endonuclease Cas9 [Streptococcus sanguinis] | SEQ ID NO: 278 |
| WP_009729476.1 | type II CRISPR RNA-guided endonuclease Cas9 [Streptococcus sp. F0441] | SEQ ID NO: 279 |
| CQR24647.1 | CRISPR-associated protein [Streptococcus sp. FF10] | SEQ ID NO: 280 |
| WP_000066813.1 | type II CRISPR RNA-guided endonuclease Cas9 [Streptococcus sp. M334] | SEQ ID NO: 281 |
| WP_009754323.1 | type II CRISPR RNA-guided endonuclease Cas9 [Streptococcus sp. taxon 056] | SEQ ID NO: 282 |
| WP_044674937.1 | type II CRISPR RNA-guided endonuclease Cas9 [Streptococcus suis] | SEQ ID NO: 283 |
| WP_044676715.1 | type II CRISPR RNA-guided endonuclease Cas9 [Streptococcus suis] | SEQ ID NO: 284 |
| WP_044680361.1 | type II CRISPR RNA-guided endonuclease Cas9 [Streptococcus suis] | SEQ ID NO: 285 |
| WP_044681799.1 | type II CRISPR RNA-guided endonuclease Cas9 [Streptococcus suis] | SEQ ID NO: 286 |
| WP_049533112.1 | CRISPR-associated protein Csn1 [Streptococcus suis] | SEQ ID NO: 287 |
| WP_029090905.1 | type II CRISPR RNA-guided endonuclease Cas9 [Brochothrix thermosphacta] | SEQ ID NO: 288 |
| WP_006506696.1 | type II CRISPR RNA-guided endonuclease Cas9 [Catenibacterium mitsuokai] | SEQ ID NO: 289 |
| AIT42264.1 | Cas9hc:NLS:HA [Cloning vector pYB196] | SEQ ID NO: 290 |
| WP_034440723.1 | type II CRISPR endonuclease Cas9 [Clostridiales bacterium S5-A11] | SEQ ID NO: 291 |
| AKQ21048.1 | Cas9 [CRISPR-mediated gene targeting vector p(bh5p68-Cas9)] | SEQ ID NO: 292 |
| WP_004636532.1 | type II CRISPR RNA-guided endonuclease Cas9 [Dolosigranulum pigrum] | SEQ ID NO: 293 |
| WP_002364836.1 | MULTISPECIES: type II CRISPR RNA-guided endonuclease Cas9 [Enterococcus] | SEQ ID NO: 294 |
| WP_016631044.1 | MULTISPECIES: type II CRISPR RNA-guided endonuclease Cas9 [Enterococcus] | SEQ ID NO: 295 |

-continued

| Accession | Description | SEQ ID NO |
|---|---|---|
| EMS75795.1 | hypothetical protein H318_06676 [Enterococcus durans IPLA 655] | SEQ ID NO: 296 |
| WP_002373311.1 | type II CRISPR RNA-guided endonuclease Cas9 [Enterococcus faecalis] | SEQ ID NO: 297 |
| WP_002378009.1 | type II CRISPR RNA-guided endonuclease Cas9 [Enterococcus faecalis] | SEQ ID NO: 298 |
| WP_002407324.1 | type II CRISPR RNA-guided endonuclease Cas9 [Enterococcus faecalis] | SEQ ID NO: 299 |
| WP_002413717.1 | type II CRISPR RNA-guided endonuclease Cas9 [Enterococcus faecalis] | SEQ ID NO: 300 |
| WP_010775580.1 | type II CRISPR RNA-guided endonuclease Cas9 [Enterococcus faecalis] | SEQ ID NO: 301 |
| WP_010818269.1 | type II CRISPR RNA-guided endonuclease Cas9 [Enterococcus faecalis] | SEQ ID NO: 302 |
| WP_010824395.1 | type II CRISPR RNA-guided endonuclease Cas9 [Enterococcus faecalis] | SEQ ID NO: 303 |
| WP_016622645.1 | type II CRISPR RNA-guided endonuclease Cas9 [Enterococcus faecalis] | SEQ ID NO: 304 |
| WP_033624816.1 | type II CRISPR RNA-guided endonuclease Cas9 [Enterococcus faecalis] | SEQ ID NO: 305 |
| WP_033625576.1 | type II CRISPR RNA-guided endonuclease Cas9 [Enterococcus faecalis] | SEQ ID NO: 306 |
| WP_033789179.1 | type II CRISPR RNA-guided endonuclease Cas9 [Enterococcus faecalis] | SEQ ID NO: 307 |
| WP_002310644.1 | type II CRISPR RNA-guided endonuclease Cas9 [Enterococcus faecium] | SEQ ID NO: 308 |
| WP_002312694.1 | type II CRISPR RNA-guided endonuclease Cas9 [Enterococcus faecium] | SEQ ID NO: 309 |
| WP_002314015.1 | type II CRISPR RNA-guided endonuclease Cas9 [Enterococcus faecium] | SEQ ID NO: 310 |
| WP_002320716.1 | type II CRISPR RNA-guided endonuclease Cas9 [Enterococcus faecium] | SEQ ID NO: 311 |
| WP_002330729.1 | type II CRISPR RNA-guided endonuclease Cas9 [Enterococcus faecium] | SEQ ID NO: 312 |
| WP_002335161.1 | type II CRISPR RNA-guided endonuclease Cas9 [Enterococcus faecium] | SEQ ID NO: 313 |
| WP_002345439.1 | type II CRISPR RNA-guided endonuclease Cas9 [Enterococcus faecium] | SEQ ID NO: 314 |
| WP_034867970.1 | type II CRISPR RNA-guided endonuclease Cas9 [Enterococcus faecium] | SEQ ID NO: 315 |
| WP_047937432.1 | type II CRISPR RNA-guided endonuclease Cas9 [Enterococcus faecium] | SEQ ID NO: 316 |
| WP_010720994.1 | type II CRISPR RNA-guided endonuclease Cas9 [Enterococcus hirae] | SEQ ID NO: 317 |
| WP_010737004.1 | type II CRISPR RNA-guided endonuclease Cas9 [Enterococcus hirae] | SEQ ID NO: 318 |
| WP_010700478.1 | type II CRISPR RNA-guided endonuclease Cas9 [Enterococcus hirae] | SEQ ID NO: 319 |
| WP_007209003.1 | type II CRISPR RNA-guided endonuclease Cas9 [Enterococcus italicus] | SEQ ID NO: 320 |
| WP_023519017.1 | type II CRISPR RNA-guided endonuclease Cas9 [Enterococcus mundtii] | SEQ ID NO: 321 |
| WP_010770040.1 | type II CRISPR RNA-guided endonuclease Cas9 [Enterococcus phoeniculicola] | SEQ ID NO: 322 |

-continued

| | |
|---|---|
| WP_048604708.1 | type II CRISPR RNA-guided endonuclease Cas9 [*Enterococcus* sp. AM1] SEQ ID NO: 323 |
| WP_010750235.1 | type II CRISPR RNA-guided endonuclease Cas9 [*Enterococcus villorum*] SEQ ID NO: 324 |
| AII16583.1 | Cas9 endonuclease [Expression vector pCas9] SEQ ID NO: 325 |
| WP_029073316.1 | type II CRISPR RNA-guided endonuclease Cas9 [*Kandleria vitulina*] SEQ ID NO: 326 |
| WP_031589969.1 | type II CRISPR RNA-guided endonuclease Cas9 [*Kandleria vitulina*] SEQ ID NO: 327 |
| KDA45870.1 | CRISPR-associated protein Cas9/Csn1, subtype II/NMEMI [*Lactobacillus animalis*] SEQ ID NO: 328 |
| WP_039099354.1 | type II CRISPR RNA-guided endonuclease Cas9 [*Lactobacillus curvatus*] SEQ ID NO: 329 |
| AKP02966.1 | hypothetical protein ABB45_04605 [*Lactobacillus farciminis*] SEQ ID NO: 330 |
| WP_010991369.1 | type II CRISPR RNA-guided endonuclease Cas9 [*Listeria innocua*] SEQ ID NO: 331 |
| WP_033838504.1 | type II CRISPR RNA-guided endonuclease Cas9 [*Listeria innocua*] SEQ ID NO: 332 |
| EHN60060.1 | CRISPR-associated protein, Csn1 family [*Listeria innocua* ATCC 33091] SEQ ID NO: 333 |
| EFR89594.1 | crispr-associated protein, Csn1 family [*Listeria innocua* FSL 54-378] SEQ ID NO: 334 |
| WP_038409211.1 | type II CRISPR RNA-guided endonuclease Cas9 [*Listeria ivanovii*] SEQ ID NO: 335 |
| EFR95520.1 | crispr-associated protein Csn1 [*Listeria ivanovii* FSL F6-596] SEQ ID NO: 336 |
| WP_003723650.1 | type II CRISPR RNA-guided endonuclease Cas9 [*Listeria monocytogenes*] SEQ ID NO: 337 |
| WP_003727705.1 | type II CRISPR RNA-guided endonuclease Cas9 [*Listeria monocytogenes*] SEQ ID NO: 338 |
| WP_003730785.1 | type II CRISPR RNA-guided endonuclease Cas9 [*Listeria monocytogenes*] SEQ ID NO: 339 |
| WP_003733029.1 | type II CRISPR RNA-guided endonuclease Cas9 [*Listeria monocytogenes*] SEQ ID NO: 340 |
| WP_003739838.1 | type II CRISPR RNA-guided endonuclease Cas9 [*Listeria monocytogenes*] SEQ ID NO: 341 |
| WP_014601172.1 | type II CRISPR RNA-guided endonuclease Cas9 [*Listeria monocytogenes*] SEQ ID NO: 342 |
| WP_023548323.1 | type II CRISPR RNA-guided endonuclease Cas9 [*Listeria monocytogenes*] SEQ ID NO: 343 |
| WP_031665337.1 | type II CRISPR RNA-guided endonuclease Cas9 [*Listeria monocytogenes*] SEQ ID NO: 344 |
| WP_031669209.1 | type II CRISPR RNA-guided endonuclease Cas9 [*Listeria monocytogenes*] SEQ ID NO: 345 |
| WP_033920898.1 | type II CRISPR RNA-guided endonuclease Cas9 [*Listeria monocytogenes*] SEQ ID NO: 346 |
| AKI42028.1 | CRISPR-associated protein [*Listeria monocytogenes*] SEQ ID NO: 347 |
| AKI50529.1 | CRISPR-associated protein [*Listeria monocytogenes*] SEQ ID NO: 348 |
| EFR83390.1 | crispr-associated protein Csn1 [*Listeria monocytogenes* FSL F2-208] SEQ ID NO: 349 |

```
                                                         -continued

WP_046323366.1         type II CRISPR RNA-guided endonuclease Cas9 [Listeria seeligeri] SEQ ID NO: 350
AKE81011.1             Cas9 [Plant multiplex genome editing vector pYLCRISPR/Cas9Pubi-H] SEQ ID NO: 351
CUO82355.1             Uncharacterized protein conserved in bacteria [Roseburia hominis] SEQ ID NO: 352
WP_033162887.1         type II CRISPR RNA-guided endonuclease Cas9 [Sharpea azabuensis] SEQ ID NO: 353
AGZ01981.1             Cas9 endonuclease [synthetic construct] SEQ ID NO: 354
AKA60242.1             nuclease deficient Cas9 [synthetic construct] SEQ ID NO: 355
AKS40380.1             Cas9 [Synthetic plasmid pFC330] SEQ ID NO: 356
4UN5_B                 Cas9, Chain B, Crystal Structure SEQ ID NO: 357

WP_010922251       1   MDKK--YSIGLDIGTNSVGWAVITDEYKVPSKKFKVLGNTDRHSIKKNLIGALLFDSGETA--EATRLKRTARRRYT    73
WP_039699303       1   MTKKnYSIGLDIGTNSVGWAVITDDYKVPAKKMKVLGNTDKKYIKKNLLGALLFDSGETA--EATRLKRTARRRYT    74
WP_045635197       1   K-KG-YSIGLDIGTNSVGFAVITDDYKVPSKKMMKVLGNTDKRFIKKNLIGALLFDEGTTA--EARRLKRTARRRYT    73
5AXW_A             1   MKRN-YILGLDIGTTSVGYGII--DYET-------RDVIDA---GVRLFKEANVEnnEGRRSKRGAARLKR        61
WP_009880683       -   ----------------------------------------------------------------------------
WP_010922251       1   MDKK--YSIGLDIGTNSVGWAVITDDYKVPSKKFKVLGNTDRHSIKKNLIGALLFDSGETA--EATRLKRTARRRYT    73
WP_011054416       1   MDKK--YSIGLDIGTNSVGWAVITDDYKVPSKKLKLGLGNTDRHGIKKNLIGALLFDSGETA--EATRLKRTARRRYT    73
WP_011284745       1   MDKK--YSIGLDIGTNSVGWAVITDDYKVPSKKFKVLGNTDKRFIKKNLIGALLFDSGETA--EATRLKRTARRRYT    73
WP_011285506       1   MDKK--YSIGLDIGTNSVGWAVITDDYKVPSKKFKVLGNTDRHSIKKNLIGALLFDSGETA--EATRLKRTARRRYT    73
WP_011527619       1   MDKK--YSIGLDIGTNSVGWAVITDDYKVPSKKFKVLGNTDRHSIKKNLIGALLFDSGETA--EATRLKRTARRRYT    73
WP_012560673       1   MDKK--YSIGLDIGTNSVGWAVITDDYKVPSKKFKVLGNTDRHSIKKNLIGALLFDSGETA--EATRLKRTARRRYT    73
WP_014407541       1   MDKK--YSIGLDIGTNSVGWAVITDDYKVPSKKFKVLGNTDRHSIKKNLIGALLFDSGETA--EATRLKRTARRRYT    73
WP_020905136       1   MDKK--YSIGLDIGTNSVGWAVITDDYKVPSKKFKVLGNTDRHSIKKNLIGALLFDSGETA--EATRLKRTARRRYT    73
WP_023080005       1   MDKK--YSIGLDIGTNSVGWAVITDDYKVPSKKLKVLGNTDRHGIKKNLIGALLFDSGETA--EATRLKRTARRRYT    73
WP_023610282       1   MDKK--YSIGLDIGTNSVGWAVITDDYKVPSKKFKVLGNTDRHGIKKNLIGALLFDSGETA--EATRLKRTARRRYT    73
WP_030125963       1   MDKK--YSIGLDIGTNSVGWAVITDDYKVPSKKFKVLGNTDRHSIKKNLIGALLFDSGETA--EATRLKRTARRRYT    73
WP_030126706       1   MDKK--YSIGLDIGTNSVGWAVITDDYKVPSKKFKVLGNTDRHSIKKNLIGALLFDSGETA--EATRLKRTARRRYT    73
WP_031488318       1   MDKK--YSIGLDIGTNSVGWAVITDDYKVPSKKFKVLGNTDRHSIKKNLIGALLFDSGETA--EATRLKRTARRRYT    73
WP_032460140       1   MDKK--YSIGLDIGTNSVGWAVITDDYKVPSKKFKVLGNTDRHSIKKNLIGALLFDSGETA--EATRLKRTARRRYT    73
```

-continued

| | | | |
|---|---|---|---|
| WP_032461047 | 1 | MDKK-YSIGLDIGTNSVGWAVITDDYKVPSKKFKVLGNTDRHSIKKNLIGALLFDSGETA--EATRLKRTARRYT | 73 |
| WP_032462016 | 1 | MDKK-YSIGLDIGTNSVGWAVITDDYKVPSKKFKVLGNTDRHSIKKNLIGALLFDSGETA--EATRLKRTARRYT | 73 |
| WP_032462936 | 1 | MDKK-YSIGLDIGTNSVGWAVITDDYKVPSKKFKVLGNTDRHSIKKNLIGALLFDSGETA--EATRLKRTARRYT | 73 |
| WP_032464890 | 1 | MDKK-YSIGLDIGTNSVGWAVITDDYKVPSKKFKVLGNTDRHSIKKNLIGALLFDSGEIA--EATRLKRTARRYT | 73 |
| WP_033888930 | | | |
| WP_038431314 | 1 | MDKK-YSIGLDIGTNSVGWAVITDDYKVPSKKFKVLGNTDRHSIKKNLIGALLFDSGETA--EATRLKRTARRYT | 73 |
| WP_038432938 | 1 | MDKK-YSIGLDIGTNSVGWAVITDDYKVPSKKFKVLGNTDRHSIKKNLIGALLFDSGETA--EATRLKRTARRYT | 73 |
| WP_038434062 | 1 | MDKK-YSIGLDIGTNSVGWAVITDDYKVPSKKFKVLGNTDRHSIKKNLIGALLFDSGETA--EATRLKRTARRYT | 73 |
| BAQ51233 | | | |
| KGE60162 | | | |
| KGE60856 | | | |
| WP_002989955 | 1 | MDKK-YSIGLDIGTNSVGWAVITDDYKVPSKKFKVLGNTDRHSIKKNLIGALLFDSGETA--EATRLKRTARRYT | 73 |
| WP_003030002 | 1 | MDQK-YSIGLDIGTNSVGWAVITDDYKVPAKKMKVLGNTDKQSIKKNLIGALLFDSGETA--EATRLKRTARRYT | 73 |
| WP_003065552 | 1 | MTKKnYSIGLDIGTNSVGWAVITDDYKVPAKKMKVLGNTDKKYIKKNLIGALLFDSGETA--EATRLKRTARRYT | 74 |
| WP_001040076 | 1 | MNKP-YSIGLDIGTNSVGWSIITDDYKVPAKKIRVLGNTDKEYIKKNLIGALLFDGGNTA--ADRRLKRTARRYT | 73 |
| WP_001040078 | 1 | MNKP-YSIGLDIGTNSVGWSIITDDYKVPAKKMRVLGNTDKEYIKKNLIGALLFDGGNTA--ADRRLKRTARRYT | 73 |
| WP_001040080 | 1 | MNKP-YSIGLDIGTNSVGWSIITDDYKVPAKKMRVLGNTDKEYIKKNLIGALLFDGGNTA--ADRRLKRTARRYT | 73 |
| WP_001040081 | 1 | MNKP-YSIGLDIGTNSVGWSIITDDYKVPAKKMRVLGNTDKEYIKKNLIGALLFDGGNTA--ADRRLKRTARRYT | 73 |
| WP_001040083 | 1 | MNKP-YSIGLDIGTNSVGWSIITDDYKVPAKKMRVLGNTDKEYIKKNLIGALLFDGGNTA--ADRRLKRTARRYT | 73 |
| WP_001040085 | 1 | MNKP-YSIGLDIGTNSVGWSIITDDYKVPAKKMRVLGNTDKEYIKKNLIGALLFDGGNTA--ADRRLKRTARRYT | 73 |
| WP_001040087 | 1 | MNKP-YSIGLDIGTNSVGWSIITDDYKVPAKKMRVLGNTDKEYIKKNLIGALLFDGGNTA--ADRRLKRTARRYT | 73 |
| WP_001040088 | 1 | MNKP-YSIGLDIGTNSVGWSIITDDYKVPAKKMRVLGNTDKEYIKKNLIGALLFDGGNTA--ADRRLKRTARRYT | 73 |
| WP_001040089 | 1 | MNKP-YSIGLDIGTNSVGWSIITDDYKVPAKKMRVLGNTDKEYIKKNLIGALLFDGGNTA--ADRRLKRTARRYT | 73 |
| WP_001040090 | 1 | MNKP-YSIGLDIGTNSVGWSIITDDYKVPAKKMRVLGNTDKEYIKKNLIGALLFDGGNTA--ADRRLKRTARRYT | 73 |
| WP_001040091 | 1 | MNKP-YSIGLDIGTNSVGWSIITDDYKVPAKKMRVLGNTDKEYIKKNLIGALLFDGGNTA--ADRRLKRTARRYT | 73 |
| WP_001040092 | 1 | MNKP-YSIGLDIGTNSVGWSIITDDYKVPAKKMRVLGNTDKEYIKKNLIGALLFDGGNTA--ADRRLKRTARRYT | 73 |
| WP_001040094 | 1 | MNKP-YSIGLDIGTNSVGWSIITDDYKVPAKKMRVLGNTDKEYIKKNLIGALLFDGGNTA--ADRRLKRTARRYT | 73 |

-continued

| | | | |
|---|---|---|---|
| WP_001040095 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040096 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040097 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040098 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040099 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040100 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040104 | 1 | MNKP-YSIGLDIGTNSVGWSIITDDYKVPAKKMRVLGNTDKEYIKKNLIGALLFDGGNTA--ADRRLKRTSRRRYT | 73 |
| WP_001040105 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040106 | 1 | MNKP-YSIGLDIGTNSVGYSVVTDDYKVPAKKMRVLGNTDKEYIKKNLIGALLFDGGNTA--ADRRLKRTARRRYT | 73 |
| WP_001040107 | 1 | MNKP-YSIGLDIGTNSVGYSVVTDDYKVPAKKMRVLGNTDKEYIKKNLIGALLFDGGNTA--SDRRLKRTARRRYT | 73 |
| WP_001040108 | 1 | MNKP-YSIGLDIGTNSVGWSIITDDYKVPAKKMRVLGNTDKEYIKKNLIGALLFDGGNTA--ADRRLKRTARRRYT | 73 |
| WP_001040109 | 1 | MNKP-YSIGLDIGTNSVGWSIITDDYKVPAKKMRVLGNTDKEYIKKNLIGALLFDGGNTA--SDRRLKRTARRRYT | 73 |
| WP_001040110 | 1 | MNKP-YSIGLDIGTNSVGWSIITDDYKVPAKKMRVLGNTDKEYIKKNLIGALLFDGGNTA--SDRRLKRTARRRYT | 73 |
| WP_015058523 | 1 | MNKP-YSIGLDIGTNSVGWSIITDDYKVPAKKMRVLGNTDKEYIKKNLIGALLFDGGNTA--ADRRLKRTARRRYT | 73 |
| WP_017643650 | 1 | MNKP-YSIGLDIGTNSVGWSIITDDYKVPAKKMRVLGNTDKEYIKKNLIGALLFDGGNTA--ADRRLKRTARRRYT | 73 |
| WP_017647151 | 1 | MNKP-YSIGLDIGTNSVGWSIITDDYKVPAKKMRVLGNTDKEYIKKNLIGALLFDGGNTA--SDRRLKRTARRRYT | 73 |
| WP_017648376 | 1 | MNKP-YSIGLDIGTNSVGWSIITDDYKVPAKKMRVLGNTDKEYIKKNLIGALLFDGGNTA--ADRRLKRTARRRYT | 73 |
| WP_017649527 | 1 | MNKP-YSIGLDIGTNSVGWSIITDDYKVPAKKMRVLGNTDKEYIKKNLIGALLFDGGNTA--SDRRLKRTARRRYT | 73 |
| WP_017771611 | 1 | MNKP-YSIGLDIGTNSVGWSIITDDYKVPAKKMRVLGNTDKEYIKKNLIGALLFDGGNTA--ADRRLKRTARRRYT | 73 |
| WP_017771984 | 1 | MNKP-YSIGLDIGTNSVGWSIITDDYKVPAKKMRVLGNTDKEYIKKNLIGALLFDGGNTA--ADRRLKRTARRRYT | 73 |
| CFQ25032 | 1 | MNKP-YSIGLDIGTNSVGWSIITDDYKVPAKKMRVLGNTDKEYIKKNLIGALLFDGGNTA--ADRRLKRTARRRYT | 73 |
| CFV16040 | 1 | MNKP-YSIGLDIGTNSVGWSIITDDYKVPAKKMRVLGNTDKEYIKKNLIGALLFDGGNTA--ADRRLKRTARRRYT | 73 |
| KLJ37842 | 1 | MNKP-YSIGLDIGTNSVGWSIITDDYKVPAKKMRVLGNTDKEYIKKNLIGALLFDGGNTA--ADRRLKRTARRRYT | 73 |
| KLJ72361 | 1 | MNKP-YSIGLDIGTNSVGWSIITDDYKVPAKKMRVLGNTDKEYIKKNLIGALLFDGGNTA--ADRRLKRTARRRYT | 73 |
| KLL20707 | 1 | MNKP-YSIGLDIGTNSVGWSIITDDYKVPAKKMRVLGNTDKEYIKKNLIGALLFDGGNTA--ADRRLKRTARRRYT | 73 |
| KLL42645 | 1 | MNKP-YSIGLDIGTNSVGWSIITDDYKVPAKKMRVLGNTDKEYIKKNLIGALLFDGGNTA--SDRRLKRTARRRYT | 73 |
| WP_047207273 | 1 | MNKP-YSIGLDIGTNSVGWSIITDDYKVPAKKMRVLGNTDKEYIKKNLIGALLFDGRNTA--ADRRLKRTARRRYT | 73 |

| ID | Start | Sequence | End |
|---|---|---|---|
| WP_047209694 | 1 | MNKP-YSIGLDIGTNSVGWSIITDDYKVPAKKMRVLGNTDKEYIKKNLIGALLFDGGNTA--ADRRLKRTARRYT | 73 |
| WP_050198062 | 1 | MNKP-YSIGLDIGTNSVGWSIITDDYKVPAKKMRVLGNTDKEYIKKNLIGALLFDGGNTA--ADRRLKRTARRYT | 73 |
| WP_050201642 | 1 | MNKP-YSIGLDIGTNSVGWSIITDDYKVPAKKMRVLGNTDKEYIKKNLIGALLFDGGNTA--ADRRLKRTARRYT | 73 |
| WP_050204027 | 1 | MNKP-YSIGLDIGTNSVGYSVVTDDYKVPAKKMRVLGNTDKEYIKKNLIGALLFDGGNTA--ADRRLKRTARRYT | 73 |
| WP_050881965 | 1 | MNKP-YSIGLDIGTNSVGWSIITDDYKVPAKKMRVLGNTDKEYIKKNLIGALLFDGGNTA--SDRRLKRTARRYT | 73 |
| WP_050886065 | 1 | MNKP-YSIGLDIGTNSVGWSIITDDYKVPAKKMRVLGNTDKEYIKKNLIGALLFDGGNTA--ADRRLKRTARRYT | 73 |
| AHN30376 | 1 | MNKP-YSIGLDIGTNSVGWSIITDDYKVPAKKMRVLGNTDKEYIKKNLIGALLFDGGNTA--ADRRLKRTARRYT | 73 |
| EAO78426 | 1 | MNKP-YSIGXDIGTNSVGWSIITDDYKVPAKKMRVLGNTDKEYIKKNLIGALLFDGGNTA--ADRRLKRTARRYT | 73 |
| CCW42055 | 1 | MNKP-YSIGLDIGTNSVGWSIITDDYKVPAKKMRVLGNTDKEYIKKNLIGALLFDGGNTA--ADRRLKRIARRYT | 73 |
| WP_003041502 | 1 | MNQK-YSIGLDIGTNSVGWAVITDDYKVPAKKMKVLGNTDKQSIKKNLLGALLFDSGETA--EATRLKRTARRYT | 74 |
| WP_037593752 | 1 | MKKE-YSIGLDIGTNSVGWAVITDDYKVPAKKMKVLGNTDKQSIKKNLLGALLFDSGETA--EATRLKRTARRYT | 74 |
| WP_049516684 | 1 | MKKE-YSIGLDIGTNSVGWAVITDDYKVPAKKMKVLGNTDKQSIKKNLLGALLFDSGETA--EATRLKRTARRYT | 73 |
| GAD46167 | 1 | MKKE-YSIGLDIGTNSVGWAVITDDYKVPAKKMKVLGNTDKKYIKKNLLGALLFDSGETA--EATRLKRTARRYT | 74 |
| WP_018363470 | 1 | MTKKnYSIGLDIGTNSVGWAVITDDYKVPAKKMKVLGNTDKKYIKKNLLGALLFDSGETA--KATRLKRTARRYT | 73 |
| WP_003043819 | 1 | MEKK-YSIGLDIGTNSVGWAVITDDYKVPSKKEKVLGNTNRKSIKKNLMGALLFDSGETA--EATRLKRTARRYT | 73 |
| WP_006269658 | 1 | MGKP-YSIGLDIGTNSVGWAVITDDYKVPSKKEKVLGNTDKQSIKKNLLGALLFDSGETA--EATRLKRTARRYT | 73 |
| WP_048800889 | 1 | MTQK-YSIGLDIGTNSVGWAIVTDDYKVPAKKMILGNTNKQYIKKNLLGALLFDSGETA--KATRLKRTARRYT | 73 |
| WP_012767106 | 1 | MDKK-YSIGLDIGTNSVGWAVITDDYKVPSKKEKVLGNTDRHSIKKNLIGALLFDSGETA--EATRLKRTARRYT | 73 |
| WP_014612333 | 1 | MDKK-YSIGLDIGTNSVGWAVITDDYKVPSKKEKVLGNTDRHSIKKNLIGALLFDSGETA--EATRLKRTARRYT | 73 |
| WP_015017095 | 1 | MDKK-YSIGLDIGTNSVGWAVITDDYKVPSKKEKVLGNTDRHSIKKNLIGALLFDSGETA--EATRLKRTARRYT | 73 |
| WP_015057649 | 1 | MDKK-YSIGLDIGTNSVGWAVITDDYKVPSKKEKVLGNTDRHSIKKNLIGALLFDSGETA--EATRLKRTARRYT | 73 |
| WP_048327215 | 1 | MDKK-YSIGLDIGTNSVGWAVITDDYKVPSKKEKVLGNTDRHSIKKNLIGALLFDSGETA--EATRLKRTARRYT | 73 |
| WP_049519324 | 1 | MDKK-YSIGLDIGTNSVGWAVITDDYKVPTKKMKVLGNTERKTIKKNLIGALLFDSGDTA--EGTRLKRTARRYT | 73 |
| WP_012515931 | 1 | MKKP-YTIALDIGTNSVGWVVVTDDYRVPTKKMKVLGNTERKTIKKNLIGALLFDSGDTA--EGTRLKRTARRYT | 73 |
| WP_021320964 | 1 | MKKP-YTIALDIGTNSVGWVVVTDDYRVPTKKMKVLGNTERKTIKKNLIGALLFDSGDTA--EGTRLKRTARRYT | 73 |
| WP_037581760 | 1 | MKKP-YTIALDIGTNSVGWVVVTDDYRVPTKKMKVLGNTERKTIKKNLIGALLFDSGDTA--EGTRLKRTARPYT | 73 |
| WP_004232481 | 1 | M-EKtYSIGLDIGTNSVGWAVITDDYKVPAKKMKVLGNTDKKYIKKNLLGALLFDSGETA--EATRLKRAARRYT | 73 |

-continued

| Accession | Start | Sequence | End |
|---|---|---|---|
| WP_009854540 | 1 | MTKKnYSIGLDIGTNSVGWAVITDDYKVPAKKMKVLGNTDKKYIKKNLLGALLFDSGETA--EATRLKRTARRYT | 74 |
| WP_012962174 | 1 | MTEKnYSIGLDIGTNSVGWAVITDDYKVPAKKMKVLGNTDKKYIKKNLLGALLFDNGETA--EATRLKRTARRYT | 74 |
| WP_039695303 | 1 | MTKKnYSIGLDIGTNSVGWAVITDDYKVPAKKMKVLGNTDKKYIKKNLLGALLFDSGETA--EATRLKRTARRYT | 74 |
| WP_014334983 | 1 | M-EKsYSIGLDIGTNSVGWAVITDDYKVPAKKMKVLGNTDKKYIKKNLLGALLFDSGETA--EVTRLKRTARRYT | 73 |
| WP_003099269 | 1 | MRKP-YSIGLDIGTNSVGWAVITDDYKVPSKKMRIQGTTDRTSIKKNLIGALLFDNGETA--EATRLKRTRRRYT | 73 |
| AHY15608 | 1 | MRKP-YSIGLDIGTNSVGWAVITDDYKVPSKKMRIQGTTDRTSIKKNLIGALLFDNGETA--EATRLKRTRRRYT | 73 |
| AHY17476 | 1 | MRKP-YSIGLDIGTNSVGWAVITDDYKVPSKKMRIQGTTDRTSIKKNLIGALLFDNGETA--EATRLKTTRRRYT | 73 |
| ESR09100 | 1 | ------------------------------------------------------------------------- |  |
| AGM98575 | 1 | MRKP-YSIGLDIGTNSVGWAVITDDYKVPSKKMRIQGTTDRTSIKKNLIGALLFDNGETA--EATRLKRTRRRYT | 73 |
| ALF27331 | 1 | MKKP-YSIGLDIGTNSVGWAVVTDDYKVPAKKMKVLGNTDKSHIKKNLLGALLFDSGNTA--EDRRLKRTARRYT | 73 |
| WP_018372492 | 1 | MKKP-YSIGLDIGTNSVGWAVVMEDYKVPSKKMKVLGNTDKQSIKKNLIGALLFDSGETA--ERRLNRTTSRRYD | 73 |
| WP_045618028 | 1 | NNKP-YSIGLDIGTNSVGWAVITDDYKVPAKKMKVLGNTDKHFIKKNLLGALLFDEGTTA--EDRRLKRTARRYT | 74 |
| WP_045635197 | 1 | K-KG-YSIGLDIGTNSVGFAVITDDYKVPAKKMKVLGNTDKRFIKKNLLGALLFDEGTTA--EARRLKRTARRYT | 73 |
| WP_002263549 | 1 | MKKP-YSIGLDIGTNSVGWAVTDDYKVPAKKMKVLGNTDKSHIEKNLLGALLFDSGNTA--EDRRLKRTARRYT | 73 |
| WP_002263887 | 1 | MKKP-YSIGLDIGTNSVGWAVVTDDYKVPAKKMKVLGNTDKSHIEKNLLGALLFDSGNTA--EDRRLKRTARRYT | 73 |
| WP_002264920 | 1 | MKKP-YSIGLDIGTNSVGWAVVTDDYKVPAKKMKVLGNTDKSHIKKNLLGALLFDSGNTA--EDRRLKRTARRYT | 73 |
| WP_002269043 | 1 | MKKP-YSIGLDIGTNSVGWAVVTDDYKVPAKKMKVLGNTDKSHIKKNLLGALLFDSGNTA--EDRRLKRTARRYT | 73 |
| WP_002269448 | 1 | MKKP-YSIGLDIGTNSVGWAVVTDDYKVPAKKMKVLGNTDKSHIKKNLLGALLFDSGNTA--EDRRLKRTARRYT | 73 |
| WP_002271977 | 1 | MKKP-YSIGLDIGTNSVGWAVVTDDYKVPAKKMKVLGNTDKSHIKKNLLGALLFDSGNTA--EDRRLKRTARRYT | 73 |
| WP_002272766 | 1 | MKKP-YSIGLDIGTNSVGWAVVTDDYKVPAKKMKVLGNTDKSHIKKNLLGALLFDSGNTA--EDRRLKRTARRYT | 73 |
| WP_002273241 | 1 | MKKP-YSIGLDIGTNSVGWAVVTDDYKVPAKKMKVLGNTDKSHIKKNLLGALLFDSGNTA--EDRRLKRTARRYT | 73 |
| WP_002275430 | 1 | MKKP-YSIGLDIGTNSVGWAVVTDDYKVPAKKMKVLGNTDKSHIKKNLLGALLFDSGNTA--ADRRLKRTARRYT | 73 |
| WP_002276448 | 1 | MKKP-YSIGLDIGTNSVGWAVVTDDYKVPAKKMKVLGNTDKSHIKKNLLGALLFDSGNTA--EDRRLKRTARRYT | 73 |
| WP_002277050 | 1 | MKKS-YSIGLDIGTNSVGWAVVTDDYKVPAKKMKVLGNTDKSHIKKNLLGALLFDSGNTA--EDRRLKRTARRYT | 73 |
| WP_002773364 | 1 | MKKP-YSIGLDIGTNSVGWAVVTDDYKVPAKKMKVLGNTDKSHIKKNLLGALLFDSGNTA--ADRRLKRTARRYT | 73 |
| WP_002279025 | 1 | MKKP-YSIGLDIGTNSVGWAVVTDDYKVPAKKMKVLGNTDKSHIEKNLLGALLFDSGNTA--EDRRLKRTARRYT | 73 |
| WP_002279859 | 1 | MKKP-YSIGLDIGTNSVGWAVVTDDYKVPAKKMKVLGNTDKSHIKKNLLGALLFDSGNTA--EDRRLKRTARRYT | 73 |

-continued

| | | | |
|---|---|---|---|
| WP_002280230 | 1 | MKKP-YSIGLDIGTNSVGWAVVTDDYKVPAKKMKVLGNTDKSHIKKNLLGALLFDSGNTA--ADRRLKRTARRRYT | 73 |
| WP_002281696 | 1 | MKKP-YSIGLDIGTNSVGWAVVTDDYKVPAKKMKVLGNTDKSHIKKNLLGALLFDSGNTA--ADRRLKRTARRRYT | 73 |
| WP_002282247 | 1 | MKKP-YSIGLDIGTNSVGWAVVTDDYKVPAKKMKVLGNTDKSHIKKNLLGALLFDSGNTA--EDRRLKRTARRRYT | 73 |
| WP_002282906 | 1 | MKKP-YSIGLDIGTNSVGWSVVTDDYKVPAKKMKVLGNTDKSHIKKNLLGALLFDSGNTA--EDRRLKRTARRRYT | 73 |
| WP_002283846 | 1 | MKKP-YSIGLDIGTNSVGWAVVTDDYKVPAKKMKVLGNTDKSHIKKNLLGALLFDSGNTA--EDRRLKRTARRRYT | 73 |
| WP_002287255 | 1 | MKKP-YSIGLDIGTNSVGWAVVTDDYKVSAKKMKVLGNTDKSHIKKNLLGALLFDSGNTA--EDRRLKRTARRRYT | 73 |
| WP_002288990 | 1 | MKKP-YSIGLDIGTNSVGWAVVTDDYKVPAKKMKVLGNTDKSHIKKNLLGALLFDSGNTA--EDRRLKRTARRRYT | 73 |
| WP_002289641 | 1 | MKKP-YSIGLDIGTNSVGWAVVTDDYKVPAKKMKVLGNTDKSHIKKNLLGALLFDSGNTA--EDRRLKRTTRRRYT | 73 |
| WP_002290427 | 1 | MKKP-YSIGLDIGTNSVGWAVVTDDYKVPAKKMKVLGNTDKSHIKKNLLGALLFDSGNTA--EDRRLKRTARRRYT | 73 |
| WP_002295753 | 1 | MKKP-YSIGLDIGTNSVGWAVVTDDYKVPAKKMKVLGNTDKSHIKKNLLGALLFDSGNTA--EDRRLKRTARRRYT | 73 |
| WP_002296423 | 1 | MKKP-YSIGLDIGTNSVGWAVVTDDYKVPAKKMKVLGNTDKSHIKKNLLGALLFDSGNTA--EDRRLKRTARRRYT | 73 |
| WP_002304487 | 1 | MKKP-YSIGLDIGTNSVGWAVVTDDYKVPAKKMKVLGNTDKSHIKKNLLGALLFDSGNTA--EDRRLKRTARRRYT | 73 |
| WP_002305844 | 1 | MKKP-YSIGLDIGTNSVGWAVVTDDYKVPAKKMKVLGNTDKSHIKKNLLGALLFDSGNTA--EDRRLKRTARRRYT | 73 |
| WP_002307203 | 1 | MKKP-YSIGLDIGTNSVGWAVVTDDYKVPAKKMKVLGNTDKSHIEKNLLGALLFDSGNTA--EDRRLKRTARRRYT | 73 |
| WP_002310390 | 1 | MKKP-YSIGLDIGTNSVGWAVVTDDYKVPAKKMKVLGNTDKSHIKKNLLGALLFDSGNTA--EDRRLKRTARRRYT | 73 |
| WP_002352408 | 1 | MKKP-YSIGLDIGTNSVGWAVVTDDYKVPAKKMKVLGNTDKSHIKKNLLGALLFDSGNTA--EDRRLKRTARRRYT | 73 |
| WP_012997688 | 1 | MKKP-YSIGLDIGTNSVGWAVVTDDYKVPAKKMKVLGNTDKSHIKKNLLGALLFDSGNTA--ADRRLKRTARRRYT | 73 |
| WP_014677909 | 1 | MKKP-YSIGLDIGTNSVGWAVVTDDYKVPDKKMKVLGNTDKSHIKKNLLGALLFDSGNTA--EDRRLKRTARRRYT | 73 |
| WP_019312892 | 1 | MKKP-YSIGLDIGTNSVGWAVVTDDYKVPAKKMKVLGNTDKSHIKKNLLGALLFDSGNTA--ADRRLKRTARRRYT | 73 |
| WP_019313659 | 1 | MKKP-YSIGLDIGTNSVGWAVVTDDYKVPAKKMKVLGNTDKSHIEKNLLGALLFDSGNTA--EDRRLKRTARRRYT | 73 |
| WP_019314093 | 1 | MKKP-YSIGLDIGTNSVGWAVVTDDYKVPAKKMKVLGNTDKSHIKKNLLGALLFDSGNTA--EDRRLKRTARRRYT | 73 |
| WP_019315370 | 1 | MKKP-YSIGLDIGTNSVGWAVVTDDYKVPAKKMKVLGNTDKSHIEKNLLGALLFDSGNTA--EDRRLKRTARRRYT | 73 |
| WP_019803776 | 1 | MKKP-YSIGLDIGTNSVGWAVVTDDYKVPAKKMKVLGNTDKSHIKKNLLGALLFDSGNTA--EDRRLKRTARRRYT | 73 |
| WP_019805234 | 1 | MKKP-YSIGLDIGTNSVGWAVVTDDYKVPAKKMKVLGNTDKSHIEKNLLGALLFDSGNTA--EDRRLKRTARRRYT | 73 |
| WP_024783594 | 1 | MKKP-YSIGLDIGTNSVGWAVVTDDYKVPAKKMKVLGNTDKSHIKKNLLGALLFDSGNTA--EDRRLKRTARRRYT | 73 |
| WP_024784288 | 1 | MKKP-YSIGLDIGTNSVGWAVVTDDYKVPAKKMKVLGNTDKSHIKKNLLGALLFDSGNTA--EDRRLKRTARRRYT | 73 |
| WP_024784666 | 1 | MKKP-YSIGLDIGTNSVGWAVVTDDYKVPAKKMKVLGNTDKSHIKKNLLGALLFDSGNTA--ADRRLKRTARRRYT | 73 |

-continued

| ID | Start | Sequence | End |
|---|---|---|---|
| WP_024784894 | 1 | MKKP-YSIGLDIGTNSVGWAVVTDDYKVPAKKMKVLGNTDKSHIKKNLLGALLFDSGNTA--EDRRLKRTTRRRYT | 73 |
| WP_024786433 | 1 | MKKP-YSIGLDIGTNSVGWAVVTDDYKVPAKKMKVLGNTDKSHIKKNLLGALLFDSGNTA--ADRRLKRTARRRYT | 73 |
| WP_049473442 | 1 | MKKP-YSIGLDIGTNSVGWAVVTDDYKVPAKKMKVLGNTDKSHIKKNLLGALLFDSGNTA--ADRRLKRTARRRYT | 73 |
| WP_049474547 | 1 | MKKP-YSIGLDIGTNSVGWAVVTDDYKVPAKKMKVLGNTDKSHIKKNLLGALLFDSGNTA--EDRRLKRTTRRRYT | 73 |
| EMC03581 | 1 | MDL------IGTNSVGWAVVTDDYKVPAKKMKVLGNTDKSHIKKNLLGALLFDSGNTA--ADRRLKRTARRRYT | 66 |
| WP_000428612 | 1 | ENKN-YSIGLDIGTNSVGWAVITDDYKVPSKKMKVLGNTDKRFIKKNLIGALLFDEGTTA--EARRLKRTARRRYT | 74 |
| WP_000428613 | 1 | ENKN-YSIGLDIGTNSVGWAVITDDYKVPSKKMKVLGNTDKRFIKKNLIGALLFDEGTTA--EARRLKRTARRRYT | 74 |
| WP_049523028 | 1 | K-KP-YSIGLDIGTNSVGWAVITDDYKVPAKKMKVLGNTNKESIKKNLIGALLFDAGNTA--ADRRLKRTARRRYT | 73 |
| WP_003107102 | 1 | ----------MKVLGNTDRQTVKKNMIGTLLFDSGETA--EARRLKRTARRRYT | 42 |
| WP_054279288 | 1 | -KKS-YSIGLDIGTNSVGWAVITDDYKVPAKKMKVLGNTSRQSIKKNMIGALLFDEGGPA--ASTRVKRTTRRRYT | 75 |
| WP_049531101 | 1 | SNKP-YSIGLDIGTNSVGWVIITDDYKVPSKKMKVLGNTDKHFIKKNLIGALLFDEGTTA--EDRRLKRTARRRYT | 74 |
| WP_049538452 | 1 | SNKP-YSIGLDIGTNSVGWVIITDDYKVPSKKMKVLGNTDKHFIKKNLIGALLFDEGTTA--EDRRLKRTARRRYT | 74 |
| WP_049549711 | 1 | SNKP-YSIGLDIGTNSVGWAVITDDYKVPAKKMTVLGNTDKHFIKKNLIGALLFDEGTTA--EDRRLKRTARRRYT | 74 |
| WP_007896501 | 1 | --YS-YSIGLDIGTNSVGWAVINEDYKVPAKKMVFGNTDRKTIKKNLLGTVLFDSGETA--QARRLKRTNRRRYT | 75 |
| EFR44625 | 1 | ---------MLGTVLFDSGETA--QARRLKRTNRRRYT | 27 |
| WP_002897477 | 1 | K-KP-YSIGLDIGTNSVGWAVVTDDYKVPAKKMVFGDTDRSHIKKNLLGTLLFDDGNTA--ESRRLKRTARRRYT | 73 |
| WP_002906454 | 1 | K-KP-YSIGLDIGTNSVGWSVVTDDYKVPSKKMKVLGNTDKHFIKKNLIGALLFDEGTTA--EDRRLKRTSRRRYT | 73 |
| WP_009729476 | 1 | ENKN-YSIGLDIGTNSVGNSVVTDDYKVPAKKMKVLGNTDKHFIKKNLIGALLFDEGTTA--EARRLKRTARRRYT | 74 |
| CQR24647 | 1 | MKKP-YSIGLDIGTNSVGNSVVTDDYKVPAKKMKVLGNTDKEYIKKNLIGALLFDSGETA--EATRMKRTARRRYT | 73 |
| WP_000066813 | 1 | SNKS-YSIGLDIGTNSVGNSVVTDDYKVPSKKMKVLGNTDKHFIKKNLIGALLFDSGETA--EDRRLKRTARRRYT | 73 |
| WP_009754323 | 1 | NNNN-YSIGLDIGTNSVGNAVITDDYKVPSKKMRVLGNTDKRFIKKNLIGALLFDEGTTA--EDRRLKRTARRRYT | 74 |
| WP_044674937 | 1 | MKKK-YAIGIDIGTNSVGWAVITDDYKVPSKKKMKVFGNTEKRYIKKNLLGTLLFDEGNTA--ENRRLKRTARRRYT | 74 |
| WP_044676715 | 1 | MKKK-YAIGIDIGTNSVGWAVITDDYKVPSKKMKVFGNTEKRYIKKNLLGTLLFDEGNTA--ENRRLKRTARRRYT | 73 |
| WP_044680361 | 1 | MKKK-YAIGIDIGTNSVGWAVITDDYKVPSKKMKVFGNTEKRYIKKNLLGTLLFDEGNTA--ENRRLKRTARRRYT | 73 |
| WP_044681799 | 1 | MKKK-YAIGIDIGTNSVGWAVITDDYKVPSKKMKVFGNTEKRYIKKNLLGTLLFDEGNTA--ENRRLKRTARRRYT | 73 |
| WP_049533112 | 1 | MDQK-YSIGLDIGTNSVGWAVVTDDYKVPAKKMKVLGNTDKQSIKKNLLGALLFDSGETA--EATRLKRTARRRYT | 73 |
| WP_029090905 | 1 | ----------MWGVSLFEAGKTA--AERRGYRSTRRRLN | 27 |

```
                                                                                                                                      -continued WP_006506696    1  I-VD-YCIGLDLGTGSVGWAVVDMNHRLMKRN------GKHLWGSRLFSNAETA--ANRRASRSIRRRYN  60
AIT42264        1  MDKK-YSIGLDIGTNSVGWAVITDEYKVPSKKFKVLGNTDRHSIKKNLIGALLFDSGETA--EATRLKRTARRRYT  73
WP_034440723    1  -MKN-YTIGLDIGTNSVGWAVIKDDLTLVRKKIKISGNTDKKEVKKNLWGSFLFEQGDTA--QDTRVKRIARRRYE  72
AKQ21048        1  MDKK-YSIGLDIGTNSVGWAVITDEYKVPSKKFKVLGNTDRHSIKKNLIGALLFDSGETA--EATRLKRTARRRYT  73
WP_004636532    1  MQKN-YTIGLDIGTNSVGWAVMKDDYTLIRKRMKVLGNTDIKKLKKNFWGVRLFDEGETA--KETRLKRGTRRRYQ  73
WP_002364836    1  MKKD-YVIGLDIGTNSVGWAVMTEDYQLVKKKMPIYGNTEKKKIKKNFWGVRLFEEGHTA--EDRRLKRTARRIS  73
WP_016631044    1  ----------------------------------MRLFEEGHTA--EDRRLKRTARRIS  24
EMS75795        1  ---------------------------------------------------------------------------
WP_002373311    1  MKKD-YVIGLDIGTNSVGWAVMTEDYQLVKKKMPIYGNTEKKKIKKNFWGVRLFEEGHTA--EDRRLKRTARRIS  73
WP_002378009    1  MKKD-YVIGLDIGTNSVGWAVMTEDYQLVKKKMPIYGNTEKKKIKKNFWGVRLFEEGHTA--EDRRLKRTARRIS  73
WP_002407324    1  MKKD-YVIGLDIGTNSVGWAVMTEDYQLVKKKMPIYGNTEKKKIKKNFWGVRLFEEGHTA--EDRRLKRTARRIS  73
WP_002413717    1  MKKD-YVIGLDIGTNSVGWAVMTEDYQLVKKKMPIYGNTEKKKIKKNFWGVRLFEEGHTA--EDRRLKRTARRIS  73
WP_010775580    1  MKKD-YVIGLDIGTNSVGWAVMTEDYQLVKKKMPIYGNTEKKKIKKNFWGVRLFEEGHTA--EDRRLKRTARRIS  73
WP_010818269    1  MKKD-YVIGLDIGTNSVGWAVMTEDYQLVKKKMPIYGNTEKKKIKKNFWGVRLFEEGHTA--EDRRLKRTARRIS  73
WP_010824395    1  MKKD-YVIGLDIGSNSVGWAVMTEDYQLVKKKMPIYGNTEKKKIKKNFWGVRLFEEGHTA--EDRRLKRTARRIS  73
WP_016622645    1  MKKD-YVIGLDIGTNSVGWAVMTEDYQLVKKKMPIYGNTEKKKIKKNFWGVRLFEEGHTA--EDRRLKRTARRIS  73
WP_033624816    1  MKKD-YVIGLDIGTNSVGWAVMTEDYQLVKKKMPIYGNTEKKKIKKNFWGVRLFEEGHTA--EDRRLKRTARRIS  73
WP_033625576    1  MKKD-YVIGLDIGTNSVGWAVMTEDYQLVKKKMPIYGNTEKKKIKKNFWGVRLFEEGHTA--EDRRLKRTARRIS  73
WP_033789179    1  MKKE-YTIGLDIGTNSVGWSVLTDDYRLVSKKKMVAGNTEKSSTKKNFWGVRLFDEGQTA--EARRSKRTARRRLA  73
WP_002310644    1  MKKE-YTIGLDIGTNSVGWSVLTDDYRLVSKKKMVAGNTEKSSTKKNFWGVRLFDEGQTA--EARRSKRTARRRLA  73
WP_002312694    1  MKKE-YTIGLDIGTNSVGWSVLTDDYRLVSKKKMVAGNTEKSSTKKNFWGVRLFDEGQTA--EARRSKRTARRRLA  73
WP_002314015    1  MKKE-YTIGLDIGTNSVGWSVLTDDYRLVSKKKMVAGNTEKSSTKKNFWGVRLFDEGQTA--EARRSKRTARRRLA  73
WP_002320716    1  MKKE-YTIGLDIGTNSVGWSVLTDDYRLVSKKKMVAGNTEKSSTKKNFWGVRLFDEGQTA--EARRSKRTARRRLA  73
WP_002330729    1  MKKE-YTIGLDIGTNSVGWSVLTDDYRLVSKKKMVAGNTEKSSTKKNFWGVRLFDEGQTA--EARRSKRTARRRLA  73
WP_002335161    1  MKKE-YTIGLDIGTNSVGWSVLTDDYRLVSKKKMVAGNTEKSSTKKNFWGVRLFDEGQTA--EARRSKRTARRRLA  73
WP_002345439    1  MKKE-YTIGLDIGTNSVGWSVLTDDYRLVSKKKMVAGNTEKSSTKKNFWGVRLFDEGQTA--EARRSKRTARRRLA  73
WP_034867970    1  MTKD-YTIGLDIGTNSVGNAVLTDDYQLMCRKMSVHGNTEKKKIKKNFWGARLFDEGQTA--EPRRTKRTNRRRLA  73
```

| Accession | Start | Sequence | End |
|---|---|---|---|
| WP_047937432 | 1 | MKKE-YTIGLDIGTNSVGWSVLTDDYRLVSKKMKVAGNTEKSSTKKNFWGVRLFDEGQTA--EARRSKRTARRRLA | 73 |
| WP_010720994 | 1 | MTKD-YTIGLDIGTNSVGWAVLTDDYQLMKRKMSVHGNTEKKKIKKNFWGARLFDEGQTA--EFRRTKRTNRRRLA | 73 |
| WP_010737004 | 1 | MTKD-YTIGLDIGTNSVGWAVLTDDYQLMKRKMSVHGNTEKKKIKKNFWGARLFDEGQTA--EFRRTKRTNRRRLA | 73 |
| WP_034700478 | 1 | MTKD-YTIGLDIGTNSVGWAVLTDDYQLMKRKMSVHGNTEKKKIKKNFWGARLFDEGQTA--EFRRTKRTNRRRLA | 73 |
| WP_007209003 | 1 | MKND-YTIGLDIGTNSVGYSVVTDDYKVISKKMNVFGNTEKKKSIKKNFWGVRLFESGQTA--QEARMKRTSRRRIA | 73 |
| WP_023519017 | 1 | MEKE-YTIGLDIGTNSVGWAVLTDDYRLVARKMSIQGDSNRKKIKKNFWGARLFEEGKTA--QFRRIKRTNRRRIA | 73 |
| WP_010770040 | 1 | MKKE-YTIGLDIGTNSVGWAVLTENYDLVKKKMKVYGNTETKYLKKNLWGVRLFDEGETA--ADRRLKRTTRRRYS | 73 |
| WP_048604708 | 1 | MGKE-YTIGLDIGTNSVGWAVLQEDLLVRRKMKVYGNTEKNYLKKNFWGVDLFDEGMTA--KDTRLKRTTRRRYF | 73 |
| WP_010750235 | 1 | MNKA-YTLGLDIGTNSVGWAVVTDDYRLMAKKMPVHSKMEKKKIKKNFWGARLFDEGQTA--EERRNKRATRRRLR | 73 |
| AII16583 | 1 | ADKK-YSIGLDIGTNSVGWAVITDEYKVPSKKFKVLGNTDRHSIKKNLIGALLFDSGETA--EATRLKRTARRRYT | 112 |
| WP_029073316 | 1 | NNKI-YNIGLDIGDASVGWAVVDEHYNLLKRH----------GKHMWGSRLFTQANTA--VERRSSRSTRRRYN | 65 |
| WP_031589969 | 1 | NNKI-YNIGLDIGDASVGWAVVDEHYNLLKRH----------GKHMWGSRLFTQANTA--VERRSSRSTRRRYN | 65 |
| KDA45870 | 1 | LKKD-YSIGLDIGTNSVGHAVVTDDYKVPTKKMKVFGDTSKKTIKKNMLGVLLFNEGQTA--ADTRLKRGARRRYT | 74 |
| WP_039099354 | 1 | MSRP-YNIGLDIGTSSIGWSVVDDQSKLVSVR----------GKYGYGVRLYDEGQTA--AERRSFTTRRRLK | 61 |
| AKP02966 | 1 | KEQP-YNIGLDIGTGSVGWAVTNDNYDLLNIK----------KKNLWGVRLFEGAQTA--KETRLNRSTRRRYR | 64 |
| WP_010991369 | 1 | MKKP-YTIGLDIGTNSVGWAVLTDQYDLVKRKMKIAGDSEKKQIKKNFWGVRLFDEGQTA--ADRRMARTARRRIE | 73 |
| WP_033838504 | 1 | MKKP-YTIGLDIGTNSVGWAVLTDQYDLVKRKMKIAGDSEKKQIKKNFWGVRLFDEGQTA--ADRRMARTARRRIE | 73 |
| EHN60060 | 1 | MKKP-YTIGLDIGTNSVGWAVLTDQYDLVKRKMKIAGDSEKKQIKKNFWGVRLFDEGQTA--ADRRMARTARRRIE | 76 |
| EFR89594 | | ---------------------------------------------------------------------- | |
| WP_038409211 | 1 | MRKP-YTIGLDIGTNSVGWAVLTDQYDLVKRKMKVAGSAEKKQIKKNFWGVRLFDEGEVA--AGRRMNRTTRRRIE | 73 |
| EFR95520 | | ---------------------------------------------------------------------- | |
| WP_003723650 | 1 | MKNP-YTIGLDIGTNSVGWAVLTNQYDLVKRKMKVAGNSDKKQIKKNFWGVRLFDDGQTA--VDRRMNRTARRRIE | 73 |
| WP_003727705 | 1 | MKNP-YTIGLDIGTNSVGWAVLTDQYDLVKRKMKVAGNSDKKQIKKNFWGVRLFDDGQTA--VDRRMNRTARRRIE | 73 |
| WP_003730785 | 1 | MKNP-YTIGLDIGTNSVGWAVLTDQYDLVKRKMKVAGNSDKKQIKKNFWGVRLFDDGQTA--VDRRMNRTARRRIE | 73 |
| WP_003733029 | 1 | MKKP-YTIGLDIGTNSVGWAVLTDQYDLVKRKMKISGDSEKKQIKKNFWGVRLFEKGETA--AKRRMSRTARRRIE | 73 |
| WP_003739838 | 1 | MKNP-YTIGLDIGTNSVGWAVLTDQYDLVKRKMKVAGNSDKKQIKKNFWGVRLFDDGQTA--ADRRMNRTARRRIE | 73 |
| WP_014601172 | 1 | MKNP-YTIGLDIGTNSVGWAVLTNQYDLVKRKMKVAGNSDKKQIKKNFWGVRLFDDGQTA--VDRRMNRTARRRIE | 73 |

| ID | Start | Sequence | End |
|---|---|---|---|
| WP_023548323 | 1 | MKNP-YTIGLDIGTNSVGWAVLTNQYDLVKRKMKVAGNSDKKQIKKNFWGVRLFDDGQTA--VDRRMNRTARRRIE | 73 |
| WP_031665337 | 1 | MKNP-YTIGLDIGTNSVGWAVLTDQYDLVKRKMKVAGNSDKKQIKKNFWGVRLFDDGQTA--VDRRMNRTARRRIE | 73 |
| WP_031669209 | 1 | MKKP-YTIGLDIGTNSVGWAVLTDQYDLVKRKMKVAGNSDKKQIKKNFWGVRLFEKGETA--AKRRMSRTARRRIE | 73 |
| WP_033920898 | 1 | MKNP-YTIGLDIGTNSVGWAVLTNQYDLVKRKMKISGDSEKKQIKKNFWGVRLFDDGQTA--VDRRMNRTARRRIE | 73 |
| AKI42028 | 1 | MKNP-YTIGLDIGTNSVGWAVLTNQYDLVKRKMKVAGNSDKKQIKKNFWGVRLFDDGQTA--VDRRMNRTARRRIE | 76 |
| AKI50529 | 1 | MKNP-YTIGLDIGTNSVGWAVLTNQYDLVKRKMKVAGNSDKKQIKKNFWGVRLFDDGQTA--VDRRMNRTARRRIE | 76 |
| EFR83390 | | | |
| WP_046323366 | 1 | MKKP-YTIGLDIGTNSVGWAALTDQYDLVKRKMKVAGNSEKKQIKKNLWGVRLVDEGKTA--AHRRVNRTTRRRIE | 73 |
| AKE81011 | 1 | ADKK-YSIGLDIGTNSVGWAVITDEYKVPSKKFKVLGNTDRHSIKKNLIGALLFDSGETA--EATRLKRTARRYT | 89 |
| CUO82355 | 1 | I-VD-YCIGLDLGTGSVGWAVVDMNHRLMKRN----------GKHLWGSRLFSNAETA--ATRRSRSIRRRYN | 64 |
| WP_033162887 | 1 | KDIR-YSIGLDIGTNSVGWAVMDEHYELLKKG----------NHHMWGSRLFDAAEPA--ATRRASRSIRRRYN | 65 |
| AGZ01981 | 1 | ADKK-YSIGLDIGTNSVGWAVITDEYKVPSKKFKVLGNTDRHSIKKNLIGALLFDSGETA--EATRLKRTARRYT | 106 |
| AKA60242 | 1 | MDKK-YSIGLDIGTNSVGWAVITDEYKVPSKKFKVLGNTDRHSIKKNLIGALLFDSGETA--EATRLKRTARRYT | 73 |
| AKS40380 | 1 | MDKK-YSIGLAIGTNSVGWAVITDEYKVPSKKFKVLGNTDRHSIKKNLIGALLFDSGETA--EATRLKRTARRYT | 73 |
| 4UN5_B | 1 | MDKK-YSIGLAIGTNSVGWAVITDEYKVPSKKFKVLGNTDRHSIKKNLIGALLFDSGETA--EATRLKRTARRYT | 77 |
| WP_010922251 | 74 | RRKNRICYLQEIFSNEMAKVDDSFFHRLEE-SFVL--EEDKK---H ERHPIFGNIV-DEVAYHEKYPTIY⬚LRKKLV | 143 |
| WP_039695303 | 75 | RRKNRLRYLQEIFANEIAKVDESFQRLDE-SFLT-DDDKT---F DSHPIFGNKA-EEDAYHQKFPTIYHLRKHLA | 144 |
| WP_045635197 | 74 | RRKNRLRYLQEIFSEEMSKVDSSFFHRLDD-SFLI--PEDKR---E SKYPIFATLT-EEKEYHKQFPTIYHLRKQLA | 143 |
| 5AXW_A | 62 | RRRHRIQRVKKLLFD----------YNLLTDhSELS------G --NPYEARVK--------GLSQKLS | 104 |
| WP_009880683 | | | |
| WP_010922251 | 74 | RRKNRICYLQEIFSNEMAKVDDSFFHRLEE-SFLV--EEDKK---H ERHPIFGNIV-DEVAYHEKYPTIYHLRKKLV | 143 |
| WP_011054416 | 74 | RRKNRICYLQEIFSNEMAKVDDSFFHRLEE-SFLV--EEDKK---H ERHPIFGNIV-DEVAYHEKYPTIYHLRKKLA | 143 |
| WP_011284745 | 74 | RRKNRICYLQEIFSNEMAKVDDSFFHRLEE-SFLV--EEDKK---H ERHPIFGNIV-DEVAYHEKYPTIYHLRKKLV | 143 |
| WP_011285506 | 74 | RRKNRICYLQEIFSNEMAKVDDSFFHRLEE-SFLV--EEDKK---H ERHPIFGNIV-DEVAYHEKYPTIYHLRKKLV | 143 |
| WP_011527619 | 74 | RRKNRICYLQEIFSNEMAKVDDSFFHRLEE-SFLV--EEDKK---H ERHPIFGNIV-DEVAYHEKYPTIYHLRKKLV | 143 |
| WP_012560673 | 74 | RRKNRICYLQEIFSNEIAKVDDSFFHRLEE-SFLV--EEDKK---H ERHPIFGNIV-DEVAYHEKYPTIYHLRKKLA | 143 |
| WP_014407541 | 74 | RRKNRICYLQEIFSNEMAKVDDSFFHRLEE-SFLV--EEDKK---H ERHPIFGNIV-DEVAYHEKYPTIYHLRKKLA | 143 |

-continued

| ID | Start | Sequence 1 | Sequence 2 | End |
|---|---|---|---|---|
| WP_020905136 | 74 | RRKNRICYLQEIFSNEMAKVDDSFFHRLEE-SFLV--EEDKK---H | ERHPIFGNIV-DEVAYHEKYPTIYHLRKKLV | 143 |
| WP_023080005 | 74 | RRKNRICYLQEIFSNEMAKVDDSFFHRLEE-SFLV--EEDKK---H | ERHPIFGNIV-DEVAYHEKYPTIYHLRKKLA | 143 |
| WP_023610282 | 74 | RRKNRICYLQEIFSNEMAKVDDSFFHRLEE-SFLV--EEDKK---H | ERHPIFGNIV-DEVAYHEKYPTIYHLRKKLA | 143 |
| WP_030125963 | 74 | RRKNRICYLQEIFSNEMAKVDDSFFHRLEE-SFLV--EEDKK---H | ERHPIFGNIV-DEVAYHEKYPTIYHLRKKLV | 143 |
| WP_030126706 | 74 | RRKNRICYLQEIFSNEMAKVDDSFFHRLEE-SFLV--EEDKK---H | ERHPIFGNIV-DEVAYHEKYPTIYHLRKKLA | 143 |
| WP_031488318 | 74 | RRKNRICYLQEIFSNEMAKVDDSFFHRLEE-SFLV--EEDKK---H | ERHPIFGNIV-DEVAYHEKYPTIYHLRKKLA | 143 |
| WP_032460140 | 74 | RRKNRICYLQEIFSNEIAKVDDSFFHRLEE-SFLV--EEDKK---H | ERHPIFGNIV-DEVAYHEKYPTIYHLRKKLA | 143 |
| WP_032461047 | 74 | RRKNRICYLQEIFSNEIAKVDDSFFHRLEE-SFLV--EEDKK---H | ERHPIFGNIV-DEVAYHEKYPTIYHLRKKLA | 143 |
| WP_032462016 | 74 | RRKNRICYLQEIFSNEMAKVDDSFFHRLEE-SFLV--EEDKK---H | ERHPIFGNIV-DEVAYHEKYPTIYHLRKKLV | 143 |
| WP_032462936 | 74 | RRKNRICYLQEIFSNEMAKVDDSFFHRLEE-SFLV--EEDKK---H | ERHPIFGNIV-DEVAYHEKYPTIYHLRKKLA | 143 |
| WP_032464890 | 74 | RRKNRICYLQEIFSNEMAKVDDSFFHRLEE-SFLV--EEDKK---H | ERHPIFGNIV-DEVAYHEKYPTIYHLRKKLV | 143 |
| WP_033888930 | | ------------------------------------------- | ------------------------------- | |
| WP_038431314 | 74 | RRKNRICYLQEIFSNEMAKVDDSFFHRLEE-SFLV--EEDKK---H | ERHPIFGNIV-DEVAYHEKYPTIYHLRKKLA | 143 |
| WP_038432938 | 74 | RRKNRICYLQEIFSNEMAKVDDSFFHRLEE-SFLV--EEDKK---H | ERHPIFGNIV-DEVAYHEKYPTIYHLRKKLA | 143 |
| WP_038434062 | 74 | RRKNRICYLQEIFSNEMAKVDDSFFHRLEE-SFLV--EEDKK---H | ERHPIFGNIV-DEVAYHEKYPTIYHLRKKLV | 143 |
| BAQ51233 | 1 | ------MAKVDDSFFHRLEE-SFLV--EEDKK---H | ERHPIFGNIV-DEVAYHEKYPTIYHLRKKLV | 54 |
| KGE60162 | | ------------------------------------------- | ------------------------------- | |
| KGE60856 | | ------------------------------------------- | ------------------------------- | |
| WP_002989955 | 74 | RRKNRICYLQEIFSNEMAKVDDSFFHRLEE-SFLV--EEDKK---H | ERHPIFGNIV-DEVAYHEKYPTIYHLRKKLV | 143 |
| WP_003030002 | 74 | RRRNLRLRYLQEIFAEEMNKVDENFQRLDD-SFLV--DEDKR---H | ERHPIFGNIA-AEVKYHDDFPTIYHLRKHLA | 143 |
| WP_003065552 | 75 | RRKNLRLRYLQEIFAEEMTKVDESFFQRLDE-SFLRwdDDNKK---L | GRYPIFGNKA-DVVKYHQEPPTIYHLRKHLA | 146 |
| WP_001040076 | 74 | RRRNRILYLQEIFAEEMSKVDDSFFHRLED-SFLV--EEDKR---G | SKYPIFATLQ-EEKDYHEKPTIYHEKPTIYHLRKELA | 143 |
| WP_001040078 | 74 | RRRNRILYLQEIFAEEMSKVDDSFFHRLED-SFLV--EEDKR---G | SKYPIFATLQ-EEKDYHEKFSTIYHLRKELA | 143 |
| WP_001040080 | 74 | RRRNRILYLQEIFAEEMSKVDDSFFHRLED-SFLV--EEDKR---G | SKYPIFATLQ-EEKDYHEKFSTIYHRKELA | 143 |
| WP_001040081 | 74 | RRRNRILYLQEIFAEEMSKVDDSFFHRLED-SFLV--EEDKR---G | SKYPIFATLQ-EEKDYHEKFSTIYHLRKELA | 143 |
| WP_001040083 | 74 | RRRNRILYLQEIFAEEMSKVDDSFFHRLED-SFLV--EEDKR---G | SKYPIFATLQ-EEKDYHEKFSTIYHLRKELA | 143 |
| WP_001040085 | 74 | RRRNRILYLQEIFAEEMSKVDDSFFHRLED-SFLV--EEDKR---G | SKYPIFATLQ-EEKDYHEKFSTIYHLRKELA | 143 |

-continued

| | | | | | |
|---|---|---|---|---|---|
| WP_001040087 | 74 | RRRNRILYLQEIFAEEMSKVDDSFFHRLED-SFLV--EEDKR---G | SKYPIFATLQ-EEKDYHEKFSTIYHLRKELA | 143 |
| WP_001040088 | 74 | RRRNRILYLQEIFAEEMSKVDDSFFHRLED-SFLV--EEDKR---G | SKYPIFATLQ-EEKDYHEKSTIYHLRKELA | 143 |
| WP_001040089 | 74 | RRRNRILYLQEIFAEEMSKVDDSFFHRLED-SFLV--EEDKR---G | SKYPIFATLQ-EEKDYHEKSTIYHLRKELA | 143 |
| WP_001040090 | 74 | RRRNRILYLQEIFAEEMSKVDDSFFHRLED-SFLV--EEDKR---G | SKYPIFATLQ-EEKDYHEKSTIYHLRKELA | 143 |
| WP_001040091 | 74 | RRRNRILYLQEIFAEEMSKVDDSFFHRLED-SFLV--EEDKR---G | SKYPIFATLQ-EEKDYHEKSTIYHLRKELA | 143 |
| WP_001040092 | 74 | RRRNRILYLQEIFAEEMSKVDDSFFHRLED-SFLV--EEDKR---G | SKYPIFATMQ-EEKDYHEKPTIYHLRKELA | 143 |
| WP_001040094 | 74 | RRRNRILYLQEIFAEEMSKVDDSFFHRLED-SFLV--EEDKR---G | SKYPIFATMQ-EEKYHEKPTIYHLRKELA | 143 |
| WP_001040095 | 74 | RRRNRILYLQEIFAEEMSKVDDSFFHRLED-SFLV--EEDKR---G | SKYPIFATMQ-EEKYHEKPTIYHLRKELA | 143 |
| WP_001040096 | 74 | RRRNRILYLQEIFAEEMSKVDDSFFHRLED-SFLV--EEDKR---G | SKYPIFATMQ-EEKYHEKPTIYHLRKELA | 143 |
| WP_001040097 | 74 | RRRNRILYLQEIFAEEMSKVDDSFFHRLED-SFLV--EEDKR---G | SKYPIFATMQ-EEKYHEKPTIYHLRKELA | 143 |
| WP_001040098 | 74 | RRRNRILYLQEIFAEEMSKVDDSFFHRLED-SFLV--EEDKR---G | SKYPIFATLQ-EEKDYHEKFSTIYHLRKELA | 143 |
| WP_001040099 | 74 | RRRNRILYLQEIFAEEMSKVDDSFFHRLED-SFLV--EEDKR---G | SKYPIFATMQ-EEKDYHEKPTIYHLRKELA | 143 |
| WP_001040100 | 74 | RRRNRILYLQEIFAEEMSKVDDSFFHRLED-SFLV--EEDKR---G | SKYXIFATLQ-EEKDYHEKPTIYHLRKELA | 143 |
| WP_001040104 | 74 | RRRNRILYLQEIFAEEMSKVDDSFFHRLED-SFLV--EEDKR---G | SKYPIFATMQ-EEKDYHEKPTIYHLRKELA | 143 |
| WP_001040105 | 74 | CRRNRILYLQEIFAEEMSKVDDSFFHRLED-SFLV--EDDKR---G | SKYPIFATMQ-EEKDYHEKPTIYHLRKELA | 143 |
| WP_001040106 | 74 | RRRNRILYLQEIFAEEMSKVDDSFFHRLED-SFLV--EDDKR---G | SKYPIFATMQ-EEKDYHEKPTIYHLRKELA | 143 |
| WP_001040107 | 74 | RRRNRILYLQEIFAEEMSKVDDSFFHRLED-SFLV--EEDKR---G | SKYPIFATMQ-EEKDYHEKPTIYHLRKELA | 143 |
| WP_001040108 | 74 | RRRNRILYLQEIFAEEMSKVDDSFFHRLED-SFLV--EEDKR---G | SKYPIFATMQ-EEKDYHEKPTIYHLRKELA | 143 |
| WP_001040109 | 74 | RRRNRILYLQEIFAEEMSKVDDSFFHRLED-SFLV--EEDKR---G | SKYPIFATMQ-EEKDYHEKPTIYHLRKELA | 143 |
| WP_001040110 | 74 | RRRNRILYLQEIFAEEMSKVDDSFFHRLED-SFLV--EEDKR---G | SKYPIFATLQ-EEKDYHEKPTIYHLRKELA | 143 |
| WP_015058523 | 74 | RRRNRILYLQEIFAEEMSKVDDSFFHRLED-SFLV--EEDKR---G | SKYPIFATMQ-EEKDYHEKPTIYHLRKELA | 143 |
| WP_017643650 | 74 | RRRNRILYLQEIFAEEMSKVDDSFFHRLED-SFLV--EEDKR---G | SKYPIFATMQ-EEKDYHEKPTIYHLRKELA | 143 |
| WP_017647151 | 74 | RRRNRILYLQEIFAEEMSKVDDSFFHRLED-SFLV--EEDKR---G | SKYPIFATMQ-EEKDYHEKPTIYHLRKELA | 143 |
| WP_017648376 | 74 | RRRNRILYLQEIFAEEMSKVDDSFFHRLED-SFLV--EEDKR---G | SKYPIFATMQ-EEKDYHEKPTIYHLRKELA | 143 |
| WP_017649527 | 74 | RRRNRILYLQEIFAEEMSKVDDSFFHRLED-SFLV--EEDKR---G | SKYPIFATMQ-EEKDYHEKPTIYHLRKELA | 143 |
| WP_017771611 | 74 | RRRNRILYLQEIFAEEMSKVDDSFFHRLED-SFLV--EEDKR---G | SKYPIFATMQ-EEKDYHEKPTIYHLRKELA | 143 |
| WP_017771984 | 74 | RRRNRILYLQEIFAEEMSKVDDSFFHRLED-SFLV--EEDKR---G | SKYPIFATLQ-EEKDYHEKFSTIYHLRKELA | 143 |

-continued

| ID | | Sequence | | |
|---|---|---|---|---|
| CFQ25032 | 74 | RRRNRILYLQEIFAEEMSKVDDSFFHRLED-SFLV--EEDKR---G | SKYPIFATLQ-EEKDYHEKFSTIYHLRKELA | 143 |
| CFV16040 | 74 | RRRNRILYLQEIFAEEMSKVDDSFFHRLED-SFLV--EEDKR---G | SKYPIFATLQ-EEKDYHEKFSTIYHLRKELA | 143 |
| KLJ37842 | 74 | RRRNRILYLQEIFAEEMSKVDDSFFHRLED-SFLV--EEDKR---G | SKYPIFATLQ-EEKDYHEKFSTIYHLRKELA | 143 |
| KLJ72361 | 74 | RRRNRILYLQEIFAEEMSKVDDSFFHRLED-SFLV--EEDKR---G | SKYPIFATLQ-EEKDYHEKFSTIYHLRKELA | 143 |
| KLL20707 | 74 | RRRNRILYLQEIFAEEMSKVDDSFFHRLED-SFLV--EEDKR---G | SKYPIFATLQ-EEKDYHEKFSTIYHLRKELA | 143 |
| KLL42645 | 74 | RRRNRILYLQEIFAEEMSKVDDSFFHRLED-SFLV--EEDKR---G | SKYPIFATMQ-EEKDYHEKFSTIYHLRKELA | 143 |
| WP_047207273 | 74 | RRRNRILYLQEIFAEEMSKVDDSFFHRLED-SFLV--EEDKR---G | SKYPIFATMQ-EEKYYHEKFPTIYHLRKELA | 143 |
| WP_047209694 | 74 | RRRNRILYLQEIFAEEMSKVDDSFFHRLED-SFLV--EEDKR---G | SKYPIFATLQ-EEKDYHEKFPTIYHLRKELA | 143 |
| WP_050198062 | 74 | RRRNRILYLQEIFAEEMSKVDDSFFHRLED-SFLV--EEDKR---G | SKYPIFATLQ-EEKDYHEKFSTIYHLRKELA | 143 |
| WP_050201642 | 74 | RRRNRILYLQEIFAEEMSKVDDSFFHRLED-SFLV--EEDKR---G | SKYPIFATMQ-EEKDYHEKFPTIYHLRKELA | 143 |
| WP_050204027 | 74 | RRRNRILYLQEIFAEEMSKVDDSFFHRLED-SFLV--EEDKR---G | SKYPIFATLQ-EEKDYHEKFSTIYHLRKELA | 143 |
| WP_050881965 | 74 | RRRNRILYLQEIFAEKMSKVDDSFFHRLED-SFLV--EEDKR---G | SKYPIFATLQ-EEKDYHEKFPTIYHLRKELA | 143 |
| WP_050886065 | 74 | RRRNRILYLQEIFAEEMSKVDDSFFHRLED-SFLV--EEDKR---G | SKYPIFATMQ-EEKDYHEKFPTIYHLRKELA | 143 |
| AHN30376 | 74 | RRRNRILYLQEIFAEEMSKVDDSFFHRLED-SFLV--EEDKR---G | SKYPIFATLQ-EEKDYHEKFSTIYHLRKELA | 143 |
| EAO78426 | 74 | RRRNRILYLQEIFAEEMSKVDDSFFHRLED-SFLV--EEDKR---G | SKYPIFATLQ-EEKDYHEKFPTIYHLRKELA | 143 |
| CCW42055 | 74 | RRRNRLRYLQEIFAEEMMQVDESFFQRLDD-SFLV--DEDKR---G | ERHPIFGNIA-AEVKYHDEFPTIYHLRKHLA | 143 |
| WP_003041502 | 74 | RRRNRLRYLQEIFTTEMNKVDENFFQRLDD-SFLV--EEDKQ---G | SKYPIFGTLK-EEKEYHKKFKTIYHLREELA | 144 |
| WP_037593752 | 75 | RRRNRLRYLQEIFAEEMMQVDESFFQRLDD-SFLV--EEDKR---G | SRYPIFGNIA-AEVKYHDDFPTIYHLRKHLV | 144 |
| WP_049516684 | 75 | RRKNRLRYLQEIFTEEMNKVDENFFQRLDD-SFLV--EEDKQ---G | SKYPIFGTLK-EEKEYHKKFKTIYHLREELA | 144 |
| GAD46167 | 75 | RRKNRLRYLQDIFTTEMAKVDDSFFQRLDE-SFLT--DNDKN---F | DSHPIFGNKA-EEDAYHQKFPTIYHLRKHLA | 143 |
| WP_018363470 | 74 | RRKNRLRYLQEIFANEMAKLDDDSFFQRLEE-SFLV--EEDKK---N | ERHPIFGNLA-DEVAYHRNYPTIYHLRKLLA | 143 |
| WP_003043819 | 74 | RRKNRLRYLQEIFTGEMNKVDENFFQRLDD-SFLV--DEDKR---G | EHHPIFGNIA-AEVKYHDDFPTIYHLRRHLA | 143 |
| WP_006269658 | 74 | RRKNRLRYLQEIFIBEMNKVDENFFQRLDD-SFLV--EEDKR---G | SKYPIFGTLK-EEKEYHKEFETIYHLRKRLA | 143 |
| WP_048800889 | 74 | RRKNRLRYLQEIFSSEMSKVDDSFFHRLEE-SFLV--TEDKR---G | ERHPIFGNIV-DEVAYHEKFPTIYHLRKKLA | 143 |
| WP_012767106 | 74 | RRKNRLRYLQEIFSSEMSKVDDSFFHRLEE-SFLV--EEDKK---H | ERHPIFGNIV-DEVAYHEKFPTIYHLRKKLA | 143 |
| WP_014612333 | 74 | RRKNRIRYLQEIFSSEMSKVDDSFFHRLEE-SFLV--EEDKK---H | ERHPIFGNIV-DEVAYHEKFPTIYHLRKKLA | 143 |
| WP_015017095 | 74 | RRKNRIRYLQEIFSSEMSKVDDSFFHRLEE-SFLV--EEDKK---H | ERHPIFGNIV-DEVAYHEKFPTIYHLRKKLA | 143 |

-continued

| | | | | |
|---|---|---|---|---|
| WP_015057649 | 74 | RRKNRIRYLQEIFSSEMSKVDDSFHRLEE-SFLV--EEDKK---H | ERHPIFGNIV-DEVAYHEKYPTIYHLRKKLA | 143 |
| WP_048327215 | 74 | RRKNRIRYLQEIFSSEMSKVDDSFHRLEE-SFLV--EEDKK---H | ERHPIFGNIV-DEVAYHEKYPTIYHLRKKLA | 143 |
| WP_049519324 | 74 | RRKNRIRYLQEIFSSEMSKVDDSFHRLEE-SFLV--EEDKK---H | ERHPIFGNIV-DEVAYHEKYPTIYHLRKKLA | 143 |
| WP_012515931 | 74 | RRKNRLRYLKEIFTEEMAKVDDGFFQRLED-SFYV--LEDKE---G | NKHPIFANLA-DEVAYHKKYPTIYHLRKELV | 143 |
| WP_021320964 | 74 | RRKNRLRYLKEIFTEEMAKVDDGFFQRLED-SFYV--LEDKE---G | NKHPIFANLA-DEVAYHKKYPTIYHLRKELV | 143 |
| WP_037581760 | 74 | RRKNRLRFLKEIFTEEMAKVDDGFFQRLED-SFYV--LEDKE---G | NKHPIFANLA-DEVAYHKKYPTIYHLRKELV | 143 |
| WP_004232481 | 74 | RRKNRLRYLQEIFAKEMAKVDESFFQRLEE-SFLT--DDDKT---F | DSHPIFGNKA-EEDTYHQEFPTIYHLRKHLA | 143 |
| WP_009854540 | 75 | RRKNRLRYLQEIFAEEMTKVDESFYRLDE-SFLT--TDEKD---F | ERHPIFGNKA-EEDAYHQKFPTIYHLRNYLA | 144 |
| WP_012962174 | 75 | RRKNRLRYLQEIFAEEMAKVDESFYRLDE-SFLT--TDDKD---F | ERHPIFGNKA-DEIKYHQEFPTIYHLRKHLA | 144 |
| WP_039695303 | 75 | RRKNRLRYLQEIFANEIAKVDESFQRLDE-SFLT--DDDKT---F | DSHPIFGNKA-EEDAYHQKFPTIYHLRKHLA | 144 |
| WP_014334983 | 74 | RRKNRLRYLQEIFAKEMTKVDESFFQRLEE-SFLT--DDDKT---F | EEDAYHQKFPTIYHLRKYLA | 143 |
| WP_003099269 | 74 | RRKYRIKELQKIFSSEMNELDIAFPPRLSE-SFLV--SDDKE---F | ENHPIFGNLK-DEITYHNDYPTIYHLRQTLA | 143 |
| AHY15608 | 74 | RRKYRIKELQKIFSSEMNELDIAFPPRLSE-SFLV--SDDKE---F | ENHPIFGNLK-DEITYHNDYPTIYHLRQTLA | 143 |
| AHY17476 | 74 | RRKYRIKELQKIFSSEMNELDIAFPPRLSE-SFLV--SDDKE---F | ENHPIFGNLK-DEITYHNDYPTIYHLRQTLA | 143 |
| ESR09100 | | | | |
| AGM98575 | 74 | RRKYRIKELQKIFSSEMNELDIAFPPRLSE-SFLV--SDDKE---F | ENHPIFGNLK-DEITYHNDYPTIYHLRQTLA | 143 |
| ALF27331 | 74 | RRRNRILYLQEIFSSEEMGKVDDSFHRLED-SFLV--TEDKR---G | ERHPIFGNLE-EEVKYHENPTIYHLRKTLA | 143 |
| WP_018372492 | 75 | RRRNRIRYLQHIFAEEMNRADENFFHRLKE-SFFV--EEDKT---Y | SKYPIFGTLE-EEKNYHKNYPTIYHLRKTLA | 144 |
| WP_045618028 | 74 | RRKNRLRYLQEIFTEEMSKVDISFFHRLDD-SFLV--PEDKR---G | SKYPIFATLE-EEKEYHKNFPTIYHLRKHLA | 143 |
| WP_045635197 | 75 | RRKNRLRYLQEIFTEEMSKVDSSFFHRLDD-SFLI--PEDKR---E | SKYPIFATLI-EEKEYHKQPPTIYHLRKQLA | 144 |
| WP_002263549 | 74 | RRRNRILYLQEIFSSEEMGKVDDSFFHRLED-SFLV--TEDKR---G | ERHPIFGNLE-EEVKYHENPTIYHLRKQLA | 143 |
| WP_002263887 | 74 | RRRNRILYLQEIFSSEEMGKVDDSFHRLED-SFLV--TEDKR---G | ERHPIFGNLE-EEVKYHENPTIYHLRQYLA | 143 |
| WP_002264920 | 74 | RRRNRILYLQEIFSSEEMGKVDDSFHRLDE-SFLT--DDDKN---F | DSYPIFGNKA-EEDAYHQKFPTIYHLRKHLA | 143 |
| WP_002269043 | 74 | RRRNRILYLQEIFSSEEMGKVDDSFHRLED-SFLV--TEDKR---G | ERHPIFGNLE-EEVKYHENPTIYHLRQYLA | 143 |
| WP_002269448 | 74 | RRRNRILYLQEIFSSEEMGKVDDSFHRLED-SFLV--TEDKR---G | ERHPIFGNLE-EEVKYHENPTIYHLRQYLA | 143 |
| WP_002271977 | 74 | RRRNRILYLQEIFSSEEMGKVDDSFHRLED-SFLV--TEDKR---G | ERHPIFGNLE-EEVKYHENPTIYHLRQYLA | 143 |
| WP_002272766 | 74 | RRRNRILYLQEIFSSEEMGKVDDSFHRLED-SFLV--TEDKR---G | ERHPIFGNLE-EEVKYHENPTIYHLRQYLA | 143 |

-continued

| | | | | |
|---|---|---|---|---|
| WP_002273241 | 74 | RRRNRILYLQEIFSEEMGKVDDSFFHRLED-SFLV--TEDKR----G | ERHPIFGNLE-EEVKYHENFPTIYHLRQYLA | 143 |
| WP_002275430 | 74 | RRRNRILYLQEIFAEEMSKVDDSFFHRLED-SFLV--TEDKR----G | ERHPIFGNLE-EEVKYHENFPTIYHLRQYLA | 143 |
| WP_002276448 | 74 | RRRNRILYLQEIFSEEMGKVDDSFFHRLED-SFLV--TEDKR----G | ERHPIFGNLE-EEVKYHENFPTIYHLRQYLA | 143 |
| WP_002277050 | 74 | RRRNRILYLQEIFSEEMGKVDDSFFHRLDE-SFLT--DDDKN----F | DSHPIFGNKA-EEDAYHQKFPTIYHLRKHLA | 143 |
| WP_002277364 | 74 | RRRNRILYLQEIFAEEMSKVDDSFFHRLED-SFLV--TEDKR----G | ERHPIFGNLE-EEVKYHENFPTIYHLRQYLA | 143 |
| WP_002279025 | 74 | RRRNRILYLQEIFSEEMGKVDDSFFHRLED-FFLV--TEDKR----G | ERHPIFGNLE-EEVKYHENFPTIYHLRQYLA | 143 |
| WP_002279859 | 74 | RRRNRILYLQEIFAEEMSKVDDSFFHRLDE-SFLT--DDDKN----F | DSHPIFGNKA-EEDAYHQKFPTIYHLRKHLA | 143 |
| WP_002280230 | 74 | RRRNRILYLQEIFSEEMGKVDDSFFHRLED-SFLV--TEDKR----G | ERHPIFGNLE-EEVKYHENFPTIYHLRQYLA | 143 |
| WP_002281696 | 74 | RRRNRILYLQEIFAEEMSKVDDSFFHRLED-SFLV--TEDKR----G | ERHPIFGNLE-EEVKYHENFPTIYHLRQYLA | 143 |
| WP_002282247 | 74 | RRRNRILYLQEIFAEEMSKVDDSFFHRLDE-SFLT--DDDKN----F | DSHPIFGNKA-EEDAYHQKFPTIYHLRKHLA | 143 |
| WP_002282906 | 74 | RRRNRILYLQEIFSEEMGKVDDSFFHRLED-SFLV--TEDKR----G | ERHPIFGNLE-EEVKYHENFPTIYHLRQYLA | 143 |
| WP_002283846 | 74 | RRRNRILYLQEIFAEEMSKVDDSFFHRLED-SFLV--TEDKR----G | ERHPIFGNLE-EEVKYHENFPTIYHLRQYLA | 143 |
| WP_002287255 | 74 | RRRNRILYLQEIFSEEMGKVDDSFFHRLED-SFLV--TEDKR----G | ERHPIFGNLE-EEVKYHENFPTIYHLRQYLA | 143 |
| WP_002288990 | 74 | RRRNRILYLQEIFSEEMGKVDDSFFHRLED-SFLV--TEDKR----G | ERHPIFGNLE-EEVKYHENFPTIYHLRQYLA | 143 |
| WP_002289641 | 74 | RRRNRILYLQEIFSEEMGKVDDSFFHRLED-SFLV--TEDKR----G | ERHPIFGNLE-EEVKYHENFPTIYHLRQYLA | 143 |
| WP_002290427 | 74 | RRRNRILYLQEIFSEEMGKVNDSFFHRLED-SFLV--TEDKR----G | ERHPIFGNLE-EEVKYHENFPTIYHLRQYLA | 143 |
| WP_002295753 | 74 | RRRNRILYLQEIFSEEMGKVDDSFFHRLED-SFLV--TEDKR----G | ERHPIFGNLE-EEVKYHENFPTIYHLRQYLA | 143 |
| WP_002296423 | 74 | RRRNRILYLQEIFAEEMMQVDESFFQRLDD-SFLV--EEDKR----G | SRYPIFGTLK-EEKKYHKEFKTIYHLREKLA | 143 |
| WP_002304487 | 74 | RRRNRILYLQEIFSEEMDKVDDSFFHRLED-SFLV--TEDKR----G | ERHPIFGNLE-EEVKYHENFPTIYHLREKLA | 143 |
| WP_002305844 | 74 | RRRNRILYLQEIFAEEMSKVDDSFFHRLED-SFLV--TEDKR----G | ERHPIFGNLE-EEVKYHENFPTIYHLRQYLA | 143 |
| WP_002307203 | 74 | RRRNRILYLQEIFSEEMGKVDDSFFHRLED-SFLV--TEDKR----G | ERHPIFGNLE-EEVKYHENFPTIYHLRQYLA | 143 |
| WP_002310390 | 74 | RRRNRILYLQEIFSEEMGKVDDSFFHRLED-SFLV--TEDKR----G | ERHPIFGNLE-EEVKYHENFPTIYHLRQYLA | 143 |
| WP_002352408 | 74 | RRRNRILYLQEIFAEEMSKVDDSFFHRLED-SFLV--TEDKR----G | ERHPIFGNLE-EEVKYHENFPTIYHLRQYLA | 143 |
| WP_012997688 | 74 | RRRNRILYLQEIFSEEMGKVDDSFFHRLED-SFLV--TEDKR----G | ERHPIFGNLE-EEVKYHENFPTIYHLRQYLA | 143 |
| WP_014677909 | 74 | RRRNRILYLQEIFAEEMSKVDDSFFHRLED-SFLV--TEDKR----G | ERHPIFGNLE-EEVKYHENFPTIYHLRQYLA | 143 |
| WP_019312892 | 74 | RRRNRILYLQEIFSEEMGKVDDSFFHRLED-SFLV--TEDKR----G | ERHPIFGNLE-EEVKYHENFPTIYHLRQYLA | 143 |
| WP_019313659 | 74 | RRRNRILYLQEIFSEEMGKVDDSFFHRLED-SFLV--TEDKR----G | ERHPIFGNLE-EEVKYHENFPTIYHLRQYLA | 143 |

```
WP_019314093   74  RRRNRILYLQEIFSEEMGKVDDSFFHRLED-SFLV--TEDKR---G  ERHPIFGNLE-EEVKYHENPTIYHLRQYLA  143
WP_019315370   74  RRRNRILYLQEIFSEEMGKVDDSFFHRLED-SFLV--TEDKR---G  ECHPIFGNLE-EEVKYHENPTIYHLRQYLA  143
WP_019803776   74  RRRNRILYLQEIFSEEMGKVDDSFFHRLED-SFLV--TEDKR---G  ERHPIFGNLE-EEVKYHENPTIYHLRQYLA  143
WP_019805234   74  RRRNRILYLQEIFSEEMGKVDDSFFHRLED-SFLV--TEDKR---G  ERHPIFGNLE-EEVKYHENPTIYHLRQYLA  143
WP_024783594   74  RRRNRILYLQEIFSEEMGKVDDSFFHRLED-SFLV--TEDKR---G  ERHPIFGNLE-EEVKYHENPTIYHLRQYLA  143
WP_024784288   74  RRRNRILYLQEIFAEEMSKVDDSFFHRLDE-SFLT--DDDKN---F  DSHPIFGNKA-EEDAYHQKFPTIYHLRQYLA 143
WP_024784666   74  RRRNRILYLQEIFSEEMSKVDDSFFHRLED-SFLV--TEDKR---G  ERHPIFGNLE-EEVKYHENPTIYHLRQYLA  143
WP_024784894   74  RRRNRILYLQEIFSEEMGKVDDSFFHRLED-SFLV--TEDKR---G  ERHPIFGNLE-EEVKYHENPTIYHLRQYLA  143
WP_024786433   74  RRRNRILYLQEIFAEEMNKVDDSFFHRLDE-SFLT--DDDKN---F  DSHPIFGNKA-EEDAYHQKFPTIYHLRKHLA 143
WP_049473442   74  RRRNRILYLQEIFAEEMSKVDDSFFHRLED-SFLV--TEDKR---G  ERHPIFGNLE-EEVKYYENPTIYHLRQYLA  143
WP_049474547   74  RRRNRILYLQEIFSEEMGKVDDSFFHRLED-SFLV--TEDKR---G  ERHPIFGNLE-EEVKYHENPTIYHLRQYLA  143
EMC03581       67  RRRNRILYLQEIFAEEMSKVDDSFFHRLED-SFLV--TEDKR---G  ERHPIFGNLE-EEVKYHENPTIYHLRKALA  136
WP_000428612   75  RRKNRLRYLQEIFAEEMSKVDSSFFHRLDD-SFLI--PEDKK---G  SKYPIFATLI-EEKEYHKQPPTIYHLRKQLA 144
WP_000428613   75  RRKNRLRYLQEIFAEEMNKVDSSFFHRLDD-SFLI--PEDKR---G  SKYPIFATLA-EEKEYHKNPTIYHLRKQLA  144
WP_049523028   74  RRRNRILYLQEIFAAEMNKVDESFFHRLDD-SFLV--PEDKR---G  SKYPIFGTLE-EEKEYHKQPPTIYHLRKQLA 143
WP_003107102   43  RRINRIKYLQSIFDDEMKIDSAFFQRIKD-SFLV--PDDKN---D  DRHPIFGNIK-DEVDYHKNYPTIYHLRKKLA  112
WP_054279288   76  RRKNRLCYLRDIFSEMHTIDKHFFLRLED-SFLH--KSDKR---Y  EAHPIFGTLQ-EEKAYHDNYPTIYHLRKALA  145
WP_049531101   75  RRKNRLRYLQEIFSEEIDSFFHRLED-SFLV--PEDKR---G  SKYPIFATLT-EEKEYYKQPPTIYHLRKQLA  144
WP_049538452   75  RRKNRLRYLQEIFAEEMNKVDSSFFHRLDD-SFLV--PEDKR---G  SKYPIFATLA-EEKEYHKNPTIYHLRKQLA  144
WP_049549711   75  RRKNRLRYLQEIFSGEMSKVDSSFFHRLDD-SFLV--PEDKR---G  SKYPIFATLA-EEKEYHKQPPTIYHLRKQLA 144
WP_007896501   76  RRRYRLCQLQNIFATEMVKVDDTFQRLSE-SFFY--YQDKA---F  DKHPIFGNSK-EERAYHKTYPTIYHLRKDLA  145
EFR44625       28  RRRYRLCQLQNIFATEMVKVDDTFQRLSE-SFFY--YQDKA---F  DKHPIFGNSK-EERAYHKTYPTIYHLRKDLA  97
WP_002897477   74  RRRNRILYLQEIFTESMNEIDESFFHRLDD-SFLV--PEDKR---G  SKYPIFATLQ-EEKEYHKQPPTIYHLRKQLA 143
WP_002906454   74  RRKNRLRYLQEIFSEEISKLDSSFFHRLDD-SFLV--PEDKR---G  SKYPIFATLE-EEKKEYHKKPTIYHLRKHLA 143
WP_009729476   75  RRKNRLRYLQEIFSEEIGKVDSSFFHRLDD-SFLI--PEDKR---G  SKYPIFATLA-EEKKYHKQPPTIYHLRKQLA 144
CQR24647       74  RRRNRILYLQDIFSPELNQVDESFLHRLDD-SFLVa-EDKR---G   ERHVIFGNIA-DEVKHKEFPTIYHLRKHLA  143
WP_000066813   75  RRKNRLRYLQEIFSQEISKVDSSFFHRLDD-FFLV--PEDKR---G  SKYPIFATLV-EEKEYHKKFPTIYHLRKHLA 144
```

-continued

| ID | | | | |
|---|---|---|---|---|
| WP_009754323 | 75 | RRKNRLRYLQEIFAEEMSKVDSSFFHRLDD-SFLV--PEDKS---G | SKYPIFATLA-EEKEYHKKFPTIYHLRKHLA | 144 |
| WP_044674937 | 74 | RRRNRILYLQEIFAEEINKIDDSFFQRLDD-SFLIv-EDKQ---G | SKHPIFGTLQ-EEKKYHKQPPTIYHLRKQLA | 143 |
| WP_044676715 | 74 | RRRNRILYLQEIFAEEINKIDDSFFQRLDD-SFLIv-EDKQ---G | SKHPIFGTLQ-EEKEYHKQPPTIYHLRKQLA | 143 |
| WP_044680361 | 74 | RRRNRILYLQEIFAEEINKIDDSFFQRLDD-SFLIv-EDKQ---G | SKHPIFGTLQ-EEKEYHKQPPTIYHLRKQLA | 143 |
| WP_044681799 | 74 | RRRNRILYLQEIFAEEINKIDDSFFQRLDD-SFLIv-EDKQ---G | SKHPIFGTLQ-EEKEYHKQPPTIYHLRKQLA | 143 |
| WP_049533112 | 74 | RRRNRLRYLQEIFAEEMNKVDENFFQRLDD-SFLV--DEDKR---G | ERHPIFGNIA-AEVKYHDDFPTIYHLRKHLA | 143 |
| WP_029090905 | 28 | HRKFRLRLLEDMFEKEILSKDPSFFIRLKE-AFLSpkDEQKQ---F | ----LFNDKDyTDADYYEQKTIYHLRYDLI | 100 |
| WP_006506696 | 61 | KRRERIRLLRAILQDMVLEKDPTFFIRLEHtSFLD--EEDKAkylG | DNYNLFIDEDfNDYTYYHKYPTIYHLRKALC | 139 |
| AIT42264 | 74 | RRKNRICYLQEIFSNEMAKVDDSFFHRLEE-SFLV--EEDKK---H | ERHPIFGNIV-DEVAYHEKYPTIYHLRKKLV | 143 |
| WP_034440723 | 73 | RRRFRIRELQKIFDKSMGEVDSNFFHRLDE-SFLV--EEDKE---Y | SKYPIFSNEK-EDKNYDKYPTIYHLRKDLA | 142 |
| AKQ21048 | 74 | RRKNRICYLQEIFSNEMAKVDDSFFHRLEE-SFLV--EEDKK---H | ERHPIFGNIV-DEVAYHEKYPTIYHLRKKLV | 143 |
| WP_004636532 | 74 | RRRNRILYLQDIFQQPMLAIDENFFHRLDD-SFFV--PDDKS---Y | DRHPIFGSLE-EEVAYHNTYPTIYHLRKKLA | 143 |
| WP_002364836 | 74 | RRRNRLRYLQAFFEEAMTDLDENFFARLQE-SFLV--PEDKK---W | HRHPIFAKLE-DEVAYHETYPTIYHLRKKLA | 143 |
| WP_016631044 | 25 | RRRNRLRYLQAFFEEAMTDLDENFFARLQE-SFLV--PEDKK---W | HRHPIFAKLE-DEVAYHETYPTIYHLRKKLA | 94 |
| EMS75795 | | ------------------------------ | ------------------------------ | |
| WP_002373311 | 74 | RRRNRLRYLQAFFEEAMTDLDENFFARLQE-SFLV--PEDKK---W | HRHPIFAKLE-DEVAYHETYPTIYHLRKKLA | 143 |
| WP_002378009 | 74 | RRRNRLRYLQAFFEEAMTALDENFFARLQE-SFLV--PEDKK---W | HRHPIFAKLE-DEVAYHETYPTIYHLRKKLA | 143 |
| WP_002407324 | 74 | RRRNRLRYLQAFFEEAMTALDENFFARLQE-SFLV--PEDKK---W | HRHPIFAKLE-DEVAYHETYPTIYHLRKKLA | 143 |
| WP_002413717 | 74 | RRRNRLRYLQAFFEEAMTDLDENFFARLQE-SFLV--PEDKK---W | HRHPIFAKLE-DEVAYHETYPTIYHLRKKLA | 143 |
| WP_010775580 | 74 | RRRNRLRYLQAFFEEAMTALDENFFARLQE-SFLV--PEDKK---W | HRHPIFAKLE-DEVAYHETYPTIYHLRKKLA | 143 |
| WP_010818269 | 74 | RRRNRLRYLQAFFEEAMTALDENFFARLQE-SFLV--PEDKK---W | HRHPIFAKLE-DEVAYHETYPTIYHLRKKLA | 143 |
| WP_010824395 | 74 | RRRNRLRYLQAFFEEAMTDLDENFFARLQE-SFLV--PEDKK---W | HRHPIFAKLE-DEVAYHETYPTIYHLRKKLA | 143 |
| WP_016622645 | 74 | RRRNRLRYLQAFFEEAMTALDENFFARLQE-SFLV--PEDKK---W | HRHPIFAKLE-DEVAYHETYPTIYHLRKKLA | 143 |
| WP_033624816 | 74 | RRRNRLRYLQAFFEEAMTALDENFFARLQE-SFLV--PEDKK---W | HRHPIFAKLE-DEVAYHETYPTIYHLRKKLA | 143 |
| WP_033625576 | 74 | RRRNRLRYLQAFFEEAMTALDENFFARLQE-SFLV--PEDKK---W | HRHPIFAKLE-DEVAYHETYPTIYHLRKKLA | 143 |
| WP_033789179 | 74 | RRRNRLRYLQAFFEEAMTALDENFFARLQE-SFLV--PEDKK---W | HRHPIFAKLE-DEVAYHETYPTIYHLRKKLA | 143 |
| WP_002310644 | 74 | RRRQRILELQKIFAPEILKIDEHFFARLNE-SFLV--LDEKK---Q | SRHPVFATIK-QEKSYHQTYPTIYHLRQALA | 143 |

```
WP_002312694    74  RRRQRILELQKIFAPEILKIDEHFFARLNE-SFLV-PDKK---Q  SRHPVFATIK-QEKSYHQTYPTIYHLRQALA  143
WP_002314015    74  RRRQRILELQKIFAPEILKIDEHFFARLNE-SFLV-LDEKK---Q  SRHPVFATIK-QEKSYHQTYPTIYHLRQALA  143
WP_002320716    74  RRRQRILELQKIFAPEILKIDEHFFARLNE-SFLV-LDEKK---Q  SRHPVFATIK-QEKSYHQTYPTIYHLRQALA  143
WP_002330729    74  RRRQRILELQKIFAPEILKIDEHFFARLNE-SFLV-LDEKK---Q  SRHPVFATIK-QEKSYHQTYPTIYHLRQALA  143
WP_002335161    74  RRRQRILELQKIFAPEILKIDEHFFARLNE-SFLV-LDEKK---Q  SRHPVFATIK-QEKSYHQTYPTIYHLRQALA  143
WP_002345439    74  RRRQRILELQKIFAPEILKIDEHFFARLNE-SFLV-LDEKK---Q  SRHPVFATIK-QEKSYHQTYPTIYHLRQALA  143
WP_038467970    74  RRKYRLSKLQDLFAEELCKQDDCFVRLEE-SFLV-PEEKQ---Y  KPASIFPTLE-EEKEYYQKYPTIYHLRQKLV  143
WP_047937432    74  RRRQRILELQKIFAPEILKIDEHFFARLNE-SFLV-LDEKK---Q  SRHPVFATIK-QEKSYHQTYPTIYHLRQALA  143
WP_010720994    74  RRKYRLSKLQDLFAEELCKQDDCFVRLEE-SFLV-PEEKQ---Y  KPASIFPTLE-EEKEYYQKYPTIYHLRQKLV  143
WP_010737004    74  RRKYRLSKLQDLFAEELCKQDDCFVRLEE-SFLV-PEEKQ---Y  KPASIFPTLE-EEKEYYQKYPTIYHLRQKLV  143
WP_034700478    74  RRKYRLSKLQDLFAEELCKQDDCFVRLEE-SFLV-PEEKQ---Y  KPASIFPTLE-EEKEYYQKYPTIYHLRQKLV  143
WP_007209903    74  RRKNRICYLQEIFQPEMNHLDNNFFYRLNE-SFLVa-DDAK---Y  DKHPIFGTLD-EEIHFHEQFPTIYHLRKYLA  143
WP_023519017    74  RRRQRVLALQDIFAEEIHKKDPNFFARLEE-GDRV-EADKR---F  AKFPVFATLS-EEKNYHRQYPTIYHLRHDLA  143
WP_010770040    74  RRRNRICRLQDLFTEEMNQVDANFFHRLQE-SFLV-PDEKE---F  ERHAIFGKME-EEVSYYREFPTIYHLRKHLA  143
WP_048604708    74  RRRQRISYLQTFFQEEMNRIDPNFFNRLDE-SFLI-EEDKL---S  ERHPIFGTIE-EEVAYHKNYATIYHLRKELA  143
WP_010750235    74  RRKYRILELQKIFSEEILKKDSHFFARLDE-SFLI-PEDKQ---Y  ARFPIFPTLL-EEKAYYQNYPTIYHLRQKLA  143
AII16583       113  RRKNRICYLQEIFSNEMAKVDDSFFHRLEE-SFLV-EEDKK---H  ERHPIFGNIV-DEVAYHEKYPTIYHLRKKLV  182
WP_029073316    66  KRRERIRLLRGIMEDMVLVDPTFFIRLANvSFLD-QEDKKdylK   SNYNLFIDKDfNDKTYYDKYPTIYHLRKHLC  144
WP_031589969    66  KRRERIRLLREIMEDMVLVDPTFFIRLANvSFLD-QEDKKdylK   SNYNLFIDKDfNDKTYYDKYPTIYHLRKHLC  144
KDA45870        75  RRKNRLRYLQEIFAPALAKVDPNFFYRLEE-SSLVa--EDKK---Y  DVYPIFGKRE-EELLYHDTHKTIYHLRSELA  144
WP_039099354    62  RRKWRLGLLREIFEPYITPVDDTFLRKKQ-SNLS--PKDQR---K  -QTSLFNDRT--DRAFYDDYPTIYHLRYKLM  132
AKP02966        65  RRKNRINWLNEIFSEELANTDPSFLIRLQN-SWVSkkDPDRK---R  DKYNLFIDNPyTDKEYYREFPTIFHLRKELI  137
WP_010991369    74  RRRNRISYLQGIFABEMSKTDANFFCRLSD-SFYV--DNEKR---N  SRHPFFATIE-EEVEYHKNYPTIYHLREELV  143
WP_033838504    74  RRRNRISYLQGIFABEMSKTDANFFCRLSD-SFYV--DNEKR---N  SRHPFFATIE-EEVEYHKNYPTIYHLREELV  143
EHN60060        77  RRRNRISYLQGIFABEMSKTDANFFCRLSD-SFYV--DNEKR---N  SRHPFFATIE-EEVEYHKNYPTIYHLREELV  146
EFR89594            ----------------------------------------------  ------------------------------
WP_038409211    74  RRRNRIAYLQEIFAAEMAEVDANFFYRLED-SFYI--ESEKR---H  SRHPFFATIE-EEVAYHEEYKTIYHLREKLV  143
```

| Name | Start | Sequence 1 | Sequence 2 | End |
|---|---|---|---|---|
| EFR95520 | | | | |
| WP_003723650 | 74 | RRRNRISYLQEIFAVEMANIDANFFCRLND-SFVV--DSEKR---N | SRHPFFATIE-EEVAYHDNYRTIYHLREKLV | 143 |
| WP_003727705 | 74 | RRRNRISYLQEIFAVEMANIDANFFCRLND-SFVV--DSEKR---N | SRHPFFATIE-EEVAYHKNYRTIYHLREELV | 143 |
| WP_003730785 | 74 | RRRNRISYLQEIFAVEMANIDANFFCRLND-SFVV--DSEKR---N | SRHPFFATIE-EEVAYHKNYRTIYHLREELV | 143 |
| WP_003733029 | 74 | RRRNRISYLQEIFAIQMNEVDDNFFNRLKE-SFYA--ESDKK---Y | NRHPFFGTVE-EEVAYYYKDFPTIYHLRKELI | 143 |
| WP_003739838 | 74 | RRRNRISYLQEIFALEMANIDANFFCRLND-SFVV--DSEKR---N | SRHPFFATIE-EEVAYHKNYRTIYHLREELV | 143 |
| WP_014601172 | 74 | RRRNRISYLQEIFAVEMANIDANFFCRLND-SFVV--DSEKR---N | SRHPFFATIE-EEVAYHKNYRTIYHLREELV | 143 |
| WP_023548323 | 74 | RRRNRISYLQEIFAVEMANIDANFFCRLND-SFVV--DSEKR---N | SRHPFFATIE-EEVAYHKNYRTIYHLREELV | 143 |
| WP_031665337 | 74 | RRRNRISYLQEIFAVEMANIDANFFCRLND-SFVV--DSEKR---N | SRHPFFATIE-EEVAYHKNYRTIYHLREELV | 143 |
| WP_031669209 | 74 | RRRNRISYLQEIFAIQMNEVDDNFFNRLKE-SFYA--ESDKK---Y | NRHPFFGTVE-EEVAYYKDFPTIYHLRKELI | 143 |
| WP_033920898 | 74 | RRRNRISYLQEIFAVEMANIDANFFCRLND-SFVV--DSEKR---N | SRHPFFATIE-EEVAYHKNYRTIYHLREELV | 143 |
| AKI42028 | 77 | RRRNRISYLQEIFAVEMANIDANFFCRLND-SFVV--DSEKR---N | SRHPFFATIE-EEVAYHKNYRTIYHLREELV | 146 |
| AKI50529 | 77 | RRRNRISYLQEIFAVEMANIDANFFCRLND-SFVV--DSEKR---N | SRHPFFATIE-EEVAYHKNYRTIYHLREELV | 146 |
| EFR83390 | | | | |
| WP_046323366 | 74 | RRRNRISYLQEIFTAEMFEVDANFFYRLED-SFYI--ESEKR---Q | SRHPFFATIE-EEVAYHENYRTIYHLREKLV | 143 |
| AKE81011 | 90 | RRKNRICYLQEIFSNEMAKVDDSFHRLEE-SFLV--EEDKK---H | ERHPIFGNIV-DEVAYHEKYPTIYHLRKKLV | 159 |
| CUO82355 | 65 | KRRERIRLLRAILQDMVLEKDPTFFIRLEHtSFLD--EEDKAKyLG | DNYNLFIDEDfNDYTYYHKYPTIYHLRKALC | 143 |
| WP_033162887 | 66 | KRRERIRLLRDLLGDMVEVDPTFFIRLLNvSFLD--EEDKQknlG | DNYNLFIEKDKTYYDKYPTIYHLRKELC | 144 |
| AGZ01981 | 107 | RRKNRICYLQEIFSNEMAKVDDSFHRLEE-SFLV--EEDKK---H | ERHPIFGNIV-DEVAYHEKYPTIYHLRKKLV | 176 |
| AKA60242 | 74 | RRKNRICYLQEIFSNEMAKVDDSFHRLEE-SFLV--EEDKK---H | ERHPIFGNIV-DEVAYHEKYPTIYHLRKKLV | 143 |
| AKS40380 | 74 | RRKNRICYLQEIFSNEMAKVDDSFHRLEE-SFLV--EEDKK---H | ERHPIFGNIV-DEVAYHEKYPTIYHLRKKLV | 143 |
| 4UN5_B | 78 | RRKNRICYLQEIFSNEMAKVDDSFHRLEE-SFLV--EEDKK---H | ERHPIFGNIV-DEVAYHEKYPTIYHLRKKLV | 147 |
| WP_010922251 | 144 | DSTDKADLRLIYLALAHMIKFRGHFLIEGD-LNPDNSDVDKL--FIQLVQTYNQL--FEEN-- | INASGVDAK---AI | 211 |
| WP_039695303 | 145 | DSSEKADLRLVYLALAHMIKFRGHFLIEGE-LNAENTDVQKI--FADFVGVYNRT--FDDS-H | LSEITVDVA---SI | 212 |
| WP_045635197 | 144 | DSKEKTDLRLIYLALAHMIKYRGHFLYEEA-FDIKNNDIQKI--FNEFISIYDNT--FEGS-S | LSGQNAQVE---AI | 211 |
| 5AXW_A | 105 | EEEFSA------ALLHLAKRRG---VHNV-----NEVE------ | ------EDT----GN--- | 134 |
| WP_009880683 | | | | |

| | | | | |
|---|---|---|---|---|
| WP_010922251 | 144 | DSTDKADLRLIYLALAHMIKFRGHFLIEGD-LNPDNSDVDKL--FIQLVQTYNQL--FEEN-- | INASGVDAK---AI | 211 |
| WP_011054416 | 144 | DSTDKVDLRLIYLALAHMIKFRGHFLIEGD-LNPDNSDVDKL--FIQLVQTYNQL--FEEN-- | INASRVDAK---AI | 211 |
| WP_011284745 | 144 | DSTDKADLRLIYLALAHMIKFRGHFLIEGD-LNPDNSDVDKL--FIQLVQTYNQL--FEEN-- | INASGVDAK---AI | 211 |
| WP_011285506 | 144 | DSTDKADLRLIYLALAHMIKFRGHFLIEGD-LNPDNSDVDKL--FIQLVQTYNQL--FEEN-- | INASGVDAK---AI | 211 |
| WP_011527619 | 144 | DSTDKADLRLIYLALAHMIKFRGHFLIEGD-LNPDNSDVDKL--FIQLVQTYNQL--FEEN-- | INASRVDAK---AI | 211 |
| WP_012560673 | 144 | DSTDKADLRLIYLALAHMIKFRGHFLIEGD-LNPDNSDVDKL--FIQLVQTYNQL--FEEN-- | INASGVDAK---AI | 211 |
| WP_014407541 | 144 | DSTDKADLRLIYLALAHMIKFRGHFLIEGD-LNPDNSDVDKL--FIQLVQIYNQL--FEEN-- | INASRVDAK---AI | 211 |
| WP_020905136 | 144 | DSTDKADLRLIYLALAHMIKFRGHFLIEGD-LNPDNSDVDKL--FIQLVQTYNQL--FEEN-- | INASGVDAK---AI | 211 |
| WP_023080005 | 144 | DSTDKADLRLIYLALAHMIKFRGHFLIEGD-LNPDNSDVDKL--FIQLVQTYNQL--FEEN-- | INASRVDAK---AI | 211 |
| WP_023610282 | 144 | DSTDKVDLRLIYLALAHMIKFRGHFLIEGD-LNPDNSDVDKL--FIQLVQTYNQL--FEEN-- | INASGVDAK---AI | 211 |
| WP_030125963 | 144 | DSTDKADLRLIYLALAHMIKFRGHFLIEGD-LNPDNSDVDKL--FIQLVQTYNQL--FEEN-- | INASRVDAK---AI | 211 |
| WP_030126706 | 144 | DSTDKVDLRLIYLALAHMIKFRGHFLIEGD-LNPDNSDVDKL--FIQLVQTYNQL--FEEN-- | INASGVDAK---AI | 211 |
| WP_031488318 | 144 | DSTDKADLRLIYLALAHMIKFRGHFLIEGD-LNPDNSDVDKL--FIQLVQTYNQL--FEEN-- | INASRVDAK---AI | 211 |
| WP_032460140 | 144 | DSTDKADLRLIYLALAHMIKFRGHFLIEGD-LNPDNSDVDKL--FIQLVQTYNQL--FEEN-- | INASRVDAK---AI | 211 |
| WP_032461047 | 144 | DSTDKADLRLIYLALAHMIKFRGHFLIEGG-LNPDNSDVDKL--FIQLVQTYNQL--FEEN-- | INANGVDAK---AI | 211 |
| WP_032462016 | 144 | DSTDKADLRLIYLALAHMIKFRGHFLIEGD-LNPDNSDVDKL--FIQLVQTYNQL--FEEN-- | INASRVDAK---AI | 211 |
| WP_032462936 | 144 | DSTDKADLRLIYLALAHMIKFRGHFLIEGD-LNPDNSDVDKL--FIQLVQTYNQL--FEEN-- | INASGVDAK---AI | 211 |
| WP_032464890 | 1 | ---------------------------PDNSDVDKL--FIQLVQTYNQL--FEEN-- | INASGVDAK---AI | 36 |
| WP_033888930 | 144 | DSTDKADLRLIYLALAHMIKFRGHFLIEGD-LNPDNSDVDKL--FIQLVQTYNQL--FEEN-- | INASRVDAK---AI | 211 |
| WP_038431314 | 144 | DSTDKVDLRLIYLALAHMIKFRGHFLIEGD-LNPDNSDVDKL--FIQLVQTYNQL--FEEN-- | INASRVDAK---AI | 211 |
| WP_038432938 | 144 | DSTDKADLRLIYLALAHMIKFRGHFLIEGD-LNPDNSDVDKL--FIQLVQTYNQL--FEEN-- | INASRVDAK---AI | 211 |
| WP_038434062 | 55 | DSTDKADLRLIYLALAHMIKFRGHFLIEGD-LNPDNSDVDKL--FIQLVQTYNQL--FEEN-- | INASGVDAK---AI | 122 |
| BAQ51233 | | ---------------------------------------------------------- | -------------- | |
| KGE60162 | | ---------------------------------------------------------- | -------------- | |
| KGE60856 | | ---------------------------------------------------------- | -------------- | |
| WP_002989955 | 144 | DSTDKADLRLVYLALAHMIKFRGHFLIEGD-LNPDNSDVDKL--FIQLVQTYNQL--FEEN-- | INASGVDAK---AI | 211 |
| WP_003030002 | 144 | DISQKADLRLVYLALAHMIKFRGHFLIEGQ-LKAENTNVQAL--FKDFVEVYDKT--VEES-H | LSEMTVDAL---SI | 211 |

-continued

```
WP_003065552  147  DSSEKADLRLIVYLALAHMIKFRGHFLIEGE-LNAENTDVQKI--FADFVGVYDRT--FDDS-H  LSEITVDAA---SI  214
WP_001040076  144  DKKEKADLRLIVYLALAHIIKFRGHFLIEDDrEDVRNTDIQKQ--YQAFLEIFDTT--FENN-D  LLSQDVDVE---AI  212
WP_001040078  144  DKQEKADLRLIYIALAHIIKFRGHFLIEDDIEDVRNTDIQKQ--YQDFLEIFDTT--FENN-H  LLSQNVDVE---AI  212
WP_001040080  144  DKKEKADLRLIYIALAHIIKFRGHFLIEDDsEDVRNTDISKQ--YQDFLEIFNIT--FENN-D  LLSQNVDVE---AI  212
WP_001040081  144  DKKEKADLRLIYIALAHIIKFRGHFLIEDDsEDVRNTDISKQ--YQDFLEIFNTI--FENN-D  LLSQNVDVE---AI  212
WP_001040083  144  DKKEKADLRLIYIALAHIIKFRGHFLIEDDsEDVRNTDISKQ--YQDFLEIFNTT--FENN-D  LLSQNVDVE---AI  212
WP_001040085  144  DKKEKADLRLIYIALAHIIKFRGHFLIEDDsEDVRNTDISKQ--YQDFLEIFNTT--FENN-D  LLSQNVDVE---AI  212
WP_001040087  144  DKKEKADLRLIYIALAHIIKFRGHFLIEDDsEDVRNTDISKQ--YQDFLEIFNTT--FENN-D  LLSQNVDVE---AI  212
WP_001040088  144  DKKEKADLRLIYIALAHIIKFRGHFLIEDDsEDVRNTDISKQ--YQDFLEIFNTT--FENN-D  LLSQNVDVE---AI  212
WP_001040089  144  DKKEKADLRLIYIALAHIIKFRGHFLIEDDsEDVRNTDISKQ--YQDFLEIFNTT--FENN-D  LLSQNVDVE---AI  212
WP_001040090  144  DKKEKADLRLIYIALAHIIKFRGHFLIEDDsEDVRNTDISKQ--YQDFLEIFNTT--FENN-D  LLSQNVDVE---AI  212
WP_001040091  144  DKKEKADLRLIYIALAHIIKFRGHFLIEDDsEDVRNTDISKQ--YQDFLEIFNTT--FENN-D  LLSQNVDVE---AI  212
WP_001040092  144  DKKEKADLRLIVYLALAHIIKFRGHFLIEDDrEDVRNTDIQKQ--YQAFLEIFDTS--FENN-H  LLSQNVDVE---AI  212
WP_001040094  144  DKKEKADLRLIVYLALAHIIKFRGHFLIEDDrEDVRNTDIQKQ--YQAFLEIFDTT--FENN-D  LLSQNVDVE---AI  212
WP_001040095  144  DKKEKADLRLIVYLALAHIIKFRGHFLIEDDrEDVRNTDIQKQ--YQAFLEIFDTT--FENN-D  LLSQNVDVE---AI  212
WP_001040096  144  DKKEKADLRLIVYLALAHIIKFRGHFLIEDDrEDVRNTDIQKQ--YQAFLEIFDTT--FENN-D  LLSQNVDVE---AI  212
WP_001040097  144  DKKEKADLRLIVYLALAHIIKFRGHFLIEDDrEDVRNTDIQKQ--YQAFLEIFDTT--FENN-D  LLSQNVDVE---AI  212
WP_001040098  144  DKKEKADLRLIVYLALAHIIKFRGHFLIEDDrEDVRNTDIQKQ--YQAFLEIFDTT--FENN-D  LLSQNVDVE---AI  212
WP_001040099  144  DKKEKADLRLIVYLALAHIIKFRGHFLIEDDrEDVRNTDIQKQ--YQAFLEIFDTT--FENN-D  LLSQNVDVE---AI  212
WP_001040100  144  DKKEKADLRLIYIALAHIIKFRGHFLIEDDsEDVRNTDISKQ--YQDFLEIFNTT--FENN-D  LLSQNVDVE---AI  212
WP_001040104  144  DKKEKADLRLIYIALAHIIKFRGHFLIEDDsEDVRNTDISKQ--YQDFLEIFNTT--FENN-D  LLSQNVDVE---AI  212
WP_001040105  144  DKKEKADLRLIVYLALAHIIKFRGHFLIEDDrEDVRNTDIQRQ--YQAFLEIFDTT--FENN-H  LLSQNVDVE---GI  212
WP_001040106  144  DKKEKANLRLIVYLALAHIIKFRGHFLIEDDrEDVRNTDIQRQ--YQAFLEIFDTT--FENN-H  LLSQNIDVE---GI  212
WP_001040107  144  DKKEKADLRLIVYLALAHIIKFRGHFLIEDDrEDVRNTDIQRQ--YQAFLEIFDTT--FENN-H  LLSQNVDVE---GI  212
WP_001040108  144  DKKEKANLRLIVYLALAHIIKFRGHFLIEDDrEDVRNTDIQRQ--YQAFLEIFDTT--FENN-H  LLSQNIDVE---GI  212
WP_001040109  144  DKKEKANLRLIVYLALAHIIKFRGHFLIEDDrEDVRNTDIQRQ--YQAFLEIFDTT--FENN-H  LLSQNIDVE---GI  212
WP_001040110  144  DKKEKANLRLIVYLALAHIIKFRGHFLIEDDrEDVRNTDIQRQ--YQAFLEIFDTT--FENN-H  LLSQNIDVE---GI  212
```

| | | | | |
|---|---|---|---|---|
| WP_015058523 | 144 | DKKEKADLRLVYLALAHIIKFRGHFLIEDDrEDVRNTDIQKQ--YQAFLEIFDTS--FENN-H | LLSQNVDVE---AI | 212 |
| WP_017643650 | 144 | DKKEKADLRLIYLALAHIIKFRGHFLIEDDrEDVRNTDIQKQ--YQAFLEIFDTT--FENN-D | LLSQNVDVE---AI | 212 |
| WP_017647151 | 144 | DKKEKADLRLFYLALAHIIKFRGHFLIEDDsEDVRNTDIQRQ--YQAFLEIFDTT--FENN-H | LLSQNIDIE---GI | 212 |
| WP_017648376 | 144 | DKKEKADLRLFYLALAHIIKFRGHFLIEDDsEDVRNTDIQRQ--YQAFLEIFDTT--FENN-H | LLSQNVDVE---GI | 212 |
| WP_017649527 | 144 | DKKEKADLRLIYLALAHIIKFRGHFLIEDDsEDVRNTDIQRQ--YQAFLEIFDTT--FENN-D | LLSQNVDVE---AI | 212 |
| WP_017771611 | 144 | DKKEKADLRLIYLALAHIIKFRGHFLIEDDsEDVRNTDIQRQ--YQDFLEIFNTT--FENN-H | LLSQNVDVE---GI | 212 |
| WP_017771984 | 144 | DKKEKADLRLIYIALAHIIKFRGHFLIEDDsEDVRNTDISKQ--YQDFLEIFNTT--FENN-D | LLSQNVDVE---AI | 212 |
| CFQ25032 | 144 | DKKEKADLRLIYIALAHIIKFRGHFLIEDDsEDVRNTDISKQ--YQDFLEIFNTT--FENN-D | LLSQNVDVE---AI | 212 |
| CFV16040 | 144 | DKKEKADLRLIYIALAHIIKFRGHFLIEDDsEDVRNTDISKQ--YQDFLEIFNTT--FENN-D | LLSQNVDVE---AI | 212 |
| KLJ37842 | 144 | DKKEKADLRLIVYLALAHIIKFRGHFLIEDDsEDVRNTDISKQ--YQDFLEIFNTT--FENN-D | LLSQNVDVE---AI | 212 |
| KLJ72361 | 144 | DKKEKADLRLIYIALAHIIKFRGHFLIEDDsEDVRNTDISKQ--YQDFLEIFNTT--FENN-D | LLSQNVDVE---AI | 212 |
| KLL20707 | 144 | DKKEKADLRLIYIALAHIIKFRGHFLIEDDsEDVRNTDISKQ--YQDFLEIFNTT--FENN-D | LLSQNVDVE---AI | 212 |
| KLL42645 | 144 | DKKEKANLRLVYLALAHIIKFRGHFLIEDDsEDVRNTDISKQ--YQAFLEIFDTT--FENN-H | LLSQNVDVE---GI | 212 |
| WP_047207273 | 144 | DKKEKADLRLIYIALAHIIKFRGHFLIEDDsEDVRNTDISKQ--YQDFLEIFNTT--FENN-D | LLSQNVDVE---AI | 212 |
| WP_047209694 | 144 | DKKEKADLRLIYIALAHIIKFRGHFLIEDDsEDVRNTDISKQ--YQAFLEIFDTT--FENN-D | LLSQNVDVE---AI | 212 |
| WP_050198062 | 144 | DKKEKADLRLIVYLALAHIIKFRGHFLIEDDsEDVRNTDISKQ--YQDFLEIFNTT--FENN-D | LLSQNVDVE---AI | 212 |
| WP_050201642 | 144 | DKKEKADLRLIYIALAHIIKFRGHFLIEDDsEDVRNTDIQRQ--YQDFLEIFNTT--FENN-D | LLSQNVDVE---AI | 212 |
| WP_050204027 | 144 | DKKEKADLRLIYIALAHIIKFRGHFLIEDDsEDVRNTDIQRQ--YQAFLEIFDTT--FENN-H | LLSQNVDVE---GI | 212 |
| WP_050881965 | 144 | DKKEKADLRLIYIALAHIIKFRGHFLIEDDsEDVRNTDISKQ--YQDFLEIFNTT--FENN-D | LLSQNVDVE---AI | 212 |
| WP_050886065 | 144 | DKKEKADLRLVYLALAHIIKFRGHFLIEDDsEDVRNTDISKQ--YQAFLEIFDTT--FENN-D | LLSQNVDVE---AI | 212 |
| AHN30376 | 144 | DKKEKADLRLVYLALAHIIKFRGHFLIEDDrEDVRNTDIQKQ--YQAFLEIFDTS--FENN-H | LLSQNVDVE---AI | 212 |
| EAO78426 | 144 | DKKEKADLRLIYLALAHIIKFRGHFLIEDDsEDVRNTDISKQ--YQDFLEIFNTT--FENN-D | LLSQNVDVE---AI | 212 |
| CCW42055 | 144 | DKKEKADLRLVYLALAHIIKFRGHFLIEDDrEDVRNTDIQKQ--YQAFLEIFDTT--FENN-H | LLSQNVDVE---AI | 212 |
| WP_003041502 | 144 | DISQKADLRLVYLALAHMIKFRGHFLIEGQ-LKAENTNVQAL--FKDFVEVYDKT--VEES-H | LSEITVDAL---SI | 211 |
| WP_037593752 | 145 | NSKEKADLRLVYLALAHMIKFRGHFLIEGD-LKAENTDVQAL--FKDFVEEYDKT--IEES-H | LSEITVDAL---SI | 212 |
| WP_049516684 | 145 | DISQKADLRLVYLALAHMIKFRGHFLIEGQ-LKAENTNVQAL--FKDFVEVYDKT--VEES-H | LSEMTVDAL---SI | 212 |
| GAD46167 | 144 | NSKEKADLRLVYLALAHMIKFRGHFLYEGD-LKAENTDVQAL--FKDFVEEYDKT--IEES-H | LSEITVDAL---SI | 211 |

| | | | | |
|---|---|---|---|---|
| WP_018363470 | 145 | DSTEKADLRLIYLALAHMIKFRGHFLIEGE-LNAENTDVQKL--FTDFVGVYDRT--FDDS-H | LSEITVDAA---SI | 212 |
| WP_003043819 | 144 | DSPEKADLRLIYLALAHIIKFRGHFLIEGK-LNAENSDVAKL--FYQLIQTYNQL--FEES- | LDEIEVDAK---GI | 211 |
| WP_006269658 | 144 | DTSKKADLRLIVYLALAHMIKFRGHFLYEGD-LKAENTDVQAL--FKDFVEEYDKT--IEES-H | LSEITVDAL---SI | 211 |
| WP_048800889 | 144 | DSTGKVDLRLIVYLALAHMIKFRGHFLIEGQ-LKAENTDVQTL--FNDFVEVYDKT--IEES-H | LAEITVDAL---SI | 211 |
| WP_012767106 | 144 | DSTDKADLRLIYLALAHMIKFRGHFLIEGD-LNPDNSDMDKL--FIQLVQTYNQL--FEEN- | INASRVDAK---AI | 211 |
| WP_014612333 | 144 | DSTDKADLRLIYLALAHMIKFRGHFLIEGD-LNPDNSDVDKL--FIQLVQTYNQL--FEEK- | INASGVDAK---AI | 211 |
| WP_015017095 | 144 | DSTDKADLRLIYLALAHMIKFRGHFLIEGD-LNPDNSDMDKL--FIQLVQTYNQL--FEEN- | INASRVDAK---AI | 211 |
| WP_015057649 | 144 | DSTDKADLRLIYLALAHMIKFRGHFLIEGD-LNPDNSDMDKL--FIQLVQTYNQL--FEEN- | INASRVDAK---AI | 211 |
| WP_048327215 | 144 | DSTDKADLRLIYLALAHMIKFRGHFLIEGD-LNPDNSDMDKL--FIQLVQTYNQL--FEEN- | INASRVDAK---AI | 211 |
| WP_049519324 | 144 | DSTDKADLRLIYLALAHMIKFRGHFLIEGD-LNPDNSDVDKL--FIQLVQTYNQL--FEEN- | INASRVDAK---AI | 211 |
| WP_012515931 | 144 | DNPQKADLRLIYLAVAHIIKFRGHFLIEGT-LSSKNNNLQKS--FDHLVDTYNLL--FEEQ- | LLTEGINAK---EL | 211 |
| WP_021320964 | 144 | DNPQKADLRLIVAHIIKFRGHFLIEGT-LSSKNNNLQKS--FDHLVDTYNLL--FEEQ- | LLTEGINAK---EL | 211 |
| WP_037581760 | 144 | DNPQKADLRLIYLAVAHIIKFRGHFLIEGT-LSSKNNNLQKS--FDHLVDTYNLL--FEEQ- | LLTEGINAK---EL | 211 |
| WP_004232481 | 144 | DSPEKVDLRLIVYLALAHMIKFRGHFLIEGQ-LNAENTDVQKI--FADFVGVYDRT--FDDS-H | LSEITVDAA---SI | 211 |
| WP_009854540 | 145 | DSSEKADLRLIVYLALAHMIKFRGHFLIEGK-LNAENTDVQKL--FTDFVGVYDRT--FDDS-H | LSEITVDVA---ST | 212 |
| WP_012962174 | 145 | DSHEKADLRLIYLALAHMIKFRGHFLIEGE-LNAENTDVQKL--FEAFVEVYDRT--FDDS-N | LSEITVDAS---SI | 212 |
| WP_039695303 | 145 | DSSEKADLRLIVYLALAHMIKFRGHFLIEGE-LNAENTDVQKI--FADFVGVYNRT--FDDS-H | LSEITVDVA---SI | 212 |
| WP_014334983 | 144 | DSQEKADLRLIVYLALAHMIKFRGHFLIEGE-LNAENTDVQKL--FNVFVETYDKI--VDES-H | LSEIEVDAS---SI | 211 |
| WP_003099269 | 144 | DSDQKADLRLIYLALAHIIKYRGHFLIEGN-LDSENTDVHVL--FLNLVNIYNNL--FEED- | VETASIDAE---KI | 211 |
| AHY15608 | 144 | DSDQKADLRLIYLALAHIIKFRGHFLIEGN-LDSENTDVHVL--FLNLVNIYNNL--FEED- | VETASIDAE---KI | 211 |
| AHY17476 | 144 | DSDQKADLRLIYLALAHIIKFRGHFLIEGN-LDSENTDVHVL--FLNLVNIYNNL--FEED- | VETASIDAE---KI | 211 |
| ESR09100 | | --------------------------------------------------------- | -------------- | |
| AGM98575 | 144 | DSDQKADLRLIYLALAHIIKFRGHFLIEGN-LDSENTDVHVL--FLNLVNIYNNL--FEED- | VETASIDAE---KI | 211 |
| ALF27331 | 144 | DNPEKTDLRLIVYLALAHIIKFRGHFLIEGK-LDSENTDVHVL--FQEFLAVYDNT--FENS-S | LQFQNVQVE---EI | 211 |
| WP_018372492 | 144 | DTPDKMDIRLIYLALAHIIKYRGHFLIEGD-LDIENIGIQDS--FKSFIEEYNTQ--FGTK- | -LDSTTKVE---AI | 209 |
| WP_045618028 | 145 | DSKEKADFRLIYLALAHIIKFRGHFLYEES-FDIKNNDIQKI--FNEFISIYDNT--FEGS-S | LNGQNAQVE---AI | 212 |
| WP_045635197 | 144 | DSKEKTDLRLIYLALAHMIKYRGHFLYEEA-FDIKNNDIQKI--FNEFISIYDNT--FEGS-S | LSGQNAQVE---AI | 211 |

| | | | |
|---|---|---|---|
| WP_002263549 | 144 | DNPEKVDLRLVYLALAHIIKFRGHFLIEGK-FDTRNNDVQRL--FQEFLAVYDNT--FENS-S LQEQNVQVE---EI | 211 |
| WP_002263887 | 144 | DNPEKVDLRLVYLALAHIIKFRGHFLIEGK-FDTRNNDVQRL--FQEFLAVYDNT--FENS-S LQEQNVQVE---EI | 211 |
| WP_002264920 | 144 | DSTEKADLRLVYLALAHMIKFRGHFLIEGE-LNAENTDVQKL--FADFVGVYDRT--FDDS-H LSEITVDAS---SI | 211 |
| WP_002269043 | 144 | DNPEKVDLRLVYLALAHIIKFRGHFLIEGK-FDTRNNDVQRL--FQEFLAVYDNT--FENS-S LQEQNVQVE---EI | 211 |
| WP_002269448 | 144 | DNPEKVDLRLVYLALAHIIKFRGHFLIEGK-FDTRNNDVQRL--FQEFLAVYDNT--FENS-S LQEQNVQVE---EI | 211 |
| WP_002271977 | 144 | DNPEKTDLRLVYLALAHIIKFRGHFLIEGK-FDTRNNDVQRL--FQEFLAVYDNT--FENS-S LQEQNVQVE---EI | 211 |
| WP_002272766 | 144 | DNPEKVDLRLVYLALAHIIKFRGHFLIEGK-FDTRNNDVQRL--FQEFLAVYDNT--FENS-S LQEQNVQVE---EI | 211 |
| WP_002273241 | 144 | DNPEKVDLRLVYLALAHIIKFRGHFLIEGK-FDTRNNDVQRL--FQEFLAVYDNT--FENS-S LQEQNVQVE---EI | 211 |
| WP_002275430 | 144 | DNPEKVDLRLVYLALAHIIKFRGHFLIEGK-FDTRNNDVQRL--FQEFLAVYDNT--FENS-S LQEQNVQVE---EI | 211 |
| WP_002276448 | 144 | DNPEKVDLRLVYLALAHIIKFRGHFLIEGK-FDTRNNDVQRL--FQEFLAVYDNT--FENS-S LQEQNVQVE---EI | 211 |
| WP_002277050 | 144 | DSTEKADLRLVYLALAHMIKFRGHFLIEGE-LNAENTDVQKL--FADFVGVYDRT--FDDS-H LSEITVDAS---SI | 211 |
| WP_002277364 | 144 | DNPEKVDLRLVYLALAHIIKFRGHFLIEGK-FDTRNNDVQRL--FQEFLAVYDNT--FENS-S LQEQNVQVE---EI | 211 |
| WP_002279025 | 144 | DNPEKTDLRLVYLALAHIIKFRGHFLIEGK-FDTRNNDVQRL--FQEFLAVYDNT--FENS-S LQEQNVQVE---EI | 211 |
| WP_002279859 | 144 | DSTEKADLRLVYLALAHMIKFRGHFLIEGE-LNAENTDVQKL--FADFVGVYDRT--FDDS-H LSEITVDAS---SI | 211 |
| WP_002280230 | 144 | DNPEKVDLRLVYLALAHIIKFRGHFLIEGK-FDTRNNDVQRL--FQEFLAVYDNT--FENS-S LQEQNVQVE---EI | 211 |
| WP_002281696 | 144 | DNPEKVDLRLVYLALAHIIKFRGHFLIEGK-FDTRNNDVQRL--FQEFLAVYDNT--FENS-S LQEQNVQVE---EI | 211 |
| WP_002282247 | 144 | DSTEKADLRLVYLALAHMIKFRGHFLIEGE-LNAENTDVQKL--FADFVGVYDRT--FDDS-H LSEITVDAS---SI | 211 |
| WP_002282906 | 144 | DNPEKVDLRLVYLALAHIIKFRGHFLIEGK-FDTRNNDVQRL--FQEFLAVYDNT--FENS-S LQEQNVQVE---EI | 211 |
| WP_002283846 | 144 | DNPEKTDLRLVYLALAHIIKFGGHFLIEGK-FDTRNNDVQRL--FQEFLAVYDNT--FENS-S LQEQNVQVE---EI | 211 |
| WP_002287255 | 144 | DNPEKTDLRLVYLALAHIIKFRGHFLIEGK-FDTRNNDVQRL--FQEFLAVYDNT--FENS-S LQEQNVQVE---EI | 211 |
| WP_002288990 | 144 | DNPEKVDLRLVYLALAHIIKFRGHFLIEGK-FDTRNNDVQRL--FQEFLAVYDNT--FENS-S LQEQNVQVE---EI | 211 |
| WP_002289641 | 144 | DNPEKVDLRLVYLALAHIIKFRGHFLIEGK-FDTRNNDVQRL--FQEFLAVYDNT--FENS-S LQEQNVQVE---EI | 211 |
| WP_002290427 | 144 | DNPEKVDLRLVYLALAHIIKFRGHFLIEGK-FDTRNNDVQRL--FQEFLAVYDNT--FENS-S LQEQNVQVE---EI | 211 |
| WP_002295753 | 144 | DNPEKVDLRLVYLSLAHMIKFRGHFLIEGQ-LKAENTNVQAL--FKDFVEVYDKT--VEES-H LSEMTVDAL---SI | 211 |
| WP_002296423 | 144 | DNPEKVDLRLVYLALAHIIKFRGHFLIEGK-FDTRNNDVQRL--FQEFLAVYDNT--FENS-S LQEQNVQVE---EI | 211 |
| WP_002304487 | 144 | NSTEKADLRLVYLSLAHMIKFRGHFLIEGK-FDTRNNDVQAL--FKDFVEVYDKT--VEES-H LSEMTVDAL---SI | 211 |
| WP_002305844 | 144 | DNPEKVDLRLVYLALAHIIKFRGHFLIEGK-FDTRNNDVQRL--FQEFLAVYDNT--FENS-S LQEQNVQVE---EI | 211 |

```
WP_002307203   144  DNPEKVDLRLIVYLALAHIIKFRGHFLIEGK-FDTRNNDVQRL--FQEFLAVYDNT--FENS-S  LQEQNVQVE----EI  211
WP_002310390   144  DNPEKTDLRLIVYLALAHIIKFRGHFLIEGK-FDTRNNDVQRL--FQEFLAVYDNT--FENS-S  LQEQNVQVE----EI  211
WP_002352408   144  DNPEKTDLRLIVYLALAHIIKFRGHFLIEGK-FDTRNNDVQRL--FQEFLAVYDNT--FENS-S  LQEQNVQVE----EI  211
WP_012997688   144  DNPEKVDLRLIVYLALAHIIKFRGHFLIEGK-FDTRNNDVQRL--FQEFLAVYDNT--FENS-S  LQEQNVQVE----EI  211
WP_014677909   144  DNPEKTDLRLIVYLALAHIIKFRGHFLIEGK-FDTRNNDVQRL--FQEFLAVYDNT--FENS-S  LQEQNVQVE----EI  211
WP_019312892   144  DNPEKVDLRLIVYLALAHIIKFRGHFLIEGK-FDTRNNDVQRL--FQEFLAVYDNT--FENS-S  LQEQNVQVE----EI  211
WP_019313659   144  DNPEKVDLRLIVYLALAHIIKFRGHFLIEGK-FDTRNNDVQKL--FQEFLAVYDNT--FENS-S  LQEQNVQVE----EI  211
WP_019314093   144  DNPEKTDLRLIVYLALAHIIKFRGHFLIEGK-FDTRNNDVQRL--FQEFLAVYDNT--FENS-S  LQEQNVQVE----EI  211
WP_019315370   144  DNPEKTDLRLIVYLALAHIIKFRGHFLIEGK-FDTRNNDVQKL--FQEFLAVYDNT--FENS-S  LQEQNVQVE----EI  211
WP_019803776   144  DNPEKVDLRLIVYLALAHIIKFRGHFLIEGK-FDTRNNDVQRL--FQEFLAVYDNT--FENS-S  LQEQNVQVE----EI  211
WP_019805234   144  DNPEKVDLRLIVYLALAHIIKFRGHFLIEGK-FDTRNNDVQRL--FQEFLAVYDNT--FENS-S  LQEQNVQVE----EI  211
WP_024783594   144  DSTEKADLRLIVYLALAHMIKFRGHFLIEGE-LNAENTDVQKL--FADFVGVYDRT--FDDS-H  LSEITVDAS----SI  211
WP_024784288   144  DNPEKVDLRLIVYLALAHIIKFRGHFLIEGK-FDTRNNDVQRL--FQEFLAVYDNT--FENS-S  LQEQNVQVE----EI  211
WP_024784666   144  DNPEKVDLRLIVYLALAHIIKFRGHFLIEGK-FDTRNNDVQRL--FQEFLAVYDNT--FENS-S  LQEQNVQVE----EI  211
WP_024784894   144  DNPEKVDLRLIVYLALAHIIKFRGHFLIEGK-FDTRNNDVQRL--FQEFLAVYDNT--FENS-S  LQEQNVQVE----EI  211
WP_024786433   144  DSTEKADLRLIVYLALAHMIKFRGHFLIEGE-LNAENTDVQKL--FADFVGVYDRT--FDDS-H  LSEITVDAS----SI  211
WP_049473442   144  DNPEKVDLRLIVYLALAHIIKFRGHFLIEGK-FDTRNNDVQRL--FQEFLAVYDNT--FENS-S  LQEQNVQVE----EI  211
WP_049745547   144  DNPEKTDLRLIVYLALAHIIKFRGHFLIEGK-FDTRNNDVQRL--FQEFLAVYDNT--FENS-S  LQEQNVQVE----EI  211
EMC03581       137  DNPEKVDLRLIVYLALAHIIKFRGHFLIEGK-FDTRNNDVQRL--FQEFLAVYDNT--FENS-S  LQEQNVQVE----EI  204
WP_000428612   145  DSKEKTDLRLIYLALAHMIKYRGHFLYEDT-FDIKNNDIQKI--FNEFISIYNNT--FEGN-S  LSGQNVQVE----AI  212
WP_000428613   145  DSKEKTDLRLIYLALAHMIKYRGHFLYEDT-FDIKNNDIQKI--FSEFISIYDNT--FEGS-S  LSGQNAQVE----AI  212
WP_049523028   144  DSKEKVDLRLIYLALAHMIKYRGHFLYEDS-FDIKNNDIQKI--FNEFTILYDNT--FEES-S  LSKGNAQVE----EI  211
WP_003107102   113  DSDEKADLRLIYLALAHIIKFRGHFLIEGD-LDSQNTDVNAL--FLKLVDTYNLM--FEDD-   IDTQTIDAT----VI  180
WP_054279288   146  DNTEKADLRLIYLALAHIIKFRGHFLIEGA-LSANNTDVQQL--VHALVDAYNIM--FEED-   LDIEAIDVK----   213
WP_049531101   145  DSKEKADLRLIYLTLAHMIKYRGHFLYEES-FDIKNNDIQKI--FNEFISIYDNT--FEGS-S  LSGQNAQVE----AI  212
WP_049538452   145  DSKEKADLRLIYLALAHMIKYRGHFLYEEA-FDIKNNDIQKI--FNEFINIYDNT--FEGS-S  LSGQNEQVE----AI  212
WP_049549711   145  DSKEKADLRLIYLVLAHMIKYRGHFLYEEA-FDIKNNDIQKI--FNEFISIYDNT--FEGS-S  LSGQNAQVE----TI  212
```

| ID | Start | Sequence | End |
|---|---|---|---|
| WP_007896501 | 146 | DRDQKADLRLIYLALSHIIKFRGHFLIEGK-LNSENTDVQKL--FIALVTVYNLL--FEEE---IAGETCDAK---AL | 213 |
| EFR44625 | 98 | DRDQKADLRLIYLALSHIIKFRGHFLIEGK-LNSENTDVQKL--FIALVTVYNLL--FEEE---IAGETCDAK---AL | 165 |
| WP_002897477 | 144 | DSKEKSDVRLIYLALAHMIKYRGHFLYEET-FDIKNNDIQKI--FNEFINIYDNT--FEGS-S-LSQNAQVE---AI | 211 |
| WP_002906454 | 144 | DSKEKTDLRLIYLALAHMIKYRGHFLYEES-FDIKNNDIQKI--FNEFISIYDNT--FEGS-S-LSGQNAQVE---AI | 211 |
| WP_009729476 | 145 | DSKEKTDLRLIYLALAHMIKYRGHFLYEEA-FDIKNNDIQKI--FNEFISIYNNT--FEGN-S-LSGQNVQVE---AI | 212 |
| CQR24647 | 144 | DSSEKADLRLVYLALAHIIKYRGHFLIDEP-IDIRNMNSQNL-FKEELLAFDGI--QVDC-Y-LASKHTDIS---GI | 211 |
| WP_000066813 | 145 | DSKEKTDLRLIYLALAHMIKYRGHFLYEES-FDIKNNDIQKI--FSEFISIYDNT--FEGK-S-LSGQNAQVE---AI | 212 |
| WP_009754323 | 145 | DSKEKADLRLIYLALAHITKYRGHFLYEEA-FDIKNNDIQKI--FNEFINIYDNT--FEGS-S-LSGQNAQVE---AI | 212 |
| WP_044674937 | 144 | DSSQKADIRLIYLALAHIIKYRGHELFEGD-LKSENKDVQHL--FNDFVEMFDKT--VEGS-Y-LSENLPNVA---DV | 211 |
| WP_044676715 | 144 | DSSQKADIRLIYLALAHIIKYRGHELFEGD-LKSENKDVQHL--FNDFVEMFDKT--VEGS-Y-LSENLPNVA---DV | 211 |
| WP_044680361 | 144 | DSSQKADIRLIYLALAHIIKYRGHELFEGD-LKSENKDVQHL--FNDFVEMFDKT--VEGS-Y-LSENLPNVA---DV | 211 |
| WP_044681799 | 144 | DSSQKADIRLIYLALAHIIKYRGHELFEGD-LKSENKDVQHL--FNDFVEMFDKT--VEGS-Y-LSENLPNVA---DV | 211 |
| WP_049533112 | 144 | DISQKADLRLVYLALAHMIKFRGHFLIEGQ-LKAENTNVQAL--FKDFVEVYDKT--VEES-H-LSEMTVDAL---SI | 211 |
| WP_029090905 | 101 | SQHRQFDIREVYLAIHHLIKYRGHFIYEDQPFTTDGNQLQHH--IKAIITMINST1---NR---IIPETIDINvfeKI | 171 |
| WP_006506696 | 140 | ESTEKADPRLIYLALHHIKYRGNFLYEGQkFNMDASNIEDK--LSDIFTQFTSFnnIPYEdD---KKNLEIL---EI | 210 |
| AIT42264 | 144 | DSTDKADLRLIYLALAHMIKFRGHFLIEGD-LNPDNSDVDKL--FIQLVQTYNQL--FEEN---INASGVDAK---AI | 211 |
| WP_034440723 | 143 | DSNQKADLRLIYLALAHMIKYRGHFLIEGD-LKMDGISISES--FQEFIDSYNEVcaLEDE-N-NDELLTQIE---NI | 217 |
| AKQ21048 | 144 | DSTDKADLRLIYLALAHMIKFRGHFLIEGD-LNPDNSDVDKL--FIQLVQTYNQL--FEEN---INASGVDAK---AI | 211 |
| WP_004636532 | 144 | DNPEKADLRLVYTALAHIVKYRGHFLIEGE-LNTNENTSISET--FEQFLDTYSDI--FKEQ---LVGDISKVE---EI | 210 |
| WP_002364836 | 144 | DSSEQADLRLIYLALAHIVKYRGHFLIEGK-LSTENISVKEQ--FQQFMIIYNQT--FVNGeS-PLPESVLIE---EE | 217 |
| WP_016631044 | 95 | DSSEQADLRLIYLALAHIVKYRGHFLIEGK-LSTENISVKDQ--FQQFMIIYNQT--FVNGeS-PLPESVLIE---EE | 168 |
| EMS75795 | | ------------------------------------------------------------------------- | |
| WP_002373311 | 144 | DSSEQADLRLIYLALAHIVKYRGHFLIEGK-LSTENISVKEQ--FQQFMIIYNQT--FVNGeS-PLPESVLIE---EE | 217 |
| WP_002378009 | 144 | DSSEQADLRLIYLALAHIVKYRGHFLIEGK-LSTENISVKEQ--FQQFMIIYNQT--FVNGeS-PLPESVLIE---EE | 217 |
| WP_002407324 | 144 | DSSEQADLRLIYLALAHIVKYRGHFLIEGK-LSTENISVKEQ--FQQFMIIYNQT--FVNGeS-PLPESVLIE---EE | 217 |
| WP_002413717 | 144 | DSSEQADLRLIYLALAHIVKYRGHFLIEGK-LSTENISVKEQ--FQQFMIIYNQT--FVNGeS-PLPESVLIE---EE | 217 |
| WP_010775580 | 144 | DSSEQADLRLIYLALAHIVKYRGHFLIEGK-LSTENISVKEQ--FQQFMIIYNQT--FVNGeS-PLPESVLIE---EE | 217 |

| | | | |
|---|---|---|---|
| WP_010818269 | 144 | DSSEQADLRLIYLALAHIVKYRGHFLIEGK-LSTENISVKEQ--FQQFMIYNQT--FVNGeS | PLPESVLIE---EE | 217 |
| WP_010824395 | 144 | DSSEQADLRLIYLALAHIVKYRGHFLIEGK-LSTENISVKDQ--FQQFMIYNQT--FVNGeS | PLPESVLIE---EE | 217 |
| WP_016622645 | 144 | DSSEQADLRLIYLALAHIVKYRGHFLIEGK-LSTENTSVKEK--FQQFMIYNQT--FVNGeS | PLPESVLIE---EE | 217 |
| WP_033624816 | 144 | DSSEQADLRLIYLALAHIVKYRGHFLIEGK-LSTENISVKDQ--FQQFMIYNQT--FVNGeG | PLPESVLIE---EE | 217 |
| WP_033625576 | 144 | DSSEQADLRLIYLALAHIVKYRGHFLIEGK-LSTENISVKEQ--FQQFMIYNQT--FVNGeS | PLPESVLIE---EE | 217 |
| WP_033789179 | 144 | DSSEQADLRLIYLALAHIVKYRGHFLIEGK-LSTENISVKEQ--FQQFMIYNQT--FVNGeS | PLPESVLIE---EE | 217 |
| WP_002310644 | 144 | DSSEKADIRLVYLAMAHLLKYRGHFLIEGE-LNTENSSVTET--FRQFLSTYNQQ--FSEA-D | KLDEAVDCS---FV | 216 |
| WP_002312694 | 144 | DSSEKADIRLVYLAMAHLLKYRGHFLIEGE-LNTENSVTET--FRQFLSTYNQQ--FSEA-G | KLDEAVDCS---FV | 216 |
| WP_002314015 | 144 | DSSEKADIRLVYLAMAHLLKYRGHFLIEGE-LNTENSSVTET--FRQFLSTYNQQ--FSEA-D | KLDEAVDCS---FV | 216 |
| WP_002320716 | 144 | DSSEKADIRLVYLAMAHLLKYRGHFLIEGE-LNTENSSVTET--FRQFLSTYNQQ--FSEA-D | KLDEAVDCS---FV | 216 |
| WP_002330729 | 144 | DSSEKADIRLVYLAMAHLLKYRGHFLIEGE-LNTENSSVTET--FRQFLSTYNQQ--FSEA-D | KLDEAVDCS---FV | 216 |
| WP_002335161 | 144 | DSSEKADIRLVYLAMAHLLKYRGHFLIEGE-LNTENSSVTET--FRQFLSTYNQQ--FSEA-D | KLDEAVDCS---FV | 216 |
| WP_002345439 | 144 | DSSEKADIRLVYLAMAHLLKYRGHFLIEGE-LNTENSSVTET--FRQFLSTYNQQ--FSEA-D | KLDEAVDCS---FV | 216 |
| WP_034867970 | 144 | DSTEKEDLRLVYLALAHLLKYRGHFLFEGD-LDTENTSIEES--FRVFLEQYSKQ--SDQP-- | -LIVHQPVL---TI | 209 |
| WP_047937432 | 144 | DSSEKADIRLVYLAMAHLLKYRGHFLIEGE-LNTENSSVTET--FRQFLSTYNQQ--FSEA-D | KLDEAVDCS---FV | 216 |
| WP_010720994 | 144 | DSTEKGDLRLVYLALAHLLKYRGHFLFEGD-LDTENTSIEES--FRVFLEQYGKQ--SDQP-- | -LIVHQPVL---TI | 209 |
| WP_010737004 | 144 | DSTEKEDLRLVYLALAHLLKYRGHFLFEGD-LDTENTSIEES--FRVFLEQYSKQ--SDQP-- | -LIVHQPVL---TI | 209 |
| WP_034700478 | 144 | DSTEKEDLRLVYLALAHLLKYRGHFLFEGD-LDTENTSIEES--FRVFLEQYGKQ--SDQP-- | -LIVHQPVL---TI | 209 |
| WP_007209003 | 144 | DGDEKADLRLVYLAIAHI IKFRGNFLIEGE-LNTENNSVIELs--KVFVQLYNQTl-SELE- | FIDESIDFS---EV | 214 |
| WP_023519017 | 144 | NSKEQADIRLVYLAIAHCLKYRGHFLFEGE-LDTENTSVTEN--YQQFlQAYQQF--FPEP-- | -IGDLDDAV---PI | 209 |
| WP_010770040 | 144 | DTSEQADLRLVYLALAHIVKYRGHFLIEGR-LNTENSSVSET--FRTFIQVYNQI--FRENe | PLAVPDNIE---EL | 212 |
| WP_048604708 | 144 | DAEEKADLRLVYLAIAHMIKYRGHFLFEGE-LSTENTSVBET--FKTFLQKYNQT--FN---- | PVDETISIG---SI | 208 |
| WP_010750235 | 144 | DSTEKADIRLVYLALAHMIKYRGHFLFEGE-LDTENTSVEET--FKEFIDIYNEQ--FEEG-- | -IIFYKDIP---LI | 209 |
| AII6583 | 183 | DSTDKADLRLIYLALAHMIKFRGHFLIEGD-LNPDNSDVDKL--FIQLVQTYNQL--FEEN-- | INASGVDAK---AI | 250 |
| WP_029073316 | 145 | ESKEKEDPRLIYLALHHIVKYRGNFLYEQQkFSMDVSNIEDK--MIDVLRQFNEInlFEYveD | --KKIDEVL---NV | 215 |
| WP_031589969 | 145 | ESKEKEDPRLIYLALIHHIVKYRGNFLYEQQkFSMDVSNIEDK--MIDVLRQFNEInlFEYveD | --KKIDEVL---NV | 215 |
| KDA45870 | 145 | NNDRPADLRLVYLALAHIIKYRGNFLLEGE-IDLRTTDINKV--FAEFSETLNEN--SDENIG | ----KLDVA---DI | 209 |

| | | | |
|---|---|---|---|
| WP_039099354 | 133 | TEKKQFDIREIYLAMHHIVKYRGHFLNEAPvSSEKSSEINLVahFDRLNTIFADL--FSESgF | -TDKLAEVK---AL | 206 |
| AKP02966 | 138 | INKNKADIRLVYLALHHNILKYRGNFTYEHQkFNISTLNSNLS---KELIELNQQLikYDIS-- | -FPDNCDWNhisDI | 208 |
| WP_010991369 | 144 | NSSEKADLRLVYLALAHIIKYRGNFLIEGA-LDTQNTSVDGI--YKQFIQTYNQV--FASGiE | KLEDNKDVA---KI | 217 |
| WP_033838504 | 144 | NSSEKADLRLVYLALAHIIKYRGNFLIEGA-LDTQNTSVDGI--YKQFIQTYNQV--FASGiE | KLEDNKDVA---KI | 217 |
| EHN60060 | 147 | NSSEKADLRLVYLALAHIIKYRGNFLIEGA-LDTQNTSVDGI--YKQFIQTYNQV--FASGiE | KLEDNKDVA---KI | 220 |
| EFR89594 | | | | |
| WP_038409211 | 144 | NSSDKADLRLVYLALAHIIKYRGNFLIEGM-LDTKNTSVDEV--FKQFIQTYNQI--FASDiE | RLEENKEVA---EI | 217 |
| EFR95520 | | | | |
| WP_003723650 | 144 | NSSEKADLRLVYLALAHIIKYRGNFLIEGA-LDTKNTSVDEV--YKQFIETYNQV--FMSNiE | KVEENIEVA---NI | 217 |
| WP_003727705 | 144 | NSSEKADLRLVYLALAHIIKYRGNFLIEGA-LDTKNTSVDEV--YKQFIQTYNQV--FMSNiE | KVEENTEVA---SI | 217 |
| WP_003730785 | 144 | NSSEKADLRLVYLALAHIIKYRGNFLIEGA-LDTKNTSVDEV--YKQFIQTYNQV--FMSNiE | KVEENTEVA---SI | 217 |
| WP_003733029 | 144 | DSQKKADLRLVYLALAHIIKYRGHFLIEGA-LDTKNTSIDEM--FKQFLQIYNQV--FANDiE | KTEKNQEVA---QI | 217 |
| WP_003739838 | 144 | NSSEKADLRLVYLALAHIIKYRGNFLIEGA-LDTKNTSVDGV--YKQFIQTYNQV--FISNiE | KVEENIEVA---DI | 217 |
| WP_014601172 | 144 | NSSEKADLRLVYLALAHIIKYRGNFLIEGA-LDTKNTSVDGV--YEQFIQTYNQV--FMSNiE | KMEENTTVA---NI | 217 |
| WP_023548323 | 144 | NSSEKADLRLVYLALAHIIKYRGNFLIEGA-LDTKNTSVDGV--YEQFILTYNQV--FMSNiE | KVEENIEVA---NI | 217 |
| WP_031665337 | 144 | NSSEKADLRLVYLALAHIIKYRGNFLIEGA-LDTKNTSVDGV--YEQFIQTYNQV--FMSNiE | KVEENIEVA---NI | 217 |
| WP_031669209 | 144 | DSQKKADLRLVYLALAHIIKYRGHFLIEGA-LDTKNTSIDEM--FKQFLQIYNQV--FANDiE | KTEKNQEVA---QI | 217 |
| WP_033920898 | 144 | NSSEKADLRLVYLALAHIIKYRGNFLIEGA-LDTKNTSVDGV--YEQFIQTYNQV--FMSNiE | KVEENIEVA---NI | 217 |
| AKI42028 | 147 | NSSEKADLRLVYLALAHIIKYRGNFLIEGA-LDTKNTSVDGV--YEQFIQTYNQV--FMSNiE | KVEENIEVA---NI | 220 |
| AKI50529 | 147 | NSSEKADLRLVYLALAHIIKYRGNFLIEGA-LDTKNTSVDGV--YEQFIQTYNQV--FMSNiE | KVEENIEVA---NI | 220 |
| EFR83390 | | | | |
| WP_046323366 | 144 | NSSDKADLRLVYLALAHIIKYRGNFLIEGK-LDTKNTSVDEV--FKQFIKTYNQV--FASDiE | RIEENNEVA---KI | 217 |
| AKE81011 | 160 | DSTDKADLRLIYLALAHMIKFRGHFLIEGD-LNPDNSDVDKL--FIQLVQTYNQL--FEEN-- | INASGVDAK---AI | 227 |
| CUO82355 | 144 | ESTEKADPRLIYLALHHIVKYRGNFLYEQEQkFNMDASNIEDK--LSDVETQFADEmnIPYEdD | -KKNLEIL---EI | 214 |
| WP_033162887 | 145 | ENKEKADPRLIYLALHHIVKYRGNFLYEQSFTMDNSDIEER--LNSAIEKFMSIneFDNRiV | --SDINSMI---AV | 215 |
| AGZ01981 | 177 | DSTDKADLRLIYLALAHMIKFRGHFLIEGD-LNPDNSDVDKL--FIQLVQTYNQL--FEEN-- | INASGVDAK---AI | 244 |
| AKA60242 | 144 | DSTDKADLRLIYLALAHMIKFRGHFLIEGD-LNPDNSDVDKL--FIQLVQTYNQL--FEEN-- | INASGVDAK---AI | 211 |

| | | | | |
|---|---|---|---|---|
| AKS40380 | 144 | DSTDKADLRLIYLALAHMIKFRGHFPLIEGD-LNPDNSDVDKL--FIQLVQTYNQL--FEEN- | | INASGVDAK---AI | 211 |
| 4UN5_B | 148 | DSTDKADLRLIYLALAHMIKFRGHFPLIEGD-LNPDNSDVDKL--FIQLVQTYNQL--FEEN- | | INASGVDAK---AI | 215 |
| WP_010922251 | 212 | LSAR-LSKSRRLENLIAQ-L-PG | EKKNGLFGNLIALSLGLTPNFKSNF--DLAED-A---KLQ--LSKDTYDDDLDN | 277 |
| WP_039695303 | 213 | LTEK-ISKSRRLENLIKY-Y-PT | EKKNTLFGNLIALALGLQPNFKTNF--KLSED-A---KLQ--FSKDTYEEDLEE | 278 |
| WP_045635197 | 212 | FTDK-ISKSAKREVLKL-F-PD | EKSTGLFSEFLKLIVGNQADFKKHF--DLEDK-A---PLQ--FSKDTYDEDLEN | 277 |
| 5AXW_A | 135 | LSTK--------EQISRN-S--K | ------------LEEKyVa-ELQ-- | 157 |
| WP_009880683 | | | | |
| WP_010922251 | 212 | LSAR-LSKSRRLENLIAQ-L-PG | EKKNGLFGNLIALSLGLTPNFKSNF--DLAED-A---KLQ--LSKDTYDDDLDN | 277 |
| WP_011054416 | 212 | LSAR-LSKSRRLENLIAQ-L-PG | EKKNGLFGNLIALSLGLTPNFKSNF--DLAED-A---KLQ--LSKDTYDDDLDN | 277 |
| WP_011284745 | 212 | LSAR-LSKSRRLENLIAQ-L-PG | EKKNGLFGNLIALSLGLTPNFKSNF--DLAED-A---KLQ--LSKDTYDDDLDN | 277 |
| WP_011285506 | 212 | LSAR-LSKSRRLENLIAQ-L-PG | EKKNGLFGNLIALSLGLTPNFKSNF--DLAED-A---KLQ--LSKDTYDDDLDN | 277 |
| WP_011527619 | 212 | LSAR-LSKSRRLENLIAQ-L-PG | EKRNGLFGNLIALSLGLTPNFKSNF--DLAED-A---KLQ--LSKDTYDDDLDN | 277 |
| WP_012560673 | 212 | LSAR-LSKSRRLENLIAQ-L-PG | EKKNGLFGNLIALSLGLTPNFKSNF--DLAED-A---KLQ--LSKDTYDDDLDN | 277 |
| WP_014407541 | 212 | LSAR-LSKSRRLENLIAQ-L-PG | EKKNGLFGNLIALSLGLTPNFKSNF--DLAED-A---KLQ--LSKDTYDDDLDN | 277 |
| WP_020905136 | 212 | LSAR-LSKSRRLENLIAQ-L-PG | EKKNGLFGNLIALSLGLTPNFKSNF--DLAED-A---KLQ--LSKDTYDDDLDN | 277 |
| WP_023080005 | 212 | LSAR-LSKSRRLENLIAQ-L-PG | EKKNGLFGNLIALSLGLTPNFKSNF--DLAED-A---KLQ--LSKDTYDDDLDN | 277 |
| WP_023610282 | 212 | LSAR-LSKSRRLENLIAQ-L-PG | EKKNGLFGNLIALSLGLTPNFKSNF--DLAED-A---KLQ--LSKDTYDDDLDN | 277 |
| WP_030125963 | 212 | LSAR-LSKSRRLENLIAQ-L-PG | EKKNGLFGNLIALSLGLTPNFKSNF--DLAED-A---KLQ--LSKDTYDDDLDN | 277 |
| WP_030126706 | 212 | LSAR-LSKSRRLENLIAQ-L-PG | EKKNGLFGNLIALSLGLTPNFKSNF--DLAED-A---KLQ--LSKDTYDDDLDN | 277 |
| WP_031488318 | 212 | LSAR-LSKSRRLENLIAQ-L-PG | EKRNGLFGNLIALSLGLTPNFKSNF--DLAED-A---KLQ--LSKDTYDDDLDN | 277 |
| WP_032460140 | 212 | LSAR-LSKSRRLENLIAQ-L-PG | EKRNGLFGNLIALSLGLTPNFKSNF--DLAED-A---KLQ--LSKDTYDDDLDN | 277 |
| WP_032461047 | 212 | LSAR-LSKSRRLENLIAQ-L-PG | EKRNGLFGNLIALSLGLTPNFKSNF--DLAED-A---KLQ--LSKDTYDDDLDN | 277 |
| WP_032462016 | 212 | LSAR-LSKSRRLENLIAQ-L-PG | EKRNGLFGNLIALSLGLTPNFKSNF--DLAED-A---KLQ--LSKDTYDDDLDN | 277 |
| WP_032462936 | 212 | LSAR-LSKSRRLENLIAQ-L-PG | EKRNGLFGNLIALLLGLTPNFKSNF--DLAED-A---KLQ--LSKDTYDDDLDN | 277 |
| WP_032464890 | 212 | LSAR-LSKSRRLENLIAQ-L-PG | EKRNGLFGNLIALSLGLTPNFKSNF--DLAED-A---KLQ--LSKDTYDDDLDN | 277 |
| WP_033888930 | 37 | LSAR-LSKSRRLENLIAQ-L-PG | EKKNGLFGNLIALSLGLTPNFKSNF--DLAED-A---KLQ--LSKDTYDDDLDN | 102 |
| WP_038431314 | 212 | LSAR-LSKSRRLENLIAQ-L-PG | EKKNGLFGNLIALSLGLTPNFKSNF--DLAED-A---KLQ--LSKDTYDDDLDN | 277 |

-continued

```
WP_038432938   212  LSAR-LSKSRRLENLIAQ-L-PG  EKKNGLFGNLIALSLGLTPNFKSNF-DLAED-T---KLQ--LSKDTYDDDLDN  277
WP_038434062   212  LSAR-LSKSRRLENLIAQ-L-PG  EKRNGLFGNLIALSLGLTPNFKSNF-DLAED-A---KLQ--LSKDTYDDDLDN  277
BAQ51233       123  LSAR-LSKSRRLENLIAQ-L-PG  EKKNGLFGNLIALSLGLTPNFKSNF-DLAED-A---KLQ--LSKDTYDDDLDN  188
KGE60162       ---  ---------------------    --------------------------------------------------
KGE60856       ---  ---------------------    --------------------------------------------------
WP_002989955   212  LSAR-LSKSRRLENLIAQ-L-PG  EKKNGLFGNLIALSLGLTPNFKSNF-DLAED-A---KLQ--LSKDTYDDDLDN  277
WP_003030002   212  LTEK-VSKSRRLENLIAH-Y-PA  EKKNTLFGNLIALSLGLQPNFKTNF-QLSED-A---KLQ--FSKDTYEEDLEG  277
WP_003065552   215  LTEK-ISKSRRLENLIKY-Y-PT  EKKNTLFGNLIALALGLQPNFKMNF-KLSED-A---KLQ--FSKDSYEEDLGE  280
WP_001040076   213  LTDK-ISKSAKKDRILAQ-Y-PN  QKSTGIFAEFLKLIVGNQADFKKYF-NLEDK-T---PLQ--FAKDSYDEDLEN  278
WP_001040078   213  ISKSAKKDRILAQ-Y-PN       QKSTGIFAEFLKLIVGNQADFKKHF-NLEDK-T---PLQ--FAKDSYDEDLEN  278
WP_001040080   213  LTDK-ISKSAKKDRILAQ-Y-PN  QKSTGIFAEFLKLIVGNQADFKKHF-NLEDK-T---PLQ--FAKDSYDEDLEN  278
WP_001040081   213  LTDK-ISKSAKKDRILAQ-Y-PN  QKSTGIFAEFLKLIVGNQADFKKYF-NLEDK-T---PLQ--FAKDSYDEDLEN  278
WP_001040083   213  LTDK-ISKSAKKDRILAQ-Y-PN  QKSTGIFAEFLKLIVGNQADFKKYF-NLEDK-T---PLQ--FAKDSYDEDLEN  278
WP_001040085   213  LTDK-ISKSAKKDRILAQ-Y-PN  QKSTGIFAEFLKLIVGNQADFKKYF-NLEDK-T---PLQ--FAKDSYDEDLEN  278
WP_001040087   213  LTDK-ISKSAKKDRILAQ-Y-PN  QKSTGIFAEFLKLIVGNQADFKKYF-NLEDK-T---PLQ--FAKDSYDEDLEN  278
WP_001040088   213  LTDK-ISKSAKKDRILAQ-Y-PN  QKSTGIFAEFLKLIVGNQADFKKYF-NLEDK-T---PLQ--FAKDSYDEDLEN  278
WP_001040089   213  LTDK-ISKSAKKDRILAQ-Y-PN  QKSTGIFAEFLKLIVGNQADFKKYF-NLEDK-T---PLQ--FAKDSYDEDLEN  278
WP_001040090   213  LTDK-ISKSAKKDRILAQ-Y-PN  QKSTGIFAEFLKLIVGNQADFKKYF-NLEDK-T---PLQ--FAKDSYDEDLEN  278
WP_001040091   213  LTDK-ISKSAKKDRILAQ-Y-PN  QKSTGIFAEFLKLIVGNQADFKKYF-NLEDK-T---PLQ--FAKDSYDEDLEN  278
WP_001040092   213  LTDK-ISKSAKKDRILAQ-Y-PN  QKSTGIFAEFLKLIVGNQADFKKHF-NLEDK-T---PLQ--FAKDSYDEDLEN  278
WP_001040094   213  LTDK-ISKSAKKDRILAQ-Y-PN  QKSTGIFAEFLKLIVGNQADFKKHF-NLEDK-T---PLQ--FAKDSYDEDLEN  278
WP_001040095   213  LTDK-ISKSAKKDRILAR-Y-PN  QKSTGIFAEFLKLIVGNQADFKKHF-NLEDK-T---PLQ--FAKDSYDEDLEN  278
WP_001040096   213  LTDK-ISKSAKKDRILAR-Y-PN  QKSTGIFAEFLKLIVGNQADFKKHF-NLEDK-T---PLQ--FAKDSYDEDLEN  278
WP_001040097   213  LTDK-ISKSAKKDRILAR-Y-PN  QKSTGIFAEFLKLIVGNQADFKKHF-NLEDK-T---PLQ--FAKDSYDEDLEN  278
WP_001040098   213  LTDK-ISKSAKKDRILAR-Y-PN  QKSTGIFAEFLKLIVGNQADFKKHF-NLEDK-T---PLQ--FAKDSYDEDLEN  278
WP_001040099   213  LTDK-ISKSAKKDRILAR-Y-PN  QKSTGIFAEFLKLIVGNQADFKKHF-NLEDK-T---PLQ--FAKDSYDEDLEN  278
WP_001040100   213  LTDK-ISKSAKKDRILAR-Y-PN  QKSTGIFAEFLKLIVGNQADFKKHF-NLEDK-T---PLQ--FAKDSYDEDLEN  278
```

-continued

| | | | | | |
|---|---|---|---|---|---|
| WP_001040104 | 213 | LTDK-ISKSAKKDRILAQ-Y-PN | QKSTGIFAEFLKLIVGNQADFKKYF | -NLEDK-T---PLQ--FAKDSYDEDLEN | 278 |
| WP_001040105 | 213 | LTDK-ISKSAKKDRILAQ-Y-PN | QKSTGIFAEFLKLIVGNQADFKKKYF | -NLEDK-T---PLQ--FAKDSYDEDLEN | 278 |
| WP_001040106 | 213 | LTDK-ISKSAKKDRILAQ-Y-PN | QKSTGIFAEFLKLIVGNQADFKKKYF | -NLEDK-T---PLQ--FAKDSYDEDLEN | 278 |
| WP_001040107 | 213 | LTDK-ISKSAKKDRILAQ-Y-PN | QKSTGIFAEFLKLIVGNQADFKKHF | -NLEDK-T---PLQ--FAKDSYDEDLEN | 278 |
| WP_001040108 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_001040109 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_001040110 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_015058523 | 213 | LTDK-ISKSAKKDRILAQ-Y-PN | QKSTGIFAEFLKLIVGNQADFKKKYF | -NLEDK-T---PLQ--FAKDSYDEDLEN | 278 |
| WP_017643650 | 213 | LTDK-ISKSAKKDRILAR-Y-PN | QKSTGIFAEFLKLIVGNQADFKKKHF | -NLEDK-T---PLQ--FAKDSYDEDLEN | 278 |
| WP_017647151 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_017648376 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_017649527 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_017771611 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_017771984 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| CFQ25032 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| CFV16040 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| KLJ37842 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| KLJ72361 | 213 | LTDK-ISKSAKKDRILAQ-Y-PN | QKSTGIFAEFLKLIVGNQADFKKKYF | -NLEDK-T---PLQ--FAKDSYDEDLEN | 278 |
| KLL20707 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| KLL42645 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_047207273 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_047209694 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_050198062 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_050201642 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_050204027 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_050881965 | 213 | LTDK-ISKSAKKDRILAQ-Y-PN | QKSTGIFAEFLKLIVGNQADFKKKHF | -NLEDK-T---PLQ--FAKDSYDEDLEN | 278 |
| WP_050886065 | 213 | LTDK-ISKSAKKDRILAQ-Y-PN | QKSTGIFAEFLKLIVGNQADFKKKHF | -NLEDK-T---PLQ--FAKDSYDEDLEN | 278 |

```
AHN30376        213 LTDK-ISKSAKKDRILAQ-Y-PN QKSTGIFAEFLKLIVGNQADFKKHF-NLEDK-T---PLQ--FAKDSYDEDLEN 278
EAO78426        213 LTDK-ISKSAKKDRILAQ-Y-PN QKSTGIFAEFLKLIVGNQADFKKYF-NLEDK-T---PLQ--FAKDSYDEDLEN 278
CCW42055        213 LTDK-ISKSAKKDRILAQ-Y-PD QKSTGIFAEFLKLIVGNQADFKKHF-NLEDK-T---PLQ--FAKDSYDEDLEN 278
WP_003041502    212 LTEK-VSKSRRLENLIAH-Y-PA EKKNTLFGNLIALFLGLQPNFKTNF-QLSED-A---KLQ--FSKDTYEEDLEG 277
WP_037593752    213 LTEK-VSKSRRLENLIAH-Y-PT EKKNTLFGNLIALSLGLQPNFKTNF-QLSED-A---KLQ--FSKDTYEEDLEE 278
WP_049516684    213 LTEK-VSKSRRLENLVEC-Y-PT EKKNTLFGNLIALSLGLQPNFKTNF-QLSED-A---KLQ--FSKDTYEEDLEG 278
GAD46167        212 LTEK-VSKSRRLENLIAH-Y-PT EKKNTLFGNLIALSLGLQPNFKTNF-QLSED-A---KLQ--FSKDTYEEDLEE 277
WP_018363470    213 LTEK-ISKSRRLENLINN-Y-PK EKKNTLFGNLIALALGLQPNFKTNF-KLSED-A---KLQ--FSKDTYEEDLEE 278
WP_003043819    212 LSAR-LSKSKRLEKLIAV-F-PN EKKNGLFGNIIALALGLTPNFKSNF-DLTED-A---KLQ--LSKDTYDDDLDE 277
WP_006269658    212 LTEK-VSKSSRLENLIAH-Y-PT EKKNTLFGNLIALSLDLHPNFKTNF-QLSED-A---KLQ--FSKDTYEEDLEG 277
WP_048800889    212 LTEK-VSKSRRLENLVKC-Y-PT EKKNTLFGNLIALSLGLQPNFKTNF-QLSED-A---KLQ--FSKDTYEEDLEE 277
WP_012767106    212 LSAR-LSKSRRLENLIAQ-L-PG EKKNGLFGNLIALSLGLTPNFKSNF-DLAED-A---KLQ--LSKDTYDDDLDN 277
WP_014612333    212 LSAR-LSKSRRLENLIAQ-L-PG EKKNGLFGNLIALSLGLTPNFKSNF-DLAED-A---KLQ--LSKDTYDDDLDN 277
WP_015017095    212 LSAR-LSKSRRLENLIAQ-L-PG EKRNGLFGNLIALSLGLTPNFKSNF-DLAED-A---KLQ--LSKDTYDDDLDN 277
WP_015057649    212 LSAR-LSKSRRLENLIAQ-L-PG EKRNGLFGNLIALSLGLTPNFKSNF-DLAED-A---KLQ--LSKDTYDDDLDN 277
WP_048327215    212 LSAR-LSKSRRLENLIAQ-L-PG EKRNGLFGNLIALSLGLTPNFKMNF-DLAED-A---KLQ--LSKDTYDDDLDN 277
WP_049519324    212 LSAR-LSKSRRLENLIAQ-L-PG EKRNGLFGNLIALSLGLTPNFKSNF-DLAED-A---KLQ--LSKDTYDDDLDN 277
WP_012515931    212 LSAA-LSKSKRLENLISL-I-PG QKKTGIFGNIIALSLGLTPNFKANF-GLSKD-V---KLQ--LAKDTYADDLDS 277
WP_021320964    212 LSAA-LSKSKRLENLISL-I-PG QKKTGIFGNIIALSLGLTPNFKANF-GLSKD-V---KLQ--LAKDTYADDLDS 277
WP_037581760    212 LSAA-LSKSKRLENLISL-I-PG QKKTGIFGNIIALSLGLTPNFKANF-GLSKD-V---KLQ--LAKDTYADDLDS 277
WP_004232481    212 LTEK-ISKSRRLENLIKQ-Y-PT EKKNTLFGNLVALALGLQPNFKTNF-KLSED-A---KLQ--FSKDTYDEDLEE 277
WP_009854540    213 LTEK-ISKSRRLENLIKH-Y-PT EKKNTLFGNLIALALGLQPNFKTNF-KLSED-A---KLQ--FSKDTYEEDLEE 278
WP_012962174    213 LTEK-FSKSRRLENLIKH-Y-PT EKKNTLFGNLIALALGLQPNFKTSF-KLSED-A---KLQ--FSKDTYEEDLEE 278
WP_039695303    213 LTEK-ISKSRRLENLIKY-Y-PT EKKNTLFGNLVALALGLQPNFKTNF-KLSED-A---KLQ--FSKDTYEEDLEE 278
WP_014334983    212 LTEK-VSKSRRLENLIKQ-Y-PT EKKNTLFGNLIALALGLQPNFKTNF-ELLED-A---KLQ--FSKDTYEEDLEE 277
WP_003099269    212 LTSK-TSKSRRLENLIAE-I-PN QKRNMLFGNLVSLALGLTPNFKTNF-ELLED-A---KLQ--ISKDSYEEDLDN 277
AHY15608        212 LTSK-TSKSRRLENLIAE-I-PN QKRNMLFGNLVSLALGLTPNFKTNF-ELLED-A---KLQ--ISKDSYEEDLDN 277
```

| ID | | | | |
|---|---|---|---|---|
| AHY17476 | 212 | LTSK-TSKSRRLENLIAE-I-PN | QKRNMLFGNLVSLALGLTPNFKTNF--ELLED-A---KLQ--ISKDSYEEDLDN | 277 |
| ESR09100 | | | | |
| AGM98575 | 212 | LTSK-TSKSRRLENLIAE-I-PN | QKRNMLFGNLVSLALGLTPNFKTNF--ELLED-A---KLQ--ISKDSYEEDLDN | 277 |
| ALF27331 | 212 | LTDK-ISKSAKKDRVLKL-F-PN | EKSNGRFAEFLKLIVGNQADFKKHF--ELEEK-A---PLQ--FSKDTYEEELEV | 277 |
| WP_018372492 | 210 | FTEN-SSKAKRVETILGL-F-PD | ETAAGNLDKFLKLMLGNQADFKKHF--DLEEK----iTLQ--FSKDSYEEDLEL | 275 |
| WP_045618028 | 213 | FTDK-ISKSAKREVRVLKL-F-PD | EKSTGLFSEFLKLIVGNQADFKKHF--DLEEK-A---PLQ--FSKDTYDEDLEN | 278 |
| WP_045635197 | 212 | FTDK-ISKSAKREVRVLKL-F-PD | EKSTGLFSEFLKLIVGNQADFKKHF--DLEDK-A---PLQ--FSKDTYDEDLEN | 277 |
| WP_002263549 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002263887 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002264920 | 212 | LTEK-ISKSRRLEKLINN-Y-PK | EKKNTLFRNLVALSLGLQPNFKTNF--KLSED-A---KLQ--FSKDTYEEDLEE | 277 |
| WP_002269043 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002269448 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002271977 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002272766 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002273241 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002275430 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002276448 | 212 | LTEK-ISKSRRLEKLINN-Y-PK | EKKNTLFGNLIALSLGLQPNFKTNF--KLSED-A---KLQ--FSKDTYEEDLEE | 277 |
| WP_002277050 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002277364 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002279025 | 212 | LTEK-ISKSRRLEKLINN-Y-PK | EKKNTLFGNLIALSLGLQPNFKTNF--KLSED-A---KLQ--FSKDTYEEELEV | 277 |
| WP_002279859 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002280230 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002281696 | 212 | LTEK-ISKSRRLEKLINN-Y-PK | EKKNTLFGNLIALSLGLQPNFKTNF--KLSED-A---KLQ--FSKDTYEEELEV | 277 |
| WP_002282247 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002282906 | 212 | LTDK-ISKSAKKDRVLKL-F-PN | EKSNGRFAEFLKLIVGNQADFKKHF--ELEEK-A---PLQ--FSKDIYEEELEV | 277 |
| WP_002283846 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002287255 | 212 | LTDK-ISKSAKKDRVLKL-F-PN | EKSNGRFAEFLKLIVGNQADFKKHF--ELEEK-A---PLQ--FSKDTYEEELEV | 277 |

| | | | | |
|---|---|---|---|---|
| WP_002288990 | 212 | LTDK-ISKSAKKDRVLKL-F-PN | EKSNGRFAEFLKLIVGNQADFKKHF--ELEEK-A---PLQ--FSKDIYEEELEV | 277 |
| WP_002289641 | 212 | LTDK-ISKSAKKDRVLKL-F-PN | EKSNGCFAEFLKLIVGNQADFKKHF--ELEEK-A---PLQ--FSKDTYEEELEV | 277 |
| WP_002290427 | 212 | LTDK-ISKSAKKDRVLKL-F-PN | EKSNGRFAEFLKLIVGNQADFKKHF--ELEEK-A---PLQ--FSKDIYEEELEV | 277 |
| WP_002295753 | 212 | LTDK-ISKSAKKDRVLKL-F-PN | EKSNGRFAEFLKLIVGNQADFKKHF--ELEEK-A---PLQ--FSKDIYEEELEV | 277 |
| WP_002296423 | 212 | LTDK-ISKSAKKDRVLKL-F-PN | EKSNGRFAEFLKLIVGNQADFKKHF--ELEEK-A---PLQ--FSKDIYEEELEV | 277 |
| WP_002304487 | 212 | LTEK-VSKSRRLENLVEC-Y-PT | EKKNTLFGNLIALSLGLQPNFKTNF--QLSED-A---KLQ--FSKDTYEEDLEG | 277 |
| WP_002305844 | 212 | LTDK-ISKSAKKDRVLKL-F-PN | EKSNGRFAEFLKLIVGNQADFKKHF--ELEEK-A---PLQ--FSKDTYEEELEV | 277 |
| WP_002307203 | 212 | LTDK-ISKSAKKDRVLKL-F-PN | EKSNGRFAEFLKLIVGNQADFKKHF--ELEEK-A---PLQ--LSKDTYEEELEV | 277 |
| WP_002310390 | 212 | LTDK-ISKSAKKDRVLKL-F-PN | EKSNGRFAEFLKLIVGNQADFKKHF--ELEEK-A---PLQ--FSKDIYEEELEV | 277 |
| WP_002352408 | 212 | LTDK-ISKSAKKDRVLKL-F-PN | EKSNGRFAEFLKLIVGNQADFKKHF--ELEEK-A---PLQ--FSKDTYEEELEV | 277 |
| WP_012997688 | 212 | LTDK-ISKSAKKDRVLKL-F-PN | EKSNGRFAEFLKLIVGNQADFKKHF--ELEEK-A---PLQ--FSKDIYEEELEV | 277 |
| WP_014677909 | 212 | LTDK-ISKSAKKDRVLKL-F-PN | EKSNGRFAEFLKLIVGNQADFKKHF--ELEEK-A---PLQ--FSKDTYEEELEV | 277 |
| WP_019312892 | 212 | LTDK-ISKSAKKDRVLKL-F-PN | EKSNGRFAEFLKLIIGNQADFKKHF--ELEEK-A---PLQ--FSKDTYEEELEV | 277 |
| WP_019313659 | 212 | LTDK-ISKSAKKDRVLKL-F-PN | EKSNGRFAEFLKLIVGNQADFKKHF--ELEEK-A---PLQ--FSKDTYEEELEV | 277 |
| WP_019314093 | 212 | LTDK-ISKSAKKDRVLKL-F-PN | EKSNGRFAEFLKLIVGNQADFKKHF--ELEEK-A---PLQ--LSKDTYEEELEV | 277 |
| WP_019315370 | 212 | LTDK-ISKSAKKDRVLKL-F-PN | EKSNGRFAEFLKLIVGNQADFKKHF--ELEEK-V---PLQ--FSKDIYEEELEV | 277 |
| WP_019803776 | 212 | LTDK-ISKSAKKDRVLKL-F-PN | EKSNGRFAEFLKLIVGNQADFKKHF--ELEEK-A---PLQ--FSKDTYEEELEV | 277 |
| WP_019805234 | 212 | LTEK-ISKSRRLEKLINN-Y-PK | EKKNTLFGNLIALSLGLQPNFKTNF--KLSED-A---KLQ--FSKDTYEEDLEE | 277 |
| WP_024783594 | 212 | LTDK-ISKSAKKDRVLKL-F-PN | EKSNGRFAEFLKLIVGNQADFKKHF--ELEEK-A---PLQ--FSKDTYEEELEV | 277 |
| WP_024784288 | 212 | LTEK-ISKSRRLEKLINN-Y-PK | EKKNTLFGNLIALSLGLQPNFKTNF--KLSED-A---KLQ--FSKDTYEEDLEE | 277 |
| WP_024784666 | 212 | LTDK-ISKSAKKDRVLKL-F-PN | EKSNGRFAEFLKLIVGNQADFKKHF--ELEEK-A---PLQ--FSKDTYEEELEE | 277 |
| WP_024784894 | 212 | LTDK-ISKSAKKDRVLKL-F-PN | EKSNGRFAEFLKLIVGNQADFKKHF--ELEEK-A---PLQ--FSKDTYEEELEV | 277 |
| WP_024786433 | 212 | LTEK-ISKSRRLEKLINN-Y-PK | EKKNTLFGNLIALSLGLQPNFKTNF--KLSED-A---KLQ--FSKDTYEEDLEE | 277 |
| WP_049473442 | 212 | LTDK-ISKSAKKDRVLKL-F-PN | EKSNGRFAEFLKLIVGNQADFKKHF--ELEEK-A---PLQ--FSKDTYEEDLEE | 277 |
| WP_049474547 | 212 | LTDK-ISKSAKKDRVLKL-F-PN | EKSNGRFAEFLKLIVGNQADFKKHF--ELEEK-A---PLQ--FSKDTYEEELEV | 277 |
| EMC03581 | 205 | LTDK-ISKSAKKDRVLKL-F-PN | EKSNGRFAEFLKLIVGNQADFKKHF--DLEEK-A---PLQ--FSKDTYEEELEV | 270 |
| WP_000428612 | 213 | FTDK-ISKSAKRERVLKL-F-PD | EKSTGLFSEFLKLIVGNQADFKKHF--DLEEK-A---PLQ--FSRDTYDEDLEN | 278 |

| | | | | |
|---|---|---|---|---|
| WP_000428813 | 213 | FTDK-ISKSAKREREVLKL-F-PD | EKSTGLFSEFLKLIVGNQADFKKHF--DLGEK-A---PLQ--FSKDTYDEDLEN | 278 |
| WP_049523028 | 212 | FTDK-ISKSAKRDRVLKL-F-PD | EKSTGLFSEFLKLIVGNQADFKKHF--DLEEK-A---PLQ--FSKDTYEEDLES | 277 |
| WP_003107102 | 181 | LTEK-MSKSRRLENLIAK-I-PN | QKKNTLFGNLISLSLGLTPNFKANF--ELSED-A---KLQ--ISKESFEEDLDN | 246 |
| WP_054279288 | 214 | LTEK-ISKTRRLENLISN-I-PG | QKKNGLFGNLIALSLGLTPNFKSHF--NLPED-A---KLQ--LAKDTYDEELNN | 279 |
| WP_049531101 | 213 | FTDK-ISKSAKREREVLKL-F-PD | QKSTGLFSEFLKLIVGNQADFKKHF--DLEEK-A---PLQ--FSKDTYDEDLEN | 278 |
| WP_049538452 | 213 | FSDK-ISKSAKREREVLKL-F-PD | EKSTGLFSEFLKLIVGNQADFKKHF--DLEEK-A---PLQ--FSKDTYDEDLEN | 278 |
| WP_049549711 | 213 | FTDK-ISKSAKREREVLKL-F-PD | EKSTGLFSEFLKLIVGNQADFKKHF--DLGEK-A---PLQ--FSKDTYDEDLEN | 278 |
| WP_007896501 | 214 | LTAK-TSKSKRLESLISE-F-PG | QKKNGLFGNLLALALGLRPNEKSNF--GLSED-A---KLQ--ITKDTYEEELDN | 279 |
| EFR44625 | 166 | LTAK-TSKSKRLESLISE-F-PG | QKKNGLFGNLLALALGLRPNEKSNF--GLSED-A---KLQ--ITKDTYEEELDN | 231 |
| WP_002897477 | 212 | FTDK-ISKSAKREREVLKL-F-PD | EKSTGLFSEFLKLIVGNQADFKKHF--DLEEK-A---PLQ--FSKDTYDEELEN | 277 |
| WP_002906454 | 212 | FTDK-ISKSTKREREVLKL-F-SD | EKSTGLFSEFLKLIVGNQADFKKHF--DLEEK-A---PLQ--FSKDTYDEDLEN | 277 |
| WP_009729476 | 213 | FTDK-ISKSAKREREVLKL-F-PD | EKSTGLFSEFLKLIVGNQADFKKHF--DLEEK-A---PLQ--FSRDTYDEDLEN | 278 |
| CQR24647 | 212 | ITAK-ISKSRKVEAVLEQ-F-PD | QKNSFFGNMVSLVFGLMPNFKSNF--ELDED-A---KLQ--FSRDSYDEDLEN | 277 |
| WP_000066813 | 213 | FTDK-ISKSTKREREVLKL-F-PD | EKSTGLFSEFLKLIVGNQADFKKHF--DLEEK-A---PLQ--FSKDTYDEDLEN | 278 |
| WP_009754323 | 213 | FTGK-ISKSVKREHVLKL-F-PD | EKSTGLFSEFLKLIVGNQADFKKHF--DLEEK-A---SLQ--FSKDTYDEDLEN | 278 |
| WP_044674937 | 212 | LVEK-VSKSRRLENILHY-F-PN | EKKNGLFGNFLALALGLQPNFKTNF--ELAED-A---KIQ--FSKETYEEDLEE | 277 |
| WP_044676715 | 212 | LVEK-VSKSRRLENILHY-F-PN | EKKNGLFGNFLALALGLQPNFKTNF--ELAED-A---KIQ--FSKETYEEDLEE | 277 |
| WP_044680361 | 212 | LVEK-VSKSRRLENILHY-F-PN | EKKNGLFGNFLALALGLQPNFKTNF--ELAED-A---KIQ--FSKETYEEDLEE | 277 |
| WP_044681799 | 212 | LVEK-VSKSRRLENILHY-F-PN | EKKNGLFGNFLALALGLQPNFKTNF--ELAED-A---KIQ--FSKETYEEDLEE | 277 |
| WP_049533112 | 212 | LTEK-VSKSRRLENLIAH-Y-PA | EKKNTLFGNLIALSLGLQPNFKTNF--QLSED-A---KLQ--FSKDTYEEDLEG | 277 |
| WP_029090905 | 172 | LLDRmMNRSSKVKFLIEL---TG | KQDKPLLKELFNLIVGLKAKPASIFe--QENlAtiveTM-nMSTEQVQLDLLT | 243 |
| WP_006506696 | 211 | LKKP-LSKKAKVDEVMTL-IaPE | KDYKSAFKELVTGIAGNKMNVTKMIlcEPIKQ-Gds-EIKlkFSDSNYDDQFSE | 283 |
| AIT42264 | 212 | LSAR-LSKSRRLENLIAQ-L-PG | EKKNGLFGNLIALSLGLTPNFKSNF--DLAED-A---KLQ--LSKDTYDDDLDN | 277 |
| WP_034440723 | 218 | FKQD-ISRSKKLDQAIAL-F-QG | -KRQSLFGIFLTLIVGNKANFQKIF--NLEDD----iKlD--LKEEDYDENLEE | 283 |
| AKQ21048 | 212 | LSAR-LSKSRRLENLIAQ-L-PG | EKKNGLFGNLIALSLGLTPNFKSNF--DLAED-A---KLQ--LSKDTYDDDLDN | 277 |
| WP_004636532 | 211 | LSSK-QSRSRKHEQIMAL-F-PN | ENKLGNFGRFMMLIVGNTSNFKPVF--DLDDE-Y---KLK--LSDETYEEDLDT | 276 |
| WP_002364836 | 218 | LTEK-ASRTKKSEKVLQQ-F-PQ | EKANGLFGQFLKLMVGNKIADFKKVF--GLEEE-A---KI--tYASESYEEDLEG | 283 |

-continued

```
WP_016631044   169  LTEK-ASRTKKSEKVLQQ-F-PQ  EKANGLFGQFLKLMVGNKADFKKVF  -GLEEE-A---KI--tYASESYEEDLEG        234
EMS75795         1  ---------------------------  -------------------------  --MDEE-A---KIQ--LSKESYEEELES         20
WP_002373311   218  LTEK-ASRTKKSEKVLQQ-F-PQ  EKANGLFGQFLKLMVGNKADFKKVF  -GLEEE-A---KI--tYASESYEEDLEG        283
WP_002378009   218  LTEK-ASRTKKSEKVLQQ-F-PQ  EKANGLFGQFLKLMVGNKADFKKVF  -GLEEE-A---KI--tYASESYEEDLEG        283
WP_002407324   218  LTEK-ASRTKKSEKVLQQ-F-PQ  EKANGLFGQFLKLMVGNKADFKKVF  -GLEEE-A---KI--tYASESYEEDLEG        283
WP_002413717   218  LTEK-ASRTKKSEKVLQQ-F-PQ  EKANGLFGQFLKLMVGNKADFKKVF  -GLEEE-A---KI--tYASESYEEDLEG        283
WP_010775580   218  LTEK-ASRTKKSEKVLQQ-F-PQ  EKANGLFGQFLKLMVGNKADFKKVF  -GLEEE-A---KIKitYASESYEEDLEG        285
WP_010818269   218  LTEK-ASRTKKSEKVLQQ-F-PQ  EKANGLFGQFLKLMVGNKADFKKVF  -GLEEE-A---KI--tYASESYEEDLEG        283
WP_010824395   218  LTEK-ASRTKKSEKVLQQ-F-PQ  EKANGLFGQFLKLMVGNKADFKKVF  -GLEEE-A---KI--tYASESYEEDLEG        283
WP_016622645   218  LTEK-ASRTKKSEKVLQQ-F-PQ  EKANGLFGQFLKLMVGNKADFKKVF  -GLEEE-A---KI--tYASESYEEDLEG        283
WP_033624816   218  LTEK-ASRTKKSEKVLQQ-F-PQ  EKANGLFGQFLKLMVGNKADFKKVF  -GLEEE-A---KI--tYASESYEEDLEG        283
WP_033625576   218  LTEK-ASRTKKSEKVLQQ-F-PQ  EKANGLFGQFLKLMVGNKADFKKVF  -GLEEE-A---KI--tYASESYEEDLEG        283
WP_033789179   218  LTEK-ASRTKKSEKVLQQ-F-PQ  EKANGLFGQFLKLMVGNKADFKKVF  -GLEEE-A---KI--tYASESYEEDLEG        283
WP_002310644   217  FTEK-MSKITKKAETLLKY-F-PH  EKSNGYLSQFIKLMVGNQGNFKNVF  -GL-EE-A---KLQ--FSKETYEEDLEE        281
WP_002312694   217  FTEK-MSKITKKAETLLKY-F-PH  EKSNGYLSQFIKLMVGNQGNFKNVF  -GL-EEeA---KLQ--FSKETYEEDLEE        282
WP_002314015   217  FTEK-MSKITKKAETLLKY-F-PH  EKSNGYLSQFIKLMVGNQGNFKNVF  -GL-EEeA---KLQ--FSKETYEEDLEE        282
WP_002320716   217  FTEK-MSKITKKAETLLKY-F-PH  EKSNGYLSQFIKLMVGNQGNFKNVF  -GL-EEeA---KLQ--FSKETYEEDLEE        282
WP_002330729   217  FTEK-MSKITKKAETLLKY-F-PH  EKSNGYLSQFIKLMVGNQGNFKNVF  -GL-EE-A---KLQ--FSKETYEEDLEE        281
WP_002335161   217  FTEK-MSKITKKAETLLKY-F-PH  EKSNGYLSQFIKLMVGNQGNFKNVF  -GL-EEeA---KLQ--FSKETYEEDLEE        282
WP_002345439   217  FTEK-MSKITKKAETLLKY-F-PH  EKSNGYLSQFIKLMVGNQGNFKNVF  -GL-EEeA---KLQ--FSKETYEEDLEE        282
WP_034867970   210  LTDK-LSKTKKVEEILKY-Y-PT  EKINSFFAQCLKLIVGNQANFKRIF  -DLEAE-V---KLQ--FSKETYEEDLES        275
WP_047937432   217  FTEK-MSKITKKAETLLKY-F-PH  EKSNGYLSQFIKLMVGNQGNFKNVF  -GL-EEeA---KLQ--FSKETYEEDLEE        282
WP_010720994   210  LTDK-LSKTKKVEEILKY-Y-PT  EKINSFFAQCLKLIVGNQANFKRIF  -DLEAE-V---KLQ--FSKETYEEDLES        275
WP_010737004   210  LTDK-LSKTKKVEEILKY-Y-PT  EKINSFFAQCLKLIVGNQANFKRIF  -DLEAE-V---KLQ--FSKETYEEDLES        275
WP_034700478   210  LTDK-LSKTKKVEEILKY-Y-PT  EKINSFFAQCLKLIVGNQANFKRIF  -DLEAE-V---KLQ--FSKETYEEDLES        275
WP_007209003   215  LTQQ-LSKSBRADNVLKL-F-PD  EKGTGIFAQFIKLIVGNQGNFKKVF  -QLEED----qKLQ--LSTDDYEENIEN        280
WP_023519017   210  LTER-LSKAKRVEKVLAY-Y-PS  EKSTGNFAQFLKLMVGNQANFKKTF  -DLEEE-M---KLN--FTRDCYEEDLNE        275
```

-continued

| ID | | | | |
|---|---|---|---|---|
| WP_010770040 | 213 | FSEK-VSRARKVEAILSV-Y-SE | EKSTGTLAQFLKLMVGNQGRFKKTF-DLEED-G---IIQ--IPKEEYEEELET | 278 |
| WP_048604708 | 209 | FADK-VSRAKKAEGVLAL-F-PD | EKRNGTEDQFLKMIVGNQNFKKTF--ELEED-A---KLQ--FSKEEYDESLEA | 274 |
| WP_010750235 | 210 | LTDK-LSKSKKVEKILQY-Y-PK | EKTGCLAQFLKLIVGNQNFKQAF--HLDEE-V---KIQ--ISKETYEEDLEK | 275 |
| AII16583 | 251 | LSAR-LSKSRRLENLIAQ-L-PG | EKKNGLFGNLIALSLGLTPNFKSNF--DLAED-A---KLQ--LSKDTYDDDLDN | 316 |
| WP_029073316 | 216 | LKEP-LSKKHKADKAFAL-FdTT | KDNKAAYKELCAALAGNKFNVTKMLkeAELHD-EdekDIsfkFSDATFDDAFVE | 289 |
| WP_031589969 | 216 | LKEP-LSKKHKAEKAFAL-FdTT | KDNKAAYKELCAALAGNKFNVTKMLkeAELHD-EdekDIsfkFSDATFDDAFVE | 289 |
| KDA45870 | 210 | FKDNtFSKTKKSEELLKL---SG | -KKNQLAHQLFKMVGNMGSFKKVL--GTDEE----hKlS--FGKDTYEDDLND | 275 |
| WP_039099354 | 207 | LLDNhQSASNRQRQALLLiYtPS | KQNKAIATELLKAILGLKAKFNVLT--GIEAEdGVktwTLT--FNAENFDEEMVK | 285 |
| AKP02966 | 209 | LIGR-GNATQKSSNILNN-F--T | KETKKLLKEVINLILGNVAHLNTIFktsLTKDeE---KLS--FSGKDIESKLDD | 278 |
| WP_010991369 | 218 | LVEK-VTRKEKLERILKL-Y-PG | EKSAGMFAQFISLIVGSKGNFQKPF--DLIEK-S---DIE--CAKDSYEEDLES | 283 |
| WP_033838504 | 218 | LVEK-VTRKEKLERILKL-Y-PG | EKSAGMFAQFISLIVGSKGNFQKPF--DLIEK-S---DIE--CAKDSYEEDLES | 283 |
| EHN60060 | 221 | LVEK-VTRKEKLERILKL-Y-PG | EKSAGMFAQFISLIVGSKGNFQKPF--DLIEK-S---DIE--CAKDSYEEDLES | 286 |
| EFR89594 | 1 | ----------LKL-Y-PG | EKSTGMFAQFISLIVGSKGNFQKVF--DLIEK-S---DIE--CAKDSYEEDLES | 52 |
| WP_038409211 | 218 | LSEK-LTRREKLDKILKL-Y-TG | EKSTGMFARFINLIIGSKGDFKKVF--DLDEK-A---EIE--CAKDTYEEDLEA | 283 |
| EFR95520 | | | -------------------------------------- | |
| WP_003723650 | 218 | LAGK-FTRREKFERILQL-Y-PG | EKSTGMFAQFISLIVGSKGNFQKVF--DLIEK-T---DIE--CAKDSYEEDLET | 283 |
| WP_003727705 | 218 | LAGK-FTRREKFERILRL-Y-PG | EKSTGMFAQFISLIVGNKGNFQKVF--NLVEK-T---DIE--CAKDSYEEDLEA | 283 |
| WP_003730785 | 218 | LAGK-FTRREKFERILRL-Y-PG | EKSTGMFAQFISLIVGNKGNFQKVF--NLVEK-T---DIE--CAKDSYEEDLEA | 283 |
| WP_003733029 | 218 | LAEK-FTRKDKLDKILSL-Y-PG | EKTTGVFAQFVNIIVGSTGKFKKHF--NLHEK-K---DIN--CAEDTYDTDLES | 283 |
| WP_003739838 | 218 | LAGK-FTRKEKLERILQL-Y-PG | EKSTGMFAQFISLIVGSKGNFQKVF--DLVEK-T---DIE--CAKDSYEEDLEA | 283 |
| WP_014601172 | 218 | LAGK-FTRREKFERILQL-Y-PG | EKSTGMFAQFISLIVGSKGNFQKVF--DLIEK-T---DIE--CAKDSYEEDLEA | 283 |
| WP_023548323 | 218 | LAGK-FTRREKFERILQL-Y-PG | EKSTGMFAQFISLIVGSKGNFQKVF--DLIEK-T---DIE--CAKDSYEEDLEA | 283 |
| WP_031665337 | 218 | LAEK-FTRKDKLDKILSL-Y-PG | EKTTGVFAQFVNIIVGSTGKFKKHF--NLHEK-K---DIN--CAEDTYDTDLES | 283 |
| WP_031669209 | 218 | LAGK-FTRREKFERILQL-Y-PG | EKSTGMFAQFISLIVGSKGNFQKVF--DLIEK-T---DIE--CAKDSYEEDLET | 283 |
| WP_033920898 | 218 | LARK-FTRREKFERILQL-Y-PG | EKSTGMFAQFISLIVGSKGNFQKVF--DLIEK-T---DIE--CAKDSYEEDLEA | 283 |
| AKI42028 | 221 | LAGK-FTRREKFERILQL-Y-PG | EKSTGMFAQFISLIVGSKGNFQKVF--DLIEK-T---DIE--CAKDSYEEDLEA | 286 |
| AKI50529 | 221 | LARK-FTRREKFERILQL-Y-PG | EKSTGMFAQFISLIVGSKGNFQKVF--DLIEK-T---DIE--CAKDSYEEDLET | 286 |

```
EFR83390      218 FSEK-LTKRKLDKILNL-Y-PN ---------------------- EKSTDLFAQFISLLIGSKNFKKFF--NLTEK-T---DIE--CAKDSYEEDLEV       283
WP_046323366  228 LSAR-LSKSRRLENLIAQ-L-PG ---------------------- EKKNGLFGNLIALSLGLTPNFKSNF--DLAED-A---KLQ--LSKDTYDDDLDN       293
AKE81011      215 LKKP-LSKKAKVDEVMAL-IsPE ---------------------- KEEKSAYKELVTGIAGNKMNVTKMIlcESIKQ-Gds-EIKIkFSDSNYDDQFSE       287
CU082355      216 LSKI-YQRSKKADDLLKI-MnPT ---------------------- KEEKAAYKEFTKALVGLKENISKMIlaQEVKK-Gdt-DIVleFSNANYDSTIDE       288
WP_033162887  245 LSAR-LSKSRRLENLIAQ-L-PG ---------------------- EKKNGLFGNLIALSLGLTPNFKSNF--DLAED-A---KLQ--LSKDTYDDDLDN       310
AGZ01981      212 LSAR-LSKSRRLENLIAQ-L-PG ---------------------- EKKNGLFGNLIALSLGLTPNFKSNF--DLAED-A---KLQ--LSKDTYDDDLDN       277
AKA60242      212 LSAR-LSKSRRLENLIAQ-L-PG ---------------------- EKKNGLFGNLIALSLGLTPNFKSNF--DLAED-A---KLQ--LSKDTYDDDLDN       277
AKS40380      216 LSAR-LSKSRRLENLIAQ-L-PG ---------------------- EKKNGLFGNLIALSLGLTPNFKSNF--DLAED-A---KLQ--LSKDTYDDDLDN       281
4UN5_B        278 LLAQIGDQYADLFLAAKNLFLAAKNLSDAILLSDILRVNTEITKAPLSASMIKRYDEHHQDLTLLKALVRQQ-LPEKYKEIFFDQSK                       356
WP_010922251  279 LLGKIGDDYADLFTSAKNLYDAILLSGILTVDDNSTKAPLSASMIKRYVEHHEDLEKLKEFIKAN-KSELYHDIFKDKNK                             357
WP_039695303  278 LLGQIGDDFTDLFVSAKKLYDAILLSGILTVTDPSTKAPLSASMIERYENHQNDLAALKQFIKNN-LPEKYDEVFSDQSK                             356
WP_045635197  158 ---------------------- ---------------------- ------LERLKDG-------EVR--------                              168
5AXW_A          1 ---------------------- ---------------------- ------------------------------                                40
WP_009880683  278 LLAQIGDQYADLFLAAKNLFLAAKNLSDAILLSDILRVNSEITKAPLSASMIKRYDEHHQDLTLLKALVRQQ-LPEKYKEIFFDQSK                       356
WP_010922251  278 LLAQIGDQYADLFLAAKNLFLAAKNLSDATLLSDILRVNSEITKAPLSASMIKRYDEHHQDLTLLKALVRQQ-LPEKYKEIFFDQSK                       356
WP_011054416  278 LLAQIGDQYADLFLAAKNLFLAAKNLSDAILLSDILRLNSEITKAPLSASMIKRYDEHHQDLTLLKALVRQQ-LPEKYKEIFFDQSK                       356
WP_011284745  278 LLAQIGDQYADLFLAAKNLFLAAKNLSDAILLSDILRLNSEITKAPLSASMIKRYDEHHQDLTLLKALVRQQ-LPEKYKEIFFDQSK                       356
WP_011285506  278 LLAQIGDQYADLFLAAKNLFLAAKNLSDAILLSDILRVNTEITKAPLSASMIKRYDEHHQDLTLLKALVRQQ-LPEKYKEIFFDQSK                       356
WP_011527619  278 LLAQIGDQYADLFLAAKNLFLAAKNLSDAILLSDILRVNSEITKAPLSASMIKRYDEHHQDLTLLKALVRQQ-LPEKYKEIFFDQSK                       356
WP_012560673  278 LLAQIGDQYADLFLAAKNLFLAAKNLSDAILLSDILRVNSEITKAPLSASMIKRYDEHHQDLTLLKALVRQQ-LPEKYKEIFFDQSK                       356
WP_014407541  278 LLAQIGDQYADLFLAAKNLFLAAKNLSDAILLSDILRVNSEITKAPLSASMIKRYDEHHQDLTLLKALVRQQ-LPEKYKEIFFDQSK                       356
WP_020905136  278 LLAQIGDQYADLFLAAKNLFLAAKNLSDAILLSDILRVNSEITKAPLSASMIKRYDEHHQDLTLLKALVRQQ-LPEKYKEIFFDQSK                       356
WP_023080005  278 LLAQIGDQYADLFLAAKNLFLAAKNLSDAILLSDILRVNSEITKAPLSASMIKRYDEHHQDLTLLKALVRQQ-LPEKYKEIFFDQSK                       356
WP_023610282  278 LLAQIGDQYADLFLAAKNLFLAAKNLSDAILLSDILRVNSEITKASLSASMIKRYDEHHQDLTLLKALVRQQ-LPEKYKEIFFDQSK                       356
WP_030125963  278 LLAQIGDQYADLFLAAKNLFLAAKNLSDATLLSDILRVNSEITKAPLSASMIKRYDEHHQDLTLLKALVRQQ-LPEKYKEIFFDQSK                       356
WP_030126706  278 LLAQIGDQYADLFLAAKNLFLAAKNLSDAILLSDILRVNSEITKAPLSASMIKRYDEHHQDLTLLKALVRQQ-LPEKYKEIFFDQSK                       356
WP_031488318  278 LLAQIGDQYADLFLAAKNLFLAAKNLSDAILLSDILRVNSEITKAPLSASMIKRYDEHHQDLTLLKALVRQQ-LPEKYKEIFFDQSK                       356
```

| | | | -continued | |
|---|---|---|---|---|
| WP_032460140 | 278 | LLAQIGDQYADLFLAAKNLSDAILLSDIIRVNTEITKAPLSASMIKRYDEHHQDLTLLKALVRQQ-LPEKYKEIFFDQSK | 356 |
| WP_032461047 | 278 | LLAQIGDQYADLFLAAKNLSDAILLSDIIRVNTEITKAPLSASMIKRYDEHHQDLTLLKALVRQQ-LPEKYKEIFFDQSK | 356 |
| WP_032462016 | 278 | LLAQIGDQYADLFLAAKNLSDAILLSDIIRVNTEITKAPLSASMIKRYDEHHQDLTLLKALVRQQ-LPEKYKEIFFDQSK | 356 |
| WP_032462936 | 278 | LLAQIGDQYADLFLAAKNLSDAILLSDIIRVNSEITKAPLSASMIKRYDEHHQDLTLLKALVRQQ-LPEKYKEIFFDQSK | 356 |
| WP_032464890 | 278 | LLAQIGDQYADLFLAAKNLSDAILLSDIIRVNSEITKAPLSASMIKRYDEHHQDLTLLKALVRQQ-LPEKYKEIFFDQSK | 356 |
| WP_033888930 | 103 | LLAQIGDQYADLFLAAKNLSDAILLSDIIRLNSEITKAPLSASMIKRYDEHHQDLTLLKALVRQQ-LPEKYKEIFFDQSK | 181 |
| WP_038431314 | 278 | LLAQIGDQYADLFLAAKNLSDAILLSDIIRVNSEITKAPLSASMIKRYDEHHQDLTLLKALVRQQ-LPEKYKEIFFDQSK | 356 |
| WP_038432938 | 278 | LLAQIGDQYADLFLAAKNLSDATLLSDIIRVNSEITKAPLSASMIKRYDEHHQDLTLLKALVRQQ-LPEKYKEIFFDQSK | 356 |
| WP_038434062 | 278 | LLAQIGDQYADLFLAAKNLSDAILLSDIIRVNSEITKAPLSASMIKRYDEHHQDLTLLKALVRQQ-LPEKYKEIFFDQSK | 356 |
| BAQ51233 | 189 | LLAQIGDQYADLFLAAKNLSDAILLSDIIRVNTEITKAPLSASMIKRYDEHHQDLTLLKALVRQQ-LPEKYKEIFFDQSK | 267 |
| KGE60162 | | ---------------------------------------------------------------- | |
| KGE60856 | | ---------------------------------------------------------------- | |
| WP_002989955 | 278 | LLAQIGDQYADLFLAAKNLSDAILLSDIIRLNSEITKAPLSASMIKRYDEHHQDLTLLKALVRQQ-LPEKYKEIFFDQSK | 356 |
| WP_003030002 | 278 | LLGEIGDEYADLFSAKNLYDAILLSGIILTVDDNSTKAPLSASMVKRYEHQKDLKKLKDFIKVN-APDQYNAIFKDKNK | 356 |
| WP_003065552 | 281 | LLGKIGDDYADLFTSAKNLYDAILLSGIILVDDNSTKAPLSASMIKRYVEHQEDLEKLKEFIKAN-KSELYHDIFKDKNIK | 359 |
| WP_001040076 | 279 | LLGQIGDEFADLFSAAKKLYDSVLLSGIILTVTDLSTKAPLSASMIQRYDEHREDLKQLKQFVKAS-LPEKYQEIVADSSK | 357 |
| WP_001040078 | 279 | LLGQIGDEFADLFSAAKKLYDSVLLSGIILTVIDLSTKAPLSASMIQRYDEHREDLKQLKQFVKAS-LPEKYQEIFADSSK | 357 |
| WP_001040080 | 279 | LLGQIGDEFADLFSAAKKLYDSVLLSGIILTVIDLSTKAPLSASMIQRYDEHREDLKQLKQFVKAS-LPEKYQEIFADSSK | 357 |
| WP_001040081 | 279 | LLGQIGDEFADLFSAAKKLYDSVLLSGIILTVIDLSTKAPLSASMIQRYDEHREDLKQLKQFVKAS-LPEKYQEIFADSSK | 357 |
| WP_001040083 | 279 | LLGQIGDEFADLFSAAKKLYDSVLLSGIILTVIDLSTKAPLSASMIQRYDEHREDLKQLKQFVKAS-LPEKYQEIFADSSK | 357 |
| WP_001040085 | 279 | LLGQIGDEFADLFSAAKKLYDSVLLSGIILTVIDLSTKAPLSASMIQRYDEHREDLKQLKQFVKAS-LPEKYQEIFADSSK | 357 |
| WP_001040087 | 279 | LLGQIGDEFADLFSAAKKLYDSVLLSGIILTVIDLSTKAPLSASMIQRYDEHREDLKQLKQFVKAS-LPEKYQEIFADSSK | 357 |
| WP_001040088 | 279 | LLGQIGDEFADLFSAAKKLYDSVLLSGIILTVIDLSTKAPLSASMIQRYDEHREDLKQLKQFVKAS-LPEKYQEIFADSSK | 357 |
| WP_001040089 | 279 | LLGQIGDEFADLFSAAKKLYDSVLLSGIILTVIDLSTKAPLSASMIQRYDEHREDLKQLKQFVKAS-LPEKYQEIFADSSK | 357 |
| WP_001040090 | 279 | LLGQIGDEFADLFSAAKKLYDSVLLSGIILTVIDLSTKAPLSASMIQRYDEHREDLKQLKQFVKAS-LPEKYQEIFADSSK | 357 |
| WP_001040091 | 279 | LLRQIGDEFADLFSAAKKLYDSVLLSGIILTVIDLSTKAPLSAYMIQRYDEHREDLKQLKQFVKAS-LPEKYQEIFADSSK | 357 |
| WP_001040092 | 279 | LLGQIGDEFADLFSAAKKLYDSVLLSGIILTVTDLSTKAPLSASMIQRYDEHREDLKQLKQFVKAS-LPEKYQEIFADSSK | 357 |

| ID | Start | Sequence | End |
|---|---|---|---|
| WP_001040094 | 279 | LLGQIGDEFADLFSAAKKLYDSVLLSGIILTVTDLSTKAPLSASMIQHYDEHREDLKQLKQFVKAS-LPEKYQEIFADSSK | 357 |
| WP_001040095 | 279 | LLGQIGDEFADLFSAAKKLYDSVLLSGIILTVTDLSTKAPLSASMIQRYDEHREDLKQLKQFVKAS-LPEKYQEIFADSSK | 357 |
| WP_001040096 | 279 | LLGQIGDEFADLFSAAKKLYDSVLLSGIILTVTDLSTKAPLSASMIQRYDEHREDLKQLKQFVKAS-LPEKYQEIFADSSK | 357 |
| WP_001040097 | 279 | LLGQIGDEFADLFSAAKKLYDSVLLSGIILTVTDLSTKAPLSASMIQRYDEHREDLKQLKQFVKAS-LPEKYQEIFADSSK | 357 |
| WP_001040098 | 279 | LLGQIGDEFADLFSAAKKLYDSVLLSGIILTVTDLSTKAPLSASMIQRYDEHREDLKQLKQFVKAS-LPEKYQEIFADSSK | 357 |
| WP_001040099 | 279 | LLGQIGDEFADLFSAAKKLYDSVLLSGIILTVTDLSTKAPLSASMIQRYDEHREDLKQLKQFVKAS-LPEKYQEIFADSSK | 357 |
| WP_001040100 | 279 | LLGQIGDEFADLFSAAKKLYDSVLLSGIILTVTDLSTKAPLSASMIQRYDEHREDLKQLKQFVKAS-LPEKYQEIFADSSK | 357 |
| WP_001040104 | 279 | LLGQIGDEFADLFSAAKKLYDSVLLSGIILTVIDLSTKAPLSASMIQRYDEHREDLKQLKQFVKAS-LPEKYQEIFADSSK | 357 |
| WP_001040105 | 279 | LLGQIGDEFADLFSAAKKLYDSVLLSGIILTVIDLSTKAPLSASMIQRYDEHREDLKQLKQFVKAS-LPEKYQEIFTDSSK | 357 |
| WP_001040106 | 279 | LLGQIGDEFADLFSVAKKLYDSVLLSGIILTVTDLSTKAPLSASMIQRYDEHREDLKQLKQFVKAS-LPEKYQEIFTDSSK | 357 |
| WP_001040107 | 279 | LLGQIGDEFADLFSAAKKLYDSVLLSGIILTVTDLSTKAPLSASMIQRYDEHREDLKQLKQFVKAS-LPEKYQEIFTDSSK | 357 |
| WP_001040108 | 279 | LLGQIGDEFADLFSVAKKLYDSVLLSGIILTVTDLSTKAPLSASMIQRYDEHREDLKQLKQFVKAS-LPEKYQEIFADSSK | 357 |
| WP_001040109 | 279 | LLGQIGDEFADLFSVAKKLYDSVLLSGIILTVIDLSTKAPLSASMIQRYDEHREDLKQLKQFVKAS-LPEKYQEIFTDSSK | 357 |
| WP_001040110 | 279 | LLGQIGDEFADLFSVAKKLYDSVLLSGIILTVIDLSTKAPLSASMIQRYDEHREDLKQLKQFVKAS-LPEKYQEIFTDSSK | 357 |
| WP_015058523 | 279 | LLGQIGDEFADLFSAAKKLYDSVLLSGIILTVTDLSTKAPLSASMIQRYDEHREDLKQLKQFVKAS-LPEKYQEIFADSSK | 357 |
| WP_017643650 | 279 | LLGQIGDEFADLFSAAKKLYDSVLLSGIILTVTDLSTKAPLSASMIQRYDEHREDLKQLKQFVKAS-LPEKYQEIFTDSSK | 357 |
| WP_017647151 | 279 | LLGQIGDEFADLFSVAKKLYDSVLLSGIILTVTDLSTKAPLSASMIQRYDEHREDLKQLKQFVKAS-LPEKYQEIFTDSSK | 357 |
| WP_017648376 | 279 | LLGQIGDEFADLFSVAKKLYDSVLLSGIILTVTDLSTKAPLSASMIQRYDEHREDLKQLKQFVKAS-LPEKYQEIFADSSK | 357 |
| WP_017649527 | 279 | LLGQIGDEFADLFSVAKKLYDSVLLSGIILTVTALSASMIQRYDEHREDLKQLKQFVKAS-LPEKYQEIFADSSK | 357 |
| WP_017771611 | 279 | LLGQIGDEFADLFSAAKKLYDSVLLSGIILTVIDLSTKASLSDSMIQRYDEHREDLKQLKQFVKAS-LPEKYQEIFADSSK | 357 |
| WP_017771984 | 279 | LLGQIGDEFADLFSVAKKLYDSVLLSGIILTVIDLSTKAPLSASMIQRYDEHREDLKQLKQFVKAS-LPEKYQEIFADSSK | 357 |
| CFQ25032 | 279 | LLGQIGDEFADLFSAAKKLYDSVLLSGIILTVTDLSTKAPLSASMIQRYDEHREDLKQLKQFVKAS-LPEKYQEIFADSSK | 357 |
| CFV16040 | 279 | LLGQIGDEFADLFSVAKKLYDSVLLSGIILTVTDLSTKAPLSASMIQRYDEHREDLKQLKQFVKAS-LPEKYQEIFADSSK | 357 |
| KLJ37842 | 279 | LLGQIGDEFADLFSAAKKLYDSVLLSGIILTVTDLSTKAPLSASMIQRYDEHREDLKQLKQFVKAS-LPEKYQEIFADSSK | 357 |
| KLJ72361 | 279 | LLGQIGDEFADLFSVAKKLYDSVLLSGIILTVTDLSTKAPLSASMIQRYDEHREDLKQLKQFVKAS-LPEKYQEIFADSSK | 357 |
| KLL20707 | 279 | LLGQIGDEFADLFSAAKKLYDSVLLSGIILTVTDLSTKAPLSASMIQRYDEHREDLKQLKQFVKAS-LPEKYQEIFADSSK | 357 |
| KLL42645 | 279 | LLGQIGDEFADLFSVAKKLYDSVLLSGIILTVTDLSTKAPLSASMIQRYDEHREDLKQLKQFVKAS-LPEKYQEIFTDSSK | 357 |

```
                                                    -continued
WP_047202273   279  LLGQIGDEFADLFSAAKKLYDSVLLSGIILTVIDLSTKAPLSASMIQRYDEHREDLKQLKQFVKAS-LPEKYQEIFADSSK  357
WP_047209694   279  LLGQIGDEFADLFSAAKKLYDSVLLSGIILTVIDLSTKAPLSASMIQRYDEHREDLKQLKQFVKAS-LPEKYQEIFADSSK  357
WP_050198062   279  LLGQIGDEFADLFSAAKKLYDSVLLSGIILTVTDLSTKAPLSASMIQRYDEHREDLKQLKQFVKAS-LPEKYQEIFADSSK  357
WP_050201642   279  LLGQIGDEFADLFSAAKKLYDSVLLSGIILTVIDLSTKAPLSASMIQRYDEHREDLKQLKQFVKAS-LPEKYQEIFADSSK  357
WP_050204027   279  LLGQIGDEFADLFSAAKKLYDSVLLSGIILTVIDLSTKAPLSASMIQRYDEHREDLKQLKQFVKAS-LPEKYQEIFTDSSK  357
WP_050881965   279  LLGQIGDEFADLFSVAKKLYDSVLLSGIILTVIDLSTKAPLSASMIQRYDEHREDLKQLKQFVKAS-LPEKYQEIFADSSK  357
WP_050886065   279  LLGQIGDEFADLFSAAKKLYDSVLLSGIILTVIDLSTKAPLSASMIQRYDEHREDLKQLKQFVKAS-LPEKYQEIFADSSK  357
AHN30376       279  LLGQIGDEFADLFSAAKKLYDSVLLSGIILTVIDLSTKAPLSASMIQRYDEHREDLKQLKQFVKAS-LPEKYQEIFADSSK  357
EAO78426       279  LLGQIGDEFADLFSAAKKLYDSVLLSGIILTVTDLSTKAPLSASMIQRYDEHREDLKQLKQFVKAS-LPEKYQEIFADSSK  357
CCW42055       279  LLGQIGDEFADLFSAAKKLYDSVLLSGIILTVTDLSTKAPLSASMIQRYDEHREDLKQLKQFVKAS-LPEKYQEIFADSSK  357
WP_003041502   278  LLGEVGDEYADLFASAKNLYDAILLSGIILTVDDNSTKAPLSASMVKRYEEHQKDLKKFEDFIKVN-ALDQYNAIFKDKNK  356
WP_037593752   279  LLGEIGDEYADLFASAKNLYDAILLSGIILAVDDNTTKAPLSASMVKRYEEHQKDLKKLKDFIKVN-APDQYNAIFKDKNK  357
WP_049516684   279  LLGEIGDEYADLFASAKNLYDAILLSGIILAVDDNSTKAPLSASMVKRYEEHQKDLKKLKDFIKVN-APAQYDDIFKDETK  357
GAD46167       278  LLGEIGDEYADLFASAKNLYDAILLSGIILAVDDNTTKAPLSASMVKRYEEHQKDLKKLKDFIKVN-APDQYNAIFKDKNK  356
WP_018363470   279  LLGKIGDDYADLFTSSKNLYDAILLSGIILTVDDNSTKAPLSASMIKRYVEHHEDLEKLKEFIKAN-KSELYHDIFKDKTQ  357
WP_003043819   278  LLGGIGDQYADLFSAAKNLSDAILLSDIILRSNSEVTKAPLSASMVKRYDEHHQDLALLKTLVRQQ-FPEKYAEIFKDDTK  356
WP_006269658   278  FLGEVGDEYADLFASAKNLYDAILLSGIILTVDDNSTKAPLSASMVKRYEEHQKDLKKLKDFIKVN-APDQYNAIFKDKNK  356
WP_048800889   278  LLGKIGDDYADLFTILLSGIILTVDTILLSGIILAVDDNSTKALLSASMIKRYEEHQKDLKKLKDFIKVN-APAQYDDIFKDETK  356
WP_012767106   278  LLAQIGDQYADLFLAAKNLSDAILLSDIILRVNSEITKAPLSASMIKRYDEHHQDLTLLKALVRQQ-LPEKYKEIFFDQSK  356
WP_014612333   278  LLAQIGNQYADLFLAAKNLSDAILLSDIILRVNSEITKAPLSASMIKRYDEHHQDLTLLKALVRQQ-LPEKYKEIFFDQSK  356
WP_015017095   278  LLAQIGDQYADLFLAAKNLSDAILLSDIILRVNSEITKAPLSASMIKRYDEHHQDLTLLKALVRQQ-LPEKYKEIFFDQSK  356
WP_015057649   278  LLAQIGDQYADLFLAAKNLSDAILLSDIILRVNSEITKAPLSASMIKRYDEHHQDLTLLKALVRQQ-LPEKYKEIFFDQSK  356
WP_048327215   278  LLAQIGDQYADLFLAAKNLSDAILLSDIILRVNSEITKAPLSASMIKRYDEHHQDLTLLKALVRQQ-LPEKYKEIFFDQSK  356
WP_049519324   278  LLAQIGDQYADLFLAAKNLSDAILLSDIILTESDEITRAPLSASMVKRYREHHKDIVTLKTLIKDQ-LPEKYQEIFLDKTK  356
WP_012515931   278  LLAQIGDQYADLFLAAKNLSDAILLSDIILTESDEITRAPLSASMVKRYREHHKDIVTLKTLIKDQ-LPEKYQEIFLDKTK  356
WP_021320964   278  LLAQIGDQYADLFLAAKNLSDAILLSDIILTESDEITRAPLSASMVKRYREHHKDIVTLKTLIKDQ-LPEKYQEIFLDKTK  356
WP_037581760   278  LLAQIGDQYADLFLAAKNLSDAILLSDIILTESDEITRAPLSASMVKRYREHHKDIVTLKTLIKDQ-LPEKYQEIFLDKTK  356
```

-continued

| ID | Start | Sequence | End |
|---|---|---|---|
| WP_004232481 | 278 | LLGKIGDDYADLFTAAKNLYDAILLSGIILTVDDNSTKAPLSASMIKRYEBHHEDLEKLKTFIKVN-NPDKYHEIFKDKSK | 356 |
| WP_009854540 | 279 | LLGKIGDDYADLFTSAKNLYDAILLSGIILTVDDNSTKAPLSASMIKRYVEHHEDLEKLKEFIKAN-KSELYHDIFKDKNK | 357 |
| WP_012962174 | 279 | LIGKIGDEYADLFTSAKNLYDAILLSGIILTVADNTTKAPLSASMIKRYNEHQVDLKKKLKEFIKAN-ASDKYDEIFNDKDK | 357 |
| WP_039695303 | 279 | LLGKIGDDYADLFTSAKNLYDAILLSGIILTVDDNSTKAPLSASMIKRYVEHHEDLEKLKEFIKAN-KSELYHDIFKDKNK | 357 |
| WP_014334983 | 278 | LLGKVGDDYADLFTSAKNLYDAILLSGIILTVDDNSTKAPLSASMIKRYVEHHEDLEKLKEFIKIN-KLKLYHDIFKDKTK | 356 |
| WP_003099269 | 278 | LLAQIGDQYADLFIAAKKLSDAILLSDIITVKGASTKAPLSASMVQRYEEHQQDLALLKNLVKKQ-IPEKYKEIFDNKEK | 356 |
| AHY15608 | 278 | LLAQIGDQYADLFIAAKKLSDAILLSDIITVKGASTKAPLSASMWQRYEEHQQDLALLKNLVKKQ-IPEKYKEIFDNKEK | 356 |
| AHY17476 | 278 | LLAQIGDQYADLFIAAKKLSDAILLSDIITVKGASTKAPLSASMVQRYEEHQQDLALLKNLVKKQ-IPEKYKEIFDNKEK | 356 |
| ESR09100 | | -------------------------------------------------------------------------------- | |
| AGM98575 | 278 | LLAQIGDQYADLFIAAKKLSDAILLSDIITVKGASTKAPLSASMVQRYEEHQQDLALLKNLVKKQ-IPEKYKEIFDNKEK | 356 |
| ALF27331 | 278 | LLAQIEDNYAELFLSAKKLYDSILLSGIILTVTDVSTKAPLSASMIQRYNEHQMDLAQLKQFIRQK-LSDKYNEVFSDVSK | 356 |
| WP_018372492 | 276 | LLSKIDEEYAALFDLAKKVYDAVLLSNILTVKEKNTKAPLSASMIKRYEEHKDDLKAFKRFFRER-LPEKYETMFKDLTK | 354 |
| WP_045618028 | 279 | LLVQIGDDFPADLFLVAKKLYDSILLSGIILTVTDPSTKAPLSASMIDRYENHQRDLAALKQFIKTN-LPEKYDEVFSDQSK | 357 |
| WP_045635197 | 278 | LLGQIGDDFTDLFVSAKKLYDSILLSGIILTVTDPSTKAPLSASMIERYENHQNDLAALKQFIKNN-LPEKYDEVFSDQSK | 356 |
| WP_002263549 | 278 | LLAQIGDNYAELFLSAKKLYDSILLSGIILTVDVGTKAPLSASMIQRYNEHQMDLAQLKQFIRQK-LSDKYNEVFSDVSK | 356 |
| WP_002263887 | 278 | LLAQIGDNYAELFLSAKKLYDSILLSGIILTVDVGTKAPLSASMIKRYAEHHEDLEKLKEFIKAN-KPELYHDIFKDETK | 356 |
| WP_002264920 | 278 | LLGKIGDDYADLFTLAKNLYDAILLSGIILTVTDADDSSTKAPLSASMIQRYNEHQMDLAQLKQFIRQK-LSDKYNEVFSDVSK | 356 |
| WP_002269043 | 278 | LLAQIGDNYAELFLSAKKLYDSILLSGIILTVTDVSTKAPLSASMIQRYNEHQMDLAQLKQFIRQK-LSDKYNEVFSDVSK | 356 |
| WP_002269448 | 278 | LLAQIGDNYAELFLSAKKLYDSILLSGIILTVTDVSTKAPLSASMIQRYNEHQMDLAQLKQFIRQK-LSDKYNEVFSDVSK | 356 |
| WP_002271977 | 278 | LLGKIGDDYADLFTLAKNLYDAILLSGIILTADDSSTKAPLSASMIQRYNEHQMDLAQLKQFIRQK-LSDKYNEVFSDVSK | 356 |
| WP_002272766 | 278 | LLGKIGDDYADLFTLAKNLYDAILLSGIILTADDSSTKAPLSASMIQRYNEHQMDLAQLKQFIRQK-LSDKYNEVFSDVSK | 356 |
| WP_002273241 | 278 | LLAQIGDNYAELFLSAKKLYDSILLSGIILTVTDVSTKAPLSASMIQRYNEHQMDLAQLKQFIRQK-LSDKYNEVFSDVSK | 356 |
| WP_002275430 | 278 | LLTQIGDNYAELFLSAKKLYDSILLSGIILTVTDVSTKAPLSASMIQRYNEHQMDLAQLKQFIRQK-LSDKYNEVFSDVSK | 356 |
| WP_002276448 | 278 | LLAQIGDNYAELFLSAKKLYDSILLSGIILTVTDVSTKAPLSASMIKRYAEHHEDLEKLKEFIKAN-KPELYHDIFKDETK | 356 |
| WP_002277050 | 278 | LLGKIGDDYADLFTLAKNLYDAILLSGIILTVTDVSTKAPLSASMIKRYAEHHEDLEKLKEFIKAN-KPELYHDIFKDETK | 356 |
| WP_002273364 | 278 | LLAQIGDNYAELFLSAKKLYDSILLSGIILTVTDVSTKAPLSASMIQRYNEHQMDLAQLKQFIRQK-LSDKYNEVFSDVSK | 356 |
| WP_002279025 | 278 | LLAQIGDNYAELFLSAKKLYDSILLSGIILTADDSSTKAPLSASMIQRYNEHQMDLAQLKQFIRQK-LSDKYNEVFSDVSK | 356 |

```
WP_002279859   278  LLAQIGDNYAELFLSAKKLYDSILLSGIILTVTDVSTKAPLSASMIQRYNEHQMDLAQLKQFIRQK-LSDKYNEVFSDVSK  356
WP_002280230   278  LLAQIGDNYAELFLSAKKLYDSILLSGIILTVTDVSTKAPLSASMIQRYNEHQMDLAQLKQFIRQK-LSDKYNEVFSDVSK  356
WP_002281696   278  LLAQIGDNYAELFLSAKKLYDSILLSGIILTVTDVSTKAPLSASMIQRYNEHQMDLAQLKQFIRQK-LSDKYNEVFSDVSK  356
WP_002282247   278  LLGKIGDDYADLFTLAKNLYDAILLSGIILTADDSTKAPLSASMIKRYAEHHEDLEKLKEFIKAN-KPELYHDIFKDETK  356
WP_002282906   278  LLAQIGDNYAELFLSAKKLYDSILLSGIILTVTDVGTKAPLSASMIQRYNEHQMDLAQLKQFIRQK-LSDKYNEVFSDVSK  356
WP_002283846   278  LLAQIGDNYAELFLSAKKLYDSILLSGIILTVTDVSTKAPLSASMIQRYNEHQMDLAQLKQFIRQK-LSDKYNEVFSDVSK  356
WP_002287255   278  LLAQIGDNYAELFLSAKKLYDSILLSGIILTVTDVSTKAPLSASMIQRYNEHQMDLAQLKQFIRQK-LSDKYNEVFSDVSK  356
WP_002288990   278  LLAQIGDNYAELFLSAKKLYDSILLSGIILTVTDVSTKAPLSASMIQRYNEHQMDLAQLKQFIRQK-LSDKYNEVFSDVSK  356
WP_002289641   278  LLAQIGDNYAELFLSAKKLYDSILLSGIILTVTDVSTKAPLSASMIQRYNEHQMDLTQLKQFIRQK-LSDKYNEVFSDVSK  356
WP_002290427   278  LLAQIGDNYAELFLSAKKLYDSILLSGIILTVTDVSTKAPLSASMIQRYNEHQMDLAQLKQFIRQK-LSDKYNEVFSDVSK  356
WP_002295753   278  LLAQIGDNYAELFLSAKNLYDSILLSGIILTVTDVSTKAPLSASMIQRYNEHQMDLAQLKQFIRQK-LSDKYNEVFSDVSK  356
WP_002296423   278  LLGEIGDEYADLFASAKNLYDAILLSGILAVDDNTTKAPLSASMVKRYKEHKEELAAFKRFIKEK-LPKKYEEIFKDDTK  356
WP_002304487   278  LLAQIGDNYAELFLSAKKLYDSILLSGIILTVTDVSTKAPLSASMIQRYNEHQMDLAQLKQFIRQK-LSDKYNEVFSDVSK  356
WP_002305844   278  LLAQIGDNYAELFLSAKKLYDSILLSGIILTVTDVSTKAPLSASMIQRYNEHQMDLAQLKQFIRQK-LSDKYNEVFSDVSK  356
WP_002307203   278  LLAQIGDNYAELFLSAKKLYDSILLSGIILTVTDVSTKAPLSASMIQRYNEHQMDLAQLKQFIRQK-LSDKYNEVFSDVSK  356
WP_002310390   278  LLAQIGDNYAELFLSAKKLYDSILLSGIILTVTDVSTKAPLSASMIQRYNEHQMDLAQLKQFIRQK-LSDKYNEVFSDVSK  356
WP_002352408   278  LLAQIGDNYAELFLSAKKLYDSILLSGIILTVTDVSTKAPLSASMIQRYNEHQMDLAQLKQFIRQK-LSDKYNEVFSDVSK  356
WP_012997688   278  LLAQIGDNYAELFLSAKKLYDSILLSGIILTVTDVSTKAPLSASMIQRYNEHQMDLAQLKQFIRQK-LSDKYNEVFSDVSK  356
WP_014677909   278  LLAQIGDNYAELFLSAKKLYDSILLSGIILTVTDVSTKAPLSASMIQRYNEHQMDLAQLKQFIRQK-LSDKYNEVFSDVSK  356
WP_019312892   278  LLAQIGDNYAELFLSAKKLYDSILLSGIILTVTDVGTKAPLSASMIQRYNEHQMDLAQLKQFIRQK-LSDKYNEVFSDVSK  356
WP_019313659   278  LLAQIGDNYAELFLSAKKLYDSILLSGIILTVTDVSTKAPLSASMIQRYNEHQMDLAQLKQFIRQK-LSDKYNEVFSDVSK  356
WP_019314093   278  LLAQIGDNYAELFLSAKKLYDSILLSGIILTVTDVGTKAPLSASMIQRYNEHQMDLAQLKQFIRQK-LSDKYNEVFSDVSK  356
WP_019315370   278  LLAQIGDNYAELFLSAKKLYDSILLSGIILTVTDVSTKAPLSASMIQRYNEHQMDLAQLKQFIRQK-LSDKYNEVFSDVSK  356
WP_019803776   278  LLAQIGDNYAELFLSAKKLYDSILLSGIILTVTDVGTKAPLSASMIQRYNEHQMDLAQLKQFIRQK-LSDKYNEVFSDVSK  356
WP_019805234   278  LLAQIGDNYAELFLSAKKLYDSILLSGIILTVTDVSTKAPLSASMIQRYNEHQMDLAQLKQFIRQK-LSDKYNEVFSDVSK  356
WP_024783594   278  LLAQIGDNYAELFLSAKKLYDSILLSGIILTVTDVGTKAPLSASMIQRYNEHQMDLAQLKQFIRQK-LSDKYNEVFSDVSK  356
WP_024784288   278  LLGKIGDDYADLFTLAKNLYDAILLSGIILTADDSTKAPLSASMIKRYAEHHEDLEKLKEFIKAN-KPELYHDIFKDETK  356
```

| | | | |
|---|---|---|---|
| WP_024784666 | 278 | LLAQIGDNYAELFLSAKKLYDSILLSGIILTVTDVSTKAPLSASMIQRYNEHQMDLVQLKQFIRQK-LSDKYNEVFSDVSK | 356 |
| WP_024784894 | 278 | LLAQIGDNYAELFLSAKKLYDSILLSGIILTVTDVSTKAPLSASMIQRYNEHQMDLTQLKQFIRQK-LSDKYNEVFSDVSK | 356 |
| WP_024786433 | 278 | LLGKIGDDYADLFTLAKNLYDAILLSGIILTADDSSTKAPLSASMIKRYAEHHEDLEKLKEFIKAN-KPELYHDIFKDETK | 356 |
| WP_049473442 | 278 | LLGKIGDDYADLFTLAKNLYDAILLSGIILTADDSSTKAPLSASMIQRYNEHQMDLAQLKQFIRQK-LSDKYNEVFSDVSK | 356 |
| WP_049474547 | 278 | LLAQIGDNYAELFLSAKKLYDSILLSGIILTVTDVSTKAPLSASMIQRYNEHQMDLTQLKQFIRQK-LSDKYNEVFSDVSK | 356 |
| EMC03581 | 271 | LLAQIGDNYAELFLSAKKLYDSILLSGIILTVTDVSTKAPLSASMIQRYNEHQMDLAQLKQFIRQK-LSDKYNEVFSDVSK | 349 |
| WP_000428612 | 279 | LLGQIGDDFADLFLVAAKKLYDAILLSGIILTVTDPSTKAPLSASMIERYENHQKDLATLKQFIKTN-LPEKYDEVFSDQSK | 357 |
| WP_000428613 | 279 | LLGQIGDDFADLFLVAKKLYDAILLSGIILTVTDPSTKAPLSASMIERYENHQKDLAVLKQFIKNN-LPEKYDEVFSDQSK | 357 |
| WP_049523028 | 278 | LLGQIGDVIYADLFVAKKLYDAILLAGIILSVKDPGTKAPLSASMIERYDNHQNDLSALKQFVRRN-LPEKYAEVFSDDSK | 356 |
| WP_003107102 | 247 | LLAQIGDQYADLFIAAKNLSDAILLSDIILTVKGVNTKAPLSASMVQRFNEHQDDLKLLKKLVKVQ-LPEKYKEIFDIKDK | 325 |
| WP_054279288 | 280 | LLTQIGDEYADLFLSAKNLSDAILLSDIILTVNGDGTQAPLSASLIKRYEEHRQDLALLKQMFKEQ-LPDLYRDVFTDENK | 358 |
| WP_049531101 | 279 | LLGQIGDDFADLFLVAKKLYDAILLSGIILTVTDPSTKAPLSASMIERYENHQKDLAALKQFIKNN-LPEKYDEVFSDQSK | 357 |
| WP_049538452 | 279 | LLGQIGDGFADLFLVAKKLYDAILLSGIILTVTDPSTKAPLSASMIERYQNHQNDLASLKQFIKNN-LPEKYDEVFSDQSK | 357 |
| WP_049549711 | 279 | LLGQIGDDFADLFLVAKKLYDAILLSGIILTVTDPSTKAPLSASMIERYENHQKDLTTLKQFIKNN-LPEKYDEVFSDQSK | 357 |
| WP_007896501 | 280 | LLAEIGDHYADLFLAAKNLSDAILLSDIILTLSDENTRAPLSASMIKRYEEHQEDLALLKKLVKEQ-MPEKYWEIFSNAKK | 358 |
| EFR44625 | 232 | LLAEIGDHYADLFLAAKNLSDAILLSDIILTLSDENTRAPLSASMIKRYEEHQKDLALLKKLVKEQ-MPEKYWEIFSNAKK | 310 |
| WP_002897477 | 278 | LLGQIGDDFADLFLIAKKLYDAILLSGIILTVTDPSTKAPLSASMIERYENHQKDLAALKQFIKNN-LPEKYVEVFSDQSK | 356 |
| WP_002906454 | 278 | LLGQIGDDFADLFLVAKKLYDAILLSGIILTVTDPSTKAPLSASMIERYENHQEDLAALKQFIKNN-LSEKYAEVFSDQSK | 356 |
| WP_009729476 | 279 | LLGQIGDDFADLFLVAKKLYDAILLSGIILTVTNPSTKAPLSASMIERYENHQKDLASLKQFIKNN-LPEKYDEVFSDQSE | 357 |
| CQR24647 | 278 | LLGIIGDEYADVFVAAKKVVDSILLSGIILTTNNHSTKAPLSASMIDRYDEHNSDKKLLRDFIRTNIGKEVEKEVFYDTSK | 357 |
| WP_000666813 | 279 | LLGQIGDDFADLFLVAKKLYDAILLSGIILTVKDLSTKAPLSASMIERYENHQKDLAALKQFIQNN-LQBKYDEVFSDQSK | 357 |
| WP_009754323 | 279 | LLGKIGDDYADLFIATKSLYDGIILLAGIILSTTDSTTKAPLSASMVNRYEBHKKDLALLKNFIHQN-LPEKYAEVFSDQSK | 357 |
| WP_044674937 | 278 | LLGKIGDDYADLFIATKSLYDGIILLAGIILSTTDSTTKAPLSASMVNRYEBHKDLALLKNFIHQN-LSDSYKEVFNDKLK | 356 |
| WP_044676715 | 278 | LLGKIGDDYADLFIATKSLYDGIILLAGIILSTTDSTTKAPLSSSMVNRYEBHQKDLALLKNFIHQN-LSDSYKEVFNDKLL | 356 |
| WP_044680361 | 278 | LLGKIGDDYADLFIATKSLYDGIILLAGIILSTTDSTTKAPLSSSMVNRYEBHKDLALLKNFIHQN-LSDSYKEVFNDKLL | 356 |
| WP_044681799 | 278 | LLGKIGDDYADLFIATKSLYDGIILLAGIILSTTDSTTKAPLSSSMVNRYEBHKKDLALLKNFIHQN-LSDSYKEVFNDKLL | 356 |
| WP_049533112 | 278 | LLGEIGDEYADLFASAKNLYDAILLSGIILTVDDNSTKAPLSASMVKRYEBHQKDLKKLKDFIKVN-APDQYNAIFKDKNK | 356 |

| ID | Start | Sequence | End |
|---|---|---|---|
| WP_029909905 | 244 | LADVLADEEYDLLLTAQKIYSAIILDESMDGYEYPA-----EAKKESYRKHQEEIVLVKKMLKSNaITNDERAKF---EY | 315 |
| WP_006506696 | 284 | VEKDLGE-YVEFVDALHNVYSWVELQTIMGATHTD-NASISEAMVSRYNKHHDDLKLLKDCIKNN-VPNKYFDMFRNDSE | 360 |
| AIT42264 | 278 | LLAQIGDQYADLFLAAKNLSDAILLSDILRVNTEITKAPLSASMIKRYDEHHQDLTLLKALVRQQ-LPEKYKEIFFDQSK | 356 |
| WP_034440723 | 284 | LLSNIDEGYRDVFLQAKNVNAIELSKILKTDGKETKAPLSAQMVELYNQHREDLKKYKDYIKAY-LPEKYGETFKDATK | 362 |
| AKQ21048 | 278 | LLAQIGDQYADLFLAAKNLSDAILLSDILRVNTEITKAPLSASMIKRYDEHHQDLTLLKALVRQQ-LPEKYKEIFFDQSK | 356 |
| WP_004636532 | 277 | LLGMTDDVFLDVFMAAKNVYDAVEMSAIISTDTGNSKAVLSNQMINFYDEHKVDLAQLKQFFKTH-LPDKYYECFSDPSK | 355 |
| WP_002364836 | 284 | ILAKVGDEYSDVFLAAKNVYDAVELSTILADSDKKSHAKLSSSMIVRFTEHQEDLKKFKRFIREN-CPDEYDNLFKNEQK | 362 |
| WP_016631044 | 235 | ILAKVGDEYSDVFLAAKNVYDAVELSTILADSDKKSHAKLSSSMIVRFTEHQEDLKKFKRFIREN-CPDEYDNLFKNEQK | 313 |
| EMS75795 | 21 | LLEKSGEEFRDVFLQAKKVYDAILLSDILSTKKQNSKAKLSLGMIERYDSHKKDLEELKQFVKAN-LPEKTAIFFKDSSK | 99 |
| WP_002373311 | 284 | ILAKVGDEYSDVFLAAKNVYDAVELSTILADSDKKSHAKLSSSMIVRFTEHQEDLKKFKRFIREN-CPDEYDNLFKNEQK | 362 |
| WP_002378009 | 284 | ILAKVGDEYSDVFLAAKNVYDAVELSTILADSDKKSHAKLSSSMIVRFTEHQEDLKNFKRFIREN-CPDEYDNLFKNEQK | 362 |
| WP_002407324 | 284 | ILAKVGDEYSDVFLAAKNVYDAVELSTILADSDKKSHAKLSSSMIVRFTEHQEDLKKFKRFIREN-CPDEYDNLFKNEQK | 362 |
| WP_002413717 | 286 | ILAKVGDEYSDVFLAAKNVYDAVELSTILADSDKKSHAKLSSSMIVRFTEHQEDLKKFKRFIREN-CPDEYDNLFKNEQK | 364 |
| WP_010775580 | 284 | ILAKVGDEYSDVFLAAKNVYDAVELSTILADSDKKSHAKLSSSMIVRFTEHQEDLKKFKRFIREN-CPDEYDNLFKNEQK | 362 |
| WP_010818269 | 284 | ILAKVGDEYSDVFLAAKNVYDAVELSTILADSDKKSHAKLSSSMIVRFTEHQEDLKKFKRFIREN-CPDEYDNLFKNEQK | 362 |
| WP_010824395 | 284 | ILAKVGDEYSDVFLAAKNVYDAVELSTILADSDKKSYAKLSSSMIVRFTEHQEDLKKFKRFIREN-CPDEYDNLFKNEQK | 362 |
| WP_016622645 | 284 | ILAKVGDEYSDVFLAAKNVYDAVELSTILADSDKKSHAKLSSSMIVRFTEHQEDLKKFKRFIREN-CPDEYDNLFKNEQK | 362 |
| WP_033624816 | 284 | ILAKVGDEYSDVFLAAKNVYDAVELSTILADSDKKSHAKLSSSMIVRFTEHQEDLKKFKRFIREN-CPDEYDNLFKNEQK | 362 |
| WP_033625576 | 284 | ILAKVGDEYSDVFLAAKNVYDAVELSTILADSDKKSHAKLSSSMIVRFTEHQEDLKKFKRFIREN-CPDEYDNLFKNEQK | 362 |
| WP_033789179 | 284 | ILAKVGDEYSDVFLAAKNVYDAVELSTILADSDKKSHAKLSSSMIVRFTEHQEDLKKFKRFIREN-CPDEYDNLFKNEQK | 362 |
| WP_002310644 | 282 | LLEKIGDDYIDLFVQAKNVYDAVLLSEILSDSTKNTRAKLSAGMIRRYDAHKEDIVLLKRFVKEN-LPKKYRAFFGDNSV | 360 |
| WP_002312694 | 283 | LLEKIGDDYIDLFVQAKNVYDAVLLSEILSDSTKNTRAKLSAGMIRRYDAHKEDIVLLKRFVKEN-LPKKYRAFFGDNSV | 361 |
| WP_002314015 | 283 | LLEKIGDDYIDLFVQAKNVYDAVLLSEILSDSTKNTRAKLSAGMIRRYDAHKEDIVLLKRFVKEN-LPKKYRAFFGDNSV | 361 |
| WP_002320716 | 283 | LLEKIGDDYIDLFVQAKNVYDAVLLSEILSDSTKNTRAKLSAGMIRRYDAHKEDIVLLKRFVKEN-LPKKYRAFFGDNSV | 361 |
| WP_002330729 | 282 | LLEKIGDDYIDLFVQAKNVYDAVLLSEILSDSTKNTRAKLSAGMIRRYDAHKEDIVLLKRFVKEN-LPKKYRAFFGDNSV | 360 |
| WP_002335161 | 283 | LLEKIGDDYIDLFVQAKNVYDAVLLSEILSDSTKNTRAKLSAGMIRRYDAHKEDIVLLKRFVKEN-LPKKYRAFFGDNSV | 361 |
| WP_002345439 | 283 | LLEKIGDDYIDLFVQAKNVYDAVLLSEILSDSTKNTRAKLSAGMIRRYDAHKEDIVLLKRFVKEN-LPKKYRAFFGDNSV | 361 |

```
WP_034867970   276  LLEKIGDEYLDIFLQAKKVHDAILLSEIISSTVKHTKAKLSSGMVERYERHKADLAKFKQFVKEN-VPQKATVFFKDTTK  354
WP_047937432   283  LLEKIGDDYIDLFVQAKNVYDAVLLSEILSDSTKNTRAKLSAGMIRRYDAHKEDIVLLKRFVKEN-LPKKYRAPFGDNSV  361
WP_010720994   276  LLEKIGDEYLDIFLQAKKVHDAILLSEIISSTVKHTQAKLSSGMVERYERHKADLAKFKQFVKEN-VPQKATVFFKDTTK  354
WP_010737004   276  LLEKIGDEYLDIFLQAKKVHDAILLSEIISSTVKHTKAKLSSGMVERYERHKADLAKFKQFVKEN-VPQKATVFFKDTTK  354
WP_034700478   276  LLEKIGDEYLDIFLQAKKVHDAILLSEIISSTVKHTQAKLSSGMVERYERHKADLAKFKQFVKEN-VPQKATVFFKDTTK  354
WP_007209003   281  LLAIIGDEYGDIFVAAQNLYQAILLAGILTSTEK-TRAKLSASMIQRYEEHAKDLKLLKRFVKEH-IPDKYAEIFNDATK  358
WP_023519017   276  LLEKTSDDYAELFLKAKGVYDAILLSQILSKSDETKAKLSANMKLRFEEHQRDLKQLELVRRD-LPKKYDDFFKNRSK    354
WP_010770040   279  LLAIIGDEYAEIFSATKSVYDAVALSGILSVTDGDTKAKLSASMVERYEAHQKDLVQFKQFIRKE-LPEMYAPIFRDNSV  357
WP_048604708   275  LLGEIGDEYADVFREAAKNVYNAVELSGLILTVTDNSTKAKLSASMIKRYEDHKTDLKLFKEFIRKN-LPEKYHEIFNDKNT  353
WP_010750235   276  LLRKSNEEMIDVFLQVKKVYDAILLSDILSTKMKDTKAKLSAGMIERYQNHKKDLEELKQFVRAH-LHEKVTVFFKDSSK  354
AII16583       317  LLAQIGDQYADLFLAAKNLSDAILLSDILRVNTEITKAPLSASMIKRYDEHHQDLTLLKALVRQQ-LPEKYKEIFFDQSK  395
WP_029073316   290  KQPLLGD-CVEFIDLLHDIYSWVELQNILGSAHTS-EPSISAAMIQRYEDHKNDLKLLKDVIRKY-LPKKYFEVFRDEKS  366
WP_031589969   290  KQPLLGD-CVEFIDLLHDIYSWVELQNILGSAHTS-EPSISAAMIQRYEDHKNDLKLLKDVIRKY-LPKKYFEVFRDEKS  366
KDA45870       276  LLAEAGDQYLDIFVAAKKVYDAAILASILDVKDTQTKTVFSQAMIERYEEHQKDLIELKRVFKKY-LPEKCHDFFSE-PK  353
WP_039099354   286  LESSLDDNAHQIIESLQELYSGVLLAGIVPENQSLS-----QAMITKYDDHQKHLKMLKAVREAL-APEDRQRLKQAYDQ  359
AKP02966       279  LDSILDDDQFTVLDTANRIYSTITLNEIL-------NGESYFSMAKVNQYENHAIDLCKLRDMWHTT----KNEKAV-GLSR  348
WP_010991369   284  LLALIGDEYAELFVAAKNAYSAVVLSSIITVAETETNAKLSASMIERFDTHEEDLGELKAFIKLH-LPKHYEEIFSNTEK  362
WP_033838504   284  LLALIGDEYAELFVAAKNAYSAVVLSSIITVAETETNAKLSASMIERFDTHEEDLGELKAFIKLH-LPKHYEEIFSNTEK  362
EHN60060       287  LLALIGDEYAELFVAAKNAYSAVVLSSIITVAETETNAKLSASMIERFDTHEEDLGELKAFIKLH-LPKHYEEIFSNTEK  365
EFR89594        53  LLAKIGDEYAELFVAAKSTYNAVVLSNIITVTDSTTRAKLSASLIERFENHKEDLKRLKAFFKMQ-LPEKFNEVFNDIEK  131
WP_038409211   284  LLAKIGDEYAELFVAAKSTYNAVVLSNIITVTDSTTRAKLSASLIERFENHKEDLKRLKAFFKMQ-LPEKFNEVFNDIEK  362
EFR95520            -------------------------------------------------------------------------------
WP_003723650   284  LLAIIGDEYAELFVAAKNTNAVVLSSIITVTDTETNAKLSASMIERFDAHEKDIVELKAFIKLN-LPKQYEEIFSNAAI   362
WP_003727705   284  LLAIIGDEYAELFVAAKNTNAVVLSSIITVTDTETNAKLSASMIERFDAHEKELGELKAFIKLH-LPKQYQEIFNNAEI   362
WP_003730785   284  LLAIIGDEYAELFVAAKNTNAVVLSSIITVTDTATETNAKLSASMIERFDAHEKELGELKAFIKLH-LPKQYQEIFNNAEI 362
WP_003733029   284  LLAIIGDEFAEVFVAAKNAYNAVVLSNIITVTDSTTRAKLSASLLERFENHKEDLKMKRFVRTY-LPKKYDEIFDDTEK   362
WP_003739838   284  LLAIIGDEYAELFVAAKNTNAVVLSSIITVTDTETNAKLSASMIERFDAHEKDLSELKAFIKLH-LPKQYEEIFSNVAI   362
```

| ID | Start | Sequence | End |
|---|---|---|---|
| WP_014601172 | 284 | LLAIIGDEYAELFVAAKNTYNAVVLSSIITVTATETNAKLSASMIERFDAHEKDLGELKAFIKLH-LPKQYQEIFNNAAI | 362 |
| WP_023548323 | 284 | LLAIIGDEYAELFVAAKNTYNAVVLSSIITVTDTETNAKLSASMIERFDAHEKDLIVELKAFIKLN-LPKQYEEIFSNAAI | 362 |
| WP_031665337 | 284 | LLAIIGDEYAELFVAAKNTYNAVVLSSIITVNDTETNAKLSASMIERFDAHEKDLIVELKAFIKLN-LPKQYEEIFSNAAI | 362 |
| WP_031669209 | 284 | LLAIIGDEFAEVFVAAKNAYNAVVLSNIITVTDSTTRAKLSASLIERFENHKEDLKKMKRFVRTY-LPEKYDEIFDDTEK | 362 |
| WP_033920898 | 284 | LLAIIGDEYAELFVAAKNTYNAVVLSSIITVTDTETNAKLSASMIERFDAHEKDLIVELKAFIKLN-LPKQYEEIFSNAAI | 362 |
| AKI42028 | 287 | LLAIIGDEYAELFVAAKNTYNAVVLSSIITVTATETNAKLSASMIERFDAHEKDLGELKAFIKLH-LPKQYQEIFNNAAI | 365 |
| AKI50529 | 287 | LLAIIGDEYAELFVAAKNTYNAVVLSSIITVTDTETNAKLSASMIERFDAHEKDLIVELKAFIKLN-LPKQYEEIFSNAAI | 365 |
| EFR83390 | | ------------------------------------------------------------------------------- | |
| WP_046323366 | 284 | LLARVGDEYAEIFVAAKNAYNAVVLSSIITVSNTETKAKLSASMIERFDKHDKDLKRMKAFFKVR-LPENFNEVFNDVEK | 362 |
| AKE81011 | 294 | LLAQIGDQYADLFLAAKNLSDAILLSDIILRVNTEITKAPLSASMIKRYDEHHQDLTLLKALVRQQ-LPEKYKEIFFDQSK | 372 |
| CUO82355 | 288 | VENDLGE-YVEFIDSLHNIYSWVELQTIMGATHTD-NASISEAMVSRYNKHHEDLQLLKKCIKDN-VPKKYFDMFRNDSE | 364 |
| WP_033162887 | 289 | LQSELGE-YIEFIEMLHNIYSWVELQAILGATHTD-NPSISAAMVERYEEHKKDLRVLKKVIREE-LPDKYNEVFRKDNR | 365 |
| AGZ01981 | 311 | LLAQIGDQYADLFLAAKNLSDAILLSDIILRVNTEITKAPLSASMIKRYDEHHQDLTLLKALVRQQ-LPEKYKEIFFDQSK | 389 |
| AKA60242 | 278 | LLAQIGDQYADLFLAAKNLSDAILLSDIILRVNTEITKAPLSASMIKRYDEHHQDLTLLKALVRQQ-LPEKYKEIFFDQSK | 356 |
| AKS40380 | 278 | LLAQIGDQYADLFLAAKNLSDAILLSDIILRVNTEITKAPLSASMIKRYDEHHQDLTLLKALVRQQ-LPEKYKEIFFDQSK | 356 |
| 4UN5_B | 282 | LLAQIGDQYADLFLAAKNLSDAILLSDIILRVNTEITKAPLSASMIKRYDEHHQDLTLLKALVRQQ-LPEKYKEIFFDQSK | 360 |
| WP_010922251 | 357 | --NGYAG YIDG G ASQEEFYKFIKPILEK-M--DGTEELLv--KLNREDLLRKQRTFDNGSIPHQIHLGEL | 419 |
| WP_039695303 | 358 | --NGYAG YIEN G VKQDEFYKYLKNILSK-IkiDGSDYFL--DKIEREDFLRKQRTFDNGSIPHQIHLQEM | 422 |
| WP_045635197 | 357 | --DGYAG YIDG K TTQETFYKYIKNLLSK-F--EGTDYFL--DKIEREDFLRKQRTFDNGSIPHQIHLQEM | 419 |
| 5AXW_A | 169 | ------G SINR - ----------------K------TSDYVk-------------------------EA | 183 |
| WP_009880683 | 41 | --NGYAG YIDG G ASQEEFYKFIKPILEK-M--DGTEELLa--KLNREDLLRKQRTFDNGSIPHQIHLGEL | 103 |
| WP_010922251 | 357 | --NGYAG YIDG G ASQEEFYKFIKPILEK-M--DGTEELLv--KLNREDLLRKQRTFDNGSIPHQIHLGEL | 419 |
| WP_011054416 | 357 | --NGYAG YIDG G ASQEEFYKFIKPILEK-M--DGTEELLa--KLNREDLLRKQRTFDNGSIPHQIHLGEL | 419 |
| WP_011284745 | 357 | --NGYAG YIDG G ASQEEFYKFIKPILEK-M--DGTEELLv--KLNREDLLRKQRTFDNGSIPYQIHLGEL | 419 |
| WP_011285506 | 357 | --NGYAG YIDG G ASQEEFYKFIKPILEK-M--DGTEELLa--KLNREDLLRKQRTFDNGSIPHQIHLGEL | 419 |
| WP_011527619 | 357 | --NGYAG YIDG G ASQEEFYKFIKPILEK-M--DGTEELLa--KLNREDLLRKQRTFDNGSIPHQIHLGEL | 419 |
| WP_012560673 | 357 | --NGYAG YIDG G ASQEEFYKFIKPILEK-M--DGTEELLa--KLNREDLLRKQRTFDNGSIPHQIHLGEL | 419 |

| | | | | | |
|---|---|---|---|---|---|
| WP_014407541 | 357 | --NGYAG | YIDG | G | ASQEEFYKFIKPILEK-M--DGTEELLv--KLNREDLLRKQRTFDNGSIPHQIHLGEL | 419 |
| WP_020905136 | 357 | --NGYAG | YIDG | G | ASQEEFYKFIKPILEK-M--DGTEELLa--KLNREDLLRKQRTFDNGSIPHQIHLGEL | 419 |
| WP_023080005 | 357 | --NGYAG | YIDG | G | ASQEEFYKFIKPILEK-M--DGTEELLa--KLNREDLLRKQRTFDNGSIPYQIHLGEL | 419 |
| WP_023610282 | 357 | --NGYAG | YIDG | G | ASQEEFYKFIKPILEK-M--DGTEELLa--KLNREDLLRKQRTFDNGSIPYQIHLGEL | 419 |
| WP_030125963 | 357 | --NGYAG | YIDG | G | ASQEEFYKFIKPILEK-M--DGTEELLv--KLNREDLLRKQRTFDNGSIPYQIHLGEL | 419 |
| WP_030126706 | 357 | --NGYAG | YIDG | G | ASQEEFYKFIKPILEK-M--DGTEELLa--KLNREDLLRKQRTFDNGSIPYQIHLGEL | 419 |
| WP_031488318 | 357 | --NGYAG | YIDG | G | ASQEEFYKFIKPILEK-M--DGTEELLa--KLNREDLLRKQRTFDNGSIPHQIHLGEL | 419 |
| WP_032460140 | 357 | --NGYAG | YIDG | G | ASQEEFYKFIKPILEK-M--DGTEELLa--KLNREDLLRKQRTFDNGSIPHQIHLGEL | 419 |
| WP_032461047 | 357 | --NGYAG | YIDG | G | ASQEEFYKFIKPILEK-M--DGTEELLa--KLNREDLLRKQRTFDNGSIPHQIHLGEL | 419 |
| WP_032462016 | 357 | --NGYAG | YIDG | G | ASQEEFYKFIKPILEK-M--DGTEELLv--KLNREDLLRKQRTFDNGSIPHQIHLGEL | 419 |
| WP_032462936 | 357 | --NGYAG | YIDG | G | ASQEEFYKFIKPILEK-M--DGTEELLa--KLNREDLLRKQRTFDNGSIPHQIHLGEL | 419 |
| WP_032464890 | 357 | --NGYAG | YIDG | G | ASQEEFYKFIKPILEK-M--DGTEELLa--KLNRKDLLRKQRTFDNGSIPHQIHLGEL | 419 |
| WP_033888930 | 182 | --NGYAG | YIDG | G | ASQEEFYKFIKPILEK-M--DGTEELLv--KLNREDLLRKQRTFDNGSIPHQIHLGEL | 244 |
| WP_038431314 | 357 | --NGYAG | YIDG | G | ASQEEFYKFIKPILEK-M--DGTEELLa--KLNREDLLRKQRTFDNGSIPYQIHLGEL | 419 |
| WP_038432938 | 357 | --NGYAG | YIDG | G | ASQEEFYKFIKPILEK-M--DGTEELLa--KLNREDLLRKQRTFDNGSIPHQIHLGEL | 419 |
| WP_038434062 | 357 | --NGYAG | YIDG | G | ASQEEFYKFIKPILEK-M--DGTEELLv--KLNREDLLRKQRTFDNGSIPHQIHLGEL | 419 |
| BAQ51233 | 268 | --NGYAG | YIDG | G | ASQEEFYKFIKPILEK-M--DGTEELLv--KLNREDLLRKQRTFDNGSIPHQIHLGEL | 330 |
| KGE60162 | | ------ | ---- | - | ---------------------------------------------------------- | |
| KGE60856 | | ------ | ---- | - | ---------------------------------------------------------- | |
| WP_002989955 | 357 | --NGYAG | YIDG | G | ASQEEFYKFIKPILEK-M--DGTEELLa--KLNREDLLRKQRTFDNGSIPHQIHLGEL | 419 |
| WP_003030002 | 357 | --KGYAG | YIEN | G | VKQDEFYKYLKGILLQ-I--NGSGDFL--DKIDREDFLRKQRTFDNGSIPHQIHLQEM | 419 |
| WP_003065552 | 360 | --NGYAG | YIEN | G | VKQDEFYKYLKNTLSK-Ia--GSDYFL--DKIEREDFLRKQRTFDNGSIPHQIHLQEM | 422 |
| WP_001040076 | 358 | --DGYAG | YIEG | K | TNQEAFYKYLSKLLTK-Q--EGSEYFL--EKIKNEDFLRKQRTFDNGSIPHQVHLTEL | 420 |
| WP_001040078 | 358 | --DGYAG | YIEG | K | TNQEAFYKYLSKLLTK-Q--EDSENFL--EKIKNEDFLRKQRTFDNGSIPHQVHLTEL | 420 |
| WP_001040080 | 358 | --DGYAG | YIEG | K | TNQEAFYKYLSKLLTK-Q--EDSENFL--EKIKNEDFLRKQRTFDNGSIPHQVHLTEL | 420 |
| WP_001040081 | 358 | --DGYAG | YIEG | K | TNQEAFYKYLSKLLTK-Q--EDSENFL--EKIKNEDFLRKQRTFDNGSIPHQVHLTEL | 420 |
| WP_001040083 | 358 | --DGYAG | YIEG | K | TNQEAFYKYLSKLLTK-Q--EDSENFL--EKIKNEDFLRKQRTFDNGSIPHQVHLTEL | 420 |

| | | | | | |
|---|---|---|---|---|---|
| WP_001040085 | 358 | --DGYAG | YIEG | K | TNQEAFYKYLSKLLTK-Q--EDSENFL--EKIKNEDFLRKQRTFDNGSIPHQVHLTEL | 420 |
| WP_001040087 | 358 | --DGYAG | YIEG | K | TNQEAFYKYLSKLLTK-Q--EDSENFL--EKIKNEDFLRKQRTFDNGSIPHQVHLTEL | 420 |
| WP_001040088 | 358 | --DGYAG | YIEG | K | TNQEAFYKYLSKLLTK-Q--EDSENFL--EKIKNEDFLRKQRTFDNGSIPHQVHLTEL | 420 |
| WP_001040089 | 358 | --DGYAG | YIEG | K | TNQEAFYKYLSKLLTK-Q--EDSENFL--EKIKNEDFLRKQRTFDNGSIPHQVHLTEL | 420 |
| WP_001040090 | 358 | --DGYAG | YIEG | K | TNQEAFYKYLSKLLTK-Q--EDSENFL--EKIKNEDFLRKQRTFDNGSIPHQVHLTEL | 420 |
| WP_001040091 | 358 | --DGYAG | YIEG | K | TNQEAFYKYLSKLLTK-Q--EDSENFL--EKIKNEDFLRKQRTFDNGSIPHQVHLTEL | 420 |
| WP_001040092 | 358 | --DGYAG | YIEG | K | TNQEAFYKYLSKLLTK-Q--EDSEYFL--EKIKNEDFLRKQRTFDNGSIPHQVHLTEL | 420 |
| WP_001040094 | 358 | --DGYAG | YIEG | K | TNQEAFYKYLSKLLTK-Q--EGSEYLL--EKIKNEDFLRKQRTFDNGSIPHQVHLTEL | 420 |
| WP_001040095 | 358 | --DGYAG | YIEG | K | TNQEAFYKYLSKLLTK-Q--EGSEYLL--EKIKNEDFLRKQRTFDNGSIPHQVHLTEL | 420 |
| WP_001040096 | 358 | --DGYAG | YIEG | K | TNQEAFYKYLSKLLTK-Q--EGSEYLL--EKIKNEDFLRKQRTFDNGSIPHQVHLTEL | 420 |
| WP_001040097 | 358 | --DGYAG | YIEG | K | TNQEAFYKYLSKLLTK-Q--EGSEYLL--EKIKNEDFLRKQRTFDNGSIPHQVHLTEL | 420 |
| WP_001040098 | 358 | --DGYAG | YIEG | K | TNQEAFYKYLSKLLTK-Q--EGSEYLL--EKIKNEDFLRKQRTFDNGSIPHQVHLTEL | 420 |
| WP_001040099 | 358 | --DGYAG | YIEG | K | TNQGAFYKYLSKLLTK-Q--EGSEYLL--EKIKNEDFLRKQRTFDNGSIPHQVHLTEL | 420 |
| WP_001040100 | 358 | --DGYAG | YIEG | K | TNQGAFYKYLSKLLTK-Q--EGSEYLL--EKIKNEDFLRKQRTFDNGSIPHQVHLTEL | 420 |
| WP_001040104 | 358 | --DGYAG | YIEG | K | TNQEAFYKYLSKLLTK-Q--EDSENFL--EKIKNEDFLRKQRTFDNGSIPHQVHLTEL | 420 |
| WP_001040105 | 358 | --DGYAG | YIEG | K | TNQGAFYKYLSKLLTK-Q--EDSENFL--EKIKNEDFLRKQRTFDNGSIPHQVHLTEL | 420 |
| WP_001040106 | 358 | --DGYAG | YIEG | K | TNQEAFYKYLSKLLTK-Q--EGSEYFL--EKIKNEDFLRKQRTFDNGSIPHQVHLTEL | 420 |
| WP_001040107 | 358 | --DGYAG | YIEG | K | TNQGAFYKYLSKLLTK-Q--EGSEYFL--EKIKNEDFLRKQRTFDNGSIPHQVHLTEL | 420 |
| WP_001040108 | 358 | --DGYAG | YIEG | K | TNQGAFYKYLSKLLTK-Q--EGSEYFL--EKIKNEDFLRKQRTFDNGSIPHQVHLTEL | 420 |
| WP_001040109 | 358 | --DGYAG | YIEG | K | TNQGAFYKYLSKLLTK-Q--EGSEYLL--EKIKNEDFLRKQRTFDNGSIPHQVHLTEL | 420 |
| WP_001040110 | 358 | --DGYAG | YIEG | K | TNQGAFYKYLSKLLTK-Q--EGSEYFL--EKIKNEDFLRKQRTFDNGSIPHQVHLTEL | 420 |
| WP_015058523 | 358 | --DGYAG | YIEG | K | TNQGAFYKYLSKLLTK-Q--EDSENFL--EKIKNEDFLRKQRTFDNGSIPHQVHLTEL | 420 |
| WP_017643650 | 358 | --DGYAG | YIEG | K | TNQGAFYKYLSKLLTK-Q--EGSEYFL--EKIKNEDFLRKQRTFDNGSIPHQVHLTEL | 420 |
| WP_017647151 | 358 | --DGYAG | YIEG | K | TNQGAFYKYLSKLLTK-Q--EGSEYFL--EKIKNEDFLRKQRTFDNGSIPHQVHLTEL | 420 |
| WP_017648376 | 358 | --DGYAG | YIEG | K | TNQGAFYKYLSKLLTK-Q--EGSEYFL--EKIKNEDFLRKQRTFDNGSIPHQVHLTEL | 420 |
| WP_017649527 | 358 | --DGYAG | YIEG | K | TNQGAFYKYLSKLLTK-Q--EDSENFL--EKIKNEDFLRKQRTFDNGSIPHQVHLTEL | 420 |
| WP_017771611 | 358 | --DGYAG | YIEG | K | TNQGAFYKYLSKLLTK-Q--EGSEYFL--EKIKNEDFLRKQRTFDNGSIPHQVHLTEL | 420 |

-continued

| ID | | | | | |
|---|---|---|---|---|---|
| WP_017771984 | 358 | --DGYAG | YIEG | K | TNQEAFYKYLSKLLTK-Q--EDSENFL--EKIKNEDFLRKQRTFDNGSIPHQVHLTEL | 420 |
| CFQ25032 | 358 | --DGYAG | YIEG | K | TNQEAFYKYLSKLLTK-Q--EDSENFL--EKIKNEDFLRKQRTFDNGSIPHQVHLTEL | 420 |
| CFV16040 | 358 | --DGYAG | YIEG | K | TNQEAFYKYLSKLLTK-Q--EDSENFL--EKIKNEDFLRKQRTFDNGSIPHQVHLTEL | 420 |
| KLJ37842 | 358 | --DGYAG | YIEG | K | TNQEAFYKYLSKLLTK-Q--EDSENFL--EKIKNEDFLRKQRTFDNGSIPHQVHLTEL | 420 |
| KLJ72361 | 358 | --DGYAG | YIEG | K | TNQEAFYKYLSKLLTK-Q--EDSENFL--EKIKNEDFLRKQRTFDNGSIPHQVHLTEL | 420 |
| KLL20707 | 358 | --DGYAG | YIEG | K | TNQEAFYKYLSKLLTK-Q--EDSENFL--EKIKNEDFLRKQRTFDNGSIPHQVHLTEL | 420 |
| KLL42645 | 358 | --DGYAG | YIEG | K | TNQGAFYKYLSKLLTK-Q--EGSEYFL--EKIKNEDFLRKQRTFDNGSIPHQVHLTEL | 420 |
| WP_047207273 | 358 | --DGYAG | YIEG | K | TNQEAFYKYLSKLLTK-Q--EDSENFL--EKIKNEDFLRKQRTFDNGSIPHQVHLTEL | 420 |
| WP_047209694 | 358 | --DGYAG | YIEG | K | TNQEAFYKYLSKLLTK-Q--EGSEYLL--EKIKNEDFLRKQRTFDNGSIPHQVHLTEL | 420 |
| WP_050198062 | 358 | --DGYAG | YIEG | K | TNQEAFYKYLSKLLTK-Q--EDSENFL--EKIKNEDFLRKQRTFDNGSIPHQVHLTEL | 420 |
| WP_050201642 | 358 | --DGYAG | YIEG | K | TNQEAFYKYLSKLLTK-Q--EDSENFL--EKIKNEDFLRKQRTFDNGSIPHQVHLTEL | 420 |
| WP_050204027 | 358 | --DGYAG | YIES | K | TNQGAFYKYLSKLLTK-Q--EGSEYFL--EKIKNEDFLRKQRTFDNGSIPHQVHLTEL | 420 |
| WP_050881965 | 358 | --DGYAG | YIEG | K | TNQEAFYKYLSKLLTK-Q--EDSENFL--EKIKNEDFLRKQRTFDNGSIPHQVHLTEL | 420 |
| WP_050886065 | 358 | --DGYAG | YIEG | K | TNQEAFYKYLSKLLTK-Q--EDSEYFL--EKIKNEDFLRKQRTFDNGSIPHQVHLTEL | 420 |
| AHN30376 | 358 | --DGYAG | YIEG | K | TNQEAFYKYLSKLLTK-Q--EDSENFL--EKIKNEDFLRKQRTFDNGSIPHQVHLTEL | 420 |
| EAO78426 | 358 | --DGYAG | YIEG | K | TNQEAFYKYLSKLLTK-Q--EDSEYLL--EKIKNEDFLRKQRTFDNGSIPHQVHLTEL | 420 |
| CCW42055 | 358 | --DGYAG | YIEG | K | TNQEAFYKYLSKLLTK-Q--EGSEYLL--EKIKNEDFLRKQRTFDNGSIPHQVHLTEL | 420 |
| WP_003041502 | 357 | --KGYAG | YIES | G | VKQDEFYKYLKGILLQ-I--NGSGDFL--DKIDREDFLRKQRTFDNGSIPHQIHLQEM | 419 |
| WP_037593752 | 358 | --KGYAG | YIES | G | VEQDEFYKYLKGILLK-I--NGSGDFL--DKIDCEDFLRKQRTFDNGSIPHQIHLQEM | 420 |
| WP_049516684 | 358 | --NGYAG | YIEN | G | VKQDEFYKYLKNTLSK-I--DGSDYFL--DKIDREDFLRKQRTFDNGSIPHQIHLQEM | 420 |
| GAD46167 | 357 | --KGYAG | YIES | G | VEQDEFYKYLKGILLK-I--NGSGDFL--DKIDCEDFLRKQRTFDNGSIPHQIHLQEM | 419 |
| WP_018363470 | 358 | --NGYAG | YIEN | G | VKQDEFYKYLKGILLK-I--NGSGDYFL--DKIEREDFLRKQRTFDNGSIPHQIHLQEM | 420 |
| WP_003043819 | 357 | --NGYAG | YVGI | G | ATQEEFYKFIKPILEK-M--DGAEELLa--KLNRDDLLRKQRTFDNGSIPHQIHLKEL | 429 |
| WP_006269658 | 357 | --KGYAS | YIES | G | VKQDEFYKYLKGILLK-I--NGSGDFL--DKIDREDFLRKQRTFDNGSIPHQIHLKEL | 419 |
| WP_048800889 | 357 | --NGYAG | YIEN | G | VKQDEFYKYLKNTLSK-I--DGSGYFL--DKIEREDFLRKQRTFDNGSIPHQIHLQEM | 419 |
| WP_012767106 | 357 | --NGYAG | YIDG | G | ASQEEFYKFIKPILEK-M--DGTEELLa--KLNREDLLRKQRTFDNGSIPHQIHLGEL | 419 |
| WP_014612333 | 357 | --NGYAG | YIDG | G | ASQEEFYKFIKPILEK-M--DGTEELLa--KLNREDLLRKQRTFDNGSIPHQIHLGEL | 419 |

-continued

| ID | | | | | |
|---|---|---|---|---|---|
| WP_015017095 | 357 | --NGYAG | YIDG | G | ASQEEFYKFIKPILEK-M--DGTEELLa--KLNREDLLRKQRTFDNGSIPHQIHLGEL | 419 |
| WP_015057649 | 357 | --NGYAG | YIDG | G | ASQEEFYKFIKPILEK-M--DGTEELLa--KLNREDLLRKQRTFDNGSIPHQIHLGEL | 419 |
| WP_048327215 | 357 | --NGYAG | YIDG | G | ASQEEFYKFIKPILEK-M--DGTEELLa--KLNREDLLRKQRTFDNGSIPHQIHLGEL | 419 |
| WP_049519324 | 357 | --NGYAG | YIDG | G | ASQEEFYKFIKPILEK-M--DGTEELLa--KLNREDLLRKQRTFDNGSIPHQIHLGEL | 419 |
| WP_012515931 | 357 | --NGYAG | YIEG | Q | VSQEEFYKYLKPILAR-L--DGSEPLLl--KIDREDFLRKQRTFDNGSIPHQIHLEEL | 419 |
| WP_021320964 | 357 | --NGYAG | YIEG | Q | VSQEEFYKYLKPILAR-L--DGSEPLLl--KIDREDFLRKQRTFDNGSIPHQIHLEEL | 419 |
| WP_037581760 | 357 | --NGYAG | YIEG | Q | VSQEEFYKYLKPILAR-L--DGSEPLLl--KIDREDFLRKQRTFDNGSIPHQIHLEEL | 419 |
| WP_004232481 | 357 | --NGYAG | YIEN | G | VKQDIFYKHLKSIISE-K--NGGQYFL--DKIEREDFLRKQRTFDNGSIPYQIHLQEM | 419 |
| WP_009854540 | 358 | --NGYAG | YIEN | G | VKQDEFYKYLKNTLSK-I--DGSDYFL--DKIEREDFLRKQRTFDNGSIPHQIHLQEM | 420 |
| WP_012962174 | 358 | --NGYAG | YIEN | G | VKQDEFYKYLKTLSK-I--DGSDYFL--DKIEREDFLRKQRTFDNGSIPHQIHLQEM | 420 |
| WP_039695303 | 358 | --NGYAG | YIEN | G | VKQDEFYKYLKNILSK-IkiDGSDYFL--DKIEREDFLRKQRTFDNGSIPHQIHLQEM | 422 |
| WP_014334983 | 357 | --NGYAG | YIDN | G | VKQDEFYKYLKTILTK-I--DDSDYFL--DKIERDDFLRKQRTFDNGSIPHQIHLQEM | 419 |
| WP_003099269 | 357 | --NGYAG | YIDG | K | TSQEEFYKYKIPILLK-L--DGTEKLIs--KLEREDFLRKQRTFDNGSIPHQIHLNEL | 419 |
| AHY15608 | 357 | --NGYAG | YIDG | K | TSQEEFYKYKIPILLK-L--DGTEKLIs--KLEREDFLRKQRTFDNGSIPHQIHLNEL | 419 |
| AHY17476 | 357 | --NGYAG | YIDG | K | TSQEEFYKYKIPILLK-L--DGTEKLIs--KLEREDFLRKQRTFDNGSIPHQIHLNEL | 419 |
| ESR09100 | | ------ | ---- | - | ---------------------------------------------------- | |
| AGM98575 | 357 | --NGYAG | YIDG | K | TSQEEFYKYIKPILLK-L--DGTEKLIs--KLEREDFLRKQRTFDNGSIPHQIHLNEL | 419 |
| ALF27331 | 357 | --DGYAG | YIDG | K | TNQEAFYKYLKGLLNK-I--EGSGYFL--DKIEREDFLRKQRTFDNGSIPHQIHLQEM | 419 |
| WP_018372492 | 355 | --PSYAA | YVSG | A | VTEDDFYKESKGLLID-V--EGAEYFL--EKIEREDFLRKQRTFDNGAIPNQVHVKEL | 432 |
| WP_045618028 | 358 | --DGYAG | YIDG | K | TTQEAFYKYIKNLLSK-L--EGADYFL--DKIEREDFLRKQRTFDNGSIPHQIHLQEM | 420 |
| WP_045635197 | 357 | --DGYAG | YIDG | K | TTQETFYKYIKNLLSK-F--EGTDYFL--DKIEREDFLRKQRTFDNGSIPHQIHLQEM | 419 |
| WP_002263549 | 357 | --DGYAG | YIDG | K | TNQEAFYKYLKGLLNK-I--EGSGYFL--DKIEREDFLRKQRTFDNGSIPHQIHLQEM | 419 |
| WP_002263887 | 357 | --DGYAG | YIDG | K | TNQEAFYKYLKGLLNK-I--EGSGYFL--DKIEREDFLRKQRTFDNGSIPHQIHLQEM | 419 |
| WP_002264920 | 357 | --NGYAG | YIEN | G | VKQDEFYKYLKNTLSK-I--AGSDYFL--DKIEREDFLRKQRTFDNGSIPHQIHLQEM | 419 |
| WP_002269043 | 357 | --DGYAG | YIDG | K | TNQEAFYKYLKGLLNK-I--EGSGYFL--DKIEREDFLRKQRTFDNGSIPHQIHLQEM | 419 |
| WP_002269448 | 357 | --DGYAG | YIDG | K | TNQEAFYKYLKGLLNK-I--EGSGYFL--DKIEREDFLRKQRTFDNGSIPHQIHLQEM | 419 |
| WP_002271977 | 357 | --DGYAG | YIDG | K | TNQEAFYKYLKGLLNK-I--EGSGYFL--DKIEREDFLRKQRTFDNGSIPHQIHLQEM | 419 |

-continued

| | | | | | | |
|---|---|---|---|---|---|---|
| WP_002272766 | 357 | --DGYAG | YIDG | K | TNQEAFYKYLKGLLNK-I--EGSGYFL--DKIEREDFLRKQRTFDNGSIPHQIHLQEM | 419 |
| WP_002273241 | 357 | --DGYAG | YIDG | K | TNQEAFYKYLKGLLNK-I--EGSGYFL--DKIEREDFLRKQRTFDNGSIPHQIHLQEM | 419 |
| WP_002275430 | 357 | --DGYAG | YIDG | K | TNQEAFYKYLKGLLNK-I--EGSGYFL--DKIEREDFLRKQRTFDNGSIPHQIHLQEM | 419 |
| WP_002276448 | 357 | --DGYAG | YIDG | K | TNQEAFYKYLKGLLNK-I--EGSGYFL--DKIEREDFLRKQRTFDNGSIPHQIHLQEM | 419 |
| WP_002277050 | 357 | --NGYAG | YIEN | G | VKQDEFYKYLKNTLSK-I--AGSDYFL--DKIEREDFLRKQRTFDNGSIPHQIHLQEM | 419 |
| WP_002277364 | 357 | --DGYAG | YIDG | K | TNQEAFYKYLKGLLNK-I--EGSGYFL--DKIEREDFLRKQRTFDNGSIPHQIHLQEM | 419 |
| WP_002279025 | 357 | --DGYAG | YIDG | K | TNQEAFYKYLKGLLNK-I--EGSGYFL--DKIEREDFLRKQRTFDNGSIPHQIHLQEM | 419 |
| WP_002279859 | 357 | --DGYAG | YIDG | K | TNQEAFYKYLKGLLNK-I--EGSGYFL--DKIEREDFLRKQRTFDNGSIPHQIHLQEM | 419 |
| WP_002280230 | 357 | --DGYAG | YIDG | K | TNQEAFYKYLKGLLNK-I--EGSGYFL--DKIEREDFLRKQRTFDNGSIPHQIHLQEM | 419 |
| WP_002281696 | 357 | --DGYAG | YIDG | K | TNQEAFYKYLKGLLNK-I--EGSGYFL--DKIEREDFLRKQRTFDNGSIPHQIHLQEM | 419 |
| WP_002282247 | 357 | --NGYAG | YIEN | G | VKQDEFYKYLKNTLSK-I--TGSDYFL--DQIEREDFLRKQRTFDNGSIPHQIHLQEM | 419 |
| WP_002282906 | 357 | --DGYAG | YIDG | K | TNQEAFYKYLKGLLNK-I--EGSGYFL--DKIEREDFLRKQRTFDNGSIPHQIHLQEM | 419 |
| WP_002283846 | 357 | --DGYAG | YIDG | K | TNQEAFYKYLKGLLNK-I--EGSGYFL--DKIEREDFLRKQRTFDNGSIPHQIHLQEM | 419 |
| WP_002287255 | 357 | --DGYAG | YIDG | K | TNQEAFYKYLKGLLNK-I--EGSGYFL--DKIEREDFLRKQRTFDNGSIPHQIHLQEM | 419 |
| WP_002288990 | 357 | --DGYAG | YIDG | K | TNQEAFYKYLKGLLNK-I--EGSGYFL--DKIEREDFLRKQRTFDNGSIPHQIHLQEM | 419 |
| WP_002289641 | 357 | --NGYAG | YVGA | D | ATEEEFYKYVKGILNK-V--EGADVWL--DKIEREDFLRKQRTFDNGSIPHQIHLQEM | 429 |
| WP_002290427 | 357 | --DGYAG | YIDG | K | TNQEAFYKYLKGLLNK-I--EGSGYFL--DKIEREDFLRKQRTFDNGSIPHQIHLQEM | 419 |
| WP_002295753 | 357 | --DGYAG | YIDG | K | TNQEAFYKYLKGLLNK-I--EGSGYFL--DKIEREDFLRKQRTFDNGSIPHQIHLQEM | 419 |
| WP_002296423 | 357 | --DGYAG | YIDG | K | TNQEAFYKYLKGLLNK-I--EGSGYFL--DKIEREDFLRKQRTFDNGSIPHQIHLQEM | 419 |
| WP_002304487 | 357 | --DGYAG | YIDG | K | TNQEAFYKYLKGLLNK-I--EGSGYFL--DKIEREDFLRKQRTFDNGSIPHQIHLQEM | 419 |
| WP_002305844 | 357 | --DGYAG | YIDG | K | TNQEAFYKYLKGLLNK-I--EGSGYFL--DKIEREDFLRKQRTFDNGSIPHQIHLQEM | 419 |
| WP_002307203 | 357 | --DGYAG | YIDG | K | TNQEAFYKYLKGLLNK-I--EGSGYFL--DKIEREDFLRKQRTFDNGSIPHQIHLQEM | 419 |
| WP_002310390 | 357 | --DGYAG | YIDG | K | TNQEAFYKYLKGLLNK-I--EGSGYFL--DKIEREDFLRKQRTFDNGSIPHQIHLQEM | 419 |
| WP_002352408 | 357 | --DGYAG | YIDG | K | TNQEAFYKYLKGLLNK-I--EGSGYFL--DKIEREDFLRKQRTFDNGSIPHQIHLQEM | 419 |
| WP_012997688 | 357 | --DGYAG | YIDG | K | TNQEAFYKYLKGLLNK-I--EGSGYFL--DKIEREDFLRKQRTFDNGSIPHQIHLQEM | 419 |
| WP_014677909 | 357 | --DGYAG | YIDG | K | TNQEAFYKYLKGLLNK-I--EGSGYFL--DKIEREDFLRKQRTFDNGSIPHQIHLQEM | 419 |
| WP_019312892 | 357 | --DGYAG | YIDG | K | TNQEAFYKYLKGLLNK-I--EGSGYFL--DKIEREDFLRKQRTFDNGSIPHQIHLQEM | 419 |

| Name | | | | | Sequence | |
|---|---|---|---|---|---|---|
| WP_019313659 | 357 | --DGYAG | YIDG | K | TNQEAFYKYLKGLLNK-I--EGSGYFL--DKIEREDFLRKQRTFDNGSIPHQIHLQEM | 419 |
| WP_019314093 | 357 | --DGYAG | YIDG | K | TNQEAFYKYLKGLLNK-I--EGSGYFL--DKIEREDFLRKQRTFDNGSIPHQIHLQEM | 419 |
| WP_019315370 | 357 | --DGYAG | YIDG | K | TNQEAFYKYLKGLLNK-I--EGNGYFL--DKIEREDFLRKQRTFDNGSIPHQIHLQEM | 419 |
| WP_019803776 | 357 | --DGYAG | YIDG | K | TNQEAFYKYLKGLLNK-I--EGSGYFL--DKIEREDFLRKQRTFDNGSIPHQIHLQEM | 419 |
| WP_019805234 | 357 | --DGYAG | YIDG | K | TNQEAFYKYLKGLLNK-I--EGSGYFL--DKIEREDFLRKQRTFDNGSIPHQIHLQEM | 419 |
| WP_024783594 | 357 | --DGYAG | YIDG | K | TNQEAFYKYLKGLLNK-I--EGSGYFL--DKIEREDFLRKQRTFDNGSIPHQIHLQEM | 419 |
| WP_024784288 | 357 | --NGYAG | YIEN | G | VKQDEFYKYLKNTLSK-I--TGSDYFL--DQIEREDFLRKQRTFDNGSIPHQIHLQEM | 419 |
| WP_024784666 | 357 | --DGYAG | YIDG | K | TNQEAFYKYLKGLLNK-I--EGSGYFL--DKIEREDFLRKQRTFDNGSIPHQIHLQEM | 419 |
| WP_024784894 | 357 | --DGYAG | YIDG | K | TNQEAFYKYLKGLLNK-I--EGSGYFL--DKIEREDFLRKQRTFDNGSIPHQIHLQEM | 419 |
| WP_024786433 | 357 | --NGYAG | YIEN | G | VKQDEFYKYLKNTLSK-I--AGSDYFL--DKIEREDFLRKQRTFDNGSIPHQIHLQEM | 419 |
| WP_049473442 | 357 | --DGYAG | YIDG | K | TNQEAFYKYLKGLLNK-I--EGSGYFL--DKIEREDFLRKQRTFDNGSIPHQIHLQEM | 419 |
| WP_049474547 | 357 | --DGYAG | YIDG | K | TNQEAFYKYLKGLLNK-I--EGSGYFL--DKIEREDFLRKQRTFDNGSIPHQIHLQEM | 419 |
| EMC03581 | 350 | --DGYAG | YIDG | K | TNQEAFYKYLKGLLNK-I--EGSGYFL--DKIEREDFLRKQRTFDNGSIPHQIHLQEM | 412 |
| WP_000428612 | 358 | --DGYAG | YIDG | K | TTQESFYKYIKNLLSK-F--EGADYFL--EKIEREDFLRKQRTFDNGSIPHQIHLQEM | 420 |
| WP_000428613 | 358 | --DGYAG | YIDG | K | TTQELFYKYIKNLLSK-F--EGTDYFL--EKIEREDFLRKQRTFDNGSIPHQIHLQEM | 420 |
| WP_049523028 | 357 | --DGYAG | YIDG | K | TTQEGFYKYIKNLISK-F--EGAEYFL--EKIEREDFLRKQRTFDNGSIPHQIHLQEM | 419 |
| WP_003107102 | 326 | --NGYAG | YING | K | TSQEDFYKYIKPILSK-L--KGAESLIs--KLEREDFLRKQRTFDNGSIPHQIHLNEL | 388 |
| WP_054279288 | 359 | --DGYAG | YISG | K | TSQEAFYKYIKPILET-L--DGAEDFLt--KINREDFLRKQRTFDNGSIPHQIHLGEL | 421 |
| WP_049531101 | 358 | -EGYAG | YIDS | K | TTQEAFYKYIKNLLSK-I--DGADYLL--DKIEREDFLRKQRTFDNGSIPHQIHLQEM | 420 |
| WP_049538452 | 358 | --DGYAG | YVDG | K | TTQEAFYKYIKNLLSK-F--EGADYFL--EKIEREDFLRKQRTFDNGSIPHQIHLQEM | 420 |
| WP_049549711 | 358 | --DGYAG | YIDG | K | TTQEAFYKYIKNLLSK-F--EGTDYFL--EKIEREDFLRKQRTFDNGSIPHQIHLQEM | 420 |
| WP_007896501 | 359 | --NGYAG | YIEG | K | VSQEDFYKYLKNLLSR-L--KGGDEFLa--KIDRDDFLRKQRTFDNGSIPHQIHLKEL | 421 |
| EFR44625 | 311 | --NGYAG | YIEG | K | VSQEDFVYRYILSR-L--KGGDEFLa--KIDRDDFLRKQRTFDNGSIPHQIHLKEL | 373 |
| WP_002897477 | 357 | --DGYAG | FIDG | K | TTQEAFYKYIKNLLSK-L--EGADYFL--NKIEREDFLRKQRTFDNGSIPHQIHLQEM | 419 |
| WP_002906454 | 357 | --DGYAG | YIDG | K | TTQETFYKYIKNLLSK-F--EGADYFL--DKIEREDFLRKQRTFDNGSIPHQIHLQEM | 419 |
| WP_009729476 | 358 | --DGYAG | YIDG | K | TNQEDFYKYLKNLLQK-V--DGGDYFI--EKIEREDFLRKQRTFDNGSIPHQVHLDEM | 420 |
| CQR24647 | 358 | --NGYAG | YIDG | K | TNQEDFYKYLKNLLQK-V--DGGDYFI--EKIEREDFLRKQRTFDNGSIPHQVHLDEM | 420 |

| | | | | | |
|---|---|---|---|---|---|
| WP_000066813 | 358 | --DGYAG | YIDG | K | TTQEAFYKYIKNLLSK-F--EGADYFL--DKIEREDFLKKQRTFDNGSIPHQIHLQEM | 420 |
| WP_009754323 | 358 | --DGYAG | YIDG | K | TTQEAFYKYIKNLLSK-F--EGADYFL--DKIEREDFLRKQRTFDNGSIPHQIHLQEM | 420 |
| WP_044674937 | 357 | --DGYAG | YIEG | K | TTQENFYRFIKKAIEK-I--EGSDYFI--DKIDREDFLRKQRTFDNGSIPHQIHLQEM | 419 |
| WP_044676715 | 357 | --DGYAG | YIEG | K | TTQENFYRFIKKAIEK-I--EGSNYFI--DKIDREDFLRKQRTFDNGSIPHQIHLQEM | 419 |
| WP_044680361 | 357 | --DGYAG | YIEG | K | TTQENFYRFIKKAIEK-I--EGSNYFI--DKIDREDFLRKQRTFDNGSIPHQIHLQEM | 419 |
| WP_044681799 | 357 | --DGYAG | YIEG | K | TTQENFYRFIKKAIEK-I--EGSDYFI--DKIDREDFLRKQRTFDNGSIPHQIHLQEM | 419 |
| WP_049533112 | 357 | --KGYAG | YIEN | G | VKQDEFYKYLKGILLQ-I--NSGDFL--DKIDREDFLRKQRTFDNGSIPHQIHLQEM | 419 |
| WP_029090905 | 316 | fyTDYIG | YEES | K | SKEERLFKHIELLLAKeNvlTTVEHALleKNITFASLLPLQRsSRNAVIPYQVHEKEL | 403 |
| WP_006506696 | 361 | ksKGTYN | YINR | K | APVDEFYKYVKKCIEK-VdtPEAKQIln--DIELENFLLKQNSRTNGSVPYQMQLDEM | 429 |
| AIT42264 | 357 | --NGYAG | YIDG | G | ASQEEFYKFIKPILEK-M--DGTEELLv--KLNREDLLRKQRTFDNGSIPHQIHLGEL | 419 |
| WP_034440723 | 363 | --NGYAG | YIDG | K | TSQEDFYKFVKAQLKG---eENGEYFL--EAIENENFLRKQRSFYNGVIPYQIHLQEL | 425 |
| AKQ21048 | 357 | --NGYAG | YIDG | G | ASQEEFYKFIKPILEK-M--DGTEELLv--KLNREDLLRKQRTFDNGSIPHQIHLGEL | 419 |
| WP_004636532 | 356 | --NGYAG | YIDG | K | TNQEDFYKYIEKVMKT-IksDKKDYFL--DKIDREVFLRKQRSFYNSVIPHQIHLQEM | 420 |
| WP_002364836 | 363 | --DGYAG | YIAH | A | VSQLKFYQYVKKIIQD-I--AGAEYFL--EKIAQENFLRKQRTFDNGVIPHQIHLAEL | 427 |
| WP_002413717 | 314 | --DGYAG | YIAH | A | VSQLKFYQYVKKIIQD-I--AGAEYFL--EKIAQENFLRKQRTFDNGVIPHQIHLAEL | 378 |
| WP_016631044 | 100 | --NGYAG | YIDG | K | TTQEDFYKFLKKELNG-I--AGSERFM--EKVDQENFLLKQRTTANGVIPHQVHLTEL | 162 |
| EMS75795 | 363 | --DGYAG | YIAH | A | VSQLKFYQYVKKIIQD-I--AGAEYFL--EKIAQENFLRKQRTFDNGVIPHQIHLAEL | 427 |
| WP_002373311 | 363 | --DGYAG | YITH | A | VSQLKFYQYVKKIIQD-I--AGAEYFL--EKIAQENFLRKQRTFDNGVIPHQIHLAEL | 427 |
| WP_002378009 | 363 | --DGYAG | YITH | A | VSQLKFYQYVKKIIQD-I--AGAEYFL--EKIAQENFLRKQRTFDNGVIPHQIHLAEL | 427 |
| WP_002407324 | 363 | --DGYAG | YIAH | A | VSQLKFYQYVKKIIQD-I--AGAEYFL--EKIAQENFLRKQRTFDNGVIPHQIHLAEL | 427 |
| WP_010775580 | 365 | --DGYAG | YIAH | A | VSQLKFYQYVKKIIQD-I--AGAEYFL--EKIAQENFLRKQRTFDNGVIPHQIHLAEL | 429 |
| WP_010818269 | 363 | --DGYAG | YIAH | A | VSQLKFYQYVKKIIQD-I--AGAEYFL--EKIAQENFLRKQRTFDNGVIPHQIHLAEL | 427 |
| WP_010824395 | 363 | --DGYAG | YITH | A | VSQLKFYQYVKKIIQD-I--AGAEYFL--EKIAQENFLRKQRTFDNGVIPHQIHLAEL | 427 |
| WP_016622645 | 363 | --DGYAG | YIAH | A | VSQLKFYQYVKKIIQD-I--AGAEYFL--EKIAQENFLRKQRTFDNGVIPHQIHLAEL | 427 |
| WP_033624816 | 363 | --DGYAG | YIAH | A | VSQLKFYQYVKKIIQD-I--AGAEYFL--EKIAQENFLRKQRTFDNGVIPHQIHLAEL | 427 |
| WP_033625576 | 363 | --DGYAG | YIAH | A | VSQLKFYQYVKKIIQD-I--AGAEYFL--EKIAQENFLRKQRTFDNGVIPHQIHLAEL | 427 |
| WP_033789179 | 363 | --DGYAG | YIAH | A | VSQLKFYQYVKKIIQD-I--AGAEYFL--EKIAQENFLRKQRTFDNGVIPHQIHLAEL | 427 |

| | | | | | |
|---|---|---|---|---|---|
| WP_002310644 | 361 | --NGYAG | YIEG | H | ATQEDFYKFVKKELTG-I--RGSEVFL--TKIEQENFLRKQRTFDNGVIPHQIHLTEL | 423 |
| WP_002312694 | 362 | --NGYAG | YIEG | H | ATQEAFYKFVKKELTG-I--RGSEVFL--TKIEQENFLRKQRTFDNGVIPHQIHLSEL | 424 |
| WP_002314015 | 362 | --NGYAG | YIEG | H | ATQEDFYKFVKKELTG-I--RGSEVFL--TKIEQENFLRKQRTFDNGVIPHQIHLTEL | 424 |
| WP_002320716 | 362 | --NGYAG | YIEG | H | ATQEDFYKFVKKELTG-I--RGSEVFL--TKIEQENFLRKQRTFDNGVIPHQIHLTEL | 424 |
| WP_002330729 | 361 | --NGYAG | YIEG | H | ATQEDFYKFVKKELTG-I--RGSEVFL--TKIEQENFLRKQRTFDNGVIPHQIHLTEL | 423 |
| WP_002335161 | 362 | --NGYAG | YIEG | H | ATQEDFYKFVKKELTG-I--RGSEVFL--TKIEQENFLRKQRTFDNGVIPHQIHLTEL | 424 |
| WP_002345439 | 362 | --NGYAG | YIEG | H | ATQEDFYKFVKKELTG-I--RGSEVFL--TKIEQENFLRKQRTFDNGVIPHQIHLTEL | 424 |
| WP_034867970 | 355 | --NGYAG | YIKG | K | TTQEEFYKFVKKELSG-V--VGSEPFL--EKIDQETFLLKQRTYTNGVIPHQVHLIEL | 417 |
| WP_047937432 | 362 | --NGYAG | YIEG | H | ATQEDFYKFVKKELTG-I--RGSEVFL--TKIEQENFLRKQRTFDNGVIPHQIHLTEL | 424 |
| WP_010720994 | 355 | --NGYAG | YIKG | K | TTQEEFYKFVKKELSG-V--VGSEPFL--EKIDQETFLLKQRTYTNGVIPHQVHLIEL | 417 |
| WP_010737004 | 355 | --NGYAG | YIKG | K | TTQEEFYKFVKKELSG-V--VGSEPFL--EKIDQETFLLKQRTYTNGVIPHQVHLIEL | 417 |
| WP_034700478 | 355 | --NGYAG | YIKG | K | TTQEEFYKFVKKELSG-V--VGSEPFL--EKIDQETFLLKQRTYTNGVIPHQVHLIEL | 417 |
| WP_007209003 | 359 | --NGYAG | YIDG | K | TKEEEFYKYLKTTLVQ---kSGYQYFI--EKIEQENFLRKQRIYDNGVIPHQVHAEEL | 421 |
| WP_023519017 | 355 | --NGYAG | YVKG | K | ATQEDFYKFLRTELAG-L--EESQSIM--EKIDLEIYLLKQRTFANGVIPHQIHLVEM | 417 |
| WP_010770040 | 358 | --SGYAG | YVEN | S | VTQAEFYKYIKKAIEK-V--PGAEYFL--EKIEQETFLDKQRTFNNGVIPHQIHLEEL | 422 |
| WP_048604708 | 354 | --DGYAG | YIDN | S | TSQEKFYKYITNLIEK-I--DGAEYFL--KKIENEDFLRKQRTFDNGIIPHQIHLEEL | 418 |
| WP_010750235 | 355 | --DGYAG | YIDG | K | TTQADFYKFLKKELTG-V--PGSEPML--AKIDQENFLLKQRTPTNGVIPHQVHLTEF | 417 |
| AII16583 | 396 | --NGYAG | YIDG | G | ASQEEFYKFIKPILEK-M--DGTEELLv--KLNREDLLRKQRTFDNGSIPHQIHLGEL | 458 |
| WP_029073316 | 367 | kkNNYCN | YINH | K | TPVDEFYKYIKKLIEK-IddPDVKTILn--KIELESFMLKQNSRTNGAVPYOMQLDEL | 435 |
| WP_031589969 | 367 | kkNNYCN | YINH | K | TPVDEFYKYIKLIEK-IdAPDVKTILn--KIELESMLKQNSRTNGAVPYOMQLDEL | 435 |
| KDA45870 | 354 | -iSGYAG | YIDG | K | VSEEDFYKYKTKKTLKG-I--PETEEILq--KIDANNVLRKQRTFDNGAIPHQVHLKEL | 417 |
| WP_039099354 | 360 | ------ | YVDG | K | -SKEDFYGDITKALKMnPdhPIVSEIKk--LIELDQFMPKQRTKDNGAIPHQLHQQEL | 425 |
| AKP02966 | 349 | --QAYDD | YINK | K | ---KELYTSLKKFPLKVaLp-TNLAKEAe-EKISKGTYLIVKPRNSENGVPYQLNKIEM | 415 |
| WP_010991369 | 363 | --HGYAG | YIDG | - | TKQADFYKYMKMTLEN-I--EGADYFI--AKIEKENFLRKQRTFDNGAIPHQLHLEEL | 425 |
| WP_033838504 | 363 | --HGYAG | YIDG | - | TKQADFYKYMKMTLEN-I--EGADYFI--AKIEKENFLRKQRTFDNGAIPHQLHLEEL | 425 |
| EHN60060 | 366 | --HGYAG | YIDG | - | TKQADFYKYMKMTLEN-I--EGADYFI--AKIEKENFLRKQRTFDNGAIPHQLHLEEL | 428 |
| EFR89594 | 132 | --HGYAG | YIDG | - | TKQADFYKYMKTTLEN-I--EGADYFI--AKIEKENFLRKQRTFDNGAIPHQLHLEEL | 194 |

-continued

| ID | Start | Seq1 | Seq2 | Seq3 | Seq4 | End |
|---|---|---|---|---|---|---|
| WP_038409211 | 363 | --DGYAG | YIDG | - | TTQEKFYKYMKKMLAN-I--DGADYFI--DQIEEENFLRKQRTFDNGTIPHQLHLEEL | 425 |
| EFR95520 | 1 | ------- | ---- | - | -------MKKMLAN-I--DGADYFI--DQIEEENFLRKQRTFDNGTIPHQLHLEEL | 44 |
| WP_003723650 | 363 | --DGYAG | YIDG | - | TKQVDFYKYLKTLEN-I--EGSDYFI--AKIEEENFLRKQRTFDNGAIPHQLHLEEL | 425 |
| WP_003727705 | 363 | --DGYAG | YIDG | - | TKQVDFYKYLKTLEN-V--EGADYFI--AKIEEENFLRKQRTFDNGVIPHQLHLEEL | 425 |
| WP_003730785 | 363 | --DGYAG | YIDG | - | TKQVDFYKYLKTLEN-V--EGADYFI--TKIEEENFLRKQRTFDNGVIPHQLHLEEL | 425 |
| WP_003733029 | 363 | --HGYAG | YISG | - | TKQADFYKYMKATLEK-I--EGADYFI--TKIEEENFLRKQRTFDNGVIPHQLHLEEL | 425 |
| WP_003739838 | 363 | --DGYAG | YIDG | - | TKQVDFYKYLKTLEN-I--EGADYFI--AKIEEENFLRKQRTFDNGAIPHQLHLEEL | 425 |
| WP_014601172 | 363 | --DGYAG | YIDG | - | TKQVDFYKYLKTILEN-I--EGADYFI--AKIEEENFLRKQRTFDNGAIPHQLHLEEL | 425 |
| WP_023548323 | 363 | --DGYAG | YIDG | - | TKQVDFYKYLKTLEN-V--EGADYFI--TKIEEENFLRKQRTFDNGVIPHQLHLEEL | 425 |
| WP_031665337 | 363 | --DGYAG | YIDG | - | TKQVDFYKYLKTILEN-I--EGSDYFI--AKIEEENFLRKQRTFDNGAIPHQLHLEEL | 425 |
| WP_031669209 | 363 | --HGYAG | YISG | - | TKQADFYKYMKATLEK-I--EGADYFI--AKIEEENFLRKQRTFDNGAIPHQLHLEEL | 425 |
| WP_033920898 | 363 | --DGYAG | YIDG | - | TKQVDFYKYLKTILEN-I--EGADYFI--AKIEEENFLRKQRTFDNGAIPHQLHLEEL | 425 |
| AKI42028 | 366 | --DGYAG | YIDG | - | TKQVDFYKYLKTILEN-I--EGADYFI--AKIEEENFLRKQRTFDNGAIPHQLHLEEL | 428 |
| AKI50529 | 366 | --DGYAG | YIDG | - | TKQVDFYKYLKTILEN-I--EGSDYFI--AKIEEENFLRKQRTFDNGAIPHQLHLEEL | 428 |
| EFR83390 | | ------- | ---- | - | ---------------------------------------- | |
| WP_046323366 | 363 | --DGYAG | YIEG | - | TKQEAFYKYMKKMLEH-V--EGADYFI--NQIEEENFLRKQRTFDNGAIPHQLHLEEL | 425 |
| AKE81011 | 373 | --NGYAG | YIDG | G | ASQEEFYKFIKPILEK-M--DGTEELLv--KLNREDLLRKQRTFDNGSIPHQIHLGEL | 435 |
| CU082355 | 365 | kvKGYYN | YINR | K | APVDEFYKFVKKCIEK-VdtPEAKQILh--DIELENFLLKQNSRTNGSVPYQMQLDEM | 433 |
| WP_033162887 | 366 | klHNVLG | YIKY | D | TPVEEFYKYIKIGLLAK-VdtDEAREIle--RIDLEKFMLKQNSRTNGSIPYQMQKDEM | 434 |
| AGZ01981 | 390 | --NGYAG | YIDG | G | ASQEEFYKFIKPILEK-M--DGTEELLv--KLNREDLLRKQRTFDNGSIPHQIHLGEL | 452 |
| AKA60242 | 357 | --NGYAG | YIDG | G | ASQEEFYKFIKPILEK-M--DGTEELLv--KLNREDLLRKQRTFDNGSIPHQIHLGEL | 419 |
| AKS40380 | 357 | --NGYAG | YIDG | G | ASQEEFYKFIKPILEK-M--DGTEELLv--KLNREDLLRKQRTFDNGSIPHQIHLGEL | 419 |
| 4UN5_B | 361 | --NGYAG | YIDG | G | ASQEEFYKFIKPILEK-M--DGTEELLv--KLNREDLLRKQRTFDNGSIPHQIHLGEL | 423 |
| WP_010922251 | 420 | HAILRRQEDFYPFLKD | -NRE | | KIEKILTFRIPYYVGPL  ARG-n-SRFAWMTR---KSEETITPWNFE V VDKGA | 486 |
| WP_039695303 | 423 | HAILRRQGDYPFFLKE | -KQD | | RIEKILTFRIPYYVGPL  VRKD--SRFAWAEY---RSDEKITPWNFDKVIDKEK | 489 |
| WP_045635197 | 420 | NAILRRQGEYYPFLKD | -NKE | | KIEKILTFRIPYYVGPL  ARGN--RDFAWLTR---NSDEAIRPWNFEEIVDKAS | 486 |
| 5AXW_A | 184 | KQLLKVQKAYHQLDQSfi | -D | | TYIDLLETRTYYEGPG  ---Eg-SPFGWKDI-------------------- | 229 |

| | | | | | |
|---|---|---|---|---|---|
| WP_009880683 | 104 | HAILRRQEDFYPFLKD--NRE | KIEKILTFRIPYYVGPL | ARG-n-SRFAWMTR---KSEETITPWNFEEVVDKGA | 170 |
| WP_010922251 | 420 | HAILRRQEDFYPFLKD--NRE | KIEKILTFRIPYYVGPL | ARG-n-SRFAWMTR---KSEETITPWNFEEVVDKGA | 486 |
| WP_011054416 | 420 | HAILRRQEDFYPFLKD--NRE | KIEKILTFRIPYYVGPL | ARG-n-SRFAWMTR---KSEETITPWNFEEVVDKGA | 486 |
| WP_011284745 | 420 | HAILRRQEDFYPFLKD--NRE | KIEKILTFRIPYYVGPL | ARG-n-SRFAWMTR---KSEETITPWNFEEVVDKGA | 486 |
| WP_011285506 | 420 | HAILRRQEDFYPFLKD--NRE | KIEKILTFRIPYYVGPL | ARG-n-SRFAWMTR---KSEETITPWNFEEVVDKGA | 486 |
| WP_011527619 | 420 | HAILRRQEDFYPFLKD--NRE | KIEKILTFRIPYYVGPL | ARG-n-SRFAWMTR---KSEETITPWNFEEVVDKGA | 486 |
| WP_012560673 | 420 | HAILRRQEDFYPFLKD--NRE | KIEKILTFRIPYYVGPL | ARG-n-SRFAWMTR---KSEETITPWNFEEVVDKGA | 486 |
| WP_014407541 | 420 | HAILRRQEDFYPFLKD--NRE | KIEKILTFRIPYYVGPL | ARG-n-SRFAWMTR---KSEETITPWNFEEVVDKGA | 486 |
| WP_020905136 | 420 | HAILRRQEDFYPFLKD--NRE | KIEKILTFRIPYYVGPL | ARG-n-SRFAWMTR---KSEETITPWNFEEVVDKGA | 486 |
| WP_023080005 | 420 | HAILRRQEDFYPFLKD--NRE | KIEKILTFRIPYYVGPL | ARG-n-SRFAWMTR---KSEETITPWNFEEVVDKGA | 486 |
| WP_023610282 | 420 | HAILRRQEDFYPFLKD--NRE | KIEKILTFRIPYYVGPL | ARG-n-SRFAWMTR---KSEETITPWNFEEVVDKGA | 486 |
| WP_030125963 | 420 | HAILRRQEDFYPFLKD--NRE | KIEKILTFRIPYYVGPL | ARG-n-SRFAWMTR---KSEETITPWNFEEVVDKGA | 486 |
| WP_030126706 | 420 | HAILRRQEDFYPFLKD--NRE | KIEKILTFRIPYYVGPL | ARG-n-SRFAWMTR---KSEETITPWNFEEVVDKGA | 486 |
| WP_031488318 | 420 | HAILRRQEDFYPFLKD--NRE | KIEKILTFRIPYYVGPL | ARG-n-SRFAWMTR---KSEETITPWNFEEVVDKGA | 486 |
| WP_032460140 | 420 | HAILRRQEDFYPFLKD--NRE | KIEKILTFRIPYYVGPL | ARG-n-SRFAWMTR---KSEETITPWNFEEVVDKGA | 486 |
| WP_032461047 | 420 | HAILRRQEDFYPFLKD--NRE | KIEKILTFRIPYYVGPL | ARG-n-SRFAWMTR---KSEETITPWNFEEVVDKGA | 486 |
| WP_032462016 | 420 | HAILRRQEDFYPFLKD--NRE | KIEKILTFRIPYYVGPL | ARG-n-SRFAWMTR---KSEETITPWNFEEVVDKGA | 486 |
| WP_032462936 | 420 | HAILRRQEDFYPFLKD--NRE | KIEKILTFRIPYYVGPL | ARG-n-SRFAWMTR---KSEETITPWNFEEVVDKGA | 486 |
| WP_032464890 | 420 | HAILRRQEDFYPFLKD--NRE | KIEKILTFRIPYYVGPL | ARG-n-SRFAWMTR---KSEETITPWNFEEVVDKGA | 486 |
| WP_033888930 | 245 | HAILRRQEDFYPFLKD--NRE | KIEKILTFRIPYYVGPL | ARG-n-SRFAWMTR---KSEETITPWNFEEVVDKGA | 311 |
| WP_038431314 | 420 | HAILRRQEDFYPFLKD--NRE | KIEKILTFRIPYYVGPL | ARG-n-SRFAWMTR---KSEETITPWNFEEVVDKGA | 486 |
| WP_038432938 | 420 | HAILRRQEDFYPFLKD--NRE | KIEKILTFRIPYYVGPL | ARG-n-SRFAWMTR---KSEETITPWNFEEVVDKGA | 486 |
| WP_038434062 | 420 | HAILRRQEDFYPFLKD--NRE | KIEKILTFRIPYYVGPL | ARG-n-SRFAWMTR---KSEETITPWNFEEVVDKGA | 486 |
| BAQ51233 | 331 | HAILRRQEDFYPFLKD--NRE | KIEKILTFRIPYYVGPL | ARG-n-SRFAWMTR---KSEETITPWNFEEVVDKGA | 397 |
| KGE60162 | | ------------------- | ----------------- | ------------------------------------ | |
| KGE60856 | | ------------------- | ----------------- | ------------------------------------ | |
| WP_002989955 | 420 | HAILRRQEDFYPFLKD--NRE | KIEKILTFRIPYYVGPL | ARG-n-SRFAWMTR---KSEETITPWNFEEVVDKGA | 486 |

-continued

| | | | | | |
|---|---|---|---|---|---|
| WP_003030002 | 420 | HAILRRQEEHYPFLKE--NQD | RIEKILTFRIPYYVGPL | ARKG--SRFAWAEY---KADEKITPWNFDDILDKEK | 486 |
| WP_003065552 | 423 | HAILRRQGDYYPFLKE--NQD | RIEKILTFRIPYYVGPL | ARKD--SRFSWAEY---HSDEKITPWNFDKVIDKEK | 489 |
| WP_001040076 | 421 | RAIIRRQSEYYPFLKE--NLD | RIEKILTFRIPYYVGPL | AREK--SDFAWMTR---KTDDSIRPWNFEDLVDKEK | 487 |
| WP_001040078 | 421 | KAIIRRQSEYYPFLKE--NQD | RIEKILTFRIPYYIGPL | AREK--SDFAWMTR---KTDDSIRPWNFEDLVDKEK | 487 |
| WP_001040080 | 421 | KAIIRRQSEYYPFLKE--NQD | RIEKILTFRIPYYIGPL | AREK--SDFAWMTR---KTDDSIRPWNFEDLVDKEK | 487 |
| WP_001040081 | 421 | KAIIRRQSEYYPFLKE--NQD | RIEKILTFRIPYYIGPL | AREK--SDFAWMTR---KTDDSIRPWNFEDLVDKEK | 487 |
| WP_001040083 | 421 | KAIIRRQSEYYPFLKE--NQD | RIEKILTFRIPYYIGPL | AREK--SDFAWMTR---KTDDSIRPWNFEDLVDKEK | 487 |
| WP_001040085 | 421 | KAIIRRQSEYYPFLKE--NQD | RIEKILTFRIPYYIGPL | AREK--SDFAWMTR---KTDDSIRPWNFEDLVDKEK | 487 |
| WP_001040087 | 421 | KAIIRRQSEYYPFLKE--NQD | RIEKILTFRIPYYIGPL | AREK--SDFAWMTR---KTDDSIRPWNFEDLVDKEK | 487 |
| WP_001040088 | 421 | KAIIRRQSEYYPFLKE--NQD | RIEKILTFRIPYYIGPL | AREK--SDFAWMTR---KTDDSIRPWNFEDLVDKEK | 487 |
| WP_001040089 | 421 | KAIIRRQSEYYPFLKE--NQD | RIEKILTFRIPYYIGPL | AREK--SDFAWMTR---KTDDSIRPWNFEDLVDKEK | 487 |
| WP_001040090 | 421 | KAIIRRQSEYYPFLKE--NQD | RIEKILTFRIPYYIGPL | AREK--SDFAWMTR---KTDDSIRPWNFEDLVDKEK | 487 |
| WP_001040091 | 421 | KAIIRRQSEYYPFLKE--NQD | KIEKILTFRIPYYIGPL | AREK--SDFAWMTR---KTDDSIRPWNFEDLVDKEK | 487 |
| WP_001040092 | 421 | KAIIRRQSEYYPFLKE--NQD | RIEKILTFRIPYYVGPL | ARGN--SDFAWMTR---KTDDSIRPWNFEDLVDKEK | 487 |
| WP_001040094 | 421 | RAIIRRQSEYYPFLKE--NLD | RIEKILTFRIPYYVGPL | AREK--SDFAWMTR---KTDDSIRPWNFEDLVDKEK | 487 |
| WP_001040095 | 421 | RAIIRRQSEYYPFLKE--NLD | RIEKILTFRIPYYVGPL | AREK--SDFAWMTR---KTDDSIRPWNFEDLVDKEK | 487 |
| WP_001040096 | 421 | RAIIRRQSEYYPFLKE--NLD | RIEKILTFRIPYYVGPL | AREK--SDFAWMTR---KTDDSIRPWNFEDLVDKEK | 487 |
| WP_001040097 | 421 | RAIIRRQSEYYPFLKE--NLD | RIEKILTFRIPYYVGPL | AREK--SDFAWMTR---KTDDSIRPWNFEDLVDKEK | 487 |
| WP_001040098 | 421 | RAIIRRQSEYYPFLKE--NLD | RIEKILTFRIPYYVGPL | AREK--SDFAWMTR---KTDDSIRPWNFEDLVDKEK | 487 |
| WP_001040099 | 421 | KAIIRRQSEYYPFLKE--NQD | RIEKILTFRIPYYIGPL | AREK--SDFAWMTR---KTDDSIRPWNFEDLVDKEK | 487 |
| WP_001040100 | 421 | RAIIRRQSEYYPLLKE--NLD | RIEKILTFRIPYYVGPL | AREK--SDFAWMTR---KTDDSIRPWNFEDLVDKEK | 487 |
| WP_001040104 | 421 | RAIIRRQSEYYPFLKE--NLD | RIEKILTFRIPYYVGPL | AREK--SDFAWMTR---KTDDSIRPWNFEDLVDKEK | 487 |
| WP_001040105 | 421 | KAIIRRQSEYYPFLKE--NQD | RIEKILTFRIPYYIGPL | AREK--SDFAWMTR---KTDDSIRPWNFEDLVDKEK | 487 |
| WP_001040106 | 421 | RAIIRRQSEYYPFLKE--NLD | RIEKILTFRIPYYVGPL | AREK--SDFAWMTR---KTDDSIRPWNFEELVDKEA | 487 |
| WP_001040107 | 421 | RAIIRRQSEYYPFLKE--NLD | RIEKILTFRIPYYVGPL | AREK--SDFAWMTR---KTDDSIRPWNFEELVDKEA | 487 |
| WP_001040108 | 421 | KAIIRRQSEYYPFLKE--NLD | RIEKILTFRIPYYVGPL | AREK--SDFAWMTR---KTDDSIRPWNFEELVDKEA | 487 |
| WP_001040109 | 421 | KAIIRRQSEYYPFLKE--NLD | RIEKILTFRIPYYVGPL | AREK--SDFAWMTR---KTDDSIRPWNFEELVDKEA | 487 |

-continued

| ID | | | | | | |
|---|---|---|---|---|---|---|
| WP_001040110 | 421 | KAIIRRQSEYYPFLKE--NLD | RIEKILTFRIPYYVGPL | AREK--SDFAWMTR---KTDDSIRPWNFEELVDKEA | 487 |
| WP_015058523 | 421 | KAIIRRQSEYYPFLKE--NQD | KIEKILTFRIPYYVGPL | ARGN--SDFAWMTR---KTDDSIRPWNFEDLVDKEK | 487 |
| WP_017643650 | 421 | RAIIRRQSEYYPFLKE--NLD | RIEKILTFRIPYYVGPL | AREK--SDFAWMTR---KTDDSIRPWNFEDLVDKEK | 487 |
| WP_017647151 | 421 | KAIIRRQSEYYPFLKE--NLD | RIEKILTFRIPYYVGPL | AREK--SDFAWMTR---KTDDSIRPWNFEELVDKEA | 487 |
| WP_017648376 | 421 | KAIIRRQSEYYPFLKE--NLD | RIEKILTFRIPYYVGPL | AREK--SDFAWMTR---KTDDSIRPWNFEELVDKEA | 487 |
| WP_017649527 | 421 | KAIIRRQSEYYPFLKE--NQD | RIEKILTFRIPYYIGPL | AREK--SDFAWMTR---KTDDSIRPWNFEDLVDKEK | 487 |
| WP_017771611 | 421 | KAIIRRQSEYYPFLKE--NLD | RIEKILTFRIPYYVGPL | AREK--SDFAWMTR---KTDDSIRPWNFEELVDKEA | 487 |
| WP_017771984 | 421 | KAIIRRQSEYYPFLKE--NQD | RIEKILTFRIPYYIGPL | AREK--SDFAWMTR---KTDDSIRPWNFEDLVDKEK | 487 |
| CFQ25032 | 421 | KAIIRRQSEYYPFLKE--NQD | RIEKILTFRIPYYIGPL | AREK--SDFAWMTR---KTDDSIRPWNFEDLVDKEK | 487 |
| CFV16040 | 421 | KAIIRRQSEYYPFLKE--NQD | RIEKILTFRIPYYIGPL | AREK--SDFAWMTR---KTDDSIRPWNFEDLVDKEK | 487 |
| KLJ37842 | 421 | KAIIRRQSEYYPFLKE--NLD | RIEKILTFRIPYYVGPL | AREK--SDFAWMTR---KTDDSIRPWNFEELVDKEA | 487 |
| KLJ72361 | 421 | KAIIRRQSEYYPFLKE--NQD | RIEKILTFRIPYYIGPL | AREK--SDFAWMTR---KTDDSIRPWNFEDLVDKEK | 487 |
| KLL20707 | 421 | KAIIRRQSEYYPFLKE--NQD | RIEKILTFRIPYYVGPL | AREK--SDFAWMTR---KTDDSIRPWNFEDLVDKEK | 487 |
| KLL42645 | 421 | KAIIRRQSEYYPFLKE--NLD | RIEKILTFRIPYYVGPL | AREK--SDFAWMTR---KTDDSIRPWNFEELVDKEA | 487 |
| WP_047207273 | 421 | KAIIRRQSEYYPFLKE--NQD | RIEKILTFRIPYYIGPL | AREK--SDFAWMTR---KTDDSIRPWNFEDLVDKEK | 487 |
| WP_047209694 | 421 | RAIIRRQSEYYPFLKE--NLD | RIEKILTFRIPYYVGPL | AREK--SDFAWMTR---KTDDSIRPWNFEDLVDKEK | 487 |
| WP_050198062 | 421 | KAIIRRQSEYYPFLKE--NQD | RIEKILTFRIPYYIGPL | AREK--SDFAWMTR---KTDDSIRPWNFEDLVDKEK | 487 |
| WP_050201642 | 421 | KAIIRRQSEYYPFLKE--NLD | RIEKILTFRIPYYVGPL | AREK--SDFAWMTR---KTDDSIRPWNFEELVDKEA | 487 |
| WP_050204027 | 421 | KAIIRRQSEYYPFLKE--NQD | RIEKILTFRIPYYIGPL | AREK--SDFAWMTR---KTDDSIRPWNFEDLVDKEK | 487 |
| WP_050881965 | 421 | KDIIRRQSEYYPFLKE--NQD | RIEKILTFRIPYYIGPL | AREK--SDFAWMTR---KTDDSIRPWNFEDLVDKEK | 487 |
| WP_050886065 | 421 | KAIIRRQSEYYPFLKE--NQD | RIEKILTFRIPYYIGPL | AREK--SDFAWMTR---KTDDSIRPWNFEDLVDKEK | 487 |
| AHN30376 | 421 | KAIIRRQSEYYPFLKE--NQD | RIEKILTFRIPYYIGPL | ARGN--SDFAWMTR---KTDDSIRPWNFEDLVDKEK | 487 |
| EAO78426 | 421 | KAIIRRQSEYYPFLKE--NQD | RIEKILTFRIPYYVGPL | AREK--SDFAWMTR---KTDDSIRPWNFEDLVDKEK | 487 |
| CCW42055 | 421 | RAIIRRQSEYYPFLKE--NLD | RIEKILTFRIPYYVGPL | AREK--SDFAWMTR---KTDDSIRPWNFEELVDKEA | 487 |
| WP_003041502 | 420 | HAILRRQGEHYPFLKE--NQD | RIEKILTFRIPYYVGPL | ARKG--SRFAWAEY---KADEKITPWNFDDILDKEK | 486 |
| WP_037593752 | 421 | HAILRRQGEHYPFLKE--NQD | KIEKILTFRIPYYVGPL | ARKG--SRFAWAEY---KADEKITPWNFDDILDKEK | 487 |
| WP_049516684 | 421 | HAILRRQGEHYPFLKE--NQD | KIEKILTFRIPYYVGPL | ARKG--SRFAWAEY---KADEKITPWNFDDILDKEK | 487 |

```
GAD46167       420 HAILRRQGEHYPFLKE-NQD KIEKILTFRIPYYVGPL ARKG--SRFAWAEY---KADEKITPWNFDDILDKEK 486
WP_018363470   421 HAILRRQGDYPFLKE-NQE EIEKILTFRIPYYVGPL ARKD--SRFAWAEY---RSDEKITPWNFDKVIDKEK 487
WP_003043819   430 HAILRRQEEFYPFLKE-NRE KIEKILTFRIPYYVGPL ARG-n-SRFAWLTR---KSEEAITPWNFEEVVDKGA 496
WP_006269658   420 HAILRRQGEHYPFLKE-NQD KIEKILTFRIPYYVGPL ARKG--SRFAWAEY---KADEKITPWNFDDILDKEK 486
WP_048800889   420 HAILRRQGEHYPFLKE-NQD KIEKILTFRIPYYVGPL VRKG--SRFAWAEY---KADEKITPWNFDDILDKEK 486
WP_012767106   420 HAILRRQEDFYPFLKD-NRE KIEKILTFRIPYYVGPL ARG-n-SRFAWMTR---KSEETITPWNFEEVVDKGA 486
WP_014612333   420 HAILRRQEDFYPFLKD-NRE KIEKILTFRIPYYVGPL ARG-n-SRFAWMTR---KSEETITPWNFEEVVDKGA 486
WP_015017095   420 HAILRRQEDFYPFLKD-NRE KIEKILTFRIPYYVGPL ARG-n-SRFAWMTR---KSEETITPWNFEEVVDKGA 486
WP_015057649   420 HAILRRQEDFYPFLKD-NRE KIEKILTFRIPYYVGPL ARG-n-SRFAWMTR---KSEETITPWNFEEVVDKGA 486
WP_048277215   420 HAILRRQEDFYPFLKD-NRE KIEKILTFRIPYYVGPL ARG-n-SRFAWMTR---KSEETITPWNFEEVVDKGA 486
WP_049519324   420 HAILRRQEDFYPFLKD-NRE KIEKILTFRIPYYVGPL ARG-n-SRFAWMTR---KSEETITPWNFEEVVDKGA 486
WP_012515931   420 HAILRRQEVEYPFLKD-NRK KIESLLTFRIPYYVGPL ARG-h-SRFAWVKR---KPDGAIRPWNFEEIVDEEA 486
WP_021320964   420 HAILRRQEVEYPFLKD-NRK KIESLLTFRIPYYVGPL ARG-h-SRFAWVKR---KPDGAIRPWNFEEIVDEEA 486
WP_037581760   420 HAILRRQEVEYPFLKD-NRK KIESLLTFRIPYYVGPL ARG-h-SRFAWVKR---KPDGAIRPWNFEEIVDEEA 486
WP_004232481   420 RTILRRQGEYYPFLKE-NQA KIEKILTFRIPYYVGPL ARKN--SRFAWAKY---HSDEPITPWNFDEVDKEK 486
WP_009854540   421 HAILRRQGDYPFLKE-KQD RIEKILTFRIPYYVGPL VRKD--SRFAWAEY---RSDEKITPWNFDKVIDKEK 487
WP_012962174   421 HAILRRQGEHYAFLKE-NQA KIEKILTFRIPYYVGPL ARKN--SRFAWAEY---HSDEKITPWNFDEIIDKEK 487
WP_039695303   423 HAILRRQGDYYPFLKE-KQD RIEKILTFRIPYYVGPL VRKD--SRFAWAEY---HSDEPITPWNFDKVIDKEK 489
WP_014334983   420 HSILRRQGDYYPFLKE-NQA KIEKILTFRIPYYVGPL ARKD--SRFAWANY---HSDEPITPWNFDEVDKEK 486
WP_003099269   420 KAIIRRQNKEYPFLKE-NQK KIEKLFTFKIPYYVGPL ANG-q-SSFAWLKR---QSNESITPWNFEEVDQEA 486
AHY15608       420 KAIIRRQEKEYPFLKE-NQK KIEKLFTFKIPYYVGPL ANG-q-SSFAWLKR---QSNESITPWNFEEVDQEA 486
AHY17476       420 KAIIRRQEKEYPFLKE-NQK KIEKLFTFKIPYYVGPL ANG-q-SSFAWLKR---QSNESITPWNFEEVDQEA 486
ESR09100                   -------------------  -----------------  -----------------------------------
AGM98575       420 KAIIRRQEKEYPFLKE-NQK KIEKILTFRIPYYVGPL ANG-q-SSFAWLKR---QSNESITPWNFEEVDQEA 486
ALF27331       420 RAIIRRQAEFYPFLAD-NQD RIEKILTFRIPYYIGPL ARGK--SDFSWLSR---KSADKITPWNFDEIVDKES 486
WP_018372492   433 QAIILNQSKYYPFLAE-NKE KIEKILTFRIPYYVGPL ARGN--SSFAWLQR---KSDEAIRPWNFEQVVDMET 499
WP_045618028   421 NAIIRRQGEHYPFLQE-NKE KIEKILTFRIPYYVGPL ARGN--RDFAWLTR---NSDQAIRPWNFEEIVDKAR 487
```

-continued

| | | | | | |
|---|---|---|---|---|---|
| WP_045635197 | 420 | NAILRRQGEYYPFLKD--NKE | KIEKILTFRIPYYVGPL | ARGN--RDFAWLTR---NSDEAIRPWNFEEIVDKAS | 486 |
| WP_002263549 | 420 | RAIIRRQAEFYPFLAD--NQD | RIEKLLTFRIPYYVGPL | ARGK--SDFAWLSR---KSADKITPWNFDEIVDKES | 486 |
| WP_002263887 | 420 | RAIIRRQAEFYPFLAD--NQD | RIEKILTFRIPYYVGPL | ARGK--SDFAWLSR---KSADKITPWNFDEIVDKES | 486 |
| WP_002264920 | 420 | HAILRRQGDYYPFLKE--NQD | RIEKILTFRIPYYVGPL | ARGK--SDFAWLSR---KSADKITPWNFDEIVDKES | 486 |
| WP_002269043 | 420 | RAIIRRQAEFYPFLAD--NQD | RIEKILTFRIPYYVGPL | ARGK--SDFAWLSR---KSADKITPWNFDEIVDKES | 486 |
| WP_002269448 | 420 | RAIIRRQAEFYPFLAD--NQD | RIEKILTFRIPYYVGPL | ARGK--SDFAWLSR---KSADKITPWNFDEIVDKES | 486 |
| WP_002271977 | 420 | RAIIRRQAEFYPFLAD--NQD | RIEKILTFRIPYYVGPL | ARGK--SDFAWLSR---KSADKITPWNFDEIVDKES | 486 |
| WP_002272766 | 420 | RAIIRRQAEFYPFLAD--NQD | RIEKILTFRIPYYVGPL | ARGK--SDFAWLSR---KSADKITPWNFDEIVDKES | 486 |
| WP_002273241 | 420 | RAIIRRQAEFYPFLAD--NQD | RIEKILTFRIPYYVGPL | ARGK--SDFAWLSR---KSADKITPWNFDEIVDKES | 486 |
| WP_002275430 | 420 | RAIIRRQAEFYPFLAD--NQD | RIEKILTFRIPYYVGPL | ARGK--SDFAWLSR---KSADKITPWNFDEIVDKES | 486 |
| WP_002276448 | 420 | RAIIRRQAEFYPFLAD--NQD | RIEKILTFRIPYYVGPL | ARKN--SRFAWAEY---HSDEAVMPWNFDQVIDKES | 486 |
| WP_002277050 | 420 | HAILRRQGDYYPFLKE--NQD | RIEKILTFRIPYYVGPL | ARGK--SDFAWLSR---KSADKITPWNFDEIVDKES | 486 |
| WP_002277364 | 420 | RAIIRRQAEFYPFLAD--NQD | RIEKILTFRIPYYVGPL | ARGK--SDFAWLSR---KSADKITPWNFDEIVDKES | 486 |
| WP_002279025 | 420 | RAIIRRQSEFYPFLAD--NQD | RIEKILTFRIPYYVGPL | ARGK--SDFAWLSR---KSADKITPWNFDEIVDKES | 486 |
| WP_002279859 | 420 | RAIIRRQAEFYPFLAD--NQD | RIEKILTFRIPYYVGPL | ARGK--SDFAWLSR---KSADKITPWNFDEIVDKES | 486 |
| WP_002280230 | 420 | RAIIRRQAEFYPFLAD--NQD | RIEKILTFRIPYYVGPL | ARGK--SDFAWLSR---KSADKITPWNFDEIVDKES | 486 |
| WP_002281696 | 420 | RAIIRRQAEFYPFLAD--NQD | RIEKILTFRIPYYVGPL | ARGK--SDFAWLSR---KSADKITPWNFDEIVDKES | 486 |
| WP_002282247 | 420 | HAILRRQGDYYPFLKE--NQD | RIEKILTFRIPYYVGPL | ARKN--SRFAWAEY---HSDEAVTPWNFDQVIDKES | 486 |
| WP_002282906 | 420 | RAIIRRQAEFYPFLAD--NQD | RIEKILTFRIPYYVGPL | ARGK--SDFAWLSR---KSADKITPWNFDEIVDKES | 486 |
| WP_002283846 | 420 | RAIIRRQAEFYPFLAD--NQD | RIEKLLTFRIPYYVGPL | ARGK--SDFAWLSR---KSADKITPWNFDEIVDKES | 486 |
| WP_002287255 | 420 | RAIIRRQAEFYPFLAD--NQD | RIEKILTFRIPYYVGPL | ARGK--SDFAWLSR---KSADKITPWNFDEIVDKES | 486 |
| WP_002288990 | 420 | RAIIRRQAEFYPFLAD--NQD | RIEKILTFRIPYYVGPL | ARGK--SDFAWLSR---KSADKITPWNFDEIVDKES | 486 |
| WP_002289641 | 420 | RAIIRRQAEFYPFLAD--NQD | RIEKILTFRIPYYVGPL | ASGK--SDFAWLSR---KSADKITPWNFDEIVDKES | 486 |
| WP_002290427 | 420 | RAIIRRQAEFYPFLAD--NQD | RIEKILTFRIPYYVGPL | ARGK--SDFAWLSR---KSADKITPWNFDEIVDKES | 486 |
| WP_002295753 | 420 | RAIIRRQAEFYPFLAD--NQD | RIEKILTFRIPYYVGPL | ARGK--SDFAWLSR---KSADKITPWNFDEIVDKES | 486 |
| WP_002296423 | 420 | RAIIRRQAEFYPFLAD--NQD | RIEKILTFRIPYYVGPL | ARGK--SDFAWLSR---KSADKITPWNFDEIVDKES | 486 |
| WP_002304487 | 430 | HAILRRQGEHYPFLKE--NQD | KIEKILTFRIPYYVGPL | VRKG--SRFAWAEY---KADEKITPWNFDDILDKEK | 496 |

```
                                              -continued

WP_002305844   420  RAIIRRQAEFYPFLAD-NQD  RIEKILTFRIPYYVGPL  ARGK--SDFAWLSR---KSADKITPWNFDEIVDKES  486
WP_002307203   420  RAIIRRQAEFYPFLAD-NQD  RIEKILTFRIPYYVGPL  ARGK--SDFAWLSR---KSADKITPWNFDEIVDKES  486
WP_002310390   420  RAIIRRQAEFYPFLAD-NQD  RIEKILTFRIPYYVGPL  ARGK--SDFAWLSR---KSADKITPWNFDEIVDKES  486
WP_002352408   420  RAIIRRQAEFYPFLAD-NQD  RIEKILTFRIPYYVGPL  ARGK--SDFAWLSR---KSADKITPWNFDEIVDKES  486
WP_012997688   420  RAIIRRQAEFYPFLAD-NQD  RIEKILTFRIPYYVGPL  ARGK--SDFAWLSR---KSADKITPWNFDEIVDKES  486
WP_014677909   420  RAIIRRQAEFYPFLAD-NQD  RIEKILTFRIPYYVGPL  ARGK--SDFAWLSR---KSADKITPWNFDEIVDKES  486
WP_019312892   420  RAIIRRQAEFYPFLAD-NQD  RIEKILTFRIPYYVGPL  ARGK--SDFAWLSR---KSADKITPWNFDEIVDKES  486
WP_019313659   420  RAIIRRQAEFYPFLAD-NQD  RIEKILTFRIPYYVGPL  ARGK--SDFAWLSR---KSADKITPWNFDEIVDKES  486
WP_019314093   420  RAIIRRQAEFYPFLAD-NQD  RIEKILTFRIPYYVGPL  ARGK--SDFAWLSR---KSADKITPWNFDEIVDKES  486
WP_019315370   420  RAIIRRQAEFYPFLAD-NQD  RIEKILTFRIPYYVGPL  ARGK--SDFAWLSR---KSADKITPWNFDEIVDKES  486
WP_019803776   420  RAIIRRQAEFYPFLAD-NQD  RIEKLLTFRIPYYVGPL  ARGK--SDFAWLSR---KSADKITPWNFDEIVDKES  486
WP_019805234   420  RAIIRRQAEFYPFLAD-NQD  RIEKILTFRIPYYVGPL  ARGK--SDFAWLSR---KSADKITPWNFDEIVDKES  486
WP_024783594   420  HAILRRQGDYYPFLKE-NQD  RIEKILTFRIPYYVGPL  ARKN--SRFAWAEY---HSDEAVTPWNFDQVIDKES  486
WP_024784288   420  RAIIRRQAEFYPFLAD-NQD  RIEKILTFRIPYYVGPL  ARGK--SDFAWLSR---KSADKITPWNFDEIVDKES  486
WP_024784666   420  RAIIRRQAEFYPFLAD-NQD  RIEKILTFRIPYYVGPL  ASGK--SDFAWLSR---KSADKITPWNFDEIVDKES  486
WP_024784894   420  HAILRRQGDYYPFLKE-NQD  RIEKILTFRIPYYVGPL  ARKN--SRFAWAEY---HSDEAVTPWNFDQVIDKES  486
WP_024786433   420  RAIIRRQAEFYPFLAD-NQD  RIEKILTFRIPYYVGPL  ARGK--SDFAWLSR---KSADKITPWNFDEIVDKES  486
WP_049473442   420  RAIIRRQAEFYPFLAD-NQD  RIEKLLTFRIPYYVGPL  ASGK--SDFAWLSR---KSADKITPWNFDEIVDKES  486
WP_049474547   420  RAIIRRQAEFYPFLAD-NQD  RIEKILTFRIPYYVGPL  ARGK--SDFAWLSR---KSADKITPWNFDEIVDKES  486
EMC03581       413  RAIIRRQAEFYPFLAD-NQD  RIEKILTFRIPYYVGPL  ARGN--RDFAWLTR---NSDQAIRPWNFEEIVDKAS  479
WP_000428612   421  NAILRRQGEHYPFLKE-NKE  KIEKILTFRIPYYVGPL  ARGN--RDFAWLTR---NSDEAIRPWNFEEIVDKAS  487
WP_000428613   421  NAILRRQGEHYPFLKD-NKE  KIEKILTFRIPYYVGPL  ARGN--RDFAWLTR---NSDEAIRPWNFEEIVDKAS  487
WP_049523028   420  NAILRHQGEYYPFLKE-NKD  KIEQILTFRIPYYVGPL  ARGN--SDFAWLSR---NSDEAIRPWNFEEMVDKSS  486
WP_003107102   389  KSIIRRQEKYYPFLKD-KQV  RIEKILTFRIPYFVGPL  ANG-n-SSFAWVKR---RSNESITPWNFEEVVEQEA  455
WP_054279288   422  QAILERQQAYYPFLKD-NQE  KIEKILTFRIPYYIGPL  ARG-n-SRFAWLTR---TSDQKITPWNFDEMVDQEA  488
WP_049531101   421  NAILRRQGEHYPFLKE-NRE  KIEKILTFRIPYYVGPL  ARGN--RDFAWLTR---NSDQAIRPWNFEEIVDKAS  487
WP_049538452   421  NAILRRQGEHYPFLKE-NKE  KIEKILTFRIPYYVGPL  ARGN--RDFAWLTR---NSDQAIRPWNFEEIVDKAS  487
```

| | | | | | |
|---|---|---|---|---|---|
| WP_049549711 | 421 | NAILRRQGEHYPFLKE--NKE | KIEKILTFRIPYYVGPL | ARGN--RDFAWLTR---NSDQAIRPWNFEEIVDKAS | 487 |
| WP_007896501 | 422 | HAILRRQEKYPFLAE--QKE | KIEQLLCFRIPYYVGPL | AKGGn-SSFAWLKR---RSDEPITPWNFKDVVDEEA | 489 |
| EFR44625 | 374 | HAILRRQEKYPFLAE--QKE | KIEQLLCFRIPYYVGPL | AKGGn-SSFAWLKR---RSDEPITPWNFKDVVDEEA | 441 |
| WP_002897477 | 420 | NAILRRQGEHYPFLKE--NRE | KIEKILTFRIPYYVGPL | ARDN--RDFSWLTR---NSDEPIRPWNFEEVVDKAR | 486 |
| WP_002906454 | 420 | NAILRRQGEHYLFLKE--NRE | KIEKILAFRIPYYVGPL | ARGN--RDFAWLTR---NSDQAIRPWNFEEVVDKAS | 486 |
| WP_009729476 | 421 | NAILRRQGEHYPFLKE--NKE | KIEKILTFRIPYYVGPL | ARGN--RDFAWLTR---NSDQAIRPWNFEEIVDKAS | 487 |
| CQR24647 | 421 | KAILRRQGEFYPFLKE--NAE | KIQQILTFKIPYYVGPL | ARGN--SRFAWASY---NSNEKMTPWNFDNVIDKTS | 487 |
| WP_000066813 | 421 | NAIIRRQGEHYPFLQE--NKE | KIEKILTFRIPYYVGPL | ARGN--GDFAWLTR---NSDQAIRPWNFEEIVDQAS | 487 |
| WP_009754323 | 421 | NAILRRQGEHYPLLKE--NKE | KIEKILTFRIPYYVGPL | ARGN--RDFAWLTR---NSDQAIRPWNFEEIVDKAS | 487 |
| WP_044674937 | 420 | HAILRRQAEFYPFLVE--NQD | KIEKILTFRIPYYVGPL | ARGK--SEFAWLNR---KSDEKIRPWNFDEMVDKET | 486 |
| WP_044676715 | 420 | HAIIRRQAEFYPFLVE--NQD | KIEKILTFRIPYYVGPL | ARGK--SEFAWLNR---KSDEKIRPWNFDEMVDKET | 486 |
| WP_044680361 | 420 | HAIIRRQAEFYPFLVE--NQD | KIEKILTFRIPYYVGPL | ARGK--SEFAWLNR---KSDEKIRPWNFDEMVDKET | 486 |
| WP_044681799 | 420 | HAIIRRQAEFYPFLVE--NQD | KIEKILTFRIPYYVGPL | ARGK--SEFAWLNR---KSDEKIRPWNFDEMVDKET | 486 |
| WP_049533112 | 420 | HAILRRQEHYPFLKE--NQD | KIEKILTFRIPYYVGPL | ARKG--SRFAWAEY---KADEKITPWNFDDILDKEK | 486 |
| WP_029090905 | 404 | VAILENQATYYPFLLE--QKD | NIHKLLTFRIPYYVGPL | ADQKd-SEFAWWVR---KQAGKITPFNFEEMVDIDA | 471 |
| WP_006506696 | 430 | IKIIDNQAEYPILKE--KRE | QLLSILTFRYFGPL | ETSEh----AWIKRlegKENQRILPWNYQDIVDVDA | 498 |
| AIT42264 | 420 | HAILRRQEDFYPFLKD--NRE | KIEKILTFRIPYYVGPL | ARG-n-SRFAWMTR---KSEETITPWNFEEVDKGA | 486 |
| WP_034440723 | 426 | TAVLDQQEKHYSFLKE--NRD | KIISLLTFRIPYYVGPL | AKGE--SRFAWLER---sNSEEKIKPWNEDKIVDIDK | 493 |
| AKQ21048 | 420 | HAILRRQEDFYPFLKD--NRE | KIEKILTFRIPYYVGPL | ARG-n-SRFAWMTR---KSEETITPWNFEEVDKGA | 486 |
| WP_004636532 | 421 | QAILDRQSQYYPFLAE--NRD | KIESLVTFRIPYYVGPL | TVSDq-SEFAWWER---QSDEPIRPWNFDEIVNKER | 488 |
| WP_002364836 | 428 | QAIIHRQAAYYPFLKE--NQE | KIEQLVTFRIPYYVGPL | SKGDa-STFAWLKR---QSEEPIRPWNLQETVDLDQ | 495 |
| WP_016631044 | 379 | QAIIHRQAAYYPFLKE--NQE | KIEQLVTFRIPYYVGPL | SKGDa-STFAWLKR---QSEEPIRPWNLQETVDLDQ | 446 |
| EMS75795 | 163 | KAIIERQKPYYPSLEE--ARD | KMIRLLTFRIPYYVGPL | AQGEetSSFAWLER---KTPEKVTPWNATEVIDYSA | 231 |
| WP_002373311 | 428 | QAIIHRQAAYYPFLKE--NQE | KIEQLVTFRIPYYVGPL | SKGDa-STFAWLKR---QSEEPIRPWNLQETVDLDQ | 495 |
| WP_002378009 | 428 | QAIIHRQAAYYPFLKE--NQE | KIEQLVTFRIPYYVGPL | SKGDa-NTFAWLKR---QSEEPIRPWNLQETVDLDQ | 495 |
| WP_002407324 | 428 | QAIIHRQAAYYPFLKE--NQE | KIEQLVTFRIPYYVGPL | SKGDa-STFAWLKR---QSEEPIRPWNLQETVDLDQ | 495 |
| WP_002413717 | 428 | QAIIHRQAAYYPFLKE--NQE | KIEQLVTFRIPYYVGPL | sKGDa-STFAWLKR---QSEEPIRPWNLQETVDLDQ | 495 |

-continued

| | | | | | |
|---|---|---|---|---|---|
| WP_010775580 | 430 | QAIIHRQAAYYPFLKE--NQK | KIEQLVTFRIPYYVGPL | SKGDa-STFAWLKR---QSEEPIRPWNLQETVDLDQ | 497 |
| WP_010818269 | 428 | QAIIHRQAAYYPFLKE--NQE | KIEQLVTFRIPYYVGPL | SKGDa-STFAWLKR---QSEEPIRPWNLQETVDLDQ | 495 |
| WP_010824395 | 428 | QAIIHRQAAYYPFLKE--NQE | KIEQLVTFRIPYYVGPL | SKGDa-STFAWLKR---QSEEPIRPWNLQETVDLDQ | 495 |
| WP_016622645 | 428 | QAIIHRQAAYYPFLKE--NQE | KIEQLVTFRIPYYVGPL | SKGDa-STFAWLKR---QSEEPIRPWNLQETVDLDQ | 495 |
| WP_033624816 | 428 | QAIIHRQAAYYPFLKE--NQE | KIEQLVTFRIPYYVGPL | SKGDa-STFAWLKR---QSEEPIRPWNLQETVDLDQ | 495 |
| WP_033625576 | 428 | QAIIHRQAAYYPFLKE--NQE | KIEQLVTFRIPYYVGPL | SKGDa-STFAWLKR---QNEKPIRPWNLQETVDLDQ | 495 |
| WP_033789179 | 428 | QAIIHRQAAYYPFLKE--NQK | KIEQLVTFRIPYYVGPL | SKGDa-STFAWLKR---QSEEPIRPWNLQETVDLDQ | 495 |
| WP_002310644 | 424 | RAIIANQKKHYPFLKE--EQE | KLESLLTFKIPYYVGPL | AKKQenSPFAWLIR---KSEEKIKPWNLPEIVDMEG | 492 |
| WP_002312694 | 425 | RAIIANQKKHYPFLKE--EQE | KLESLLTFKIPYYVGPL | AKKQenSPFAWLIR---KSEEKIKPWNLPEIVDMEG | 493 |
| WP_002314015 | 425 | RAIIANQKKHYPFLKE--EQE | KLESLLTFKIPYYVGPL | AKKQenSPFAWLIR---KSEEKIKPWNLPEIVDMEG | 493 |
| WP_002320716 | 425 | RAIIANQKKHYPFLKE--EQE | KLESLLTFKIPYYVGPL | AKKQenSPFAWLIR---KSEEKIKPWNLPEIVDMEG | 493 |
| WP_002330729 | 424 | RAIIANQKKHYPFLKE--EQE | KLESLLTFKIPYYVGPL | AKKQenSPFAWLIR---KSEEKIKPWNLPEIVDMEG | 492 |
| WP_002335161 | 425 | RAIIANQKKHYPFLKE--EQE | KLESLLTFKIPYYVGPL | AKKQenSPFAWLIR---KSEEKIKPWNLPEIVDMEG | 493 |
| WP_002345439 | 425 | RAIIANQKKHYPFLKE--EQE | KLESLLTFKIPYYVGPL | AKKQenSPFAWLIR---KSEEKIKPWNLPEIVDMEG | 493 |
| WP_034867970 | 418 | KAIIDQQKQHYPFLEE--AGP | KIIALFKFKRIPYYVGPL | AKEQeaSSFAWIER---KTAEKINPWNFSEVVDIEK | 486 |
| WP_047937432 | 425 | RAIIANQKKHYPFLKE--EQE | KLESLLTFKIPYYVGPL | AKKQenSPFAWLIR---KSEEKIKPWNLPEIVDMEG | 493 |
| WP_010720994 | 418 | KAIIDQQKQHYPFLEE--AGP | KIIALFKFKRIPYYVGPL | AKEQeaSSFAWIER---KTAEKINPWNFSEVVDIEK | 486 |
| WP_010737004 | 418 | KAIIDQQKQHYPFLEE--AGP | KIIALFKFKRIPYYVGPL | AKEQeaSSFAWIER---KTAEKINPWNFSEVVDIEK | 486 |
| WP_034700478 | 418 | KAIIDQQKQHYPFLEE--AGP | KIIALFKFKRIPYYVGPL | AKEQeaSSFAWIER---KTAEKINPWNFSEVVDIEK | 486 |
| WP_007209003 | 422 | RAILRKQEKYYSFLKE--NHE | KIEQIPKVRIPYYVGPL | AKHNeqSRFAWNIR---KSDEPIRPWNMNDVVDENA | 490 |
| WP_023519017 | 418 | REIMDRQKRFYPFLKG--AQG | KIEKLLTFRIPYYVGPL | AQEGq-SPFAWIKR---KSPSQITPWNFAEVVDKEN | 485 |
| WP_010770040 | 423 | EAIIQKQATYYPFLAD--NKE | EMKQLVTFRIPYYVGPL | ADGN--SPFAWLER---ISSEPIRPGNLAEVVDIKK | 489 |
| WP_048604708 | 419 | KAILHHQAMYPFLQE--KFS | NFVDLLTFRIPYYVGPL | ANGN--SRFSWLSR---KSDEPIRPWNLAEVVDLSK | 485 |
| WP_010750235 | 418 | KAIIDQQKQYYPFLEK--SKE | KMIQLLTFRIPYYVGPL | AQDKetSSFAWLER---KTTEKIKPWNAKDVIDYGA | 486 |
| AII16583 | 459 | HAILRRQEDFYPFLKD--NRE | KIEKILTFRIPYYVGPL | ARG-n-SRFAWMTR---KSEETITPWNFEEVVDKGA | 525 |
| WP_029073316 | 436 | NKILENQSVYYSDLKD--NED | KIRSILTFRIPYYFGPL | ITKDr--QFDWIIKegKENERILPWNANEIVDVDK | 506 |
| WP_031589969 | 436 | NKILENQSVYYSDLKD--NED | KIRSILTFRIPYYFGPL | ITKDr--QFDWIIKegKENERILPWNANEIVDVDK | 506 |

| ID | Start | Sequence | | | | End |
|---|---|---|---|---|---|---|
| KDA45870 | 418 | VAIVENQGKYYPFLRE-NKD | KPEKILNFRIPYYVGPL | ARGN--SKFAWLTR-a-GEGKITPYNFDEMIDKET | | 484 |
| WP_039099354 | 426 | DRIIENQQQYYPWLAE-lNPN | KLDELVAFRVPYYVGPL | QQQssdAKFAWMIR---KAEGQITPWNFDDKVDRQA | | 509 |
| AKP02966 | 416 | EKIDNQSQYYPFLKE-NKE | KLLSILSFRIPYYVGPL | -QSSekNPFAWMER---KSNGHARPWNFDEIVDREK | | 483 |
| WP_010991369 | 426 | EAIIHQQAKYYPFLKE-NYD | KIKSLVTFRIPYFVGPL | ANGQ--SEFAWLTR---KADGEIRPWNIEEKVDFGK | | 492 |
| WP_033838504 | 426 | EAIIHQQAKYYPFLKE-NYD | KIKSLVTFRIPYFVGPL | ANGQ--SEFAWLTR---KADGEIRPWNIEEKVDFGK | | 492 |
| EHN60060 | 429 | EAIIHQQAKYYPFLKE-NYD | KIKSLVTFRIPYFVGPL | ANGQ--SEFAWLTR---KADGEIRPWNIEEKVDFGK | | 495 |
| EFR89594 | 195 | EAIIHQQAKYYPFLKE-NYD | KIKSLVTFRIPYFVGPL | ANGQ--SEFAWLTR---KADGEIRPWNIEEKVDFGK | | 261 |
| WP_038409211 | 426 | EAIIHQQAKYYPFLRK-DYE | KIRSLVTFRIPYFIGPL | ANGQ--SDFAWLTR---KADGEIRPWNIEEKVDFGK | | 492 |
| EFR95520 | 45 | EAIIHQQAKYYPFLRK-DYE | KIRSLVTFRIPYFIGPL | ANGQ--SDFAWLTR---KADGEIRPWNIEEKVDFGK | | 111 |
| WP_003723650 | 426 | EAIIHQQAKYYPFLKE-DYD | KIKSLVTFRIPYFVGPL | ANGQ--SEFAWLTR---KADGEIRPWNIEEKVDFGK | | 492 |
| WP_003727705 | 426 | EAIIHQQAKYYPFLRE-GYD | KIKSLVTFRIPYFVGPL | ANGQ--SEFAWLTR---KDDGEIRPWNIEEKVDFGK | | 492 |
| WP_003730785 | 426 | EAIIHQQAKYYPFLRE-GYD | KIKSLVTFRIPYFVGPL | ANGQ--SEFAWLTR---KADGEIRPWNIEEKVDFGK | | 492 |
| WP_003733029 | 426 | EAIIHQQAKYYPFLRE-DYE | KIKSLVTFRIPYFVGPL | AKGQ--SEFAWLTR---KADGEIRPWNIEEKVDFGK | | 492 |
| WP_003739838 | 426 | EAIIHQQAKYYPFLRE-AYD | KIKSLVTFRIPYFVGPL | ANGQ--SDFAWLTR---KADGEIRPWNIEEKVDFGK | | 492 |
| WP_014601172 | 426 | EAIIHQQAKYYPFLRE-DYE | KIKSLVTFRIPYFVGPL | AKGQ--SEFAWLTR---KADGEIRPWNIEEKVDFGK | | 492 |
| WP_023548323 | 426 | EAIIHQQAKYYPFLRE-GYD | KIKSLVTFRIPYFVGPL | AKGQ--SEFAWLTR---KADGEIRPWNIEEKVDFGK | | 492 |
| WP_031665337 | 426 | EAIIHQQAKYYTFLRE-DYD | KIKSLVTFRIPYFVGPL | ANGQ--SEFAWLTR---KADGEIRPWNIEEKVDFGK | | 492 |
| WP_031669209 | 426 | EAIIHQQAKYYPFLRE-DYE | KIKSLVTFRIPYFVGPL | AKGQ--SEFAWLTR---KADGEIRPWNIEEKVDFGK | | 492 |
| WP_033920898 | 426 | EAIIHQQAKYYPFLRE-DYE | KIKSLVTFRIPYFVGPL | AKGQ--SEFAWLTR---KADGEIRPWNIEEKVDFGK | | 492 |
| AKI42028 | 429 | EAIIHQQAKYYPFLRE-DYE | KIKSLVTFRIPYFVGPL | AKGQ--SEFAWLTR---KADGEIRPWNIEEKVDFGK | | 495 |
| AKI50529 | 429 | EAIIHQQAKYYPFLRE-DYE | KIKSLVTFRIPYFVGPL | AKGQ--SEFAWLTR---KADGEIRPWNIEEKVDFGK | | 495 |
| EFR83390 | | ------------------- | ----------------- | ---------------------------------- | | |
| WP_046323366 | 426 | EAIIHQQAKYYPFLKV-DYE | KIKSLVTFRIPYFVGPL | ANGQ--SEFSWLTR---KADGEIRPWNIEEKVDFGK | | 492 |
| AKE81011 | 436 | HAILRRQEDFYPFLKD-NRE | KIEKILTFRIPYYVGPL | ARG-n-SRFAWMTR---KSEETITPWNFEEVVDKGA | | 502 |
| CUO82355 | 434 | IKIIDNQAKYYPVLKE-KRE | QLLSILTFRIPYYFGPL | ETSEh---AWIKRlegKENQRILPWNYQDTVDVDA | | 502 |
| WP_033162887 | 435 | IQIIDNQSVVYPQLKE-NRD | KLISILEFRIPYYFGPL | AHSE---FAWIKKfedKQKERILPWNYDQIVDIDA | | 503 |
| AGZ01981 | 453 | HAILRRQEDFYPFLKD-NRE | KIEKILTFRIPYYVGPL | ARG-n-SRFAWMTR---KSEETITPWNFEEVVDKGA | | 519 |

-continued

```
AKA60242      420 HAILRRQEDFYPFLKD--NRE  KIEKILTFRIPYYVGPL  ARG-n-SRFAWMTR---KSEETITPWNFEEVVDKGA                                       486
AKS40380      420 HAILRRQEDFYPFLKD--NRE  KIEKILTFRIPYYVGPL  ARG-n-SRFAWMTR---KSEETITPWNFEEVVDKGA                                       486
4UN5_B        424 HAILRRQEDFYPFLKD--NRE  KIEKILTFRIPYYVGPL  ARG-n-SRFAWMTR---KSEETITPWNFEEVVDKGA                                       490
WP_010922251  487 SAQSFIERMTNFDKNLPNEKVLPKHSLLYEYFTVNELTKVKYVT--EGMRKPaFLSGEQKKAIVDLLFK--TNR-KVTV                                       561
WP_039695303  490 SAEKFITRMTLNDLYLPEEKVLPKHSHVETYAVYNELTKIKYVN--EQGKES-FFDSNMKQEIFDHVFK--ENR-KVTK                                       563
WP_045635197  487 SAEDFINKMTNYDLYLPEEKVLPKHSLLYETFAVYNELTKVKFIA--EGLRDYqFLDSQKKQIVNQLFK--ENR-KVTE                                       561
5AXW_A        230 ---KEWYEMLGHCTYFPEELRSVKYAYNADLYNALNDLNNLVITR--DENEKLeYYE---KFQIIENVFK--QKK-KPTL                                       299
WP_009880683  171 SAQSFIERMTNFDKNLPNEKVLPKHSLLYEYFTVNELTKVKYVT--EGMRKPaFLSGEQKKAIVDLLFK--TNR-KVTV                                       245
WP_010922251  487 SAQSFIERMTNFDKNLPNEKVLPKHSLLYEYFTVNELTKVKYVT--EGMRKPaFLSGEQKKAIVDLLFK--TNR-KVTV                                       561
WP_011054416  487 SAQSFIERMTNFDKNLPNEKVLPKHSLLYEYFTVNELTKVKYVT--EGMRKPaFLSGEQKKAIVDLLFK--TNR-KVTV                                       561
WP_011284745  487 SAQSFIERMTNFDKNLPNEKVLPKHSLLYEYFTVNELTKVKYVT--EGMRKPaFLSGEQKKAIVDLLFK--TNR-KVTV                                       561
WP_011285506  487 SAQSFIERMTNFDKNLPNEKVLPKHSLLYEYFTVNELTKVKYVT--EGMRKPaFLSGEQKKAIVDLLFK--TNR-KVTV                                       561
WP_011527619  487 SAQSFIERMTNFDKNLPNEKVLPKHSLLYEYFTVNELTKVKYVT--EGMRKPaFLSGEQKKAIVDLLFK--TNR-KVTV                                       561
WP_012560673  487 SAQSFIERMTNFDKNLPNEKVLPKHSLLYEYFTVNELTKVKYVT--EGMRKPaFLSGEQKKAIVDLLFK--TNR-KVTV                                       561
WP_014407541  487 SAQSFIERMTNFDKNLPNEKVLPKHSLLYEYFTVNELTKVKYVT--EGMRKPaFLSGEQKKAIVDLLFK--TNR-KVTV                                       561
WP_020905136  487 SAQSFIERMTNFDKNLPNEKVLPKHSLLYEYFTVNELTKVKYVT--EGMRKPaFLSGEQKKAIVDLLFK--TNR-KVTV                                       561
WP_023080005  487 SAQSFIERMTNFDKNLPNEKVLPKHSLLYEYFTVNELTKVKYVT--EGMRKPaFLSGEQKKAIVDLLFK--TNR-KVTV                                       561
WP_023610282  487 SAQSFIERMTNFDKNLPNEKVLPKHSLLYEYFTVNELTKVKYVT--EGMRKPaFLSGEQKKAIVDLLFK--TNR-KVTV                                       561
WP_030125963  487 SAQSFIERMTNFDKNLPNEKVLPKHSLLYEYFTVNELTKVKYVT--EGMRKPaFLSGEQKKAIVDLLFK--TNR-KVTV                                       561
WP_030126706  487 SAQSFIERMTNFDKNLPNEKVLPKHSLLYEYFTVNELTKVKYVT--EGMRKPaFLSGEQKKAIVDLLFK--TNR-KVTV                                       561
WP_031488318  487 SAQSFIERMTNFDKNLPNEKVLPKHSLLYEYFTVNELTKVKYVT--EGMRKPaFLSGEQKKAIVDLLFK--TNR-KVTV                                       561
WP_032460140  487 SAQSFIERMTNFDKNLPNEKVLPKHSLLYEYFTVNELTKVKYVT--EGMRKPeFLSGEQKKAIVDLLFK--TNR-KVTV                                       561
WP_032461047  487 SAQSFIERMTNFDKNLPNEKVLPKHSLLYEYFTVNELTKVKYVT--EGMRKPaFLSGEQKKAIVDLLFK--TNR-KVTV                                       561
WP_032462016  487 SAQSFIERMTNFDKNLPNEKVLPKHSLLYEYFTVNELTKVKYVT--EGMRKPaFLSGEQKKAIVDLLFK--TNR-KVTV                                       561
WP_032462936  487 SAQSFIERMTNFDKNLPNEKVLPKHSLLYEYFTVNELTKVKYVT--EGMRKPaFLSGEQKKAIVDLLFK--TNR-KVTV                                       561
WP_032464890  487 SAQSFIERMTNFDKNLPNEKVLPKHSLLYEYFTVNELTKVKYVT--EGMRKPaFLSGEQKKAIVDLLFK--TNR-KVTV                                       561
WP_033888930  312 SAQSFIERMTNFDKNLPNEKVLPKHSLLYEYFTVNELTKVKYVT--EGMRKPaFLSGEQKKAIVDLLFK--TNR-KVTV                                       386
```

| | | | |
|---|---|---|---|
| WP_038431314 | 487 | SAQSFIERMTNFDKNLPNEKVLPKHSLLYEYFTVNELTKVKYVT--EGMRKPaFLSGEQKKAIVDLLFK--TNR-KVTV | 561 |
| WP_038432938 | 487 | SAQSFIERMTNFDKNLPNEKVLPKHSLLYEYFTVNELTKVKYVT--EGMRKPaFLSGEQKKAIVDLLFK--TNR-KVTV | 561 |
| WP_038434062 | 487 | SAQSFIERMTNFDKNLPNEKVLPKHSLLYEYFTVNELTKVKYVT--EGMRKPaFLSGEQKKAIVDLLFK--TNR-KVTV | 561 |
| BAQ51233 | 398 | SAQSFIERMTNFDKNLPNEKVLPKHSLLYEYFTVNELTKVKYVT--EGMRKPaFLSGEQKKAIVDLLFK--TNR-KVTV | 472 |
| KGE60162 | | ---------------------------------------------------------------------------- | |
| KGE60856 | | ---------------------------------------------------------------------------- | |
| WP_002989955 | 487 | SAQSFIERMTNFDKNLPNEKVLPKHSLLYEYFTVNELTKVKYVT--EGMRKPaFLSGEQKKAIVDLLFK--TNR-KVTV | 561 |
| WP_003030002 | 487 | SAEKFITRMTLNDLYLPEEKVLPKHSLLYETFTVNELTKVKVN--EQGEAK-FFDANMKQEIFDHVFK--ENR-KVTK | 560 |
| WP_003065552 | 490 | SAEKFITRMTLNDLYLPEEKVLPKHSHVETYAVVNELTKIKVN--EQGKDS-FFDSNMKQEIFDHVFK--ENR-KVTK | 563 |
| WP_001040076 | 488 | SAEAFIHRMTNNDLYLPEEKVLPKHSLIYEKFTVNELTKVRFLA--EGFKDFqFLNRKQETIENSLEK--EKR-KVTE | 562 |
| WP_001040078 | 488 | SAEAFIHRMTNNDLYLPEEKVLPKHSLIYEKFTVNELTKVRYKN--EQGETY-FFDSNIKQEIFDGVEK--EHR-KVSK | 561 |
| WP_001040080 | 488 | SAEAFIHRMTNNDLYLPEEKVLPKHSLIYEKFTVNELTKVRYKN--EQGETY-FFDSNIKQEIFDGVEK--EHR-KVSK | 561 |
| WP_001040081 | 488 | SAEAFIHRMTNNDLYLPEEKVLPKHSLIYEKFTVNELTKVRYKN--EQGETY-FFDSNIKQEIFDGVEK--EHR-KVSK | 561 |
| WP_001040083 | 488 | SAEAFIHRMTNNDLYLPEEKVLPKHSLIYEKFTVNELTKVRYKN--EQGETY-FFDSNIKQEIFDGVFK--EHR-KVSK | 561 |
| WP_001040085 | 488 | SAEAFIHRMTNNDLYLPEEKVLPKHSLIYEKFTVNELTKVRYKN--EQGETY-FFDSNIKQEIFDGVEK--EHR-KVSK | 561 |
| WP_001040087 | 488 | SAEAFIHRMTNNDLYLPEEKVLPKHSLIYEKFTVNELTKVRYKN--EQGETY-FFDSNIKQEIFDGVEK--EHR-KVSK | 561 |
| WP_001040088 | 488 | SAEAFIHRMTNNDLYLPEEKVLPKHSLIYEKFTVNELTKVRYKN--EQGETY-FFDSNIKQEIFDGVEK--EHR-KVSK | 561 |
| WP_001040089 | 488 | SAEAFIHRMTNNDLYLPEEKVLPKHSLIYEKFTVNELTKVRYKN--EQGETY-FFDSNIKQEIFDGVPK--EHR-KVSK | 561 |
| WP_001040090 | 488 | SAEAFIHRMTNNDLYLPEEKVLPKHSLIYEKFTVNELTKVRYKN--EQGETY-FFDSNIKQEIFDGVEK--EHR-KVSK | 561 |
| WP_001040091 | 488 | SAEAFIHRMTNNDLYLPEEKVLPKHSLIYEKFTVNELTKVRYKN--EQGETY-FFDSNIKQEIFDGVFK--EHR-KVSK | 561 |
| WP_001040092 | 488 | SAEAFIHRMTNNDLYLPEEKVLPKHSLIYEKFTVNELTKVRYKN--EQGETY-FFDENVKQEIFDGVFK--EHR-KVSK | 561 |
| WP_001040094 | 488 | SAEAFIHRMTNNDLYLPEEKVLPKHSLIYEKFTVNELTKVRFLA--EGFKDFqFLNRKQETIFNELFK--EKR-KVTE | 562 |
| WP_001040095 | 488 | SAEAFIHRMTNNDLYLPEEKVLPKHSLIYEKFTVNELTKVRFLA--EGFKDFqFLNRKQETIFNELFK--EKR-KVTE | 562 |
| WP_001040096 | 488 | SAEAFIHRMTNNDLYLPEEKVLPKHSLIYEKFTVNELTKVRFLA--EGFKDFqFLNRKQETIFNELFK--EKR-KVTE | 562 |
| WP_001040097 | 488 | SAEAFIHRMTNNDLYLPEEKVLPKHSLIYEKFTVNELTKVRFLA--EGFKDFqFLNRKQETIFNELFK--EKR-KVTE | 562 |
| WP_001040098 | 488 | SAEAFIHRMTNNDLYLPEEKVLPKHSLIYEKFTVNELTKVRFLA--EGFKDFqFLNRKQETIFNELFK--EKR-KVTE | 562 |
| WP_001040099 | 488 | SAEAFIHRMTNNDLYLPEEKVLPKHSLIYEKFTVNELTKVRFLA--EGFKDFqFLNRKQETIFNELFK--EKR-KVTE | 562 |

-continued

| ID | | Sequence | |
|---|---|---|---|
| WP_001040100 | 488 | SAEAFIHRMTNNDLYLPEEKVLPKHSLIYEKFTVNELTKVRYKN--EQGETY-FFDSNIKQEIFDGVFK--EGFKDFqFLNRKQETIFNELFK--EKR-KVTE | 562 |
| WP_001040104 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_001040105 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_001040106 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_001040107 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_001040108 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_001040109 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_001040110 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_015058523 | 488 | SAEAFIHRMTNNDFYLPEEKVLPKHSLIYEKFTVNELTKVRYKN--EQGETY-FFDENVKQEIFDGVFK--EHR-KVSK | 561 |
| WP_017643650 | 488 | SAEAFIHRMTNNDLYLPEEKVLPKHSLIYEKFTVNELTKVRFLA--EGFKDFqFLNRKQETIFNELFK--EKR-KVTE | 562 |
| WP_017647151 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_017648376 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_017649527 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_017771611 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_017771984 | 488 | SAEAFIHRMTNNDFYLPEEKVLPKHSLIYEKFTVNELTKVRYKN--EQGETY-FFDSNIKQEIFDGVFK--EHR-KVSK | 561 |
| CFQ25032 | 488 | SAEAFIHRMTNNDFYLPEEKVLPKHSLIYEKFTVNELTKVRYKN--EQGETY-FFDSNIKQEIFDGVFK--EHR-KVSK | 561 |
| CFV16040 | 488 | SAEAFIHRMTNNDFYLPEEKVLPKHSLIYEKFTVNELTKVRYKN--EQGETY-FFDSNIKQEIFDGVFK--EHR-KVSK | 561 |
| KLJ37842 | 488 | SAEAFIHRMTNNDFYLPEEKVLPKHSLIYEKFTVNELTKVRYKN--EQGETY-FFDSNIKQEIFDGVFK--EHR-KVSK | 561 |
| KLJ72361 | 488 | SAEAFIHRMTNNDFYLPEEKVLPKHSLIYEKFTVNELTKVRYKN--EQGETY-FFDSNIKQEIFDGVFK--EHR-KVSK | 561 |
| KLL20707 | 488 | SAEAFIHRMTNNDFYLPEEKVLPKHSLIYEKFTVNELTKVRYKN--EQGETY-FFDSNIKQEIFDGVFK--EHR-KVSK | 561 |
| KLL42645 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_047207273 | 488 | SAEAFIHRMTNNDLYLPEEKVLPKHSLIYEKFTVNELTKVRFLA--EGFKDFqFLNRKQETIFNELFK--EKR-KVTE | 562 |
| WP_047209694 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_050198062 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_050201642 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_050204027 | 488 | SAEAFIHRMTNNDFYLPEEKVLPKHSLIYEKFTVNELTKVRYKN--EQGETY-FFDSNIKQEIFDGVFK--EHR-KVSK | 561 |
| WP_050881965 | 488 | SAEAFIHRMTNNDFYLPEEKVLPKHSLIYEKFTVNELTKVRYKN--EQGETY-FFDSNIKQEIFDGVFK--EHR-KVSK | 561 |

-continued

| ID | Start | Sequence | End |
|---|---|---|---|
| WP_050886065 | 488 | SAEAFIHRMTNNDFYLPEEKVLPKHSLIYEKFTVNELTKVRYKN--EQGETY-FFDSNIKQEIFDGVFK--EHR-KVSK | 561 |
| AHN30376 | 488 | SAEAFIHRMTNNDFYLPEEKVLPKHSLIYEKFTVNELTKVRYKN--EQGETY-FFDENVKQEIFDGVFK--EHR-KVSK | 561 |
| EAO78426 | 488 | SAEAFIHRMTNNDFYLPEEKVLPKHSLIYEKFTVNELTKVRYKN--EQGETY-FFDSNIKQEIFDGVFK--EHR-KVSK | 561 |
| CCW42055 | 488 | SAEAFIHCMTNNDFYLPEEKVLPKHSLIYEKFTVNELTKVRYKN--EQGETY-FFDSNIKQEIFDGVFK--EYR-KVSK | 560 |
| WP_003041502 | 488 | SAEKFITRMTLNDLYLPEEKVLPKHSLLYETFTVNELTKVKYVN--EQGEAK-FFDANMKQEIFDHVFK--ENR-KVTK | 561 |
| WP_037593752 | 488 | SAEKFITRMTLNDLYLPEEKVLPKHSPLYETFTVNELTKVKYVN--EQGEAK-FFDTNMKQEIFDHVFK--ENR-KVTK | 561 |
| WP_049516684 | 488 | SAEKFITRMTLNDLYLPEEKVLPKHSPLYETFTVNELTKVKYVN--EQGEAK-FFDTNMKQEIFDHVFK--ENR-KVTK | 560 |
| GAD46167 | 487 | SAEKFITRMTLNDLYLPEEKVLPKHSPLYETFTVNELTKVKYVN--EQGEAK-FFDTNMKQEIFDHVFK--ENR-KVTK | 561 |
| WP_018363470 | 488 | SAEKFITRMTLNDLYLPEEKVLPKHSVETFAVNELTKVKYVN--EQGKDS-FFDSNMKQEIFDHVFK--ENR-KVTK | 571 |
| WP_003043819 | 497 | SAQSFIERMTNFDEQLPNKVLPKHSLLYEYFTVNELTKVKYVT--ERMRKPeFLSGEQKKAIVDLLFK--TNR-KVTV | 560 |
| WP_006269658 | 487 | SAEKFITRMTLNDLYLPEEKVLPKHSPLYEAFTVNELTKVKYVN--EQGEAK-FFDTNMKQEIFDHVFK--ENR-KVTK | 560 |
| WP_048800889 | 487 | SAEKFITRMTLNDLYLPEEKVLPKHSLLYEIFTVNELTKVKYVT--EGMRKPeFLSGKQKEAIVDLLFK--TNR-KVTV | 561 |
| WP_012767106 | 487 | SAQSFIERMTNFDKNLPNEKVLPKHSLLYEYFTVNELTKVKYVT--EGMRKPeFLSGKQKEAIVDLLFK--TNR-KVTV | 561 |
| WP_014612333 | 487 | SAQSFIERMTNFDKNLPNEKVLPKHSLLYEYFTVNELTKVKYVT--EGMRKPeFLSGKQKEAIVDLLFK--TNR-KVTV | 561 |
| WP_015017095 | 487 | SAQSFIERMTNFDKNLPNEKVLPKHSLLYEYFTVNELTKVKYVT--EGMRKPeFLSGKQKEAIVDLLFK--TNR-KVTV | 561 |
| WP_015057649 | 487 | SAQSFIERMTNFDKNLPNEKVLPKHSLLYEYFTVNELTKVKYVT--EGMRKPeFLSGKQKEAIVDLLFK--TNR-KVTV | 561 |
| WP_048327215 | 487 | SAQSFIERMTNFDKNLPNEKVLPKHSLLYEYFTVNELTKVKYVT--EGMRKPaFLSGQKKAIVDLLFK--TNR-KVTV | 561 |
| WP_049519324 | 487 | SAQIFIEKMTKNDLYLPNEKVLPKHSLLYETFTVNELTKVKYAT--EGMTRPqFLSADQKQAIVDLLFK--TNR-KVTV | 561 |
| WP_012515931 | 487 | SAQIFIEKMTKNDLYLPNEKVLPKHSLLYETFTVNELTKVKYAT--EGMTRPqFLSADQKQAIVDLLFK--TNR-KVTV | 561 |
| WP_021320964 | 487 | SAQIFIEKMTKNDLYLPNEKVLPKHSLLYETFTVNELTKVKYAT--EGMTRPqFLSADQKQAIVDLLFK--TNR-KVTV | 561 |
| WP_037581760 | 487 | SAQIFIEKMTKNDLYLPNEKVLPKHSLLYETFTVNELTKVKYAT--EGMTRPqFLSADQKQAIVDLLFK--TNR-KVTV | 560 |
| WP_004232481 | 488 | SAEKFITRMTLNDLYLPNEKVLPKHSLLYETFTVNELTKVKIKYVN--EQGKSF-FFDKES-FFDANMKQEIFDHVFK--ENR-KVTK | 561 |
| WP_009854540 | 488 | SAEKFITRMTLNDLYLPNEKVLPKHSYVNELTKVKIKYVN--EQGKES-FFDANMKQEIFDHVFK--ENR-KVTK | 561 |
| WP_012962174 | 487 | SAEKFITRMTLNDLYLPNEKVLPKHSHVLVYETYAVNELTKVKIKYVN--EQGKSN-FFDANMKQEIFEHVFK--ENR-KVTK | 561 |
| WP_039695303 | 490 | SAEKFITRMTLNDLYLPNEKVLPKHSHVETYAVNELTKVKIKYVN--EQGKES-FFDANMKQEIFDHVFK--ENR-KVTK | 563 |
| WP_014334983 | 487 | SAEKFITRMTLNDLYLPNEKVLPKHSHVETFVVNELTKVKIKYVN--EQGESF-FFDANMKQEIFDHVFK--ENR-KVTK | 560 |
| WP_003099269 | 487 | SARAFIERMTNFDTYLPEEKVLPKHSPLYEMFMVNELTKVKYQT--EGMKRPvFLSSEDKEEIVNLLFK--KER-KVTV | 561 |

```
                                                                                                         -continued AHY15608         487  SARAFIERMTNFDTYLPEEKVLPKHSPLYEMFMVNELTKVKYQT--EGMKRPvFLSSEDKEEIVNLLFK--KER-KVTV  561
AHY17476         487  SARAFIERMTNFDTYLPEEKVLPKHSPLYEMFMVNELTKVKYQT--EGMKRPvFLSSEDKEEIVNLLFK--KER-KVTV  561
ESR09100              ----------------------------------------------------------------------------
AGM98575         487  SARAFIERMTNFDTYLPEEKVLPKHSPLYEMFMVNELTKVKYQT--EGMKRPvFLSSEDKEEIVNLLFK--KER-KVTV  561
ALF27331         487  SASRFIERMTLHDLYLPDEKVLPRHSLIYEKYTVNELTKVKRFTP--EGGKEV-YESKTDKENIFDSLEK--RYR-KVTK  560
WP_018372492     500  SAEDFINKMTNYDLYLPEEKVLPKHSLLYETFAVNELTKVKFIA--EGLRDYqFLDSGQKQQIVTQLFK--EKR-KVTE  573
WP_045618028     488  SAEDFINKMTNYDLYLPNQKVLPKHSLLYETFAVNELTKVKFIA--EGLRDYqFLDSQKKQIVNQLFK--ENR-KVTE  562
WP_045635197     487  SAEAFINRMTNYDLYLPNQKVLPKHSLLYEKFTVNELTKVKYKT--EQGKTA-FFDANMKQEIFDGVEK--VYR-KVTK  561
WP_002263549     487  SAEAFINRMTNYDLYLPNQKVLPKHSLLYEKFTVNELTKVKYKT--EQGKTA-FFDANMKQEIFDGVEK--VYR-KVTK  560
WP_002263887     487  SAEAFINRMTNYDLYLPNQKVLPKHSLLYEKFTVNELIKVKYKT--EQGKTA-FFDANMKQEIFDGVEK--VYR-KVTK  560
WP_002264920     487  SVEAFINRMTNYDLYLPNQKVLPKHSLLYEKFTVNELTKVKYKT--EQGKTA-FFDANMKQEIFDGVEK--VYR-KVTK  560
WP_002269043     487  SVEAFINRMTNYDLYLPNQKVLPKHSLLYEKFTVNELTKVKYKT--EQGKTA-FFDANMKQEIFDGVEK--VYR-KVTK  560
WP_002269448     487  SAEAFINRMTNYDLYLPNQKVLPKHSLLYEKFTVNELTKVKYKT--EQGKTA-FFDANMKQEIFDGVEK--VYR-KVTK  560
WP_002271977     487  SAEAFINRMTNYDLYLPNQKVLPKHSLLYEKFTVNELTKVKYKT--EQGKTA-FFDANMKQEIFDGVEK--VYR-KVTK  560
WP_002272766     487  SAEAFINRMTNYDLYLPNQKVLPKHSLLYEKFTVNELTKVKYKT--EQGKTA-FFDANMKQEIFDGVEK--VYR-KVTK  560
WP_002273241     487  SAEAFINRMTNYDLYLPNQKVLPKHSLLYEKFTVNELTKVKYKT--EQGKTA-FFDANMKQEIFDGVEK--VYR-KVTK  560
WP_002275430     487  SAEAFINRMTNYDLYLPNQKVLPKHSLLYEKFTVNELTKVKYKT--EQGKTA-FFDANMKQEIFDGVEK--VYR-KVTK  560
WP_002276448     487  SAQAFIEHMTNNDLYLPNEKVLPKHSPLYEKFTVNELTKIKYVT--EIGEAK-FFDANLKQEIFDGLEK--HER-KVTK  560
WP_002277050     487  SAEAFINRMTNYDLYLPNEKVLPKHSLLYEKFTVNELTKIKIKYVT--EQGKTA-FFDANMKQEIFDGVEK--VYR-KVTK  560
WP_002277364     487  SAEAFINRMTNYDLYLPNEKVLPKHSPLYEKFTVNELTKVKYKT--EQGKTA-FFDANMKQEIFDGVEK--VYR-KVTK  560
WP_002279025     487  SAEAFINRMTNYDLYLPNQKVLPKHSLLYEKFTVNELTKVKYKT--EQGETA-FFDANMKQEIFDGVEK--VYR-KVTK  560
WP_002279859     487  SVEAFINRMTNYDLYLPNQKVLPKHSLLYEKFTVNELTKVKYKT--EQGKTA-FFDANMKQEIFDGVEK--VYR-KVTK  560
WP_002280230     487  SAEAFINRMTNYDLYLPNQKVLPKHSLLYEKFTVNELTKVKYKT--EQGKTA-FFDANLKQEIFDGLEK--HER-KVTK  560
WP_002281696     487  SAEAFINRMTNYDLYLPNEKVLPKHSPLYEKYTVNELTKIKYVT--EIGEAK-FFDANLKQEIFDGLEK--HER-KVTK  560
WP_002282247     487  SAQAFIEHMTNNDLYLPNQKVLPKHSLLYEKYTVNELTKIKYVT--EQGKTA-FFDANLKQEIFDGLEK--HER-KVTK  560
WP_002282906     487  SAEAFINRMTNYDLYLPNQKVLPKHSPLYEKFTVNELTKVKYKT--EIGEAK-FFDANLKQEIFDGLEK--HER-KVTK  560
WP_002283846     487  SVEAFINRMTNYDLYLPNQKVLPKHSLLYEKFTVNELTKVKYKT--EQGKTA-FFDANMKQEIFDGVEK--VYR-KVTK  560
```

| ID | Start | Sequence | End |
|---|---|---|---|
| WP_002287255 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_002288990 | 487 | SVEAFINRMTNYDLYLPNQKVLPKHSLLYEKFTVNELTKVKYKT--EQGKTA-FFDANMKQEIFDGVEK--VYR-KVTK | 560 |
| WP_002289641 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_002290427 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_002295753 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_002296423 | 487 | SVEAFINRMTNYDLYLPNQKVLPKHSLLYEKFTVNELTKVKYKT--EQGKTA-FFDANMKQEIFDGVEK--VYR-KVTK | 560 |
| WP_002304487 | 497 | SAEKFITRMLNDLYLPEEKVLPKHSLLYETFTVNELTKVKVN--EQGEAK-FFDANMKQEIFDHVFK--ENR-KVTK | 570 |
| WP_002305844 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_002307203 | 487 | SVEAFINRMTNYDLYLPNQKVLPKHSLLYEKFTVNELTKVKYKT--EQGKTA-FFDANMKQEIFDGVEK--VYR-KVTK | 560 |
| WP_002310390 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_002352408 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_012997688 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_014677909 | 487 | SVEAFINRMTNYDLYLPNQKVLPKHSLLYEKFTVNELTKVKYKT--EQGKTA-FFDANMKQEIFDGVEK--VYR-KVTK | 560 |
| WP_019312892 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_019313659 | 487 | SVEAFINRMTNYDLYLPNQKVLPKHSLLYEKFTVNELTKVKYKT--EQGKTA-FFDANMKQEIFDGVEK--VYR-KVTK | 560 |
| WP_019314093 | 487 | SAQAFIEHMTNYDLYLPNQKVLPKHSPLYEKYTVNELTKIKIKYVT--EIGEAK-FFDANLKQEIFDGLEK--HER-KVTK | 560 |
| WP_019315370 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_019803776 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_019805234 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_024783594 | 487 | SAQAFIEHMTNNDLYLPNEKVLPKHSPLYEKFTVNELTKIKYVT--EIGEAK-FFDANLKQEIFDGLEK--HER-KVTK | 560 |
| WP_024784288 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_024784666 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_024784894 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_024786433 | 487 | SAQAFIEHMTNNDLYLPNEKVLPKHSPLYEKFTVNELTKIKYVT--EIGEAK-FFDANLKQEIFDGLEK--HER-KVTK | 560 |
| WP_049473442 | 487 | SAEAFINRMTNYDLYLPNQKVLPKHSLLYEKFTVNELTKVKYKT--EQGKTA-FFDANMKQEIFDGVEK--VYR-KVTK | 560 |
| WP_049474547 | 487 | SAEAFINRMTNYDLYLPNQKVLPKHSLLYEKFTVNELTKVKYKT--EQGKTA-FFDANMKQEIFDGVEK--VYR-KVTK | 560 |
| EMC03581 | 480 | SAEAFINRMTNYDLYLPNQKVLPKHSLLYEKFTVNELTKVKYKT--EQGKTA-FFDANMKQEIFDGVEK--VYR-KVTK | 553 |

-continued

| ID | Start | Sequence | End |
|---|---|---|---|
| WP_000428612 | 488 | SAEDFINKMTNYDLYLPEEKVLPKHSLLYETFAVVNELTKVKFIA--EGLRDYqFLDSQKKDIFYTLFKaeDKR-KVTE | 564 |
| WP_000428613 | 488 | SAEDFINKMTNYDLYLPEEKVLPKHSLLYETFAVVNELTKVKFIA--EGLRDYqFLDSQKKQIVTQLFK---EKR-KVTE | 562 |
| WP_049523028 | 487 | SAEDFIHRMTNYDLYLPEEKVLPKHSLLYETFAVVNELTKVKFIA--EGLRDYqFLDSQKKQIVNQLFK---EKR-KVTE | 561 |
| WP_003107102 | 456 | SAKVFIERMTNFDTYLPEEKVLPKHSLLYEMFTVVNELTKVKQA---EGMKDYqFLDSQKKQIVNQLFK---EKR-KVTE | 530 |
| WP_054279288 | 489 | SAQAFIERMTNFDEYLPQEKVLPKHSLTYEYFTVVNELTKVKVT---EGMRKPeFLSSEKIEIVSNLFK---TER-KVTV | 563 |
| WP_049531101 | 488 | SAEAFINKMTNYDLYLPEEKVLPKHSLLYETFAVVNELTKVKFIA--EGMTKPeFLSAQKEQIVELLFK---KYR-KVTV | 562 |
| WP_049538452 | 488 | SAEDFINKMTNYDLYLPEEKVLPKHSLLYETFAVVNELTKVKFIA--EGLRDYqFLDSGQKKKIINQLFK---EKR-KVTE | 562 |
| WP_049549711 | 488 | SAEDFINKMTNYDLYLPEEKVLPKHSLLYETFAVVNELTKVKFIA--EGLRDYqFLDSQKKQIVNQLFK---EKR-KVTE | 562 |
| WP_007896501 | 490 | SAEDFINKMTNYDLYLPEEKVLPKHSPLYEMFTVVNELTKVKFIA--EGLRDYqFLDSQKKQIVNQLFK---EKR-KVTE | 564 |
| EFR44625 | 442 | SAQAFIEGMTNYDTYLPEEKVLPKHSPLYEMFTVVNELTKVKYIA--ENMTKP1YLSAEQKEATIDHLFK---QTR-KVTV | 516 |
| WP_002897477 | 487 | SAEDFIHRMTNYDLYLPEEKVLPKHSLLYETFAVVNELTKVKFIA--EGLRDYqFLDSQKKQIVNQLFK---EKR-KVTE | 561 |
| WP_002906454 | 487 | SAEDFINKMTNYDLYLPEEKVLPKHSLLYETFAVVNELTKVKFIA--EGLRDYqFLDSGQKKQIVNQLFK---DKR-KVTE | 561 |
| WP_009729476 | 488 | SAEDFINKMTNYDLYLPEEKVLPKHSLLYETFAVVNELTKVKFIA--EGLRDYqFLDSQKKQIVTQLFK---EKR-KVTE | 562 |
| CQR24647 | 488 | SAQAFIERMTNNDLYLPDQKVLPKHSLLYQKFAVVNELTKIKYVT--ETGEAR-LEDVFLKKEIFDGLEK---KER-KVTK | 561 |
| WP_000066813 | 488 | SAEDFINKMTNYDLYLPEEKVLPKHSLLYETFAVVNELTKVKFIA--EGLTRYqFLDKKQKKDIFDTFFKaeNKR-KVTE | 564 |
| WP_009754323 | 488 | SAESFINKMTNYDLYLPEEKVLPKHSLLYETFAVVNELTKVKFIA--EGLRDYqFFDSGQKKQIVNQLFK---EKR-KVTE | 562 |
| WP_044674937 | 487 | SAENFITRMTNYDQYLPDQKVLPKHSLLYEKFAVVNELTKVRYVT--EGMRDYqFLDSGQKKDIVKTLFK---TKR-KVTA | 561 |
| WP_044676715 | 487 | SAENFITRMTNYDQYLPDQKVLPKHSLLYEKFAVVNELTKVRYVT--EQGKSF-FFDANMKQEIFDGVEK---VVR-KVTK | 560 |
| WP_044680361 | 487 | SAENFITRMTNYDQYLPDQKVLPKHSLLYEKFAVVNELTKVRYVT--EQGKSF-FFDANMKQEIFDGVEK---VVR-KVTK | 560 |
| WP_044681799 | 487 | SAENFITRMTNYDQYLPDQKVLPKHSLLYEKFAVVNELTKVKFIA--EGMRDYqFLDSGQKKDIVKTLFK---TKR-KVTA | 561 |
| WP_049533112 | 487 | SAEKFITRMTLNDLYLPEEKVLPKHSLLYETFTVVNELTKVKYVN--EQGEAK-FFDANMKQEIFDHVEK---ENR-KVTK | 560 |
| WP_029909005 | 472 | SSEAPIKRMTNKCTYLIHEDVIPKHSFSYAKFEVLNELNKIRLDG------KP--IDIPLKKRIFEGLFL1--EKtKVTQ | 540 |
| WP_006506696 | 499 | TAEGFIKRMRSYCTYFPDEEVLPKNSLIVSKYEVVNELNKIRVDD--------kLLEVDVKNDIYNELFM--KNK-TVTE | 567 |
| AIT42264 | 487 | SAQSFIERMTNEDKNLPNEKVLPKHSLLYEYFTVVNELTKVKYVT--EGMRKPaFLSGEQKKAIVDLLFK---TNR-KVTV | 561 |
| WP_034440723 | 494 | SAELFIENLTSRDTYLPDEPVLPKRSLIYQKFTIFNELTKVKISYID-ERGILQ-NESSREKIAIENDLEK---NKsKVTK | 567 |
| AKQ21048 | 487 | SAQSFIERMTNEDKNLPNEKVLPKHSLLYEYFTVVNELTKVKYVT--EGMRKPaFLSGEQKKAIVDLLFK---TNR-KVTV | 561 |
| WP_004636532 | 489 | SAEKFIERMTNMDTYLLEEKVLPKRSLLYQTFEVVNELTKVRYTN--EQGKTE-KLNRQQKAEIIETLFK--qKNR-VRE | 562 |

| | | | |
|---|---|---|---|
| WP_002364836 | 496 | SATAFIERMTNEDTYLPSEKVLPKHSLLYEKFMVFNELTKISYTD--DRGIKA-NFSGKEKEKIFDYLEK--TRR-KVKK | 569 |
| WP_016631044 | 447 | SATAFIERMTNEDTYLPSEKVLPKHSLLYEKFMVFNELTKISYTD--DRGIKA-NFSGKEKEKIFDYLEK--TRR-KVKK | 520 |
| EMS75795 | 232 | SAMKFIQRMINYDTYLPTEKVLPKHSILYQKYTIFNELTKVAYKD--ERGIKH-QFSSKEKREIFKELFQ--KQR-KVTV | 305 |
| WP_002373311 | 496 | SATAFIERMTNEDTYLPSEKVLPKHSLLYEKFMVFNELTKISYTD--DRGIKA-NFSGKEKEKIFDYLEK--TRR-KVKK | 569 |
| WP_002378009 | 496 | SATAFIERMTNEDTYLPSEKVLPKHSLLYEKFMVFNELTKISYTD--DRGIKA-NFSGKEKEKIFDYLEK--TRR-KVKK | 569 |
| WP_002407324 | 496 | SATAFIERMTNEDTYLPSEKVLPKHSLLYEKFMVFNELTKISYTD--DRGIKA-NFSGKEKEKIFDYLEK--TRR-KVKK | 569 |
| WP_002413717 | 496 | SATAFIERMTNEDTYLPSEKVLPKHSLLYEKFMVFNELTKISYTD--DRGIKA-NFSGKEKEKIFDYLEK--TRR-KVKK | 569 |
| WP_010775580 | 498 | SATAFIERMTNEDTYLPSEKVLPKHSLLYEKFMVFNELTKISYTD--DRGIKA-NFSGKEKEKIFDYLEK--TRR-KVKK | 571 |
| WP_010818269 | 496 | SATAFIERMTNEDTYLPSEKVLPKHSLLYEKFMVFNELTKISYTD--DRGIKA-NFSGKEKEKIFDYLEK--TRR-KVKK | 569 |
| WP_010824395 | 496 | SATAFIERMTNEDTYLPSEKVLPKHSLLYEKFMVFNELTKISYTD--DRGIKA-NFSGKEKEKIFDYLEK--TRR-KVKK | 569 |
| WP_016622645 | 496 | SATAFIERMTNEDTYLPSEKVLPKHSLLYEKFMVFNELTKISYTD--DRGIKA-NFSGKEKEKIFDYLEK--TRR-KVKK | 569 |
| WP_033624816 | 496 | SATAFIERMTNEDTYLPSEKVLPKHSLLYEKFMVFNELTKISYTD--DRGIKA-NFSGKEKEKIFDYLEK--TRR-KVKK | 569 |
| WP_033625576 | 496 | SATAFIERMTNEDTYLPSEKVLPKHSLLYEKFMVFNELTKISYTD--DRGIKA-NFSGKEKEKIFDYLEK--TRR-KVKK | 569 |
| WP_033789179 | 496 | SATAFIERMTNEDTYLPSEKVLPKHSLLYEKFMVFNELTKISYTD--DRGIKA-NFSGKEKEKIFDYLEK--TRR-KVKK | 569 |
| WP_002310644 | 493 | SAVRFIERMINTDMYMPHNKVLPKNSLLYQKFSIYNELTKVRYQD--ERGQMN-YFSSIEKKEIFHELFE--KNR-KVTK | 566 |
| WP_002312694 | 494 | SAVRFIERMINTDMYIPHNKVLPKNSLLYQKFSIYNELTKVRYQD--ERGQMN-YFSSIEKKEIFHELFE--KNR-KVTK | 567 |
| WP_002314015 | 494 | SAVRFIERMINTDMYIPHNKVLPKNSLLYQKFSIYNELTKVRYQD--ERGQMN-YFSSIEKKEIFHELFE--KNR-KVTK | 567 |
| WP_002320716 | 494 | SAVRFIERMNNTDMYIPHNKVLPKNSLLYQKFSIYNELTKVRYQD--ERGQMN-YFSSIEKKEIFHELFE--KNR-KVTK | 567 |
| WP_002330729 | 493 | SAVRFIERMINTDMYIPHNKVLPKNSLLYQKFSIYNELTKVRYQD--ERGQMN-YFSSIEKKEIFHELFE--KNR-KVTK | 566 |
| WP_002335161 | 494 | SAVRFIERMINTDMYIPHNKVLPKNSLLYQKFSIYNELTKVRYQD--ERGQMN-YFSSIEKKEIFHELFE--KNR-KVTK | 567 |
| WP_002345439 | 494 | SAVRFIERMINTDMYIPHNKVLPKNSLLYQKFSIYNELTKVRYQD--ERGQMN-YFSSIEKKEIFHELFE--KNR-KVTK | 567 |
| WP_034867970 | 487 | SAMRFIQRMTKQDTYLPTEKVLPKNSLLYQKYMIFNELTKVSYKD--ERGVKQ-YFSGDEKQQIFKQLFQ--KERgKITV | 561 |
| WP_047937432 | 494 | SAVRFIERMINTDMYMPHNKVLPKNSLLYQKFSIYNELTKVRYQD--ERGQMN-YFSSIEKKEIFHELFE--KNR-KVTK | 567 |
| WP_010720994 | 487 | SAMRFIQRMTKQDTYLPTEKVLPKNSLLFYQKYMIFNELTKVSYKD--ERGVKQ-YFSGDEKQQIFKQLFQ--KERgKITV | 561 |
| WP_010737004 | 487 | SAMRFIQRMTKQDTYLPTEKVLPKNSLLYQKYMIFNELTKVSYKD--ERGVKQ-YFSGDEKQQIFKQLFQ--KERgKITV | 561 |
| WP_034700478 | 487 | SAMRFIQRMTKQDTYLPTEKVLPKNSLLYQKYMIFNELTKVSYKD--ERGVKQ-YFSGDEKQQIFKQLFQ--KERgKITV | 561 |
| WP_007209003 | 491 | SAVAFIERMTIKDIYL-NENVLPRHSLIYEKFTVNELTKVLYAD--DRGVFQ-RFSAEEKEDIFEKLFK--SER-KVTK | 563 |

-continued

```
WP_023519017   486 SAIEFIERMTNQDTYLPKEKVLPKQSLIYQRFMIFNELTKVSYTD--ERGKSH-YESSEQKRKIFNELFK---QHP-RVTE  559
WP_010770040   490 SATKFIERMTNEDTYLPTEKVLPKHSMIYEKYMVNELTKVSYVD--ERGMNQ-RFSGEEKKQIVEELFK---QSR-KVTK  563
WP_048604708   486 SAELFIERMTNFDLYLPSEKVLPKHSMLYEKYTVNELTKVTYKD--EQGKVQ-NFSSEEKERIFIDLFK---QHR-KVTK  559
WP_010750235   487 SATKFIQRMINYDTYLPTEKVLPKYSMLYQKYTIFNELTKVAYKD--DRGIKH-QESSEEKLRIFQELFK---KQR-RVTK  560
AII16583       526 SAQSFIERMTNFDKNLPNEKVLPKHSLLYEYFTVNELTKVKVT--EGMRKPaFLSGEQKKAIVDLLFK---TNR-KVTV  600
WP_029073316   507 TADEFIKRMRNFCTYFPDEPVLAKNSLTVSKYEVLNEINKLRIND------hLIKRDIKDKMLHTLFM--DHK-SISA  575
WP_031589969   507 TADEFIKRMRNFCTYFPDEPVMAKNSLTVSKYEVLNEINKLRIND------hLIKRDMKDKMLHTLFM--DHK-SISA  575
KDA45870       485 SAEDFIKRMTINDLYLPTEPVLPKHSLLYERYTIFNELAGVRYVT--ENGEAK-YEDAQTKRSIFE-LPK1--DR-KVSE  557
WP_039099354   510 SANEFIKRMTTTDTYLLAEDVLPKQSLIYQRFEVLNELNGLKIDD----QPITTE-----LKQAIFTDLFM---QKtSVTV  578
AKP02966       484 SSNKFIRRMTVTDSYLVGEPVLPKNSLIYQRYEVLNELNNIRITEn1KTNPTGsRLTVETKQHIYNELFK---NYK-KITV  560
WP_010991369   493 SAVDFIEKMTNKDTYLPKENVLPKHSLCYQKYLVNELTKVRYIN--DQGKTS-YFSGQEKEQIFNDLFK---QKR-KVKK  566
WP_033838504   493 SAVDFIEKMTNKDTYLPKENVLPKHSLCYQKYLVNELTKVRYIN--DQGKTS-YFSGQEKEQIFNDLFK---QKR-KVKK  566
EHN60060       496 SAVDFIEKMTNKDTYLPKENVLPKHSLCYQKYLVNELTKVRYIN--DQGKTS-YFSGQEKEQIFNDLFK---QKR-KVKK  569
EFR89594       262 SAVDFIEKMTNKDTYLPKENVLPKHSLCYQKYMVNELTKVRYIN--DQGKTS-YFSGQEKEQIFNDLFK---QKR-KVKK  335
WP_038409211   493 SAIDFIEKMTNKDTYLPKENVLPKHSLCYQKYMVNELTKIRYID--DQGKTH-HFSGQEKQQIENGLEK---QQR-KVKK  566
EFR95520       112 SAIDFIEKMTNKDTYLPKENVLPKHSLCYQKYMVNELTKIRYID--DQGKTH-HFSGQEKQQIENGLEK---QQR-KVKK  185
WP_003723650   493 SAVDFIEKMTNKDTYLPKENVLPKHSLCYQKYMVNELTKIRYID--DQGKTN-YFSGREKQQVFNDLFK---QKR-KVKK  566
WP_003727705   493 SAVDFIEKMTNKDTYLPKENVLPKHSLCYQKYMVNELTKIRYID--DQGKTN-YFSGREKQQIFNDLFK---QKR-KVKK  566
WP_003730785   493 SAVDFIEKMTNKDTYLPKENVLPKHSLCYQKYMVNELTKIRYID--DQGKTN-YFSGREKQQIFNDLFK---QKR-KVKK  566
WP_003733029   493 SAVDFIEKMTNKDTYLPKENVLPKHSLCYQKYMVNELTKIRYID--DQGKTN-YFSGQEKQQIFNDLFK---QKR-KVKK  566
WP_003739838   493 SAVDFIEKMTNKDTYLPKENVLPKHSLCYYQKYMVNELTKVRYID--DQGKTN-YFSGQEKQQIENDYPK---QKR-KVSK  566
WP_014601172   493 SAVDFIEKMTNKDTYLPKENVLPKHSLCYQKYMVNELTKVRYID--DQGKTN-YFSGQEKQQIFNDLFK---QKR-KVKK  566
WP_023548323   493 SAVDFIEKMTNKDTYLPKENVLPKHSLCYQKYMVNELTKVRYID--DQGKTN-YFSGQEKQQIFNDLFK---QKR-KVKK  566
WP_031665337   493 SAVDFIEKMTNKDTYLPKENVLPKHSLCYQKYMVNELTKVRYID--DQGKTN-YFSGQEKQQIFNDLFK---QKR-KVKK  566
WP_031669209   493 SAVDFIEKMTNKDTYLPKENVLPKHSLCYQKYMVNELTKVRYID--DQGKTN-YFSGQEKQQIFNDLFK---QKR-KVKK  566
WP_033920898   493 SAVDFIEKMTNKDTYLPKENVLPKHSLCYQKYMVNELTKVRYID--DQGKTN-YFSGQEKQQIFNDLFK---QKR-KVKK  566
AKI42028       496 SAVDFIEKMTNKDTYLPKENVLPKHSLCYQKYMVNELTKVRYID--DQGKTN-YFSGQEKQQIFNDLFK---QKR-KVKK  569
```

```
AKI50529        496  SAVDFIEKMTNKDTYLPKENVLPKHSLCYQKYMVNELTKIRYID--DQGKTN-YFSGQEKQQIFNDLFK--QKR-KVKK           569
EFR83390          1  ------------------------------------------------------IFNDLFK--QKR-KVKK            14
WP_046323366    493  SAIDFIEKMTNKDTYLPKENVLPKHSMCYQKYMVNELTKIRYTD--DQGKTH-YFSGQEKQQIFNDLFK--QKR-KVKK           566
AKE81011        503  SAQSFIERMTNFDKNLPNEKVLPKHSLLYEYFTVNELTKVKYVT--EGMRKPaFLSGEQKKAIVDLLFK--TNR-KVTV           577
CUO82355        503  TAEGFIKRMRSYCYFPDEEVLPKNSLIVSKYEVNELNKIRVDD------kLLEVDVKNDIYNELFM--KNK-TVTE            571
WP_033162887    504  TAEGFIERMKNTGTYFPDEPVMAKNSLTVSKFEVLNELNKIRING------kLIAVETKKELLSDLFM--KNK-TITD           572
AGZ01981        520  SAQSFIERMTNFDKNLPNEKVLPKHSLLYEYFTVNELTKVKYVT--EGMRKPaFLSGEQKKAIVDLLFK--TNR-KVTV           594
AKA60242        487  SAQSFIERMTNFDKNLPNEKVLPKHSLLYEYFTVNELTKVKYVT--EGMRKPaFLSGEQKKAIVDLLFK--TNR-KVTV           561
AKS40380        487  SAQSFIERMTNFDKNLPNEKVLPKHSLLYEYFTVNELTKVKYVT--EGMRKPaFLSGEQKKAIVDLLFK--TNR-KVTV           561
4UN5_B          491  SAQSFIERMTNFDKNLPNEKVLPKHSLLYEYFTVNELTKVKYVT--EGMRKPaFLSGEQKKAIVDLLFK--TNR-KVTV           565
WP_010922251    562  KQLKEDYFKK--IECFDSVEISGVEDR---FNASLGTYHDLLKIIKDK                  DFLDNEENEDILEDIVLTLTLFEDREMIE   633
WP_039695303    564  EKLLNYLNKE--FPEYRIKDLIGLDKEnkSFNASLGTYHDLKKIL-DK                  AFLDDKVNEEVIEDIIKTLTLFEDKDMIH   637
WP_045635197    562  KDIIHYLHN---VDGYDGIELKGIEKQ---FNASLSTYHDLLKIIKDK                  EFMDDAKNEAILENIVHTLTIFEDREMIK   632
5AXW_A          300  KQIAKEILVNe-EDIKGYRTSTGKPe---FTNLKVYHDIKDITARK                  ------ENAELLDQIAKILTIYQSSEDIQ   368
WP_009880683    246  KQLKEDYFKK--IECFDSVEISGVEDR---FNASLGTYHDLLKIIKDK                  DFLDNEENEDILEDIVLTLTLFEDREMIE   317
WP_010922251    562  KQLKEDYFKK--IECFDSVEISGVEDR---FNASLGTYHDLLKIIKDK                  DFLDNEENEDILEDIVLTLTLFEDREMIE   633
WP_011054416    562  KQLKEDYFKK--IECFDSVEISGVEDR---FNASLGTYHDLLKIIKDK                  DFLDNEENEDILEDIVLTLTLFEDREMIE   633
WP_011284745    562  KQLKEDYFKK--IECFDSVEISGVEDR---FNASLGTYHDLLKIIKDK                  DFLDNEENEDILEDIVLTLTLFEDREMIE   633
WP_011285506    562  KQLKEDYFKK--IECFDSVEISGVEDR---FNASLGTYHDLLKIIKDK                  DFLDNEENEDILEDIVLTLTLFEDREMIE   633
WP_011527619    562  KQLKEDYFKK--IECFDSVEISGVEDR---FNASLGTYHDLLKIIKDK                  DFLDNEENEDILEDIVLTLTLFEDREMIE   633
WP_012560673    562  KQLKEDYFKK--IECFDSVEISGVEDR---FNASLGAYHDLLKIIKDK                  DFLDNEENEDILEDIVLTLTLFEDREMIE   633
WP_014407541    562  KQLKEDYFKK--IECFDSVEISGVEDR---FNASLGTYHDLLKIIKDK                  DFLDNEENEDILEDIVLTLTLFEDRGMIE   633
WP_020905136    562  KQLKEDYFKK--IECFDSVEISGVEDR---FNTSLGTYHDLLKIIKDK                  DFLDNEENEDILEDIVLTLTLFEDKEMIE   633
WP_023080005    562  KQLKEDYFKK--IECFDSVEISGVEDR---FNTSLGTYHDLLKIIKDK                  DFLDNEENEDILEDIVLTLTLFEDKEMIE   633
WP_023610282    562  KQLKEDYFKK--IECFDSVEISGVEDR---FNASLGTYHDLLKIIKDK                  DFLDNEENEDILEDIVLTLTLFEDKEMIE   633
WP_030125963    562  KQLKEDYFKK--IECFDSVEISGVEDR---FNASLGTYHDLLKIIKDK                  DFLDNEENEDILEDIVLTLTLFEDKEMIE   633
WP_030126706    562  KQLKEDYFKK--IECFDSVEISGVEDR---FNASLGTYHDLLKIIKDK                  DFLDNEENEDILEDIVLTLTLFEDREMIE   633
```

-continued

| | | | | |
|---|---|---|---|---|
| WP_031488318 | 562 | KQLKEDYFKK--IECFDSVEISGVEDR---FNASLGTYHDLLKIIKDK | DFLDNEENEDILEDIVLTLTLFEDREMIE | 633 |
| WP_032460140 | 562 | KQLKEDYFKK--IECFDSVEISGVEDR---FNASLGTYHDLLKIIKDK | DFLDNEENEDILEDIVLTLTLFEDREMIE | 633 |
| WP_032461047 | 562 | KQLKEDYFKK--IECFDSVEISGVEDR---FNASLGTYHDLLKIIKDK | DFLDNEENEDILEDIVLTLTLFEDREMIE | 633 |
| WP_032462016 | 562 | KQLKEDYFKK--IECFDSVEISGVEDR---FNASLGTYHDLLKIIKDK | DFLDNEENEDILEDIVLTLTLFEDREMIE | 633 |
| WP_032462936 | 562 | KQLKEDYFKK--IECFDSVEISGVEDR---FNASLGTYHDLLKIIKDK | DFLDNEENEDILEDIVLTLTLFEDREMIE | 633 |
| WP_032464890 | 562 | KQLKEDYFKK--IECFDSVEISGVEDR---FNASLGTYHDLLKIIKDK | DFLDNEENEDILEDIVLTLTLFEDREMIE | 633 |
| WP_033888930 | 387 | KQLKEDYFKK--IECFDSVEISGVEDR---FNASLGTYHDLLKIIKDK | DFLDNEENEDILEDIVLTLTLFEDREMIE | 458 |
| WP_038431314 | 562 | KQLKEDYFKK--IECFDSVEISGVEDR---FNASLGTYHDLLKIIKDK | DFLDNEENEDILEDIVLTLTLFEDREMIE | 633 |
| WP_038432938 | 562 | KQLKEDYFKK--IECFDSVEISGVEDR---FNTSLGTYHDLLKIIKDK | DFLDNEENEDILEDIVLTLTLFEDKEMIE | 633 |
| WP_038434062 | 562 | KQLKEDYFKK--IECFDSVEISGVEDR---FNASLGTYHDLLKIIKDK | DFLDNEENEDILEDIVLTLTLFEDREMIE | 633 |
| BAQ51233 | 473 | KQLKEDYFKK--IECFDSVEISGVEDR---FNASLGTYHDLLKIIKDK | DFLDNEENEDILEDIVLTLTLFEDREMIE | 544 |
| KGE60162 | | ------------------------------ | ------------------------------ | |
| KGE60856 | | ------------------------------ | ------------------------------ | |
| WP_002989955 | 562 | KQLKEDYFKK--IECFDSVEISGVEDR---FNASLGTYHDLLKIIKDK | DFLDNEENEDILEDIVLTLTLFEDREMIE | 633 |
| WP_003030002 | 561 | DKLLNYLNKE--FEEFRIVNLTGLDKEnkAFNSSLGTYHDLRKIL-DK | SFLDDKANEKTIEDIIQTLFEDREMIR | 634 |
| WP_003065552 | 564 | EKLLNYLNKE--FPEYRIKDLIGLDKEnkSFNASLGTYHDLKKIL-DK | AFLDDKVNEEVIEDIIKTLFEDKDMIH | 637 |
| WP_001040076 | 563 | KDIISFLNK---VDGYEGIAIKGIEKQ---FNASLSTYHDLKKIL-GK | DFLDNTDNELILEDIVQTLFEDREMIK | 632 |
| WP_001040078 | 562 | KKLLDFLAKE--YEEFRIVDVIGLDKEnkAFNASLGTYHDLEKIL-DK | DFLDNPDNESILEDIVQTLFEDREMIK | 635 |
| WP_001040080 | 562 | KKLLDFLAKE--YEEFRIVDVIGLDKEnkAFNASLGTYHDLEKIL-DK | DFLDNPDNESILEDIVQTLFEDREMIK | 635 |
| WP_001040081 | 562 | KKLLDFLAKE--YEEFRIVDVIGLDKEnkAFNASLGTYHDLEKIL-DK | DFLDNPDNESILEDIVQTLFEDREMIK | 635 |
| WP_001040083 | 562 | KKLLDFLAKE--YEEFRIVDVIGLDKEnkAFNASLGTYHDLEKIL-DK | DFLDNPDNESILEDIIQTLFEDREMIK | 635 |
| WP_001040085 | 562 | KKLLDFLAKE--YEEFRIVDVIGLDKEnkAFNASLGTYHDLEKIL-DK | DFLDNPDNESILEDIVQTLFEDREMIK | 635 |
| WP_001040087 | 562 | KKLLDFLAKE--YEEFRIVDVIGLDKEnkAFNASLGTYHDLEKIL-DK | DFLDNPDNESILEDIVQTLFEDREMIK | 635 |
| WP_001040088 | 562 | KKLLDFLAKE--YEEFRIVDVIGLDKEnkAFNASLGTYHDLEKIL-DK | DFLDNPDNESILEDIVQTLFEDREMIK | 635 |
| WP_001040089 | 562 | KKLLDFLAKE--YEEFRIVDVIGLDKEnkAFNASLGTYHDLEKIL-DK | DFLDNPDNESILEDIVQTLFEDREMIK | 635 |
| WP_001040090 | 562 | KKLLDFLAKE--YEEFRIVDVIGLDKEnkAFNASLGTYHDLEKIL-DK | DFLDNPDNESILEDIVQTLFEDREMIK | 635 |
| WP_001040091 | 562 | KKLLDFLAKE--YEEFRIVDVIGLDKEnkAFNASLGTYHDLEKIL-DK | DFLDNPDNESILEDIVQTLFEDREMIK | 635 |

| | | | | |
|---|---|---|---|---|
| WP_001040092 | 562 | KQLLDFLAKE--FEEFRIVDVTGLDKEhkAFNASLGTYHDLKKIL-DK | DFLDNPDNESILEDIVQTITLFEDREMIK | 635 |
| WP_001040094 | 563 | KDIISFLNK---VDGYEGIAIKGIEKQ---FNASLSTYHDLKKIL-GK | DFLDNTDNELILEDIVQTLTLFEDREMIR | 632 |
| WP_001040095 | 563 | KDIISFLNK---VDGYEGIAIKGIEKQ---FNASLSTYHDLKKIL-GK | DFLDNTDNELILEDIVQTLTLFEDREMIR | 632 |
| WP_001040096 | 563 | KDIISFLNK---VDGYEGIAIKGIEKQ---FNASLSTYHDLKKIL-GK | DFLDNTDNELILEDIVQTLTLFEDREMIR | 632 |
| WP_001040097 | 563 | KDIISFLNK---VDGYEGIAIKGIEKQ---FNASLSTYHDLKKIL-GK | DFLDNTDNELILEDIVQTLTLFEDREMIR | 632 |
| WP_001040098 | 563 | KDIISFLNK---VDGYEGIAIKGIEKQ---FNASLSTYHDLKKIL-GK | DFLDNTDNELILEDIVQTLTLFEDREMIR | 632 |
| WP_001040099 | 563 | KDIISFLNK---VDGYEGIAIKGIEKQ---FNASLSTYHDLKKIL-GK | DFLDNTDNELILEDIVQTLTLFEDREMIR | 632 |
| WP_001040100 | 563 | KDIISFLNK---VDGYEGIAIKGIEKQ---FNASLSTYHDLKKIL-GK | DFLDNTDNELILEDIVQTLTLFEDREMIR | 632 |
| WP_001040104 | 562 | KKLLDFLAKE--YEEFRIVDVIGLDKEhkAFNASLGTYHDLEKIL-DK | DFLDNPDNESILEDIVQTLTLFEDREMIR | 635 |
| WP_001040105 | 562 | KKLLDFLAKE--YEEFRIVDVIGLDKEhkAFNASLGTYHDLEKIL-DK | DFLDNPDNESILEDIVQTLTLFEDREMIR | 635 |
| WP_001040106 | 562 | KKLLDFLAKE--YEEFRIVDVIGLDKEhkAFNASLGTYHDLKKIL-DK | DFLDNPDNESILEDIVQTLTLFEDREMIR | 635 |
| WP_001040107 | 562 | KKLLDFLAKE--YEEFRIVDVIGLDKEhkAFNASLGTYHDLKKIL-DK | DFLDNPDNESILEDIVQTLTLFEDREMIR | 635 |
| WP_001040108 | 562 | KKLLDFLAKE--YEEFRIVDVIGLDKEhkAFNASLGTYHDLKKIL-DK | DFLDNPDNESILEDIVQTLTLFEDREMIR | 635 |
| WP_001040109 | 562 | KKLLDFLAKE--YEEFRIVDVIGLDKEhkAFNASLGTYHDLKKIL-DK | DFLDNPDNESILEDIVQTLTLFEDREMIR | 635 |
| WP_001040110 | 562 | KKLLDFLAKE--YEEFRIVDVIGLDKEhkAFNASLGTYHDLKKIL-DK | DFLDNPDNESILEDIVQTLTLFEDREMIR | 635 |
| WP_015058823 | 562 | KQLLDFLAKE--FEEFRIVDVTGLDKEhkAFNASLGTYHDLKKIL-DK | DFLDNPDNESILEDIVQTITLFEDREMIR | 635 |
| WP_017643650 | 563 | KDIISFLNK---VDGYEGIAIKGIEKQ---FNASLSTYHDLKKIL-GK | DFLDNTDNELILEDIVQTLTLFEDREMIR | 632 |
| WP_017647151 | 562 | KKLLDFLAKE--YEEFRIVDVIGLDKEhkAFNASLGTYHDLKKIL-DK | DFLDNPDNESILEDIVQTLTLFEDREMIR | 635 |
| WP_017648376 | 562 | KKLLDFLAKE--YEEFRIVDVIGLDKEhkAFNASLGTYHDLKKIL-DK | DFLDNPDNESILEDIVQTLTLFEDREMIR | 635 |
| WP_017649527 | 562 | KKLLDFLAKE--YEEFRIVDVIGLDKEhkAFNASLGTYHDLKKIL-DK | DFLDNPDNESILEDIVQTLTLFEDREMIR | 635 |
| WP_017771611 | 562 | KKLLDFLAKE--YEEFRIVDVIGLDKEhkAFNASLGTYHDLKKIL-DK | DFLDNPDNESILEDIVQTLTLFEDREMIR | 635 |
| WP_017771984 | 562 | KKLLDFLAKE--YEEFRIVDVIGLDKEhkAFNASLGTYHDLKKIL-DK | DFLDNPDNESILEDIVQTLTLFEDREMIR | 635 |
| CFQ25032 | 562 | KKLLDFLAKE--YEEFRIVDVIGLDKEhkAFNASLGTYHDLEKIL-DK | DFLDNPDNESILEDIVQTLTLFEDREMIR | 635 |
| CFV16040 | 562 | KKLLDFLAKE--YEEFRIVDVIGLDKEhkAFNASLGTYHDLEKIL-DK | DFLDNPDNESILEDIVQTLTLFEDREMIR | 635 |
| KLJ37842 | 562 | KKLLDFLAKE--YEEFRIVDVIGLDKEhkAFNASLGTYHDLEKIL-DK | DFLDNPDNESILEDIVQTLTLFEDREMIR | 635 |
| KLJ72361 | 562 | KKLLDFLAKE--YEEFRIVDVIGLDKEhkAFNASLGTYHDLEKIL-DK | DFLDNPDNESILEDIVQTLTLFEDREMIR | 635 |
| KLL20707 | 562 | KKLLDFLAKE--YEEFRIVDVIGLDKEhkAFNASLGTYHDLEKIL-DK | DFLDNPDNESILEDIVQTLTLFEDREMIR | 635 |

| | | | | |
|---|---|---|---|---|
| KLL42645 | 562 | KKLLDFLAKE--YEEFRIVDVIGLDKEhkAFNASLGTYHDLKKIL-DK | DFLDNPDNESILEDIVQTLTLFEDREMIK | 635 |
| WP_047207273 | 562 | KKLLDFLAKE--YEEFRIVDVIGLDKEnkAFNASLGTYHDLEKIL-DK | DFLDNPDNESILEDIVQTLTLFEDREMIK | 635 |
| WP_047209694 | 563 | KDIISFLNK---VDGYEGIAIKGIEKQ---FNASLSTYHDLKKIL-GK | DFLDNTDNELILEDIVQTLTLFEDREMIK | 632 |
| WP_050198062 | 562 | KKLLDFLAKE--YEEFRIVDVIGLDKEnkAFNASLGTYHDLEKIL-DK | DFLDNPDNESILEDIVQTLTLFEDREMIK | 635 |
| WP_050201642 | 562 | KKLLDFLAKE--YEEFRIVDVIGLDKEnkAFNASLGTYHDLEKIL-DK | DFLDNPDNESILEDIVQTLTLFEDREMIK | 635 |
| WP_050204027 | 562 | KKLLDFLAKE--YEEFRIVDVIGLDKEnkAFNASLGTYHDLEKIL-DK | DFLDNPDNESILEDIVQTLTLFEDREMIK | 635 |
| WP_050881965 | 562 | KKLLDFLAKE--YEEFRIVDVIGLDKEnkAFNASLGTYHDLEKIL-DK | DFLDNPDNESILEDIVQTLTLFEDREMIK | 635 |
| WP_050886065 | 562 | KKLLDFLAKE--YEEFRIVDVIGLDKEnkAFNASLGTYHDLEKIL-DK | DFLDNPDNESILEDIVQTLTLFEDREMIK | 635 |
| AHN30376 | 562 | KQLLDFLAKE--FEEFRIVDVTGLDKEnkAFNASLGTYHDLKKIL-DK | DFLDNPDNESILEDIVQTITLFEDREMIK | 635 |
| EAO78426 | 562 | KKLLDFLAKE--YEEFRIVDVIGLDKEnkAFNASLGTYHDLEKIL-DK | DFLDNPDNESILEDIVQTLTLFEDREMIK | 635 |
| CCW42055 | 562 | KQLLDFLAKE--FEEFRIVDVTGLDKEnkAFNASLGTYHDLEKIL-GK | DFLDNPDNESILEDIVQTLTLFEDREMIK | 635 |
| WP_003041502 | 561 | DKLLNYLNKE--FEEFRIVNLTGLDKEnkVFNSSLGTYHDLRKIL-NK | SFLDNKENAQIIEDIIQTLTLFEDREMIR | 634 |
| WP_037593752 | 562 | DKLLNYLNKE--FEEFRIVNLTGLDKEnkAFNSSLGTYHDLRKIL-DK | SFLDDKANEKTIEDIIQTLTLFEDREMIR | 635 |
| WP_049516684 | 562 | DKLLNYLNKE--FEEFRIVNLTGLDKEnkAFNASLGTYHDLRKIL-DK | SFLDDKANEKTIEDIIQTLTLFEDREMIR | 635 |
| GAD46167 | 561 | DKLLNYLDKE--PDEFRIVDLTGLDKEnkAFNASLGTYHDLRKIL-DK | SFLDDKVNEKIIEDIIQTLTLFEDREMIR | 634 |
| WP_018363470 | 562 | EKLLNYLDKE--PPEYRIQDLVGLDKEnkSFNASLGTYHDLKKIL-DK | SFLDDKVNEEVIEDIIKTLTLFEDREMIQ | 635 |
| WP_003043819 | 572 | KQLKEDYFKK--IECFDSVEIIGVEDR---FNASLGTYHDLKIIKDK | DFLDNEENEDILEDIVLTLFEDREMIE | 643 |
| WP_006269658 | 561 | DKLLNYLNKE--FEEFRIVNLTGLDKEnkAFNSSLGTYHDLRKIL-DK | SFLDDKANEKTIEDIIQTLTLFEDREMIR | 634 |
| WP_048800889 | 561 | KQLKEDYFKK--IECFDSVEISGVEDR---FNASLGTYHDLLKIIKDK | SFLDDKANEKTIEDIIQTLTLFEDREMIR | 634 |
| WP_012767106 | 562 | KQLKEDYFKK--IECFDSVEISGVEDR---FNASLGTYHDLLKIIKDK | DFLDNEENEDILEDIVLTLFEDKEMIE | 633 |
| WP_014612333 | 562 | KQLKEDYFKK--IECFDSVEISGVEDR---FNASLGTYHDLLKIIKDK | DFLDNEENEDILEDIVLTLFEDKEMIE | 633 |
| WP_015017095 | 562 | KQLKEDYFKK--IECFDSVEISGVEDR---FNASLGTYHDLLKIIKDK | DFLDNEENEDILEDIVLTLFEDKEMIE | 633 |
| WP_015057649 | 562 | KQLKEDYFKK--IECFDSVEISGVEDR---FNASLGTYHDLLKIIKDK | DFLDNEENEDILEDIVLTLFEDKEMIE | 633 |
| WP_048327215 | 562 | KQLKEDYFKK--IECFDSVEISGVEDR---FNASLGTYHDLLKIIKDK | DFLDNEENEDILEDIVLTLFEDKEMIE | 633 |
| WP_049519324 | 562 | KQLKENYFKK--IECWDSVEITGVEDS---FNASLGTYHDLLKIIQDK | DFLDNEENEDILEDIVLTLFEDKEMIE | 633 |
| WP_012515931 | 562 | KQLKENYFKK--IECWDSVEITGVEDS---FNASLGTYHDLLKIIQDK | DFLDNPDNQKIIEDIILTLFEDKKMIS | 633 |
| WP_021320964 | 562 | KQLKENYFKK--IECWDSVEITGVEDS---FNASLGTYHDLLKIIQDK | DFLDNPDNQKIIEDIILTLFEDKKMLS | 633 |

| | | | | |
|---|---|---|---|---|
| WP_037581760 | 562 | KQLKENYFKK---IECWDSVBITGVEDS---FNASLGTYHDLLKKIIQDK | DFLDNPDNQKIIEDIILTLFEDKKMIS | 633 |
| WP_004232481 | 561 | AKLLSYLNNE--FEEFRINDLIGLDKDskSFNASLGTYHDLKKKIL-DK | SFLDDKTNEQIIEDIVLTLFEDRDMIH | 634 |
| WP_009854540 | 562 | EKLLNYLNKE--FPEYRIKDLIGLDKEnkSFNASLGTYHDLKKKIL-DK | AFLDDKVNEEVIEDIIKTLTLFEDKDMIH | 635 |
| WP_012962174 | 562 | DKFLNYLNKE--FPEYRIQDLIGLDKEnkSFNASLGTYHDLKKKIL-DK | SFLDDKTNETIIEDIIQTLTLFEDRDMIR | 635 |
| WP_039695303 | 564 | EKLLNYLNKE--FPEYRIKDLIGLDKEnkSFNASLGTYHDLKKKIL-DK | AFLDDKVNEEVIEDIIKTLTLFEDKDMIH | 637 |
| WP_014334983 | 561 | AKLLSYLNNE--FEEFRINDLIGLDKDskSFNASLGTYHDLKKKIL-DK | SFLDDKTNGQIIEDIVLTLFEDRDMIH | 634 |
| WP_003099269 | 562 | KQLKEEYFSK--MKCFHTVTILGVEDR---FNASLGTYHDLLKKIFKDK | AFLDDEANQDILEEIVWTLTLFEDQAMIE | 633 |
| AHY15608 | 562 | KQLKEEYFSK--MKCFHTVTILGVEDR---FNASLGTYHDLLKKIFKDK | AFLDDEANQDILEEIVWTLTLFEDQAMIE | 633 |
| AHY17476 | 562 | KQLKEEYFSK--MKCFHTVTILGVEDR---FNASLGTYHDLLKKIFKDK | AFLDDEANQDILEEIVWTLTLFEDQAMIE | 633 |
| ESR09100 | | ------------------------------------------------ | --------------------------- | |
| AGM98575 | 562 | KQLKEEYFSK--MKCFHTVTILGVEDR---FNASLGTYHDLLKKIFKDK | AFLDDEANQDILEEIVWTLTLFEDQAMIE | 633 |
| ALF27331 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_018372492 | 574 | RKLKDFIEKElgYGYIDIDNIKGVEEQ---FNASYTTYQDLLKKIIGDK | EFLDNEENKDLLEEIIYILTVFEDRKMIE | 647 |
| WP_045618028 | 563 | KDIIQYLHN---VDSYDGIELKGIEKQ---FNASLSTYHDLLKKIIKDK | EFMDDSKNEAILENIVHTLTIFEDREMIK | 633 |
| WP_045635197 | 562 | KDIIHYLHN---VDGYDGIELKGIEKQ---FNASLSTYHDLLKKIIKDK | EFMDDAKNEAILENIVHTLTIFEDREMIR | 632 |
| WP_002263549 | 561 | DKLMDFLEKE--FDEFRIVDLTGLDKEnkVFNASYGTYHDLCKIL-DK | DFLDNSKNEKILEDIVLTLTLFEDREMIR | 634 |
| WP_002263887 | 561 | DKLMDFLEKE--FDEFRIVDLTGLDKEnkVFNASYGTYHDLCKIL-DK | DFLDNSKNEKILEDIVLTLTLFEDREMIR | 634 |
| WP_002264920 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_002269043 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_002269448 | 561 | DKLMDFLEKE--FDEFRIVDLTGLDKEnkVFNASYGTYHDLCKIL-DK | DFLDNSKNEKILEDIVLTLTLFEDREMIR | 634 |
| WP_002271977 | 561 | DKLMDFLEKE--FDEFRIVDLTGLDKEnkVFNASYGTYHDLCKIL-DK | DFLDNSKNEKILEDIVLTLTLFEDREMIR | 634 |
| WP_002272766 | 561 | DKLMDFLEKE--FDEFRIVDLTGLDKEnkVFNASYGTYHDLCKIL-DK | DFLDNSKNEKILEDIVLTLTLFEDREMIR | 634 |
| WP_002273241 | 561 | DKLMDFLEKE--FDEFRIVDLTGLDKEnkVFNASYGTYHDLCKIL-DK | DFLDNSKNEKILEDIVLTLTLFEDREMIR | 634 |
| WP_002275430 | 561 | DKLMDFLEKE--FDEFRIVDLTGLDKEnkVFNASYGTYHDLCKIL-DK | DFLDNSKNEKILEDIVLTLTLFEDREMIR | 634 |
| WP_002276448 | 561 | DKLMDFLEKE--FDEFRIVDLTGLDKEnkVFNASYGTYHDLCKIL-DK | DFLDNSKNEKILEDIVLTLTLFEDREMIR | 634 |
| WP_002277050 | 561 | KKLRTFLDKN--FDEFRIVDIQGLDKEtFNASYATYQDLLKVIKDK | VFMDNPENAEILENIVLTLTLFEDREMIK | 635 |
| WP_002773364 | 561 | DKLMDFLEKE--FDEFRIVDLTGLDKEnkAFNASYGTYHDLRKIL-DK | DFLDNSKNEKILEDIVLTLTLFEDREMIR | 634 |

-continued

| | | | | |
|---|---|---|---|---|
| WP_002279025 | 561 | DKLMDFLEKE--FDEFRIVDLTGLDKEhkAFNASYGTYHDLRKIL-DK | DFLDNSKNEKILEDIVLTLTLFEDREMIR | 634 |
| WP_002279859 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_002280230 | 561 | DKLMDFLEKE--FDEFRIVDLTGLDKEhkAFNASYGTYHDLRKIL-DK | DFLDNSKNEKILEDIVLTLTLFEDREMIR | 634 |
| WP_002281696 | 561 | DKLMDFLEKE--FDEFRIVDLTGLDKEnkVFNASYGTYHDLRKIL-DK | DFLDNSKNEKILEDIVLTLTLFEDREMIR | 634 |
| WP_002282247 | 561 | KKLRTFLDKN--FDEFRIVDIQGLDKEteTFNASYATYQDLLKVIKDK | VFMDNPENAEILENIVLTLTLFEDREMIK | 635 |
| WP_002282906 | 561 | DKLMDFLEKE--FDEFRIVDLTGLDKEnkVFNASYGTYHDLRKIL-DK | DFLDNSKNEKILEDIVLTLTLFEDREMIR | 634 |
| WP_002283846 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_002287255 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_002288990 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_002289641 | 561 | DKLMDFLEKE--FDEFRIVDLTGLDKEnkVFNASYGTYHDLCKIL-DK | DFLDNSKNEKILEDIVLTLTLFEDREMIR | 634 |
| WP_002290427 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_002295753 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_002296423 | 561 | DKLLNYLNKE--FEEFRIVNLTGLDKEnkVFNSSLGTYHDLRKIL-NK | SFLDNKENEQIIEDIIQTLTLFEDREMIR | 644 |
| WP_002304487 | 571 | DKLMDFLEKE--FDEFRIVDLTGLDKEnkVFNASYGTYHDLRKIL-NK | DFLDNSKNEKILEDIVLTLTLFEDREMIR | 634 |
| WP_002305844 | 561 | DKLMDFLEKE--FDEFRIVDLTGLDKEnkAFNASYGTYHDLCKIL-DK | DFLDNSKNEKILEDIVLTLTLFEDREMIR | 634 |
| WP_002307203 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_002310390 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_002352408 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_012997688 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_014677909 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_019312892 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_019313659 | 561 | DKLMDFLEKE--FDEFRIVDLTGLDKEnkAFNASYGTYHDLCKIL-DK | DFLDNSKNEKILEDIVLTLTLFEDREMIR | 634 |
| WP_019314093 | 561 | DKLMDFLEKE--FDEFRIVDLTGLDKEnkAFNASYGTYHDLCKIL-DK | DFLDNSKNEKILEDIVLTLTLFEDREMIR | 634 |
| WP_019315370 | 561 | DKLMDFLEKE--FDEFRIVDLTGLDKEnkAFNASYGTYHDLCKIL-DK | DFLDNSKNEKILEDIVLTLTLFEDREMIR | 634 |
| WP_019803776 | 561 | DKLMDFLEKE--FDEFRIVDLTGLDKEnkAFNASYGTYHDLCKIL-DK | DFLDNSKNEKILEDIVLTLTLFEDREMIR | 634 |
| WP_019805234 | 561 | DKLMDFLEKE--FDEFRIVDLTGLDKEnkAFNASYGTYHDLCKIL-DK | DFLDNSKNEKILEDIVLTLTLFEDREMIR | 634 |
| WP_024783594 | 561 | DKLMDFLEKE--FDEFRIVDLTGLDKEnkVFNASYGTYHDLCKIL-DK | DFLDNSKNEKILEDIVLTLTLFEDREMIR | 634 |

-continued

| | | | | |
|---|---|---|---|---|
| WP_024784288 | 561 | KKLRTFLDKN--FDEFRIVDIQGLDKEteTFNASYATYQDLLKVIKDK | VFMDNPENAEILENIVLTLTLFEDREMIK | 635 |
| WP_024784666 | 561 | DKLMDFLEKE--FDEFRIVDLTGLDKEnkAFNASYGTYHDLRKIL-DK | DFLDNSKNEKILEDIVLTLTLFEDREMIR | 634 |
| WP_024784894 | 561 | DKLMDFLEKE--FDEFRIVDLTGLDKEnkVFNASYGTYHDLCKIL-DK | DFLDNSKNEKILEDIVLTLTLFEDREMIR | 634 |
| WP_024786433 | 561 | KKLRTFLDKN--FDEFRIVDIQGLDKEteTFNASYATYQDLLKVIKDK | VFMDNPENAEILENIVLTLTLFEDREMIK | 635 |
| WP_049473442 | 561 | DKLMDFLEKE--FDEFRIVDLTGLDKEnkVFNASYGTYHDLCKIL-DK | DFLDNSKNEKILEDIVLTLTLFEDREMIR | 634 |
| WP_049474547 | 561 | DKLMDFLEKE--FDEFRIVDLTGLDKEnkAFNASYGTYHDLCKIL-DK | DFLDNSKNEKILEDIVLTLTLFEDREMIR | 634 |
| EMC03581 | 554 | DKLMDFLEKE--FDEFRIVDLTGLDKEnkAFNASYGTYHDLRKIL-DK | DFLDNSKNEKILEDIVLTLTLFEDREMIR | 627 |
| WP_000428612 | 565 | KDIIQYLHT---VDGYDGIELKGIEKQ---FNASLSTYHDLLKIIKDK | EFMDDPNNEEILENIVHTLTIFEDREMIK | 635 |
| WP_000428613 | 563 | KDIIQFLHN---VDGYDGIELKGIEKQ---FNASLLSTYHDLLKIIKDK | EFMDDSKNEEILENIVHTLTIFEDREMIK | 633 |
| WP_049523028 | 562 | KDIIHYLHN---VDGYDGIELKGIEKH---FNSSLSTYHDLLKIIKDK | EFMDDPKNEEIFENIVHTLTIFEDRVMIK | 632 |
| WP_003107102 | 531 | KQLKENYFNK--IRCLDSITISGVEDK---FNASLGTYHDLLNIIKNQ | KILLDDEQNQDSLEDIVLTLTLFEDREKMIA | 602 |
| WP_054279288 | 564 | KQLKEDFFSK--IECFDTVDISGVEDK---FNASLGTYHDLLKIIKDK | AFLDNSENENIIEDIILTLTLFEDREKMIA | 635 |
| WP_049531101 | 563 | KDLIHYLHN---VDGYDGIELKGIEKQ---FNASLSTYHDLLKIIKDK | RFMDEPKNQEILENIVHTLTIFEDREMIK | 633 |
| WP_049538452 | 563 | KDIIQYLHN---VDGYDGIELKGIEKQ---FNASLSTYHDLLKIIKDK | EFMDDSKNEEILENIVHTLTIFEDREMIK | 633 |
| WP_049549711 | 563 | KDIIHYLHT---VDGYDGIELKGIEKQ---FNASLSTYHDLLKIIKDK | EFMDDSKNEAILENIVHTLTIFEDREMIK | 633 |
| WP_007896501 | 565 | KDLKEKYFSQ--IEGLENVDTGVEGA---FNASLGTYNDLLKIIKDK | AFLDDEANAEILEEIVLILTLFQDEKLIE | 636 |
| EFR44625 | 517 | KDLKEKYFSQ--IEGLENVDTGVEGA---FNASLGTYNDLLKIIKDK | AFLDDEANAEILEEIVLILTLFQDEKLIE | 588 |
| WP_002897477 | 562 | KDIIHYLHN---VDGYDGIELKGIEKQ---FNANLSTYHDLLKITKDK | EFMDDPKNEEILENIVHTLTIFEDREMIK | 632 |
| WP_002906454 | 562 | KDIIHYLHN---VDGYDGIELKGIEKQ---FNASLSTYHDLLKIIKDK | EFMDNPKNQEILENIIHTLTIFEDREMIK | 632 |
| WP_009729476 | 563 | KDIIQFLHN---VDGYDGIELKGIEKQ---FNASLSTYHDLLKIIKDK | AFMDDAKNEAILENIVHTLTIFEDREMIK | 633 |
| CQR24647 | 562 | KKILNFLDKN--FDEFRITDIQGLDNEtgNFNASYGTYHDLLKIIGDK | EFMDSSDNVDVLEDIVLSLTLFEDREMIK | 636 |
| WP_000066813 | 565 | KDIIHYLHN---VDGYDGIELKGIEKQ---FNASLSTYHDLLKIIKDK | AFMDDSKNEEILENIIHTLTIFEDREMIR | 635 |
| WP_009754323 | 563 | KDIIHYLHN---VDGYDGIELKGIEKQ---FNASLSTYHDLLKIIKDK | EFMDNHKNQEILENIVHTLTIFEDREMIK | 633 |
| WP_044674937 | 562 | KDIKAYL-EN--SNGYAGVELKGLEEQ---FNASLPTYHDLLKILRDK | AFIDAEENQEILEDIVLTLTLFEDREMIR | 632 |
| WP_044676715 | 561 | EKLMDFLGKE--FDEFRIVDLLGLDKDnkSFNASLGTYHDLKKIV-SK | DLLDNPENEDILENVLTLTLFEDREMIR | 634 |
| WP_044680361 | 561 | EKLMDFLGKE--FDEFRIVDLLGLDKDnkSFNASLGTYHDLKKIV-SK | DLLDNPENEDILENVVLTLTLFEDREMIR | 634 |
| WP_044681799 | 562 | KDIKAYL-EN--SNGYAGVELKGLEEQ---FNASLPTYHDLLKILRDK | AFIDAEENQEILEDIVLTLTLFEDREMIR | 632 |

| | | | | |
|---|---|---|---|---|
| WP_049533112 | 561 | DKLLNYLGKE--PDEFRIVDLTGLDKEhkVFNSSLGTYHDLRKLL-DK | SFLDKENEQIIEDIIQTITLFEDREMIR | 634 |
| WP_029090905 | 541 | TSLKKWLAEH---EHMTVSVQGTQKet-EFATSLQAEHREVKIP-DR | ETVSNPANEMFEKIIYWSTVFEDKKIMR | 612 |
| WP_006506696 | 568 | KKLKNWLVNNqcCS--KDAEIKGFQKEn-QFSTSLTPWIDETNIFGKI | ----DQSNFDLIENIIYDLTVFEDKKIMK | 637 |
| AIT42264 | 562 | KQLKEDYFKK--IECEDSVEISGVEDR--FNASLGTYHDLLKIIKDK | DFLDNEENEDILEDIVLTLTLFEDREMIE | 633 |
| WP_034440723 | 568 | NQLVKYIENK---EQIIAPEIKGIEDS--FNSNSYTYIDLSKIPDMK | --LLEKDEDEILEEIIKILTLFEDRKMRK | 637 |
| AKQ21048 | 562 | KQLKEDYFKK--IECEDSVEISGVEDR--FNASLGTYHDLLKIIKDK | DFLDNEENEDILEDIVLTLTLFEDREMIE | 633 |
| WP_004636532 | 563 | KDIANYLEQ---YGYVDGTDIKGVEDK--FNASLSTYNDLAKIDGAK | AYLDDPEYADVWEDIIKLTIFEDKAMRK | 633 |
| WP_002364836 | 570 | KDIIQFYRNE--YN-TEIVTLSGLEED--QFNASFSTYQDLLKCGLTR | AELDHPDNAEKLEDIIKILTIFEDRQRIR | 641 |
| WP_002407324 | 521 | KDIIQFYRNE--YN-TEIVTLSGLEED--QFNASFSTYQDLLKCGLTR | AELDHPDNAEKLEDIIKILTIFEDRQRIR | 592 |
| EMS75795 | 306 | KKLQQFLSAN--YN-IEDAEILGVDKA--FNSSYATYHDFLDLAKPN | ELLEQPEMNAMFEDIVKLTIFEDREMIR | 381 |
| WP_002373311 | 570 | KDIIQFYRNE--YN-TEIVTLSGLEED--QFNASFSTYQDLLKCGLTR | AELDHPDNAEKLEDIIKILTIFEDRQRIR | 641 |
| WP_002378009 | 570 | KDIIQFYRNE--YN-TEIVTLSGLEED--QFNASFSTYQDLLKCGLTR | AELDHPDNAEKLEDIIKILTIFEDRQRIR | 641 |
| WP_002407324 | 570 | KDIIQFYRNE--YN-TEIVTLSGLEED--QFNASFSTYQDLLKCGLTR | AELDHPDNAEKLEDIIKILTIFEDRQRIR | 641 |
| WP_002413717 | 572 | KDIIQFYRNE--YN-TEIVTLSGLEED--QFNASFSTYQDLLKCGLTR | AELDHPDNAEKLEDIIKILTIFEDRQRIR | 643 |
| WP_010775580 | 570 | KDIIQFYRNE--YN-TEIVTLSGLEED--QFNASFSTYQDLLKCGLTR | AELDHPDNAEKLEDIIKILTIFEDRQRIR | 641 |
| WP_010818269 | 570 | KDIIQFYRNE--YN-TEIVTLSGLEED--QFNASFSTYQDLLKCGLTR | AELDHPDNAEKLEDIIKILTIFEDRQRIR | 641 |
| WP_010824395 | 570 | KDIIQFYRNE--YN-TEIVTLSGLEED--QFNASFSTYQDLLKCGLTR | AELDHPDNAEKLEDIIKILTIFEDRQRIR | 641 |
| WP_016622645 | 570 | KDIIQFYRNE--YN-TEIVTLSGLEED--QFNASFSTYQDLLKCGLTR | AELDHPDNAEKLEDIIKILTIFEDRQRIR | 641 |
| WP_033624816 | 570 | KDIIQFYRNE--YN-TEIVTLSGLEED--QFNASFSTYQDLLKCGLTR | AELDHPDNAEKLEDIIKILTIFEDRQRIR | 641 |
| WP_033625576 | 570 | KDIIQFYRNE--YN-TEIVTLSGLEED--QFNASFSTYQDLLKCGLTR | AELDHPDNAEKLEDIIKILTIFEDRQRIR | 641 |
| WP_033789179 | 570 | KDIIQFYRNE--YN-TEIVTLSGLEED--QFNASFSTYQDLLKCGLTR | AELDHPDNAEKLEDIIKILTIFEDRQRIR | 641 |
| WP_002310644 | 567 | KDLQEFLYLK--YD-IKHAELSGIEKA---FNASYTTYHDFLTMSENK | QWLEDPELASMFEEIIKTLTVFEDREMIK | 641 |
| WP_002312694 | 568 | KDLQEFLYLK--YD-IKHAELSGIEKA---FNASYTTYHDFLTMSENK | QWLEDPELASMFEEIIKTLTVFEDREMIK | 642 |
| WP_002314015 | 568 | KDLQEFLYLK--YD-IKHAELSGIEKA---FNASYTTYHDFLTMSENK | QWLEDPELASMFEEIIKTLTVFEDREMIK | 642 |
| WP_002320716 | 568 | KDLQEFLYLK--YD-IKHAELSGIEKA---FNASYTTYHDFLTMSENK | QWLEDPELASMFEEIIKTLTVFEDREMIK | 642 |
| WP_002330729 | 567 | KDLQEFLYLK--YD-IKHAELSGIEKA---FNASYTTYHDFLTMSENK | QWLEDPELASMFEEIIKTLTVFEDREMIK | 641 |
| WP_002335161 | 568 | KDLQEFLYLK--YD-IKHAELSGIEKA---FNASYTTYHDFLTMSENK | QWLEDPELASMFEEIIKTLTVFEDREMIK | 642 |

| | | -continued | | |
|---|---|---|---|---|
| WP_002345439 | 568 | KDLQEFLYLK--YD-IKHAELSGIEKA---FNASYTTYHDFLTMSENK | QWLEDPELASMFEEIIKLTIFEDREMIK | 642 |
| WP_034867970 | 562 | KKLQNFLYTH--YH-IENAQIFGIEKA---FNASYSTYHDFMKLAKTN | EWLEQPEMEPIFEDIVKLTIFEDRQMIK | 637 |
| WP_047937432 | 568 | KDLQEFLYLK--YD-IKHAELSGIEKA---FNASYTTYHDFLTMSENK | QWLEDPELASMFEEIIKLTIFEDREMIK | 642 |
| WP_010720994 | 562 | KKLQNFLYTH--YH-IENAQIFGIEKA---FNASYSTYHDFMKLAKTN | EWLEQPEMEPIFEDIVKLTIFEDRQMIK | 637 |
| WP_010737004 | 562 | KKLQNFLYTH--YH-IENAQIFGIEKA---FNASYSTYHDFMKLAKTN | EWLEQPEMEPIFEDIVKLTIFEDRQMIK | 637 |
| WP_034700478 | 562 | KKLQNFLYTH--YH-IENAQIFGIEKA---FNASYSTYHDFMKLAKTN | EWLEQPEMEPIFEDIVKLTIFEDRQMIK | 637 |
| WP_007209003 | 564 | KKLENYLRIEl---SISSPSVKGIEEQ--FNANFGTYLDLKKFDELH | PYLDDEKYQDTLEEVIKVLTVFEDRSMIQ | 634 |
| WP_023519017 | 560 | KQLRKFLELN--EQ-IDSTEIKGIETS---FNASYSTYHDLLKLS--- | TLLDDPDMTTMFEEIIKILTIFEDREMIR | 631 |
| WP_010770040 | 564 | KLLEKFLSNE--FG-LVDVAIKGIE-T--SFNAGYGTYHDFLKIGITR | EQLDKEENSETLEEIVKILTVFEDRKMIR | 634 |
| WP_048604708 | 560 | KDLSNFLRNE--YN-LDDVIIDGIE-N--KFNASFNTYHDFLKLKIDP | KVLDDPANEPMFEEIVKLTIFEDRKMLR | 630 |
| WP_010750235 | 561 | KKLQHFLSAN--YN-IEDAEILGVDKV---FNSSYATYHDFLELAKPY | ELLEQPEMEEMFEDIVKLITIFEDREMVR | 636 |
| AII16583 | 601 | KQLKEDYFKK--IECFDSVEISGVEDR---FNASLGTYHDLLKIIKDK | DFLDNEENEDILEDIVLTLFEDREMIE | 672 |
| WP_029073316 | 576 | NAMKKWLVKNqyFSNTDDIKIEGFQKEn-ACSTSLTPWIDFTKIFGEI | ----NNSNYELIEKIIYDTVFEDKKILR | 647 |
| WP_031589969 | 576 | NAMKKWLVKNqyFSNTDDIKIEGFQKEn-ACSTSLTPWIDFTKIFGKI | ----NESNYDFIEKIIYDVTVFEDKKILR | 647 |
| KDA45870 | 558 | KMVIKHLKVV--MPAIRIQALKGLDNGk--FNASYGTYKDLVDMGVAP | ELLNDEVNSEKWEDIIKTLTIFEGRKLIK | 630 |
| WP_039099354 | 579 | KNIQDYLVSEk--RYASRPAITGLSDEnk-FNSRLSTYHDLKTIVGDA | --VDDDKQADLEKCIEWSTIFEDGKIYS | 650 |
| AKP02966 | 561 | KKLTKWLIAQg---YYKNPILIGLSQKd-EFNSTLTTYLDMKKIFGSS | -FMENNKNYNQIEELIEWLTIFEDKQILN | 632 |
| WP_010991369 | 567 | KDLELFLRNM--SH-VESPTIEGLE-D--SFNSSYSTYHDLLKVGIKQ | EILDNPVNTEMLENIVKILTVFEDKRMIK | 637 |
| WP_033388504 | 567 | KDLELFLRNM--SH-VESPTIEGLE-D--SFNSSYSTYHDLLKVGIKQ | EILDNPVNTEMLENIVKILTVFEDKRMIK | 637 |
| EHN60060 | 570 | KDLELFLRNM--SH-VESPTIEGLE-D--SFNSSYSTYHDLLKVGIKQ | EILDNPVNTEMLENIVKILTVFEDKRMIK | 640 |
| EFR89594 | 336 | KDLELFLRNM--SH-VESPTIEGLE-D--SFNSSYSTYHDLLKVGIKQ | EILDNPVNTEMLENIVKILTVFEDKRMIK | 406 |
| WP_038409211 | 567 | KDLERFLYTI--NH-IESPTIEGVE-D--AFNSSFATYHDLQKGGVTQ | EILDNPLNADMLEEIVKILTVFEDKRMIK | 637 |
| EFR95520 | 186 | KDLERFLYTI--NH-IESPTIEGVE-D--AFNSSFATYHDLQKGGVTQ | EILDNPLNADMLEEIVKILTVFEDKRMIK | 256 |
| WP_003723650 | 567 | KDLELFLRNI--NH-IESPTIEGLE-D--SFNASYATYHDLLKVGMKQ | EILDNPLNTEMLEDIVKILTVFEDKPMIK | 637 |
| WP_003727705 | 567 | KDLELFLRNI--NH-IESPTIEGLE-D--SFNASYATYHDLLKVGLKQ | EILDNPLNTEILEDIVKILTVFEDKRMIK | 637 |
| WP_003730785 | 567 | KDLELFLRNI--NH-IESPTIEGLE-D--SFNASYATYHDLLKVGLKQ | EILDNPLNTEILEDIVKILTVFEDKRMIK | 637 |
| WP_003733029 | 567 | KDLELFLRNI--NQ-IESPTIEGLE-D--SFNASYATYHDLLKVGMKQ | EILDNPLNTEMLEDIVKILTVFEDKRMIK | 637 |

```
WP_003739838   567  KDLEQFLRNM--SH-IESPTIEGLE-D-SFNSSYATYHDLLKVGIKQ  EVLENPLNTEMLEDIVKILTVFEDKRMIK  637
WP_014601172   567  KDLELFLRNI--NH-IESPTIEGLE-D-SFNASYATYHDLLKVGMKQ  EILDNPLNTEMLEDIVKILTVFEDKPMIK  637
WP_023548323   567  KDLELFLRNI--NH-VESPTIEGLE-D-SFNASYATYHDLMKVGIKQ  EILDNPLNTEMLEDIVKILTVFEDKRMIK  637
WP_031665337   567  KDLELFLRNI--NQ-IESPTIEGLE-D-SFNASYATYHDLLKVGMKQ  EILDNPLNTEMLEDIVKILTVFEDKRMIK  637
WP_031669209   567  KDLELFLRNI--NQ-IESPTIEGLE-D-SFNASYATYHDLLKVGMKQ  EILDNPLNTEMLEDIVKILTVFEDKRMIK  637
WP_033920898   567  KDLELFLRNI--NH-VESPTIEGLE-D-SFNASYATYHDLMKVGIKQ  EILDNPLNTEMLEDIVKILTVFEDKRMIK  637
AKI42028       570  KDLELFLRNI--NH-IESPTIEGLE-D-SFNASYATYHDLLKVGMKQ  EILDNPLNTEMLEDIVKILTVFEDKPMIK  640
AKI50529       570  KDLELFLRNI--NH-VESPTIEGLE-D-SFNASYATYHDLMKVGIKQ  EILDNPLNTEMLEDIVKILTVFEDKRMIK  640
EFR83390        15  KDLELFLRNI--NQ-IESPTIEGLE-D-SFNASYATYHDLLKVGMKQ  EILDNPLNTEMLEDIVKILTVFEDKRMIK   85
WP_046323366   567  KDLELFLYNM--NH-VESPTVEGVE-D-AFNSSFTTYHDLQKVGVPQ  EILDDPLNTEMLEEIIKILTVFEDKRMIN  637
AKE81011       578  KQLKEDYFKK--IECFDSVEISGVEDR---FNASLGTYHDLLKIIKDK DFLDNEENEDILEDIVLTLTLFEDREMIE  649
CU082355       572  KKLKNWLVNNqcCR--KDAEIKGFQKEn-QFSTSLTPWIDFTNIFGKI ----DQSNFDLIEKIIYDLTVFEDKKIMK  641
WP_033162887   573  KKLKDWLVTHqyYDINEELKIEGYQKDl-QFSTSLAPWIDFTKIFGEI ----NASNYQLIEKIIYDISIFEDKKILK  644
AGZ01981       595  KQLKEDYFKK--IECFDSVEISGVEDR---FNASLGTYHDLLKIIKDK DFLDNEENEDILEDIVLTLTLFEDREMIE  666
AKA60242       562  KQLKEDYFKK--IECFDSVEISGVEDR---FNASLGTYHDLLKIIKDK DFLDNEENEDILEDIVLTLTLFEDREMIE  633
AKS40380       562  KQLKEDYFKK--IECFDSVEISGVEDR---FNASLGTYHDLLKIIKDK DFLDNEENEDILEDIVLTLTLFEDREMIE  633
4UN5_B         566  KQLKEDYFKK--IECFDSVEISGVEDR---FNASLGTYHDLLKIIKDK DFLDNEENEDILEDIVLTLTLFEDREMIE  637
WP_010922251   634  ERLKTYAHLFDDKVMKQLKR-RRYTGWGRLSRKLINGIRDK  QSGKTILDFLK  -Dgf---ANRNFMQLIHDDSL  702
WP_039695303   638  ERLQKYSDIFTANQLKKLER-RHYTGWGRLSYKLINGIRNK  ENNKTILDYLI  DDG---SANRNFMQLINDDTL  706
WP_045635197   633  QRLAQYDSLFDEKVIKALTR-RHYTGWGKLSAKLINGICDK  QTGNTILDYLI  DDG---KINRNFMQLINDDGL  701
5AXW_A         369  EELTNLNSELTQEEIEQISNIKGYTGTHNLSLKAINLIIDE  ---------LW  ------TNDNQIAIFNRLKL   426
WP_009880683   318  ERLKTYAHLFDDKVMKQLKR-RRYTGWGRLSRKLINGIRDK  QSGKTILDFLK  -Dgf---ANRNFMQLIHDDSL  386
WP_010922251   634  ERLKTYAHLFDDKVMKQLKR-RRYTGWGRLSRKLINGIRDK  QSGKTILDFLK  -Dgf---ANRNFMQLIHDDSL  702
WP_011054416   634  ERLKTYAHLFDDKVMKQLKR-RRYTGWGRLSRKLINGIRDK  QSGKTILDFLK  -Dgf---ANRNFMQLIHDDSL  702
WP_011284745   634  ERLKTYAHLFDDKVMKQLKR-RRYTGWGRLSRKLINGIRDK  QSGKTILDFLK  -Dgf---ANRNFMQLIHDDSL  702
WP_011285506   634  ERLKTYAHLFDDKVMKQLKR-RRYTGWGRLSRKLINGIRDK  QSGKTILDFLK  -Dgf---ANRNFMQLIHDDSL  702
WP_011527619   634  ERLKTYAHLFDDKVMKQLKR-RRYTVWGRLSRKLINGIRDK  QSGKTILDFLK  -Dgf---ANRNFMQLIHDDSL  702
```

| ID | | | | | |
|---|---|---|---|---|---|
| WP_012560673 | 634 | ERLKTYAHLFDDKVMKQLKR-RRYTGWGRLSRKLINGIRDK | QSGKTILDFLK | -DGf---ANRNFMQLIHDDSL | 702 |
| WP_014407541 | 634 | ERLKTYAHLFDDKVMKQLKR-RRYTGWGRLSRKLINGIRDK | QSGKTILDFLK | -DGf---ANRNFMQLIHDDSL | 702 |
| WP_020905136 | 634 | ERLKKYANLFDDKVMKQLKR-RRYTGWGRLSRKLINGIRDK | QSGKTILDFLK | -DGf---ANRNFMQLIHDDSL | 702 |
| WP_023080005 | 634 | ERLKTYAHLFDDKVMKQLKR-RHYTGWGRLSRKLINGIRDK | QSGKTILDFLK | -DGf---ANRNFMQLIHDDSL | 702 |
| WP_023610282 | 634 | ERLKTYANLFDDKVMKQLKR-RRYTGWGRLSRKLINGIRDK | QSGKTILDFLK | -DGf---ANRNFMQLINDDSL | 702 |
| WP_030125963 | 634 | ERLKKYANLFDDKVMKQLKR-RRYTGWGRLSRKLINGIRDK | QSGKTILDFLK | -DGf---ANRNFMQLIHDDSL | 702 |
| WP_030126706 | 634 | ERLKTYAHLFDDKVMKQLKR-RRYTGWGRLSRKLINGIRDK | QSGKTILDFLK | -DGf---ANRNFMQLIHDDSL | 702 |
| WP_031488318 | 634 | ERLKTYAHLFDDKVMKQLKR-RRYTGWGRLSRKLINGIRDK | QSGKTILDFLK | -DGf---ANRNFMQLIHDDSL | 702 |
| WP_032460140 | 634 | ERLKTYAHLFDDKVMKQLKR-RRYTGWGRLSRKLINGIRDK | QSGKTILDFLK | -DGf---ANRNFMQLIHDDSL | 702 |
| WP_032461047 | 634 | ERLKTYAHLFDDKVMKQLKR-RRYTGWGRLSRKLINGIRDK | QSGKTILDFLK | -DGf---ANRNFMQLIHDDSL | 702 |
| WP_032462016 | 634 | ERLKKYANLFDDKVMKQLKR-RRYTGWGRLSRKLINGIRDK | QSGKTILDFLK | -DGf---ANRNFMQLIHDDSL | 702 |
| WP_032462936 | 634 | ERLKTYAHLFDDKVMKQLKR-RRYTGWGRLSRKLINGIRDK | QSGKTILDFLK | -DGf---ANRNFMQLIHDDSL | 702 |
| WP_032464890 | 634 | ERLKTYAHLFDDKVMKQLKR-RRYTGWGRLSRKLINGIRDK | QSGKTILDFLK | -DGf---ANRNFMQLIHDDSL | 702 |
| WP_033888930 | 459 | ERLKTYAHLFDDKVMKQLKR-RRYTGWGRLSRKLINGIRDK | QSGKTILDFLK | -DGf---ANRNFMQLINDDSL | 527 |
| WP_038431314 | 634 | ERLKTYAHLFDDKVMKQLKR-RRYTGWGRLSRKLINGIRDK | QSGKTILDFLK | -DGf---ANRNFMQLIHDDSL | 702 |
| WP_038432938 | 634 | ERLKKYANLFDDKVMKQLKR-RRYTGWGRLSRKLINGIRDK | QSGKTILDFLK | -DGf---ANRNFMQLIHDDSL | 702 |
| WP_038434062 | 634 | ERLKTYAHLFDDKVMKQLKR-RRYTGWGRLSRKLINGIRDK | QSGKTILDFLK | -DGf---ANRNFMQLIHDDSL | 702 |
| BAQ51233 | 545 | ERLKTYAHLFDDKVMKQLKR-RRYTGWGRLSRKLINGIRDK | QSGKTILDFLK | -DGf---ANRNFMQLIHDDSL | 613 |
| KGE60162 | | | | | |
| KGE60856 | | | | | |
| WP_002989955 | 634 | ERLKTYAHLFDDKVMKQLKR-RRYTGWGRLSRKLINGIRDK | QSGKTILDFLK | -DGf---ANRNFMQLIHDDSL | 702 |
| WP_003030002 | 635 | QRLQKYSDIPTKAQLKKLER-RHYTGWGRLSYKLINGIRNK | ENKKTILDYLI | DDG---YANRNFMQLINDDAL | 703 |
| WP_003065552 | 638 | ERLQKYSDIPTADQLKKLER-RHYTGWGRLSYKLINGIRNK | ENNKTILDYLI | DDG---SANRNFMQLINDDTL | 706 |
| WP_001040076 | 633 | KRLDIYKDFPTESQLKKLYR-RHYTGWGRLSAKLINGIRNK | ENQKTILDYLI | DDG---SANRNFMQLIKDAGL | 701 |
| WP_001040078 | 636 | KRLENYKDLFTESQLKKLYR-RHYTGWGRLSAKLINGIRDK | ESQKTILDYLI | DDG---RSNRNFMQLINDDGL | 704 |
| WP_001040080 | 636 | KRLENYKDLFTESQLKKLYR-RHYTGWGRLSAKLINGIRDK | ESQKTILDYLI | DDG---RSNRNFMQLINDDGL | 704 |
| WP_001040081 | 636 | KRLENYKDLFTESQLKKLYR-RHYTGWGRLSAKLINGIRDK | ESQKTILDYLI | DDG---RSNRNFMQLINDDGL | 704 |

-continued

| | | | | |
|---|---|---|---|---|
| WP_001040083 | 636 | KRLENYKDLFTESQLKKLYR-RHYTGWGRLSAKLINGIRDK | ESQKTILDYLI | DDG---RSNRNFMQLINDDGL | 704 |
| WP_001040085 | 636 | KRLENYKDLFTESQLKKLYR-RHYTGWGRLSAKLINGIRDK | ESQKTILDYLI | DDG---RSNRNFMQLINDDGL | 704 |
| WP_001040087 | 636 | KRLENYKDLFTESQLKKLYR-RHYTGWGRLSAKLINGIRDK | ESQKTILDYLI | DDG---RSNRNFMQLINDDGL | 704 |
| WP_001040088 | 636 | KRLENYKDLFTESQLKKLYR-RHYTGWGRLSAKLINGIRDK | ESQKTILDYLI | DDG---RSNRNFMQLINDDGL | 704 |
| WP_001040089 | 636 | KRLENYKDLFTESQLKKLYR-RHYTGWGRLSAKLINGIRDK | ESQKTILDYLI | DDG---RSNRNFMQLINDDGL | 704 |
| WP_001040090 | 636 | KRLENYKDLFTESQLKKLYR-RHYTGWGRLSAKLINGIRDK | ESQKTILDYLI | DDG---RSNRNFMQLINDDGL | 704 |
| WP_001040091 | 636 | KRLENYKDLFTESQLKKLYR-RHYTGWGRLSAKLINGIRDK | ESQKTILDYLI | SDG---RANRNFMQLINDDGL | 704 |
| WP_001040092 | 633 | KRLDIYKDLFTESQLKKLYR-RHYTGWGRLSAKLINGIRDR | ESQKTILDYLI | DDG---RANRNFMQLIKDAGL | 701 |
| WP_001040094 | 633 | KRLDIYKDFFTESQLKKLYR-RHYTGWGRLSAKLINGIRNK | ENQKTILDYLI | DDG---SANRNFMQLIKDAGL | 701 |
| WP_001040095 | 633 | KRLDIYKDFFTESQLKKLYR-RHYTGWGRLSAKLINGIRNK | ENQKTILDYLI | DDG---SANRNFMQLIKDAGL | 701 |
| WP_001040096 | 633 | KRLDIYKDFFTESQLKKLYR-RHYTGWGRLSAKLINGIRNK | ENQKTILDYLI | DDG---SANRNFMQLIKDAGL | 701 |
| WP_001040097 | 633 | KRLDIYKDFFTESQLKKLYR-RHYTGWERLSAKLINGIRNK | ENQKTILDYLI | DDG---SANRNFMQLIKDAGL | 701 |
| WP_001040098 | 633 | KRLDIYKDFFTESQLKKLYR-RHYTGWGRLSAKLINGIRNK | ENQKTILDYLI | DDG---SANRNFMQLIKDAGL | 701 |
| WP_001040099 | 636 | KRLENYKDLFTESQLKKLYR-RHYTGWGRLSAKLINGIRNK | ENQKTILDYLI | DDG---RSNRNFMQLINDDGL | 704 |
| WP_001040100 | 636 | KRLENYKDLFTESQLKKLYR-RHYTGWGRLSAKLINGIRDK | ESQKTILDYLI | SDG---RSNRNFMQLIHDDGL | 704 |
| WP_001040104 | 636 | KRLENYKDLFTESQLKKLYR-RHYTGWGRLSAKLINGIRNK | ESQKTILDYLI | SDG---RANRNFMQLIHDDGL | 704 |
| WP_001040105 | 636 | KRLENYKDLFTESQLKKLYR-RHYTGWGRLSAKLINGIRNK | ESQKTILDYLI | SDG---SANRNFMQLIHDDGL | 704 |
| WP_001040106 | 636 | KRLENYKDLFTESQLKKLYR-RHYTGWGRLSAKLINGIRNK | ESQKTILDYLI | SDG---SANRNFMQLIHDDGL | 704 |
| WP_001040107 | 636 | KRLENYKDLFTESQLKKLYR-RHYTGWGRLSAKLINGIRDR | ESQKTILDYLI | SDG---RANRNFMQLIHDDGL | 704 |
| WP_001040108 | 636 | KRLENYKDLFTESQLKKLYR-RHYTGWGRLSAKLINGIRDK | ESQKTILDYLI | DDG---RANRNFMQLIHDDGL | 704 |
| WP_001040109 | 636 | KRLDIYKDLFTESQLKKLYR-RHYTGWGRLSAKLINGIRNK | ENQKTILDYLI | DDG---SANRNFMQLIHDDGL | 704 |
| WP_001040110 | 636 | KRLENYKDLFTESQLKKLYR-RHYTGWGRLSAKLINGIRDK | ESQKTILDYLI | DDG---KSNRNFMQLIHDDGL | 704 |
| WP_015058523 | 633 | KRLENYKDLFTESQLKKLYR-RHYTGWGRLSAKLINGIRDK | ESQKTILDYLI | DDG---KSNRNFMQLIHDDGL | 701 |
| WP_017643650 | 636 | KRLENYKDLFTESQLKKLYR-RHYTGWGRLSAKLINGIRDK | ESQKTILDYLI | DDG---RSNRNFMQLIHDDGL | 704 |
| WP_017647151 | 636 | KRLENYKDLFTESQLKKLYR-RHYTGWGRLSAKLINGIRDK | ESQKTILDYLI | DDG---RSNRNFMQLINDDGL | 704 |
| WP_017648376 | 636 | KRLENYKDLFTESQLKKLYR-RHYTGWGRLSAKLINGIRDK | ESQKTILDYLI | DDG---RSNRNFMQLINDDGL | 704 |
| WP_017649527 | 636 | KRLENYKDLFTESQLKKLYR-RHYTGWGRLSAKLINGIRDK | ESQKTILDYLI | DDG---RSNRNFMQLINDDGL | 704 |

```
WP_017771611    636  KRLENYKDLFTESQLKKLYR-RHYTGWGRLSAKLINGIRDK  ESQKTILDYLI  SDG---RANRNFMQLIHDDGL  704
WP_017771984    636  KRLENYKDLFTESQLKKLYR-RHYTGWGRLSAKLINGIRDK  ESQKTILDYLI  DDG---RSNRNFMQLINDDGL  704
CFQ25032        636  KRLENYKDLFTESQLKKLYR-RHYTGWGRLSAKLINGIRDK  ESQKTILDYLI  DDG---RSNRNFMQLINDDGL  704
CFV16040        636  KRLENYKDLFTESQLKKLYR-RHYTGWGRLSAKLINGIRDK  ESQKTILDYLI  DDG---RSNRNFMQLINDDGL  704
KLJ37842        636  KRLENYKDLFTESQLKKLYR-RHYTGWGRLSAKLINGIRDK  ESQKTILDYLI  DDG---RSNRNFMQLINDDGL  704
KLJ72361        636  KRLENYKDLFTESQLKKLYR-RHYTGWGRLSAKLINGIRDK  ESQKTILDYLI  DDG---RSNRNFMQLINDDGL  704
KLL20707        636  KRLENYKDLFTESQLKKLYR-RHYTGWGRLSAKLINGIRDK  ESQKTILDYLI  DDG---RSNRNFMQLINDDGL  718
KLL42645        636  KRLENYKDLFTESQLKKLYR-RHYTGWGRLSAKLINGIRDK  ESQKTILDYLI  SDG---RANRNFMQLIHDDGL  704
WP_047207273    633  KRLDIYKDFFTESQLKKLYR-RHYTGWGRLSAKLINGIRDK  ESQKTILDYLI  DDG---RSNRNFMQLIKDAGL  701
WP_047209694    636  KRLENYKDLFTESQLKKLYR-RHYTGWGRLSAKLINGIRDK  ENQKTILDYLI  DDG---SANRNFMQLINDDGL  704
WP_050198062    636  KRLENYKDLFTESQLKKLYR-RHYTGWGRLSAKLINGIRDK  ESQKTILDYLI  DDG---RSNRNFMQLINDDGL  704
WP_050201642    636  KRLENYKDLFTESQLKKLYR-RHYTGWGRLSAKLINGIRDK  ESQKTILDYLI  DDG---RSNRNFMQLIHDDGL  704
WP_050204027    636  KRLENYKDLFTESQLKKLYR-RHYTGWGRLSAKLINGIRDK  ESQKTILDYLI  SDG---RANRNFMQLINDDGL  704
WP_050881965    636  KRLENYKDLFTESQLKKLYR-RHYTGWGRLSAKLINGIRDK  ESQKTILDYLI  DDG---RSNRNFMQLINDDGL  704
WP_050886065    636  KRLENYKDLFTESQLKKLYR-RHYTGWGRLSAKLINGIRDK  ESQKTILDYLI  SDG---RANRNFMQLINDDGL  704
AHN30376        636  KRLENYKDLFTESQLKKLYR-RHYTGWGRLSAKLINGIRDR  ESQKTILDYLI  DDG---RSNRNFMQLINDDGL  704
EAO78426        636  KRLENYKDLFTESQLKKLYR-RHYTGWGRLSAKLINGIRDK  ESQKTILDYLI  DDG---RSNRNFMQLIKDAGL  704
CCW42055        635  KRLDIYKDFFTESQLKKLYR-RHYTGWGRLSAKLINGIRNK  ENQKTILDYLI  DDG---SANRNFMQLIKDAGL  703
WP_003041502    636  QRLQKYSDIFTKAQLKKLER-RHYTGWGRLSYKLINGIRNK  ENKKTILDYLI  DDG---YANRNFMQLINDDAL  704
WP_037593752    635  QRLQKYSDIFTKAQLKKLER-RHYTGWGRLSYKLINGIRNK  ENKKTILDYLI  DDG---YANRNFMQLINDDAL  703
WP_049516684    636  QRLQKYSDIFTTQQLKKLER-RHYTGWGRLSYKLINGIRNK  ENKKTILDYLI  DDG---YANRNFMQLINDDAL  704
GAD46167        635  QRLQKYSDIFTKAQLKKLER-RHYTGWGRLSYKLINGIRNK  ENKKTILDYLI  DDG---YANRNFMQLINDDAL  703
WP_018363470    636  QRLQKYSDIFTKQQLKKLER-RHYTGWGRLSYKLINGIRNK  ENNKTILDYLI  DDG---SANRNFMQLINDDAL  704
WP_003043819    644  ERLKTYAHLFDDKVMKQLKR-RHYTGWGRLSRKMINGIRDK  QSGKTILDFLK  -DGf--SNRNFMQLIHDDSL  712
WP_006269658    635  QRLQKYSDIFTKAQLKKLER-RHYTGWGRLSYKLINGIRNK  ENKKTILDYLI  DDG---YANRNFMQLINDDAL  703
WP_048800889    635  QRLQKYSDIFTKAQLKKLER-RHYTGWGRLSYKLINGIRNK  ENNKTILEYLV  DDG---YANRNFMQLINDDTL  703
WP_012767106    634  ERLKKYANLFDDKVMKQLKR-RHYTGWGRLSRKLINGIRDK  QSGKTILDFLK  -DGf--ANRNFMQLINDDSL  702
```

| | | | | |
|---|---|---|---|---|
| WP_014612333 | 634 | ERLKKYANLFDDKVMKQLKR-RHYTGWGRLSRKLINGIRDK | QSGKTILDFLK | -DGf---ANRNFMQLINDDSL | 702 |
| WP_015017095 | 634 | ERLKTYAHLFDDKVMKQLKR-RHYTGWGRLSRKLINGIRDK | QSGKTILDFLK | -DGf---ANRNFIQLIHDDSL | 702 |
| WP_015057649 | 634 | ERLKKYANLFDDKVMKQLKR-RHYTGWGRLSRKLINGIRDK | QSGKTILDFLK | -DGf---ANRNFIQLIHDDSL | 702 |
| WP_048327215 | 634 | ERLKTYAHLFDDKVMKQLKR-RHYTGWGRLSRKLINGIRDK | QSGKTILDFLK | -DGf---ANRNFIQLIHDDSL | 702 |
| WP_049519324 | 634 | ERLKTYAHLFDDKVMKQLKR-RHYTGWGRLSRKLINGIRDK | QSGKTILDFLK | -DGf---ANRNFMQLIHDDSL | 702 |
| WP_012515931 | 634 | KRLDQYAHLFDKVVLNKLER-HHYTGWGRLSGKLINGIRDK | QSGKTILDFLK | -DGf---ANRNFMQLIHDSEL | 702 |
| WP_021320964 | 634 | KRLDQYAHLFDKVVLNKLER-HHYTGWGRLSGKLINGIRDK | QSGKTILDFLK | -DGf---ANRNFMQLIHDSEL | 702 |
| WP_037581760 | 634 | KRLDQYAHLFDKVVLNKLER-HHYTGWGRLSGKLINGIRDK | QSGKTILDFLK | -DGf---ANRNFMQLIHDSEL | 702 |
| WP_004232481 | 635 | ERLQKYSDIFTSQQLKKLER-RHYTGWGRLSYKLINGIRNK | ENNKTILDFLI | DDG---DANRNFMQLINDDTL | 703 |
| WP_009854540 | 636 | ERLQKYSDIFTANQLKKLER-RHYTGWGRLSYKLINGIRNK | ENNKTILDYLI | DDG---SANRNFMQLINDDTL | 704 |
| WP_012962174 | 636 | ERLQKYSDIFTPQQLKKLER-RHYTGWGRLSYKLINGIRNK | ENGKSILDYLI | DDG---YANRNFMQLISDDTL | 704 |
| WP_039695303 | 638 | ERLQKYSDIFTANQLKKLER-RHYTGWGRLSYKLINGIRNK | ENNKTILDFLI | DDG---SANRNFMQLINDDTL | 706 |
| WP_014334983 | 635 | ERLQKYSDFFTSQQLKKLER-RHYTGWGRLSYKLINGIRNK | ENNKTILDFLI | DDG---HANRNFMQLINDESL | 703 |
| WP_003099269 | 634 | RRLVKYADVFEKSVLKKLKK-RHYTGWGRLSQKLINGIKDK | QTGKTILGFLK | -DGv---ANRNFMQLINDSSL | 702 |
| AHY15608 | 634 | RRLVKYADVFEKSVLKKLKK-RHYTGWGRLSQKLINGIKDK | QTGKTILGFLK | -DGv---ANRNFMQLINDSSL | 702 |
| AHY17476 | 634 | RRLVKYADVFEKSVLKKLKK-RHYTGWGRLSQKLINGIKDK | QTGKTILGFLK | -DGv---ANRNFMQLINDSSL | 702 |
| ESR09100 | | | | | |
| AGM98575 | 634 | RRLVKYADVFEKSVLKKLKK-RHYTGWGRLSQKLINGIKDK | QTGKTILGFLK | -DGv---ANRNFMQLINDSSL | 702 |
| ALF27331 | 635 | KRLENYSDLLTKEQVKNLER-RHYTGWGRLSAELIHGIRNK | ESRKTILDYLI | DDG---NSNRNFMQLINDDAL | 703 |
| WP_018372492 | 648 | KRLSELNIPPENKIIKKLAR-KKYTGWGNLSRKLIDGIRNR | ETNRTILGHLI | DDGf---SNRNLMQLINDDGL | 716 |
| WP_045618028 | 634 | QRLAHYASIFDEKVIKALTR-RHYTGWGKLSAKLINGIYDK | QSKKTILDYLI | DDG---EINRNFMQLINDDGL | 702 |
| WP_045635197 | 633 | QRLAQYDSLFDEKVIKALTR-RHYTGWGKLSAKLINGICDK | QTGNTILDYLI | DDG---KINRNFMQLINDDGL | 701 |
| WP_002263549 | 635 | KRLENYSDLLTKEQVKKLER-RHYTGWGRLSAELIHGIRNK | ESRKTILDYLI | DDG---NSNRNFMQLINDDAL | 703 |
| WP_002263887 | 635 | KRLENYSDLLTKEQVKKLER-RHYTGWGRLSAELIHGIRNK | ESRKTILDYLI | DDG---NSNRNFMQLINDDAL | 703 |
| WP_002264920 | 635 | KRLKNYSDLLTKEQLKKLER-RHYTGWGRLSAELIHGIRNK | ESRKTILDYLI | DDG---NSNRNFMQLINDDAL | 703 |
| WP_002269043 | 635 | KRLKNYSDLLTKEQLKKLER-RHYTGWGRLSAELIHGIRNK | ESRKTILDYLI | DDG---NSNRNFMQLINDDAL | 703 |
| WP_002269448 | 635 | KRLENYSDLLTKEQVKKLER-RHYTGWGRLSAELIHGIRNK | ESRKTILDYLI | DDG---NSNRNFMQLINDDAL | 703 |

```
WP_002271977  635  KRLENYSDLLTKEQVKKLER-RHYTGWGRLSAELIHGIRNK  ESRKTILDYLI  DDG---NSNRNFMQLINDDAL  703
WP_002272766  635  KRLENYSDLLTKEQVKKLER-RHYTGWGRLSAELIHGIRNK  ESRKTILDYLI  DDG---NSNRNFMQLINDDAL  703
WP_002273241  635  KRLENYSDLLTKEQVKKLER-RHYTGWGRLSAELIHGIRNK  ESRKTILDYLI  DDG---NSNRNFMQLINDDAL  703
WP_002275430  635  KRLENYSDLLTKEQVKKLER-RHYTGWGRLSAELIHGIRNK  ESRKTILDYLI  DDG---NSNRNFMQLINDDAL  703
WP_002276448  635  KRLENYSDLLTKEQVKKLER-RHYTGWGRLSAELIHGIRNK  ESRKTILDYLI  DDG---NSNRNFMQLINDDAL  703
WP_002277050  636  QRLAKYADVFDKKVIDQLAR-RHYTGWGRLSAKLLNGIRDK  QSCKTIMDYLI  DDA---QSNRNLMQLITDDNL  704
WP_002277364  635  KRLENYSDLLTKEQVKKLER-RHYTGWGRLSAELIHGIRNK  ESRKTILDYLI  DDG---NSNRNFMQLINDDAL  703
WP_002279025  635  KRLKNYSDLLTKEQLKKLER-RHYTGWGRLSAELIHGIRNK  ESRKTILDYLI  DDG---NSNRNFMQLINDDAL  703
WP_002279859  635  KRLKNYSDLLTKEQVKKLER-RHYTGWGRLSAELIHGIRNK  ESRKTILDYLI  DDG---NSNRNFMQLINDDAL  703
WP_002280230  635  KRLENYSDLLTKEQVKKLER-RHYTGWGRLSAELIHGIRNK  ESRKTILDYLI  DDG---NSNRNFMQLINDDAL  703
WP_002281696  635  KRLENYSDLLTKEQVKKLER-RHYTGWGRLSAELIHGIRNK  ESRKTILDYLI  DDG---NSNRNFMQLINDDAL  703
WP_002282247  636  QRLAKYADVFDKKVIDQLAR-RHYTGWGRLSAKLLNGIRDK  QSCKTIMDYLI  DDA---QSNRNLMQLITDDNL  704
WP_002282906  635  KRLENYSDLLTKEQVKKLER-RHYTGWGRLSAELIHGIRNK  ESRKTILDYLI  DDG---NSNRNFMQLINDDAL  703
WP_002283846  635  KRLKNYSDLLTKEQVKKLER-RHYTGWGRLSAELIHGIRNK  ESRKTILDYLI  DDG---NSNRNFMQLINDDAL  703
WP_002287255  635  KRLENYSDLLTKEQVKKLER-RHYTGWGRLSAELIHGIRNK  ESRKTILDYLI  DDG---NSNRNFMQLINDDAL  703
WP_002288990  635  KRLKNYSDLLTKEQVKKLER-RHYTGWGRLSAELIHGIRNK  ESRKTILDYLI  DDG---NSNRNFMQLINDDAL  703
WP_002289641  635  KRLENYSDLLTKEQVKKLER-RHYTGWGRLSAELIHGIRNK  ESRKTILDYLI  DDG---NSNRNFMQLINDDAL  703
WP_002290427  635  KRLKNYSDLLTKEQVKKLER-RHYTGWGRLSAELIHGIRNK  ESRKTILDYLI  DDG---NSNRNFMQLINDDAL  703
WP_002295753  645  QRLQKYSDIFTKAQLKKLER-RHYTGWGRLSYKLINGIRDK  QSNKTILGYLI  DDG---YSNRNFMQLINDDAL  713
WP_002296423  635  KRLENYSDLLTKEQVKKLER-RHYTGWGRLSAELIHGIRNK  ESRKTILDYLI  DDG---NSNRNFMQLINDDAL  703
WP_002304487  635  KRLENYSDLLTKEQVKKLER-RHYTGWGRLSAELIHGIRNK  ESRKTILDYLI  DDG---NSNRNFMQLINDDAL  703
WP_002305844  635  KRLENYSDLLTKEQVKKLER-RHYTGWGRLSAELIHGIRNK  ESRKTILDYLI  DDG---NSNRNFMQLINDDAL  703
WP_002307203  635  KRLENYSDLLTKEQVKKLER-RHYTGWGRLSAELIHGIRNK  ESRKTILDYLI  DDG---NSNRNFMQLINDDAL  703
WP_002310390  635  KRLKNYSDLLTKEQVKKLER-RHYTGWGRLSAELIHGIRNK  ESRKTILDYLI  DDG---NSNRNFMQLINDDAL  703
WP_002352408  635  KRLENYSDLLTKEQVKKLER-RHYTGWGRLSAELIHGIRNK  ESRKTILDYLI  DDG---NSNRNFMQLINDDAL  703
WP_012997688  635  KRLKNYSDLLTKEQVKKLER-RHYTGWGRLSAELIHGIRNK  ESRKTILDYLI  DDG---NSNRNFMQLINDDAL  703
WP_014677909  635  KRLKNYSDLLTKEQLKKLER-RHYTGWGRLSAELIHGIRNK  ESRKTILDYLI  DDG---NSNRNFMQLINDDAL  703
```

-continued

| | | | | |
|---|---|---|---|---|
| WP_019312892 | 635 | KRLENYSDLLTKEQVKKLER-RHYTGWGRLSAELIHGIRNK | ESRKTILDYLI | DDG---NSNRNFMQLINDDAL | 703 |
| WP_019313659 | 635 | KRLENYSDLLTKEQVKKLER-RHYTGWGRLSAELIHGIRNK | ESRKTILDYLI | DDG---NSNRNFMQLINDDAL | 703 |
| WP_019314093 | 635 | KRLENYSDLLTKEQVKKLER-RHYTGWGRLSAELIHGIRNK | ESRKTILDYLI | DDG---NSNRNFMQLINDDAL | 703 |
| WP_019315370 | 635 | KRLENYSDLLTKEQVKKLER-RHYTGWGRLSAELIHGIRNK | ESRKTILDYLI | DDG---NSNRNFMQLINDDAL | 703 |
| WP_019803776 | 635 | KRLENYSDLLTKEQVKKLER-RHYTGWGRLSAELIHGIRNK | ESRKTILDYLI | DDG---NSNRNFMQLINDDAL | 703 |
| WP_019805234 | 635 | KRLKNYSDLLTKEQLKKLER-RHYTGWGRLSAELIHGIRNK | ESRKTILDYLI | DDG---NSNRNFMQLINDDAL | 703 |
| WP_024783594 | 635 | KRLENYSDLLTKEQVKKLER-RHYTGWGRLSAELIHGIRNK | ESRKTILDYLI | DDG---NSNRNFMQLINDDAL | 703 |
| WP_024784288 | 636 | QRLAKYADVFDKKVIDQLAR-RHYTGWGRLSAKLLNGIRDK | QSCKTIMDYLI | DDA---QSNRNLMQLITDDNL | 704 |
| WP_024784666 | 635 | KRLENYSDLLTKEQVKKLER-RHYTGWGRLSAELIHGIRNK | ESRKTILDYLI | DDG---NSNRNFMQLINDDAL | 703 |
| WP_024784894 | 635 | KRLENYSDLLTKEQVKKLER-RHYTGWGRLSAELIHGIRNK | ESRKTILDYLI | DDG---NSNRNFMQLINDDAL | 703 |
| WP_024786433 | 636 | QRLAKYADVFDKKVIDQLAR-RHYTGWGRLSAKLLNGIRDK | QSCKTIMDYLI | DDA---QSNRNLMQLITDDNL | 704 |
| WP_049473442 | 635 | KRLENYSDLLTKEQVKKLER-RHYTGWGRLSAELIHGIRNK | ESRKTILDYLI | DDG---NSNRNFMQLINDDAL | 703 |
| WP_049474547 | 628 | KRLENYSDLLTKEQVKKLER-RHYTGWGRLSAELIHGIRNK | ESRKTILDYLI | DDG---NSNRNFMQLINDDAL | 696 |
| EMC03581 | 636 | QRLAQYDSLFDEKVIKALTR-RHYTGWGKLSSKLINGIRDK | QTGKTILDYLM | DDG---YNNRNFMQLINDDEL | 704 |
| WP_000428612 | 634 | QRLAQYDSLFDEKVIKALTR-RHYTGWGKLSAKLIDGICDK | QTGNTILDYLI | DDG---KNNRNFMQLINDDGL | 702 |
| WP_000428613 | 633 | QRLNQYDSIFDEKVIKALTR-RHYTGWGKLSAKLINGIRDK | KTSKTILDYLI | DDG---YSNRNFMQLINDDGL | 701 |
| WP_049523028 | 603 | KRLSKYESIFDPSILKKLKK-RHYTGWGRLSQKLINGIRDK | QTGKTILDFLI | -DGq---ANRNFMQLINDPSL | 671 |
| WP_003107102 | 636 | NRLAVYEDLFDQNVLKQLKR-RHYTGWGRLSKQLINGMRDK | HTGKTILDFLK | -Dgf---INRNFMQLINDDNL | 704 |
| WP_054279288 | 634 | QRLAQYASIFDEKVIKTLTR-RHYTGWGKLSAKLINCIRDR | KTGKTILDYLI | DDG---YNNRNFMQLINDDGL | 702 |
| WP_049531101 | 634 | QRLAQYDSIFDEKVIKALTR-RHYTGWGKLSAKLINGIRDK | QTGKTILDYLI | DDG---YSNRNFMQLINDDGL | 702 |
| WP_049538452 | 634 | QRLAQYDSLFDEKVIKALTR-RHYTGWGKLSAKLINGICDK | QTGNTILDYLI | DDG---EINRNFMQLINDDGL | 702 |
| WP_049549711 | 637 | KRLAKYANLFEKSVLKKLRK-RHYRGWGRLSRQLIDGMKDK | ASGKTILDFLK | -DDf---ANRNFIQLINDSSL | 705 |
| WP_007896501 | 589 | KRLAKYANLFEKSVLKKLRK-RHYRGWGRLSRQLIDGMKDK | ASGKTILDFLK | -DDf---ANRNFIQLINDSSL | 657 |
| EFR44625 | 633 | QRLAQYDTLFDEKVIKALTR-RHYTGWGKLSAKLINGIRDK | QSGKTILDYLI | DDD---KINRNFMQLINDDGL | 701 |
| WP_002897477 | 633 | QRLAQYDTLFDEKVIKALTR-RHYTGWGKLSAKLINGIRDK | QTGKTILEYLI | DDG---DCNRNFMQLINDDGL | 701 |
| WP_002906454 | 634 | QRLAQYDSLFDEKVIKALTR-RHYTGWGKLSAKLINGISDK | QTGNTILDYLI | DDG---EINRNFMQLINDDGL | 702 |
| WP_009729476 | | | | | |

-continued

| | | | | |
|---|---|---|---|---|
| CQR24647 | 637 | QRLLKYEDIFSKKVIANLTR-RHYTGWGRLSAKLINGIKDK | HSRKTILDYLI | DDG---HSNRNFMQLINDDNL | 705 |
| WP_000066813 | 636 | QRLAQYDSLFPDEKVIKALTR-RHYTGWGKLSAKLINGIRDK | KSGKTILDYLI | DDG---EINRNFMQLIHDDGL | 704 |
| WP_009754323 | 634 | QRLAQYDSIFPDEKVIKALTR-RHYTGWGKLSAKLINGICDK | KTGKTILDYLI | DDG---YNNRNFMQLINDDGL | 702 |
| WP_044674937 | 633 | KRLEKYKDILTEEQRKKLER-RHYTGWGRLSAKLINGILDK | VTRKTILGYLI | DDG---TSNRNFMQLINDDTL | 701 |
| WP_044676715 | 635 | KRLEKYKDVLTEEQRKKLER-RHYTGWGRLSAKLINGIRDK | VTRKTILDYLI | DDG---TSNRNFMQLINDDTL | 703 |
| WP_044680361 | 635 | KRLEKYKDVLTEEQRKKLER-RHYTGWGRLSAKLINGIRDK | VTRKTILDYLI | DDG---TSNRNFMQLINDDTL | 703 |
| WP_044681799 | 633 | KRLEKYKDILTEEQRKKLER-RHYTGWGRLSAKLINGILDK | VTRKTILDYLI | DDG---TSNRNFMQLINDDTL | 701 |
| WP_049533112 | 635 | QRLQKYSDIFTKAQLKKLER-CHYTGWGRLSYKLINGIRNK | ENKKTILDYLI | DDG---YANRNFMQLINDDAL | 703 |
| WP_029090905 | 613 | RKLSEYPQLTEQQQVQLAQV--RFRGWGRLSQRLINRIKTP | EDHKLSINEIL | ------QTNENFMQIIRNKDY | 682 |
| WP_006506696 | 638 | RRLKKKYALPDDKVKQILKL--KYKDWSRLSKKLLDGIVAD | SV--TVLDVLE | ------SRLNLMEIINDKDL | 705 |
| AIT42264 | 634 | ERLKTYAHLFDDKVMKQLKR-RRYTGWGRLSRKLINGIRDK | QSGKTILDFLK | -DGf---ANRNFMQLIHDDSL | 702 |
| WP_034440723 | 638 | RQLMKFKDKLSEKAINQLSK-KHYTGWGQLSEKLINGIRDE | QSNKTILDYLI | DNGcpkNMNRNFMQLINDDTL | 710 |
| AKQ21048 | 634 | ERLKTYAHLFDDKVMKQLKR-RRYTGWGRLSRKLINGIRDK | QSGKTILDFLK | -DGf---ANRNFMQLIHDDSL | 702 |
| WP_004636532 | 634 | KQLQTYSDTLSPEILKKLER-KHYTGWGRPSKKLINGLRDE | GSNKTILDYLK | DEGssgPTNRNFMQLIRDNTL | 706 |
| WP_002364836 | 642 | TQLSTFKGQFSAEVLKKLER-KHYTGWGRLSKKLINGIYDK | ESGKTILDYLI | DDGvskHYNRNFMQLINDSQL | 714 |
| WP_016631044 | 593 | TQLSTFKGQFSEEVLKKLER-KHYTGWGRLSKKLINGIYDK | ESGKTILDYLI | DDGvskHYNRNFMQLINDSQL | 665 |
| EMS75795 | 382 | TQLKKYQSVLGDGFEKKLVK-KHYTGWGRLSERLINGIRDK | KTNKTILDYLI | DDDfpyNRNRNFMQLINDDSL | 454 |
| WP_002373311 | 642 | TQLSTFKGQFSAEVLKKLER-KHYTGWGRLSKKLINGIYDK | ESGKTILDYLV | DDGvskHYNRNFMQLINDSQL | 714 |
| WP_002378009 | 642 | TQLSTFKGQFSAEVLKKLER-KHYTGWGRLSKKLINGIYDK | ESGKTILDYLV | DDGvskHYNRNFMQLINDSQL | 714 |
| WP_002407324 | 642 | TQLSTFKGQFSAEVLKKLER-KHYTGWGRLSKKLINGIYDK | ESGKTILDYLV | DDGvskHYNRNFMQLINDSQL | 714 |
| WP_002413717 | 642 | TQLSTFKGQFSAEVLKKLER-KHYTGWGRLSKKLINGIYDK | ESGKTILDYLI | DDGvskHYNRNFMQLINDSQL | 714 |
| WP_010775580 | 644 | TQLSTFKGQFSAEVLKKLER-KHYTGWGRLSKKLINGIYDK | ESGKTILDYLI | DDGvskHYNRNFMQLINDSQL | 716 |
| WP_010818269 | 642 | TQLSTFKGQFSAEVLKKLER-KHYTGWGRLSKKLINGIYDK | ESGKTILGYLI | DDGvskHYNRNFMQLINDSQL | 714 |
| WP_010824395 | 642 | TQLSTFKGQFSAEVLKKLER-KHYTGWGRLSKKLINGIYDK | ESGKTILDYLV | DDGvskHYNRNFMQLINDSQL | 714 |
| WP_016622645 | 642 | TQLSTFKGQFSAEVLKKLER-KHYTGWGRLSKKLINGIYDK | ESGKTILDYLI | DDGvskHYNRNFMQLINDSQL | 714 |
| WP_033624816 | 642 | TQLSTFKGQFSAEVLKKLER-KHYTGWGRLSKKLINGIYDK | ESGKTILDYLI | DDGvskHYNRNFMQLINDSQL | 714 |
| WP_033625576 | 642 | TQLSTFKGQFSAEVLKKLER-KHYTGWGRLSKKLINGIYDK | ESGKTILDYLI | DDGvskHYNRNFMQLINDSQL | 714 |

| | | | | |
|---|---|---|---|---|
| WP_033789179 | 642 | TQLSTFKGQPSEEVLKKKLER-KHYTGWGRLSKKLINGIYDK | ESGKTILDYLI | DDGvskHYNRNFMQLINDSQL | 714 |
| WP_002310644 | 642 | TRLSHHEATLGKHIIKKLTK-KHYTGWGRLSKELIQGIRDK | QSNKTILDYLI | DDDfphHRNRNFMQLINDDSL | 714 |
| WP_002312694 | 643 | TRLSHHEATLGKHIIKKLTK-KHYTGWGRLSKELIQGIRDK | QSNKTILDYLI | DDDfphHRNRNFMQLINDDSL | 715 |
| WP_002314015 | 643 | TRLSHHEATLGKHIIKKLTK-KHYTGWGRLSKELIQGIRDK | QSNKTILDYLI | DDDfphHRNRNFMQLINDDSL | 715 |
| WP_002320716 | 643 | TRLSHHEATLGKHIIKKLTK-KHYTGWGRLSKELIQGIRDK | QSNKTILDYLI | DDDfphHRNRNFMQLINDDSL | 715 |
| WP_002330729 | 642 | TRLSHHEATLGKHIIKKLTK-KHYTGWGRLSKELIQGIRDK | QSNKTILDYLI | DDDfphHRNRNFMQLINDDSL | 714 |
| WP_002335161 | 643 | TRLSHHEATLGKHIIKKLTK-KHYTGWGRLSKELIQGIRDK | QSNKTILDYLI | DDDfphHRNRNFMQLINDDSL | 715 |
| WP_002345439 | 643 | TRLSHHEATLGKHIIKKLTK-KHYTGWGRLSKELIQGIRDK | QSNKTILDYLI | DDDfphHRNRNCMQLINDDSL | 715 |
| WP_034867970 | 638 | HQLSKYQEVFGEKLLKEFAR-KHYTGWGRPSAKLIHGIRDR | KTNKTILDYLI | DDDvpaNRNRNLMQLINDEHL | 710 |
| WP_047937432 | 643 | TRLSHHEATLGKHIIKKLTK-KHYTGWGRLSKELIQGIRDK | QSNKTILDYLI | DDDfphHRNRNFMQLINDDSL | 715 |
| WP_010720994 | 638 | HQLSKYQEVFGEKLLKEFAR-KHYTGWGRPSAKLIHGIRDR | KTNKTILDYLI | DDDvpaNRNRNLMQLINDEHL | 710 |
| WP_010737004 | 638 | HQLSKYQEVFGEKLLKEFAR-KHYTGWGRPSAKLIHGIRDR | KTNKTILDYLI | DDDvpaNRNRNLMQLINDEHL | 710 |
| WP_034700478 | 638 | HQLSKYQEVFGEKLLKEFAR-KHYTGWGRPSAKLIHGIRDR | KTNKTILDYLI | DDDvpaNRNRNLMQLINDEHL | 710 |
| WP_007209903 | 635 | NQLEQLPLNLSTKTIKALSR-RKYTGWGRLSARLIDGIHDK | NSGKTILDYLI | DESdsyIVNRNFMQLINDDHL | 707 |
| WP_023519017 | 632 | EQLKPYETVLGLPAIKKLAK-KHYTGWGRLSEKMIQGMREK | QSRKTILDYLI | DDDfpcNRNRNFMQLINDDHL | 704 |
| WP_010770040 | 635 | EQLKKYTYLFDEEVLKKLER-RHYTGWGRLSAKLLIGIKEK | RTHKTILDYLI | DDGgkqPINRNLMQLINDSDL | 707 |
| WP_048604708 | 631 | EQLSKFSDRLSEKTIKDLER-RHYTGWGRLSAKLINGIHDK | QSNKTILDYLI | DDApkkNINRNFMQLINDNRL | 703 |
| WP_010750235 | 637 | TQLKKYQRIILGEEIFPKKLVK-KKYTGWGRLSRKLINGIRDQ | KTNKTILDYLI | DDDfpyNRNRNFMQLINDDHL | 709 |
| AII16583 | 673 | ERLKTYAHLFDDKVMKQLKR-RRYTGWGRLSRKLINGIRDK | QSGKTILDFLK | -Dgf--ANRNFMQLIHDDSL | 741 |
| WP_029073316 | 648 | RRLKKEYDLDEEKIKKILKI--KYSGWSRLSKKLLSGIKTK | RTPETVLEVME | -------TNMNLMQVINDEKL | 717 |
| WP_031589969 | 648 | RRLKKEYDLDEEKIKKILKI--KYSGWSRLSKKLLSGIKTK | RTPETVLEVME | -------TNMNLMQVINDEKL | 717 |
| KDA45870 | 631 | RRLENYRDFLGEDILRKLSR-KKYTGWGRLSAKLLDGIYDK | KTHKTILDCLM | EDYs------QNFMQLINDDTY | 698 |
| WP_039099354 | 651 | AKLNEIDWLTDQQRVQLAAK--RYRGWGRLSAKLLTQIVN- | ANGQRIMDLLW | ---------TTDNFMRIVHSE-- | 712 |
| AKP02966 | 633 | EKLHSSNYSYTSDQIKKISN-MRYKGWGRLSKKLILTCITTE | TNTPKSLQLSN | -DLm-wTTNNNFISIISNDKY | 706 |
| WP_010991369 | 638 | EQLQQFSDVLDGVVLKKLER-RHYTGWGRLSAKLMGIRDK | QSHLTILDYLM | DDG----LNRNLMQLINDSNL | 706 |
| WP_033838504 | 638 | EQLQQFSDVLDGVVLKKLER-RHYTGWGRLSAKLMGIRDK | QSHLTILDYLM | DDG----LNRNLMQLINDSNL | 706 |
| EHN60060 | 641 | EQLQQFSDVLDGVVLKKLER-RHYTGWGRLSAKLMGIRDK | QSHLTILDYLM | DDG----LNRNLMQLINDSNL | 709 |

```
EFR89594       407  EQLQQFSDVLDGVLKKKLER-RHYTGWGRLSAKLLMGIRDK  QSHLTILDYLM  DDG----LNRNLMQLINDSNL                                        475
WP_038409211   638  EQLQSFSDVLDGTILKKKLER-RHYTGWGRLSAKLLTGIRDK  HSHLTILDYLM  DDG----LNRNLMQLINDSNL                                        706
EFR95520       257  EQLQSFSDVLDGTILKKKLER-RHYTGWGRLSAKLLTGIRDK  HSHLTILDYLM  DDG----LNRNLMQLINDSNL                                        325
WP_003723650   638  EQLQQFSDVLDGGVLKKKLER-RHYTGWGRLSAKLLVGIREK  QSHLTILDYLM  DDG----LNRNLMQLINDSNL                                        706
WP_003727705   638  EQLEQFSDVLDGVVLKKKLER-RHYTGWGRLSAKLLVGIREK  QSHLTILDYLM  DDG----LNRNLMQLINDSNL                                        706
WP_003730785   638  EQLEQFSDVLDGVVLKKLER-RHYTGWGRLSAKLLVGIRDK  QSHLTILDYLM  DDG----LNRNLMQLINDSNL                                        706
WP_003733029   638  EQLQQFSDVLDGTVLKKKLER-RHYTGWGRLSAKLLVGIRDK  QSHLTILDYLM  DDG----LNRNLMQLINDSNL                                        706
WP_003739838   638  EQLQQFSDVLDGAVLKKLER-RHYTGWGRLSAKLLVGIRDK  QSHLTILDYLM  DDG----LNRNLMQLINDSNL                                        706
WP_014601172   638  EQLQQFSDVLDGGVLKKLER-RHYTGWGRLSAKLLVGIREK  QSHLTILDYLM  DDG----LNRNLMQLINDSNL                                        706
WP_023548323   638  EQLQQFSDVLDGTVLDGVLKKLER-RHYTGWGRLSAKLLVGIRDK  QSHLTILDYLM  DDG----LNRNLMQLINDSNL                                      706
WP_031665337   638  EQLQQFSDVLDGVLKKLER-RHYTGWGRLSAKLLVGIRDK  QSHLTILEYLM  DDG----LNRNLMQLINDSNL                                        706
WP_031669209   638  EQLQQFSDVLDGTVLKKLER-RHYTGWGRLSAKLLVGIRDK  QSHLTILDYLM  DDG----LNRNLMQLINDSNL                                        706
WP_033920898   638  EQLQQFSDVLDGTVLKKLER-RHYTGWGRLSAKLLVGIRDK  QSHLTILDYLM  DDG----LNRNLMQLINDSNL                                        706
AKI42028       641  EQLQQFSDVLDGGVLDGTVLKKLER-RHYTGWGRLSAKLLVGIREK  QSHLTILDYLM  DDG----LNRNLMQLINDSNL                                    709
AKI50529       641  EQLQQFSDVLDGVLKKLER-RHYTGWGRLSAKLLVGIRDK  QSHLTILDYLM  DDG----LNRNLMQLINDSNL                                        709
EFR83390        86  EQLQQFSDVLDGVLKKLER-RHYTGWGRLSAKLLIGIRDK  QSHLTILEYLM  DDG----LNRNLMQLINDSNL                                        154
WP_046323366   638  EQLQFFSNVLDEAVLKKLER-RHYTGWGRLSAKLLVGIRDK  ESHLTILDYLM  DDK----HNRNLMQLINDSNL                                        706
AKE81011       650  ERLKTYAHLFDDKVMKQLKR-RRYTGWGRLSRKLINGIRDK  QSGKTILDFLK  -DGf----ANRNFMQLIHDDSL                                       718
CUO82355       642  RRLKKKYALPDDKIKQIKLI--KYKDWSRLSKKLLDGIVAD  SV--TVLDVLE  -----SRLNLMEIINDKEL                                          709
WP_033162887   645  RRLKKVYQLDDLLLVDKILKI--NYTGWSRLSEKLLTGMTAD  KA--TVLFVLE  -----SNKNLMEIINDEKL                                          712
AGZ01981       667  ERLKTYAHLFDDKVMKQLKR-RRYTGWGRLSRKLINGIRDK  QSGKTILDFLK  -DGf----ANRNFMQLIHDDSL                                       735
AKA60242       634  ERLKTYAHLFDDKVMKQLKR-RRYTGWGRLSRKLINGIRDK  QSGKTILDFLK  -DGf----ANRNFMQLIHDDSL                                       702
AKS40380       634  ERLKTYAHLFDDKVMKQLKR-RRYTGWGRLSRKLINGIRDK  QSGKTILDFLK  -DGf----ANRNFMQLIHDDSL                                       702
4UN5_B         638  ERLKTYAHLFDDKVMKQLKR-RRYTGWGRLSRKLINGIRDK  QSGKTILDFLK  -DGf----ANRNFMQLIHDDSL                                       706
WP_010922251   703  TFKEDIQKAQVSG-QGDS-LHEHIANLAGSPAIKKGILQTVKGILQTVKVVDELVKVMGFHKPENIVIEMARENQ  TTQKGQKNS            777
WP_039695303   707  PFKQIIQKSQVVG-DVDD-IEAVVHDLPGSPAIKKGILQSVKIVDELVKVMG-GNPDNIVIEMARENQ  TTNRGRSQS                  780
WP_045635197   702  SFKEIIQKAQVIG-KTDD-VKQVVQELSGSPAIKKGILQSIKIVDELVKVMG-HAPESIVIEMARENQ  TTARGKKNS                  775
```

| | | | | |
|---|---|---|---|---|
| 5AXW_A | 427 | VPKKVDLSQQKEI---PT---TLVDDFILSPVVKRSFIQSIKVINAIIKKYG--LPNDIIIELAREKN | ---------S | 487 |
| WP_009880683 | 387 | TFKEDLQKAQVSG-QGDS-LHEHIANLAGSPAIKKGILQTVKVDELVKVMGrHKPENIVIEMARENQ | TTQKGQKNS | 461 |
| WP_010922251 | 703 | TFKEDIQKAQVSG-QGDS-LHEHIANLAGSPAIKKGILQTVKVDELVKVMGrHKPENIVIEMARENQ | TTQKGQKNS | 777 |
| WP_011054416 | 703 | TFKEDIQKAQVSG-QGDS-LHEHIANLAGSPAIKKGILQTVKVDELVKVMGrHKPENIVIEMARENQ | TTQKGQKNS | 777 |
| WP_011284745 | 703 | TFKEDIQKAQVSG-QGDS-LHEHIANLAGSPAIKKGILQTVKVDELVKVMGrHKPENIVIEMARENQ | TTQKGQKNS | 777 |
| WP_011285506 | 703 | TFKEDIQKAQVSG-QGDS-LHEHIANLAGSPAIKKGILQTVKVDELVKVMGrHKPENIVIEMARENQ | TTQKGQKNS | 777 |
| WP_011527619 | 703 | TFKEDLQKAQVSG-QGDS-LHEHIANLAGSPAIKKGILQTVKVDELVKVMGrHKPENIVIEMARENQ | TTQKGQKNS | 777 |
| WP_012560673 | 703 | TFKEDIQKAQVSG-QGDS-LHEHIANLAGSPAIKKGILQTVKVDELVKVMGrHKPENIVIEMARENQ | TTQKGQKNS | 777 |
| WP_014407541 | 703 | TFKEDIQKAQVSG-QGHS-LHEQIANLAGSPAIKKGILQTVKIVDELVKVMG-HKPENIVIEMARENQ | TTQKGQKNS | 776 |
| WP_020905136 | 703 | TFKEDIQKAQVSG-QGDS-LHEHIANLAGSPAIKKGILQTVKVDELVKVMGrHKPENIVIEMARENQ | TTQKGQKNS | 777 |
| WP_023080005 | 703 | TFKERAIQKAQVSG-QGHS-LHEQIANLAGSPAIKKGILQTVKIVDELVKVMG-HKPENIVIEMARENQ | TTQKGQKNS | 776 |
| WP_023610282 | 703 | TFKEAIQKAQVSG-QGDS-LHEQIANLAGSPAIKKGILQTVKVDELVKVMGrHKPENIVIEMARENQ | TTQKGQKNS | 776 |
| WP_030125963 | 703 | TFKEDIQKAQVSG-QGDS-LHEHIANLAGSPAIKKGILQTVKVDELVKVMGrHKPENIVIEMARENQ | TTQKGQKNS | 777 |
| WP_030126706 | 703 | TFKEDIQKAQVSG-QGDS-LHEHIANLAGSPAIKKGILQTVKVDELVKVMGrHKPENIVIEMARENQ | TTQKGQKNS | 777 |
| WP_031488318 | 703 | TFKEDIQKAQVSG-QGDS-LHEHIANLAGSPAIKKGILQTVKVDELVKVMGrHKPENIVIEMARENQ | TTQKGQKNS | 777 |
| WP_032460140 | 703 | TFKEDIQKAQVSG-QGDS-LHEHIANLAGSPAIKKGILQTVKVDELVKVMGrHKPENIVIEMARENQ | TTQKGQKNS | 777 |
| WP_032461047 | 703 | TFKEDIQKAQVSG-QGDS-LHEHIANLAGSPAIKKGILQTVKVDELVKVMGrHKPENIVIEMARENQ | TTQKGQKNS | 777 |
| WP_032462016 | 703 | TFKEDIQKAQVSG-QGDS-LHEHIANLAGSPAIKKGILQTVKVDELVKVMGrHKPENIVIEMARENQ | TTQKGQKNS | 777 |
| WP_032462936 | 703 | TFKEDIQKAQVSG-QGDS-LHEHIANLAGSPAIKKGILQTVKVDELVKVMGrHKPENIVIEMARENQ | TTQKGQKNS | 777 |
| WP_032464890 | 703 | TFKEDIQKAQVSG-QGDS-LHEHIANLAGSPAIKKGILQTVKVDELVKVMGrHKPENIVIEMARENQ | TTQKGQKNS | 777 |
| WP_033888930 | 528 | TFKEDIQKAQVSG-QGDS-LHEHIANLAGSPAIKKGILQTVKVDELVKVMGrHKPENIVIEMARENQ | TTQKGQKNS | 602 |
| WP_038431314 | 703 | TFKEDIQKAQVSG-QGDS-LHEHIANLAGSPAIKKGILQTVKVDELVKVMGrHKPENIVIEMARENQ | TTQKGQKNS | 777 |
| WP_038432938 | 703 | TFKERAIQKAQVSG-QGHS-LHEQIANLAGSPAIKKGILQTVKIVDELVKVMG-HKPENIVIEMARENQ | TTQKGQKNS | 776 |
| WP_038434062 | 703 | TFKEDIQKAQVSG-QGDS-LHEHIANLAGSPAIKKGILQTVKVDELVKVMGrHKPENIVIEMARENQ | TTQKGQKNS | 777 |
| BAQ51233 | 614 | TFKEDIQKAQVSG-QGDS-LHEHIANLAGSPAIKKGILQTVKVDELVKVMGrHKPENIVIEMARENQ | TTQKGQKNS | 688 |
| KGE60162 | | ---------------------------------------------------------------- | --------- | |
| KGE60856 | | ---------------------------------------------------------------- | --------- | |

| | | | |
|---|---|---|---|
| WP_002989955 | 703 | TFKEDIQKAQVSG-QGDS-LHEHIANLAGSPAIKKGILQTVKVVDELVKVMGrHKPENIVIEMARENQ | TTQKGQKNS | 777 |
| WP_003030002 | 704 | SFKEEIARAQIIG-DVDD-IANVVHDLPGSPAIKKGILQSVKIVDELVKVMG-HNPANIIEMARENQ | MTDKGRRNS | 777 |
| WP_003065552 | 707 | PFKQIIQKSQVVG-DVDD-IEAVVHDLPGSPAIKKGILQSLKIVDELVKVMG-DNPDNIVIEMARENQ | TTNRGRSQS | 780 |
| WP_001040076 | 702 | SFKPIIDKARTGS-HSDN-LKEVIGELAGSPAIKKGILQSLKIVDELVKVMG-YEPEQIVEMARENQ | TTAKGLSRS | 775 |
| WP_001040078 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040080 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040081 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040083 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040085 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040087 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040088 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040089 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040090 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040091 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040092 | 705 | SFKSIISKAQSGS-HSDN-LKEVVGELAGSPAIKKGILQSLKIVDELVKVMG-YEPEQIVEMARENQ | TTNQGRRNS | 778 |
| WP_001040094 | 702 | SFKPIIDKARTGS-HSDN-LKEVVGELAGSPAIKKGILQSLKIVDELVKVMG-YEPEQIVEMARENQ | TTAKGLSRS | 775 |
| WP_001040095 | 702 | SFKPIIDKARTGS-HLDN-LKEVVGELAGSPAIKKGILQSLKIVDELVKVMG-YEPEQIVEMARENQ | TTAKGLSRS | 775 |
| WP_001040096 | 702 | SFKPIIDKARTGS-HLDN-LKEVVGELAGSPAIKKGILQSLKIVDELVKVMG-YEPEQIVEMARENQ | TTAKGLSRS | 775 |
| WP_001040097 | 702 | SFKPIIDKARTGS-HSDN-LKEVVGELAGSPAIKKGILQSLKIVDELVKVMG-YEPEQIVEMARENQ | TTAKGLSRL | 775 |
| WP_001040098 | 702 | SFKPIIDKARTGS-HSDN-LKEVVGELAGSPAIKKGILQSLKIVDELVKVMG-YEPEQIVEMARENQ | TTAKGLSRS | 775 |
| WP_001040099 | 702 | SFKPIIDKARTGS-HSDN-LKEVVGELAGSPAIKKGILQSLKIVDELVKVMG-YEPEQIVEMARENQ | TTAKGLSRS | 775 |
| WP_001040100 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040104 | 705 | SFKSIISKAQAGS-HSDN-LKEVVGELAGSPAIKKGILQSLKIVDELVKVMG-YEPEQIVEMARENQ | TTNQGRRNS | 778 |
| WP_001040105 | 705 | SFKPIIDKAQAGS-HSDN-LKEVVGELAGSPAIKKGILQSLKIVDELVKVMG-YEPEQVVEMARENQ | TTNQGRRNT | 778 |
| WP_001040106 | 705 | SFKPIIDKAQAGS-HSDN-LKEVVGELAGSPAIKKGILQSLKIVDELVKVMG-YEPEQVVEMARENQ | TTNQGRRNT | 778 |
| WP_001040107 | 705 | SFKPIIDKAQAGS-HSDN-LKEVVGELAGSPAIKKGILQSLKIVDELVKVMG-YEPEQVVEMARENQ | TTNQGRRNT | 778 |
| WP_001040108 | 705 | SFKPIIDKAQAGS-HSDN-LKEVVGELAGSPAIKKGILQSLKIVDELVKVMG-YEPEQVVEMARENQ | TTNQGRRNT | 778 |

-continued

| | | | | |
|---|---|---|---|---|
| WP_001040109 | 705 | SFKPIIDKAQAGS-HSDN-LKEVVGELAGSPAIKKGILQSLKIVDELVKVMG-YEPEQVVEMARENQ | TTNQGRRNT | 778 |
| WP_001040110 | 705 | SFKPIIDKAQAGS-HSDN-LKEVVGELAGSPAIKKGILQSLKIVDELVKVMG-YEPEQVVEMARENQ | TTNQGRRNT | 778 |
| WP_015058523 | 705 | SFKSIISKAQSGS-HSDN-LKEVVGELAGSPAIKKGILQSLKIVDELVKVMG-YEPEQVVEMARENQ | TTNQGRRNS | 778 |
| WP_017643650 | 702 | SFKPIIDKARTGS-HSDN-LKEVVGELAGSPAIKKGILQSLKIVDELVKVMG-YEPEQIVEMARENQ | TTAKGLSRL | 775 |
| WP_017647151 | 705 | SFKSIISKAQAGS-HSDN-LKEVVGELAGSPAIKKGILQSLKIVDELVKVMG-YEPEQIVEMARENQ | TTNQGRRNS | 778 |
| WP_017648376 | 705 | SFKSIISKAQAGS-HSDN-LKEVVGELAGSPAIKKGILQSLKIVDELVKVMG-YEPEQIVEMARENQ | TTNQGRRNS | 778 |
| WP_017649527 | 705 | SFKPIIDKAQAGS-HSDN-LKEVVGELAGSPAIKKGILQSLKIVDELVKVMG-YEPEQVVEMARENQ | TTNQGRRNT | 778 |
| WP_017771611 | 705 | SFKSIISKAQAGS-HSDN-LKEVVGELAGSPAIKKGILQSLKIVDELVKVMG-YEPEQIVEMARENQ | TTNQGRRNS | 778 |
| WP_017771984 | 705 | SFKSIISKAQAGS-HSDN-LKEVVGELAGSPAIKKGILQSLKIVDELVKVMG-YEPEQIVEMARENQ | TTNQGRRNS | 778 |
| CFQ25032 | 705 | SFKSIISKAQAGS-HSDN-LKEVVGELAGSPAIKKGILQSLKIVDELVKVMG-YEPEQIVEMARENQ | TTNQGRRNS | 778 |
| CFV16040 | 705 | SFKSIISKAQAGS-HSDN-LKEVVGELAGSPAIKKGILQSLKIVDELVKVMG-YEPEQIVEMARENQ | TTNQGRRNS | 778 |
| KLJ37842 | 705 | SFKSIISKAQAGS-HSDN-LKEVVGELAGSPAIKKGILQSLKIVDELVKVMG-YEPEQIVEMARENQ | TTNQGRRNS | 778 |
| KLJ72361 | 719 | SFKSIISKAQAGS-HSDN-LKEVVGELAGSPAIKKGILQSLKIVDELVKVMG-YEPEQIVEMARENQ | TTNQGRRNS | 792 |
| KLL20707 | 705 | SFKPIIDKAQAGS-HSDN-LKEVVGELAGSPAIKKGILQSLKIVDELVKVMG-YEPEQVVEMARENQ | TTNQGRRNT | 778 |
| KLL42645 | 705 | SFKSIISKAQAGS-HSDN-LKEVVGELAGSPAIKKGILQSLKIVDELVKVMG-YEPEQIVEMARENQ | TTNQGRRNS | 778 |
| WP_047207273 | 702 | SFKPIIDKARTGS-HSDN-LKEVVGELAGSPAIKKGILQSLKIVDELVKVMG-YEPEQIVEMARENQ | TTAKGLSRS | 775 |
| WP_047209694 | 705 | SFKSIISKAQAGS-HSDN-LKEVVGELAGSPAIKKGILQSLKIVDELVKVMG-YEPEQIVEMARENQ | TTNQGRRNS | 778 |
| WP_050198062 | 705 | SFKPIIDKAQAGS-HSDN-LKEVVGELAGSPAIKKGILQSLKIVDELVKVMG-YEPEQVVEMARENQ | TTNQGRRNT | 778 |
| WP_050201642 | 705 | SFKSIISKAQAGS-HSDN-LKEVVGELAGSPAIKKGILQSLKIVDELVKVMG-YEPEQIVEMARENQ | TTNQGRRNS | 778 |
| WP_050204027 | 705 | SFKSIISKAQAGS-HSDN-LKEVVGELAGSPAIKKGILQSLKIVDELVKVMG-YEPEQIVEMARENQ | TTNQGRRNS | 778 |
| WP_050881965 | 705 | SFKSIISKAQAGS-HSDN-LKEVVGELAGSPAIKKGILQSLKIVDELVKVMG-YEPEQIVEMARENQ | TTNQGRRNS | 778 |
| WP_050886065 | 705 | SFKSIISKAQSGS-HSDN-LKEVSELAGSPAIKKGILQSLKIVDELVKVMG-YEPEQIVEMARENQ | TTNQGRRNS | 778 |
| AHN30376 | 705 | SFKSIISKAQSGS-HSDN-LKEVSELAGSPAIKKGILQSLKIVDELVKVMG-YEPEQIVEMARENQ | TTNQGRRNS | 778 |
| EAO78426 | 705 | SFKSIISKAQAGS-HSDN-LKEVVGELAGSPAIKKGILQSLKIVDELVKVMG-YKPEQIVEMARENQ | TTNQGRRNS | 778 |
| CCW42055 | 705 | SFKSIISKAQSGS-HSDN-LKEVVGELAGSPAIKKGILQSLKIVDELVKVMG-YEPEQIVEMARENQ | TTNQGRRNS | 778 |
| WP_003041502 | 704 | SFKEEIAKAQIIG-DVDD-IANVVHDLPGSPAIKKGIQSVKIVDELVKVMG-HNPANIIIEMARENQ | TTDRGRRNS | 777 |
| WP_037593752 | 705 | SFKEEIARAQIIG-DVDD-IANVVHDLPGSPAIKKGILQSVKIVDELVKVMG-HNPANIIIEMARENQ | TTDKGRRNS | 778 |

| ID | Start | Sequence | End |
|---|---|---|---|
| WP_049516684 | 705 | SFKEEIARAQIIG-DVDD-IANVVHDLPGSPAIKKGILQSVKIVDELVKVMG-HNPANIIIEMARENQ TTDKGRRNS | 778 |
| GAD46167 | 704 | SFKEEIARAQIIG-DVDD-IANVVHDLPGSPAIKKGILQSVKIVDELVKVMG-HNPANIIIEMARENQ TTDKGRRNS | 777 |
| WP_018363470 | 705 | SFKQIIQEAQVVG-DVDD-IETVVHDLPGSPAIKKGILQSVKIVDELIKVMG-DNPDNIVIEMARENQ TTNRGRSQS | 778 |
| WP_003043819 | 713 | TFKEEIEKAQVSG-QGDS-LHEQIADLAGSPAIKKGILQTVKIVDELVKVMG-HKPENIVIEMARENQ TTTKGLQQS | 786 |
| WP_006269658 | 704 | SFKEEIARAQIID-DVDD-IANVVHDLPGSPAIKKGILQSVKIVDELVKVMG-HNPANIIIEMARENQ TTDKGRRNS | 777 |
| WP_048800889 | 704 | PFKQIIKDAQAID-DVDD-IELIVHDLPGSPAIKKGILQSIKIVDELVKVMG-YNPDNIVIEMARENQ TTTKGRRNS | 777 |
| WP_012767106 | 703 | TFKEAIQKAQVSG-QGHS-LHEQIANLAGSPAIKKGILQSVKVVDELVKVMG-HKPGQKNS TTQKGQKNS | 776 |
| WP_014612333 | 703 | TFKEAIQKAQVSG-QGHS-LHEQIANLAGSPAIKKGILQSVKIVDELVKVMG-HKPENIVIEMARENQ TTQKGQKNS | 776 |
| WP_015017095 | 703 | TFKEAIQKAQVSG-QGHS-LHEQIANLAGSPAIKKGILQTVKIVDELVKVMG-HKPENIVIEMARENQ TTQKGQKNS | 776 |
| WP_015057649 | 703 | TFKEAIQKAQVSG-QGHS-LHEQIANLAGSPAIKKGILQSVKVVDELVKVMG-HKPENIVIEMARENQ TTQKGQKNS | 776 |
| WP_048327215 | 703 | TFKEAIQKAQVSG-QGHS-LHEQIANLAGSPAIKKGILQSIKIVDELVKVMG-HKPENIVIEMARENQ TTQKGQKNS | 776 |
| WP_049519324 | 703 | TFKEAIQKAQVSG-QGHS-LHEQIANLAGSPAIKKGILQSVKVVDELVKVMG-HKPENIVIEMARENQ TTQKGQKNS | 776 |
| WP_012515931 | 703 | SFIDEIAKAQVIG-KTEY-SKDLVGNLAGSPAIKKGISQTIKIVDELVKIMG-YLPQQIVIEMARENQ TTAQGIKNA | 776 |
| WP_021320964 | 703 | SFIDEIAKAQVIG-KTEY-SKDLVGNLASSPAIKKGISQTIKIVDELVKIMG-YLPQQIVIEMARENQ TTAQGIKNA | 776 |
| WP_037581760 | 703 | SFIDEIAKAQVIG-KTEY-SKDLVGNLAGSPAIKKGISQTIKIVDELVKIMG-YLPQQIVIEMARENQ TTAQGIKNA | 776 |
| WP_004232481 | 704 | SFKTTIQEAQVVG-DVDD-IEAVVHDLPGSPAIKKGILQSVKIVDELVKVMG-HNPQNIVIEMARENQ ITGYGRNRS | 777 |
| WP_009854540 | 705 | PFKQIIQKSQVVG-DVDD-IEAVVHDLPGSPAIKKGILQSVKIVDELVKVMG-DNPDNIVIEMARENQ TTNRGRSQS | 778 |
| WP_012962174 | 705 | PFKQIIKDAQIID-DIDD-VTSVVRELPGSPAIKKGILQSVKIVDELVKVMG-HNPDNIVIEMARENQ TTNRGRNQS | 778 |
| WP_039695303 | 707 | PFKQIIQKSQVVG-DVDD-IEAVVHDLPGSPAIKKGILQSVKIVDELVKVMG-GNPDNIVIEMARENQ TTNRGRSQS | 780 |
| WP_014334983 | 704 | SFKTIIQEAQVVG-DVDD-IEAVVHDLPGSPAIKKGILQSVKIVDELVKVMG-DNPDNIVIEMARENQ TTGYGRNKS | 777 |
| WP_003099269 | 703 | DFAKIIKNEQEKTIKNES-LEETIANLAGSPAIKKGILQSIKIVDEIVKIMG-QNPDNIVIEMARENQ TTGYGRNKS | 777 |
| AHY15608 | 703 | DFAKIIKNEQEKTIKNES-LEETIANLAGSPAIKKGILQSIKIVDEIVKIMG-QNPDNIVIEMARENQ STMQGIKNS | 777 |
| AHY17476 | 703 | DFAKIIKNEQEKTIKNES-LEETIANLAGSPAIKKGILQSIKIVDEIVKIMG-QNPDNIVIEMARENQ STMQGIKNS | 777 |
| ESR09100 | | ------------------------------------------------------------------------ ---------- | |
| AGM98575 | 703 | DFAKIIKNEQEKTIKNES-LEETIANLAGSPAIKKGILQSIKIVDEIVKIMG-QNPDNIVIEMARENQ STMQGIKNS | 777 |
| ALF27331 | 704 | SFKEEIAKAQVIG-ETDN-LNQVVSDIAGSPAIKKGILQSLKIVDELVKIMG-HQPENIVVEMARENQ FTNQGRRNS | 777 |
| WP_018372492 | 717 | DFKEIIRKAQTIE-NIDT-NQALVSSLPGSPAIKKGILQSLNIVDEIIAIMG-YAPTNIVIEMARENQ TTQKGRDNS | 790 |

-continued

| | | | |
|---|---|---|---|
| WP_045618028 | 703 | SFKEIIQKAQVVG-KTND-VKQVVQELPGSPAIKKGIKLVDELVKVMG-HAPESIVIEMARENQ | TTARGKKNS | 776 |
| WP_045635197 | 702 | SFKEIIQKAQVIG-KTDD-VKQVVQELSGSPAIKKGIKLVDELVKVMG-HAPESIVIEMARENQ | TTARGKKNS | 775 |
| WP_002263549 | 704 | SFKEIAKAQVIG-ETDN-LNQVVSDIAGSPAIKKGILQSLKIVDELVKIMG-HQPENIVVEMARENQ | FTNQGRRNS | 777 |
| WP_002263887 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002264920 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002269043 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002269448 | 704 | SFKEEIAKAQVIG-ETDN-LNQVVSDIAGSPAIKKGILQSLKIVDELVKIMG-HQPENIVVEMARENQ | FTNQGRQNS | 777 |
| WP_002271977 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002272766 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002273241 | 704 | SFKEEIAKAQVIG-ETDN-LNQVVSDIAGSPAIKKGILQSLKIVDELVKIMG-HQPENIVVEMARENQ | FTKQGRRNS | 777 |
| WP_002275430 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002276448 | 704 | SFKEEIAKAQVIG-ETDN-LNQVVSDIAGSPAIKKGILQSLKIVDELVKIMG-HQPENIVVEMARENQ | FTKQGRRNS | 777 |
| WP_002277050 | 705 | TFKDDIVKAQYVD-NSDD-LHQVVQSLAGSPAIKKGILQSLKIVDELVKVMG-KEPEQIVVEMARENQ | TTAKGRRNS | 778 |
| WP_002277364 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002279025 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002279859 | 704 | SFKEEIAKAQVIG-ETDN-LNQVVSDIAGSPAIKKGILQSLKIVDELVKIMG-HQPENIVVEMARENQ | FTKQGRRNS | 777 |
| WP_002280230 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002281696 | 705 | TFKDDIVKAQYVD-NSDD-LHQVVQSLAGSPAIKKGILQSLKIVDELVKVMG-KEPEQIVVEMARENQ | TTAKGRRNS | 778 |
| WP_002282247 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002282906 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002283846 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002287255 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002288990 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002289641 | 704 | SFKEEIAKAQVIG-ETDN-LNQVVSDIAGSLAIKKGILQSLKIVDELVKIMG-HQPENIVVEMARENQ | TTAKGRRNS | 777 |
| WP_002290427 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002295753 | 704 | SFKEEIAKAQVIG-ETDN-LNQVVSDIAGSPAIKKGILQSLKIVDELVKIMG-HQPENIVVEMARENQ | FTKQGRRNS | 777 |
| WP_002296423 | 704 | SFKEEIAKAQVIG-ETDN-LNQVVSDIAGSPAIKKGILQSLKIVDELVKIMG-HQPENIVVEMARENQ | FTNQGRRNS | 777 |

| | | | |
|---|---|---|---|
| WP_002304487 | 714 | SFKEEIAKAQVIG-EMDG-LNQVVSDIAGSPAIKKGILQSLKIVDELVKIMG-HNPANIVIEMARENQ | TTAKGRRSS | 787 |
| WP_002305844 | 704 | SFKEEIAKAQVIG-ETDN-LNQVVSDIAGSPAIKKGILQSLKIVDELVKIMG-HQPENIVVEMARENQ | FTKQGRRNS | 777 |
| WP_002307203 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_002310390 | 704 | SFKEEIAKAQVIG-ETDN-LNQVVSDIAGSLAIKKGILQSLKIVDELVKIMG-HQPENIVVEMARENQ | FTNQGRRNS | 777 |
| WP_002352408 | 704 | SFKEEIAKAQVIG-ETDN-LNQVVSDIAGSPAIKKGILQSLKIVDELVKIMG-HQPENIVVEMARENQ | FTNQGQRNS | 777 |
| WP_012997688 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_014677909 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_019312892 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_019313659 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_019314093 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_019315370 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_019803776 | 705 | TFKDDIVKAQYVD-NSDD-LHQVVQSLAGSPAIKKGILQSLKIVDELVKIMG-HQPENIVVEMARENQ | FTNQGRRNS | 778 |
| WP_019805234 | 704 | SFKEEIAKAQVIG-ETDN-LNQVVSDIAGSPAIKKGILQNLKIVDELVKIMG-HQPENIVVEMARENQ | FTNQGRRNS | 777 |
| WP_024783594 | 704 | SFKEEIAKAQVIG-ETDN-LNQVVSDIAGSLAIKKGILQSLKIVDELVKIMG-HQPENIVVEMARENQ | FTNQGRRNS | 777 |
| WP_024784288 | 705 | TFKDDIVKAQYVD-NSDD-LHQVVQSLAGSPAIKKGILQSLKIVDELVKVMG-KEPEQIVVEMARENQ | TTAKGRRNS | 778 |
| WP_024784666 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_024784894 | 705 | SFKEEIAKAQVIG-ETDN-LNQVVSDIAGSPAIKKGILQSLKIVDELVKIMG-HQPENIVVEMARENQ | FTNQGRRNS | 778 |
| WP_024786433 | 704 | TFKDDIVKAQYVD-NSDD-LHQVVQSLAGSPAIKKGILQSLKIVDELVKIMG-KEPEQIVVEMARENQ | TTAKGRRNS | 777 |
| WP_049473442 | 704 | SFKEEIAKAQVIG-ETDN-LNQVVSDIAGSPAIKKGILQSLKIVDELVKIMG-HQPENIVVEMARENQ | FTNQGRRNS | 777 |
| WP_049474547 | 704 | SFKEEIAKAQVIG-ETDN-LNQVVSDIAGSPAIKKGILQSLKIVDELVKIMG-HQPENIVVEMARENQ | FTNQGRRNS | 777 |
| EMC03581 | 697 | SFKEEIAKAQVIG-ETDN-LNQVVSDIAGSPAIKKGILQSLKIVDELVKIMG-HQPENIVVEMARENQ | FTNQGRRNS | 770 |
| WP_000428612 | 705 | SFKEIIKKAQVVG-KTDD-VKQVVQELPGSPAIKKGILQSIKLVDELVKVMG-HEPESIVIEMARENQ | TTARGKKNS | 778 |
| WP_000428613 | 703 | SFKEITQKAQVVG-KTDD-VKQVVQELPGSPAIKKGILQSIKIVDELVKIMG-HTPESIVIEMARENQ | TTARGKKNS | 776 |
| WP_049523028 | 702 | SFKEETIQKAQVIG-ETND-VKQVVQELPGSPAIKKGILQSIKIVDELVKVMG-HAPESVVIEMARENQ | TTNKGKSKS | 775 |
| WP_003107102 | 672 | DFASIIKEAQEKTIKSEK-LEETIANLAGSPAIKKGILQSVKIVDEVVKVMG-YEPSNIVIEMARENQ | STQRGINNS | 746 |
| WP_054279288 | 705 | SFKEEIKKAQEGG-LKDS-INDQIRDLAGSPAIKKGILQTINIVDEIVKIMG-KAPQHIVVEMARDVQ | KTDIGVKQS | 778 |
| WP_049531101 | 703 | SFKEIQESQVVG-KPDD-VKQIVQELPGSSAIKKGILQSIKLVDELVKVMG-HDPESIVIEMARENQ | TTARGKKNS | 776 |

| | | | |
|---|---|---|---|
| WP_049538452 | 703 | SFKEIIQKAQVFG-KTND-VKQVVQELPGSPAIKKGILQSIKIVEELVKVMG-HEPESIVIEMARENQ | TTTRGKKNS | 776 |
| WP_049549711 | 703 | SFKKIIQKSQVVG-ETDD-VKQVVRELPGSPAIKKGILQSIKIVDELVKVMD-HAPESIVIEMARENQ | TTARGKKNS | 776 |
| WP_007896501 | 706 | DFEKLIDDAQKKAiKRES-LTEAVANLAGSPAIKKGILQSLKVVDEIVKVMG-HNPDNIVIEMSRENQ | TTAQGLKNA | 780 |
| EFR44625 | 658 | DFEKLIDDAQKKAiKRES-LTEAVANLAGSPAIKKGILQSLKVVDEIVKVMG-HNPDNIVIEMSRENQ | TTAQGLKNA | 732 |
| WP_002897477 | 702 | SFKEIIQKAQVVG-KTDD-VKQVVQELPGSPAIKKGILQSIKIVDELVKVMG-YALESIVIEMARENQ | TTARGKKNS | 775 |
| WP_002906454 | 702 | SFKEIIQKAQVVG-KTDD-VKQVVQEIPGSPAIKKGILQSIKIVDELVKVMG-HNPESIVIEMARENQ | TTAKGKKNS | 775 |
| WP_009729476 | 703 | SFKEIIQKAQVVG-KTND-VKQVVQELPGSPAIKKGILQSIKIVDELVKVMG-HAPESIVIEMARENQ | TTARGKKNS | 776 |
| CQR24647 | 706 | SFKDEIANSQVIG-DGDD-LHQVVQELAGSPAIKKGILQSLKIVDELVKVMG-YNPEQIVVEMARENQ | TTARGRNNS | 779 |
| WP_000066813 | 705 | SFKEIIQKAQVFG-KTND-VKQVVQELPGSPAIKKGILQSIKIVDELVKVMG-HAPESIVIEMARENQ | TTARGKKNS | 778 |
| WP_009754323 | 703 | SFKEIIQKAQVVG-KTDD-LTQVVRELSGSPAIKKGILQSIKIVDELVKVMG-YAPESIVIEMARENQ | TTAKGKKNS | 776 |
| WP_044674937 | 702 | SFVDEIRLAQGSG-EAED-YRAEVQNLAGSPAIKKGILQSLKIVDELIEVMG-YDPEHIVVEMARENQ | FTNQGRRNS | 775 |
| WP_044676715 | 704 | SFVDEIRLAQGSG-EAED-YRAEVQNLAGSPAIKKGILQSLKIVDELIEVMG-YDPEHIVVEMARENQ | FTNQGRRNS | 777 |
| WP_044680361 | 704 | SFVDEIRLAQGSG-EAED-YRAEVQNLAGSPAIKKGILQSLKIVDELIEVMG-YDPEHIVVEMARENQ | FTNQGRRNS | 777 |
| WP_044681799 | 702 | SFVDEIRLAQGSG-EAED-YRAEVQNLAGSPAIKKGILQSLKIVDELIEVMG-YDPEHIVVEMARENQ | FTNQGRRNS | 775 |
| WP_049533112 | 704 | SFKEEIAKAQVIG-ETDD-LNQVVSDIAGSPAIKKGILQSLKIVDELVKVMG-YNPANIVIEMARENQ | TTDKGRRNS | 777 |
| WP_029090905 | 683 | LFKKIIEEQFENEtALLN-KQRIDELAASPANKKGIWQAIKIVKELEKVLQ-QPAENIFIEFARSDE | ES----KRS | 752 |
| WP_006506696 | 706 | GYAQMIEERATSCPeDGKF-TYEEVERLAGSPALKRGIWQLQIVEEITKVMK-CRPKYIYIEFERSEE | -----KERT | 776 |
| AIT42264 | 703 | TFKEDIQKAQVSG-QGDS-LHEHIANLAGSPAIKKGILQTVKVVDELVKVMGrHKPENIVIEMARENQ | TTQKGQKNS | 777 |
| WP_034440723 | 711 | SFKEKIRKAQDIN-QVND-IKEIVKDLPGSPAIKKGIYQSIRIVDEIIRKMK-DRPKNIVIEMARENQ | TTQEGKNKS | 784 |
| AKQ21048 | 703 | TFKEDIQKAQVSG-QGDS-LHEHIANLAGSPAIKKGILQTVKVVDELVKVMGrHKPENIVIEMARENQ | TTQKGQKNS | 777 |
| WP_004636532 | 707 | SFKKKIEDAQTIE-DTTH-IYDTVAELPGSPAIKKGIRQALKIVEEIIDIG-YEPENIVVEMARESQ | TTKKGKDLS | 780 |
| WP_002364836 | 715 | SFKNAIQKAQSSE-HEET-LSETVNELAGSPAIKKGIYQSLKIVDELVAIMG-YAPKRIVVEMARENQ | TTSTGKRRS | 788 |
| WP_016631044 | 666 | SFKNAIQKAQSSE-HEET-LSETVNELAGSPAIKKGIYQSLKIVEELIELIG-YNPKIVVEELIELIG | RT----NRS | 739 |
| EMS75795 | 455 | SFKEELANELALA-GNQS-LLEVEALLGSPAIKKGIWQTLKIVEELIELIG-YNPKIVVEELIELIG | RT----NRS | 524 |
| WP_002373311 | 715 | SFKNAIQKAQSSE-HEET-LSETVNELAGSPAIKKGIYQSLKIVDELVAIMG-YAPKRIVVEMARENQ | TTSTGKRRS | 788 |
| WP_002378009 | 715 | SFKNAIQKAQSSE-HEET-LSETVNELAGSPAIKKGIYQSLKIVDELVAIMG-YAPKRIVVEMARENQ | TTSTGKRRS | 788 |
| WP_002407324 | 715 | SFKNAIQKAQSSE-HEET-LSETVNELAGSPAIKKGIYQSLKIVDELVAIMG-YAPKRIVVEMARENQ | TTSTGKRRS | 788 |

-continued

```
WP_002413717  715 SFKNAIQKAQSSE-HEET-LSETVNELAGSPAIKKGIYQSLKIVDELVAIMG-YAPKRIVVEMARENQ  TTSTGKRRS  788
WP_010775580  717 SFKNAIQKAQSSE-HEET-LSETVNELAGSPAIKKGIYQSLKIVDELVAIMG-YAPKRIVVEMARENQ  TTSTGKRRS  790
WP_010818269  715 SFKNAIQKAQSSE-HEET-LSETVNELAGSPAIKKGIYQSLKIVDELVAIMG-YAPKRIVVEMARENQ  TTSTGKRRS  788
WP_010824395  715 SFKNAIQKAQSSE-HEET-LSETVNELAGSPAIKKGIYQSLKIVDELVAIMG-YAPKRIVVEMARENQ  TTSTGKRRS  788
WP_016622645  715 SFKNAIQKAQSSE-HEET-LSETVNELAGSPAIKKGIYQSLKIVDELVAIMG-YAPKRIVVEMARENQ  TTSTGKRRS  788
WP_033624816  715 SFKNAIQKAQSSE-HEET-LSETVNELAGSPAIKKGIYQSLKIVDELVAIMG-YAPKRIVVEMARENQ  TTSTGKRRS  788
WP_033625576  715 SFKNAIQKAQSSE-HEET-LSETVNELAGSPAIKKGIYQSLKIVDELVAIMG-YAPKRIVVEMARENQ  TTSTGKRRS  788
WP_033789179  715 SFKNAIQKAQSSE-HEET-LSETVNELAGSPAIKKGIYQSLKIVDELVAIMG-YAPKRIVVEMARENQ  TTSTGKRRS  788
WP_002310644  715 SFKKEIKKAQMIT-DTEN-LEEIVKELTGSPAIKKGILQSLKIVDEIVGIMG-YEPANIVVEMARENQ  TTGRGLKSS  788
WP_002312694  716 SFKKEIKKAQMIT-DTEN-LEEIVKELTGSPAIKKGILQSLKIVDEIVGIMG-YEPANIVVEMARENQ  TTGRGLKSS  789
WP_002314015  716 SFKKEIKKAQMIT-DTEN-LEEIVKELTGSPAIKKGILQSLKIVDEIVGIMG-YEPANIVVEMARENQ  TTGRGLKSS  789
WP_002320716  715 SFKKEIKKAQMIT-DTEN-LEEIVKELTGSPAIKKGILQSLKIVDEIVGIMG-YEPANIVVEMARENQ  TTGRGLKSS  788
WP_002330729  716 SFKKEIKKAQMIT-DTEN-LEEIVKELTGSPAIKKGILQSLKIVDEIVGIMG-YEPANIVVEMARENQ  TTGRGLKSS  789
WP_002335161  716 SFKKEIKKAQMIT-DTEN-LEEIVKELTGSPAIKKGILQSLKIVDEIVGIMG-YEPANIVVEMARENQ  TTGRGLKSS  789
WP_002345439  711 SFKKEEIAKATVFS-KHKS-LVDVIQDLPGSPAIKKGILQSLKIVEELIAIIG-YKPKNIVIEMARENQ  KT---HRT   780
WP_034867970  716 SFKKEEIAKATVFS-KHKS-LVDVIQDLPGSPAIKKGILQSLKIVEELIAIIG-YKPKNIVIEMARENQ  TTGRGLKSS  789
WP_047937432  711 SFKKEEIAKATVFS-KHKS-LVDVIQDLPGSPAIKKGILQSLKIVEELIAIIG-YKPKNIVIEMARENQ  KT---HRT   780
WP_010720994  711 SFKKEEIAKATVFS-KHKS-LVDVIQDLPGSPAIKKGILQSLKIVEELIAIIG-YKPKNIVIEMARENQ  KT---HRT   780
WP_010737004  711 SFKKEEIAKATVFS-KHKS-LVDVIQDLPGSPAIKKGIWQSLKIVEELIAIIG-YKPKNIVIEMARENQ  KT---HRT   780
WP_034700478  708 SFKKIIEDSQPYK-EQQS-AEEIVSELSGSPAIKKGILQSLKIVDELVAIMG-YKPKNIVVEMARENQ  TTGRGKQNS  781
WP_007209003  705 SFKETIANELIMS-DSNV-LLDQVKAIPGSPAVKKGIWQSIKIVEEIIGIIG-KAPKNIVIEMARENQ  RTSR----S  774
WP_023519017  708 SFKSEIAEAQSDM-NTED-LHEVVQNLAGSPAIKKGILQSLKIVDELVDIMG-SLPKNIVVEMARENQ  TTSRGRTNS  781
WP_010770040  704 TFKEEIEKEQLKA-NSEESLIEIVQNLAGSPAIKKGIFQSLKIVEEIVEIMG-YAPTNIVVEMARENQ  TTANGRRNS  778
WP_048604708  710 SFKEEIAKELTLS-DKQS-LLEVEAIPGSPAIKKGIWQTLKIVEELIAIIG-YKPKNIVIEMARENQ   TTTGGKNRS  783
WP_010750235  742 TFKEDIQKAQVSG-QGDS-LHEHIANLAGSPAIKKGILQTVKVVDELVKVMGIHKPENIVIEMARENQ  TTQKGQKNS  816
AII16583      718 GFKKTIDDANSTSvSGKF-SYAEVQELAGSPAIKRGIWQALLIVDEIKKIMK-HEPAHVYIEFARNED  -----KERK  788
WP_029073316
```

| | | | |
|---|---|---|---|
| WP_031589969 | 718 | GFKKTIDDANSTS-vSGKF-SYAEVQELAGSPAIKRGIWQALLIVDEIKKIMK-HEPAHVYIEFARNED | -----KERK | 788 |
| KDA45870 | 699 | SFKETIKNAQVIE-KEET-LAKTVQELPGSPAIKKGILQSLEIVDEIIKVMG-YKPKSIVEMARETQ | --THGTRKR | 771 |
| WP_039099354 | 713 | DFDKLITEANQMM-LAENGVQDVINDLYTSPQNKKALRQILLVVNDIQKAMKgQAPERILIEFARDE | VNPRLSVQR | 788 |
| AKP02966 | 707 | DFKNYIENHHLNKnEDQN-ISNLVNDIHVSPALKRGITQSIKIVQEIVKFMG-HAPKYIFIEVTRETK | TTSRGKRIQ | 785 |
| WP_010991369 | 707 | SFKSIIEKEQVTT-ADKD-IQSIVADLAGSPAIKKGILQSLKIVDELVSVMG-YPPQTIVVEMARENQ | TTGKGKNNS | 780 |
| WP_033838504 | 707 | SFKSIIEKEQVTT-ADKD-IQSIVADLAGSPAIKKGILQSLKIVDELVSVMG-YPPQTIVVEMARENQ | TTGKGKNNS | 780 |
| EHN60060 | 710 | SFKSIIEKEQVTT-ADKD-IQSIVADLAGSPAIKKGILQSLKIVDELVSVMG-YPPQTIVVEMARENQ | TTGKGKNNS | 783 |
| EFR89594 | 476 | SFKSIIEKEQVTT-ADKD-IQSIVADLAGSPAIKKGILQSLKIVDELVSVMG-YPPQTIVVEMARENQ | TTGKGKNNS | 549 |
| WP_038409211 | 707 | SFKSIIEKEQVST-ADKG-IQSIVAELAGSPAIKKGILQSLKIVDELVGIMG-YPPQTIVVEMARENQ | TTGKGKNNS | 780 |
| EFR95520 | 326 | SFKSIIEKEQVST-ADKG-IQSIVAELAGSPAIKKGILQSLKIVDELVGIMG-YPPQTIVVEMARENQ | TTGKGKNNS | 399 |
| WP_003723650 | 707 | SFKSIIEKEQVST-TDKD-LQSIVADLAGSPAIKKGILQSLKIVDELVSIMG-YPPQTIVVEMARENQ | TTGKGKNNS | 780 |
| WP_003727705 | 707 | SFKSIIEKEQVST-ADKD-LQSIVADLAGSPAIKKGILQSLKIVDELVSIMG-YPPQTIVVEMARENQ | TTGKGKNNS | 780 |
| WP_003730785 | 707 | SFKSIIEKEQVST-TDKD-LQSIVADLAGSPAIKKGILQSLKIVDELVSVMG-YPPQTIVVEMARENQ | TTGKGKNNS | 780 |
| WP_003733029 | 707 | SFKSIIEKEQVST-TDKD-LQSIVAELAGSPAIKKGILQSLKIVDELVSIMG-YPPQTIVVEMARENQ | TTNKGKNNS | 780 |
| WP_003739838 | 707 | SFKSIIEKEQVST-TDKD-LQSIVADLAGSPAIKKGILQSLKIVDELVSIMG-YPPQTIVVEMARENQ | TTVKGKNNS | 780 |
| WP_014601172 | 707 | SFKSIIEKEQVST-TDKD-LQSIVADLAGSPAIKKGILQSLKVVEELVSVMG-YPPQTIVVEMARENQ | TTGKGKNNS | 780 |
| WP_023548323 | 707 | SFKSIIEKEQVST-ADKD-LQSIVADLAGSPAIKKGILQSLKIVDELVSIMG-YPPQTIVVEMARENQ | TTNKGKNNS | 780 |
| WP_031665337 | 707 | SFKSIIEKEQVST-TDKD-LQSIVADLAGSPAIKKGILQSLKIVDELVSIMG-YPPQTIVVEMARENQ | TTGKGKNNS | 780 |
| WP_031669209 | 707 | SFKSIIEKEQVST-ADKD-LQSIVADLAGSPAIKKGILQSLKIVDELVSVMG-YPPQTIVVEMARENQ | TTNKGKNNS | 780 |
| WP_033920898 | 707 | SFKSIIEKEQVST-ADKD-LQSIVADLAGSPAIKKGILQSLKVVEELVSIMG-YPPQTIVVEMARENQ | TTNKGKNNS | 780 |
| AKI42028 | 710 | SFKSIIEKEQVST-TDKD-LQSIVADLAGSPAIKKGILQSLKIVDELVSIMG-YPPQTIVVEMARENQ | TTGKGKNNS | 783 |
| AKI50529 | 710 | SFKSIIEKEQVST-TDKD-LQSIVADLAGSPAIKKGILQSLKVVEELVSIMG-YPPQTIVVEMARENQ | TTNKGKNNS | 783 |
| EFR83390 | 155 | SFKSIIEKEQVST-TDKD-LQSIVADLAGSPAIKKGILQSLKIVDELVSIMG-YPPQTIVVEMARENQ | TTVKGKNNS | 228 |
| WP_046323366 | 707 | SFKSIIEKEQVST-ADKD-IQSIVADLAGSPAIKKGILQSLKIVDELVGIMG-YPPQTIVVEMARENQ | TTGKGKNNS | 780 |
| AKE81011 | 719 | TFKEDIQKAQVSG-QGDS-LHEHIANLAGSPAIKKGILQTVKVVDELVKVMGrHKPENIVIEMARENQ | TTQKGQKNS | 793 |
| CUO82355 | 710 | GYAQMIEEASSCPkDGKF-TYEEVAKLAGSPALKRGIWQSLQIVEEITKVMK-CRPKIYIYEFERSEE | -----KERT | 780 |
| WP_033162887 | 713 | GYKQIIEESNMQDiEGPF-KYDEVKKLAGSPAIKRGIWQALLVVREITKFMK-HEPSHIYIEFAREEQ | -----KVRK | 783 |

| | | | | | |
|---|---|---|---|---|---|
| AGZ01981 | 736 | TFKEDIQKAQVSG-QGDS-LHEHIANLAGSPAIKKGILQTVKVVDELVKVMG:HKPENIVIEMARENQ | TTQKGQKNS | 810 |
| AKA60242 | 703 | TFKEDIQKAQVSG-QGDS-LHEHIANLAGSPAIKKGILQTVKVVDELVKVMG:HKPENIVIEMARENQ | TTQKGQKNS | 777 |
| AKS40380 | 703 | TFKEDIQKAQVSG-QGDS-LHEHIANLAGSPAIKKGILQTVKVVDELVKVMG:HKPENIVIEMARENQ | TTQKGQKNS | 777 |
| 4UN5_B | 707 | TFKEDIQKAQVSG-QGDS-LHEHIANLAGSPAIKKGILQTVKVVDELVKVMG:HKPENIVIEMARENQ | TTQKGQKNS | 781 |
| WP_010922251 | 778 | RERMKRIEEGIK ELGS QILKEHP--VE---NTQLQNEKLYLYLYIQNGRDMYDQEL--D--INRLSDYDVDHI | 841 |
| WP_039695303 | 781 | QQRLKKLQNSLK PSYI E----DK--VE---NSHLQNDQLFLYYIQNGKDMYTGDEL--D--IDHLSDYDIDHI | 851 |
| WP_045635197 | 776 | QQRYKRIEDSLK ILAS NILKENP--TD---NNQLQNDRLFLYYLQNGKDMYTGEAL--D--INQLSSYDIDHI | 843 |
| 5AXW_A | 488 | KDAQKMINEMQK QTNE EIIRTTGk-E---NAKYLIEKIKLHDMQEGKCLYSLEAIp1EdILNNPFNYEVDHI | 561 |
| WP_009880683 | 462 | RERMKRIEEGIK ELGS DILKEYP--VE---NTQLQNEKLYLYLYLQNGRDMYDQEL--D--INRLSDYDVDHI | 525 |
| WP_010922251 | 778 | RERMKRIEEGIK ELGS QILKEHP--VE---NTQLQNEKLYLYLYLQNGRDMYDQEL--D--INRLSDYDVDHI | 841 |
| WP_011054416 | 778 | RERMKRIEEGIK ELGS QILKEHP--VE---NTQLQNEKLYLYLYLQNGRDMYDQEL--D--INRLSDYDVDHI | 841 |
| WP_011284745 | 778 | RERMKRIEEGIK ELGS QILKEHP--VE---NTQLQNEKLYLYLYLQNGRDMYDQEL--D--INRLSDYDVDHI | 841 |
| WP_011285506 | 778 | RERMKRIEEGIK ELGS QILKEHP--VE---NTQLQNEKLYLYLYLQNGRDMYDQEL--D--INRLSDYDVDHI | 841 |
| WP_011527619 | 778 | RERMKRIEEGIK ELGS DILKEYP--VE---NTQLQNEKLYLYLYLQNGRDMYDQEL--D--INRLSDYDVDHI | 841 |
| WP_012560673 | 778 | RERMKRIEEGIK ELGS QILKEHP--VE---TTQLQNEKLYLYLYLQNGRDMYDQEL--D--INRLSDYDVDHI | 841 |
| WP_014407541 | 777 | RERMKRIEEGIK ELGS QILKEHP--VE---NTQLQNEKLYLYLYLQNGRDMYDQEL--D--INRLSDYDVDHI | 840 |
| WP_020905136 | 778 | RERMKRIEEGIK ELGS QILKEHP--VE---NTQLQNEKLYLYLYLQNGRDMYDQEL--D--INRLSDYDVDHI | 841 |
| WP_023080005 | 777 | RERMKRIEEGIK ELGS QILKEHP--VE---NTQLQNEKLYLYLYLQNGRDMYDQEL--D--INRLSDYDVDHI | 840 |
| WP_023610282 | 777 | RERMKRIEEGIK ELGS QILKEHP--VE---NTQLQNEKLYLYLYLQNGRDMYDQEL--D--INRLSDYDVDHI | 840 |
| WP_030125963 | 778 | RERMKRIEEGIK ELGS DILKEYP--VE---NTQLQNEKLYLYLYLQNGRDMYDQEL--D--INRLSDYDVDHI | 841 |
| WP_030126706 | 778 | RERMKRIEEGIK ELGS DILKEYP--VE---NTQLQNEKLYLYLYLQNGRDMYDQEL--D--INRLSDYDVDHI | 841 |
| WP_031488318 | 778 | RERMKRIEEGIK ELGS DILKEYP--VE---NTQLQNEKLYLYLYLQNGRDMYDQEL--D--INRLSDYDVDHI | 841 |
| WP_032460140 | 778 | RERMKRIEEGIK ELGS DILKEYP--VE---NTQLQNEKLYLYLYLQNGRDMYDQEL--D--INRLSDYDVDHI | 841 |
| WP_032461047 | 778 | RERMKRIEEGIK ELGS DILKEYP--VE---NTQLQNEKLYLYLYLQNGRDMYDQEL--D--INRLSDYDVDHI | 841 |
| WP_032462016 | 778 | RERMKRIEEGIK ELGS QILKEHP--VE---NTQLQNEKLYLYLYLQNGRDMYDQEL--D--INRLSDYDVDHI | 841 |
| WP_032462936 | 778 | RERMKRIEEGIK ELGS DILKEYP--VE---NTQLQNEKLYLYLYLQNGRDMYDQEL--D--INRLSDYDVDHI | 841 |
| WP_032464890 | 778 | RERMKRIEEGIK ELGS QILKEHP--VE---NTQLQNEKLYLYLYLQNGRDMYDQEL--D--INRLSDYDVDHI | 841 |

| | | | | | |
|---|---|---|---|---|---|
| WP_033888930 | 603 | RERMKRIEEGIK | ELGS | QILKEHP--VE---NTQLQNEKLYLYYLQNGRDMYVDQEL---D--INRLSDYDVDHI | 666 |
| WP_038431314 | 778 | RERMKRIEEGIK | ELGS | DILKEYP--VE---NTQLQNEKLYLYYLQNGRDMYVDQEL---D--INRLSDYDVDHI | 841 |
| WP_038432938 | 777 | RERMKRIEEGIK | ELGS | QILKEHP--VE---NTQLQNEKLYLYYLQNGRDMYVDQEL---D--INRLSDYDVDHI | 840 |
| WP_038434062 | 778 | RERMKRIEEGIK | ELGS | DILKEYP--VE---NTQLQNEKLYLYYLQNGRDMYVDQEL---D--INRLSDYDVDHI | 841 |
| BAQ51233 | 689 | RERMKRIEEGIK | ELGS | QILKEHP--VE---NTQLQNEKLYLYYLQNGRDMYVDQEL---D--INRLSDYDVDHI | 752 |
| KGE60162 | 1 | ------------ | ---- | ------------------------------------QEL---D--INRLSGYDVDHI | 16 |
| KGE60856 | 1 | ------------ | ---- | ---------------------------------------------------------- | |
| WP_002989955 | 778 | RERMKRIEEGIK | ELGS | QILKEHP--VE---NTQLQNEKLYLYYLQNGRDMYVDQEL---D--INRLSDYDVDHI | 841 |
| WP_003030002 | 778 | QQRLKLLQDSLK | PVNI | K------N--VE---NQQLQNDRLFLYYIQNGKDMTGETL---D--INNLSQYDIDHI | 840 |
| WP_003065552 | 781 | QQRLKKLQNSLK | PSYI | E-----DK--VE---NSHLQNDQLFLYYIQNGKDMYTGDEL---D--IDHLSQYDIDHI | 851 |
| WP_001040076 | 776 | RQRLTTLRESLA | NLKS | EKKPKVV--KDqveNHHLSDDRLFLYYLQNGKDMYTDDEL---D--IDNLSQYDIDHI | 846 |
| WP_001040078 | 779 | RQRYKLLDDGVK | NLAS | NILKEYP--TD---NQALQNERLFLYYLQNGKDMYTGEAL---D--IDNLSQYDIDHI | 846 |
| WP_001040080 | 779 | RQRYKLLDDGVK | NLAS | NILKEYP--TD---NQALQNERLFLYYLQNGKDMYTGEAL---D--IDNLSQYDIDHI | 846 |
| WP_001040081 | 779 | RQRYKLLDDGVK | NLAS | NILKEYP--TD---NQALQNERLFLYYLQNGKDMYTGEAL---D--IDNLSQYDIDHI | 846 |
| WP_001040083 | 779 | RQRYKLLDDGVK | NLAS | NILKEYP--TD---NQALQNERLFLYYLQNGKDMYTGEAL---D--IDNLSQYDIDHI | 846 |
| WP_001040085 | 779 | RQRYKLLDDGVK | NLAS | NILKEYP--TD---NQALQNERLFLYYLQNGKDMYTGEAL---D--IDDLSQYDIDHI | 846 |
| WP_001040087 | 779 | RQRYKLLDDGVK | NLAS | NILKEYP--TD---NQALQNERLFLYYLQNGKDMYTDDEL---D--IDNLSQYDIDHI | 846 |
| WP_001040088 | 779 | RQRYKLLDDGVK | NLAS | NILKEYP--TD---NQALQNERLFLYYLQNGKDMYTDDEL---D--IDNLSQYDIDHI | 846 |
| WP_001040089 | 779 | RQRYKLLDDGVK | NLAS | NILKEYP--TD---NQALQNERLFLYYLQNGKDMYTDDEL---D--IDNLSQYDIDHI | 846 |
| WP_001040090 | 779 | RQRYKLLDDGVK | NLAS | NILKEYP--TD---NQALQNERLFLYYLQNGKDMYTDDEL---D--IDNLSQYDIDHI | 846 |
| WP_001040091 | 779 | RQRYKLLDDGVK | NLAS | NILKEYP--TD---NQALQNERLFLYYLQNGKDMYTDDEL---D--IDNLSQYDIDHI | 846 |
| WP_001040092 | 779 | RQRYKLLEDGVK | NLAS | DILKEYP--TD---NQALQNERLFLYYLQNGKDMYTDDEL---D--IDNLSQYDIDHI | 846 |
| WP_001040094 | 776 | RQRLTTLRESLA | NLKS | EKKPKVV--KDqveNHHLSDDRLFLYYLQNGKDMYTDDEL---D--IDNLSQYDIDHI | 846 |
| WP_001040095 | 776 | RQRLTTLRESLA | NLKS | EKKPKVV--KDqveNHHLSDDRLFLYYLQNGKDMYTDDEL---D--IDNLSQYDIDHI | 846 |
| WP_001040096 | 776 | RQRLTTLRESLA | NLKS | EKKPKVV--KDqveNHHLSDDRLFLYYLQNGKDMYTDDEL---D--IDNLSQYDIDHI | 846 |
| WP_001040097 | 776 | RQRLTTLRESLA | NLKS | EKKPKVV--KDqveNHHLSDDRLFLYYLQNGKDMYTDDEL---D--IDNLSQYDIDHI | 846 |
| WP_001040098 | 776 | RQRLTTLRESLA | NLKS | EKKPKVV--KDqveNHHLSDDRLFLYYLQNGKDMYTDDEL---D--IDNLSQYDIDHI | 846 |

| | | | | | | |
|---|---|---|---|---|---|---|
| WP_001040099 | 776 | RQRLTTLRESLA | NLKS | EKKPKVV--KDqveNHHLSDDRLFLYYLQNGKDMYTDDEL--D--IDNLSQYDIDHI | 846 |
| WP_001040100 | 776 | RQRLTTLRESLA | NLKS | EKKPKVV--KDqveNHHLSDDRLFLYYLQNGKDMYTDDEL--D--IDNLSQYDIDHI | 846 |
| WP_001040104 | 779 | RQRYKLLDDGVK | NLAS | NILKEYP--TD---NQALQNERLFLYYLQNGRDMYTGEAL--D--IDNLSQYDIDHI | 846 |
| WP_001040105 | 779 | RQRYKLLDDGVK | NLAS | NILKEYP--TD---NQALQNERLFLYYLQNGRDMYTGEAL--D--IDNLSQYDIDHI | 846 |
| WP_001040106 | 779 | RQRYKLLEEGVK | NLAS | NILKEYP--TD---NQALQNERLFLYYLQNGRDMYTGEAL--D--IDNLSQYDIDHI | 846 |
| WP_001040107 | 779 | RQRYKLLEEGVK | NLAS | NILKEYP--TD---NQALQNERLFLYYLQNGRDMYTGEAL--D--IDNLSQYDIDHI | 846 |
| WP_001040108 | 779 | RQRYKLLEEGVK | NLAS | NILKEYP--TD---NQALQNERLFLYYLQNGRDMYTGETL--D--IDNLSQYDIDHI | 846 |
| WP_001040109 | 779 | RQRYKLLEEGVK | NLAS | NILKEYP--TD---NQALQNERLFLYYLQNGRDMYTGEAL--D--IDNLSQYDIDHI | 846 |
| WP_001040110 | 779 | RQRYKLLEEGVK | NLAS | NILKEYP--TD---NQALQNERLFLYYLQNGRDMYTGEAL--D--IDNLSQYDIDHI | 846 |
| WP_015058523 | 779 | RQRYKLLEDGVK | NLAS | DILKEYP--TD---NQALQNERLFLYYLQNGRDMYTGEAL--D--IDNLSQYDIDHI | 846 |
| WP_017643650 | 776 | RQRLTTLRESLA | NLKS | EKKPKVV--KDqveNHHLSDDRLFLYYLQNGRDMYTDDEL--D--IDNLSQYDIDLI | 846 |
| WP_017647151 | 779 | RQRYKLLDDGVK | NLAS | NILKEYP--TD---NQALQNERLFLYYLQNGRDMYTGKAL--D--IDNLSQYDIDHI | 846 |
| WP_017648376 | 779 | RQRYKLLDDGVK | NLAS | NILKEYP--TD---NQALQNERLFLYYLQNGRDMYTGKAL--D--IDNLSQYDIDHI | 846 |
| WP_017649527 | 779 | RQRYKLLDDGVK | NLAS | NILKEYP--TD---NQALQNERLFLYYLQNGRDMYTGEAL--D--IDNLSQYDIDHI | 846 |
| WP_017771611 | 779 | RQRYKLLEEGVK | NLAS | NILKEYP--TD---NQALQNERLFLYYLQNGRDMYTGEAL--D--IDNLSQYDIDHI | 846 |
| WP_017771984 | 779 | RQRYKLLDDGVK | NLAS | NILKEYP--TD---NQALQNERLFLYYLQNGRDMYTGEAL--D--IDNLSQYDIDHI | 846 |
| CFQ25032 | 779 | RQRYKLLDDGVK | NLAS | NILKEYP--TD---NQALQNERLFLYYLQNGRDMYTGEAL--D--IDNLSQYDIDHI | 846 |
| CFV16040 | 779 | RQRYKLLDDGVK | NLAS | NILKEYP--TD---NQALQNERLFLYYLQNGRDMYTGEAL--D--IDNLSQYDIDHI | 846 |
| KLJ37842 | 779 | RQRYKLLDDGVK | NLAS | NILKEYP--TD---NQALQNERLFLYYLQNGRDMYTGEAL--D--IDNLSQYDIDHI | 846 |
| KLJ72361 | 779 | RQRYKLLDDGVK | NLAS | NILKEYP--TD---NQALQNERLFLYYLQNGRDMYTGEAL--D--IDNLSQYDIDHI | 846 |
| KLL20707 | 793 | RQRYKLLDDGVK | NLAS | NILKEYP--TD---NQALQNERLFLYYLQNGRDMYTGEAL--D--IDNLSQYDIDHI | 860 |
| KLL42645 | 779 | RQRYKLLEEGVK | NLAS | NILKEYP--TD---NQALQNERLFLYYLQNGRDMYTGEAL--D--IDNLSQYDIDHI | 846 |
| WP_047207273 | 776 | RQRLTTLRESLA | NLKS | EKKPKVV--KDqveNHHLSDDRLFLYYLQNGRDMYTDDEL--D--IDNLSQYDIDHI | 846 |
| WP_047209694 | 779 | RQRYKLLDDGVK | NLAS | NILKEYP--TD---NQALQNERLFLYYLQNGRDMYTGEAL--D--IDNLSQYDIDHI | 846 |
| WP_050198062 | 779 | RQRYKLLDDGVK | NLAS | NILKEYP--TD---NQALQNERLFLYYLQNGRDMYTGEAL--D--IDNLSQYDIDHI | 846 |
| WP_050201642 | 779 | RQRYKLLDDGVK | NLAS | NILKEYP--TD---NQALQNERLFLYYLQNGRDMYTGEAL--D--IDNLSQYDIDHI | 846 |
| WP_050204027 | 779 | RQRYKLLEEGVK | NLAS | NILKEYP--TD---NQALQNERLFLYYLQNGRDMYTGEAL--D--IDNLSQYDIDHI | 846 |

-continued

| ID | Pos1 | Seq1 | Seq2 | Seq3 | Seq4 | Pos2 |
|---|---|---|---|---|---|---|
| WP_050881965 | 779 | RQRYKLLDDGVK | NLAS | NILKEYP--TD---NQALQNERLFLYLQNGRDMYTGEAL--D--IDNLSQYDIDHI | | 846 |
| WP_050886065 | 779 | RQRYKLLDDGVK | NLAS | NILKEYP--TD---NQALQNERLFLYLQNGRDMYTGEAL--D--IDNLSQYDIDHI | | 846 |
| AHN30376 | 779 | RQRYKLLEDGVK | NLAS | DILKEYP--TD---NQALQNERLFLYLQNGRDMYTGEAL--D--IDSLSQYDIDHI | | 846 |
| EAO78426 | 779 | RQRYKLLDDGVK | NLAS | NILKEYP--TD---NQALQNERLFLYLQNGRDMYTGEAL--D--IDNLSQYDIDHI | | 846 |
| CCW42055 | 779 | RQRYKLLDDGVR | NLAS | NILKEYP--TD---NQALQNERLFLYLQNGRDMYTEKAL--D--IDNLSQYDIDHI | | 846 |
| WP_003041502 | 778 | QQRLKLLQDSLK | PVNI | K-----N--VE---NQQLQNDRLFLFLYIQNGKDMYTGETL--D--INNLSQYDIDHI | | 840 |
| WP_037593752 | 779 | QQRLKLLQDSLK | PVNI | K-----N--VE---NQQLQNDRLFLFLYIQNGKDMYTGETL--D--INNLSQYDIDHI | | 841 |
| WP_049516684 | 778 | QQRLKLLQDSLK | PVNI | K-----N--VE---NQQLQNDRLFLFLYIQNGKDMYTGETL--D--INNLSQYDIDHI | | 841 |
| GAD46167 | 779 | QQRLKKLQNSLK | PSYI | E-----DK--VE---NSHLQNDQLFLYLYIQNGKDMYTGDEL--D--IDHLSDYDIDHI | | 840 |
| WP_018363470 | 787 | RERKKRIEEGIK | ELES | QILKENP--VE---NTQLQNEKLYLYLYLQNGRDMYDQEL--D--INRLSDYDVDHI | | 849 |
| WP_003043819 | 778 | QQRLKLLQDSLK | PVNI | K-----N--VE---NQQLQNDRLFLFLYIQNGKDMYTGETL--D--INNLSQYDIDHI | | 850 |
| WP_006269658 | 778 | QQRLKLLQDSLT | PVSI | K-----N--VE---NQQLQNDRLFLFLYIQNGKDMYTGETL--D--IHHLSDYDIDHI | | 840 |
| WP_048800889 | 777 | RERMKRIEEGIK | ELGS | QILKEHP--VE---NTQLQNEKLYLYLYLQNGRDMYDQEL--D--INRLSDYDVDHI | | 840 |
| WP_012767106 | 777 | RERMKRIEEGIK | ELGS | QILKEHP--VE---NTQLQNEKLYLYLYLQNGRDMYDQEL--D--INRLSDYDVDHI | | 840 |
| WP_014612333 | 777 | RERMKRIEEGIK | ELGS | QILKEHP--VE---NTQLQNEKLYLYLYLQNGRDMYDQEL--D--INRLSDYDVDHI | | 840 |
| WP_015017095 | 777 | RERMKRIEEGIK | ELGS | QILKEHP--VE---NTQLQNEKLYLYLYLQNGRDMYDQEL--D--INRLSDYDVDHI | | 840 |
| WP_015057649 | 777 | RERMKRIEEGIK | ELGS | QILKEHP--VE---NTQLQNEKLYLYLYLQNGRDMYDQEL--D--INRLSDYDVDHI | | 840 |
| WP_048327215 | 777 | RERMKRIEEGIK | ELGS | QILKEHP--VE---NTQLQNEKLYLYLYLQNGRDMYDQEL--D--INRLSDYDVDHI | | 840 |
| WP_049519324 | 777 | RERMKRIEEGIK | ELGS | QILKEHP--VE---NTQLQNEKLYLYLYLQNGRDMYDQEL--D--INRLSDYDVDHI | | 840 |
| WP_012515931 | 777 | RQRMKKLEETAK | KLGS | NILKEHP--VD---NSQLQNDKRYLYLYYIQNGKDMYGDDL--D--IDYLSSYDIDHI | | 840 |
| WP_021320964 | 777 | RQRMKKLEETAK | KLGS | NILKEHP--VD---NSQLQNDKRYLYLYYIQNGKDMYGDDL--D--IDYLSSYDIDHI | | 840 |
| WP_037581760 | 777 | RQRMKKLEETAK | KLGS | NILKEHP--VD---NSQLQNDKRYLYLYYIQNGKDMYGDDL--D--IDYLSSYDIDHI | | 840 |
| WP_004232481 | 778 | NQRLKRLQDSLK | PSYV | D-----SK--VE---NSHLQNDRLFLFLYIQNGKDMYTGEEL--D--IDHLSDYDIDHI | | 848 |
| WP_009854540 | 779 | QQRLKKLQSSLK | PSYI | E-----DK--VE---NSHLQNDQLFLFLYIQNGKDMYTGDEL--D--IDHLSDYDIDHI | | 849 |
| WP_012962174 | 779 | QQRLKKLQDSLK | PSYI | E-----GK--VE---NNHLQDDRLFLFLYIQNGKDMYTGDEL--D--IDHLSDYDIDHI | | 849 |
| WP_039695303 | 781 | QQRLKKLQNSLK | PSYI | E-----DK--VE---NSHLQNDQLFLFLYIQNGKDMYTGDEL--D--IDHLSDYDIDHI | | 851 |
| WP_014334983 | 778 | NQRLKRLQDSLK | PSYV | D-----SK--VE---NSHLQNDRLFLFLYIQNGKDMYTGEEL--D--IDRLSDYDIDHI | | 848 |

| | | | | | |
|---|---|---|---|---|---|
| WP_003092269 | 778 | RQRLRKLEEVHK | NTGS | KILKEYN--VS----NTQLQSDRLYLYLLQDGKDMYTGKEL--D--YDNLSQYDIDHI | 841 |
| AHY15608 | 778 | RQRLRKLEEVHK | NTGS | KILKEYN--VS----NTQLQSDRLYLYLLQDGKDMYTGKEL--D--YDNLSQYDIDHI | 841 |
| AHY17476 | 778 | RQRLRKLEEVHK | NTGS | KILKEYN--VS----NTQLQSDRLYLYLLQDGKDMYTGKEL--D--YDNLSQYDIDHI | 841 |
| ESR09100 | | ------------ | ---- | ---------------------------------------------------------- | |
| AGM98575 | 778 | RQRLRKLEEVHK | NTGS | KILKEYN--VS----NTQLQSDRLYLYLLQDGKDMYTGKEL--D--YDNLSQYDIDHI | 841 |
| ALF27331 | 778 | QQRLKGLTDSIK | EFGS | QILKEHP--VE----NSQLQNDRLFLYYLQNGRDMYTGEEL--D--IDYLSQYDIDHI | 841 |
| WP_018372492 | 791 | AQRLKKIEDGIK | -LGS | DLLKQNP--IQd--NKDLQKEKLFLYYMQNGIDLYTGQPLncD--PDSLAFYDVDHI | 857 |
| WP_045618028 | 777 | QQRYKRIEDALK | NLAH | NILKEHP--TD----NIQLQNDRLFLYYLQNGKDMYTGKSL--D--INQLSCDIDHI | 844 |
| WP_045635197 | 776 | QQRYKRIEDSLK | ILAS | NILKENP--TD----NNQLQNDRLFLYYLQNGKDMYTGEAL--D--INQLSSYDIDHI | 843 |
| WP_002263549 | 778 | QQRLKGLTDSIK | EFGS | QILKEHP--VE----NSQLQNDRLFLYYLQNGRDMYTGEEL--D--IDYLSQYDIDHI | 841 |
| WP_002263887 | 778 | QQRLKGLTDSIK | EFGS | QILKEHP--VE----NSQLQNDRLFLYYLQNGRDMYTGEEL--D--IDYLSQYDIDHI | 841 |
| WP_002264920 | 778 | QQRLKGLTDSIK | EFGS | QILKEHP--VE----NSQLQNDRLFLYYLQNGRDMYTGEEL--D--IDYLSQYDIDHI | 841 |
| WP_002269043 | 778 | QQRLKGLTDSIK | EFGS | QILKEHP--VE----NSQLQNDRLFLYYLQNGRDMYTGEEL--D--IDYLSQYDIDHI | 841 |
| WP_002269448 | 778 | QQRLKGLTDSIK | EFGS | QILKEHP--VE----NSQLQNDRLFLYYLQNGRDMYTGEEL--D--IDYLSQYDIDHI | 841 |
| WP_002271977 | 778 | QQRLKGLTDSIK | EFGS | QILKEHP--VE----NSQLQNDRLFLYYLQNGRDMYTGEEL--D--IDYLSQYDIDHI | 841 |
| WP_002272766 | 778 | QQRLKGLTDSIK | EFGS | QILKEHP--VE----NSQLQNDRLFLYYLQNGRDMYTGEEL--D--IDYLSQYDIDHI | 841 |
| WP_002273241 | 778 | QQRLKGLTDSIK | EFGS | QILKEHP--VE----NSQLQNDRLFLYYLQNGRDMYTGEEL--D--IDYLSQYDIDHI | 841 |
| WP_002275430 | 778 | QQRLKGLTDSIK | EFGS | QILKEHP--VE----NSQLQNDRLFLYYLQNGRDMYTGEEL--D--IDYLSQYDIDHI | 841 |
| WP_002276448 | 778 | QQRLKGLTDSIK | EFGS | QILKEHP--VE----NSQLQNDRLFLYYLQNGRDMYTGEEL--D--IDYLSQYDIDHI | 841 |
| WP_002277050 | 779 | QQRYKRLKEAIK | DLNH | KILKEHP--TD----NQALQNNRLFLYYLQNGRDMYTGESL--D--INRLSDYDIDHV | 846 |
| WP_002277364 | 778 | QQRLKGLTDSIK | EFGS | QILKEHP--VE----HSQLQNDRLFLYYLQNGRDMYTGEEL--D--IDYLSQYDIDHI | 841 |
| WP_002279025 | 778 | QQRLKGLTDSIK | EFGS | QILKEHP--VE----NSQLQNDRLFLYYLQNGRDMYTGEEL--D--IDYLSQYDIDHI | 841 |
| WP_002279859 | 778 | QQRLKGLTDSIK | EFGS | QILKEHP--VE----NSQLQNDRLFLYYLQNGRDMYTGEEL--D--IDYLSQYDIDHI | 841 |
| WP_002280230 | 778 | QQRLKGLTDSIK | EFGS | QILKEHP--VE----NSQLQNDRLFLYYLQNGRDMYTGEEL--D--IDYLSQYDIDHI | 841 |
| WP_002281696 | 778 | QQRLKGLTDSIK | EFGS | QILKEHP--VE----NSQLQNDRLFLYYLQNGRDMYTGEEL--D--IDYLSQYDIDHI | 841 |
| WP_002282247 | 779 | QQRYKRLKEAIK | DLNH | KILKEHP--TD----NQALQNNRLFLYYLQNGRDMYTGESL--D--INRLSDYDIDHV | 846 |
| WP_002282906 | 778 | QQRLKGLTDSIK | EFGS | QILKEHP--VE----NSQLQNDRLFLYYLQNGRDMYTGEEL--D--IDYLSQYDIDHI | 841 |

| | | | | | |
|---|---|---|---|---|---|
| WP_002283846 | 778 | QQRLKGLTDSIK | EFGS | QILKEHP--VE---NSQLQNDRLFLYYLQNGRDMYTGEEL--D--IDYLSQYDIDHI | 841 |
| WP_002287255 | 778 | QQRLKGLTDSIK | EFGS | QILKEHP--VE---HSQLQNDRLFLYYLQNGRDMYTGEEL--D--IDYLSQYDIDHI | 841 |
| WP_002288990 | 778 | QQRLKGLTDSIK | EFGS | QILKEHP--VE---NSQLQNDRLFLYYLQNGRDMYTGEEL--D--IDYLSQYDIDHI | 841 |
| WP_002289641 | 778 | QQRLKGLTDSIK | EFGS | QILKEHP--VE---NSQLQNDRLFLYYLQNGRDMYTGEEL--D--IDYLSQYDIDHI | 841 |
| WP_002290427 | 778 | QQRLKGLTDSIK | EFGS | QILKEHP--VE---NSQLQNDRLFLYYLQNGRDMYTGEEL--D--IDYLSQYDIDHI | 841 |
| WP_002295753 | 778 | QQRLKGLTDSIK | EFGS | QILKEHP--VE---NSQLQNDRLFLYYLQNGRDMYTGEEL--D--IDYLSQYDIDHI | 841 |
| WP_002296423 | 778 | QQRLKGLTDSIK | EFGS | QILKEHP--VE---NSQLQNDRLFLYYLQNGRDMYTGEEL--D--IDYLSQYDIDHI | 841 |
| WP_002304487 | 788 | QKRYKRLEEAIK | DLNH | KILKEHP--TD---NQALQNDRLFLYYLQNGRDMYTEDPL--D--INRLSDYDIDHI | 855 |
| WP_002305844 | 778 | QQRLKGLTDSIK | EFGS | QILKEHP--VE---NSQLQNDRLFLYYLQNGRDMYTGEEL--D--IDYLSQYDIDHI | 841 |
| WP_002307203 | 778 | QQRLKGLTDSIK | EFGS | QILKEHP--VE---NSQLQNDRLFLYYLQNGRDMYTGEEL--D--IDYLSQYDIDHI | 841 |
| WP_002310390 | 778 | QQRLKGLTDSIK | EFGS | QILKEHP--VE---NSQLQNDRLFLYYLQNGRDMYTGEEL--D--IDYLSQYDIDHI | 841 |
| WP_002352408 | 778 | QQRLKGLTDSIK | EFGS | QILKEHP--VE---NSQLQNDRLFLYYLQNGRDMYTGEEL--D--IDYLSQYDIDHI | 841 |
| WP_012997688 | 778 | QQRLKGLTDSIK | EFGS | QILKEHP--VK---HSQLQNDRLFLYYLQNGRDMYTGEEL--D--IDYLSQYDIDHI | 841 |
| WP_014677909 | 778 | QQRLKGLTDSIK | EFGS | QILKEHP--VE---NSQLQNDRLFLYYLQNGRDMYTGEEL--D--IDYLSQYDIDHI | 841 |
| WP_019312892 | 778 | QQRLKGLTDSIK | EFGS | QILKEHP--VE---NSQLQNDRLFLYYLQNGRDMYTGEEL--D--IDYLSQYDIDHI | 841 |
| WP_019313659 | 778 | QQRLKGLTDSIK | EFGS | QILKEHP--VE---NSQLQNDRLFLYYLQNGRDMYTGEEL--D--IDYLSQYDIDHI | 841 |
| WP_019314093 | 778 | QQRLKGLTDSIK | EFGS | QILKEHP--VE---NSQLQNDRLFLYYLQNGRDMYTGEEL--D--IDYLSQYDIDHI | 841 |
| WP_019315370 | 778 | QQRLKGLTDSIK | EFGS | QILKEHP--VE---NSQLQNDRLFLYYLQNGRDMYTGEEL--D--IDYLSQYDIDHI | 841 |
| WP_019803776 | 778 | QQRLKGLTDSIK | EFGS | QILKEHP--VE---NSQLQNDRLFLYYLQNGRDMYTGEEL--D--IDYLSQYDIDHI | 841 |
| WP_019805234 | 778 | QQRLKGLTDSIK | EFGS | QILKEHP--VE---NSQLQNDRLFLYYLQNGRDMYTGEEL--D--IDYLSQYDIDHI | 841 |
| WP_024783594 | 778 | QQRLKGLTDSIK | EFGS | QILKEHP--VE---NSQLQNDRLFLYYLQNGRDMYTGEEL--D--IDYLSQYDIDHI | 841 |
| WP_024784288 | 779 | QQRYKRLKEAIK | EFGS | QILKEHP--VE---NSQLQNDRLFLYYLQNGRDMYTGESL--D--INRLSDYDIDHV | 846 |
| WP_024784666 | 778 | QQRLKGLTDSIK | EFGS | QILKEHP--VE---HSQLQNDRLFLYYLQNGRDMYTGEEL--D--IDYLSQYDIDHI | 841 |
| WP_024784894 | 778 | QQRLKGLTDSIK | EFGS | QILKEHP--TD---NQALQNNRLFLYYLQNGRDMYTGESL--D--IDYLSQYDIDHI | 841 |
| WP_024786433 | 779 | QQRYKRLKEAIK | DLNH | KILKEHP--TD---NQALQNNRLFLYYLQNGRDMYTGESL--D--INRLSDYDIDHV | 846 |
| WP_049473442 | 778 | QQRLKGLTDSIK | EFGS | QILKEHP--VE---NSQLQNDRLFLYYLQNGRDMYTGEEL--D--IDYLSQYDIDHI | 841 |
| WP_049474547 | 778 | QQRLKGLTDSIK | EFGS | QILKEHP--VE---NSQLQNDRLFLYYLQNGRDMYTGEEL--D--IDYLSQYDIDHI | 841 |

-continued

| | | | | | |
|---|---|---|---|---|---|
| EMCO3581 | 771 | QQRLKGLTDSIK | EFGS | QILKEHP--VE---HSQLQNDRLFLYYLQNGRDMYTGEEL--D--IDYLSQYDIDHI | 834 |
| WP_000428612 | 779 | QQRYKRIEDSLK | ILAS | KILKEHP--TD---NIQLQNDRLFLYYLQNGRDMYTGKPL--D--INQLSSYDIDHI | 846 |
| WP_000428613 | 777 | QQRYKRIEDALK | NLAS | NILKEHP--TN---NIQLQNDRLFLYYLQNGRDMYTGKPL--D--INQLSSYDIDHI | 844 |
| WP_049523028 | 776 | QQRLKTLSDAIS | ELG- | NILKEHP--TD---NIQLQNDRLFLYYLQNGKDMYTGEAL--D--INQLSNYDIDHI | 839 |
| WP_003107102 | 747 | RERLRKLEEVHK | NIGS | KILKEHE--IS---NAQLQSDRVYLYLLQDGKDMYTGKDL--D--FDRLSQYDIDHI | 810 |
| WP_054279288 | 779 | RERMKRVQEVLK | KLGS | QLLKEHP--VE---NFQLQNERLYLYLQNGKDMYTGEEL--S--ISNLSHYDIDHI | 842 |
| WP_049531101 | 777 | QQRYKRIEDSLK | ILAS | NILKEHP--TD---NIQLQNDRLFLYYLQNGKDMYTGNPL--D--INHLSSYDIDHI | 844 |
| WP_049538452 | 777 | QQRYKRIENSLK | ILAS | KILKEHP--TD---NNQLQNDRLFLYYLQNGKDMYTGEAL--D--INQLSSCDIDHI | 844 |
| WP_049549711 | 777 | QQRYKRIEDSLK | ILAS | NILKENP--TD---NNQLQNDRLFLYYLQNGKDMYTGEAL--D--INQLSSYDIDHI | 844 |
| WP_007896501 | 781 | RQRLKKIKEVHK | KTGS | RILEDNSerIT-----NLTLQDNRLYLYLLQDGKDMYTGQDL--D--INNLSQYDIDHI | 846 |
| EFR44625 | 733 | RQRLKKIKEVHK | KTGS | RILEDNSerIT-----NLTLQDNRLFLYLYLLQDGKDMYTGQDL--D--INQLSSYDIDHI | 798 |
| WP_002897477 | 776 | QQRYKRIEDALK | NLAP | NILKENP--TD---NIQLQNDRLFLYYLQNGRDMYTGKPL--D--INQLSSYDIDHI | 843 |
| WP_002906454 | 776 | QQRYKRIEDALK | NLAP | NILKENP--TD---NIQLQNDRLFLYYLQNGKDMYTGKAI--D--INQLSNYDIDHI | 843 |
| WP_009729476 | 777 | QQRYKRIEDSLK | ILAS | KILKEHP--TD---NIQLQNDRLFLYYLQNGKDMYTGEAL--D--INQLSCCDIDHI | 844 |
| CQR24647 | 780 | QQRLGSLTKAIQ | DFGS | DILKRYP--VE---NNQLQNDQLYLYLQNGKDMYTGDTL--D--IHNLSQYDIDHI | 843 |
| WP_000066813 | 779 | QQRYKRIEDSLK | NLAS | NILKEHP--TD---NIQLQNDRLFLYYLQNGRDMYTGKPL--E--INQLSNYDIDHI | 846 |
| WP_009754323 | 777 | QQRYKRIEDALK | NLAP | TISKENP--TD---NIQLQNDRLFLYYLQNGKDMYTGEAL--D--INQLSSYDIDHI | 844 |
| WP_044674937 | 776 | QQRYKKIENAIK | NLNS | KILKEYP--TN---NQALQNDRLFLYFLQNGKDMYTDEEL--D--IDQLSQYDIDHI | 843 |
| WP_044676715 | 778 | QQRYKKIENAIK | NLNS | KILKEYP--TN---NQALQNDRLFLYYLQNGKDMYTDEEL--D--IDQLSQYDIDHI | 845 |
| WP_044680361 | 778 | QQRYKKIENAIK | NLNS | KILKEYP--TN---NQALQNDRLFLYYLQNGKDMYTDEEL--D--IDQLSQYDIDHI | 845 |
| WP_044681799 | 776 | QQRYKKIENAIK | NLNS | KILKEYP--TN---NQALQNDRLFLYIQNGKDMYTGETL--D--IDQLSQYDIDHI | 843 |
| WP_049533112 | 778 | QQRLKLLQDSLK | PVNI | K-----N--VE---NQQLQNDRLFLYYLQNGKDMYTGEHL--D--INNLSQYDIDHI | 840 |
| WP_029090905 | 753 | TPRDKFIEKAYA | ETDT | EHLKELK---Qr--SKQLSSQRLFLYFIQNGKCMYSGEHL--D--IERLDSYEVDHI | 823 |
| WP_006506696 | 777 | ESKIKKLENVYK | DEQT | SVLEELKg-FDn--TKKISSDSLFLYFTQLGKCMYSGKKL--D--IDSLDKYQIDHI | 849 |
| AIT42264 | 778 | RERMKRIEEGIK | ELGS | QILKEHP--VE---NTQLQNEKLYLYLQNGRDMVDQEL--D--INRLSDYDVDHI | 841 |
| WP_034440723 | 785 | KARLKKIQEGLE | NLDS | HVEKQAL---D----EEMLKSPKYYLVCLQNGKDIYTGKDL--D--IGQLQTYDIDHI | 848 |
| AKQ21048 | 778 | RERMKRIEEGIK | ELGS | QILKEHP--VE---NTQLQNEKLYLYLQNGRDMVDQEL--D--INRLSDYDVDHI | 841 |

-continued

| | | | | | |
|---|---|---|---|---|---|
| WP_004636532 | 781 | KERLEKLTEAIK | EFDG | --VKVKD--LK----NENLRNDRLYYLQNGRDMYTNEPL--D--INNLSKYDIDHI | 845 |
| WP_002364836 | 789 | IQRLKIVEKAMA | EIGS | NLLKEQP--TT----NEQLRDTRLFLYYMQNGKDMYTGDEL--S--LHRLSHYDIDHI | 852 |
| WP_016631044 | 740 | IQRLKIVEKAMA | EIGS | NLLKEQP--TT----NEQLRDTRLFLYYMQNGKDMYTGDEL--S--LHRLSHYDIDHI | 803 |
| EMS75795 | 525 | KPRLKALEEALK | SFDS | PLLKEQP--VD----NQALQKDRLYLYLQNGKDMYTGDEL--D--IDRLSEYDIDHI | 588 |
| WP_002373311 | 789 | IQRLKIVEKAMA | EIGS | NLLKEQP--TT----NEQLRDTRLFLYYMQNGKDMYTGDEL--S--LHRLSHYDIDHI | 852 |
| WP_002378009 | 789 | IQRLKIVEKAMA | EIGS | NLLKEQP--TT----NEQLRDTRLFLYYMQNGKDMYTGDEL--S--LHRLSHYDIDHI | 852 |
| WP_002407324 | 789 | IQRLKIVEKAMA | EIGS | NLLKEQP--TT----NEQLRDTRLFLYYMQNGKDMYTGDEL--S--LHRLSHYDIDHI | 852 |
| WP_002413717 | 789 | IQRLKIVEKAMA | EIGS | NLLKEQP--TT----NEQLRDTRLFLYYMQNGKDMYTGDEL--S--LHRLSHYDIDHI | 852 |
| WP_010775580 | 791 | IQRLKIVEKAMA | EIGS | NLLKEQP--TT----NEQLRDTRLFLYYMQNGKDMYTGDEL--S--LHRLSHYDIDHI | 854 |
| WP_010818269 | 789 | IQRLKIVEKAMA | EIGS | NLLKEQP--TT----NEQLRDTRLFLYYMQNGKDMYTGDEL--S--LHRLSHYDIDHI | 852 |
| WP_010824395 | 789 | IQRLKIVEKAMA | EIGS | NLLKEQP--TT----NEQLRDTRLFLYYMQNGKDMYTGDEL--S--LHRLSHYDIDHI | 852 |
| WP_016622645 | 789 | IQRLKIVEKAMA | EIGS | NLLKEQP--TT----NEQLRDTRLFLYYMQNGKDMYTGDEL--S--LHRLSHYDIDHI | 852 |
| WP_033624816 | 789 | IQRLKIVEKAMA | EIGS | NLLKEQP--TT----NEQLRDTRLFLYYMQNGKDMYTGDEL--S--LHRLSHYDIDHI | 852 |
| WP_033625576 | 789 | IQRLKIVEKAMA | EIGS | NLLKEQP--TT----NEQLRDTRLFLYYMQNGKDMYTGDEL--S--LHRLSHYDIDHI | 852 |
| WP_033789179 | 789 | IQRLKIVEKAMA | EIGS | NLLKEQP--TT----NEQLRDTRLFLYYMQNGKDMYTGDEL--S--LHRLSHYDIDHI | 852 |
| WP_002310644 | 789 | RPRLKALEESLK | DFGS | QLLKEYP--TD----NSSLQKDRLYLYLYLQNGRDMYTGAPL--D--IHRLSDYDIDHI | 852 |
| WP_002312694 | 790 | RPRLKALEESLK | DFGS | QLLKEYP--TD----NSSLQKDRLYLYLYLQNGRDMYTGAPL--D--IHRLSDYDIDHI | 853 |
| WP_002314015 | 790 | RPRLKALEESLK | DFGS | QLLKEYP--TD----NSSLQKDRLYLYLYLQNGRDMYTGAPL--D--IHRLSDYDIDHI | 853 |
| WP_002320716 | 790 | RPRLKALEESLK | DFGS | QLLKEYP--TD----NSSLQKDRLYLYLYLQNGRDMYTGAPL--D--IHRLSDYDIDHI | 853 |
| WP_002330729 | 789 | RPRLKALEESLK | DFGS | QLLKEYP--TD----NSSLQKDRLYLYLYLQNGRDMYTGAPL--D--IHRLSDYDIDHI | 852 |
| WP_002335161 | 790 | RPRLKALEESLK | DFGS | QLLKEYP--TD----NSSLQKDRLYLYLYLQNGRDMYTGAPL--D--IHRLSDYDIDHI | 853 |
| WP_002345439 | 790 | RPRLKALEESLK | DFGS | QLLKEYP--TD----NSSLQKDRLYLYLYLQNGRDMYTGAPL--D--IHRLSDYDIDHI | 853 |
| WP_034867970 | 781 | SPRLKALENGLK | QIGS | TLLKEQP--TD----NKALQKERLYLYLYLQNGRDMYTGEPL--E--IENLHQYEVDHI | 844 |
| WP_047937432 | 790 | RPRLKALEESLK | DFGS | QLLKEYP--TD----NSSLQKDRLYLYLYLQNGRDMYTGAPL--D--IHRLSDYDIDHI | 853 |
| WP_010720994 | 781 | KPRLKALENGLK | QIGS | TLLKEQP--TD----NKALQKERLYLYLYLQNGRDMYTGEPL--E--IENLHQYEVDHI | 844 |
| WP_010737004 | 781 | SPRLKALENGLK | QIGS | TLLKEQP--TD----NKALQKERLYLYLYLQNGRDMYTGEPL--E--IENLHQYEVDHI | 844 |
| WP_034700478 | 781 | KPRLKALENGLK | QIGS | TLLKEQP--TD----NKALQKERLYLYLYLQNGRDMYTGEPL--E--IENLHQYEVDHI | 844 |

-continued

| | | | | | |
|---|---|---|---|---|---|
| WP_007209003 | 782 | KPRLKGIENGLK | EFSD | SVLKGSS--ID---NKQLQNDRLYLYLQNGKDMYTGHEL--D--IDHLSTYDIDHI | 845 |
| WP_023519017 | 775 | RPRLKALEEALK | NIDS | PLLKDYP--TD---NQALQKDRLYLYLQNGKDMYTGEPL--E--IHRLSEYDIDHI | 838 |
| WP_010770040 | 782 | NPRMKALEEAMR | NLRS | NLLKEYP--TD---NQALQNDRLYLYLQNGKDMYTGLDL--S--LHNLSNYDIDHI | 845 |
| WP_048604708 | 779 | RPRLKNLEKAID | DLDS | EILKKHP--VD---NKALQKDRLYLYLQNGKDMYTNEEL--D--IHKLSTYDIDHI | 842 |
| WP_010750235 | 784 | KPRLKSLEEALK | NFDS | QLLKEHP--VD---NQSLQKDRLYLYLQNGKDMYTGESL--D--IDRLSEYDIDHI | 847 |
| AII16583 | 817 | RERMKRIEEGIK | ELGS | QILKEHP--VE---NTQLQNEKLYLYLQNGRDMVYDQEL--D--INRLSDYDVDHI | 880 |
| WP_029073316 | 789 | DSFVNQMLKLYK | DFED | EANKHLKg-EDa--KSKIRSERLKLYTQMGKCMYTGKSL--D--IDRLDTYQVDHI | 860 |
| WP_031589969 | 789 | DSFVNQMLKLYK | DFED | EANKHLKg-EDa--KSKIRSERLKLYTQMGKCMYTGKSL--D--IDRLDTYQVDHI | 860 |
| KDA45870 | 772 | EDRVQQIVKNLK | ELPK | ------P--S---NAELSDERKYLCLQNGRDMYTGAPL--D--YDHLQFYDVDHI | 833 |
| WP_039099354 | 789 | KRQVEQVYQNIS | EL-- | EIRNELK--D1-sNSALSNTRLFLYFMQGGRDMYTGDSL--N--IDRLSTYDIDHI | 856 |
| AKP02966 | 786 | RLQSKLLNKANG | -LVP | EELKKHKn-D----LSSERIMLYFLQNGKSLIYSEESL--N--INKLSDYQVDHI | 858 |
| WP_010991369 | 781 | RPRYKSLEKAIK | EFGS | QILKEHP--TD---NQELRNNRLYLYLQNGKDMYTGQDL--D--IHNLSNYDIDHI | 844 |
| WP_033838504 | 781 | RPRYKSLEKAIK | EFGS | QILKEHP--TD---NQELRNNRLYLYLQNGKDMYTGQDL--D--IHNLSNYDIDHI | 844 |
| EHN60060 | 784 | RPRYKSLEKAIK | EFGS | QILKEHP--TD---NQELRNNRLYLYLQNGKDMYTGQDL--D--IHNLSNYDIDHI | 847 |
| EFR89594 | 550 | RPRYKSLEKAIK | EFGS | QILKEHP--TD---NQELRNNRLYLYLQNGKDMYTGQDL--D--IHNLSNYDIDHI | 613 |
| WP_038409211 | 781 | KPRFISLEKAIK | EFGS | QILKEHP--TD---NQCLKNDRLYLYLQNGKDMYTGKEL--D--IHNLSNYDIDHI | 844 |
| EFR95520 | 400 | KPRFISLEKAIK | EFGS | QILKEHP--TD---NQCLKNDRLYLYLQNGKDMYTGKEL--D--IHNLSNYDIDHI | 463 |
| WP_003723650 | 781 | KPRYKSLEKAIK | EFGS | QILKEHP--TD---NQELKNNRLYLYLQNGKDMYTGQEL--D--IHNLSNYDIDHI | 844 |
| WP_003727705 | 781 | KPRYKSLEKAIK | DEGS | QILKEHP--TD---NQELKNNRLYLYLQNGKDIYTGQEL--D--IHNLSNYDIDHI | 844 |
| WP_003730785 | 784 | KPRYKSLEKAIK | DEGS | QILKEHP--TD---NQELKNNRLYLYLQNGKDMYTGQEL--D--IHNLSNYDIDHI | 847 |
| WP_003733029 | 781 | RPRYKSLEKAIK | EFGS | QILKEHP--TD---NQELRNNRLYLYLQNGKDMYTGQEL--D--IHNLSNYDIDHI | 844 |
| WP_003739838 | 781 | KPRYKSLEKAIK | EFGS | QILKEHP--TD---NQELKNNRLYLYLQNGKDMYTGQEL--D--IHNLSNYDIDHI | 844 |
| WP_014601172 | 781 | KPRYKSLEKAIK | EFGS | KILKEHP--TD---NQELKNNRLYLYLQNGKDMYTGQEL--D--IHNLSNYDIDHI | 844 |
| WP_023548323 | 781 | KPRYKSLEKAIK | EFGS | QILKEHP--TD---NQELKNNRLYLYLQNGKDMYTGQEL--D--IHNLSNYDIDHI | 844 |
| WP_031665337 | 781 | KPRYKSLEKAIK | EFGS | QILKEHP--TD---NQELKNNRLYLYLQNGKDMYTGQEL--D--IHNLSNYDIDHI | 844 |
| WP_031669209 | 781 | KPRYKSLEKAIK | EFGS | QILKEHP--TD---NQELKNNRLYLYLQNGKDMYTGQEL--D--IHNLSNYDIDHI | 844 |
| WP_033920898 | 781 | KPRYKSLEKAIK | EFGS | QILKEHP--TD---NQELKNNRLYLYLQNGKDMYTGQEL--D--IHNLSNYDIDHI | 844 |

```
AKI42028       784  KPRYKSLEKAIK   EFGS   KILKEHP--TD---NQELKNNRLYLYYLQNGKDMYTGQEL--D--IHNLSNVDIDHI                                      847
AKI50529       784  KPRYKSLEKAIK   EFGS   QILKEHP--TD---NQELKNNRLYLYYLQNGKDMYTGQEL--D--IHNLSNVDIDHI                                      847
EFR83390       229  RPRYKSLEKAIK   EFGS   QILKEHP--TD---NQGLKNDRLYLYYLQNGKDIYTGQEL--D--IHNLSNVDIDHV                                      292
WP_046323366   781  KPRFTSLEKAIK   ELGS   QILKEHP--TD---NQGLKNDRLYLYYLQNGKDMYTGQEL--D--IHNLSNVDIDHV                                      844
AKE81011       794  RERMKRIEEGIK   ELGS   QILKEHP--VE---NTQLQNEKLYLYLYLQNGRDMVDQEL--D--INRLSDYDVDHI                                      857
CUO82355       781  ESKIKKLENVYK   DEQT   SVLEELKg-FDn--TKKISSDSLFLYFTQLGKCMYSGKKL--D--IDSLDKYQIDHI                                      853
WP_033162887   784  ESKIAKLQKIYE   NLQT   QVYESLKk-EDa--KKRMETDALYLYLYLQMGKSMYSGKPL--D--IDKLSTYQIDHI                                      855
AGZ01981       811  RERMKRIEEGIK   ELGS   QILKEHP--VE---NTQLQNEKLYLYLYLQNGRDMVDQEL--D--INRLSDYDVDHI                                      874
AKA60242       778  RERMKRIEEGIK   ELGS   QILKEHP--VE---NTQLQNEKLYLYLYLQNGRDMVDQEL--D--INRLSDYDVDAI                                      841
AKS40380       778  RERMKRIEEGIK   ELGS   QILKEHP--VE---NTQLQNEKLYLYLYLQNGRDMVDQEL--D--INRLSDYDVDHI                                      841
4UN5_B         782  RERMKRIEEGIK   ELGS   QILKEHP--VE---NTQLQNEKLYLYLYLQNGRDMVDQEL--D--INRLSDYDVDAI                                      845
WP_010922251   842  VPQSFLKDDSIDNKVLTRSDKNRG-KSDN--VP   S--EEVVKKMKN--YWRQLLNAKLITQRKFPDNLTKA--ERGGLSE                                910
WP_039695303   852  IPQAFIKDDSIDNRVLTSSAKNRG-KSDD--VP   S--LDIVRARKA-EWVRLYKSGLISKRKFDNLTKA--ERGGLTE                                 920
WP_045635197   844  IPQAFIKDDSLDNRVLTSSKDNRG-KSDN--VP   S--IEVVQKRKA-FWQQLLDSKLISERKFNNLTKA--ERGGLDE                                 912
5AXW_A         562  IPRSVSFDNSFNNKVLVKQBEASK-KGNR--TP   FQy-LSSSDSKI-SYETFKKHILNLAKGKGRISKTk-KEYLLEE                                 632
WP_099880683   526  VPQSFLKDDSIDNKVLTRSDKNRG-KSDN--VP   S--EEVVKKMKN--YWKQLLNAKLITQRKFPDNLTKA--ERGGLSE                                594
WP_010922251   842  VPQSFLKDDSIDNKVLTRSDKNRG-KSDN--VP   S--EEVVKKMKN--YWRQLLNAKLITQRKFPDNLTKA--ERGGLSE                                910
WP_011054416   842  VPQSFLKDDSIDNKVLTRSDKNRG-KSDN--VP   S--EEVVKKMKN--YWRQLLNAKLITQRKFPDNLTKA--ERGGLSE                                910
WP_011284745   842  VPQSFLKDDSIDNKVLTRSDKNRG-KSDN--VP   S--EEVVKKMKN--YWRQLLNAKLITQRKFPDNLTKA--ERGGLSE                                910
WP_011285506   842  VPQSFLKDDSIDNKVLTRSDKNRG-KSDN--VP   S--EEVVKKMKN--YWRQLLNAKLITQRKFPDNLTKA--ERGGLSE                                910
WP_011527619   842  VPQSFLKDDSIDNKVLTRSDKNRG-KSDN--VP   S--EEVVKKMKN--YWRQLLNAKLITQRKFPDNLTKA--ERGGLSE                                910
WP_012560673   842  VPQSFLKDDSIDNKVLTRSDKNRG-KSDN--VP   S--EEVVKKMKN--YWRQLLNAKLITQRKFPDNLTKA--ERGGLSE                                910
WP_014407541   841  VPQSFLKDDSIDNKVLTRSDKNRG-KSDN--VP   S--EEVVKKMKN--YWRQLLNAKLITQRKFPDNLTKA--ERGGLSE                                909
WP_020905136   842  VPQSFLKDDSIDNKVLTRSDKNRG-KSDN--VP   S--EEVVKKMKN--YWRQLLNAKLITQRKFPDNLTKA--ERGGLSE                                910
WP_023080005   841  VPQSFLKDDSIDNKVLTRSDKNRG-KSDN--VP   S--EEVVKKMKN--YWRQLLNAKLITQRKFPDNLTKA--ERGGLSE                                909
WP_023610282   841  VPQSFLKDDSIDNKVLTRSDKNRG-KSDN--VP   S--EEVVKKMKN--YWRQLLNAKLITQRKFPDNLTKA--ERGGLSE                                909
WP_030125963   842  VPQSFLKDDSIDNKVLTRSDKNRG-KSDN--VP   S--EEVVKKMKN--YWRQLLNAKLITQRKFPDNLTKA--ERGGLSE                                910
```

-continued

| | | | | |
|---|---|---|---|---|
| WP_030126706 | 842 | VPQSFLKDDSIDNKVLTRSDKNRG-KSDN--VP | S--EEVVKKMKN-YWRQLLNAKLITQRKFDNLTKA--ERGGLSE | 910 |
| WP_031488318 | 842 | VPQSFLKDDSIDNKVLTRSDKNRG-KSDN--VP | S--EEVVKKMKN-YWKQLLNAKLITQRKFPDNLTKA--ERGGLSE | 910 |
| WP_032460140 | 842 | VPQSFLKDDSIDNKVLTRSDKNRG-KSDN--VP | S--EEVVKKMKN-YWKQLLNAKLITQRKFPDNLTKA--ERGGLSE | 910 |
| WP_032461047 | 842 | VPQSFLKDDSIDNKVLTRSDKNRG-KSDN--VP | S--EEVVKKMKN-YWKQLLNAKLITQRKFPDNLTKA--ERGGLSE | 910 |
| WP_032462016 | 842 | VPQSFLKDDSIDNKVLTRSDKNRG-KSDN--VP | S--EEVVKKMKN-YWKQLLNAKLITQRKFPDNLTKA--ERGGLSE | 910 |
| WP_032462936 | 842 | VPQSFLKDDSIDNKVLTRSDKNRG-KSDN--VP | S--EEVVKKMKN-YWKQLLNAKLITQRKFPDNLTKA--ERGGLSE | 910 |
| WP_032464890 | 842 | VPQSFLKDDSIDNKVLTRSDKNRG-KSDN--VP | S--EEVVKKMKN-YWKQLLNAKLITQRKFPDNLTKA--ERGGLSE | 910 |
| WP_033888930 | 667 | VPQSFLKDDSIDNKVLTRSDKNRG-KSDN--VP | S--EEVVKKMKN-YWKQLLNAKLITQRKFPDNLTKA--ERGGLSE | 735 |
| WP_038431314 | 842 | VPQSFLKDDSIDNKVLTRSDKNRG-KSDN--VP | S--EEVVKKMKN-YWRQLLNAKLITQRKFPDNLTKA--ERGGLSE | 910 |
| WP_038432938 | 841 | VPQSFLKDDSIDNKVLTRSDKNRG-KSDN--VP | S--EEVVKKMKN-YWKQLLNAKLITQRKFPDNLTKA--ERGGLSE | 909 |
| WP_038434062 | 842 | VPQSFLKDDSIDNKVLTRSDKNRG-KSDN--VP | S--EEVVKKMKN-YWRQLLNAKLITQRKFPDNLTKA--ERGGLSE | 910 |
| BAQ51233 | 753 | VPQSFLKDDSIDNKVLTRSDKNRG-KSDN--VP | S--EEVVKKMKN-YWRQLLNAKLITQRKFPDNLTKA--ERGGLSE | 821 |
| KGE60162 | 17 | VPQSFLKDDSIDNKVLTRSDKNRG-KSDN--VP | S--EEVVKKMKN-YWRQLLNAKLITQRKFPDNLTKA--ERGGLSE | 85 |
| KGE60856 | | ---------------------------- | ---------------------------------- | |
| WP_002989955 | 842 | VPQSFIKDDSIDNKVLTRSDKNRG-KSDN--VP | S--EEVVKKMKN-YWRQLLNAKLITQRKFDNLTKA--ERGGLSE | 910 |
| WP_003030002 | 841 | IPQAFIKDDSIDNSLDNRVLTRSSAKNRG-KSDD--VP | S--IEVVHEMKS-FWSKLLSVKLITQRKFPDNLTKA--ERGGLTE | 909 |
| WP_003065552 | 852 | IPQAFIKDDSIDNRVLTSSAKNRG-KSDD--VP | S--LDIVRARKA-EWVRLYKSGLISKRKFPDNLTKA--ERGGLTE | 920 |
| WP_001040076 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040078 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040080 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040081 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040083 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040085 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040087 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040088 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040089 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040090 | 847 | IPQAFIKDDSIDNRVLVSSAKNRG-KSDD--VP | S--LEIVKDCKV-FWKKLLDAKLMSQRKYDNLTKA--ERGGLTS | 915 |

-continued

| | | | | |
|---|---|---|---|---|
| WP_001040091 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040092 | 847 | VPQAFIKDDSIDNRVLVSSAKNRG-KSDD--VP | S--IDIVKARKA-FWKKLLDAKLISQRKYDNLTKA--ERGGLTP | 915 |
| WP_001040094 | 847 | IPQAFIKDDSIDNRVLVSSAKNRG-KSDD--VP | S--VEIVKDCKV-FWKKLLDAKLMSQRKYDNLTKA--ERGGLTS | 915 |
| WP_001040095 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040096 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040097 | 847 | IPQAFIKDDSIDNRVLVSSAKNRG-KSDD--VP | S--VEIVKDCKV-FWKKLLDAKLMSQRKYDNLTKA--ERGGLTS | 915 |
| WP_001040098 | 847 | IPQAFIKDDSIDNRVLVSSAKNRG-KSDD--VP | S--VEIVKDCKV-FWKKLLDAKLMSQRKYDNLTKA--ERGGLTS | 915 |
| WP_001040099 | 847 | IPQAFIKDDSIDNRVLVSSAKNRG-KSDD--VP | S--VEIVKDCKV-FWKKLLDAKLMSQRKYDNLTKA--ERGGLTS | 915 |
| WP_001040100 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040104 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_001040105 | 847 | VPQAFIKDDSIDNRVLVSSAKNRG-KSDN--VP | S--IDIVKARKA-FWKKLLDAKLMSQRKYDNLTKA--ERGGLTS | 915 |
| WP_001040106 | 847 | VPQAFIKDDSIDNRVLVSSAKNRG-KSDN--VP | S--IDIVKARKA-FWKKLLDAKLMSQRKYDNLTKA--ERGGLTS | 915 |
| WP_001040107 | 847 | VPQAFIKDDSIDNRVLVSSAKNRG-KSDN--VP | S--IDIVKARKA-FWKKLLDAKLMSQRKYDNLTKA--ERGGLTS | 915 |
| WP_001040108 | 847 | VPQAFIKDDSIDNRVLVSSAKNRG-KSDD--VP | S--IDIVKARKA-FWKKLLDAKLMSQRKYDNLTKA--ERGGLTS | 915 |
| WP_001040109 | 847 | IPQAFIKDDSIDNRVLVSSAKNRG-KSDD--VP | S--IDIVKARKA-FWKKLLDAKLMSQRKYDNLTKA--ERGGLTS | 915 |
| WP_001040110 | 847 | VPQAFIKDDSIDNRVLVSSAKNRG-KSDN--VP | S--IDIVKARKA-FWKKLLDAKLMSQRKYDNLTKA--ERGGLTP | 915 |
| WP_015058523 | 847 | VPQAFIKDDSIDNRVLVSSAKNRG-KSDD--VP | S--VEIVKDCKV-FWKKLLDAKLMSQRKYDNLTKA--ERGGLTS | 915 |
| WP_017643650 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_017647151 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_017648376 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_017649527 | 847 | VPQAFIKDDSIDNRVLVSSAKNRG-KSDN--VP | S--IDIVKARKA-FWKKLLDAKLMSQRKYDNLTKA--ERGGLTS | 915 |
| WP_017771611 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_017771984 | 847 | IPQAFIKDDSIDNRVLVSSAKNRG-KSDD--VP | S--LEIVKDCKV-FWKKLLDAKLMSQRKYDNLTKA--ERGGLTS | 915 |
| CFQ25032 | 847 | IPQAFIKDDSIDNRVLVSSAKNRG-KSDD--VP | S--LEIVKDCKV-FWKKLLDAKLMSQRKYDNLTKA--ERGGLTS | 915 |
| CFV16040 | 847 | IPQAFIKDDSIDNRVLVSSAKNRG-KSDD--VP | S--LEIVKDCKV-FWKKLLDAKLMSQRKYDNLTKA--ERGGLTS | 915 |
| KLJ37842 | 847 | IPQAFIKDDSIDNRVLVSSAKNRG-KSDD--VP | S--LEIVKDCKV-FWKKLLDAKLMSQRKYDNLTKA--ERGGLTS | 915 |
| KLJ72361 | 847 | IPQAFIKDDSIDNRVLVSSAKNRG-KSDD--VP | S--LEIVKDCKV-FWKKLLDAKLMSQRKYDNLTKA--ERGGLTS | 915 |

-continued

| | | | | | |
|---|---|---|---|---|---|
| KLL20707 | 861 | IPQAFIKDDSIDNRVLVSSAKNRG-KSDD--VP | S--LEIVKDCKV-FWKKLLDAKLMSQRKYDNLTKA--ERGGLTS | 929 |
| KLL42645 | 847 | VPQAFIKDDSIDNRVLVSSAKNRG-KSDN--VP | S--IDIVKARKA-FWKKLLDAKLMSQRKYDNLTKA--ERGGLTS | 915 |
| WP_047207273 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_047209694 | 847 | IPQAFIKDDSIDNRVLVSSAKNRG-KSDD--VP | S--VEIVKDCKV-FWKKLLDAKLMSQRKYDNLTKA--ERGGLTS | 915 |
| WP_050198062 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_050201642 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_050204027 | 847 | VPQAFIKDDSIDNRVLVSSAKNRG-KSDN--VP | S--IDIVKARKA-FWKKLLDAKLMSQRKYDNLTKA--ERGGLTS | 915 |
| WP_050881965 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_050886065 | 847 | IPQAFIKDDSIDNRVLVSSAKNRG-KSDD--VP | S--LEIVKDCKV-FWKKLLDAKLMSQRKYDNLTKA--ERGGLTS | 915 |
| AHN30376 | 847 | VPQAFIKDDSIDNRVLVSSAKNRG-KSDD--VP | S--IDIVKARKA-FWKKLLDAKLISQRKYDNLTKA--ERGGLTP | 915 |
| EAO78426 | 847 | IPQAFIKDDSIDNRVLVSSAKNRG-KSDD--VP | S--LEIVKDCKV-FWKKLLDAKLMSQRKYDNLTKA--ERGGLTS | 915 |
| CCW42055 | 847 | IPQAFIKDDSIDNRVLVSSAKNRG-KSDD--VP | S--LEIVKDCKV-FWKKLLDAKLMSQRKYDNLTKA--ERGGLTS | 915 |
| WP_003041502 | 841 | IPQAYIKDDSFDNRVLTSSENRG-KSDN--VP | S--IEVVCARKA-DWMRLRKAGLISQRKFDNLTKA--ERGGLTE | 909 |
| WP_037593752 | 842 | IPQAFIKDNSLDNRVLTRSDKNRG-KSDD--VP | S--IEVVHEMKS-FWSKLLSVKLITQRKFDNLTKA--ERGGLTE | 910 |
| WP_049516684 | 842 | IPQAFIKDNSLDNRVLTRSDKNRG-KSDD--VP | S--IEVVHEMKS-FWSKLLSVKLITQRKFDNLTKA--ERGGLTE | 910 |
| GAD46167 | 841 | IPQAFIKDDSIDNRVLTRSDKNRG-KSDD--VP | S--IEVVHEMKS-FWSKLLSVKLITQRKFDNLTKA--ERGGLTE | 909 |
| WP_018363470 | 850 | IPQAFIKDDSIDNRVLTSSAKNRG-KSDD--VP | S--LGIVRARKA-EWVRLYKSGLISKRKFDNLTKA--ERGGLTE | 918 |
| WP_003043819 | 851 | VPQSFIKDDSIDNRVLTRSVENRG-KSDN--VP | S--EEVVKKMKN-YWRQLLNAKLITQRKFDNLTKA--ERGGLSE | 919 |
| WP_006269658 | 841 | IPQAFIKDNSLDNRVLTRSDKNRG-KSDD--VP | S--IEVVHEMKS-FWSKLLSVKLITQRKFDNLTKA--ERGGLTE | 909 |
| WP_048800889 | 841 | IPQAFIKDDSIDNRVLTRSSAKNRG-KSDD--VP | N--LEVVCDRKA-DWIRLREAGLISQRKFDNLTKA--ERGGLTE | 909 |
| WP_012767106 | 841 | VPQSFIKDDSIDNKILTRSDKNRG-KSDD--VP | S--EEVVKKMKN-YWRQLLNAKLITQRKFDNLTKA--ERGGLSE | 909 |
| WP_014612333 | 841 | VPQSFIKDDSIDNKVLTRSDKNRG-KSDD--VP | S--EEVVKKMKN-YWRQLLNAKLITQRKFDNLTKA--ERGGLSE | 909 |
| WP_015017095 | 841 | VPQSFIKDDSIDNKVLTRSDKNRG-KSDD--VP | S--EEVVKKMKN-YWRQLLNAKLITQRKFDNLTKA--ERGGLSE | 909 |
| WP_015057649 | 841 | VPQSFIKDDSIDNKVLTRSDKNRG-KSDD--VP | S--EEVVKKMKN-YWRQLLNAKLITQRKFDNLTKA--ERGGLSE | 909 |
| WP_048327215 | 841 | VPQSFIKDDSIDNKVLTRSDKNRG-KSDD--VP | S--EEVVKKMKN-YWRQLLNAKLITQRKFDNLTKA--ERGGLSE | 909 |
| WP_049519324 | 841 | VPQSFIKDDSIDNKVLTRSDKNRG-KSDN--VP | S--EEVVKKMKN-YWRQLLNAKLITQRKFDNLTKA--ERGGLSE | 909 |
| WP_012515931 | 841 | IPQSFIKNNSIDNKVLTSQGANRG-KLDN--VP | S--EAIVRKMKG-YWQSLLRAGAISKQKFDNLTKA--ERGGLTQ | 909 |

-continued

| ID | | | | |
|---|---|---|---|---|
| WP_021329964 | 841 | IPQSFIKNNSIDNKVLTSQGANRG-KLDN--VP | S--EAIVRKMKG-YWQSLLRAGAISKQKFDNLTKA--ERGGLTQ | 909 |
| WP_037581760 | 841 | IPQSFIKNNSIDNKVLTSQGANRG-KLDN--VP | S--EAIVRKMKG-YWQSLLRAGAISKQKFDNLTKA--ERGGLTQ | 909 |
| WP_004232481 | 849 | IPQAFIKDNSIDNRVLTSSAKNRG-KSDD--VP | S--IEIVRNRKS-YWYKLLSKRKFDNLTKA--ERGGLTE | 917 |
| WP_009854540 | 850 | IPQAFIKDSIDNRVLTSSAKNRG-KSDD--VP | S--LDIVRARKA-EWVRLYKSGLISKRKFDNLTKA--ERGGLTE | 918 |
| WP_012962174 | 850 | IPQAFIKDSIDNRVLTSSAKNRG-KSDD--VP | S--LDIVHDRKA-DWIRLYKSGLISKRKFDNLTKA--ERGGLTE | 918 |
| WP_039695303 | 852 | IPQAFIKDSIDNRVLTSSAKNRG-KSDD--VP | S--LDIVRARKA-EWVRLYKSGLISKRKFDNLTKA--ERGGLTE | 920 |
| WP_014334983 | 849 | IPQAFIKDNSIDNKVLTSSAKNRG-KSDD--VP | S--IEIVRNRRS-YWYKLYKSGLISKRKFDNLTKA--ERGGLTE | 917 |
| WP_003099269 | 842 | IPQSFIKDNSIDNTVLTTQASNRG-KSDN--VP | N--IETVNKMKS-FWYKQLKSGAISQRKFDHLTKA--ERGALSD | 910 |
| AHY15608 | 842 | IPQSFIKDNSIDNTVLTTQASNRG-KSDN--VP | N--IETVNKMKS-FWYKQLKSGAISQRKFDHLTKA--ERGALSD | 910 |
| AHY17476 | 842 | IPQSFIKDNSIDNTVLTTQASNRG-KSDN--VP | N--IETVNKMKS-FWYKQLKSGAISQRKFDHLTKA--ERGALSD | 910 |
| ESR09100 | | | | |
| AGM98575 | 842 | IPQSFIKDNSIDNTVLTTQASNRG-KSDD--VP | N--IETVNKMKS-FWYKQLKSGAISQRKFDHLTKA--ERGALSD | 910 |
| ALF27331 | 842 | IPQAFIKDNSIDNRVLTSSKENRG-KSDD--VP | S--KDVVRKMKS-YWSKLLSAKLITQRKFDNLTKA--ERGGLTD | 910 |
| WP_018372492 | 858 | VPRSYIKNDSEDNKVLTSKGNRK-KLDD--VP | A--KEVVEKMEN-TWRRLHAAGLISDIKLSYLMKGe----LTE | 923 |
| WP_045618028 | 845 | IPQAFIKDDSLDNRVLTSSKDNRG-KSDN--VP | S--LEIVQKRKA-FWQQLLDSKLISERKFPNNLTKA--ERGGLDE | 913 |
| WP_045635197 | 844 | IPQAFIKDDSLDNRVLTSSKDNRG-KSDN--VP | S--IEVVQKRKA-FWQQLLDSKLISERKFPNNLTKA--ERGGLDE | 912 |
| WP_002263549 | 842 | IPQAFIKDNSIDNRVLTSSKENRG-KSDD--VP | S--KDVVRKMKS-YWSKLLSAKLITQRKFDNLTKA--ERGGLTD | 910 |
| WP_002263887 | 842 | IPQAFIKDNSIDNRVLTSSKENRG-KSDD--VP | S--KDVVRKMKS-YWSKLLSAKLITQRKFDNLTKA--ERGGLTD | 910 |
| WP_002264920 | 842 | IPQAFIKDNSIDNRVLTSSKENRG-KSDD--VP | S--KDVVRKMKS-YWSKLLSAKLITQRKFDNLTKG--ERGGLTD | 910 |
| WP_002269043 | 842 | IPQAFIKDNSIDNRVLTSSKENRG-KSDD--VP | S--KDVVRKMKP-YWSKLLSAKLITQRKFDNLTKA--ERGGLTD | 910 |
| WP_002269448 | 842 | IPQAFIKDNSIDNRVLTSSKENRG-KSDD--VP | S--KDVVRKMKP-YWSKLLSAKLITQRKFDNLTKA--ERGGLTD | 910 |
| WP_002271977 | 842 | IPQAFIKDNSIDNRVLTSSKENRG-KSDD--VP | S--KDVVRKMKS-YWSKLLSAKLITQRKFDNLTKA--ERGGLTD | 910 |
| WP_002272766 | 842 | IPQAFIKDNSIDNRVLTSSKENRG-KSDD--VP | S--KDVVRKMKP-YWSKLLSAKLITQRKFDNLTKA--ERGGLTD | 910 |
| WP_002273241 | 842 | IPQAFIKDNSIDNRVLTSSKENRG-KSDD--VP | S--KDVVRKMKP-YWSKLLSAKLITQRKFDNLTKA--ERGGLTD | 910 |
| WP_002275430 | 842 | IPQAFIKDNSIDNRVLTSSKENRG-KSDD--VP | S--KDVVRKMKS-YWSKLLSAKLITQRKFDNLTKA--ERGGLTD | 910 |
| WP_002276448 | 842 | IPQAFIKDNSIDNRVLTSSKANRG-KSDD--VP | S--KDVVRKMKS-YWSKLLSAKLITQRKFDNLTKA--ERGGLTD | 910 |
| WP_002277050 | 847 | IPQAFIKDNSIDNRVLTSSKANRG-KSDD--VP | S--EDVVNRMRP-FWNKLLSSGLISQRKYNNLTKK--E---LTP | 912 |

-continued

| | | | | |
|---|---|---|---|---|
| WP_002773364 | 842 | IPQAFIKDNSIDNRVLTSSKENRG-KSDD--VP | S--KNVVRKMKS-YWSKLLSAKLITQRKFDNLTKA--ERGGLTD | 910 |
| WP_002279025 | 842 | IPQAFIKDNSIDNRVLTSSKENRG-KSDD--VP | S--KDVVRKMKP-YWSKLLSAKLITQRKFDNLTKG--ERGGLTD | 910 |
| WP_002279859 | 842 | IPQAFIKDNSIDNRVLTSSKENRG-KSDD--VP | S--KDVVRKMKS-YWSKLLSAKLITQRKFDNLTKG--ERGGLTD | 910 |
| WP_002280230 | 842 | IPQAFIKDNSIDNRVLTSSKENRG-KSDD--VP | S--KDVVRKMKS-YWSKLLSAKLITQRKFDNLTKA--ERGGLTD | 910 |
| WP_002281696 | 842 | IPQAFIKDNSIDNRVLTSSKENRG-KSDD--VP | S--KNVVRKMKS-YWSKLLSAKLITQRKFDNLTKA--ERGGLTD | 910 |
| WP_002282247 | 847 | IPQAFIKDNSIDNRVLTSSKANRG-KSDD--VP | S--EDVVNRMRP-FWNKLLSSGLISQRKYNNLTKK--E---LTL | 912 |
| WP_002282906 | 842 | IPQAFIKDNSIDNRVLTSSKENRG-KSDD--VP | S--KDVVRKMKS-YWSKLLSAKLITQRKFDNLTKA--ERGGLTD | 910 |
| WP_002283846 | 842 | IPQAFIKDNSIDNRVLTSSKENRG-KSDD--VP | S--KNVVRKMKS-YWSKLLSAKLITQRKFDNLTKA--ERGGLTD | 910 |
| WP_002287255 | 842 | IPQAFIKDNSIDNRVLTSSKENRG-KSDD--VP | S--KNVVRKMKS-YWSKLLSAKLITQRKFDNLTKG--ERGGLTD | 910 |
| WP_002288990 | 842 | IPQAFIKDNSIDNRVLTSSKENRG-KSDD--VP | S--KDVVRKMKS-YWSKLLSAKLITQRKFDNLTKA--ERGGLTD | 910 |
| WP_002289641 | 842 | IPQAFIKDNSIDNRVLTSSKENRG-KSDD--VP | S--KDVVRKMKS-YWSKLLSAKLITQRKFDNLTKA--ERGGLTD | 910 |
| WP_002290427 | 842 | IPQAFIKDNSIDNRVLTSSKENRG-KSDD--VP | S--KDVVRKMKS-YWSKLLSAKLITQRKFDNLTKG--ERGGLTD | 910 |
| WP_002295753 | 842 | IPQAFIKDNSIDNRVLTSSKENRG-KSDD--VP | S--KDVVRKMKS-YWSKLLSAKLITQRKFDNLTKA--ERGGLTD | 910 |
| WP_002296423 | 842 | IPQAFIKDNSIDNRVLTSSKENRG-KSDD--VP | S--KNVVRKMKS-YWSKLLSAKLITQRKFDNLTKA--ERGGLTD | 910 |
| WP_002304487 | 856 | IPQAFIKDNSIDNRVLTRSDKNRG-KSDD--VP | S--EEVVHKMKP-FWSKLLSAKLITQRKFDNLTKA--ERGGLTD | 924 |
| WP_002305844 | 842 | IPQAFIKDNSIDNRVLTSSKENRG-KSDD--VP | S--KDVVRKMKS-YWSKLLSAKLITQRKFDNLTKA--ERGGLTD | 910 |
| WP_002307203 | 842 | IPQAFIKDNSIDNRVLTSSKENRG-KSDD--VP | S--KDVVRKMKS-YWSKLLSAKLITQRKFDNLTKG--ERGGLTD | 910 |
| WP_002310390 | 842 | IPQAFIKDNSIDNRVLTSSKENRG-KSDD--VP | S--KDVVRKMKS-YWSKLLSAKLITQRKFDNLTKA--ERGGLTD | 910 |
| WP_002352408 | 842 | IPQAFIKDNSIDNRVLTSSKENRG-KSDD--VP | S--KDVVRKMKS-YWSKLLSAKLITQRKFDNLTKA--ERGGLTD | 910 |
| WP_012997688 | 842 | IPQAFIKDNSIDNRVLTSSKENRG-KSDD--VP | S--KNVVRKMKS-YWSKLLSAKLITQRKFDNLTKA--ERGGLTD | 910 |
| WP_014677909 | 842 | IPQAFIKDNSIDNRVLTSSKENRG-KSDD--VP | S--KDVVRKMKS-YWSKLLSAKLITQRKFDNLTKA--ERGGLTD | 910 |
| WP_019312892 | 842 | IPQAFIKDNSIDNRVLTSSKENRG-KSDD--VP | S--KNVVRKMKS-YWSKLLSAKLITQRKFDNLTKA--ERGGLTD | 910 |
| WP_019313659 | 842 | IPQAFIKDNSIDNRVLTSSKENRG-KSDD--VP | S--KDVVRKMKS-YWSKLLSAKLITQRKFDNLTKA--ERGGLTD | 910 |
| WP_019314093 | 842 | IPQAFIKDNSIDNRVLTSSKENRG-KSDD--VP | S--KDVVRKMKS-YWSKLLSAKLITQRKFDNLTKA--ERGGLTD | 910 |
| WP_019315370 | 842 | IPQAFIKDNSIDNRVLTSSKENRG-KSDD--VP | S--KDVVRKMKP-YWSKLLSAKLITQRKFDNLTKA--ERGGLTD | 910 |
| WP_019803776 | 842 | IPQAFIKDNSIDNRVLTSSKENRG-KSDD--VP | S--KDVVRKMKS-YWSKLLSAKLITQRKFDNLTKA--ERGGLTD | 910 |
| WP_019805234 | 842 | IPQAFIKDNSIDNRVLTSSKENRG-KSDD--VP | S--KDVVRKMKS-YWSKLLSAKLITQRKFDNLTKG--ERGGLTD | 910 |

-continued

| ID | start | seq1 | seq2 | end |
|---|---|---|---|---|
| WP_024785594 | 842 | IPQAFIKDNSIDNRVLTSSKENRG-KSDD--VP | S--KDVVRKMKS-YWSKLLSAKLITQRKFDNLTKA--ERGGLTD | 910 |
| WP_024784288 | 847 | IPQAFIKDNSIDNRVLTSSKANRG-KSDD--VP | S--EDVVNRMRP-FWNKLLSSGLISQRKYNNLTKK--E---LTL | 912 |
| WP_024784666 | 842 | IPQAFIKDNSIDNRVLTSSKENRG-KSDD--VP | S--KNVVRKMKS-YWSKLLSAKLITQRKFDNLTKA--ERGGLTD | 910 |
| WP_024784894 | 842 | IPQAFIKDNSIDNRVLTSSKENRG-KSDD--VP | S--KDVVRKMKS-YWSKLLSAKLITQRKFDNLTKA--ERGGLTD | 910 |
| WP_024786433 | 847 | IPQAFIKDNSIDNRVLTSSKANRG-KSDD--VP | S--EDVVNRMRP-FWNKLLSSGLISQRKYNNLTKK--E---LTL | 912 |
| WP_049473442 | 842 | IPQAFIKDNSIDNRVLTSSKENRG-KSDD--VP | S--KDVVRKMKP-YWSKLLSAKLITQRKFDNLTKA--ERGGLTD | 910 |
| WP_049474547 | 842 | IPQAFIKDNSIDNRVLTSSKENRG-KSDD--VP | S--KDVVRKMKS-YWSKLLSAKLITQRKFDNLTKA--ERGGLTD | 910 |
| EMC03581 | 835 | IPQAFIKDNSIDNRVLTSSKENRG-KSDD--VP | S--KNVVRKMKS-YWSKLLSAKLITQRKFDNLTKA--ERGGLTD | 903 |
| WP_000428612 | 847 | VPQAFIKDDSLDNRVLTSLKDNRG-KSDN--VP | S--LEIVEKMKT-FWQQLLDSKLISYRKFNNLTKA--ERGGLDE | 915 |
| WP_000428613 | 845 | VPQAFIKDDSLDNRVLTSLKDNRG-KSDN--VP | S--IEVVQKRKA-FWQQLLDSKLISERKFNNLTKA--ERGGLDE | 913 |
| WP_049523028 | 840 | IPQAFIKDDSLDNRVLTSSKDNRG-KSDN--VP | S--LEIVEKMKG-FWQQLLDSKLISERKFNNLTKA--ERGGLDE | 908 |
| WP_003107102 | 811 | IPQSFIKDNSIDNIVLTSQESNRG-KSDN--VP | Y--IAIVNKMKS-YWQHQLKSGAISQRKFDNLTKA--ERGGLSE | 879 |
| WP_054279288 | 843 | IPRSFIKDDSIDNRVLTRSEHNRG-KTDN--VP | S--IEVVKRMKP-YWQKLLDTKVISQRKFDNLTKA--ERGGLQE | 911 |
| WP_049531101 | 845 | IPQAFIKDDSLDNRVLTSSKDNRG-KSDN--VP | S--LEVVQKRKA-FWQQLLESKLISERKFNNLTKA--ERGGLNE | 913 |
| WP_049538452 | 845 | IPQAFIKDDSLDNRVLTSSKDNRG-KSDN--VP | C--LEVVQKRKA-FWQQLLDFKLISYRKFNNLTKA--ERGGLDE | 913 |
| WP_049549711 | 845 | IPQAFIKDDSLDNRVLTSSKENRG-KSDN--VP | S--LEVVQKRKA-FWQQLLDSKLISERKFNNLTKAer-ERDGLNE | 915 |
| WP_007896501 | 847 | IPQSFIKDNSIDNLVLTTQKANRG-KSDN--VP | S--IEVVRDMKDrVWRRQLANGAISRQKFPDHLTKA--ERGGLAD | 916 |
| EFR44625 | 799 | IPQSFIKDNSIDNLVLTTQKANRG-KSDN--VP | S--IEVVRDMKDrVWRRQLANGAISRQKFPDHLTKA--ERGGLAD | 868 |
| WP_002897477 | 844 | IPQAFIKDDSIDNRVLTSSKDNRG-KSDN--VP | S--LEVVQKRKA-FWQQLLDSKLISERKFNNLTKA--ERGGLDE | 912 |
| WP_002906454 | 844 | IPQAFIKDDSLDNRVLTSSKDNRG-KSDN--VP | S--LEVVQKRKA-FWQQLLDSKLISERKFNNLTKA--KRGGLDE | 912 |
| WP_009729476 | 845 | IPQAFIKDDSLDNRVLTSSKDNRG-KSDN--VP | S--LEVVDKMKV-FWQQLLDSKLISYRKFNNLTKA--ERGGLNE | 913 |
| CQR24647 | 844 | IPQSFIKDNSLDNRVLTNSKSNRG-KSDN--VP | S--NEVVKRMKG-FWLKQLLDAKLISQRKFDNLTKA--ERGGLSA | 912 |
| WP_000666813 | 847 | IPQAFIKDDSLDNRVLTSSKDNRG-KSDN--VP | S--LEVVEKMKA-FWQQLLDSKLISERKFNNLTKAer-ERGGLNE | 917 |
| WP_009754323 | 845 | IPQAFIKDDSLDNRVLTSSKDNRG-KSDN--VP | S--LEVVKKRKA-FWQQLLDSKLISERKFNNLTKA--ERGGLDE | 913 |
| WP_044674937 | 844 | IPQAFIKDDSLDNKVLTKSAKNRG-KSDD--VP | S--LEIVHKKKN-FWKQLLDSQLISQRKFDNLTKA--ERGGLTN | 912 |
| WP_044676715 | 846 | IPQAFIKDDSLDNKVLTKSAKNRG-KSDD--VP | S--LEIVHKKKN-FWKQLLDSQLISQRKFDNLTKA--ERGGLTN | 914 |
| WP_044680361 | 846 | IPQAFIKDDSLDNKVLTKSAKNRG-KSDD--VP | S--LEIVHKKKN-FWKQLLDSQLISQRKFDNLTKA--ERGGLTN | 914 |

-continued

| ID | Start | Sequence | End |
|---|---|---|---|
| WP_044681799 | 844 | IPQAFIKDDSLDNKVLTKSAKNRG-KSDD--VP | S--LEIVHKKKN-FWKQLLDSQLISQRKFDNLTKA--ERGGLTN | 912 |
| WP_049533112 | 841 | IPQAFIKDDSEDNRVLTSSSENRG-KSDN--VP | S--IEVVRARKA-DWMRLRKAGLISQRKFPDNLTKA--ERGGLTE | 909 |
| WP_029090905 | 824 | LPQSYIKDNSIENILALVKKVENQR-KKDSllLN | S---SIINQNYS-RWEQLKNAGLIGEKKFRNLTRTk-----ITD | 890 |
| WP_006506696 | 850 | VPQSLVKDDSEDNRVLVVPSENQR-KLDDlvVP | ---FDIRDKMYR-FWKLLFDHELISPKKFYSLIKTe-----YTE | 916 |
| AIT42264 | 842 | VPQSFLKDDSIDNKVLTRSDKNRG-KSDN--VP | S--EEVVKKMKN-YWRQLNAKLITQRKFDNLTKA--ERGGLSE | 910 |
| WP_034440723 | 849 | IPRSFITDNSEDNLVLTSSTVNRG-KLDN--VP | Sp--DIVRQQKG-FWKQLLRAGLMSQRKFNNLTKGk-----LTD | 914 |
| AKQ21048 | 842 | VPQSFLKDDSIDNKVLTRSDKNRG-KSDN--VP | S--EEVVKKMKN-YWRQLNAKLITQRKFDNLTKA--ERGGLSE | 910 |
| WP_004636532 | 846 | IPQSFTTDNSIDNKVLVSRTKNQGnKSDD--VP | S--INIVHMKP-FWRQLHKAGLISDREKNLTKA--EHGGLTE | 915 |
| WP_002364836 | 853 | IPQSFMKDDSLDNLVLVGSTENRG-KSDD--VP | S--KEVVKDMKA-YWEKLYAAGLISQRKFQRLTKG--EQGGLTL | 921 |
| WP_016631044 | 804 | IPQSFMKDDSLDNLVLVGSTENRG-KSDD--VP | S--KEVVKDMKA-YWEKLYAAGLISQRKFQRLTKG--EQGGLTL | 872 |
| EMS75795 | 589 | IPRSFIVDNSIDNKVLVSSKENRL-KMDD--VP | D--QKVVIRMRR-YWEKLLRANLISERKFAYLTKLe-----LTP | 654 |
| WP_002373311 | 853 | IPQSFMKDDSLDNLVLVGSTENRG-KSDD--VP | S--KKVVKKMKA-YWEKLYAAGLISQRKFQRLTKG--EQGGLTL | 921 |
| WP_002378009 | 853 | IPQSFMKDDSLDNLVLVGSTENRG-KSDD--VP | S--KEVVKDMKA-YWEKLYAAGLISQRKFQRLTKG--EQGGLTL | 921 |
| WP_002407324 | 853 | IPQSFMKDDSLDNLVLVGSTENRG-KSDD--VP | S--KEVVKDMKA-YWEKLYAAGLISQRKFQRLTKG--EQGGLTL | 921 |
| WP_002413717 | 855 | IPQSFMKDDSLDNLVLVGSTENRG-KSDD--VP | S--KEVVKDMKA-YWEKLYAAGLISQRKFQRLTKG--EQGGLTL | 923 |
| WP_010775580 | 853 | IPQSFMKDDSLDNLVLVGSTENRG-KSDD--VP | S--KEVVKKMKA-YWEKLYAAGLISQRKFQRLTKG--EQGGLTL | 921 |
| WP_010818269 | 853 | IPQSFMKDDSLDNLVLVGSTENRG-KSDD--VP | S--KEVVKDMKA-YWEKLYAAGLISQRKFQRLTKG--EQGGLTL | 921 |
| WP_010824395 | 853 | IPQSFMKDDSLDNLVLVGSTENRG-KSDD--VP | S--KEVVKDMKA-YWEKLYAAGLISQRKFQRLTKG--EQGGLTL | 921 |
| WP_016622645 | 853 | IPQSFMKDDSLDNLVLVGSTENRG-KSDD--VP | S--KEVVKDMKA-YWEKLYAAGLISQRKFQRLTKG--EQGGLTL | 921 |
| WP_033624816 | 853 | IPQSFMKDDSLDNLVLVGSTENRG-KSDD--VP | S--KEVVKKMKA-YWEKLYAAGLISQRKFQRLTKG--EQGGLTL | 921 |
| WP_033625576 | 853 | IPQSFMKDDSLDNLVLVGSTENRG-KSDD--VP | S--KEVVKKMKA-YWEKLYAAGLISQRKFQRLTKG--EQGGLTL | 921 |
| WP_033789179 | 853 | IPQSFMKDDSLDNLVLVGSTENRG-KSDD--VP | S--KEVVKKMKA-YWEKLYAAGLISQRKFQRLTKG--EQGGLTL | 921 |
| WP_002310644 | 853 | IPRSFTTDNSIDNKVLVSSKENRL-KKDD--VP | S--EKVVKKMRS-FWYDLYSSKLISKRKLDNLTKIk-----LTE | 918 |
| WP_002312694 | 854 | IPRSFTTDNSIDNKVLVSSKENRL-KKDD--VP | S--EKVVKKMRS-FWYDLYSSKLISKRKLDNLTKIk-----LTE | 919 |
| WP_002314015 | 854 | IPRSFTTDNSIDNKVLVSSKENRL-KKDD--VP | S--EKVVKKMRS-FWYDLYSSKLISKRKLDNLTKIk-----LTE | 919 |
| WP_002320716 | 854 | IPRSFTTDNSIDNKVLVSSKENRL-KKDD--VP | S--EKVVKKMRS-FWYDLYSSKLISKRKLDNLTKIk-----LTE | 919 |
| WP_002330729 | 853 | IPRSFTTDNSIDNKVLVSSKENRL-KKDD--VP | S--EKVVKKMRS-FWYDLYSSKLISKRKLDNLTKIk-----LTE | 918 |

| | | | |
|---|---|---|---|
| WP_002335161 | 854 | IPRSFTTDNSIDNKVLVSSKENRL-KKDD--VP | S--EKVVKKMRS-FWYDLYSSKLISKRKLDNLTKIk-----LTE | 919 |
| WP_002345439 | 854 | IPRSFTTDNSIDNKVLVSSKENRL-KKDD--VP | S--EKVVKKMRS-FWYDLYSSKLISKRKLDNLTKIk-----LTE | 919 |
| WP_034867970 | 845 | IPRSFIVDNSIDDKVLVASKQNQK-KRDD--VP | K--KQIVNEQRI-FWNQLKEAKLISTKKYAYLTKIe-----LTP | 910 |
| WP_047937432 | 854 | IPRSFTTDNSIDNKVLVSSKENRL-KKDD--VP | S--EKVVKKMRS-FWYDLYSSKLISKRKLDNLTKIk-----LTE | 919 |
| WP_010720994 | 845 | IPRSFIVDNSIDNKVLVASKQNQK-KRDD--VP | K--KQIVNEQRI-FWNQLKEAKLISPKKYAYLTKIe-----LTP | 910 |
| WP_010737004 | 845 | IPRSFIVDNSIDNKVLVASKQNQK-KRDD--VP | K--KQIVNEQRI-FWNQLKEAKLISPKKYAYLTKIe-----LTP | 910 |
| WP_034700478 | 845 | IPRSFIVDNSIDNKVLVASKQNQK-KRDD--VP | N--KQIVNEQRI-FWNQLKEAKLISPKKYAYLTKIe-----LTP | 910 |
| WP_007209003 | 846 | IPQSFLTDNSIDNRVLTTSKSNRG-KSDN--VP | S--EEVVRKMDR-FWRKLLNAKLISERKYTNLTKKe-----LTE | 911 |
| WP_023351917 | 839 | IPRSFIVDNSLDNRVLVSSKVNRG-KLDN--AP | D--PLVVKRMRS-HWEKLHQAKLISDKKLANLTKQn-----LTE | 904 |
| WP_010770040 | 846 | VPQSFTTDNSLDNRVLVSSKENRG-KKDD--VP | S--KEVVQKNIT-LWETLKNSNLISQKKYDNLTKG--LRGGLTE | 914 |
| WP_048604708 | 843 | IPQSFIVDNSLDNRVLVSSKNRG-KLDD--VP | S--KEVVKKMRA-FWESLYRSGLISKKKFDNLVKA--ESGGLSE | 911 |
| WP_010750235 | 848 | IPRSFIVDHSLDNKVLVSSKENRL-KKDD--VP | D--SKVVKRMKA-YWEKLLRANLISERKFSYLTKLe-----LTD | 913 |
| AII16583 | 881 | VPQSFLKDDSIDNKVLTRSDKNRG-KSDN--VP | S--EEVVKKMKN-YWRQLLNAKLITQRKFDNLTKA--ERGGLSE | 949 |
| WP_029073316 | 861 | VPQSLLKDDSIDNKVLVLSSENQR-KLDDlVIP | ---EMIRNKMFG-FWNKLYENKIISPKKFYSLLIKSe-----YSD | 927 |
| WP_031589969 | 861 | VPQSLLKDDSIDNKVLVLSSENQR-KLDDlVIP | ---SSIRNKMYG-FWEKLFNNKIISPKKFYSLLIKTe-----FNE | 927 |
| KDA45870 | 834 | IPQFLKDDSIENKVLTIKKENVR-KING--LP | S--EAVIQKMGS-FWKKLLDAGAMTNKKYDNLRRN1--HGGLNE | 902 |
| WP_039099354 | 857 | LPQSFIKDNSLDNRVLVSQRMNRS-KADQ--VP | S--VELGQKMQI-QWEQMLRAGLITKKKYDNLTLNp-------- | 923 |
| AKP02966 | 859 | LPRTYIPDDSLENKALVLAKENQR-KADDllLN | S--NVIDKNLE-RWTYMLNNNMMGLKKFKNLTRRv----ITD | 925 |
| WP_010991369 | 845 | VPQSFITDNSIDNLVLTSSAGNRE-KGDD--VP | P--LEIVRKRKV-FWEKLYQGNLMSKRKFPDYLTKA--ERGGLTE | 913 |
| WP_033838504 | 845 | VPQSFITDNSIDNLVLTSSAGNRE-KGDD--VP | P--LEIVRKRKV-FWEKLYQGNLMSKRKFPDYLTKA--ERGGLTE | 913 |
| EHN60060 | 848 | VPQSFITDNSIDNLVLTSSAGNRE-KGDD--VP | P--LEIVRKRKV-FWEKLYQGNLMSKRKFPDYLTKA--ERGGLTE | 916 |
| EFR89594 | 614 | VPQSFITDNSIDNLVLTSSAGNRE-KGND--VP | P--LEIVQKRKV-FWEKLYQGNLMSKRKFPDYLTKA--ERGGLTE | 682 |
| WP_038409211 | 845 | VPQSFITDNSIDNRVLVSSTANRE-KGDN--VP | L--LEVVRKRKA-FWEKLYQAKLMSKRKFPDYLTKA--ERGGLTE | 913 |
| EFR95520 | 464 | VPQSFITDNSIDNRVLVSSTANRE-KGDN--VP | L--LEVVRKRKA-FWEKLYQGNLMSKRKFPDYLTKA--ERGGLTE | 532 |
| WP_003723650 | 845 | VPQSFITDNSIDNLVLTSSAGNRE-KGGD--VP | P--LEIVRKRKV-FWEKLYQGNLMSKRKFPDYLTKA--ERGGLTE | 913 |
| WP_003727705 | 845 | VPQSFITDNSIDNLVLTSSAGNRE-KGGD--VP | P--LEIVRKRKV-FWEKLYQGNLMSKRKFPDYLTKA--ERGGLTE | 913 |
| WP_003730785 | 845 | VPQSFITDNSIDNLVLTSSAGNRE-KGGD--VP | P--LEIVRKRKV-FWEKLYQGNLMSKRKFPDYLTKA--ERGGLTE | 913 |

| ID | | | | |
|---|---|---|---|---|
| WP_003733029 | 845 | VPQSFITDNSVDNLVLTSSAGNRE-KGDN--VP | P--LEIVQKRKI-FWEKLYQGNLMSKRKFPDYLTKA--ERGGLTE | 913 |
| WP_003739838 | 845 | VPQSFITDNSIDNLVLTSSAGNRE-KGDD--VP | P--LEIVRKRKV-FWEKLYQGNLMSKRKFPDYLTKA--ERGGLTE | 913 |
| WP_014601172 | 845 | VPQSFITDNSIDNLVLTSSAGNRE-KGGD--VP | P--LEIVRKRKV-FWEKLYQGNLMSKRKFPDYLTKA--ERGGLTD | 913 |
| WP_023548323 | 845 | VPQSFITDNSIDNLVLTSSAGNRE-KGDN--VP | P--LEIVQKRKI-FWEKLYQGNLMSKRKFPDYLTKA--ERGGLTE | 913 |
| WP_031665337 | 845 | VPQSFITDNSVDNLVLTSSAGNRE-KGDN--VP | P--LEIVQKRKI-FWEKLYQGNLMSKRKFPDYLTKA--ERGGLTE | 913 |
| WP_031669209 | 845 | VPQSFITDNSIDNLVLTSSAGNRE-KGDN--VP | P--LEIVRKRKI-FWEKLYQGNLMSKRKFPDYLTKA--ERGGLTE | 913 |
| WP_033920898 | 845 | VPQSFITDNSIDNLVLTSSAGNRE-KGDN--VP | P--LEIVRKRKV-FWEKLYQGNLMSKRKFPDYLTKA--ERGGLTE | 913 |
| AKI42028 | 848 | VPQSFITDNSIDNLVLTSSAGNRE-KGGD--VP | P--LEIVRKRKV-FWEKLYQGNLMSKRKFPDYLTKA--ERGGLTD | 916 |
| AKI50529 | 848 | VPQSFITDNSIDNLVLTSSAGNRE-KGDN--VP | P--LEIVRKRKV-FWEKLYQGNLMSKRKFPDYLTKA--ERGGLTE | 916 |
| EFR83390 | 293 | VPQSFITDNSIDNLVLTSSAGNRE-KGGD--VP | P--LEIVRKRKV-FWEKLYQGNLMSKRKFPDYLTKA--ERGGLTE | 361 |
| WP_046323366 | 845 | VPQSFITDNSIDNRVLASSAANRE-KGDN--VP | S--LEIVRKRKV-YWEKLYQAKLMSKRKFPDYLTKA--ERGGLTE | 913 |
| AKE81011 | 858 | VPQSFLKDDSIDNKVLTRSDKNRG-KSDN--VP | S--EEVVKKMKN-YWRQLLNAKLITQRKFPDNLTKA--ERGGLSE | 926 |
| CU082355 | 854 | VPQSLVKDDSFDNRVLVLPSENQR-KLDD1vVP | ---FDIRDKMYR-FWKLLFDHELISPKKFYSLLIKTe----YTE | 920 |
| WP_033162887 | 856 | LPQSLIKDDSFDNRVLVLPEENQW-KLDSetVP | ---FEIRNKMIG-FWQMLHENGLMSNKKFFSLIRTd----FSD | 922 |
| AGZ01981 | 875 | VPQSFLKDDSIDNKVLTRSDKNRG-KSDN--VP | S--EEVVKKMKN-YWRQLLNAKLITQRKFPDNLTKA--ERGGLSE | 943 |
| AKA60242 | 842 | VPQSFLKDDSIDNKVLTRSDKNRG-KSDN--VP | S--EEVVKKMKN-YWRQLLNAKLITQRKFPDNLTKA--ERGGLSE | 910 |
| AKS40380 | 842 | VPQSFLKDDSIDNKVLTRSDKNRG-KSDN--VP | S--EEVVKKMKN-YWRQLLNAKLITQRKFPDNLTKA--ERGGLSE | 910 |
| 4UN5_B | 846 | VPQSFLKDDSIDNKVLTRSDKNRG-KSDN--VP | S--EEVVKKMKN-YWRQLLNAKLITQRKFPDNLTKA--ERGGLSE | 914 |
| WP_010922251 | 911 | LD KAGFIKRQLVETRQITKHVAQILDSRMNTKYDENDKLIR--EVKVITLKSKLVSKFRKDF | QFYKVREINNY | 981 |
| WP_039695303 | 921 | AD KAGFIKRQLVETRQITKHVAQILDARFNTEHDENDKVIR--DVKVITLKSNLVSQFRKDF | EFYKVREINDY | 991 |
| WP_045635197 | 913 | RD KVGFIKRQLVETRQITKHVAQILDARYNTEVNEKDKKNR--TVKIITLKSNLVSNFRKEF | RLYKVREINDY | 983 |
| 5AXW_A | 633 | RD QKDFINRNLVDTRYATRGLMNLLRSYFR---------VNnlDVKVKSINGGFTSFLRRKW | KFKKERNKGYK | 702 |
| WP_009880683 | 595 | LD KAGFIKRQLVETRQITKHVAQILDSRMNTKYDENDKLIR--EVRVITLKSKLVSDFRKDF | QFYKVREINNY | 665 |
| WP_010922251 | 911 | LD KAGFIKRQLVETRQITKHVAQILDSRMNTKYDENDKLIR--EVRVITLKSKLVSDFRKDF | QFYKVREINNY | 981 |
| WP_011054416 | 911 | LD KVGFIKRQLVETRQITKHVAQILDSRMNTKYDENDKLIR--EVRVITLKSKLVSDFRKDF | QFYKVREINNY | 981 |
| WP_011284745 | 911 | LD KAGFIKRQLVETRQITKHVAQILDSRMNTKYDENDKLIR--EVRVITLKSKLVSDFRKDF | QFYKVREINNY | 981 |
| WP_011285506 | 911 | LD KAGFIKRQLVETRQITKHVAQILDSRMNTKYDENDKLIR--EVKVITLKSKLVSDFRKDF | QFYKVREINNY | 981 |

| ID | | | | |
|---|---|---|---|---|
| WP_011527619 | 911 | LD KAGFIKRQLVETRQITKHVAQILDSRMNTKYDENDKLIR--EVKVITLKSKLVSDFRKDF | QFYKVREINNY | 981 |
| WP_012560673 | 911 | LD KAGFIKRQLVETRQITKHVAQILDSRMNTKYDENDKLIR--EVRVITLKSKLVSDFRKDF | QFYKVREINNY | 981 |
| WP_014407541 | 910 | LD KAGFIKRQLVETRQITKHVAQILDSRMNTKYDENDKLIR--EVKVITLKSKLVSDFRKDF | QFYKVREINNY | 980 |
| WP_020905136 | 911 | LD KAGFIKRQLVETRQITKHVAQILDSRMNTKYDENDKLIR--EVKVITLKSKLVSDFRKDF | QFYKVREINNY | 981 |
| WP_023080005 | 910 | LD KAGFIKRQLVETRQITKHVAQILDSRMNTKYDENDKLIR--EVKVITLKSKLVSDFRKDF | QFYKVREINNY | 980 |
| WP_023610282 | 910 | LD KAGFIKRQLVETRQITKHVAQILDSRMNTKYDENDKLIR--EVKVITLKSKLVSDFRKDF | QFYKVREINNY | 980 |
| WP_030125963 | 911 | LD KAGFIKRQLVETRQITKHVAQILDSRMNTKYDENDKLIR--EVKVITLKSKLVSDFRKDF | QFYKVREINNY | 981 |
| WP_030126706 | 911 | LD KAGFIKRQLVETRQITKHVAQILDSRMNTKYDENDKLIR--EVKVITLKSKLVSDFRKDF | QFYKVREINNY | 981 |
| WP_031488318 | 911 | LD KAGFIKRQLVETRQITKHVAQILDSRMNTKYDENDKLIR--EVKVITLKSKLVSDFRKDF | QFYKVREINNY | 981 |
| WP_032460140 | 911 | LD KAGFIKRQLVETRQITKHVAQILDSRMNTKYDENDKLIR--EVKVITLKSKLVSDFRKDF | QFYKVREINNY | 981 |
| WP_032461047 | 911 | LD KAGFIKRQLVETRQITKHVAQILDSRMNTKYDENDKLIR--EVKVITLKSKLVSDFRKDF | QFYKVREINNY | 981 |
| WP_032462016 | 911 | LD KAGFIKRQLVETRQITKHVAQILDSRMNTKYDENDKLIR--EVKVITLKSKLVSDFRKDF | QFYKVREINNY | 981 |
| WP_032462936 | 911 | LD KAGFIKRQLVETRQITKHVAQILDSRMNTKYDENDKLIR--EVKVITLKSKLVSDFRKDF | QFYKVREINNY | 981 |
| WP_032464890 | 911 | LD KAGFIKRQLVETRQITKHVAQILDSRMNTKYDENDKLIR--EVKVITLKSKLVSDFRKDF | QFYKVREINNY | 981 |
| WP_033888930 | 736 | LD KAGFIKRQLVETRQITKHVAQILDSRMNTKYDENDKLIR--EVKVITLKSKLVSDFRKDF | QFYKVREINNY | 806 |
| WP_038431314 | 911 | LD KAGFIKRQLVETRQITKHVAQILDSRMNTKYDENDKLIR--EVKVITLKSKLVSDFRKDF | QFYKVREINNY | 981 |
| WP_038432938 | 910 | LD KAGFIKRQLVETRQITKHVAQILDSRMNTKYDENDKLIR--EVKVITLKSKLVSDFRKDF | QFYKVREINNY | 980 |
| WP_038434062 | 911 | LD KAGFIKRQLVETRQITKHVAQILDSRMNTKYDENDKLIR--EVKVITLKSKLVSDFRKDF | QFYKVREINNY | 981 |
| BAQ51233 | 822 | LD KVGFIKRQLVETRQITKHVAQILDSRMNTKYDENDKLIR--EVRVITLKSKLVSDFRKDF | QFYKVREINNY | 892 |
| KGE60162 | 86 | -- ------------------------------------------------------------ | ----------- | 156 |
| KGE60856 | | | | |
| WP_002989955 | 911 | LD KAGFIKRQLVETRQITKHVAQILDERENTEDGNKRRIR--EVKIITLKSNLVSDFRKEF | QFYKVREINNY | 981 |
| WP_003030002 | 910 | ED KAGFIKRQLVETRQITKHVAQILDERENTEDGNKRRIR--NVKIITLKSNLVSNFRKEF | ELYKVREINDY | 980 |
| WP_003065552 | 921 | AD KAGFIKRQLVETRQITKHVAQILDARFNTESDENDKVIR--DVKVITLKSNLVSQFRKDF | EFYKVREINDY | 991 |
| WP_001040076 | 916 | DD KARFIKRQLVETRQITKHVARILDERFNNELDSKGRRIR--KVKVITLKSNLVSNFRKEF | VFYKIREVNNY | 986 |
| WP_001040078 | 916 | DD KARFIQRQLVETRQITKHVARILDERFNNELDSKGRRIR--KVKIVTLKSNLVSNFRKEF | GFYKIREVNDY | 986 |
| WP_001040080 | 916 | DD KARFIQRQLVETRQITKHVARILDERFNNELDSKGRRIR--KVKIVTLKSNLVSNFRKEF | GFYKIREVNNY | 986 |

-continued

| | | | | |
|---|---|---|---|---|
| WP_001040081 | 916 | DD KARFIQRQLVETRQITKHVARILDERFNNELDSKGRRIR--KVKIVTLKSNLVSNFRKEF | GFYKIREVNNY | 986 |
| WP_001040083 | 916 | DD KARFIQRQLVETRQITKHVARILDERFNNELDSKGRRIR--KVKIVTLKSNLVSNFRKEF | GFYKIREVNNY | 986 |
| WP_001040085 | 916 | DD KARFIQRQLVETRQITKHVARILDERFNNELDSKGRRIR--KVKIVTLKSNLVSNFRKEF | GFYKIREVNNY | 986 |
| WP_001040087 | 916 | DD KARFIQRQLVETRQITKHVARILDERFNNELDSKGRRIR--KVKIVTLKSNLVSNFRKEF | GFYKIREVNNY | 986 |
| WP_001040088 | 916 | DD KARFIQRQLVETRQITKHVARILDERFNNELDSKGRRIR--KVKIVTLKSNLVSNFRKEF | GFYKIREVNNY | 986 |
| WP_001040089 | 916 | DD KARFIQRQLVETRQITKHVARILDERFNNELDSKGRRIR--KVKIVTLKSNLVSNFRKEF | GFYKIREVNNY | 986 |
| WP_001040090 | 916 | DD KARFIQRQLVETRQITKHVARILDERFNNELDSKGRRIR--KVKIVTLKSNLVSNFRKEF | GFYKIREVNNY | 986 |
| WP_001040091 | 916 | DD KARFIQRQLVETRQITKHVARILDERFNNELDSKGRRIR--KVKIVTLKSNLVSNFRKEF | GFYKIREVNNY | 986 |
| WP_001040092 | 916 | DD KAGFIQRQLVETRQITKHVARILDERFNNKVDDNNKPIR--KVKIVTLKSNLVSNFRKEF | GFYKIREVNNY | 986 |
| WP_001040094 | 916 | DD KARFIQRQLVETRQITKHVARILDERFNNELDSKGRRIR--KVKIVTLKSNLVSNFRKEF | GFYKIREVNNY | 986 |
| WP_001040095 | 916 | DD KARFIQRQLVETRQITKHVARILDERFNNELDSKGRRIR--KVKIVTLKSNLVSNFRKEF | GFYKIREVNNY | 986 |
| WP_001040096 | 916 | DD KARFIQRQLVETRQITKHVARILDERFNNELDSKGRRIR--KVKIVTLKSNLVSNFRKEF | GFYKIREVNNY | 986 |
| WP_001040097 | 916 | DD KARFIQRQLVETRQITKHVARILDERFNNELDSKGRRIR--KVKIVTLKSNLVSNFRKEF | GFYKIREVNNY | 986 |
| WP_001040098 | 916 | DD KARFIQRQLVETRQITKHVARILDERFNNELDSKGRRIR--KVKIVTLKSNLVSNFRKEF | GFYKIREVNNY | 986 |
| WP_001040099 | 916 | DD KARFIQRQLVETRQITKHVARILDERFNNELDSKGRRIR--KVKIVTLKSNLVSNFRKEF | GFYKIREVNNY | 986 |
| WP_001040100 | 916 | DD KARFIQRQLVETRQITKHVARILDERFNNELDSKGRRIR--KVKIVTLKSNLVSNFRKEF | GFYKIREVNNY | 986 |
| WP_001040104 | 916 | DD KARFIQRQLVETRQITKHVARILDERFNNELDSKGRRIR--KVKIVTLKSNLVSNFRKEF | GFYKIREVNNY | 986 |
| WP_001040105 | 916 | DD KARFIQRQLVETRQITKHVARILDERFNNELDSKGRRIR--KVKIVTLKSNLVSNFRKEF | GFYKIREVNDY | 986 |
| WP_001040106 | 916 | DD KARFIQRQLVETRQITKHVARILDERFNNELDSKGRRIR--KVKIVTLKSNLVSNFRKEF | GFYKIREVNDY | 986 |
| WP_001040107 | 916 | DD KARFIQRQLVETRQITKHVARILDERFNNELDSKGRRIR--KVKIVTLKSNLVSNFRKEF | GFYKIREVNDY | 986 |
| WP_001040108 | 916 | DD KARFIQRQLVETRQITKHVARILDERFNNELDSKGRRIR--KVKIVTLKSNLVSNFRKEF | GFYKIREVNDY | 986 |
| WP_001040109 | 916 | DD KARFIQRQLVETRQITKHVARILDERFNNELDSKGRRIR--KVKIVTLKSNLVSNFRKEF | GFYKIREVNDY | 986 |
| WP_001040110 | 916 | DD KARFIQRQLVETRQITKHVARILDERFNNELDSKGRRIR--KVKIVTLKSNLVSNFRKEF | GFYKIREVNDY | 986 |
| WP_015058523 | 916 | DD KAGFIQRQLVETRQITKHVARILDERFNNKVDDNNKPIR--KVKIVTLKSNLVSNFRKEF | GFYKIREVNDY | 986 |
| WP_017643650 | 916 | DD KARFIQRQLVETRQITKHVARILDERFNNELDSKGRRIR--KVKIVTLKSNLVSNFRKEF | GFYKIREVNDY | 986 |
| WP_017647151 | 916 | DD KARFIQRQLVETRQITKHVARILDERFNNELDSKGRRIR--KVKIVTLKSNLVSNFRKEF | GFYKIREVNNY | 986 |
| WP_017648376 | 916 | DD KARFIQRQLVETRQITKHVARILDERFNNELDSKGRRIR--KVKIVTLKSNLVSNFRKEF | GFYKIREVNNY | 986 |

-continued

| | | | | |
|---|---|---|---|---|
| WP_017649527 | 916 | DD KARFIQRQLVETRQITKHVARILDERFNNELDSKGRRIR--KVKIVTLKSNLVSNFRKEF | GFYKIREVNNY | 986 |
| WP_017771611 | 916 | DD KARFIQRQLVETRQITKHVARILDERFNNELDSKGRRIR--KVKIVTLKSNLVSNFRKEF | GFYKIREVNDY | 986 |
| WP_017771984 | 916 | DD KARFIQRQLVETRQITKHVARILDERFNNELDSKGRRIR--KVKIVTLKSNLVSNFRKEF | GFYKIREVNNY | 986 |
| CFQ25032 | 916 | DD KARFIQRQLVETRQITKHVARILDERFNNELDSKGRRIR--KVKIVTLKSNLVSNFRKEF | GFYKIREVNNY | 986 |
| CFV16040 | 916 | DD KARFIQRQLVEIRQITKHVARILDERFNNELDSKGRRIR--KVKIVTVKSNLVSNFRKEF | GFYKIREVNNY | 986 |
| KLJ37842 | 916 | DD KARFIQRQLVETRQITKHVARILDERFNNELDSKGRRIR--KVKIVTLKSNLVSNFRKEF | GFYKIREVNNY | 986 |
| KLJ72361 | 916 | DD KARFIQRQLVETRQITKHVARILDELFNNELDSKGRRIR--KVKIVTLKSNLVSNFRKEF | GFYKIREVNNY | 986 |
| KLL20707 | 930 | DD KARFIQRQLVETRQITKHVARILDERFNNELDSKGRRIR--KVKIVTLKSNLVSNFRKEF | GFYKIREVNDY | 1000 |
| KLL42645 | 916 | DD KARFIQRQLVETRQITKHVARILDERFNNELDSKGRRIR--KVKIVTLKSNLVSNFRKEF | GFYKIREVNNY | 986 |
| WP_047207273 | 916 | DD KARFIQRQLVETRQITKHVARILDERFNNELDSKGRRIR--KVKIVTLKSNLVSNFRKEF | GFYKIREVNDY | 986 |
| WP_047209694 | 916 | DD KARFIQRQLVETRQITKHVARILDERFNNELDSKGRRIR--KVKIVTLKSNLVSNFRKEF | GFYKIREVNNY | 986 |
| WP_050198062 | 916 | DD KARFIQRQLVETRQITKHVASILDERFNNELDSKGRRIR--KVKIVTLKSNLVSNFRKEF | GFYKIREVNNY | 986 |
| WP_050201642 | 916 | DD KARFIQRQLVETRQITKHVARILDERFNNELDSKGRRIR--KVKIVTLKSNLVSNFRKEF | GFYKIREVNDY | 986 |
| WP_050204027 | 916 | DD KARFIQRQLVETRQITKHVARILDERFNNELDSKGRRIR--KVKIVTLKSNLVSNFRKEF | GFYKIREVNNY | 986 |
| WP_050881965 | 916 | DD KARFIQRQLVETRQITKHVARILDERFNNELDSKGRRIR--KVKIVTLKSNLVSNFRKEF | GFYKIREVNNY | 986 |
| WP_050886065 | 916 | DD KARFIQRQLVETRQITKHVARILDERFNNKVDDNNKPIR--KVKIVTLKSNLVSNFRKEF | GFYKIREVNNY | 986 |
| AHN30376 | 916 | DD KARFIQRQLVETRQITKHVARILDERFNNELDSKGRRIR--KVKIVTLKSNLVSNFRKEF | GFYKIREVNNY | 986 |
| EA078426 | 916 | DD KARFIQRQLVETRQITKHVARILDERFNNELDSKGRRIR--KVKIVTLKSNLVSNFRKEF | GFYKIREVNNY | 986 |
| CCW42055 | 916 | DD KARFIQRQLVETRQITKHVARILDERFNNELDSKGRRIR--KVKIVTLKSNLVSNFRKEF | GFYKIREVNNY | 986 |
| WP_003041502 | 910 | ND KAGFIKRQLVETRQLVETRQITKHVAQVLDARFNAKHDENKKVIR--DVKIITLKSNLVSNFRKDF | KFYKVREINDY | 980 |
| WP_037593752 | 911 | ED KAGFIKRQLVETRQITKHVAQILDERFNTEFDGAQRRIR--NVKIITLKSNLVSNFRKEF | ELYKVREINDY | 981 |
| WP_049516684 | 911 | ED KAGFIKRQLVETRQITKHVAQILDERFNTEFDGAQRRIR--NVKIITLKSNLVSNFRKEF | ELYKVREINDY | 981 |
| GAD46167 | 910 | ED KAGFIKRQLVETRQITKHVAQILDERFNTEFDGAQRRIR--NVKIITLKSNLVSNFRKEF | ELYKVREINDY | 980 |
| WP_018363470 | 919 | AD KAGFIKRQLVETRQITKHVAQILDARFNTERDENDKVIR--DVKIITLKSNLVSNFRKEF | KFYKVREINDY | 989 |
| WP_003043819 | 920 | AD KAGFIKRQLVETRQITKHVARILDSRMNTKRDKNDKPIR--EVKIITLKSKLVSDFRKDF | QLYKVRDINNY | 990 |
| WP_006269658 | 910 | ED KAGFIKRQLVETRQITKHVAQILDERFNTEFDGNKRRIR--NVKIITLKSNLVSNFRKEF | ELYKVREINDY | 980 |
| WP_048800889 | 910 | ND KAGFIHRQLVETRQITKHVAQILDARFNPKRDDNKKVIR--DVKIITLKSNLVSQFRRDF | KLYKVREINDY | 980 |

| ID | Start | | Sequence | | End |
|---|---|---|---|---|---|
| WP_012767106 | 910 | LD | KAGFIKRQLVETRQITKHVAQILDSRMNTKYDENDKLIR--EVKVITLKSKLVSDFRKDF | QFYKVREINNY | 980 |
| WP_014612333 | 910 | LD | KAGFIKRQLVETRQITKHVAQILDSRMNTKYDENDKLIR--EVKVITLKSKLVSDFRKDF | QFYKVREINNY | 980 |
| WP_015017095 | 910 | LD | KAGFIKRQLVETRQITKHVAQILDSRMNTKYDENDKLIR--EVKVITLKSKLVSDFRKDF | QFYKVREINNY | 980 |
| WP_015057649 | 910 | LD | KAGFIKRQLVETRQITKHVAQILDSRMNTKYDENDKLIR--EVKVITLKSKLVSDFRKDF | QFYKVREINNY | 980 |
| WP_048327215 | 910 | LD | KAGFIKRQLVETRQITKHVAQILDSRMNTKYDENDKLIR--EVKVITLKSKLVSDFRKDF | QFYKVREINNY | 980 |
| WP_049519324 | 910 | LD | KAGFIKRQLVETRQITKHVAQILDSRMNTKYDENDKLIR--EVKVITLKSKLVSDFRKDF | QFYKVREINNY | 980 |
| WP_012515931 | 910 | VD | KAGFIQRQLVETRQITKHVAQILDSRFNTEFDDHNKRIR--KVHIITLKSKLVSDFRKEF | GLYKIRDINHY | 980 |
| WP_021320964 | 910 | VD | KAGFIQRQLVETRQITKHVAQILDSRFNTEFDDHNKRIR--KVHIITLKSKLVSDFRKEF | GLYKIRDINHY | 980 |
| WP_037581760 | 910 | VD | KAGFIQLQLVETRQITKHVAQILDSRFNTEFDDHNKRIR--KVHIITLKSKLVSDFRKEF | GLYKIRDINHY | 980 |
| WP_004232481 | 918 | TD | KAGFIKRQLVETRQITKHVAQILDARFNTKCDENDKVIR--DVKVITLKSSLVSQFRKEF | KFYKVREINDY | 988 |
| WP_009854540 | 919 | AD | KAGFIKRQLVETRQITKHVAQILDARFNTEHDENDKVIR--DVKVITLKSNLVSQFRKDF | EFYKVREINDY | 989 |
| WP_012962174 | 919 | ND | KAGFIKRQLVETRQITKHVAQILDSRFNTERDENDKVIR--NVKVITLKSNLVSQFRKEF | KFYKVREINDY | 989 |
| WP_039695303 | 921 | AD | KAGFIKRQLVETRQITKHVAQILDSRFNTEHDENDKVIR--DVKVITLKSNLVSDFRKDF | EFYKVREINDY | 991 |
| WP_014334983 | 918 | AD | KAGFIKRQLVETRQITKHVAQILDARFNTKRDENDKVIR--DVKVITLKSNLVSNFRKEF | KFYKVREINDY | 988 |
| WP_003099269 | 911 | FD | KAGFIKRQLVETRQITKHVAQILDSRFNSNLTEDSKSNR--NVKIITLKSKMVSDFRKDF | GFYKLREVNDY | 981 |
| AHY15608 | 911 | FD | KAGFIKRQLVETRQITKHVAQILDSRFNSNLTEDSKSNR--NVKIITLKSKMVSDFRKDF | GFYKLREVNDY | 981 |
| AHY17476 | 911 | FD | KAGFIKRQLVETRQITKHVAQILDSRFNSNLTEDSKSNR--NVKIITLKSKMVSDFRKDF | GFYKLREVNDY | 981 |
| ESR09100 | | -- | ------------------------------------------------------------ | ----------- | |
| AGM98575 | 911 | FD | KAGFIKRQLVETRQITKHVAQILDSRFNSNLTEDSKSNR--NVKIITLKSKMVSDFRKDF | GFYKLREINDY | 981 |
| ALF27331 | 911 | DD | KAGFIKRRQLVETRQITKHVAQILDSRFNTEDERFNTETDENNKKIR--QVKIVTLKSNLVSNFRKEF | ELYKVREINDY | 981 |
| WP_018372492 | 924 | ED | KAGFIKRQLVETRQITKHVARLLDEKLNRKKNENGEKLR--TTKIITLKSVFASRFPRANF | DLYKLRELNHY | 994 |
| WP_045618028 | 914 | RD | KVGFIKRQLVETRQITKHVAQILDARFNTEVTEKDKKDR--SVKIITLKSNLVSNFRKEF | RLYKVREINDY | 984 |
| WP_045635197 | 913 | RD | KVGFIKRQLVETRQITKHVAQILDARYNTEVNEKDKKNR--TVKIITLKSNLVSNFRKEF | RLYKVREINDY | 983 |
| WP_002263549 | 911 | DD | KAGFIKRQLVETRQITKHVARILDERFNTETDENNKKIR--QVKIVTLKSNLVSNFRKEF | ELYKVREINDY | 981 |
| WP_002263887 | 911 | DD | KAGFIKRQLVETRQITKHVARILDERFNTETDENNKKIR--QVKIVTLKSNLVSNFRKEF | ELYKVREINDY | 981 |
| WP_002264920 | 911 | DD | KAGFIKRQLVETRQITKHVARILDERFNTETDENNKKIR--QVKIVTLKSNLVSNFRKEF | ELYKVREINDY | 981 |
| WP_002269043 | 911 | DD | KAGFIKRQLVETRQITKHVARILDERFNTETDENNKKIR--QVKIVTLKSNLVSNFRKEF | ELYKVREINDY | 981 |

| | | | | |
|---|---|---|---|---|
| WP_002269448 | 911 | DD KAGFIKRQLVETRQITKHVARILDERFYTETDENNKKIR--QVKIVTLKSNLVSNFRKEF | ELYKVREINDY | 981 |
| WP_002271977 | 911 | DD KAGFIKRQLVETRQITKHVARILDERFYTETDENNKKIR--QVKIVTLKSNLVSNFRKEF | ELYKVREINDY | 981 |
| WP_002272766 | 911 | DD KAGFIKRQLVETRQITKHVARILDERFYTETDENNKKIR--QVKIVTLKSNLVSNFRKEF | ELYKVREINDY | 981 |
| WP_002273241 | 911 | DD KAGFIKRQLVETRQITKHVARILDERFNTETDENNKKIR--QVKIVTLKSNLVSNFRKEF | ELYKVREINDY | 981 |
| WP_002275430 | 911 | DD KAGFIKRQLVETRQITKHVARILDERFYTETDENNKKIR--QVKIVTLKSNLVSNFRKEF | ELYKVREINDY | 981 |
| WP_002276448 | 911 | DD KAGFIKRQLVETRQITKHVARILDERFYTETDENNKKIR--QVKIVTLKSNLVSNFRKEF | ELYKVREINDY | 981 |
| WP_002277050 | 913 | DD KAGFIKRQLVETRQITKHVARMLDERFNKEFDDNNKRIR--RVKIVTLKSNLVSSFRKEF | ELYKVREINDY | 983 |
| WP_002773364 | 911 | DD KAGFIKRQLVETRQITKHVARILDERFHTETDENNKKIR--QVKIVTLKSNLVSNFRKEF | ELYKVREINDY | 981 |
| WP_002279025 | 911 | DD KAGFIKRQLVETRQITKHVARILDERFNTETDENNKKIR--QVKIVTLKSNLVSNFRKEF | ELYKVREINDY | 981 |
| WP_002279859 | 911 | DD KAGFIKRQLVETRQITKHVARILDERFNTETDENNKKIR--QVKIVTLKSNLVSNFRKEF | ELYKVREINDY | 981 |
| WP_002280230 | 911 | DD KAGFIKRQLVETRQITKHVARILDERFYTETDENNKKIR--QVKIVTLKSNLVSNFRKEF | ELYKVREINDY | 981 |
| WP_002281696 | 911 | DD KAGFIKRQLVETRQITKHVARILDERFHTETDENNKKIR--QVKIVTLKSNLVSNFRKEF | ELYKVREINDY | 981 |
| WP_002282247 | 913 | DD KAGFIKRQLVETRQITKHVARMLDERFNKEFDDNNKRIR--RVKIVTLKSNLVSSFRKEF | ELYKVREINDY | 983 |
| WP_002282906 | 911 | DD KAGFIKRQLVETRQITKHVARILDERFNTETDENNKKIR--QVKIVTLKSNLVSNFRKEF | ELYKVREINDY | 981 |
| WP_002283846 | 911 | DD KAGFIKRQLVETRQITKHVARILDERFHTETDENNKKIR--QVKIVTLKSNLVSNFRKEF | ELYKVREINDY | 981 |
| WP_002287255 | 911 | DD KAGFIKRQLVETRQITKHVARILDERFNTETDENNKKIR--QVKIVTLKSNLVSNFRKEF | ELYKVREINDY | 981 |
| WP_002288990 | 911 | DD KAGFIKRQLVETRQITKHVARILDERFYTETDENNKKIR--QVKIVTLKSNLVSNFRKEF | ELYKVREINDY | 981 |
| WP_002289641 | 911 | DD KAGFIKRQLVETRQITKHVARILDERFNTETDENNKKIR--QVKIVTLKSNLVSNFRKEF | ELYKVREINDY | 981 |
| WP_002290427 | 911 | DD KAGFIKRQLVETRQITKHVARILDERFNTETDENNKKIR--QVKIVTLKSNLVSNFRKEF | ELYKVREINDY | 981 |
| WP_002295753 | 911 | DD KAGFIKRQLVETRQITKHVARILDERFHTETDENNKKIR--QVKIVTLKSNLVSNFRKEF | ELYKVREINDY | 981 |
| WP_002296423 | 911 | DD KAGFIKRQLVETRQITKHVARILDERFYTETDENNKKIR--QVKIVTLKSNLVSNFRKEF | ELYKVREINDY | 981 |
| WP_002304487 | 925 | DD KAGFIKRQLVETRQITKHVARILDERFHTETDENNKKIR--QVKIVTLKSNLVSNFRKEF | ELYKVREINDY | 995 |
| WP_002305844 | 911 | DD KAGFIKRQLVETRQITKHVARILDERFYTETDENNKKIR--QVKIVTLKSNLVSNFRKEF | ELYKVREINDY | 981 |
| WP_002307203 | 911 | DD KAGFIKRQLVETRQITKHVARILDERFNTETDENNKKIR--QVKIVTLKSNLVSNFRKEF | ELYKVREINDY | 981 |
| WP_002310390 | 911 | DD KAGFIKHQLVETRQITKHVARILDERFNTETDENNKKIR--QVKIVTLKSNLVSNFRKEF | ELYKVREINDY | 981 |
| WP_002352408 | 911 | DD KAGFIKRQLVETRQITKHVARILDERFYTETDENNKKIR--QVKIVTLKSNLVSNFRKEF | ELYKVREINDY | 981 |
| WP_012997688 | 911 | DD KAGFIKRQLVETRQITKHVARILDERFHTETDENNKKIR--QVKIVTLKSNLVSNFRKEF | ELYKVREINDY | 981 |

-continued

| ID | Start | | Sequence | | End |
|---|---|---|---|---|---|
| WP_014677909 | 911 | DD | KAGFIKRQLVETRQITKHVARILDERFYTETDENNKKIR--QVKIVTLKSNLVSNFRKEF | ELYKVREINDY | 981 |
| WP_019312892 | 911 | DD | KAGFIKRQLVETRQITKHVARILDERFHTETDENNKKIR--QVKIVTLKSNLVSNFRKEF | ELYKVREINDY | 981 |
| WP_019313659 | 911 | DD | KAGFIKRQLVETRQITKHVARILDERFNTETDENNKKIR--QVKIVTLKSNLVSNFRKEF | ELYKVREINDY | 981 |
| WP_019314093 | 911 | DD | KAGFIKRQLVETRQITKHVARILDERFNTETDENNKKIR--QVKIVTLKSNLVSNFRKEF | ELYKVREINDY | 981 |
| WP_019315370 | 911 | DD | KAGFIKRQLVETRQITKHVARILDERFNTETDENNKKIR--QVKIVTLKSNLVSNFRKEF | ELYKVREINDY | 981 |
| WP_019803776 | 911 | DD | KAGFIKRQLVETRQITKHVARILDERFNTETDENNKKIR--QVKIVTLKSNLVSNFRKEF | ELYKVREINDY | 981 |
| WP_019805234 | 911 | DD | KAGFIKRQLVETRQITKHVARILDERFNTETDENNKKIR--QVKIVTLKSNLVSNFRKEF | ELYKVREINDY | 981 |
| WP_024783594 | 911 | DD | KAGFIKRQLVETRQITKHVARILDERFNTETDENNKKIR--QVKIVTLKSNLVSNFRKEF | ELYKVREINDY | 981 |
| WP_024784288 | 913 | DD | KAGFIKRQLVETRQITKHVARMLDERFNKEFDDNNKRIR--RVKIVTLKSNLVSSFRKEF | ELYKVREINDY | 983 |
| WP_024784666 | 911 | DD | KAGFIKRQLVETRQITKHVARILDERFHTETDENNKKIR--QVKIVTLKSNLVSNFRKEF | ELYKVREINDY | 981 |
| WP_024784894 | 911 | DD | KAGFIKRQLVETRQITKHVARILDERFNTETDENNKKIR--QVKIVTLKSNLVSNFRKEF | ELYKVREINDY | 981 |
| WP_024786433 | 913 | DD | KAGFIKRQLVETRQITKHVARMLDERFNKEFDDNNKRIR--RVKIVTLKSNLVSSFRKEF | ELYKVREINDY | 983 |
| WP_024786442 | 911 | DD | KAGFIKRQLVETRQITKHVARILDERFNTETDENNKKIR--QVKIVTLKSNLVSNFRKEF | ELYKVREINDY | 981 |
| WP_049473442 | 911 | DD | KAGFIKRQLVETRQITKHVARILDERFHTETDENNKKIR--QVKIVTLKSNLVSNFRKEF | ELYKVREINDY | 981 |
| WP_049474547 | 904 | DD | KAGFIKRQLVETRQITKHVARILDERFHTETDENNKKIR--QVKIVTLKSNLVSNFRKEF | ELYKVREINDY | 974 |
| EMC03581 | 916 | RD | KVGFIKRQLVETRQITKHVAQILDARYNTEVNEKDKKNR--TVKIITLKSNLVSNFRKEF | RLYKIREINDY | 986 |
| WP_000428612 | 914 | RD | KVGFIKRQLVETRQITKHVAQILDARFNKEVNEKDKKNR--TVKIITLKSNLVSNFRKEF | RLYKVREINDY | 984 |
| WP_000428613 | 909 | RD | KVGFIKRQLVETRQITKHVAQILDDRFNAEVNEKNQKLR--SVKIITLKSNLVSNFRKEF | GLYKVREINDY | 979 |
| WP_049523028 | 880 | YD | KAGFIKRQLVETRQITKHVAQILNNRFNNNVDDSSKNKR--PVKIITLKSKMVSDFRKEF | GFYKIREVNDY | 950 |
| WP_003107102 | 912 | SD | KANFIQRQLVETRQITKHVAQILDSRFNTERDEKDRPIR--RVKVITLKSKFVSDFRQDF | GFYKLREVNDY | 982 |
| WP_054279288 | 914 | RD | KVGFIKRQLVETRQITKHVAQILDSRFNTEVNEKNQKIR--TVKIITLKSNLVSNFRKEF | RLYKVREINDY | 984 |
| WP_049531101 | 914 | RD | KVGFIRRQLVETRQITKHVAQILDSRFNTEVTEKDKKNR--NVKIITLKSNLVSNFRKEF | GLYKVREINDY | 984 |
| WP_049538452 | 916 | LD | KVGFIRRQLVETRQITKHVAQILDARFNKEVTEKDKKNR--NVKIITLKSNLVSNFRKEF | RLYKVREINDY | 986 |
| WP_049549711 | 917 | SD | KARFLRRQLVETRQITKHVAQLLDSRFNSKSNQNKKLAR--NVKIITLKSKIVSDFRKDF | GLYKLREINDY | 987 |
| WP_007896501 | 869 | SD | KARFLRRQLVETQQITKHVAQLLDSRFNSKSNQNKKLAR--NVKIITLKSKIVSDFRKDF | GLYKLREVNNY | 939 |
| EFR44625 | 913 | RD | KVGFIRRQLVETQQITKNVAQILDARFNTEVKEKNQKIR--TVKIITLKSNLVSNFRKEF | GLYKLREINNY | 983 |
| WP_002897477 | 913 | RD | KVGFIKRQLVETQQITKHVAQLLDTRFNTEVNEENQKIR--TVKIITLKSNLVSNFRKEF | GLYKVREINDY | 983 |
| WP_002906454 | | | | | |

| | | | | |
|---|---|---|---|---|
| WP_009729476 | 914 | LD | KVGFIKRQLVETRQITKHVAQILDARFNKEVTEKDKKNR--TVKIITLKSNLVSNFRKEF | ELYKVREINDY | 984 |
| CQR24647 | 913 | ED | KAGFIKRQLVETRQITKHVAQFLDARFNKEVTEKDKKNR--NVKIVTLKSNLVSNERKEF | GFYKVREINNF | 983 |
| WP_000066813 | 918 | LD | KVGFIKRQLVETRQITKHVARILDERFNRDFDKNDKRIR--NVKIITLKSNLVSNFRKEF | GLYKVREINDY | 988 |
| WP_009754323 | 914 | RD | KVGFIKRQLVETRQITKHVARILDARFNTEVSEKNQKIR--SVKIITLKSNLVSNFRKEF | KLYKVREINDY | 984 |
| WP_044674937 | 913 | ED | KARFIQRQLVETRQITKHVARILDTRFNTKLDEAGNRIRdpKVNIITLKSNLVSQFRKDY | QLYKVREINNY | 985 |
| WP_044676715 | 915 | ED | KARFIQRQLVETRQITKHVARILDTRFNTKLDEAGNRIRdpKVNIITLKSNLVSQFRKDY | QLYKVREINNY | 987 |
| WP_044680361 | 915 | ED | KARFIQRQLVETRQITKHVARILDTRFNTKLDEAGNRIRdpKVNIITLKSNLVSQFRKDY | QLYKVREINNY | 987 |
| WP_044681799 | 913 | ED | KARFIQRQLVETRQITKHVARILDTRFNTKLDEAGNRIRdpKVNIITLKSNLVSQFRKDY | QLYKVREINNY | 985 |
| WP_049533112 | 910 | ND | KAGFIQRQLVETRQITKHVAQVLDARFNAKHDENKKVIR--DVKIITLKSNLVSQFRKDF | KFYKVREINDY | 980 |
| WP_029090905 | 891 | RD | KEGFIARQLVETRQITKHVTQLLQQEY---------------K--dTTKVFAIKATLVSGLRRKF | EFIKNRNVNDY | 951 |
| WP_006506696 | 917 | RD | EERFINRQLVETRQITKNVTQIIEDHYST---------------TKVAAIRANLSHEFRVKN | HIYKNRDINDY | 976 |
| AIT42264 | 911 | LD | KAGFIKRQLVETRQITKHVAQILDSRMNTKYDENDKLIR--EVKVITLKSKLVSDFRKDF | QFYKVREINNY | 981 |
| WP_034440723 | 915 | RD | RQQFINRQLVETRQITKHVANLLSHHLNEK-------KEVG--EINIVLLKSALTSQFRKKF | DFYKVREVNDY | 980 |
| AKQ21048 | 911 | LD | KAGFIKRQLVETRQITKHVAQILDSRMNTKYDENDKLIR--EVKVITLKSKLVSDFRKDF | QFYKVREINNY | 981 |
| WP_004636532 | 916 | AD | RAHFLNRQLVETRQITKHVANLLDSQYNTAEEQ-------R--INIVLLKSSMTSRFRKEF | KLYKVREINDY | 980 |
| WP_002364836 | 922 | ED | KAHFIQRQLVETRQITKNVAGILDQRYNANSKE--------K--KVQIITLKASLTSQFRSIF | GLYKVREVNDY | 987 |
| WP_016631044 | 873 | ED | KAHFIQRQLVETRQITKNVAGILDQRYNAKSKE--------K--KVQIITLKASLTSQFRSIF | GLYKVREVNDY | 938 |
| EMS75795 | 655 | ED | KARFIQRQLVETRQITKHVAAILDQYFN-QPEE-SK-NK--GIRIITLKSSLVSQFRKTF | GINKVREINNH | 722 |
| WP_002373311 | 922 | ED | KAHFIQRQLVETRQITKNVAGILDQRYNAKSKE--------K--KVQIITLKASLTSQFRSIF | GLYKVREVNDY | 987 |
| WP_002378009 | 922 | ED | KAHFIQRQLVETRQITKNVAGILDQRYNAKSKE--------K--KVQIITLKASLTSQFRSIF | GLYKVREVNDY | 987 |
| WP_002407324 | 922 | ED | KAHFIQRQLVETRQITKNVAGILDQRYNAKSKE--------K--KVQIITLKASLTSQFRSIF | GLYKVREVNDY | 987 |
| WP_002413717 | 922 | ED | KAHFIQRQLVETRQITKNVAGILNQRYNANSKE--------K--KVQIITLKASLTSQFRSIF | GLYKVREVNDY | 987 |
| WP_010775580 | 924 | ED | KAHFIQRQLVETRQITKNVAGILNQRYNAKSKE--------K--KVQIITLKASLTSQFRSIF | GLYKVREVNDY | 989 |
| WP_010818269 | 922 | ED | KAHFIQRQLVETRQITKNVAGILDQLYNAKSKE--------K--KVQIITLKASLTSQFRSIF | GLYKVREVNDY | 987 |
| WP_010824395 | 922 | ED | KAHFIQRQLVETRQITKNVAGILDQRYNAKSKE--------K--KVQIITLKASLTSQFRSIF | GLYKVREVNDY | 987 |
| WP_016622645 | 922 | ED | KAHFIQRQLVETRQITKNVAGILDQRYNAKSKE--------K--KVQIITLKASLTSQFRSIF | GLYKVREVNDY | 987 |
| WP_033624816 | 922 | ED | KAHFIQRQLVETRQITKNVAGILDQRYNAKSKE--------K--KVQIITLKASLTSQFRSIF | GLYKVREVNDY | 987 |

| | | | | |
|---|---|---|---|---|
| WP_033625576 | 922 | ED | KAHFIQRQLVETRQITKNVAGILDQRYNAKSKE-----K--KVQIITLKASLTSQFRSIF | GLYKVREVNDY | 987 |
| WP_033789179 | 922 | ED | KAHFIQRQLVETRQITKNVAGILDQRYNAKSKE-----K--KVQIITLKASLTSQFRSIF | GLYKVREVNDY | 987 |
| WP_002310644 | 919 | ED | KAGFIKRQLVETRQITKHVAGILHHRFN-KAEDTNEPIR--KVRIITLKSALVSQFRNRF | GIYKVREINEY | 988 |
| WP_002312694 | 920 | ED | KAGFIKRQLVETRQITKHVAGILHHRFN-KAEDTNDPIR--KVRIITLKSALVSQFRNRF | GIYKVREINEY | 989 |
| WP_002314015 | 920 | ED | KAGFIKRQLVETRQITKHVAGILHHRFN-KAEDTNEPIR--KVRIITLKSALVSQFRNRF | GIYKVREINEY | 989 |
| WP_002320716 | 920 | ED | KAGFIKRQLVETRQITKHVAGILHHRFN-KAEDTNEPIR--KVRIITLKSALVSQFRNRF | GIYKVREINEY | 989 |
| WP_002330729 | 919 | ED | KAGFIKRQLVETRQITKHVAGILHHRFN-KAEDTNEPIR--KVRIITLKSALVSQFRNRF | GIYKVREINEY | 988 |
| WP_002335161 | 920 | ED | KAGFIKRQLVETRQITKHVAGILHHRFN-KAEDTNEPIR--KVRIITLKSALVSQFRNRF | GIYKVREINEY | 989 |
| WP_002345439 | 920 | ED | KAGFIKRQLVETRQITKHVAGILHHRFN-KAEDTNEPIR--KVRIITLKSALVSQFRNRF | GIYKVREINEY | 989 |
| WP_034867970 | 911 | ED | KARFIQRQLVETRQITKHVANILHQSFN-QEEEGTD-CD--GVQIITLKATLTSQFRQTF | GLYKVREINPH | 979 |
| WP_047937432 | 920 | ED | KAGFIKRQLVETRQITKHVAGILHHRFN-KAEDTNEPIR--KVRIITLKSALVSQFRNRF | GIYKVREINEY | 989 |
| WP_010720994 | 911 | ED | KARFIQRQLVETRQITKHVANILHQSFN-QEEEGTD-CD--GVQIITLKATLTSQFRQTF | GLYKVREINPH | 979 |
| WP_010737004 | 911 | ED | KARFIQRQLVETRQITKHVANILHQSFN-QEEEGTD-CD--GVQIITLKATLTSQFRQTF | GLYKVREINPH | 979 |
| WP_034700478 | 911 | ED | KARFIQRQLVETRQITKHVANILHQSFN-QEEEGTD-CD--GVQIITLKATLTSQFRQTF | GLYKVREINPH | 979 |
| WP_007209003 | 912 | SD | KAGFLKRQLVETRQITKHVATILDSKFNE--DSNNRDVQ-----IITLKSALVSEFRKTF | NLYKVREINDL | 977 |
| WP_023519017 | 905 | AD | KARFIQRQLVETRQITKHVANLLHQHFN-LPEEVSA-TE--KTSIITLKSTLTSQFRQMF | DIYKVREINHH | 973 |
| WP_010770040 | 915 | DD | RAHFIKRQLVETRQITKHVARILDQRFNSQKDEEGKTIR--AVRVTLKSSLTSQFRKQF | AIHKVREINDY | 985 |
| WP_048604708 | 912 | DD | KAGFIHRQLVETRQITKHVARILHQRFNSEKDEEGNLIR--KVRIITLKSALVSQFRKNY | GIYKIREINDY | 982 |
| WP_010750235 | 914 | DD | KARFIQRQLVETRQITKHVAAILHQYFN-QTQELEK-EK--DIRIITLKSSLVSQFRQVF | GIHKVREINHH | 982 |
| AII16583 | 950 | LD | KAGFIKRQLVETRQITKHVAQILDSRMNTKYDENDKLIR--EVKVITLKSKLVSDFRKDF | QFYKVREINNY | 1020 |
| WP_029073316 | 928 | KD | KERFINRQIVETRQITKHVAQIISNHYET-------------TKVVTVRADLSHAFRERY | HIYKNRDINDF | 987 |
| WP_031589969 | 928 | KD | QERFINRQIVETRQITKHVAQIIDNHYEN-------------TKVVTVRADLSHQFRERY | HIYKNRDINDF | 987 |
| KDA45870 | 903 | KL | KERFIERQLVETRQITKYVAQLLDQRLN-YDGNGVELD-eKIAIVTLKAQLASQFRSEF | KLRKVRALNNL | 972 |
| WP_039099354 | 924 | -D | MKGFINRQLVETRQVIKLATNLLMEQYGED------------NIELITVKSGLTHQMRTEF | DFPKNRNLNNH | 990 |
| AKP02966 | 926 | KD | KLGFIHRQLVQTSQMVKGVANILNSMYK---NQGTCIQ-------ARANLSTAFRKAL | ELVKNRNINDF | 999 |
| WP_010991369 | 914 | AD | KARFIHRQLVETRQITKNVANILHQRFNYEKDDHGNTMK--QVRIVTLKSALVSQFRKQF | QLYKVRDVNDY | 984 |
| WP_033838504 | 914 | AD | KARFIHRQLVETRQITKNVANILHQRFNYEKDDHGNTMK--QVRIVTLKSALVSQFRKQF | QLYKVRDVNDY | 984 |

-continued

| ID | Pos1 | Seq1 | Seq2 | Seq3 | Pos2 |
|---|---|---|---|---|---|
| EHN60060 | 917 | AD | KARFIHRQLVETRQITKNVANILHQRFNYEKDDHGNTMK--QVRIVTLKSALVSQFRKQF | QLYKVRDVNDY | 987 |
| EFR89594 | 683 | AD | KARFIHRQLVETRQITKNVANILHQRFNYGKDDHGNTMK--QVRIVTLKSALVSQFRKQF | QLYKVRGVNDY | 753 |
| WP_038409211 | 914 | AD | KANFIQRQLVETRQITKNVANILHQRFNYGKDDHGNEVE--QVRIVTLKSTLVSQFRKQF | QLYKVREVNDY | 984 |
| EFR95520 | 533 | AD | KANFIQRQLVETRQITKNVANILYQRFNCKQDENGNEVE--QVRIVTLKSTLVSQFRKQF | QLYKVREVNDY | 603 |
| WP_003723650 | 914 | AD | KARFIHRQLVETRQITKNVANILYQRFNCKQDENGNEVE--QVRIVTLKSALVSQFRKQF | QLYKVREVNGY | 984 |
| WP_003727705 | 914 | AD | KARFIHRQLVETRQITKNVANILHQRFNKETDNHGNTME--QVRIVTLKSALVSQFRKQF | QLYKVREVNDY | 984 |
| WP_003730785 | 914 | AD | KARFIHRQLVETRQITKNVANILHQRFNKETDNHGNTME--QVRIVTLKSALVSQFRKQF | QLYKVREVNDY | 984 |
| WP_003733029 | 914 | AD | KARFIHRQLVETRQITKNVANILHQRFNYKTDGNKDTME--TVRIVTLKSALVSQFRKQF | QFYKVREVNDY | 984 |
| WP_003739838 | 914 | AD | KATFIHRQLVETRQITKNVANILHQRFNNETDNHGNNME--QVRIVMLKSALVSQFRKQF | QLYKVREVNDY | 984 |
| WP_014601172 | 914 | AD | KARFIHRQLVETRQITKNVANILHQRFNNETDNHGNTME--QVRIVTLKSALVSQFRKQF | QLYKVREVNDY | 984 |
| WP_023548323 | 914 | AD | KARFIHRQLVETRQITKNVANILHQRFNYKTDDNEDTME--PVRIVTLKSALVSQFRKQF | QLYKVREVNDY | 984 |
| WP_031665337 | 914 | AD | KARFIHRQLVETRQITKNVANILHQRFNKETDNHGNTME--QVRIVTLKSALVSQFRKQF | QLYKVREVNDY | 984 |
| WP_031669209 | 914 | AD | KARFIHRQLVETRQITKNVANILHQRFNYKTDGNKDTME--TVRIVTLKSALVSQFRKQF | QFYKVREVNDY | 984 |
| WP_033920898 | 914 | AD | KARFIHRQLVETRQITKNVANILHQRFNYKTDDNEDTME--PVRIVTLKSALVSQFRKQF | QLYKVREVNDY | 984 |
| AKI42028 | 917 | AD | KARFIHRQLVETRQITKNVANILHQRFNNETDNHGNTME--QVRIVTLKSALVSQFRKQF | QLYKVREVNDY | 987 |
| AKI50529 | 917 | AD | KARFIHRQLVETRQITKNVANILHQRFNYKTDDNEDTME--PVRIVTLKSALVSQFRKQF | QLYKVREVNDY | 987 |
| EFR83390 | 362 | AD | KARFIHRQLVETRQITKNVANILHQRFNNETDNHGNTME--QVRIVTLKSALVSQFRKQF | QLYKVREVNDY | 432 |
| WP_046323366 | 914 | AD | KARFIHRQLVETRQITKNVANILHQRFNCKDESGNVIE--QVRIVTLKAALVSQFRKQF | QLYKVREVNDY | 984 |
| AKE81011 | 927 | LD | KAGFIKRQLVETRQITKHVAQILDSRMNTKYDENDKLIR--EVKVITLKSKLVSDFRKDF | QFYKVREINNY | 997 |
| CUO82355 | 921 | RD | EERFINRQLVETRQITKNVTQIIEDHYST----------- --TKVAAIRANLSHEFRVKN | HIYKNRDINDY | 980 |
| WP_033162887 | 923 | KD | KERFINRQLVETRQIIKNVAVIINDHYTN----------- --TNIVTVRAELSHQFRERY | KIYKNRDINDF | 982 |
| AGZ01981 | 944 | LD | KAGFIKRQLVETRQITKHVAQILDSRMNTKYDENDKLIR--EVKVITLKSKLVSDFRKDF | QFYKVREINNY | 1014 |
| AKA60242 | 911 | LD | KAGFIKRQLVETRQITKHVAQILDSRMNTKYDENDKLIR--EVKVITLKSKLVSDFRKDF | QFYKVREINNY | 981 |
| AKS40380 | 911 | LD | KAGFIKRQLVETRQITKHVAQILDSRMNTKYDENDKLIR--EVKVITLKSKLVSDFRKDF | QFYKVREINNY | 981 |
| 4UN5_B | 915 | LD | KAGFIKRQLVETRQITKHVAQILDSRMNTKYDENDKLIR--EVKVITLKSKLVSDFRKDF | QFYKVREINNY | 985 |
| WP_010922251 | 982 | HHAHDAYLNAVGTALIKKYPKL-ESEFVYGDYKVYDV | S---EQEI--GK | ATAKY--F-FYSNIM-NFFKTEI | 1051 |
| WP_039695303 | 992 | HHAHDAYLNAVGTALLKKYPKL-ASEFVYGEYKKYDI | S---SD------ | KATAK--YfFYSNLM-NFFKTKVK | 1058 |

| | | | | |
|---|---|---|---|---|
| WP_045635197 | 984 | HHAHDAYLNAVVAKAILKKYPKL-EPEFVVGEYQKYDL | SkqpKEV---EK | ATEKY--F-FYSNLL-NFFKEEVH | 1055 |
| 5AXW_A | 703 | HHAHEDALI---------IaNADFIPKEWKKLDK | Nq-mFE----EK | ETEQEykEiFITPHQiKHiKDFKD | 771 |
| WP_009880683 | 666 | HHAHDAYLNAVVGTALIKKYPKL-ESEFVVGDYKVYDI | S---EQEi-GK | ATAKY--F-FYSNIM-NFFKTEIT | 735 |
| WP_010922251 | 982 | HHAHDAYLNAVVGTALIKKYPKL-ESEFVVGDYKVYDV | S---EQEi-GK | ATAKY--F-FYSNIM-NFFKTEIT | 1051 |
| WP_011054416 | 982 | HHAHDAYLNAVVGTALIKKYPKL-ESEFVVGDYKVYDV | S---EQEi-GK | ATAKY--F-FYSNIM-NFFKTEIT | 1051 |
| WP_011284745 | 982 | HHAHDAYLNAVVGTALIKKYPKL-ESEFVVGDYKVYDV | S---EQEi-GK | ATAKY--F-FYSNIM-NFFKTEIT | 1051 |
| WP_011285506 | 982 | HHAHDAYLNAVVGTALIKKYPKL-ESEFVVGDYKVYDV | S---EQEi-GK | ATAKY--F-FYSNIM-NFFKTEIT | 1051 |
| WP_011527619 | 982 | HHAHDAYLNAVVGTALIKKYPKL-ESEFVVGDYKVYDV | S---EQEi-GK | ATAKY--F-FYSNIM-NFFKTEIT | 1051 |
| WP_012560673 | 982 | HHAHDAYLNAVVGTALIKKYPKL-ESEFVVGDYKVYDI | S---EQEi-GK | ATAKY--F-FYSNIM-NFFKTEIT | 1051 |
| WP_014407541 | 981 | HHAHDAYLNAVVGTALIKKYPKL-ESEFVVGDYKVYDV | S---EQEi-GK | ATAKY--F-FYSNIM-NFFKTEIT | 1050 |
| WP_020905136 | 982 | HHAHDAYLNAVVGTALIKKYPKL-ESEFVVGDYKVYDV | S---EQEi-GK | ATAKY--F-FYSNIM-NFFKTEIT | 1051 |
| WP_023080005 | 981 | HHAHDAYLNAVVGTALIKKYPKL-ESEFVVGDYKVYDV | S---EQEi-GK | ATAKY--F-FYSNIM-NFFKTEIT | 1050 |
| WP_023610282 | 981 | HHAHDAYLNAVVGTALIKKYPKL-ESEFVVGDYKVYDV | S---EQEi-GK | ATAKY--F-FYSNIM-NFFKTEIT | 1050 |
| WP_030125963 | 982 | HHAHDAYLNAVVGTALIKKYPKL-ESEFVVGDYKVYDI | S---EQEi-GK | ATAKY--F-FYSNIM-NFFKTEIT | 1051 |
| WP_030126706 | 982 | HHAHDAYLNAVVGTALIKKYPKL-ESEFVVGDYKVYDV | S---EQEi-GK | ATAKY--F-FYSNIM-NFFKTEIT | 1051 |
| WP_031488318 | 982 | HHAHDAYLNAVVGTALIKKYPKL-ESEFVVGDYKVYDV | S---EQEi-GK | ATAKY--F-FYSNIM-NFFKTEIT | 1051 |
| WP_032460140 | 982 | HHAHDAYLNAVVGTALIKKYPKL-ESEFVVGDYKVYDV | S---EQEi-GK | ATAKY--F-FYSNIM-NFFKTEIT | 1051 |
| WP_032461047 | 982 | HHAHDAYLNAVVGTALIKKYPKL-ESEFVVGDYKVYDI | S---EQEi-GK | ATAKY--F-FYSNIM-NFFKTEIT | 1051 |
| WP_032462016 | 982 | HHAHDAYLNAVVGTALIKKYPKL-ESEFVVGDYKVYDV | S---EQEi-GK | ATAKY--F-FYSNIM-NFFKTEIT | 1051 |
| WP_032462936 | 982 | HHAHDAYLNAVVGTALIKKYPKL-ESEFVVGDYKVYDV | S---EQEi-GK | ATAKY--F-FYSNIM-NFFKTEIT | 1051 |
| WP_032464890 | 982 | HHAHDAYLNAVVGTALIKKYPKL-ESEFVVGDYKVYDV | S---EQEi-GK | ATAKY--F-FYSNIM-NFFKTEIT | 1051 |
| WP_033888930 | 807 | HHAHDAYLNAVVGTALIKKYPKL-ESEFVVGDYKVYDV | S---EQEi-GK | ATAKY--F-FYSNIM-NFFKTEIT | 876 |
| WP_038431314 | 982 | HHAHDAYLNAVVGTALIKKYPKL-ESEFVVGDYKVYDI | S---EQEi-GK | ATAKY--F-FYSNIM-NFFKTEIT | 1051 |
| WP_038432938 | 981 | HHAHDAYLNAVVGTALIKKYPKL-ESEFVVGDYKVYDV | S---EQEi-GK | ATAKY--F-FYSNIM-NFFKTEIT | 1050 |
| WP_038434062 | 982 | HHAHDAYLNAVVGTALIKKYPKL-ESEFVVGDYKVYDV | S---EQEi-GK | ATAKY--F-FYSNIM-NFFKTEIT | 1051 |
| BAQ51233 | 893 | HHAHDAYLNAVVGTALIKKYPKL-ESEFVVGDYKVYDV | S---EQEi-GK | ATAKY--F-FYSNIM-NFFKTEIT | 962 |
| KGE60162 | 157 | HHAHDAYLNAVVGTALIKKYPKL-ESEFVVGDYKVYDV | S---EQEi-GK | ATAKY--F-FYSNIM-NFFKTEIT | 226 |

| | | | | | |
|---|---|---|---|---|---|
| KGE60856 | | | | | |
| WP_002989955 | 982 | HHAHDAYLNAVVGTALIKKYPKL-ESEFVVGDYKVYDV | S---EQEi--GK | ATAKY--F-FYSNIM-NFFKTEIT | 1051 |
| WP_003030002 | 981 | HHAHDAYLNAVVGNALLLKYPQL-EPEFVVGEYGEYPKN- | S---YR----sRK | SATEK-FlFYSNIL-RFFKKE-- | 1041 |
| WP_003065552 | 992 | HHAHDAYLNAVVGTALLKKYPKL-ASEFVVGEYKKYDI | S---SD------ | KATAK-YfFYSNLM-NFFKRVIR | 1058 |
| WP_001040076 | 987 | HHAHDAYLNAVVAKAILTKYPQL-EPEFVVGDYPKYN- | S---YKT---RK | ATEKL--F-FYSNIM-NFFKTKVT | 1049 |
| WP_001040078 | 987 | HHAHDAYLNAVVAKAILTKYPQL-EPEFVVGLYRRKK- | L---SKI---VR | ATRKM--F-FYSNIM-NMFKRVVR | 1057 |
| WP_001040080 | 987 | HHAHDAYLNAVVAKAILTKYPQL-EPEFVVGDYPKYN- | S---YKT---RK | ATRKL--F-FYSNIM-NFFKTKVT | 1049 |
| WP_001040081 | 987 | HHAHDAYLNAVVAKAILTKYPQL-EPEFVVGDYPKYN- | S---YKT---RK | ATEKL--F-FYSNIM-NFFKTKVT | 1049 |
| WP_001040083 | 987 | HHAHDAYLNAVVAKAILTKYPQL-EPEFVVGDYPKYN- | S---YKT---RK | ATEKL--F-FYSNIM-NFFKTKVT | 1049 |
| WP_001040085 | 987 | HHAHDAYLNAVVAKAILTKYPQL-EPEFVVGDYPKYN- | S---YKT---RK | ATEKL--F-FYSNIM-NFFKTKVT | 1049 |
| WP_001040087 | 987 | HHAHDAYLNAVVAKAILTKYPQL-EPEFVVGDYPKYN- | S---YKT---RK | ATEKL--F-FYSNIM-NFFKTKVT | 1049 |
| WP_001040088 | 987 | HHAHDAYLNAVVAKAILTKYPQL-EPEFVVGDYPKYN- | S---YKT---RK | ATEKL--F-FYSNIM-NFFKTKVT | 1049 |
| WP_001040089 | 987 | HHAHDAYLNAVVAKAILTKYPQL-EPEFVVGDYPKYN- | S---YKT---RK | ATEKL--F-FYSNIM-NFFKTKVT | 1049 |
| WP_001040090 | 987 | HHAHDAYLNAVVAKAILTKYPQL-EPEFVVGDYPKYN- | S---YKT---RK | ATEKL--F-FYSNIM-NFFKTKVT | 1049 |
| WP_001040091 | 987 | HHAHDAYLNAVVAKAILTKYPQL-EPEFVVGDYPKYN- | S---YKT---RK | ATEKL--F-FYSNIM-NFFKTKVT | 1049 |
| WP_001040092 | 987 | HHAHDAYLNAVVAKAILTKYPQL-EPEFVVGDYPKYN- | S---YKT---RK | ATEKL--F-FYSNIM-NFFKTKVT | 1049 |
| WP_001040094 | 987 | HHAHDAYLNAVVAKAILTKYPQL-EPEFVVGDYPKYN- | S---YKT---RK | ATEKL--F-FYSNIM-NFFKTKVT | 1049 |
| WP_001040095 | 987 | HHAHDAYLNAVVAKAILTKYPQL-EPEFVVGDYPKYN- | S---YKT---RK | ATEKL--F-FYSNIM-NFFKTKVT | 1049 |
| WP_001040096 | 987 | HHAHDAYLNAVVAKAILTKYPQL-EPEFVVGDYPKYN- | S---YKT---RK | ATEKL--F-FYSNIM-NFFKTKVT | 1049 |
| WP_001040097 | 987 | HHAHDAYLNAVVAKAILTKYPQL-EPEFVVGDYPKYN- | S---YKT---RK | ATEKL--F-FYSNIM-NFFKTKVT | 1049 |
| WP_001040098 | 987 | HHAHDAYLNAVVAKAILTKYPQL-EPEFVVGDYPKYN- | S---YKT---RK | ATEKL--F-FYSNIM-NFFKTKVT | 1049 |
| WP_001040099 | 987 | HHAHDAYLNAVVAKAILTKYPQL-EPEFVVGDYPKYN- | S---YKT---RK | ATEKL--F-FYSNIM-NFFKTKVT | 1049 |
| WP_001040100 | 987 | HHAHDAYLNAVVAKAILTKYPQL-EPEFVVGDYPKYN- | S---YKT---RK | ATEKL--F-FYSNIM-NFFKTKVT | 1049 |
| WP_001040104 | 987 | HHAHDAYLNAVVAKAILTKYPQL-EPEFVVGDYPKYN- | S---YKT---RK | ATEKL--F-FYSNIM-NFFKTKVT | 1049 |
| WP_001040105 | 987 | HHAHDAYLNAVVAKAILTKYPQL-EPEFVVGDYPKYN- | S---YKT---RK | ATEKL--F-FYSNIM-NFFKTKVT | 1049 |
| WP_001040106 | 987 | HHAHDAYLNAVVAKAILTKYPQL-EPEFVVGDYPKYN- | S---YKT---RK | ATEKL--F-FYSNIM-NFFKTKVT | 1049 |
| WP_001040107 | 987 | HHAHDAYLNAVVAKAILTKYPQL-EPEFVVGDYPKYN- | S---YKT---RK | ATEKL--F-FYSNIM-NFFKTKVT | 1049 |

-continued

| | | | | | |
|---|---|---|---|---|---|
| WP_001040108 | 987 | HHAHDAYLNAVVAKAILTKYPQL-EREFVVGDYPKYN- | S---YKT---RK | ATEKL--F-FYSNIM-NFFKTKVT | 1049 |
| WP_001040109 | 987 | HHAHDAYLNAVVAKAILTKYPQL-EPEFVVGDYPKYN- | S---YKT---RK | ATEKL--F-FYSNIM-NFFKTKVT | 1049 |
| WP_001040110 | 987 | HHAHDAYLNAVVAKAILTKYPQL-EPEFVVGDYPKYN- | S---YKT---RK | ATEKL--F-FYSNIM-NFFKTKVT | 1049 |
| WP_015058523 | 987 | HHAHDAYLNAVVAKAILTKYPQL-EPEFVVGDYPKYN- | S---YKT---RK | ATEKL--F-FYSNIM-NFFKTKVT | 1049 |
| WP_017643650 | 987 | HHAHDAYLNAVVAKAILTKYPQL-EPEFVVGDYPKYN- | S---YKT---RK | ATEKL--F-FYSNIM-NFFKTKVT | 1049 |
| WP_017647151 | 987 | HHAHDAYLNAVVAKAILTKYPQL-EPEFVVGDYPKYN- | S---YKT---RK | ATEKL--F-FYSNIM-NFFKTKVT | 1049 |
| WP_017648376 | 987 | HHAHDAYLNAVVAKAILTKYPQL-EPEFVVGDYPKYN- | S---YKT---RK | ATEKL--F-FYSNIM-NFFKTKVT | 1049 |
| WP_017649527 | 987 | HHAHDAYLNAVVAKAILTKYPQL-EPEFVVGDYPKYN- | S---YKT---RK | ATEKL--F-FYSNIM-NFFKTKVT | 1049 |
| WP_017771611 | 987 | HHAHDAYLNAVVAKAILTKYPQL-EPEFVVGDYPKYN- | S---YKT---RK | ATEKL--F-FYSNIM-NFFKTKVT | 1049 |
| WP_017771984 | 987 | HHAHDAYLNAVVAKAILTKYPQL-EPEFVVGDYPKYN- | S---YKT---RK | ATEKL--F-FYSNIM-NFFKTKVT | 1049 |
| CFQ25032 | 987 | HHAHDAYLNAVVAKAILTKYPQL-EPEFVVGDYPKYN- | S---YKT---RK | ATEKL--F-FYSNIM-NFFKTKVT | 1049 |
| CFV16040 | 987 | HHAHDAYLNAVVAKAILTKYPQL-EPEFVVGDYPKYN- | S---YKT---RK | ATEKL--F-FYSNIM-NFFKTKVT | 1049 |
| KLJ37842 | 987 | HHAHDAYLNAVVAKAILTKYPQL-EPEFVVGDYPKYN- | S---YKT---RK | ATEKL--F-FYSNIM-NFFKTKVT | 1049 |
| KLJ72361 | 987 | HHAHDAYLNAVVAKAILTKYPQL-EPEFVVGDYPKYN- | S---YKT---RK | ATEKL--F-FYSNIM-NFFKTKVT | 1049 |
| KLL20707 | 1001 | HHAHDAYLNAVVAKAILTKYPQL-EPEFVVGDYPKYN- | S---YKT---RK | ATEKL--F-FYSNIM-NFFKTKVT | 1063 |
| KLL42645 | 987 | HHAHDAYLNAVVAKAILTKYPQL-EPEFVVGDYPKYN- | S---YKT---RK | ATEKL--F-FYSNIM-NFFKTKVT | 1049 |
| WP_047207273 | 987 | HHAHDAYLNAVVAKAILTKYPQL-EPEFVVGDYPKYN- | S---YKT---RK | ATEKL--F-FYSNIM-NFFKTKVT | 1049 |
| WP_047209694 | 987 | HHAHDAYLNAVVAKAILTKYPQL-EPEFVVGDYPKYN- | S---YKT---RK | ATEKL--F-FYSNIM-NFFKTKVT | 1049 |
| WP_050198062 | 987 | HHAHDAYLNAVVAKAILTKYPQL-EPEFVVGDYPKYN- | S---YKT---RK | ATEKL--F-FYSNIM-NFFKTKVT | 1049 |
| WP_050201642 | 987 | HHAHDAYLNAVVAKAILTKYPQL-EPEFVVGDYPKYN- | S---YKT---RK | ATEKL--F-FYSNIM-NFFKTKVT | 1049 |
| WP_050204027 | 987 | HHAHDAYLNAVVAKAILTKYPQL-EPEFVVGDYPKYN- | S---YKT---RK | ATEKL--F-FYSNIM-NFFKTKVT | 1049 |
| WP_050881965 | 987 | HHAHDAYLNAVVAKAILTKYPQL-EPEFVVGDYPKYN- | S---YKT---RK | ATEKL--F-FYSNIM-NFFKTKVT | 1049 |
| WP_050886065 | 987 | HHAHDAYLNAVVAKAILTKYPQL-EPEFVVGDYPKYN- | S---YKT---RK | ATEKL--F-FYSNIM-NFFKTKVT | 1049 |
| AHN30376 | 987 | HHAHDAYLNAVVAKAILTKYPQL-EPEFVVGDYPKYN- | S---YKT---RK | ATEKL--F-FYSNIM-NFFKTKVT | 1049 |
| EAO78426 | 987 | HHAHDAYLNAVVAKAILTKYPQL-EPEFVVGDYPKYN- | S---YKT---RK | ATEKL--F-FYSNIM-NFFKTKVT | 1049 |
| CCW42055 | 987 | HHAHDAYLNAVVAKAILTKYPQL-EPEFVVGDYPKYN- | S---YKT---RK | ATEKL--F-FYSNIM-NFFKTKVT | 1049 |
| WP_003041502 | 981 | HHAHDAYLNAVIGTALLKKYPKL-ASEFVVGEFKKYDV | S---DK---eIG | KATAK--YfFYSNLM-NFFKKEVK | 1050 |

```
WP_037593752  982  HHAHDAYLNAVVGNALLLKYPQL-EPEFVVGEYPKYN-  S---YR---sRK  SATEK--FlFYSNIL-RPFKKE--  1042
WP_049516684  982  HHAHDAYLNAVVGNALLLKYPQL-EPEFVVGEYPKYN-  S---YR---sRK  SATEK--FlFYSNIL-RPFKKE--  1042
GAD46167      981  HHAHDAYLNAVVGNALLLKYPQL-EPEFVVGEYPKYN-  S---YR---sRK  SATEK--FlFYSNIL-RPFKKE--  1041
WP_018363470  990  HHAHDAYLNAVVGTALLKKYPKL-APEFVVGEYKKYDV  S---SDDhseMG  KATAK--YfFYSNLM-NFFKRVIR  1062
WP_003043819  991  HHAHDAYLNAVVGTALIKKYPKL-ESEFVVGDYKVYDV  S---EQEi--GK  ATAKR--F-FYSNIM-NFFKTEVK  1060
WP_006269658  981  HHAHDAYLNAVVGNALLLKYPQL-EPEFVVGEYPKYN-  S---YR---sRK  SATEK--FlFYSNIL-RPFKKE--  1041
WP_048800889  981  HHAHDAYLNAVVGTALIKKYTKL-TSEFVYGEYKKYDV  S---DND--eIG  KATAK--YfFYSNLM-NFFKTEVK  1051
WP_012767106  981  HHAHDAYLNAVVGTALIKKYPKL-ESEFVYGDYKVYDV  S---EQEi--GK  ATAKR--F-FYSNIM-NFFKTEIT  1050
WP_014612333  981  HHAHDAYLNAVVGTALIKKYPKL-ESEFVYGDYKVYDV  S---EQEi--GK  ATAKR--F-FYSNIM-NFFKTEIT  1050
WP_015017095  981  HHAHDAYLNAVVGTALIKKYPKL-ESEFVYGDYKVYDV  S---EQEi--GK  ATAKR--F-FYSNIM-NFFKTEIT  1050
WP_015057649  981  HHAHDAYLNAVVGTALIKKYPKL-ESEFVYGDYKVYDV  S---EQEi--GK  ATAKR--F-FYSNIM-NFFKTEIT  1050
WP_048272215  981  HHAHDAYLNAVVGTALIKKYPKL-ESEFVYGDYKVYDV  S---EQEi--GK  ATAKR--F-FYSNIM-NFFKTEIT  1050
WP_049519324  981  HHAHDAYLNAVVAKAILGKYPQL-APEFVVGDYPKYN-  S---EQEi--GK  ATQKM--L-FYSNIL-KFFKDQES  1043
WP_012515931  981  HHAHDAYLNAVVAKAILGKYPQL-APEFVVGDYPKYN-  S---FKEr--QK  ATQKT--L-FYSNIL-KFFKDQES  1043
wP_021320964  981  HHAHDAYLNAVVAKAILGKYPQL-APEFVVGDYPKYN-  S---FKEr--QK  ATQKT--L-FYSNIL-KFFKDQES  1043
WP_037581760  981  HHAHDAYLNAVVGTALIKKYPKL-APEFVVGDYPKYN-  S---FKEr--QK  ATQKT--L-FYSNIL-KFFKDQES  1061
WP_004232481  989  HHAQDAYLNAVVGTALLKKYPKL-APEFVVGEYKKYDV  S---SDNhseLG  KATAK--YfFYSNLM-NFFKTEVK  1056
WP_009854540  990  HHAQDAYLNAVVGTALLKKYPKL-APEFVVGEYKKYDI  S---SD-----   KATAK--YfFYSNLM-NFFKTKVK  1056
WP_012962174  990  HHAQDAYLNAVVGTALLKKYPKL-APEFVVGEYKKYDI  S---GD-----   KATAK--YfFYSNLM-NFFKRVIR  1058
WP_039695303  992  HHAQDAYLNAVVGTALLKKYPKL-ASEFVVGEYKKYDI  S---SD-----   KATAK--YfFYSNLM-NFFKTKVK  1061
WP_014334983  989  HHAQDAYLNAVVGTALLKKYPKL-TPEFVVGEYKKYDV  S---SDDyseMG  KATAK--YfFYSNLM-NFFKTEVK  1051
WP_003092269  982  HHAQDAYLNAVVGTALLKKYPKL-EAEFVVGDYKHYDL  P---DSSl--GK  ATTRM--F-FYSNLM-NFFKKEIK  1051
AHY15608      982  HHAQDAYLNAVVGTALLKKYPKL-EAEFVVGDYKHYDL  P---DSSl--GK  ATTRM--F-FYSNLM-NFFKKEIK  1051
AHY17476      982  HHAQDAYLNAVVGTALLKKYPKL-EAEFVVGDYKHYDL  P---DSSl--GK  ATTRM--F-FYSNLM-NFFKKEIK  1051
ESR09100           -------------------------------------  ------------  ------------------------
AGM98575      982  HHAQDAYLNAVVGTALLKKYPKL-EAEFVVGDYKHYDL  P---DSSl--GK  ATAKK--F-FYSNIM-NFFKKEIK  1051
ALF27331      982  HHAHDAYLNAVIGKALLGVVPQL-EPEFVVGDYPHFH-  G---HK---eNK  ATAKK--F-FYSNIM-NFFKKD--  1041
```

| | | | | | |
|---|---|---|---|---|---|
| WP_018372492 | 995 | HHAHDAYLNAVVAQALLKVYPKF-ERELVYGSYVKESI | ----FS----RK | ATERM---rMYNNIL-KFISKD-- | 1055 |
| WP_045618028 | 985 | HHAHDPYLNAVVAKAILKKYPKL-EPEFVVGDYQKYDL | TkdpKEV---EK | ATEKY--F-FYSNLL-NFFKEEVH | 1056 |
| WP_045635197 | 984 | HHAHDPYLNAVVAKAILKKYPKL-EPEFVVGEYQKYDL | SkdpKEV---EK | ATEKY--F-FYSNLL-NFFKEEVH | 1055 |
| WP_002263549 | 982 | HHAHDAYLNAVIGKALLGVYPQL-EPEFVVGDYPHFH | G---HK---eNK | ATAKK--F-FYSNIM-NFFKKD-- | 1041 |
| WP_002263887 | 982 | HHAHDAYLNAVIGKALLGVYPQL-EPEFVVGDYPHFH | G---HK---eNK | ATAKK--F-FYSNIM-NFFKKD-- | 1041 |
| WP_002264920 | 982 | HHAHDAYLNAVIGKALLGVYPQL-EPEFVVGDYPHFH | G---HK---eNK | ATAKK--F-FYSNIM-NFFKKD-- | 1041 |
| WP_002269043 | 982 | HHAHDAYLNAVIGKALLGVYPQL-EPEFVVGDYPHFH | G---HK---eNK | ATAKK--F-FYSNIM-NFFKKD-- | 1041 |
| WP_002269448 | 982 | HHAHDAYLNAVIGKALLGVYPQL-EPEFVVGDYPHFH | G---HK---eNK | ATAKK--F-FYSNIM-NFFKKD-- | 1041 |
| WP_002271977 | 982 | HHAHDAYLNAVIGKALLGVYPQL-EPEFVVGDYPHFH | G---HE---eNK | ATAKK--F-FYSNIM-NFFKKD-- | 1041 |
| WP_002272766 | 982 | HHAHDAYLNAVIGKALLGVYPQL-EPEFVVGDYPHFH | G---HK---eNK | ATAKK--F-FYSNIM-NFFKKD-- | 1041 |
| WP_002273241 | 982 | HHAHDAYLNAVIGKALLGVYPQL-EPEFVVGDYPHFH | G---HE---eNK | ATAKK--F-FYSNIM-NFFKKD-- | 1041 |
| WP_002275430 | 982 | HHAHDAYLNAVIGKALLGVYPQL-EPEFVVGDYPHFH | G---HK---eNK | ATAKK--F-FYSNIM-NFFKKD-- | 1041 |
| WP_002276448 | 984 | HHAHDAYLNAVVVKALLVKYPKL-EPEFVVGDYPHFH | S---YR---eRK | ATQKM--F-FYSNIM-NMFKSKVK | 1046 |
| WP_002277050 | 982 | HHAHDAYLNAVIGKALLGVYPQL-EPEFVVGEYPKYN | G---HK---eNK | ATAKK--F-FYSNIM-NFFKKD-- | 1041 |
| WP_002277364 | 982 | HHAHDAYLNAVIGKALLGVYPQL-EPEFVVGDYPHFH | G---HK---eNK | ATAKK--F-FYSNIM-NFFKKD-- | 1041 |
| WP_002279025 | 982 | HHAHDAYLNAVIGKALLGVYPQL-EPEFVVGDYPHFH | G---HE---eNK | ATAKK--F-FYSNIM-NFFKKD-- | 1041 |
| WP_002279859 | 982 | HHAHDAYLNAVIGKALLGVYPQL-EPEFVVGDYPHFH | G---HK---eNK | ATAKK--F-FYSNIM-NFFKKD-- | 1041 |
| WP_002280230 | 982 | HHAHDAYLNAVIGKALLGVYPQL-EPEFVVGDYPHFH | G---HK---eNK | ATAKK--F-FYSNIM-NFFKKD-- | 1041 |
| WP_002281696 | 984 | HHAHDAYLNAVVVKALLVKYPKL-EPEFVVGEYPKYN | S---YR---eRK | ATQKM--F-FYSNIM-NMFKSKVK | 1046 |
| WP_002282247 | 982 | HHAHDAYLNAVIGKALLGVYPQL-EPEFVVGDYPHFH | G---HK---eNK | ATAKK--F-FYSNIM-NFFKKD-- | 1041 |
| WP_002282906 | 982 | HHAHDAYLNAVIGKALLGVYPQL-EPEFVVGDYPHFH | G---HK---eNK | ATAKK--F-FYSNIM-NFFKKD-- | 1041 |
| WP_002283846 | 982 | HHTHDAYLNAVIGKALLGVYPQL-EPEFVVGDYPHFH | G---HK---eNK | ATAKK--F-FYSNIM-NFFKKD-- | 1041 |
| WP_002287255 | 982 | HHAHDAYLNAVIGKALLGVYPQL-EPEFVVGDYPHFH | G---HK---eNK | ATAKK--F-FYSNIM-NFFKKD-- | 1041 |
| WP_002288990 | 982 | HHAHDAYLNAVIGKALLGVYPQL-EPEFVVGDYPHFH | G---HK---eNK | ATAKK--F-FYSNIM-NFFKKD-- | 1041 |
| WP_002289641 | 982 | HHAHDAYLNAVIGKALLGVYPQL-EPEFVVGDYPHFH | G---HK---eNK | ATAKK--F-FYSNIM-NFFKKD-- | 1041 |
| WP_002290427 | 982 | HHAHDAYLNAVIGKALLGVYPQL-EPEFVVGDYPHFH | G---HK---eNK | ATAKK--F-FYSNIM-NFFKKD-- | 1041 |
| WP_002295753 | 982 | HHAHDAYLNAVIGKALLGVYPQL-EPEFVVGDYPHFH | G---HK---eNK | ATAKK--F-FYSNIM-NFFKKD-- | 1041 |

| | | | | | |
|---|---|---|---|---|---|
| WP_002296423 | 982 | HHAHDAYLNAVIGKALLGVYPQL-EPEFVVGDYPHFH- | G---HK---eNK | ATAKK--F-FYSNIM-NFFKKD-- | 1041 |
| WP_002304487 | 996 | HHAHDAYLNAVIGKALLGVYPQL-EPEFVVGDYPHFH- | G---HK---eNK | ATAKK--F-FYSNIM-NFFKKKG-- | 1055 |
| WP_002305844 | 982 | HHAHDAYLNAVIGKALLGVYPQL-EPEFVVGDYPHFH- | G---HK---eNK | ATAKK--F-FYSNIM-NFFKKD-- | 1041 |
| WP_002307203 | 982 | HHAHDAYLNAVIGKALLGVYPQL-EPEFVVGDYPHFH- | G---HK---eNK | ATAKK--F-FYSNIM-NFFKKD-- | 1041 |
| WP_002310390 | 982 | HHAHDAYLNAVIGKALLGVYPQL-EPEFVVGDYPHFH- | G---HK---eNK | ATAKK--F-FYSNIM-NFFKKD-- | 1041 |
| WP_002352408 | 982 | HHAHDAYLNAVIGKALLGVYPQL-EPEFVVGDYPHFH- | G---HK---eNK | ATAKK--F-FYSNIM-NFFKKD-- | 1041 |
| WP_012997688 | 982 | HHAHDAYLNAVIGKALLGVYPQL-EPEFVVGDYPHFH- | G---HK---eNK | ATAKK--F-FYSNIM-NFFKKD-- | 1041 |
| WP_014677909 | 982 | HHAHDAYLNAVIGKALLGVYPQL-EPEFVVGDYPHFH- | G---HK---eNK | ATAKK--F-FYSNIM-NFFKKD-- | 1041 |
| WP_019312892 | 982 | HHAHDAYLNAVIGKALLGVYPQL-EPEFVVGDYPHFH- | G---HK---eNK | ATAKK--F-FYSNIM-NFFKKD-- | 1041 |
| WP_019313659 | 982 | HHAHDAYLNAVIGKALLGVYPQL-EPEFVVGDYPHFH- | G---HK---eNK | ATAKK--F-FYSNIM-NFFKKD-- | 1041 |
| WP_019314093 | 982 | HHAHDAYLNAVIGKALLGVYPQL-EPEFVVGDYPHFH- | G---HK---eNK | ATAKK--F-FYSNIM-NFFKKD-- | 1041 |
| WP_019315370 | 982 | HHAHDAYLNAVIGKALLGVYPQL-EPEFVVGDYPHFH- | G---HE---eNK | ATAKK--F-FYSNIM-NFFKKD-- | 1041 |
| WP_019803776 | 982 | HHAHDAYLNAVIGKALLGVYPQL-EPEFVVGDYPHFH- | G---HK---eNK | ATAKK--F-FYSNIM-NFFKKD-- | 1041 |
| WP_019805234 | 984 | HHAHDAYLNAVIGKALLGVYPQL-EPEFVVGDYPHFH- | G---HK---eNK | ATAKK--F-FYSNIM-NFFKKD-- | 1041 |
| WP_024783594 | 982 | HHAHDAYLNAVIGKALLGVYPQL-EPEFVVGDYPHFH- | G---HK---eNK | ATAKK--F-FYSNIM-NFFKKD-- | 1041 |
| WP_024784288 | 984 | HHAHDAYLNAVVKALLVKYPKL-EPEFVVYGEYLKYN- | S---YR---eRK | ATQKM--F-FYSNIM-NMFKSKVK | 1046 |
| WP_024784666 | 982 | HHAHDAYLNAVIGKALLGVYPQL-EPEFVVGDYPHFH- | G---HK---eNK | ATAKK--F-FYSNIM-NFFKKD-- | 1041 |
| WP_024784894 | 984 | HHAHDAYLNAVVKALLVKYPKL-EPEFVVGEYPKYN- | S---YR---eRK | ATQKM--F-FYSNIM-NMFKSKVK | 1046 |
| WP_024786433 | 982 | HHAHDAYLNAVIGKALLGVYPQL-EPEFVVGDYPHFH- | G---HK---eNK | ATAKK--F-FYSNIM-NFFKKD-- | 1041 |
| WP_049473442 | 982 | HHAHDAYLNAVIGKALLGVYPQL-EPEFVVGDYPHFH- | G---HK---eNK | ATAKK--F-FYSNIM-NFFKKD-- | 1041 |
| WP_049474547 | 975 | HHAHDAYLNAVIGKALLGVYPQL-EPEFVVGDYPHFH- | G---HK---eNK | ATAKK--F-FYSNIM-NFFKKD-- | 1034 |
| EMC03581 | 987 | HHAHDAYLNAVVAKAILKKYPKL-EPEFVVGDYQKYDL | SkdpKEI---EK | ATEKY--F-FYSNLL-NFFKEEVH | 1058 |
| WP_000428612 | 985 | HHAHDAYLNAVVAKAILKKYPKL-EPEFVVGDYQKYDL | SmpKEV---EK | ATEKY--F-FYSNLL-NFFKEEVH | 1056 |
| WP_000428613 | 980 | HHAHDAYLNAVVGTALLKKYPKL-EPEFVVGDYQKYDL | TkdpKEI---EK | ATEKY--F-FYSNIM-NFFKDKVY | 1051 |
| WP_049523028 | 951 | HHAHDAYLNAVVGTALLKKYPKL-EAEFVVGDYKHYDL | S---DTS1--GK | ATAKM--F-FYSNIM-NFFKKEVR | 1020 |
| WP_003107102 | 983 | HHAHDAYLNAVVGTALLKMYPKL-ASEFVVGDYQKYDL | S---GKAs--GH | ATAKY--F-FYSNLM-NFFKSEVK | 1052 |
| WP_054279288 | | | | | |

| | | | | |
|---|---|---|---|---|
| WP_049531101 | 985 | HHAHDAYLNAVVAKAILKKYPKL-EPEFVVGDYQKYDL | SrdpKEI---EK | ATEKY--F-FYSNLL-NFFKEEVH | 1056 |
| WP_049538452 | 985 | HHAHDAYLNAVVAKAILKKYPKL-EPEFVVGDYQKYDL | SkdpKDI---EK | ATEKY--F-FYSNLL-NFFKEEVH | 1056 |
| WP_049549711 | 987 | HHAHDAYLNAVVAKAILKKYPKL-EPEFVVGDYQKNDL | SkdpKDI---EK | ATEKY--F-FYSNLL-NFFKEEVH | 1058 |
| WP_007896501 | 988 | HHAHDAYLNAVVGTALLKKYPKL-EAEFVVGDYKHFDL | S---DPsl--GK | ATAKV--F-FYSNIM-NFFKEELS | 1057 |
| EFR44625 | 940 | HHAHDAYLNAVVGTALLKKYPKL-EAEFVVGDYKHFDL | S---DPsl--GK | ATAKV--F-FYSNIM-NFFKEELS | 1009 |
| WP_002897477 | 984 | HHAHDAYLNAVVAKAILKKYPKL-EPEFVVGDYQKYDL | FkpsKEI---EK | ATEKY--F-FYSNLL-NFFKEEVL | 1055 |
| WP_002906454 | 984 | HHAHDAYLNAVVAKAILKKYPKL-EPEFVVGDYQKYDL | SkasNTI---DK | ATEKY--F-FYSNLL-NFFKEKVR | 1055 |
| WP_009729476 | 985 | HHAHDAYLNAVVAKAILKKYPKL-EPEFVVGDYQKYDL | SkdpKEI---EK | ATEKY--F-FYSNLL-NFFKEEVH | 1056 |
| CQR24647 | 984 | HHAHDAYLNAVVAKALLIRYPKL-EPEFVYGEYPKYN- | S---YRE---RK | ATEKM--F-FYSNIM-NMFKTTIK | 1046 |
| WP_000066813 | 989 | HHAHDAYLNAVLAKAILKKYPKL-EPEFVVGDYQKYDL | SrepKEV---EK | ATQKY--F-FYSNLL-NFFKEEVH | 1060 |
| WP_009754323 | 985 | HHAHDAYLNAVVAKAILKKYPKL-EPEFVVGDYQKYDL | SkdpKEV---EK | ATEKY--F-FYSNIM-NFFKEEVH | 1056 |
| WP_044674937 | 986 | HHAHDAYLNAVVATALLKKYPQL-APEFVVGDYPKYN- | S---YKS---RK | ATEKV--L-FYSNIM-NFFRRVLV | 1048 |
| WP_044676715 | 988 | HHAHDAYLNAVVATALLKKYPQL-APEFVVGDYPKYN- | S---YKS---RK | ATEKV--L-FYSNIM-NFFRRVLV | 1050 |
| WP_044680361 | 988 | HHAHDAYLNAVVATALLKKYPQL-APEFVVGDYPKYN- | S---YKS---RK | ATEKV--L-FYSNIM-NFFRRVLV | 1050 |
| WP_044681799 | 986 | HHAHDAYLNAVVATALLKKYPQL-APEFVVGDYPKYN- | S---YKS---RK | ATEKV--L-FYSNIM-NFFRRVLV | 1048 |
| WP_049533112 | 981 | HHAHDAYLNAVIGTALLKKYPKL-ASEFVYGEFKKYDV | S---DK---eIG | KATAK--YfFYSNLM-NFFKKEVK | 1050 |
| WP_029090905 | 952 | HHAQDAFLVAFLGTNITSNYPKI-EMEYLFKGYQHYLN | ------Ev--GK | AAKPKftF-IVENLS-------- | 1007 |
| WP_006506696 | 977 | HHAHDAYIVALIGGFMRDRYPNMhDSKAVYSEYMKMFR | ------NKNq-QK | ------g---FVINSM-NYPY-EV- | 1038 |
| AIT42264 | 982 | HHAHDAYLNAVVGTALIKKYPKL-ESEFVVGDYKVYDV | S---EQEi--GK | ATAKY--F-FYSNIM-NFFKTEIT | 1051 |
| WP_034440723 | 981 | HHAHDAYLNGVIALKLLELYPYM-AKDLIYGKYSYHRK | G--------DK | ATQAK--Y-KMSNII-ERFSQDL- | 1041 |
| AKQ21048 | 982 | HHAHDAYLNAVVGTALIKKYPKL-ESEFVVGDYKVYDV | S---EQEi--GK | ATAKY--F-FYSNIM-NFFKTEIT | 1051 |
| WP_004636532 | 981 | HHGQDAYLNAVVATTIMKVYPNL-KPQFVVGQYKKTSM | S---FKE---EK | ATARK--H-FYSNIT-KFFKKEKV | 1042 |
| WP_002364836 | 988 | HHGQDAYLNCVVATTLLKVYPNL-APEFVVGEYPKFQT | ----FKE---NK | ATAKA--I-IYTNLL-RFFTED-- | 1047 |
| WP_016631044 | 939 | HHAHDAYLNGVVAIALLKKYPKL-APEFVVGEYPKFQT | ----AT---eNK | ATAKT--I-IYTNLL-RFFTED-- | 998 |
| EMS75795 | 723 | HHGQDAYLNCVVATTLLKVYPNL-APEFVVGNYTKFNL | ----FKE---NK | ATAKK--E-FYSNIL-RFFKEKE- | 782 |
| WP_002373311 | 988 | HHGQDAYLNCVVATTLLKVYPNL-APEFVVGEYPKFQA | ----FKE---NK | ATAKT--I-IYTNLM-RFFTED-- | 1047 |
| WP_002378009 | 988 | HHGQDAYLNCVVATTLLKVYPNL-APEFVVGEYPKFQT | ----FKE---NK | ATAKA--I-IYTNLL-RFFTED-- | 1047 |

```
-continued

WP_002407324  988   HHGQDAYLNCVVATTLLKVYPNL-APEFVVGEYPKFQT  ----FKE---NK  ATAKA--I-IYTNLL-RFFTED-  1047
WP_002413717  988   HHGQDAYLNCVVATTLLKVYPNL-APEFVVGEYPKFQT  ----FKE---NK  ATAKA--I-IYTNLL-RFFTED-  1047
WP_010775580  990   HHGQDAYLNCVVATTLLKVYPNL-APEFVVGEYPKFQA  ----FKE---NK  ATAKA--I-IYTNLL-RFFTED-  1049
WP_010818269  988   HHGQDAYLNCVVATTLLKVYPNL-APEFVVGEYPKFQT  ----FKE---NK  ATAKA--I-IYTNLM-RFFTED-  1047
WP_010824395  988   HHGQDAYLNCVVATTLLKVYPNL-APEFVVGEYPKFQT  ----FKE---NK  ATAKT--I-IYTNLL-RFFTED-  1047
WP_016622645  988   HHGQDAYLNCVVATTLLKVYPNL-APEFVVGEYPKFQT  ----FKE---NK  ATAKA--I-IYTNLL-RFFTED-  1047
WP_033624816  988   HHGQDAYLNCVVATTLLKVYPNL-APEFVVGEYPKFQA  ----FKE---NK  AMAKA--I-IYTNLL-RFFTED-  1047
WP_033625576  988   HHGQDAYLNCVVATTLLKVYPNL-APEFVVGEYPKFQA  ----FKE---NK  ATAKA--I-IYTNLL-RFFTEV-  1047
WP_033789179  988   HHGQDAYLNCVVATTLLKVYPNL-APEFVVGEYPKFQA  ----FKE---NK  ATAKA--I-IYTNLL-RFFTED-  1047
WP_002310644  989   HHAHDAYLNGVVALALLKKYPQL-APEFVVGEYLKFNA  ----HK---aNK  ATVKK--E-FYSNIM-KFFESD-  1048
WP_002312694  990   HHAHDAYLNGVVALALLKKYPQL-APEFVVGEYLKFNA  ----HK---aNK  ATVKK--E-FYSNIM-KFFESD-  1049
WP_002314015  990   HHAHDAYLNGVVALALLKKYPQL-APEFVVGEYLKFNA  ----HK---aNK  ATVKK--E-FYSNIM-KFFESD-  1049
WP_002320716  990   HHAHDAYLNGVVALALLKKYPQL-APEFVVGEYLKFNA  ----HK---aNK  ATVKK--E-FYSNIM-KFFESD-  1049
WP_002330729  989   HHAHDAYLNGFIANVLLKKYPQL-APEFVVGEYLKFNA  ----HK---aNK  ATVKK--E-FYSNIM-KFFESD-  1048
WP_002335161  990   HHAHDAYLNGFIANVLLKKYPQL-APEFVVGEYLKFNA  ----HK---aNK  ATVKK--E-FYSNIM-KFFESD-  1049
WP_002345439  990   HHAHDAYLNGFIANVLLKKYPQL-APEFVVGEYLKFNA  ----HK---aNK  ATVKK--E-FYSNIM-KFFESD-  1049
WP_034867970  980   HHAHDAYLNGVIALALLKKYPKL-APEFVVGKYVKYSL  ----AR---eNK  ATAKK--E-FYSNIL-KFFESD-  1039
WP_047937432  990   HHAHDAYLNGFIANVLLKKYPQL-APEFVVGEYLKFNA  ----HK---aNK  ATAKK--E-FYSNIL-KFFESD-  1049
WP_010720994  980   HHAHDAYLNGFIANVLLKRYPKL-APEFVVGKYVKYSL  ----AR---eNK  ATAKK--E-FYSNIL-KFLESD-  1039
WP_010737004  980   HHAHDAYLNGFIANVLLKRYPKL-APEFVVGKYVKYSL  ----AR---eNK  ATAKK--E-FYSNIL-KFLESD-  1039
WP_034700478  980   HHAHDAYLNGFIANVLLKRYPKL-APEFVVGKYVKYSL  ----AR---eNK  ATAKK--E-FYSNIL-KFLESD-  1039
WP_007209003  978   HHAHDAYLNAVVALSLLRVVPQL-KPEFVVGEYGKNS-  ----IHDq--NK  ATIKK---qFYSNIT-RYFASK-  1037
WP_023519017  974   HHGHDAYLNGVVAMTLLKKYPKL-APEFVVGKYIKGDI  ----NQ---iNK  ATAKK--E-FYSNIM-KFFESE-  1033
WP_010770040  986   HHAHDAYLNGVVANSLLRVVPQL-QPEFVVGDYPKFNA  ----YKA---NK  ATAKK--Q-LYTNIM-KFFAED-  1045
WP_048604708  983   HHAHDAYLNGVVATALLKIYPQL-EPEFVVGEFHRFNA  ----FKE---NK  ATAKK--Q-FYSNLM-EFSKSD-  1042
WP_010750235  983   HHAHDAYLNAVVALALLKKYPRL-APEFVVGSFAKFHL  ----VK---eNK  ATAKK--E-FYSNIL-KFFEKE-  1042
AII16583      1021  HHAHDAYLNAVVGTALIKKYPKL-ESEFVVGDYKVYDV  S---EQEi--GK  ATAKY--F-FYSNIM-NFFKTEIT 1090
```

| | | -continued | | |
|---|---|---|---|---|
| WP_029073316 | 988 | HHAHDAYIATILGTYIGHRPESL-DAKYIYGEYQKIFR | ---NKNk---DK | ---KDg----FILNSM-RNLYADK- | 1052 |
| WP_031589969 | 988 | HHAHDAYIATILGTYIGHRPESL-DAKYIYGEYKRIFR | ---QKNk---GK | ---NDg----FILNSM-RNIYADK- | 1052 |
| KDA45870 | 973 | HHAHDAYLNAVVANLIMAKYPEL-EPEFVVGKYRKTK- | ----FKGl--GK | ATAKN---tLYANVL-YPLKENEV | 1034 |
| WP_039099354 | 991 | HHAFDAYLTAPVGLYLLKRYPKL-KPYFVVGEYQKAS- | ----QQ----DK | ---RN--F----NFL-NGLKKD-- | 1043 |
| AKP02966 | 1000 | HHAQDAYLASFLGTYRLRFPPTD-EMLLMNGEYNKFYG | -----KElysKK | -SRKN-gF-IISPLV--------- | 1062 |
| WP_010991369 | 985 | HHAHDAYLNGVVANTLLKVYPQL-EPEFVVGDYHQFDW | ----FKA---NK | ATAKK---Q-FYTNIM-LFFAQK- | 1044 |
| WP_033838504 | 985 | HHAHDAYLNGVVANTLLKVYPQL-EPEFVVGDYHQFDW | ----FKA---NK | ATAKK---Q-FYTNIM-LFFAQK- | 1044 |
| EHN60060 | 988 | HHAHDAYLNGVVANTLLKVYPQL-EPEFVVGDYHQFDW | ----FKA---NK | ATAKK---Q-FYTNIM-LFFAQK- | 1047 |
| EFR89594 | 754 | HHAHDAYLNGVVANTLLKVYPQL-EPEFVVGDYHQFDW | ----FKA---NK | ATAKK---Q-FYTNIM-LFFAQK- | 813 |
| WP_038409211 | 985 | HHAHDAYLNGVVANTLLKVYPQL-EPEFVVGDYHQFDW | ----FKA---NK | ATAKK---Q-FYTNIM-RFFAKE- | 1044 |
| EFR95520 | 604 | HHAHDAYLNGVVANTLLKVYPQL-EPEFVVGDYHQFDW | ----FKA---NK | ATAKK---Q-FYTNIM-RFFAKE- | 663 |
| WP_003723650 | 985 | HHAHDAYLNGVVANTLLKVYPQL-EPEFVVGDYHQFDW | ----FKA---NK | ATAKK---Q-FYTNIM-LFFAQK- | 1044 |
| WP_003727705 | 985 | HHAHDAYLNGVVANTLLKVYPQL-EPEFVVGDYHQFDW | ----FKA---NK | ATAKK---Q-FYTNIM-LFFAQK- | 1044 |
| WP_003730785 | 985 | HHAHDAYLNGVVANTLLKVYPQL-EPEFVVGDYHQFDW | ----FKA---NK | ATAKK---Q-FYTNIM-LFFAQK- | 1044 |
| WP_003733029 | 985 | HHAHDAYLNGVVANTLLKVYPQL-EPEFVVGDYHQFGW | ----FKA---NK | ATAKK---Q-FYTNIM-LFFAQK- | 1044 |
| WP_003739838 | 985 | HHAHDAYLNGVVANTLLKVYPQL-EPEFVVGDYHQFDW | ----FKA---NK | ATAKK---Q-FYTNIM-LFFAQK- | 1044 |
| WP_014601172 | 985 | HHAHDAYLNGVVANTLLKVYPQL-EPEFVVGDYHQFDW | ----FKA---NK | ATAKK---Q-FYTNIM-LFFGQK- | 1044 |
| WP_023548323 | 985 | HHAHDAYLNGVVANTLLKVYPQL-EPEFVVGDYHQFDW | ----FKA---NK | ATAKK---Q-FYTNIM-LFFAQK- | 1044 |
| WP_031665337 | 985 | HHAHDAYLNGVVANTLLKVYPQL-EPEFVVGDYHQFDW | ----FKA---NK | ATAKK---Q-FYTNIM-LFFAQK- | 1044 |
| WP_031669209 | 985 | HHAHDAYLNGVVANTLLKVYPQL-EPEFVVGDYHQFDW | ----FKA---NK | ATAKK---Q-FYTNIM-LFFAQK- | 1044 |
| WP_033920898 | 985 | HHAHDAYLNGVVANTLLKVYPQL-EPEFVVGDYHQFDW | ----FKA---NK | ATAKK---Q-FYTNIM-LFFAQK- | 1044 |
| AKI42028 | 988 | HHAHDAYLNGVVANTLLKVYPQL-EPEFVVGDYHQFDW | ----FKA---NK | ATAKK---Q-FYTNIM-LFFGQK- | 1047 |
| AKI50529 | 988 | HHAHDAYLNGVVANTLLKVYPQL-EPEFVVGDYHQFDW | ----FKA---NK | ATAKK---Q-FYTNIM-LFFAQK- | 1047 |
| EFR83390 | 433 | HHAHDAYLNCVVANTLLKVYPQL-EPEFVVGDYHQFDW | ----FKA---NK | ATAKK---Q-FYTNIM-LFFAQK- | 492 |
| WP_046323366 | 985 | HHAHDAYLNGVVANTLLKVYPQL-EPEFVVGDYHQFDW | ----FKA---NK | ATAKK---Q-FYTNIM-LFFAKK- | 1044 |
| AKE81011 | 998 | HHAHDAYLNAVVGTALIKKYPKL-ESEFVVGDYKVYDV | S---EQEi--GK | ATAKY--F-FYSNIM-NFFKTEIT | 1067 |
| CUO82355 | 981 | HHAHDAYIVALIGGFMRDRYPNMhDSKAVVSEYMKMFR | ---NKNg--QK | -----g----FVINSM-NYPY-EV- | 1042 |

| ID | Start | Sequence | End |
|---|---|---|---|
| WP_033162887 | 983 | HHAHDAYIACIVGQPMHQNFEHL-DAKIIYGQYK---- -----KNy--KK ---NYg---FILNSM-NHLQSDI- | 1042 |
| AGZ01981 | 1015 | HHAHDAYLNAVVGTALIKKYPKL-ESEFVVGDYKVYDV S---EQEi--GK ATAKY--F-FYSNIM-NFFKTEIT | 1084 |
| AKA60242 | 982 | HHAHDAYLNAVVGTALIKKYPKL-ESEFVVGDYKVYDV S---EQEi--GK ATAKY--F-FYSNIM-NFFKTEIT | 1051 |
| AKS40380 | 982 | HHAHDAYLNAVVGTALIKKYPKL-ESEFVVGDYKVYDV S---EQEi--GK ATAKY--F-FYSNIM-NFFKTEIT | 1051 |
| 4UN5_B | 986 | HHAHDAYLNAVVGTALIKKYPKL-ESEFVVGDYKVYDV S---EQEi--GK ATAKY--F-FYSNIM-NFFKTEIT | 1055 |
| WP_010922251 | 1052 | LAN-GEIRKRPLIE TNGET-GE-IVWDKGRDFATVRKVLS-MPQVNIVKKTEVQT GGFSK ESIL-PKR- | 1114 |
| WP_039695303 | 1059 | YAD-GTVFERPIIE T-NAD-GE-IAWNKQIDFEKVRKVLS-YPQVNIVKKVETQT GGFSK ESIL-PKG- | 1120 |
| WP_045635197 | 1056 | YAD-GTIVKRENIE Y-SKDtGE-IAWNKEKDFAIIKKVLS-LPQVNIVKKREVQT GGFSK ESIL-PKG- | 1118 |
| 5AXW_A | 772 | YKYsHRVDKKPNRE VNNLN-GL---YDKDND--KLKKLINkSPEKLLMYHHDPQT --YQK KLIMeQYGd | 852 |
| WP_009880683 | 736 | LAN-GEIRKRPLIE TNGET-GE-IVWDKGRDFATVRKVLS-MPQVNIVKKTEVQT --YQK KLIMeQYGd | 798 |
| WP_010922251 | 1052 | LAN-GEIRKRPLIE TNGET-GE-IVWDKGRDFATVRKVLS-MPQVNIVKKTEVQT GGFSK ESIL-PKR- | 1114 |
| WP_011054416 | 1052 | LAN-GEIRKRPLIE TNGET-GE-IVWDKGRDFATVRKVLS-MPQVNIVKKTEVQT GGFSK ESIL-PKR- | 1114 |
| WP_011284745 | 1052 | LAN-GEIRKRPLIE TNGET-GE-IVWDKGRDFATVRKVLS-MPQVNIVKKTEVQT GGFSK ESIL-PKR- | 1114 |
| WP_011285506 | 1052 | LAN-GEIRKRPLIE TNGET-GE-IVWDKGRDFATVRKVLS-MPQVNIVKKTEVQT GGFSK ESIL-PKR- | 1114 |
| WP_011527619 | 1052 | LAN-GEIRKRPLIE TNGET-GE-IVWDKGRDFATVRKVLS-MPQVNIVKKTEVQT GGFSK ESIL-PKR- | 1114 |
| WP_012560673 | 1052 | LAN-GEIRKRPLIE TNGET-GE-IVWDKGRDFATVRKVLS-MPQVNIVKKTEVQT GGFSK ESIL-PKR- | 1114 |
| WP_014407541 | 1051 | LAN-GEIRKRPLIE TNGET-GE-IVWDKGRDFATVRKVLS-MPQVNIVKKTEVQT GGFSK ESIL-PKR- | 1113 |
| WP_020905136 | 1052 | LAN-GEIRKRPLIE TNGET-GE-IVWDKGRDFATVRKVLS-MPQVNIVKKTEVQT GGFSK ESIL-PKR- | 1114 |
| WP_023080005 | 1051 | LAN-GEIRKRPLIE TNGET-GE-IVWDKGRDFATVRKVLS-MPQVNIVKKTEVQT GGFSK ESIL-PKR- | 1113 |
| WP_023610282 | 1052 | LAN-GEIRKRPLIE TNGET-GE-IVWDKGRDFATVRKVLS-MPQVNIVKKTEVQT GGFSK ESIL-PKR- | 1114 |
| WP_030125963 | 1052 | LAN-GEIRKRPLIE TNGET-GE-IVWDKGRDFATVRKVLS-MPQVNIVKKTEVQT GGFSK ESIL-PKR- | 1114 |
| WP_030126706 | 1052 | LAN-GEIRKRPLIE TNGET-GE-IVWDKGRDFATVRKVLS-MPQVNIVKKTEVQT GGFSK ESIL-PKR- | 1114 |
| WP_031488318 | 1052 | LAN-GEIRKRPLIE TNGET-GE-IVWDKGRDFATVRKVLS-MPQVNIVKKTEVQT GGFSK ESIL-PKR- | 1114 |
| WP_032460140 | 1052 | LAN-GEIRKRPLIE TNGET-GE-IVWDKGRDFATVRKVLS-MPQVNIVKKTEVQT GGFSK ESIL-PKR- | 1114 |
| WP_032461047 | 1052 | LAN-GEIRKRPLIE TNGET-GE-IVWDKGRDFATVRKVLS-MPQVNIVKKTEVQT GGFSK ESIL-PKR- | 1114 |
| WP_032462016 | 1052 | LAN-GEIRKRPLIE TNGET-GE-IVWDKGRDFATVRKVLS-MPQVNIVKKTEVQT GGFSK ESIL-PKR- | 1114 |
| WP_032462936 | 1052 | LAN-GEIRKRPLIE TNGET-GE-IVWDKGRDFATVRKVLS-MPQVNIVKKTEVQT GGFSK ESIL-PKR- | 1114 |

-continued

| ID | | | | | | | |
|---|---|---|---|---|---|---|---|
| WP_032464890 | 1052 | LAN-GEIRKRPLIE | TNGET-GE-IVWDKGRDFATVRKVLS-MPQVNIVKKTEVQT | GGFSK | ESIL-PKR- | 1114 |
| WP_033888930 | 877 | LAN-GEIRKRPLIE | TNGET-GE-IVWDKGRDFATVRKVLS-MPQVNIVKKTEVQT | GGFSK | ESIL-PKR- | 939 |
| WP_038431314 | 1052 | LAN-GEIRKRPLIE | TNGET-GE-IVWDKGRDFATVRKVLS-MPQVNIVKKTEVQT | GGFSK | ESIL-PKR- | 1114 |
| WP_038432938 | 1051 | LAN-GEIRKRPLIE | TNGET-GE-IVWDKGRDFATVRKVLS-MPQVNIVKKTEVQT | GGFSK | ESIL-PKR- | 1113 |
| WP_038434062 | 1052 | LAN-GEIRKRPLIE | TNGET-GE-IVWDKGRDFATVRKVLS-MPQVNIVKKTEVQT | GGFSK | ESIL-PKR- | 1114 |
| BAQ51233 | 963 | LAN-GEIRKRPLIE | TNGET-GE-IVWDKGRDFATVRKVLS-MPQVNIVKKTEVQT | GGFSK | ESIL-PKR- | 1025 |
| KGE60162 | 227 | LAN-GEIRKRPLIE | TNGET-GE-IVWDKGRDFATVRKVLS-MPQVNIVKKTEVQT | GGFSK | ESIL-PKR- | 289 |
| KGE60856 | 1 | ---------IE | TNGET-GE-IVWDKGRDFATVRKVLS-MPQVNIVKKTEVQT | GGFSK | ESIL-PKR- | 52 |
| WP_002989955 | 1052 | LAN-GEIRKRPLIE | TNGET-GE-IVWDKGRDFATVRKVLS-MPQVNIVKKTEVQT | GGFSK | ESIL-PKR- | 1114 |
| WP_003030002 | 1042 | ---------DIQ | T-NED-GE-IAWNKEKHIKILRKVLS-YPQVNIVKKTEEQT | GGFSK | ESIL-PKG- | 1093 |
| WP_003065552 | 1059 | YSN-GKVIVRPVVE | Y-SKD-TEGIAWDKKSNFRTICKVLS-YPQVNIVKKVETQT | GGFSK | ESIL-PKG- | 1121 |
| WP_001040076 | 1050 | LAD-GTVVVKDDIE | VNNDT-GE-IVWDKKKHFATVRKVLS-YPQNNIVKKTEIQT | GGFSK | ESIL-AHG- | 1112 |
| WP_001040078 | 1058 | LAD-GSIVVRPVIE | TGRYM-GK-TAWDKKKKHFATVRKVLS-YPQNNIVKKTEIQT | GGFSK | ESIL-AHG- | 1120 |
| WP_001040080 | 1050 | LAD-GTVVVKDDIE | VNNDT-GE-IVWDKKKHFATVRKVLS-YPQNNIVKKTEIQT | GGFSK | ESIL-AHG- | 1112 |
| WP_001040081 | 1050 | LAD-GTVVVKDDIE | VNNDT-GE-IVWDKKKHFATVRKVLS-YPQNNIVKKTEIQT | GGFSK | ESIL-AHG- | 1112 |
| WP_001040083 | 1050 | LAD-GTVVVKDDIE | VNNDT-GE-IVWDKKKHFATVRKVLS-YPQNNIVKKTEIQT | GGFSK | ESIL-AHG- | 1112 |
| WP_001040085 | 1050 | LAD-GTVVVKDDIE | VNNDT-GE-IAWDKKKHFATVRKVLS-YPQNNIVKKTEIQT | GGFSK | ESIL-AHG- | 1112 |
| WP_001040087 | 1050 | LAD-ETVVVKDDIE | VNNET-GE-IVWDKKKHFATVRKVLS-YPQVNIVKKTEVQT | GGFSK | ESIL-AHS- | 1112 |
| WP_001040088 | 1050 | LAD-GTVVVKDDIE | VNNDT-GE-IVWDKKKHFATVRKVLS-YPQVNIVKKTEVQT | GGFSK | ESIL-AHG- | 1112 |
| WP_001040089 | 1050 | LAD-GTVVVKDDIE | VNNDT-GE-IVWDKKKHFATVRKVLS-YPQVNIVKKTEVQT | GGFSK | ESIL-AHG- | 1112 |
| WP_001040090 | 1050 | LAD-GTVVVKDDIE | VNNDT-GE-IVWDKKKHFATVRKVLS-YPQVNIVKKTEVQT | GGFSK | ESIL-AHG- | 1112 |
| WP_001040091 | 1050 | LAD-GTVVVKDDIE | VNNDT-GE-IVWDKKKHFATVRKVLS-YPQVNIVKKTEVQT | GGFSK | ESIL-AHG- | 1112 |
| WP_001040092 | 1050 | LAD-GTVVVKDDIE | VNNDT-GE-IVWDKKKHFATVRKVLS-YPQVNIVKKTEVQT | GGFSK | ESIL-AHG- | 1112 |
| WP_001040094 | 1050 | LAD-GTVVVKDDIE | VNNDT-GE-IVWDKKKHFATVRKVLS-YPQVNIVKKTEVQT | GGFSK | ESIL-AHG- | 1112 |
| WP_001040095 | 1050 | LAD-GTVVVKDDIE | VNNDT-GE-IVWDKKKHFATVRKVLS-YPQVNIVKKTEVQT | GGFSK | ESIL-AHG- | 1112 |
| WP_001040096 | 1050 | LAD-GTVVVKDDIE | VNNDT-GE-IVWDKKKHFATVRKVLS-YPQVNIVKKTEVQT | GGFSK | ESIL-AHG- | 1112 |
| WP_001040097 | 1050 | LAD-GTVVVKDDIE | VNNDT-GE-IVWDKKKHFATVRKVLS-YPQVNIVKKTEVQT | GGFSK | ESIL-AHG- | 1112 |

-continued

| | | | | | | |
|---|---|---|---|---|---|---|
| WP_001040098 | 1050 | LAD-GTVVVKDDIE | VNNDT-GE-IVWDKKKHFATVRKVLS-YPQVNIVKKTEIQT | GGFSK | ESIL-AHG- | 1112 |
| WP_001040099 | 1050 | LAD-GTVVVKDDIE | VNNDT-GE-IVWDKKKHFATVRKVLS-YPQVNIVKKTEIQT | GGFSK | ESIL-AHG- | 1112 |
| WP_001040100 | 1050 | LAD-GTVVVKDDIE | VNNDT-GE-IVWDKKKHFATVRKVLS-YPQVNIVKKTEIQT | GGFSK | ESIL-AHG- | 1112 |
| WP_001040104 | 1050 | LAD-GTVVVKDDIE | VNNDT-GE-IVWDKKKHFATVRKVLS-YPQNNIVKKTEIQT | GGFSK | ESIL-AHG- | 1112 |
| WP_001040105 | 1050 | LAD-GTVVVKDDIE | VNNDT-GE-IVWDKKKHFATVRKVLS-YPQNNIVKKTEIQT | GGFSK | ESIL-AHG- | 1112 |
| WP_001040106 | 1050 | LAD-GTVVVKDDIE | VNNDT-GE-IVWDKKKHFATVRKVLS-YPQVNIVKKTEIQT | GGFSK | ESIL-AHG- | 1112 |
| WP_001040107 | 1050 | LAD-GTVVVKDDIE | VNNDT-GE-IVWDKKKHFATVRKVLS-YPQNNIVKKTEIQT | GGFSK | ESIL-AHG- | 1112 |
| WP_001040108 | 1050 | LAD-GTVVVKDDIE | VNNDT-GE-IVWDKKKHFATVRKVLS-YPQVNIVKKTEIQT | GGFSK | ESIL-AHG- | 1112 |
| WP_001040109 | 1050 | LAD-GTVVVKDDIE | VNNDT-GE-IVWDKKKHFATVRKVLS-YPQVNIVKKTEIQT | GGFSK | ESIL-AHG- | 1112 |
| WP_001040110 | 1050 | LAD-GTVVVKDDIE | VNNDT-GE-IVWDKKKHFATVRKVLS-YPQNNIVKKTEIQT | GGFSK | ESIL-AHG- | 1112 |
| WP_015058523 | 1050 | LAD-ETVVVKDDIE | VNNET-GE-IAWDKKKHFATVRKVLS-YPQVNIVKKTEVQT | GGFSK | ESIL-AHS- | 1112 |
| WP_017643650 | 1050 | LAD-GTVVVKDDIE | VNNDT-GE-IVWDKKKHFATVRKVLS-YPQNNIVKKTEIQT | GGFSK | ESIL-AHG- | 1112 |
| WP_017647151 | 1050 | LAD-GTVVVKDDIE | VNNDT-GE-IVWDKKKHFATVRKVLS-YPQNNIVKKTEIQT | GGFSK | ESIL-AHG- | 1112 |
| WP_017648376 | 1050 | LAD-GTVVVKDDIE | VNNDT-GE-IVWDKKKHFATVRKVLS-YPQNNIVKKTEIQT | GGFSK | ESIL-AHG- | 1112 |
| WP_017649527 | 1050 | LAD-GTVVVKDDIE | VNNDT-GE-IVWDKKKHFATVRKVLS-YPQNNIVKKTEIQT | GGFSK | ESIL-AHG- | 1112 |
| WP_017771611 | 1050 | LAD-GTVVVKDDIE | VNNDT-GE-IVWDKKKHFATVRKVLS-YPQVNIVKKTEIQT | GGFSK | ESIL-AHG- | 1112 |
| WP_017771984 | 1050 | LAD-GTVVVKDDIE | VNNDT-GE-IVWDKKKHFATVRKVLS-YPQNNIVKKTEIQT | GGFSK | ESIL-AHG- | 1112 |
| CFQ25032 | 1050 | LAD-GTVVVKDDIE | VNNDT-GE-IVWDKKKHFATVRKVLS-YPQNNIVKKTEIQT | GGFSK | ESIL-AHG- | 1112 |
| CFV16040 | 1050 | LAD-GTVVVKDDIE | VNNDT-GE-IVWDKKKHFATVRKVLS-YPQVNIVKKTEIQT | GGFSK | ESIL-AHG- | 1112 |
| KLJ37842 | 1050 | LAD-GTVVVKDDIE | VNNDT-GE-IVWDKKKHFATVRKVLS-YPQNNIVKKTEIQT | GGFSK | ESIL-AHG- | 1112 |
| KLJ72361 | 1064 | LAD-GTVVVKDDIE | VNNDT-GE-IVWDKKKHFATVRKVLS-YPQVNIVKKTEIQT | GGFSK | ESIL-AHG- | 1126 |
| KLL20707 | 1050 | LAD-GTVVVKDDIE | VNNDT-GE-IVWDKKKHFATVRKVLS-YPQVNIVKKTEIQT | GGFSK | ESIL-AHG- | 1112 |
| KLL42645 | 1050 | LAD-GTVVIKDDIE | VNNDT-GE-IVWDKKKHFATVRKVLS-YPQNNIVKKTEIQT | GGFSK | ESIL-AHG- | 1112 |
| WP_047207273 | 1050 | LAD-GTVVVKDDIE | VNNDT-GE-IVWDKKKHFATVRKVLS-YPQVNIVKKTEIQT | GGFSK | ESIL-AHG- | 1112 |
| WP_047209694 | 1050 | LAD-GTVVVKDDIE | VNNDT-GE-IVWDKKKHFATVRKVLS-YPQVNIVKKTEIQT | GGFSK | ESIL-AHG- | 1112 |
| WP_050198062 | 1050 | LAD-GTVVVKDDIE | VNNDT-GE-IVWDKKKHFATVRKVLS-YPQNNIVKKTEIQT | GGFSK | ESIL-AHG- | 1112 |
| WP_050201642 | 1050 | LAD-GTVVVKDDIE | VNNDT-GE-IVWDKKKHFATVRKVLS-YPQNNIVKKTEIQT | GGFSK | ESIL-AHG- | 1112 |

-continued

| | | | | | | |
|---|---|---|---|---|---|---|
| WP_050204027 | 1050 | LAD-GTVVVKDDIE | VNNDT-GE-IVWDKKKHFATVRKVLS-YPQNIVKKTEIQT | GGFSK | ESIL-AHG- | 1112 |
| WP_050881965 | 1050 | LAD-GTVVVKDDIE | VNNDT-GE-IVWDKKKHFATVRKVLS-YPQNIVKKTEIQT | GGFSK | ESIL-AHG- | 1112 |
| WP_050886065 | 1050 | LAD-GTVVVKDDIE | VNNDT-GE-IVWDKKKHFATVRKVLS-YPQNNIVKKTEIQT | GGFSK | ESIL-AHG- | 1112 |
| AHN30376 | 1050 | LAD-ETVVVKDDIE | VNNET-GE-IAWDKKKHFATVRKVLS-YPQVNIVKKTEVQT | GGFSK | ESIL-AHS- | 1112 |
| EAO78426 | 1050 | LAD-GTVVVKDDIE | VNNDT-GE-IVWDKKKHFATVRKVLS-YPQNNIVKKTEIQT | GGFSK | ESIL-AHG- | 1112 |
| CCW42055 | 1050 | LAD-GTVVVKDDIE | VNNDT-GE-IVWDKKKHFATVRKVLS-YPQNNIVKKTEIQT | GGFSK | ESIL-AHG- | 1112 |
| WP_003041502 | 1051 | FAD-GTVVERPDIE | T-SED-GE-IAWNKQTDFKIVRKVLS-YPQVNIVKKTEVQT | HGLDR | PSPK-PKP- | 1122 |
| WP_037593752 | 1043 | ---------DIQ | T-NED-GE-IAWNKEKHIKILRKVLS-YPQVNIVKKTEEQT | GGFSK | ESIL-PKG- | 1094 |
| WP_049516684 | 1043 | ---------DIQ | T-NED-GE-IAWNKEKHIKILLRKVLS-YPQVNIVKKTEEQT | GGFSK | ESIL-PKG- | 1094 |
| GAD46167 | 1042 | ---------DIQ | T-NED-GE-IAWNKEKHIKILRKVLS-YPQVNIVKKTEEQT | GGFSK | ESIL-PKG- | 1093 |
| WP_018363470 | 1063 | YSN-GKVIVRPVVE | Y-SKDtGE-IAWNKRTDFEKVRKVLS-YPQVNIVKKTEVQT | GGFSK | ESIL-PKG- | 1125 |
| WP_003043819 | 1061 | LAN-GEIRKRPLIE | TNGET-GE-VVWNKEKDFATVRKVLA-MPQVNIVKKTEVQT | GGFSK | ESIL-SKR- | 1123 |
| WP_006269658 | 1042 | ---------DIQ | T-NED-GE-IAWNKEKHIKILRKVLS-YPQVNIVKKTEEQT | GGFSK | ESIL-PKG- | 1093 |
| WP_048800889 | 1052 | FAD-GTVVERPDIE | T-SED-GE-IAWNKQTDFKIVRKVLS-YPQVNIVKKVEKQT | GRFSK | ESIY-ARG- | 1113 |
| WP_012767106 | 1051 | LAN-GEIRKRPLIE | TNEET-GE-IVWDKGRDFATVRKVLS-MPQVNIVKKTEVQT | GALTN | ESIY-ARG- | 1113 |
| WP_014612333 | 1051 | LAN-GEIRKRPLIE | TNEET-GE-IVWDKGRDFATVRKVLS-MPQVNIVKKTEVQT | GALTN | ESIY-ARG- | 1113 |
| WP_015017095 | 1051 | LAN-GEIRKRPLIE | TNEET-GE-IVWDKGRDFATVRKVLS-MPQVNIVKKTEVQT | GALTN | ESIY-ARG- | 1113 |
| WP_015057649 | 1051 | LAN-GEIRKRPLIE | TNEET-GE-IVWDKGRDFATVRKVLS-MPQVNIVKKTEVQT | GALTN | ESIY-ARG- | 1113 |
| WP_048327215 | 1051 | LAN-GEIRKRPLIE | TNEET-GE-IVWDKGRDFATVRKVLS-MPQVNIVKKTEVQT | GALTN | ESIY-ARG- | 1113 |
| WP_049519324 | 1051 | LAN-GEIRKRPLIE | TNEET-GE-IVWDKGRDFATVRKVLS-MPQVNIVKKTEVQT | GALTN | ESIY-ARG- | 1113 |
| WP_012515931 | 1044 | L---------H | VNSD--GE-EIWNNANKHLPIIKNVLS-IPQVNIVKKTEVQT | GGFYK | ESIL-SKG- | 1094 |
| WP_021320964 | 1044 | L---------H | VNSD--GE-EIWNNANKHLPIIKNVLS-IPQVNIVKKTEVQT | GGFYK | ESIL-SKG- | 1094 |
| WP_037581760 | 1044 | L---------H | VNSD--GE-EIWNNANKHLPIIKNVLS-IPQVNIVKKTEVQT | GGFYK | ESIL-SKG- | 1094 |
| WP_004232481 | 1062 | YAD-GRVFERPDIE | T-NAD-GE-VVWNKQRDFNIVRKVLS-YPQVNIVKKVEVQS | GGFSK | ESIL-PKG- | 1123 |
| WP_009854540 | 1057 | YAD-GTVFERPIIE | T-NAD-GE-IAWNKQIDFEKVRKVLS-YPQVNIVKKTEVQT | GGFSK | ESIL-PKG- | 1118 |
| WP_012962174 | 1057 | YSN-GKVVVRPVIE | C-SKDtGE-IAWNKQIDFEKVRRVLS-YPQVNIVKKTEVQT | GGFSK | ESIL-PKG- | 1119 |
| WP_039695303 | 1059 | YAD-GTVFERPIIE | T-NAD-GE-IAWNKQIDFEKVRKVLS-YPQVNIVKKVETQT | GGFSK | ESIL-PKG- | 1120 |

| | | | | | |
|---|---|---|---|---|---|
| WP_014334983 | 1062 | YAD-GRVFERPDIE | T-NAD-GE-VVWNKQKDFDIVRKVLS-YPQNIVKKVEAQT | GGFSK | ESIL-SKG- | 1123 |
| WP_003099269 | 1052 | LAD-DTIFTRPQIE | VNTET-GE-IVWDKVKDMQTIRKVMS-YPQNIVMKTEVQT | GGFSK | ESIW-PKG- | 1114 |
| AHY15608 | 1052 | LAD-DTIFTRPQIE | VNTET-GE-IVWDKVKDMQTIRKVMS-YPQNIVMKTEVQT | GGFSK | ESIW-PKG- | 1114 |
| AHY17476 | 1052 | LAD-DTIFTRPQIE | VNTET-GE-IVWDKVKDMQTIRKVMS-YPQNIVMKTEVQT | GGFSK | ESIW-PKG- | 1114 |
| ESR09100 | | | | | | |
| AGM98575 | 1052 | LAD-DTIFTRPQIE | VNTET-GE-IVWDKVKDMQTIRKVMS-YPQNIVMTEVQT | GGFSK | ESIW-PKG- | 1114 |
| ALF27331 | 1042 | ---------DVR | T-DKN-GE-IIWKKDDEHISNIKKVLS-YPQNIVKKVEEQT | GGFSK | ESIL-PKG- | 1093 |
| WP_018372492 | 1056 | --K-------K | --DQEtGE-IVWDKKEIENIVKKVIY-SSPVNIVKKREEQS | GALFK | QSNM-AVGy | 1108 |
| WP_045618028 | 1057 | YAD-GTIVKRENIE | Y-SKDtGE-IAWNKEKDFATIKKVLS-LPQNIVKKTEEQT | GGLFD | NNIV-SKKk | 1124 |
| WP_045635197 | 1056 | YAD-GTIVKRENIE | Y-SKDtGE-IAWNKEKDFAIIKKVLS-LPQNIVKREVQT | GGFSK | ESIL-PKG- | 1118 |
| WP_002263549 | 1042 | ---------DVR | T-DKN-GE-IIWKKDDEHISNIKKVLS-YPQNIVKKVEEQT | GGFSK | ESIL-PKG- | 1093 |
| WP_002263887 | 1042 | ---------DVR | T-DKN-GE-IIWKKDDEHISNIKKVLS-YPQNIVKKVEEQT | GGFSK | ESIL-PKG- | 1093 |
| WP_002264920 | 1042 | ---------DVR | T-DKN-GE-IIWKKDDEHIYISNIKKVLS-YPQNIVKKVEEQT | GGFSK | ESIL-PKG- | 1093 |
| WP_002269043 | 1042 | ---------DVR | T-DKN-GE-IIWKKDDEHISNIKKVLS-YPQNIVKKVEEQT | GGFSK | ESIL-PKG- | 1093 |
| WP_002269448 | 1042 | ---------DVR | T-DKN-GE-IIWKKDDEHISNIKKVLS-YPQNIVKKVEEQT | GGFSK | ESIL-PKG- | 1093 |
| WP_002271977 | 1042 | ---------DVR | T-DRN-GE-IIWKKDDEHISNIKKVLS-YPQNIVKKVEEQT | GGFSK | ESIL-PKG- | 1093 |
| WP_002272766 | 1047 | LAD-DQIERPMIE | VNDET-GE-IAWDKTKHITTVKKVLS-YPQNIVKKVEEQT | GGFSK | -----PKS- | 1111 |
| WP_002273241 | 1042 | ---------DVR | T-DKN-GE-IIWKKDDEHISNIKKVLS-YPQNIVKKVEEQT | GGFSK | ESIL-PKG- | 1093 |
| WP_002275430 | 1042 | ---------DVR | T-DKN-GE-IIWKKDDEYISNIKKVLS-YPQNIVKKVEEQT | GGFSK | ESIL-PKG- | 1093 |
| WP_002276448 | 1042 | ---------DVR | T-DKN-GE-IIWKKDDEHISNIKKVLS-YPQNIVKKVEEQT | GGFSK | ESIL-PKG- | 1093 |
| WP_002277050 | 1047 | LAD-DQIERPMIE | VNDET-GE-IAWDKTKHITTVKKVLS-YPQNIVKKVEEQT | GGFSK | ESIL-PKG- | 1111 |
| WP_002277364 | 1042 | ---------DVR | T-DKN-GE-IIWKKDDEHISNIKKVLS-YPQNIVKKVEEQT | GGFSK | ESIL-PKG- | 1093 |
| WP_002279025 | 1042 | ---------DVR | T-DKN-GE-IIWKKDDEHISNIKKVLS-YPQNIVKKVEEQT | GGFSK | ESIL-PKG- | 1093 |
| WP_002279859 | 1042 | ---------DVR | T-DKN-GE-IIWKKDDEHISNIKKVLS-YPQNIVKKVEEQT | GGFSK | ESIL-PKG- | 1093 |
| WP_002280230 | 1042 | ---------DVR | T-DKN-GE-IIWKKDDEHISNIKKVLS-YPQNIVKKVEEQT | GGFSK | ESIL-PKG- | 1093 |
| WP_002281696 | 1042 | ---------DVR | T-DKN-GE-IIWKKDDEHISNIKKVLS-YPQNIVKKVEEQT | GGFSK | ESIL-PKG- | 1093 |
| WP_002282247 | 1047 | LAD-DQIVERPMIE | VNDET-GE-IAWDKTKHITTVKKVLS-YPQNIVKKVEEQT | GGLFD | -----PKS- | 1111 |

| | | | | | | |
|---|---|---|---|---|---|---|
| WP_002282906 | 1042 | ---------DVR | I-DKN-GE-IIWKKDEHISNIKKVLS-YPQVNIVKKVEEQT | GGFSK | ESIL-PKG- | 1093 |
| WP_002283846 | 1042 | ---------DVR | T-DKN-GE-IIWKKDEHISNIKKVLS-YPQVNIVKKVEEQT | GGFSK | ESIL-PKG- | 1093 |
| WP_002287255 | 1042 | ---------DVR | T-DKN-GE-IIWKKDEHISNIKKVLS-YPQVNIVKKVEEQT | GGFSK | ESIL-PKG- | 1093 |
| WP_002288990 | 1042 | ---------DVR | T-DKN-GE-IIWKKDEHISNIKKVLS-YPQVNIVKKVEEQT | GGFSK | ESIL-PKG- | 1093 |
| WP_002289641 | 1042 | ---------DVR | T-DKN-GE-IIWKKDEYISNIKKVLS-YPQVNIVKKVEEQT | GGFFK | ESIL-PKG- | 1093 |
| WP_002290427 | 1042 | ---------DVR | T-DKN-GE-IIWKKDEHISNIKKVLS-YPQVNIVKKVEEQT | GGFSK | ESIL-PKG- | 1093 |
| WP_002295753 | 1042 | ---------DVR | T-DKN-GE-IIWKKDEYISNIKKVLS-YPQVNIVKKVEEQT | GGFSK | ESIL-PKG- | 1093 |
| WP_002296423 | 1042 | ---------DVR | T-DKN-GE-IIWKKDEHISNIKKVLS-YPQVNIVKKVEEQT | GGFSK | ESIL-PKG- | 1093 |
| WP_002304487 | 1056 | ---------DVR | T-DKN-GE-IIWKKDEHISNIKKVLS-YPQVNIVKKVEEQT | GGFSK | ESIL-PKG- | 1107 |
| WP_002305844 | 1042 | ---------DVR | T-DKN-GE-IIWKKDEHISNIKKVLS-YPQVNIVKKVEEQT | GGFSK | ESIL-PKG- | 1093 |
| WP_002307203 | 1042 | ---------DVR | T-DKN-GE-IIWKKDEHISNIKKVLS-YPQVNIVKKVEEQT | GGFSK | ESIL-PKG- | 1093 |
| WP_002310390 | 1042 | ---------DVR | T-DKN-GE-IIWKKDEYISNIKKVLS-YPQVNIVKKVEEQT | GGFFK | ESIL-PKG- | 1093 |
| WP_002352408 | 1042 | ---------DVR | T-DKN-GE-IIWKKDEHISNIKKVLS-YPQVNIVKKVEEQT | GGFSK | ESIL-PKG- | 1093 |
| WP_012997688 | 1042 | ---------DVR | T-DKN-GE-IIWKKDEHISNIKKVLS-YPQVNIVKKVEEQT | GGFSK | ESIL-PKG- | 1093 |
| WP_014677909 | 1042 | ---------DVR | T-DKN-GE-IIWKKDEHISNIKKVLS-YPQVNIVKKVEEQT | GGFSK | ESIL-PKG- | 1093 |
| WP_019312892 | 1042 | ---------DVR | T-DKN-GE-IIWKKDEHISNIKKVLS-YPQVNIVKKVEEQT | GGFFK | ESIL-PKG- | 1093 |
| WP_019313659 | 1042 | ---------DVR | T-DKN-GE-IIWKKDEHISNIKKVLS-YPQVNIVKKVEEQT | GGFSK | ESIL-PKG- | 1093 |
| WP_019314093 | 1042 | ---------DVR | T-DKN-GE-IIWKKDEHISNIKKVLS-YPQVNIVKKVEEQT | GGFSK | ESIL-PKG- | 1093 |
| WP_019315370 | 1042 | ---------DVR | T-DKN-GE-IIWKKDEHISNIKKVLS-YPQVNIVKKVEEQT | GGFSK | ESIL-PKG- | 1093 |
| WP_019803776 | 1042 | ---------DVR | T-DKN-GE-IIWKKDEHISNIKKVLS-YPQVNIVKKVEEQT | GGFSK | ESIL-PKG- | 1093 |
| WP_019805234 | 1042 | ---------DVR | T-DKN-GE-IIWKKDEHISNIKKVLS-YPQVNIVKKVEEQT | GGFFK | ESIL-PKG- | 1093 |
| WP_024783594 | 1042 | ---------DVR | T-DKN-GE-IIWKKDEHISNIKKVLS-YPQVNIVKKVEEQT | GGFSK | ESIL-PKG- | 1093 |
| WP_024784288 | 1047 | LAD-DQIVERPMIE | VNDET-GE-IAWDKTKHITTVKKVLS-YPQVNIVKKVEEQT | GGLFD | ------PKS- | 1111 |
| WP_024784666 | 1042 | ---------DVR | T-DKN-GE-IIWKKDEHISNIKKVLS-YPQVNIVKKVEEQT | GGFSK | ESIL-PKG- | 1093 |
| WP_024786894 | 1042 | ---------DVR | T-DKN-GE-IIWKKDEHISNIKKVLS-YPQVNIVKKVEEQT | GGFSK | ESIL-PKG- | 1093 |
| WP_024786433 | 1047 | LAD-DQIVERPMIE | VNDET-GE-IAWDKTKHITTVKKVLS-YPQVNIVKKVEEQT | GGLFD | ------PKS- | 1111 |
| WP_049473442 | 1042 | ---------DVR | T-DKN-GE-IIWKKDEHISNIKKVLS-YPQVNIVKKVEEQT | GGFSK | ESIL-PKG- | 1093 |

-continued

| | | | | | |
|---|---|---|---|---|---|
| WP_049474547 | 1042 | ---------DVR | T-DKN-GE-IIWKKDEHISNIKKVLS-YPQVNIVKKVEEQT | GGFSK | ESIL-PKG- | 1093 |
| EMC03581 | 1035 | ---------DVR | T-DKN-GE-IIWKKDEHISNIKKVLS-YPQVNIVKKVEEQT | GGFSK | ESIL-PKG- | 1086 |
| WP_000428812 | 1059 | YAD-GTIVKRENIE | Y-SKDtGE-IAWNKEKDFATIKKVLS-LPQVNIVKKREVQT | GGFSK | ESIL-PKG- | 1121 |
| WP_000428813 | 1057 | YAD-GTIVKRENIE | Y-SKDtGE-IAWNKEKDFATIKKVLS-YPQVNIVKRREVQT | GGFSK | ESIL-PKG- | 1119 |
| WP_049523028 | 1052 | YAD-GTIIQRGNVE | Y-SKDtGE-IAWNKKRDFAIVRKVLS-YPQVNIVKKTEEQT | GGFSK | ESIL-PKG- | 1114 |
| WP_003107102 | 1021 | LAD-GTVITRPQIE | TNTET-GE-IVWDKVKDIKTIRKVLS-IPQINVVKKTEVQT | GGFSK | ESIL-SKR- | 1083 |
| WP_054279288 | 1053 | LAN-GNIIKRSPIE | VNEET-GE-IVWDKTKDFGTVRKVLS-APQVNIVKKTEIQT | GGFSN | ETIL-SKG- | 1115 |
| WP_049531101 | 1057 | YAD-GTIVKRENIE | Y-SKDtGE-IAWNKEIDFATIRKILS-LSQVNIVKKTEEQT | GGLFD | NNIV-SKKk | 1124 |
| WP_049538452 | 1057 | YAD-GTIVKRENIE | Y-SKDtGE-IAWNKEKDFATIKKILS-LPQVNIVKKTEEQT | GGLFD | NNIV-SKKk | 1124 |
| WP_049549711 | 1059 | YAD-GTIVKRENIE | Y-SKDtGE-IAWNKEKDFATIKKVLS-YPQVNIVKKTEEQT | GGLFD | NNIV-SKEk | 1126 |
| WP_007896501 | 1058 | LAD-GTLMKRPVIE | TNTET-GE-VVWDKVKDFKTIRKVLS-YPQVNIVKKTEIQS | GAFSK | ESVL-SKG- | 1120 |
| EFR44625 | 1010 | LAD-GTLMKRPVIE | TNTET-GE-IVWDKVKDFKTIRKVLS-LPQVNIVKKTEIQS | GAFSK | ESVL-SKG- | 1072 |
| WP_002897477 | 1056 | YAD-GTIRKRENIE | Y-SKDtGE-IAWNKEKDFATIKKVLS-YPQVNIVKKREVQT | GGFSK | ESIL-PKG- | 1118 |
| WP_002906454 | 1056 | YAD-GTIKKRENIE | Y-SNDtGE-IAWNKEKDFATIKKVLS-LPQVNIVKKTEEQT | GGLFD | NNIV-SKKk | 1123 |
| WP_009729476 | 1057 | YAD-GTIVKRENIE | Y-SKDtGE-IAWNKEKDFATIKKVLS-LPQVNIVKKREVQT | GGFSK | ESIL-PKG- | 1119 |
| CQR24647 | 1047 | LAD-GRVVEKPVIE | ANEET-GE-IAWDKTKHFANVKKVLS-YPQVSIVKVEEQT | GGFSK | ESIL-PKG- | 1109 |
| WP_000066813 | 1061 | YAD-GTIVKRENIE | Y-SKDtGE-IAWNKEKDFATVKKVLS-LPQVNIVKKREVQT | GGFSK | ESIL-PKG- | 1123 |
| WP_009754323 | 1057 | YAD-GTIVKRENIE | Y-SKDtGE-IAWNKEKDFVTIKKVLS-YPQVNIVKKREVQT | GGFSK | ESIL-PKG- | 1119 |
| WP_044674937 | 1049 | YSKtGEVRIRPVIE | VNKET-GE-IVWDKKSDFRTVRKVLS-YPQVNVVKKVEMQT | GGFSK | ESIL-QHG- | 1112 |
| WP_044676715 | 1051 | YSKtGEVRIRPVIE | VNKET-GE-IVWDKKSDFRTVRKVLS-YPQVNVVKKVEMQT | GGFSK | ESIL-QHG- | 1114 |
| WP_044680361 | 1051 | YSKtGEVRIRPVIE | VNKET-GE-IVWDKKSDFRTVRKVLS-YPQVNVVKKVEMQT | GGFSK | ESIL-QHG- | 1114 |
| WP_044681799 | 1049 | YSKtGEVRIRPVIE | VNKET-GE-IVWDKKSDFKTVRKVLS-YPQVNVVKKVEMQT | GGFSK | ESIL-QHG- | 1112 |
| WP_049533112 | 1051 | FAD-GTVVERPDIE | T-SED-GE-IAWNKQTDFKIVRKVLS-YPQVNIVKKTEVQT | HGLDR | PSPK-PKP- | 1122 |
| WP_029909905 | 1008 | -KQ--------Q | --NSTtGE-VKMNPEVDIAKLKRILN-FKQCNIVRKVEEQS | GALFK | ETIY-PVEe | 1061 |
| WP_006506696 | 1039 | --D-------- | -----GK-LIMNP-DLINEIKKCFY-YKDCYCTTKLDQKS | GQLFN | -TVL-SNDa | 1084 |
| AIT42264 | 1052 | LAN-GEIRKRPLIE | TNGET-GE-IVWDKGRDFATVRKKVLS-MPQVNIVKKTEVQT | GGFSK | ESIL-PKR- | 1114 |
| WP_034440723 | 1042 | ---------LA | --NPD-GE-IAWEKDKDLNTIRKVLS-SKQINIIKKAEEGK | GRLFK | ETIN-SRPs | 1092 |

| | | | | | |
|---|---|---|---|---|---|
| AKQ21048 | 1052 | LAN-GEIRKRPLIE | TNGET-GE-IVWDKGRDFATVRKVLS-MPQVNIVKKTEVQT | GGFSK | ESIL-PKR- | 1114 |
| WP_004636532 | 1043 | ------------- | VNEET-GE-IILMDTERHLSTIKRVLS-WKQMNIVKKVEKQK | GQLWK | ETIY-PKG- | 1092 |
| WP_002364836 | 1048 | --E---------- | RFTKD-GE-ILMSN-SYLKTIKKELN-YHQMNIVKKVEVQK | GGFSK | ESIK-PKG- | 1098 |
| WP_016631044 | 999 | --E---------- | RFTKD-GE-ILMSN-SYLKTIKKELN-YHQMNIVKKVEVQK | GGFSK | ESIK-PKG- | 1049 |
| EMS75795 | 783 | --E---------Y | SYDEN-GE-IFWDKARHIPQIKKVIS-SHQVNIVKKTEVQT | GGFYK | ETVN-PKG- | 834 |
| WP_002373311 | 1048 | --E---------- | RFTKD-SE-ILMSN-SYLKTIKKELN-YHQMNIVKKVEVQK | GGFSK | ESIK-PKG- | 1098 |
| WP_002378009 | 1048 | --E---------- | RFTKD-GE-ILMSN-SYLKTIKKELN-YHQMNIVKKVEVQK | GGFSK | ESIK-PKG- | 1098 |
| WP_002407324 | 1048 | --E---------- | RFTKD-GE-ILMSN-SYLKTIKKELN-YHQMNIVKKVEVQK | GGFSK | ESIK-PKG- | 1098 |
| WP_002413717 | 1048 | --E---------- | RFTKD-GE-ILMSN-SYLKTIKKELN-YHQMNIVKKVEVQK | GGFSK | ESIK-PKG- | 1098 |
| WP_010775580 | 1050 | --E---------- | RFTKD-GE-ILMSN-SYLKTIKKELN-YHQMNIVKKVEVQK | GGFSK | ESIK-PKG- | 1100 |
| WP_010818269 | 1048 | --E---------- | RFTKD-GE-ILMSN-SYLKTIKKELN-YHQMNIVKKVEVQK | GGFSK | ESIK-PKG- | 1098 |
| WP_010824395 | 1048 | --E---------- | RFTKD-GE-ILMSN-SYLKTIKKELN-YHQMNIVKKVEVQK | GGFSK | ESIK-PKG- | 1098 |
| WP_016622645 | 1048 | --E---------- | RFTKD-GE-ILMSN-SYLKTIKKELN-YHQMNIVKKVEVQK | GGFSK | ESIK-PKG- | 1098 |
| WP_033624816 | 1048 | --E---------- | RFTKD-GE-ILMSN-SYLKTIKKELN-YHQMNIVKKVEVQK | GGFSK | ESIK-PKG- | 1098 |
| WP_033625576 | 1048 | --E---------- | RFTKD-GE-ILMSN-SYLKTIKKELN-YHQMNIVKKVEVQK | GGFSK | ESIK-PKG- | 1098 |
| WP_033789179 | 1048 | --E---------- | RFTKD-GE-ILMSN-SYLKTIKKELN-YHQMNIVKKVEVQK | GGFSK | ESIK-PKG- | 1098 |
| WP_002310644 | 1049 | --T---------- | VCDEN-GE-IFWDKSKSIAQVKKVIN-HHHMNIVKKTEIQK | GGFSK | ETVE-PKK- | 1100 |
| WP_002312694 | 1050 | --T---------- | VCDEN-GE-IFWDKSKSIAQVKKVIN-HHHMNIVKKTEIQK | GGFSK | ETVE-PKK- | 1101 |
| WP_002314015 | 1050 | --T---------- | VCDEN-GE-IFWDKSKSIAQVKKVIN-HHHMNIVKKTEIQK | GGFSK | ETVE-PKK- | 1101 |
| WP_002320716 | 1050 | --T---------- | VCDEN-GE-IFWDKSKSIAQVKKVIN-HHHMNIVKKTEIQK | GGFSE | ETVE-PKK- | 1101 |
| WP_002330729 | 1049 | --T---------- | VCDEN-GE-IFWDKSKSIAQVKKVIN-HHHMNIVKKTEIQK | GGFSK | ETVE-PKK- | 1100 |
| WP_002335161 | 1050 | --T---------- | VCDEN-GE-IFWDKSKSIAQVKKVIN-HHHMNIVKKTEIQK | GGFSK | ETVE-PKK- | 1101 |
| WP_002345439 | 1050 | --E---------- | VCDEN-GE-IFWDKSKSIAQVKKVIN-HHHMNIVKKTEIQK | GGFSK | ETVE-PKK- | 1101 |
| WP_034867970 | 1040 | --E---------- | FCDEN-GE-IYWEKSHHLPRIKKVLS-SHQVNVVKKVEQQK | GGFYK | ETVN-SKE- | 1091 |
| WP_047937432 | 1050 | --E---------- | VCDEN-GE-IFWDKSKSIAQVKKVIN-HHHMNIVKKTEIQK | GGFSK | ETVE-PKK- | 1101 |
| WP_010720994 | 1040 | --E---------- | FCDEN-GE-IYWEKSHHLPRIKKVLS-SHQVNVVKKVEQQK | GGFYK | ETVN-SKE- | 1091 |
| WP_010737004 | 1040 | --E---------- | FCDEN-GE-IYWEKSHHLPRIKKVLS-SHQVNVVKKVEQQK | GGFYK | ETVN-SKE- | 1091 |

-continued

| ID | | | | | |
|---|---|---|---|---|---|
| WP_034700478 | 1040 | --E--------P | FCDEN-GE-IVWEKSHHLPRIKKVLS-SHQVNVKKVEQQK | GGFYK | ETVN-SKE- | 1091 |
| WP_007209003 | 1038 | --D-------- | IINDD-GE-ILWNKQETIAQVIKTLG-MHQVNVVKKVEIQK | GGFSK | ESIQ-PKG- | 1089 |
| WP_023519017 | 1034 | --E--------- | ICDEQ-GE-VIWNKKRDLSTIKKTIG-AHQVNIVKKVEKQK | GGFYK | ETIN-SKA- | 1085 |
| WP_010770040 | 1046 | --A--------V | IIDEN-GE-ILWMDK-KNIATVKKVMS-YPQMNIVKKPEIQT | GSFSK | ETIK-PKG- | 1096 |
| WP_048604708 | 1043 | --K--------V | IIDEN-GE-ILWMDK-ILWNQ-KKIVTVKKVMN-YRQMNIVKKVEIQK | GGFSK | ESIL-PKG- | 1093 |
| WP_010750235 | 1043 | --E--------Q | FCDEN-GE-IFWDKRKHIQQIKKVIS-SHQVNIVKKVEVQT | GSFYK | ETVN-TKE- | 1094 |
| AII16583 | 1091 | LAN-GEIRKRPLIE | TNGET-GE-IVWDKGRDFATVRKVLS-MPQVNIVKKTEVQT | GGFSK | ESIL-PKR- | 1153 |
| WP_029073316 | 1053 | --D--------- | -----T-GE-VVWDP-EWISRIKKCFY-YKDCFVTKKLEENN | GSFFN | -TVR-PNDe | 1099 |
| WP_031589969 | 1053 | --D--------- | -----T-GE-IVWDP-NYIDRIKKCFY-YKDCFVTKKLEENN | GTFFN | -TVL-PNDt | 1099 |
| KDA45870 | 1035 | YPF--------- | --------WDKARDLPTIKRYLY-RAQVNKVRKAERQT | GGFSD | EMLV-PKS- | 1078 |
| WP_039099354 | 1044 | -----------E | LVDEN-TEaVIWNKESGLAYLNKIYQ-FKKILLVTREVHENS | GALFN | QTIYaAkDd | 1097 |
| AKP02966 | 1063 | --N------GTTQ | --DRNt.GE-IIWNVG-FRDKILKIFN-YHQCNVTRKTEIKT | GQFYD | QTIYsPKNp | 1118 |
| WP_010991369 | 1045 | --D--------R | IIDKN-GE-ILWMDN-RYLDTIKKVLS-YRQMNIVKKTEIQK | GEFSK | ATIK-PKG- | 1095 |
| WP_033838504 | 1045 | --D--------R | IIDEN-GE-ILWMDK-KYLDTVKKVMS-YRQMNIVKKTEIQK | GEFSK | ATIK-PKG- | 1095 |
| EHN60060 | 1048 | --D--------R | IIDEN-GE-ILWMDK-KYLDTVKKVMS-YRQMNIVKKTEIQK | GEFSK | ATIK-PKG- | 1098 |
| EFR89594 | 814 | --D--------R | IIDEN-GE-ILWMDK-KYLDTVKKVMS-YRQMNIVKKTEIQK | GEFSK | ATIK-PKG- | 864 |
| WP_038409211 | 1045 | --N--------Q | IIDKN-GE-ILWMDN-RYLDTIKKVLS-YRQMNIVKKTEIQK | GEFSN | ATVN-PKG- | 1095 |
| EFR95520 | 664 | --N--------Q | IIDKN-GE-ILWMDN-RYLDTIKKVLS-YRQMNIVKKTEIQK | GEFSN | ATVN-PKG- | 714 |
| WP_003723650 | 1045 | --E--------R | IIDEN-GE-ILWMDK-KYLETIKKVLD-YRQMNIVKKTEIQK | GEFSK | ATIK-PKG- | 1095 |
| WP_003727705 | 1045 | --E--------R | IIDEN-GE-ILWMDK-KYLETIKKVLD-YRQMNIVKKTEIQK | GEFSK | ATIK-PKG- | 1095 |
| WP_003730785 | 1045 | --E--------R | IIDEN-GE-ILWMDK-KYLETIKKVLD-YRQINIVKKTEIQK | GEFSK | ATIK-PKG- | 1095 |
| WP_003733029 | 1045 | --D--------R | IIDEN-GE-ILWMDK-KYLETVKKVLG-YRQMNIVKKTEIQK | GEFSN | VTPN-PKG- | 1095 |
| WP_003739838 | 1045 | --E--------R | IIDEN-GE-ILWMDK-KYLETIKKVLD-YRQMNIVKKTEIQK | GEFSK | ATIK-PKG- | 1095 |
| WP_014601172 | 1045 | --E--------R | IIDEN-GE-ILWMDK-KYLETIKKVLN-YRQMNIVKKTEIQK | GEFSK | ATIK-PKG- | 1095 |
| WP_023548323 | 1045 | --E--------R | IIDEN-GE-ILWMDK-KYLETIKKVLD-YRQMNIVKKTEIQK | GEFSN | QNPK-PRG- | 1095 |
| WP_031665337 | 1045 | --E--------R | IIDEN-GE-ILWMDK-KYLETIKKVLD-YRQMNIVKKTEIQK | GEFSK | ATIK-PKG- | 1095 |
| WP_031669209 | 1045 | --D--------R | IIDEN-GE-ILWMDK-RYLETVKKVLG-YRQMNIVKKTEIQK | GEFSN | VTPN-PKG- | 1095 |

```
WP_033920898  1045  --E---------R  IIDEN-GE-IIMDK-KYLETIKKKVLN-YRQMNIVKKTEIQK  GEFSN  QNPK-PRG-  1095
AKI42028      1048  --E---------R  IIDEN-GE-IIMDK-KYLETIKKKVLD-YRQMNIVKKTEIQK  GEFSK  ATIK-PKG-  1098
AKI50529      1048  --E---------R  IIDEN-GE-IIMDK-KYLETIKKKVLN-YRQMNIVKKTEIQK  GEFSN  QNPK-PRG-  1098
EFR83390       493  --E---------R  IIDEN-GE-IIMDK-KYLETIKKKVLD-YRQMNIVKKTEIQK  GEFSK  ATIK-PKG-   543
WP_046323366  1045  --D---------R  IIDEN-GE-IIMDK-KYLDTIKKKVLN-YRQMNIVKKTEIQK  GEFSN  ATAN-PKG-  1095
AKE81011      1068  LAN-GEIRKRPLIE TNGET-GE-IVWDKGRDFATVRKVLS-MPQVNIVKKTEVQT  GGFSK  ESIL-PKR-  1130
CUO82355      1043  --D----------  ------GK-LIWNP-DLINEIKKCFY-YKDCYCTTKLDQKS  GQMFN  -TVL-PNDa  1088
WP_033162887  1043  --D----------  ----T-GE-VMWDP-AKIGKIKSCFY-YKDVYVTKKLEQNS  GTLFN  -TVL-PNDa  1089
AGZ01981      1085  LAN-GEIRKRPLIE TNGET-GE-IVWDKGRDFATVRKVLS-MPQVNIVKKTEVQT  GGFSK  ESIL-PKR-  1147
AKA60242      1052  LAN-GEIRKRPLIE TNGET-GE-IVWDKGRDFATVRKVLS-MPQVNIVKKTEVQT  GGFSK  ESIL-PKR-  1114
AKS40380      1052  LAN-GEIRKRPLIE TNGET-GE-IVWDKGRDFATVRKVLS-MPQVNIVKKTEVQT  GGFSK  ESIL-PKR-  1114
4UN5_B        1056  LAN-GEIRKRPLIE TNGET-GE-IVWDKGRDFATVRKVLS-MPQVNIVKKTEVQT  GGFSK  ESIL-PKR-  1118
WP_010922251  1115  --NSD          KLIA----RKKDW-DPKKYGGPDSPTVAYSV-LVVAK--VE--KGKSKKLKSVKELVGITIME  RSSFEK  1176
WP_039695303  1121  --DSD          KLIPRKTKKV-YW-DTKKYGGPDSPTVAYSV-FVVAD--VE--KGKAKKLKTVKELVGISIME  RSFFEE  1185
WP_045635197  1119  --NSD          KLIPRKT-KDILL-DTTKYGGPDSPTVIAYSI-LLIAD--IE--KGKAKKLKTVKTLVGITIME  KAAFEE  1183
5AXW_A         853  --EKN          -LYKYYEeTGNYL--TKYSKKDNGPVIKKI---------KYYGNKLNAHLDITDDYPNS  -VKLSL   912
WP_009880683   799  --NSD          KLIA----RKKDW-DPKKYGGPDSPTVAYSV-LVVAK--VE--KGKSKKLKSVKELVGITIME  RSSFEK   860
WP_010922251  1115  --NSD          KLIA----RKKDW-DPKKYGGPDSPTVAYSV-LVVAK--VE--KGKSKKLKSVKELLGITIME  RSSFEK  1176
WP_011054416  1115  --NSD          KLIA----RKKDW-DPKKYGGPDSPTVAYSV-LVVAK--VE--KGKSKKLKSVKELLGITIME  RSSFEK  1176
WP_011284745  1115  --NSD          KLIA----RKKDW-DPKKYGGPDSPTVAYSV-LVVAK--VE--KGKSKKLKSVKELLGITIME  RSSFEK  1176
WP_011285506  1115  --NSD          KLIA----RKKDW-DPKKYGGPDSPTVAYSV-LVVAK--VE--KGKSKKLKSVKELLGITIME  RSSFEK  1176
WP_011527619  1115  --NSD          KLIA----RKKDW-DPKKYGGPDSPTVAYSV-LVVAK--VE--KGKSKKLKSVKELLGITIME  RSSFEK  1176
WP_012560673  1115  --NSD          KLIA----RKKDW-DPKKYGGPDSPTVAYSV-LVVAK--VE--KGKSKKLKSVKELVGITIME  RSSFEK  1176
WP_014407541  1114  --NSD          KLIA----RKKDW-DPKKYGGPDSPTVAYSV-LVVAK--VE--KGKSKKLKSVKELLGITIME  RSSFEK  1175
WP_020905136  1115  --NSD          KLIA----RKKDW-DPKKYGGPDSPTVAYSV-LVVAK--VE--KGKSKKLKSVKELLGLTIME  RSSFEK  1176
WP_023080005  1114  --NSD          KLIA----RKKDW-DPKKYGGPDSPTVAYSV-LVVAK--VE--KGKSKKLKSVKELLGITIME  RSSFEK  1175
WP_023610282  1114  --NSD          KLIA----RKKDW-DPKKYGGPDSPTVAYSV-LVVAK--VE--KGKSKKLKSVKELLGITIME  RSSFEK  1175
```

| | | | | | |
|---|---|---|---|---|---|
| WP_030125963 | 1115 | --NSD | KLIA----RKKDW-DPKKYGGFDSPTVAYSV-LVVAK--VE--KGKSKKLKSVKELLGITIME | RSSFEK | 1176 |
| WP_030126706 | 1115 | --NSD | KLIA----RKKDW-DPKKYGGFDSPTVAYSV-LVVAK--VE--KGKSKKLKSVKELLGITIME | RSSFEK | 1176 |
| WP_031488318 | 1115 | --NSD | KLIA----RKKDW-DPKKYGGFDSPTVAYSV-LVVAK--VE--KGKSKKLKSVKELLGITIME | RSSFEK | 1176 |
| WP_032460140 | 1115 | --NSD | KLIA----RKKDW-DPKKYGGFDSPTVAYSV-LVVAK--VE--KGKSKKLKSVKELVGITIME | RSSFEK | 1176 |
| WP_032461047 | 1115 | --NSD | KLIA----RKKDW-DPKKYGGFDSPTVAYSV-LVVAK--VE--KGKSKKLKSVKELVGITIME | RSSFEK | 1176 |
| WP_032462016 | 1115 | --NSD | KLIA----RKKDW-DPKKYGGFDSPTVAYSV-LVVAK--VE--KGKSKKLKSVKELLGITIME | RSSFEK | 1176 |
| WP_032462936 | 1115 | --NSD | KLIA----RKKDW-DPKKYGGFDSPTVAYSV-LVVAK--VE--KGKSKKLKSVKELLGITIME | RSSFEK | 1176 |
| WP_032464890 | 1115 | --NSD | KLIA----RKKDW-DPKKYGGFDSPTVAYSV-LVVAK--VE--KGKSKKLKSVKELLGITIME | RSSFEK | 1176 |
| WP_033888930 | 940 | --NSD | KLIA----RKKDW-DPKKYGGFDSPTVAYSV-LVVAK--VE--KGKSKKLKSVKELLGITIME | RSSFEK | 1001 |
| WP_038431314 | 1115 | --NSD | KLIA----RKKDW-DPKKYGGFDSPTVAYSV-LVVAK--VE--KGKSKKLKSVKELLGITIME | RSSFEK | 1176 |
| WP_038432938 | 1114 | --NSD | KLIA----RKKDW-DPKKYGGFDSPTVAYSV-LVVAK--VE--KGKSKKLKSVKELLGITIME | RSSFEK | 1175 |
| WP_038434062 | 1115 | --NSD | KLIA----RKKDW-DPKKYGGFDSPTVAYSV-LVVAK--VE--KGKSKKLKSVKELLGITIME | RSSFEK | 1176 |
| BAQ51233 | 1026 | --NSD | KLIA----RKKDW-DPKKYGGFDSPTVAYSV-LVVAK--VE--KGKSKKLKSVKELLGITIME | RSSFEK | 1087 |
| KGE60162 | 290 | --NSD | KLIA----RKKDW-DPKKYGGFDSPTVAYSV-LVVAK--VE--KGKSKKLKSVKELLGITIME | RSSFEK | 351 |
| KGE60856 | 53 | --NSD | KLIA----RKKDW-DPKKYGGFDSPTVAYSV-LVVAK--VE--KGKSKKLKSVKELLGITIME | RSSFEK | 114 |
| WP_002989955 | 1115 | --NSD | KLIA----RKKDW-DPKKYGGFDSPTVAYSV-LVVAK--VE--KGKSKKLRKVQDMVGITIME | RSSFEK | 1176 |
| WP_003030002 | 1094 | --ESD | KLIPRKT-KNSYW-NPKKYGGFDSPVVAYSI-LVFAD--VE--KGKSKKLKSVKELVGISIME | KKRFEK | 1158 |
| WP_003065552 | 1122 | --DSD | KLIPRKTkKA-YW-DTKKYGGFDSPTVAYSV-FVVAD--VE--KGKAKKLKTVKELVTELLGITIME | RSFFEE | 1186 |
| WP_001040076 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040078 | 1121 | --NSD | KLIPRKT-KDIYL-DPKKYGGFDSPIVAYSV-LVVAD--IK--KGKAQKLKTVTELLGITIME | RSKFEK | 1185 |
| WP_001040080 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040081 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040083 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040085 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040087 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040088 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040089 | 1113 | --NSD | KLIPRKT-KDIYL-DPKKYGGFDSPIVAYSV-LVVAD--IK--KGKAQKLKTVTELLGITIME | RSRFEK | 1177 |

| ID | | | | | |
|---|---|---|---|---|---|
| WP_001040090 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040091 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040092 | 1113 | --NSD | KLIPRKT-KDIYL-DPKKYGGFDSPIVAYSV-LVLAD--IK--KGKAQKLKTVKELLGITIME | RERFEK | 1177 |
| WP_001040094 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040095 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040096 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040097 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040098 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040099 | 1113 | --NSD | KLIPRKT-KDIYL-DPKKYGGFDSPKVAYSV-LVVAD--IK--KGKAQKLKTVTELLGITIME | RSRFEK | 1177 |
| WP_001040100 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040104 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040105 | 1113 | --NSD | KLIPRKT-KDIYL-DPKKYGGFDSPIVAYSV-LVVAD--IK--KGKAQKLKTVTELLGITIME | RSRFEK | 1177 |
| WP_001040106 | 1113 | --NSD | KLIPRKT-KDIYL-DPKKYGGFDSPIVAYSV-LVVAD--IK--KGKAQKLKTVTELLGITIME | RFRFEK | 1177 |
| WP_001040107 | 1113 | --NSD | KLIPRKT-KDIYL-DPKKYGGFDSPIVAYSV-LVVAD--IK--KGKAQKLKTVTELLGITIME | RFRFEK | 1177 |
| WP_001040108 | 1113 | --NSD | KLIPRKT-KDIYL-DPKKYGGFDSPIVAYSV-LVVAD--IK--KGKAQKLKTVTELLGITIME | RFRFEK | 1177 |
| WP_001040109 | 1113 | --NSD | KLIPRKT-KDIYL-DPKKYGGFDSPIVAYSV-LVVAD--IK--KGKAQKLKTVTELLGITIME | RFRFEK | 1177 |
| WP_001040110 | 1113 | --NSD | KLIPRKT-KDIYL-DPKKYGGFDSPIVAYSV-LVLAD--IK--KGKAQKLKTVTELLGITIME | RERFEK | 1177 |
| WP_015058523 | 1113 | --NSD | KLIPRKT-KDIYL-DPKKYGGFDSPIVAYSV-LVVAD--IK--KGKAQKLKTVKELLGITIME | RSRFEK | 1177 |
| WP_017643650 | 1113 | --NSD | KLIPRKT-KDIYL-DPKKYGGFDSPIVAYSV-LVVAD--IK--KGKAQKLKTVTELLGITIME | RSRFEK | 1177 |
| WP_017647151 | 1113 | --NSD | KLIPRKT-KDIYL-DPKKYGGFDSPIVAYSV-LVVAD--IK--KGKAQKLKTVTELLGITIME | RSRFEK | 1177 |
| WP_017648376 | 1113 | --NSD | KLIPRKT-KDIYL-DPKKYGGFDSPIVAYSV-LVAAD--IK--KGKAQKLKTVTELLGITIME | RSRFEK | 1177 |
| WP_017649527 | 1113 | --NSD | KLIPRKT-KDIYL-DPKKYGGFDSPIVAYSV-LVVAD--IK--KGKAQKLKTVTELLGITIME | RSRFEK | 1177 |
| WP_017771611 | 1113 | --NSD | KLIPRKT-KDIYL-DPKKYGGFDSPIVAYSV-LVVAD--IK--KGKAQKLKTVTELLGITIME | RFRFEK | 1177 |
| WP_017771984 | 1113 | --NSD | KLIPRKT-KDIYL-DPKKYGGFDSPIVAYSV-LVVAD--IK--KGKAQKLKTVTELLGITIME | RSRFEK | 1177 |
| CFQ25032 | 1113 | --NSD | KLIPRKT-KDIYL-DPKKYGGFDSPIVAYSV-LVVAD--IK--KGKAQKLKTVTELLGITIME | RSRFEK | 1177 |
| CFV16040 | 1113 | --NSD | KLIPRKT-KDIYL-DPKKYGGFDSPIVAYSV-LVVAD--IK--KGKAQKLKTVTELLGITIME | RFRFEK | 1177 |
| KLJ37842 | 1113 | --NSD | KLIPRKT-KDIYL-DPKKYGGFDSPIVAYSV-LVVAD--IK--KGKAQKLKTVTELLGITIME | RSRFEK | 1177 |

-continued

| | | | | | |
|---|---|---|---|---|---|
| KLJ72361 | 1113 | --NSD | KLIPRKT-KDIYL-DPKKYGGFDSPIVAYSV-LVVAD--IK--KGKAQKLKTVTELLGITIME | RSRFEK | 1177 |
| KLL20707 | 1127 | --NSD | KLIPRKT-KDIYL-DPKKYGGFDSPIVAYSV-LVVAD--IK--KGKAQKLKTVTELLGITIME | RSRFEK | 1191 |
| KLL42645 | 1113 | --NSD | KLIPRKT-KDIYL-DPKKYGGFDSPIVAYSV-LVVAD--IK--KGKAQKLKTVTELLGITIME | RFRFEK | 1177 |
| WP_047207273 | 1113 | --NSD | KLIPRKT-KDIYL-DPKKYGGFDSPIVAYSV-LVVAD--IK--KGKAQKLKTVTELLGITIME | RSRFEK | 1177 |
| WP_047209694 | 1113 | --NSD | KLIPRKT-KDIYL-DPKKYGGFDSPIVAYSV-LVVAD--IK--KGKAQKLKTVTELLGITIME | RSRFEK | 1177 |
| WP_050198062 | 1113 | --NSD | KLIPRKT-KDIYL-DPKKYGGFDSPIVAYSV-LVVAD--IK--KGKAQKLKTVTELLGITIME | RSRFEK | 1177 |
| WP_050201642 | 1113 | --NSD | KLIPRKT-KDIYL-DPKKYGGFDSPIVAYSV-LVVAD--IK--KGKAQKLKTVTELLGITIME | RSRFEK | 1177 |
| WP_050204027 | 1113 | --NSD | KLIPRKT-KDIYL-DPKKYGGFDSPIVAYSV-LVVAD--IK--KGKAQKLKTVTELLGITIME | RFRFEK | 1177 |
| WP_050881965 | 1113 | --NSD | KLIPRKT-KDIYL-DPKKYGGFDSPIVAYSV-LVVAD--IK--KGKAQKLKTVTELLGITIME | RSRFEK | 1177 |
| WP_050886065 | 1113 | --NSD | KLIPRKT-KDIYL-DPKKYGGFDSPIVAYSV-LVVAD--IK--KGKAQKLKTVTELLGITIME | RSRFEK | 1177 |
| AHN30376 | 1113 | --NSD | KLIPRKT-KDIYL-DPKKYGGFDSPIVAYSV-LVLAD--IK--KGKAQKLKTVKELIGITIME | RERFEK | 1177 |
| EAO78426 | 1113 | --NSD | KLIPRKT-KDIYL-DPKKYGGFDSPIVAYSV-LVVAD--IK--KGKAQKLKTVTELLGITIME | RSRFEK | 1177 |
| CCW42055 | 1113 | --NSD | KLIPRKT-KDIYL-DPKKYGGFDSPIVAYSV-LVVAD--IK--KGKAQKLKTVTELLGITIME | RSRFEK | 1177 |
| WP_003041502 | 1123 | --DSS | ENLVGVK-RNL---DPKKYGGYAGISNSYAV-LVKAI--IE--KGVKKKETMVLEFQGISILD | RITFEK | 1185 |
| WP_037593752 | 1095 | --ESD | KLIPRKT-KNSYW--NPKKYGGFDSPVVAYSI-LVFAD--VE--KGKSKKLLRKVQDMVGITIME | KKRFEK | 1159 |
| WP_049516684 | 1095 | --ESD | KLIPRKT-KNSYW--NPKKYGGFDSPVVAYSI-LVFAD--VE--KGKSKKLLRKVQDMVGITIME | KKRFEK | 1159 |
| GAD46167 | 1094 | --ESD | KLIPRKT-KNSYW--NPKKYGGFDSPVVAYSI-LVFAD--VE--KGKSKKLLRKVQDMVGITIME | KKRFEK | 1158 |
| WP_018363470 | 1126 | --DSD | KLIPRKTkKV-LW-EPKKYGGFDSPTVAYSV-LVVAD--VE--KGKTKKLLKTVKELVGISIME | RSFFEK | 1190 |
| WP_003043819 | 1124 | --ESA | KLIP----RKKGW-DTRKYGGEGSPTVAYSI-LVVAK--VE--KGKAKKLKSVKVLVGITIME | KGSYEK | 1185 |
| WP_006269658 | 1094 | --ESD | KLIPRKT-KNSYW--DPKKYGGFDSPVVAYSI-LVFAD--VE--KGKSKKLKTVKELVGISIME | KKRFEK | 1158 |
| WP_048800889 | 1114 | --DSD | KLIARKTkEN-YW-DTKKYGGFDSPTVAYSV-LVVAD--IK--KGKAKKLKTVKELVGISIME | RPFFEK | 1178 |
| WP_012767106 | 1114 | --SFD | KLIS----RKHRF-ESSKYGGEGSPTVTYSV-LVVAKskVQ--DGKVKKIKTGKELIGMTLLD | KLVFEK | 1177 |
| WP_014612333 | 1114 | --SFD | KLIS----RKHRF-ESSKYGGEGSPTVTYSV-LVVAKskVQ--DGKVKKIKTGKELIGITLLD | KLVFEK | 1177 |
| WP_015017095 | 1114 | --SFD | KLIS----RKHRF-ESSKYGGEGSPTVTYSV-LVVAKskVQ--DGKVKKIKTGKELIGITLLD | KLVFEK | 1177 |
| WP_015057649 | 1114 | --SFD | KLIS----RKHRF-ESSKYGGEGSPTVTYSV-LVVAKskVQ--DGKVKKIKTGKELIGITLLD | KLVFEK | 1177 |
| WP_048327215 | 1114 | --SFD | KLIS----RKHRF-ESSKYGGEGSPTVTYSV-LVVAKckVQ--DGKVKKIKTGKELIGITLLD | KLVFEK | 1177 |
| WP_049519324 | 1114 | --SFD | KLIS----RKHRF-ESSKYGGEGSPTVTYSV-LVVAKskVQ--DGKVKKIKTGKELIGITLLD | KLVFEK | 1177 |

-continued

| | | | | |
|---|---|---|---|---|
| WP_012515931 | 1095 | --NSD | KLIP----RKNNW-DTRKYGGFDSPTVAYSV-LVIAK--ME--KGKAKVLKPVKEMVGITIME | RTAFEE | 1156 |
| WP_021320964 | 1095 | --NSD | KLIP----RKNNW-DTRKYGGFDSPTVAYSV-LVIAK--ME--KGKAKVLKPVKEMVGITIME | RIAFEE | 1156 |
| WP_037581760 | 1095 | --NSD | KLIP----RKNNW-DTRKYGGFDSPTVAYSV-LVIAK--ME--KGKAKVLKPVKEMVGITIME | RIAFEE | 1156 |
| WP_004232481 | 1124 | --DSD | KLIPRKTkKL-QW-ETQKYGGFDSPTVAYSV-LVVAD--VE--KGKTRKLKTVKELVGISIME | RSSFEE | 1188 |
| WP_009854540 | 1119 | --DSD | KLIPRKTkKV-YW-DTKKYGGFDSPTVAYSV-LVVAD--VE--KGKAKKLKTVKELVGISIME | RSSFEE | 1183 |
| WP_012962174 | 1120 | --NSD | KLIPRKTkKF-RW-DTPKYGGFDSPNIAYSV-EVIAD--VE--KGKAKKLKTVKELVGISIME | RSSFEE | 1184 |
| WP_039695303 | 1121 | --DSD | KLIPRKTkKV-YW-DTKKYGGFDSPTVAYSV-FVVAD--VE--KGKAKKLKTVKELVGISIME | RSFFEE | 1185 |
| WP_014334983 | 1124 | --DSD | KLIPRKTkKV-YW-NTKKYGGFDSPTVAYSV-LVVAD--IE--KGKAKKLKTVKELVGISIME | RSFFEE | 1188 |
| WP_003099269 | 1115 | --DSD | KLIA----RKKSW-DPKKYGGFDSPIIAYSV-LVVAK--IA--KGKTQKLKTIKELVGIKIME | QDEFEK | 1176 |
| AHY15608 | 1115 | --DSD | KLIA----RKKSW-DPKKYGGFDSPIIAYSV-LVVAK--IA--KGKTQKLKTIKELVGIKIME | QDEFEK | 1176 |
| AHY17476 | 1115 | --DSD | KLIA----RKKSW-DPKKYGGFDSPIIAYSV-LVVAK--IA--KGKTQKLKTIKELVGIKIME | QDEFEK | 1176 |
| ESR09100 | 1 | ------ | --------------------------------------------------------ME | QDEFEK | 8 |
| AGM98575 | 1115 | --DSD | KLIA----RKKSW-DPKKYGGFDSPIIAYSV-LVVAK--IA--KGKTQKLKTIKELVGIKIME | QDEFEK | 1176 |
| ALF27331 | 1094 | --NSD | KLIPRKT-KKFYW-DTKKYGGFDSPIVAYSI-LVIAN--IE--KGKSKKLKLVKDLVGITIME | RTIFEK | 1158 |
| WP_018372492 | 1109 | ---NN | KLIP----RKKDW-SVDKYGGFIEPAESYSLaIFYTD--IN-----GKKPKKKSTIIAISRME | KKDYEK | 1167 |
| WP_045618028 | 1125 | vvDAS | KLTPIKS-G---L-SPEKYGGYARPTIAYSV-LVIAD--IE--KGKAKKLRIKEMVGITVQD | KKKFEA | 1188 |
| WP_045635197 | 1119 | --NSD | KLIPRKT-KDILL-DTTKYGGFDSPVIAYSI-LLIAD--IE--KGKAKKLKTVKTLVGITIME | KAAFEE | 1183 |
| WP_002263549 | 1094 | --NSD | KLIPRKT-KKFYW-DTKKYGGFDSPIVAYSI-LVIAD--IE--KGKSKKKLKTVKALVGVTIME | KMTFER | 1158 |
| WP_002263887 | 1094 | --NSD | KLIPRKT-KKFYW-DTKKYGGFDSPIVAYSI-LVIAD--IE--KGKSKKKLKTVKALVGVTIME | KMTFER | 1158 |
| WP_002264920 | 1094 | --DSD | KLIPRKT-KKFYW-DTKKYGGFDSPIVAYSI-LVIAD--IE--KGKSKKKLKTVKALVGVTIME | KMTFER | 1158 |
| WP_002269043 | 1094 | --NSD | KLIPRKT-KKFYW-DTKKYGGFDSPIVAYSI-LVIAD--IE--KGKSKKKLKTVKALVGVTIME | KMTFER | 1158 |
| WP_002269448 | 1094 | --NSD | KLIPRKT-KKFYW-DTKKYGGFDSPIVAYSI-LVIAD--IE--KGKSKKKLKTVKALVGVTIME | KMTFER | 1158 |
| WP_002271977 | 1094 | --NSD | KLIPRKT-KKFYW-DTKKYGGFDSPIVAYSI-LVIAD--IE--KGKSKKKLKTVKALVGVTIME | KMTFER | 1158 |
| WP_002272766 | 1094 | --NSD | KLIPRKT-KKFYW-DTKKYGGFDSPIVAYSI-LVIAD--IE--KGKSKKKLKTVKALVGVTIME | KMTFER | 1158 |
| WP_002273241 | 1094 | --NSD | KLIPRKT-KKFYW-DTKKYGGFDSPIVAYSI-LVIAD--IE--KGKSKKKLKTVKALVGVTIME | KMTFER | 1158 |
| WP_002275430 | 1094 | --NSD | KLIPRKT-KKFYW-DTKKYGGFDSPIVAYSI-LVIAD--IE--KGKSKKKLKTVKALVGVTIME | KMTFER | 1158 |
| WP_002276448 | 1094 | --NSD | KLIPRKT-KKFYW-DTKKYGGFDSPIVAYSI-LVIAD--IE--KGKSKKKLKTVKALVGVTIME | KMTFER | 1158 |

-continued

| | | | | |
|---|---|---|---|---|
| WP_002277050 | 1112 | --PLE | KLVPLKK----AL-NPEKYGGYQKPTTAYPI-LLIVD---------IE--TKQLIPISVMD | KKRFEQ | 1166 |
| WP_002773364 | 1094 | --NSD | KLIPRKT-KKFYW-DTKKYGGFDSPIVAYSI-LVIAD--IE--KGKSKKLKTVKALVGVTIME | KMTFER | 1158 |
| WP_002279025 | 1094 | --NSD | KLIPRKT-KKFYW-DTKKYGGFDSPIVAYSI-LVIAD--IE--KGKSKKLKTVKALVGVTIME | KMTFER | 1158 |
| WP_002279859 | 1094 | --DSD | KLIPRKT-KKFYW-DTKKYGGFDSPIVAYSI-LVIAD--IE--KGKSKKLKTVKALVGVTIME | KMTFER | 1158 |
| WP_002280230 | 1094 | --NSD | KLIPRKT-KKFYW-DTKKYGGFDSPIVAYSI-LVIAD--IE--KGKSKKLKTVKALVGVTIME | KMTFER | 1158 |
| WP_002281696 | 1094 | --NSD | KLIPRKT-KKFYW-DTKKYGGFDSPIVAYSI-LVIAD--IE--KGKSKKLKTVKALVGVTIME | KMTFER | 1158 |
| WP_002282247 | 1112 | --PLE | KLVPLKK----AL-NPEKYGGYQKPTTAYPI-LLIVD---------IE--TKQLIPISVMD | KKRFEQ | 1166 |
| WP_002282906 | 1094 | --NSD | KLIPRKT-KKFYW-DTKKYGGFDSPIVAYSI-LVIAD--IE--KGKSKKLKTVKALVGVTIME | KMTFER | 1158 |
| WP_002283846 | 1094 | --NSD | KLIPRKT-KKFYW-DTKKYGGFDSPIVAYSI-LVIAD--IE--KGKSKKLKTVKALVGVTIME | KMTFER | 1158 |
| WP_002287255 | 1094 | --NSD | KLIPRKT-KKFYW-DTKKYGGFDSPIVAYSI-LVIAD--IE--KGKSKKLKTVKALVGVTIME | KMTFER | 1158 |
| WP_002288990 | 1094 | --NSY | KLIPRKT-KKFYW-DTKKYGGFDSPIVAYSI-LVIAD--IE--KGKSKKLKTVKALVGVTIME | KMTFER | 1158 |
| WP_002289641 | 1094 | --NSD | KLIPRKT-KKFYW-DTKKYGGFDSPIVAYSI-LVIAD--IE--KGKSKKLKTVKALVGVTIME | KMTFER | 1158 |
| WP_002290427 | 1094 | --DSD | KLIPRKT-KKFYW-DTKKYGGFDSPIVAYSI-LVIAD--IE--KGKSKKLKTVKALVGVTIME | KMTFER | 1158 |
| WP_002295753 | 1094 | --NSD | KLIPRKT-KKFYW-DTKKYGGFDSPIVAYSI-LVIAD--IE--KGKSKKLKTVKALVGVTIME | KMTFER | 1158 |
| WP_002296423 | 1094 | --NSD | KLIPRKT-KKFYW-DTKKYGGFDSPIVAYSI-LVIAD--IE--KGKSKKLKTVKALVGVTIME | KMTFER | 1158 |
| WP_002304487 | 1108 | --NSD | KLIPRKT-KKFYW-DTKKYGGFDSPIVAYSI-LVIAD--IE--KGKSKKLKTVKALVGVTIME | KMTFER | 1172 |
| WP_002305844 | 1094 | --NSD | KLIPRKT-KKFYW-DTKKYGGFDSPIVAYSI-LVIAD--IE--KGKSKKLKTVKALVGVTIME | KMTFER | 1158 |
| WP_002307203 | 1094 | --NSD | KLIPRKT-KKFYW-DTKKYGGFDSPIVAYSI-LVIAD--IE--KGKSKKLKTVKALVGVTIME | KMTFER | 1158 |
| WP_002310390 | 1094 | --DSD | KLIPRKT-KKFYW-DTKKYGGFDSPIVAYSI-LVIAD--IE--KGKSKKLKTVKALVGVTIME | KMTFER | 1158 |
| WP_002352408 | 1094 | --DSD | KLIPRKT-KKFYW-DTKKYGGFDSPIVAYSI-LVIAD--IE--KGKSKKLKTVKALVGVTIME | KMTFER | 1158 |
| WP_012997688 | 1094 | --NSD | KLIPRKT-KKFYW-DTKKYGGFDSPIVAYSI-LVIAD--IE--KGKSKKLKTVKALVGVTIME | KMTFER | 1158 |
| WP_014677909 | 1094 | --NSD | KLIPRKT-KKFYW-DTKKYGGFDSPIVAYSI-LVIAD--IE--KGKSKKLKTVKALVGVTIME | KMTFER | 1158 |
| WP_019312892 | 1094 | --NSD | KLIPRKT-KKFYW-DTKKYGGFDSPIVAYSI-LVIAD--IE--KGKSKKLKTVKALVGVTIME | KMTFER | 1158 |
| WP_019313659 | 1094 | --NSD | KLIPRKT-KKFYW-DTKKYGGFDSPIVAYSI-LVIAD--IE--KGKSKKLKTVKALVGVTIME | KMTFER | 1158 |
| WP_019314093 | 1094 | --NSD | KLIPRKT-KKFYW-DTKKYGGFDSPIVAYSI-LVIAD--IE--KGKSKKLKTVKALVGVTIME | KMTFER | 1158 |
| WP_019315370 | 1094 | --NSD | KLIPRKT-KKFYW-DTKKYGGFDSPIVAYSI-LVIAD--IE--KGKSKKLKTVKALVGVTIME | KMTFER | 1158 |
| WP_019803776 | 1094 | --NSD | KLIPRKT-KKFYW-DTKKYGGFDSPIVAYSI-LVIAD--IE--KGKSKKLKTVKALVGVTIME | KMTFER | 1158 |

| | | | | |
|---|---|---|---|---|
| WP_019805234 | 1094 | --DSD | KLIPRKT-KKFYW-DTKKYGGFDSPIVAYSI-LVIAD--IE--KGKSKKKLKTVKALVGVTIME | KMTFER | 1158 |
| WP_024783594 | 1094 | --NSD | KLIPRKT-KKFYW-DTKKYGGFDSPIVAYSI-LVIAD--IE--KSKSKKKLKTVKALVGVTIME | KMTFER | 1158 |
| WP_024784288 | 1112 | --PLE | KLVPLKK----AL-NPEKYGGYQKPTTAYPI-LLIVD----------TKQLIPISVMD | KKRFEQ | 1166 |
| WP_024784666 | 1094 | --NSD | KLIPRKT-KKFYW-DTKKYGGFDSPIVAYSI-LVIAD--IE--KGKSKKKLKTVKALVGVTIME | KMTFER | 1158 |
| WP_024784894 | 1094 | --NSD | KLIPRKT-KKFYW-DTKKYGGFDSPIVAYSI-LVIAD--IE--KGKSKKKLKTVKALVGVTIME | KMTFER | 1158 |
| WP_024786433 | 1112 | --PLE | KLVPLKK----AL-NPEKYGGYQKPTTAYPI-LLIVD----------TKQLIPISVMD | KKRFEQ | 1166 |
| WP_049473442 | 1094 | --NSD | KLIPRKT-KKFYW-DTKKYGGFDSPIVAYSI-LVIAD--IE--KGKSKKKLKTVKALVGVTIME | KMTFER | 1158 |
| WP_049474547 | 1094 | --NSD | KLIPRKT-KKFYW-DTKKYGGFDSPIVAYSI-LVIAD--IE--KGKSKKKLKTVKALVGVTIME | KMTFER | 1158 |
| EMC03581 | 1087 | --NSD | KLIPRKT-KDILW-DTTKYGGFDSPVIAYSI-LLIAD--IE--KGKAKRLKTVKTLVGITIME | KATFEK | 1151 |
| WP_000428612 | 1122 | --NSD | KLIPRKT-KDILW-ETTKYGGFDSPVIAYSI-LLIAD--IE--KGKAKKLKTVKTLVGITIME | KAAFEE | 1186 |
| WP_000428613 | 1120 | --NSD | KLIPRKT-KNVQL-DTTKYGGFDSPVIAYSI-LLVAD--VE--KGKSKKLKTVKSLIGITIME | KVKFEA | 1184 |
| WP_049523028 | 1115 | --NSD | KLIP-----RKNNW-DPKKYGGEGSPITAYSV-LVVAK--VT--KGKSQKTKSVKELVGITIME | QNEFEK | 1179 |
| WP_003107102 | 1084 | --DSD | KLIP-----RKNKWrDTTKYGGENTPTVAYSV-LVVAK--VE--KGKAKKLKPVKELVGITIME | RTKFEA | 1145 |
| WP_054279288 | 1116 | --KSS | KLIPIKS-G---L-SPEKYGGYARPTIAYSV-LVIAD--IE--KGKAKKLKRIKEMVGITIQD | KKKFEA | 1178 |
| WP_049531101 | 1125 | vvDAS | KLIPIKS-G---L-SPEKYGGYARPTIAYSV-LVIAD--IE--KGKTKKLKRIKEMIGITVQD | KKIFES | 1188 |
| WP_049538452 | 1125 | vvDAS | KLIPIKS-G---L-SPEKYGGYARPTIAYSV-LVIAD--IE--KGKTKKLKRIKEMIGITVQD | KKKFEA | 1188 |
| WP_049549711 | 1127 | vvDAS | KLIE-----RKKGW-DPKKYGGFDSPNTAYSI-FVVAK--VA--KRKAQKLKTVKEIVGITIME | KKKFEA | 1190 |
| WP_007896501 | 1121 | --NSD | KLIE-----RKKGW-DPKKYGGFDSPNTAYSI-FVVAK--VA--KRKAQKLKTVKEIVGITIME | QAEYEK | 1182 |
| EFR44625 | 1073 | --NSD | KLIPRKT-KDILW-DTTKYGGFDSPVIAYSI-LLIAD--IE--KGKAKKLKTVKTLVGITIME | QAEYEK | 1134 |
| WP_002897477 | 1119 | --NSD | KLIPIKS-S---L-SPEKYGGYARPTIAYSV-LVIAD--IE--IEkgKGKAKKLKRIKEIVGITIQD | KAAFEE | 1183 |
| WP_002906454 | 1124 | vvDAS | KLIPIKS-S---L-SPEKYGGYARPTIAYSV-LVIAD--IE--KGKAKKLKTVKTLVGITIQD | KKKFES | 1189 |
| WP_009729476 | 1120 | --NSD | KLIPRKT-KDILW-DTTKYGGFDSPVIAYSI-LLIAD--IE--KGKAKKLKTVKTLVGITIME | KDAFEK | 1184 |
| CQR24647 | 1110 | --GSD | KLIARKT-KNNYL-STQKYGGFDSPTVAYSI-MFVAD--IE--KGKSKRLKTVKEMIGITIME | RSRFES | 1174 |
| WP_000066813 | 1124 | --NSD | KLIARKT-KEILM-DTTKYGGFDSPVIAYSI-LLIAD--IE--KGKSKRLKTVKEMIGITIME | KATFEK | 1188 |
| WP_009754323 | 1120 | --NSD | KLIPRKT-KDILW-DTTKYGGFDSPVIAYSI-LLIAD--IE--KGKAKKLKTVKTLVGITIME | KAAFEK | 1184 |
| WP_044674937 | 1113 | --DSD | KLIPRKT-EKFYL-DTKKYGGFDSPTIAYSV-LLIAD--IE--KGKAKKLKRVKELIGITIME | RMAFEK | 1177 |
| WP_044676715 | 1115 | --DSD | KLIPRKT-EKFYL-DTKKYGGFDSPTIAYSV-LLIAD--IE--KGKAKKLKRVKELIGITIME | RMAFEK | 1179 |

| ID | | | | |
|---|---|---|---|---|
| WP_044680361 | 1115 | --DSD | KLIPRKT-EKFYL-DTKKYGGFDSPTIAYSV-LLIAD--IE--KGKAKKLKRVKELIGITIME | RMAFEK | 1179 |
| WP_044681799 | 1113 | --DSD | KLIPRKT-EKFYL-DTKKYGGFDSPTIAYSV-LLIAD--IE--KGKAKKLKRVKELIGITIME | RMAFEK | 1177 |
| WP_049533112 | 1123 | --DSS | ENLVGVK-RNL---DPKKYGGYAGISNSYAV-LVKAI--IE--KGVKKKETMVLEFQGISILD | RITFEK | 1185 |
| WP_029090905 | 1062 | --SSS | KTIP----LKKHL-DTAIYGGYTAVNVASYA--LIQ--FK---KGRKLK--REIIGIPLAV | QTRIDN | 1117 |
| WP_006506696 | 1085 | haDKG | AVVP---vNKNRS-DVHKYGGFSG--LQYTI----VA--IEgqKKKGKKTELVKKISGVPLHL | KAASIN | 1149 |
| AIT42264 | 1115 | --NSD | KLIA----RKKDW-DPKKYGGFDSPTVAYSV-LVVAK--VE--KGKSKKLKSVKELLGITIME | RSSFEK | 1176 |
| WP_034440723 | 1093 | k-KTE | KRIP----IKNNL-DPNIYGGYIEEKMAYYI----AInyLE--NGKTKK----AIVGISIKD | KKDFEG | 1149 |
| AKQ21048 | 1115 | --NSD | KLIA----RKKDW-DPKKYGGFDSPTVAYSV-LVVAK--VE--KGKSKKLKSVKELLGITIME | RSSFEK | 1176 |
| WP_004636532 | 1093 | --DSS | KLIP----VKEGM-DPQKYGGLSQVSEAFAV-VIT---HE--KGKKKQLK--SDLISIPIVD | QKAYEQ | 1150 |
| WP_002364836 | 1099 | --PSN | KLIP----VKNGL-DPQKYGGFDSPIVAYTV-LF----T--HE--KGK-KPL-IKQEILGITIME | KTRFEQ | 1156 |
| WP_016631044 | 1050 | --PSN | KLIP----VKNGL-DPQKYGGFDSPIVAYTV-LF----T--HE--KGK-KPL-IKQEILGITIME | KTRFEQ | 1107 |
| EMS75795 | 835 | --KPD | KLIQ----RKAGW-DVSKYGGFGSPVVAYAV-AFI-------YE--KGKAR--KKAKAIEGITIMK | QSLFEQ | 892 |
| WP_002373311 | 1099 | --PSN | KLIP----VKNGL-DPQKYGGFDSPIVAYTV-LF----T--HE--KGK-KPL-IKQEILGITIME | KTRFEQ | 1156 |
| WP_002378009 | 1099 | --PSN | KLIP----VKNGL-DPQKYGGFDSPIVAYTV-LF----T--HE--KGK-KPL-IKQEILGITIME | KTRFEQ | 1156 |
| WP_002407324 | 1099 | --PSN | KLIP----VKNGL-DPQKYGGFDSPIVAYTV-LF----T--HE--KGK-KPL-IKQEILGITIME | KTRFEQ | 1156 |
| WP_002413717 | 1099 | --PSN | KLIP----VKNGL-DPQKYGGFDSPVVAYTV-LF----T--HE--KGK-KPL-IKQEILGITIME | KTRFEQ | 1156 |
| WP_010775580 | 1101 | --PSN | KLIP----VKNGL-DPQKYGGFDSPVVAYTV-LF----T--HE--KGK-KPL-IKQEILGITIME | KTRFEQ | 1158 |
| WP_010818269 | 1099 | --PSN | KLIP----VKNGL-DPQKYGGFDSPVVAYTV-LF----T--HE--KGK-KPL-IKQEILGITIME | KTRFEQ | 1156 |
| WP_010824395 | 1099 | --PSN | KLIP----VKNGL-DPQKYGGFDSPVVAYTV-LF----T--HE--KGK-KPL-IKQEILGITIME | KTRFEQ | 1156 |
| WP_016622645 | 1099 | --PSN | KLIP----VKNGL-DPQKYGGFDSPVVAYTV-LF----T--HE--KGK-KPL-IKQEILGITIME | KTRFEQ | 1156 |
| WP_033624816 | 1099 | --PSN | KLIP----VKNGL-DPQKYGGFDSPVVAYTV-LF----T--HE--KGK-KPL-IKQEILGITIME | KTRFEQ | 1156 |
| WP_033625576 | 1099 | --PSN | KLIP----VKNGL-DPQKYGGFDSPVVAYTV-LF----T--HE--KGK-KPL-IKQEILGITIME | KTKFEQ | 1156 |
| WP_033789179 | 1099 | --PSN | KLIP----VKNGL-DPQKYGGFDSPVVAYTV-LF----T--HE--KGK-KPL-IKQEILGITIME | KTRFEQ | 1156 |
| WP_002310644 | 1101 | --DSS | KLLP----RKNNW-DPAKYGGLGSPNVAYTV-AFT------YE--KGKAR--KRTNALEGITIME | REAFEQ | 1158 |
| WP_002312694 | 1102 | --DSS | KLLP----RKNNW-DPAKYGGLGSPNVAYTV-AFT------YE--KGKAR--KRTNALEGITIME | REAFEQ | 1159 |
| WP_002314015 | 1102 | --DSS | KLLP----RKNNW-DPAKYGGLGSPNVAYTV-AFT------YE--KGKAR--KRTNALEGITIME | REAFEQ | 1159 |
| WP_002320716 | 1102 | --DSS | KLLP----RKNNW-DPAKYGGLGSPNVAYTV-AFT------YE--KGKAR--KRTNALEGITIME | REAFEQ | 1159 |

| | | | | | |
|---|---|---|---|---|---|
| WP_002330729 | 1101 | --DSS | KLLP----RKNNW-DPAKYGGLGSPNVAYTV-AFT----YE--KGKAR--KRTNALEGITIME | REAFEQ | 1158 |
| WP_002335161 | 1102 | --DSS | KLLP----RKNNW-DPAKYGGLGSPNVAYTV-AFT----YE--KGKAR--KRTNALEGITIME | REAFEQ | 1159 |
| WP_002345439 | 1102 | --DSS | KLLP----RKNNW-DPTKYGGLGSPNVAYTV-AFT----YE--KGKAR--KRTNALEGITIME | REAFEQ | 1159 |
| WP_034867970 | 1092 | --KPD | KLIE----RKNNW-DVTKYGGFGSPVIAYAI-AFV----YA--KGKTQ--KKTRAIEGITIME | QAAFEK | 1149 |
| WP_047937432 | 1102 | --DSS | KLIE----RKNNW-DPAKYGGLGSPNVAYTV-AFT----YE--KGKAR--KRTNALEGITIME | REAFEQ | 1159 |
| WP_010720994 | 1092 | --KPD | KLIE----RKNNW-DVTKYGGFGSPVIAYAI-AFV----YA--KGKTQ--KKTKAIEGITIME | QAAFEK | 1149 |
| WP_010737004 | 1092 | --KPD | KLIE----RKNNW-DVTKYGGFGSPVIAYAI-AFV----YA--KGKTQ--KKTRAIEGITIME | QAAFEK | 1149 |
| WP_034700478 | 1092 | --KPD | KLIE----RKNNW-DVTKYGGFGSPVIAYAI-AFV----YA--KGKTQ--KKTRAIEGITIME | QAAFEK | 1149 |
| WP_007209003 | 1090 | --ESQ | KLIR----RKQQW-NTKKYGGFDSPVVAYAI-LLS----FD--KGK-RKARSFK-IVGITIQD | RESFEG | 1147 |
| WP_023519017 | 1086 | --NPE | KLIP----RKASL-DPLKYGGYGSPLVAYTV-IFI----FE--KGKQK--KVTKGIEGITVME | QLRFEQ | 1143 |
| WP_010770040 | 1097 | --DSD | KLIS----RKTNW-SPKLYGGFDSPQVAYSV-II-----T---YE--KGK-KKVRA-KAIVGITIME | QSLFKK | 1154 |
| WP_048604708 | 1094 | --DSD | KLIS----RKKEW-DTTKYGGFDSPNVAYSV-VI-----R---YE--KGK-TRKLV-KTIVGITIME | RAAFEK | 1151 |
| WP_010750235 | 1095 | --KPD | KLIK----RKNNW-DVTKYGGFGSPVVAYAV-VFT----YE--KGKNH--KKAKAIEGITIME | QALFEK | 1152 |
| AII16583 | 1154 | --NSD | KLIA----RKKDW-DPKKYGGFDSPTVAYSV-LVVAK--VE--KGKSKKLKSVKELLGITIME | RSSFEK | 1215 |
| WP_029073316 | 1100 | hsEKG | AKVP----VNKLRS-NVHKYGGFEG--LKYSI----VA--IKgkKKKGKKI IDVNKLVGIPLMY | KNVDDE | 1164 |
| WP_031589969 | 1100 | nsDKD | ATVP----VNKYRS-NVNKYGGFSG--VNSFI----VA--IKgkKKKGKKVIEVNKLTGIPLMY | KNADEE | 1164 |
| KDA45870 | 1079 | --DSG | KLLP----RKEGL-DPVKYGGYAKAVESYAV-LITAD-eVK--KGKTKKVKT--LVNIPIID | SKKYEA | 1138 |
| WP_039099354 | 1098 | k-ASG | QLIPAKQdRPTAL----YGGYSGKTVAYMC--IVR----IKnkKGDLYKVCGVETSWLAQLKQ | KKAFLK | 1170 |
| AKP02966 | 1119 | k---- | KLIA----QKKDM-DPNIYGGFSGDNKSSIT--IVK--ID----NNKIKPVA--IPIRLIN | ---DK | 1172 |
| WP_010991369 | 1096 | --NSS | KLIP----RKTNW-DPMKYGGLDSPNMAYAV-VI-----E---YA--KGK-NKLVFEKKIIRVTIME | RKAFEK | 1154 |
| WP_033838504 | 1096 | --NSS | KLIS----RKTNW-DPMKYGGLDSPNMAYAV-VI-----E---YA--KGK-NKLVFEKKIIRVTIME | RKAFEK | 1154 |
| EHN60060 | 1099 | --NSS | KLIS----RKTNW-DPMKYGGLDSPNMAYAV-VI-----E---YA--KGK-NKLVFEKKIIRVTIME | RKAFEK | 1157 |
| EFR89594 | 865 | --NSS | KLIS----RKTNW-DPMKYGGLDSPNMAYAV-VI-----E---YA--KGK-NKLVFEKKIIRVTIME | RKAFEK | 923 |
| WP_038409211 | 1096 | --NSS | KLIS----RKADW-NPIKYGGFDGSNMAYSI-VI-----E---YE--KGK-KRK-KKTVIKKELIQINIME | RVAFEK | 1154 |
| EFR95520 | 715 | --NSS | KLIS----RKADM-NPIKYGGFDGSNMAYSI-VI-----E---YE--KGK-KRK-KKTVIKKELIQINIME | RVAFEK | 773 |
| WP_003723650 | 1096 | --NSS | KLIP----RKENW-DPMKYGGLDSPNMAYAV-II-----E---HA--KGK-KKIVIEKKLIQINIME | RKMFEK | 1154 |
| WP_003727705 | 1096 | --NSS | KLIP----RKENW-DPMKYGGLDSPNMAYAV-II-----E---HA--KGK-KKIVIEKKLIQINIME | RKMFEK | 1154 |

-continued

| ID | | | | | | |
|---|---|---|---|---|---|---|
| WP_003730785 | 1096 | --NSS | KLIP----RKENW-DPVKYGGLDSPNMAYAV-II--E---HA--KGK-KKIVIEKKLIQINIME | RKMFEK | 1154 |
| WP_003733029 | 1096 | --KSN | KLIP----RKKDW-DPIKYGGFDGSKMAYAI-II--E---YE--KQK-RKVRIEKKLIQINIME | REAFEK | 1154 |
| WP_003739838 | 1096 | --NSS | KLIP----RKENW-DPMKYGGLDSPNMAYAV-II--E---HA--KGK-KKVFEKKLIRITIME | RKAFEK | 1154 |
| WP_014601172 | 1096 | --NSS | KLIP----RKENW-DPMKYGGLDSPNMAYAV-II--E---HA--KGK-KKLIFEKKIRITIME | RKMFEK | 1154 |
| WP_023548323 | 1096 | --DSS | KLIP----KKTNL-NPIKYGGFEGSNMAYAI-II--E---KRK-KGK-KKVTIEKKLIQINIME | RKMFEK | 1154 |
| WP_031665337 | 1096 | --NSS | KLIP----RKENW-DPMKYGGLDSPNMAYAV-II--E---HA--KGK-KRK-RKVRIEKKLIQINIME | RKMFEK | 1154 |
| WP_031669209 | 1096 | --KSN | KLIP----RKKDW-DPIKYGGFDGSKMAYAI-II--E---YE--KQK-RKVRIEKKLIQINIME | REAFEK | 1154 |
| WP_033920898 | 1096 | --DSS | KLIP----KKTNL-NPIKYGGFEGSNMAYAI-II--E---HE--KRK-KKVTIEKKLIFEKKIRITIME | RKAFEK | 1154 |
| AKI42028 | 1099 | --NSS | KLIP----RKENW-DPMKYGGLDSPNMAYAV-II--E---HE--KRK-KKGK-KKVTIEKKLIQINIME | RKMFEK | 1157 |
| AKI50529 | 1099 | --DSS | KLIP----KKTNL-NPIKYGGFEGSNMAYAI-II--E---HE--KRK-KKVTIEKKLIQINIME | RKAFEK | 1157 |
| EFR83390 | 544 | --NSS | KLIP----RKENW-DPMKYGGLDSPNMAYAV-II--E---HA--KGK-KKIVIEKKLIQINIME | RKMFEK | 602 |
| WP_046323366 | 1096 | --NSS | KLIP----RKADW-DPIKYGGFDGSNMAYAV-VI--E---HE--KRK-KKTVIKKELIQINIME | RTAFEK | 1154 |
| AKE81011 | 1131 | --NSD | KLIA----RKKDW-DPKKYGGFDSPTVAYSV-LVVAK--VE--KGKSKKLKSVKELLGITIME | RSSFEK | 1192 |
| CU082355 | 1089 | hsAKG | AVIP----vNKNRK-DVNKYGGFSG--LQYVI----AA--IEgtKKKKGKKLVKRKLSGIPLYL | KQADIK | 1153 |
| WP_033162887 | 1090 | hsEKG | ATVP----1NKYRA-DVHKYGGFGN--VQSII----VA--IEgkKKKKGKKLIDVRKLTSIPLHL | KNAPVE | 1154 |
| AGZ01981 | 1148 | --NSD | KLIA----RKKDW-DPKKYGGFDSPTVAYSV-LVVAK--VE--KGKSKKLKSVKELLGITIME | RSSFEK | 1209 |
| AKA60242 | 1115 | --NSD | KLIA----RKKDW-DPKKYGGFDSPTVAYSV-LVVAK--VE--KGKSKKLKSVKELLGITIME | RSSFEK | 1176 |
| AKS40380 | 1115 | --NSD | KLIA----RKKDW-DPKKYGGFDSPTVAYSV-LVVAK--VE--KGKSKKLKSVKELLGITIME | RSSFEK | 1176 |
| 4UN5_B | 1119 | --NSD | KLIA----RKKDW-DPKKYGGFDSPTVAYSV-LVVAK--VE--KGKSKKLKSVKELLGITIME | RSSFEK | 1180 |
| WP_010922251 | 1177 | NPI----DFLE---AKGYKE--V-KKDLIIK--LPKYSLFE---LENGRKRMLAS | -GELQKGNELALPSKYVNFLYLA | 1239 |
| WP_039695303 | 1186 | NPV----EFLE---NKGYHN--I-REDKLIK--LPKYSLFE---PEGGRRRLLAS | ASELQKGNEMVLPGYLVELLYHA | 1248 |
| WP_045635197 | 1184 | NPI----TFLE---NKGYHN--V-RKENILC--LPKYSLFE---LENGRRRLLAS | AKELQKGNEIVLPVYLTTLLYHS | 1246 |
| 5AXW_A | 913 | KPYrfdVYLD----NGVYKFvtV-KNLDVIK---KENYE---VNSKAYEEAKK | -KKISNQAEFIASFYNNDLIKIN | 978 |
| WP_009880683 | 861 | DPV----DFLE---AKGYKE--V-RKDLIIK--LPKYSLFE---LENGRKRMLAS | -GELQKGNELALPSKYVNFLYLA | 923 |
| WP_010922251 | 1177 | NPI----DFLE---AKGYKE--V-RKDLIIK--LPKYSLFE---LENGRKRMLAS | -GELQKGNELALPSKYVNFLYLA | 1239 |
| WP_011054416 | 1177 | DPI----DFLE---AKGYKE--V-RKDLIIK--LPKYSLFE---LENGRKRMLAS | -GELQKGNELALPSKYVNFLYLA | 1239 |
| WP_011284745 | 1177 | NPI----DFLE---AKGYKE--V-RKDLIVK--LPKYSLFE---LENGRKRMLAS | -GELQKGNELALPSKYVNFLYLA | 1239 |

-continued

| | | | | | | |
|---|---|---|---|---|---|---|
| WP_011285506 | 1177 | NPI---DFLE---AKGYKE--V-KKDLIIK--LPKYSLFE---LENGRKRMLAS | -GELQKGNELALPSKYVNFLYLA | 1239 |
| WP_011527619 | 1177 | NPI---DFLE---AKGYKE--V-RKDLIIK--LPKYSLFE---LENGRKRMLAS | -GELQKGNELALPSKYVNFLYLA | 1239 |
| WP_012560673 | 1177 | DPV---DFLE---AKGYKE--V-RKDLIIK--LPKYSLFE---LENGRKRMLAS | -GELQKGNELALPSKYVNFLYLA | 1239 |
| WP_014407541 | 1176 | NPI---DFLE---AKGYKE--V-KKDLIIK--LPKYSLFE---LENGRKRMLAS | -GELQKGNELALPSKYVNFLYLA | 1238 |
| WP_020905136 | 1177 | NPI---DFLE---AKGYKE--V-RKDLIIK--LPKYSLFE---LENGRKRMLAS | -GELQKGNELALPSKYVNFLYLA | 1239 |
| WP_023080005 | 1176 | NPI---DFLE---AKGYKE--V-RKDLIIK--LPKYSLFE---LENGRKRMLAS | -GELQKGNELALPSKYVNFLYLA | 1238 |
| WP_023610282 | 1176 | NPI---DFLE---AKGYKE--V-RKDLIIK--LPKYSLFE---LENGRKRMLAS | -GELQKGNELALPSKYVNFLYLA | 1238 |
| WP_030125963 | 1177 | NPI---DFLE---AKGYKE--V-RKDLIIK--LPKYSLFE---LENGRKRMLAS | -GELQKGNELALPSKYVNFLYLA | 1239 |
| WP_030126706 | 1177 | NPI---DFLE---AKGYKE--V-RKDLIIK--LPKYSLFE---LENGRKRMLAS | -GELQKGNELALPSKYVNFLYLA | 1239 |
| WP_031488318 | 1177 | NPI---DFLE---AKGYKE--V-RKDLIIK--LPKYSLFE---LENGRKRMLAS | -GELQKGNELALPSKYVNFLYLA | 1239 |
| WP_032460140 | 1177 | DPV---DFLE---AKGYKE--V-RKDLIIK--LPKYSLFE---LENGRKRMLAS | -GELQKGNELALPSKYVNFLYLA | 1239 |
| WP_032461047 | 1177 | NPI---DFLE---AKGYKE--V-RKDLIIK--LPKYSLFE---LENGRKRMLAS | -GELQKGNELALPSKYVNFLYLA | 1239 |
| WP_032462016 | 1177 | NPI---DFLE---AKGYKE--V-RKDLIIK--LPKYSLFE---LENGRKRMLAS | -GELQKGNELALPSKYVNFLYLA | 1239 |
| WP_032462936 | 1177 | NPI---DFLE---AKGYKE--V-RKDLIIK--LPKYSLFE---LENGRKRMLAS | -GELQKGNELALPSKYVNFLYLA | 1239 |
| WP_032464890 | 1177 | NPI---DFLE---AKGYKE--V-RKDLIIK--LPKYSLFE---LENGRKRMLAS | -GELQKGNELALPSKYVNFLYLA | 1239 |
| WP_033888930 | 1002 | NPI---DFLE---AKGYKE--V-RKDLIIK--LPKYSLFE---LENGRKRMLAS | -GELQKGNELALPSKYVNFLYLA | 1064 |
| WP_038431314 | 1177 | DPI---DFLE---AKGYKE--V-RKDLIIK--LPKYSLFE---LENGRKRMLAS | -GELQKGNELALPSKYVNFLYLA | 1239 |
| WP_038432938 | 1176 | DPI---DFLE---AKGYKE--V-RKDLIIK--LPKYSLFE---LENGRKRMLAS | -GELQKGNELALPSKYVNFLYLA | 1238 |
| WP_038434062 | 1177 | NPI---DFLE---AKGYKE--V-RKDLIIK--LPKYSLFE---LENGRKRMLAS | -GELQKGNELALPSKYVNFLYLA | 1239 |
| BAQ51233 | 1088 | HPV---DFLE---QRGYRN--V-RLEKIIK--LPKYSLFE---LENKRRRLLAS | ARELQKGNELVIPQRFTTLLYHS | 1150 |
| KGE60162 | 352 | NPV---EFLE---NKGYHN--I-REDKLIK--LPKYSLFE---PEGGKRRLLAS | ASELQKGNEMVIPGHLVKLLYHA | 414 |
| KGE60856 | 115 | AFLE---SKGYLN--I-RTDKLII--LPKYSLFE---LENGRRRLLAS | AGELQKGNELALPTQFMKFLYLA | 177 |
| WP_002989955 | 1177 | NPI---DFLE---AKGYKE--V-RKDLIIK--LPKYSLFE---LENGRKRMLAS | -GELQKGNELALPSKYVNFLYLA | 1239 |
| WP_003030002 | 1159 | HPV---DFLE---QRGYRN--V-RLEKIIK--LPKYSLFE---LENKRRRLLAS | ARELQKGNELVIPQRFTTLLYHS | 1221 |
| WP_003065552 | 1187 | NPV---EFLE---NKGYHN--I-REDKLIK--LPKYSLFE---PEGGKRRLLAS | ASELQKGNEMVIPGHLVKLLYHA | 1249 |
| WP_001040076 | 1178 | NPS---AFLE---SKGYLN--I-RTDKLII--LPKYSLFE---LENGRRRLLAS | AGELQKGNELALPTQFMKFLYLA | 1240 |
| WP_001040078 | 1186 | NPS---AFLE---SKGYLN--I-RDDKLMI--LPKYSLFE---LENGRRRLLAS | AGELQKGNELALPTQFMKFLYLA | 1248 |

-continued

| ID | | | | | |
|---|---|---|---|---|---|
| WP_001040080 | 1178 | NPS---AFLE---SKGYLN--I-RADKLII--LPKYSLFE---LENGRRRLLAS | AGELQKGNELALPTQFMKFLYLA | 1240 |
| WP_001040081 | 1178 | NPS---AFLE---SKGYLN--I-RADKLII--LPKYSLFE---LENGRRRLLAS | AGETIDRLQKGNELALPTQFMKFLYLA | 1240 |
| WP_001040083 | 1178 | NPS---AFLE---SKGYLN--I-RADKLII--LPKYSLFE---LENGRRRLLAS | AGELQKGNELALPTQFMKFLYLA | 1240 |
| WP_001040085 | 1178 | NPS---AFLE---SKGYLN--I-RADKLII--LPKYSLFE---LENGRRRLLAS | AGELQKGNELALPTQFMKFLYLA | 1240 |
| WP_001040087 | 1178 | NPS---AFLE---SKGYLN--I-RADKLII--LPKYSLFE---LENGRRRLLAS | AGELQKGNELALPTQFMKFLYLA | 1240 |
| WP_001040088 | 1178 | NPS---AFLE---SKGYLN--I-RADKLII--LPKYSLFE---LENGRRRLLAS | AGELQKGNELALPTQFMKFLYLA | 1240 |
| WP_001040089 | 1178 | NPS---AFLE---SKGYLN--I-RDDKLMI--LPKYSLFE---LENGRRRLLAS | AGELQKGNELALPTQFMKFLYLA | 1240 |
| WP_001040090 | 1178 | NPS---AFLE---SKGYLN--I-RADKLII--LPKYSLFE---LENGRRRLLAS | AGELQKGNELALPTQFMKFLYLA | 1240 |
| WP_001040091 | 1178 | NPS---AFLE---SKGYLN--I-RADKLII--LPKYSLFE---LENGRRRLLAS | AGELQKGNELALPTQFMKFLYLA | 1240 |
| WP_001040092 | 1178 | NPS---AFLE---SKGYLN--I-RTDKLII--LPKYSLFE---LENGRRRLLAS | AGELQKGNELALPTQYMKFLYLA | 1240 |
| WP_001040094 | 1178 | NPS---AFLE---SKGYLN--I-RDDKLMI--LPKYSLFE---LENGRRRLLAS | ADELQKGNELALPTQYMKFLYLA | 1240 |
| WP_001040095 | 1178 | NPS---AFLE---SKGYLN--I-RTDKLII--LPKYSLFE---LENGRRRLLAS | AGELQKGNELALPTQYMKFLYLA | 1240 |
| WP_001040096 | 1178 | NPS---AFLE---SKGYLN--I-RTDKLII--LPKYSLFE---LENGRRRLLAS | AGELQKGNELALPTQFMKFLYLA | 1240 |
| WP_001040097 | 1178 | NPS---AFLE---SKGYLN--I-RDDKLMI--LPKYSLFE---LENGRRRLLAS | ADELQKGNELALPTQFMKFLYLA | 1240 |
| WP_001040098 | 1178 | NPS---AFLE---SKGYLN--I-RDDKLMI--LPKYSLFE---LENGRRRLLAS | AGELQKGNELALPTQFMKFLYLA | 1240 |
| WP_001040099 | 1178 | NPS---AFLE---SKGYLN--I-RDDKLMI--LPKYSLFE---LENGRRRLLAS | AGELQKGNELALPTQFMKFLYLA | 1240 |
| WP_001040100 | 1178 | NPS---AFLE---SKGYLN--I-RADKLII--LPKYSLFE---LENGRRRLLAS | AGELQKGNELALPTQFMKFLYLA | 1240 |
| WP_001040104 | 1178 | NPS---AFLE---SKGYLN--I-RADKLII--LPKYSLFE---LENGRRRLLAS | AGELQKGNELALPTQFMKFLYLA | 1240 |
| WP_001040105 | 1178 | NPS---AFLE---SKGYLN--I-RDDKLMI--LPKYSLFE---LENGRRRLLAS | AGELQKGNELALPTQYMKFLYLA | 1240 |
| WP_001040106 | 1178 | NPS---AFLE---SKGYLN--I-RDDKLMI--LPKYSLFE---LENGRRRLLAS | AGELQKGNELALPTQYMKFLYLA | 1240 |
| WP_001040107 | 1178 | NPS---AFLE---SKGYLN--I-RDDKLMI--LPKYSLFE---LENGRRRLLAS | AGELQKGNELALPTQYMKFLYLA | 1240 |
| WP_001040108 | 1178 | NPS---AFLE---SKGYLN--I-RDDKLMI--LPKYSLFE---LENGRRRLLAS | AGELQKGNELALPTQYMKFLYLA | 1240 |
| WP_001040109 | 1178 | NPS---AFLE---SKGYLN--I-RDDKLMI--LPKYSLFE---LENGRRRLLAS | AGELQKGNELALPTQYMKFLYLA | 1240 |
| WP_001040110 | 1178 | NPS---AFLE---SKGYLN--I-RDDKLMI--LPKYSLFE---LENGRRRLLAS | AGELQKGNELALPTQYMKFLYLA | 1240 |
| WP_015058523 | 1178 | NPS---AFLE---SKGYLN--I-RTDKLII--LPKYSLFE---LENGRRRLLAS | AGELQKGNELALPTQYMKFLYLA | 1240 |
| WP_017643650 | 1178 | NPS---AFLE---SKGYLN--I-RDDKLMI--LPKYSLFE---LENGRRRLLAS | ADELQKGNELALPTQFMKFLYLA | 1240 |
| WP_017647151 | 1178 | NPS---AFLE---SKGYLD--I-RDDKLMI--LPKYSLFE---LENGRRRLLAS | AGELQKGNELALPTQFMKFLYLA | 1240 |

| | | | | |
|---|---|---|---|---|
| WP_017648376 | 1178 | NPS---AFLE---SKGYLN--I-RDDKLMI--LPKYSLFE---LENGRRLLAS | AGELQKGNELALPTQFMKFLYLA | 1240 |
| WP_017649527 | 1178 | NPS---AFLE---SKGYLN--I-RADKLII--LPKYSLFE---LENGRRLLAS | AGELQKGNELALPTQFMKFLYLA | 1240 |
| WP_017771611 | 1178 | NPS---AFLE---SKGYLN--I-RDDKLMI--LPKYSLFE---LENGRRLLAS | AGELQKGNELALPTQFMKFLYLA | 1240 |
| WP_017771984 | 1178 | NPS---AFLE---SKGYLN--I-RADKLII--LPKYSLFE---LENGRRLLAS | AGELQKGNELALPTQYMKFLYLA | 1240 |
| CFQ25032 | 1178 | NPS---AFLE---SKGYLN--I-RADKLII--LPKYSLFE---LENGRRLLAS | AGELQKGNELALPTQFMKFLYLA | 1240 |
| CFV16040 | 1178 | NPS---AFLE---SKGYLN--I-RADKLII--LPKYSLFE---LENGRRLLAS | AGELQKGNELALPTQFMKFLYLA | 1240 |
| KLJ37842 | 1178 | NPS---AFLE---SKGYLN--I-RADKLII--LPKYSLFE---LENGRRLLAS | AGELQKGNELALPTQFMKFLYLA | 1240 |
| KLJ72361 | 1178 | NPS---AFLE---SKGYLN--I-RADKLII--LPKYSLFE---LENGRRLLAS | AGELQKGNELALPTQFMKFLYLA | 1240 |
| KLL20707 | 1192 | NPS---AFLE---SKGYLN--I-RADKLII--LPKYSLFE---LENGRRLLAS | AGELQKGNELALPTQFMKFLYLA | 1254 |
| KLL42645 | 1178 | NPS---AFLE---SKGYLN--I-RDDKLMI--LPKYSLFE---LENGRRLLAS | AGELQKGNELALPTQYMKFLYLA | 1240 |
| WP_047207273 | 1178 | NPS---AFLE---SKGYLN--I-RADKLII--LPKYSLFE---LENGRRLLAS | AGELQKGNELALPTQFMKFLYLA | 1240 |
| WP_047209694 | 1178 | NPS---AFLE---SKGYLN--I-RDDKLMI--LPKYSLFE---LENGRRLLAS | AGELQKGNELALPTQFMKFLYLA | 1240 |
| WP_050198062 | 1178 | NPS---AFLE---SKGYLN--I-RADKLII--LPKYSLFE---LENGRRLLAS | AGELQKGNELALPTQFMKFLYLA | 1240 |
| WP_050201642 | 1178 | NPS---AFLE---SKGYLN--I-RADKLII--LPKYSLFE---LENGRRLLAS | AGELQKGNELALPTQYMKFLYLA | 1240 |
| WP_050204027 | 1178 | NPS---AFLE---SKGYLN--I-RDDKLMI--LPKYSLFE---LENGRRLLAS | AGELQKGNELALPTQFMKFLYLA | 1240 |
| WP_050881965 | 1178 | NLS---AFLE---SKGYLN--I-RADKLII--LPKYSLFE---LENGRRLLAS | AGELQKGNELALPTQFMKFLYLA | 1240 |
| WP_050886065 | 1178 | NPS---AFLE---SKGYLN--I-RADKLII--LPKYSLFE---LENGRRLLAS | AGELQKGNELALPTQFMKFLYLA | 1240 |
| AHN30376 | 1178 | NPS---AFLE---SKGYLN--I-RTDKLII--LPKYSLFE---LENGRRLLAS | AGELQKGNELALPTQYMKFLYLA | 1240 |
| EAO78426 | 1178 | NPS---AFLE---SKGYLN--I-RADKLII--LPKYSLFE---LENGRRLLAS | AGELQKGNELALPTQFMKFLYLA | 1240 |
| CCW42055 | 1178 | NPS---AFLE---SKGYLN--I-RTDKLII--LPKYSLFE---LENGRRLLAS | AGELQKGNELALPTQFMKFLYLA | 1240 |
| WP_003041502 | 1186 | DKR---AFLL---GKGYKD--I-K--KIIE--LPKYSLFE---LKDGSRRMLAS | RGEIHKGNELFVPQKFTTLLYHA | 1253 |
| WP_037593752 | 1160 | NPV---DFLE---QRGYRN--V-RLEKIIK--LPKYSLFE---LENKRRLLAS | ARELQKGNELVIPQRFTTLLYHS | 1222 |
| WP_049516684 | 1160 | HPV---DFLE---QRGYRN--V-RLEKIIK--LPKYSLFE---LENKRRLLAS | ARELQKGNELVIPQRFTTLLYHS | 1222 |
| GAD46167 | 1159 | NPV---DFLE---QRGYRN--V-RLEKIIK--LPKYSLFE---LENKRRLLAS | ARELQKGNELVIPQRFTTLLYHS | 1221 |
| WP_018363470 | 1191 | NPV---EFLK---NKGYQN--V-QEDKLMK--LPKYSLFE---PEGGRRRLLAS | ATELQKGNEIMLSAHLVALLYHA | 1253 |
| WP_003043819 | 1186 | DPI---GFLE---AKGYKD--I-KKELIFK--LPKYSLFE---LENGRRMLAS | -ELQKANELVLPQHLVRLLYYT | 1248 |
| WP_006269658 | 1159 | NPV---DFLE---QRGYRN--V-RLEKIIK--LPKYSLFE---LENKRRLLAS | AKELQKGNELVIPQRFTTLLYHS | 1221 |

| | | | | | |
|---|---|---|---|---|---|
| WP_048800889 | 1179 | NPI---MFLE---SKGYRN--I-QKDKLIK--LPKYSLFE----FEGGRRRLLAS | AVELQKGNEMVLPQYLNNLLYHA | 1241 |
| WP_012767106 | 1178 | NPL---KFIE---DKGYGN--V-QIDKCIK--LPKYSLFE----FENGTRRMLAS | RGDLQKANEMFLPAKLVTLLY-- | 1245 |
| WP_014612333 | 1178 | NPL---KFIE---DKGYGN--V-QIDKCIK--LPKYSLFE----FENGTRRMLAS | RGDLQKANEMFLPAKLVTLLY-- | 1245 |
| WP_015017095 | 1178 | NPL---KFIE---DKGYGN--V-QIDKCIK--LPKYSLFE----FENGTRRMLAS | RGDLQKANEMFLPAKLVTLLY-- | 1245 |
| WP_015057649 | 1178 | NPL---KFIE---DKGYGN--V-QIDKCIK--LPKYSLFE----FENGTRRMLAS | RGDLQKANEMFLPAKLVTLLY-- | 1245 |
| WP_048327215 | 1178 | NPL---KFIE---DKGYGN--V-QIDKCIK--LPKYSLFE----FENGTRRMLAS | RGDLQKANEMFLPAKLVTLLY-- | 1245 |
| WP_049519324 | 1178 | NPL---KFIE---DKGYGN--V-QIDKCIK--LPKYSLFE----FENGTRRMLAS | RGDLQKANEMFLPAKLVTLLY-- | 1245 |
| WP_012515931 | 1157 | NPV---VFLE---ARGYRE--I-QEHLIIK--LPKYSLFE----LENGRRRLLAS | -SELQKGNELFLPVDYMTFLYLA | 1219 |
| WP_021320964 | 1157 | NPV---VFLE---AKGYRE--I-QEHLIIK--LPKYSLFE----LENGRRRLLAS | -SELQKGNELFLPVDYMTFLYLA | 1219 |
| WP_037581760 | 1157 | NPV---VFLE---AKGYRE--I-QEHLIIK--LPKYSLFE----LENGRRRLLAS | -SELQKGNELFLPVDYMTFLYLA | 1219 |
| WP_004232481 | 1189 | NPV---SFLE---KKGYHN--V-QEDKLIK--LPKYSLFE----FEGGRRRLLAS | ATELQKGNEVVLPQYMVNLLYHS | 1251 |
| WP_009854540 | 1184 | NPV---EFLE---NKGYHN--I-REDKLIK--LPKYSLFE----FEGGRRRLLAS | ASELQKGNEMVLPGYLVELLYHA | 1246 |
| WP_012962174 | 1185 | NPV---VFLE---KKGYQN--V-QEDNLIK--LPKYSLFE----FEGGRRRLLAS | ASELQKGNEVVLSRHLVELLYHA | 1247 |
| WP_039695303 | 1186 | NPV---EFLE---NKGYHN--I-REDKLIK--LPKYSLFE----FEGGRRRLLAS | ASELQKGNEMVLPGYLVELLYHA | 1248 |
| WP_014334983 | 1189 | NPV---SFLE---KKGYHN--V-QEDKLIK--LPKYSLFE----FEGGRRRLLAS | ATELQKGNEVMLPAHLVELLYHA | 1251 |
| WP_003099269 | 1177 | DPI---AFLE---KKGYQD--I-QTSSIIK--LPKYSLFE----LENGRKRLLAS | --ELQKGNELALPNKYVKFLYLA | 1239 |
| AHY15608 | 1177 | DPI---AFLE---KKGYQD--I-QTSSIIK--LPKYSLFE----LENGRKRLLAS | --ELQKGNELALPNKYVKFLYLA | 1239 |
| AHY17476 | 1177 | DPI---AFLE---KKGYQD--I-QTSSIIK--LPKYSLFE----LENGRKRLLAS | --ELQKGNELALPNKYVKFLYLA | 1239 |
| ESR09100 | 9 | DPI---AFLE---KKGYQD--I-QTSSIIK--LPKYSLFE----LENGRKRLLAS | -KELQKGNELALPNKYVKFLYLA | 71 |
| AGM98575 | 1177 | DPI---AFLE---KKGYQD--I-QTSSIIK--LPKYSLFE----LENGRKRLLAS | --ELQKGNELALPNKYVKFLYLA | 1239 |
| ALF27331 | 1159 | NPV---AFLE---RKGYHN--V-QEENIVK--LPKYSLFE----LENGRRRLLAS | ARELQKGNEIVLPNHLGTMLYHA | 1221 |
| WP_018372492 | 1168 | EPEr---FLA---QKGFER--V-EKT--IK--LPKYSLFE----MEKGRRRLLAS | SGELQKGNQVLLPEHLIRLLSYA | 1228 |
| WP_045618028 | 1189 | NPI---AYLE---ECGYKN--I-NPNLIIK--LPKYSLFE----FNNGQRRLLAS | SIELQKGNELIVPYHFTALLYHA | 1251 |
| WP_045635197 | 1184 | NPI---TFLE---NKGYHN--V-RKENILC--LPKYSLFE----LENGRRRLLAS | AKELQKGNELIVPYLTLLYHS | 1246 |
| WP_002263549 | 1159 | DPV---AFLE---RKGYRN--V-QEENIIK--LPKYSLFK----LENGRKRLLAS | ARELQKGNEIVLPNHLGTLLYHA | 1221 |
| WP_002263887 | 1159 | DPV---AFLE---RKGYRN--V-QEENIIK--LPKYSLFK----LENGRKRLLAS | ARELQKGNEIVLPNHLGTLLYHA | 1221 |
| WP_002264920 | 1159 | DPV---AFLE---RKGYRN--V-QEENIIK--LPKYSLFK----LENGRKRLLAS | ARELQKGNEIVLPNHLGTLLYHA | 1221 |

```
WP_002269943  1159  DPV---AFLE---RKGYRN--V-QEENIIK--LPKYSLFK----LENGRKRLLAS  ARELQKGNEIVLPNHLGTLLYHA  1221
WP_002269448  1159  DPV---AFLE---RKGYRN--V-QEENIIK--LPKYSLFK----LENGRKRLLAS  ARELQKGNEIVLPNHLGTLLYHA  1221
WP_002271977  1159  DPV---AFLE---RKGYRN--V-QEENIIK--LPKYSLFK----LENGRKRLLAS  ARELQKGNEIVLPNHLGTLLYHA  1221
WP_002272766  1159  DPV---AFLE---RKGYRN--V-QEENIIK--LPKYSLFK----LENGRKRLLAS  ARELQKGNEIVLPNHLGTLLYHA  1221
WP_002273241  1159  DPV---AFLE---RKGYRN--V-QEENIIK--LPKYSLFK----LENGRKRLLAS  ARELQKGNEIVLPNHLGTLLYHA  1221
WP_002275430  1159  DPV---AFLE---RKGYRN--V-QEENIIK--LPKYSLFK----LENGRKRLLAS  ARELQKGNEIVLPNHLGTLLYHA  1221
WP_002276448  1159  DPV---AFLE---RKGYRN--V-QEENIIK--LPKYSLFK----LENGRKRLLAS  ARELQKGNEIVLPNHLGTLLYHA  1221
WP_002277050  1167  NPV---KFLK---DKGYQQ--I-EKNNFVK--LPKYTLVD----IGNGIKRLWAS  SKEVHKGNQLVVSKKSQDLLYHA  1229
WP_002277364  1159  DPV---AFLE---RKGYRN--V-QEENIIK--LPKYSLFK----LENGRKRLLAS  ARELQKGNEIVLPNHLGTLLYHA  1221
WP_002279025  1159  DPV---AFLE---RKGYRN--V-QEENIIK--LPKYSLFK----LENGRKRLLAS  ARELQKGNEIVLPNHLGTLLYHA  1221
WP_002279859  1159  DPV---AFLE---RKGYRN--V-QEENIIK--LPKYSLFK----LENGRKRLLAS  ARELQKGNEIVLPNHLGTLLYHA  1221
WP_002280230  1159  DPV---AFLE---RKGYRN--V-QEENIIK--LPKYSLFK----LENGRKRLLAS  ARELQKGNEIVLPNHLGTLLYHA  1221
WP_002281696  1159  DPV---AFLE---RKGYRN--V-QEENIIK--LPKYSLFK----LENGRKRLLAS  ARELQKGNEIVLPNHLGTLLYHA  1221
WP_002282247  1167  NPV---KFLK---DKGYQQ--I-EKNNFVK--LPKYTLVD----IGNGIKRLWAS  SKEVHKGNQLVVSKKSQDLLYHA  1229
WP_002282906  1159  DPV---AFLE---RKGYRN--V-QEENIIK--LPKYSLFK----LENGRKRLLAS  ARELQKGNEIVLPNHLGTLLYHA  1221
WP_002283846  1159  DPV---AFLE---RKGYRN--V-QEENIIK--LPKYSLFK----LENGRKRLLAS  ARELQKGNEIVLPNHLGTLLYHA  1221
WP_002287255  1159  DPI---AFLE---RKGYRN--V-QEENIIK--LPKYSLFK----LENGRKRLLAS  ARELQKGNEIVLPNHLGTLLYHA  1221
WP_002289990  1159  DPV---AFLE---RKGYRN--V-QEENIIK--LPKYSLFK----LENGRKRLLAS  ARELQKGNEIVLPNHLGTLLYHA  1221
WP_002289641  1159  DPV---AFLE---RKGYRN--V-QEENIIK--LPKYSLFK----LENGRKRLLAS  ARELQKGNEIVLPNHLGTLLYHA  1221
WP_002290427  1159  DPV---AFLE---RKGYRN--V-QEENIIK--LPKYSLFK----LENGRKRLLAS  ARELQKGNEIVLPNHLGTLLYHA  1221
WP_002295753  1173  DPV---AFLE---RKGYRN--V-QEENIIK--LPKYSLFK----LENGRKRLLAS  ARELQKGNEIVLPNHLGTLLYHA  1235
WP_002296423  1159  DPV---AFLE---RKGYRN--V-QEENIIK--LPKYSLFK----LENGRKRLLAS  ARELQKGNEIVLPNHLGTLLYHA  1221
WP_002304487  1159  DPI---AFLE---RKGYRN--V-QEENIIK--LPKYSLFK----LENGRKRLLAS  ARELQKGNEIVLPNHLETLLYHA  1221
WP_002305844  1159  DPV---AFLE---RKGYRN--V-QEENIIK--LPKYSLFK----LENGRKRLLAS  ARELQKGNEIVLPNHLGTLLYHA  1221
WP_002307203  1159  DPV---AFLE---RKGYRN--V-QEENIIK--LPKYSLFK----LENGRKRLLAS  ARELQKGNEIVLPDHLGTLLYHA  1221
WP_002310390  1159  DPV---AFLE---RKGYRN--V-QEENIIK--LPKYSLFK----LENGRKRLLAS  ARELQKGNEIVLPNHLGTLLYHA  1221
WP_002352408  1159  DPV---AFLE---RKGYRN--V-QEENIIK--LPKYSLFK----LENGRKRLLAS  ARELQKGNEIVLPDHLGTLLYHA  1221
```

| | | | | |
|---|---|---|---|---|
| WP_012997688 | 1159 | DPV---AFLE---RKGYRN---V-QEENIIK---LPKYSLFK----LENGRKRLLAS | ARELQKGNEIVLPNHLGTLLYHA | 1221 |
| WP_014677909 | 1159 | DPV---AFLE---RKGYRN---V-QEENIIK---LPKYSLFK----LENGRKRLLAS | ARELQKGNEIVLPNHLGTLLYHA | 1221 |
| WP_019312892 | 1159 | DPV---AFLE---RKGYRN---V-QEENIIK---LPKYSLFK----LENGRKRLLAS | ARELQKGNEIVLPNHLGTLLYHA | 1221 |
| WP_019313659 | 1159 | DPV---AFLE---RKGYRN---V-QEENIIK---LPKYSLFK----LENGRKRLLAS | ARELQKGNEIVLPNHLGTLLYHA | 1221 |
| WP_019314093 | 1159 | DPI---AFLE---RKGYRN---V-QEENIIK---LPKYSLFK----LENGRKRLLAS | ARELQKGNEIVLPNHLGTLLYHA | 1221 |
| WP_019315370 | 1159 | DPV---AFLE---RKGYRN---V-QEENIIK---LPKYSLFK----LENGRKRLLAS | ARELQKGNEIVLPNHLGTLLYHA | 1221 |
| WP_019803776 | 1159 | DPV---AFLE---RKGYRN---V-QEENIIK---LPKYSLFK----LENGRKRLLAS | ARELQKGNEIVLPNHLGTLLYHA | 1221 |
| WP_019805234 | 1159 | DPV---AFLE---RKGYRN---V-QEENIIK---LPKYSLFK----LENGRKRLLAS | ARELQKGNEIVLPNHLGTLLYHA | 1221 |
| WP_024783594 | 1159 | DPV---AFLE---RKGYRN---V-QEENIIK---LPKYSLFK----LENGRKRLLAS | ARELQKGNEIVLPNHLGTLLYHA | 1221 |
| WP_024784288 | 1167 | NPV---KFLK---DKGYQQ--I-EKNNFVK---LPKYTLVD---IGNGIKRLWAS | SKEVHKGNQLVVSKKSQDLLYHA | 1229 |
| WP_024784666 | 1159 | DPV---AFLE---RKGYRN---V-QEENIIK---LPKYSLFK----LENGRKRLLAS | ARELQKGNEIVLPNHLGTLLYHA | 1221 |
| WP_024784894 | 1159 | DPV---AFLE---RKGYRN---V-QEENIIK---LPKYSLFK----LENGRKRLLAS | ARELQKGNEIVLPNHLGTLLYHA | 1221 |
| WP_024786433 | 1167 | NPV---KFLK---DKGYQQ--I-EKNNFVK---LPKYTLVD---IGNGIKRLWAS | SKEVHKGNQLVVSKKSQDLLYHA | 1229 |
| WP_049473442 | 1159 | DPV---AFLE---RKGYRN---V-QEENIIK---LPKYSLFK----LENGRKRLLAS | ARELQKGNEIVLPNHLGTLLYHA | 1221 |
| WP_049474547 | 1159 | DPV---AFLE---RKGYRN---V-QEENIIK---LPKYSLFK----LENGRKRLLAS | ARELQKGNEIVLPNHLGTLLYHA | 1221 |
| EMC03581 | 1152 | SPI---AFLE---NKGYHN---V-RKENILC---LPKYSLFE----LKNGRRRMLAS | AKELQKGNEIVLPVHLTTLLYHA | 1214 |
| WP_000428612 | 1187 | NPI---TFLE---NKGYHN---V-RKENILC---LPKYSLFE----LENGRRRLLAS | AKELQKGNEIVLPVYLTTLLYHS | 1249 |
| WP_000428613 | 1185 | NPV---AFLE---GKGYQN---V-VEENIIR---LPKYSLFE----LENGRRRMLAS | AKELQKGNEMVLPSYLIALLYHA | 1247 |
| WP_049523028 | 1180 | DRI---TFLE---KKGYQD--I-QESLIIK---LPKFSLFE----LENGRKRLLAS | -ELQKGNELSLPNKYIQFLYLA | 1242 |
| WP_003107102 | 1146 | NPI---AFLE---SKGYHD--I-QEHLMIT---LPKYSLFE----LENGRRRLLAS | -ELQKGNEMVLPQHLVTELYRV | 1208 |
| WP_054279288 | 1179 | NPT---AYLE---EYGYKN---I-NPNLIIK---LPKYSLFK----LENGRRRLLAS | SIELQKGNELILPYHFTTLLYHA | 1241 |
| WP_049531101 | 1189 | NPI---AYLE---ECGYKN---I-NPNLIIK---LPKYSLFE----FNDGQRRLLAS | SIELQKGNELILPYHFTALLYHT | 1251 |
| WP_049538452 | 1189 | NPI---AYLE---ECGYKN---I-NPNLIIK---LPKYSLFE----FNGGQRRLLAS | SIELQKGNELILPYHFTALLYHA | 1251 |
| WP_049549711 | 1191 | DNI---AFLE---KKGYQD--I-QEKLLIK---LPKYSLFE----FNGGQRRLLAS | -EFQKGNELALSGKYMKELYLA | 1253 |
| WP_007896501 | 1183 | DNI---AFLE---KKGYQD--I-QEKLLIK---LPKYSLFE----LENGRRRLLAS | -EFQKGNELALSGKYMKELYLA | 1245 |
| EFR44625 | 1135 | | | 1197 |
| WP_002897477 | 1184 | NPI---TFLE---NKGYHN---V-RKENILC---LPKYSLFE----LENGRRRLLAS | AKELQKGNEIVLPVCLTTLLYHS | 1246 |

| ID | | | | | |
|---|---|---|---|---|---|
| WP_002906454 | 1190 | NPV---TYLE---ECGYKN--I-NSNLIIK--LPKYSLFE----ENDGQRRLLAS | SIELQKGNELILPYHLTALLYHA | 1252 |
| WP_009729476 | 1185 | NPI---AFLE---NKGYHN--V-CKENILC--LPKYSLFE----LENGRRRLLAS | AKELQKCNEIVLPVYLTLLYHS | 1247 |
| CQR24647 | 1175 | NSV---TFLE---EKGYRN--I-RENTIIK--PPKYSLFE----LENGRRRLLAS | AIELQKGNEMFLPQQEVNLLYHA | 1237 |
| WP_000066813 | 1189 | NPI---TFLE---NKGYHN--V-RKENILC--LPKYSLFE----LESGRRRMLAS | AKELQKGNEIVLPVYLTLLYHS | 1251 |
| WP_009754323 | 1185 | NPI---TFLE---NKGYHN--V-RKENILC--LPKYSLFE----LENGRRRLLAS | AKELQKGNEIVLPVYLTLLYHS | 1247 |
| WP_044674937 | 1178 | NPI---EFLE---HKGYKN--I-LEKNIIK--LPKYSLFE----LENGRRRLLAS | AKELQKGNEMILPPHLVTLLYHS | 1240 |
| WP_044676715 | 1180 | NPI---EFLE---HKGYKN--I-LEKNIIK--LPKYSLFE----LENGRRRLLAS | AKELQKGNEMILPPHLVTLLYHS | 1242 |
| WP_044680361 | 1180 | NPI---EFLE---HKGYKN--I-LEKNIIK--LPKYSLFE----LENGRRRLLAS | AKELQKGNEMILPPHLVTLLYHS | 1242 |
| WP_044681799 | 1178 | NPI---EFLE---HKGYKN--I-LEKNIIK--LPKYSLFE----LENGRRRLLAS | AKELQKGNEMILPPHLVTLLYHS | 1240 |
| WP_049533112 | 1186 | DKR---AFLL---GKGYKD--I-K--KIIE--LPKYSLFE----LKDGSRRMLAS | RGEIHKGNELFVPQKETTLLYHA | 1253 |
| WP_029090905 | 1118 | SETSlqAYIA---EQIKSE--VeILN----grILKYQLLS----NNGNRLYIAG | -SERHNARQLIVSDEAAKVIWLI | 1181 |
| WP_006506696 | 1150 | EKI---NYIE--eKEGLSD--VrIIK--Dn-IPVNQMIEm----DGGEYLLTS | --EYVNARQLVLNEKQCALIADI | 1211 |
| AIT42264 | 1177 | NPI---DFLE---AKGYKE--V-KKDLIIK--LPKYSLFE----LENGRKRMLAS | -GELQKGNELALPSKYVNELYLA | 1239 |
| WP_034440723 | 1150 | QTT---EYLG---KIGFNK--AsIIN----S--FKNYTLFE----LENGSRRMIVG | KGELQKGNQMVLPQNLLEEVYHL | 1217 |
| AKQ21048 | 1177 | NPI---DFLE---AKGYKE--V-KKDLIIK--LPKYSLFE----LENGRKRMLAS | -GELQKGNELALPSKYVNELYLA | 1239 |
| WP_004636532 | 1151 | HPT---AYLE---EAGYNN--P-TV--LHE--LFKYQLFE----LEDGSRRMIAS | AKEEQKGNQMVLPLELVELLYHA | 1211 |
| WP_002364836 | 1157 | NPI---LFLE---EKGFLR--P-RV--LMK--LPKYTLYE----FPEGRRRLLAS | AKEAQKGNQMVLPEHLLTLLYHA | 1217 |
| WP_016631044 | 1108 | NPI---LFLE---AKGYKE--V-KKDLIIK--LPKYSLFE----LENGRKRMLAS | AKEAQKGNQMVLPEHLLTLLYHA | 1168 |
| EMS75795 | 893 | DPI---GFLS---NKGYSN--V-TKF--IK--LSKYTLYE----LENGRRRMVAS | -KEAQKANSFILPEKLVTLLYHA | 953 |
| WP_002373311 | 1157 | NPI---LFLE---EKGFLR--P-RV--LMK--LPKYTLYE----FPEGRRRLLAS | AKEAQKGNQMVLPEHLLTLLYHA | 1217 |
| WP_002378009 | 1157 | NPI---LFLE---EKGFLR--P-RV--LMK--LPKYTLYQ----FPEGRRRLLAS | AKEAQKGNQMVLPEHLLTLLYHA | 1217 |
| WP_002407324 | 1157 | NPI---LFLE---EKGFLR--P-RV--LMK--LPKYTLYE----FPEGRRRLLAS | AKEAQKGNQMVLPEHLLTLLYHA | 1217 |
| WP_002413717 | 1157 | NPI---LFLE---EKGFLR--P-RV--LMK--LPKYTLYE----FPEGRRRLLAS | AKEAQKGNQMVLPEHLLTLLYHA | 1217 |
| WP_010775580 | 1159 | NPI---LFLE---EKGFLR--P-RV--LMK--LPKYTLYE----FPEGRRRLLAS | AKEAQKGNQMVLPEHLLTLLYHA | 1219 |
| WP_010818269 | 1157 | NPI---LFLE---EKGFLR--P-RV--LMK--LPKYTLYE----FPEGRRRLLAS | AKEAQKGNQMVLPEHLLTLLYHA | 1217 |
| WP_010823395 | 1157 | NPI---LFLE---EKGFLR--P-RV--LMK--LPKYTLYE----FPEGRRRLLAS | AKEAQKGNQMVLPEHLLTLLYHA | 1217 |
| WP_016622645 | 1157 | NPI---LFLE---EKGFLR--P-RV--LMK--LPKYTLYE----FPEGRRRLLAS | AKEAQKGNQMVLPEHLLTLLYHA | 1217 |

| ID | Seq Start | Sequence | End |
|---|---|---|---|
| WP_033624816 | 1157 | NPI---LFLE---EKGFLR---P-RV--LMK--LPKYTLYE---FPEGRRRLLAS-AKEAQKGNQMVLPERLLTLLYHA | 1217 |
| WP_033625576 | 1157 | NPI---LFLE---EKGFLR---P-RV--LMK--LPKYTLYE---FPEGRRRLLAS-AKEAQKGNQMVLPEHLLTLLYHA | 1217 |
| WP_033789179 | 1157 | NPI---LFLE---EKGFLR---P-RV--LMK--LPKYTLYE---FPEGRRRLLAS-AKEAQKGNQMVLPEHLLTLLYHA | 1217 |
| WP_002310644 | 1159 | SPV---LFLK---NKGYEQ---A-EIE--MK--LPKYALFE---LENGRKRMVAS-KEAQKANSFLLPEHLVTLLYHA | 1219 |
| WP_002312694 | 1160 | SPV---LFLK---NKGYEQ---A-EIE--MK--LPKYALFE---LENGRKRMVAS-KEAQKANSFLLPEHLVTLLYHA | 1220 |
| WP_002314015 | 1160 | SPV---LFLK---NKGYEQ---A-EIE--MK--LPKYALFE---LENGRKRMVAS-KEAQKANSFLLPEHLVTLLYHA | 1220 |
| WP_002320716 | 1160 | SPV---LFLK---NKGYEQ---A-EIE--MK--LPKYALFE---LENGRKRMVAS-KEAQKANSFLLPEHLVTLLYHA | 1220 |
| WP_002330729 | 1159 | SPV---LFLK---NKGYEQ---A-EIE--MH--LPKYALFE---LENGRKRMVAS-KEAQKANSFLLPEHLVTLLYHA | 1219 |
| WP_002335161 | 1160 | SPV---LFLK---NKGYEQ---A-EIE--MH--LPKYALFE---LENGRKRMVAS-KEAQKANSFLLPEHLVTLLYHA | 1220 |
| WP_002345439 | 1160 | SPV---LFLK---NKGYEQ---A-EIE--MH--LPKYALFE---LENGRKRMVAS-KEAQKANSFLLPEHLVTLLYHA | 1220 |
| WP_034867970 | 1150 | DPT---TFLK---EKGFPQ---V-TEF--IK--LPKYTLFE---FDNGRRRFLAS-KESQKGNPFILSDQLVTLLYHA | 1210 |
| WP_047937432 | 1160 | SPV---LFLK---NKGYEQ---A-EIE--MH--LPKYALFE---LENGRKRMVAS-KEAQKANSFLLPEHLVTLLYHA | 1220 |
| WP_010720994 | 1150 | DPT---TFLK---DKGFPQ---V-TEF--IK--LPKYTLFE---FDNGRRRFLAS-KESQKGNPFILSDQLVTLLYHA | 1210 |
| WP_010737004 | 1150 | DPT---TFLK---EKGFPQ---V-TEF--IK--LPKYTLFE---FDNGRRRFLAS-KESQKGNPFILSDQLVTLLYHA | 1210 |
| WP_034700478 | 1150 | DPT---TFLK---DKGFPH---V-TEF--IK--LPKYTLFE---FDNGRRRFLAS-KESQKGNPFILSDQLVTLLYHA | 1210 |
| WP_007209003 | 1148 | NPII--YLS----KKDYHN---pKVEAI----LPKYSLFE---FENGRRRMVAS-SETQKGNQLIIPGHLMELLYHS | 1208 |
| WP_023519017 | 1144 | DPR---EFLK---TKGYEG---V-KQW--LI--LPKYILFE---AQGGYRRMIAS-QETQKANSLILPENLVTLLYHA | 1204 |
| WP_010770040 | 1155 | DPV---SLLE---EKGYAN---P-EV--LIH--LPKYTLYE---LENGRRRLLAS-ANEAQKGNQLVLPASLVTLLYHA | 1215 |
| WP_048604708 | 1152 | NER---EFLK---NKGYQN---P-QI--CMK--LPKYSLYE---FDDGRRRLLAS-AKEAQKGNQMVLPAHLVTFLYHA | 1212 |
| WP_010750235 | 1153 | DPI---SFLI---EKGYSN---V-NQF--IK--LPKYTLFE---LANGQRRMLAS-QELQKANSFILPEKLVTLLYHA | 1213 |
| AII16583 | 1216 | NPI---DFLE---AKGYKE---V-KKDLIIK--LPKYSLFE---LENGRKRMLAS-GELQKGNELALPSKYVNFLYLA | 1278 |
| WP_029073316 | 1165 | TKI---NYIK---eSEGLEE---VkIIK----E--ILKNQLIEi---NGGLEYVTS-EIVNARQLIIDFNCTRIIDGI | 1225 |
| WP_031589969 | 1165 | IKI---NYLK---qAEDLEE---VqIGK----E--ILKNQLIEk---DGGLYYIVA-EIINAKQLILNESQTKLVCEI | 1225 |
| KDA45870 | 1139 | DPT---AYLA---SRGYTNvtNsFIL-----PKYSLLEd---PEGRRRYLAS-KEFQKANELILPQHLVELLYWV | 1199 |
| WP_039099354 | 1171 | QKI sPQFTKv---KKQKGtiV-KVVEDFEv-IAPHILNqrfFDNGQELTLGS----HNEQELILDKTAVKLLNGA | 1241 |
| AKP02966 | 1173 | KTL---qNWLE---ENVKHKsIqIIK---Nn-VPIGQIIY-----SKKVGLLS-REIANRQQLIIPPEHSALLRIL | 1237 |
| WP_010991369 | 1155 | DEK---AFLE---EQGYRQ---P-KV--LAK--LPKYTLYE---CEEGRRRMLAS-ANEAQKGNQQVLPNHLVTLLHHA | 1215 |

| ID | Start | Sequence | End |
|---|---|---|---|
| WP_033835504 | 1155 | DEK---AFLE---EQGYRQ--P-KV--LAK--LPKYTLYE----CEEGRRRMLAS ANEAQKGNQQVLPNHLVTLLHHV | 1215 |
| EHN60060 | 1158 | DEK---AFLE---EQGYRQ--P-KV--LAK--LPKYTLYE----CEEGRRRMLAS ANEAQKGNQQVLPNHLVTLLHHV | 1218 |
| EFR89594 | 924 | DEK---AFLE---EQGYRQ--P-KV--LAK--LPKYTLYE----CEEGRRRMLAS ANEAQKGNQQVLPNHLVTLLHHA | 984 |
| WP_038409211 | 1155 | DQK---AFLE---EKGYYS--P-KV--LTK--IPKYTLYE----CENGRRRMLGS ANEAQKGNQMVLPNHLMTLLYHA | 1215 |
| EFR95520 | 774 | DQK---AFLE---EKGYYS--P-KV--LTK--IPKYTLYE----CENGRRRMLGS ANEAQKGNQMVLPNHLMTLLYHA | 834 |
| WP_003723650 | 1155 | DEE---AFLE---EKGYRH--P-KV--LTK--LPKYTLYE----CEKGRRRMLAS ANEAQKGNQLVLSNHLVSLLYHA | 1215 |
| WP_003727705 | 1155 | DEE---AFLE---EKGYHQ--P-KV--LTK--LPKYTLYE----CEKGRRRMLSS ANEAQKGNQLVLSNHLVSLLYHA | 1215 |
| WP_003730785 | 1155 | DEE---AFLE---EKGYHQ--P-KV--LTK--LPKYTLYE----CEKGRRRMLGS ANEAQKGNQLVLSNHLVSLLYHA | 1215 |
| WP_003733029 | 1155 | DEE---TFLE---EKGYHQ--P-KV--LTK--LPKYTLYE----CENGRRRMLGS ANEAHKGNQMLLPNHLMALLYHA | 1215 |
| WP_003739838 | 1155 | DEK---SFLE---KQGYRQ--P-KV--LTK--LPKYTLYE----CENGRRRMLGS ANEAQKGNQQVLKGQLITLLHHA | 1215 |
| WP_014601172 | 1155 | DEE---AFLE---EKGYRH--P-KV--LTK--LPKYTLYE----CEKGRRRMLAS ANEAQKGNQLVLSNHLVSLLYHA | 1215 |
| WP_023548323 | 1155 | DEK---VFLE---GKGYHQ--P-KV--LTK--LPKYALYE----CENGRRRMLGS ANEVHKGNQMLLPNHLMTLLYHA | 1215 |
| WP_031665337 | 1155 | DEE---AFLE---EKGYRH--P-KV--LTK--LPKYTLYE----CEKGRRRMLAS ANEAQKGNQLVLSNHLVSLLYHA | 1215 |
| WP_031669209 | 1155 | DEK---TFLE---EKGYHQ--P-KV--LTK--VPKYTLYE----CENGRRRMLGS ANEAHKGNQMLLPNHLMALLYHA | 1215 |
| WP_033920898 | 1155 | DEK---VFLE---GKGYHQ--P-KV--LTK--LPKYALYE----CENGRRRMLGS ANEVHKGNQMLLPNHLMTLLYHA | 1215 |
| AKI42028 | 1158 | DEE---AFLE---EKGYRH--P-KV--LTK--LPKYTLYE----CEKGRRRMLAS ANEAQKGNQLVLSNHLVSLLYHA | 1218 |
| AKI50529 | 1158 | DEE---VFLE---GKGYHQ--P-KV--LTK--LPKYALYE----CENGRRRMLGS ANEVHKGNQMLLPNHLMTLLYHA | 1218 |
| EFR83390 | 603 | DEE---AFLE---EKGYRH--P-KV--LTK--LPKYTLYE----CEKGRRRMLAS ANEAQKGNQLVLSNHLVSLLYHA | 663 |
| WP_046323366 | 1155 | DQK---EFLE---GKGYRN--P-KV--ITK--IPKYTLYE----CENGRRRMLGS ANEAQKGNQMVLPNHLMTLLYHA | 1215 |
| AKE81011 | 1193 | NPI---DFLE---AKGYKE--V-KKDLIIK--LPKYSLFE----LENGRKRMLAS -GELQKGNELALPSKYVNFLYLA | 1255 |
| CUO82355 | 1154 | EQI---EYVE--kEEKLSD--VkIIK----Nn-IPlNQLIEi---DGRQYLLTS --ECVNAMQLVLNEEQCKLIADI | 1215 |
| WP_033162887 | 1155 | EQL---SYIAspeHEDLID--VrIVK--E---ILKNQLIEi---DGGlYYVTS --EYVTARQLSLNEQSCKLISEI | 1217 |
| AGZ01981 | 1210 | NPI---DFLE---AKGYKE--V-KKDLIIK--LPKYSLFE----LENGRKRMLAS -GELQKGNELALPSKYVNFLYLA | 1272 |
| AKA60242 | 1177 | NPI---DFLE---AKGYKE--V-KKDLIIK--LPKYSLFE----LENGRKRMLAS -GELQKGNELALPSKYVNFLYLA | 1239 |
| AKS40380 | 1177 | NPI---DFLE---AKGYKE--V-KKDLIIK--LPKYSLFE----LENGRKRMLAS -GELQKGNELALPSKYVNFLYLA | 1239 |
| 4UN5_B | 1181 | NPI---DFLE---AKGYKE--V-KKDLIIK--LPKYSLFE----LENGRKRMLAS -GELQKGNELALPSKYVNFLYLA | 1243 |
| WP_010922251 | 1240 | SHYEKLKgSPEDnEQKQL--FVEQHKHYLDEIIEQISEFSKRVlAD--ANLDKVL-S AYN-KH---RDKPIREq- | 1305 |

| | | | | |
|---|---|---|---|---|
| WP_039695303 | 1249 | HRAD----NFNS-TEYLN--YVSEHKKEPEKVLSCVEDFANLYDVE--KNLSKIR-A | VAD-SM---DNFSIEE-- | 1308 |
| WP_045635197 | 1247 | KNVH----KLDE-PGHLE--YIQKHRNEFKDLLNLVSEFSQKYVLAD--ANLEKIK-S | LYA-DN---EQADIEI-- | 1306 |
| 5AXW_A | 979 | GELYRVIgVNNDllNRIE---VNMIDITYREYLENMNDKRPPRIIKTiaSKTQSIK-K | LYEvKSk--KHPQIIKkg | 1056 |
| WP_009880683 | 924 | SHYEKLKgSPEDnEQKQL--FVEQHKHYLDEIIEQISEFSKRVILAD--ANLDKVL-S | AYN-KH---RDKPIREq- | 989 |
| WP_010922251 | 1240 | SHYEKLKgSPEDnEQKQL--FVEQHKHYLDEIIEQISEFSKRVILAD--ANLDKVL-S | AYN-KH---RDKPIREq- | 1305 |
| WP_011054416 | 1240 | SHYEKLKgSPEDnEQKQL--FVEQHKHYLDEIIEQISEFSKRVILAD--ANLDKVL-S | AYN-KH---RDKPIREq- | 1305 |
| WP_011284745 | 1240 | SHYEKLKgSPEDnEQKQL--FVEQHKHYLDEIIEQISEFSKRVILAD--ANLDKVL-S | AYN-KH---RDKPIREq- | 1305 |
| WP_011285506 | 1240 | SHYEKLKgSPEDnEQKQL--FVEQHKHYLDEIIEQISEFSKRVILAD--ANLDKVL-S | AYN-KH---RDKPIREq- | 1305 |
| WP_011527619 | 1240 | SHYEKLKgSPEDnEQKQL--FVEQHKHYLDEIIEQISEFSKRVILAD--ANLDKVL-S | AYN-KH---RDKPIREq- | 1305 |
| WP_012560673 | 1240 | SHYEKLKgSPEDnEQKQL--FVEQHKHYLDEIIEQISEFSKRVILAD--ANLDKVL-S | AYN-KH---RDKPIREq- | 1305 |
| WP_014407541 | 1239 | SHYEKLKgSPEDnEQKQL--FVEQHKHYLDEIIEQISEFSKRVILAD--ANLDKVL-S | AYN-KH---RDKPIREq- | 1304 |
| WP_020905136 | 1240 | SHYEKLKgSPEDnEQKQL--FVEQHKHYLDEIIEQISEFSKRVILAD--ANLDKVL-S | AYN-KH---RDKPIREq- | 1305 |
| WP_023080005 | 1239 | SHYEKLKgSPEDnEQKQL--FVEQHKHYLDEIIEQISEFSKRVILAD--ANLDKVL-S | AYN-KH---RDKPIREq- | 1304 |
| WP_023610282 | 1239 | SHYEKLKgSPEDnEQKQL--FVEQHKHYLDEIIEQISEFSKRVILAD--ANLDKVL-S | AYN-KH---RDKPIREq- | 1304 |
| WP_030125963 | 1240 | SHYEKLKgSPEDnEQKQL--FVEQHKHYLDEIIEQISEFSKRVILAD--ANLDKVL-S | AYN-KH---RDKPIREq- | 1305 |
| WP_030126706 | 1240 | SHYEKLKgSPEDnEQKQL--FVEQHKHYLDEIIEQISEFSKRVILAD--ANLDKVL-S | AYN-KH---RDKPIREq- | 1305 |
| WP_031488318 | 1240 | SHYEKLKgSPEDnEQKQL--FVEQHKHYLDEIIEQISEFSKRVILAD--ANLDKVL-S | AYN-KH---RDKPIREq- | 1305 |
| WP_032460140 | 1240 | SHYEKLKgSPEDnEQKQL--FVEQHKHYLDEIIEQISEFSKRVILAD--ANLDKVL-S | AYN-KH---RDKPIREq- | 1305 |
| WP_032461047 | 1240 | SHYEKLKgSPEDnEQKQL--FVEQHKHYLDEIIEQISEFSKRVILAD--ANLDKVL-S | AYN-KH---RDKPIREq- | 1305 |
| WP_032462016 | 1240 | SHYEKLKgSPEDnEQKQL--FVEQHKHYLDEIIEQISEFSKRVILAD--ANLDKVL-S | AYN-KH---RDKPIREq- | 1305 |
| WP_032462936 | 1240 | SHYEKLKgSPEDnEQKQL--FVEQHKHYLDEIIEQISEFSKRVILAD--ANLDKVL-S | AYN-KH---RDKPIREq- | 1305 |
| WP_032464890 | 1240 | SHYEKLKgSPEDnEQKQL--FVEQHKHYLDEIIEQISEFSKRVILAD--ANLDKVL-S | AYN-KH---RDKPIREq- | 1305 |
| WP_033888930 | 1065 | SHYEKLKgSPEDnEQKQL--FVEQHKHYLDEIIEQISEFSKRVILAD--ANLDKVL-S | AYN-KH---RDKPIREq- | 1130 |
| WP_038431314 | 1240 | SHYEKLKgSPEDnEQKQL--FVEQHKHYLDEIIEQISEFSKRVILAD--ANLDKVL-S | AYN-KH---RDKPIREq- | 1305 |
| WP_038432938 | 1239 | SHYEKLKgSPEDnEQKQL--FVEQHKHYLDEIIEQISEFSKRVILAD--ANLDKVL-S | AYN-KH---RDKPIREq- | 1304 |
| WP_038434062 | 1240 | SHYEKLKgSPEDnEQKQL--FVEQHKHYLDEIIEQISEFSKRVILAD--ANLDKVL-S | AYN-KH---RDKPIREq- | 1305 |
| BAQ51233 | 1151 | SHYEKLKgSPEDnEQKQL--FVEQHKHYLDEIIEQISEFSKRVILAD--ANLDKVL-S | AYN-KH---RDKPIREq- | 1216 |

-continued

| | | | | |
|---|---|---|---|---|
| KGE60162 | 415 | SHYEKLKgSPEDnEQKQL--FVEQKHYLDEIIEQISEFSKRVILAD--ANLDKVL-S | 480 | AYN-KH---RDKPIREq- |
| KGE60856 | 178 | SHYEKLKgSPEDnEQKQL--FVEQKHYLDEIIEQISEFSKRVILAD--ANLDKVL-S | 243 | AYN-KH---RDKPIREq- |
| WP_002989955 | 1240 | SHYEKLKgSPEDnEQKQL--FVEQKHYLDEIIEQISEFSKRVILAD--ANLDKVL-S | 1305 | AYN-KH---RDKPIREq- |
| WP_003030002 | 1222 | YQIE----KNYE-PEHRE-YVEKHKDEFKELLEYISVFSRKYVILAD--NNLTKIE-M | 1281 | LFS-KN---KDAEVSS- |
| WP_003065552 | 1250 | QRIN----SFNS-TKYLD-YVSAHKKEFKVLSCVEDFANLYDVE-KNLSKIR-A | 1309 | VAD-SM---DNFSIEE- |
| WP_001040076 | 1241 | SRYNESKgKPEEiEKKQE--FVNQHVSYFDDIFQIINDFSKRVILAD--ANLEKIN-R | 1306 | LYQ-DNK--ENIPVDE- |
| WP_001040078 | 1249 | SRYNESKgKPEEiEKKQE--FVNQHVSYFDDILQLINDFSKRVILAD--ANLEKIN-K | 1314 | LYQ-DNK--ENISVDE- |
| WP_001040080 | 1241 | SRYNESKgKPEEiEKKQE--FVNQHVSYFDDILQLINDFSKRVILAD--ANLEKIN-K | 1306 | LYQ-DNK--ENISVDE- |
| WP_001040081 | 1241 | SRYNESKgKPEEiEKKQE--FVNQHVSYFDDILQLINDFSKRVILAD--ANLEKIN-K | 1306 | LYQ-DNK--ENISVDE- |
| WP_001040083 | 1241 | SRYNESKgKPEEiEKKQE--FVNQHVSYFDDILQLINDFSKRVILAD--ANLEKIN-K | 1306 | LYQ-DNK--ENISVDE- |
| WP_001040085 | 1241 | SRYNESKgKPEEiEKKQE--FVNQHVSYFDDILQLINDFSKRVILAD--ANLEKIN-K | 1306 | LYQ-DNK--ENISVDE- |
| WP_001040087 | 1241 | SRYNESKgKPEEiEKKQE--FVNQHVSYFDDILQLINDFSKRVILAD--ANLEKIN-K | 1306 | LYQ-DNK--ENISVDE- |
| WP_001040088 | 1241 | SRYNESKgKPEEiEKKQE--FVNQHISYFDDILQLINDFSKRVILAD--ANLEKIN-K | 1306 | LYS-DNK--DNTPVDE- |
| WP_001040089 | 1241 | SRYNELKgKPEEiEQKQE--FVVQHVSYFDDILQLINDFSNRVILAD--ANLEKIN-K | 1306 | LYQ-DNK--ENIPVDE- |
| WP_001040090 | 1241 | SRYNELKgKPEEiEQKQE--FVVQHVSYFDDILQLINDFSNRVILAD--ANLEKIN-K | 1306 | LYQ-DNK--ENIPVDE- |
| WP_001040091 | 1241 | SRYNELKgKPEEiEQKQE--FVVQHVSYFDDILQLINDFSNRVILAD--ANLEKIN-K | 1306 | LYQ-DNK--ENIPVDE- |
| WP_001040092 | 1241 | SRYNELKgKPEEiEQKQE--FVVQHVSYFDDILQLINDFSNRVILAD--ANLEKIN-K | 1306 | LYQ-DNK--ENIPVDE- |
| WP_001040094 | 1241 | SRYNELKgKPEEiEQKQE--FVVQHVSYFDDILQLINDFSNRVILAD--ANLEKIN-K | 1306 | LYQ-DNK--ENIPVDE- |
| WP_001040095 | 1241 | SRYNELKgKPEEiEQKQE--FVVQHVSYFDDILQLINDFSNRVILAD--ANLEKIN-K | 1306 | LYQ-DNK--ENIPVDE- |
| WP_001040096 | 1241 | SRYNELKgKPEEiEQKQE--FVVQHVSYFDDILQLINDFSNRVILAD--ANLEKIN-K | 1306 | LYQ-DNK--ENIPVDE- |
| WP_001040097 | 1241 | SRYNELKgKPEEiEQKQE--FVVQHVSYFDDILQLINDFSNRVILAD--ANLEKIN-K | 1306 | LYQ-DNK--ENIPVDE- |
| WP_001040098 | 1241 | SRYNELKgKPEEiEQKQE--FVVQHVSYFDDILQLINDFSNRVILAD--ANLEKIN-K | 1306 | LYQ-DNK--ENIPVDE- |
| WP_001040099 | 1241 | SRYNELKgKPEEiEQKQE--FVVQHVSYFDDILQLINDFSNRVILAD--ANLEKIN-K | 1306 | LYQ-DNK--ENIPVDE- |
| WP_001040100 | 1241 | SRYNESKgKPEEiEKKQE--FVNQHVSYFDDILQLINDFSKRVILAD--ANLEKIN-K | 1306 | LYQ-DNK--ENISVDE- |
| WP_001040104 | 1241 | SRYNESKgKPEEiEKKQE--FVNQHVSYFDDILQLINDFSKRVILAD--ANLEKIN-K | 1306 | LYQ-DNK--ENISVDE- |
| WP_001040105 | 1241 | SRYNELKgKPEEiEQKQE--FVVQHVSYFDDILQLINDFSNRVILAD--ANLEKIN-K | 1306 | LYQ-DNK--ENISVDE- |
| WP_001040106 | 1241 | SRYNELKgKPEEiEQKQE--FVVQHVSYFDDILQLINDFSNRVILAD--ANLEKIN-K | 1306 | LYQ-DNK--ENISVDE- |

| | | | |
|---|---|---|---|
| WP_001040107 | 1241 SRYNELKgKPEEiEQKQE--FVVQHVSYFDDILQIINDFSNRVILAD--ANLEKIN-K | LYQ-DNK--ENISVDE-- | 1306 |
| WP_001040108 | 1241 SRYNELKgKPEEiEQKQE--FVVQHVSYFDDILQIINDFSNRVILAD--ANLEKIN-K | LYQ-DNK--ENISVDE-- | 1306 |
| WP_001040109 | 1241 SRYNELKgKPEEiEQKQE--FVVQHVSYFDDILQIINDFSNRVILAD--ANLEKIN-K | LYQ-DNK--ENISVDE-- | 1306 |
| WP_001040110 | 1241 SRYNELKgKPEEiEQKQE--FVVQHVSYFDDILQIINDFSNRVILAD--ANLEKIN-K | LYQ-DNK--ENISVDE-- | 1306 |
| WP_015058523 | 1241 SRYNELKgKPEEiEKKQE--FVVQHVSYFDDILQIINDFSNRVILAD--ANLEKIN-K | LYS-DNK--DNTPVDE-- | 1306 |
| WP_017643650 | 1241 SRYNELKgKPEEiEQKQE--FVNQHVSYFDDILQIINDFSNRVILAD--ANLEKIN-K | LYQ-DNK--ENIPVDE-- | 1306 |
| WP_017647151 | 1241 SRYNELKgKPEEiEQKQE--FVVQHVSYFDDILQIINDFSNRVILAD--ANLEKIN-K | LYQ-DNK--ENISVDE-- | 1306 |
| WP_017648376 | 1241 SRYNELKgKPEEiEKKQE--FVVQHVSYFDDILQIINDFSNRVILAD--ANLEKIN-K | LYQ-DNK--ENISVDE-- | 1306 |
| WP_017649527 | 1241 SRYNESKgKPEEiEKKQE--FVNQHVSYFDDILQIINDFSKRVILAD--ANLEKIN-K | LYQ-DNK--ENISVDE-- | 1306 |
| WP_017771611 | 1241 SRYNELKgKPEEiEQKQE--FVNQHVSYFDDILQIINDFSNRVILAD--ANLEKIN-K | LYQ-DNK--ENISVDE-- | 1306 |
| WP_017771984 | 1241 SRYNELKgKPEEiEKKQE--FVNQHVSYFDDILQIINDFSKRVILAD--ANLEKIN-K | LYQ-DNK--ENISVDE-- | 1306 |
| CFQ25032 | 1241 SRYNELKgKPEEiEKKQE--FVVQHVSYFDDILQIINDFSKRVILAD--ANLEKIN-K | LYQ-DNK--ENISVDE-- | 1306 |
| CFV16040 | 1241 SRYNELKgKPEEiEKKQE--FVNQHVSYFDDILQIINDFSKRVILAD--ANLEKIN-K | LYQ-DNK--ENISVDE-- | 1306 |
| KLJ37842 | 1241 SRYNELKgKPEEiEKKQE--FVNQHVSYFDDILQIINDFSKRVILAD--ANLEKIN-K | LYQ-DNK--ENISVDE-- | 1306 |
| KLJ72361 | 1241 SRYNELKgKPEEiEKKQE--FVNQHVSYFDDILQIINDFSKRVILAD--ANLEKIN-K | LYQ-DNK--ENISVDE-- | 1306 |
| KLL20707 | 1255 SRYNELKgKPEEiEQKQE--FVNQHVSYFDDILQIINDFSKRVILAD--ANLEKIN-K | LYQ-DNK--ENISVDE-- | 1320 |
| KLL42645 | 1241 SRYNELKgKPEEiEQKQE--FVNQHVSYFDDILQIINDFSKRVILAD--ANLEKIN-K | LYQ-DNK--ENISVDE-- | 1306 |
| WP_047207273 | 1241 SRYNELKgKPEEiEKKQE--FVVQHVSYFDDILQIINDFSNRVILAD--ANLEKIN-K | LYQ-DNK--ENISVDE-- | 1306 |
| WP_047209694 | 1241 SRYNESKgKPEEiEKKQE--FVNQHVSYFDDILQIINDFSKRVILAD--ANLEKIN-K | LYQ-DNK--ENISVDE-- | 1306 |
| WP_050198062 | 1241 SRYNESKgKPEEiEKKQE--FVNQHVSYFDDILQIINDFSKRVILAD--ANLEKIN-K | LYQ-DNK--ENISVDE-- | 1306 |
| WP_050201642 | 1241 SRYNESKgKPEEiEKKQE--FVNQHVSYFDDILQIINDFSKRVILAD--ANLEKIN-K | LYQ-DNK--ENISVDE-- | 1306 |
| WP_050204027 | 1241 SRYNELKgKPEEiEKKQE--FVNQHVSYFDDILQIINDFSKRVILAD--ANLEKIN-K | LYQ-DNK--ENISVDE-- | 1306 |
| WP_050881965 | 1241 SRYNESKgKPEEiEKKQE--FVNQHVSYFDDILQIINDFSKRVILAD--ANLEKIN-K | LYQ-DNK--ENISVDE-- | 1306 |
| WP_050886065 | 1241 SRYNESKgKPEEiEKKQE--FVNQHVSYFDDILQIINDFSKRVILAD--ANLEKIN-K | LYQ-DNK--ENISVDE-- | 1306 |
| AHN30376 | 1241 SRYNESKgKPEEiEKKQE--FVNQHVSYFDDILQIINDFSKRVILAD--ANLEKIN-K | LYS-DNK--DNTPVDE-- | 1306 |
| EAO78426 | 1241 SRYNESKgKPEEiEKKQE--FVNQHVSYFDDILQIINDFSKRVILAD--ANLEKIN-K | LYQ-DNK--ENISVDE-- | 1306 |
| CCW42055 | 1241 SRYNESKgKPEEiEKKQE--FVNQHVSYFDDILQIINDFSKRVILAD--ANLEKIN-K | LYQ-DNK--ENISVDE-- | 1306 |

| | | | |
|---|---|---|---|
| WP_003041502 | 1254 | KRIN----NPIN-KDHIE--YVKKHRDDFKELLNVLEFNEKYVGAT-KNGERLK-E | AVA-DF---DSKSNEE-- | 1313 |
| WP_037593752 | 1223 | YQIE----KNYE-PEHRE--YVEKHKDEFKELLEYISVFSRKYVLAD--NNLTKIE-M | LFS-KN---KDAEVSS-- | 1282 |
| WP_049516684 | 1223 | YRIE----KDYE-PEHRE--YVEKHKDEFKELLEYISVFSRKYVLAD--NNLTKIE-M | LFS-KN---KDAEVSS-- | 1282 |
| GAD46167 | 1222 | YQIE----KNYE-PEHRE--YVEKHKDEFKELLEYISVFSRKYVLAD--NNLTKIE-M | LFS-KN---KDAEVSS-- | 1281 |
| WP_018363470 | 1254 | HRIG----NFNS-AEHLK--YVSEHKKEFEVLSCVENFANVYVDVE--KNLSKIR-A | AAD-SM---DNFSIEE-- | 1313 |
| WP_003043819 | 1249 | QNISATTgSNNLg------YIEQHREEFKEIFEKIIDFSEKYILKN--KVNSNLK-S | SFD-EQfavSDSIL--l- | 1310 |
| WP_006269658 | 1222 | YRIE----KDYE-PEHRE--YVEKHKDEFKELLEYISVFSRKYVLAD--NNLTKIE-M | LFS-KN---KDAEVSS-- | 1281 |
| WP_048800889 | 1242 | HRID----NSDN-SEHLK--YITEHKEEFGKLLSYIENFAKSYVDVD--KNLEKIQ-L | AVE-KI---DSFSVKE-- | 1301 |
| WP_012767106 | 1246 | -HAHKIEsSKE--LEHEA--YILDHYNDLYQLLSYIERFASLYVDVE--KNISKVK-E | LFS-NI---ESYSISE1- | 1308 |
| WP_014612333 | 1246 | -HAHKIEsSKE--LEHEA--YILDHYNDLYQLLSYIERFASLYVDVE--KNISKVK-E | LFS-NI---ESYSISE1- | 1308 |
| WP_015017095 | 1246 | -HAHKIEsSKE--LEHEA--YILDHYNDLYQLLSYIERFASLYVDVE--KNISKVK-E | LFS-NI---ESYSISE1- | 1308 |
| WP_015057649 | 1246 | -HAHKIEsSKE--LEHEA--YILDHYNDLYQLLSYIERFASLYVDVE--KNISKVK-E | LFS-NI---ESYSISE1- | 1308 |
| WP_048327215 | 1246 | -HAHKIEsSKE--LEHEA--YILDHYNDLYQLLSYIERFASLYVDVE--KNISKVK-E | LFS-NI---ESYSISE1- | 1308 |
| WP_049519324 | 1246 | -HAHKIEsSKE--LEHEA--YILDHYNDLYQLLSYIERFASLYVDVE--KNISKVK-E | LFS-NI---ESYSISE1- | 1308 |
| WP_012515931 | 1220 | AHYHELTgSSEDvLRKKY--FVDRHLHYFDDIIQMINDFAERHILAS--SNLEKIN-H | TYH-NN---SDLPVNEr- | 1285 |
| WP_021320964 | 1220 | AHYHELTgSSEDvLRKKY--FVERHLHYFDDIIQMINDFAERHILAS--SNLEKIN-H | TYH-NN---SDLPINEr- | 1285 |
| WP_037581760 | 1220 | AHYHELTgSSEDvLRKKY--FVERHLHYFDDIIQMINDFAERHILAS--SNLEKIN-H | TYH-NN---SDLPVNEr- | 1285 |
| WP_004232481 | 1252 | QHVN----NSHK-PEHLN--YVKQHKDEFKDIFNLIISIARINILKP--KVVDNL--- | -IN-EF---TEYGQED-- | 1308 |
| WP_009854540 | 1247 | HRAD----NFNS-TEYLN--YVSEHKKEFEKVLSCVEDFANLYVDVE--KNLSKIR-A | VAD-SM---DNFSIEE-- | 1306 |
| WP_012962174 | 1248 | HRVN----SFNN-SEHLK--YVSEHKKEFGEVLSCVENFAKSYVDVE--KNLGKIR-A | VAD-KI---DTFSIED-- | 1307 |
| WP_039695303 | 1249 | HRAD----NFNS-TEYLN--YVSEHKKEFEKVLSCVEDFANLYVDVE--KNLSKIR-A | VAD-SM---DNFSIEE-- | 1308 |
| WP_014334983 | 1252 | HRID----SFNS-TEHLK--YVSEHKKEFEKVLSCVENFSNLYVDVE--KNLSKVR-A | AAE-SM---TNFSLEE-- | 1311 |
| WP_003099269 | 1240 | SHYTKFTgKEEDrEKKRS--YVESHLYYFDEIMQIIVEYSNRYILAD--SNLIKIQ-N | LYK-EKq---NFSIEEq- | 1305 |
| AHY15608 | 1240 | SHYTKFTgKEEDrEKKRS--YVESHLYYFXEVKSSF---------------------- | ------------------ | 1273 |
| AHY17476 | 1240 | SHYTKFTgKEEDrEKKRS--YVESHLYXFX---------------------------- | ------------------ | 1267 |
| ESR09100 | 72 | SHYTKFTgKEEDrEKKRS--YVESHLYYFDEIMQIIVEYSNRYILAD--SNLIKIQ-N | LYK-Ek---DNFSIEEq- | 137 |
| AGM98575 | 1240 | SHYTKFTgKEEDrEKKRS--YVESHLYYFDVRLSQVFRVTNVEF-------------- | ------------------ | 1281 |

-continued

| | | | | |
|---|---|---|---|---|
| ALF27331 | 1222 | KNIH-----KVDE-PKHLD--YVKKHKDEFKELLDVVSNFSKKNILAE--SNLEKIE-E | LYA-QN---NNKDITE-- | 1281 |
| WP_018372492 | 1229 | KKVDVLVkSKDD---DYD--LEEHRAEFAELLDCIKKFNDMYILAS--SNMSKIE-E | IYQ-KNi---DAPIEE-- | 1289 |
| WP_045610028 | 1252 | QRIN----KISE-PIHKQ-YVETHQSEFKELLTAIISLSKKYI-QK--PNVESL--- | LQQ-AF---DQSDKDIyq | 1310 |
| WP_045635197 | 1247 | KNVH-----KLDE-PGHLE-YIQKHRNEFKDLLNLVSEFSQKYVLAD--ANLEKIK-S | LYA-DN---EQADIEI-- | 1306 |
| WP_002263549 | 1222 | KNIH-----KVDE-PKHLD--YVDKHKDEFKELLDVVSNFSKKYTLAE--GNLEKIK-E | LYA-QN---NGEDLKE-- | 1281 |
| WP_002263887 | 1222 | KNIH-----KVDE-PKHLD--YVDKHKDEFKELLDVVSNFSKKYTLAE--GNLEKIK-E | LYA-QN---NGEDLKE-- | 1281 |
| WP_002264920 | 1222 | KNIH-----KVDE-PKHLD--YVDKHKDEFKELLDVVSNFSKKYTLAE--GNLEKIK-E | LYA-QN---NGEDLKE-- | 1281 |
| WP_002269043 | 1222 | KNIH-----KVDE-PKHLD--YVDKHKDEFKELLDVVSNFSKKYTLAE--GNLEKIK-E | LYA-QN---NGEDLKE-- | 1281 |
| WP_002269448 | 1222 | KNIH-----KVDE-PKHLD--YVDKHKDEFKELLDVVSNFSKKYTLAE--GNLEKIK-E | LYA-QN---NGEDLKE-- | 1281 |
| WP_002271977 | 1222 | KNIH-----KVDE-PKHLD--YVDKHKDEFKELLDVVSNFSKKYTLAE--GNLEKIK-E | LYA-QN---NGEDLKE-- | 1281 |
| WP_002272766 | 1222 | KNIH-----KVDE-PKHLD--YVDKHKDEFKELLDVVSNFSKKYTLAE--GNLEKIK-E | LYA-QN---NGEDLKE-- | 1281 |
| WP_002273241 | 1222 | KNIH-----KVDE-PKHLD--YVDKHKDEFKELLDVVSNFSKKYTLAE--GNLEKIK-E | LYA-QN---NGEDLKE-- | 1281 |
| WP_002275430 | 1222 | KNIH-----KVDE-PKHLD--YVDKHKDEFKELLDVVSNFSKKYTLAE--GNLEKIK-E | LYA-QN---NGEDLKE-- | 1281 |
| WP_002276448 | 1222 | KNIH-----KVDE-PKHLD--YVDKHKDEFKELLDVVSNFSKKYTLAE--GNLEKIK-E | LYA-QN---NGEDLKE-- | 1281 |
| WP_002277050 | 1230 | HHL------DN-DYSNE--YVKNHYQQFDILFNEITSFSKKCKLGK--EHIQKIE-E | AYSkER---DSASIEE-- | 1287 |
| WP_002277364 | 1222 | KNIH-----KVDE-PKHLD--YVDKHKDEFKELLDVVSNFSKKYTLAE--GNLEKIK-E | LYA-QN---NGEDLKE-- | 1281 |
| WP_002279025 | 1222 | KNIH-----KVDE-PKHLD--YVDKHKDEFKELLDVVSNFSKKYTLAE--GNLEKIK-E | LYA-QN---NGEDLKE-- | 1281 |
| WP_002279859 | 1222 | KNIH-----KVDE-PKHLD--YVDKHKDEFKELLDVVSNFSKKYTLAE--GNLEKIK-E | LYA-QN---NGEDLKE-- | 1281 |
| WP_002280230 | 1222 | KNIH-----KVDE-PKHLD--YVDKHKDEFKELLDVVSNFSKKYTLAE--GNLEKIK-E | LYA-QN---NGEDLKE-- | 1281 |
| WP_002281696 | 1222 | KNIH-----KVDE-PKHLD--YVDKHKDEFKELLDVVSNFSKKYTLAE--GNLEKIK-E | LYA-QN---NGEDLKE-- | 1281 |
| WP_002282247 | 1230 | HHL------DN-DYSNE--YVKNHYQQFDILFNEITSFSKKCKLGK--EHIQKIE-E | AYSkER---DFASIEE-- | 1287 |
| WP_002282906 | 1222 | KNIH-----KVDE-PKHLD--YVDKHKDEFKELLDVVSNFSKKYTLAE--GNLEKIK-E | LYA-QN---NGEDLKE-- | 1281 |
| WP_002283846 | 1222 | KNIH-----KVDE-PKHLD--YVDKHKDEFKELLDVVSNFSKKYTLAE--GNLEKIK-E | LYA-QN---NGEDLKE-- | 1281 |
| WP_002287255 | 1222 | KNIH-----KVDE-PKHLD--YVDKHKDEFKELLDVVSNFSKKYTLAE--GNLEKIK-E | LYA-QN---NGEDLKE-- | 1281 |
| WP_002288990 | 1222 | KNIH-----KVDE-PKHLD--YVDKHKDEFKELLDVVSNFSKKYTLAE--GNLEKIK-E | LYA-QN---NGEDLKE-- | 1281 |
| WP_002289641 | 1222 | KNIH-----KVDE-PKHLD--YVDKHKDEFKELLDVVSNFSKKYTLAE--GNLEKIK-E | LYA-QN---NGEDLKE-- | 1281 |
| WP_002290427 | 1222 | KNIH-----KVDE-PKHLD--YVDKHKDEFKELLDVVSNFSKKYTLAE--GNLEKIK-E | LYA-QN---NGEDLKE-- | 1281 |

| | | | | |
|---|---|---|---|---|
| WP_002295753 | 1222 | KNIH----KVDE-PKHLD--YVDKHKDEFKELLDVVSNFSKKYTLAE--GNLEKIK-E | LYA-QN---NGEDLKE-- | 1281 |
| WP_002296423 | 1222 | KNIH----KVDE-PKHLD--YVDKHKDEFKELLDVVSNFSKKYTLAE--GNLEKIK-E | LYA-QN---NGEDLKE-- | 1281 |
| WP_002304487 | 1236 | KNIH----KVDE-PKHLD--YVDKHKDEFKELLDVVSNFSKKYTLAE--GNLEKIK-E | LYA-QN---NGEDLKE-- | 1295 |
| WP_002305844 | 1222 | KNIH----KVDE-PKHLD--YVDKHKDEFKELLDVVSNFSKKYTLAE--GNLEKIK-E | LYA-QN---NGEDLKE-- | 1281 |
| WP_002307203 | 1222 | KNIH----KVDE-PKHLD--YVDKHKDEFKELLDVVSNFSKKYTLAE--GNLEKIK-E | LYA-QN---NGEDLKE-- | 1281 |
| WP_002310390 | 1222 | KNIH----KVDE-PKHLD--YVDKHKDEFKELLDVVSNFSKKYTLAE--GNLEKIK-E | LYA-QN---NGEDLKE-- | 1281 |
| WP_002352408 | 1222 | KNIH----KVDE-PKHLD--YVDKHKDEFKELLDVVSNFSKKYTLAE--GNLEKIK-E | LYA-QN---NGEDLKE-- | 1281 |
| WP_012997688 | 1222 | KNIH----KVDE-PKHLD--YVDKHKDEFKELLDVVSNFSKKYTLAE--GNLEKIK-E | LYA-QN---NGEDLKE-- | 1281 |
| WP_014677909 | 1222 | KNIH----KVDE-PKHLD--YVDKHKDEFKELLDVVSNFSKKYTLAE--GNLEKIK-E | LYA-QN---NGEDLKE-- | 1281 |
| WP_019312892 | 1222 | KNIH----KVDE-PKHLD--YVDKHKDEFKELLDVVSNFSKKYTLAE--GNLEKIK-E | LYA-QN---NGEDLKE-- | 1281 |
| WP_019313659 | 1222 | KNIH----KVDE-PKHLD--YVDKHKDEFKELLDVVSNFSKKYTLAE--GNLEKIK-E | LYA-QN---NGEDLKE-- | 1281 |
| WP_019314093 | 1222 | KNIH----KVDE-PKHLD--YVDKHKDEFKELLDVVSNFSKKYTLAE--GNLEKIK-E | LYA-QN---NGEDLKE-- | 1281 |
| WP_019315370 | 1222 | KNIH----KVDE-PKHLD--YVDKHKDEFKELLDVVSNFSKKYTLAE--GNLEKIK-E | LYA-QN---NGEDLKE-- | 1281 |
| WP_019803776 | 1222 | KNIH----KVDE-PKHLD--YVDKHKDEFKELLDVVSNFSKKYTLAE--GNLEKIK-E | LYA-QN---NGEDLKE-- | 1281 |
| WP_019805234 | 1222 | KNIH----KVDE-PKHLD--YVDKHKDEFKELLDVVSNFSKKYTLAE--GNLEKIK-E | LYA-QN---NGEDLKE-- | 1281 |
| WP_024783594 | 1230 | HHL-------DN-DYSNE--YVKNHYQQFDILFNEITSFSKKCKLGK--EHIQKIE-E | AYSkER---DFASIEE-- | 1287 |
| WP_024784288 | 1222 | KNIH----KVDE-PKHLD--YVDKHKDEFKELLDVVSNFSKKYTLAE--GNLEKIK-E | LYA-QN---NGEDLKE-- | 1281 |
| WP_024784666 | 1222 | KNIH----KVDE-PKHLD--YVDKHKDEFKELLDVVSNFSKKYTLAE--GNLEKIK-E | LYA-QN---NGEDLKE-- | 1281 |
| WP_024784994 | 1230 | HHL-------DN-DYSNE--YVKNHYQQFDILFNEITSFSKKCKLGK--EHIQKIE-E | AYSkER---DSASIEE-- | 1287 |
| WP_024786433 | 1222 | KNIH----KVDE-PKHLD--YVDKHKDEFKELLDVVSNFSKKYTLAE--GNLEKIK-E | LYA-QN---NGEDLKE-- | 1281 |
| WP_049473442 | 1222 | KNIH----KVDE-PKHLD--YVDKHKDEFKELLDVVSNFSKKYTLAE--GNLEKIK-E | LYA-QN---NGEDLKE-- | 1281 |
| WP_049474547 | 1215 | KNIH----KVDE-PKHLD--YVDKHKDEFKELLDVVSNFSKKYTLAE--GNLEKIK-E | LYA-QN---NGEDLKE-- | 1274 |
| EMC03581 | 1250 | KNIH----RLDE-PEHLE--YIQKHRNEFKGLLNLVSEFSQKYVLAD--ANLEKIK-N | LYA-DN---EQADIEI-- | 1309 |
| WP_000428612 | 1248 | KNVH----KLDE-PEHLE--YIQKHRNEFKDLLNLVSEFSQKYVLAD--ANLEKIQ-N | LYA-DN---EQADIEI-- | 1307 |
| WP_000428613 | 1243 | KRIQ----KKDE-PEHLE--YIKQHHSEFNDLLNFVSEFSQKYVLAE--SNLEKIK-N | LYI-DN---EQTNMEE-- | 1302 |
| WP_049523028 | 1209 | SRYTSFSgKpEDrEKHRH--FVESHLHYFDEIKDIIADFSRRYIlAD--ANLEKIL-T | LYN-EKn---QFSIEEq- | 1274 |
| WP_003107102 | | | | |

```
WP_054279288  1242  SKRDK-gTQSEnME-----YISNHKEKFIEIFHYIIRYAEKNVIKP--KVIERLN-D  TFNQkF---NDSDLTE1-  1303
WP_049531101  1252  QRIN----KISE-PIHKQ-YVETHQSEFELLTTIISLSKKYI-QK--PIVESL---  LQQ-AF--EQADKDIyq  1310
WP_049538452  1252  QRIN----KISE-PIHKQ-YVEAHQNEFKELLTTIISLSKKYI-QK--PNVESL---  LQQ-AF--EQADKDIyq  1310
WP_049549711  1254  QRIN----KFSE-PIHKQ-YVEAHQNEFKELLTTIISLSKKYI-QK--PNVESL---  LHQ-AF--EQADNDIyq  1312
WP_007896501  1246  SRYDKLSsKIESeQQKKL-FVEQHLHYFDEILDIVVKHATCYIKAE--NNLKKII-S  LYK-KK--EAYSINEq-  1311
EFR44625      1198  SRYDKLSsKIESeQQKKL-FVEQHLHYFDEILDIVVKHATCYIKAE--NNLKKII-S  LYK-KK--EAYSINEq-  1263
WP_002897477  1247  KNLH----KLDE-PEHLE-YIQKHRNEFKDLLNLVSEFSQKYILAE--ANLEKIK-D  LYA-DN--EQADIEI--  1306
WP_002906454  1253  QRIN----KISE-PIHKQ-YVEAHQNEFKELLTTIISLSKKYI-QK--PNVELL---  LQQ-AF--DQADKDIyq  1311
WP_009729476  1248  KNVH----KLDE-PGHLE-YIQKHRNEFKDLLNLVSEFSQKVLAD--ANLEKIK-N  LYA-DN--EQADIEI--  1307
CQR24647      1238  QHAN----KEDS----VI-YLEKHRHELSELFHHIIGVSEKTLKP--KVEMTLN-E  AFE-KHf--EPDEVSE-  1295
WP_000066813  1252  KNVH----KLDE-PEHLE-YIQKHRYEFKDLLNLVSEFSQKVLAD--ANLEKIK-N  LYA-DN--EQADIEI--  1311
WP_009754323  1248  KNVH----KLDE-PEHLE-YIQKHRYEFKDLLNLVSEFSQKVLAE--ANLEKIK-S  LYV-DN--EQADIEI--  1307
WP_044674937  1241  SNIH----KITE-PIHLN-YVNKNKHEFKELLRHISDFSTRYILAQ--DRLSKIE-E  LYD-KN--DGDDISD--  1300
WP_044676715  1243  SNIH----KITE-PIHLN-YVNKNKHEFKELLRHISDFSTRYILAQ--DRLSKIE-E  LYD-KN--DGDDISD--  1302
WP_044680361  1243  SNIH----KITE-PIHLN-YVNKNKHEFKELLRHISDFSTRYILAQ--DRLSKIE-E  LYD-KN--DGDDISD--  1302
WP_044681799  1241  SNIH----KITE-PIHLN-YVNKNKHEFKELLRHISDFSTRYILAQ--DRLSKIE-E  LYD-KN--DGDDISD--  1300
WP_049533112  1254  KRIN----NPIN-KDHIE-YVKKHRDDFKELLNYVLEFNEKYVGAT--KNGERLK-E  AVA-DF--DSKSNEE--  1313
WP_029090905  1182  STKQA---DE-AMFLKyYRLEHLEAVFBEL------IRKQAADYQIFE--KLIKKIEvN  FYS---c----TYNEk-  1240
WP_006506696  1212  YNAIYKQ-DYDN1DDILMi--------QLYIELTNKMKVLYPAY-rGIAEKFE-s  YVV--i----SKEEk-  1268
AIT42264      1240  SHYEKLKgSPEDnEQKQL-FVEQHKHYLDEIIEQISEFSKRVILAD--ANLDKVL-S  AYN-KH--RDKPIREq-  1305
WP_034440723  1218  KHYNE---DE--TSHK--FIVEHKAYFDELLNVIVEFANKYLELE--NSIEKIK-D  LYH-----gKGPDVEEke  1276
AKQ21048      1240  SHYEKLKgSPEDnEQKQL-FVEQHKHYLDEIIEQISEFSKRVILAD--ANLDKVL-S  AYN-KH--RDKPIREq-  1305
WP_004636532  1212  NRYDKVK-----fPDSIE-YVHDNLAKFDDLLEVIDFSNKYINAD--KNVQKIQ-K  IYK-EH--GTEDVEL--  1271
WP_002364836  1218  KQCLL---PNQ-SESLA-YVEQHQPEFQEILERVVDFAEVHTLAK--SKVQQIV-K  LFE-AN--QTADVKE--  1277
WP_016631044  1169  KQCLL---PNQ-SESLA-YVEQHQPEFQEILERVVDFAEVHTLAK--SKVQQIV-K  LFE-AN--QTADVKE--  1228
EMS75795       954  QHYDEIAhKESF-----D-YVNDHLSEFREILDQVIDFSNRYTIAA--KNTEKIA-E  LFE-QN--QESTVQS--  1013
WP_002373311  1218  KQCLL---PNQ-SESLA-YVEQHQPEFQEILERVVDFAEVHTLAK--SKVQQIV-K  LFE-AN--QTADVKE--  1277
```

| | | | | |
|---|---|---|---|---|
| WP_002378009 | 1218 | KQCLL----PNQ-SESLA--YVEQHQPEFQEILERVVDFAEVHTLAK--SKVQQIV-K | LFE-AN---QTADVKE- | 1277 |
| WP_002407324 | 1218 | KQCLL----PNQ-SESLA--YVEQHQPEFQEILERVVDFAEVHTLAK--SKVQQIV-K | LFE-AN---QTADVKE- | 1277 |
| WP_002413717 | 1218 | KQCLL----PNQ-SESLA--YVEQHQPEFQEILERVVDFAEVHTLAK--SKVQQIV-K | LFE-AN---QTADVKE- | 1277 |
| WP_010775580 | 1220 | KQCLL----PNQ-SESLA--YVEQHQPEFQEILERVVDFAEVHTLAK--SKVQQIV-K | LFE-AN---QTADVKE- | 1279 |
| WP_010818269 | 1218 | KQCLL----PNQ-SESLA--YVEQHQPEFQEILERVVDFAEVHTLAK--SKVQQIV-K | LFE-AN---QTADVKE- | 1277 |
| WP_010824395 | 1218 | KQCLL----PNQ-SESLA--YVEQHQPEFQEILERVVDFAEVHTLAK--SKVQQIV-K | LFE-AN---QTADVKE- | 1277 |
| WP_016622645 | 1218 | KQCLL----PNQ-SESLA--YVEQHQPEFQEILERVVDFAEVHTLAK--SKVQQIV-K | LFE-AN---QTADVKE- | 1277 |
| WP_033624816 | 1218 | KQCLL----PNQ-SESLA--YVEQHQPEFQEILERVVDFAEVHTLAK--SKVQQIV-K | LFE-AN---QTADVKE- | 1277 |
| WP_033625576 | 1218 | KQCLL----PNQ-SESLA--YVEQHQPEFQEILERVVDFAEVHTLAK--SKVQQIV-K | LFE-TN---QTADVKE- | 1277 |
| WP_033789179 | 1218 | KQCLL----PNQ-SESLA--YVEQHQPEFQEILERVVDFAEVHTLAK--SKVQQIV-K | LFE-AN---QTADVKE- | 1277 |
| WP_002310644 | 1220 | KQYDEIShKESF------D--YVNEHHKEFSEVFARVLEFAGKYTLAE--KNIEKLE-K | IYK-EN---QTDDLAK- | 1279 |
| WP_002312694 | 1221 | KQYDEIShKESF------D--YVNEHHKEFSEVFARVLEFAGKYTLAE--KNIEKLE-K | IYK-EN---QTDDLAK- | 1280 |
| WP_002314015 | 1221 | KQYDEIShKESF------D--YVNEHHKEFSEVFARVLEFAGKYTLAE--KNIEKLE-K | IYK-EN---QTDDLAK- | 1280 |
| WP_002320716 | 1220 | KQYDEIShKESF------D--YVNEHHKEFSEVFARVLEFAGKYTLAE--KNIEKLE-K | IYK-EN---QTDDLAK- | 1279 |
| WP_002330729 | 1221 | KQYDEIShKESF------D--YVNEHHKEFSEVFARVLEFAGKYTLAE--KNIEKLE-K | IYK-EN---QTDDLAK- | 1280 |
| WP_002335161 | 1221 | KQYDEIShKESF------D--YVNEHHKEFSEVFARVLEFAGKYTLAE--KNIEKLE-K | IYK-EN---QTDDLAK- | 1280 |
| WP_002345439 | 1221 | QHYDKITyQESF------D--YVNTHLSDFSAILTEVLARAEKYTLAD--KNIERIQ-E | LYE-EN---KYGETSM- | 1270 |
| WP_034867970 | 1221 | KQYDEIShKESF------D--YVNEHHKEFSEVFARVLEFAGKYTLAE--KNIEKLE-K | IYK-EN---QTDDLAK- | 1280 |
| WP_047937432 | 1221 | QHYDKITyQESF------D--YVNTHLSDFSAILTEVLARAEKYTLAD--KNIERIQ-E | LYE-EN---KYGEISM- | 1270 |
| WP_010720994 | 1211 | QHYDKITyQESF------D--YVNTHLSDFSAILTEVLARAEKYTLAD--KNIERIQ-E | LYE-EN---KYGETSM- | 1270 |
| WP_010737004 | 1211 | QHYDKITyQESF------D--YVNTHLSDFSAILTEVLARAEKYTLAD--KNIERIQ-E | LYE-EN---KYGEISM- | 1270 |
| WP_034700478 | 1211 | QHYDKITyQESF------D--YVNTHLSDFSAILTEVLARAEKYTLAD--KNIERIQ-E | LYE-EN---KYGEISM- | 1270 |
| WP_007209003 | 1209 | KKIIN-gKNSD----SVS--YIQNNKEKPREIFEYIVDFSSKYISAD--ANLNKIE-K | IFE-NNfh---KASEqe | 1269 |
| WP_023519017 | 1205 | RHYDEINhKVSF------D--YVNAHKEGFNDIFDFISDPGVRYILAP--QHLEKIK-V | AYE-KN---KEVDLKE- | 1264 |
| WP_010770040 | 1216 | KQVDE----DS-GKSEE--YVREHRAEFAEILNVQAFSETKILAN--KNLQTIL-K | LYE-EN---KEADIKE- | 1274 |
| WP_048604708 | 1213 | KHCNE----KP-D-SLK--YVTEHQSGFSEIMAHVKDFAEKYTLVD--KNLEKIL-S | LYA-KN---MDSEVKE- | 1270 |
| WP_010750235 | 1214 | NHYDEIAyKDSY------D--YVNEHFSNFQDILDKVIIFAEKYTSAP--QKLNQII-A | TYE-KN---QEADRKI- | 1273 |

-continued

| ID | | | | |
|---|---|---|---|---|
| AII16583 | 1279 | SHYEKLKgSPEDnEQKQL--FVEQHKYLDEIIEQISEFSKRVILAD--ANLDKVL-S | AYN-KH---RDKPIREq- | 1344 |
| WP_029073316 | 1226 | YKAMKYK-NYSE1SQEEIm----------NVYDIFVEKLKLYYPTY-kNIATNPFE-N | FEN----i----SDEEk- | 1282 |
| WP_031589969 | 1226 | YKAMKYK-NVDNIDSEKIi----------DLYRLLINKMELYYPEYrKQLVKKFE-D | LKV----i----SIEEk- | 1283 |
| KDA45870 | 1200 | NAKDG-------EQKLE----DHKAEFKELFDKIMEFADKYVVAP--KNSEKIR-R | LYE-ENq-----DATPme | 1253 |
| WP_039099354 | 1242 | LPLTQ-------SEeLAEQV--------YDEILDQVMHYFPLYDTNQfrAKLSAGKaA | DGN-KMv-----QVGQqv | 1306 |
| AKP02966 | 1238 | QIPDE------DpDQILAf----YDKNILVEILQELITKMKKFYPFY--KNEQEFLaS | FNQ---------ATTSEk- | 1296 |
| WP_010991369 | 1216 | ANCEV------SD-GKSLD--YIESNREMFAELLAHVSEFAKRYTLAE--ANLNKIN-Q | LFE-QN----KEGDIKA- | 1274 |
| WP_033838504 | 1216 | ANCEV------SD-GKSLD--YIESNREMFAELLAHVSEFAKRYTLAE--ANLNKIN-Q | LFE-QN----KEGDIKA- | 1274 |
| EHN60060 | 1219 | ANCEV------SD-GKSLD--YIESNREMFAELLAHVSEFAKRYTLAE--ANLNKIN-Q | LFE-QN----KEGDIKA- | 1277 |
| EFR89594 | 985 | ANCEV------SD-GKSLD--YIESNREMFAELLAHVSEFAKRYTLAE--ANLNKIN-Q | LFE-QN----KEGDIKA- | 1043 |
| WP_038409211 | 1216 | KNCEA------ND-GESLA--YIEMHREMFAELLAYISEFAKRYTLAN--DRLEKIN-M | FFE-QN----KKGDIKV- | 1274 |
| EFR95520 | 835 | KNCEA------ND-GESLA--YIEMHREMFAELLAYISEFAKRYTLAN--DRLEKIN-M | FFE-QN----KKGDIKV- | 893 |
| WP_003723650 | 1216 | KNCEA------SD-GKSLK--YIEAHRETFSELLAQVSEFATRYTLAD--ANLSKIN-N | LFE-QN----KEGDIKA- | 1274 |
| WP_003727705 | 1216 | KNCEA------SD-GKSLK--YIEAHRETFSELLAQVSEFATKYTLAD--ANLSKIN-N | LFE-QN----KEGDIKA- | 1274 |
| WP_003730785 | 1216 | KNCEA------SD-GKSLK--YIEAHRETFSELLAQVSEFATKYTLAD--ANLSKIN-N | LFE-QN----KEGDIKA- | 1274 |
| WP_003733029 | 1216 | EKYEA------ID-GESLA--YIEVHRALFDELLAYISEFARKYTLSN--DRLDEIN-M | LYE-RN----KDGDIKV- | 1274 |
| WP_003739838 | 1216 | KNCEA------SD-GKSLD--YIESNREMFGELLAHVSEFAKRYTLAD--ANLSKIN-Q | LFE-QN----KDNDIKV- | 1274 |
| WP_014601172 | 1216 | KNCEA------SD-GESLA--YIEAHRETFSELLAQVSEFATRYTLAD--ANLSKIN-N | LFE-QN----KEGDIQA- | 1274 |
| WP_023548323 | 1216 | EKREA------ID-GESLA--YIEAHKAVFGELLAHISEFATRYTLAN--DKLDEIN-M | LYE-RN----KDGDVKS- | 1274 |
| WP_031665337 | 1216 | KNCEA------SD-GKSLK--YIEAHRETFSELLAQVSEFATRYTLAD--ANLSKIN-N | LFE-QN----KEGDIKA- | 1274 |
| WP_031669209 | 1216 | EKYEA------ID-GESLA--YIEVHRALFDELLAYISEFARKYTLSN--DRLDEIN-M | LYE-RN----KDGDVKS- | 1274 |
| WP_033920898 | 1216 | EKREA------ID-GESLA--YIEAHKAVFGELLAHISEFATRYTLAN--DKLDEIN-M | LYE-RN----KDGDVKS- | 1274 |
| AKI42028 | 1219 | KNCEA------SD-GKSLK--YIEAHRETFSELLAQVSEFATRYTLAD--ANLSKIN-N | LFE-QN----KEGDIQA- | 1277 |
| AKI50529 | 1219 | EKREA------ID-GESLA--YIEAHKAVFGELLAHISEFATRYTLAD--DKLDEIN-M | LYE-RN----KDGDVKS- | 1277 |
| EFR83390 | 664 | KNCEA------SD-GKSLK--YTEAHRETFSELLAQVSEFATRYTLAD--ANLSKIN-N | LFE-QN----KEGDIKX- | 722 |
| WP_046323366 | 1216 | KNCEA------SD-GKSLA--YIESHREMFAELLDSISEFASRYTLAD--ANLEKIN-T | IFE-QN----KSGDVKV- | 1274 |
| AKE81011 | 1256 | SHYEKLKgSPEDnEQKQL--FVEQHKHYLDEIIEQISEFSKRVILAD--ANLDKVL-S | AYN-KH---RDKPIREq- | 1321 |

```
CU082355         1216  YNAIYKQ-DFDGIDNMLMi----------QLYIQLIDKLKTLYPIY-mGIVEKFE-K  FVS----i-----SKEEk-  1272
WP_033162887     1218  YAAMLKK-RYEYIDEEIf----------DLYLQLLQKMDTLYPAY-kGIAKRPF-D  FKN----i-----DVVEk-  1274
AGZ01981         1273  SHYEKLKgSPEDnEQKQL--FVEQHKHYLDEIIEQISEFSKRVILAD--ANLDKVL-S  AYN-KH---RDKPIREq-  1338
AKA60242         1240  SHYEKLKgSPEDnEQKQL--FVEQHKHYLDEIIEQISEFSKRVILAD--ANLDKVL-S  AYN-KH---RDKPIREq-  1305
AKS40380         1240  SHYEKLKgSPEDnEQKQL--FVEQHKHYLDEIIEQISEFSKRVILAD--ANLDKVL-S  AYN-KH---RDKPIREq-  1305
4UN5_B           1244  SHYEKLKgSPEDnEQKQL--FVEQHKHYLDEIIEQISEFSKRVILAD--ANLDKVL-S  AYN-KH---RDKPIREq-  1309
WP_010922251     1306  -AE---NII  HLFTLTNLGAP-AAFKYFD-TTI--DRK--R-YTSTKEVL  DATLIHQSITGLYETRIDLSQL--  1365
WP_039695303     1309  ISN---SFI  NLLTLTALGAP-ADFNFLG-EKI--PRK--R-YTSTKECL  NATLIHQSITGLYETRIDLSKL--  1369
WP_045635197     1307  LAN---SFI  NLLTFTALGAP-AAFKFPG-KDI--DRK--R-YTTVSEIL  NATLIHQSITGLYETWIDLSKL--  1367
5AXW_A                                                                                         1049
WP_009880683      990  -AE---NII  HLFTLTNLGAP-AAFKCPD-TTI--GRN--R-YKSIKEVL  DATLIHQSITGLYETRIDLSQL--  1365
WP_010922251     1306  -AE---NII  HLFTLTNLGAP-AAFKYFD-TTI--DRK--R-YTSTKEVL  DATLIHQSITGLYETRIDLSQL--  1365
WP_011054416     1306  -AE---NII  HLFTLTNLGAP-AAFKYFD-TTI--DRK--R-YTSTKEVL  DATLIHQSITGLYETRIDLSQL--  1365
WP_011284745     1306  -AE---NII  HLFTLTNLGAP-AAFKYFD-TTI--DRK--R-YTSTKEVL  DATFIHQSITGLYETRIDLSQL--  1365
WP_011285506     1306  -AE---NII  HLFTLTNLGAP-AAFKYFD-TTI--DRK--R-YKSIKEVL  DATFIHQSITGLYETRIDLSQL--  1365
WP_011527619     1306  -AE---NII  HLFTLTNLGAP-TAFKYFD-TTI--DRK--R-YTSTKEVL  DATLIHQSITGLYETRIDLSQL--  1365
WP_012560673     1306  -AE---NII  HLFTLTNLGAP-AAFKYFD-TTI--GRN--R-YKSIKEVL  DATLIHQSITGLYETRIDLSQL--  1365
WP_014407541     1305  -AE---NII  HLFTLTNLGAP-AAFKYFD-TTI--DRK--R-YTSTKEVL  DATLIHQSITGLYETRIDLSQL--  1364
WP_020905136     1306  -AE---NII  HLFTLTNLGAP-AAFKYFD-TTI--DRK--R-YTSTKEVL  DATLIHQSITGLYETRIDLSQL--  1365
WP_023080005     1305  -AK---NII  HLFTLTNLGAP-AAFKYFD-TTI--ERN--R-YKSIKEVL  DATLIHQSITGLYETRIDLSQL--  1364
WP_023610282     1305  -AK---NII  HLFTLTNLGAP-AAFKYFD-TTI--ERN--R-YKSIKEVL  DATLIHQSITGLYETRIDLSQL--  1364
WP_030125963     1305  -AE---NII  HLFTLTNLGAP-AAFKYFD-TTI--GRN--R-YKSIKEVL  DATLIHQSITGLYEIRIDLSQL--  1364
WP_030126706     1306  -AE---NII  HLFTLTNLGAP-AAFKYFD-TTI--DRK--R-YTSTKEVL  DATLIHQSITGLYETRIDLSQL--  1365
WP_031488318     1306  -AE---NII  HLFTLTNLFGAP-AAFIYFD-TTI--GRN--R-YKSIKEVL DATLIHQSITGLYETRIDLSQL-- 1365
WP_032460140     1306  -AE---NII  HLFTLTNLGAP-AAFKYFD-TTI--GRN--R-YKSIKEVL  DATLIHQSITGLYETRIDLSQL--  1365
WP_032461047     1306  -AE---NII  HLFTLTNLGAP-AAFKYFD-TTI--GRN--R-YKSIKEVL  DATLIHQSITGLYETRIDLSQL--  1365
WP_032462016     1306  -AE---NII  HLFTLTNLGAP-AAFKYFD-TTI--DRK--R-YTSTKEVL  DATLIHQSITGLYETRIDLSQL--  1365
```

-continued

| | | | | | |
|---|---|---|---|---|---|
| WP_032462936 | 1306 | -AE---NII | HLFTLTNLGAP-AAFKYPD--TTI--DRK--R--YTSTKEVL | DATLIHQSITGLYETRIDLSQL-- | 1365 |
| WP_032464890 | 1306 | -AE---NII | HLFTLTNLGAP-TAFKYPD--TTI--DRK--R--YTSTKEVL | DATPIHQSITGLYETRIDLSQL-- | 1365 |
| WP_033888930 | 1131 | -AE---NII | HLFTLTNLGAP-AAFKYPD--TTI--DRK--R--YTSTKEVL | DATLIHQSITGLYETRIDLSQL-- | 1190 |
| WP_038431314 | 1306 | -AE---NII | HLFTLTNLGAP-AAFKYPD--TTI--DRK--R--YTSTKEVL | DATLIHQSITGLYETRIDLSQL-- | 1365 |
| WP_038432938 | 1305 | -AK---NII | HLFTLTNLGAP-AAFKYPD--TTI--ERN--R--YKSIKEVL | DATLIHQSITGLYETRIDLSQL-- | 1364 |
| WP_038434062 | 1306 | -AE---NII | HLFTLTNLGAP-AAFKYPD--TTI--GRN--R--YKSIKEVL | DATLIHQSITGLYETRIDLSQL-- | 1365 |
| BAQ51233 | 1217 | -AE---NII | HLFTLTNLGAP-AAFKYPD--TTI--DRK--R--YTSTKEVL | DATLIHQSITGLYETRIDLSQL-- | 1276 |
| KGE60162 | 481 | -AE---NII | HLFTLTNLGAP-AAFKYPD--TTI--DRK--R--YTSTKEVL | DATLIHQSITGLYETRIDLSQL-- | 540 |
| KGE60856 | 244 | -AE---NII | HLFTLTNLGAP-TAFKYPD--TTI--DRK--R--YTSTKEVL | DATPIHQSITGLYETRIDLSQL-- | 303 |
| WP_002989955 | 1306 | -AE---NII | HLFTLTNLGAP-AAFKYPD--TTI--DRK--R--YTSTKEVL | DATLIHQSITGLYETRIDLSQL-- | 1365 |
| WP_003030002 | 1282 | LAK---SFI | SLLTFTAFGAP-AAFNPFG--ENI--DRK--R--YTSVTECL | NATLIHQSITGLYETRIDLSKI-- | 1342 |
| WP_003065552 | 1310 | ISN---SFI | NLLTLTALGAP-ADFNFLG--EKI--PRK--R--YTSTKECL | NATLIHQSITGLYETRIDLSKI-- | 1370 |
| WP_001040076 | 1307 | LAN---NII | NLFTFTSLGAP-AAFKFPD--KIV--DRK--R--YTSTKEVL | NSTLIHQSITGLYETRIDLSKL-- | 1367 |
| WP_001040078 | 1315 | LAN---NII | NLFTFTSLGAP-AAFKFPD--KIV--DRK--R--YTSTKEVL | NSTLIHQSITGLYETRIDLGKL-- | 1375 |
| WP_001040080 | 1307 | LAN---NII | NLFTFTSLGAP-AAFKFPD--KIV--DRK--R--YTSTKEVL | NSTLIHQSITGLYETRIDLGKL-- | 1367 |
| WP_001040081 | 1307 | LAN---NII | NLFTFTSLGAP-AAFKFPD--KIV--DRK--R--YTSTKEVL | NSTLIHQSITGLYETRIDLGKL-- | 1367 |
| WP_001040083 | 1307 | LAN---NII | NLFTFTSLGAP-AAFKFPD--KIV--DRK--R--YTSTKEVL | NSTLIHQSITGLYETRIDLGKL-- | 1367 |
| WP_001040085 | 1307 | LAN---NII | NLFTFTSLGAP-AAFKFPD--KIV--DRK--R--YTSTKEVL | NSTLIHQSITGLYETRIDLGKL-- | 1367 |
| WP_001040087 | 1307 | LAN---NII | NLFTFTSLGAP-AAFKFPD--KIV--DRK--R--YTSTKEVL | NSTLIHQSITGLYETRIDLGKL-- | 1367 |
| WP_001040088 | 1307 | LAN---NII | NLFTFTSLGAP-AAFKFPD--KIV--DRK--R--YTSTKEVL | NSTLIHQSITGLYETRIDLGKL-- | 1367 |
| WP_001040089 | 1307 | LAN---NII | NLFTFTSLGAP-AAFKFPD--KIV--DRK--R--YTSTKEVL | NSTLIHQSITGLYETRIDLGKL-- | 1367 |
| WP_001040090 | 1307 | LAN---NII | NLFTFTSLGAP-AAFKFPD--KIV--DRK--R--YTSTKEVL | NSTLIHQSITGLYETRIDLGKL-- | 1367 |
| WP_001040091 | 1307 | LAN---NII | NLFTFTSLGAP-AAFKFPD--KIV--DRK--R--YTSTKEVL | NSTLIHQSITGLYETRIDLGKL-- | 1367 |
| WP_001040092 | 1307 | LAK---NII | NLFTFTSLGAP-AAFKFPD--KSV--DRK--R--YTSTKEVL | DSTLIHQSITGLYETRIDLGKL-- | 1367 |
| WP_001040094 | 1307 | LAN---NII | NLFTFTSLGAP-AAFKFPD--KIV--DRK--R--YTSTKEVL | NSTLIHQSITGLYETRIDLGKL-- | 1367 |
| WP_001040095 | 1307 | LAN---NII | NLFTFTSLGAP-AAFKFPD--KIV--DRK--R--YTSTKEVL | NSTLIHQSITGLYETRIDLGKL-- | 1367 |
| WP_001040096 | 1307 | LAN---NII | NLFTFTSLGAP-AAFKFPD--KIV--DRK--R--YTSTKEVL | NSTLIHQSITGLYETRIDLGKL-- | 1367 |

| | | | | | | |
|---|---|---|---|---|---|---|
| WP_001040097 | 1307 | LAN---NII | NLFTFTSLGAP-AAFKFPD--KIV--DRK--R--YTSTKEVL | NSTLIHQSITGLYETRIDLGKL-- | 1367 |
| WP_001040098 | 1307 | LAN---NII | NLFTFTSLGAP-AAFKFPD--KIV--DRK--R--YTSTKEVL | NSTLIHQSITGLYETRIDLGKL-- | 1367 |
| WP_001040099 | 1307 | LAN---NII | NLFTFTSLGAP-AAFKFPD--KIV--DRK--R--YTSTKEVL | NSTLIHKSITGLYETRIDLGKL-- | 1367 |
| WP_001040100 | 1307 | LAN---NII | NLFTFTSLGAP-AAFKFPD--KIV--DRK--R--YTSTKEVL | NSTLIHQSITGLYETRIDLGKL-- | 1367 |
| WP_001040104 | 1307 | LAN---NII | NLFTFTSLGAP-AAFKFPD--KIV--DRK--R--YTSTKEVL | NSTLIHQSITGLYETRIDLGKL-- | 1367 |
| WP_001040105 | 1307 | LAN---NII | NLFTFTSLGAP-AAFKFPD--KIV--DRK--R--YTSTKEVL | NSTLIHQSITGLYETRIDLGKL-- | 1367 |
| WP_001040106 | 1307 | LAN---NII | NLFTFTSLGAP-AAFKFPD--KIV--DRK--R--YTSTKEVL | NSTLIHQSITGLYETRIDLGKL-- | 1367 |
| WP_001040107 | 1307 | LAN---NII | NLFTFTSLGAP-AAFKFPD--KIV--DRK--R--YTSTKEVL | NSTLIHQSITGLYETRIDLGKL-- | 1367 |
| WP_001040108 | 1307 | LAN---NII | NLFTFTSLGAP-AAFKFPD--KIV--DRK--R--YTSTKEVL | NSTLIHQSITGLYETRIDLGKL-- | 1367 |
| WP_001040109 | 1307 | LAN---NII | NLFTFTSLGAP-AAFKFPD--KIV--DRK--R--YTSTKEVL | NSTLIHQFITGLYETRIDLGKL-- | 1367 |
| WP_001040110 | 1307 | LAK---NII | NLFTFTSLGAP-AAFKFPD--KSV--DRK--R--YTSTKEVL | DSTLIHQSITGLYETRIDLGKL-- | 1367 |
| WP_015058523 | 1307 | LAN---NII | NLFTFTSLGAP-AAFKFPD--KIV--DRK--R--YTSTKEVL | NSTLIHQSITGLYETRIDLGKL-- | 1367 |
| WP_017643650 | 1307 | LAN---NII | NLFTFTSLGAP-AAFKFPD--KIV--DRK--R--YTSTKEVL | NSTLIHQSITGLYETRIDLGKL-- | 1367 |
| WP_017647151 | 1307 | LAN---NII | NLFTFTSLGAP-AAFKFPD--KIV--DRK--R--YTSTKEVL | NSTLIHQSITGLYETRIDLGKL-- | 1367 |
| WP_017648376 | 1307 | LAN---NII | NLFTFTSLGAP-AAFKFPD--KIV--DRK--R--YTSTKEVL | NSTLIHQSITGLYETRIDLGKL-- | 1367 |
| WP_017649527 | 1307 | LAN---NII | NLFTFTSLGAP-AAFKFPD--KIV--DRK--R--YTSTKEVL | NSTLIHQSITGLYETRIDLGKL-- | 1367 |
| WP_017771611 | 1307 | LAN---NII | NLFTFTSLGAP-AAFKFPD--KIV--DRK--R--YTSTKEVL | NSTLIHQSITGLYETRIDLGKL-- | 1367 |
| WP_017771984 | 1307 | LAN---NII | NLFTFTSLGAP-AAFKFPD--KIV--DRK--R--YTSTKEVL | NSTLIHQSITGLYETRIDLGKL-- | 1367 |
| CFQ25032 | 1307 | LAN---NII | NLFTFTSLGAP-AAFKFPD--KIV--DRK--R--YTSTKEVL | NSTLIHQSITGLYETRIDLGKL-- | 1367 |
| CFV16040 | 1307 | LAN---NII | NLFTFTSLGAP-AAFKFPD--KIV--DRK--R--YTSTKEVL | NSTLIHQSITGLYETRIDLGKL-- | 1367 |
| KLJ37842 | 1307 | LAN---NII | NLFTFTSLGAP-AAFKFPD--KIV--DRK--R--YTSTKEVL | NSTLIHQSITGLYETRIDLGKL-- | 1367 |
| KLJ72361 | 1321 | LAN---NII | NLFTFTSLGAP-AAFKFPD--KIV--DRK--R--YTSTKEVL | NSTLIHQSITGLYETRIDLGKL-- | 1381 |
| KLL20707 | 1307 | LAN---NII | NLFTFTSLGAP-AAFKFPD--KIV--DRK--R--YTSTKEVL | NSTLIHQSITGLYETRIDLGKL-- | 1367 |
| KLL42645 | 1307 | LAN---NII | NLFTFTSLGAP-AAFKFPD--KIV--DRK--R--YTSTKEVL | NSTLIHQSITGLYETRIDLGKL-- | 1367 |
| WP_047207273 | 1307 | LAN---NII | NLFTFTSLGAP-AAFKFPD--KIV--DRK--R--YTSTKEVL | NSTLIHKSITGLYETRIDLGKL-- | 1367 |
| WP_047209694 | 1307 | LAN---NII | NLFTFTSLGAP-AAFKFPD--KIV--DRK--R--YTSTKEVL | NSTLIHQSITGLYETRIDLGKL-- | 1367 |
| WP_050198062 | 1307 | LAN---NII | NLFTFTSLGAP-AAFKFPD--KIV--DRK--R--YTSTKEVL | NSTLIHQSITGLYETRIDLGKL-- | 1367 |

| | | | | | |
|---|---|---|---|---|---|
| WP_050201642 | 1307 | LAN---NII | NLFTFTSLGAP-AAFKFPD--KIV-DRK--R-YTSTKEVL | NSTLIHQSITGLYETRIDLGKL-- | 1367 |
| WP_050204027 | 1307 | LAN---NII | NLFTFTSLGAP-AAFKFPD--KIV-DRK--R-YTSTKEVL | NSTLIHQSITGLYETRIDLGKL-- | 1367 |
| WP_050881965 | 1307 | LAN---NII | NLFTFTSLGAP-AAFKFPD--KII-DRK--R-YTSTKEVL | NSTLIHQSITGLYETRIDLGKL-- | 1367 |
| WP_050886065 | 1307 | LAN---NII | NLFTFTSLGAP-AAFKFPD--KIV-DRK--R-YTSTKEVL | NSTLIHQSITGLYETRIDLGKL-- | 1367 |
| AHN30376 | 1307 | LAK---NII | NLFTFTSLGAP-AAFKFPD--KSV-DRK--R-YTSTKEVL | DSTLIHQSITGLYETRIDLGKL-- | 1367 |
| EAO78426 | 1307 | LAN---NII | NLFTFTSLGAP-AAFKFPD--KIV-DRK--R-YTSTKEVL | NSTLIHQSITGLYETRIDLGKL-- | 1367 |
| CCW42055 | 1307 | LAN---NII | NLFTFTSLGAP-AAFKFPD--KIV-DRK--R-YTSTKEVL | NSTLIHQSITGLYETRIDLGKL-- | 1367 |
| WP_003041502 | 1314 | ICT---SFL | GLPELTSLGSA-SDFEFLG--VKI-PRY--RdYTPSSLLK | DSTLIHQSITGLYETRIDLSKL-- | 1383 |
| WP_037593752 | 1283 | LAK---SFI | SLLTFTAFGAP-AAFNFFG--ENI-DRK--R-YTSVTECL | NATLIHQSITGLYETRIDLSKL-- | 1343 |
| WP_049516684 | 1283 | LAK---SFI | SLLTFTAFGAP-AAFNFFG--ENI-DRK--R-YTSVTECL | NATLIHQSITGLYETRIDLSKL-- | 1343 |
| GAD46167 | 1282 | LAK---SFI | SLLTFTAFGAP-AAFNFFG--ENI-DRK--R-YTSVTECL | NATLIHQSITGLYETRIDLSKL-- | 1342 |
| WP_018363470 | 1314 | ISD---SFI | NLLTLTALGAP-ADFNFLG--EKI-PRK--R-YNSTKECL | NATLIHQSITGLYETRIDLSKL-- | 1374 |
| WP_003043819 | 1311 | -SN---SFV | SLLKYTSFGAS-GGFTFLD--LDVkgGRL--R-YQTVTEVL | DATLIYQSITGLYETRTDLSQL-- | 1372 |
| WP_006269658 | 1282 | LAK---SFI | SLLTFTAFGAP-AAFNFFG--ENI-DRK--R-YTSVTECL | NATLIHQSITGLYETRIDLSKL-- | 1342 |
| WP_048800889 | 1302 | ISN---SFI | HLLTLTALGAP-ADFKFLG--EKI-PRK--R-YTSTKECL | NATLIHQSITGLYETQTDLSKL-- | 1362 |
| WP_012767106 | 1309 | -CS---SVI | NLLTLTASGAP-ADFKFLG--TTI-PRK--R-YGSPQSIL | SSTLIHQSITGLYETRIDLSQL-- | 1368 |
| WP_014612333 | 1309 | -CS---SVI | NLLTLTASGAP-ADFKFLG--TTI-PRK--R-YGSPQSIL | SSTLIHQSITGLYETRIDLSQL-- | 1368 |
| WP_015017095 | 1309 | -CS---SVI | NLLTLTASGAP-ADFKFLG--TTI-PRK--R-YGSPQSIL | SSTLIHQSITGLYETRIDLSQL-- | 1368 |
| WP_015057649 | 1309 | -CS---SVI | NLLTLTASGAP-ADFKFLG--TTI-PRK--R-YGSPQSIL | SSTLIHQSITGLYETRIDLSQL-- | 1368 |
| WP_048327215 | 1309 | -CS---SVI | NLLTLTASGAP-ADFKFLG--TTI-PRK--R-YGSPQSIL | SSTLIHQSITGLYETRIDLSQL-- | 1368 |
| WP_049519324 | 1309 | -CS---SVI | NLLTLTASGAP-ADFKFLG--TTI-PRK--R-YGSPQSIL | SSTLIHQSITGLYETRIDLSQL-- | 1368 |
| WP_012515931 | 1286 | -AE---NII | NVFTFVALGAP-AAFKFPD--ATI-DRK--R-YTSTKEVL | NATLIHQSVTGLYETRIDLSQL-- | 1345 |
| WP_021320964 | 1286 | -AE---NII | NVFTFVALGAP-AAFKFPD--ATI-DRK--R-YTSTKEVL | NATLIHQSVTGLYETRIDLSQL-- | 1345 |
| WP_037581760 | 1286 | -AE---NII | NVFTFVALGAP-AAFKFPD--ATI-DRK--R-YTSTKEVL | NATLIHQSVTGLYETRIDLSQL-- | 1345 |
| WP_004232481 | 1309 | ISSlseSFI | NLLKFISFGAP-GAFKFLK--LDV-KQSn1R-YKSTTEAL | SATLIHQSVTGLYETRIDLSKL-- | 1374 |
| WP_009854540 | 1307 | ISN---SFI | NLLTLTALGAP-ADFNFLG--EKI-PRK--R-YTSTKECL | TATLIHQSITGLYETRIDLSKL-- | 1367 |
| WP_012962174 | 1308 | ISI---SFV | NLLTLTALGAP-ADFNFLG--EKI-PRK--R-YTSTKECL | NATLIHQSITGLYETRIDLSKL-- | 1368 |

| | | | | | |
|---|---|---|---|---|---|
| WP_039695303 | 1309 | ISN---SFI | NLLTLTAIGAP-ADFNFLG--EKI--PRK--R-YTSTKECL | NATLIHQSITGLYETRIDLSKL-- | 1369 |
| WP_014334983 | 1312 | ISA---SFI | NLLTLTAIGAP-ADFNFLG--EKI--PRK--R-YTSTKECL | SATLIHQSVTGLYETRIDLSKL-- | 1372 |
| WP_003099269 | 1306 | -AI---NML | NLFTFTDLGAP-SAFKFFN--GDI--DRK--R-YSSTNEII | NSTLIYQSPTGLYETRIDLSKL-- | 1365 |
| AHY15608 | | | | | |
| AHY17476 | | | | | |
| ESR09100 | 138 | -AI---NML | NLFTFTDLGAP-SAFKFFNg--DI--DRK--R-YSSTNEII | NSTLIYQSPTGLYETRIDLSKL-- | 197 |
| AGM98575 | | | | | |
| ALF27331 | 1282 | LAS---SFI | NLLTFTAIGAP-AAFKFPD--NNI--DRK--R-YTSTTEIL | NATLIHQSITGLYETRIDLSRL-- | 1342 |
| WP_018372492 | 1290 | VAR---SFV | -LLNFTMMGAA-TDFKFFG--QII--PRK--R-YPSTTECL | KSTLIHQSVTGLYETRIDLSKL-- | 1350 |
| WP_045618028 | 1311 | LSE---SFI | SLLKLISPGAP-GTFKFLG--VEI--SQSnvR-YQSVSSCF | NATLIHQSITGLYETRIDLSKL-- | 1373 |
| WP_045635197 | 1307 | LAN---SFI | NLLTFTAIGAP-AAFKFFG--KDI--DRK--R-YTTVSEIL | NATLIHQSITGLYETWIDLSKL-- | 1367 |
| WP_002263549 | 1282 | LAS---SFI | NLLTFTAIGAP-ATFKFPD--KNI--DRK--R-YTSTTEIL | NATLIHQSITGLYETRIDLNKL-- | 1342 |
| WP_002263887 | 1282 | LAS---SFI | NLLTFTAIGAP-ATFKFFD--KNI--DRK--R-YTSTTEIL | NATLIHQSITGLYETRIDLNKL-- | 1342 |
| WP_002264920 | 1282 | LAS---SFI | NLLTFTAIGAP-ATFKFFD--KNI--DRK--R-YTSTTEIL | NATLIHQSITGLYETRIDLSKL-- | 1342 |
| WP_002269043 | 1282 | LAS---SFI | NLLTFTAIGAP-ATFKFFD--KNI--DRK--R-YTSTTEIL | NATLIHQSITGLYETRIDLSKL-- | 1342 |
| WP_002269448 | 1282 | LAS---SFI | NLLTFTAIGAP-ATFKFFD--KNI--DRK--R-YTSTTEIL | NATLIHQSITGLYETRIDLSKL-- | 1342 |
| WP_002271977 | 1282 | LAS---SFI | NLLTFTAIGAP-ATFKFFD--KNI--DRK--R-YTSTTEIL | NATLIHQSITGLYETRIDLSKL-- | 1342 |
| WP_002272766 | 1282 | LAS---SFI | NLLTFTAIGAP-ATFKFFD--KNI--DRK--R-YTSTTEIL | NATLIHQSITGLYETRIDLSKL-- | 1342 |
| WP_002273241 | 1282 | LAS---SFI | NLLTFTAIGAP-AAFKFFD--KNI--DRK--R-YTSTTEIL | NATLIHQSITGLYETRIDLSKL-- | 1342 |
| WP_002275430 | 1282 | LSS---SFI | NLLTFTAIGAP-ATFKFFD--KNI--DRK--R-YTSTTEIL | NATLIHQSITGLYETRIDLSKL-- | 1342 |
| WP_002276448 | 1282 | LAS---SFI | NLLTFTAIGAP-ATFKFFD--KNI--DRK--R-YTSTTEIL | NATLIHQSITGLYETRIDLSKL-- | 1342 |
| WP_002277050 | 1288 | LAD---GFI | KLLGFTQLGAT-SPFSFLG--IKL--NQK--Q-YTGKKDYL | EATLIHQSITGLYETRIDLNKL-- | 1352 |
| WP_002277364 | 1282 | LAS---SFI | NLLTFTAIGAP-ATFKFFD--KNI--DRK--R-YTSTTEIL | NATLIHQSITGLYETRIDLSKL-- | 1342 |
| WP_002279025 | 1282 | LAS---SFI | NLLTFTAIGAP-ATFKFFD--KNI--DRK--R-YTSTTEIL | NATLIHQSITGLYETRIDLSKL-- | 1342 |
| WP_002279859 | 1282 | LAS---SFI | NLLTFTAIGAP-ATFKFFD--KNI--DRK--R-YTSTTEIL | NATLIHQSITGLYETRIDLSKL-- | 1342 |
| WP_002280230 | 1282 | LAS---SFI | NLLTFTAIGAP-ATFKFFD--KNI--DRK--R-YTSTTEIL | NATLIHQSITGLYETRIDLSKL-- | 1342 |
| WP_002281696 | 1282 | LSS---SFI | NLLTFTAIGAP-ATFKFFD--KNI--DRK--R-YTSTTEIL | NATLIHQSITGLYETRIDLSKL-- | 1342 |

-continued

| | | | | | | | |
|---|---|---|---|---|---|---|---|
| WP_002282247 | 1288 | LAD---GFI | KLLGFTQLGAT-SPFSFLG--IKL--NQK--Q-YTGKKDYL | EATLIHQSITGLYETRIDLSKL-- | 1352 |
| WP_002282906 | 1282 | LAS---SFI | NLLTFTAIGAP-ATFKFFD--KNI--DRK--R-YTSTTEIL | NATLIHQSITGLYETRIDLSKL-- | 1342 |
| WP_002283846 | 1282 | LAS---SFI | NLLTFTAIGAP-ATFKFFD--KNI--DRK--R-YTSTTEIL | NATLIHQSITGLYETRIDLSKL-- | 1342 |
| WP_002287255 | 1282 | LAS---SFI | NLLTFTAIGAP-ATFKFFD--KNI--DRK--R-YTSTTEIL | NATLIHQSITGLYETRIDLSKL-- | 1342 |
| WP_002288990 | 1282 | LAS---SFI | NLLTFTAIGAP-AAFKFFD--KNI--DRK--R-YTSTTEIL | NATLIHQSITGLYETRIDLSKL-- | 1342 |
| WP_002289641 | 1282 | LAS---SFI | NLLTFTAIGAP-ATFKFFD--KNI--DRK--R-YTSTTEIL | NATLIHQSITGLYETRIDLSKL-- | 1342 |
| WP_002290427 | 1282 | LAS---SFI | NLLTFTAIGAP-ATFKFFD--KNI--DRK--R-YTSTTEIL | NATLIHQSITGLYETRIDLSKL-- | 1342 |
| WP_002295753 | 1282 | LAS---SFI | NLLTFTAIGAP-AAFKFFD--KNI--DRK--R-YTSTTEIL | NATLIHQSITGLYETRIDLSKL-- | 1342 |
| WP_002296423 | 1282 | LAS---SFI | NLLTFTAIGAP-ATFKFFD--KNI--DRK--R-YTSTTEIL | NATLIHQSITGLYETRIDLSKL-- | 1342 |
| WP_002304487 | 1296 | LAS---SFI | NLLTFTAIGAP-AAFKFFD--KNI--DRK--R-YTSTTEIL | NATLIHQSITGLYETRIDLNKL-- | 1356 |
| WP_002305844 | 1282 | LAS---SFI | NLLTFTAIGAP-ATFKFFD--KNI--DRK--R-YTSTTEIL | NATLIHQSITGLYETRIDLSKL-- | 1342 |
| WP_002307203 | 1282 | LAS---SFI | NLLTFTAIGAP-ATFKFFD--KNI--DRK--R-YTSTTEIL | NATLIHQSITGLYETRIDLSKL-- | 1342 |
| WP_002310390 | 1282 | LAS---SFI | NLLTFTAIGAP-ATFKFFD--KNI--DRK--R-YTSTTEIL | NATLIHQSITGLYETRIDLSKL-- | 1342 |
| WP_002352408 | 1282 | LAS---SFI | NLLTFTAIGAP-ATFKFFD--KNI--DRK--R-YTSTTEIL | NATLIHQSITGLYETRIDLSKL-- | 1342 |
| WP_012997688 | 1282 | LAS---SFI | NLLTFTAIGAP-ATFKFFD--KNI--DRK--R-YTSTTEIL | NATLIHQSITGLYETRIDLSKL-- | 1342 |
| WP_014677909 | 1282 | LAS---SFI | NLLTFTAIGAP-ATFKFFD--KNI--DRK--R-YTSTTEIL | NATLIHQSITGLYETRIDLSKL-- | 1342 |
| WP_019312892 | 1282 | LAS---SFI | NLLTFTAIGAP-ATFKFFD--KNI--DRK--R-YTSTTEIL | NATLIHQSITGLYETRIDLSKL-- | 1342 |
| WP_019313659 | 1282 | LAS---SFI | NLLTFTAIGAP-ATFKFFD--KNI--DRK--R-YTSTTEIL | NATLIHQSITGLYETRIDLNKL-- | 1342 |
| WP_019314093 | 1282 | LAS---SFI | NLLTFTAIGAP-AAFKFFD--KNI--DRK--R-YTSTTEIL | NATLIHQSITGLYETRIDLNKL-- | 1342 |
| WP_019315370 | 1282 | LSS---SFI | NLLTFTAIGAP-AAFKFFD--KNI--DRK--R-YTSTTEIL | NATLIHQSITGLYETRIDLNKL-- | 1342 |
| WP_019803776 | 1282 | LAS---SFI | NLLTFTAIGAP-ATFKFFD--KNI--DRK--R-YTSTTEIL | NATLIHQSITGLYETRIDLNKL-- | 1342 |
| WP_019805234 | 1282 | LAS---SFI | NLLTFTAIGAP-ATFKFFD--KNI--DRK--R-YTSTTEIL | NATLIHQSITGLYETRIDLNKL-- | 1342 |
| WP_024783594 | 1282 | LAS---SFI | NLLTFTAIGAP-ATFKFFD--KNI--DRK--R-YTSTTEIL | NATLIHQSITGLYETRIDLNKL-- | 1342 |
| WP_024784288 | 1288 | LAD---GFI | KLLGFTQLGAT-SPFSFLG--IKL--NQK--Q-YTGKKDYL | EATLIHQSITGLYETRIDLSKL-- | 1352 |
| WP_024784666 | 1282 | LAS---SFI | NLLTFTAIGAP-ATFKFFD--KNI--DRK--R-YTSTTEIL | NATLIHQSITGLYETRIDLNKL-- | 1342 |
| WP_024784894 | 1282 | LAS---SFI | NLLTFTAIGAP-ATFKFFD--KNI--DRK--R-YTSTTEIL | NATLIHQSITGLYETRIDLSKL-- | 1342 |
| WP_024786433 | 1288 | LAD---GFI | KLLGFTQLGAT-SPFSFLG--IKL--NQK--Q-YTGKKDYL | EATLIHQSITGLYETRIDLSKL-- | 1352 |

| | | | | |
|---|---|---|---|---|
| WP_049473442 | 1282 LAS---SFI | NLLTFTAIGAP-ATFKFPD--KNI--DRK--R-YTSTTEIL | NATLIHQSITGLYETRIDLSKL-- | 1342 |
| WP_049474547 | 1282 LAS---SFI | NLLTFTAIGAP-ATFKFPD--KNI--DRK--R-YTSTTEIL | KATLIHQSITGLYETRIDLSKL-- | 1342 |
| EMC03581 | 1275 LAS---SFI | NLLTFTAIGAP-ATFKFPD--KNI--DRK--R-YTSTTEIL | NATLIHQSITGLYETRIDLSKL-- | 1335 |
| WP_000428612 | 1310 LAN---SFI | NLLTFTALGAP-AAFKFPG--KDV--DRK--R-YTTVSEIL | NATLIHQSITGLYETRIDLSKL-- | 1370 |
| WP_000428613 | 1308 LAN---SFI | NLLTFTALGAP-AAFKFPG--KDI--DRK--R-YTTVSEIL | NATLIHQSITGLYETRIDLSKL-- | 1368 |
| WP_049523028 | 1303 IAN---SFI | NLLTFTAPGAP-AVFKFPG--KDI--ERK--R-YSTVTEIL | NATLIHQSLTGLYETRIDLSKL-- | 1363 |
| WP_003107102 | 1275 -AT---NML | NLFTFTGLGAP-ATLKFFN--VDI--DRK--R-YTSSTEIL | KATLIHQSITGLYETRIDLSKI-- | 1334 |
| WP_054279288 | 1304 -SI---SFL | NLFKFTSPGAP-EKFTFLN--SEIkqDDV--R-YRSTKECL | NSTLIRQSITGLYETRIDLSQF-- | 1365 |
| WP_049531101 | 1311 LSE---SFI | SLLKLTSPGAP-GAFRFLG--VEI--SQSnvR-YQSVSSCF | NATLIHQSVTGLYETRIDLSKL-- | 1373 |
| WP_049538452 | 1311 LSE---SFI | SLLKLTSPGAP-GAFKFLG--VEI--SQSsvR-YKPNSQFL | DATLIHQSITGLYETRIDLSKL-- | 1373 |
| WP_049549711 | 1313 LSE---SFI | SLLKLTSPGAP-GAFKFLG--AEI--SQSsvR-YKPNSQFL | DTTLIHQSITGLYETRIDLSKL-- | 1375 |
| WP_007896501 | 1312 -AL---NML | NLFIFTSLGAP-STFVFFD--ETI--DRK--R-YTTSSDVL | NGILIQQSITGLYETRIDLSRF-- | 1371 |
| EFR44625 | 1264 -AL---NML | NLFIFTSLGAP-STFVFFD--ETI--DRK--R-YTTSSDVL | NGILIQQSITGLYETRIDLSRF-- | 1323 |
| WP_002897477 | 1307 LAN---SFI | NLLTFTALGAP-AAFKFPG--KDV--DRK--R-YTTVSEIL | NATLIHQSITGLYETRIDLSKL-- | 1367 |
| WP_002906454 | 1312 LSE---SFI | SLLKLTSPGAP-GAFKFLG--VEI--SQSsvR-YKPNSQFL | DTTLIHQSITGLYETRIDLSKL-- | 1374 |
| WP_009729476 | 1308 LAN---SFI | NLLTFTALGAP-AAFKFPG--KDV--DRK--R-YTTVSEIL | NATLIHQSITGLYETRIDLSKL-- | 1368 |
| CQR24647 | 1296 LAQ---SFI | SLLKFTAPGAP-GGFKFLD--ADI--KQSnlR-YQTVTEVL | SSTLIHQSVTGLYETRIDLSKL-- | 1358 |
| WP_000066813 | 1312 LAN---SFI | NLLTFTALGAP-AAFKFPG--KDV--DRK--R-YTTVSEIL | NATLIHQSITGLYETRIDLSKL-- | 1372 |
| WP_009754323 | 1308 LAN---SFI | NLLTFTALGAP-AAFKFPG--KDV--DRK--R-YTTVSEIL | NATLIHQSITGLYETRIDLSKL-- | 1368 |
| WP_044674937 | 1301 LTS---SFV | NLLTFTAIGAP-AAFKFLG--SVI--DRK--R-YTSIAEIL | EATLIHQSVTGLYETRIDLSKL-- | 1361 |
| WP_044676715 | 1303 LTS---SFV | NLLTFTAIGAP-AAFKFLG--SVI--DRK--R-YTSIAEIL | EATLIHQSVTGLYETRIDLSKL-- | 1363 |
| WP_044680361 | 1303 LTS---SFV | NLLTFTAIGAP-AAFKFLG--SVI--DRK--R-YTSIAEIL | EATLIHQSVTGLYETRIDLSKL-- | 1363 |
| WP_044681799 | 1301 LTS---SFV | NLLTFTAIGAP-AAFKFLG--SVI--DRK--R-YTSIAEIL | EATLIHQSVTGLYETRIDLSKL-- | 1361 |
| WP_049533112 | 1314 ICT---SFL | GLFELTSLGSA-SDFEFLG--VKI--PRY--RdYTPSSLLK | DSTLIHQSVTGLYETRIDLSKL-- | 1383 |
| WP_029090905 | 1241 -VK---VI | ELLKITQANATnGDLKLLK---M-sNREg--R-LGSVSVAL | DFKIINQSVTGLYQSIEDYNN--- | 1300 |
| WP_006506696 | 1269 -AN---II | QMLIVMHRGPQnGNIVYDDf--KI-sDRIg--KI-LKTKNHNL | NIVFISQSPTGIYTKKYKL---- | 1329 |
| AIT42264 | 1306 -AE---NII | HLFTLTNLGAP-AAFKYPD--TTI--DRK--R-YTSTKEVL | DATLIHQSITGLYETRIDLSQL-- | 1365 |

| | | | | | |
|---|---|---|---|---|---|
| WP_034440723 | 1277 | LVE---SFI | NLLAITKCGPA-ADITFLG--EKI--SRK--R-YRSTNCLW | GSEVIFQSPTGLYETRLRLE---- | 1335 |
| AKQ21048 | 1306 | -AE---NII | HLFTLTNLGAP-AAFKYPD--TTI--DRK--R-YTSTKEVL | DATLIHQSPTGLYETRIDLSQL-- | 1365 |
| WP_004636532 | 1272 | TVE---SFV | NLMTFTAMGAP-ATFKFYG--ESI--TRS--R-YTSITEFR | GSTLIFQSITGLYETRYKL----- | 1329 |
| WP_002364836 | 1278 | IAA---SFI | QLMQFNAMGAP-STFKFFQ--DKI--ERA--R-YTSIKEIF | DATIIYQSTTGLYETRRKV----- | 1335 |
| WP_016631044 | 1229 | IAA---SFI | QLMQFNAMGAP-STFKFFQ--DKI--ERA--R-YTSIKEIF | DATIIYQSPTGLYETRRKV----- | 1286 |
| EMS75795 | 1014 | LSQ---SFI | NLMQLNAMGAP-ADFKFFD--VII--PRK--R-YPSLTEIW | ESTIIYQSITGLRETRTRMATLwd | 1076 |
| WP_002373311 | 1278 | IAA---SFI | QLMQFNAMGAP-STFKFFQ--DKI--ERA--R-YTSIKEIF | DATIIYQSTTGLYETRRKV----- | 1335 |
| WP_002378009 | 1278 | IAA---SFI | QLMQFNAMGAOP-STFKFFQ--DKI--ERA--R-YTSIKEIF | DATIIYQSTTGLYETRRKV----- | 1335 |
| WP_002407324 | 1278 | IAA---SFI | QLMQFNAMGAP-STFKFFQ--DKI--ERA--R-YTSIKEIF | DATIIYQSTTGLYETRRKV----- | 1335 |
| WP_002413717 | 1278 | IAA---SFI | QLMQFNAMGAP-STFKFFQ--DKI--ERA--R-YTSIKEIF | DATIIYQSTTGLYETRRKV----- | 1335 |
| WP_010775580 | 1280 | IAA---SFI | QLMQFNAMGAP-ADFKFFD--VII--PRK--R-YPSLTEIW | ESTIIYQSITGLRETRTRMATLwd | 1337 |
| WP_002318269 | 1278 | IAA---SFI | QLMQFNAMGAP-STFKFFQ--DKI--ERA--R-YTSIKEIF | DATIIYQSTTGLYETRRKV----- | 1335 |
| WP_010824395 | 1278 | IAA---SFI | QLMQFNAMGAP-STFKFFQ--DKI--ERA--R-YTSIKEIF | DATIIYQSTTGLYETRRKV----- | 1335 |
| WP_016622645 | 1278 | IAA---SFI | QLMQFNAMGAP-STFKFFQ--DKI--ERA--R-YTSIKEIF | DATIIYQSTTGLYETRRKV----- | 1335 |
| WP_033624816 | 1278 | IAA---SFI | QLMQFNAMGAP-STFKFFQ--DKI--ERA--R-YTSIKEIF | DATIIYQSTTGLYETRRKV----- | 1335 |
| WP_033625576 | 1278 | IAA---SFI | QLMQFNAMGAP-STFKFFQ--DKI--ERA--R-YTSIKEIF | DATIIYQSTTGLYETRRKV----- | 1335 |
| WP_033789179 | 1278 | IAA---SFI | QLMQFNAMGAP-STFKFFQ--DKI--ERA--R-YTSIKEIF | DATIIYQSTTGLYETRRKV----- | 1335 |
| WP_002310644 | 1280 | LAS---SFV | NLMQFNAMGAP-ADFKFFD--VTI--PRK--R-YTSLTEIW | QSTIIHQSITGLYETRIRMGK--- | 1339 |
| WP_002312694 | 1281 | LAS---SFV | NLMQFNAMGAP-ADFKFFD--VTI--PRK--R-YTSLTEIW | QSTIIHQSITGLYETRIRMGK--- | 1340 |
| WP_002314015 | 1281 | LAS---SFV | NLMQFNAMGAP-ADFKFFD--VTI--PRK--R-YTSLTEIW | QSTIIHQSITGLYETRIRMGK--- | 1340 |
| WP_002320716 | 1281 | LAS---SFV | NLMQFNAMGAP-ADFKFFD--VTI--PRK--R-YTSLTEIW | QSTIIHQSITGLYETRIRMGK--- | 1340 |
| WP_002330729 | 1280 | LAS---SFV | NLMQFNAMGAP-ADFKFFD--VTI--PRK--R-YTSLTEIW | QSTIIHQSITGLYETRIRMGK--- | 1339 |
| WP_002335161 | 1281 | LAS---SFV | NLMQFNAMGAP-ADFKFFD--VTI--PRK--R-YTSLTEIW | QSTIIHQSITGLYETRIRMGK--- | 1340 |
| WP_002345439 | 1281 | IAQ---SFL | QLLQFNAIGAP-ADFKFPG--VTI--PRK--R-YTSLTEIW | QSTIIHQSITGLYETRIRMGK--- | 1340 |
| WP_034867970 | 1271 | LAS---SFV | NLMQFNAMGAP-ADFKFFD--VTI--PRK--R-YTSLTEIW | DATIIYQSVTGLYETRIRMGDLwa | 1333 |
| WP_047937432 | 1281 | LAS---SFV | NLMQFNAMGAP-ADFKFFG--VTI--PRK--R-YTSLTEIW | QSTIIHQSITGLYETRIRMGK--- | 1340 |
| WP_010720994 | 1271 | IAQ---SFL | QLLQFNAIGAP-ADFKFPG--VTI--PRK--R-YTSLTEIW | DATIIYQSVTGLYETRIRMGDLwa | 1333 |

| ID | Start | | | | End |
|---|---|---|---|---|---|
| WP_010737004 | 1271 | IAQ---SFL | QLLQFNAIGAP-ADFKFFG--VTI--PRK--R-YTSLTEIW | DATIIYQSVTGLYETRIRMGDLwa | 1333 |
| WP_034700478 | 1271 | IAQ---SFL | QLLQFNAIGAP-ADFKFPG--VTI--PRK--R-YTSLTEIW | DATIIYQSVTGLYETRIRMGDLwa | 1333 |
| WP_007209003 | 1270 | IAK---SFI | NLLTFTAMGAP-ADFEFFG--EKI--PRK--R-YVSISEII | DAVFIHQSITGLYETRVRLTEV- | 1330 |
| WP_023519017 | 1265 | MID---AIL | SLLKFTLFGAS-VEFKFPD--IKI---LK--R-YKSLTDIW | EATIIYQSVTGLYERRVEVRKLwd | 1326 |
| WP_010770040 | 1275 | IAE---SFV | NLMKFSAYGAP-MDFKFFG--KTI--PRS--R-YTSVGELL | SATINQSITGLYETRRRL----- | 1332 |
| WP_048604708 | 1271 | IAQ---SFV | DLMQLNAFGAP-ADFKFFG--ETI--PRK--R-YTSVNELL | EATINQSITGLYETRRRL----- | 1328 |
| WP_010750235 | 1274 | MAH---SFV | NLMQFNALGAP-ADFKFFD--TTI--TRK--R-YTSLTEIW | QSTIIYQSVTGLYETRRRMADLwd | 1336 |
| AII16583 | 1345 | -AE---NII | HLFTLTNLGAP-AAFKYFD--TTI--DRK--R-YTSTKEVL | DATLIHQSITGLYETRIDLSQL- | 1404 |
| WP_029073316 | 1283 | -CE---VI | QMLVVMHAGPQnGNITFDDf--KL-sNRLg-R-LNCKTISL | TTVFIADSPTGMYSKKYKL---- | 1343 |
| WP_031589969 | 1284 | -CN---II | QILATLHCNSSiGKIMYSDf--KI-sTTIg-R-LNGRTISL | DISFIAESPTGMYSKKYKL---- | 1344 |
| KDA45870 | 1254 | LGK---NFV | ELLRYTADGAA-SDFKFFG--ENI--PRK--R-YNSAGSLL | NGTLIYQSKTGLYETRIDLGKL- | 1314 |
| WP_039099354 | 1307 | ILDr----V | -LIGLHANAAV-SDLGVLKiSTPL--GKM--Q---QPSGIS | DTQIIYQSPTGLFERRVALRDL- | 1368 |
| AKP02966 | 1297 | INSl-eELI | TLLHANSTSAH-LIFNNIE-kKAF--GRK------THGLT | DTDFIYQSVTGLYETRIHIE--- | 1356 |
| WP_010991369 | 1275 | IAQ---SFV | DLMAFNAMGAP-ASFKFFE--TTI--ERK--R-YNNLKELL | NSTIIYQSITGLYESRKRL---- | 1332 |
| WP_033838504 | 1275 | IAQ---SFV | DLMAFNAMGAP-ASFKFFE--TTI--ERK--R-YNNLKELL | NSTIIYQSITGLYESRKRL---- | 1332 |
| EHN60060 | 1278 | IAQ---SFV | DLMAFNAMGAP-ASFKFFE--TTI--ERK--R-YNNLKELL | NSTIIYQSITGLYESRKRL---- | 1335 |
| EFR89594 | 1044 | IAQ---SFV | DLMAFNAMGAP-ASFKFFE--TTI--ERK--R-YNNLKELL | NSTIIYQSITGLYESRKRL---- | 1101 |
| WP_038409211 | 1275 | IAK---SFD | KLKVFNAFGAP-RDFEFFE--TTI--KRK--R-YYNIKELL | NATIIYQSITGLYEARKRL---- | 1332 |
| EFR95520 | 894 | IAK---SFD | KLKVFNAFGAP-RDFEFFE--TTI--KRK--R-YYNIKELL | NATIIYQSITGLYEARKRL---- | 951 |
| WP_003723650 | 1275 | IAQ---SFV | DLMAFNAMGAP-ASFKFFE--ATI--DRK--R-YTNLKELL | SSTIIYQSITGLYESRKRL---- | 1332 |
| WP_003727705 | 1275 | IAQ---SFV | DLMAFNAMGAP-ASFKFFE--TTI--DRK--R-YTNLKELL | SSTIIYQSITGLYESRKRL---- | 1332 |
| WP_003730785 | 1275 | IAE---SFV | SLKKFNAFPGVH-QDFSFFG--TKI--ERK--R-DRKLNELL | NSTIIYQSITGLYESRKRL---- | 1332 |
| WP_003733029 | 1275 | IAE---SFV | NLMAFNAMGAP-ASFKFFE--ATI--ERK--R-YTNLKELL | SATIIYQSITGLYEARKRL---- | 1332 |
| WP_003739838 | 1275 | IAQ---SFV | DLMAFNAMGAP-ASFKFFE--ATI--DRK--R-YTNLKELL | SSTIIYQSITGLYESRKRL---- | 1332 |
| WP_014601172 | 1275 | IAE---SFV | SLKKFNAFPGVH-KDFNFFG--TTI--KRK--R-DRKLKELL | NSTIIYQSITGLYESRKRL---- | 1332 |
| WP_023548323 | 1275 | IAE---SFV | SLKKFNAFPGVH-KDFNFFG--TTI--KRK--R-DRKLKELL | NSTIIYQSITGLYESRKRL---- | 1332 |
| WP_031665337 | 1275 | IAQ---SFV | DLMAFNAMGAP-ASFKFFE--ATI--DRK--R-YTNLKELL | SSTIIYQSITGLYESRKRL---- | 1332 |

| Name | Start | Seq1 | Seq2 | End |
|---|---|---|---|---|
| WP_031669209 | 1275 | IAE---SFV | SLKKFNAFGVH-QDFSFPG--TKI--ERK--R-DRKLNELL NSTIIYQSITGLYESRKRL----- | 1332 |
| WP_033920898 | 1275 | IAE---SFV | SLKKFNAFGVH-KDFNFPG--TTI--KRK--R-DRKLKELL NSTIIYQSITGLYESRKRL----- | 1332 |
| AKI42028 | 1278 | IAQ---SFV | DLMAFNAMGAP-ASFKFFE--ATI--DRK--R-YTNLKELL SSTIIYQSITGLYESRKRL----- | 1335 |
| AKI50529 | 1278 | IAE---SFV | SLKKFNAFGVH-KDFNFPG--TTI--KRK--R-DRKLKELL NSTIIYQSITGLYESRKRL----- | 1335 |
| EFR83390 | 723 | IAQ---SFV | DLMVFNAMGAP-ASFKFFE--ATI--DRK--R-YTNLKELL SSTIIYQSITGLYESRKRL----- | 780 |
| WP_046323366 | 1275 | IAQ---SFV | NLLEFNAMGAP-ASFKYFE--TNI--ERK--R-YNNLKELL NATIIYQSITGLYEARKRL----- | 1332 |
| AKE81011 | 1322 | -AE---NII | HLFTLTNLGAP-AAFKYFD--TTI--DRK--R-YTSTKEVL DATLIHQSITGLYETRIDLSQL- | 1381 |
| CUO82355 | 1273 | -AN----VI | QMLIIMHKGPQnGNIIYDDf--NV-gKRig-R-LNGRTFYL NIEFISQSPTGIYTKKKYKL---- | 1333 |
| WP_033162887 | 1275 | -CD----VI | QILIIMHAGPMnGNIMYDDf--KF-tNRig-R-FTHKNIDL KTTFISTSVTGLFSKKKYKL---- | 1335 |
| AGZ01981 | 1339 | -AE---NII | HLFTLTNLGAP-AAFKYFD--TTI--DRK--R-YTSTKEVL DATLIHQSITGLYETRIDLSQL- | 1398 |
| AKA60242 | 1306 | -AE---NII | HLFTLTNLGAP-AAFKYFD--TTI--DRK--R-YTSTKEVL DATLIHQSITGLYETRIDLSQL- | 1365 |
| AKS40380 | 1306 | -AE---NII | HLFTLTNLGAP-AAFKYFD--TTI--DRK--R-YTSTKEVL DATLIHQSITGLYETRIDLSQL- | 1365 |
| 4UN5_B | 1310 | -AE---NII | HLFTLTNLGAP-AAFKYFD--TTI--DRK--R-YTSTKEVL DATLIHQSITGLYETRIDLSQL- | 1369 |
| WP_010922251 | 1366 | GGD | | 1368 |
| WP_039695303 | 1370 | GEE | | 1372 |
| WP_045635197 | 1368 | GED | | 1370 |
| 5AXW_A | | --- | | |
| WP_009880683 | 1050 | GGD | | 1052 |
| WP_010922251 | 1366 | GGD | | 1368 |
| WP_011054416 | 1366 | GGD | | 1368 |
| WP_011284745 | 1366 | GGD | | 1368 |
| WP_011285506 | 1366 | GGD | | 1368 |
| WP_011527619 | 1366 | GGD | | 1368 |
| WP_012566673 | 1366 | GGD | | 1368 |
| WP_014407541 | 1365 | GGD | | 1367 |
| WP_020905136 | 1366 | GGD | | 1368 |
| WP_023080005 | 1365 | GGD | | 1367 |

-continued

| | | | | |
|---|---|---|---|---|
| WP_023610282 | 1365 | GGD | 1367 | |
| WP_030125963 | 1366 | GGD | 1368 | |
| WP_030126706 | 1366 | GGD | 1368 | |
| WP_031488318 | 1366 | GGD | 1368 | |
| WP_032460140 | 1366 | GGD | 1368 | |
| WP_032461047 | 1366 | GGD | 1368 | |
| WP_032462016 | 1366 | GGD | 1368 | |
| WP_032462936 | 1366 | GGD | 1368 | |
| WP_032464890 | 1366 | GGD | 1368 | |
| WP_033888930 | 1191 | GGD | 1193 | |
| WP_038431314 | 1366 | GGD | 1368 | |
| WP_038432938 | 1365 | GGD | 1367 | |
| WP_038434062 | 1366 | GGD | 1368 | |
| BAQ51233 | 1277 | GGD | 1279 | |
| KGE60162 | 541 | GGD | 543 | |
| KGE60856 | 304 | GGD | 306 | |
| WP_002989955 | 1366 | GGD | 1368 | |
| WP_003030002 | 1343 | GED | 1345 | |
| WP_003065552 | 1371 | GEE | 1373 | |
| WP_001040076 | 1368 | GED | 1370 | |
| WP_001040078 | 1376 | GED | 1378 | |
| WP_001040080 | 1368 | GED | 1370 | |
| WP_001040081 | 1368 | GED | 1370 | |
| WP_001040083 | 1368 | GED | 1370 | |
| WP_001040085 | 1368 | GED | 1370 | |
| WP_001040087 | 1368 | GED | 1370 | |
| WP_001040088 | 1368 | GGD | 1370 | |

-continued

| | | |
|---|---|---|
| WP_001040089 | 1368 GED | 1370 |
| WP_001040090 | 1368 GED | 1370 |
| WP_001040091 | 1368 GED | 1370 |
| WP_001040092 | 1368 GED | 1370 |
| WP_001040094 | 1368 GED | 1370 |
| WP_001040095 | 1368 GEG | 1370 |
| WP_001040096 | 1368 GEG | 1370 |
| WP_001040097 | 1368 GED | 1370 |
| WP_001040098 | 1368 GED | 1370 |
| WP_001040099 | 1368 GED | 1370 |
| WP_001040100 | 1368 GED | 1370 |
| WP_001040104 | 1368 GED | 1370 |
| WP_001040105 | 1368 GED | 1370 |
| WP_001040106 | 1368 GED | 1370 |
| WP_001040107 | 1368 GED | 1370 |
| WP_001040108 | 1368 GED | 1370 |
| WP_001040109 | 1368 GED | 1370 |
| WP_001040110 | 1368 GED | 1370 |
| WP_015058523 | 1368 GED | 1370 |
| WP_017643650 | 1368 GED | 1370 |
| WP_017647151 | 1368 GED | 1370 |
| WP_017648376 | 1368 GED | 1370 |
| WP_017649527 | 1368 GED | 1370 |
| WP_017771611 | 1368 GED | 1370 |
| WP_017771984 | 1368 GED | 1370 |
| CFQ25032 | 1368 GED | 1370 |
| CFV16040 | 1368 GED | 1370 |

-continued

| | | | | |
|---|---|---|---|---|
| KLJ37842 | 1368 | GED | | 1370 |
| KLJ72361 | 1368 | GGD | | 1370 |
| KLL20707 | 1382 | GED | | 1384 |
| KLL42645 | 1368 | GED | | 1370 |
| WP_047207273 | 1368 | GED | | 1370 |
| WP_047209694 | 1368 | GED | | 1370 |
| WP_050198062 | 1368 | GED | | 1370 |
| WP_050201642 | 1368 | GED | | 1370 |
| WP_050204027 | 1368 | GED | | 1370 |
| WP_050881965 | 1368 | GED | | 1370 |
| WP_050886065 | 1368 | GED | | 1370 |
| AHN30376 | 1368 | GED | | 1370 |
| EAO78426 | 1368 | GED | | 1370 |
| CCW42055 | 1368 | GED | | 1370 |
| WP_003041502 | 1384 | GED | | 1386 |
| WP_037593752 | 1344 | GED | | 1346 |
| WP_049516684 | 1344 | GED | | 1346 |
| GAD46167 | 1343 | GED | | 1345 |
| WP_018363470 | 1375 | GEE | | 1377 |
| WP_003043819 | 1373 | GGD | | 1375 |
| WP_006269658 | 1343 | GED | | 1345 |
| WP_048800889 | 1363 | GED | | 1365 |
| WP_012767106 | 1369 | GGD | | 1371 |
| WP_014612333 | 1369 | GGD | | 1371 |
| WP_015017095 | 1369 | GGD | | 1371 |
| WP_015057649 | 1369 | GGD | | 1371 |
| WP_048327215 | 1369 | GGD | | 1371 |

-continued

| | | | | |
|---|---|---|---|---|
| WP_049519324 | 1369 | GGD | | 1371 |
| WP_012515931 | 1346 | GEN | | 1348 |
| WP_021320964 | 1346 | GEN | | 1348 |
| WP_037581760 | 1346 | GEN | | 1348 |
| WP_004232481 | 1375 | GEE | | 1377 |
| WP_009854540 | 1368 | GEE | | 1370 |
| WP_012962174 | 1369 | GEE | | 1371 |
| WP_039695303 | 1370 | GEE | | 1372 |
| WP_014334983 | 1373 | GEE | | 1375 |
| WP_003099269 | 1366 | GGK | | 1368 |
| AHY15608 | | --- | | |
| AHY17476 | | --- | | |
| ESR09100 | 198 | GGK | | 200 |
| AGM98575 | | --- | | |
| ALF27331 | 1343 | GGD | | 1345 |
| WP_018372492 | 1351 | GEN | | 1353 |
| WP_045618028 | 1374 | GED | | 1376 |
| WP_045635197 | 1368 | GED | | 1370 |
| WP_002263549 | 1343 | GGD | | 1345 |
| WP_002263887 | 1343 | GGD | | 1345 |
| WP_002264920 | 1343 | GGD | | 1345 |
| WP_002269043 | 1343 | GGD | | 1345 |
| WP_002269448 | 1343 | GGD | | 1345 |
| WP_002271977 | 1343 | GGD | | 1345 |
| WP_002272766 | 1343 | GGD | | 1345 |
| WP_002273241 | 1343 | GGD | | 1345 |
| WP_002275430 | 1343 | GGD | | 1345 |

-continued

| | | | |
|---|---|---|---|
| WP_002276448 | 1343 | GGD | 1345 |
| WP_002277050 | 1353 | GGD | 1355 |
| WP_002277364 | 1343 | GGD | 1345 |
| WP_002279025 | 1343 | GGD | 1345 |
| WP_002279859 | 1343 | GGD | 1345 |
| WP_002280230 | 1343 | GGD | 1345 |
| WP_002281696 | 1343 | GGD | 1345 |
| WP_002282247 | 1353 | GGD | 1355 |
| WP_002282906 | 1343 | GGD | 1345 |
| WP_002283846 | 1343 | GGD | 1345 |
| WP_002287255 | 1343 | GGD | 1345 |
| WP_002288990 | 1343 | GGD | 1345 |
| WP_002289641 | 1343 | GGD | 1345 |
| WP_002290427 | 1343 | GGD | 1345 |
| WP_002295753 | 1343 | GGD | 1345 |
| WP_002296423 | 1343 | GGD | 1345 |
| WP_002304487 | 1357 | GGD | 1359 |
| WP_002305844 | 1343 | GGD | 1345 |
| WP_002307203 | 1343 | GGD | 1345 |
| WP_002310390 | 1343 | GGD | 1345 |
| WP_002352408 | 1343 | GGD | 1345 |
| WP_012997688 | 1343 | GGD | 1345 |
| WP_014677909 | 1343 | GGD | 1345 |
| WP_019311892 | 1343 | GGD | 1345 |
| WP_019313659 | 1343 | GGD | 1345 |
| WP_019314093 | 1343 | GGD | 1345 |
| WP_019315370 | 1343 | GGD | 1345 |

| | | |
|---|---|---|
| WP_019803776 | 1343 GGD | 1345 |
| WP_019805234 | 1343 GGD | 1345 |
| WP_024783594 | 1343 GGD | 1345 |
| WP_024784288 | 1353 GGD | 1355 |
| WP_024784666 | 1343 GGD | 1345 |
| WP_024784894 | 1343 GGD | 1345 |
| WP_024786433 | 1353 GGD | 1355 |
| WP_049473442 | 1343 GGD | 1345 |
| WP_049474547 | 1343 GGD | 1345 |
| EMC03581 | 1336 GGD | 1338 |
| WP_000428612 | 1371 GED | 1373 |
| WP_000428613 | 1369 GED | 1371 |
| WP_049523028 | 1364 GEE | 1366 |
| WP_003107102 | 1335 GGD | 1337 |
| WP_054279288 | 1366 GGD | 1368 |
| WP_049531101 | 1374 GED | 1376 |
| WP_049538452 | 1374 GED | 1376 |
| WP_049549711 | 1376 GED | 1378 |
| WP_007896501 | 1372 GGD | 1374 |
| EFR44625 | 1324 GGD | 1326 |
| WP_002897477 | 1368 GEE | 1370 |
| WP_002906454 | 1375 GED | 1377 |
| WP_009729476 | 1369 GED | 1371 |
| CQR24647 | 1359 GGE | 1361 |
| WP_000066813 | 1373 GED | 1375 |
| WP_009754323 | 1369 GED | 1371 |
| WP_044674937 | 1362 GGD | 1364 |

| | | | |
|---|---|---|---|
| WP_044676715 | 1364 | GGD | 1366 |
| WP_044680361 | 1364 | GGD | 1366 |
| WP_044681799 | 1362 | GGD | 1364 |
| WP_049533112 | 1384 | GED | 1386 |
| WP_029090905 | | --- | |
| WP_006506696 | | --- | |
| AIT42264 | 1366 | GGD | 1389 |
| WP_034440723 | | --- | |
| AKQ21048 | 1366 | GGD | 1384 |
| WP_004636532 | 1330 | -ED | 1332 |
| WP_002364836 | 1336 | -VD | 1337 |
| WP_016631044 | 1287 | -VD | 1288 |
| EMS75795 | 1077 | GEQ | 1079 |
| WP_002373311 | 1336 | -VD | 1337 |
| WP_002378009 | 1336 | -VD | 1337 |
| WP_002407324 | 1336 | -VD | 1337 |
| WP_002413717 | 1338 | -VD | 1339 |
| WP_010775580 | 1336 | -VD | 1337 |
| WP_010818269 | 1336 | -VD | 1337 |
| WP_010824395 | 1336 | -VD | 1337 |
| WP_016622645 | 1336 | -VD | 1337 |
| WP_033624816 | 1336 | -VD | 1337 |
| WP_033625576 | 1336 | -VD | 1337 |
| WP_033789179 | 1336 | -VD | 1337 |
| WP_002310644 | | --- | |
| WP_002312694 | | --- | |
| WP_002314015 | | --- | |

-continued

| | | | |
|---|---|---|---|
| WP_002320716 | | --- | |
| WP_002330729 | | --- | |
| WP_002335161 | | --- | |
| WP_002345439 | | --- | |
| WP_034867970 | 1334 | GEQ | 1336 |
| WP_047937432 | 1334 | --- | 1336 |
| WP_010720994 | 1334 | GEQ | 1336 |
| WP_010737004 | 1334 | GEQ | 1336 |
| WP_034700478 | 1334 | GEQ | 1336 |
| WP_007209003 | 1334 | --- | |
| WP_023519017 | 1327 | GER | 1330 |
| WP_010770040 | 1333 | -VD | 1334 |
| WP_048604708 | 1329 | -GD | 1330 |
| WP_010750235 | 1337 | GVQ | 1339 |
| AII16583 | 1405 | GGD | 1424 |
| WP_029073316 | | --- | |
| WP_031589969 | | --- | |
| KDA45870 | | | |
| WP_039099354 | | --- | |
| AKP02966 | | | |
| WP_010991369 | 1333 | -DD | 1334 |
| WP_033838504 | 1333 | -DD | 1334 |
| EHN60060 | 1336 | -DD | 1337 |
| EFR89594 | 1102 | -DD | 1103 |
| WP_038409211 | 1333 | -ED | 1334 |
| EFR95520 | 952 | -ED | 953 |
| WP_003723650 | 1333 | -DD | 1334 |

-continued

| | | | |
|---|---|---|---|
| WP_003727705 | 1333 | -DD | 1334 |
| WP_003730785 | 1333 | -DD | 1334 |
| WP_003733029 | 1333 | -DN | 1334 |
| WP_003739838 | 1333 | -DG | 1334 |
| WP_014601172 | 1333 | -DD | 1334 |
| WP_023548323 | 1333 | -DS | 1334 |
| WP_031665337 | 1333 | -DD | 1334 |
| WP_031669209 | 1333 | -DN | 1334 |
| WP_033920898 | 1333 | -DS | 1334 |
| AKI42028 | 1336 | -DD | 1337 |
| AKI50529 | 1336 | -DS | 1337 |
| EFR83390 | 781 | -DD | 782 |
| WP_046323366 | 1333 | -DD | 1334 |
| AKE81011 | 1382 | GGD | 1400 |
| CUO82355 | | --- | |
| WP_033162887 | | --- | |
| AGZ01981 | 1399 | GGD | 1417 |
| AKA60242 | 1366 | GGD | 1368 |
| AKS40380 | 1366 | GGD | 1376 |
| 4UN5_B | 1370 | GGD | 1372 |

EQUIVALENTS AND SCOPE, INCORPORATION BY REFERENCE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

---

LENGTHY TABLES

The patent contains a lengthy table section. A copy of the table is available in electronic form from the USPTO web site (https://seqdata.uspto.gov/?pageRequest=docDetail&DocID=US11702651B2). An electronic copy of the table will also be available from the USPTO upon request and payment of the fee set forth in 37 CFR 1.19(b)(3).

---

SEQUENCE LISTING

The patent contains a lengthy sequence listing. A copy of the sequence listing is available in electronic form from the USPTO web site (https://seqdata.uspto.gov/?pageRequest=docDetail&DocID=US11702651B2). An electronic copy of the sequence listing will also be available from the USPTO upon request and payment of the fee set forth in 37 CFR 1.19(b)(3).

What is claimed is:

1. A nucleic acid molecule encoding an adenosine deaminase comprising an amino acid sequence that is at least 85% identical to the amino acid sequence of SEQ ID NOs: 1, 8, 9, 371, 372, 373, 374, or 375, with the exception of one or more substitutions at positions selected from the group consisting of amino acid residues corresponding to positions 8, 17, 18, 23, 34, 36, 45, 48, 51, 56, 59, 84, 85, 94, 95, 102, 104, 106, 107, 108, 110, 118, 123, 127, 138, 142, 146, 147, 149, 151, 152, 153, 154, 155, 156, and 157 of the amino acid sequence of SEQ ID NO: 1, wherein the adenosine deaminase deaminates adenine in deoxyribonucleic acid (DNA).

2. The nucleic acid molecule of claim 1, wherein the adenosine deaminase is a TadA deaminase.

3. The nucleic acid molecule of claim 1, wherein the nucleic acid molecule comprises deoxyribonucleic acid (DNA).

4. The nucleic acid molecule of claim 1, wherein the nucleic acid molecule comprises ribonucleic acid (RNA).

5. The nucleic acid molecule of claim 1, wherein the nucleic acid molecule is an mRNA.

6. The nucleic acid molecule of claim 5, wherein the mRNA is a modified mRNA.

7. The nucleic acid molecule of claim 1, wherein the nucleic acid molecule comprises one or more natural nucleosides, nucleoside analogs, chemically modified bases, biologically modified bases, intercalated bases, modified sugars, and/or modified phosphate groups.

8. The nucleic acid molecule of claim 7, wherein the nucleoside analog is selected from the group consisting of 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine.

9. The nucleic acid molecule of claim 7, wherein the modified phosphate group is a phosphorothioate.

10. The nucleic acid molecule of claim 7, wherein the biologically modified base is a methylated base.

11. The nucleic acid molecule of claim 1, wherein the adenosine deaminase comprises an amino acid sequence that is at least 85% identical to the amino acid sequence of SEQ ID NO: 1 or 8.

12. The nucleic acid molecule of claim 1, wherein said one or more substitutions are at positions selected from the group consisting of amino acid residues corresponding to positions 23, 36, 48, 51, 84, 106, 108, 123, 142, 146, 147, 152, 155, 156, and 157 of the amino acid sequence of SEQ ID NO: 1.

13. The nucleic acid molecule of claim 12, wherein said one or more substitutions are substitutions selected from the group consisting of W23R, W23L, H36L, P48S, P48A, R51L, L84F, A106V, D108N, H123Y, A142N, S146C, D147Y, R152P, E155V, I156F, and K157N of the amino acid sequence of SEQ ID NO: 1.

14. The nucleic acid molecule of claim 12, wherein said one or more substitutions comprise a group of substitutions at positions selected from the group of substitutions at positions consisting of:
(i) W23, H36, P48, R51, L84, A106, D108, H123, A142, 5146, D147, R152, E155, I156, and K157;
(ii) W23, H36, P48, R51, L84, A106, D108, H123, S146, D147, R152, E155, I156, and K157;
(iii) H36, P48, R51, L84, A106, D108, H123, A142, 5146, D147, E155, I156, and K157;

(iv) H36, P48, R51, L84, A106, D108, H123, S146, D147, E155, I156, and K157;
(v) H36, R51, L84, A106, D108, H123, S146, D147, E155, I156, and K157;
(vi) L84, A106, D108, H123, D147, E155, and I156;
(vii) A106, D108, D147, and E155;
(viii) A106 and D108; and
(ix) D108; of the amino acid sequence of SEQ ID NO: 1.

15. The nucleic acid molecule of claim 12, wherein said one or more substitutions comprise a group of substitutions selected from the groups of substitutions consisting of:
(i) W23L, H36L, P48A, R51L, L84F, A106V, D108N, H123Y, A142N, S146C, D147Y, R152P, E155V, I156F, and K157N;
(ii) W23R, H36L, P48A, R51L, L84F, A106V, D108N, H123Y, S146C, D147Y, R152P, E155V, I156F, and K157N;
(iii) H36L, P48S, R51L, L84F, A106V, D108N, H123Y, A142N, S146C, D147Y, E155V, I156F, and K157N;
(iv) H36L, P48S, R51L, L84F, A106V, D108N, H123Y, S146C, D147Y, E155V, I156F, and K157N;
(v) H36L, R51L, L84F, A106V, D108N, H123Y, S146C, D147Y, E155V, I156F, and K157N;
(vi) L84F, A106V, D108N, H123Y, D147Y, E155V, and I156F;
(vii) A106V, D108N, D147Y, and E155V;
(viii) A106V and D108N; and
(ix) D108N; of the amino acid sequence of SEQ ID NO: 1.

16. A nucleic acid molecule encoding a base editor for modifying a base within a nucleic acid sequence, wherein the base editor comprises:
a) a nucleic acid programmable DNA binding protein (napDNAbp) domain, wherein said napDNAbp domain site specifically binds said nucleic acid sequence when associated with a bound nucleic acid; and
b) an adenosine deaminase domain comprising said adenosine deaminase encoded by the nucleic acid molecule of claim 1.

17. The nucleic acid molecule of claim 16, wherein said napDNAbp domain comprises a Cas9 domain, a Cpf1 domain, a CasX domain, a CasY domain, a C2c1 domain, a C2c2 domain, or a C2c3 domain.

18. The nucleic acid molecule of claim 17, wherein said napDNAbp domain comprises a Cas9 domain.

19. The nucleic acid molecule of claim 18, wherein said Cas9 domain comprises a nuclease dead Cas9 (dCas9) domain, a Cas9 nickase (nCas9) domain, or a nuclease active Cas9 domain.

20. The nucleic acid molecule of claim 18, wherein said Cas9 domain comprises an amino acid sequence that is at least 85% identical to any one of SEQ ID NOs: 34-36.

21. The nucleic acid molecule of claim 18, wherein said Cas9 domain comprises the amino acid sequence of any one of SEQ ID NOs: 34-36.

22. The nucleic acid molecule of claim 16, wherein said adenosine deaminase domain is a TadA deaminase.

23. The nucleic acid molecule of claim 16, wherein said adenosine deaminase domain is fused to the N-terminus of said napDNAbp domain.

24. The nucleic acid molecule of claim 23, wherein said adenosine deaminase domain is fused via a linker.

25. The nucleic acid molecule of claim 16, wherein said base editor further comprises a second adenosine deaminase domain.

26. The nucleic acid molecule of claim 25, wherein said second adenosine deaminase domain is fused to the N-terminus of said adenosine deaminase domain.

27. The nucleic acid molecule of claim 25, wherein said second adenosine deaminase domain does not deaminate adenine in DNA.

28. The nucleic acid molecule of claim 25, wherein said second adenosine deaminase domain is capable of deaminating adenine in DNA.

29. The nucleic acid molecule of claim 16 further comprising an inhibitor of base excision repair.

30. The nucleic acid molecule of claim 29, wherein the inhibitor of base excision repair is a catalytically inactive inosine specific nuclease (dISN).

31. The nucleic acid molecule of claim 25, wherein said second adenosine deaminase domain is fused to the C-terminus of said adenosine deaminase domain.

32. The nucleic acid molecule of claim 25, wherein said second adenosine deaminase domain is a TadA adenosine deaminase.

33. The nucleic acid molecule of claim 25, wherein said second adenosine deaminase comprises an amino acid sequence that is at least 85% identical to the amino acid sequence of SEQ ID NO: 1.

34. The nucleic acid molecule of claim 16, wherein the nucleic acid molecule comprises deoxyribonucleic acid (DNA).

35. The nucleic acid molecule of claim 16, wherein the nucleic acid molecule comprises ribonucleic acid (RNA).

36. The nucleic acid molecule of claim 16, wherein the nucleic acid is an mRNA.

37. The nucleic acid molecule of claim 36, wherein the mRNA is a modified mRNA.

38. The nucleic acid molecule of claim 16, wherein the nucleic acid molecule comprises one or more natural nucleosides, nucleoside analogs, chemically modified bases, biologically modified bases, intercalated bases, modified sugars, and/or modified phosphate groups.

39. The nucleic acid molecule of claim 38, wherein the nucleoside analog is selected from the group consisting of 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine.

40. The nucleic acid molecule of claim 38, wherein the modified phosphate group is a phosphorothioate.

41. The nucleic acid molecule of claim 38, wherein the biologically modified base is a methylated base.

42. A vector comprising the nucleic acid molecule of claim 1.

43. The vector of claim 42, wherein the vector comprises a heterologous promoter driving expression of the polynucleotide.

44. The vector of claim 42, wherein the vector is a viral vector.

45. The vector of claim 44, wherein the viral vector is an adeno-associated virus (AAV) vector.

46. A vector comprising the nucleic acid molecule of claim 16.

47. The vector of claim 46, wherein the vector comprises a heterologous promoter driving expression of the nucleic acid molecule.

48. The vector of claim 46, wherein the vector is a viral vector.

49. The vector of claim 48, wherein the viral vector is an adeno-associated virus (AAV) vector.

50. A cell comprising the vector of claim 42.

51. A cell comprising the vector of claim 46.

52. A pharmaceutical composition comprising the nucleic acid molecule of claim 1 encapsulated within a lipid particle.

53. The pharmaceutical composition of claim 52, wherein the nucleic acid molecule is an mRNA.

54. The pharmaceutical composition of claim 52 further comprising a pharmaceutically acceptable excipient.

55. A pharmaceutical composition comprising the nucleic acid molecule of claim 16 encapsulated within a lipid particle.

56. The pharmaceutical composition of claim 55, wherein the nucleic acid molecule is an mRNA.

57. The pharmaceutical composition of claim 55 further comprising a pharmaceutically acceptable excipient.

58. A kit comprising a vector comprising a heterologous promoter that drives expression of the nucleic acid molecule of claim 1.

59. The kit of claim 58, wherein the vector is an AAV vector.

60. A kit comprising a vector comprising a heterologous promoter that drives expression of the nucleic acid molecule of claim 16.

61. The kit of claim 60, wherein the vector is an AAV vector.

* * * * *

UNITED STATES PATENT AND TRADEMARK OFFICE
CERTIFICATE OF CORRECTION

PATENT NO. : 11,702,651 B2  
APPLICATION NO. : 17/148059  
DATED : July 18, 2023  
INVENTOR(S) : David R. Liu et al.

Page 1 of 1

It is certified that error appears in the above-identified patent and that said Letters Patent is hereby corrected as shown below:

In the Claims

In Claim 14, at Column 635, Line 63, the text: "5146, D147, R152, E155, I156, and K157;" should be replaced with: -- S146, D147, R152, E155, I156, and K157; --.

In Claim 14, at Column 635, Line 66, the text: "(iii) H36, P48, R51, L84, A106, D108, H123, A142, 5146," should be replaced with: -- (iii) H36, P48, R51, L84, A106, D108, H123, A142, S146, --.

Signed and Sealed this  
Twenty-fourth Day of October, 2023

Katherine Kelly Vidal  
*Director of the United States Patent and Trademark Office*